US007747395B2

(12) United States Patent
Scheinberg et al.

(10) Patent No.: US 7,747,395 B2
(45) Date of Patent: Jun. 29, 2010

(54) METHOD OF INHIBITOR DESIGN AND IDENTIFICATION USING A 3-D STRUCTURE OF HUMAN PEPTIDE DEFORMYLASE

(75) Inventors: David A. Scheinberg, New York, NY (US); Sindy Noemi Escobar-Alvarez, New York, NY (US); Yehuda Goldgur, Fair Lawn, NJ (US); Yueming Li, New York, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 61 days.

(21) Appl. No.: 11/787,237

(22) Filed: Apr. 13, 2007

(65) Prior Publication Data

US 2008/0254442 A1 Oct. 16, 2008

(51) Int. Cl.
*G01N 31/00* (2006.01)
*C12Q 1/34* (2006.01)
*C12Q 1/00* (2006.01)
(52) U.S. Cl. .............................. 702/27; 435/18; 435/4; 435/5; 435/7.21; 435/7.22; 435/7.32
(58) Field of Classification Search ........................ None
See application file for complete search history.

(56) References Cited

U.S. PATENT DOCUMENTS

2008/0124808 A1* 5/2008 Rodgers et al. ............... 436/86

OTHER PUBLICATIONS

Lee et al., J. Clin. Invest. 114:1107-1116, 2004.*
Lee et al., "A new human peptide deformylase inhibitable by actinonin", Biochem. Biophys. Res. Comm. 312:309-315, 2003.*
Altschul et al., Basic local alignment search tool. J Mol Biol. Oct. 5, 1990;215(3):403-10.
Antczak et al., High-throughput identification of inhibitors of human mitochondrial peptide deformylase. J Biomol. Screen. 2007;12(4):521-35.
Apfel et al., Peptide deformylase as an antibacterial drug target: target validation and resistance development. Antimicrob Agents Chemother. Apr. 2001;45(4):1058-64.
Bailey et al., The *CCP4* Suite: Programs for Protein Crystallography. Acta Crystallogr D. 1994;50:760-63.
Balakrishnon et al., Metalloprotease inhibitors GM6001 and TAPI-0 inhibit the obligate intracellular human pathogen Chlamydia trachomatis by targeting peptide deformylase of the bacterium. J Biol Chem. Jun. 16, 2006;281(24):16691-9. Epub Mar. 24, 2006.
Baldwin et al., Crystal structure of type II peptide deformylase from Staphylococcus aureus. J Biol Chem. Aug. 23, 2002;277(34):31163-71. Epub Jun. 4, 2002.
Bartlett et al., Molecular Recognition in Chemical and Biological Problems, Special Pub., Royal Chem Soc. 1989;78:182-96.
Becker et al., Iron center, substrate recognition and mechanism of peptide deformylase. Nat Struct Biol. Dec. 1998;5(12):1053-8.
Becker et al., Structure of peptide deformylase and identification of the substrate binding site. J Biol Chem. May 8, 1998;273(19):11413-6.

Bingel-Erlenmeyer et al., A peptide deformylase-ribosome complex reveals mechanism of nascent chain processing. Nature. Mar. 6, 2008;452(7183):108-11. Epub Feb. 20, 2008.
Böhm, The computer program LUDI: a new method for the de novo design of enzyme inhibitors. J Comput Aided Mol Des. Feb. 1992;6(1):61-78.
Bonnet et al., A mitochondria-K+ channel axis is suppressed in cancer and its normalization promotes apoptosis and inhibits cancer growth. Cancer Cell. Jan. 2007;11(1):37-51.
Boularot et al., Discovery and refinement of a new structural class of potent peptide deformylase inhibitors. J Med Chem. Jan. 11, 2007;50(1):10-20.
Brünger et al., Crystallography & NMR system: A new software suite for macromolecular structure determination. Acta Crystallogr D Biol Crystallogr. Sep. 1, 1998;54(Pt 5):905-21.
Chan et al., Crystal structure of the *Escherichia coli* peptide deformylase. Biochemistry. Nov. 11, 1997;36(45):13904-9.
Chen et al., Actinonin, a naturally occurring antibacterial agent, is a potent deformylase inhibitor. Biochemistry. Feb. 15, 2000;39(6):1256-62.
Clamp et al., The Jalview Java alignment editor. Bioinformatics. Feb. 12, 2004;20(3):426-7. Epub Jan. 22, 2004.
Clements et al., Antibiotic activity and characterization of BB-3497, a novel peptide deformylase inhibitor. Antimicrob Agents Chemother. Feb. 2001;45(2):563-70.
Cohen et al., Molecular modeling software and methods for medicinal chemistry. J Med Chem. Mar. 1990;33(3):883-94.
Don et al., Mitochondria as cancer drug targets. Trends Mol Med. Aug. 2004;10(8):372-8.
Escobar-Alvarez et al., Structure and activity of human mitochondrial peptide deformylase, a novel cancer target. J Mol Biol. Apr. 17, 2009;387(5):1211-28. Epub Feb. 21, 2009.
Fearnley et al., Two overlapping genes in bovine mitochondrial DNA encode membrane components of ATP synthase. EMBO J. Aug. 1986;5(8):2003-8.
Fieulaine et al., The crystal structure of mitochondrial (Type 1A) peptide deformylase provides clear guidelines for the design of inhibitors specific for the bacterial forms. J Biol Chem. Dec. 23, 2005;280(51):42315-24. Epub Sep. 28, 2005.
Giglione et al., Control of protein life-span by N-terminal methionine excision. EMBO J. Jan. 2, 2003;22(1):13-23.
Giglione et al., Identification of eukaryotic peptide deformylases reveals universality of N-terminal protein processing mechanisms. EMBO J. Nov. 1, 2000;19(21):5916-29.
Giglione et al., Organellar peptide deformylases: universality of the N-terminal methionine cleavage mechanism. Trends Plant Sci. Dec. 2001;6(12):566-72.

(Continued)

*Primary Examiner*—David J Steadman
(74) *Attorney, Agent, or Firm*—Wolf, Greenfield & Sacks, P.C.; C. Hunter Baker

(57) ABSTRACT

The present invention provides the three-dimensional structure of human mitochondrial *Homo sapiens* peptide deformylase (HsPDF) protein, and HsPDF complexed to a binding compound, such as a PDF inhibitor. This crystallographic information will aid in the identification and development of novel binding compounds of HsPDF and other PDF family members which have anti-bacterial, anti-viral, anti-parasitical, anti-inflammatory, and/or anti-cancer activity.

10 Claims, 24 Drawing Sheets

OTHER PUBLICATIONS

Golovchenko et al., Analysis of pH-dependent protein interactions with gel filtration medium. J Chromatogr. Feb. 7, 1992;591(1-2):121-8.

Good et al., Hydrogen ion buffers for biological research. Biochemistry. Feb. 1966;5(2):467-77.

Goodford, A computational procedure for determining energetically favorable binding sites on biologically important macromolecules. J Med Chem. Jul. 1985;28(7):849-57.

Goodsell et al., Automated docking of substrates to proteins by simulated annealing. Proteins. 1990;8(3):195-202.

Grant et al., Inhibition and structure-activity studies of methionine hydroxamic acid derivatives with bacterial peptide deformylase. Bioorg Chem. Aug. 2001;29(4):211-22.

Grujic et al., Actinonin induces apoptosis in U937 leukemia cells. Cancer Lett. Jun. 8, 2005;223(2):211-8. Epub Dec. 13, 2004.

Guilloteau et al., The crystal structures of four peptide deformylases bound to the antibiotic actinonin reveal two distinct types: a platform for the structure-based design of antibacterial agents. J Mol Biol. Jul. 26, 2002;320(5):951-62.

Harris et al., Co-crystallization of *Staphylococcus aureus* peptide deformylase (PDF) with potent inhibitors. Acta Crystallogr D Biol Crystallogr. Dec. 2002;58(Pt 12):2153-6. Epub Nov. 23, 2002.

Howard et al., A novel class of inhibitors of peptide deformylase discovered through high-throughput screening and virtual ligand screening. J Med Chem. Dec. 30, 2004;47(27):6669-72.

Jain et al., Bacterial Peptide deformylase inhibitors: a new class of antibacterial agents. Curr Med Chem. 2005;12(14):1607-21.

Jenkins et al., Catalytic domain of human immunodeficiency virus type 1 integrase: identification of a soluble mutant by systematic replacement of hydrophobic residues. Proc Natl Acad Sci U S A. Jun. 20, 1995;92(13):6057-61.

Jones et al., Potential utility of a peptide deformylase inhibitor (NVP PDF-713) against oxazolidinone-resistant or streptogramin-resistant Gram-positive organism isolates. J Antimicrob Chemother. May 2004;53(5):804-7. Epub Mar. 31, 2004.

Kierzek et al., Models of protein crystal growth. Biophys Chem. Jun. 15, 2001;91(1):1-20.

Kreusch et al., Structure analysis of peptide deformylases from *Streptococcus pneumoniae, Staphylococcus aureus, Thermotoga maritima* and *Pseudomonas aeruginosa*: snapshots of the oxygen sensitivity of peptide deformylase. J Mol Biol. Jul. 4, 2003;330(2):309-21.

Kroemer, Mitochondria in cancer. Oncogene. Aug. 7, 2006;25(34):4630-2.

Kuntz et al., A geometric approach to macromolecule-ligand interactions. J Mol Biol. Oct. 25, 1982;161(2):269-88.

Lazennec et al., Formate dehydrogenase-coupled spectrophotometric assay of peptide deformylase. Anal Biochem. Jan. 1, 1997;244(1):180-2.

Leeds et al., Peptide deformylase as an antibacterial target: a critical assessment. Curr Opin Pharmacol. Oct. 2006;6(5):445-52. Epub Aug. 9, 2006.

Liao et al., Identification and initial characterization of translational initiation factor 2 from bovine mitochondria. J Biol Chem. Aug. 15, 1990;265(23):13618-22.

Lofland et al., in vitro antibacterial activity of the peptide deformylase inhibitor BB-83698. J Antimicrob Chemother. Apr. 2004;53(4):664-8. Epub Feb. 18, 2004.

Martin, 3D database searching in drug design. J Med Chem. Jun. 12, 1992;35(12):2145-54.

Mazel et al., Genetic characterization of polypeptide deformylase, a distinctive enzyme of eubacterial translation. EMBO J. Feb. 15, 1994;13(4):914-23.

Meinnel et al., A new subclass of the zinc metalloproteases superfamily revealed by the solution structure of peptide deformylase. J Mol Biol. Sep. 27, 1996;262(3):375-86.

Miranker et al., Functionality maps of binding sites: a multiple copy simultaneous search method. Proteins. 1991;11(1):29-34.

Murshudov et al., Refinement of macromolecular structures by the maximum-likelihood method. Acta Crystallogr D Biol Crystallogr. May 1, 1997;53(Pt 3):240-55.

Navaza, *AMoRe*: an Automated Package for Molecular Replacement. Acta Crystallogr D. 1994;A50:157-163.

Navia et al., Use of structural information in drug design. Current Opinions in Structural Biology. 1992;2:202-10.

Nguyen et al., Characterization of a human peptide deformylase: implications for antibacterial drug design. Biochemistry. Aug. 26, 2003;42(33):9952-8.

Nishibata et al., Automatic Creation of Drug Candidate Structure Based on Receptor Structure. Starting Point for Artificial Lead Generation. Tetrahedron. 1991;47:8985-90.

Park et al., Crystallization and preliminary X-ray crystallographic analysis of peptide deformylase (PDF) from *Bacillus cereus* in ligand-free and actinonin-bound forms. Acta Crystallogr Sect F Struct Biol Cryst Commun. Jan. 1, 2005;61(Pt 1):150-2. Epub Dec. 24, 2004.

Ragusa et al., Substrate recognition and selectivity of peptide deformylase. Similarities and differences with metzincins and thermolysin. J Mol Biol. Jun. 25, 1999;289(5):1445-57.

Schechter et al., On the active site of proteases. III. Mapping the active site of papain; specific peptide inhibitors of papain. Biochem Biophys Res Commun. Sep. 6, 1968;32(5):898-902.

Schechter et al., On the size of the active site in proteases. I. Papain. Biochem Biophys Res Commun. Apr. 20, 1967;27(2):157-62.

Schwede et al, Swiss-Model: An automated protein homology-modeling server. Nucleic Acids Res. Jul. 1, 2003;31(13):3381-5.

Serero et al., An unusual peptide deformylase features in the human mitochondrial N-terminal methionine excision pathway. J Biol Chem. Dec. 26, 2003;278(52):52953-63. Epub Oct. 7, 2003.

Sharma et al., Structure of the mammalian mitochondrial ribosome reveals an expanded functional role for its component proteins. Cell. Oct. 3, 2003;115(1):97-108.

Smith et al., Structural variation and inhibitor binding in polypeptide deformylase from four different bacterial species. Protein Sci. Feb. 2003;12(2):349-60.

Spencer et al., Interaction of mitochondrial initiation factor 2 with mitochondrial fMet-tRNA. Nucleic Acids Res. Oct. 11, 2004;32(18):5464-70. Print 2004.

Takenga et al., In vitro metabolism of a new anticancer agent, 6-N-formylamino-12, 13-dihydro-1,11-dihydroxy-13-(beta-D-glucopyranosil)5H-indolo+ ++[2,3-a]pyrrolo[3,4-c]carbazole-5,7(6H)-dione (NB-506), in mice, rats, dogs, and humans. Drug Metab Dispos. Feb. 1999;27(2):213-20.

Takeuchi et al., Mammalian mitochondrial methionyl-tRNA transformylase from bovine liver. Purification, characterization, and gene structure. J Biol Chem. Jun. 12, 1998;273(24):15085-90.

Takeuchi et al., Recognition of tRNAs by Methionyl-tRNA transformylase from mammalian mitochondria. J Biol Chem. Jun. 8, 2001;276(23):20064-8. Epub Mar. 23, 2001.

Teo et al., Peptide deformylase inhibitors as potent antimycobacterial agents. Antimicrob Agents Chemother. Nov. 2006;50(11):3665-73. Epub Sep. 11, 2006.

Thompson et al., Clustal W: improving the sensitivity of progressive multiple sequence alignment through sequence weighting, position-specific gap penalties and weight matrix choice. Nucleic Acids Res. Nov. 11, 1994;22(22):4673-80.

Walker et al., Identification of the subunits of F1F0-ATPase from bovine heart mitochondria. Biochemistry. Jun. 4, 1991;30(22):5369-78.

Wallace et al., LIGPLOT: a program to generate schematic diagrams of protein-ligand interactions. Protein Eng. Feb. 1995;8(2):127-34.

Wang et al., Docking studies of Nickel-Peptide deformylase (PDF) inhibitors: exploring the new binding pockets. Biophys Chem. Jun. 20, 2006;122(1):43-9. Epub Mar. 6, 2006.

Watters et al, Antimicrobial activity of a novel peptide deformylase inhibitor, LBM415, tested against respiratory tract and cutaneous infection pathogens: a global surveillance report (2003-2004). J Antimicrob Chemother. May 2006;57(5):914-23. Epub Mar. 20, 2006.

Wei et al, Continuous spectrophotometric assay of peptide deformylase. Anal Biochem. Jul. 15, 1997;250(1):29-34.

Weiss et al., Global indicators of X-ray data quality. J. Appl. Crystallogr. 2001;34:130-35.

Wiencek, New strategies for protein crystal growth. Annu Rev Biomed Eng. 1999;1:505-34.

Wise et al., In vitro activities of peptide deformylase inhibitors against gram-positive pathogens Antimicrob Agents Chemother. Apr. 2002;46(4):1117-8.

Xu et al., Antitumor activity of actinonin in vitro and in vivo. Clin Cancer Res. Jan. 1998;4(1):171-6.

Yagi et al., Identification of the dicyclohexylcarbodiimide-binding subunit of NADH-ubiquinone oxidoreductase (Complex I). J Biol Chem. Nov. 5, 1988;263(31):16150-5.

Yoon et al., Crystal structure of peptide deformylase from *Staphylococcus aureus* in complex with actinonin, a naturally occurring antibacterial agent. Proteins. Nov. 15, 2004;57(3):639-42.

Zhou et al., Co-crystallization of Leptospira interrogans peptide deformylase with a potent inhibitor and molecular-replacement schemes with eight subunits in an asymmetric unit. Acta Crystallogr D Biol Crystallogr. Jan. 2004;60(Pt 1):137-9. Epub Dec. 18, 2003.

Zhou et al., Novel conformational states of peptide deformylase from pathogenic bacterium Leptospira interrogans: implications for population shift. J Biol Chem. Dec. 23, 2005;280(51):42391-6. Epub Oct. 20, 2005.

Zhou et al., Unique structural characteristics of peptide deformylase from pathogenic bacterium Leptospira interrogans. J Mol Biol. May 21, 2004;339(1):207-15.

\* cited by examiner

HsPDF in red

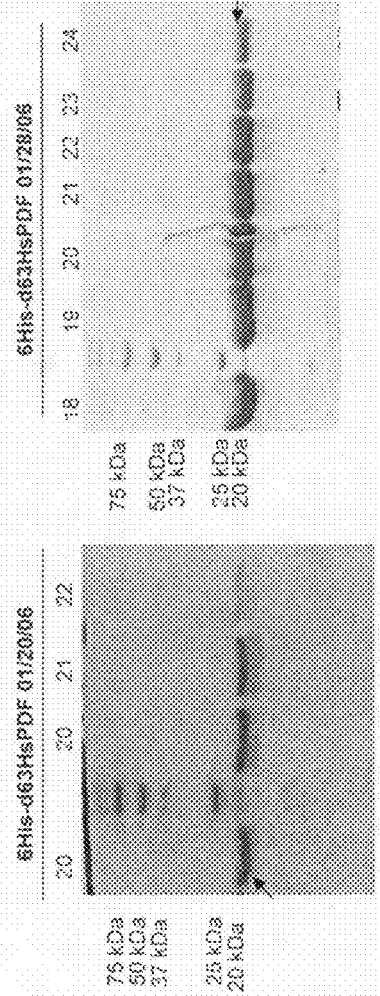
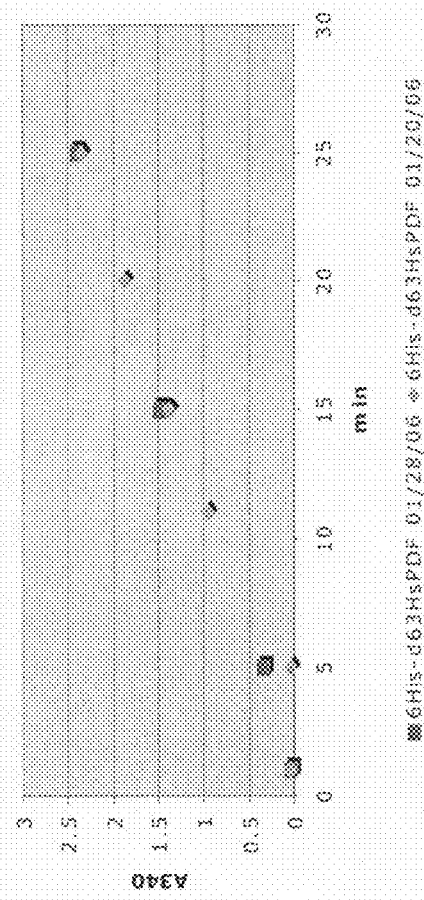
Figure 10A
Figure 10B
Figure 11

63HsPDF (SEQ ID NO: 18)

| Cycle #: | 1 | 2 | 3 | 4 | 5 | 6 | 7 | 8 | 9 | 10 |
|---|---|---|---|---|---|---|---|---|---|---|
| AA: | G | S | H | M | S | F | S | H | V | x |

\* At the level of sensitivities employed, free Cysteines are not detected during Edman degradation analysis.

\*\* During HPLC analysis of the PTH-amino acid derivatives, Tryptophan co-elutes with a chemical by-product; this residue is therefore not called during sequence analysis.

Figure 14

SEQUENCE LISTING

<160> NUMBER OF SEQ ID NOS: 18

<210> SEQ ID NO 1
<211> LENGTH: 202
<212> TYPE: PRT
<213> ORGANISM: Homo sapiens

<400> SEQUENCE: 1

Met Gly Ser Ser His His His His His His Ser Ser Gly Leu Val Pro
1               5                   10                  15

Arg Gly Ser His Met Ser Phe Ser His Val Cys Gln Val Gly Asp Pro
            20                  25                  30

Val Leu Arg Gly Val Ala Ala Pro Val Glu Arg Ala Gln Leu Gly Gly
        35                  40                  45

Pro Glu Leu Gln Arg Leu Thr Gln Arg Leu Val Gln Val Met Arg Arg
    50                  55                  60

Arg Arg Cys Val Gly Leu Ser Ala Pro Gln Leu Gly Val Pro Arg Gln
65                  70                  75                  80

Val Leu Ala Leu Glu Leu Pro Glu Ala Leu Cys Arg Glu Cys Pro Pro
                85                  90                  95

Arg Gln Arg Ala Leu Arg Gln Met Glu Pro Phe Pro Leu Arg Val Phe
            100                 105                 110

Val Asn Pro Ser Leu Arg Val Leu Asp Ser Arg Leu Val Thr Phe Pro
        115                 120                 125

Glu Gly Cys Glu Ser Val Ala Gly Phe Leu Ala Cys Val Pro Arg Phe
    130                 135                 140

Gln Ala Val Gln Ile Ser Gly Leu Asp Pro Asn Gly Glu Gln Val Val
145                 150                 155                 160

Trp Gln Ala Ser Gly Trp Ala Ala Arg Ile Ile Gln His Glu Met Asp
                165                 170                 175

His Leu Gln Gly Cys Leu Phe Ile Asp Lys Met Asp Ser Arg Thr Phe
            180                 185                 190

Thr Asn Val Tyr Trp Met Lys Val Asn Asp
        195                 200

<210> SEQ ID NO 2
<211> LENGTH: 202
<212> TYPE: PRT
<213> ORGANISM: Artificial Sequence
<220> FEATURE:
<223> OTHER INFORMATION: The pET-15 Delta63HsPDF clone amino acid
      sequence

<400> SEQUENCE: 2

Met Gly Ser Ser His His His His His His Ser Ser Gly Leu Val Pro
1               5                   10                  15

Arg Gly Ser His Met Ser Phe Ser His Val Cys Gln Val Gly Asp Pro
            20                  25                  30

Val Leu Arg Gly Val Ala Ala Pro Val Glu Arg Ala Gln Leu Gly Gly
        35                  40                  45

Pro Glu Leu Gln Arg Leu Thr Gln Arg Leu Val Gln Val Met Arg Arg
    50                  55                  60

Arg Arg Cys Val Gly Leu Ser Ala Pro Gln Leu Gly Val Pro Arg Gln
65                  70                  75                  80

Val Leu Ala Leu Glu Leu Pro Glu Ala Leu Cys Arg Glu Cys Pro Pro
                85                  90                  95

```
Arg Gln Arg Ala Leu Arg Gln Met Glu Pro Phe Pro Leu Arg Val Phe
            100                 105                 110

Val Asn Pro Ser Leu Arg Val Leu Asp Ser Arg Leu Val Thr Phe Pro
            115                 120                 125

Glu Gly Cys Glu Ser Val Ala Gly Phe Leu Ala Cys Val Pro Arg Phe
            130                 135                 140

Gln Ala Val Gln Ile Ser Gly Leu Asp Pro Asn Gly Glu Gln Val Val
145                 150                 155                 160

Trp Gln Ala Ser Gly Trp Ala Ala Arg Ile Ile Gln His Glu Met Asp
                165                 170                 175

His Leu Gln Gly Cys Leu Phe Ile Asp Lys Met Asp Ser Arg Thr Phe
            180                 185                 190

Thr Asn Val Tyr Trp Met Lys Val Asn Asp
            195                 200
```

<210> SEQ ID NO 3
<211> LENGTH: 185
<212> TYPE: PRT
<213> ORGANISM: Artificial Sequence
<220> FEATURE:
<223> OTHER INFORMATION: Delta63HsPDF amino acid sequence

<400> SEQUENCE: 3

```
Gly Ser His Met Ser Phe Ser His Val Cys Gln Val Gly Asp Pro Val
1               5                   10                  15

Leu Arg Gly Val Ala Ala Pro Val Glu Arg Ala Gln Leu Gly Gly Pro
            20                  25                  30

Glu Leu Gln Arg Leu Thr Gln Arg Leu Val Gln Val Met Arg Arg Arg
            35                  40                  45

Arg Cys Val Gly Leu Ser Ala Pro Gln Leu Gly Val Pro Arg Gln Val
        50                  55                  60

Leu Ala Leu Glu Leu Pro Glu Ala Leu Cys Arg Glu Cys Pro Pro Arg
65                  70                  75                  80

Gln Arg Ala Leu Arg Gln Met Glu Pro Phe Pro Leu Arg Val Phe Val
                85                  90                  95

Asn Pro Ser Leu Arg Val Leu Asp Ser Arg Leu Val Thr Phe Pro Glu
            100                 105                 110

Gly Cys Glu Ser Val Ala Gly Phe Leu Ala Cys Val Pro Arg Phe Gln
            115                 120                 125

Ala Val Gln Ile Ser Gly Leu Asp Pro Asn Gly Glu Gln Val Val Trp
        130                 135                 140

Gln Ala Ser Gly Trp Ala Ala Arg Ile Ile Gln His Glu Met Asp His
145                 150                 155                 160

Leu Gln Gly Cys Leu Phe Ile Asp Lys Met Asp Ser Arg Thr Phe Thr
                165                 170                 175

Asn Val Tyr Trp Met Lys Val Asn Asp
            180                 185
```

<210> SEQ ID NO 4
<211> LENGTH: 6249
<212> TYPE: DNA
<213> ORGANISM: Artificial Sequence
<220> FEATURE:
<223> OTHER INFORMATION: The pET-15b-6His-Delta63HsPDF nucleotide
      sequence

<400> SEQUENCE: 4

-continued

```
ttctcatgtt tgacagctta tcatcgataa gctttaatgc ggtagtttat cacagttaaa    60
ttgctaacgc agtcaggcac cgtgtatgaa atctaacaat gcgctcatcg tcatcctcgg   120
caccgtcacc ctggatgctg taggcatagg cttggttatg ccggtactgc cgggcctctt   180
gcgggatatc cggatatagt tcctcctttc agcaaaaaac ccctcaagac ccgtttagag   240
gccccaaggg gttatgctag ttattgctca gcggtggcag cagccaactc agcttccttt   300
cgggctttgt tagcagccgg atccttagtc attcaccttc atccaataga cgtttgtgaa   360
cgtcctgctg tccattttgt caataaacag gcagccctgc aggtggtcca tctcgtgctg   420
gatgatgcgc gctgcccacc cgctcgcctg ccacaccacc tgttctccat tggggtccag   480
ccctgagatc tgcaccgcct ggaagcgggg cacgcaggcc aggaagccgg cgacgctctc   540
gcagccctcg ggaaaggtga ccaggcggct gtcaagcact cgcaggctgg ggttcacgaa   600
cacgcgcagg gggaagggct ccatttggcg gagcgcgcgc tggcggggcg ggcactcccg   660
acacagcgcc tcggggagct ccagcgccag cacctgccgc ggcaccccca gctgcggcgc   720
gcttaggccc acgcagcgcc gccgccgcat cacctggacc agccgttgcg tcagccgctg   780
cagctcgggc ccgcctagct gcgcccgctc caccggggcc gccacgccgc gcagcaccgg   840
gtccccgact tggcacacgt gcgagaatga catatggctg ccgcgcggca ccaggccgct   900
gctgtgatga tgatgatgat ggctgctgcc catggtatat ctccttctta aagttaaaca   960
aaattatttc tagaggggaa ttgttatccg ctcacaattc cctatagtg agtcgtatta  1020 atttcgcggg atcgagatct cgatcctcta cgccggacgc atcgtggccg gcatcaccgg  1080
cgccacaggt gcggttgctg cgcctatat cgccgacatc accgatgggg aagatcgggc  1140
tcgccacttc gggctcatga gcgcttgttt cggcgtgggt atggtggcag gccccgtggc  1200
cgggggactg ttgggcgcca tctccttgca tgcaccattc cttgcggcgg cggtgctcaa  1260
cggcctcaac ctactactgg gctgcttcct aatgcaggag tcgcataagg gagagcgtcg  1320
agatcccgga caccatcgaa tggcgcaaaa cctttcgcgg tatggcatga tagcgcccgg  1380
aagagagtca attcagggtg gtgaatgtga accagtaac gttatacgat gtcgcagagt  1440
atgccggtgt ctcttatcag accgtttccc gcgtggtgaa ccaggccagc cacgtttctg  1500
cgaaaacgcg ggaaaagtg gaagcggcga tggcggagct gaattacatt cccaaccgcg  1560
tggcacaaca actggcgggc aaacagtcgt tgctgattgg cgttgccacc tccagtctgg  1620
ccctgcacgc gccgtcgcaa attgtcgcgc gattaaatc tcgcgccgat caactgggtg  1680
ccagcgtggt ggtgtcgatg gtagaacgaa gcggcgtcga agcctgtaaa gcggcggtgc  1740
acaatcttct cgcgcaacgc gtcagtgggc tgatcattaa ctatccgctg gatgaccagg  1800
atgccattgc tgtggaagct gcctgcacta atgttccggc gttatttctt gatgtctctg  1860
accagacacc catcaacagt attatttct cccatgaaga cggtacgcga ctgggcgtgg  1920
agcatctggt cgcattgggt caccagcaaa tcgcgctgtt agcgggccca ttaagttctg  1980
tctcggcgcg tctgcgtctg gctggctggc ataaatatct cactcgcaat caaattcagc  2040
cgatagcgga acgggaaggc gactggagtg ccatgtccgg ttttcaacaa accatgcaaa  2100
tgctgaatga gggcatcgtt cccactgcga tgctggttgc caacgatcag atggcgctgg  2160
gcgcaatgcg cgccattacc gagtccggc tgcgcgttgg tgcggatatc tcggtagtgg  2220
gatacgacga taccgaagac agctcatgtt atatcccgcc gttaaccacc atcaaacagg  2280
attttcgcct gctggggcaa accagcgtgg accgcttgct gcaactctct cagggccagg  2340
cggtgaaggg caatcagctg ttgcccgtct cactggtgaa aagaaaaacc accctggcgc  2400
```

```
ccaatacgca aaccgcctct ccccgcgcgt tggccgattc attaatgcag ctggcacgac    2460
aggtttcccg actggaaagc gggcagtgag cgcaacgcaa ttaatgtaag ttagctcact    2520
cattaggcac cgggatctcg accgatgccc ttgagagcct tcaacccagt cagctccttc    2580
cggtgggcgc ggggcatgac tatcgtcgcc gcacttatga ctgtcttctt tatcatgcaa    2640
ctcgtaggac aggtgccggc agcgctctgg gtcattttcg gcgaggaccg ctttcgctgg    2700
agcgcgacga tgatcggcct gtcgcttgcg gtattcggaa tcttgcacgc cctcgctcaa    2760
gccttcgtca ctggtcccgc caccaaacgt ttcggcgaga agcaggccat tatcgccggc    2820
atggcggccg acgcgctggg ctacgtcttg ctggcgttcg cgacgcgagg ctggatggcc    2880
ttccccatta tgattcttct cgcttccggc ggcatcggga tgcccgcgtt gcaggccatg    2940
ctgtccaggc aggtagatga cgaccatcag ggacagcttc aaggatcgct cgcggctctt    3000
accagcctaa cttcgatcac tggaccgctg atcgtcacgg cgatttatgc cgcctcggcg    3060
agcacatgga acgggttggc atggattgta ggcgccgccc tataccttgt ctgcctcccc    3120
gcgttgcgtc gcggtgcatg gagcgggggcc acctcgacct gaatggaagc cggcggcacc    3180
tcgctaacgg attcaccact ccaagaattg gagccaatca attcttgcgg agaactgtga    3240
atgcgcaaac caaccttgg cagaacatat ccatcgcgtc cgccatctcc agcagccgca    3300
cgcggcgcat ctcgggcagc gttgggtcct ggccacgggt gcgcatgatc gtgctcctgt    3360
cgttgaggac ccggctaggc tggcggggtt gccttactgg ttagcagaat gaatcaccga    3420
tacgcgagcg aacgtgaagc gactgctgct gcaaaacgtc tgcgacctga gcaacaacat    3480
gaatggtctt cggtttccgt gtttcgtaaa gtctggaaac gcggaagtca gcgccctgca    3540
ccattatgtt ccggatctgc atcgcaggat gctgctggct accctgtgga acacctacat    3600
ctgtattaac gaagcgctgg cattgaccct gagtgatttt tctctggtcc cgccgcatcc    3660
ataccgccag ttgtttaccc tcacaacgtt ccagtaaccg ggcatgttca tcatcagtaa    3720
cccgtatcgt gagcatcctc tctcgtttca tcggtatcat taccccatg aacagaaatc    3780 ccccttacac ggaggcatca gtgaccaaac aggaaaaaac cgcccttaac atggcccgct    3840
ttatcagaag ccagacatta acgcttctgg agaaactcaa cgagctggac gcggatgaac    3900
aggcagacat ctgtgaatcg cttcacgacc acgctgatga gctttaccgc agctgcctcg    3960
cgcgtttcgg tgatgacggt gaaaacctct gacacatgca gctcccggag acggtcacag    4020
cttgtctgta gcggatgcc gggagcagac aagcccgtca gggcgcgtca gcgggtgttg    4080
gcgggtgtcg gggcgcagcc atgacccagt cacgtagcga tagcggagtg tatactggct    4140
taactatgcg gcatcagagc agattgtact gagagtgcac catatatgcg gtgtgaaata    4200
ccgcacagat gcgtaaggag aaaataccgc atcaggcgct cttccgcttc ctcgctcact    4260
gactcgctgc gctcggtcgt tcggctgcgg cgagcggtat cagctcactc aaaggcggta    4320
atacggttat ccacagaatc aggggataac gcaggaaaga acatgtgagc aaaaggccag    4380
caaaaggcca ggaaccgtaa aaaggccgcg ttgctggcgt ttttccatag gctccgcccc    4440
cctgacgagc atcacaaaaa tcgacgctca agtcagaggt ggcgaaaccc gacaggacta    4500
taaagatacc aggcgtttcc ccctggaagc tccctcgtgc gctctcctgt tccgaccctg    4560
ccgcttaccg gatacctgtc cgcctttctc ccttcgggaa gcgtggcgct ttctcatagc    4620
tcacgctgta ggtatctcag ttcggtgtag gtcgttcgct ccaagctggg ctgtgtgcac    4680
gaaccccccg ttcagcccga ccgctgcgcc ttatccggta actatcgtct tgagtccaac    4740
```

```
ccggtaagac acgacttatc gccactggca gcagccactg gtaacaggat tagcagagcg    4800
aggtatgtag gcggtgctac agagttcttg aagtggtggc ctaactacgg ctacactaga    4860
aggacagtat ttggtatctg cgctctgctg aagccagtta ccttcggaaa aagagttggt    4920
agctcttgat ccggcaaaca aaccaccgct ggtagcggtg gttttttttgt ttgcaagcag    4980 cagattacgc gcagaaaaaa aggatctcaa gaagatcctt tgatcttttc tacggggtct    5040
gacgctcagt ggaacgaaaa ctcacgttaa gggattttgg tcatgagatt atcaaaaagg    5100
atcttcacct agatcctttt aaattaaaaa tgaagtttta aatcaatcta agtatatat    5160 gagtaaactt ggtctgacag ttaccaatgc ttaatcagtg aggcacctat ctcagcgatc    5220
tgtctatttc gttcatccat agttgcctga ctccccgtcg tgtagataac tacgatacgg    5280
gagggcttac catctggccc cagtgctgca atgataccgc gagacccacg ctcaccggct    5340
ccagatttat cagcaataaa ccagccagcc ggaagggccg agcgcagaag tggtcctgca    5400
actttatccg cctccatcca gtctattaat tgttgccggg aagctagagt aagtagttcg    5460
ccagttaata gtttgcgcaa cgttgttgcc attgctgcag gcatcgtggt gtcacgctcg    5520
tcgtttggta tggcttcatt cagctccggt tcccaacgat caaggcgagt tacatgatcc    5580
cccatgttgt gcaaaaaagc ggttagctcc ttcggtcctc cgatcgttgt cagaagtaag    5640
ttggccgcag tgttatcact catggttatg gcagcactgc ataattctct tactgtcatg    5700
ccatccgtaa gatgcttttc tgtgactggt gagtactcaa ccaagtcatt ctgagaatag    5760
tgtatgcggc gaccgagttg ctcttgcccg gcgtcaacac gggataatac cgcgccacat    5820
agcagaactt taaaagtgct catcattgga aaacgttctt cggggcgaaa actctcaagg    5880
atcttaccgc tgttgagatc cagttcgatg taacccactc gtgcacccaa ctgatcttca    5940
gcatctttta ctttcaccag cgtttctggg tgagcaaaaa caggaaggca aaatgccgca    6000
aaaaagggaa taagggcgac acggaaatgt tgaatactca tactcttcct ttttcaatat    6060
tattgaagca tttatcaggg ttattgtctc atgagcggat acatatttga atgtatttag    6120
aaaaataaac aaatagggt tccgcgcaca tttccccgaa aagtgccacc tgacgtctaa    6180
gaaaccatta ttatcatgac attaacctat aaaaataggc gtatcacgag gccctttcgt    6240
cttcaagaa                                                            6249
```

<210> SEQ ID NO 5
<211> LENGTH: 40
<212> TYPE: DNA
<213> ORGANISM: Artificial Sequence
<220> FEATURE:
<223> OTHER INFORMATION: The forward primer nucleotide sequence NdeI_F

<400> SEQUENCE: 5
ggaattccat atgtcattct cgcacgtgtg ccaagtcggg                           40

<210> SEQ ID NO 6
<211> LENGTH: 39
<212> TYPE: DNA
<213> ORGANISM: Artificial Sequence
<220> FEATURE:
<223> OTHER INFORMATION: The reverse primer nucleotide sequence BamHI_R

<400> SEQUENCE: 6
cgcggatcct tagtcattca ccttcatcca atagacgtt                            39

<210> SEQ ID NO 7
<211> LENGTH: 22

```
<212> TYPE: PRT
<213> ORGANISM: Homo sapiens

<400> SEQUENCE: 7

Leu Pro Glu Ala Leu Cys Arg Glu Cys Pro Pro Arg Gln Arg Ala Leu
1               5                   10                  15

Arg Gln Met Glu Pro Phe
            20

<210> SEQ ID NO 8
<211> LENGTH: 10
<212> TYPE: PRT
<213> ORGANISM: Homo sapiens

<400> SEQUENCE: 8

Thr Asn Val Tyr Trp Met Lys Val Asn Asp
1               5                   10

<210> SEQ ID NO 9
<211> LENGTH: 6
<212> TYPE: PRT
<213> ORGANISM: Homo sapiens

<400> SEQUENCE: 9

Asp Ser Arg Leu Val Thr
1               5

<210> SEQ ID NO 10
<211> LENGTH: 7
<212> TYPE: PRT
<213> ORGANISM: Homo sapiens

<400> SEQUENCE: 10

Trp Ala Ala Arg Ile Ile Gln
1               5

<210> SEQ ID NO 11
<211> LENGTH: 8
<212> TYPE: PRT
<213> ORGANISM: Homo sapiens

<400> SEQUENCE: 11

Cys Val Gly Leu Ser Ala Pro Gln
1               5

<210> SEQ ID NO 12
<211> LENGTH: 5
<212> TYPE: PRT
<213> ORGANISM: Homo sapiens

<400> SEQUENCE: 12

Glu Gly Cys Glu Ser
1               5

<210> SEQ ID NO 13
<211> LENGTH: 6
<212> TYPE: PRT
<213> ORGANISM: Homo sapiens

<400> SEQUENCE: 13

His Glu Met Asp His Leu
1               5

<210> SEQ ID NO 14
```

```
<211> LENGTH: 5
<212> TYPE: PRT
<213> ORGANISM: Artificial Sequence
<220> FEATURE:
<223> OTHER INFORMATION: synthetic sequence from vector

<400> SEQUENCE: 14

Gly Ser His Met Ser
1               5

<210> SEQ ID NO 15
<211> LENGTH: 8
<212> TYPE: PRT
<213> ORGANISM: Artificial Sequence
<220> FEATURE:
<223> OTHER INFORMATION: HsPDF consensus sequence
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 15

Gly Xaa Gly Xaa Ala Ala Xaa Gln
1               5

<210> SEQ ID NO 16
<211> LENGTH: 5
<212> TYPE: PRT
<213> ORGANISM: Artificial Sequence
<220> FEATURE:
<223> OTHER INFORMATION: HsPDF consensus sequence
<220> FEATURE:
<221> NAME/KEY: misc_feature
<222> LOCATION: (4)..(4)
<223> OTHER INFORMATION: Xaa can be any naturally occurring amino acid

<400> SEQUENCE: 16

Glu Cys Gly Xaa Ser
1               5

<210> SEQ ID NO 17
<211> LENGTH: 183
<212> TYPE: PRT
<213> ORGANISM: Artificial Sequence
<220> FEATURE:
<223> OTHER INFORMATION: Delta63HsPDF amino acid sequence

<400> SEQUENCE: 17

His Met Ser Phe Ser His Val Cys Gln Val Gly Asp Pro Val Leu Arg
1               5                   10                  15

Gly Val Ala Ala Pro Val Glu Arg Ala Gln Leu Gly Gly Pro Glu Leu
                20                  25                  30

Gln Arg Leu Thr Gln Arg Leu Val Gln Val Met Arg Arg Arg Arg Cys
            35                  40                  45

Val Gly Leu Ser Ala Pro Gln Leu Gly Val Pro Arg Gln Val Leu Ala
        50                  55                  60

Leu Glu Leu Pro Glu Ala Leu Cys Arg Glu Cys Pro Pro Arg Gln Arg
65                  70                  75                  80

Ala Leu Arg Gln Met Glu Pro Phe Pro Leu Arg Val Phe Val Asn Pro
```

-continued

```
                        85                    90                    95
Ser Leu Arg Val Leu Asp Ser Arg Leu Val Thr Phe Pro Glu Gly Cys
            100                   105                   110

Glu Ser Val Ala Gly Phe Leu Ala Cys Val Pro Arg Phe Gln Ala Val
            115                   120                   125

Gln Ile Ser Gly Leu Asp Pro Asn Gly Glu Gln Val Val Trp Gln Ala
            130                   135                   140

Ser Gly Trp Ala Ala Arg Ile Ile Gln His Glu Met Asp His Leu Gln
145                     150                   155                   160

Gly Cys Leu Phe Ile Asp Lys Met Asp Ser Arg Thr Phe Thr Asn Val
                    165                   170                   175

Tyr Trp Met Lys Val Asn Asp
                180

<210> SEQ ID NO 18
<211> LENGTH: 10
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 18

Gly Ser His Met Ser Phe Ser His Val Xaa
1               5                   10
```

METHOD OF INHIBITOR DESIGN AND IDENTIFICATION USING A 3-D STRUCTURE OF HUMAN PEPTIDE DEFORMYLASE

GOVERNMENT FUNDING

The work described herein was supported, in part, by a grant from the National Institutes of Health (CA-55349). The United States government may have certain rights in the invention.

BACKGROUND

Peptide deformylase (PDF) has been long recognized as important in protein synthesis. Removal of the formyl moiety on methionine of nascent proteins by PDF is a necessary activity for prokaryotic cell viability (Mazel et al., *Embo J* (1994) 13:914-923). The central role of PDF in bacterial protein synthesis has led to significant efforts to discover antibiotics that selectively target bacterial PDFs (Howard et al., *J Med Chem* (2004) 47:6669-6672; Leeds and Dean *Current Opinion in Pharmacology* (2006) 6: 445-452). PDF inhibitors are a promising drug class, as has been demonstrated by the broad spectrum activity in vitro against drug resistant bacterial strains of the clinical drug candidates LBM415 (Watters et al., *J Antimicrob Chemother* (2006) 57:914-923) and BB-83698 (Lofland et al., *J Antimicrob Chemother* (2004) 53:664-668). The PDF inhibitor BB-83698 has been proposed as a tuberculosis treatment (Teo et al, *Antimicrob Agents Chemother* (2006) 50:3665-3673).

PDF activity was not believed to be important in eukaryotic cells until recently because nuclear encoded proteins are not N-formylated (Serero et al., *J Biol Chem* (2003) 278:52953-52963). However, in eukaryotes, mitochondrial protein synthesis involves the formylation and deformylation of proteins, as evidenced by the presence of the enzymatic machinery to perform these activities in mammals and plants, among other eukaryotes (Giglione et al., *Embo J* (2000). 19:5916-5929; Takeuchi et al., *J Biol Chem* (2001) 276:20064-20068; Takeuchi et al., *J Biol Chem* (1998) 273:15085-15090). The human mitochondrial *Homo sapiens* peptide deformylase (HsPDF) protein, which participates in the N-methionine excision pathway of newly synthesized peptides encoded by the mitochondrial genome, removes the N-terminal formyl group on the initiator methionine, and is important for cancer cell viability (Lee et al., *Biochem Biophys Res Commun* (2003) 312: 309-315; Lee et al., *J Clin Invest* (2004) 114:1107-1116; Serero et al. (2003) supra). For example, cancer cell lines appear to be more sensitive to HsPDF inhibition than normal non-cancer cell lines (Lee (2003) and Lee (2004) supra). As well, ATP depletion and mitochondrial membrane depolarization result from the inhibition of HsPDF with the PDF inhibitor actinonin. siRNA interference and pharmacologic inhibition both decrease human cell growth. Furthermore, the PDF inhibitor actinonin and its analogs exhibit anti-cancer activity in vitro and in vivo (Xu et al., *Clin Cancer Res* (1998) 4:171-176).

The wealth of information made available through efforts in structural genomics and advances in computation has allowed structure-based drug design to emerge as a valuable tool in medicinal chemistry. In the past combinatorial chemistry, coupled with high-throughput approaches, shifted attention away from structure-based drug discovery. Protein x-ray crystal structure determination is reversing the drug discovery process by starting with the protein crystal structure to identify and design new ligands. It is the integration of structure-based methods, virtual screening, and combinatorial chemistry that will provide the basis for more efficient drug design in the future, significantly reducing the time of the design cycle and the cost per marketed drug.

SUMMARY OF THE INVENTION

The present invention provides purification and crystallization methods for human mitochondrial *Homo sapiens* peptide deformylase (HsPDF) protein. The present invention also provides detailed three-dimensional structural information provided from single crystal X-ray crystallography of HsPDF and HsPDF complexed with a binding compound. Such information will aid in the identification and development of novel compounds which bind to HsPDF and/or related PDF family members, and which may possess anti-bacterial, anti-viral, anti-parasitical, anti-inflammatory, and/or anti-cancer activity.

In one embodiment of the invention, three-dimensional structure information is provided from a crystal of N-truncated HsPDF, i.e., Δ63HsPDF (SEQ ID NO:2). The Δ63HsPDF crystal belongs to the monoclinic space group C2 and has unit cell dimensions of a=115.938 Å, b=77.642 Å, c=110.711 Å, α=90.00°, β=107.820°, and γ=90.00°. Atomic structure coordinates for Δ63HsPDF are provided in Table 1, as set forth in Appendix A, provided herewith.

In another aspect, the present invention provides the three-dimensional structure of Δ63HsPDF bound to the antibiotic and PDF inhibitor actinonin. Crystalline actinonin-bound Δ63HsPDF belongs to the monoclinic space group C2 and has unit dimensions of a=116.158 Å, b=77.884 Å, c=110.596 Å, α=90.00°, β=107.409°, γ=90.00°. Atomic structure coordinates for crystalline actinonin-bound Δ63HsPDF are provided in Table 2, as set forth in Appendix B, provided herewith.

Both Tables 1 and 2 provide information useful in the design of novel compounds which bind to HsPDF and/or PDF family members, and which may also possess anti-bacterial, anti-viral, anti-parasitical, anti-inflammatory, and/or anti-cancer activity.

In other embodiments, methods of designing and identifying a binding compound of HsPDF and/or related PDF family members are provided.

For instance, one method includes the steps of: (a) providing a three-dimensional structure of HsPDF as defined by the atomic coordinates provided in Tables 1 and/or 2; (b) employing the three-dimensional structure to design and/or select a potential binding compound; and (c) synthesizing and/or choosing the potential binding compound.

In certain embodiments, the method further comprises the steps of: (d1) contacting the potential binding compound with HsPDF and/or a PDF family member in the presence of a formylated substrate; and (e1) determining the percent inhibition of deformylase activity to determine the activity of the potential binding compound.

Alternatively, in certain embodiments, the above method further comprises the steps of: (d2) contacting the potential binding compound with a cell, virus, bacterium, and/or parasite; and (e2) determining the cytotoxicity of the potential binding compound to the cell, virus, bacterium, and/or parasite. In certain embodiments, the cell is a cancer cell.

Another method comprises the steps of (a) using a three-dimensional structure of HsPDF as defined by the atomic coordinates provided in Tables 1 and/or 2 by characterizing: (i) an active site or accessory binding site of HsPDF and/or a PDF family member from the atomic structure coordinates found in Tables 1 and/or 2, or (ii) an active site or accessory binding site of HsPDF and/or a PDF family member by comparison to the atomic structure coordinates found in Tables 1 and/or 2, and (b) designing and/or selecting a potential binding compound that is capable of binding to at least one amino acid in the active site and/or accessory binding site (i) or (ii) of HsPDF and/or a PDF family member in the absence of a known inhibitor; (c) synthesizing and/or choosing the potential binding compound.

In certain embodiments, the above method further comprises the steps of: (d1) contacting the potential binding compound with HsPDF and/or a PDF family member in the presence of a formylated substrate; and (e1) determining the percent inhibition of deformylase activity of HsPDF and/or a PDF family member to determine the activity of the potential binding compound.

Alternatively, in certain embodiments, the above method further comprises the steps of: (d2) contacting the potential binding compound with a cell, virus, bacterium, and/or parasite; and (e2) determining the cytotoxicity of the potential binding compound to the cell, virus, bacterium, and/or parasite. In certain embodiments, the cell is a cancer cell.

The present invention also provides methods for solving unknown crystal structures by performing molecular replacement using the atomic structure coordinates provided in Tables 1 or 2.

Thus, in certain embodiments, the present invention provides a method for solving the structure of HsPDF or a PDF family member comprising the steps of: (a) collecting X-ray diffraction data of a HsPDF crystal or a PDF-family member crystal; (b) using the atomic coordinates of HsPDF according to Tables 1 and/or 2 to perform molecular replacement with the X-ray diffraction data of the HsPDF crystal or the PDF-family member crystal; and (c) determining the structure of HsPDF or the PDF-family member.

Furthermore, in certain embodiments, the present invention provides a method for solving the structure of HsPDF or a PDF family member complexed to a binding compound comprising the steps of: (a) collecting X-ray diffraction data of a HsPDF crystal complexed to a binding compound or a PDF-family member crystal complexed to a binding compound; (b) using the atomic coordinates of HsPDF according to Tables 1 and/or 2 to perform molecular replacement with the X-ray diffraction data of the HsPDF crystal or PDF-family member crystal; and (c) determining the structure of HsPDF complexed to a binding compound or PDF-family member complexed to a binding compound.

Additionally, the present invention provides a method of evaluating the binding properties of a potential binding compound comprising the steps of: (a) soaking a potential binding compound with crystalline HsPDF or a crystalline PDF family member to provide a crystalline HsPDF complexed to a binding compound or a crystalline PDF-family member complexed to a binding compound; (b) determining the three-dimensional structure of the crystalline HsPDF complexed to a binding compound or the crystalline PDF-family member complexed to a binding compound by molecular replacement using the three-dimensional structure of HsPDF as defined by atomic coordinates according to Tables 1 and/or 2; and (c) analyzing the three-dimensional structure of the a crystalline HsPDF complexed to a binding compound or a crystalline PDF-family member complexed to a binding compound to the unbound potential binding compound to evaluate the binding characteristics of the potential binding compound.

The details of one or more embodiments of the invention are set forth herein. Other features, objects, and advantages of the invention will be apparent from the description, the figures, the examples, and the claims.

All references cited herein, including patents, published patent applications and publications, are incorporated by reference in their entirety.

Definitions

Amino acid residues in peptides shall herein after be abbreviated as follows: Phenylalanine is Phe or F; Leucine is Leu or L; Isoleucine is Ile or I; Methionine is Met or M; Valine is Val or V; Serine is Ser or S; Proline is Pro or P; Threonine is Thr or T; Alanine is Ala or A; Tyrosine is Tyr or Y; Histidine is H is or H; Glutamine is Gln or Q; Asparagine is Asn or N; Lysine is Lys or K; Aspartic Acid is Asp or D; Glutamic Acid is Glu or E; Cysteine is Cys or C; Tryptophan is Trp or W; Arginine is Arg or R; and Glycine is Gly or G. For further description of amino acids, please refer to *Proteins: Structure and Molecular Properties* by Creighton, T. E., W. H. Freeman & Co., New York 1983, incorporated herein by reference.

HsPDF: As used herein "HsPDF" refers to not only to native HsPDF (SEQ ID NO.:1), but also includes any structural modifications thereof. Structural modifications include any additions, deletions, and/or substitutions to the native HsPDF amino acid sequence, of bound metal(s), and/or of coordinating solvates, hydrates, or non-covalently bound ligands. Such structurally modified HsPDF's include, for example, 6His-d63HsPDF (SEQ ID NO.:2) and N-truncated Δ63HsPDF (SEQ ID NO.:3), as described herein.

Active site: The active site of an enzyme contains catalytic sites and binding sites. The structure and chemical properties of the active site allow the recognition and binding of a binding compound or substrate. The active site is typically a small pocket at the surface of the enzyme that contains residues responsible for the binding specificity (e.g., charge, hydrophobicity, and/or steric hindrance) and catalytic residues which often act as proton donors or acceptors. The active site is also the site of inhibition of enzymes. The term "active site," as used herein, comprises any or all of the following sites in HsPDF: the site where cleavage of a formyl group from a substrate occurs, the metal binding site, the HsPDF site where a binding compound of the PDF family binds or, more particularly, the HsPDF site where a binding compound of the HsPDF family binds. In certain embodiments, the active site may be defined as consisting of three regions: the atrium or entrance to the active site, the substrate binding site, and the catalytic core. The atrium to the HsPDF active site is formed by residues $^{69}$LPEALCRECPPRQRALRQMEPF$^{90}$ (SEQ ID NO: 7), as well as by the topology of the C-terminus residues $^{176}$TNVYWMKVND$^{185}$ (SEQ ID NO: 8). Further past the entrance to the active site of HsPDF is the substrate binding site delineated by V51, Q57, $^{104}$DSRLVT$^{109}$ (SEQ ID NO: 9), $^{117}$VAG$^{119}$, and $^{149}$WAARIIQ$^{155}$ (SEQ ID NO: 10). The core of the HsPDF active site is defined by residues $^{50}$CVGLSAPQ$^{57}$ (SEQ ID NO: 11), $^{112}$EGCES$^{116}$ (SEQ ID NO: 12), and $^{156}$HEMDHL$^{161}$ (SEQ ID NO: 13). The active site of HsPDF is provided by the atomic structure coordinates listed in Tables 1 and 2. The metal which binds may be a divalent or trivalent cation selected from the group consisting of zinc, cobalt, iron, manganese, selenium, nickel. In certain embodiments, the cation is cobalt. In certain embodiments, the cation is $Co^{2+}$.

Accessory binding site: The term "accessory binding site" comprises any binding site other than the active site. An "allosteric binding site" is an assessory binding site which facilitates a change in the conformation and activity of an enzyme upon being bound by a binding compound or a substrate to the site in question.

Atomic structure coordinates: The term "atomic structure coordinates" refers to mathematical coordinates derived from mathematical equations related to the patterns obtained on diffraction of a monochromatic beam of X-rays by the atoms (scattering centers) of a protein molecule in crystal form. The diffraction data are used to calculate an electron density map of the repeating unit of the crystal. The electron density maps are used to establish the positions of the individual atoms within the unit cell of the crystal. The coordinates can also be obtained by means of computational analysis.

Unit cell: The term "unit cell" refers to the basic parallelipiped shaped block. The entire volume of a crystal may be constructed by regular assembly of such blocks.

Space group: The term "space group" refers to the arrangement of symmetry elements in a crystal.

PDF or PDF family or PDF family member: As used herein, "PDF" or "PDF family" or "PDF family member" refers to both bacterial and human peptide deformylase proteins. Exemplary bacterial PDF include, but are not limited to, *Escherichia coli* PDF; *Streptococcus pneumoniae* PDF; *Haemophilus influenzae* PDF; *Sthaphylococcus aureus* PDF; *Arabidopsis thaliana* PDF; *Pseudomonas aeruginosa* PDF; *Leptospira interrogans* PDF; *Thermotoga maritima* PDF; *Bacillus stearothermophilus* PDF; *B. subtilis* PDF; *P. aeruginosa* PDF; Malaria parasite (*Plasmodium falciparum* PDF); *Thermus thermophilus* PDF; *T. maritima* PDF; *Chlamydia trachomatis* PDF; *C. pneumoniae* PDF; *C. psittaci* PDF; and *C. pecorum* PDF. Crystal structures of many of these PDF family members are available, as discussed in Jain et al., *Current Medicinal Chemistry* (2005) 12:1607-1621, and references cited therewith, the entirety of which are incorporated herein by reference.

Binding compound: As used herein, a "binding compound" refers to a compound which reversibly or irreversibly binds to PDF. In certain embodiments, the binding compound binds to an active site or an accessory site of PDF. A binding compound may be an inhibitor of PDF (i.e., illiciting inhibition or reduction in enzymatic activity), an activator of PDF (i.e., illiciting an increase in enzymatic activity), or may not illicit any change in the enzymatic activity (e.g., deformylase activity) of PDF. In certain embodiments, the binding compound binds to HsPDF and/or another PDF family member and illicits a change (e.g., an inhibition, reduction, or activation) in PDF enzymatic activity.

Inhibitor compound: By "inhibitor" or "inhibitor compound" is meant a binding compound which reduces or inhibits PDF enzymatic activity. A "competitive" inhibitor compound is one that reduces or inhibits PDF activity by binding to the same kinetic form of PDF as another substrate binds, and thus directly competes with the substrate for the active site of PDF. Competitive inhibition can be reversed completely by increasing the substrate concentration. An "uncompetitive" inhibitor compound is one that reduces or inhibits PDF activity by binding to a different kinetic form of the active site than does the substrate. Such inhibitors bind to PDF already bound with the substrate and not to the free enzyme. Uncompetitive inhibition cannot be reversed completely by increasing the substrate concentration. A "noncompetitive" inhibitor compound is one that reduces or inhibits PDF activity by binding to either the free- or substrate-bound form of PDF.

Substrate: By "substrate" is meant a compound which bears a formyl group which may be cleaved upon contacting a PDF protein.

Modulate: The term "modulate," as used herein, means to increase, reduce, or inhibit, HsPDF enzymatic activity.

By "design" or "designing" is meant to provide a novel molecular structure.

By "select" or "selecting" is meant to provide a pre-existing molecular structure.

By "synthesizing" is meant making a novel or pre-existing molecular structure from natural and/or unnatural precursors by chemical or enzymatic methods. Synthesizing implies making at least one inhibitor compound, but is not limited to one compound. In certain aspects, synthesizing implies making more than one compound, such as a series of compounds synthesized in an effort to study structure activity relationships (SAR) using standard medicinal chemistry methods, and/or a series of structurally similar compounds made using standard combinatorial techniques.

By "choosing" is meant obtaining a pre-existing molecular structure from a chemical library or commercially available source.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIGS. 10A-10B. 6His-Δ63HsPDF has PDF activity. Two different 6His-Δ63HsPDF purifications, 6His-d63HsPDF Jan. 20, 2006 (FIG. 10A) and 6His-d63HsPDF Jan. 28, 2006 (FIG. 10B), were prepared for an initial assessment of PDF activity in 6His-Δ63HsPDF expressed in a bacterial system. Protein elution fractions from the $Ni^{2+}$ affinity column were confirmed to contain 6His-Δ63HsPDF by SDS-PAGE. Selected fractions run on gels are shown for each independent preparation. Numbers above each lane gel correspond to the elution fraction number. 6His-Δ63HsPDF is the band running at approximately 20 kDa and indicated by an arrow. High 6His-Δ63HsPDF purity (>90%) was obtained by loading the affinity column above its binding capacity limit. The purity and concentration of the $Ni^{2+}$ affinity column protein eluate enabled further, rapid, concentration of Δ63HsPDF with ammonium sulfate to obtain highly pure Δ63HsPDF. The initial high purity of 6His-Δ63HsPDF was key to minimizing the purification time of Δ63HsPDF by decreasing the number of steps necessary to obtain the final Δ63HsPDF used for crystallization. A lower purity of the $Ni^{2+}$ affinity column protein eluate resulted in protein loss due to protein precipitation and overall low yield and heterogeneity of the final purified Δ63HsPDF. The heterogeneity of Δ63HsPDF originated from the uncontrolled precipitation and aggregation of Δ63HsPDF. The total purification time of Δ63HsPDF using this method takes approximately 3 days.

FIG. 11. Pooled fractions from each purification were normalized by protein concentration and the HsPDF activity measured using the formate dehydrogenate assay.

FIG. 14. N-terminal Edman degradation sequencing of Δ63HsPDF.

SEQUENCE IDENTIFICATION NUMBERS

Figures 1A, 1B:
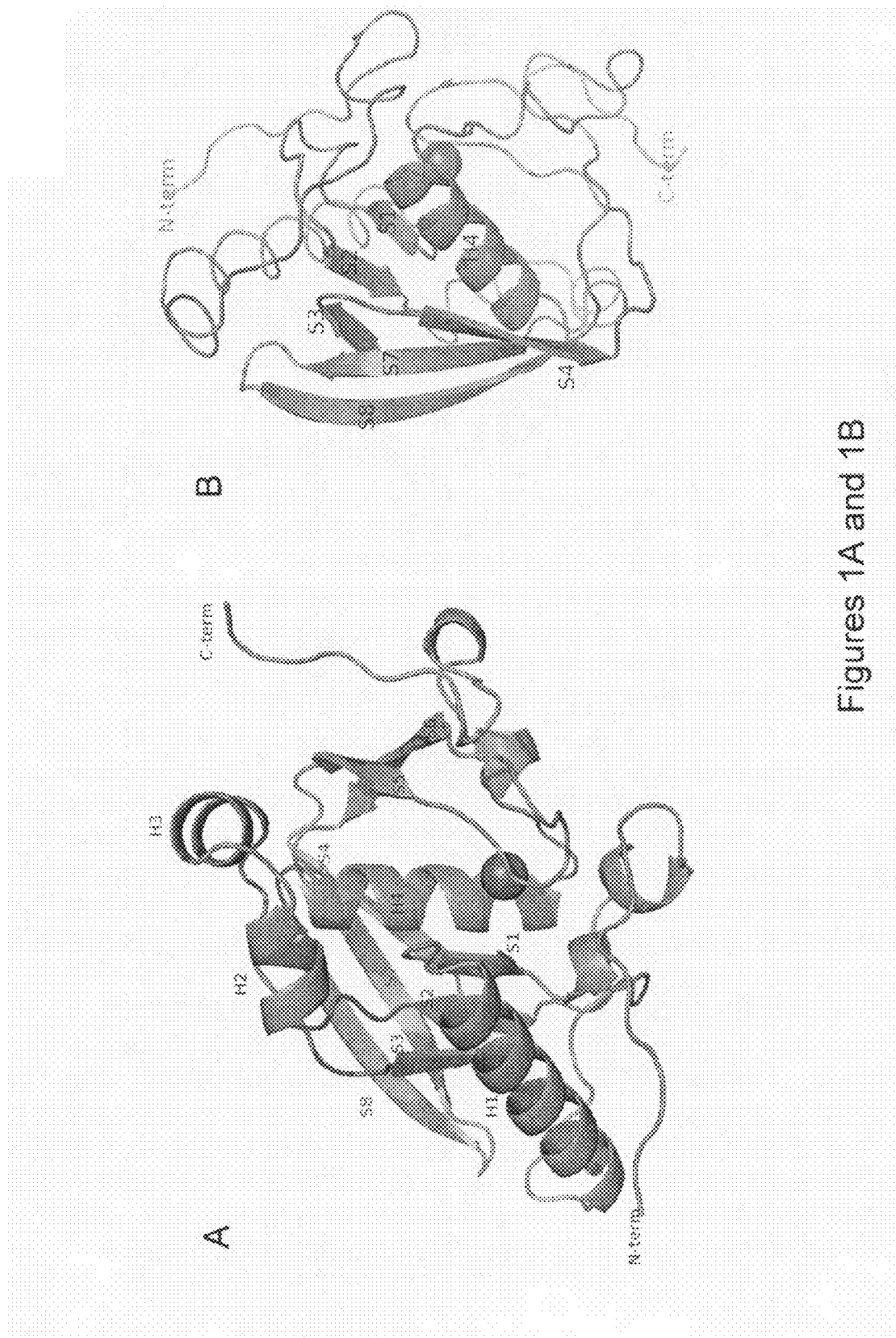
FIG. 1A. Δ63HsPDF monomer showing the conserved fold of the enzyme family. Secondary structure elements are numbered. Alpha-helix is symbolized by "H", while beta-strand is represented by "S". The $Co^{2+}$ atom is a purple sphere.
FIG. 1B. Two beta sheets house the central alpha helix H4. Two antiparallel beta sheets (S1, S2, S3, and S4, S7, S8) form an angle, creating a cavity that houses the central alpha helix H4.

SEQ ID NO. 1: native *Homo sapiens* peptide deformylase (HsPDF) amino acid sequence
MARLWGALSLWPLWAAVPWGGAAAVGVRACSSTAAPDGVEGPALRRSYWRHLRRLV

LGPPEPPFSHVCQVGDPVLRGVAAPVERAQLGGPELQRLTQRLVQVMRRRRCVGLSAQ

LGVPRQVLALELPEALCRECPPRQRALRQMEPFPLRVFVNPSLRVLDSRLVTFPEGCESV

AGFLACVPRFQAVQISGLDPNGEQVVWQASGWAARIIQHEMDHLQGCLFIDKMDSRTF

TNVYWMKVND

SEQ ID NO. 2: The pET-15 Δ63HsPDF clone amino acid sequence
MGSSHHHHHHSSGLVPRGSHMSFSHVCQVGDPVLRGVAAPVERAQLGGPELQRLTQRL

VQVMRRRRCVGLSAPQLGVPRQVLALELPEALCRECPPRQRALRQMEPFPLRVFVNPSL

RVLDSRLVTFPEGCESVAGFLACVPRFQAVQISGLDPNGEQVVWQASGWAARIIQHEM

DHLQGCLFIDKMDSRTFTNVYWMKVND

SEQ ID NO. 3: Δ63HsPDF amino acid sequence
GSHMSFSHVCQVGDPVLRGVAAPVERAQLGGPELQRLTQRLVQVMRRRRCVGLSAPQ

LGVPRQVLALELPEALCRECPPRQRALRQMEPFPLRVFVNPSLRVLDSRLVTFPEGCESV

AGFLACVPRFQAVQISGLDPNGEQVVWQASGWAARIIQHEMDHLQGCLFIDKMDSRTF

TNVYWMKVND

SEQ ID NO. 4: The pET-15b-6His-Δ63HsPDF nucleotide sequence
TTCTCATGTTTGACAGCTTATCATCGATAAGCTTTAATGCGGTAGTTTATCACAGTTA

AATTGCTAACGCAGTCAGGCACCGTGTATGAAATCTAACAATGCGCTCATCGTCATC

CTCGGCACCGTCACCCTGGATGCTGTAGGCATAGGCTTGGTTATGCCGGTACTGCCG

GGCCTCTTGCGGGATATCCGGATATAGTTCCTCCTTTCAGCAAAAAACCCCTCAAGA

CCCGTTTAGAGGCCCCAAGGGGTTATGCTAGTTATTGCTCAGCGGTGGCAGCAGCCA

ACTCAGCTTCCTTTCGGGCTTTGTTAGCAGCCGGATCCTTAGTCATTCACCTTCATCC

AATAGACGTTTGTGAACGTCCTGCTGTCCATTTTGTCAATAAACAGGCAGCCCTGCA

GGTGGTCCATCTCGTGCTGGATGATGCGGGCTGCCCACCCGCTCGCCTGCCACACCA

CCTGTTCTCCATTGGGGTCCAGCCCTGAGATCTGCACCGCCTGGAAGCGGGGCACGC

AGGCCAGGAAGCCGGCGACGCTCTCGCAGCCCTCGGGAAAGGTGACCAGGCGGCTG

TCAAGCACTCGCAGGCTGGGGTTCACGAACACGCGCAGGGGGAAGGGCTCCATTTG

GCGGAGCGCGCGCTGGCGGGGCGGGCACTCCCGACACAGCGCCTCGGGGAGCTCCA

GCGCCAGCACCTGCCGCGGCACCCCCAGCTGCGGCGCGCTTAGGCCCACGCAGCGC

CGCCGCCGCATCACCTGGACCAGCCGTTGCGTCAGCCGCTGCAGCTCGGGCCCGCCT

AGCTGCGCCCGCTCCACCGGGGCCGCCACGCCGCGCAGCACCGGGTCCCCGACTTG

GCACACGTGCGAGAATGACATATGGCTGCCGCGCGGCACCAGGCCGCTGCTGTGAT

GATGATGATGATGGCTGCTGCCCATGGTATATCTCCTTCTTAAAGTTAAACAAAATT

ATTTCTAGAGGGGAATTGTTATCCGCTCACAATTCCCCTATAGTGAGTCGTATTAATT

TCGCGGGATCGAGATCTCGATCCTCTACGCCGGACGCATCGTGGCCGGCATCACCGG

CGCCACAGGTGCGGTTGCTGGCGCCTATATCGCCGACATCACCGATGGGGAAGATC

GGGCTCGCCACTTCGGGCTCATGAGCGCTTGTTTCGGCGTGGGTATGGTGGCAGGCC

CCGTGGCCGGGGGACTGTTGGGCGCCATCTCCTTGCATGCACCATTCCTTGCGGCGG

CGGTGCTCAACGGCCTCAACCTACTACTGGGCTGCTTCCTAATGCAGGAGTCGCATA

-continued

```
AGGGAGAGCGTCGAGATCCCGGACACCATCGAATGGCGCAAAACCTTTCGCGGTAT
GGCATGATAGCGCCCGGAAGAGAGTCAATTCAGGGTGGTGAATGTGAAACCAGTAA
CGTTATACGATGTCGCAGAGTATGCCGGTGTCTCTTATCAGACCGTTTCCCGCGTGG
TGAACCAGGCCAGCCACGTTTCTGCGAAAACGCGGGAAAAAGTGGAAGCGGCGATG
GCGGAGCTGAATTACATTCCCAACCGCGTGGCACAACAACTGGCGGGCAAACAGTC
GTTGCTGATTGGCGTTGCCACCTCCAGTCTGGCCCTGCACGCGCCGTCGCAAATTGT
CGCGGCGATTAAATCTCGCGCCGATCAACTGGGTGCCAGCGTGGTGGTGTCGATGGT
AGAACGAAGCGGCGTCGAAGCCTGTAAAGCGGCGGTGCACAATCTTCTCGCGCAAC
GCGTCAGTGGGCTGATCATTAACTATCCGCTGGATGACCAGGATGCCATTGCTGTGG
AAGCTGCCTGCACTAATGTTCCGGCGTTATTTCTTGATGTCTCTGACCAGACACCCAT
CAACAGTATTATTTTCTCCCATGAAGACGGTACGCGACTGGGCGTGGAGCATCTGGT
CGCATTGGGTCACCAGCAAATCGCGCTGTTAGCGGGCCCATTAAGTTCTGTCTCGGC
GCGTCTGCGTCTGGCTGGCTGGCATAAATATCTCACTCGCAATCAAATTCAGCCGAT
AGCGGAACGGGAAGGCGACTGGAGTGCCATGTCCGGTTTTCAACAAACCATGCAAA
TGCTGAATGAGGGCATCGTTCCCACTGCGATGCTGGTTGCCAACGATCAGATGGCGC
TGGGCGCAATGCGCGCCATTACCGAGTCCGGGCTGCGCGTTGGTGCGGATATCTCGG
TAGTGGGATACGACGATACCGAAGACAGCTCATGTTATATCCCGCCGTTAACCACCA
TCAAACAGGATTTTCGCCTGCTGGGGCAAACCAGCGTGGACCGCTTGCTGCAACTCT
CTCAGGGCCAGGCGGTGAAGGGCAATCAGCTGTTGCCCGTCTCACTGGTGAAAAGA
AAAACCACCCTGGCGCCCAATACGCAAACCGCCTCTCCCCGCGCGTTGGCCGATTCA
TTAATGCAGCTGGCACGACAGGTTTCCCGACTGGAAAGCGGGCAGTGAGCGCAACG
CAATTAATGTAAGTTAGCTCACTCATTAGGCACCGGGATCTCGACCGATGCCCTTGA
GAGCCTTCAACCCAGTCAGCTCCTTCCGGTGGGCGCGGGGCATGACTATCGTCGCCG
CACTTATGACTGTCTTCTTTATCATGCAACTCGTAGGACAGGTGCCGGCAGCGCTCT
GGGTCATTTTCGGCGAGGACCGCTTTCGCTGGAGCGCGACGATGATCGGCCTGTCGC
TTGCGGTATTCGGAATCTTGCACGCCCTCGCTCAAGCCTTCGTCACTGGTCCCGCCA
CCAAACGTTTCGGCGAGAAGCAGGCCATTATCGCCGGCATGGCGGCCGACGCGCTG
GGCTACGTCTTGCTGGCGTTCGCGACGCGAGGCTGGATGGCCTTCCCCATTATGATT
CTTCTCGCTTCCGGCGGCATCGGGATGCCCGCGTTGCAGGCCATGCTGTCCAGGCAG
GTAGATGACGACCATCAGGGACAGCTTCAAGGATCGCTCGCGGCTCTTACCAGCCT
AACTTCGATCACTGGACCGCTGATCGTCACGGCGATTTATGCCGCCTCGGCGAGCAC
ATGGAACGGGTTGGCATGGATTGTAGGCGCCGCCCTATACCTTGTCTGCCTCCCCGC
GTTGCGTCGCGGTGCATGGAGCCGGGCCACCTCGACCTGAATGGAAGCCGGCGGCA
CCTCGCTAACGGATTCACCACTCCAAGAATTGGAGCCAATCAATTCTTGCGGAGAAC
TGTGAATGCGCAAACCAACCCTTGGCAGAACATATCCATCGCGTCCGCCATCTCCAG
CAGCCGCACGCGGCGCATCTCGGGCAGCGTTGGGTCCTGGCCACGGGTGCGCATGA
TCGTGCTCCTGTCGTTGAGGACCCGGCTAGGCTGGCGGGGTTGCCTTACTGGTTAGC
AGAATGAATCACCGATACGCGAGCGAACGTGAAGCGACTGCTGCTGCAAAACGTCT
GCGACCTGAGCAACAACATGAATGGTCTTCGGTTTCCGTGTTTCGTAAAGTCTGGAA
ACGCGGAAGTCAGCGCCCTGCACCATTATGTTCCGGATCTGCATCGCAGGATGCTGC
```

-continued

```
TGGCTACCCTGTGGAACACCTACATCTGTATTAACGAAGCGCTGGCATTGACCCTGA
GTGATTTTTCTCTGGTCCCGCCGCATCCATACCGCCAGTTGTTTACCCTCACAACGTT
CCAGTAACCGGGCATGTTCATCATCAGTAACCCGTATCGTGAGCATCCTCTCTCGTTT
CATCGGTATCATTACCCCCATGAACAGAAATCCCCCTTACACGGAGGCATCAGTGAC
CAAACAGGAAAAAACCGCCCTTAACATGGCCCGCTTTATCAGAAGCCAGACATTAA
CGCTTCTGGAGAAACTCAACGAGCTGGACGCGGATGAACAGGCAGACATCTGTGAA
TCGCTTCACGACCACGCTGATGAGCTTTACCGCAGCTGCCTCGCGCGTTTCGGTGAT
GACGGTGAAAACCTCTGACACATGCAGCTCCCGGAGACGGTCACAGCTTGTCTGTA
AGCGGATGCCGGGAGCAGACAAGCCCGTCAGGGCGCGTCAGCGGGTGTTGGCGGGT
GTCGGGCGCAGCCATGACCCAGTCACGTAGCGATAGCGGAGTGTATACTGGCTTA
ACTATGCGGCATCAGAGCAGATTGTACTGAGAGTGCACCATATATGCGGTGTGAAA
TACCGCACAGATGCGTAAGGAGAAAATACCGCATCAGGCGCTCTTCCGCTTCCTCGC
TCACTGACTCGCTGCGCTCGGTCGTTCGGCTGCGGCGAGCGGTATCAGCTCACTCAA
AGGCGGTAATACGGTTATCCACAGAATCAGGGGATAACGCAGGAAAGAACATGTGA
GCAAAAGGCCAGCAAAAGGCCAGGAACCGTAAAAAGGCCGCGTTGCTGGCGTTTTT
CCATAGGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCTCCCTC
GTGCGCTCTCCTGTTCCGACCCTGCCGCTTACCGGATACCTGTCCGCCTTTCTCCCTT
CGGGAAGCGTGGCGCTTTCTCATAGCTCACGCTGTAGGTATCTCAGTTCGGTGTAGG
TCGTTCGCTCCAAGCTGGGCTGTGTGCACGAACCCCCCGTTCAGCCCGACCGCTGCG
CCTTATCCGGTAACTATCGTCTTGAGTCCAACCCGGTAAGACACGACTTATCGCCAC
TGGCAGCAGCCACTGGTAACAGGATTAGCAGAGCGAGGTATGTAGGCGGTGCTACA
GAGTTCTTGAAGTGGTGGCCTAACTACGGCTACACTAGAAGGACAGTATTTGGTATC
TGCGCTCTGCTGAAGCCAGTTACCTTCGGAAAAAGAGTTGGTAGCTCTTGATCCGGC
AAACAAACCACCGCTGGTAGCGGTGGTTTTTTTGTTTGCAAGCAGCAGATTACGCGC
AGAAAAAAAGGATCTCAAGAAGATCCTTTGATCTTTTCTACGGGGTCTGACGCTCAG
TGGAACGAAAACTCACGTTAAGGGATTTTGGTCATGAGATTATCAAAAAGGATCTTC
ACCTAGATCCTTTTAAATTAAAAATGAAGTTTTAAATCAATCTAAAGTATATATGAG
TAAACTTGGTCTGACAGTTACCAATGCTTAATCAGTGAGGCACCTATCTCAGCGATC
TGTCTATTTCGTTCATCCATAGTTGCCTGACTCCCCGTCGTGTAGATAACTACGATAC
GGGAGGGCTTACCATCTGGCCCCAGTGCTGCAATGATACCGCGAGACCCACGCTCA
CCGGCTCCAGATTTATCAGCAATAAACCAGCCAGCCGGAAGGGCCGAGCGCAGAAG
TGGTCCTGCAACTTTATCCGCCTCCATCCAGTCTATTAATTGTTGCCGGGAAGCTAGA
GTAAGTAGTTCGCCAGTTAATAGTTTGCGCAACGTTGTTGCCATTGCTGCAGGCATC
GTGGTGTCACGCTCGTCGTTTGGTATGGCTTCATTCAGCTCCGGTTCCCAACGATCAA
GGCGAGTTACATGATCCCCCATGTTGTGCAAAAAAGCGGTTAGCTCCTTCGGTCCTC
CGATCGTTGTCAGAAGTAAGTTGGCCGCAGTGTTATCACTCATGGTTATGGCAGCAC
TGCATAATTCTCTTACTGTCATGCCATCCGTAAGATGCTTTTCTGTGACTGGTGAGTA
CTCAACCAAGTCATTCTGAGAATAGTGTATGCGGCGACCGAGTTGCTCTTGCCCGGC
GTCAACACGGGATAATACCGCGCCACATAGCAGAACTTTAAAAGTGCTCATCATTG
```

-continued

```
GAAAACGTTCTTCGGGGCGAAAACTCTCAAGGATCTTACCGCTGTTGAGATCCAGTT

CGATGTAACCCACTCGTGCACCCAACTGATCTTCAGCATCTTTTACTTTCACCAGCGT

TTCTGGGTGAGCAAAAACAGGAAGGCAAAATGCCGCAAAAAAGGGAATAAGGGCG

ACACGGAAATGTTGAATACTCATACTCTTCCTTTTTCAATATTATTGAAGCATTTATC

AGGGTTATTGTCTCATGAGCGGATACATATTTGAATGTATTTAGAAAAATAAACAAA

TAGGGGTTCCGCGCACATTTCCCCGAAAAGTGCCACCTGACGTCTAAGAAACCATTA

TTATCATGACATTAACCTATAAAAATAGGCGTATCACGAGGCCCTTTCGTCTTCAAG

AA

SEQ ID NO. 5: The forward primer nucleotide sequence NdeI_F
GGAATTCCATATGTCATTCTCGCACGTGTGCCAAGTCGGG SEQ ID NO. 6: The reverse primer nucleotide sequence BamHI_R
CGCGGATCCTTAGTCATTCACCTTCATCCAATAGACGTT3
```

DETAILED DESCRIPTION OF CERTAIN EMBODIMENTS

As previously stated, the present invention provides purification and crystallization methods for human mitochondrial *Homo sapiens* peptide deformylase (HsPDF) protein. The present invention also provides detailed three-dimensional structural information provided from single crystal X-ray crystallography of HsPDF and HsPDF complexed with a binding compound. Such information will aid in the identification and development of novel compounds which bind to HsPDF and/or related PDF family members, and which may possess anti-bacterial, anti-viral, anti-parasitical, anti-inflammatory, and/or anti-cancer activity.

Specifically, the present invention provides crystalline N-terminally truncated HsPDF lacking the first 63 amino acids which correspond to the mitochondrial targeting sequence (i.e., Δ63HsPDF). Δ63HsPDF may be sub-cloned from preparation by the polymerase chain reaction (PCR) and then inserted into a vector to be expressed (Lee et al., *Biochem Biophys Res Commun*(2003) 312: 309-315, the entirety of which is incorporated herein by reference) The amino acid sequence 6His-Δ63HsPDF (SEQ ID NO:2) is initially provided from vector expression. 6His-Δ63HsPDF can be treated with thrombin to remove the 6His-tag to liberate Δ63HsPDF. Cleavage of the tag with thrombin results in the Δ63HsPDF sequence (SEQ ID NO: 3), which includes an additional five amino-acids, GSHMS (SEQ ID NO: 14), that arise from the vector. Δ63HsPDF may be expressed and/or purified as the catalytically active $Co^{2+}$ form (Lee (2003) supra). The atomic structure coordinates for crystalline Δ63HsPDF are provided in Table 1 (SEQ ID NO: 17), as set forth in Appendix A, provided herewith.

Additionally, the present invention provides crystalline Δ63HsPDF bound to the PDF antibiotic actinonin. The atomic structure coordinates for crystalline actinonin-bound Δ63HsPDF are provided in Table 2 (SEQ ID NO: 17), as set forth in Appendix B, provided herewith.

It should be understood that while Tables 1 and 2 provide atomic structure coordinates for crystalline Δ63HsPDF and crystalline actinonin-bound Δ63HsPDF, respectively, the present invention also contemplates the crystal structures of native HsPDF, and other structural modifications thereof, as described herein, as well as other PDF-family members, as having significant structural homology (e.g., significant structural overlap), particularly in the areas recognized as active and accessory binding sites, and thus providing the same or similar structural information as provided herewith. Significant structural homology refers to at least one of the following criteria: (i) at least 60%, 65%, 70%, 75%, 80%, 85%, 90%, 95%, or 99% structural homology with crystalline Δ63HsPDF and/or crystalline actinonin-bound Δ63HsPDF; or (ii) at least 60%, 65%, 70%, 75%, 80%, 85%, 90%, 95%, or 99% structural homology with a recognized active and/or accessory binding site of crystalline Δ63HsPDF and/or crystalline actinonin-bound Δ63HsPDF. In certain embodiments, significant structural homology may also refer to at least 60%, 65%, 70%, 75%, 80%, 85%, 90%, 95%, or 99% structural homology with the primary amino acid sequence of HsPDF (e.g., for example, native HsPDF, Δ63HsPDF, and 6His-Δ63HsPDF). Furthermore, the primary amino acid sequence of HsPDF may be a sequence included as a segment in a larger amino acid sequence, or may be a fragment thereof. The present invention contemplates any and all such variations and modifications of HsPDF.

Structural modifications include any additions, deletions, and/or substitutions to the native HsPDF amino acid sequence, and also includes any additions, deletions, and/or substitutions of complexed metal(s), and/or of coordinating solvates, hydrates, or non-covalently bound ligands.

In certain embodiments, the present invention contemplates native HsPDF (SEQ ID No.: 1), N-truncated 6His-d63HsPDF (SEQ ID NO.:2), and/or Δ63HsPDF (SEQ ID NO.:3) comprising at least ten (10) substitutions, additions, or deletions thereof. In certain embodiments, the present invention contemplates native HsPDF (SEQ ID No.:1), N-truncated 6His-d63HsPDF (SEQ ID NO.:2), and/or Δ63HsPDF (SEQ ID NO.:3) comprising at least five (5) substitutions, additions, or deletions thereof. In certain embodiments, the present invention contemplates native HsPDF (SEQ ID No.: 1), N-truncated 6His-d63HsPDF (SEQ ID NO.:2), and/or Δ63HsPDF (SEQ ID NO.:3) comprising at least two (2) substitutions, additions, or deletions thereof. In certain embodiments, the present invention contemplates native HsPDF (SEQ ID No.:1), N-truncated 6His-d63HsPDF (SEQ ID NO.: 2), and/or Δ63HsPDF (SEQ ID NO.:3) comprising at least one (1) substitutions, additions, or deletions thereof.

In certain embodiments, the present invention contemplates native HsPDF (SEQ ID No.:1), N-truncated 6His-d63HsPDF (SEQ ID NO.:2), and/or Δ63HsPDF (SEQ ID NO.:3) comprising at least one to ten substitutions, additions, or deletions thereof. In certain embodiments, the present invention contemplates native HsPDF (SEQ ID No.:1), N-truncated 6His-d63HsPDF (SEQ ID NO.:2), and/or Δ63HsPDF (SEQ ID NO.:3) comprising at least one to five substitutions, additions, or deletions thereof. In certain embodiments, the present invention contemplates native HsPDF (SEQ ID No.:1), N-truncated 6His-d63HsPDF (SEQ ID NO.:2), and/or Δ63HsPDF (SEQ ID NO.:3) comprising at least one to two substitutions, additions, or deletions thereof.

In certain embodiments, the present invention contemplates N-truncated 6His-d63HsPDF (SEQ ID NO.:2) and/or Δ63HsPDF (SEQ ID NO.:3) comprising at least sixty-three (63) additions thereof. In certain embodiments, the present invention contemplates N-truncated 6His-d63HsPDF (SEQ ID NO.:2) and/or Δ63HsPDF (SEQ ID NO.:3) comprising at least sixty (60) additions thereof. In certain embodiments, the present invention contemplates N-truncated 6His-d63HsPDF (SEQ ID NO.:2) and/or Δ63HsPDF (SEQ ID NO.:3) comprising at least fifty-five (55) additions thereof. In certain embodiments, the present invention contemplates N-truncated 6His-d63HsPDF (SEQ ID NO.:2) and/or Δ63HsPDF (SEQ ID NO.:3) comprising at least fifty (50) additions thereof. In certain embodiments, the present invention contemplates N-truncated 6His-d63HsPDF (SEQ ID NO.:2) and/or Δ63HsPDF (SEQ ID NO.:3) comprising at least forty-five (45) additions thereof. In certain embodiments, the present invention contemplates N-truncated 6His-d63HsPDF (SEQ ID NO.:2) and/or Δ63HsPDF (SEQ ID NO.:3) comprising at least forty (40) additions thereof. In certain embodiments, the present invention contemplates N-truncated 6His-d63HsPDF (SEQ ID NO.:2) and/or Δ63HsPDF (SEQ ID NO.:3) comprising at least thirty-five (35) additions thereof. In certain embodiments, the present invention contemplates N-truncated 6His-d63HsPDF (SEQ ID NO.:2) and/or Δ63HsPDF (SEQ ID NO.:3) comprising at least thirty (30) additions thereof. In certain embodiments, the present invention contemplates N-truncated 6His-d63HsPDF (SEQ ID NO.:2) and/or Δ63HsPDF (SEQ ID NO.:3) comprising at least twenty-five (25) additions thereof. In certain embodiments, the present invention contemplates N-truncated 6His-d63HsPDF (SEQ ID NO.:2) and/or Δ63HsPDF (SEQ ID NO.:3) comprising at least twenty (20) additions thereof. In certain embodiments, the present invention contemplates N-truncated 6His-d63HsPDF (SEQ ID NO.:2) and/or Δ63HsPDF (SEQ ID NO.:3) comprising at least fifteen (15) additions thereof.

In general, peptide deformylase proteins comprise one or more complexing metal cations. In certain embodiments, the metal complexed to HsPDF and/or a PDF family member comprises a divalent or trivalent metal cation. In certain embodiments, the metal cation is a transition metal cation. In certain embodiments, the transition metal cation is selected from the group consisting of zinc, cobalt, iron, manganese, selenium, nickel. In certain embodiments, the transition metal cation is a cobalt cation. In certain embodiments, the transition metal cobalt cation is $Co^{2+}$.

Purification of HsPDF

Figure 12:
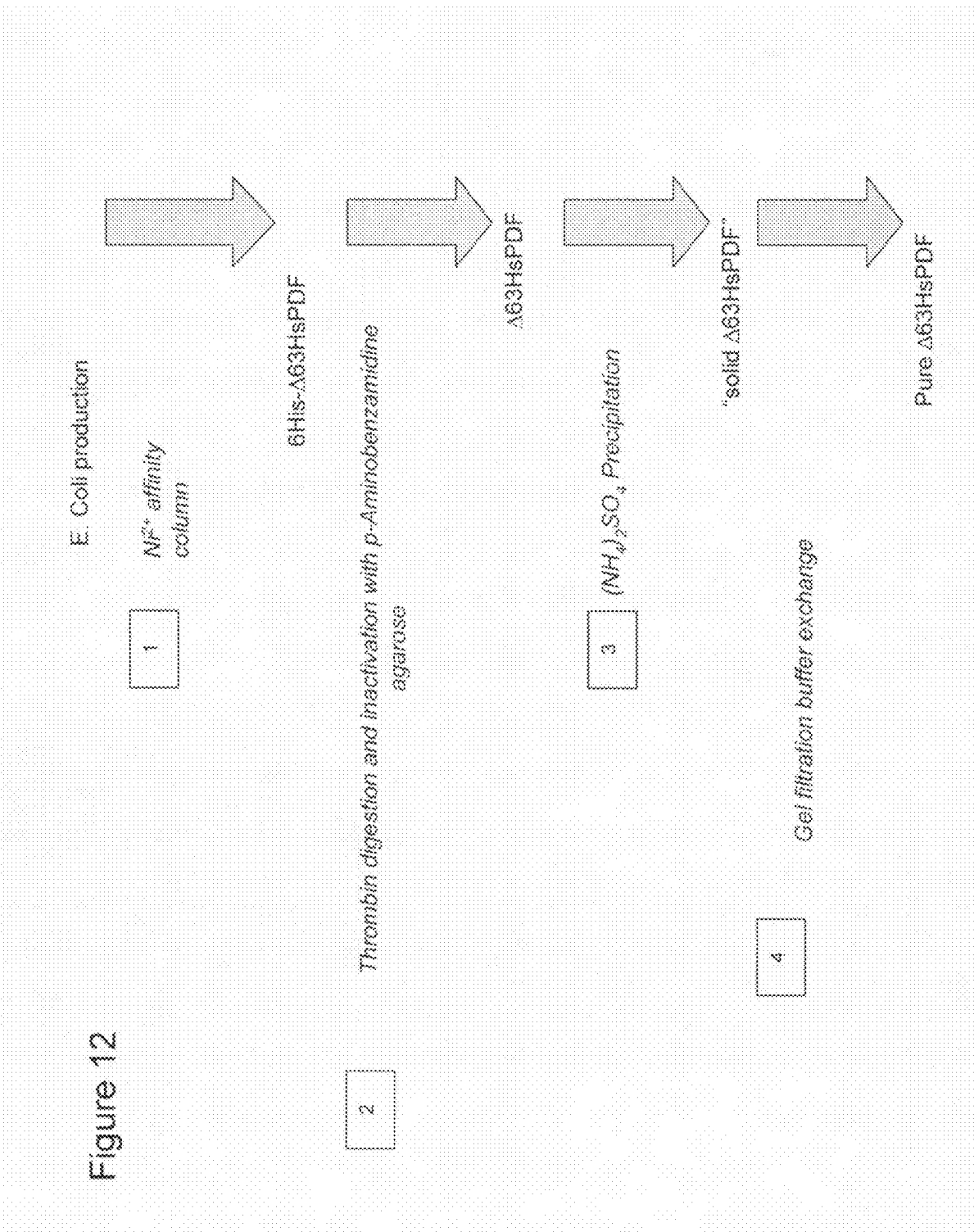
FIG. 12. Diagram of the steps followed to purify 6His-Δ63HsPDF to obtain Δ63HsPDF utilized for screening of crystallization conditions. Steps are shown in blue and numbered. $Ni^{2+}$ affinity purified 6His-Δ63HsPDF was treated with thrombin to remove the 6His-tag, with the thrombin subsequently being removed by p-aminobenzamidine agarose. Δ63HsPDF was concentrated by precipitation with ammonium sulfate, $(NH_4)_2SO_4$. Ammonium sulfate was removed by buffer exchange of the soluble Δ63HsPDF. The final, pure, and concentrated, Δ63HsPDF is in 20 mM HEPES, 20 mM NaCl, pH 6.2 with 5 mM TCEP.
Figure 13A:
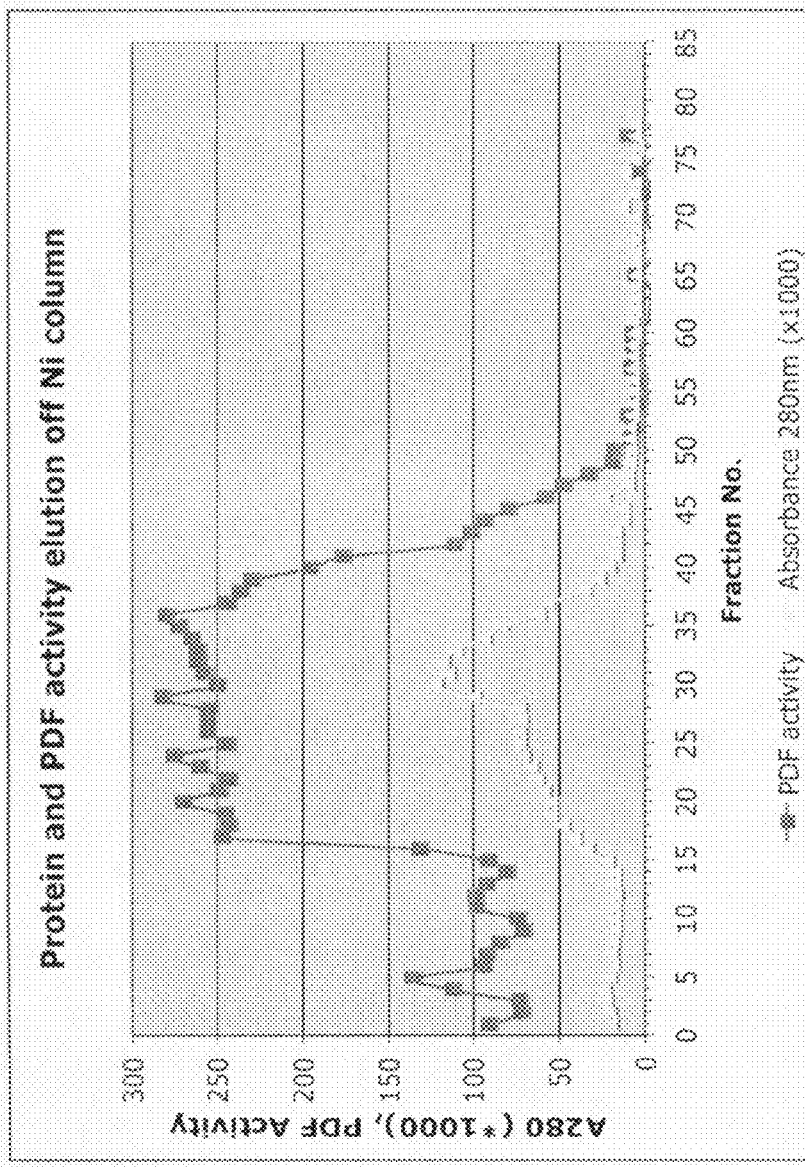
FIG. 13 A. Purification of 6His-Δ63HsPDF from a bacterial cell lysate by $Ni^{2+}$ affinity. Fractions containing protein and PDF activity were pooled for the next step.
FIG. 13B. 6His-Δ63HsPDF pool obtained from the $Ni^{2+}$ affinity purification was digested with thrombin and precipitated with 35% ammonium sulfate. The SDS-PAGE gel was run to confirm the integrity and purity of HsPDF.
FIG. 13C. Ammonium sulfate in the re-solubilized 35% ammonium sulfate Δ63HsPDF protein was removed by gel filtration. Red marks in the X axis represent the fraction number.
FIG. 13D. Gel filtration chromatogram measuring protein elution by absorbance at 280 nm.
FIG. 13E. The protein elution peak corresponded to the PDF activity elution peak. PDF activity was confirmed at various steps along the purification of Δ63HsPDF.
Figure 13B:
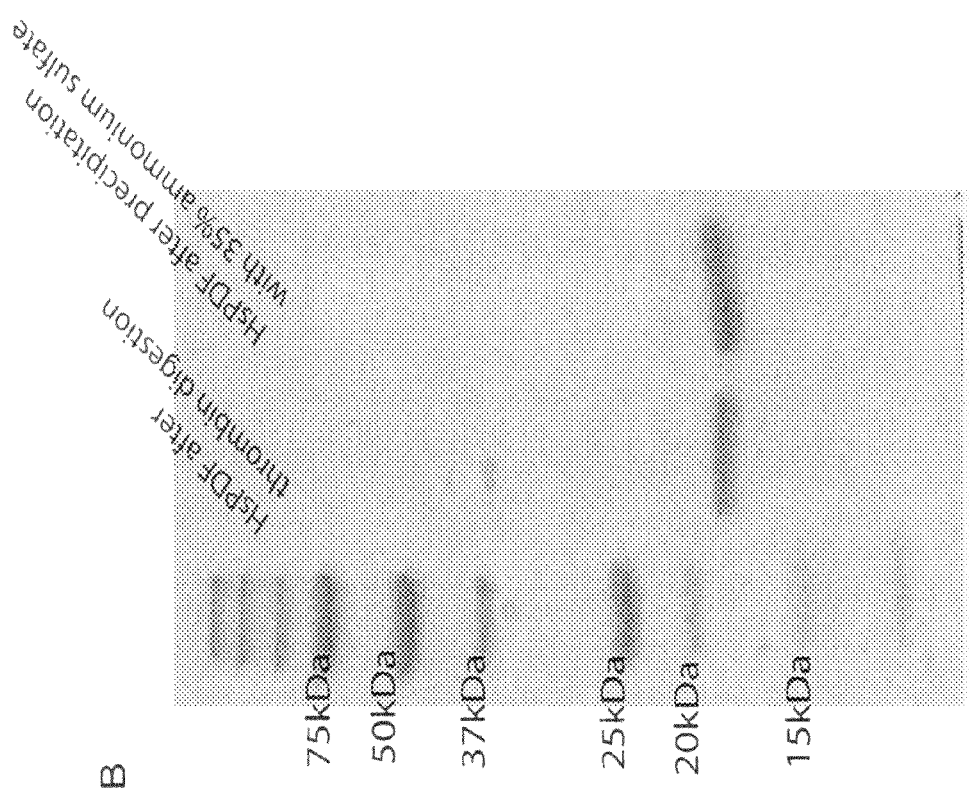
Figures 13C, 13D:
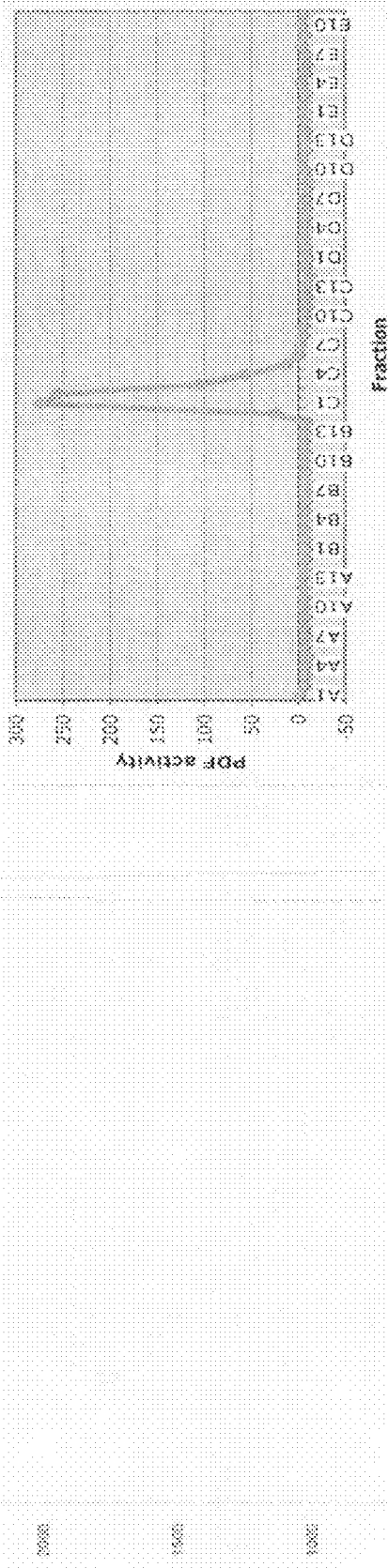
Figure 13E:
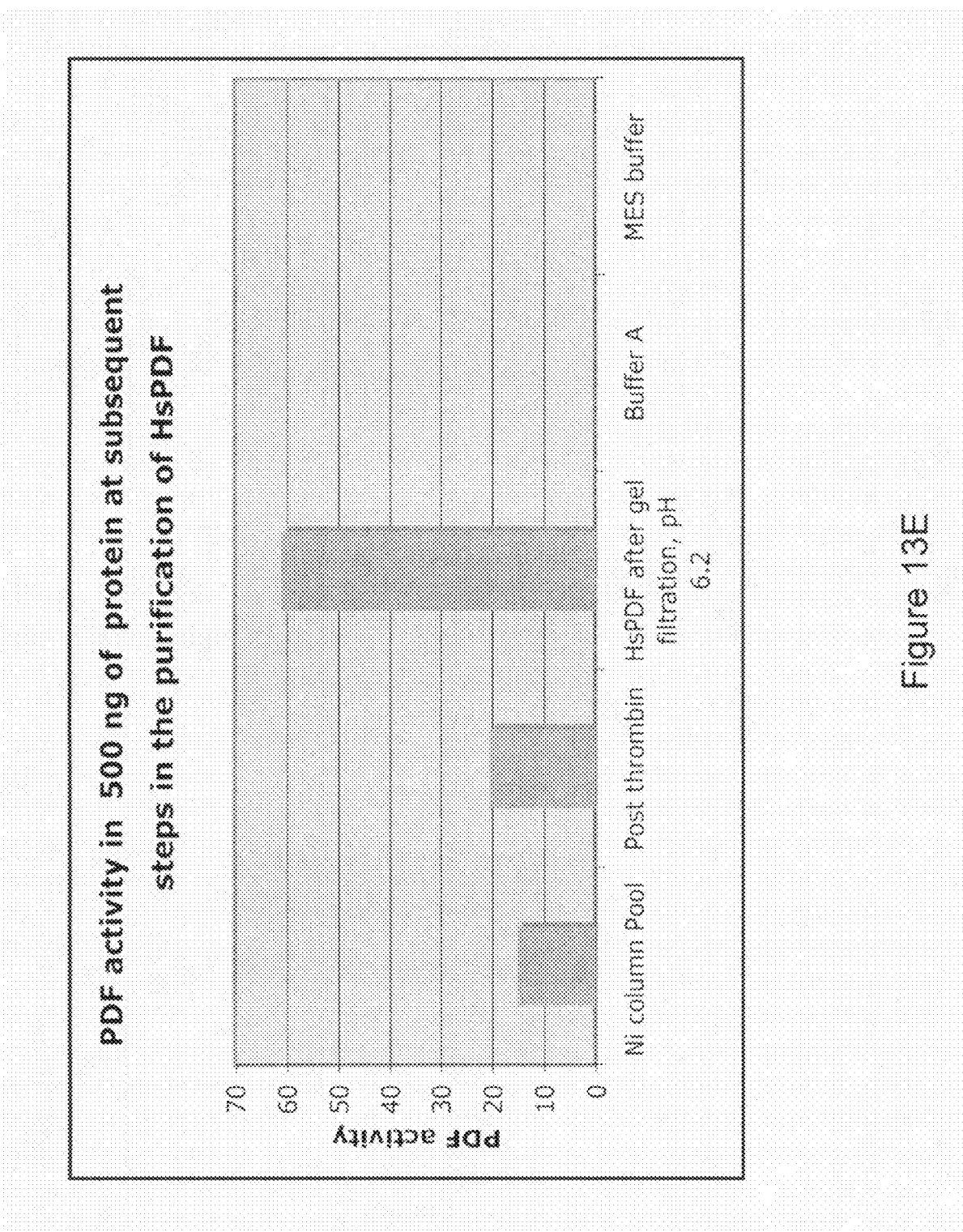
Figure 15:
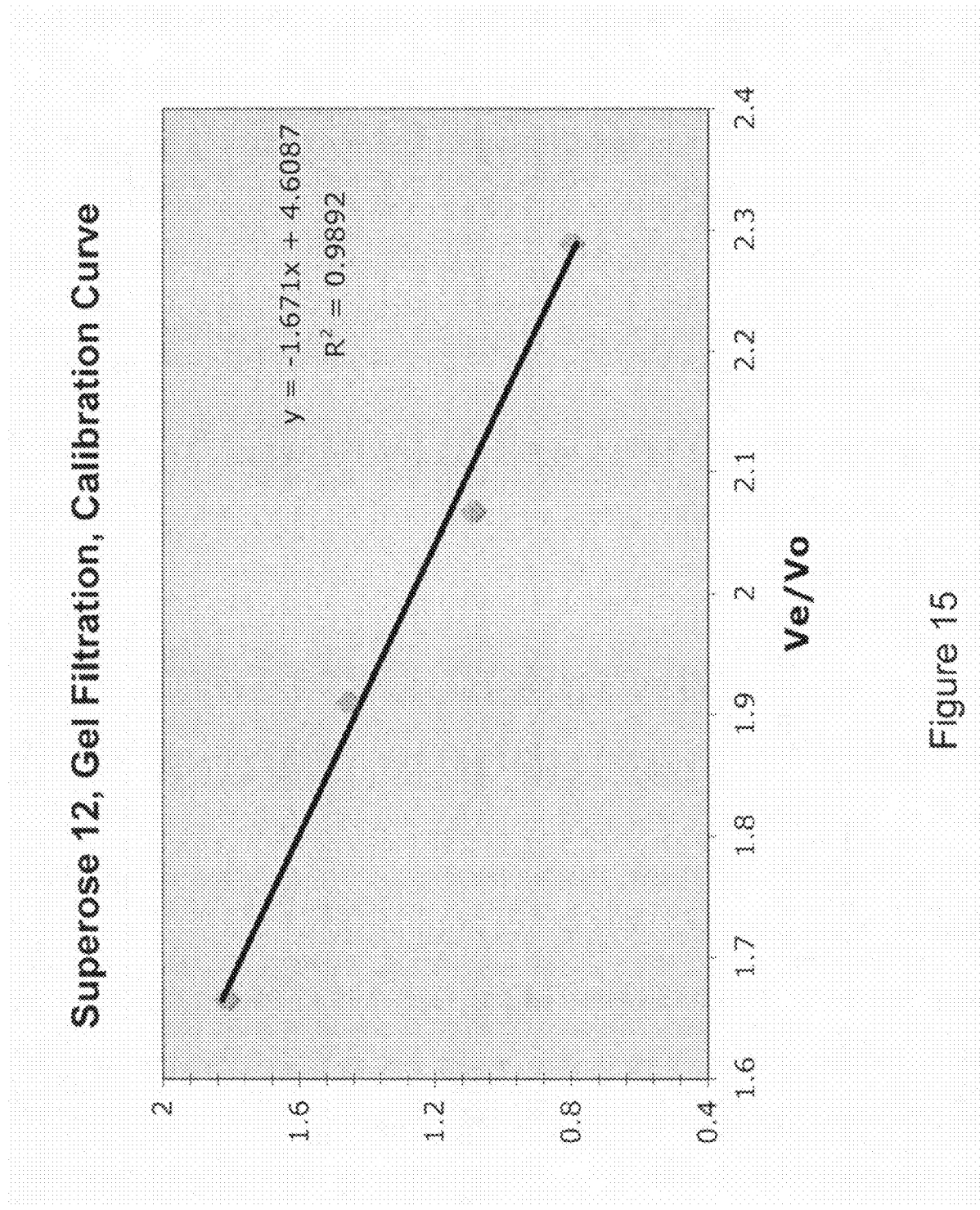
FIG. 15. Estimation of Δ63HsPDF molecular weight by gel filtration using a Superose 12 column. Based on the calibration curve shown, and the elution time of Δ63HsPDF (13.68 min), Δ63HsPDF was estimated to be a 22 kDa protein, which is comparable to the molecular weight of a monomer (20.7 kDa based on amino-acid sequence). The calibration curve was done with Δ63HsPDF in 20 mM HEPES, 300 mM NaCl, 100 μM $CoCl_2$, 20 mM imidazole, pH 7.4.
Figure 16A:
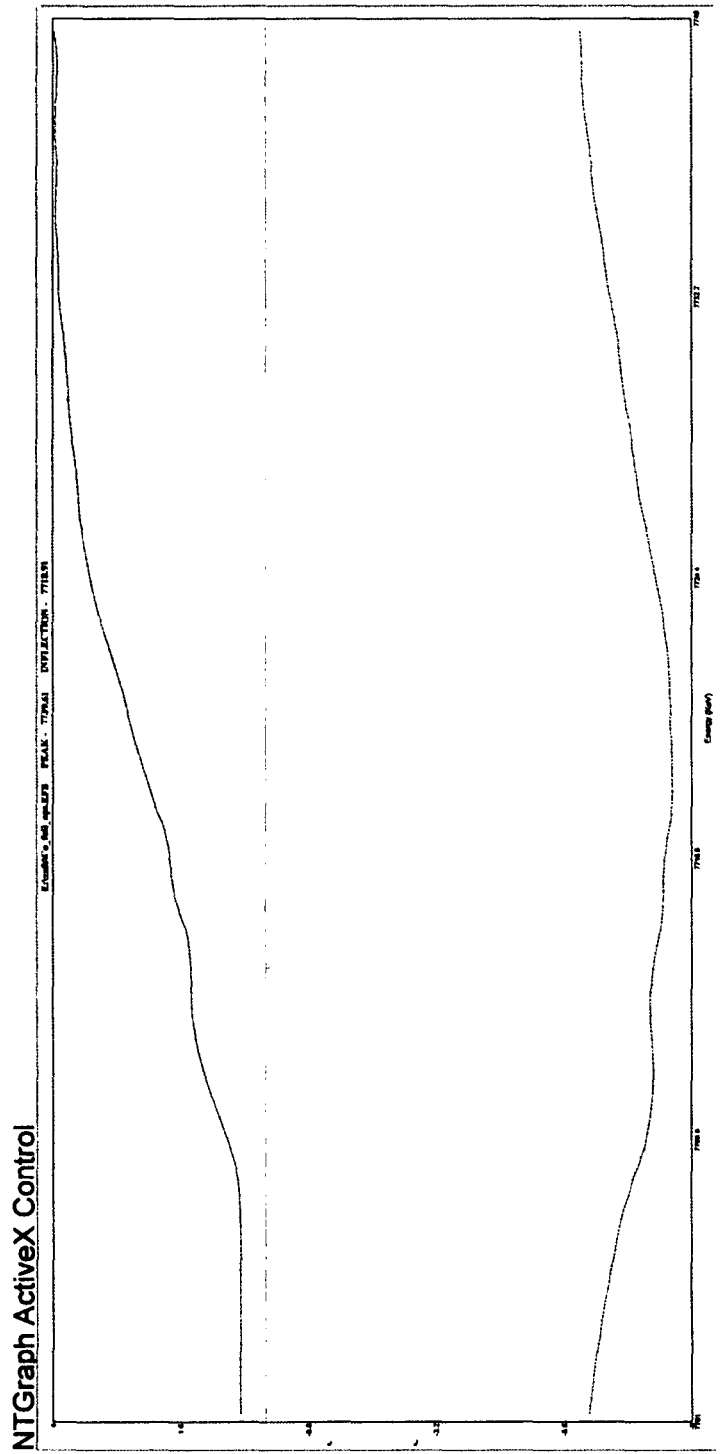
FIGS. 16A-16B. The nature of the metal ion at the active site of the pure HsPDF was confirmed as $Co^{2+}$ from a X-ray fluorescence scan spectrum of an Δ63HsPDF crystal (FIG. 16B) compared to that of a $Co^{2+}$ foil standard (FIG. 16A).
Figure 16B:

FIG. 12 provides one exemplary strategy for obtaining pure Δ63HsPDF (SEQ ID NO. 3) from 6His-Δ63HsPDF (SEQ ID NO. 2). 6His-Δ63HsPDF may be purified by $Ni^{2+}$ affinity column chromatography, and then treated with thrombin to remove the 6His-tag, with the thrombin subsequently being removed by p-aminobenzamidine agarose. Δ63HsPDF may be concentrated by precipitation with an appropriate salt, such as ammonium sulfate, $(NH_4)_2SO_4$. The salt may then be removed by gel filtration buffer exchange to provide pure Δ63HsPDF. Δ63HsPDF may then be prepared as a metal-complexed form (Lee (2003) supra).

Crystallization of HsPDF

One of ordinary skill in the art will appreciate that a wide variety of crystallization conditions may be employed to provide single crystals of HsPDF, therefore, a wide variety of crystallization conditions are envisioned; see generally, Kierzek and Zielenkiewicz, *Biophysical Chemistry* (2001) 91:1-20, and Wiencek *Annu. Rev. Biomed. Eng.* (1999) 1:505-534, the entirety of both of which are hereby incorporated herein by reference.

Each protein crystallizes under a unique set of conditions, such as, for example, supersaturating the solution containing the protein; and/or adding precipitating or crystallizing agents, salts, metals, and/or buffers to the solution containing the protein.

Any crystallization technique known to those skilled in the art may be employed to obtain the crystals of the present invention, including, but not limited to, batch crystallization, vapor diffusion (e.g., either by sitting drop or hanging drop), and micro dialysis. Seeding of the crystals in some instances may be required to obtain X-ray quality crystals. Standard micro and/or macro seeding of crystals may therefore be used.

The present invention provides crystals of HsPDF. In certain embodiments, the crystals are HsPDF, or any structural modifications thereof. In certain embodiments, the crystals are native HsPDF. In certain embodiments, the crystals are Δ63HsPDF.

In certain embodiments, the crystals of the present invention are grown by the hanging-drop vapor-diffusion method.

In certain embodiments, the crystals of the present invention are grown at a temperature of between 0° C. to 10° C. In certain embodiments, the crystals of the present invention are grown at a temperature of between 0° C. to 5° C. In certain embodiments, the crystals of the present invention are grown at a temperature of 4° C.

In certain embodiments, the crystals of the present invention are grown from a crystallization solution comprising one or more precipitants. In certain embodiments, these precipitants are selected from the group consisting of monomethyl ether (MME); Polyethylene glycol (PEG)-400; PEG-1000; PEG-2000; PEG-3000; PEG-8000; PEG 20,000; $(NH_4)_2SO_4$; 2-propanol; 1,4-butanediol; K/Na tartrate; ethanol; NaCl; sodium citrate; $NaH_2PO_4/K_2HPO_4$; ethylene glycol; dioxane; 2-methyl-2,4-pentanediol (MPD); polyethyleneimine; tert-butanol; and 1,6-hexanediol.

In certain embodiments, the crystallization solution may further comprise one or more salts and/or buffers. Thus, in certain embodiments the crystallization further comprises one or more salts selected from the group consisting of $MgCl_2$, $Zn(OAc)_2$, $Li_2SO_4$, $Ca(OAc)_2$, NaCl; $(NH_4)_2SO_4$; $CdCl_2$; $COCl_2$; $MgSO_4$; and $NiCl_2$. In certain embodiments the crystallization further comprises one or more buffers selected from the group consisting of 2-(cyclohexylamino) ethanesulfonic acid (CHES); 2-(N-morpholino)ethanesulfonic acid (MES); N-cyclohexyl-3-aminopropanesulfonic acid (CAPS); N-cyclohexyl-2-hydroxyl3-aminopropanesulfonic acid (CASPO); 4-(2-hydroxyethyl)piperazine-1-ethanesulfonic acid (HEPES); 3-(N-morpholino)propanesulfonic acid (MOPS); 2-amino-2-(hydroxymethyl)-1,3-propanediol (Tris); piperazine-N,N'-bis(2-ethanesulfonic acid) (PIPES); N-(2-Acetamido)-2-aminoethanesulfonic acid (ACES); N,N-Bis(2-hydroxyethyl)-2-aminoethanesulfonic acid (BES); N-Tris(hydroxymethyl)methyl-2-aminoethanesulfonic acid (TES); N-(2-acetamido)iminodiacetic acid (ADA); tris(2-carboxylethyl)phosphine (TCEP); acetamidoglycine; cholamine chloride; glycinamide; bicine; N-(2-Hydroxy-1,1-bis(hydroxymethyl)ethyl)glycine (tricine); imidazole; sodium citrate; sodium acetate; cacodylate; Na/K phosphate, and buffers as described in Good et al., *Biochemistry* (1966) 5:467-477, the entirety of which is incorporated herein by reference.

In certain embodiments, the pH of the crystallization solution is between about a pH of 4 to about pH of 7. In certain embodiments, the pH of the crystallization solution is between about a pH of 5 to about pH of 6. In certain embodiments, the pH of the crystallization solution is about a pH of 5.6.

In certain embodiments, the crystals of the present invention further comprise complexation with a binding compound. Thus, in certain embodiments, the crystallization solution of the above method further comprises a binding compound in order to provide a binding compound-HsPDF complex. In certain embodiments, the HsPDF crystal provided by the above method is soaked in a solution of a binding compound to provide a binding compound-HsPDF complex. In certain embodiments, the binding compound is complexed to the active site of HsPDF. In certain embodiments, the binding compound is complexed to an accessory site of HsPDF.

In certain embodiments, the binding compound is a PDF inhibitor. Any HsPDF- or PDF-inhibitor compound that may be complexed with HsPDF may be used to form a binding compound-HsPDF complex of the present invention. Exemplary PDF inhibitors include, but are not limited to, actinonin and anctinonin analogs (Lee (2004) supra), as well as other PDF inhibitors as described in Apfel et al., *Antimicrobial Agents and Chemotherapy* (2001) 45:1058-1064; Wise et al., *Antimicrobial Agents and Chemotherapy* (2002) 46:1117-1118; Jones et al., *Journal of Antimicrobial Chemotherapy* (2004) 53, 804-807; Balakrishnon et al., *J. Biol. Chem.* (2006) 281:16691-16699; Wang et al., *Biophysical Chem.* (2006) 122:43-49; and Jain et al., *Current Medicinal Chemistry* (2005) 12:1607-1621; the entirety of each of which is incorporated herein by reference. Typical pathogens to PDF inhibitors include, but are not limited to, *S. aureus, S. pneumoniae, H. influenzae, M. catarrhalis, E. faecalis, E. faecium. E. oralis, H. pylori, Mycoplasma,* Anaerobes (G−), Anaerobes (G+), *Enterobacteriaceae, Chlamydia trachomatis; C. pneumoniae; C. psittaci;* and *C. pecorum.*

In certain embodiments, the binding compound is the antibiotic actinonin. Actinonin has previously been used to lead structure activity relation (SAR) efforts in the generation of more potent microbial PDF inhibitors (Grant et al., *Bioorganic Chemistry* (2001) 29:211-222). The present invention provides crystals of actinonin-bound Δ63HsPDF. In certain embodiments, crystalline actinonin-bound Δ63HsPDF is provided by soaking Δ63HsPDF crystals in a solution containing actinonin.

Crystalline HsPDF

The present invention provides crystal structures of HsPDF. In certain embodiments, the crystal structure is of Δ63HsPDF. In certain embodiments, the crystal structure is of actinonin-bound Δ63HsPDF.

A crystal of the present invention may take a variety of forms, all of which are contemplated by the present invention.

In one aspect of the invention, the present invention provides three-dimensional structure information from a crystal of N-truncated HsPDF, i.e., Δ63HsPDF (SEQ ID NO.:3, FIG. 10B). Table 1 provides the atomic structural coordinates of crystalline Δ63HsPDF as a $Co^{2+}$ complex. Crystalline Δ63HsPDF has a space group of C2 and with unit cell dimensions of a=115.938 Å, b=77.642 Å, c=110.711 Å, α=90.00°, β=107.820°, and γ=90.00°. The three dimensional structure of crystalline Δ63HsPDF displays a type 1A fold, an N-terminal alpha helix H1, a beta sheet formed by beta strands S1, S2, and S3, a "loop" containing alpha helices H2 and H3, a beta-hairpin S5, S6, and a second beta sheet formed by three beta strands S4, S7 and S8. Crystalline Δ63HsPDF also lacks a C-terminal alpha helix observed in type 1B PDF.

In another aspect of the invention, the present invention provides three-dimensional structure information from the complexation of Δ63HsPDF with a binding compound.

For example, the present invention provides three-dimensional structure information from actinonin-bound Δ63HsPDF. Table 2 provides the atomic structural coordinates of crystalline actinonin-bound Δ63HsPDF as a $Co^{2+}$ complex (the atomic structure coordinates of actinonin present in Table 2 correspond to the atom type listed as BB2). Crystalline actinonin-bound Δ63HsPDF has a space group of C2 and with unit dimensions of a=116.158 Å, b=77.884 Å, c=110.596 Å, α=90.00°, β=107.409°, γ=90.00°. Like crystalline Δ63HsPDF, the three dimensional structure of actinonin-bound Δ63HsPDF displays a type 1A fold, an N-terminal alpha helix H1, a beta sheet formed by beta strands S1, S2, and S3, a "loop" containing alpha helices H2 and H3, a beta-hairpin S5, S6, and a second beta sheet formed by three beta strands S4, S7 and S8. Crystalline actinonin-bound Δ63HsPDF also lacks a C-terminal alpha helix observed in type 1B PDF.

The crystals and co-crystals of the present invention diffract to a resolution limit of at least equal to or greater than 8 angstrom (Å). In certain embodiments, the crystals diffract to a resolution limit of at least equal to or greater than 6 angstrom (Å). In certain embodiments, the crystals diffract to a resolution limit of at least equal to or greater than 4 angstrom (Å). In certain embodiments, the crystals diffract to a resolution limit of at least equal to or greater than 2.5 angstrom (Å).

Methods of Using Crystalline HsPDF

It is one object of the present invention to use the atomic structure coordinates of Δ63HsPDF (e.g., Tables 1 and/or 2) to design, identify, and screen potential binding compounds that bind to HsPDF and/or a related PDF family member and alter its physical, chemical, or physiological properties. Novel compounds obtained from this screen may further be identified as possessing anti-bacterial, anti-viral, anti-parasitical, anti-inflammatory, and/or anti-cancer activity.

The atomic structure coordinates of Δ63HsPDF (e.g., Tables 1 and/or 2) can also be used to computationally screen small molecule data for compounds that bind to HsPDF and/or a PDF family member in order to select, design, and develop potential binding compounds of HsPDF and/or a PDF family member. It should be understood that a potential binding compound according to this invention may bind to an active site and/or an accessory binding site and/or to a site which is not identified as an active site or accessory binding site.

In certain embodiments, the potential binding compound is a potential inhibitor compound. In certain embodiments, the potential binding compound is a potential PDF inhibitor compound. In certain embodiments, the potential inhibitor compound is a competitive, uncompetitive or non-competitive inhibitor compound. Those of skill in the art may identify potential inhibitors as competitive, uncompetitive or non-competitive inhibitors by computer fitting enzyme kinetic data using standard equations according to, for example, Segel, *Enzyme Kinetics*, J. Wiley & Sons, (1975), incorporated herein by reference, or by employing assays which measure the ability of a potential inhibitor to modulate HsPDF enzymatic activity (e.g., deformylase activity). Exemplary assays include, but are not limited to, fluorescamine based assays (Antczak et al., JBMS in press); *aeromonas proteolytica*-p-nitroaniline assay (Wei and Pei, *Anal Biochem* (1997) 250:29-34), and formate-dehydrogenase (FDH) assay (Lazennec and Meinnel, *Anal Biochem* (1997) 244:180-182, and *Takenaga, Drug, Metabolism, and Disposition* (1999) 27:213-220), the entirety of each of which is incorporated herein by reference.

Thus, in one embodiment, the present invention provides a method for the design and identification of a potential binding compound for HsPDF and/or a PDF family member, comprising the steps of: (a) using a three-dimensional structure of HsPDF as defined by the atomic coordinates provided in Tables 1 and/or 2; (b) employing the three-dimensional structure to design and/or select the potential binding compound; and (c) synthesizing and/or choosing the potential binding compound.

In certain embodiments, the potential binding compound is a potential inhibitor compound. In certain embodiments, the potential binding compound is a potential PDF inhibitor compound. In certain embodiments, the potential inhibitor compound is a competitive, uncompetitive or non-competitive inhibitor compound.

Suitable computer programs which may be used in the design and selection of potential binding compounds (e.g., by selecting suitable chemical fragments) include, but are not limited to, GRID (Goodford; *J. Med. Chem.* (1985) 28:849 857); MCSS (Miranker, A. and M. Karplus, *Proteins: Structure. Function and Genetics*, (1991) 11:29-34); AUTODOCK (Goodsell, D. S, and A. J. Olsen, *Proteins: Structure. Function, and Genetics* (1990) 8:195 202); and DOCK (Kuntz, I. D. et al, *J. Mol. Biol.* (1982) 161:269-288), the entirety of each of which is incorporated herein by reference.

Suitable computer programs which may be used in connecting the individual chemical entities or fragments include, but are not limited to, CAVEAT (Bartlett, *Molecular Recognition in Chemical and Biological Problems*, Special Pub., Royal Chem. Soc. (1989) 78:182-196); and 3D Database systems such as MACCS-3D (MDL Information Systems, San Leandro, Calif.), HOOK (Molecular Simulations, Burlington, Mass.) and as reviewed in Martin, Y. C., *J. Med. Chem.*, (1992) 35:2145 2154), the entirety of each of which is hereby incorporated herein by reference.

In addition to the method of building or identifying a potential binding compound in a step-wise fashion (e.g., one fragment or chemical entity at a time as described above), potential binding compounds may be designed as a whole or "de novo" using either an empty active site or, optionally, including some portion(s) of a known inhibitor(s). Suitable computer programs include, but are not limited to, LUDI (Bohm, J. Comp. Aid. Molec. Design (1992) 6:61-78); LEGEND (Nishibata, Y. and A. Itai, Tetrahedron, 47, p. 8985 (1991)); and LEAPFROG (Tripos Associates, St. Louis, Mo.). Other molecular modeling techniques may also be employed in accordance with this invention; see, for example, Cohen, N. C. et al., *J. Med. Chem.* (1990) 33: 883-894, and Navia, *Current Opinions in Structural Biology* (1992) 2:202-210, the entirety of each of which is hereby incorporated herein by reference.

Once a potential binding compound has been designed and/or selected and/or synthesized and/or chosen by the above methods, the efficiency with which that compound binds to HsPDF and/or a PDF family member may be tested and optimized by computational evaluation. A compound designed and/or selected and/or synthesized and/or chosen as potential inhibitor compound may be further computationally optimized so that in its bound state it would preferably lack repulsive electrostatic interaction with the target site. Such non-complementary (e.g., electrostatic) interactions include repulsive charge-charge, dipole-dipole and charge-dipole interactions. Specifically, the sum of all electrostatic interactions between the potential inhibitory compound and the site at which it is bound to HsPDF and/or a PDF family member, in certain embodiments, make a neutral or favorable contribution to the enthalpy of binding. Suitable computer software which may be used to evaluate compound deformation energy and electrostatic interactions, includes, but is not limited to, Gaussian 92, revision C (M. J. Frisch, Gaussian, Inc., Pittsburgh, Pa., 1992); AMBER, version 4.0 (P. A. Kollman, University of California at San Francisco, 1994); QUANTA/CHARMM (Molecular Simulations, Inc., Burlington, Mass. 1994); and Insight II/Discover (Biosysm Technologies Inc., San Diego, Calif., 1994). These programs may be implemented, for example, using a Silicon Graphics workstation, IRIS 4D/35 or IBM RISC/6000 workstation model 550. Other hardware systems and software packages will be known to those skilled in the art of which the speed and capacity are continually modified.

Thus, in certain embodiments, the above method comprises using a suitable computer program in designing and/or selecting a potential binding compound.

Additionally, in certain embodiments, the above method step (c) comprises using a suitable computer program in conjunction with synthesizing and/or choosing the potential binding compound.

Furthermore, in certain embodiments, the above method further comprises the steps of using a suitable assay, as described herein, to characterize the potential binding compound's inhibitory activity. Thus, in certain embodiments, the above method further comprises: (d1) contacting the potential binding compound with HsPDF and/or a related PDF family member in the presence of a formylated substrate; and (e1) determining the percent inhibition of deformylase activity to determine the activity of the potential binding compound.

Figure 17:
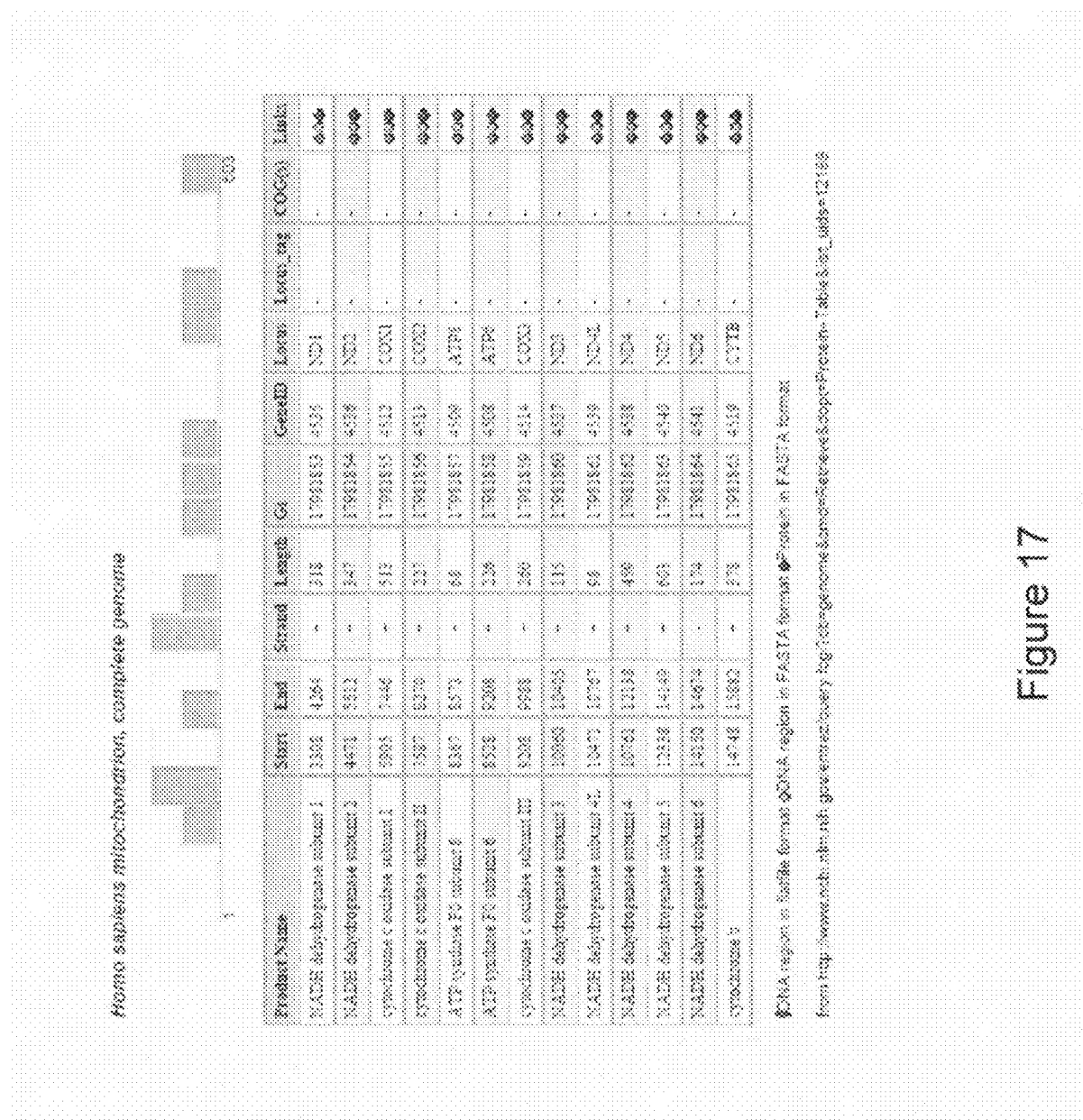
FIG. 17. The thirteen subunits of the mitochondrial respiratory complexes (National Center for Biotechnology Information, NCBI).

A formylated substrate is a substrate which contains an N-formyl group (formyl is understood to mean a —CHO group). It is understood that there are many different formulated substrates suitable for the above method. Exemplary formylated substrates include, but are not limited to, formyl-methionine-alanine-serine (FMAS), formyl-methionine-leucine-p-nitroaniline, formyl-methionine-alanine-histidine-alanine (FMAHA), formyl-methionine-serine-asparagine-glutamate (FMSAG), and formyl-methionine-leucine-glutamate (FMLG) (Lee (2003); Lee (2004), and Serero (2003), supra). Other exemplary formulated substrates include N-formylated peptides encoded by the mitochondrial genome (NCBI, FIG. 17).

Alternatively, in certain embodiments, the above method further comprises the steps of: (d2) contacting the potential binding compound with a cell, virus, bacterium, and/or parasite; and (e2) determining the cytotoxicity of the potential binding compound to the cell, virus, bacterium, and/or parasite. In certain embodiments, the cell is a cancer cell.

The present invention is also directed to a method for the design and identification of potential binding compounds for HsPDF and/or a related PDF family member comprising the steps of: (a) using a three-dimensional structure of HsPDF as defined by the atomic coordinates provided in Tables 1 and/or 2 by characterizing: (a) (i) an active site or accessory binding site of HsPDF and/or a related PDF family member from the atomic structure coordinates found in Tables 1 and/or 2, or (ii) an active site or accessory binding site of HsPDF and/or a related PDF family member by comparison to the atomic structure coordinates found in Tables 1 and/or 2, and (b) designing and/or selecting a potential binding compound that is capable of binding to at least one amino acid in the active site or accessory binding site of HsPDF and/or a related PDF family member (i) or (ii) in the absence of a known inhibitor; (c) synthesizing and/or choosing the potential binding compound.

In certain embodiments, the potential binding compound is a potential inhibitor compound. In certain embodiments, the potential binding compound is a potential PDF inhibitor compound. In certain embodiments, the potential inhibitor compound is a competitive, uncompetitive or non-competitive inhibitor compound.

In certain embodiments, the known inhibitor is actinonin or an actinonin analog.

In certain embodiments, the above method further comprises the steps of: (d1) contacting the potential binding compound with HsPDF and/or a PDF family member in the presence of a formylated substrate; and (e1) determining the percent inhibition of deformylase activity of HsPDF or PDF family member to determine the activity of the potential binding compound.

Alternatively, in certain embodiments, the above method further comprises the steps of: (d2) contacting the potential binding compound with a cell, virus, bacterium, and/or parasite; and (e2) determining the cytotoxicity of the potential binding compound to the cell, virus, bacterium, and/or parasite. In certain embodiments, the cell is a cancer cell.

It is another object of the invention to provide methods for solving the structures of crystallized proteins which belong to HsPDF or PDF family member, albeit free or complexed with a binding compound, by molecular replacement. Structures of crystallized proteins which are thought to be similar in structure based on function or sequence similarity or identity to HsPDF may be solved by molecular replacement with HsPDF structural information provided by the present invention (e.g., Tables 1 and/or 2).

The term "molecular replacement" refers to a method that involves generating a preliminary model of the three-dimensional structure of a HsPDF or HsPDF-inhibitor complex whose structure coordinates are not known, by orienting and positioning a HsPDF structure whose atomic structure coordinates are known (e.g., Δ63HsPDF (Table 1), or Δ63HsPDF-actinonin complex (Table 2)). Phases can then be calculated from this model and combined with the observed amplitudes of the unknown crystal structure to give an approximate structure. This, in turn, can be subject to any of several forms of refinement to provide a final, accurate structure. Any program known to the skilled artisan may be employed to determine the structure by molecular replacement. Suitable molecular replacement programs include, but are not limited to, AMORE (the CCP4 suite: *Acta Crystallogr. D.* (1994) 50:760-763; Navaza, *Acta Cryst.* (1994) A50, 157-163) and CNS (*Acta Crystallogr. D* (1998) 54:905 921).

Thus, in certain embodiments, the present invention provides a method for solving the structure of HsPDF or a PDF family member comprising the steps of: (a) collecting X-ray diffraction data of a HsPDF crystal or a PDF-family member crystal; (b) using the atomic coordinates of HsPDF according to Tables 1 and/or 2 to perform molecular replacement with the X-ray diffraction data of the HsPDF crystal or the PDF-family member crystal; and (c) determining the structure of HsPDF or the PDF-family member.

Furthermore, in certain embodiments, the present invention provides a method for solving the structure of HsPDF or a PDF family member complexed to a binding compound comprising the steps of: (a) collecting X-ray diffraction data of a HsPDF crystal complexed to a binding compound or a PDF-family member crystal complexed to a binding compound; (b) using the atomic coordinates of HsPDF according to Tables 1 and/or 2 to perform molecular replacement with the X-ray diffraction data of the HsPDF crystal or PDF-family member crystal; and (c) determining the structure of HsPDF complexed to a binding compound or PDF-family member complexed to a binding compound.

Additionally, the present invention provides a method of evaluating the binding properties of a potential binding compound comprising the steps of: (a) soaking a potential binding compound with crystalline HsPDF or a crystalline PDF family member to provide a crystalline HsPDF complexed to a binding compound or a crystalline PDF-family member complexed to a binding compound; (b) determining the three-dimensional structure of the crystalline HsPDF complexed to a binding compound or the crystalline PDF-family member complexed to a binding compound by molecular replacement using the three-dimensional structure of HsPDF as defined by atomic coordinates according to Tables 1 and/or 2; and (c) analyzing the three-dimensional structure of the a crystalline HsPDF complexed to a binding compound or a crystalline PDF-family member complexed to a binding compound to the unbound potential binding compound to evaluate the binding characteristics of the potential binding compound.

Binding Compounds

Binding compounds identified using the above methods may further be identified as possessing anti-bacterial, anti-viral, anti-parasitical, anti-inflammatory, and/or anti-cancer activity. Biologically active binding compounds may be used to treat cancer, bacterial diseases, viral diseases, parasitical diseases, and/or inflammatory diseases, or may be used to develop other anti-bacterial, anti-viral, anti-parasitical, anti-inflammatory, and/or anti-cancer agents via standard medicinal chemistry or combinatorial methods.

Exemplary bacterial diseases which these biologically active binding compounds may be used to treat include, but are not limited to, Actinomycosis; Acute prostatitis; *Aeromonas hydrophila*; Annual ryegrass toxicity; Anthrax; Bacteremia; Bacterial meningitis; Bacterial pneumonia; Brazilian purpuric fever; Brodie's abscess; Bubonic plague; Brucellosis; *Burkholderia cepacia* complex; Buruli ulcer; Campylobacteriosis; *Capnocytophaga canimorsus*; Caries; Carrion's disease; *Chlamydia*; Cholera; Diphtheria; Diphtheritic stomatitis; Donovanosis; Erythema migrans; Fitz-Hugh-Curtis syndrome; Fournier gangrene; Group A streptococcal infection; Human granulocytic ehrlichiosis; Impetigo; Late congenital syphilis; Late congenital syphilitic oculopathy; *Legionella*; Lemierre's syndrome; Leprosy; Leptospirosis; Listeriosis; Ludwig's angina; Lyme disease; Melioidosis; Meningococcemia; Methicillin-resistant *Staphylococcus aureus*; Miliary tuberculosis; *Mycobacterium; Mycobacterium avium* complex; Necrotizing fasciitis; Nontuberculous mycobacteria; Omphalitis; Orbital cellulitis; Osteomyelitis; Paratyphoid fever; *Pasteurella multocida*; Periorbital cellulitis; Peritonsillar abscess; Pertussis; Pott's disease; Pseudomembranous colitis; Psittacosis; Pyomyositis; Q fever; Rheumatic fever; *Rickettsia prowazekii*; Rickettsialpox; Salmonellosis; Scarlet fever; Scrub typhus; Spondylitis; Staphylococcal infection; Strep throat; Syphilis; Syphilitic aortitis; Tetanus; Tuberculosis; Tularemia; Typhoid fever; Typhus.

Exemplary viral diseases which these biologically active binding compounds may be used to treat include, but are not limited to, Acquired Immunodeficiency Syndrome; Adenoviridae Infections; Alphavirus Infections; Arbovirus Infections; Borna Disease; Bunyaviridae Infections; Caliciviridae Infections; Chickenpox; Condyloma Acuminata; Coronaviridae Infections; Coxsackievirus Infections; Cytomegalovirus Infections; Dengue; DNA Virus Infections; Eethyma; Encephalitis; Arbovirus; Epstein-Barr Virus Infections; Erythema Infectiosum; Hantavirus Infections; Hemorrhagic Fevers; Hepatitis; Herpes; Herpesviridae Infections; Infectious Mononucleosis; Influenza in birds; Influenza in humans; Lassa Fever; Measles; Molluscum Contagiosum; Mumps; Paramyxoviridae Infections; Phlebotomus Fever; Polyomavirus Infections; Rabies; Respiratory Syncytial Virus Infections; Rift Valley Fever; RNA Virus Infections; Rubella; Slow Virus Diseases; Smallpox; Subacute Sclerosing Panencephalitis; Tumor Virus Infections; Warts; West Nile Fever; Yellow Fever.

Exemplary parasitical diseases which these biologically active binding compounds may be used to treat include, but are not limited to, Amebiasis; Anisakiasis; *Ascariasis*; Babesiosis; Blastocystis hominis infections; Cestode Infections; Chagas Disease; Cryptosporidiosis; Cyclosporiasis; Cysticercosis; Dientamoebiasis; Diphyllobothriasis; Dracunculiasis; Echinococcosis; Ectoparasitic Infestations; Filariasis; Giardiasis; Helminthiasis; Hookworm Infections; Intestinal Diseases, Parasitic; Larva Migrans; Leishmaniasis; Lice Infestations; Loiasis; Malaria; Mite Infestations; Myiasis; Neurocysticercosis; Onchocerciasis; Protozoan Infections; Scabies; Schistosomiasis; Skin Diseases, Parasitic; Strongyloidiasis; Taeniasis; Toxocariasis; Toxoplasmosis; Trichinosis; Trichomonas Infections; Trypanosomiasis; Whipworm Infections Exemplary inflammatory diseases which these biologically active binding compounds may be used to treat include, but are not limited to, rheumatoid arthritis, osteoarthritis inflammatory lung disease, inflammatory bowel disease, atherosclerosis and psoriasis.

Exemplary cancers which these biologically active binding compounds may be used to treat include, but are not limited to, bone cancer, brain cancer, blood cancer, breast cancer, pancreatic cancer, lung cancer, kidney cancer, stomach cancer, ovarian cancer, prostate cancer, colorectal cancer, endometrial cancer, bladder cancer, non-Hodgkin lymphoma, leukemia, neuroblastoma, lymphomas, rhabdomyosarcoma, Wilms' tumor, osteosarcoma and Ewing's sarcoma.

The present invention will be more specifically illustrated by the following examples. However, it should be understood that the present invention is not limited by these examples in any manner.

EXAMPLES

Cloning and Expression of Δ63HsPDF. A truncated HsPDF lacking the first 63 amino-acids (Δ63HsPDF) which correspond to the mitochondrial targeting sequence was cloned, and expressed. This truncated PDF circumvents the low yields of production in a bacterial host while retaining the key residues for PDF activity (Giglione et al., *Embo J* (2000). 19:5916-5929, incorporated herein by reference).

Previous cloning of Δ63HsPDF with a C-terminal 6-Histidine tag, Δ63HsPDF-6His, (Lee et al. (2003) supra) resulted in low protein yields. The low protein yields and the poor stability of Δ63HsPDF-6His in solution proved this particular HsPDF clone inadequate for producing the concentration and purity required for protein crystallography. The poor stability and precipitation of PDF family proteins has been attributed to lose of the active site metal and oxidation of the cysteine residue which coordinates the metal at the active site.

In order to improve the yield of HsPDF production, Δ63HsPDF-6His was cloned by restriction digestion into the NdeI and XhoI restriction sites of the pIAD16 vector to give an N-terminal maltose binding protein fusion with a thrombin cleavable site that would enable removal of the maltose binding protein tag.

However this HsPDF clone, pIAD16-Δ63HsPDF-6His, retained the C-terminal 6His-tag, whose presence was undesirable for crystallization. Therefore HsPDF was cloned by PCR with the pIAD16-Δ63HsPDF-6His vector as a template and using adaptor forward and reverse primers to include the NdeI and BamHI restriction sites, respectively.

Figure 8:
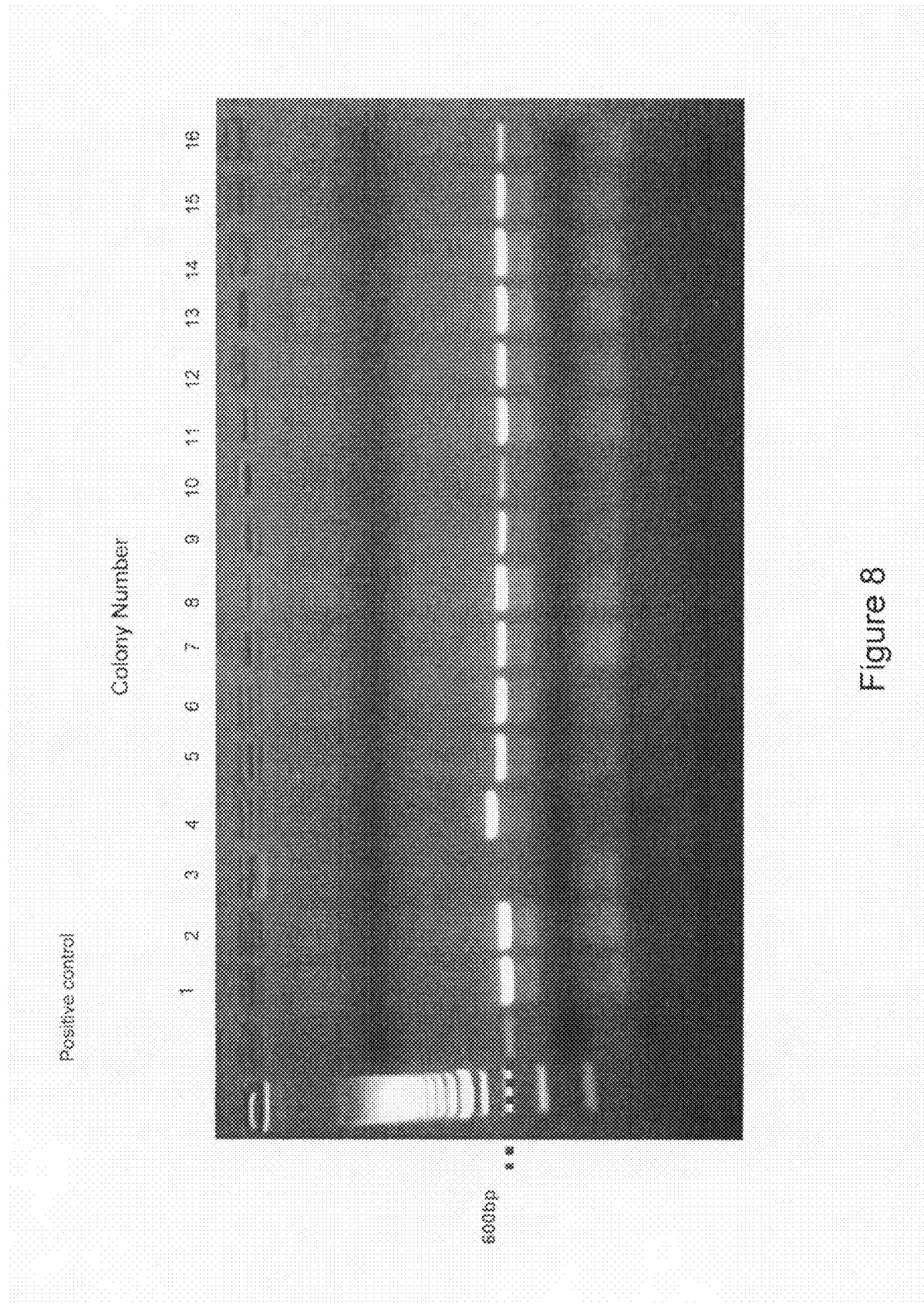
FIG. 8. Screening of cell colonies, transformed with the Δ63HsPDF PCR fragment pET15 vector ligation reaction product, for the presence of the Δ63HsPDF insert. Δ63HsPDF was amplified directly from each colony using the NdeI_F and BamHI_R1 primers described herein. Numbers above the lanes represent the colony number. The positive control PCR product is the result of amplification of a colony bearing the pIAD16-Δ63HsPDF-6His vector.

The forward and reverse primers used, correspondingly, are NdeI_F, 5'GGAATTCCATATGTCATTCTCGCACGT-GTGCCAAGTCGGG3' (SEQ ID NO. 5) and BamHI_R, 5'CGCGGATCCTTAGTCATTCACCTTCATC-CAATAGACGTT3' (SEQ ID NO. 6) (Genelink, Hawthorne N.Y.). The gel purified NdeI/BamHI restriction digested HsPDF PCR fragment was cloned into the expression vector pET-15b by ligation into plasmid vector that had been digested with the same restriction enzymes. XL-10 Gold ultracompetent cells (Stratagene, La Jolla Calif.) transformed with the plasmid-PCR ligation product were screened for the presence of the HsPDF insert by colony PCR (FIG. 8). The presence of the HsPDF insert in the pET-15b vector was further confirmed by restriction digestion of plasmid extracted from the same colonies with NdeI and BamHI, as well as with EcoRV.

The NdeI/BamHI (New England Biolabs, Ipswich, Mass.) restriction digested PCR fragment was cloned into the expression vector pET-15b (Novagen, San Diego Calif.), resulting in an N-terminal 6-Histidine tagged Δ63HsPDF, 6His-Δ63HsPDF, with a thrombin cleavage signal sequence plus an additional five amino-acid insertion, GSHMS, between the tag and the Δ63HsPDF sequence. 6His-Δ63HsPDF was expressed in BL-21 (DE3) pLys (Invitrogen, Carlsbad Calif.). Briefly, transformed bacteria were grown overnight at 37° C. in Lennox LB Broth (Fisher Scientific, Fair Lawn N.J.) in the presence of 200 μg/mL ampicillin (Sigma, St Louis Mo.) and 34 μg/mL chloramphenicol (Fisher Scientific, Fair Lawn N.J.) and diluted 1:50 in fresh media with the same antibiotic concentrations at 37° C. until OD600 reached 0.4-0.8. Protein expression was induced with 0.4 mM IPTG (Fisher Scientific, Fair Lawn N.J.) and in the presence of 100 μM $CoCl_2$ for 3 h at 37° C. Cells were collected by centrifugation at 5000 rpm in a Sorvall SLC4000 rotor (Sorvall, Asheville, N.C.) for 30 min at 4° C.

Figure 9:
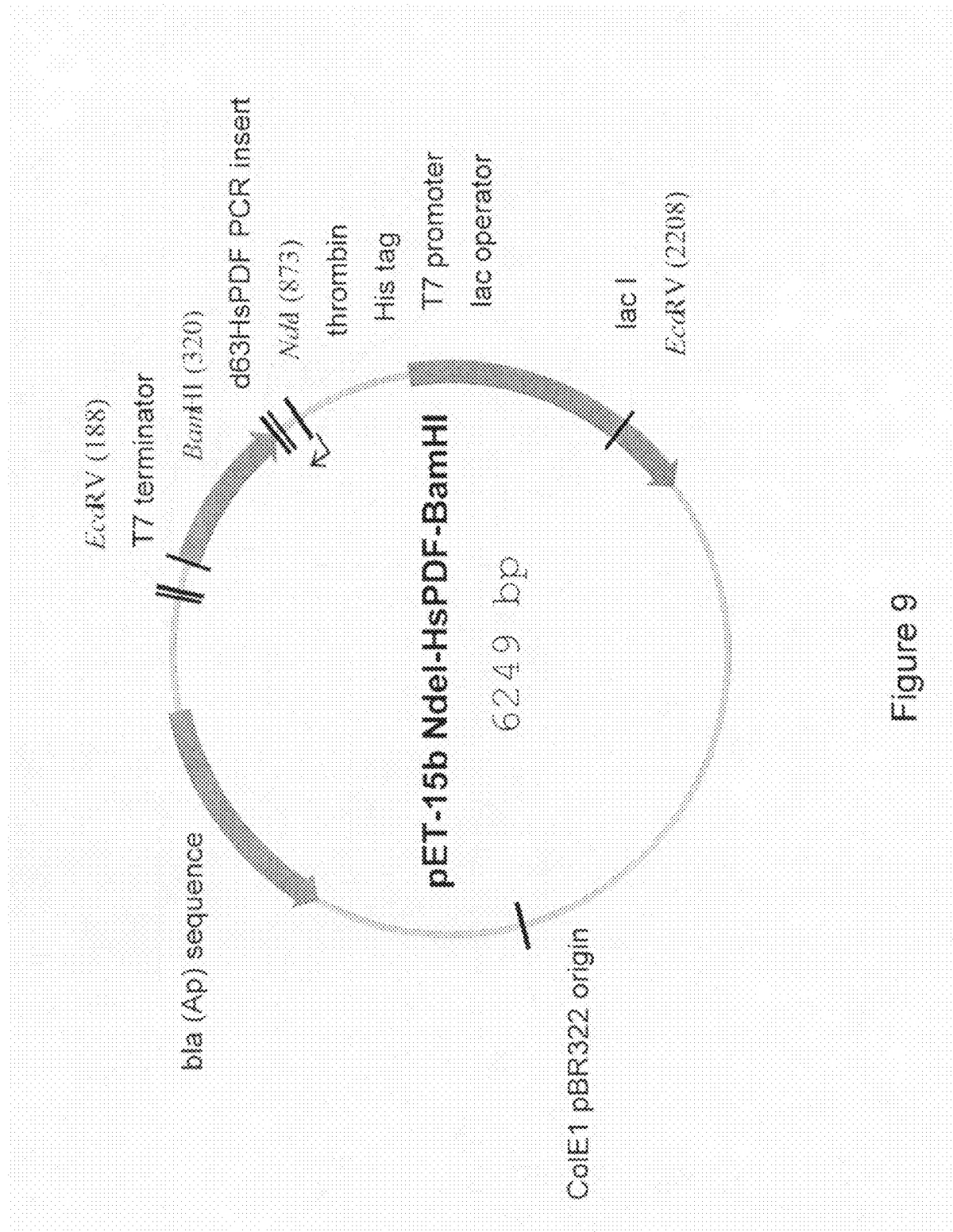
FIG. 9. The pET-15b-6His-Δ63HsPDF vector map.

The pET-15 HsPDF clone codes for an N-terminal 6-Histidine tagged Δ63HsPDF, 6His-Δ63HsPDF (FIG. 9A). The vector construct sequence is provided in FIG. 9B. In 6His-Δ63HsPDF, the N-terminal 6His-tag is followed by a thrombin cleavage signal that in turn is followed by the Δ63HsPDF sequence. Cloning of Δ63HsPDF into the chosen restriction sites of the pET-15 vector resulted in the addition of five amino-acids, GSHMS, at the N-terminus of Δ63HsPDF (FIG. 9B).

The activity of 6His-Δ63HsPDF produced from a selected pET-1Sb vector clone was initially verified by two independent purifications of 6His-Δ63HsPDF over a $Ni^{2+}$ affinity column (FIG. 11A) and measurement of HsPDF activity using a formate dehydrogenase assay described previously (Lazennec and Meinnel (1997) (FIG. 11B). An average of 7 mg of 6His-Δ63HsPDF per liter of culture were obtained from this initial purification step.

6His-Δ63HsPDF was toxic to competent cell strains routinely used for protein expression, such as BL-21 (DE3), therefore 6His-Δ63HsPDF was expressed in BL-21 (DE3) pLys (Invitrogen, Carlsbad Calif.). Briefly, transformed bacteria were grown overnight at 37° C. in Lennox LB Broth (Fisher Scientific, Fair Lawn N.J.) in the presence of 200 μg/mL ampicillin (Sigma, St Louis Mo.) and 34 μg/mL chloramphenicol (Fisher Scientific, Fair Lawn N.J.) and diluted 1:50 in fresh media with the same antibiotic concentrations at 37° C. until OD600 reached 0.4-0.8. Protein expression was induced with 0.4 mM IPTG (Fisher Scientific, Fair Lawn N.J.) and in the presence of 100 μM $CoCl_2$ for 3 h at 37° C. Cells were collected by centrifugation at 5000 rpm in a Sorvall SLC4000 rotor (Sorvall, Asheville, N.C.) for 30 min at 4° C.

Purification of Δ63HsPDF. The bacterial cell pellet was resuspended in Buffer A (20 mM HEPES, 300 mM NaCl, 5% glycerol, 20 mM Imidazole, pH 7.4) and lysed by sonication. The cell lysate was cleared by centrifugation at 14,000 g for 20 min at 4° C., and the supernatant loaded onto a $Ni^{2+}$ sepharose high performance resin packed column (Amersham Biosciences, Piscataway N.J.). Protein elution was performed with an imidazole gradient using Buffer A and Buffer B (20 mM HEPES, 300 mM NaCl, 5% glycerol, 500 mM Imidazole pH 7.4). Δ63HsPDF elution was assessed following the protein elution at absorbance 280 nm combined with Δ63HsPDF activity elution. Fractions containing HsPDF activity were pooled. The purity of the purified 6His-Δ63HsPDF was determined by SDS-PAGE. 6His-Δ63HsPDF was then digested with 8 units of thrombin/mg of protein (Amersham Biosciences, Piscataway N.J.) overnight at 16° C. Thrombin was removed by incubation of the digested protein solution with 100 μL of 50% p-aminobenzamidine, agarose (Sigma, St. Louis Mo.) for 3 h at 4° C. Digested Δ63HsPDF was precipitated over a range of increasing ammonium sulfate percentages. The protein pellets obtained at each percentage of ammonium sulfate saturation were resuspended in Buffer A and the fraction containing HsPDF determined from the presence of HsPDF activity measured by the formate-dehydrogenase, FDH, assay described elsewhere Lazennec and Meinnel, *Anal Biochem* (1997) 244:180-182, incorporated herein by reference. The ammonium sulfate in the fraction containing HsPDF was reduced by exchanging the buffer to 20 mM MES, 20 mM NaCl pH 6.2 using a Superose 12 gel filtration column (Amersham Biosciences, Piscataway N.J.). PDF activity was measured in the single $A_{280nm}$ peak eluted from the gel filtration column. The purified HsPDF was stored in 5 mM TCEP.

6His-Δ63HsPDF was purified in four steps to yield the Δ63HsPDF utilized for crystallization screening (FIG. 12). $Ni^{2+}$ affinity purified 6His-Δ63HsPDF was treated with thrombin to remove the 6His-tag, with the thrombin subsequently being removed by p-aminobenzamidine agarose. Δ63HsPDF was concentrated by precipitation with ammonium sulfate, $(NH_4)_2SO_4$. Ammonium sulfate was removed by buffer exchange of the soluble Δ63HsPDF. The final, pure and concentrated, Δ63HsPDF is in 20 mM HEPES, 20 mM NaCl, pH 6.2 with 5 mM TCEP. The thrombin digestion conditions proved optimal to obtain Δ63HsPDF that was not over or under-digested. In addition ammonium sulfate precipitation was necessary to rapidly concentrate the protein while minimizing losses due to precipitation of Δ63HsPDF. Other concentration methods such as the use of Centricon devices resulted in protein loss due to precipitation and protein adherence to the device. FIGS. 13A-13E shows the results from one purification process to obtain Δ63HsPDF for screening of crystallization conditions. The identity of the protein purified was further confirmed by N-terminal Edman degradation of the first nine amino-acid residues at the Microchemistry and Proteomics core facility at Sloan-Kettering Institute (FIG. 14).

The monomeric or dimeric state of the purified Δ63HsPDF was confirmed by gel filtration through comparison of the elution volume of Δ63HsPDF to those of gel filtration standards. A second run of Δ63HsPDF and the gel filtration standards in 20 mM MES, 20 mM NaCl pH 6.2 resulted in an estimated molecular weight of 27 kDa for Δ63HsPDF.

Crystallization of Δ63HsPDF. Crystallization conditions were screened by the hanging drop method at 4° C. Initial screenings for crystallization of Δ63HsPDF were done with varying concentrations of Δ63HsPDF, as well as in the presence and absence of the 6His-tag (Table 3), using both Emerald Biosystems Wizard I and II Random sparse matrix crystallization screens (Emerald BioSystems, Bainbridge Island, Wash.), and Hampton Research Crystal Screen and Crystal Screen 2 (Hampton Research, Aliso Viejo, Calif.). Some of the buffers resulted in crystal formation, shown as "promising buffers", and one of them also presented crystal formation, however these crystals were confirmed to be salt crystals. Δ63HsPDF and 6His-Δ63HsPDF used for these crystallization screens were from different purification preparations of HsPDF, which varied in the type of protein concentration method used, purification method after the $Ni^{2+}$ affinity purification, and pH, relative to the purification method. Crystal screens were inspected for crystal formation a week to two weeks after they were set-up and followed up on for at least a month after the initial inspection.

The hanging drop was a 1:2 mixture of Δ63HsPDF solution to precipitation buffer in a total volume of 3 μL. Reproducible crystals grew in 0.1M sodium citrate tribasic dihydrate pH 5.6, 1.0 M ammonium phosphate monobasic (Buffer 11 in the Hampton Research Crystal Screen) at 4° C., and at a protein concentration of about 2 mg/ml. The quality of the crystals, in terms of size of the crystals as well as formation of monocrystals rather than poly-crystals was further refined by testing for the best protein to buffer ratio. The best crystals were obtained by the hanging drop being a 1:2 mixture of Δ63HsPDF solution to precipitation buffer in a total volume of 3 μL.

To obtain the Δ63HsPDF structures in complex with the inhibitors, all inhibitor stocks in dimethylsulfoxide (Sigma, St Louis Mo.), were diluted to 0.5 mM in 23% glycerol in mother liquor, where the crystals were soaked overnight. Crystals were cryoprotected with 25% glycerol in mother liquor upon data collection. Actinonin was synthesized by the Organic Synthesis core facility at Sloan Kettering Institute.

TABLE 3

Summary of conditions tested for Δ63HsPDF crystallization.

| Tag | Concentration (mg/mL) | Crystallization screen | # Conditions tested | Important Observations |
|---|---|---|---|---|
| no | 0.4 | Emerald Wizard I, II | 96 | Too dilute |
| + | 1.8 | Emerald Wizard I, II | 96 | Possible Crystal* |
| − | 1.7 | Emerald Wizard I, II | 96 | Precipitation at most condition |
| +/− | 1.8/1.7 | Hampton Research (HR2-110) | 48 | 3 "promising buffers" |
| +/− | 1.8/1.7 | Hampton Research (HR2-112) | 48 | 2 "promising buffers" |

TABLE 4

Emerald Wizard I random sparse matrix crystallization screen technical sheet

|   | crystallant | buffer (0.1M) | salt (0.2M) |
|---|---|---|---|
| 1 | 20% (w/v) PEG-8000 | CHES pH 9.5 | none |
| 2 | 10% (v/v) 2-propanol | HEPES pH 7.5 | NaCl |
| 3 | 15% (v/v) ethanol | CHES pH 9.5 | none |
| 4 | 35% (v/v) 2-methyl-2,4-pentanediol | imidazole pH 8.0 | $MgCl_2$ |
| 5 | 30% (v/v) PEG-400 | CAPS pH 10.5 | none |
| 6 | 20% (w/v) PEG-3000 | citrate pH 5.5 | none |
| 7 | 10% (w/v) PEG-8000 | MES pH 6.0 | $Zn(OAc)_2$ |
| 8 | 2.0M $(NH_4)_2SO_4$ | citrate pH 5.5 | none |
| 9 | 1.0M $(NH_4)_2HPO_4$ | acetate pH 4.5 | none |
| 10 | 20% (w/v) PEG-2000 MME | Tris pH 7.0 | none |
| 11 | 20% (v/v) 1,4-butanediol | MES pH 6.0 | $Li_2SO_4$ |
| 12 | 20% (w/v) PEG-1000 | imidazole pH 8.0 | $Ca(OAc)_2$ |
| 13 | 1.26M $(NH_4)_2SO_4$ | cacodylate pH 6.5 | none |
| 14 | 1.0M sodium citrate | cacodylate pH 6.5 | none |
| 15 | 10% (w/v) PEG-3000 | imidazole pH 8.0 | $Li_2SO_4$ |
| 16 | 2.5M NaCl | Na/K phosphate pH 6.2 | none |
| 17 | 30% (w/v) PEG-8000 | acetate pH 4.5 | $Li_2SO_4$ |
| 18 | 1.0M K/Na tartrate | imidazole pH 8.0 | NaCl |
| 19 | 20% (w/v) PEG-1000 | Tris pH 7.0 | none |
| 20 | 0.4M $NaH_2PO_4$/1.6M $K_2HPO_4$ | imidazole pH 8.0 | NaCl |
| 21 | 20% (w/v) PEG-8000 | HEPES pH 7.5 | none |
| 22 | 10% (v/v) 2-propanol | Tris pH 8.5 | none |
| 23 | 15% (v/v) ethanol | imidazole pH 8.0 | $MgCl_2$ |
| 24 | 35% (v/v) 2-methyl-2,4-pentanediol | Tris pH 7.0 | NaCl |
| 25 | 30% (v/v) PEG-400 | Tris pH 8.5 | $MgCl_2$ |
| 26 | 10% (w/v) PEG-3000 | CHES pH 9.5 | none |
| 27 | 1.2M $NaH_2PO_4$/0.8M $K_2HPO_4$ | CAPS pH 10.5 | $Li_2SO_4$ |
| 28 | 20% (w/v) PEG-3000 | HEPES pH 7.5 | NaCl |
| 29 | 10% (w/v) PEG-8000 | CHES pH 9.5 | NaCl |
| 30 | 1.26M $(NH_4)_2SO_4$ | acetate pH 4.5 | NaCl |
| 31 | 20% (w/v) PEG-8000 | phosphate-citrate pH 4.2 | NaCl |
| 32 | 10% (w/v) PEG-3000 | Na/K phosphate pH 6.2 | none |
| 33 | 2.0M $(NH_4)_2SO_4$ | CAPS pH 10.5 | $Li_2SO_4$ |
| 34 | 1.0M $(NH_4)_2HPO_4$ | imidazole pH 8.0 | none |
| 35 | 20% (v/v) 1,4-butanediol | acetate pH 4.5 | none |
| 36 | 1.0M sodium citrate | imidazole pH 8.0 | none |
| 37 | 2.5M NaCl | imidazole pH 8.0 | none |
| 38 | 1.0M K/Na tartrate | CHES pH 9.5 | $Li_2SO_4$ |
| 39 | 20% (w/v) PEG-1000 | phosphate-citrate pH 4.2 | $Li_2SO_4$ |
| 40 | 10% (v/v) 2-propanol | MES pH 6.0 | $Ca(OAc)_2$ |
| 41 | 30% (w/v) PEG-3000 | CHES pH 9.5 | none |
| 42 | 15% (v/v) ethanol | Tris pH 7.0 | none |
| 43 | 35% (v/v) 2-methyl-2,4-pentanediol | Na/K phosphate pH 6.2 | none |
| 44 | 30% (v/v) PEG-400 | acetate pH 4.5 | $Ca(OAc)_2$ |
| 45 | 20% (w/v) PEG-3000 | acetate pH 4.5 | none |
| 46 | 10% (w/v) PEG-8000 | imidazole pH 8.0 | $Ca(OAc)_2$ |
| 47 | 1.26M $(NH_4)_2SO_4$ | Tris pH 8.5 | $Li_2SO_4$ |
| 48 | 20% (w/v) PEG-1000 | acetate pH 4.5 | $Zn(OAc)_2$ |

TABLE 5

Emerald Wizard II random sparse matrix crystallization screen technical sheet

|   | crystallant | buffer (0.1M) | salt (0.2M) |
|---|---|---|---|
| 1 | 10% (w/v) PEG-3000 | acetate pH 4.5 | $Zn(OAc)_2$ |
| 2 | 35% (v/v) 2-methyl-2,4-pentanediol | MES pH 6.0 | $Li_2SO_4$ |
| 3 | 20% (w/v) PEG-8000 | Tris pH 8.5 | $MgCl_2$ |
| 4 | 2.0M $(NH_4)_2SO_4$ | cacodylate pH 6.5 | NaCl |
| 5 | 20% (v/v) 1,4-butanediol | HEPES pH 7.5 | NaCl |
| 6 | 10% (v/v) 2-propanol | phosphate-citrate pH 4.2 | $Li_2SO_4$ |
| 7 | 30% (w/v) PEG-3000 | Tris pH 7.0 | NaCl |
| 8 | 10% (w/v) PEG-8000 | Na/K phosphate pH 6.2 | NaCl |
| 9 | 2.0M $(NH_4)_2SO_4$ | phosphate-citrate pH 4.2 | none |
| 10 | 1.0M $(NH_4)_2HPO_4$ | Tris pH 8.5 | none |
| 11 | 10% (v/v) 2-propanol | cacodylate pH 6.5 | $Zn(OAc)_2$ |
| 12 | 30% (v/v) PEG-400 | cacodylate pH 6.5 | $Li_2SO_4$ |
| 13 | 15% (v/v) ethanol | citrate pH 5.5 | $Li_2SO_4$ |
| 14 | 20% (w/v) PEG-1000 | Na/K phosphate pH 6.2 | NaCl |
| 15 | 1.26M $(NH_4)_2SO_4$ | HEPES pH 7.5 | none |
| 16 | 1.0M sodium citrate | CHES pH 9.5 | none |
| 17 | 2.5M NaCl | Tris pH 7.0 | $MgCl_2$ |
| 18 | 20% (w/v) PEG-3000 | Tris pH 7.0 | $Ca(OAc)_2$ |
| 19 | 1.6M $NaH_2PO_4$/0.4M $K_2HPO_4$ | phosphate-citrate pH 4.2 | none |
| 20 | 15% (v/v) ethanol | MES pH 6.0 | $Zn(OAc)_2$ |
| 21 | 35% (v/v) 2-methyl-2,4-pentanediol | acetate pH 4.5 | none |
| 22 | 10% (v/v) 2-propanol | imidazole pH 8.0 | none |
| 23 | 15% (v/v) ethanol | HEPES pH 7.5 | $MgCl_2$ |
| 24 | 30% (w/v) PEG-8000 | imidazole pH 8.0 | NaCl |
| 25 | 35% (v/v) 2-methyl-2,4-pentanediol | HEPES pH 7.5 | NaCl |
| 26 | 30% (v/v) PEG-400 | CHES pH 9.5 | none |
| 27 | 10% (w/v) PEG-3000 | cacodylate pH 6.5 | $MgCl_2$ |
| 28 | 20% (w/v) PEG-8000 | MES pH 6.0 | $Ca(OAc)_2$ |
| 29 | 1.26M $(NH_4)_2SO_4$ | CHES pH 9.5 | NaCl |
| 30 | 20% (v/v) 1,4-butanediol | imidazole pH 8.0 | $Zn(OAc)_2$ |
| 31 | 1.0M sodium citrate | Tris pH 7.0 | NaCl |
| 32 | 20% (w/v) PEG-1000 | Tris pH 8.5 | none |
| 33 | 1.0M $(NH_4)_2HPO_4$ | citrate pH 5.5 | NaCl |
| 34 | 10% (w/v) PEG-8000 | imidazole pH 8.0 | none |
| 35 | 0.8M $NaH_2PO_4$/1.2M $K_2HPO_4$ | acetate pH 4.5 | none |
| 36 | 10% (w/v) PEG-3000 | phosphate-citrate pH 4.2 | NaCl |
| 37 | 1.0M K/Na tartrate | Tris pH 7.0 | $Li_2SO_4$ |
| 38 | 2.5M NaCl | acetate pH 4.5 | $Li_2SO_4$ |
| 39 | 20% (w/v) PEG-8000 | CAPS pH 10.5 | NaCl |
| 40 | 20% (w/v) PEG-3000 | imidazole pH 8.0 | $Zn(OAc)_2$ |
| 41 | 2.0M $(NH_4)_2SO_4$ | Tris pH 7.0 | $Li_2SO_4$ |
| 42 | 30% (v/v) PEG-400 | HEPES pH 7.5 | NaCl |
| 43 | 10% (w/v) PEG-8000 | Tris pH 7.0 | $MgCl_2$ |
| 44 | 20% (w/v) PEG-1000 | cacodylate pH 6.5 | $MgCl_2$ |
| 45 | 1.26M $(NH_4)_2SO_4$ | MES pH 6.0 | none |
| 46 | 1.0M $(NH_4)_2HPO_4$ | imidazole pH 8.0 | NaCl |
| 47 | 2.5M NaCl | imidazole pH 8.0 | $Zn(OAc)_2$ |
| 48 | 1.0M K/Na tartrate | MES pH 6.0 | none |

TABLE 6

Hamptom Research Crystal Screen (HR2-112)

1. 10% PEG 6000, 2.0M Sodium Chloride
2. 0.5M Sodium Chloride, 0.01M CTAB, 0.01M Magnesium Chloride
3. 25% Ethylene Glycol
4. 35% Dioxane
5. 5% iso-Propanol, 2.0M Ammonium Sulfate
6. 1.0M Imidazole pH 7.0
7. 10% PEG 1000, 10% PEG 8000
8. 10% Ethanol, 1.5M Sodium Chloride
9. 2.0M Sodium Chloride, 0.1M Na Acetate pH 4.6
10. 30% MPD, 0.1M Na Acetate pH 4.6, 0.2M Sodium Chloride
11. 1.0M 1,6 Hexanediol, 0.1M Na Acetate pH 4.6, 0.01M Cobalt Chloride
12. 30% PEG 400, 0.1M Na Acetate pH 4.6, 0.1M Cadmium Chloride
13. 30% PEG MME 2000, 0.1M Na Acetate pH 4.6, 0.2M Ammonium Sulfate
14. 2.0M Ammonium Sulfate, 0.1M Na Citrate pH 5.6, 0.2M K/Na Tartrate
15. 1.0M Lithium Sulfate, 0.1M Na Citrate pH 5.6, 0.5M Ammonium Sulfate
16. 2% Polyethyleneimine, 0.1M Na Citrate pH 5.6, 0.5M Sodium Chloride
17. 35% tert-Butanol, 0.1M Na Citrate pH 5.6
18. 10% Jeffamine M-600, 0.1M Na Citrate pH 5.6, 0.01M Ferric Chloride
19. 2.5M 1,6 Hexanediol, 0.1M Na Citrate pH 5.6
20. 1.6M Magnesium Sulfate, 0.1M MES pH 6.5
21. 2.0M Sodium Chloride, 0.1M MES pH 6.5, 0.2M Na/K Phosphate
22. 12% PEG 20,000, 0.1M MES pH 6.5
23. 10% Dioxane, 0.1M MES pH 6.5, 1.6M Ammonium Sulfate
24. 30% Jeffamine M-600, 0.1M MES pH 6.5, 0.05M Cesium Chloride
25. 1.8M Ammonium Sulfate, 0.1M MES pH 6.5, 0.01M Cobalt Chloride
26. 30% PEG MME 5000, 0.1M MES pH 6.5, 0.2M Ammonium Sulfate
27. 25% PEG MME 550, 0.1M MES pH 6.5, 0.01M Zinc Sulfate
28. 1.6M Sodium Citrate pH 6.5
29. 30% MPD, 0.1M Hepes pH 7.5, 0.5M Ammonium Sulfate
30. 10% PEG 6000, 0.1M Hepes pH 7.5, 5% MPD
31. 20% Jeffamine M-600, 0.1M Hepes pH 7.5
32. 1.6M Ammonium Sulfate, 0.1M Hepes pH 7.5, 0.1M Sodium Chloride
33. 2.0M Ammonium Formate, 0.1M Hepes pH 7.5
34. 1.0M Sodium Acetate, 0.1M Hepes pH 7.5, 0.05M Cadmium Sulfate
35. 70% MPD, 0.1M Hepes pH 7.5
36. 4.3M Sodium Chloride, 0.1M Hepes pH 7.5
37. 10% PEG 8000, 0.1M Hepes pH 7.5, 8% Ethylene Glycol
38. 20% PEG 10,000, 0.1M Hepes pH 7.5
39. 3.4M 1,6 Hexanediol, 0.1M Tris pH 8.5, 0.2M Magnesium Chloride
40. 25% tert-Butanol, 0.1M Tris pH 8.5
41. 1.0M Lithium Sulfate, 0.1M Tris pH 8.5, 0.01M Nickel (II) Chloride
42. 12% Glycerol, 0.1M Tris pH 8.5, 1.5M Ammonium Sulfate
43. 50% MPD, 0.1M Tris pH 8.5, 0.2M Ammonium Phosphate
44. 20% Ethanol, 0.1M Tris pH 8.5
45. 20% PEG MME 2000, 0.1M Tris pH 8.5, 0.01M Nickel (II) Chloride
46. 20% PEG MME 550, 0.1M Bicine pH 9.0, 0.1M Sodium Chloride
47. 2.0M Magnesium Chloride, 0.1M Bicine pH 9.0
48. 10% PEG 20,000, 0.1M Bicine pH 9.0, 2% Dioxane X-ray Crystallography of Δ63HsPDF. The crystal structures of the N-terminally truncated HsPDF (Δ63HsPDF), in the absence of inhibitor (Table 1), as well as in complex with actinonin (Table 2), were elucidated.

Δ63HsPDF atomic structure coordinates (Table 1). A single crystal of Δ63HsPDF (unbound Δ63HsPDF) was obtained via the crystallization method as described herein. The space group was determined to be C2. The atomic structure coordinates are provided in Table 1 (coordinates from restrained individual B-factor refinement; refinement resolution: 500.0-1.6 A; final R-factor=0.1947 free R-factor=0.2145; B rmsd for bonded mainchain atoms=1.055 (target=1.5); B rmsd for bonded sidechain atoms=1.995 (target=2.0); B rmsd for angle mainchain atoms=1.638 (target=2.0); B rmsd for angle sidechain atoms=2.976 (target=2.5; space group=C2 (a=115.938 b=77.642 c=110.711 alpha=90.000 beta=107.820 gamma=90.000); B-correction resolution: 6.0-1.6; initial B-factor correction applied to fobs: B11=−1.567, B22=1.081, B33=0.486, B12=0.000 B13=1.018 B23=0.000; B-factor correction applied to coordinate array B: −0.047; bulk solvent: density level=0.388278 e/A$^3$, B-factor=45.5952 A$^2$; reflections with |Fobs|/sigma_F<0.0 rejected; reflections with |Fobs|>10000*rms (Fobs) rejected; anomalous diffraction data was input; theoretical total number of refl. in resol. range: 242655 (100.0%); number of unobserved reflections (no entry or |F|=0): 15190 (6.3%); number of reflections rejected: 0 (0.0%); total number of reflections used: 227465 (93.7%); number of reflections in working set: 216276 (89.1%); number of reflections measured was 243350 (99.2% completeness). Five percent of reflections selected randomly were included into the test set for the calculation of the free R-factor. The metal cation complexed to Δ63HsPDF was confirmed as Co$^{2+}$ from an X-ray fluorescence scan spectrum.

Actinonin-bound Δ63HsPDF atomic structure coordinates (Table 2). A single crystal of Δ63HsPDF (actinonin-bound Δ63HsPDF) was obtained via the crystallization method as described herein. The space group was determined to be C2. The atomic structure coordinates are provided in Table 2 (coordinates from minimization refinement; refinement resolution: 500.0; −1.6 A; final R-factor=0.1987; free R-factor=0.2172; rmsd bonds=0.004556 rmsd angles=1.27441;

wa=0.301503; target=mlf cycles=1 steps=100; space group=C2 (a=116.158 b=77.884 c=110.596 alpha=90.0000 beta=107.409 gamma=90.000); B-correction resolution: 6.0-1.6; initial B-factor correction applied to fobs: B11=−2.576 B22=1.720 B33=0.856 B12=0.000 B13=1.327 B23=0.000; B-factor correction applied to coordinate array B: −0.547; bulk solvent: density level=0.381382 e/A^3, B-factor=41.9966 A^2; reflections with |Fobs|/sigma_F<0.0 rejected; reflections with |Fobs|>10000*rms(Fobs) rejected; theoretical total number of refl. in resol. range: 123934 (100.0%); number of unobserved reflections (|F|=0): 4780 (3.9%); number of reflections rejected: 0 (0.0%); total number of reflections used: 119154 (96.1%); number of reflections in working set: 113108 (91.3%); number of reflections in test set: 6046 (4.9%)). Non-anomalous data was input, number of measured reflections was 152326 (99.5% completeness). Five percent of reflections selected randomly were included into the test set for the calculation of the free R-factor.

Diffraction data was measured at 100K, cryoprotectant was 23% glycerol. Data processed with HKL2000 (Otwinowski and Minor, "Processing of X-ray Diffraction Data Collected in Oscillation Mode", in *Methods in Enzymology*, 276: Macromolecular Crystallography, part A, 307-326, C. W. Carter, Jr. & R. M. Sweet, Eds., Academic Press, New York, 1997. Structure solved by molecular replacement using CCP4 package program AMORE (J. Navaza, *Acta Cryst.* (1994) A50, 157-163) with PDB entry 1ZXZ as a search model and refined with CNS (Brunger et al. *Acta Cryst.* (1998) D54, 905-921).

Figure 2:
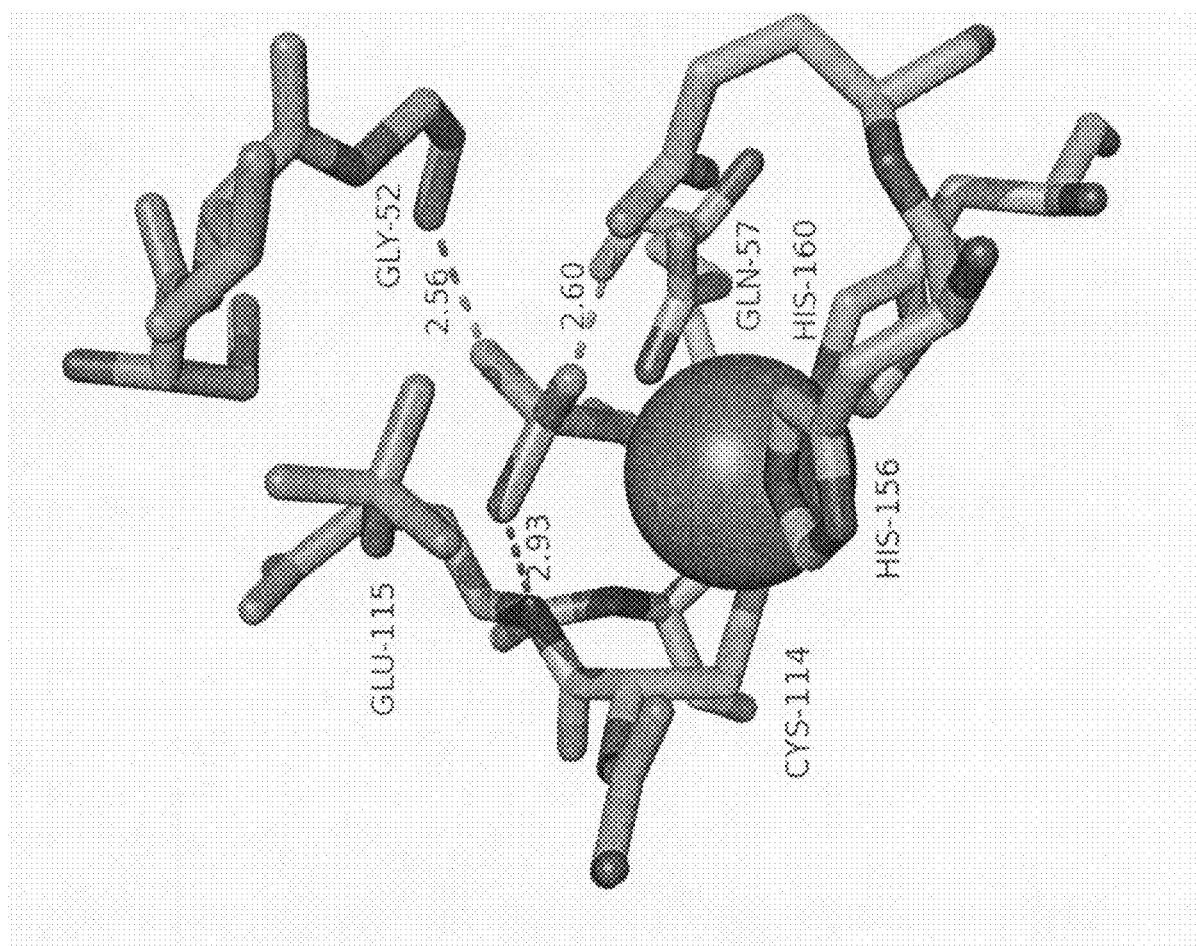
FIG. 2. The metal coordination in Δ63HsPDF is tetrahedral. The four ligands of the $Co^{2+}$ atom, in purple, are H156, H160, C114, and a fourth molecule modeled as phosphate, in orange. The distances of the presumed oxygen atoms in the phosphate molecule to neighboring atoms are shown as dotted lines. Water molecules are shown as red crosses.

Discussion. Δ63HsPDF was expressed and purified as a $Co^{2+}$ enzyme because this was the only metal that allowed reconstitution of enzymatic activity of the Δ63HsPDF (Lee et al., (2003) supra). The geometry of the metal is tetrahedral, and $Co^{2+}$ is kept at the active site by coordination to the side chain N atoms of H156 and H160, the side chain sulfur atom of C114, and a fourth unexpected ligand. Other non-mammalian PDF structures have shown a water molecule as the fourth metal ligand (Becker et al., *Nat Struct Biol* (1998) 5:1053-1058). Interestingly however, model building revealed the presence of two tetrahedral molecules at the active site of HsPDF, one of which replaces the water molecule as the fourth metal coordinating molecule (FIG. 2). These molecules were modeled as inorganic phosphate, as the crystallization buffer contains this ion. These phosphate molecules were not observed in the actinonin bound molecule, and were presumably displaced by the inhibitor molecule.

Figure 3A:
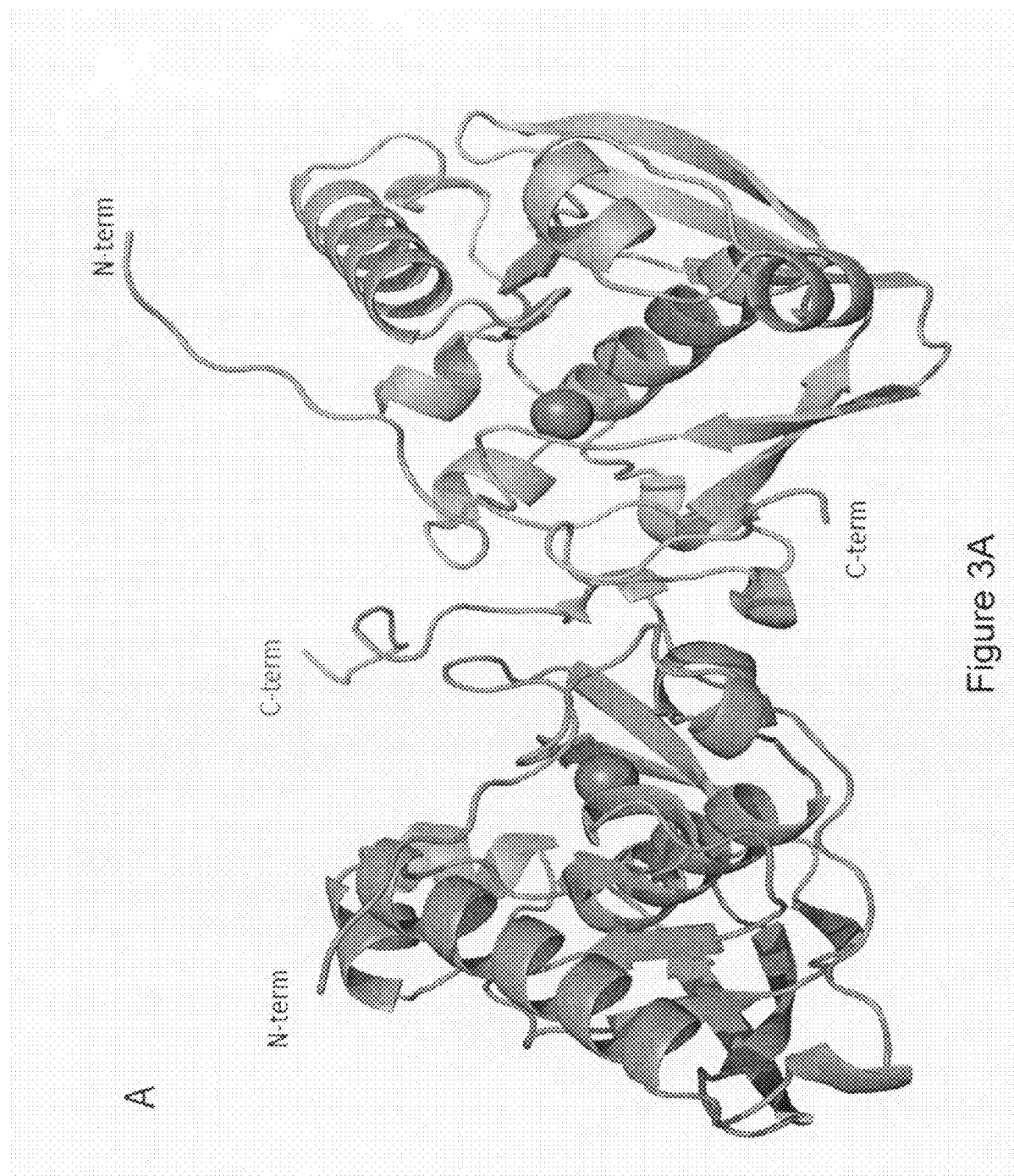
FIG. 3A. The Δ63HsPDF asymmetric unit is constituted by two Δ63HsPDF dimers. Each monomer is shown in a different color, with their respective N-terminus and C-terminus indicated as N-term, and C-term accordingly. The $Co^{2+}$ atom is a purple sphere.
Figure 3B:
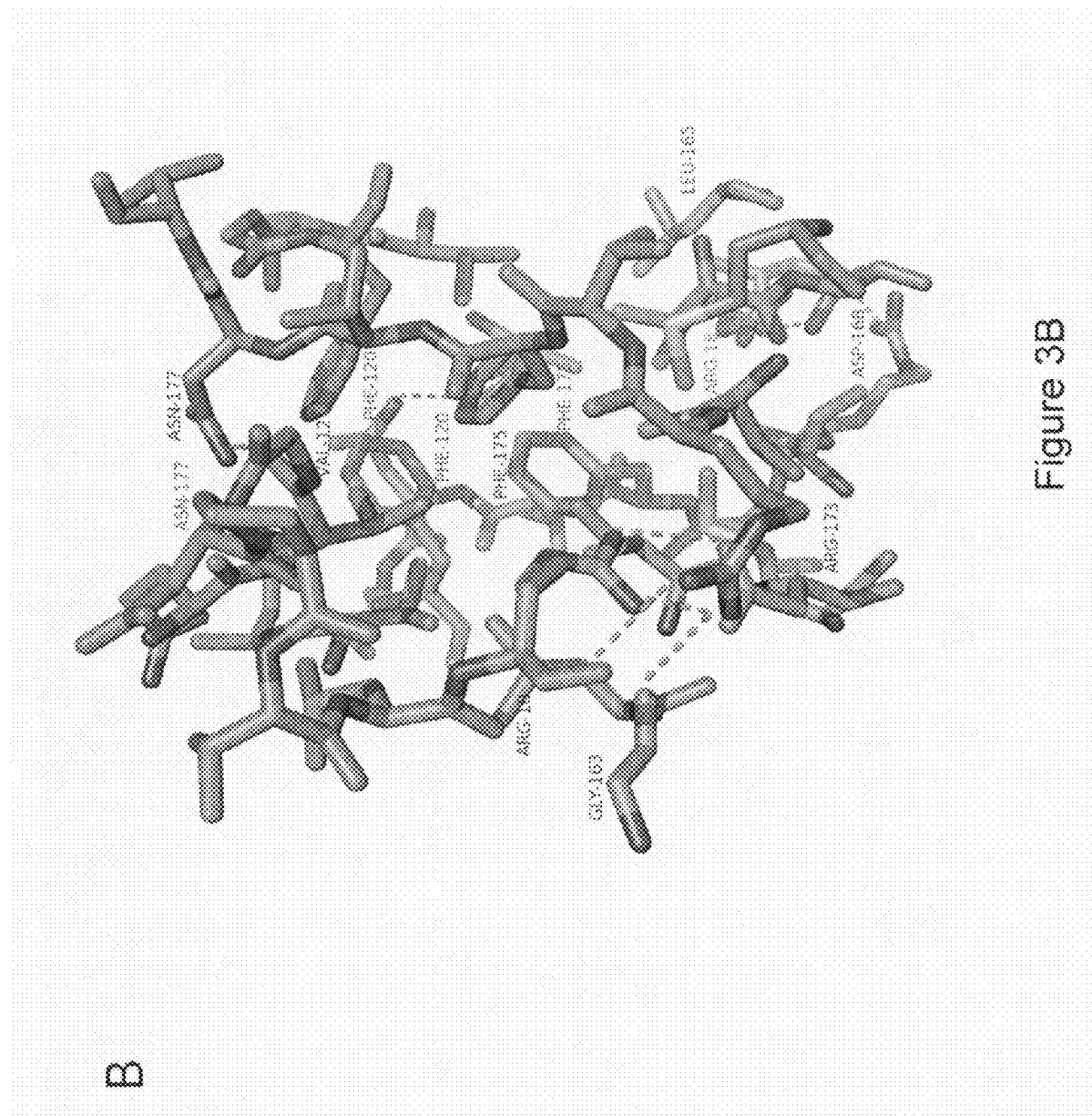
FIG. 3B. The dimer interphase is formed through electrostatic and hydrophobic interactions between the Δ63HsPDF monomers. The carbon backbone of each of the monomers is in a different color, green or cyan, with nitrogen atoms in blue, oxygen atoms in red, and sulfur atoms in yellow. Salt bridges are indicated by orange dotted lines.

The crystal structure of Δ63HsPDF was resolved as a dimer (FIG. 3A). The topology of the monomers is rotated 180°, in both the vertical and horizontal axes, relative to each other. As a result one monomer appears upside down and with a counter-clockwise rotation of 180° relative to the other monomer. The interaction between the two Δ63HsPDF monomers occurs through a hydrophobic core, which is zippered at the edges by intra and inter monomer hydrogen bonding (FIG. 3B). The carbonyl oxygen of R18 in each monomer presumably interacts with the nitrogen-bound hydrogen atom in the R173 side chain of the opposite monomer, judging from the proximity between such carbonyl and R173 side chain N. Similar interactions occur between the pairs G163-R173 and V12-N177, each of these residues in a different monomer. In addition, intra-monomer electrostatic interactions such as D168-R18 are also present at the dimer interphase. F120, F175, and M170 of each subunit are positioned at the dimer interface, each one facing their counterpart in the opposite dimer, building the core of the hydrophobic dimer interaction. V117, I167, and V12 in both monomers also take part in the hydrophobic interaction of the Δ63HsPDF monomers. An interesting observation is the proximity of the metal binding loop to the dimer interface. Analytical size exclusion chromatography resolved Δ63HsPDF as a monomer, but sedimentation equilibrium of the protein used for crystallization suggested that HsPDF can exist as a mixture of monomer and dimer. Whether Δ63HsPDF is monomeric or dimeric in its native form is not proven by these data.

Figures 4A, 4B, 4C:
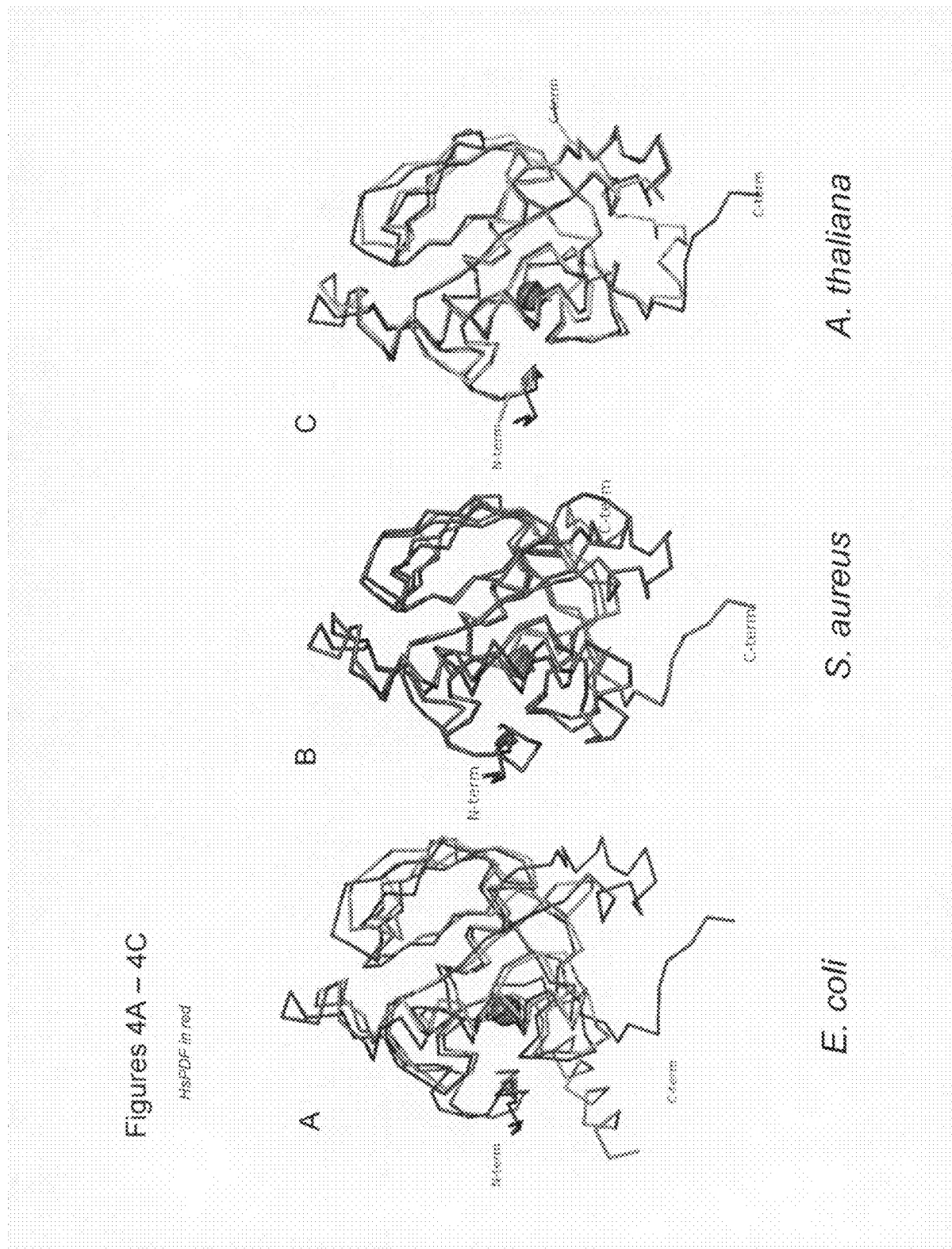
FIG. 4A. Δ63HsPDF has the conserved PDF fold observed in other type 1B, type 2, and type 1A PDFs. Δ63HsPDF, red in all panels, is superimposed on *E. coli* PDF (EcPDF) type 1B (Protein data bank 1G2A), green. The Δ63HsPDF $Co^{2+}$ metal is represented as a purple sphere in all panels.
FIG. 4B. Superimposed on Δ63HsPDF is *S. aureus* PDF (SaPDF) type 2 (Protein data bank 1G2A), blue.
FIG. 4C. Δ63HsPDF is superimposed on *A. thaliana* PDF (AtPDF) type 1A (Protein data bank 1ZXZ), cyan.

HsPDF, a type 1A PDF, shares the same fold as other PDFs such as *E. coli* PDF, EcPDF (Protein databank 1G2A) type 1B, *Staphylococcus aureus*, SaPDF, (Protein data bank 1LQW) type 2, and *Arabidopsis thaliana*, AtPDF (Protein data bank 1ZXZ) type 1A (FIG. 4A-C). HsPDF and EcPDF differ mainly in the presence of the loop containing alpha helices H2 and H3, and the lack of a C-terminal alpha helix in HsPDF. Other secondary structure features differ between the human and the bacterial PDF, such as beta strands S3 and S4 in HsPDF appearing as a single strand in EcPDF (Chan et al., *Biochemistry* (1997) 36:13904-13909), or the presence the two beta strands, S5 and S6, which are not observed in EcPDF, however these differences could be a result of the algorithm used to assign secondary structure in different reports.

Figures 5A, 5B:
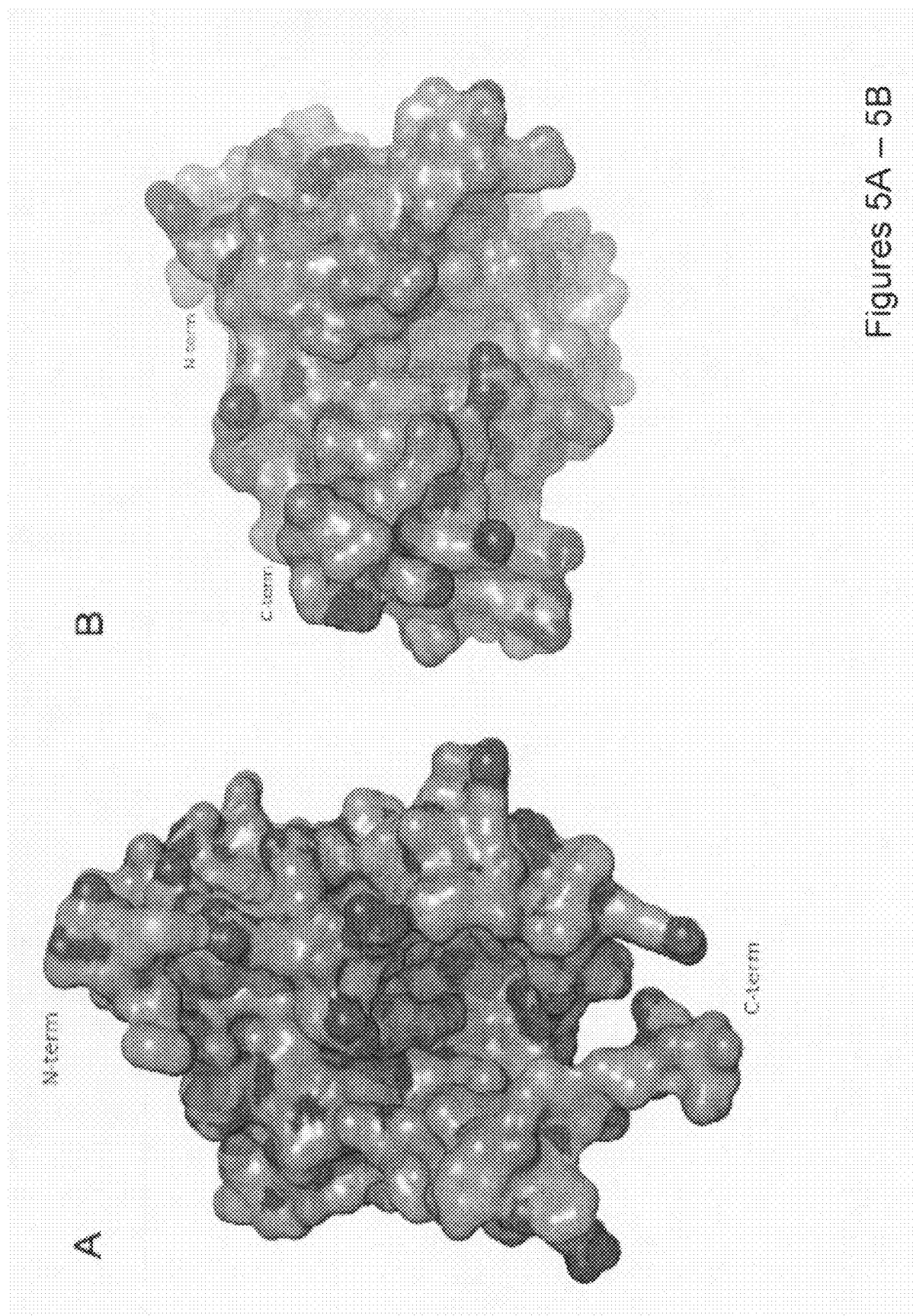
FIG. 5A. The entrance to the binding site of Δ63HsPDF differs from those of other PDFs. Surface view of PDF from various organisms in grey with oxygen atoms in red, nitrogen atoms in blue, and sulfur atoms in yellow.
FIG. 5B. The entrance to the EcPDF active site is occluded compared to HsPDF.

Importantly, while the outer atrium in EcPDF is wider than Δ63HsPDF, the inner entrance into the active site of Δ63HsPDF is more accessible to substrate (FIG. 5A) than that of EcPDF (FIG. 5B) due to the side chains of residues E87, E95, and R97 (EcPDF numbering). These residues face the active site cavity opening, and are replaced by P111, G119, and L121, correspondingly, in Δ63HsPDF. P111 is located on beta strand S4, on the metal binding loop. The other two residues, also found on the metal binding loop, localize to a region that contacts the main chain atoms of the C-terminus through hydrogen bonding.

Δ63HsPDF lacks the insertion between alpha helix H1 and beta strand S1 present in type II PDFs. The entrance to the active and binding sites of PDFs, delineated by the metal binding loop containing beta strands 5 and 6, and helix 2 in the alpha helical "CD loop", are also different between HsPDF and the type II PDF, with the entrance being narrower in the former (FIG. 5C), while access to the active site in SaPDF is provided by an unshielded open cavity. This is due to differences in the C-terminal conformations of both enzymes, as well as the presence of a short "pseudo" CD loop in *S. aureus*'s PDF.

Figures 5C, 5D:
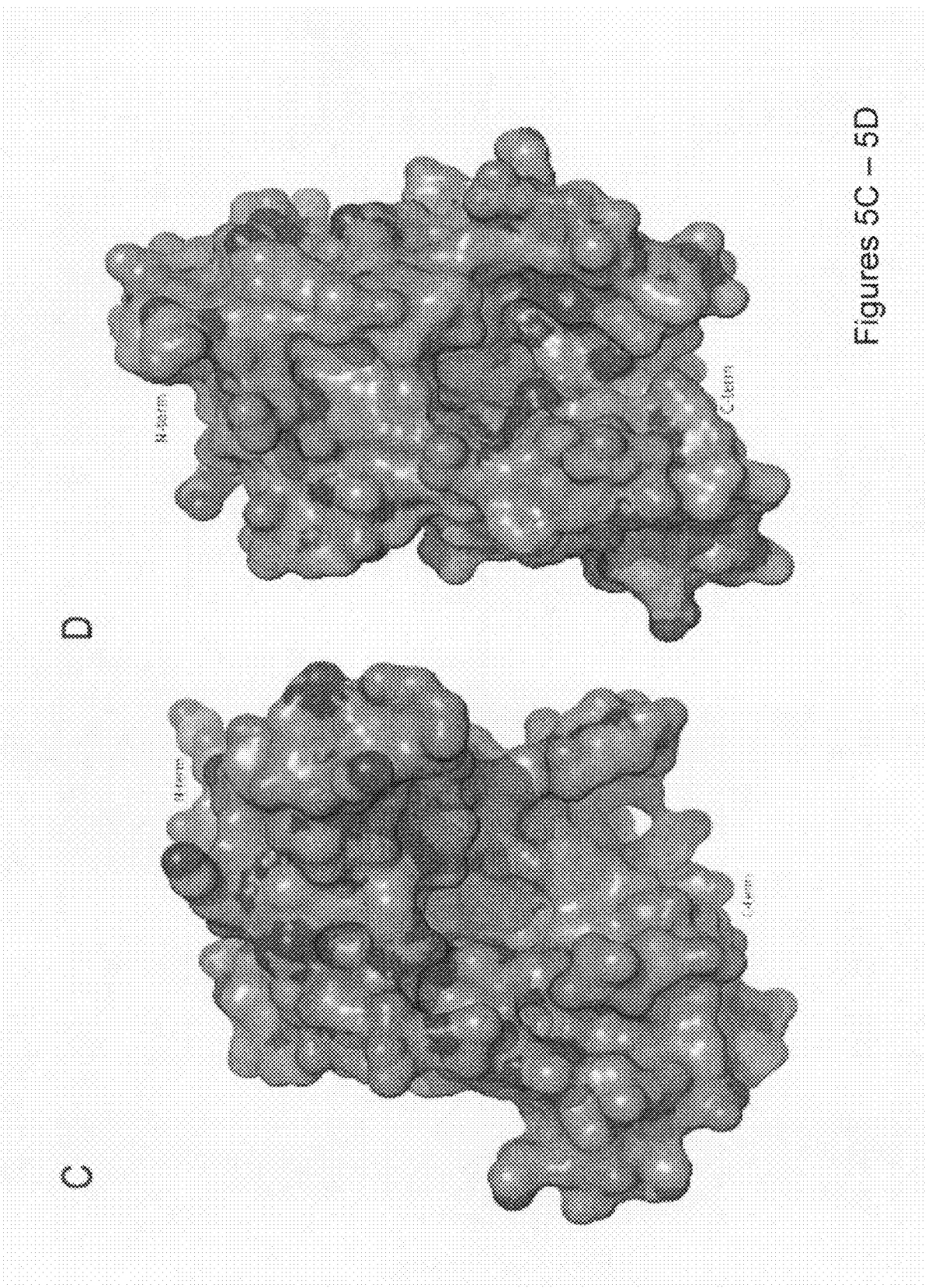
FIG. 5C. The entrance to the active and binding sites of the type II SaPDF is wider than that of Δ63HsPDF.
FIG. 5D. The active site entrance of AtPDF differs from Δ63HsPDF due to the conformation of the C-terminus in AtPDF.

AtPDF has been proposed as a representative member of Type 1A peptide deformylases (Fieulain et al. (2005) supra), and as a model for Δ63HsPDF, however significant structural differences exist between them. The main difference is observed at the C-terminus, which is not only shorter in Δ63HsPDF but also shows a different topology than that of AtPDF, which impacts the shape of the entrance to the active site. The entrance to the Δ63HsPDF active site is far narrower than in AtPDF. The C-terminus in Δ63HsPDF does not loop back towards beta strand 5, as is the case with the corresponding strand in AtPDF (FIGS. 4C and 5D). The rather perpendicular position of Δ63HsPDF's C-terminus with respect to beta strand 5 results in a narrower entrance to the substrate binding and active sites of the enzyme.

Figures 6A, 6B, 6C, 6D:
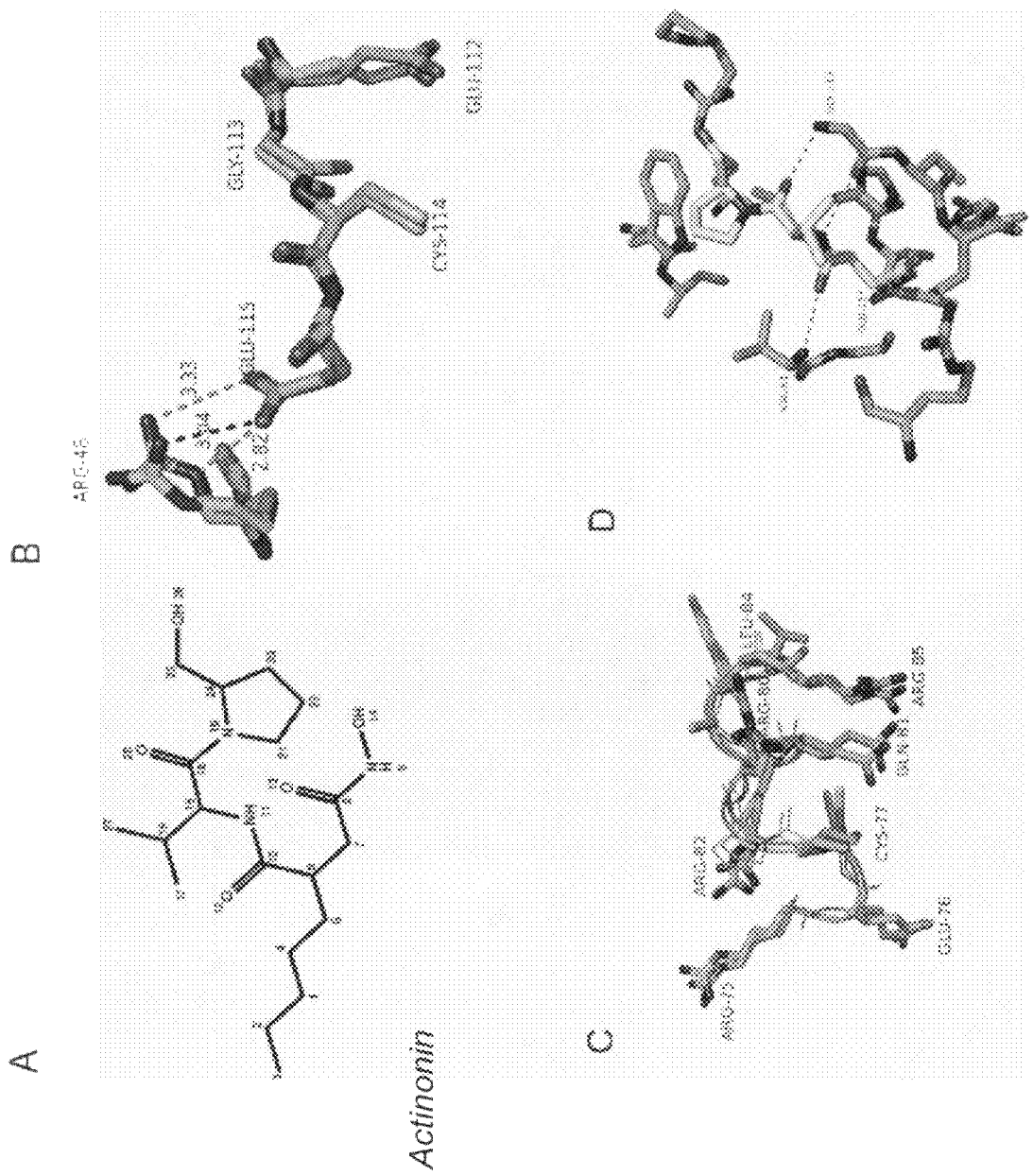
FIG. 6A. Actinonin binding to Δ63HsPDF results in rearrangement of residue side chains. Structure of the peptidomimetic inhibitor actinonin. N9 and hydroxyl 14 constitute the hydroxamic acid moiety of the inhibitor. The carbons in the aliphatic pentyl chain are numbered 1-5, and the valine side chain carbons are numbered 15-17 and 27.
FIG. 6B. Shifts in catalytically important residues occur upon actinonin binding to Δ63HsPDF. The orientation of the residues in one of the inhibitor free Δ63HsPDF monomers is shown in green. Superimposed are the same residues in the actinonin bound Δ63HsPDF monomer, in cyan. The electrostatic interaction between the side chain oxygens of G115 with the backbone nitrogen of R48 and one of its side chain nitrogens, represented as orange dotted lines, is replaced with only one electrostatic interaction between the side chains of G115 and R48, black dotted line. Distances between atoms are shown in Å.
FIG. 6C. Conformational changes occur in the helix 2 and helix 3 regions of Δ63HsPDF upon actinonin binding. The orientation of the residues in one of the inhibitor free Δ63HsPDF monomers is shown in green. Superimposed are the same residues in the actinonin bound Δ63HsPDF monomer, in cyan.
FIG. 6D. Actinonin binds Δ63HsPDF through hydrogen bonding and hydrophobic interactions. The Δ63HsPDF backbone, green, with the residues contacting actinonin, yellow, are shown as sticks. Hydrogen bonding is represented by orange dotted lines. Distances in Å.
Figure 6E:
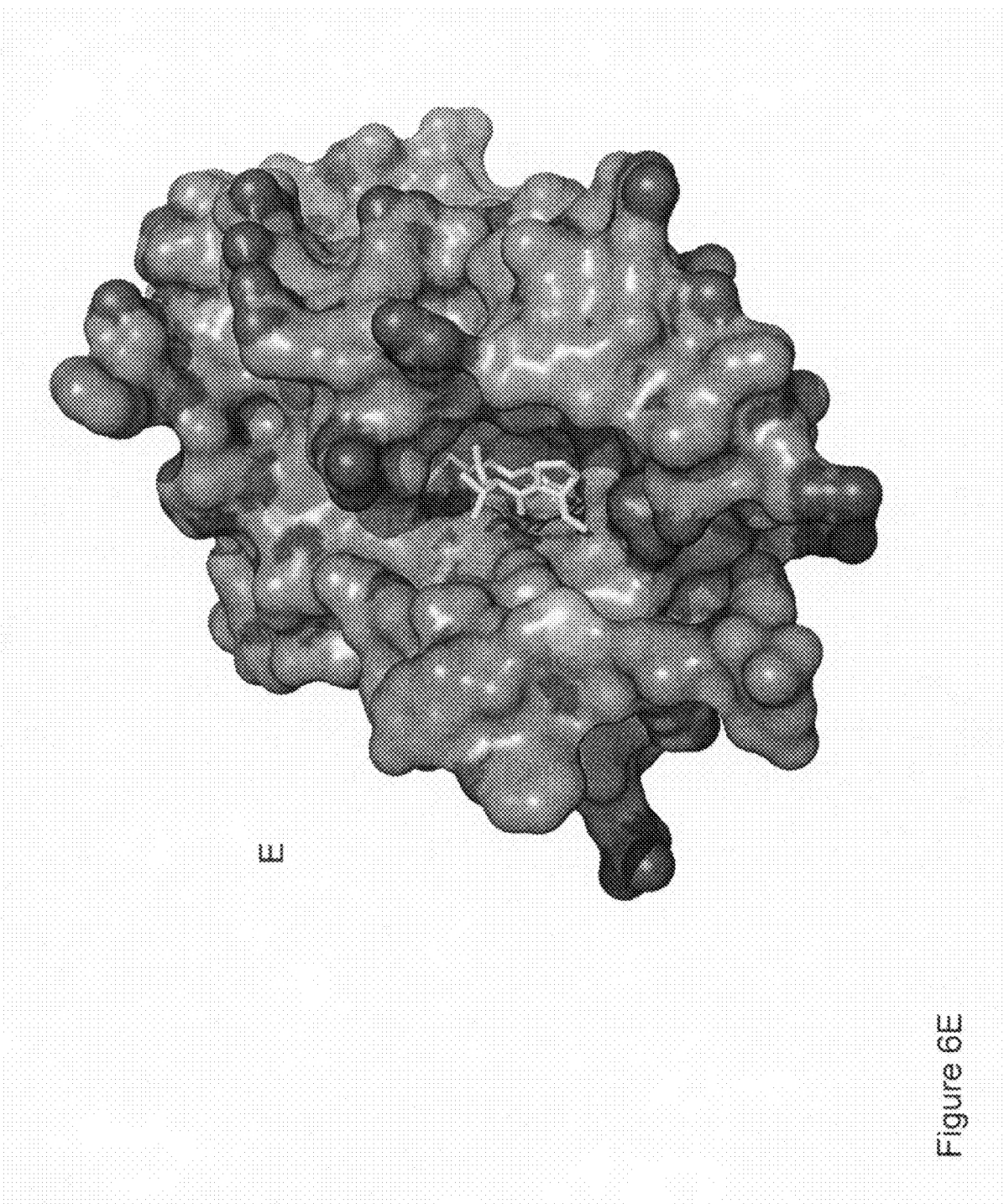
FIG. 6E. Model of the HsPDF structure in complex with the antibiotic inhibitor actinonin, in yellow.

Actinonin (FIG. 6A) binds PDFs due to its peptidomimetic nature and inhibits their activity through chelation and disruption of the metal dependent catalysis. In the absence of a non-hydrolizable substrate of HsPDF, we solved the structure of Δ63HsPDF in complex with actinonin by soaking Δ63HsPDF crystals in a solution of this inhibitor. The main chain backbones of the native and actinonin bound Δ63HsPDF are practically indistinguishable when superimposed. In the presence of actinonin, the metal is still coordinated by the C114, H156, and H160 residues, however there are two additional ligands, the oxygen atoms in the hydroxamic acid moiety of actinonin. Although the spatial arrangement of residues involved in the metal coordination does not change upon actinonin binding, shifts occur in catalytically important residues. There is a minor rearrangement in the position of carbonyl in G113, and the E115 side chain, the last of which disrupts the salt bridge with R48, resulting in a change in the conformation of the R48 side chain (FIG. 6B). A similar side chain orientation change is observed for E112. Interestingly, significant side chain orientation changes are observed in the actinonin bound Δ63HsPDF alpha helical region containing helices 2 and 3, $R^{75}ECPPRQRALRQ^{86}$, with the most striking conformational differences in residues R75, E76, R80, Q81, R82, L84, and R85 (FIG. 6C). A noteworthy change is that of the I153 side chain, which is pushed away from its position in the native structure to allow for the hydrophobic side chain in actinonin to position itself.

Actinonin fits in the Δ63HsPDF active site in a linear conformation, with its backbone kept in place through a series of hydrogen bonds with main chain atoms in Δ63HsPDF and hydrophobic interaction (FIG. 6D). The N atom in the hydroxamic acid moiety of actinonin, N9, hydrogen bonds to carbonyl oxygen of E157. The main chain N atom of V51 also hydrogen bonds to the carbonyl oxygen, O12, in actinonin. G113 carbonyl forms a hydrogen bond to the actinonin amide nitrogen, N11, and the same residue's main chain nitrogen hydrogen bonds to the carbonyl oxygen, O20, of the valine residue in actinonin. V51, I153 and R152 make up a hydrophobic environment, with which the aliphatic pentyl chain of actinonin interacts. The floor of the HsPDF active site, where the metal lies and where the hydroxamic acid chain of actinonin fits, is hydrophilic, with N57, and S54 at the base of the floor and C114, E157, and the two H156 and H160 making up the sides of the cavity. Other residues that define this depression are L53 and E115.

Figure 7A:
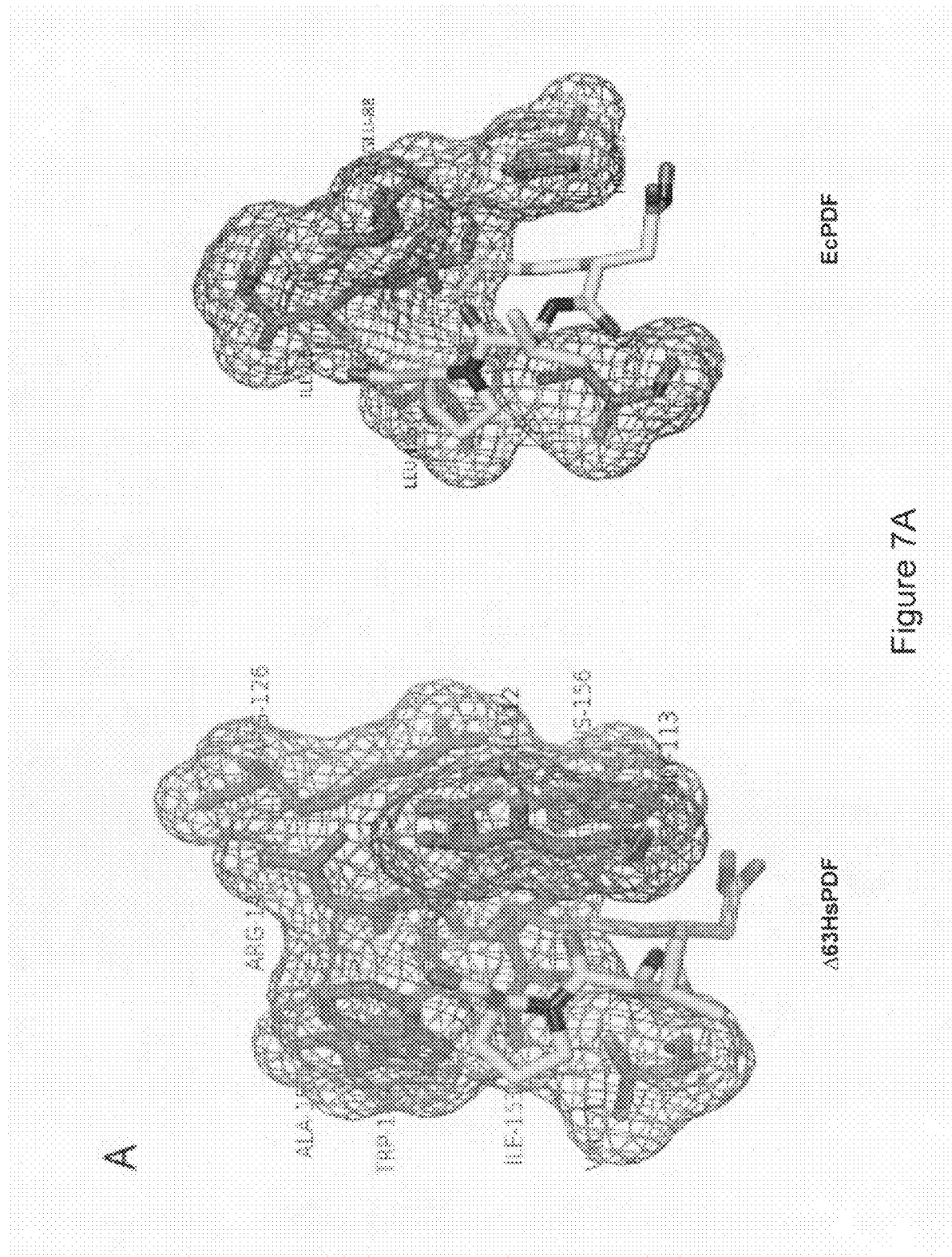
FIG. 7A. The substrate binding pockets of Δ63HsPDF differ from that of EcPDF. The S1' binding pocket in Δ63HsPDF is narrower than that of EcPDF. The left panel shows the Δ63HsPDF S1' pocket with the protein residues in gray, and the actinonin molecule in yellow. The right panel shows the same pocket for EcPDF (1G2A), cyan.

The aliphatic chain in the actinonin (FIG. 6A, atoms 1-5) peptidomimetic resembles the methionine side chain present in N-formylated nascent peptides. The S1' binding pocket where the hydrophobic chain fits is defined by residues E112, W149, R152, and I153. This cleft is narrower in HsPDF than in EcPDF due to the presence of W149 and R152 instead of L125 and I128 in EcPDF, respectively (FIG. 7A). R152 contacts the hydrophobic actinonin side chain, similar to EcPDF I128, however it pushes actinonin's C3 away due to its bigger size compared to Ile. Other than S1', there are no other well-defined pockets that could potentially accommodate the side chains of peptide substrates. Analogous to EcPDF, in Δ63HsPDF the valine side chain of actinonin, C17 and C27 face the edge of a depression delineated by residues $G^{113}CE^{115}$. The floor and ceiling of this cavity are further delineated by V117, G119, and the backbone of F120.

Figure 7B:
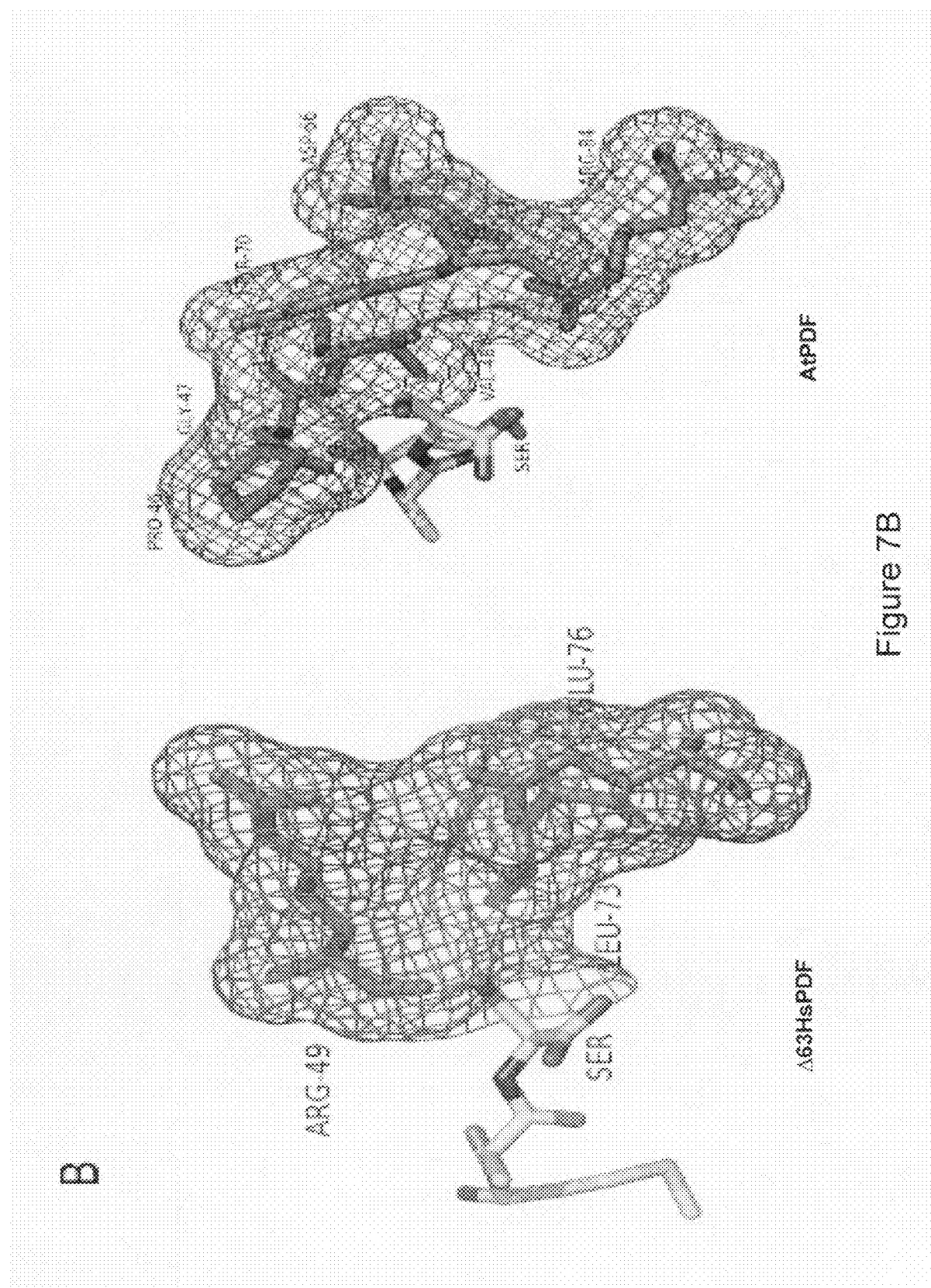
FIG. 7B. The substrate binding pockets of Δ63HsPDF differ from that of AtPDF. Δ63HsPDF has no well-defined S3' pocket. AtPDF has an S3' pocket formed by the residues shown as a mesh, where the side chain of the peptide methionine-alanine-serine (MAS), yellow, fits, (PDB 1ZY1) left panel. However Δ63HsPDF, has no S3' pocket, right panel. The MAS product was modeled from that of AtPDF (PDB 1ZY1)

Comparison of Δ63HsPDF with AtPDF in complex with the catalysis reaction product MAS (Protein data bank 1ZY1), highlights differences in the putative substrate binding site between these two eukaryotic PDFs. The architecture of the metal binding site and S1' pocket, are conserved between HsPDF and AtPDF. The S3' pocket, which accommodates the side chain of the amino acid residue in the third position of the peptide substrate, is defined in AtPDF by residues P46, V48, D66, and Y70, AtPDF numbering. However there is no well defined S3' pocket in Δ63HsPDF due to the lack of sequence conservation between the two PDFs at the respective positions in HsPDF. Specifically, the presence of R49 in Δ63HsPDF instead of P46, and L73 rather than Y70 in AtPDF make this area in Δ63HsPDF less concave (FIG. 7B). There is, however, a hydrophobic depression made by residues V51, L69, C77, Q81, M87, and F90. Some of the equivalent residues have been previously described as taking part of the AtPDF S3', nevertheless it is clear that the residues mentioned in Δ63HsPDF create a different cavity than what would be considered as S3'.

Despite the surprising presence of two tetrahedral molecules at the active site, one of which coordinates to $Co^{2+}$ instead of the expected water molecule, the presence and topology of the amino-acid residues involved in the reaction mechanism and metal coordination are conserved, which suggest that the mechanism of catalysis of Δ63HsPDF is also conserved. The presence of such presumed phosphate molecules at the active site might be an artifact from the purification and crystallization process. Since Δ63HsPDF was confirmed to be catalytically active up to its crystallization, the presence of the catalytic water molecules described previously cannot be excluded when the protein is in solution.

Another unexpected finding was the crystallization of Δ63HsPDF as a dimer. Two other PDF structures have been described as dimers from x-ray crystallography studies, *L. interrogans* (Zhou et al., *J Mol Biol* (2004) 339:207-215) and *A. thaliana* (Fieulain et al. (2005) supra).

Δ63HsPDF shares the common fold observed previously for other PDFs. Δ63HsPDF resembles the *A. thaliana* PDF, both being type 1A PDFs, albeit with topological differences in their C-terminus. The Δ63HsPDF structure differs from those of bacterial types 1B and 2 mostly in the topology of the C-terminus and in the presence of the loop containing alpha helices 2 and 3 in Δ63HsPDF. The characteristic conformation of the C-terminus and the presence of the alpha helices mentioned in Δ63HsPDF, together with particular residues in the metal binding loop that face the C-terminus, impact the shape and hydrophobic properties at the active site opening in a way that distinguish Δ63HsPDF from those of other organisms. The nature of the amino-acids making up this substrate binding site entrance, as well as the topology of the C-terminus are potential determinants of Δ63HsPDF inhibitor binding selectivity. The characteristic shape of the active site opening of Δ63HsPDF could enable HsPDF-inhibitor interactions that otherwise would not occur with PDFs from other organisms that lack a similar C-terminal conformation or alpha helices 2 and 3. It is important to notice the significant differences between the architecture of the Δ63HsPDF and AtPDF active site entrances, particularly since AtPDF has been proposed as a surrogate of HsPDF in the design of more specific antibacterials.

Despite the similarity of the Δ63HsPDF backbone to those of other organisms, at the amino-acid level, Δ63HsPDF differs at key positions that influence features relevant to substrate binding or catalysis. Examples are the residues that constitute the putative substrate binding S1' pocket of Δ63HsPDF. Although conserved among PDFs, the S1' pocket in Δ63HsPDF is narrower. This characteristic feature of type 1A PDFs has already been exploited for the design of bacterial PDF inhibitors (Boularot et al., *J Med Chem* (2007) 50:10-20). On the other hand, there are no other determinants of binding specificity analogous to the S3' pocket described for AtPDF. There is, however, a hydrophobic depression at the base of the entrance to the active site cavity (residues V51, L69, C77, Q81, M87, and F90), which could be taken advantage of for structure based design of inhibitors (See preliminary data attached).

The effect on catalysis of amino-acid residues that are conserved among PDF family members, but which differ in HsPDF, is uncertain; these changes include the substitution of G for C50 in the GXGXAAXQ (SEQ ID NO: 15) conserved element and the substitution of X, a hydrophobic amino-acid, for E115 in the ECGXS (SEQ ID NO: 16) sequence. The equivalent position to HsPDF's C50 in *E. coli*, L91, participates in the mechanism of reaction and the presence of L rather than C together with G rather than E115 are necessary for an increase in the catalytic efficiency, $k_{cat}/K_m$, of HsPDF (Serero et al. (2003) supra). The contribution of C50 to catalysis is not evident from the HsPDF structure where its side chain faces away from the active site core towards the hydrophobic patch formed by L41, V44, M45, and L53. The conservation of C50 among mammals, however, highlights the importance of this residue for catalysis. The salt bridge between E115 and R48 could explain the slower kinetics of HsPDF compared to other PDFs. The structure of A63HsPDF in complex with actinonin suggests that a rearrangement of the E115 side chain is necessary for catalysis. The energetic cost of breaking the hydrogen bonding and electrostatic interaction with R48 might constitute a negative energetic contribution to catalysis that is not present in other PDFs where no hydrogen bonding or electrostatic interactions occur between the residues at these positions. Conversely, the possibility of other factors impacting the catalytic properties of HsPDF, such as mitochondrial environment, protein modulators, or amino terminal truncation of the studied HsPDF, cannot be excluded.

The contribution of this study towards understanding the structural basis for inhibition of HsPDF in a species specific way enables further drug development for cancer treatment as well as aid in the design of more specific antibacterials. The effects of HsPDF inhibition, mitochondrial membrane depolarization, ATP depletion (Lee et al., (2004) supra) and apoptosis (Grujic et al., *Cancer Lett* (2005) 223:211-218) suggest that inhibition of HsPDF function affects the energetic balance of the cell. Targeting of HsPDF is a viable anti-cancer approach that may take advantage of the altered bioenergetics in cancer cells.

Appendix A

Table 1, pp 50-175

TABLE 1

| Atom | Atom Type | Residue | # | X | Y | Z | OCC | B |
|---|---|---|---|---|---|---|---|---|
| 1 | CB | HIS | 3 | 34.651 | 34.279 | 27.703 | 1 | 44.66 |
| 2 | CG | HIS | 3 | 33.505 | 33.625 | 28.408 | 1 | 45.84 |
| 3 | CD2 | HIS | 3 | 32.304 | 33.198 | 27.951 | 1 | 45.92 |
| 4 | ND1 | HIS | 3 | 33.529 | 33.333 | 29.755 | 1 | 46.57 |
| 5 | CE1 | HIS | 3 | 32.392 | 32.753 | 30.097 | 1 | 46.49 |
| 6 | NE2 | HIS | 3 | 31.631 | 32.66 | 29.021 | 1 | 46.69 |
| 7 | C | HIS | 3 | 35.77 | 32.124 | 27.098 | 1 | 43.8 |
| 8 | O | HIS | 3 | 35.878 | 32.008 | 25.876 | 1 | 44 |
| 9 | N | HIS | 3 | 37.052 | 34.245 | 27.108 | 1 | 44.38 |
| 10 | CA | HIS | 3 | 35.957 | 33.482 | 27.772 | 1 | 44.21 |
| 11 | N | MET | 4 | 35.495 | 31.099 | 27.888 | 1 | 43.04 |
| 12 | CA | MET | 4 | 35.296 | 29.754 | 27.367 | 1 | 42.28 |
| 13 | CB | MET | 4 | 36.471 | 28.847 | 27.74 | 1 | 43.7 |
| 14 | CG | MET | 4 | 37.784 | 29.221 | 27.08 | 1 | 45.39 |
| 15 | SD | MET | 4 | 39.056 | 27.965 | 27.323 | 1 | 50.76 |
| 16 | CE | MET | 4 | 38.793 | 26.928 | 25.881 | 1 | 46.87 |
| 17 | C | MET | 4 | 34.008 | 29.126 | 27.878 | 1 | 40.41 |
| 18 | O | MET | 4 | 33.417 | 29.589 | 28.855 | 1 | 40.76 |
| 19 | N | SER | 5 | 33.581 | 28.064 | 27.205 | 1 | 37.92 |
| 20 | CA | SER | 5 | 32.372 | 27.344 | 27.576 | 1 | 35.08 |
| 21 | CB | SER | 5 | 31.151 | 27.991 | 26.931 | 1 | 35.85 |
| 22 | OG | SER | 5 | 31.301 | 28.044 | 25.527 | 1 | 38.33 |
| 23 | C | SER | 5 | 32.502 | 25.905 | 27.102 | 1 | 32.6 |
| 24 | O | SER | 5 | 33.553 | 25.502 | 26.604 | 1 | 33.91 |
| 25 | N | PHE | 6 | 31.434 | 25.131 | 27.251 | 1 | 29.45 |
| 26 | CA | PHE | 6 | 31.463 | 23.737 | 26.837 | 1 | 25.64 |
| 27 | CB | PHE | 6 | 31.031 | 22.818 | 27.987 | 1 | 26.29 |
| 28 | CG | PHE | 6 | 31.953 | 22.841 | 29.17 | 1 | 26.07 |
| 29 | CD1 | PHE | 6 | 31.963 | 23.927 | 30.041 | 1 | 26.8 |
| 30 | CD2 | PHE | 6 | 32.809 | 21.772 | 29.419 | 1 | 26.32 |
| 31 | CE1 | PHE | 6 | 32.812 | 23.946 | 31.145 | 1 | 25.33 |
| 32 | CE2 | PHE | 6 | 33.662 | 21.781 | 30.522 | 1 | 27.4 |
| 33 | CZ | PHE | 6 | 33.662 | 22.87 | 31.386 | 1 | 26.67 |
| 34 | C | PHE | 6 | 30.578 | 23.444 | 25.638 | 1 | 24.62 |
| 35 | O | PHE | 6 | 29.53 | 24.061 | 25.446 | 1 | 24.81 |
| 36 | N | SER | 7 | 31.018 | 22.489 | 24.831 | 1 | 22.3 |
| 37 | CA | SER | 7 | 30.265 | 22.052 | 23.67 | 1 | 20.49 |
| 38 | CB | SER | 7 | 30.941 | 22.492 | 22.37 | 1 | 24.04 |
| 39 | OG | SER | 7 | 30.766 | 23.883 | 22.151 | 1 | 29.29 |
| 40 | C | SER | 7 | 30.262 | 20.541 | 23.755 | 1 | 18.94 |
| 41 | O | SER | 7 | 31.161 | 19.945 | 24.341 | 1 | 17.31 |
| 42 | N | HIS | 8 | 29.241 | 19.913 | 23.198 | 1 | 16.92 |
| 43 | CA | HIS | 8 | 29.204 | 18.469 | 23.234 | 1 | 16.12 |
| 44 | CB | HIS | 8 | 28.41 | 17.974 | 24.449 | 1 | 19.24 |
| 45 | CG | HIS | 8 | 26.934 | 18.199 | 24.35 | 1 | 21.22 |
| 46 | CD2 | HIS | 8 | 26.189 | 19.318 | 24.512 | 1 | 23.17 |
| 47 | ND1 | HIS | 8 | 26.046 | 17.187 | 24.055 | 1 | 23.94 |
| 48 | CE1 | HIS | 8 | 24.818 | 17.672 | 24.04 | 1 | 24.3 |
| 49 | NE2 | HIS | 8 | 24.876 | 18.963 | 24.314 | 1 | 27.33 |
| 50 | C | HIS | 8 | 28.596 | 17.945 | 21.958 | 1 | 14.7 |
| 51 | O | HIS | 8 | 27.74 | 18.59 | 21.347 | 1 | 15.67 |
| 52 | N | VAL | 9 | 29.077 | 16.786 | 21.539 | 1 | 14.66 |
| 53 | CA | VAL | 9 | 28.566 | 16.141 | 20.345 | 1 | 12 |
| 54 | CB | VAL | 9 | 29.665 | 15.331 | 19.632 | 1 | 13.55 |
| 55 | CG1 | VAL | 9 | 29.065 | 14.568 | 18.457 | 1 | 12.12 |
| 56 | CG2 | VAL | 9 | 30.771 | 16.27 | 19.147 | 1 | 13.77 |
| 57 | C | VAL | 9 | 27.463 | 15.204 | 20.816 | 1 | 12.53 |
| 58 | O | VAL | 9 | 27.711 | 14.288 | 21.598 | 1 | 12.8 |
| 59 | N | CYS | 10 | 26.241 | 15.463 | 20.364 | 1 | 12.72 |
| 60 | CA | CYS | 10 | 25.092 | 14.644 | 20.731 | 1 | 12.53 |
| 61 | CB | CYS | 10 | 23.837 | 15.19 | 20.052 | 1 | 12.25 |
| 62 | SG | CYS | 10 | 23.501 | 16.919 | 20.463 | 1 | 16.47 |
| 63 | C | CYS | 10 | 25.329 | 13.197 | 20.304 | 1 | 11.66 |
| 64 | O | CYS | 10 | 25.875 | 12.941 | 19.23 | 1 | 12.12 |
| 65 | N | GLN | 11 | 24.918 | 12.26 | 21.155 | 1 | 10.93 |
| 66 | CA | GLN | 11 | 25.09 | 10.832 | 20.895 | 1 | 11.47 |
| 67 | CB | GLN | 11 | 25.622 | 10.131 | 22.144 | 1 | 11.52 |
| 68 | CG | GLN | 11 | 27.006 | 10.606 | 22.566 | 1 | 11.29 |
| 69 | CD | GLN | 11 | 28.032 | 10.421 | 21.469 | 1 | 11.22 |
| 70 | OE1 | GLN | 11 | 28.315 | 9.296 | 21.052 | 1 | 11.77 |
| 71 | NE2 | GLN | 11 | 28.595 | 11.527 | 20.988 | 1 | 10.67 |
| 72 | C | GLN | 11 | 23.788 | 10.174 | 20.464 | 1 | 10.48 |
| 73 | O | GLN | 11 | 22.701 | 10.64 | 20.816 | 1 | 11.32 |
| 74 | N | VAL | 12 | 23.909 | 9.068 | 19.731 | 1 | 10.35 |
| 75 | CA | VAL | 12 | 22.741 | 8.364 | 19.222 | 1 | 11.57 |
| 76 | CB | VAL | 12 | 23.15 | 7.076 | 18.45 | 1 | 11.6 |
| 77 | CG1 | VAL | 12 | 23.81 | 6.074 | 19.372 | 1 | 12.33 |
| 78 | CG2 | VAL | 12 | 21.925 | 6.488 | 17.758 | 1 | 12.32 |
| 79 | C | VAL | 12 | 21.739 | 8.071 | 20.331 | 1 | 11.7 |
| 80 | O | VAL | 12 | 22.073 | 7.53 | 21.392 | 1 | 12.4 |
| 81 | N | GLY | 13 | 20.5 | 8.464 | 20.065 | 1 | 12.05 |
| 82 | CA | GLY | 13 | 19.426 | 8.341 | 21.029 | 1 | 12.45 |
| 83 | C | GLY | 13 | 18.797 | 9.721 | 21.083 | 1 | 12.9 |
| 84 | O | GLY | 13 | 17.586 | 9.865 | 21.257 | 1 | 13.19 |
| 85 | N | ASP | 14 | 19.633 | 10.748 | 20.937 | 1 | 11.73 |
| 86 | CA | ASP | 14 | 19.152 | 12.127 | 20.922 | 1 | 13.15 |
| 87 | CB | ASP | 14 | 20.328 | 13.106 | 20.881 | 1 | 13.06 |
| 88 | CG | ASP | 14 | 19.895 | 14.551 | 21.043 | 1 | 14.36 |
| 89 | OD1 | ASP | 14 | 18.753 | 14.892 | 20.66 | 1 | 13.24 |
| 90 | OD2 | ASP | 14 | 20.707 | 15.357 | 21.542 | 1 | 13.23 |
| 91 | C | ASP | 14 | 18.337 | 12.259 | 19.634 | 1 | 13.11 |
| 92 | O | ASP | 14 | 18.86 | 12.055 | 18.539 | 1 | 13.26 |
| 93 | N | PRO | 15 | 17.046 | 12.609 | 19.746 | 1 | 13.41 |
| 94 | CD | PRO | 15 | 16.277 | 12.94 | 20.958 | 1 | 14.47 |
| 95 | CA | PRO | 15 | 16.213 | 12.743 | 18.547 | 1 | 15.13 |
| 96 | CB | PRO | 15 | 14.829 | 13.055 | 19.119 | 1 | 15.95 |
| 97 | CG | PRO | 15 | 15.138 | 13.766 | 20.392 | 1 | 15.77 |
| 98 | C | PRO | 15 | 16.673 | 13.769 | 17.515 | 1 | 15.44 |
| 99 | O | PRO | 15 | 16.293 | 13.683 | 16.342 | 1 | 15.3 |
| 100 | N | VAL | 16 | 17.493 | 14.731 | 17.933 | 1 | 14.41 |

TABLE 1-continued

| Atom | Atom Type | Residue | # | X | Y | Z | OCC | B |
|---|---|---|---|---|---|---|---|---|
| 101 | CA | VAL | 16 | 17.976 | 15.748 | 17.001 | 1 | 14.74 |
| 102 | CB | VAL | 16 | 18.85 | 16.811 | 17.72 | 1 | 15.77 |
| 103 | CG1 | VAL | 16 | 20.206 | 16.223 | 18.097 | 1 | 16.77 |
| 104 | CG2 | VAL | 16 | 19.027 | 18.037 | 16.82 | 1 | 16.91 |
| 105 | C | VAL | 16 | 18.789 | 15.113 | 15.866 | 1 | 13.44 |
| 106 | O | VAL | 16 | 18.87 | 15.656 | 14.764 | 1 | 15.18 |
| 107 | N | LEU | 17 | 19.374 | 13.952 | 16.135 | 1 | 12.59 |
| 108 | CA | LEU | 17 | 20.184 | 13.252 | 15.145 | 1 | 12.27 |
| 109 | CB | LEU | 17 | 21.106 | 12.251 | 15.849 | 1 | 12.23 |
| 110 | CG | LEU | 17 | 22.153 | 12.859 | 16.786 | 1 | 11.83 |
| 111 | CD1 | LEU | 17 | 22.878 | 11.745 | 17.533 | 1 | 11.44 |
| 112 | CD2 | LEU | 17 | 23.139 | 13.698 | 15.981 | 1 | 11.85 |
| 113 | C | LEU | 17 | 19.364 | 12.52 | 14.085 | 1 | 11.68 |
| 114 | O | LEU | 17 | 19.889 | 12.152 | 13.03 | 1 | 11.96 |
| 115 | N | ARG | 18 | 18.077 | 12.323 | 14.358 | 1 | 13.11 |
| 116 | CA | ARG | 18 | 17.208 | 11.604 | 13.433 | 1 | 12.8 |
| 117 | CB | ARG | 18 | 16.495 | 10.472 | 14.175 | 1 | 13.28 |
| 118 | CG | ARG | 18 | 17.138 | 9.098 | 13.999 | 1 | 13.09 |
| 119 | CD | ARG | 18 | 18.625 | 9.084 | 14.344 | 1 | 12.41 |
| 120 | NE | ARG | 18 | 19.139 | 7.714 | 14.343 | 1 | 12.88 |
| 121 | CZ | ARG | 18 | 19.43 | 7.011 | 13.249 | 1 | 14.63 |
| 122 | NH1 | ARG | 18 | 19.274 | 7.542 | 12.041 | 1 | 12.96 |
| 123 | NH2 | ARG | 18 | 19.859 | 5.759 | 13.364 | 1 | 13.8 |
| 124 | C | ARG | 18 | 16.182 | 12.465 | 12.71 | 1 | 14.92 |
| 125 | O | ARG | 18 | 15.442 | 11.969 | 11.862 | 1 | 15.05 |
| 126 | N | GLY | 19 | 16.124 | 13.746 | 13.051 | 1 | 15.84 |
| 127 | CA | GLY | 19 | 15.182 | 14.624 | 12.384 | 1 | 17.25 |
| 128 | C | GLY | 19 | 15.783 | 15.145 | 11.093 | 1 | 17.63 |
| 129 | O | GLY | 19 | 16.961 | 14.919 | 10.816 | 1 | 16.23 |
| 130 | N | VAL | 20 | 14.974 | 15.821 | 10.284 | 1 | 17.66 |
| 131 | CA | VAL | 20 | 15.462 | 16.401 | 9.039 | 1 | 17.27 |
| 132 | CB | VAL | 20 | 14.411 | 16.308 | 7.907 | 1 | 18.79 |
| 133 | CG1 | VAL | 20 | 14.928 | 17.019 | 6.664 | 1 | 19.6 |
| 134 | CG2 | VAL | 20 | 14.108 | 14.85 | 7.589 | 1 | 19.06 |
| 135 | C | VAL | 20 | 15.73 | 17.868 | 9.359 | 1 | 17.33 |
| 136 | O | VAL | 20 | 14.802 | 18.626 | 9.64 | 1 | 17.95 |
| 137 | N | ALA | 21 | 17 | 18.256 | 9.335 | 1 | 15.79 |
| 138 | CA | ALA | 21 | 17.393 | 19.626 | 9.65 | 1 | 16.67 |
| 139 | CB | ALA | 21 | 18.898 | 19.793 | 9.47 | 1 | 16.84 |
| 140 | C | ALA | 21 | 16.654 | 20.651 | 8.801 | 1 | 16.21 |
| 141 | O | ALA | 21 | 16.451 | 20.452 | 7.604 | 1 | 16.96 |
| 142 | N | ALA | 22 | 16.256 | 21.748 | 9.434 | 1 | 17.34 |
| 143 | CA | ALA | 22 | 15.541 | 22.812 | 8.742 | 1 | 18.79 |
| 144 | CB | ALA | 22 | 14.732 | 23.623 | 9.736 | 1 | 19.23 |
| 145 | C | ALA | 22 | 16.535 | 23.713 | 8.028 | 1 | 18.43 |
| 146 | O | ALA | 22 | 17.672 | 23.871 | 8.469 | 1 | 17.26 |
| 147 | N | PRO | 23 | 16.119 | 24.319 | 6.909 | 1 | 19.24 |
| 148 | CD | PRO | 23 | 14.851 | 24.132 | 6.186 | 1 | 20.43 |
| 149 | CA | PRO | 23 | 17.019 | 25.206 | 6.169 | 1 | 19.43 |
| 150 | CB | PRO | 23 | 16.222 | 25.538 | 4.906 | 1 | 21.01 |
| 151 | CG | PRO | 23 | 15.271 | 24.382 | 4.767 | 1 | 23.43 |
| 152 | C | PRO | 23 | 17.315 | 26.465 | 6.979 | 1 | 19.15 |
| 153 | O | PRO | 23 | 16.539 | 26.842 | 7.857 | 1 | 20.35 |
| 154 | N | VAL | 24 | 18.445 | 27.102 | 6.692 | 1 | 20.11 |
| 155 | CA | VAL | 24 | 18.8 | 28.348 | 7.36 | 1 | 21.57 |
| 156 | CB | VAL | 24 | 20.323 | 28.601 | 7.312 | 1 | 21.25 |
| 157 | CG1 | VAL | 24 | 20.64 | 30.007 | 7.812 | 1 | 20.66 |
| 158 | CG2 | VAL | 24 | 21.039 | 27.568 | 8.17 | 1 | 19.29 |
| 159 | C | VAL | 24 | 18.074 | 29.431 | 6.565 | 1 | 22.94 |
| 160 | O | VAL | 24 | 18.204 | 29.497 | 5.342 | 1 | 23.92 |
| 161 | N | GLU | 25 | 17.294 | 30.259 | 7.252 | 1 | 24.74 |
| 162 | CA | GLU | 25 | 16.539 | 31.32 | 6.594 | 1 | 26.33 |
| 163 | CB | GLU | 25 | 15.569 | 31.968 | 7.585 | 1 | 29.92 |
| 164 | CG | GLU | 25 | 14.456 | 31.042 | 8.052 | 1 | 34.2 |
| 165 | CD | GLU | 25 | 13.599 | 30.543 | 6.902 | 1 | 36.81 |
| 166 | OE1 | GLU | 25 | 13.038 | 31.384 | 6.169 | 1 | 40.37 |
| 167 | OE2 | GLU | 25 | 13.485 | 29.311 | 6.731 | 1 | 39.41 |
| 168 | C | GLU | 25 | 17.439 | 32.385 | 5.982 | 1 | 26.39 |
| 169 | O | GLU | 25 | 18.497 | 32.709 | 6.519 | 1 | 24.83 |
| 170 | N | ARG | 26 | 17.002 | 32.929 | 4.851 | 1 | 26.83 |
| 171 | CA | ARG | 26 | 17.756 | 33.952 | 4.142 | 1 | 27.56 |
| 172 | CB | ARG | 26 | 16.923 | 34.481 | 2.972 | 1 | 30.31 |
| 173 | CG | ARG | 26 | 17.74 | 35.037 | 1.828 | 1 | 34.84 |
| 174 | CD | ARG | 26 | 16.843 | 35.477 | 0.682 | 1 | 37.28 |
| 175 | NE | ARG | 26 | 17.605 | 35.747 | −0.534 | 1 | 40.57 |
| 176 | CZ | ARG | 26 | 18.585 | 36.641 | −0.622 | 1 | 42.04 |
| 177 | NH1 | ARG | 26 | 18.93 | 37.363 | 0.438 | 1 | 42.53 |
| 178 | NH2 | ARG | 26 | 19.221 | 36.811 | −1.774 | 1 | 42.48 |
| 179 | C | ARG | 26 | 18.13 | 35.101 | 5.077 | 1 | 26.61 |
| 180 | O | ARG | 26 | 19.223 | 35.659 | 4.983 | 1 | 25.2 |
| 181 | N | ALA | 27 | 17.221 | 35.441 | 5.986 | 1 | 26.17 |
| 182 | CA | ALA | 27 | 17.445 | 36.528 | 6.934 | 1 | 25.93 |
| 183 | CB | ALA | 27 | 16.158 | 36.825 | 7.696 | 1 | 26.46 |
| 184 | C | ALA | 27 | 18.578 | 36.246 | 7.918 | 1 | 26.3 |
| 185 | O | ALA | 27 | 19.098 | 37.166 | 8.549 | 1 | 25.44 |
| 186 | N | GLN | 28 | 18.955 | 34.978 | 8.055 | 1 | 24.46 |
| 187 | CA | GLN | 28 | 20.029 | 34.6 | 8.969 | 1 | 24.6 |
| 188 | CB | GLN | 28 | 19.735 | 33.233 | 9.593 | 1 | 26.98 |
| 189 | CG | GLN | 28 | 18.598 | 33.246 | 10.598 | 1 | 31.69 |
| 190 | CD | GLN | 28 | 18.904 | 34.117 | 11.801 | 1 | 36.01 |
| 191 | OE1 | GLN | 28 | 19.105 | 35.325 | 11.674 | 1 | 40.01 |
| 192 | NE2 | GLN | 28 | 18.943 | 33.505 | 12.979 | 1 | 39.16 |
| 193 | C | GLN | 28 | 21.402 | 34.565 | 8.308 | 1 | 22.44 |
| 194 | O | GLN | 28 | 22.427 | 34.562 | 8.991 | 1 | 21.35 |
| 195 | N | LEU | 29 | 21.428 | 34.534 | 6.98 | 1 | 20.54 |
| 196 | CA | LEU | 29 | 22.697 | 34.491 | 6.264 | 1 | 20.37 |
| 197 | CB | LEU | 29 | 22.451 | 34.426 | 4.756 | 1 | 20.57 |
| 198 | CG | LEU | 29 | 21.713 | 33.176 | 4.264 | 1 | 21.79 |
| 199 | CD1 | LEU | 29 | 21.412 | 33.316 | 2.78 | 1 | 21.93 |
| 200 | CD2 | LEU | 29 | 22.56 | 31.933 | 4.528 | 1 | 22.14 |
| 201 | C | LEU | 29 | 23.558 | 35.704 | 6.604 | 1 | 20.03 |
| 202 | O | LEU | 29 | 23.063 | 36.834 | 6.672 | 1 | 19.65 |
| 203 | N | GLY | 30 | 24.847 | 35.45 | 6.821 | 1 | 19.41 |
| 204 | CA | GLY | 30 | 25.784 | 36.506 | 7.159 | 1 | 21.55 |
| 205 | C | GLY | 30 | 25.635 | 37.027 | 8.578 | 1 | 21.05 |
| 206 | O | GLY | 30 | 26.443 | 37.84 | 9.029 | 1 | 21.45 |
| 207 | N | GLY | 31 | 24.61 | 36.551 | 9.281 | 1 | 21.03 |
| 208 | CA | GLY | 31 | 24.352 | 36.996 | 10.642 | 1 | 21.31 |
| 209 | C | GLY | 31 | 25.273 | 36.462 | 11.726 | 1 | 22.88 |
| 210 | O | GLY | 31 | 26.002 | 35.495 | 11.51 | 1 | 21.2 |
| 211 | N | PRO | 32 | 25.255 | 37.086 | 12.917 | 1 | 23.52 |
| 212 | CD | PRO | 32 | 24.513 | 38.332 | 13.179 | 1 | 24.98 |
| 213 | CA | PRO | 32 | 26.07 | 36.722 | 14.082 | 1 | 23.93 |
| 214 | CB | PRO | 32 | 25.727 | 37.815 | 15.097 | 1 | 24.63 |
| 215 | CG | PRO | 32 | 25.362 | 38.981 | 14.235 | 1 | 25.87 |
| 216 | C | PRO | 32 | 25.783 | 35.328 | 14.635 | 1 | 23.7 |
| 217 | O | PRO | 32 | 26.701 | 34.606 | 15.025 | 1 | 24.03 |
| 218 | N | GLU | 33 | 24.508 | 34.957 | 14.682 | 1 | 23.79 |
| 219 | CA | GLU | 33 | 24.132 | 33.648 | 15.204 | 1 | 25.01 |
| 220 | CB | GLU | 33 | 22.611 | 33.526 | 15.29 | 1 | 27.89 |
| 221 | CG | GLU | 33 | 22.14 | 32.29 | 16.037 | 1 | 34.24 |
| 222 | CD | GLU | 33 | 20.633 | 32.238 | 16.186 | 1 | 38.58 |
| 223 | OE1 | GLU | 33 | 20.054 | 33.208 | 16.723 | 1 | 40.9 |
| 224 | OE2 | GLU | 33 | 20.028 | 31.228 | 15.77 | 1 | 42.19 |
| 225 | C | GLU | 33 | 24.696 | 32.527 | 14.338 | 1 | 23.51 |
| 226 | O | GLU | 33 | 25.217 | 31.537 | 14.854 | 1 | 21.6 |
| 227 | N | LEU | 34 | 24.592 | 32.681 | 13.022 | 1 | 22.69 |
| 228 | CA | LEU | 34 | 25.116 | 31.676 | 12.108 | 1 | 22.14 |
| 229 | CB | LEU | 34 | 24.714 | 32 | 10.664 | 1 | 21.3 |
| 230 | CG | LEU | 34 | 25.208 | 31.035 | 9.578 | 1 | 20.11 |
| 231 | CD1 | LEU | 34 | 24.794 | 29.604 | 9.92 | 1 | 22.14 |
| 232 | CD2 | LEU | 34 | 24.631 | 31.449 | 8.227 | 1 | 19.71 |
| 233 | C | LEU | 34 | 26.637 | 31.632 | 12.232 | 1 | 22.78 |
| 234 | O | LEU | 34 | 27.248 | 30.565 | 12.13 | 1 | 21.5 |
| 235 | N | GLN | 35 | 27.248 | 32.793 | 12.452 | 1 | 22.32 |
| 236 | CA | GLN | 35 | 28.697 | 32.861 | 12.606 | 1 | 24.24 |
| 237 | CB | GLN | 35 | 29.166 | 34.317 | 12.685 | 1 | 26.17 |
| 238 | CG | GLN | 35 | 29.259 | 35.014 | 11.339 | 1 | 32.65 |
| 239 | CD | GLN | 35 | 29.719 | 36.454 | 11.466 | 1 | 35.68 |
| 240 | OE1 | GLN | 35 | 30.677 | 36.749 | 12.182 | 1 | 39.32 |
| 241 | NE2 | GLN | 35 | 29.044 | 37.358 | 10.766 | 1 | 37.31 |
| 242 | C | GLN | 35 | 29.142 | 32.12 | 13.86 | 1 | 22.71 |
| 243 | O | GLN | 35 | 30.159 | 31.425 | 13.851 | 1 | 23.62 |
| 244 | N | ARG | 36 | 28.385 | 32.273 | 14.943 | 1 | 22.92 |
| 245 | CA | ARG | 36 | 28.729 | 31.592 | 16.184 | 1 | 22.57 |
| 246 | CB | ARG | 36 | 27.836 | 32.07 | 17.333 | 1 | 23.67 |
| 247 | CG | ARG | 36 | 28.124 | 33.504 | 17.78 | 1 | 27 |
| 248 | CD | ARG | 36 | 27.517 | 33.793 | 19.146 | 1 | 27.9 |
| 249 | NE | ARG | 36 | 26.058 | 33.818 | 19.119 | 1 | 30.32 |
| 250 | CZ | ARG | 36 | 25.335 | 34.833 | 18.654 | 1 | 31.79 |
| 251 | NH1 | ARG | 36 | 25.934 | 35.916 | 18.175 | 1 | 32.5 |
| 252 | NH2 | ARG | 36 | 24.011 | 34.763 | 18.668 | 1 | 32.3 |

TABLE 1-continued

| Atom | Atom Type | Residue | # | X | Y | Z | OCC | B |
|---|---|---|---|---|---|---|---|---|
| 253 | C | ARG | 36 | 28.587 | 30.085 | 15.995 | 1 | 21.21 |
| 254 | O | ARG | 36 | 29.38 | 29.308 | 16.525 | 1 | 21.15 |
| 255 | N | LEU | 37 | 27.581 | 29.675 | 15.23 | 1 | 20.64 |
| 256 | CA | LEU | 37 | 27.361 | 28.257 | 14.975 | 1 | 20.01 |
| 257 | CB | LEU | 37 | 26.026 | 28.039 | 14.26 | 1 | 20.4 |
| 258 | CG | LEU | 37 | 25.768 | 26.609 | 13.771 | 1 | 19.37 |
| 259 | CD1 | LEU | 37 | 25.834 | 25.632 | 14.942 | 1 | 20.26 |
| 260 | CD2 | LEU | 37 | 24.409 | 26.548 | 13.085 | 1 | 21.47 |
| 261 | C | LEU | 37 | 28.487 | 27.651 | 14.143 | 1 | 19.47 |
| 262 | O | LEU | 37 | 29.015 | 26.593 | 14.487 | 1 | 18.45 |
| 263 | N | THR | 38 | 28.858 | 28.317 | 13.052 | 1 | 18.19 |
| 264 | CA | THR | 38 | 29.925 | 27.811 | 12.194 | 1 | 19.53 |
| 265 | CB | THR | 38 | 30.062 | 28.647 | 10.9 | 1 | 20.84 |
| 266 | OG1 | THR | 38 | 30.407 | 29.997 | 11.229 | 1 | 25.7 |
| 267 | CG2 | THR | 38 | 28.755 | 28.635 | 10.124 | 1 | 20.52 |
| 268 | C | THR | 38 | 31.265 | 27.796 | 12.929 | 1 | 20.25 |
| 269 | O | THR | 38 | 32.076 | 26.889 | 12.743 | 1 | 20.13 |
| 270 | N | GLN | 39 | 31.494 | 28.802 | 13.766 | 1 | 21.29 |
| 271 | CA | GLN | 39 | 32.73 | 28.882 | 14.533 | 1 | 22.41 |
| 272 | CB | GLN | 39 | 32.767 | 30.186 | 15.335 | 1 | 24.93 |
| 273 | CG | GLN | 39 | 33.935 | 30.302 | 16.297 | 1 | 31.36 |
| 274 | CD | GLN | 39 | 33.986 | 31.652 | 16.99 | 1 | 34.86 |
| 275 | OE1 | GLN | 39 | 33.011 | 32.085 | 17.61 | 1 | 38.4 |
| 276 | NE2 | GLN | 39 | 35.127 | 32.324 | 16.89 | 1 | 36.84 |
| 277 | C | GLN | 39 | 32.806 | 27.688 | 15.478 | 1 | 20.93 |
| 278 | O | GLN | 39 | 33.85 | 27.052 | 15.613 | 1 | 21.58 |
| 279 | N | ARG | 40 | 31.683 | 27.388 | 16.118 | 1 | 21.25 |
| 280 | CA | ARG | 40 | 31.593 | 26.273 | 17.056 | 1 | 21.58 |
| 281 | CB | ARG | 40 | 30.194 | 26.222 | 17.666 | 1 | 25.38 |
| 282 | CG | ARG | 40 | 30.155 | 25.724 | 19.093 | 1 | 30.33 |
| 283 | CD | ARG | 40 | 30.839 | 26.722 | 20.012 | 1 | 33.99 |
| 284 | NE | ARG | 40 | 30.288 | 26.685 | 21.362 | 1 | 38.4 |
| 285 | CZ | ARG | 40 | 30.529 | 27.605 | 22.29 | 1 | 40.54 |
| 286 | NH1 | ARG | 40 | 31.315 | 28.64 | 22.016 | 1 | 40.27 |
| 287 | NH2 | ARG | 40 | 29.972 | 27.496 | 23.488 | 1 | 41.93 |
| 288 | C | ARG | 40 | 31.878 | 24.958 | 16.343 | 1 | 19.95 |
| 289 | O | ARG | 40 | 32.636 | 24.124 | 16.838 | 1 | 18.06 |
| 290 | N | LEU | 41 | 31.254 | 24.766 | 15.185 | 1 | 18.99 |
| 291 | CA | LEU | 41 | 31.465 | 23.547 | 14.415 | 1 | 17.8 |
| 292 | CB | LEU | 41 | 30.698 | 23.601 | 13.091 | 1 | 18.17 |
| 293 | CG | LEU | 41 | 29.217 | 23.232 | 13.104 | 1 | 20.4 |
| 294 | CD1 | LEU | 41 | 28.621 | 23.47 | 11.719 | 1 | 18.46 |
| 295 | CD2 | LEU | 41 | 29.062 | 21.773 | 13.508 | 1 | 19.41 |
| 296 | C | LEU | 41 | 32.935 | 23.324 | 14.113 | 1 | 18.53 |
| 297 | O | LEU | 41 | 33.471 | 22.242 | 14.354 | 1 | 18.97 |
| 298 | N | VAL | 42 | 33.586 | 24.349 | 13.571 | 1 | 17.87 |
| 299 | CA | VAL | 42 | 34.994 | 24.235 | 13.229 | 1 | 18.82 |
| 300 | CB | VAL | 42 | 35.496 | 25.5 | 12.5 | 1 | 20.22 |
| 301 | CG1 | VAL | 42 | 36.978 | 25.367 | 12.191 | 1 | 20.67 |
| 302 | CG2 | VAL | 42 | 34.709 | 25.697 | 11.212 | 1 | 21.46 |
| 303 | C | VAL | 42 | 35.857 | 23.973 | 14.459 | 1 | 18.87 |
| 304 | O | VAL | 42 | 36.791 | 23.178 | 14.399 | 1 | 19.47 |
| 305 | N | GLN | 43 | 35.541 | 24.622 | 15.578 | 1 | 19.03 |
| 306 | CA | GLN | 43 | 36.315 | 24.421 | 16.804 | 1 | 20.77 |
| 307 | CB | GLN | 43 | 35.809 | 25.33 | 17.925 | 1 | 23.52 |
| 308 | CG | GLN | 43 | 36.072 | 26.81 | 17.704 | 1 | 31.08 |
| 309 | CD | GLN | 43 | 35.653 | 27.653 | 18.894 | 1 | 35.58 |
| 310 | OE1 | GLN | 43 | 36.182 | 27.498 | 19.997 | 1 | 39.97 |
| 311 | NE2 | GLN | 43 | 34.695 | 28.55 | 18.679 | 1 | 38.7 |
| 312 | C | GLN | 43 | 36.243 | 22.972 | 17.269 | 1 | 20.2 |
| 313 | O | GLN | 43 | 37.259 | 22.367 | 17.6 | 1 | 19.48 |
| 314 | N | VAL | 44 | 35.035 | 22.419 | 17.297 | 1 | 19.11 |
| 315 | CA | VAL | 44 | 34.849 | 21.035 | 17.719 | 1 | 19.36 |
| 316 | CB | VAL | 44 | 33.351 | 20.687 | 17.841 | 1 | 17.54 |
| 317 | CG1 | VAL | 44 | 33.18 | 19.199 | 18.11 | 1 | 20.21 |
| 318 | CG2 | VAL | 44 | 32.721 | 21.505 | 18.956 | 1 | 19.89 |
| 319 | C | VAL | 44 | 35.497 | 20.093 | 16.717 | 1 | 19.28 |
| 320 | O | VAL | 44 | 36.156 | 19.123 | 17.089 | 1 | 19.68 |
| 321 | N | MET | 45 | 35.312 | 20.393 | 15.437 | 1 | 20.43 |
| 322 | CA | MET | 45 | 35.874 | 19.579 | 14.374 | 1 | 21.96 |
| 323 | CB | MET | 45 | 35.47 | 20.182 | 13.023 | 1 | 22.85 |
| 324 | CG | MET | 45 | 35.734 | 19.311 | 11.818 | 1 | 26.97 |
| 325 | SD | MET | 45 | 35.078 | 20.066 | 10.307 | 1 | 28.71 |
| 326 | CE | MET | 45 | 36.268 | 21.368 | 10.033 | 1 | 30.72 |
| 327 | C | MET | 45 | 37.397 | 19.493 | 14.505 | 1 | 22.83 |
| 328 | O | MET | 45 | 37.982 | 18.419 | 14.369 | 1 | 24.26 |
| 329 | N | ARG | 46 | 38.039 | 20.621 | 14.792 | 1 | 22.78 |
| 330 | CA | ARG | 46 | 39.49 | 20.647 | 14.934 | 1 | 23.21 |
| 331 | CB | ARG | 46 | 39.996 | 22.083 | 14.786 | 1 | 24.97 |
| 332 | CG | ARG | 46 | 39.862 | 22.6 | 13.358 | 1 | 25.3 |
| 333 | CD | ARG | 46 | 40.179 | 24.077 | 13.234 | 1 | 27.05 |
| 334 | NE | ARG | 46 | 40.19 | 24.491 | 11.833 | 1 | 27.69 |
| 335 | CZ | ARG | 46 | 40.186 | 25.755 | 11.422 | 1 | 27.44 |
| 336 | NH1 | ARG | 46 | 40.169 | 26.743 | 12.307 | 1 | 27.56 |
| 337 | NH2 | ARG | 46 | 40.2 | 26.03 | 10.125 | 1 | 26.87 |
| 338 | C | ARG | 46 | 39.992 | 20.035 | 16.241 | 1 | 23.54 |
| 339 | O | ARG | 46 | 41.089 | 19.477 | 16.291 | 1 | 24.45 |
| 340 | N | ARG | 47 | 39.195 | 20.124 | 17.298 | 1 | 21.99 |
| 341 | CA | ARG | 47 | 39.613 | 19.556 | 18.573 | 1 | 22.27 |
| 342 | CB | ARG | 47 | 38.801 | 20.16 | 19.72 | 1 | 23.42 |
| 343 | CG | ARG | 47 | 38.96 | 21.669 | 19.81 | 1 | 29.57 |
| 344 | CD | ARG | 47 | 38.775 | 22.191 | 21.218 | 1 | 33.24 |
| 345 | NE | ARG | 47 | 38.964 | 23.639 | 21.266 | 1 | 37.2 |
| 346 | CZ | ARG | 47 | 39.289 | 24.317 | 22.362 | 1 | 39.06 |
| 347 | NH1 | ARG | 47 | 39.465 | 23.678 | 23.51 | 1 | 40.64 |
| 348 | NH2 | ARG | 47 | 39.438 | 25.634 | 22.309 | 1 | 39.49 |
| 349 | C | ARG | 47 | 39.489 | 18.039 | 18.574 | 1 | 21.38 |
| 350 | O | ARG | 47 | 40.323 | 17.343 | 19.151 | 1 | 21.31 |
| 351 | N | ARG | 48 | 38.454 | 17.531 | 17.912 | 1 | 19.76 |
| 352 | CA | ARG | 48 | 38.216 | 16.094 | 17.832 | 1 | 20.22 |
| 353 | CB | ARG | 48 | 36.713 | 15.819 | 17.747 | 1 | 19.71 |
| 354 | CG | ARG | 48 | 35.973 | 16.003 | 19.064 | 1 | 21.09 |
| 355 | CD | ARG | 48 | 36.495 | 15.023 | 20.102 | 1 | 21.68 |
| 356 | NE | ARG | 48 | 36.423 | 13.652 | 19.607 | 1 | 24.04 |
| 357 | CZ | ARG | 48 | 37.392 | 12.753 | 19.742 | 1 | 26.67 |
| 358 | NH1 | ARG | 48 | 38.518 | 13.075 | 20.364 | 1 | 27.46 |
| 359 | NH2 | ARG | 48 | 37.243 | 11.536 | 19.24 | 1 | 27.81 |
| 360 | C | ARG | 48 | 38.921 | 15.477 | 16.633 | 1 | 20.6 |
| 361 | O | ARG | 48 | 38.969 | 14.255 | 16.482 | 1 | 20.87 |
| 362 | N | ARG | 49 | 39.466 | 16.335 | 15.78 | 1 | 20.73 |
| 363 | CA | ARG | 49 | 40.172 | 15.898 | 14.59 | 1 | 21.71 |
| 364 | CB | ARG | 49 | 41.428 | 15.125 | 14.992 | 1 | 24.05 |
| 365 | CG | ARG | 49 | 42.345 | 15.974 | 15.85 | 1 | 28.64 |
| 366 | CD | ARG | 49 | 43.559 | 15.227 | 16.333 | 1 | 32.42 |
| 367 | NE | ARG | 49 | 44.327 | 16.051 | 17.259 | 1 | 35.18 |
| 368 | CZ | ARG | 49 | 45.498 | 15.699 | 17.777 | 1 | 37.56 |
| 369 | NH1 | ARG | 49 | 46.04 | 14.531 | 17.457 | 1 | 38.46 |
| 370 | NH2 | ARG | 49 | 46.124 | 16.514 | 18.616 | 1 | 37.27 |
| 371 | C | ARG | 49 | 39.29 | 15.067 | 13.668 | 1 | 20.96 |
| 372 | O | ARG | 49 | 39.738 | 14.092 | 13.066 | 1 | 20.72 |
| 373 | N | CYS | 50 | 38.02 | 15.447 | 13.579 | 1 | 20.57 |
| 374 | CA | CYS | 50 | 37.104 | 14.762 | 12.684 | 1 | 20.56 |
| 375 | CB | CYS | 50 | 35.709 | 14.618 | 13.313 | 1 | 21.27 |
| 376 | SG | CYS | 50 | 35.001 | 16.086 | 14.072 | 1 | 21.51 |
| 377 | C | CYS | 50 | 37.073 | 15.605 | 11.41 | 1 | 20.95 |
| 378 | O | CYS | 50 | 37.041 | 16.831 | 11.466 | 1 | 22.71 |
| 379 | N | VAL | 51 | 37.118 | 14.931 | 10.27 | 1 | 20.69 |
| 380 | CA | VAL | 51 | 37.143 | 15.576 | 8.961 | 1 | 18.14 |
| 381 | CB | VAL | 51 | 37.4 | 14.515 | 7.869 | 1 | 18.08 |
| 382 | CG1 | VAL | 51 | 37.463 | 15.163 | 6.498 | 1 | 17.71 |
| 383 | CG2 | VAL | 51 | 38.699 | 13.788 | 8.167 | 1 | 19.86 |
| 384 | C | VAL | 51 | 35.886 | 16.375 | 8.619 | 1 | 17.71 |
| 385 | O | VAL | 51 | 35.923 | 17.276 | 7.78 | 1 | 18.86 |
| 386 | N | GLY | 52 | 34.774 | 16.039 | 9.261 | 1 | 15.62 |
| 387 | CA | GLY | 52 | 33.534 | 16.749 | 9.01 | 1 | 14.51 |
| 388 | C | GLY | 52 | 32.66 | 16.763 | 10.247 | 1 | 14.86 |
| 389 | O | GLY | 52 | 32.893 | 15.997 | 11.179 | 1 | 14.46 |
| 390 | N | LEU | 53 | 31.657 | 17.633 | 10.264 | 1 | 13.35 |
| 391 | CA | LEU | 53 | 30.744 | 17.728 | 11.397 | 1 | 13.15 |
| 392 | CB | LEU | 53 | 31.426 | 18.428 | 12.579 | 1 | 11.93 |
| 393 | CG | LEU | 53 | 30.701 | 18.417 | 13.928 | 1 | 12.96 |
| 394 | CD1 | LEU | 53 | 30.563 | 16.978 | 14.419 | 1 | 13.7 |
| 395 | CD2 | LEU | 53 | 31.481 | 19.241 | 14.948 | 1 | 12.88 |
| 396 | C | LEU | 53 | 29.529 | 18.521 | 10.945 | 1 | 12.92 |
| 397 | O | LEU | 53 | 29.648 | 19.406 | 10.099 | 1 | 13.81 |
| 398 | N | SER | 54 | 28.367 | 18.202 | 11.504 | 1 | 12.32 |
| 399 | CA | SER | 54 | 27.129 | 18.88 | 11.136 | 1 | 13.28 |
| 400 | CB | SER | 54 | 26.155 | 17.877 | 10.515 | 1 | 14.13 |
| 401 | OG | SER | 54 | 25.778 | 16.895 | 11.465 | 1 | 15.98 |
| 402 | C | SER | 54 | 26.466 | 19.55 | 12.333 | 1 | 13.07 |
| 403 | O | SER | 54 | 26.662 | 19.14 | 13.48 | 1 | 13.36 |
| 404 | N | ALA | 55 | 25.657 | 20.568 | 12.059 | 1 | 12.29 |

TABLE 1-continued

| Atom | Atom Type | Residue | # | X | Y | Z | OCC | B |
|---|---|---|---|---|---|---|---|---|
| 405 | CA | ALA | 55 | 24.969 | 21.301 | 13.114 | 1 | 12.53 |
| 406 | CB | ALA | 55 | 24.133 | 22.428 | 12.507 | 1 | 13.7 |
| 407 | C | ALA | 55 | 24.102 | 20.423 | 14.019 | 1 | 12.6 |
| 408 | O | ALA | 55 | 24.102 | 20.604 | 15.234 | 1 | 13.07 |
| 409 | N | PRO | 56 | 23.346 | 19.466 | 13.448 | 1 | 12.14 |
| 410 | CD | PRO | 56 | 23.062 | 19.204 | 12.023 | 1 | 13.11 |
| 411 | CA | PRO | 56 | 22.514 | 18.616 | 14.308 | 1 | 11.96 |
| 412 | CB | PRO | 56 | 21.91 | 17.623 | 13.323 | 1 | 13.38 |
| 413 | CG | PRO | 56 | 21.732 | 18.471 | 12.085 | 1 | 13.55 |
| 414 | C | PRO | 56 | 23.331 | 17.92 | 15.398 | 1 | 11.58 |
| 415 | O | PRO | 56 | 22.829 | 17.653 | 16.491 | 1 | 13.76 |
| 416 | N | GLN | 57 | 24.592 | 17.632 | 15.095 | 1 | 11.94 |
| 417 | CA | GLN | 57 | 25.462 | 16.963 | 16.057 | 1 | 12.67 |
| 418 | CB | GLN | 57 | 26.73 | 16.469 | 15.37 | 1 | 12.49 |
| 419 | CG | GLN | 57 | 26.465 | 15.308 | 14.43 | 1 | 13.74 |
| 420 | CD | GLN | 57 | 27.685 | 14.933 | 13.639 | 1 | 14.49 |
| 421 | OE1 | GLN | 57 | 27.966 | 15.52 | 12.594 | 1 | 14.27 |
| 422 | NE2 | GLN | 57 | 28.439 | 13.963 | 14.143 | 1 | 12.27 |
| 423 | C | GLN | 57 | 25.809 | 17.858 | 17.234 | 1 | 13.63 |
| 424 | O | GLN | 57 | 26.25 | 17.374 | 18.276 | 1 | 13.13 |
| 425 | N | LEU | 58 | 25.626 | 19.164 | 17.068 | 1 | 13.84 |
| 426 | CA | LEU | 58 | 25.88 | 20.091 | 18.167 | 1 | 16.33 |
| 427 | CB | LEU | 58 | 26.682 | 21.309 | 17.693 | 1 | 16.77 |
| 428 | CG | LEU | 58 | 28.138 | 21.057 | 17.285 | 1 | 19.09 |
| 429 | CD1 | LEU | 58 | 28.824 | 22.387 | 17.021 | 1 | 21.4 |
| 430 | CD2 | LEU | 58 | 28.869 | 20.302 | 18.388 | 1 | 19.39 |
| 431 | C | LEU | 58 | 24.539 | 20.53 | 18.745 | 1 | 17.69 |
| 432 | O | LEU | 58 | 24.449 | 21.547 | 19.443 | 1 | 21.28 |
| 433 | N | GLY | 59 | 23.498 | 19.756 | 18.439 | 1 | 16.36 |
| 434 | CA | GLY | 59 | 22.163 | 20.037 | 18.941 | 1 | 15.51 |
| 435 | C | GLY | 59 | 21.362 | 21.092 | 18.199 | 1 | 15.81 |
| 436 | O | GLY | 59 | 20.31 | 21.522 | 18.68 | 1 | 16.41 |
| 437 | N | VAL | 60 | 21.845 | 21.509 | 17.035 | 1 | 14.77 |
| 438 | CA | VAL | 60 | 21.161 | 22.532 | 16.245 | 1 | 15.47 |
| 439 | CB | VAL | 60 | 22.132 | 23.674 | 15.891 | 1 | 17.18 |
| 440 | CG1 | VAL | 60 | 21.421 | 24.735 | 15.065 | 1 | 16.99 |
| 441 | CG2 | VAL | 60 | 22.692 | 24.276 | 17.171 | 1 | 17.3 |
| 442 | C | VAL | 60 | 20.595 | 21.919 | 14.968 | 1 | 15.62 |
| 443 | O | VAL | 60 | 21.341 | 21.574 | 14.051 | 1 | 14.48 |
| 444 | N | PRO | 61 | 19.259 | 21.778 | 14.893 | 1 | 17.2 |
| 445 | CD | PRO | 61 | 18.282 | 22.135 | 15.939 | 1 | 18.08 |
| 446 | CA | PRO | 61 | 18.585 | 21.194 | 13.729 | 1 | 17.29 |
| 447 | CB | PRO | 61 | 17.208 | 20.844 | 14.279 | 1 | 18.19 |
| 448 | CG | PRO | 61 | 16.95 | 21.98 | 15.217 | 1 | 18.08 |
| 449 | C | PRO | 61 | 18.513 | 22.108 | 12.512 | 1 | 17.79 |
| 450 | O | PRO | 61 | 17.427 | 22.412 | 12.009 | 1 | 19.03 |
| 451 | N | ARG | 62 | 19.679 | 22.531 | 12.042 | 1 | 15.96 |
| 452 | CA | ARG | 62 | 19.783 | 23.413 | 10.885 | 1 | 16.01 |
| 453 | CB | ARG | 62 | 20.318 | 24.781 | 11.318 | 1 | 18.26 |
| 454 | CG | ARG | 62 | 19.376 | 25.525 | 12.231 | 1 | 21.41 |
| 455 | CD | ARG | 62 | 18.12 | 25.977 | 11.48 | 1 | 27.65 |
| 456 | NE | ARG | 62 | 17.158 | 26.642 | 12.355 | 1 | 30.79 |
| 457 | CZ | ARG | 62 | 16.006 | 27.162 | 11.943 | 1 | 33.73 |
| 458 | NH1 | ARG | 62 | 15.665 | 27.099 | 10.662 | 1 | 34.98 |
| 459 | NH2 | ARG | 62 | 15.189 | 27.738 | 12.815 | 1 | 35.81 |
| 460 | C | ARG | 62 | 20.711 | 22.797 | 9.847 | 1 | 16.34 |
| 461 | O | ARG | 62 | 21.638 | 22.053 | 10.189 | 1 | 14.47 |
| 462 | N | GLN | 63 | 20.467 | 23.121 | 8.58 | 1 | 15.78 |
| 463 | CA | GLN | 63 | 21.263 | 22.586 | 7.483 | 1 | 14.92 |
| 464 | CB | GLN | 63 | 20.465 | 22.662 | 6.174 | 1 | 16.54 |
| 465 | CG | GLN | 63 | 19.144 | 21.91 | 6.246 | 1 | 17.17 |
| 466 | CD | GLN | 63 | 18.327 | 21.994 | 4.966 | 1 | 19.24 |
| 467 | OE1 | GLN | 63 | 17.142 | 21.653 | 4.952 | 1 | 22.41 |
| 468 | NE2 | GLN | 63 | 18.954 | 22.435 | 3.889 | 1 | 16.94 |
| 469 | C | GLN | 63 | 22.599 | 23.298 | 7.329 | 1 | 15.42 |
| 470 | O | GLN | 63 | 22.777 | 24.139 | 6.45 | 1 | 15.55 |
| 471 | N | VAL | 64 | 23.535 | 22.948 | 8.203 | 1 | 13.8 |
| 472 | CA | VAL | 64 | 24.867 | 23.524 | 8.183 | 1 | 12.52 |
| 473 | CB | VAL | 64 | 25.034 | 24.619 | 9.259 | 1 | 14.5 |
| 474 | CG1 | VAL | 64 | 26.402 | 25.267 | 9.129 | 1 | 14.33 |
| 475 | CG2 | VAL | 64 | 23.933 | 25.655 | 9.126 | 1 | 14.34 |
| 476 | C | VAL | 64 | 25.861 | 22.415 | 8.485 | 1 | 14.1 |
| 477 | O | VAL | 64 | 25.651 | 21.615 | 9.402 | 1 | 14.15 |
| 478 | N | LEU | 65 | 26.931 | 22.361 | 7.705 | 1 | 13.48 |
| 479 | CA | LEU | 65 | 27.963 | 21.358 | 7.912 | 1 | 13.74 |
| 480 | CB | LEU | 65 | 27.664 | 20.099 | 7.082 | 1 | 14.38 |
| 481 | CG | LEU | 65 | 27.664 | 20.187 | 5.552 | 1 | 14.82 |
| 482 | CD1 | LEU | 65 | 29.094 | 20.107 | 5.03 | 1 | 17.85 |
| 483 | CD2 | LEU | 65 | 26.838 | 19.04 | 4.977 | 1 | 16.32 |
| 484 | C | LEU | 65 | 29.313 | 21.947 | 7.535 | 1 | 14.78 |
| 485 | O | LEU | 65 | 29.391 | 22.912 | 6.771 | 1 | 15.18 |
| 486 | N | ALA | 66 | 30.373 | 21.374 | 8.092 | 1 | 14.35 |
| 487 | CA | ALA | 66 | 31.726 | 21.832 | 7.816 | 1 | 14.21 |
| 488 | CB | ALA | 66 | 32.288 | 22.564 | 9.024 | 1 | 16.17 |
| 489 | C | ALA | 66 | 32.609 | 20.641 | 7.454 | 1 | 14.82 |
| 490 | O | ALA | 66 | 32.383 | 19.512 | 7.913 | 1 | 14.3 |
| 491 | N | LEU | 67 | 33.619 | 20.906 | 6.635 | 1 | 13.75 |
| 492 | CA | LEU | 67 | 34.537 | 19.877 | 6.161 | 1 | 15.95 |
| 493 | CB | LEU | 67 | 34.123 | 19.438 | 4.755 | 1 | 17.67 |
| 494 | CG | LEU | 67 | 32.658 | 19.042 | 4.566 | 1 | 19.1 |
| 495 | CD1 | LEU | 67 | 32.23 | 19.278 | 3.12 | 1 | 20.84 |
| 496 | CD2 | LEU | 67 | 32.477 | 17.594 | 4.973 | 1 | 20.26 |
| 497 | C | LEU | 67 | 35.95 | 20.438 | 6.091 | 1 | 15.82 |
| 498 | O | LEU | 67 | 36.149 | 21.551 | 5.606 | 1 | 16.25 |
| 499 | N | GLU | 68 | 36.925 | 19.664 | 6.557 | 1 | 14.95 |
| 500 | CA | GLU | 68 | 38.32 | 20.089 | 6.505 | 1 | 16.77 |
| 501 | CB | GLU | 68 | 38.588 | 21.214 | 7.513 | 1 | 18.29 |
| 502 | CG | GLU | 68 | 40.041 | 21.695 | 7.518 | 1 | 20.26 |
| 503 | CD | GLU | 68 | 40.314 | 22.736 | 8.59 | 1 | 23.96 |
| 504 | OE1 | GLU | 68 | 39.95 | 22.496 | 9.761 | 1 | 25.96 |
| 505 | OE2 | GLU | 68 | 40.902 | 23.79 | 8.265 | 1 | 26.06 |
| 506 | C | GLU | 68 | 39.258 | 18.925 | 6.787 | 1 | 18.31 |
| 507 | O | GLU | 68 | 39.064 | 18.175 | 7.746 | 1 | 17.53 |
| 508 | N | LEU | 69 | 40.266 | 18.764 | 5.937 | 1 | 18.09 |
| 509 | CA | LEU | 69 | 41.239 | 17.699 | 6.12 | 1 | 18.82 |
| 510 | CB | LEU | 69 | 41.001 | 16.558 | 5.127 | 1 | 19 |
| 511 | CG | LEU | 69 | 42.021 | 15.414 | 5.18 | 1 | 20.8 |
| 512 | CD1 | LEU | 69 | 42.247 | 14.971 | 6.619 | 1 | 22.34 |
| 513 | CD2 | LEU | 69 | 41.523 | 14.253 | 4.333 | 1 | 23.46 |
| 514 | C | LEU | 69 | 42.646 | 18.253 | 5.95 | 1 | 20.25 |
| 515 | O | LEU | 69 | 43.177 | 18.311 | 4.838 | 1 | 18.31 |
| 516 | N | PRO | 70 | 43.259 | 18.689 | 7.058 | 1 | 21.02 |
| 517 | CD | PRO | 70 | 42.65 | 18.81 | 8.394 | 1 | 22.76 |
| 518 | CA | PRO | 70 | 44.614 | 19.247 | 7.055 | 1 | 23.29 |
| 519 | CB | PRO | 70 | 44.831 | 19.634 | 8.517 | 1 | 22.85 |
| 520 | CG | PRO | 70 | 43.441 | 19.942 | 8.997 | 1 | 22.74 |
| 521 | C | PRO | 70 | 45.623 | 18.21 | 6.583 | 1 | 23.67 |
| 522 | O | PRO | 70 | 45.399 | 17.009 | 6.722 | 1 | 22.28 |
| 523 | N | GLU | 71 | 46.734 | 18.679 | 6.024 | 1 | 24.6 |
| 524 | CA | GLU | 71 | 47.77 | 17.783 | 5.532 | 1 | 26.57 |
| 525 | CB | GLU | 71 | 48.924 | 18.592 | 4.935 | 1 | 29.36 |
| 526 | CG | GLU | 71 | 50.038 | 17.741 | 4.346 | 1 | 35.1 |
| 527 | CD | GLU | 71 | 51.129 | 18.576 | 3.702 | 1 | 39.11 |
| 528 | OE1 | GLU | 71 | 51.766 | 19.381 | 4.417 | 1 | 40.55 |
| 529 | OE2 | GLU | 71 | 51.347 | 18.428 | 2.481 | 1 | 41.3 |
| 530 | C | GLU | 71 | 48.294 | 16.891 | 6.652 | 1 | 25.12 |
| 531 | O | GLU | 71 | 48.538 | 15.703 | 6.445 | 1 | 25.4 |
| 532 | N | ALA | 72 | 48.459 | 17.473 | 7.836 | 1 | 25.67 |
| 533 | CA | ALA | 72 | 48.96 | 16.746 | 8.998 | 1 | 26.32 |
| 534 | CB | ALA | 72 | 49.064 | 17.687 | 10.192 | 1 | 26.85 |
| 535 | C | ALA | 72 | 48.068 | 15.562 | 9.344 | 1 | 26.64 |
| 536 | O | ALA | 72 | 48.533 | 14.424 | 9.435 | 1 | 26.21 |
| 537 | N | LEU | 73 | 46.782 | 15.839 | 9.539 | 1 | 26.93 |
| 538 | CA | LEU | 73 | 45.819 | 14.799 | 9.876 | 1 | 27.25 |
| 539 | CB | LEU | 73 | 44.423 | 15.406 | 10.02 | 1 | 26.81 |
| 540 | CG | LEU | 73 | 43.291 | 14.431 | 10.345 | 1 | 26.78 |
| 541 | CD1 | LEU | 73 | 43.619 | 13.665 | 11.622 | 1 | 26.03 |
| 542 | CD2 | LEU | 73 | 41.991 | 15.202 | 10.496 | 1 | 25.87 |
| 543 | C | LEU | 73 | 45.807 | 13.741 | 8.785 | 1 | 28.11 |
| 544 | O | LEU | 73 | 45.628 | 12.552 | 9.046 | 1 | 29.02 |
| 545 | N | CYS | 74 | 46.005 | 14.193 | 7.555 | 1 | 29.11 |
| 546 | CA | CYS | 74 | 46.021 | 13.312 | 6.403 | 1 | 28.71 |
| 547 | CB | CYS | 74 | 46.022 | 14.157 | 5.13 | 1 | 30.13 |
| 548 | SG | CYS | 74 | 45.543 | 13.271 | 3.653 | 1 | 29.31 |
| 549 | C | CYS | 74 | 47.252 | 12.406 | 6.442 | 1 | 30.81 |
| 550 | O | CYS | 74 | 47.194 | 11.242 | 6.044 | 1 | 29.57 |
| 551 | N | ARG | 75 | 48.365 | 12.944 | 6.932 | 1 | 31.73 |
| 552 | CA | ARG | 75 | 49.602 | 12.177 | 7.017 | 1 | 33.63 |
| 553 | CB | ARG | 75 | 50.806 | 13.118 | 7.114 | 1 | 34.27 |
| 554 | CG | ARG | 75 | 51.048 | 13.939 | 5.861 | 1 | 37.48 |
| 555 | CD | ARG | 75 | 52.342 | 14.729 | 5.966 | 1 | 38.82 |
| 556 | NE | ARG | 75 | 52.624 | 15.479 | 4.745 | 1 | 41.53 |

TABLE 1-continued

| Atom | Atom Type | Residue | # | X | Y | Z | OCC | B |
|---|---|---|---|---|---|---|---|---|
| 557 | CZ | ARG | 75 | 53.728 | 16.192 | 4.543 | 1 | 42.08 |
| 558 | NH1 | ARG | 75 | 54.662 | 16.255 | 5.483 | 1 | 42.88 |
| 559 | NH2 | ARG | 75 | 53.899 | 16.842 | 3.399 | 1 | 43.28 |
| 560 | C | ARG | 75 | 49.607 | 11.209 | 8.197 | 1 | 33.67 |
| 561 | O | ARG | 75 | 50.47 | 10.335 | 8.284 | 1 | 34.88 |
| 562 | N | GLU | 76 | 48.651 | 11.369 | 9.108 | 1 | 33.92 |
| 563 | CA | GLU | 76 | 48.552 | 10.478 | 10.26 | 1 | 34.29 |
| 564 | CB | GLU | 76 | 47.53 | 11.006 | 11.271 | 1 | 35.08 |
| 565 | CG | GLU | 76 | 48.042 | 12.124 | 12.169 | 1 | 35.77 |
| 566 | CD | GLU | 76 | 46.999 | 12.589 | 13.171 | 1 | 36.23 |
| 567 | OE1 | GLU | 76 | 46.306 | 11.726 | 13.75 | 1 | 38.97 |
| 568 | OE2 | GLU | 76 | 46.877 | 13.812 | 13.391 | 1 | 35.59 |
| 569 | C | GLU | 76 | 48.123 | 9.097 | 9.777 | 1 | 34.53 |
| 570 | O | GLU | 76 | 48.219 | 8.112 | 10.506 | 1 | 34.07 |
| 571 | N | CYS | 77 | 47.646 | 9.039 | 8.538 | 1 | 33.96 |
| 572 | CA | CYS | 77 | 47.2 | 7.788 | 7.937 | 1 | 34.63 |
| 573 | CB | CYS | 77 | 45.959 | 8.041 | 7.074 | 1 | 34.89 |
| 574 | SG | CYS | 77 | 45.257 | 6.578 | 6.273 | 1 | 36.32 |
| 575 | C | CYS | 77 | 48.324 | 7.211 | 7.08 | 1 | 34.81 |
| 576 | O | CYS | 77 | 48.882 | 7.904 | 6.23 | 1 | 34.76 |
| 577 | N | PRO | 78 | 48.677 | 5.934 | 7.299 | 1 | 34.89 |
| 578 | CD | PRO | 78 | 48.083 | 4.988 | 8.262 | 1 | 34.79 |
| 579 | CA | PRO | 78 | 49.743 | 5.29 | 6.524 | 1 | 35.51 |
| 580 | CB | PRO | 78 | 49.571 | 3.816 | 6.871 | 1 | 35.55 |
| 581 | CG | PRO | 78 | 49.108 | 3.876 | 8.296 | 1 | 35.88 |
| 582 | C | PRO | 78 | 49.573 | 5.564 | 5.031 | 1 | 35.92 |
| 583 | O | PRO | 78 | 48.458 | 5.542 | 4.513 | 1 | 36.1 |
| 584 | N | PRO | 79 | 50.683 | 5.82 | 4.32 | 1 | 36.07 |
| 585 | CD | PRO | 79 | 52.073 | 5.651 | 4.778 | 1 | 36.95 |
| 586 | CA | PRO | 79 | 50.642 | 6.103 | 2.881 | 1 | 36.05 |
| 587 | CB | PRO | 79 | 52.121 | 6.223 | 2.513 | 1 | 36.46 |
| 588 | CG | PRO | 79 | 52.785 | 5.304 | 3.496 | 1 | 36.56 |
| 589 | C | PRO | 79 | 49.915 | 5.053 | 2.044 | 1 | 35.87 |
| 590 | O | PRO | 79 | 49.194 | 5.393 | 1.106 | 1 | 35.59 |
| 591 | N | ARG | 80 | 50.104 | 3.781 | 2.379 | 1 | 36.12 |
| 592 | CA | ARG | 80 | 49.458 | 2.707 | 1.635 | 1 | 36.29 |
| 593 | CB | ARG | 80 | 49.987 | 1.348 | 2.101 | 1 | 38.4 |
| 594 | CG | ARG | 80 | 49.526 | 0.181 | 1.242 | 1 | 40.89 |
| 595 | CD | ARG | 80 | 50.297 | −1.088 | 1.574 | 1 | 43.6 |
| 596 | NE | ARG | 80 | 49.954 | −2.189 | 0.678 | 1 | 46.33 |
| 597 | CZ | ARG | 80 | 50.569 | −3.368 | 0.672 | 1 | 47.27 |
| 598 | NH1 | ARG | 80 | 51.564 | −3.604 | 1.517 | 1 | 48.02 |
| 599 | NH2 | ARG | 80 | 50.19 | −4.313 | −0.18 | 1 | 47.49 |
| 600 | C | ARG | 80 | 47.944 | 2.768 | 1.817 | 1 | 35.16 |
| 601 | O | ARG | 80 | 47.185 | 2.668 | 0.851 | 1 | 33.76 |
| 602 | N | GLN | 81 | 47.513 | 2.935 | 3.061 | 1 | 34.44 |
| 603 | CA | GLN | 81 | 46.094 | 3.017 | 3.374 | 1 | 33.68 |
| 604 | CB | GLN | 81 | 45.891 | 2.926 | 4.886 | 1 | 35.54 |
| 605 | CG | GLN | 81 | 44.446 | 3.012 | 5.325 | 1 | 39.35 |
| 606 | CD | GLN | 81 | 44.276 | 2.747 | 6.809 | 1 | 41.48 |
| 607 | OE1 | GLN | 81 | 44.793 | 3.486 | 7.647 | 1 | 43.53 |
| 608 | NE2 | GLN | 81 | 43.552 | 1.683 | 7.139 | 1 | 43.11 |
| 609 | C | GLN | 81 | 45.528 | 4.332 | 2.852 | 1 | 32.01 |
| 610 | O | GLN | 81 | 44.366 | 4.412 | 2.453 | 1 | 30.53 |
| 611 | N | ARG | 82 | 46.346 | 5.36 | 2.857 | 1 | 30.66 |
| 612 | CA | ARG | 82 | 45.98 | 6.682 | 2.389 | 1 | 29.81 |
| 613 | CB | ARG | 82 | 47.118 | 7.67 | 2.648 | 1 | 32.29 |
| 614 | CG | ARG | 82 | 46.761 | 9.127 | 2.442 | 1 | 33.83 |
| 615 | CD | ARG | 82 | 48.022 | 9.973 | 2.414 | 1 | 36.51 |
| 616 | NE | ARG | 82 | 48.878 | 9.705 | 3.566 | 1 | 38.86 |
| 617 | CZ | ARG | 82 | 50.15 | 10.08 | 3.655 | 1 | 40.74 |
| 618 | NH1 | ARG | 82 | 50.718 | 10.742 | 2.657 | 1 | 42.09 |
| 619 | NH2 | ARG | 82 | 50.854 | 9.792 | 4.74 | 1 | 41.36 |
| 620 | C | ARG | 82 | 45.674 | 6.625 | 0.894 | 1 | 28.57 |
| 621 | O | ARG | 82 | 44.682 | 7.187 | 0.43 | 1 | 28.2 |
| 622 | N | ALA | 83 | 46.53 | 5.94 | 0.144 | 1 | 27.25 |
| 623 | CA | ALA | 83 | 46.35 | 5.81 | −1.299 | 1 | 26.32 |
| 624 | CB | ALA | 83 | 47.599 | 5.202 | −1.926 | 1 | 27.29 |
| 625 | C | ALA | 83 | 45.136 | 4.943 | −1.609 | 1 | 25.44 |
| 626 | O | ALA | 83 | 44.355 | 5.243 | −2.514 | 1 | 26.02 |
| 627 | N | LEU | 84 | 44.985 | 3.866 | −0.848 | 1 | 24.83 |
| 628 | CA | LEU | 84 | 43.875 | 2.941 | −1.027 | 1 | 24.37 |
| 629 | CB | LEU | 84 | 43.986 | 1.809 | −0.005 | 1 | 25.83 |
| 630 | CG | LEU | 84 | 43.006 | 0.644 | −0.118 | 1 | 29.26 |
| 631 | CD1 | LEU | 84 | 43.174 | −0.043 | −1.47 | 1 | 29.85 |
| 632 | CD2 | LEU | 84 | 43.265 | −0.339 | 1.015 | 1 | 29.93 |
| 633 | C | LEU | 84 | 42.543 | 3.665 | −0.857 | 1 | 22.97 |
| 634 | O | LEU | 84 | 41.605 | 3.461 | −1.63 | 1 | 22.52 |
| 635 | N | ARG | 85 | 42.475 | 4.517 | 0.16 | 1 | 20.51 |
| 636 | CA | ARG | 85 | 41.265 | 5.275 | 0.456 | 1 | 20.8 |
| 637 | CB | ARG | 85 | 41.222 | 5.61 | 1.949 | 1 | 20.98 |
| 638 | CG | ARG | 85 | 41.015 | 4.409 | 2.864 | 1 | 23.55 |
| 639 | CD | ARG | 85 | 41.26 | 4.808 | 4.312 | 1 | 24.75 |
| 640 | NE | ARG | 85 | 40.708 | 3.86 | 5.278 | 1 | 28.24 |
| 641 | CZ | ARG | 85 | 41.005 | 2.566 | 5.334 | 1 | 30.48 |
| 642 | NH1 | ARG | 85 | 41.859 | 2.031 | 4.471 | 1 | 34.03 |
| 643 | NH2 | ARG | 85 | 40.45 | 1.804 | 6.267 | 1 | 32.87 |
| 644 | C | ARG | 85 | 41.165 | 6.568 | −0.351 | 1 | 20.24 |
| 645 | O | ARG | 85 | 40.19 | 7.307 | −0.221 | 1 | 19.03 |
| 646 | N | GLN | 86 | 42.166 | 6.832 | −1.186 | 1 | 20.6 |
| 647 | CA | GLN | 86 | 42.191 | 8.049 | −1.994 | 1 | 21.77 |
| 648 | CB | GLN | 86 | 41.132 | 7.982 | −3.097 | 1 | 21.78 |
| 649 | CG | GLN | 86 | 41.334 | 6.8 | −4.038 | 1 | 24.9 |
| 650 | CD | GLN | 86 | 40.377 | 6.794 | −5.213 | 1 | 26.58 |
| 651 | OE1 | GLN | 86 | 40.367 | 5.855 | −6.012 | 1 | 31.32 |
| 652 | NE2 | GLN | 86 | 39.571 | 7.84 | −5.331 | 1 | 26.11 |
| 653 | C | GLN | 86 | 41.943 | 9.235 | −1.071 | 1 | 21.32 |
| 654 | O | GLN | 86 | 41.04 | 10.047 | −1.289 | 1 | 22.54 |
| 655 | N | MET | 87 | 42.76 | 9.313 | −0.029 | 1 | 20.99 |
| 656 | CA | MET | 87 | 42.663 | 10.372 | 0.963 | 1 | 22.48 |
| 657 | CB | MET | 87 | 42.977 | 9.805 | 2.345 | 1 | 24.48 |
| 658 | CG | MET | 87 | 42.635 | 10.723 | 3.499 | 1 | 26.33 |
| 659 | SD | MET | 87 | 43.127 | 9.988 | 5.063 | 1 | 29.59 |
| 660 | CE | MET | 87 | 42.293 | 8.416 | 4.966 | 1 | 30 |
| 661 | C | MET | 87 | 43.65 | 11.482 | 0.628 | 1 | 23.15 |
| 662 | O | MET | 87 | 44.863 | 11.266 | 0.625 | 1 | 24.09 |
| 663 | N | GLU | 88 | 43.123 | 12.664 | 0.339 | 1 | 22.06 |
| 664 | CA | GLU | 88 | 43.953 | 13.811 | 0.009 | 1 | 22.6 |
| 665 | CB | GLU | 88 | 43.813 | 14.158 | −1.475 | 1 | 25.83 |
| 666 | CG | GLU | 88 | 44.141 | 13.007 | −2.417 | 1 | 32.78 |
| 667 | CD | GLU | 88 | 45.619 | 12.664 | −2.444 | 1 | 36.7 |
| 668 | OE1 | GLU | 88 | 46.189 | 12.373 | −1.371 | 1 | 40.21 |
| 669 | OE2 | GLU | 88 | 46.212 | 12.681 | −3.546 | 1 | 40.07 |
| 670 | C | GLU | 88 | 43.49 | 14.983 | 0.859 | 1 | 21.31 |
| 671 | O | GLU | 88 | 42.305 | 15.107 | 1.175 | 1 | 20.09 |
| 672 | N | PRO | 89 | 44.417 | 15.864 | 1.247 | 1 | 20.56 |
| 673 | CD | PRO | 89 | 45.881 | 15.864 | 1.085 | 1 | 20.74 |
| 674 | CA | PRO | 89 | 43.975 | 16.99 | 2.064 | 1 | 19.21 |
| 675 | CB | PRO | 89 | 45.291 | 17.583 | 2.568 | 1 | 20.42 |
| 676 | CG | PRO | 89 | 46.241 | 17.283 | 1.462 | 1 | 23.88 |
| 677 | C | PRO | 89 | 43.134 | 18 | 1.292 | 1 | 19.27 |
| 678 | O | PRO | 89 | 43.235 | 18.106 | 0.069 | 1 | 20.28 |
| 679 | N | PHE | 90 | 42.273 | 18.707 | 2.015 | 1 | 17.44 |
| 680 | CA | PHE | 90 | 41.445 | 19.751 | 1.43 | 1 | 18.48 |
| 681 | CB | PHE | 90 | 40.117 | 19.208 | 0.871 | 1 | 18.3 |
| 682 | CG | PHE | 90 | 39.334 | 18.349 | 1.828 | 1 | 18.12 |
| 683 | CD1 | PHE | 90 | 39.411 | 16.961 | 1.756 | 1 | 18 |
| 684 | CD2 | PHE | 90 | 38.475 | 18.924 | 2.76 | 1 | 17.89 |
| 685 | CE1 | PHE | 90 | 38.636 | 16.157 | 2.596 | 1 | 17.48 |
| 686 | CE2 | PHE | 90 | 37.697 | 18.129 | 3.604 | 1 | 17.15 |
| 687 | CZ | PHE | 90 | 37.778 | 16.745 | 3.52 | 1 | 16.66 |
| 688 | C | PHE | 90 | 41.187 | 20.826 | 2.475 | 1 | 19.06 |
| 689 | O | PHE | 90 | 41.146 | 20.552 | 3.679 | 1 | 18.48 |
| 690 | N | PRO | 91 | 41.027 | 22.077 | 2.028 | 1 | 19.93 |
| 691 | CD | PRO | 91 | 41.075 | 22.552 | 0.627 | 1 | 19.63 |
| 692 | CA | PRO | 91 | 40.781 | 23.2 | 2.934 | 1 | 19.66 |
| 693 | CB | PRO | 91 | 41.023 | 24.409 | 2.039 | 1 | 20.38 |
| 694 | CG | PRO | 91 | 40.5 | 23.929 | 0.721 | 1 | 20.65 |
| 695 | C | PRO | 91 | 39.389 | 23.207 | 3.547 | 1 | 18.68 |
| 696 | O | PRO | 91 | 38.498 | 22.47 | 3.121 | 1 | 19.47 |
| 697 | N | LEU | 92 | 39.213 | 24.056 | 4.551 | 1 | 17.98 |
| 698 | CA | LEU | 92 | 37.938 | 24.186 | 5.229 | 1 | 17.05 |
| 699 | CB | LEU | 92 | 38.072 | 25.112 | 6.439 | 1 | 17.73 |
| 700 | CG | LEU | 92 | 36.754 | 25.556 | 7.086 | 1 | 17.29 |
| 701 | CD1 | LEU | 92 | 36.054 | 24.361 | 7.726 | 1 | 17.33 |
| 702 | CD2 | LEU | 92 | 37.038 | 26.625 | 8.129 | 1 | 18.62 |
| 703 | C | LEU | 92 | 36.861 | 24.745 | 4.312 | 1 | 17.9 |
| 704 | O | LEU | 92 | 37.075 | 25.73 | 3.599 | 1 | 18.04 |
| 705 | N | ARG | 93 | 35.704 | 24.096 | 4.332 | 1 | 16.42 |
| 706 | CA | ARG | 93 | 34.551 | 24.537 | 3.564 | 1 | 17.8 |
| 707 | CB | ARG | 93 | 34.342 | 23.685 | 2.305 | 1 | 19.14 |
| 708 | CG | ARG | 93 | 35.242 | 24.041 | 1.125 | 1 | 21.09 |

TABLE 1-continued

| Atom | Atom Type | Residue | # | X | Y | Z | OCC | B |
|---|---|---|---|---|---|---|---|---|
| 709 | CD | ARG | 93 | 34.714 | 23.375 | −0.146 | 1 | 24.36 |
| 710 | NE | ARG | 93 | 35.486 | 23.71 | −1.343 | 1 | 25.37 |
| 711 | CZ | ARG | 93 | 36.673 | 23.193 | −1.645 | 1 | 26.16 |
| 712 | NH1 | ARG | 93 | 37.245 | 22.307 | −0.842 | 1 | 26.69 |
| 713 | NH2 | ARG | 93 | 37.288 | 23.56 | −2.761 | 1 | 29.36 |
| 714 | C | ARG | 93 | 33.349 | 24.387 | 4.479 | 1 | 16.79 |
| 715 | O | ARG | 93 | 33.19 | 23.363 | 5.142 | 1 | 17.45 |
| 716 | N | VAL | 94 | 32.522 | 25.423 | 4.533 | 1 | 16.08 |
| 717 | CA | VAL | 94 | 31.318 | 25.408 | 5.354 | 1 | 15.87 |
| 718 | CB | VAL | 94 | 31.306 | 26.581 | 6.36 | 1 | 16.61 |
| 719 | CG1 | VAL | 94 | 30.006 | 26.58 | 7.15 | 1 | 17.01 |
| 720 | CG2 | VAL | 94 | 32.503 | 26.47 | 7.297 | 1 | 16.33 |
| 721 | C | VAL | 94 | 30.139 | 25.553 | 4.404 | 1 | 16.34 |
| 722 | O | VAL | 94 | 30.1 | 26.486 | 3.595 | 1 | 16.28 |
| 723 | N | PHE | 95 | 29.19 | 24.625 | 4.49 | 1 | 15.02 |
| 724 | CA | PHE | 95 | 28.012 | 24.653 | 3.632 | 1 | 15.51 |
| 725 | CB | PHE | 95 | 27.87 | 23.343 | 2.847 | 1 | 15.99 |
| 726 | CG | PHE | 95 | 28.877 | 23.177 | 1.75 | 1 | 16.24 |
| 727 | CD1 | PHE | 95 | 30.145 | 22.675 | 2.02 | 1 | 16.17 |
| 728 | CD2 | PHE | 95 | 28.558 | 23.526 | 0.443 | 1 | 17.68 |
| 729 | CE1 | PHE | 95 | 31.085 | 22.519 | 1.002 | 1 | 19.02 |
| 730 | CE2 | PHE | 95 | 29.488 | 23.377 | −0.584 | 1 | 18.7 |
| 731 | CZ | PHE | 95 | 30.753 | 22.872 | −0.305 | 1 | 18.71 |
| 732 | C | PHE | 95 | 26.72 | 24.895 | 4.399 | 1 | 16.83 |
| 733 | O | PHE | 95 | 26.492 | 24.325 | 5.469 | 1 | 16.6 |
| 734 | N | VAL | 96 | 25.878 | 25.748 | 3.829 | 1 | 14.25 |
| 735 | CA | VAL | 96 | 24.583 | 26.082 | 4.398 | 1 | 15.79 |
| 736 | CB | VAL | 96 | 24.478 | 27.6 | 4.677 | 1 | 16.31 |
| 737 | CG1 | VAL | 96 | 23.086 | 27.949 | 5.182 | 1 | 17.29 |
| 738 | CG2 | VAL | 96 | 25.534 | 28.014 | 5.699 | 1 | 17.28 |
| 739 | C | VAL | 96 | 23.554 | 25.671 | 3.347 | 1 | 16.01 |
| 740 | O | VAL | 96 | 23.739 | 25.94 | 2.156 | 1 | 15.82 |
| 741 | N | ASN | 97 | 22.49 | 25.005 | 3.79 | 1 | 15.95 |
| 742 | CA | ASN | 97 | 21.426 | 24.525 | 2.903 | 1 | 17.23 |
| 743 | CB | ASN | 97 | 20.54 | 25.689 | 2.453 | 1 | 18.16 |
| 744 | CG | ASN | 97 | 19.953 | 26.455 | 3.618 | 1 | 19.16 |
| 745 | OD1 | ASN | 97 | 19.786 | 25.912 | 4.711 | 1 | 17.94 |
| 746 | ND2 | ASN | 97 | 19.621 | 27.722 | 3.389 | 1 | 21.56 |
| 747 | C | ASN | 97 | 21.977 | 23.807 | 1.675 | 1 | 17.7 |
| 748 | O | ASN | 97 | 21.571 | 24.084 | 0.545 | 1 | 17.19 |
| 749 | N | PRO | 98 | 22.897 | 22.852 | 1.881 | 1 | 17.11 |
| 750 | CD | PRO | 98 | 23.484 | 22.408 | 3.161 | 1 | 17.64 |
| 751 | CA | PRO | 98 | 23.485 | 22.118 | 0.762 | 1 | 16.84 |
| 752 | CB | PRO | 98 | 24.732 | 21.506 | 1.383 | 1 | 18.16 |
| 753 | CG | PRO | 98 | 24.252 | 21.165 | 2.758 | 1 | 16.09 |
| 754 | C | PRO | 98 | 22.608 | 21.059 | 0.112 | 1 | 17.44 |
| 755 | O | PRO | 98 | 21.642 | 20.566 | 0.701 | 1 | 17.56 |
| 756 | N | SER | 99 | 22.965 | 20.729 | −1.124 | 1 | 16.68 |
| 757 | CA | SER | 99 | 22.286 | 19.699 | −1.891 | 1 | 18.33 |
| 758 | CB | SER | 99 | 21.473 | 20.311 | −3.037 | 1 | 21.17 |
| 759 | OG | SER | 99 | 22.299 | 21.054 | −3.913 | 1 | 27.64 |
| 760 | C | SER | 99 | 23.405 | 18.818 | −2.432 | 1 | 17.36 |
| 761 | O | SER | 99 | 24.529 | 19.286 | −2.649 | 1 | 15.54 |
| 762 | N | LEU | 100 | 23.107 | 17.543 | −2.641 | 1 | 16.67 |
| 763 | CA | LEU | 100 | 24.11 | 16.606 | −3.126 | 1 | 16.75 |
| 764 | CB | LEU | 100 | 24.311 | 15.494 | −2.096 | 1 | 18.21 |
| 765 | CG | LEU | 100 | 25.408 | 14.459 | −2.346 | 1 | 19.95 |
| 766 | CD1 | LEU | 100 | 26.775 | 15.113 | −2.239 | 1 | 23.56 |
| 767 | CD2 | LEU | 100 | 25.283 | 13.342 | −1.316 | 1 | 24.36 |
| 768 | C | LEU | 100 | 23.735 | 15.983 | −4.463 | 1 | 17.75 |
| 769 | O | LEU | 100 | 22.586 | 15.608 | −4.684 | 1 | 17.82 |
| 770 | N | ARG | 101 | 24.716 | 15.879 | −5.348 | 1 | 18.32 |
| 771 | CA | ARG | 101 | 24.51 | 15.275 | −6.656 | 1 | 19.28 |
| 772 | CB | ARG | 101 | 24.643 | 16.326 | −7.761 | 1 | 22.69 |
| 773 | CG | ARG | 101 | 24.345 | 15.801 | −9.154 | 1 | 29.29 |
| 774 | CD | ARG | 101 | 24.291 | 16.934 | −10.169 | 1 | 33.51 |
| 775 | NE | ARG | 101 | 23.939 | 16.46 | −11.505 | 1 | 38.58 |
| 776 | CZ | ARG | 101 | 24.666 | 15.6 | −12.212 | 1 | 40.67 |
| 777 | NH1 | ARG | 101 | 25.792 | 15.111 | −11.712 | 1 | 40.82 |
| 778 | NH2 | ARG | 101 | 24.267 | 15.229 | −13.422 | 1 | 42.26 |
| 779 | C | ARG | 101 | 25.574 | 14.202 | −6.823 | 1 | 17.87 |
| 780 | O | ARG | 101 | 26.755 | 14.448 | −6.581 | 1 | 17.92 |
| 781 | N | VAL | 102 | 25.157 | 13.006 | −7.219 | 1 | 17.07 |
| 782 | CA | VAL | 102 | 26.101 | 11.911 | −7.409 | 1 | 17.38 |
| 783 | CB | VAL | 102 | 25.395 | 10.545 | −7.296 | 1 | 17.59 |
| 784 | CG1 | VAL | 102 | 26.401 | 9.42 | −7.482 | 1 | 17.54 |
| 785 | CG2 | VAL | 102 | 24.701 | 10.435 | −5.945 | 1 | 18.17 |
| 786 | C | VAL | 102 | 26.742 | 12.028 | −8.786 | 1 | 17.88 |
| 787 | O | VAL | 102 | 26.042 | 12.112 | −9.797 | 1 | 19.78 |
| 788 | N | LEU | 103 | 28.072 | 12.034 | −8.825 | 1 | 16.87 |
| 789 | CA | LEU | 103 | 28.795 | 12.153 | −10.089 | 1 | 17.39 |
| 790 | CB | LEU | 103 | 29.979 | 13.107 | −9.928 | 1 | 17.14 |
| 791 | CG | LEU | 103 | 29.608 | 14.486 | −9.379 | 1 | 18.18 |
| 792 | CD1 | LEU | 103 | 30.849 | 15.345 | −9.329 | 1 | 19.27 |
| 793 | CD2 | LEU | 103 | 28.544 | 15.134 | −10.253 | 1 | 17.63 |
| 794 | C | LEU | 103 | 29.29 | 10.803 | −10.592 | 1 | 18.08 |
| 795 | O | LEU | 103 | 29.324 | 10.556 | −11.794 | 1 | 19.69 |
| 796 | N | ASP | 104 | 29.687 | 9.941 | −9.663 | 1 | 18.17 |
| 797 | CA | ASP | 104 | 30.16 | 8.599 | −9.99 | 1 | 17.46 |
| 798 | CB | ASP | 104 | 31.68 | 8.507 | −9.833 | 1 | 19.36 |
| 799 | CG | ASP | 104 | 32.242 | 7.188 | −10.336 | 1 | 20.57 |
| 800 | OD1 | ASP | 104 | 31.49 | 6.189 | −10.364 | 1 | 20.66 |
| 801 | OD2 | ASP | 104 | 33.441 | 7.144 | −10.692 | 1 | 23.16 |
| 802 | C | ASP | 104 | 29.469 | 7.71 | −8.961 | 1 | 17.31 |
| 803 | O | ASP | 104 | 29.805 | 7.751 | −7.777 | 1 | 16.44 |
| 804 | N | SER | 105 | 28.494 | 6.925 | −9.41 | 1 | 17.75 |
| 805 | CA | SER | 105 | 27.731 | 6.061 | −8.515 | 1 | 18.12 |
| 806 | CB | SER | 105 | 26.358 | 5.752 | −9.119 | 1 | 20.28 |
| 807 | OG | SER | 105 | 26.48 | 5.111 | −10.375 | 1 | 23.24 |
| 808 | C | SER | 105 | 28.408 | 4.763 | −8.105 | 1 | 17.65 |
| 809 | O | SER | 105 | 27.815 | 3.959 | −7.381 | 1 | 17.64 |
| 810 | N | ARG | 106 | 29.639 | 4.552 | −8.562 | 1 | 17.03 |
| 811 | CA | ARG | 106 | 30.375 | 3.35 | −8.192 | 1 | 17.71 |
| 812 | CB | ARG | 106 | 31.758 | 3.343 | −8.846 | 1 | 18.76 |
| 813 | CG | ARG | 106 | 32.663 | 2.224 | −8.35 | 1 | 20.68 |
| 814 | CD | ARG | 106 | 33.888 | 2.059 | −9.236 | 1 | 21.54 |
| 815 | NE | ARG | 106 | 34.742 | 0.97 | −8.767 | 1 | 22.02 |
| 816 | CZ | ARG | 106 | 35.727 | 0.43 | −9.477 | 1 | 24.24 |
| 817 | NH1 | ARG | 106 | 35.995 | 0.874 | −10.699 | 1 | 23.27 |
| 818 | NH2 | ARG | 106 | 36.443 | −0.561 | −8.965 | 1 | 24.07 |
| 819 | C | ARG | 106 | 30.518 | 3.361 | −6.675 | 1 | 16.68 |
| 820 | O | ARG | 106 | 30.816 | 4.399 | −6.086 | 1 | 16.39 |
| 821 | N | LEU | 107 | 30.304 | 2.209 | −6.049 | 1 | 16.71 |
| 822 | CA | LEU | 107 | 30.396 | 2.106 | −4.598 | 1 | 16.26 |
| 823 | CB | LEU | 107 | 29.334 | 1.131 | −4.076 | 1 | 15.25 |
| 824 | CG | LEU | 107 | 27.887 | 1.588 | −4.285 | 1 | 15.12 |
| 825 | CD1 | LEU | 107 | 26.934 | 0.522 | −3.783 | 1 | 17.04 |
| 826 | CD2 | LEU | 107 | 27.651 | 2.906 | −3.546 | 1 | 16.51 |
| 827 | C | LEU | 107 | 31.772 | 1.69 | −4.097 | 1 | 16.17 |
| 828 | O | LEU | 107 | 32.423 | 0.814 | −4.665 | 1 | 15.44 |
| 829 | N | VAL | 108 | 32.201 | 2.337 | −3.019 | 1 | 15.4 |
| 830 | CA | VAL | 108 | 33.487 | 2.066 | −2.393 | 1 | 15.55 |
| 831 | CB | VAL | 108 | 34.405 | 3.302 | −2.455 | 1 | 17.94 |
| 832 | CG1 | VAL | 108 | 35.745 | 2.984 | −1.824 | 1 | 19.9 |
| 833 | CG2 | VAL | 108 | 34.588 | 3.739 | −3.9 | 1 | 21.54 |
| 834 | C | VAL | 108 | 33.171 | 1.75 | −0.938 | 1 | 14.01 |
| 835 | O | VAL | 108 | 32.435 | 2.492 | −0.289 | 1 | 13.72 |
| 836 | N | THR | 109 | 33.726 | 0.658 | −0.426 | 1 | 13.43 |
| 837 | CA | THR | 109 | 33.452 | 0.243 | 0.946 | 1 | 13.02 |
| 838 | CB | THR | 109 | 32.83 | −1.169 | 0.954 | 1 | 15.65 |
| 839 | OG1 | THR | 109 | 31.629 | −1.156 | 0.17 | 1 | 15.71 |
| 840 | CG2 | THR | 109 | 32.496 | −1.606 | 2.374 | 1 | 16.6 |
| 841 | C | THR | 109 | 34.674 | 0.261 | 1.858 | 1 | 14.33 |
| 842 | O | THR | 109 | 35.681 | −0.399 | 1.587 | 1 | 15.43 |
| 843 | N | PHE | 110 | 34.564 | 1.027 | 2.941 | 1 | 14.75 |
| 844 | CA | PHE | 110 | 35.625 | 1.172 | 3.933 | 1 | 14.44 |
| 845 | CB | PHE | 110 | 36.505 | 2.386 | 3.627 | 1 | 15.64 |
| 846 | CG | PHE | 110 | 37.493 | 2.173 | 2.525 | 1 | 15.62 |
| 847 | CD1 | PHE | 110 | 38.544 | 1.275 | 2.676 | 1 | 17.18 |
| 848 | CD2 | PHE | 110 | 37.396 | 2.903 | 1.344 | 1 | 16.48 |
| 849 | CE1 | PHE | 110 | 39.493 | 1.107 | 1.663 | 1 | 18.3 |
| 850 | CE2 | PHE | 110 | 38.338 | 2.744 | 0.325 | 1 | 17.02 |
| 851 | CZ | PHE | 110 | 39.388 | 1.845 | 0.487 | 1 | 17.85 |
| 852 | C | PHE | 110 | 35.003 | 1.41 | 5.298 | 1 | 13.7 |
| 853 | O | PHE | 110 | 33.848 | 1.827 | 5.403 | 1 | 12.99 |
| 854 | N | PRO | 111 | 35.766 | 1.157 | 6.367 | 1 | 14.83 |
| 855 | CD | PRO | 111 | 37.027 | 0.398 | 6.442 | 1 | 14.64 |
| 856 | CA | PRO | 111 | 35.216 | 1.382 | 7.703 | 1 | 15.24 |
| 857 | CB | PRO | 111 | 36.254 | 0.735 | 8.621 | 1 | 16.79 |
| 858 | CG | PRO | 111 | 36.881 | −0.323 | 7.756 | 1 | 17.54 |
| 859 | C | PRO | 111 | 35.121 | 2.881 | 7.967 | 1 | 15.58 |
| 860 | O | PRO | 111 | 35.995 | 3.649 | 7.555 | 1 | 15.99 |

TABLE 1-continued

| Atom | Atom Type | Residue | # | X | Y | Z | OCC | B |
|---|---|---|---|---|---|---|---|---|
| 861 | N | GLU | 112 | 34.053 | 3.306 | 8.625 | 1 | 15.79 |
| 862 | CA | GLU | 112 | 33.932 | 4.707 | 8.985 | 1 | 16.92 |
| 863 | CB | GLU | 112 | 33.148 | 5.517 | 7.929 | 1 | 21.43 |
| 864 | CG | GLU | 112 | 31.679 | 5.207 | 7.759 | 1 | 20.7 |
| 865 | CD | GLU | 112 | 30.985 | 6.197 | 6.811 | 1 | 19.74 |
| 866 | OE1 | GLU | 112 | 31.311 | 6.224 | 5.603 | 1 | 15.86 |
| 867 | OE2 | GLU | 112 | 30.107 | 6.951 | 7.277 | 1 | 19.03 |
| 868 | C | GLU | 112 | 33.283 | 4.777 | 10.359 | 1 | 15.66 |
| 869 | O | GLU | 112 | 32.652 | 3.815 | 10.815 | 1 | 14.05 |
| 870 | N | GLY | 113 | 33.492 | 5.894 | 11.041 | 1 | 14.98 |
| 871 | CA | GLY | 113 | 32.924 | 6.066 | 12.361 | 1 | 14.36 |
| 872 | C | GLY | 113 | 32.092 | 7.325 | 12.391 | 1 | 13.7 |
| 873 | O | GLY | 113 | 31.838 | 7.932 | 11.353 | 1 | 14.82 |
| 874 | N | CYS | 114 | 31.674 | 7.726 | 13.583 | 1 | 13.51 |
| 875 | CA | CYS | 114 | 30.859 | 8.917 | 13.729 | 1 | 11.74 |
| 876 | CB | CYS | 114 | 29.391 | 8.57 | 13.482 | 1 | 12.09 |
| 877 | SG | CYS | 114 | 28.246 | 9.95 | 13.655 | 1 | 13.12 |
| 878 | C | CYS | 114 | 31.031 | 9.457 | 15.135 | 1 | 11.78 |
| 879 | O | CYS | 114 | 30.939 | 8.71 | 16.114 | 1 | 11.82 |
| 880 | N | GLU | 115 | 31.286 | 10.755 | 15.238 | 1 | 11.37 |
| 881 | CA | GLU | 115 | 31.46 | 11.373 | 16.543 | 1 | 12.78 |
| 882 | CB | GLU | 115 | 31.805 | 12.855 | 16.377 | 1 | 13.8 |
| 883 | CG | GLU | 115 | 33.23 | 13.113 | 15.911 | 1 | 16.89 |
| 884 | CD | GLU | 115 | 34.263 | 12.743 | 16.963 | 1 | 20.53 |
| 885 | OE1 | GLU | 115 | 34.07 | 13.104 | 18.144 | 1 | 21.3 |
| 886 | OE2 | GLU | 115 | 35.274 | 12.103 | 16.61 | 1 | 22.27 |
| 887 | C | GLU | 115 | 30.203 | 11.217 | 17.393 | 1 | 11.9 |
| 888 | O | GLU | 115 | 30.271 | 11.276 | 18.621 | 1 | 13.01 |
| 889 | N | SER | 116 | 29.06 | 11.019 | 16.737 | 1 | 11.24 |
| 890 | CA | SER | 116 | 27.788 | 10.849 | 17.434 | 1 | 10.27 |
| 891 | CB | SER | 116 | 26.652 | 11.429 | 16.59 | 1 | 10.53 |
| 892 | OG | SER | 116 | 26.724 | 12.849 | 16.581 | 1 | 12.52 |
| 893 | C | SER | 116 | 27.484 | 9.396 | 17.832 | 1 | 10.93 |
| 894 | O | SER | 116 | 26.434 | 9.107 | 18.404 | 1 | 12.49 |
| 895 | N | VAL | 117 | 28.394 | 8.482 | 17.502 | 1 | 10.22 |
| 896 | CA | VAL | 117 | 28.267 | 7.077 | 17.9 | 1 | 11.09 |
| 897 | CB | VAL | 117 | 27.853 | 6.153 | 16.733 | 1 | 10.66 |
| 898 | CG1 | VAL | 117 | 27.558 | 4.758 | 17.272 | 1 | 14.59 |
| 899 | CG2 | VAL | 117 | 26.611 | 6.708 | 16.036 | 1 | 11.69 |
| 900 | C | VAL | 117 | 29.688 | 6.75 | 18.332 | 1 | 11.62 |
| 901 | O | VAL | 117 | 30.344 | 5.87 | 17.786 | 1 | 12.1 |
| 902 | N | ALA | 118 | 30.154 | 7.506 | 19.319 | 1 | 13.81 |
| 903 | CA | ALA | 118 | 31.509 | 7.399 | 19.829 | 1 | 14.31 |
| 904 | CB | ALA | 118 | 31.647 | 8.259 | 21.082 | 1 | 16.17 |
| 905 | C | ALA | 118 | 32.043 | 6.001 | 20.114 | 1 | 14.37 |
| 906 | O | ALA | 118 | 31.383 | 5.189 | 20.763 | 1 | 14.44 |
| 907 | N | GLY | 119 | 33.247 | 5.743 | 19.608 | 1 | 14.94 |
| 908 | CA | GLY | 119 | 33.925 | 4.484 | 19.852 | 1 | 14.83 |
| 909 | C | GLY | 119 | 33.634 | 3.282 | 18.982 | 1 | 14.73 |
| 910 | O | GLY | 119 | 34.083 | 2.186 | 19.302 | 1 | 13.74 |
| 911 | N | PHE | 120 | 32.915 | 3.473 | 17.882 | 1 | 14.18 |
| 912 | CA | PHE | 120 | 32.584 | 2.359 | 16.999 | 1 | 14.28 |
| 913 | CB | PHE | 120 | 31.095 | 2.029 | 17.118 | 1 | 14.02 |
| 914 | CG | PHE | 120 | 30.692 | 1.515 | 18.469 | 1 | 15.81 |
| 915 | CD1 | PHE | 120 | 30.868 | 0.175 | 18.798 | 1 | 15.55 |
| 916 | CD2 | PHE | 120 | 30.15 | 2.375 | 19.417 | 1 | 16.62 |
| 917 | CE1 | PHE | 120 | 30.508 | −0.304 | 20.059 | 1 | 17.7 |
| 918 | CE2 | PHE | 120 | 29.786 | 1.908 | 20.684 | 1 | 19.71 |
| 919 | CZ | PHE | 120 | 29.967 | 0.563 | 21.003 | 1 | 19.46 |
| 920 | C | PHE | 120 | 32.9 | 2.652 | 15.541 | 1 | 15.97 |
| 921 | O | PHE | 120 | 32.935 | 3.805 | 15.117 | 1 | 16.69 |
| 922 | N | LEU | 121 | 33.133 | 1.59 | 14.781 | 1 | 13.59 |
| 923 | CA | LEU | 121 | 33.408 | 1.696 | 13.355 | 1 | 14.13 |
| 924 | CB | LEU | 121 | 34.896 | 1.48 | 13.058 | 1 | 15.94 |
| 925 | CG | LEU | 121 | 35.903 | 2.564 | 13.435 | 1 | 17.18 |
| 926 | CD1 | LEU | 121 | 37.317 | 2.025 | 13.241 | 1 | 19.93 |
| 927 | CD2 | LEU | 121 | 35.677 | 3.795 | 12.573 | 1 | 21.34 |
| 928 | C | LEU | 121 | 32.62 | 0.601 | 12.657 | 1 | 14.02 |
| 929 | O | LEU | 121 | 32.254 | −0.398 | 13.273 | 1 | 12.94 |
| 930 | N | ALA | 122 | 32.349 | 0.8 | 11.374 | 1 | 12.97 |
| 931 | CA | ALA | 122 | 31.649 | −0.203 | 10.579 | 1 | 12.14 |
| 932 | CB | ALA | 122 | 30.156 | −0.213 | 10.901 | 1 | 11.89 |
| 933 | C | ALA | 122 | 31.864 | 0.149 | 9.118 | 1 | 12.17 |
| 934 | O | ALA | 122 | 31.99 | 1.32 | 8.764 | 1 | 13.7 |
| 935 | N | CYS | 123 | 31.928 | −0.867 | 8.269 | 1 | 12.34 |
| 936 | CA | CYS | 123 | 32.103 | −0.624 | 6.847 | 1 | 12.93 |
| 937 | CB | CYS | 123 | 32.469 | −1.921 | 6.131 | 1 | 14.57 |
| 938 | SG | CYS | 123 | 34.152 | −2.446 | 6.458 | 1 | 19.6 |
| 939 | C | CYS | 123 | 30.819 | −0.057 | 6.256 | 1 | 13.8 |
| 940 | O | CYS | 123 | 29.721 | −0.531 | 6.553 | 1 | 13.03 |
| 941 | N | VAL | 124 | 30.961 | 0.965 | 5.419 | 1 | 13.41 |
| 942 | CA | VAL | 124 | 29.809 | 1.59 | 4.781 | 1 | 13.31 |
| 943 | CB | VAL | 124 | 29.46 | 2.952 | 5.428 | 1 | 13.08 |
| 944 | CG1 | VAL | 124 | 28.234 | 3.553 | 4.743 | 1 | 12.01 |
| 945 | CG2 | VAL | 124 | 29.214 | 2.786 | 6.918 | 1 | 13.66 |
| 946 | C | VAL | 124 | 30.117 | 1.854 | 3.314 | 1 | 12.81 |
| 947 | O | VAL | 124 | 31.152 | 2.434 | 2.987 | 1 | 12.72 |
| 948 | N | PRO | 125 | 29.23 | 1.414 | 2.408 | 1 | 13.77 |
| 949 | CD | PRO | 125 | 28.068 | 0.536 | 2.616 | 1 | 14.8 |
| 950 | CA | PRO | 125 | 29.458 | 1.646 | 0.979 | 1 | 13.66 |
| 951 | CB | PRO | 125 | 28.46 | 0.704 | 0.3 | 1 | 14.88 |
| 952 | CG | PRO | 125 | 28.099 | −0.295 | 1.367 | 1 | 19.09 |
| 953 | C | PRO | 125 | 29.119 | 3.105 | 0.694 | 1 | 13.68 |
| 954 | O | PRO | 125 | 28.104 | 3.609 | 1.176 | 1 | 14.31 |
| 955 | N | ARG | 126 | 29.959 | 3.779 | −0.083 | 1 | 13.45 |
| 956 | CA | ARG | 126 | 29.728 | 5.181 | −0.425 | 1 | 12.7 |
| 957 | CB | ARG | 126 | 30.654 | 6.097 | 0.376 | 1 | 13.8 |
| 958 | CG | ARG | 126 | 30.437 | 6.077 | 1.876 | 1 | 12.91 |
| 959 | CD | ARG | 126 | 29.121 | 6.726 | 2.249 | 1 | 13.04 |
| 960 | NE | ARG | 126 | 29.016 | 6.917 | 3.694 | 1 | 11.25 |
| 961 | CZ | ARG | 126 | 27.94 | 7.398 | 4.307 | 1 | 11.15 |
| 962 | NH1 | ARG | 126 | 26.867 | 7.74 | 3.604 | 1 | 13.18 |
| 963 | NH2 | ARG | 126 | 27.934 | 7.539 | 5.627 | 1 | 12.41 |
| 964 | C | ARG | 126 | 30.019 | 5.399 | −1.899 | 1 | 12.48 |
| 965 | O | ARG | 126 | 30.806 | 4.666 | −2.494 | 1 | 13.23 |
| 966 | N | PHE | 127 | 29.391 | 6.416 | −2.481 | 1 | 12.37 |
| 967 | CA | PHE | 127 | 29.621 | 6.732 | −3.885 | 1 | 12.99 |
| 968 | CB | PHE | 127 | 28.65 | 7.816 | −4.355 | 1 | 13.65 |
| 969 | CG | PHE | 127 | 27.215 | 7.398 | −4.317 | 1 | 14.65 |
| 970 | CD1 | PHE | 127 | 26.284 | 8.136 | −3.597 | 1 | 15.79 |
| 971 | CD2 | PHE | 127 | 26.786 | 6.273 | −5.013 | 1 | 14.9 |
| 972 | CE1 | PHE | 127 | 24.944 | 7.762 | −3.571 | 1 | 15.78 |
| 973 | CE2 | PHE | 127 | 25.447 | 5.89 | −4.995 | 1 | 16.28 |
| 974 | CZ | PHE | 127 | 24.526 | 6.636 | −4.273 | 1 | 16.92 |
| 975 | C | PHE | 127 | 31.054 | 7.223 | −4.044 | 1 | 13.17 |
| 976 | O | PHE | 127 | 31.602 | 7.868 | −3.15 | 1 | 13.98 |
| 977 | N | GLN | 128 | 31.653 | 6.912 | −5.187 | 1 | 13.06 |
| 978 | CA | GLN | 128 | 33.025 | 7.303 | −5.49 | 1 | 13.93 |
| 979 | CB | GLN | 128 | 33.476 | 6.586 | −6.768 | 1 | 14.42 |
| 980 | CG | GLN | 128 | 34.77 | 7.091 | −7.399 | 1 | 16.31 |
| 981 | CD | GLN | 128 | 35.977 | 6.959 | −6.492 | 1 | 17.97 |
| 982 | OE1 | GLN | 128 | 36.004 | 6.127 | −5.583 | 1 | 18.27 |
| 983 | NE2 | GLN | 128 | 36.995 | 7.772 | −6.749 | 1 | 18.73 |
| 984 | C | GLN | 128 | 33.207 | 8.813 | −5.647 | 1 | 14.31 |
| 985 | O | GLN | 128 | 34.237 | 9.364 | −5.254 | 1 | 14.81 |
| 986 | N | ALA | 129 | 32.218 | 9.483 | −6.228 | 1 | 14.21 |
| 987 | CA | ALA | 129 | 32.323 | 10.927 | −6.431 | 1 | 15.23 |
| 988 | CB | ALA | 129 | 32.991 | 11.218 | −7.774 | 1 | 15.28 |
| 989 | C | ALA | 129 | 30.977 | 11.624 | −6.355 | 1 | 14.38 |
| 990 | O | ALA | 129 | 29.963 | 11.109 | −6.829 | 1 | 13.55 |
| 991 | N | VAL | 130 | 30.976 | 12.807 | −5.751 | 1 | 15.17 |
| 992 | CA | VAL | 130 | 29.757 | 13.583 | −5.598 | 1 | 14.91 |
| 993 | CB | VAL | 130 | 29.096 | 13.351 | −4.214 | 1 | 14.16 |
| 994 | CG1 | VAL | 130 | 28.753 | 11.883 | −4.023 | 1 | 15.12 |
| 995 | CG2 | VAL | 130 | 30.033 | 13.84 | −3.101 | 1 | 14.53 |
| 996 | C | VAL | 130 | 30.077 | 15.062 | −5.679 | 1 | 15 |
| 997 | O | VAL | 130 | 31.238 | 15.461 | −5.603 | 1 | 14.88 |
| 998 | N | GLN | 131 | 29.037 | 15.867 | −5.843 | 1 | 14.69 |
| 999 | CA | GLN | 131 | 29.202 | 17.308 | −5.858 | 1 | 16.92 |
| 1000 | CB | GLN | 131 | 28.849 | 17.92 | −7.215 | 1 | 18.23 |
| 1001 | CG | GLN | 131 | 28.996 | 19.44 | −7.2 | 1 | 21.44 |
| 1002 | CD | GLN | 131 | 28.438 | 20.108 | −8.436 | 1 | 24.75 |
| 1003 | OE1 | GLN | 131 | 27.232 | 20.086 | −8.676 | 1 | 27.82 |
| 1004 | NE2 | GLN | 131 | 29.315 | 20.71 | −9.227 | 1 | 26.77 |
| 1005 | C | GLN | 131 | 28.259 | 17.875 | −4.815 | 1 | 16.53 |
| 1006 | O | GLN | 131 | 27.055 | 17.598 | −4.836 | 1 | 17.47 |
| 1007 | N | ILE | 132 | 28.802 | 18.646 | −3.883 | 1 | 16.23 |
| 1008 | CA | ILE | 132 | 27.965 | 19.269 | −2.879 | 1 | 15.15 |
| 1009 | CB | ILE | 132 | 28.556 | 19.114 | −1.447 | 1 | 15.98 |
| 1010 | CG2 | ILE | 132 | 29.989 | 19.607 | −1.409 | 1 | 16 |
| 1011 | CG1 | ILE | 132 | 27.684 | 19.867 | −0.443 | 1 | 15.52 |
| 1012 | CD1 | ILE | 132 | 27.989 | 19.533 | 1.016 | 1 | 16.19 |

TABLE 1-continued

| Atom | Atom Type | Residue | # | X | Y | Z | OCC | B |
|---|---|---|---|---|---|---|---|---|
| 1013 | C | ILE | 132 | 27.875 | 20.735 | −3.271 | 1 | 15.99 |
| 1014 | O | ILE | 132 | 28.878 | 21.352 | −3.635 | 1 | 16.76 |
| 1015 | N | SER | 133 | 26.663 | 21.273 | −3.243 | 1 | 15.71 |
| 1016 | CA | SER | 133 | 26.447 | 22.667 | −3.592 | 1 | 18.21 |
| 1017 | CB | SER | 133 | 25.779 | 22.779 | −4.968 | 1 | 18.98 |
| 1018 | OG | SER | 133 | 24.506 | 22.159 | −4.966 | 1 | 26.67 |
| 1019 | C | SER | 133 | 25.565 | 23.306 | −2.539 | 1 | 18.32 |
| 1020 | O | SER | 133 | 24.642 | 22.682 | −2.019 | 1 | 18.78 |
| 1021 | N | GLY | 134 | 25.86 | 24.556 | −2.214 | 1 | 18.25 |
| 1022 | CA | GLY | 134 | 25.069 | 25.251 | −1.225 | 1 | 18.71 |
| 1023 | C | GLY | 134 | 25.501 | 26.695 | −1.151 | 1 | 19.46 |
| 1024 | O | GLY | 134 | 25.907 | 27.283 | −2.154 | 1 | 19.46 |
| 1025 | N | LEU | 135 | 25.417 | 27.261 | 0.043 | 1 | 18.33 |
| 1026 | CA | LEU | 135 | 25.798 | 28.646 | 0.276 | 1 | 19.74 |
| 1027 | CB | LEU | 135 | 24.583 | 29.454 | 0.736 | 1 | 19.72 |
| 1028 | CG | LEU | 135 | 23.359 | 29.524 | −0.173 | 1 | 21.32 |
| 1029 | CD1 | LEU | 135 | 22.21 | 30.214 | 0.548 | 1 | 21.96 |
| 1030 | CD2 | LEU | 135 | 23.732 | 30.272 | −1.428 | 1 | 23.76 |
| 1031 | C | LEU | 135 | 26.826 | 28.665 | 1.391 | 1 | 20.51 |
| 1032 | O | LEU | 135 | 26.823 | 27.779 | 2.243 | 1 | 19.38 |
| 1033 | N | ASP | 136 | 27.725 | 29.644 | 1.38 | 1 | 19.83 |
| 1034 | CA | ASP | 136 | 28.669 | 29.74 | 2.479 | 1 | 20.71 |
| 1035 | CB | ASP | 136 | 29.988 | 30.411 | 2.059 | 1 | 22.95 |
| 1036 | CG | ASP | 136 | 29.814 | 31.836 | 1.573 | 1 | 24.06 |
| 1037 | OD1 | ASP | 136 | 28.782 | 32.474 | 1.867 | 1 | 23.3 |
| 1038 | OD2 | ASP | 136 | 30.744 | 32.325 | 0.899 | 1 | 28.88 |
| 1039 | C | ASP | 136 | 27.913 | 30.57 | 3.512 | 1 | 20.81 |
| 1040 | O | ASP | 136 | 26.801 | 31.021 | 3.243 | 1 | 20.44 |
| 1041 | N | PRO | 137 | 28.481 | 30.76 | 4.711 | 1 | 20.97 |
| 1042 | CD | PRO | 137 | 29.701 | 30.125 | 5.241 | 1 | 20.5 |
| 1043 | CA | PRO | 137 | 27.804 | 31.541 | 5.754 | 1 | 21.95 |
| 1044 | CB | PRO | 137 | 28.83 | 31.556 | 6.882 | 1 | 21.89 |
| 1045 | CG | PRO | 137 | 29.485 | 30.215 | 6.738 | 1 | 22.51 |
| 1046 | C | PRO | 137 | 27.351 | 32.951 | 5.357 | 1 | 22.36 |
| 1047 | O | PRO | 137 | 26.496 | 33.54 | 6.02 | 1 | 24.15 |
| 1048 | N | ASN | 138 | 27.914 | 33.485 | 4.279 | 1 | 21.19 |
| 1049 | CA | ASN | 138 | 27.56 | 34.828 | 3.827 | 1 | 22.66 |
| 1050 | CB | ASN | 138 | 28.822 | 35.58 | 3.406 | 1 | 21.98 |
| 1051 | CG | ASN | 138 | 29.717 | 35.908 | 4.584 | 1 | 23.12 |
| 1052 | OD1 | ASN | 138 | 30.942 | 35.851 | 4.484 | 1 | 25.75 |
| 1053 | ND2 | ASN | 138 | 29.105 | 36.263 | 5.708 | 1 | 19.92 |
| 1054 | C | ASN | 138 | 26.541 | 34.832 | 2.692 | 1 | 23.06 |
| 1055 | O | ASN | 138 | 26.235 | 35.883 | 2.125 | 1 | 23.22 |
| 1056 | N | GLY | 139 | 26.018 | 33.655 | 2.363 | 1 | 22.21 |
| 1057 | CA | GLY | 139 | 25.023 | 33.56 | 1.311 | 1 | 22.03 |
| 1058 | C | GLY | 139 | 25.559 | 33.452 | −0.103 | 1 | 22.77 |
| 1059 | O | GLY | 139 | 24.802 | 33.598 | −1.061 | 1 | 23.58 |
| 1060 | N | GLU | 140 | 26.856 | 33.208 | −0.249 | 1 | 21.54 |
| 1061 | CA | GLU | 140 | 27.442 | 33.075 | −1.573 | 1 | 23.54 |
| 1062 | CB | GLU | 140 | 28.903 | 33.527 | −1.567 | 1 | 23.28 |
| 1063 | CG | GLU | 140 | 29.078 | 35.027 | −1.409 | 1 | 25.86 |
| 1064 | CD | GLU | 140 | 30.472 | 35.484 | −1.776 | 1 | 28.07 |
| 1065 | OE1 | GLU | 140 | 31.372 | 35.433 | −0.911 | 1 | 28.89 |
| 1066 | OE2 | GLU | 140 | 30.666 | 35.885 | −2.943 | 1 | 29.2 |
| 1067 | C | GLU | 140 | 27.36 | 31.635 | −2.061 | 1 | 25.55 |
| 1068 | O | GLU | 140 | 27.637 | 30.7 | −1.308 | 1 | 23.5 |
| 1069 | N | GLN | 141 | 26.976 | 31.467 | −3.324 | 1 | 27.05 |
| 1070 | CA | GLN | 141 | 26.862 | 30.144 | −3.929 | 1 | 29.46 |
| 1071 | CB | GLN | 141 | 26.332 | 30.247 | −5.361 | 1 | 30.87 |
| 1072 | CG | GLN | 141 | 24.915 | 30.761 | −5.493 | 1 | 35.63 |
| 1073 | CD | GLN | 141 | 23.903 | 29.847 | −4.842 | 1 | 37.48 |
| 1074 | OE1 | GLN | 141 | 23.957 | 28.626 | −5 | 1 | 40.05 |
| 1075 | NE2 | GLN | 141 | 22.96 | 30.434 | −4.116 | 1 | 39.91 |
| 1076 | C | GLN | 141 | 28.22 | 29.461 | −3.966 | 1 | 28.62 |
| 1077 | O | GLN | 141 | 29.176 | 29.995 | −4.527 | 1 | 30.53 |
| 1078 | N | VAL | 142 | 28.305 | 28.28 | −3.366 | 1 | 27.65 |
| 1079 | CA | VAL | 142 | 29.548 | 27.527 | −3.355 | 1 | 25.79 |
| 1080 | CB | VAL | 142 | 30.174 | 27.479 | −1.943 | 1 | 28.05 |
| 1081 | CG1 | VAL | 142 | 30.587 | 28.879 | −1.513 | 1 | 28.71 |
| 1082 | CG2 | VAL | 142 | 29.188 | 26.895 | −0.951 | 1 | 27.79 |
| 1083 | C | VAL | 142 | 29.292 | 26.105 | −3.835 | 1 | 24.9 |
| 1084 | O | VAL | 142 | 28.222 | 25.543 | −3.605 | 1 | 23.65 |
| 1085 | N | VAL | 143 | 30.278 | 25.533 | −4.513 | 1 | 22.95 |
| 1086 | CA | VAL | 143 | 30.16 | 24.179 | −5.033 | 1 | 21.99 |
| 1087 | CB | VAL | 143 | 29.748 | 24.192 | −6.524 | 1 | 23.95 |
| 1088 | CG1 | VAL | 143 | 29.686 | 22.778 | −7.062 | 1 | 26.86 |
| 1089 | CG2 | VAL | 143 | 28.399 | 24.867 | −6.679 | 1 | 23.66 |
| 1090 | C | VAL | 143 | 31.498 | 23.475 | −4.893 | 1 | 21.21 |
| 1091 | O | VAL | 143 | 32.552 | 24.106 | −4.987 | 1 | 22.25 |
| 1092 | N | TRP | 144 | 31.456 | 22.17 | −4.652 | 1 | 19.21 |
| 1093 | CA | TRP | 144 | 32.674 | 21.388 | −4.514 | 1 | 18.47 |
| 1094 | CB | TRP | 144 | 33.1 | 21.308 | −3.038 | 1 | 18.6 |
| 1095 | CG | TRP | 144 | 34.379 | 20.54 | −2.814 | 1 | 18.89 |
| 1096 | CD2 | TRP | 144 | 34.736 | 19.777 | −1.652 | 1 | 19.25 |
| 1097 | CE2 | TRP | 144 | 36.033 | 19.26 | −1.873 | 1 | 19.13 |
| 1098 | CE3 | TRP | 144 | 34.088 | 19.481 | −0.445 | 1 | 19.71 |
| 1099 | CD1 | TRP | 144 | 35.444 | 20.456 | −3.666 | 1 | 21.31 |
| 1100 | NE1 | TRP | 144 | 36.441 | 19.69 | −3.109 | 1 | 20.89 |
| 1101 | CZ2 | TRP | 144 | 36.695 | 18.46 | −0.932 | 1 | 18.75 |
| 1102 | CZ3 | TRP | 144 | 34.748 | 18.684 | 0.494 | 1 | 19.23 |
| 1103 | CH2 | TRP | 144 | 36.038 | 18.185 | 0.241 | 1 | 17.69 |
| 1104 | C | TRP | 144 | 32.472 | 19.988 | −5.076 | 1 | 19.14 |
| 1105 | O | TRP | 144 | 31.587 | 19.255 | −4.636 | 1 | 18.56 |
| 1106 | N | GLN | 145 | 33.282 | 19.642 | −6.072 | 1 | 19.48 |
| 1107 | CA | GLN | 145 | 33.238 | 18.326 | −6.695 | 1 | 20.09 |
| 1108 | CB | GLN | 145 | 33.538 | 18.434 | −8.192 | 1 | 22.88 |
| 1109 | CG | GLN | 145 | 33.481 | 17.112 | −8.93 | 1 | 27.86 |
| 1110 | CD | GLN | 145 | 34.01 | 17.21 | −10.348 | 1 | 31.41 |
| 1111 | OE1 | GLN | 145 | 33.725 | 18.171 | −11.067 | 1 | 32.41 |
| 1112 | NE2 | GLN | 145 | 34.779 | 16.209 | −10.761 | 1 | 33.82 |
| 1113 | C | GLN | 145 | 34.343 | 17.538 | −6.004 | 1 | 19.93 |
| 1114 | O | GLN | 145 | 35.499 | 17.965 | −6.004 | 1 | 18.87 |
| 1115 | N | ALA | 146 | 33.994 | 16.402 | −5.408 | 1 | 18.31 |
| 1116 | CA | ALA | 146 | 34.983 | 15.597 | −4.702 | 1 | 17.6 |
| 1117 | CB | ALA | 146 | 34.885 | 15.86 | −3.202 | 1 | 18.17 |
| 1118 | C | ALA | 146 | 34.858 | 14.104 | −4.967 | 1 | 17.16 |
| 1119 | O | ALA | 146 | 33.789 | 13.605 | −5.316 | 1 | 16.63 |
| 1120 | N | SER | 147 | 35.968 | 13.396 | −4.799 | 1 | 17.49 |
| 1121 | CA | SER | 147 | 35.987 | 11.956 | −4.997 | 1 | 17.5 |
| 1122 | CB | SER | 147 | 36.631 | 11.61 | −6.347 | 1 | 20.88 |
| 1123 | OG | SER | 147 | 37.946 | 12.13 | −6.443 | 1 | 25.49 |
| 1124 | C | SER | 147 | 36.757 | 11.299 | −3.859 | 1 | 18.17 |
| 1125 | O | SER | 147 | 37.335 | 11.981 | −3.008 | 1 | 16.74 |
| 1126 | N | GLY | 148 | 36.742 | 9.973 | −3.832 | 1 | 17.47 |
| 1127 | CA | GLY | 148 | 37.461 | 9.25 | −2.801 | 1 | 16.15 |
| 1128 | C | GLY | 148 | 36.992 | 9.556 | −1.392 | 1 | 15 |
| 1129 | O | GLY | 148 | 35.799 | 9.734 | −1.147 | 1 | 14.6 |
| 1130 | N | TRP | 149 | 37.94 | 9.641 | −0.465 | 1 | 14.87 |
| 1131 | CA | TRP | 149 | 37.609 | 9.894 | 0.931 | 1 | 13.77 |
| 1132 | CB | TRP | 149 | 38.882 | 9.887 | 1.785 | 1 | 14.42 |
| 1133 | CG | TRP | 149 | 38.602 | 9.558 | 3.215 | 1 | 14.06 |
| 1134 | CD2 | TRP | 149 | 38.235 | 8.277 | 3.738 | 1 | 15.61 |
| 1135 | CE2 | TRP | 149 | 38.027 | 8.435 | 5.128 | 1 | 16.72 |
| 1136 | CE3 | TRP | 149 | 38.059 | 7.009 | 3.166 | 1 | 16.89 |
| 1137 | CD1 | TRP | 149 | 38.604 | 10.419 | 4.275 | 1 | 16.49 |
| 1138 | NE1 | TRP | 149 | 38.258 | 9.751 | 5.431 | 1 | 17.56 |
| 1139 | CZ2 | TRP | 149 | 37.653 | 7.369 | 5.958 | 1 | 17.82 |
| 1140 | CZ3 | TRP | 149 | 37.686 | 5.945 | 3.994 | 1 | 17.08 |
| 1141 | CH2 | TRP | 149 | 37.487 | 6.137 | 5.374 | 1 | 18.07 |
| 1142 | C | TRP | 149 | 36.837 | 11.188 | 1.151 | 1 | 13.61 |
| 1143 | O | TRP | 149 | 35.941 | 11.245 | 1.992 | 1 | 12.9 |
| 1144 | N | ALA | 150 | 37.176 | 12.231 | 0.4 | 1 | 14.24 |
| 1145 | CA | ALA | 150 | 36.478 | 13.502 | 0.546 | 1 | 13.69 |
| 1146 | CB | ALA | 150 | 37.065 | 14.538 | −0.411 | 1 | 14.39 |
| 1147 | C | ALA | 150 | 34.991 | 13.305 | 0.266 | 1 | 13.24 |
| 1148 | O | ALA | 150 | 34.136 | 13.841 | 0.975 | 1 | 12.83 |
| 1149 | N | ALA | 151 | 34.689 | 12.531 | −0.775 | 1 | 11.93 |
| 1150 | CA | ALA | 151 | 33.308 | 12.252 | −1.152 | 1 | 12.51 |
| 1151 | CB | ALA | 151 | 33.276 | 11.446 | −2.442 | 1 | 11.97 |
| 1152 | C | ALA | 151 | 32.588 | 11.494 | −0.04 | 1 | 12.55 |
| 1153 | O | ALA | 151 | 31.4 | 11.703 | 0.196 | 1 | 12.1 |
| 1154 | N | ARG | 152 | 33.317 | 10.614 | 0.638 | 1 | 12.78 |
| 1155 | CA | ARG | 152 | 32.748 | 9.837 | 1.736 | 1 | 12.7 |
| 1156 | CB | ARG | 152 | 33.762 | 8.804 | 2.24 | 1 | 12.01 |
| 1157 | CG | ARG | 152 | 33.358 | 8.107 | 3.548 | 1 | 12.6 |
| 1158 | CD | ARG | 152 | 34.328 | 6.985 | 3.883 | 1 | 11.91 |
| 1159 | NE | ARG | 152 | 34.342 | 5.969 | 2.833 | 1 | 12.59 |
| 1160 | CZ | ARG | 152 | 33.583 | 4.876 | 2.827 | 1 | 13.02 |
| 1161 | NH1 | ARG | 152 | 32.742 | 4.63 | 3.824 | 1 | 14.18 |
| 1162 | NH2 | ARG | 152 | 33.654 | 4.037 | 1.805 | 1 | 13.88 |
| 1163 | C | ARG | 152 | 32.33 | 10.744 | 2.887 | 1 | 12.35 |
| 1164 | O | ARG | 152 | 31.222 | 10.627 | 3.405 | 1 | 11.75 |

TABLE 1-continued

| Atom | Atom Type | Residue | # | X | Y | Z | OCC | B |
|---|---|---|---|---|---|---|---|---|
| 1165 | N | ILE | 153 | 33.219 | 11.65 | 3.286 | 1 | 11.75 |
| 1166 | CA | ILE | 153 | 32.915 | 12.557 | 4.386 | 1 | 11.81 |
| 1167 | CB | ILE | 153 | 34.142 | 13.416 | 4.754 | 1 | 13.86 |
| 1168 | CG2 | ILE | 153 | 33.804 | 14.337 | 5.919 | 1 | 16.51 |
| 1169 | CG1 | ILE | 153 | 35.316 | 12.502 | 5.126 | 1 | 16.29 |
| 1170 | CD1 | ILE | 153 | 35.024 | 11.547 | 6.274 | 1 | 19.69 |
| 1171 | C | ILE | 153 | 31.73 | 13.451 | 4.029 | 1 | 10.52 |
| 1172 | O | ILE | 153 | 30.868 | 13.711 | 4.865 | 1 | 11.77 |
| 1173 | N | ILE | 154 | 31.679 | 13.914 | 2.784 | 1 | 11.4 |
| 1174 | CA | ILE | 154 | 30.568 | 14.747 | 2.338 | 1 | 11.47 |
| 1175 | CB | ILE | 154 | 30.735 | 15.158 | 0.859 | 1 | 12.32 |
| 1176 | CG2 | ILE | 154 | 29.429 | 15.758 | 0.333 | 1 | 12.16 |
| 1177 | CG1 | ILE | 154 | 31.888 | 16.155 | 0.727 | 1 | 12.65 |
| 1178 | CD1 | ILE | 154 | 32.308 | 16.399 | −0.712 | 1 | 14.67 |
| 1179 | C | ILE | 154 | 29.255 | 13.977 | 2.485 | 1 | 11.44 |
| 1180 | O | ILE | 154 | 28.267 | 14.502 | 3.001 | 1 | 12.88 |
| 1181 | N | GLN | 155 | 29.242 | 12.729 | 2.024 | 1 | 12.17 |
| 1182 | CA | GLN | 155 | 28.039 | 11.916 | 2.12 | 1 | 10.71 |
| 1183 | CB | GLN | 155 | 28.24 | 10.589 | 1.393 | 1 | 11.81 |
| 1184 | CG | GLN | 155 | 28.387 | 10.758 | −0.113 | 1 | 12.16 |
| 1185 | CD | GLN | 155 | 28.913 | 9.512 | −0.788 | 1 | 11.23 |
| 1186 | OE1 | GLN | 155 | 28.244 | 8.472 | −0.817 | 1 | 12.65 |
| 1187 | NE2 | GLN | 155 | 30.123 | 9.601 | −1.329 | 1 | 12.88 |
| 1188 | C | GLN | 155 | 27.666 | 11.665 | 3.576 | 1 | 11.18 |
| 1189 | O | GLN | 155 | 26.486 | 11.659 | 3.929 | 1 | 12.2 |
| 1190 | N | HIS | 156 | 28.672 | 11.465 | 4.422 | 1 | 10.51 |
| 1191 | CA | HIS | 156 | 28.425 | 11.227 | 5.839 | 1 | 10.97 |
| 1192 | CB | HIS | 156 | 29.747 | 10.933 | 6.564 | 1 | 10.95 |
| 1193 | CG | HIS | 156 | 29.583 | 10.602 | 8.018 | 1 | 11.72 |
| 1194 | CD2 | HIS | 156 | 29.365 | 11.397 | 9.092 | 1 | 11.86 |
| 1195 | ND1 | HIS | 156 | 29.618 | 9.311 | 8.498 | 1 | 14.07 |
| 1196 | CE1 | HIS | 156 | 29.43 | 9.325 | 9.807 | 1 | 13.57 |
| 1197 | NE2 | HIS | 156 | 29.272 | 10.578 | 10.192 | 1 | 11.06 |
| 1198 | C | HIS | 156 | 27.75 | 12.448 | 6.475 | 1 | 11.77 |
| 1199 | O | HIS | 156 | 26.765 | 12.319 | 7.21 | 1 | 12.84 |
| 1200 | N | GLU | 157 | 28.267 | 13.641 | 6.188 | 1 | 11.68 |
| 1201 | CA | GLU | 157 | 27.685 | 14.84 | 6.776 | 1 | 13.24 |
| 1202 | CB | GLU | 157 | 28.631 | 16.035 | 6.631 | 1 | 12.56 |
| 1203 | CG | GLU | 157 | 30.071 | 15.798 | 7.115 | 1 | 13.01 |
| 1204 | CD | GLU | 157 | 30.183 | 15.081 | 8.461 | 1 | 15.67 |
| 1205 | OE1 | GLU | 157 | 29.269 | 15.194 | 9.303 | 1 | 14.83 |
| 1206 | OE2 | GLU | 157 | 31.215 | 14.411 | 8.679 | 1 | 15.31 |
| 1207 | C | GLU | 157 | 26.317 | 15.173 | 6.189 | 1 | 11.22 |
| 1208 | O | GLU | 157 | 25.426 | 15.626 | 6.909 | 1 | 12.34 |
| 1209 | N | MET | 158 | 26.137 | 14.952 | 4.889 | 1 | 12.38 |
| 1210 | CA | MET | 158 | 24.838 | 15.223 | 4.281 | 1 | 14.05 |
| 1211 | CB | MET | 158 | 24.891 | 15.007 | 2.763 | 1 | 15.82 |
| 1212 | CG | MET | 158 | 25.583 | 16.124 | 1.999 | 1 | 16.85 |
| 1213 | SD | MET | 158 | 24.75 | 17.726 | 2.181 | 1 | 16.98 |
| 1214 | CE | MET | 158 | 23.237 | 17.428 | 1.287 | 1 | 18.75 |
| 1215 | C | MET | 158 | 23.794 | 14.298 | 4.912 | 1 | 13.58 |
| 1216 | O | MET | 158 | 22.655 | 14.701 | 5.152 | 1 | 14.64 |
| 1217 | N | ASP | 159 | 24.191 | 13.059 | 5.184 | 1 | 13.26 |
| 1218 | CA | ASP | 159 | 23.291 | 12.097 | 5.818 | 1 | 12.97 |
| 1219 | CB | ASP | 159 | 23.993 | 10.754 | 6.034 | 1 | 13.15 |
| 1220 | CG | ASP | 159 | 23.966 | 9.869 | 4.803 | 1 | 17.03 |
| 1221 | OD1 | ASP | 159 | 23.347 | 10.255 | 3.786 | 1 | 19.34 |
| 1222 | OD2 | ASP | 159 | 24.564 | 8.774 | 4.86 | 1 | 15.49 |
| 1223 | C | ASP | 159 | 22.831 | 12.647 | 7.167 | 1 | 11.95 |
| 1224 | O | ASP | 159 | 21.667 | 12.511 | 7.535 | 1 | 12.57 |
| 1225 | N | HIS | 160 | 23.745 | 13.269 | 7.905 | 1 | 12.3 |
| 1226 | CA | HIS | 160 | 23.393 | 13.837 | 9.203 | 1 | 12.25 |
| 1227 | CB | HIS | 160 | 24.609 | 14.503 | 9.858 | 1 | 11.27 |
| 1228 | CG | HIS | 160 | 25.447 | 13.567 | 10.675 | 1 | 12.51 |
| 1229 | CD2 | HIS | 160 | 26.755 | 13.23 | 10.585 | 1 | 13.94 |
| 1230 | ND1 | HIS | 160 | 24.945 | 12.871 | 11.754 | 1 | 12.03 |
| 1231 | CE1 | HIS | 160 | 25.909 | 12.145 | 12.294 | 1 | 12.31 |
| 1232 | NE2 | HIS | 160 | 27.018 | 12.344 | 11.603 | 1 | 11.86 |
| 1233 | C | HIS | 160 | 22.272 | 14.86 | 9.075 | 1 | 12.14 |
| 1234 | O | HIS | 160 | 21.399 | 14.936 | 9.933 | 1 | 13.44 |
| 1235 | N | LEU | 161 | 22.299 | 15.65 | 8.005 | 1 | 13.39 |
| 1236 | CA | LEU | 161 | 21.272 | 16.667 | 7.809 | 1 | 13.94 |
| 1237 | CB | LEU | 161 | 21.705 | 17.662 | 6.731 | 1 | 12.88 |
| 1238 | CG | LEU | 161 | 23.009 | 18.409 | 7.037 | 1 | 12.82 |
| 1239 | CD1 | LEU | 161 | 23.219 | 19.498 | 5.991 | 1 | 14.15 |
| 1240 | CD2 | LEU | 161 | 22.954 | 19.022 | 8.431 | 1 | 14.34 |
| 1241 | C | LEU | 161 | 19.923 | 16.065 | 7.454 | 1 | 13.88 |
| 1242 | O | LEU | 161 | 18.894 | 16.734 | 7.567 | 1 | 13.98 |
| 1243 | N | GLN | 162 | 19.932 | 14.804 | 7.025 | 1 | 13.49 |
| 1244 | CA | GLN | 162 | 18.707 | 14.097 | 6.673 | 1 | 15.93 |
| 1245 | CB | GLN | 162 | 18.921 | 13.247 | 5.418 | 1 | 18.68 |
| 1246 | CG | GLN | 162 | 19.081 | 14.056 | 4.148 | 1 | 24.94 |
| 1247 | CD | GLN | 162 | 17.879 | 14.935 | 3.877 | 1 | 27.79 |
| 1248 | OE1 | GLN | 162 | 16.741 | 14.459 | 3.83 | 1 | 30.44 |
| 1249 | NE2 | GLN | 162 | 18.122 | 16.227 | 3.698 | 1 | 31.7 |
| 1250 | C | GLN | 162 | 18.237 | 13.2 | 7.813 | 1 | 15.73 |
| 1251 | O | GLN | 162 | 17.221 | 12.516 | 7.688 | 1 | 15.83 |
| 1252 | N | GLY | 163 | 18.98 | 13.208 | 8.919 | 1 | 13.78 |
| 1253 | CA | GLY | 163 | 18.624 | 12.396 | 10.074 | 1 | 13.76 |
| 1254 | C | GLY | 163 | 19.102 | 10.962 | 9.944 | 1 | 13.51 |
| 1255 | O | GLY | 163 | 18.603 | 10.062 | 10.624 | 1 | 14.45 |
| 1256 | N | CYS | 164 | 20.079 | 10.758 | 9.069 | 1 | 13.21 |
| 1257 | CA | CYS | 164 | 20.636 | 9.438 | 8.804 | 1 | 13.66 |
| 1258 | CB | CYS | 164 | 20.718 | 9.225 | 7.288 | 1 | 15.82 |
| 1259 | SG | CYS | 164 | 21.392 | 7.642 | 6.751 | 1 | 17.12 |
| 1260 | C | CYS | 164 | 22.018 | 9.261 | 9.422 | 1 | 13.22 |
| 1261 | O | CYS | 164 | 22.883 | 10.131 | 9.293 | 1 | 12.33 |
| 1262 | N | LEU | 165 | 22.214 | 8.135 | 10.104 | 1 | 12.8 |
| 1263 | CA | LEU | 165 | 23.497 | 7.819 | 10.724 | 1 | 12.77 |
| 1264 | CB | LEU | 165 | 23.303 | 7.449 | 12.198 | 1 | 12.05 |
| 1265 | CG | LEU | 165 | 22.703 | 8.548 | 13.077 | 1 | 13.63 |
| 1266 | CD1 | LEU | 165 | 22.602 | 8.047 | 14.508 | 1 | 13.91 |
| 1267 | CD2 | LEU | 165 | 23.567 | 9.803 | 13.009 | 1 | 13.81 |
| 1268 | C | LEU | 165 | 24.116 | 6.648 | 9.969 | 1 | 12.77 |
| 1269 | O | LEU | 165 | 23.4 | 5.879 | 9.314 | 1 | 12.77 |
| 1270 | N | PHE | 166 | 25.435 | 6.498 | 10.061 | 1 | 12.2 |
| 1271 | CA | PHE | 166 | 26.099 | 5.425 | 9.334 | 1 | 12.42 |
| 1272 | CB | PHE | 166 | 27.628 | 5.509 | 9.507 | 1 | 13.93 |
| 1273 | CG | PHE | 166 | 28.143 | 4.942 | 10.801 | 1 | 13.03 |
| 1274 | CD1 | PHE | 166 | 28.821 | 3.724 | 10.819 | 1 | 15.46 |
| 1275 | CD2 | PHE | 166 | 27.988 | 5.637 | 11.993 | 1 | 14.75 |
| 1276 | CE1 | PHE | 166 | 29.344 | 3.207 | 12.007 | 1 | 15.88 |
| 1277 | CE2 | PHE | 166 | 28.506 | 5.132 | 13.192 | 1 | 15.31 |
| 1278 | CZ | PHE | 166 | 29.186 | 3.915 | 13.199 | 1 | 15.4 |
| 1279 | C | PHE | 166 | 25.59 | 4.036 | 9.704 | 1 | 13.16 |
| 1280 | O | PHE | 166 | 25.677 | 3.109 | 8.898 | 1 | 13.56 |
| 1281 | N | ILE | 167 | 25.05 | 3.889 | 10.912 | 1 | 12.56 |
| 1282 | CA | ILE | 167 | 24.532 | 2.592 | 11.34 | 1 | 11.96 |
| 1283 | CB | ILE | 167 | 24.212 | 2.57 | 12.853 | 1 | 12.27 |
| 1284 | CG2 | ILE | 167 | 25.501 | 2.748 | 13.649 | 1 | 12.52 |
| 1285 | CG1 | ILE | 167 | 23.193 | 3.657 | 13.201 | 1 | 13.54 |
| 1286 | CD1 | ILE | 167 | 22.641 | 3.543 | 14.621 | 1 | 14.11 |
| 1287 | C | ILE | 167 | 23.282 | 2.191 | 10.552 | 1 | 12.4 |
| 1288 | O | ILE | 167 | 22.831 | 1.043 | 10.632 | 1 | 12.87 |
| 1289 | N | ASP | 168 | 22.73 | 3.131 | 9.787 | 1 | 12.6 |
| 1290 | CA | ASP | 168 | 21.547 | 2.846 | 8.973 | 1 | 12.31 |
| 1291 | CB | ASP | 168 | 20.732 | 4.12 | 8.693 | 1 | 12.12 |
| 1292 | CG | ASP | 168 | 20.249 | 4.819 | 9.952 | 1 | 13.61 |
| 1293 | OD1 | ASP | 168 | 20.006 | 4.147 | 10.978 | 1 | 13.61 |
| 1294 | OD2 | ASP | 168 | 20.088 | 6.058 | 9.896 | 1 | 14.82 |
| 1295 | C | ASP | 168 | 21.953 | 2.266 | 7.614 | 1 | 13.72 |
| 1296 | O | ASP | 168 | 21.123 | 1.681 | 6.912 | 1 | 14.36 |
| 1297 | N | LYS | 169 | 23.219 | 2.441 | 7.244 | 1 | 13.22 |
| 1298 | CA | LYS | 169 | 23.727 | 1.987 | 5.943 | 1 | 13.98 |
| 1299 | CB | LYS | 169 | 24.181 | 3.195 | 5.121 | 1 | 14.45 |
| 1300 | CG | LYS | 169 | 23.092 | 4.19 | 4.782 | 1 | 15.67 |
| 1301 | CD | LYS | 169 | 23.67 | 5.342 | 3.971 | 1 | 17.09 |
| 1302 | CE | LYS | 169 | 22.575 | 6.248 | 3.441 | 1 | 15.43 |
| 1303 | NZ | LYS | 169 | 23.127 | 7.364 | 2.619 | 1 | 16.81 |
| 1304 | C | LYS | 169 | 24.901 | 1.023 | 6.023 | 1 | 13.38 |
| 1305 | O | LYS | 169 | 25.408 | 0.553 | 5.003 | 1 | 15.02 |
| 1306 | N | MET | 170 | 25.337 | 0.733 | 7.237 | 1 | 13.39 |
| 1307 | CA | MET | 170 | 26.488 | −0.127 | 7.44 | 1 | 12.9 |
| 1308 | CB | MET | 170 | 26.948 | −0.026 | 8.89 | 1 | 13.57 |
| 1309 | CG | MET | 170 | 25.953 | −0.67 | 9.849 | 1 | 13.54 |
| 1310 | SD | MET | 170 | 26.548 | −0.768 | 11.534 | 1 | 14.19 |
| 1311 | CE | MET | 170 | 25.094 | −1.356 | 12.375 | 1 | 13.29 |
| 1312 | C | MET | 170 | 26.281 | −1.597 | 7.138 | 1 | 13.46 |
| 1313 | O | MET | 170 | 25.151 | −2.085 | 7.021 | 1 | 13.76 |
| 1314 | N | ASP | 171 | 27.409 | −2.285 | 7.012 | 1 | 13.76 |
| 1315 | CA | ASP | 171 | 27.444 | −3.727 | 6.843 | 1 | 14.91 |
| 1316 | CB | ASP | 171 | 28.728 | −4.147 | 6.133 | 1 | 18.27 |

TABLE 1-continued

| Atom | Atom Type | Residue | # | X | Y | Z | OCC | B |
|---|---|---|---|---|---|---|---|---|
| 1317 | CG | ASP | 171 | 28.881 | −5.649 | 6.055 | 1 | 22.14 |
| 1318 | OD1 | ASP | 171 | 28.271 | −6.353 | 6.886 | 1 | 21.93 |
| 1319 | OD2 | ASP | 171 | 29.624 | −6.124 | 5.171 | 1 | 28.66 |
| 1320 | C | ASP | 171 | 27.532 | −4.073 | 8.33 | 1 | 14.03 |
| 1321 | O | ASP | 171 | 28.611 | −4.001 | 8.922 | 1 | 13.75 |
| 1322 | N | SER | 172 | 26.401 | −4.422 | 8.934 | 1 | 13.79 |
| 1323 | CA | SER | 172 | 26.359 | −4.696 | 10.368 | 1 | 13.04 |
| 1324 | CB | SER | 172 | 24.941 | −5.087 | 10.802 | 1 | 14.93 |
| 1325 | OG | SER | 172 | 24.558 | −6.338 | 10.272 | 1 | 16 |
| 1326 | C | SER | 172 | 27.354 | −5.716 | 10.901 | 1 | 12.78 |
| 1327 | O | SER | 172 | 27.767 | −5.625 | 12.057 | 1 | 13.39 |
| 1328 | N | ARG | 173 | 27.751 | −6.682 | 10.078 | 1 | 12.6 |
| 1329 | CA | ARG | 173 | 28.702 | −7.687 | 10.55 | 1 | 13.18 |
| 1330 | CB | ARG | 173 | 28.755 | −8.868 | 9.579 | 1 | 15.29 |
| 1331 | CG | ARG | 173 | 27.5 | −9.731 | 9.619 | 1 | 18.65 |
| 1332 | CD | ARG | 173 | 27.691 | −10.992 | 8.802 | 1 | 17.84 |
| 1333 | NE | ARG | 173 | 28.771 | −11.821 | 9.327 | 1 | 17.67 |
| 1334 | CZ | ARG | 173 | 28.62 | −12.73 | 10.285 | 1 | 18.33 |
| 1335 | NH1 | ARG | 173 | 27.429 | −12.932 | 10.827 | 1 | 19.51 |
| 1336 | NH2 | ARG | 173 | 29.66 | −13.442 | 10.692 | 1 | 18.3 |
| 1337 | C | ARG | 173 | 30.107 | −7.134 | 10.776 | 1 | 12.55 |
| 1338 | O | ARG | 173 | 30.956 | −7.805 | 11.372 | 1 | 14.13 |
| 1339 | N | THR | 174 | 30.349 | −5.907 | 10.324 | 1 | 11.9 |
| 1340 | CA | THR | 174 | 31.662 | −5.29 | 10.493 | 1 | 11.87 |
| 1341 | CB | THR | 174 | 32.146 | −4.61 | 9.192 | 1 | 12.31 |
| 1342 | OG1 | THR | 174 | 31.303 | −3.495 | 8.889 | 1 | 13.37 |
| 1343 | CG2 | THR | 174 | 32.126 | −5.596 | 8.035 | 1 | 14.14 |
| 1344 | C | THR | 174 | 31.668 | −4.248 | 11.616 | 1 | 13.14 |
| 1345 | O | THR | 174 | 32.686 | −3.589 | 11.858 | 1 | 12.45 |
| 1346 | N | PHE | 175 | 30.533 | −4.093 | 12.293 | 1 | 12.41 |
| 1347 | CA | PHE | 175 | 30.422 | −3.134 | 13.397 | 1 | 12.17 |
| 1348 | CB | PHE | 175 | 28.998 | −3.141 | 13.951 | 1 | 13.49 |
| 1349 | CG | PHE | 175 | 28.717 | −2.052 | 14.949 | 1 | 13.18 |
| 1350 | CD1 | PHE | 175 | 28.498 | −0.742 | 14.532 | 1 | 13.54 |
| 1351 | CD2 | PHE | 175 | 28.612 | −2.349 | 16.304 | 1 | 13.29 |
| 1352 | CE1 | PHE | 175 | 28.17 | 0.255 | 15.452 | 1 | 12.56 |
| 1353 | CE2 | PHE | 175 | 28.287 | −1.36 | 17.234 | 1 | 13.23 |
| 1354 | CZ | PHE | 175 | 28.063 | −0.054 | 16.805 | 1 | 13.01 |
| 1355 | C | PHE | 175 | 31.402 | −3.596 | 14.466 | 1 | 12.39 |
| 1356 | O | PHE | 175 | 31.457 | −4.785 | 14.794 | 1 | 12.36 |
| 1357 | N | THR | 176 | 32.171 | −2.666 | 15.02 | 1 | 11.5 |
| 1358 | CA | THR | 176 | 33.161 | −3.043 | 16.017 | 1 | 11.25 |
| 1359 | CB | THR | 176 | 34.449 | −3.567 | 15.319 | 1 | 12.47 |
| 1360 | OG1 | THR | 176 | 35.449 | −3.889 | 16.296 | 1 | 14.27 |
| 1361 | CG2 | THR | 176 | 35.014 | −2.507 | 14.384 | 1 | 14.84 |
| 1362 | C | THR | 176 | 33.565 | −1.911 | 16.953 | 1 | 10.73 |
| 1363 | O | THR | 176 | 33.537 | −0.736 | 16.586 | 1 | 11.05 |
| 1364 | N | ASN | 177 | 33.908 | −2.279 | 18.183 | 1 | 11.32 |
| 1365 | CA | ASN | 177 | 34.413 | −1.314 | 19.149 | 1 | 11.41 |
| 1366 | CB | ASN | 177 | 34.617 | −1.98 | 20.507 | 1 | 12.06 |
| 1367 | CG | ASN | 177 | 33.387 | −1.919 | 21.373 | 1 | 12.18 |
| 1368 | OD1 | ASN | 177 | 33.138 | −0.915 | 22.038 | 1 | 13.89 |
| 1369 | ND2 | ASN | 177 | 32.602 | −2.988 | 21.366 | 1 | 12.03 |
| 1370 | C | ASN | 177 | 35.773 | −0.955 | 18.562 | 1 | 12.95 |
| 1371 | O | ASN | 177 | 36.429 | −1.807 | 17.962 | 1 | 12.3 |
| 1372 | N | VAL | 178 | 36.205 | 0.289 | 18.732 | 1 | 13.35 |
| 1373 | CA | VAL | 178 | 37.493 | 0.705 | 18.188 | 1 | 15.77 |
| 1374 | CB | VAL | 178 | 37.726 | 2.217 | 18.376 | 1 | 17.71 |
| 1375 | CG1 | VAL | 178 | 36.712 | 2.997 | 17.558 | 1 | 19.52 |
| 1376 | CG2 | VAL | 178 | 37.634 | 2.58 | 19.847 | 1 | 20.05 |
| 1377 | C | VAL | 178 | 38.675 | −0.047 | 18.79 | 1 | 13.99 |
| 1378 | O | VAL | 178 | 39.739 | −0.13 | 18.171 | 1 | 15.4 |
| 1379 | N | TYR | 179 | 38.498 | −0.604 | 19.985 | 1 | 12.99 |
| 1380 | CA | TYR | 179 | 39.591 | −1.334 | 20.611 | 1 | 12.58 |
| 1381 | CB | TYR | 179 | 39.457 | −1.314 | 22.139 | 1 | 12.44 |
| 1382 | CG | TYR | 179 | 38.143 | −1.806 | 22.694 | 1 | 12.85 |
| 1383 | CD1 | TYR | 179 | 37.849 | −3.168 | 22.749 | 1 | 14.8 |
| 1384 | CE1 | TYR | 179 | 36.66 | −3.621 | 23.316 | 1 | 14.74 |
| 1385 | CD2 | TYR | 179 | 37.211 | −0.906 | 23.214 | 1 | 13.37 |
| 1386 | CE2 | TYR | 179 | 36.023 | −1.346 | 23.781 | 1 | 13.12 |
| 1387 | CZ | TYR | 179 | 35.756 | −2.704 | 23.832 | 1 | 15.07 |
| 1388 | OH | TYR | 179 | 34.59 | −3.134 | 24.415 | 1 | 15.78 |
| 1389 | C | TYR | 179 | 39.779 | −2.756 | 20.082 | 1 | 13.3 |
| 1390 | O | TYR | 179 | 40.621 | −3.5 | 20.576 | 1 | 13 |
| 1391 | N | TRP | 180 | 38.988 | −3.123 | 19.073 | 1 | 11.48 |
| 1392 | CA | TRP | 180 | 39.117 | −4.415 | 18.401 | 1 | 11.55 |
| 1393 | CB | TRP | 180 | 37.795 | −5.195 | 18.369 | 1 | 12.08 |
| 1394 | CG | TRP | 180 | 37.639 | −6.145 | 19.52 | 1 | 12.36 |
| 1395 | CD2 | TRP | 180 | 38.296 | −7.408 | 19.68 | 1 | 12.92 |
| 1396 | CE2 | TRP | 180 | 37.896 | −7.932 | 20.93 | 1 | 12.63 |
| 1397 | CE3 | TRP | 180 | 39.187 | −8.146 | 18.89 | 1 | 12.79 |
| 1398 | CD1 | TRP | 180 | 36.886 | −5.96 | 20.641 | 1 | 13.23 |
| 1399 | NE1 | TRP | 180 | 37.036 | −7.029 | 21.495 | 1 | 12.79 |
| 1400 | CZ2 | TRP | 180 | 38.356 | −9.164 | 21.409 | 1 | 12.01 |
| 1401 | CZ3 | TRP | 180 | 39.644 | −9.374 | 19.366 | 1 | 12.94 |
| 1402 | CH2 | TRP | 180 | 39.225 | −9.869 | 20.615 | 1 | 13.47 |
| 1403 | C | TRP | 180 | 39.505 | −4.04 | 16.98 | 1 | 14.31 |
| 1404 | O | TRP | 180 | 38.874 | −3.173 | 16.379 | 1 | 13.72 |
| 1405 | N | MET | 181 | 40.537 | −4.681 | 16.441 | 1 | 14.82 |
| 1406 | CA | MET | 181 | 40.981 | −4.355 | 15.092 | 1 | 18.56 |
| 1407 | CB | MET | 181 | 41.918 | −3.141 | 15.146 | 1 | 20.27 |
| 1408 | CG | MET | 181 | 43.187 | −3.387 | 15.952 | 1 | 20.96 |
| 1409 | SD | MET | 181 | 43.921 | −1.877 | 16.641 | 1 | 21.8 |
| 1410 | CE | MET | 181 | 43.021 | −1.767 | 18.187 | 1 | 21.08 |
| 1411 | C | MET | 181 | 41.696 | −5.517 | 14.419 | 1 | 21.09 |
| 1412 | O | MET | 181 | 42.166 | −6.441 | 15.08 | 1 | 19.49 |
| 1413 | N | LYS | 182 | 41.766 | −5.466 | 13.093 | 1 | 25.37 |
| 1414 | CA | LYS | 182 | 42.457 | −6.496 | 12.33 | 1 | 29.07 |
| 1415 | CB | LYS | 182 | 41.753 | −6.753 | 10.997 | 1 | 31.63 |
| 1416 | CG | LYS | 182 | 40.322 | −7.24 | 11.121 | 1 | 33.75 |
| 1417 | CD | LYS | 182 | 39.724 | −7.556 | 9.754 | 1 | 37.46 |
| 1418 | CE | LYS | 182 | 39.727 | −6.334 | 8.842 | 1 | 37.6 |
| 1419 | NZ | LYS | 182 | 39.155 | −6.631 | 7.496 | 1 | 40.47 |
| 1420 | C | LYS | 182 | 43.858 | −5.967 | 12.069 | 1 | 30.68 |
| 1421 | O | LYS | 182 | 44.031 | −4.789 | 11.755 | 1 | 31.42 |
| 1422 | N | VAL | 183 | 44.857 | −6.829 | 12.212 | 1 | 32.29 |
| 1423 | CA | VAL | 183 | 46.239 | −6.431 | 11.988 | 1 | 34.23 |
| 1424 | CB | VAL | 183 | 46.997 | −6.268 | 13.32 | 1 | 34.02 |
| 1425 | CG1 | VAL | 183 | 46.409 | −5.113 | 14.116 | 1 | 34.35 |
| 1426 | CG2 | VAL | 183 | 46.918 | −7.558 | 14.121 | 1 | 34.38 |
| 1427 | C | VAL | 183 | 46.971 | −7.461 | 11.137 | 1 | 36.46 |
| 1428 | O | VAL | 183 | 46.508 | −8.589 | 10.98 | 1 | 36.81 |
| 1429 | N | ASN | 184 | 48.113 | −7.06 | 10.586 | 1 | 39.02 |
| 1430 | CA | ASN | 184 | 48.918 | −7.947 | 9.756 | 1 | 42.07 |
| 1431 | CB | ASN | 184 | 49.74 | −7.134 | 8.753 | 1 | 43 |
| 1432 | CG | ASN | 184 | 48.876 | −6.283 | 7.847 | 1 | 43.9 |
| 1433 | OD1 | ASN | 184 | 48.054 | −6.798 | 7.088 | 1 | 44.79 |
| 1434 | ND2 | ASN | 184 | 49.058 | −4.97 | 7.921 | 1 | 45.11 |
| 1435 | C | ASN | 184 | 49.857 | −8.761 | 10.638 | 1 | 43.38 |
| 1436 | O | ASN | 184 | 50.465 | −8.228 | 11.567 | 1 | 44.25 |
| 1437 | N | ASP | 185 | 49.974 | −10.052 | 10.347 | 1 | 45.25 |
| 1438 | CA | ASP | 185 | 50.846 | −10.923 | 11.124 | 1 | 46.81 |
| 1439 | CB | ASP | 185 | 50.47 | −12.389 | 10.895 | 1 | 47.53 |
| 1440 | CG | ASP | 185 | 49.076 | −12.716 | 11.392 | 1 | 48.4 |
| 1441 | OD1 | ASP | 185 | 48.828 | −12.573 | 12.608 | 1 | 48.69 |
| 1442 | OD2 | ASP | 185 | 48.228 | −13.116 | 10.58 | 1 | 49.23 |
| 1443 | C | ASP | 185 | 52.307 | −10.702 | 10.747 | 1 | 47.42 |
| 1444 | O | ASP | 185 | 52.559 | −9.923 | 9.803 | 1 | 47.96 |
| 1445 | OXT | ASP | 185 | 53.18 | −11.313 | 11.399 | 1 | 48.89 |
| 1446 | CB | HIS | 3 | 38.577 | −19.515 | 45.071 | 1 | 44.56 |
| 1447 | CG | HIS | 3 | 39.11 | −18.696 | 46.205 | 1 | 44.86 |
| 1448 | CD2 | HIS | 3 | 40.133 | −17.81 | 46.263 | 1 | 44.71 |
| 1449 | ND1 | HIS | 3 | 38.575 | −18.745 | 47.475 | 1 | 44.71 |
| 1450 | CE1 | HIS | 3 | 39.245 | −17.926 | 48.266 | 1 | 44.64 |
| 1451 | NE2 | HIS | 3 | 40.196 | −17.346 | 47.555 | 1 | 44.72 |
| 1452 | C | HIS | 3 | 36.949 | −17.788 | 44.265 | 1 | 44.98 |
| 1453 | O | HIS | 3 | 35.861 | −17.216 | 44.35 | 1 | 45.38 |
| 1454 | N | HIS | 3 | 36.632 | −20.179 | 43.693 | 1 | 45.65 |
| 1455 | CA | HIS | 3 | 37.108 | −19.232 | 44.739 | 1 | 44.96 |
| 1456 | N | MET | 4 | 38.034 | −17.204 | 43.766 | 1 | 44.53 |
| 1457 | CA | MET | 4 | 38.007 | −15.827 | 43.283 | 1 | 43.99 |
| 1458 | CB | MET | 4 | 38.681 | −14.898 | 44.299 | 1 | 45.85 |
| 1459 | CG | MET | 4 | 38.009 | −14.879 | 45.668 | 1 | 48.34 |
| 1460 | SD | MET | 4 | 38.842 | −13.807 | 46.868 | 1 | 53.04 |
| 1461 | CE | MET | 4 | 37.966 | −12.251 | 46.61 | 1 | 50.33 |
| 1462 | C | MET | 4 | 38.702 | −15.704 | 41.93 | 1 | 42.37 |
| 1463 | O | MET | 4 | 39.93 | −15.752 | 41.844 | 1 | 43.54 |
| 1464 | N | SER | 5 | 37.907 | −15.547 | 40.876 | 1 | 39.82 |
| 1465 | CA | SER | 5 | 38.438 | −15.414 | 39.525 | 1 | 35.77 |
| 1466 | CB | SER | 5 | 38.22 | −16.716 | 38.751 | 1 | 36.54 |
| 1467 | OG | SER | 5 | 38.787 | −16.651 | 37.456 | 1 | 39.93 |
| 1468 | C | SER | 5 | 37.734 | −14.261 | 38.815 | 1 | 33.15 |

TABLE 1-continued

| Atom | Atom Type | Residue | # | X | Y | Z | OCC | B |
|---|---|---|---|---|---|---|---|---|
| 1469 | O | SER | 5 | 36.941 | −13.543 | 39.423 | 1 | 33.45 |
| 1470 | N | PHE | 6 | 38.033 | −14.081 | 37.532 | 1 | 28.69 |
| 1471 | CA | PHE | 6 | 37.425 | −13.016 | 36.741 | 1 | 24.68 |
| 1472 | CB | PHE | 6 | 38.464 | −11.941 | 36.4 | 1 | 24.22 |
| 1473 | CG | PHE | 6 | 38.753 | −10.992 | 37.526 | 1 | 23.3 |
| 1474 | CD1 | PHE | 6 | 37.929 | −9.895 | 37.756 | 1 | 24.04 |
| 1475 | CD2 | PHE | 6 | 39.841 | −11.199 | 38.365 | 1 | 24.6 |
| 1476 | CE1 | PHE | 6 | 38.183 | −9.016 | 38.806 | 1 | 25.49 |
| 1477 | CE2 | PHE | 6 | 40.105 | −10.326 | 39.421 | 1 | 24.99 |
| 1478 | CZ | PHE | 6 | 39.273 | −9.233 | 39.642 | 1 | 26.12 |
| 1479 | C | PHE | 6 | 36.831 | −13.552 | 35.447 | 1 | 23 |
| 1480 | O | PHE | 6 | 37.39 | −14.446 | 34.815 | 1 | 23.26 |
| 1481 | N | SER | 7 | 35.686 | −13 | 35.064 | 1 | 20.23 |
| 1482 | CA | SER | 7 | 35.017 | −13.383 | 33.827 | 1 | 19.37 |
| 1483 | CB | SER | 7 | 33.774 | −14.233 | 34.103 | 1 | 22.47 |
| 1484 | OG | SER | 7 | 34.119 | −15.579 | 34.376 | 1 | 29.41 |
| 1485 | C | SER | 7 | 34.599 | −12.111 | 33.117 | 1 | 16.39 |
| 1486 | O | SER | 7 | 34.427 | −11.066 | 33.742 | 1 | 15.61 |
| 1487 | N | HIS | 8 | 34.438 | −12.187 | 31.805 | 1 | 15.06 |
| 1488 | CA | HIS | 8 | 34.025 | −11.006 | 31.075 | 1 | 15.89 |
| 1489 | CB | HIS | 8 | 35.248 | −10.226 | 30.59 | 1 | 19.05 |
| 1490 | CG | HIS | 8 | 35.994 | −10.894 | 29.479 | 1 | 21.43 |
| 1491 | CD2 | HIS | 8 | 36.774 | −12.001 | 29.466 | 1 | 24.08 |
| 1492 | ND1 | HIS | 8 | 35.981 | −10.42 | 28.185 | 1 | 24.54 |
| 1493 | CE1 | HIS | 8 | 36.722 | −11.204 | 27.423 | 1 | 24.75 |
| 1494 | NE2 | HIS | 8 | 37.214 | −12.171 | 28.176 | 1 | 25.54 |
| 1495 | C | HIS | 8 | 33.157 | −11.383 | 29.898 | 1 | 14.96 |
| 1496 | O | HIS | 8 | 33.311 | −12.458 | 29.318 | 1 | 15.01 |
| 1497 | N | VAL | 9 | 32.221 | −10.505 | 29.57 | 1 | 13.23 |
| 1498 | CA | VAL | 9 | 31.356 | −10.737 | 28.428 | 1 | 12.66 |
| 1499 | CB | VAL | 9 | 29.96 | −10.132 | 28.645 | 1 | 13.54 |
| 1500 | CG1 | VAL | 9 | 29.122 | −10.313 | 27.39 | 1 | 13.86 |
| 1501 | CG2 | VAL | 9 | 29.28 | −10.809 | 29.831 | 1 | 13.65 |
| 1502 | C | VAL | 9 | 32.031 | −10.052 | 27.245 | 1 | 12.79 |
| 1503 | O | VAL | 9 | 32.262 | −8.842 | 27.269 | 1 | 12.9 |
| 1504 | N | CYS | 10 | 32.371 | −10.836 | 26.227 | 1 | 11.17 |
| 1505 | CA | CYS | 10 | 33.024 | −10.308 | 25.035 | 1 | 10.9 |
| 1506 | CB | CYS | 10 | 33.303 | −11.442 | 24.053 | 1 | 11.58 |
| 1507 | SG | CYS | 10 | 34.339 | −12.736 | 24.751 | 1 | 15.5 |
| 1508 | C | CYS | 10 | 32.167 | −9.242 | 24.363 | 1 | 11.31 |
| 1509 | O | CYS | 10 | 30.947 | −9.386 | 24.267 | 1 | 11.29 |
| 1510 | N | GLN | 11 | 32.813 | −8.177 | 23.899 | 1 | 10.46 |
| 1511 | CA | GLN | 11 | 32.115 | −7.071 | 23.25 | 1 | 11 |
| 1512 | CB | GLN | 11 | 32.646 | −5.737 | 23.776 | 1 | 10.68 |
| 1513 | CG | GLN | 11 | 32.401 | −5.536 | 25.268 | 1 | 10.88 |
| 1514 | CD | GLN | 11 | 30.929 | −5.591 | 25.617 | 1 | 11.64 |
| 1515 | OE1 | GLN | 11 | 30.139 | −4.759 | 25.162 | 1 | 12.17 |
| 1516 | NE2 | GLN | 11 | 30.549 | −6.574 | 26.425 | 1 | 9.92 |
| 1517 | C | GLN | 11 | 32.254 | −7.116 | 21.732 | 1 | 10.71 |
| 1518 | O | GLN | 11 | 33.234 | −7.648 | 21.205 | 1 | 11.62 |
| 1519 | N | VAL | 12 | 31.281 | −6.528 | 21.04 | 1 | 11.28 |
| 1520 | CA | VAL | 12 | 31.278 | −6.53 | 19.585 | 1 | 11.92 |
| 1521 | CB | VAL | 12 | 30.079 | −5.718 | 19.026 | 1 | 11.07 |
| 1522 | CG1 | VAL | 12 | 30.192 | −4.25 | 19.394 | 1 | 11.29 |
| 1523 | CG2 | VAL | 12 | 29.986 | −5.921 | 17.52 | 1 | 11.1 |
| 1524 | C | VAL | 12 | 32.612 | −6.041 | 19.025 | 1 | 12.8 |
| 1525 | O | VAL | 12 | 33.128 | −4.98 | 19.397 | 1 | 12.37 |
| 1526 | N | GLY | 13 | 33.169 | −6.861 | 18.14 | 1 | 12.51 |
| 1527 | CA | GLY | 13 | 34.469 | −6.598 | 17.554 | 1 | 12.88 |
| 1528 | C | GLY | 13 | 35.259 | −7.881 | 17.738 | 1 | 11.27 |
| 1529 | O | GLY | 13 | 36.107 | −8.236 | 16.918 | 1 | 12.54 |
| 1530 | N | ASP | 14 | 34.977 | −8.582 | 18.835 | 1 | 11.68 |
| 1531 | CA | ASP | 14 | 35.63 | −9.854 | 19.12 | 1 | 11.16 |
| 1532 | CB | ASP | 14 | 35.258 | −10.331 | 20.526 | 1 | 12.59 |
| 1533 | CG | ASP | 14 | 36.025 | −11.571 | 20.95 | 1 | 13.43 |
| 1534 | OD1 | ASP | 14 | 36.462 | −12.349 | 20.07 | 1 | 12.5 |
| 1535 | OD2 | ASP | 14 | 36.173 | −11.778 | 22.177 | 1 | 13.48 |
| 1536 | C | ASP | 14 | 35.079 | −10.834 | 18.086 | 1 | 12.28 |
| 1537 | O | ASP | 14 | 33.872 | −11.086 | 18.049 | 1 | 13.26 |
| 1538 | N | PRO | 15 | 35.95 | −11.405 | 17.238 | 1 | 12.47 |
| 1539 | CD | PRO | 15 | 37.42 | −11.293 | 17.229 | 1 | 13.27 |
| 1540 | CA | PRO | 15 | 35.491 | −12.35 | 16.212 | 1 | 14.43 |
| 1541 | CB | PRO | 15 | 36.78 | −12.725 | 15.481 | 1 | 14.97 |
| 1542 | CG | PRO | 15 | 37.83 | −12.576 | 16.541 | 1 | 16.43 |
| 1543 | C | PRO | 15 | 34.723 | −13.571 | 16.715 | 1 | 13.47 |
| 1544 | O | PRO | 15 | 33.964 | −14.179 | 15.961 | 1 | 13.55 |
| 1545 | N | VAL | 16 | 34.906 | −13.927 | 17.981 | 1 | 12.84 |
| 1546 | CA | VAL | 16 | 34.207 | −15.084 | 18.53 | 1 | 12.69 |
| 1547 | CB | VAL | 16 | 34.645 | −15.371 | 19.989 | 1 | 11.51 |
| 1548 | CG1 | VAL | 16 | 34.062 | −14.321 | 20.94 | 1 | 13.51 |
| 1549 | CG2 | VAL | 16 | 34.21 | −16.779 | 20.394 | 1 | 14.38 |
| 1550 | C | VAL | 16 | 32.692 | −14.874 | 18.481 | 1 | 12.71 |
| 1551 | O | VAL | 16 | 31.928 | −15.835 | 18.411 | 1 | 13.36 |
| 1552 | N | LEU | 17 | 32.258 | −13.616 | 18.497 | 1 | 11.78 |
| 1553 | CA | LEU | 17 | 30.829 | −13.309 | 18.464 | 1 | 12.35 |
| 1554 | CB | LEU | 17 | 30.585 | −11.886 | 18.972 | 1 | 11.39 |
| 1555 | CG | LEU | 17 | 30.961 | −11.608 | 20.43 | 1 | 10.95 |
| 1556 | CD1 | LEU | 17 | 30.901 | −10.104 | 20.678 | 1 | 11.7 |
| 1557 | CD2 | LEU | 17 | 30.018 | −12.362 | 21.368 | 1 | 13.16 |
| 1558 | C | LEU | 17 | 30.206 | −13.456 | 17.08 | 1 | 12.56 |
| 1559 | O | LEU | 17 | 28.98 | −13.512 | 16.952 | 1 | 12.89 |
| 1560 | N | ARG | 18 | 31.044 | −13.512 | 16.049 | 1 | 12.3 |
| 1561 | CA | ARG | 18 | 30.549 | −13.64 | 14.683 | 1 | 12.74 |
| 1562 | CB | ARG | 18 | 31.155 | −12.547 | 13.799 | 1 | 13.09 |
| 1563 | CG | ARG | 18 | 30.214 | −11.379 | 13.515 | 1 | 13.62 |
| 1564 | CD | ARG | 18 | 29.676 | −10.758 | 14.793 | 1 | 15.28 |
| 1565 | NE | ARG | 18 | 29.005 | −9.485 | 14.537 | 1 | 13.35 |
| 1566 | CZ | ARG | 18 | 27.788 | −9.35 | 14.018 | 1 | 14.08 |
| 1567 | NH1 | ARG | 18 | 27.066 | −10.416 | 13.686 | 1 | 11.96 |
| 1568 | NH2 | ARG | 18 | 27.288 | −8.133 | 13.831 | 1 | 12.39 |
| 1569 | C | ARG | 18 | 30.803 | −15.005 | 14.058 | 1 | 13.74 |
| 1570 | O | ARG | 18 | 30.472 | −15.233 | 12.895 | 1 | 14.97 |
| 1571 | N | GLY | 19 | 31.394 | −15.911 | 14.824 | 1 | 12.73 |
| 1572 | CA | GLY | 19 | 31.644 | −17.239 | 14.302 | 1 | 15 |
| 1573 | C | GLY | 19 | 30.429 | −18.107 | 14.559 | 1 | 15.71 |
| 1574 | O | GLY | 19 | 29.484 | −17.673 | 15.22 | 1 | 15.47 |
| 1575 | N | VAL | 20 | 30.425 | −19.32 | 14.021 | 1 | 15.37 |
| 1576 | CA | VAL | 20 | 29.307 | −20.226 | 14.254 | 1 | 15.29 |
| 1577 | CB | VAL | 20 | 28.879 | −20.964 | 12.965 | 1 | 15.36 |
| 1578 | CG1 | VAL | 20 | 27.688 | −21.861 | 13.259 | 1 | 15.17 |
| 1579 | CG2 | VAL | 20 | 28.509 | −19.963 | 11.887 | 1 | 15.91 |
| 1580 | C | VAL | 20 | 29.794 | −21.237 | 15.28 | 1 | 14.58 |
| 1581 | O | VAL | 20 | 30.701 | −22.024 | 15.007 | 1 | 15.85 |
| 1582 | N | ALA | 21 | 29.199 | −21.196 | 16.468 | 1 | 14.41 |
| 1583 | CA | ALA | 21 | 29.576 | −22.085 | 17.562 | 1 | 15.84 |
| 1584 | CB | ALA | 21 | 28.633 | −21.872 | 18.738 | 1 | 15.8 |
| 1585 | C | ALA | 21 | 29.587 | −23.557 | 17.161 | 1 | 15.84 |
| 1586 | O | ALA | 21 | 28.681 | −24.027 | 16.479 | 1 | 15.86 |
| 1587 | N | ALA | 22 | 30.617 | −24.278 | 17.595 | 1 | 16.29 |
| 1588 | CA | ALA | 22 | 30.745 | −25.698 | 17.284 | 1 | 17.26 |
| 1589 | CB | ALA | 22 | 32.207 | −26.123 | 17.368 | 1 | 16.29 |
| 1590 | C | ALA | 22 | 29.906 | −26.531 | 18.244 | 1 | 16.49 |
| 1591 | O | ALA | 22 | 29.684 | −26.144 | 19.389 | 1 | 15.92 |
| 1592 | N | PRO | 23 | 29.424 | −27.694 | 17.788 | 1 | 16.81 |
| 1593 | CD | PRO | 23 | 29.539 | −28.323 | 16.459 | 1 | 18.83 |
| 1594 | CA | PRO | 23 | 28.617 | −28.511 | 18.691 | 1 | 17.69 |
| 1595 | CB | PRO | 23 | 27.976 | −29.526 | 17.75 | 1 | 18.69 |
| 1596 | CG | PRO | 23 | 29.048 | −29.734 | 16.722 | 1 | 20.07 |
| 1597 | C | PRO | 23 | 29.465 | −29.179 | 19.765 | 1 | 17.87 |
| 1598 | O | PRO | 23 | 30.677 | −29.347 | 19.609 | 1 | 19.06 |
| 1599 | N | VAL | 24 | 28.818 | −29.541 | 20.864 | 1 | 18.55 |
| 1600 | CA | VAL | 24 | 29.487 | −30.235 | 21.954 | 1 | 19.75 |
| 1601 | CB | VAL | 24 | 28.75 | −30.013 | 23.287 | 1 | 18.36 |
| 1602 | CG1 | VAL | 24 | 29.383 | −30.856 | 24.383 | 1 | 18.57 |
| 1603 | CG2 | VAL | 24 | 28.795 | −28.537 | 23.663 | 1 | 18.3 |
| 1604 | C | VAL | 24 | 29.421 | −31.714 | 21.575 | 1 | 20.54 |
| 1605 | O | VAL | 24 | 28.345 | −32.231 | 21.281 | 1 | 20.96 |
| 1606 | N | GLU | 25 | 30.566 | −32.388 | 21.559 | 1 | 23.55 |
| 1607 | CA | GLU | 25 | 30.6 | −33.805 | 21.195 | 1 | 26.38 |
| 1608 | CB | GLU | 25 | 32.043 | −34.245 | 20.941 | 1 | 29.06 |
| 1609 | CG | GLU | 25 | 32.727 | −33.515 | 19.793 | 1 | 33.32 |
| 1610 | CD | GLU | 25 | 32.004 | −33.691 | 18.468 | 1 | 37.12 |
| 1611 | OE1 | GLU | 25 | 31.769 | −34.85 | 18.063 | 1 | 40 |
| 1612 | OE2 | GLU | 25 | 31.672 | −32.671 | 17.827 | 1 | 39.9 |
| 1613 | C | GLU | 25 | 29.963 | −34.698 | 22.261 | 1 | 27.5 |
| 1614 | O | GLU | 25 | 30.007 | −34.385 | 23.451 | 1 | 27.01 |
| 1615 | N | ARG | 26 | 29.372 | −35.81 | 21.825 | 1 | 28.61 |
| 1616 | CA | ARG | 26 | 28.717 | −36.751 | 22.734 | 1 | 30.45 |
| 1617 | CB | ARG | 26 | 28.353 | −38.05 | 22.003 | 1 | 32.87 |
| 1618 | CG | ARG | 26 | 27.305 | −37.896 | 20.92 | 1 | 36.02 |
| 1619 | CD | ARG | 26 | 26.893 | −39.246 | 20.336 | 1 | 38.94 |
| 1620 | NE | ARG | 26 | 26.162 | −40.084 | 21.288 | 1 | 40.63 |

TABLE 1-continued

| Atom | Atom Type | Residue | # | X | Y | Z | OCC | B |
|---|---|---|---|---|---|---|---|---|
| 1621 | CZ | ARG | 26 | 26.671 | −41.144 | 21.909 | 1 | 41.99 |
| 1622 | NH1 | ARG | 26 | 27.926 | −41.513 | 21.686 | 1 | 42.97 |
| 1623 | NH2 | ARG | 26 | 25.92 | −41.846 | 22.748 | 1 | 42.87 |
| 1624 | C | ARG | 26 | 29.58 | −37.104 | 23.937 | 1 | 30.62 |
| 1625 | O | ARG | 26 | 29.098 | −37.132 | 25.07 | 1 | 30.85 |
| 1626 | N | ALA | 27 | 30.855 | −37.374 | 23.68 | 1 | 30.39 |
| 1627 | CA | ALA | 27 | 31.798 | −37.751 | 24.726 | 1 | 31.59 |
| 1628 | CB | ALA | 27 | 33.164 | −38.035 | 24.108 | 1 | 30.42 |
| 1629 | C | ALA | 27 | 31.935 | −36.715 | 25.839 | 1 | 31.77 |
| 1630 | O | ALA | 27 | 32.285 | −37.06 | 26.966 | 1 | 32.11 |
| 1631 | N | GLN | 28 | 31.659 | −35.453 | 25.526 | 1 | 32.38 |
| 1632 | CA | GLN | 28 | 31.772 | −34.384 | 26.516 | 1 | 32.12 |
| 1633 | CB | GLN | 28 | 32.128 | −33.059 | 25.834 | 1 | 34.3 |
| 1634 | CG | GLN | 28 | 33.606 | −32.899 | 25.506 | 1 | 37.72 |
| 1635 | CD | GLN | 28 | 34.107 | −33.93 | 24.518 | 1 | 40.48 |
| 1636 | OE1 | GLN | 28 | 33.657 | −33.978 | 23.373 | 1 | 42.42 |
| 1637 | NE2 | GLN | 28 | 35.046 | −34.763 | 24.954 | 1 | 42.02 |
| 1638 | C | GLN | 28 | 30.522 | −34.192 | 27.367 | 1 | 31.02 |
| 1639 | O | GLN | 28 | 30.574 | −33.544 | 28.412 | 1 | 31.13 |
| 1640 | N | LEU | 29 | 29.4 | −34.747 | 26.923 | 1 | 30.35 |
| 1641 | CA | LEU | 29 | 28.154 | −34.618 | 27.668 | 1 | 30.66 |
| 1642 | CB | LEU | 29 | 27.019 | −35.33 | 26.928 | 1 | 30.02 |
| 1643 | CG | LEU | 29 | 26.648 | −34.761 | 25.556 | 1 | 29.49 |
| 1644 | CD1 | LEU | 29 | 25.625 | −35.666 | 24.893 | 1 | 28.77 |
| 1645 | CD2 | LEU | 29 | 26.098 | −33.345 | 25.71 | 1 | 28.09 |
| 1646 | C | LEU | 29 | 28.309 | −35.202 | 29.068 | 1 | 31.99 |
| 1647 | O | LEU | 29 | 28.822 | −36.309 | 29.236 | 1 | 32.11 |
| 1648 | N | GLY | 30 | 27.866 | −34.449 | 30.07 | 1 | 31.5 |
| 1649 | CA | GLY | 30 | 27.975 | −34.907 | 31.443 | 1 | 32.63 |
| 1650 | C | GLY | 30 | 29.406 | −34.861 | 31.952 | 1 | 32.27 |
| 1651 | O | GLY | 30 | 29.688 | −35.308 | 33.064 | 1 | 33.07 |
| 1652 | N | GLY | 31 | 30.308 | −34.317 | 31.139 | 1 | 32.2 |
| 1653 | CA | GLY | 31 | 31.708 | −34.231 | 31.525 | 1 | 31.78 |
| 1654 | C | GLY | 31 | 32.055 | −33.03 | 32.39 | 1 | 31.8 |
| 1655 | O | GLY | 31 | 31.297 | −32.06 | 32.443 | 1 | 31.3 |
| 1656 | N | PRO | 32 | 33.209 | −33.062 | 33.08 | 1 | 31.23 |
| 1657 | CD | PRO | 32 | 34.191 | −34.162 | 33.082 | 1 | 31.72 |
| 1658 | CA | PRO | 32 | 33.656 | −31.969 | 33.951 | 1 | 30.4 |
| 1659 | CB | PRO | 32 | 34.913 | −32.542 | 34.603 | 1 | 31.35 |
| 1660 | CG | PRO | 32 | 35.443 | −33.467 | 33.552 | 1 | 31.49 |
| 1661 | C | PRO | 32 | 33.921 | −30.641 | 33.239 | 1 | 29.57 |
| 1662 | O | PRO | 32 | 33.597 | −29.578 | 33.769 | 1 | 27.54 |
| 1663 | N | GLU | 33 | 34.512 | −30.7 | 32.048 | 1 | 28.28 |
| 1664 | CA | GLU | 33 | 34.803 | −29.485 | 31.293 | 1 | 28.13 |
| 1665 | CB | GLU | 33 | 35.585 | −29.82 | 30.021 | 1 | 30.35 |
| 1666 | CG | GLU | 33 | 35.953 | −28.604 | 29.183 | 1 | 34.97 |
| 1667 | CD | GLU | 33 | 36.739 | −28.965 | 27.934 | 1 | 38.66 |
| 1668 | OE1 | GLU | 33 | 36.222 | −29.75 | 27.108 | 1 | 40.43 |
| 1669 | OE2 | GLU | 33 | 37.873 | −28.46 | 27.776 | 1 | 40.26 |
| 1670 | C | GLU | 33 | 33.508 | −28.76 | 30.933 | 1 | 27.25 |
| 1671 | O | GLU | 33 | 33.423 | −27.535 | 31.031 | 1 | 25.41 |
| 1672 | N | LEU | 34 | 32.5 | −29.518 | 30.515 | 1 | 25.71 |
| 1673 | CA | LEU | 34 | 31.215 | −28.927 | 30.158 | 1 | 23.68 |
| 1674 | CB | LEU | 34 | 30.295 | −29.978 | 29.532 | 1 | 22.88 |
| 1675 | CG | LEU | 34 | 28.9 | −29.477 | 29.144 | 1 | 21.21 |
| 1676 | CD1 | LEU | 34 | 29.027 | −28.362 | 28.111 | 1 | 20.4 |
| 1677 | CD2 | LEU | 34 | 28.076 | −30.626 | 28.587 | 1 | 21.89 |
| 1678 | C | LEU | 34 | 30.568 | −28.363 | 31.415 | 1 | 23.97 |
| 1679 | O | LEU | 34 | 29.919 | −27.318 | 31.381 | 1 | 24.2 |
| 1680 | N | GLN | 35 | 30.754 | −29.061 | 32.529 | 1 | 24.3 |
| 1681 | CA | GLN | 35 | 30.194 | −28.628 | 33.802 | 1 | 25.2 |
| 1682 | CB | GLN | 35 | 30.503 | −29.658 | 34.888 | 1 | 28.28 |
| 1683 | CG | GLN | 35 | 29.92 | −29.313 | 36.245 | 1 | 33.88 |
| 1684 | CD | GLN | 35 | 30.543 | −30.128 | 37.361 | 1 | 37.75 |
| 1685 | OE1 | GLN | 35 | 30.589 | −31.359 | 37.297 | 1 | 40.85 |
| 1686 | NE2 | GLN | 35 | 31.027 | −29.445 | 38.393 | 1 | 39.91 |
| 1687 | C | GLN | 35 | 30.769 | −27.276 | 34.209 | 1 | 24.53 |
| 1688 | O | GLN | 35 | 30.05 | −26.407 | 34.703 | 1 | 24.62 |
| 1689 | N | ARG | 36 | 32.072 | −27.103 | 34.011 | 1 | 23.35 |
| 1690 | CA | ARG | 36 | 32.714 | −25.844 | 34.361 | 1 | 23.82 |
| 1691 | CB | ARG | 36 | 34.23 | −25.932 | 34.158 | 1 | 26.84 |
| 1692 | CG | ARG | 36 | 34.952 | −26.779 | 35.202 | 1 | 31.11 |
| 1693 | CD | ARG | 36 | 36.456 | −26.532 | 35.175 | 1 | 32.7 |
| 1694 | NE | ARG | 36 | 37.101 | −27.075 | 33.981 | 1 | 35.92 |
| 1695 | CZ | ARG | 36 | 37.341 | −28.367 | 33.78 | 1 | 36.41 |
| 1696 | NH1 | ARG | 36 | 36.991 | −29.261 | 34.696 | 1 | 36.97 |
| 1697 | NH2 | ARG | 36 | 37.935 | −28.767 | 32.664 | 1 | 37.48 |
| 1698 | C | ARG | 36 | 32.143 | −24.72 | 33.509 | 1 | 22.09 |
| 1699 | O | ARG | 36 | 31.872 | −23.625 | 34.005 | 1 | 21.7 |
| 1700 | N | LEU | 37 | 31.952 | −24.998 | 32.224 | 1 | 21.81 |
| 1701 | CA | LEU | 37 | 31.412 | −24.001 | 31.308 | 1 | 20.69 |
| 1702 | CB | LEU | 37 | 31.435 | −24.532 | 29.873 | 1 | 19.53 |
| 1703 | CG | LEU | 37 | 30.76 | −23.638 | 28.829 | 1 | 18.77 |
| 1704 | CD1 | LEU | 37 | 31.413 | −22.26 | 28.817 | 1 | 20.93 |
| 1705 | CD2 | LEU | 37 | 30.868 | −24.295 | 27.463 | 1 | 20 |
| 1706 | C | LEU | 37 | 29.988 | −23.589 | 31.671 | 1 | 19.91 |
| 1707 | O | LEU | 37 | 29.685 | −22.402 | 31.761 | 1 | 18.96 |
| 1708 | N | THR | 38 | 29.109 | −24.567 | 31.87 | 1 | 19.05 |
| 1709 | CA | THR | 38 | 27.729 | −24.248 | 32.206 | 1 | 19.65 |
| 1710 | CB | THR | 38 | 26.847 | −25.513 | 32.243 | 1 | 20.71 |
| 1711 | OG1 | THR | 38 | 27.341 | −26.417 | 33.233 | 1 | 23.67 |
| 1712 | CG2 | THR | 38 | 26.854 | −26.199 | 30.889 | 1 | 19.51 |
| 1713 | C | THR | 38 | 27.638 | −23.522 | 33.542 | 1 | 19.68 |
| 1714 | O | THR | 38 | 26.826 | −22.615 | 33.706 | 1 | 19.31 |
| 1715 | N | GLN | 39 | 28.48 | −23.911 | 34.494 | 1 | 20.35 |
| 1716 | CA | GLN | 39 | 28.479 | −23.268 | 35.801 | 1 | 21.73 |
| 1717 | CB | GLN | 39 | 29.437 | −23.991 | 36.752 | 1 | 25.3 |
| 1718 | CG | GLN | 39 | 28.853 | −25.25 | 37.364 | 1 | 32.84 |
| 1719 | CD | GLN | 39 | 27.654 | −24.954 | 38.248 | 1 | 36.66 |
| 1720 | OE1 | GLN | 39 | 27.768 | −24.245 | 39.252 | 1 | 40.11 |
| 1721 | NE2 | GLN | 39 | 26.496 | −25.49 | 37.877 | 1 | 38.47 |
| 1722 | C | GLN | 39 | 28.881 | −21.803 | 35.688 | 1 | 20.41 |
| 1723 | O | GLN | 39 | 28.271 | −20.934 | 36.305 | 1 | 18.92 |
| 1724 | N | ARG | 40 | 29.909 | −21.535 | 34.891 | 1 | 20.87 |
| 1725 | CA | ARG | 40 | 30.386 | −20.172 | 34.707 | 1 | 20.18 |
| 1726 | CB | ARG | 40 | 31.724 | −20.184 | 33.956 | 1 | 23.4 |
| 1727 | CG | ARG | 40 | 32.362 | −18.809 | 33.777 | 1 | 26.84 |
| 1728 | CD | ARG | 40 | 32.406 | −18.028 | 35.087 | 1 | 31.49 |
| 1729 | NE | ARG | 40 | 33.222 | −18.673 | 36.116 | 1 | 34.34 |
| 1730 | CZ | ARG | 40 | 34.548 | −18.772 | 36.074 | 1 | 37.13 |
| 1731 | NH1 | ARG | 40 | 35.225 | −18.269 | 35.049 | 1 | 38 |
| 1732 | NH2 | ARG | 40 | 35.201 | −19.366 | 37.064 | 1 | 36.64 |
| 1733 | C | ARG | 40 | 29.353 | −19.348 | 33.944 | 1 | 18.89 |
| 1734 | O | ARG | 40 | 29.103 | −18.184 | 34.26 | 1 | 17.95 |
| 1735 | N | LEU | 41 | 28.742 | −19.964 | 32.939 | 1 | 18.2 |
| 1736 | CA | LEU | 41 | 27.737 | −19.29 | 32.134 | 1 | 16.89 |
| 1737 | CB | LEU | 41 | 27.237 | −20.246 | 31.045 | 1 | 18.67 |
| 1738 | CG | LEU | 41 | 26.342 | −19.721 | 29.924 | 1 | 19.75 |
| 1739 | CD1 | LEU | 41 | 27.062 | −18.641 | 29.129 | 1 | 18.32 |
| 1740 | CD2 | LEU | 41 | 25.969 | −20.889 | 29.018 | 1 | 19.73 |
| 1741 | C | LEU | 41 | 26.576 | −18.837 | 33.018 | 1 | 16.49 |
| 1742 | O | LEU | 41 | 26.138 | −17.688 | 32.955 | 1 | 15.82 |
| 1743 | N | VAL | 42 | 26.082 | −19.741 | 33.858 | 1 | 16.36 |
| 1744 | CA | VAL | 42 | 24.969 | −19.413 | 34.739 | 1 | 16.73 |
| 1745 | CB | VAL | 42 | 24.451 | −20.679 | 35.46 | 1 | 19.32 |
| 1746 | CG1 | VAL | 42 | 23.354 | −20.312 | 36.447 | 1 | 19.62 |
| 1747 | CG2 | VAL | 42 | 23.918 | −21.667 | 34.431 | 1 | 19.87 |
| 1748 | C | VAL | 42 | 25.343 | −18.353 | 35.773 | 1 | 15.9 |
| 1749 | O | VAL | 42 | 24.544 | −17.471 | 36.086 | 1 | 15.4 |
| 1750 | N | GLN | 43 | 26.565 | −18.431 | 36.291 | 1 | 17.55 |
| 1751 | CA | GLN | 43 | 27.024 | −17.474 | 37.29 | 1 | 19.53 |
| 1752 | CB | GLN | 43 | 28.409 | −17.871 | 37.799 | 1 | 22.28 |
| 1753 | CG | GLN | 43 | 28.764 | −17.237 | 39.127 | 1 | 29.22 |
| 1754 | CD | GLN | 43 | 30.205 | −17.471 | 39.515 | 1 | 32.69 |
| 1755 | OE1 | GLN | 43 | 30.752 | −18.555 | 39.304 | 1 | 36.34 |
| 1756 | NE2 | GLN | 43 | 30.829 | −16.456 | 40.099 | 1 | 34.32 |
| 1757 | C | GLN | 43 | 27.082 | −16.058 | 36.719 | 1 | 18.83 |
| 1758 | O | GLN | 43 | 26.652 | −15.1 | 37.363 | 1 | 18.67 |
| 1759 | N | VAL | 44 | 27.622 | −15.929 | 35.512 | 1 | 17.32 |
| 1760 | CA | VAL | 44 | 27.722 | −14.625 | 34.872 | 1 | 17.04 |
| 1761 | CB | VAL | 44 | 28.547 | −14.7 | 33.573 | 1 | 16.97 |
| 1762 | CG1 | VAL | 44 | 28.478 | −13.372 | 32.838 | 1 | 16.22 |
| 1763 | CG2 | VAL | 44 | 29.996 | −15.056 | 33.901 | 1 | 18.31 |
| 1764 | C | VAL | 44 | 26.333 | −14.1 | 34.551 | 1 | 17.1 |
| 1765 | O | VAL | 44 | 26.033 | −12.927 | 34.764 | 1 | 16.95 |
| 1766 | N | MET | 45 | 25.482 | −14.978 | 34.036 | 1 | 16.28 |
| 1767 | CA | MET | 45 | 24.123 | −14.585 | 33.7 | 1 | 16.75 |
| 1768 | CB | MET | 45 | 23.362 | −15.784 | 33.132 | 1 | 16.89 |
| 1769 | CG | MET | 45 | 21.927 | −15.48 | 32.758 | 1 | 18.25 |
| 1770 | SD | MET | 45 | 21.141 | −16.91 | 31.997 | 1 | 21.2 |
| 1771 | CE | MET | 45 | 20.905 | −17.951 | 33.421 | 1 | 20.96 |
| 1772 | C | MET | 45 | 23.4 | −14.037 | 34.927 | 1 | 17.39 |

TABLE 1-continued

| Atom | Atom Type | Residue | # | X | Y | Z | OCC | B |
|---|---|---|---|---|---|---|---|---|
| 1773 | O | MET | 45 | 22.739 | −13.003 | 34.861 | 1 | 16.96 |
| 1774 | N | ARG | 46 | 23.532 | −14.728 | 36.054 | 1 | 18.16 |
| 1775 | CA | ARG | 46 | 22.88 | −14.296 | 37.283 | 1 | 18.73 |
| 1776 | CB | ARG | 46 | 22.938 | −15.417 | 38.323 | 1 | 19.66 |
| 1777 | CG | ARG | 46 | 21.991 | −16.557 | 37.995 | 1 | 18.55 |
| 1778 | CD | ARG | 46 | 22.113 | −17.725 | 38.955 | 1 | 21.51 |
| 1779 | NE | ARG | 46 | 21.043 | −18.689 | 38.716 | 1 | 20.45 |
| 1780 | CZ | ARG | 46 | 20.997 | −19.91 | 39.235 | 1 | 23.11 |
| 1781 | NH1 | ARG | 46 | 21.968 | −20.336 | 40.032 | 1 | 23.86 |
| 1782 | NH2 | ARG | 46 | 19.974 | −20.703 | 38.958 | 1 | 21.92 |
| 1783 | C | ARG | 46 | 23.465 | −13.007 | 37.853 | 1 | 20.44 |
| 1784 | O | ARG | 46 | 22.733 | −12.162 | 38.363 | 1 | 21.53 |
| 1785 | N | ARG | 47 | 24.782 | −12.854 | 37.758 | 1 | 20.84 |
| 1786 | CA | ARG | 47 | 25.444 | −11.655 | 38.26 | 1 | 21.3 |
| 1787 | CB | ARG | 47 | 26.961 | −11.808 | 38.145 | 1 | 23.83 |
| 1788 | CG | ARG | 47 | 27.758 | −10.633 | 38.7 | 1 | 30.76 |
| 1789 | CD | ARG | 47 | 27.611 | −10.533 | 40.212 | 1 | 36.64 |
| 1790 | NE | ARG | 47 | 28.428 | −9.459 | 40.77 | 1 | 42.34 |
| 1791 | CZ | ARG | 47 | 28.546 | −9.206 | 42.071 | 1 | 44.62 |
| 1792 | NH1 | ARG | 47 | 27.897 | −9.95 | 42.958 | 1 | 46.54 |
| 1793 | NH2 | ARG | 47 | 29.317 | −8.209 | 42.486 | 1 | 46.9 |
| 1794 | C | ARG | 47 | 24.995 | −10.428 | 37.471 | 1 | 20.52 |
| 1795 | O | ARG | 47 | 24.695 | −9.381 | 38.044 | 1 | 19.32 |
| 1796 | N | ARG | 48 | 24.945 | −10.57 | 36.15 | 1 | 18.05 |
| 1797 | CA | ARG | 48 | 24.548 | −9.48 | 35.264 | 1 | 19.7 |
| 1798 | CB | ARG | 48 | 25.112 | −9.723 | 33.861 | 1 | 18.82 |
| 1799 | CG | ARG | 48 | 26.619 | −9.529 | 33.76 | 1 | 21.56 |
| 1800 | CD | ARG | 48 | 26.982 | −8.093 | 34.1 | 1 | 21.98 |
| 1801 | NE | ARG | 48 | 26.222 | −7.165 | 33.268 | 1 | 22.97 |
| 1802 | CZ | ARG | 48 | 25.648 | −6.053 | 33.712 | 1 | 24.06 |
| 1803 | NH1 | ARG | 48 | 25.747 | −5.717 | 34.99 | 1 | 26.31 |
| 1804 | NH2 | ARG | 48 | 24.962 | −5.283 | 32.881 | 1 | 26.87 |
| 1805 | C | ARG | 48 | 23.037 | −9.308 | 35.181 | 1 | 19.86 |
| 1806 | O | ARG | 48 | 22.542 | −8.315 | 34.649 | 1 | 20.01 |
| 1807 | N | ARG | 49 | 22.31 | −10.284 | 35.71 | 1 | 20.31 |
| 1808 | CA | ARG | 49 | 20.857 | −10.253 | 35.69 | 1 | 20.75 |
| 1809 | CB | ARG | 49 | 20.341 | −9.083 | 36.53 | 1 | 24.11 |
| 1810 | CG | ARG | 49 | 20.731 | −9.198 | 37.995 | 1 | 28.11 |
| 1811 | CD | ARG | 49 | 20.272 | −8 | 38.795 | 1 | 32.72 |
| 1812 | NE | ARG | 49 | 20.725 | −8.083 | 40.18 | 1 | 36.97 |
| 1813 | CZ | ARG | 49 | 20.525 | −7.134 | 41.088 | 1 | 39.4 |
| 1814 | NH1 | ARG | 49 | 19.877 | −6.025 | 40.758 | 1 | 41.15 |
| 1815 | NH2 | ARG | 49 | 20.975 | −7.292 | 42.327 | 1 | 40.86 |
| 1816 | C | ARG | 49 | 20.301 | −10.176 | 34.276 | 1 | 20.56 |
| 1817 | O | ARG | 49 | 19.256 | −9.569 | 34.036 | 1 | 20.06 |
| 1818 | N | CYS | 50 | 21.016 | −10.773 | 33.329 | 1 | 18.96 |
| 1819 | CA | CYS | 50 | 20.529 | −10.8 | 31.959 | 1 | 18.9 |
| 1820 | CB | CYS | 50 | 21.694 | −10.816 | 30.957 | 1 | 20.34 |
| 1821 | SG | CYS | 50 | 23.024 | −11.984 | 31.281 | 1 | 19.32 |
| 1822 | C | CYS | 50 | 19.7 | −12.083 | 31.898 | 1 | 19.83 |
| 1823 | O | CYS | 50 | 20.038 | −13.076 | 32.535 | 1 | 21.96 |
| 1824 | N | VAL | 51 | 18.599 | −12.056 | 31.161 | 1 | 20.3 |
| 1825 | CA | VAL | 51 | 17.72 | −13.216 | 31.077 | 1 | 17.69 |
| 1826 | CB | VAL | 51 | 16.388 | −12.823 | 30.408 | 1 | 18.66 |
| 1827 | CG1 | VAL | 51 | 15.445 | −14.006 | 30.385 | 1 | 19.57 |
| 1828 | CG2 | VAL | 51 | 15.757 | −11.659 | 31.167 | 1 | 20.92 |
| 1829 | C | VAL | 51 | 18.331 | −14.415 | 30.349 | 1 | 17.82 |
| 1830 | O | VAL | 51 | 17.928 | −15.555 | 30.568 | 1 | 17.59 |
| 1831 | N | GLY | 52 | 19.308 | −14.16 | 29.488 | 1 | 15.8 |
| 1832 | CA | GLY | 52 | 19.938 | −15.247 | 28.76 | 1 | 15.2 |
| 1833 | C | GLY | 52 | 21.389 | −14.938 | 28.475 | 1 | 14.66 |
| 1834 | O | GLY | 52 | 21.801 | −13.783 | 28.553 | 1 | 15.81 |
| 1835 | N | LEU | 53 | 22.164 | −15.966 | 28.153 | 1 | 12.48 |
| 1836 | CA | LEU | 53 | 23.579 | −15.788 | 27.851 | 1 | 13.32 |
| 1837 | CB | LEU | 53 | 24.383 | −15.609 | 29.143 | 1 | 12.63 |
| 1838 | CG | LEU | 53 | 25.827 | −15.119 | 28.989 | 1 | 13.8 |
| 1839 | CD1 | LEU | 53 | 25.827 | −13.725 | 28.372 | 1 | 13.33 |
| 1840 | CD2 | LEU | 53 | 26.505 | −15.087 | 30.355 | 1 | 13.78 |
| 1841 | C | LEU | 53 | 24.082 | −17.005 | 27.088 | 1 | 13.86 |
| 1842 | O | LEU | 53 | 23.617 | −18.127 | 27.317 | 1 | 15.19 |
| 1843 | N | SER | 54 | 25.028 | −16.784 | 26.18 | 1 | 12.81 |
| 1844 | CA | SER | 54 | 25.577 | −17.871 | 25.376 | 1 | 12.57 |
| 1845 | CB | SER | 54 | 25.302 | −17.616 | 23.896 | 1 | 13.11 |
| 1846 | OG | SER | 54 | 26.062 | −16.516 | 23.428 | 1 | 12.98 |
| 1847 | C | SER | 54 | 27.077 | −18.047 | 25.581 | 1 | 13.32 |
| 1848 | O | SER | 54 | 27.785 | −17.095 | 25.914 | 1 | 12.93 |
| 1849 | N | ALA | 55 | 27.556 | −19.267 | 25.363 | 1 | 12.81 |
| 1850 | CA | ALA | 55 | 28.97 | −19.58 | 25.529 | 1 | 12.9 |
| 1851 | CB | ALA | 55 | 29.223 | −21.045 | 25.175 | 1 | 14.5 |
| 1852 | C | ALA | 55 | 29.916 | −18.673 | 24.727 | 1 | 12.27 |
| 1853 | O | ALA | 55 | 30.95 | −18.257 | 25.239 | 1 | 12.83 |
| 1854 | N | PRO | 56 | 29.582 | −18.361 | 23.46 | 1 | 11.54 |
| 1855 | CD | PRO | 56 | 28.503 | −18.893 | 22.604 | 1 | 11.92 |
| 1856 | CA | PRO | 56 | 30.48 | −17.494 | 22.687 | 1 | 12.32 |
| 1857 | CB | PRO | 56 | 29.751 | −17.342 | 21.356 | 1 | 12.05 |
| 1858 | CG | PRO | 56 | 29.068 | −18.682 | 21.209 | 1 | 12.25 |
| 1859 | C | PRO | 56 | 30.74 | −16.149 | 23.364 | 1 | 11.66 |
| 1860 | O | PRO | 56 | 31.814 | −15.557 | 23.204 | 1 | 13.19 |
| 1861 | N | GLN | 57 | 29.756 | −15.672 | 24.119 | 1 | 10.82 |
| 1862 | CA | GLN | 57 | 29.88 | −14.398 | 24.815 | 1 | 12.78 |
| 1863 | CB | GLN | 57 | 28.524 | −13.969 | 25.354 | 1 | 13.4 |
| 1864 | CG | GLN | 57 | 27.556 | −13.606 | 24.244 | 1 | 15.03 |
| 1865 | CD | GLN | 57 | 26.187 | −13.282 | 24.771 | 1 | 15.14 |
| 1866 | OE1 | GLN | 57 | 25.346 | −14.17 | 24.943 | 1 | 14.62 |
| 1867 | NE2 | GLN | 57 | 25.953 | −12.007 | 25.054 | 1 | 13.41 |
| 1868 | C | GLN | 57 | 30.912 | −14.451 | 25.93 | 1 | 13.99 |
| 1869 | O | GLN | 57 | 31.383 | −13.415 | 26.403 | 1 | 12.64 |
| 1870 | N | LEU | 58 | 31.257 | −15.664 | 26.352 | 1 | 13.8 |
| 1871 | CA | LEU | 58 | 32.279 | −15.843 | 27.375 | 1 | 16.14 |
| 1872 | CB | LEU | 58 | 31.842 | −16.875 | 28.418 | 1 | 15.66 |
| 1873 | CG | LEU | 58 | 30.659 | −16.467 | 29.3 | 1 | 17.53 |
| 1874 | CD1 | LEU | 58 | 30.474 | −17.496 | 30.405 | 1 | 19.96 |
| 1875 | CD2 | LEU | 58 | 30.906 | −15.094 | 29.898 | 1 | 18.79 |
| 1876 | C | LEU | 58 | 33.566 | −16.3 | 26.695 | 1 | 16.81 |
| 1877 | O | LEU | 58 | 34.482 | −16.805 | 27.346 | 1 | 19.18 |
| 1878 | N | GLY | 59 | 33.619 | −16.124 | 25.376 | 1 | 16.59 |
| 1879 | CA | GLY | 59 | 34.796 | −16.497 | 24.609 | 1 | 15.52 |
| 1880 | C | GLY | 59 | 34.912 | −17.96 | 24.229 | 1 | 15.64 |
| 1881 | O | GLY | 59 | 35.952 | −18.389 | 23.728 | 1 | 16.43 |
| 1882 | N | VAL | 60 | 33.847 | −18.725 | 24.45 | 1 | 14.34 |
| 1883 | CA | VAL | 60 | 33.843 | −20.158 | 24.148 | 1 | 15.56 |
| 1884 | CB | VAL | 60 | 33.372 | −20.961 | 25.378 | 1 | 15.31 |
| 1885 | CG1 | VAL | 60 | 33.353 | −22.445 | 25.064 | 1 | 15.58 |
| 1886 | CG2 | VAL | 60 | 34.289 | −20.672 | 26.56 | 1 | 17.67 |
| 1887 | C | VAL | 60 | 32.925 | −20.455 | 22.959 | 1 | 14.99 |
| 1888 | O | VAL | 60 | 31.702 | −20.411 | 23.083 | 1 | 14.7 |
| 1889 | N | PRO | 61 | 33.512 | −20.78 | 21.794 | 1 | 15.7 |
| 1890 | CD | PRO | 61 | 34.966 | −20.907 | 21.572 | 1 | 16.39 |
| 1891 | CA | PRO | 61 | 32.774 | −21.082 | 20.563 | 1 | 16.39 |
| 1892 | CB | PRO | 61 | 33.842 | −20.922 | 19.491 | 1 | 18.09 |
| 1893 | CG | PRO | 61 | 35.039 | −21.503 | 20.17 | 1 | 18.21 |
| 1894 | C | PRO | 61 | 32.125 | −22.464 | 20.533 | 1 | 16.52 |
| 1895 | O | PRO | 61 | 32.419 | −23.281 | 19.656 | 1 | 17.57 |
| 1896 | N | ARG | 62 | 31.237 | −22.709 | 21.489 | 1 | 15.41 |
| 1897 | CA | ARG | 62 | 30.536 | −23.983 | 21.592 | 1 | 15.06 |
| 1898 | CB | ARG | 62 | 31.038 | −24.764 | 22.806 | 1 | 18.35 |
| 1899 | CG | ARG | 62 | 32.547 | −24.962 | 22.824 | 1 | 21.57 |
| 1900 | CD | ARG | 62 | 32.994 | −25.718 | 24.06 | 1 | 25.77 |
| 1901 | NE | ARG | 62 | 32.679 | −27.141 | 23.972 | 1 | 28.14 |
| 1902 | CZ | ARG | 62 | 32.805 | −28 | 24.98 | 1 | 28.39 |
| 1903 | NH1 | ARG | 62 | 33.237 | −27.584 | 26.164 | 1 | 29.19 |
| 1904 | NH2 | ARG | 62 | 32.502 | −29.277 | 24.801 | 1 | 30.6 |
| 1905 | C | ARG | 62 | 29.041 | −23.714 | 21.719 | 1 | 14.67 |
| 1906 | O | ARG | 62 | 28.625 | −22.689 | 22.275 | 1 | 13.49 |
| 1907 | N | GLN | 63 | 28.239 | −24.643 | 21.211 | 1 | 14.12 |
| 1908 | CA | GLN | 63 | 26.787 | −24.509 | 21.227 | 1 | 14.93 |
| 1909 | CB | GLN | 63 | 26.174 | −25.435 | 20.173 | 1 | 13.81 |
| 1910 | CG | GLN | 63 | 26.686 | −25.149 | 18.76 | 1 | 14.14 |
| 1911 | CD | GLN | 63 | 26.154 | −26.101 | 17.714 | 1 | 14.98 |
| 1912 | OE1 | GLN | 63 | 26.677 | −26.186 | 16.602 | 1 | 17.54 |
| 1913 | NE2 | GLN | 63 | 25.111 | −26.853 | 18.059 | 1 | 13.45 |
| 1914 | C | GLN | 63 | 26.172 | −24.784 | 22.59 | 1 | 15.37 |
| 1915 | O | GLN | 63 | 25.623 | −25.862 | 22.839 | 1 | 15.83 |
| 1916 | N | VAL | 64 | 26.266 | −23.791 | 23.468 | 1 | 13.65 |
| 1917 | CA | VAL | 64 | 25.718 | −23.886 | 24.811 | 1 | 13.59 |
| 1918 | CB | VAL | 64 | 26.806 | −24.263 | 25.839 | 1 | 13.29 |
| 1919 | CG1 | VAL | 64 | 26.186 | −24.402 | 27.228 | 1 | 13.75 |
| 1920 | CG2 | VAL | 64 | 27.496 | −25.555 | 25.422 | 1 | 14.36 |
| 1921 | C | VAL | 64 | 25.147 | −22.525 | 25.184 | 1 | 14.2 |
| 1922 | O | VAL | 64 | 25.787 | −21.49 | 24.965 | 1 | 14.43 |
| 1923 | N | LEU | 65 | 23.932 | −22.527 | 25.715 | 1 | 13.06 |
| 1924 | CA | LEU | 65 | 23.284 | −21.295 | 26.132 | 1 | 13.31 |

TABLE 1-continued

| Atom | Atom Type | Residue | # | X | Y | Z | OCC | B |
|---|---|---|---|---|---|---|---|---|
| 1925 | CB | LEU | 65 | 22.389 | −20.747 | 25.007 | 1 | 14.58 |
| 1926 | CG | LEU | 65 | 21.241 | −21.612 | 24.475 | 1 | 12.78 |
| 1927 | CD1 | LEU | 65 | 20.055 | −21.5 | 25.411 | 1 | 14.97 |
| 1928 | CD2 | LEU | 65 | 20.84 | −21.152 | 23.076 | 1 | 15.62 |
| 1929 | C | LEU | 65 | 22.472 | −21.55 | 27.394 | 1 | 14.14 |
| 1930 | O | LEU | 65 | 22.118 | −22.691 | 27.704 | 1 | 14.09 |
| 1931 | N | ALA | 66 | 22.199 | −20.485 | 28.135 | 1 | 13.62 |
| 1932 | CA | ALA | 66 | 21.427 | −20.594 | 29.358 | 1 | 14.41 |
| 1933 | CB | ALA | 66 | 22.346 | −20.488 | 30.571 | 1 | 15.44 |
| 1934 | C | ALA | 66 | 20.39 | −19.483 | 29.377 | 1 | 15.07 |
| 1935 | O | ALA | 66 | 20.583 | −18.429 | 28.769 | 1 | 13.5 |
| 1936 | N | LEU | 67 | 19.28 | −19.742 | 30.057 | 1 | 14.32 |
| 1937 | CA | LEU | 67 | 18.191 | −18.782 | 30.184 | 1 | 15.82 |
| 1938 | CB | LEU | 67 | 17.133 | −18.988 | 29.091 | 1 | 22.29 |
| 1939 | CG | LEU | 67 | 17.284 | −18.273 | 27.745 | 1 | 26.47 |
| 1940 | CD1 | LEU | 67 | 18.278 | −19.008 | 26.871 | 1 | 29.44 |
| 1941 | CD2 | LEU | 67 | 15.926 | −18.219 | 27.06 | 1 | 27.75 |
| 1942 | C | LEU | 67 | 17.528 | −18.968 | 31.537 | 1 | 15.16 |
| 1943 | O | LEU | 67 | 17.39 | −20.094 | 32.02 | 1 | 15.38 |
| 1944 | N | GLU | 68 | 17.116 | −17.861 | 32.138 | 1 | 15.06 |
| 1945 | CA | GLU | 68 | 16.448 | −17.896 | 33.432 | 1 | 15.99 |
| 1946 | CB | GLU | 68 | 17.446 | −18.256 | 34.539 | 1 | 17.48 |
| 1947 | CG | GLU | 68 | 16.853 | −18.245 | 35.944 | 1 | 19.22 |
| 1948 | CD | GLU | 68 | 17.897 | −18.488 | 37.021 | 1 | 21.87 |
| 1949 | OE1 | GLU | 68 | 18.919 | −17.772 | 37.033 | 1 | 23.19 |
| 1950 | OE2 | GLU | 68 | 17.696 | −19.391 | 37.86 | 1 | 23.5 |
| 1951 | C | GLU | 68 | 15.828 | −16.54 | 33.722 | 1 | 16.06 |
| 1952 | O | GLU | 68 | 16.473 | −15.502 | 33.552 | 1 | 15.52 |
| 1953 | N | LEU | 69 | 14.566 | −16.543 | 34.135 | 1 | 16.71 |
| 1954 | CA | LEU | 69 | 13.892 | −15.299 | 34.473 | 1 | 18.1 |
| 1955 | CB | LEU | 69 | 12.898 | −14.889 | 33.38 | 1 | 18.1 |
| 1956 | CG | LEU | 69 | 12.139 | −13.584 | 33.658 | 1 | 18.35 |
| 1957 | CD1 | LEU | 69 | 13.124 | −12.458 | 33.965 | 1 | 21.79 |
| 1958 | CD2 | LEU | 69 | 11.279 | −13.222 | 32.461 | 1 | 21.44 |
| 1959 | C | LEU | 69 | 13.165 | −15.456 | 35.801 | 1 | 20.02 |
| 1960 | O | LEU | 69 | 12.003 | −15.873 | 35.847 | 1 | 18.93 |
| 1961 | N | PRO | 70 | 13.854 | −15.139 | 36.909 | 1 | 21.26 |
| 1962 | CD | PRO | 70 | 15.277 | −14.767 | 36.991 | 1 | 22.93 |
| 1963 | CA | PRO | 70 | 13.27 | −15.244 | 38.248 | 1 | 23.05 |
| 1964 | CB | PRO | 70 | 14.421 | −14.821 | 39.161 | 1 | 23.82 |
| 1965 | CG | PRO | 70 | 15.636 | −15.224 | 38.38 | 1 | 22.77 |
| 1966 | C | PRO | 70 | 12.075 | −14.307 | 38.366 | 1 | 23.87 |
| 1967 | O | PRO | 70 | 11.974 | −13.324 | 37.632 | 1 | 22.48 |
| 1968 | N | GLU | 71 | 11.175 | −14.611 | 39.294 | 1 | 25.22 |
| 1969 | CA | GLU | 71 | 9.99 | −13.792 | 39.499 | 1 | 27.36 |
| 1970 | CB | GLU | 71 | 9.127 | −14.405 | 40.604 | 1 | 29.95 |
| 1971 | CG | GLU | 71 | 7.821 | −13.678 | 40.868 | 1 | 33.99 |
| 1972 | CD | GLU | 71 | 7.011 | −14.338 | 41.969 | 1 | 37.82 |
| 1973 | OE1 | GLU | 71 | 6.629 | −15.516 | 41.802 | 1 | 39.95 |
| 1974 | OE2 | GLU | 71 | 6.759 | −13.682 | 43.004 | 1 | 40.51 |
| 1975 | C | GLU | 71 | 10.35 | −12.347 | 39.855 | 1 | 26.77 |
| 1976 | O | GLU | 71 | 9.803 | −11.407 | 39.278 | 1 | 26.99 |
| 1977 | N | ALA | 72 | 11.274 | −12.176 | 40.797 | 1 | 28.42 |
| 1978 | CA | ALA | 72 | 11.698 | −10.846 | 41.235 | 1 | 29.44 |
| 1979 | CB | ALA | 72 | 12.8 | −10.966 | 42.282 | 1 | 29.45 |
| 1980 | C | ALA | 72 | 12.177 | −9.985 | 40.072 | 1 | 29.63 |
| 1981 | O | ALA | 72 | 11.686 | −8.874 | 39.867 | 1 | 30.25 |
| 1982 | N | LEU | 73 | 13.14 | −10.498 | 39.314 | 1 | 30.6 |
| 1983 | CA | LEU | 73 | 13.669 | −9.767 | 38.171 | 1 | 30.63 |
| 1984 | CB | LEU | 73 | 14.726 | −10.608 | 37.45 | 1 | 30.41 |
| 1985 | CG | LEU | 73 | 15.396 | −9.98 | 36.225 | 1 | 30.46 |
| 1986 | CD1 | LEU | 73 | 16.043 | −8.658 | 36.609 | 1 | 28.21 |
| 1987 | CD2 | LEU | 73 | 16.431 | −10.945 | 35.663 | 1 | 28.89 |
| 1988 | C | LEU | 73 | 12.525 | −9.444 | 37.22 | 1 | 30.43 |
| 1989 | O | LEU | 73 | 12.498 | −8.388 | 36.589 | 1 | 31.44 |
| 1990 | N | CYS | 74 | 11.571 | −10.363 | 37.137 | 1 | 31.47 |
| 1991 | CA | CYS | 74 | 10.417 | −10.198 | 36.267 | 1 | 30.26 |
| 1992 | CB | CYS | 74 | 9.649 | −11.519 | 36.191 | 1 | 31.61 |
| 1993 | SG | CYS | 74 | 8.588 | −11.68 | 34.753 | 1 | 28.13 |
| 1994 | C | CYS | 74 | 9.497 | −9.078 | 36.758 | 1 | 31.5 |
| 1995 | O | CYS | 74 | 8.985 | −8.293 | 35.962 | 1 | 31.07 |
| 1996 | N | ARG | 75 | 9.292 | −9.005 | 38.072 | 1 | 32.63 |
| 1997 | CA | ARG | 75 | 8.435 | −7.975 | 38.66 | 1 | 33.97 |
| 1998 | CB | ARG | 75 | 8.072 | −8.34 | 40.101 | 1 | 34.76 |
| 1999 | CG | ARG | 75 | 7.145 | −9.533 | 40.229 | 1 | 38.15 |
| 2000 | CD | ARG | 75 | 6.757 | −9.76 | 41.681 | 1 | 41.12 |
| 2001 | NE | ARG | 75 | 5.8 | −10.852 | 41.83 | 1 | 44.27 |
| 2002 | CZ | ARG | 75 | 5.29 | −11.243 | 42.994 | 1 | 45.75 |
| 2003 | NH1 | ARG | 75 | 5.644 | −10.628 | 44.115 | 1 | 46.24 |
| 2004 | NH2 | ARG | 75 | 4.424 | −12.248 | 43.039 | 1 | 46.77 |
| 2005 | C | ARG | 75 | 9.122 | −6.616 | 38.644 | 1 | 34.76 |
| 2006 | O | ARG | 75 | 8.532 | −5.597 | 39.004 | 1 | 34.77 |
| 2007 | N | GLU | 76 | 10.381 | −6.615 | 38.226 | 1 | 34.84 |
| 2008 | CA | GLU | 76 | 11.167 | −5.396 | 38.144 | 1 | 35.13 |
| 2009 | CB | GLU | 76 | 12.626 | −5.77 | 37.882 | 1 | 37.02 |
| 2010 | CG | GLU | 76 | 13.655 | −4.768 | 38.347 | 1 | 38.94 |
| 2011 | CD | GLU | 76 | 15.058 | −5.35 | 38.328 | 1 | 39.59 |
| 2012 | OE1 | GLU | 76 | 15.325 | −6.289 | 39.111 | 1 | 39.09 |
| 2013 | OE2 | GLU | 76 | 15.888 | −4.876 | 37.526 | 1 | 40.96 |
| 2014 | C | GLU | 76 | 10.601 | −4.559 | 36.995 | 1 | 35.04 |
| 2015 | O | GLU | 76 | 10.788 | −3.344 | 36.938 | 1 | 34.02 |
| 2016 | N | CYS | 77 | 9.898 | −5.23 | 36.085 | 1 | 34.05 |
| 2017 | CA | CYS | 77 | 9.287 | −4.58 | 34.93 | 1 | 34.16 |
| 2018 | CB | CYS | 77 | 9.315 | −5.527 | 33.725 | 1 | 33.35 |
| 2019 | SG | CYS | 77 | 8.612 | −4.854 | 32.193 | 1 | 34.05 |
| 2020 | C | CYS | 77 | 7.843 | −4.195 | 35.246 | 1 | 34.67 |
| 2021 | O | CYS | 77 | 7.067 | −5.019 | 35.728 | 1 | 35.07 |
| 2022 | N | PRO | 78 | 7.466 | −2.933 | 34.978 | 1 | 35.55 |
| 2023 | CD | PRO | 78 | 8.308 | −1.871 | 34.399 | 1 | 35.79 |
| 2024 | CA | PRO | 78 | 6.109 | −2.436 | 35.233 | 1 | 35.94 |
| 2025 | CB | PRO | 78 | 6.102 | −1.087 | 34.522 | 1 | 36.44 |
| 2026 | CG | PRO | 78 | 7.507 | −0.623 | 34.702 | 1 | 36.5 |
| 2027 | C | PRO | 78 | 5.033 | −3.38 | 34.697 | 1 | 36.46 |
| 2028 | O | PRO | 78 | 5.185 | −3.955 | 33.62 | 1 | 36.39 |
| 2029 | N | PRO | 79 | 3.93 | −3.546 | 35.445 | 1 | 36.28 |
| 2030 | CD | PRO | 79 | 3.666 | −2.896 | 36.742 | 1 | 37.08 |
| 2031 | CA | PRO | 79 | 2.812 | −4.419 | 35.07 | 1 | 36.27 |
| 2032 | CB | PRO | 79 | 1.748 | −4.071 | 36.107 | 1 | 37.53 |
| 2033 | CG | PRO | 79 | 2.568 | −3.761 | 37.318 | 1 | 36.71 |
| 2034 | C | PRO | 79 | 2.309 | −4.228 | 33.641 | 1 | 35.86 |
| 2035 | O | PRO | 79 | 2.071 | −5.203 | 32.928 | 1 | 35.5 |
| 2036 | N | ARG | 80 | 2.146 | −2.973 | 33.233 | 1 | 35.51 |
| 2037 | CA | ARG | 80 | 1.665 | −2.654 | 31.892 | 1 | 35.82 |
| 2038 | CB | ARG | 80 | 1.488 | −1.142 | 31.743 | 1 | 37.45 |
| 2039 | CG | ARG | 80 | 0.949 | −0.711 | 30.387 | 1 | 40.95 |
| 2040 | CD | ARG | 80 | 0.913 | 0.804 | 30.26 | 1 | 42.88 |
| 2041 | NE | ARG | 80 | 0.344 | 1.232 | 28.985 | 1 | 45.54 |
| 2042 | CZ | ARG | 80 | 0.239 | 2.501 | 28.601 | 1 | 46.7 |
| 2043 | NH1 | ARG | 80 | 0.667 | 3.475 | 29.394 | 1 | 47.41 |
| 2044 | NH2 | ARG | 80 | −0.295 | 2.797 | 27.423 | 1 | 46.95 |
| 2045 | C | ARG | 80 | 2.619 | −3.163 | 30.814 | 1 | 34.75 |
| 2046 | O | ARG | 80 | 2.204 | −3.859 | 29.886 | 1 | 33.55 |
| 2047 | N | GLN | 81 | 3.895 | −2.806 | 30.937 | 1 | 33.73 |
| 2048 | CA | GLN | 81 | 4.907 | −3.231 | 29.975 | 1 | 33.36 |
| 2049 | CB | GLN | 81 | 6.24 | −2.542 | 30.272 | 1 | 35.54 |
| 2050 | CG | GLN | 81 | 6.235 | −1.042 | 30.036 | 1 | 40.33 |
| 2051 | CD | GLN | 81 | 7.548 | −0.389 | 30.422 | 1 | 42.97 |
| 2052 | OE1 | GLN | 81 | 8.618 | −0.804 | 29.973 | 1 | 45.42 |
| 2053 | NE2 | GLN | 81 | 7.474 | 0.644 | 31.256 | 1 | 44.34 |
| 2054 | C | GLN | 81 | 5.09 | −4.744 | 30.034 | 1 | 31.48 |
| 2055 | O | GLN | 81 | 5.321 | −5.395 | 29.015 | 1 | 29.71 |
| 2056 | N | ARG | 82 | 4.987 | −5.291 | 31.239 | 1 | 29.88 |
| 2057 | CA | ARG | 82 | 5.136 | −6.722 | 31.461 | 1 | 29.58 |
| 2058 | CB | ARG | 82 | 4.983 | −7.023 | 32.952 | 1 | 32.29 |
| 2059 | CG | ARG | 82 | 5.466 | −8.39 | 33.388 | 1 | 34.67 |
| 2060 | CD | ARG | 82 | 5.073 | −8.631 | 34.836 | 1 | 36.77 |
| 2061 | NE | ARG | 82 | 5.44 | −7.501 | 35.683 | 1 | 39.03 |
| 2062 | CZ | ARG | 82 | 4.936 | −7.276 | 36.892 | 1 | 39.61 |
| 2063 | NH1 | ARG | 82 | 4.036 | −8.101 | 37.404 | 1 | 40.35 |
| 2064 | NH2 | ARG | 82 | 5.324 | −6.215 | 37.587 | 1 | 39.04 |
| 2065 | C | ARG | 82 | 4.076 | −7.481 | 30.666 | 1 | 27.8 |
| 2066 | O | ARG | 82 | 4.368 | −8.487 | 30.022 | 1 | 27.32 |
| 2067 | N | ALA | 83 | 2.842 | −6.988 | 30.712 | 1 | 26.59 |
| 2068 | CA | ALA | 83 | 1.737 | −7.613 | 29.996 | 1 | 24.68 |
| 2069 | CB | ALA | 83 | 0.412 | −7.014 | 30.458 | 1 | 25.42 |
| 2070 | C | ALA | 83 | 1.888 | −7.443 | 28.487 | 1 | 23.99 |
| 2071 | O | ALA | 83 | 1.658 | −8.38 | 27.724 | 1 | 22.53 |
| 2072 | N | LEU | 84 | 2.268 | −6.243 | 28.059 | 1 | 22.64 |
| 2073 | CA | LEU | 84 | 2.445 | −5.965 | 26.639 | 1 | 23.29 |
| 2074 | CB | LEU | 84 | 2.787 | −4.488 | 26.425 | 1 | 25.89 |
| 2075 | CG | LEU | 84 | 1.605 | −3.519 | 26.497 | 1 | 29.88 |
| 2076 | CD1 | LEU | 84 | 2.101 | −2.086 | 26.405 | 1 | 31.43 |

TABLE 1-continued

| Atom | Atom Type | Residue | # | X | Y | Z | OCC | B |
|---|---|---|---|---|---|---|---|---|
| 2077 | CD2 | LEU | 84 | 0.637 | −3.826 | 25.362 | 1 | 30.7 |
| 2078 | C | LEU | 84 | 3.529 | −6.832 | 26.013 | 1 | 21.19 |
| 2079 | O | LEU | 84 | 3.399 | −7.273 | 24.87 | 1 | 20.46 |
| 2080 | N | ARG | 85 | 4.595 | −7.076 | 26.767 | 1 | 19.87 |
| 2081 | CA | ARG | 85 | 5.711 | −7.878 | 26.282 | 1 | 19.47 |
| 2082 | CB | ARG | 85 | 7.014 | −7.391 | 26.918 | 1 | 20.53 |
| 2083 | CG | ARG | 85 | 7.36 | −5.952 | 26.572 | 1 | 22.38 |
| 2084 | CD | ARG | 85 | 8.672 | −5.516 | 27.204 | 1 | 22.96 |
| 2085 | NE | ARG | 85 | 9.076 | −4.199 | 26.717 | 1 | 26.41 |
| 2086 | CZ | ARG | 85 | 10.275 | −3.66 | 26.914 | 1 | 27.85 |
| 2087 | NH1 | ARG | 85 | 11.202 | −4.322 | 27.595 | 1 | 27.84 |
| 2088 | NH2 | ARG | 85 | 10.55 | −2.463 | 26.414 | 1 | 30.42 |
| 2089 | C | ARG | 85 | 5.534 | −9.363 | 26.567 | 1 | 20.15 |
| 2090 | O | ARG | 85 | 6.403 | −10.171 | 26.236 | 1 | 19.76 |
| 2091 | N | GLN | 86 | 4.405 | −9.719 | 27.171 | 1 | 20.44 |
| 2092 | CA | GLN | 86 | 4.122 | −11.106 | 27.516 | 1 | 21.52 |
| 2093 | CB | GLN | 86 | 3.835 | −11.926 | 26.256 | 1 | 22.63 |
| 2094 | CG | GLN | 86 | 3.044 | −13.195 | 26.522 | 1 | 27.41 |
| 2095 | CD | GLN | 86 | 2.746 | −13.973 | 25.257 | 1 | 28.86 |
| 2096 | OE1 | GLN | 86 | 2.421 | −13.393 | 24.215 | 1 | 28.12 |
| 2097 | NE2 | GLN | 86 | 2.838 | −15.294 | 25.343 | 1 | 29.41 |
| 2098 | C | GLN | 86 | 5.349 | −11.656 | 28.232 | 1 | 21.04 |
| 2099 | O | GLN | 86 | 5.903 | −12.689 | 27.856 | 1 | 20.77 |
| 2100 | N | MET | 87 | 5.772 | −10.933 | 29.26 | 1 | 21.8 |
| 2101 | CA | MET | 87 | 6.935 | −11.308 | 30.045 | 1 | 22.36 |
| 2102 | CB | MET | 87 | 7.706 | −10.054 | 30.455 | 1 | 23.45 |
| 2103 | CG | MET | 87 | 9.025 | −10.323 | 31.152 | 1 | 24.67 |
| 2104 | SD | MET | 87 | 9.78 | −8.789 | 31.726 | 1 | 27.25 |
| 2105 | CE | MET | 87 | 10.289 | −8.063 | 30.171 | 1 | 28.1 |
| 2106 | C | MET | 87 | 6.493 | −12.072 | 31.283 | 1 | 22.24 |
| 2107 | O | MET | 87 | 5.786 | −11.536 | 32.137 | 1 | 22.96 |
| 2108 | N | GLU | 88 | 6.908 | −13.329 | 31.367 | 1 | 20.7 |
| 2109 | CA | GLU | 88 | 6.562 | −14.175 | 32.5 | 1 | 21.25 |
| 2110 | CB | GLU | 88 | 5.482 | −15.175 | 32.088 | 1 | 24.37 |
| 2111 | CG | GLU | 88 | 4.293 | −14.505 | 31.414 | 1 | 30.59 |
| 2112 | CD | GLU | 88 | 3.311 | −15.496 | 30.835 | 1 | 34.22 |
| 2113 | OE1 | GLU | 88 | 3.757 | −16.436 | 30.143 | 1 | 37.43 |
| 2114 | OE2 | GLU | 88 | 2.094 | −15.33 | 31.06 | 1 | 37.17 |
| 2115 | C | GLU | 88 | 7.809 | −14.908 | 32.977 | 1 | 19.35 |
| 2116 | O | GLU | 88 | 8.712 | −15.204 | 32.196 | 1 | 18.23 |
| 2117 | N | PRO | 89 | 7.876 | −15.211 | 34.275 | 1 | 18.93 |
| 2118 | CD | PRO | 89 | 6.905 | −14.945 | 35.352 | 1 | 19.7 |
| 2119 | CA | PRO | 89 | 9.052 | −15.911 | 34.787 | 1 | 18.43 |
| 2120 | CB | PRO | 89 | 8.856 | −15.843 | 36.3 | 1 | 19.12 |
| 2121 | CG | PRO | 89 | 7.367 | −15.894 | 36.436 | 1 | 21.28 |
| 2122 | C | PRO | 89 | 9.164 | −17.343 | 34.28 | 1 | 18.27 |
| 2123 | O | PRO | 89 | 8.168 | −17.964 | 33.903 | 1 | 19.24 |
| 2124 | N | PHE | 90 | 10.392 | −17.847 | 34.246 | 1 | 16.7 |
| 2125 | CA | PHE | 90 | 10.657 | −19.219 | 33.841 | 1 | 16.83 |
| 2126 | CB | PHE | 90 | 10.755 | −19.377 | 32.309 | 1 | 17.59 |
| 2127 | CG | PHE | 90 | 11.716 | −18.431 | 31.634 | 1 | 17.73 |
| 2128 | CD1 | PHE | 90 | 11.252 | −17.27 | 31.02 | 1 | 17.28 |
| 2129 | CD2 | PHE | 90 | 13.073 | −18.732 | 31.555 | 1 | 17.12 |
| 2130 | CE1 | PHE | 90 | 12.124 | −16.425 | 30.329 | 1 | 17.31 |
| 2131 | CE2 | PHE | 90 | 13.954 | −17.894 | 30.868 | 1 | 17.5 |
| 2132 | CZ | PHE | 90 | 13.479 | −16.743 | 30.254 | 1 | 16.07 |
| 2133 | C | PHE | 90 | 11.935 | −19.685 | 34.518 | 1 | 17.51 |
| 2134 | O | PHE | 90 | 12.859 | −18.896 | 34.729 | 1 | 17.47 |
| 2135 | N | PRO | 91 | 11.993 | −20.971 | 34.892 | 1 | 17.42 |
| 2136 | CD | PRO | 91 | 10.949 | −21.994 | 34.686 | 1 | 17.39 |
| 2137 | CA | PRO | 91 | 13.159 | −21.552 | 35.56 | 1 | 17.2 |
| 2138 | CB | PRO | 91 | 12.647 | −22.913 | 36.015 | 1 | 17.28 |
| 2139 | CG | PRO | 91 | 11.712 | −23.283 | 34.903 | 1 | 16.95 |
| 2140 | C | PRO | 91 | 14.388 | −21.668 | 34.678 | 1 | 16.17 |
| 2141 | O | PRO | 91 | 14.307 | −21.588 | 33.452 | 1 | 17.65 |
| 2142 | N | LEU | 92 | 15.528 | −21.865 | 35.325 | 1 | 16.42 |
| 2143 | CA | LEU | 92 | 16.798 | −22.004 | 34.638 | 1 | 16.18 |
| 2144 | CB | LEU | 92 | 17.924 | −22.209 | 35.653 | 1 | 16.88 |
| 2145 | CG | LEU | 92 | 19.288 | −22.573 | 35.055 | 1 | 16.32 |
| 2146 | CD1 | LEU | 92 | 19.837 | −21.387 | 34.268 | 1 | 16.96 |
| 2147 | CD2 | LEU | 92 | 20.25 | −22.962 | 36.168 | 1 | 17.68 |
| 2148 | C | LEU | 92 | 16.809 | −23.17 | 33.662 | 1 | 17.22 |
| 2149 | O | LEU | 92 | 16.368 | −24.276 | 33.982 | 1 | 16.41 |
| 2150 | N | ARG | 93 | 17.312 | −22.905 | 32.464 | 1 | 16.77 |
| 2151 | CA | ARG | 93 | 17.447 | −23.925 | 31.44 | 1 | 17.57 |
| 2152 | CB | ARG | 93 | 16.337 | −23.822 | 30.388 | 1 | 21.2 |
| 2153 | CG | ARG | 93 | 14.969 | −24.285 | 30.854 | 1 | 22.66 |
| 2154 | CD | ARG | 93 | 15.002 | −25.736 | 31.312 | 1 | 26.85 |
| 2155 | NE | ARG | 93 | 13.659 | −26.251 | 31.557 | 1 | 29.62 |
| 2156 | CZ | ARG | 93 | 13.393 | −27.484 | 31.976 | 1 | 32.9 |
| 2157 | NH1 | ARG | 93 | 14.381 | −28.341 | 32.204 | 1 | 31.74 |
| 2158 | NH2 | ARG | 93 | 12.135 | −27.864 | 32.157 | 1 | 33.71 |
| 2159 | C | ARG | 93 | 18.785 | −23.718 | 30.76 | 1 | 16.96 |
| 2160 | O | ARG | 93 | 19.124 | −22.6 | 30.363 | 1 | 16.76 |
| 2161 | N | VAL | 94 | 19.557 | −24.791 | 30.661 | 1 | 14.45 |
| 2162 | CA | VAL | 94 | 20.84 | −24.749 | 29.981 | 1 | 15.36 |
| 2163 | CB | VAL | 94 | 21.991 | −25.217 | 30.888 | 1 | 15.27 |
| 2164 | CG1 | VAL | 94 | 23.285 | −25.269 | 30.086 | 1 | 18.7 |
| 2165 | CG2 | VAL | 94 | 22.14 | −24.267 | 32.071 | 1 | 16.16 |
| 2166 | C | VAL | 94 | 20.691 | −25.723 | 28.825 | 1 | 15.16 |
| 2167 | O | VAL | 94 | 20.361 | −26.893 | 29.035 | 1 | 15.5 |
| 2168 | N | PHE | 95 | 20.898 | −25.236 | 27.606 | 1 | 13.45 |
| 2169 | CA | PHE | 95 | 20.785 | −26.08 | 26.424 | 1 | 15.2 |
| 2170 | CB | PHE | 95 | 19.833 | −25.471 | 25.39 | 1 | 15.57 |
| 2171 | CG | PHE | 95 | 18.385 | −25.598 | 25.745 | 1 | 15.81 |
| 2172 | CD1 | PHE | 95 | 17.744 | −24.606 | 26.475 | 1 | 15.14 |
| 2173 | CD2 | PHE | 95 | 17.659 | −26.72 | 25.353 | 1 | 17.05 |
| 2174 | CE1 | PHE | 95 | 16.398 | −24.726 | 26.811 | 1 | 17.79 |
| 2175 | CE2 | PHE | 95 | 16.316 | −26.85 | 25.684 | 1 | 17.17 |
| 2176 | CZ | PHE | 95 | 15.684 | −25.85 | 26.415 | 1 | 16.95 |
| 2177 | C | PHE | 95 | 22.12 | −26.316 | 25.746 | 1 | 16.38 |
| 2178 | O | PHE | 95 | 22.935 | −25.402 | 25.598 | 1 | 16.25 |
| 2179 | N | VAL | 96 | 22.327 | −27.557 | 25.328 | 1 | 15.72 |
| 2180 | CA | VAL | 96 | 23.535 | −27.946 | 24.621 | 1 | 16.55 |
| 2181 | CB | VAL | 96 | 24.25 | −29.105 | 25.335 | 1 | 16.65 |
| 2182 | CG1 | VAL | 96 | 25.452 | −29.55 | 24.522 | 1 | 17.68 |
| 2183 | CG2 | VAL | 96 | 24.69 | −28.66 | 26.726 | 1 | 16.93 |
| 2184 | C | VAL | 96 | 23.071 | −28.393 | 23.236 | 1 | 16.95 |
| 2185 | O | VAL | 96 | 22.095 | −29.134 | 23.117 | 1 | 16.85 |
| 2186 | N | ASN | 97 | 23.76 | −27.919 | 22.201 | 1 | 15.46 |
| 2187 | CA | ASN | 97 | 23.429 | −28.238 | 20.812 | 1 | 16.35 |
| 2188 | CB | ASN | 97 | 23.837 | −29.677 | 20.482 | 1 | 16.17 |
| 2189 | CG | ASN | 97 | 25.291 | −29.947 | 20.783 | 1 | 19.35 |
| 2190 | OD1 | ASN | 97 | 26.122 | −29.04 | 20.737 | 1 | 16.02 |
| 2191 | ND2 | ASN | 97 | 25.613 | −31.201 | 21.084 | 1 | 19.72 |
| 2192 | C | ASN | 97 | 21.947 | −28.047 | 20.495 | 1 | 16.45 |
| 2193 | O | ASN | 97 | 21.314 | −28.911 | 19.882 | 1 | 16.87 |
| 2194 | N | PRO | 98 | 21.375 | −26.901 | 20.888 | 1 | 15.66 |
| 2195 | CD | PRO | 98 | 21.98 | −25.759 | 21.604 | 1 | 17.02 |
| 2196 | CA | PRO | 98 | 19.956 | −26.652 | 20.622 | 1 | 16.08 |
| 2197 | CB | PRO | 98 | 19.644 | −25.474 | 21.535 | 1 | 15.69 |
| 2198 | CG | PRO | 98 | 20.917 | −24.684 | 21.467 | 1 | 15.76 |
| 2199 | C | PRO | 98 | 19.608 | −26.345 | 19.17 | 1 | 17.22 |
| 2200 | O | PRO | 98 | 20.439 | −25.859 | 18.401 | 1 | 17.01 |
| 2201 | N | SER | 99 | 18.365 | −26.642 | 18.811 | 1 | 16.19 |
| 2202 | CA | SER | 99 | 17.846 | −26.37 | 17.481 | 1 | 18.74 |
| 2203 | CB | SER | 99 | 17.527 | −27.672 | 16.738 | 1 | 20.66 |
| 2204 | OG | SER | 99 | 16.465 | −28.37 | 17.361 | 1 | 25.5 |
| 2205 | C | SER | 99 | 16.573 | −25.569 | 17.716 | 1 | 18.13 |
| 2206 | O | SER | 99 | 15.907 | −25.733 | 18.745 | 1 | 17.52 |
| 2207 | N | LEU | 100 | 16.234 | −24.699 | 16.775 | 1 | 17.1 |
| 2208 | CA | LEU | 100 | 15.05 | −23.866 | 16.919 | 1 | 17.85 |
| 2209 | CB | LEU | 100 | 15.464 | −22.386 | 16.95 | 1 | 19.1 |
| 2210 | CG | LEU | 100 | 14.435 | −21.269 | 17.19 | 1 | 22.47 |
| 2211 | CD1 | LEU | 100 | 15.174 | −19.942 | 17.292 | 1 | 24.89 |
| 2212 | CD2 | LEU | 100 | 13.417 | −21.197 | 16.065 | 1 | 24.89 |
| 2213 | C | LEU | 100 | 14.039 | −24.088 | 15.804 | 1 | 18.44 |
| 2214 | O | LEU | 100 | 14.402 | −24.228 | 14.635 | 1 | 20.02 |
| 2215 | N | ARG | 101 | 12.768 | −24.118 | 16.182 | 1 | 18.06 |
| 2216 | CA | ARG | 101 | 11.681 | −24.276 | 15.228 | 1 | 18.22 |
| 2217 | CB | ARG | 101 | 11.014 | −25.645 | 15.381 | 1 | 20.67 |
| 2218 | CG | ARG | 101 | 9.787 | −25.815 | 14.498 | 1 | 25.21 |
| 2219 | CD | ARG | 101 | 9.198 | −27.21 | 14.615 | 1 | 29.95 |
| 2220 | NE | ARG | 101 | 8.042 | −27.383 | 13.738 | 1 | 33.72 |
| 2221 | CZ | ARG | 101 | 7.356 | −28.516 | 13.62 | 1 | 35.3 |
| 2222 | NH1 | ARG | 101 | 7.705 | −29.584 | 14.326 | 1 | 35.98 |
| 2223 | NH2 | ARG | 101 | 6.319 | −28.581 | 12.797 | 1 | 37.39 |
| 2224 | C | ARG | 101 | 10.673 | −23.174 | 15.521 | 1 | 18.12 |
| 2225 | O | ARG | 101 | 10.283 | −22.97 | 16.674 | 1 | 17.89 |
| 2226 | N | VAL | 102 | 10.265 | −22.449 | 14.487 | 1 | 16.85 |
| 2227 | CA | VAL | 102 | 9.299 | −21.373 | 14.66 | 1 | 17.06 |
| 2228 | CB | VAL | 102 | 9.428 | −20.321 | 13.537 | 1 | 17.26 |

TABLE 1-continued

| Atom | Atom Type | Residue | # | X | Y | Z | OCC | B |
|---|---|---|---|---|---|---|---|---|
| 2229 | CG1 | VAL | 102 | 8.387 | −19.23 | 13.723 | 1 | 18.94 |
| 2230 | CG2 | VAL | 102 | 10.832 | −19.719 | 13.555 | 1 | 19.64 |
| 2231 | C | VAL | 102 | 7.896 | −21.969 | 14.642 | 1 | 18.38 |
| 2232 | O | VAL | 102 | 7.548 | −22.717 | 13.723 | 1 | 18.94 |
| 2233 | N | LEU | 103 | 7.103 | −21.645 | 15.659 | 1 | 17.4 |
| 2234 | CA | LEU | 103 | 5.739 | −22.16 | 15.763 | 1 | 18.25 |
| 2235 | CB | LEU | 103 | 5.489 | −22.685 | 17.181 | 1 | 18.47 |
| 2236 | CG | LEU | 103 | 6.427 | −23.814 | 17.619 | 1 | 20.62 |
| 2237 | CD1 | LEU | 103 | 6.106 | −24.218 | 19.045 | 1 | 22.98 |
| 2238 | CD2 | LEU | 103 | 6.283 | −25.003 | 16.681 | 1 | 22.25 |
| 2239 | C | LEU | 103 | 4.693 | −21.112 | 15.398 | 1 | 18.83 |
| 2240 | O | LEU | 103 | 3.614 | −21.445 | 14.909 | 1 | 18.9 |
| 2241 | N | ASP | 104 | 5.013 | −19.846 | 15.642 | 1 | 17.86 |
| 2242 | CA | ASP | 104 | 4.12 | −18.734 | 15.319 | 1 | 18.98 |
| 2243 | CB | ASP | 104 | 3.445 | −18.192 | 16.583 | 1 | 19.35 |
| 2244 | CG | ASP | 104 | 2.362 | −17.172 | 16.279 | 1 | 21.01 |
| 2245 | OD1 | ASP | 104 | 2.452 | −16.491 | 15.236 | 1 | 20.29 |
| 2246 | OD2 | ASP | 104 | 1.423 | −17.034 | 17.092 | 1 | 21.25 |
| 2247 | C | ASP | 104 | 5.035 | −17.67 | 14.719 | 1 | 19.75 |
| 2248 | O | ASP | 104 | 5.8 | −17.024 | 15.438 | 1 | 17.87 |
| 2249 | N | SER | 105 | 4.956 | −17.495 | 13.404 | 1 | 18.91 |
| 2250 | CA | SER | 105 | 5.812 | −16.539 | 12.71 | 1 | 19.43 |
| 2251 | CB | SER | 105 | 5.948 | −16.942 | 11.24 | 1 | 21.52 |
| 2252 | OG | SER | 105 | 4.692 | −16.904 | 10.592 | 1 | 24.7 |
| 2253 | C | SER | 105 | 5.387 | −15.078 | 12.801 | 1 | 18.96 |
| 2254 | O | SER | 105 | 6.043 | −14.209 | 12.222 | 1 | 18.92 |
| 2255 | N | ARG | 106 | 4.298 | −14.796 | 13.511 | 1 | 17.63 |
| 2256 | CA | ARG | 106 | 3.854 | −13.413 | 13.661 | 1 | 18.65 |
| 2257 | CB | ARG | 106 | 2.621 | −13.326 | 14.565 | 1 | 20.66 |
| 2258 | CG | ARG | 106 | 2.144 | −11.9 | 14.825 | 1 | 24.24 |
| 2259 | CD | ARG | 106 | 0.725 | −11.866 | 15.388 | 1 | 26.1 |
| 2260 | NE | ARG | 106 | 0.603 | −12.517 | 16.692 | 1 | 28.61 |
| 2261 | CZ | ARG | 106 | 0.98 | −11.976 | 17.847 | 1 | 29.11 |
| 2262 | NH1 | ARG | 106 | 1.513 | −10.762 | 17.877 | 1 | 31.19 |
| 2263 | NH2 | ARG | 106 | 0.812 | −12.65 | 18.978 | 1 | 30.51 |
| 2264 | C | ARG | 106 | 5.017 | −12.656 | 14.292 | 1 | 18.14 |
| 2265 | O | ARG | 106 | 5.641 | −13.155 | 15.225 | 1 | 17.66 |
| 2266 | N | LEU | 107 | 5.311 | −11.466 | 13.778 | 1 | 17.4 |
| 2267 | CA | LEU | 107 | 6.421 | −10.668 | 14.293 | 1 | 17.33 |
| 2268 | CB | LEU | 107 | 7.117 | −9.93 | 13.145 | 1 | 17.98 |
| 2269 | CG | LEU | 107 | 7.805 | −10.792 | 12.087 | 1 | 17.9 |
| 2270 | CD1 | LEU | 107 | 8.321 | −9.892 | 10.973 | 1 | 20.94 |
| 2271 | CD2 | LEU | 107 | 8.946 | −11.585 | 12.714 | 1 | 19.72 |
| 2272 | C | LEU | 107 | 6.015 | −9.664 | 15.365 | 1 | 17.78 |
| 2273 | O | LEU | 107 | 5.037 | −8.929 | 15.22 | 1 | 17.54 |
| 2274 | N | VAL | 108 | 6.791 | −9.639 | 16.443 | 1 | 17.04 |
| 2275 | CA | VAL | 108 | 6.554 | −8.743 | 17.561 | 1 | 16.01 |
| 2276 | CB | VAL | 108 | 6.333 | −9.543 | 18.858 | 1 | 18.57 |
| 2277 | CG1 | VAL | 108 | 6.085 | −8.602 | 20.016 | 1 | 19.87 |
| 2278 | CG2 | VAL | 108 | 5.155 | −10.495 | 18.68 | 1 | 21.09 |
| 2279 | C | VAL | 108 | 7.81 | −7.886 | 17.694 | 1 | 15.75 |
| 2280 | O | VAL | 108 | 8.92 | −8.41 | 17.683 | 1 | 14.3 |
| 2281 | N | THR | 109 | 7.633 | −6.576 | 17.812 | 1 | 15.42 |
| 2282 | CA | THR | 109 | 8.77 | −5.665 | 17.913 | 1 | 16.51 |
| 2283 | CB | THR | 109 | 8.754 | −4.646 | 16.757 | 1 | 16.96 |
| 2284 | OG1 | THR | 109 | 8.833 | −5.339 | 15.506 | 1 | 17.88 |
| 2285 | CG2 | THR | 109 | 9.925 | −3.673 | 16.879 | 1 | 17.87 |
| 2286 | C | THR | 109 | 8.834 | −4.892 | 19.226 | 1 | 16.18 |
| 2287 | O | THR | 109 | 7.88 | −4.213 | 19.607 | 1 | 17.74 |
| 2288 | N | PHE | 110 | 9.977 | −4.997 | 19.902 | 1 | 16.71 |
| 2289 | CA | PHE | 110 | 10.23 | −4.304 | 21.162 | 1 | 15.36 |
| 2290 | CB | PHE | 110 | 9.884 | −5.19 | 22.365 | 1 | 16.87 |
| 2291 | CG | PHE | 110 | 8.417 | −5.3 | 22.645 | 1 | 16.96 |
| 2292 | CD1 | PHE | 110 | 7.703 | −4.204 | 23.119 | 1 | 19.41 |
| 2293 | CD2 | PHE | 110 | 7.75 | −6.502 | 22.445 | 1 | 18.85 |
| 2294 | CE1 | PHE | 110 | 6.342 | −4.304 | 23.39 | 1 | 20.05 |
| 2295 | CE2 | PHE | 110 | 6.388 | −6.612 | 22.713 | 1 | 19.79 |
| 2296 | CZ | PHE | 110 | 5.684 | −5.51 | 23.186 | 1 | 19.78 |
| 2297 | C | PHE | 110 | 11.715 | −3.982 | 21.241 | 1 | 16.11 |
| 2298 | O | PHE | 110 | 12.526 | −4.597 | 20.544 | 1 | 14.38 |
| 2299 | N | PRO | 111 | 12.089 | −3.007 | 22.086 | 1 | 17.11 |
| 2300 | CD | PRO | 111 | 11.24 | −2.033 | 22.792 | 1 | 18.28 |
| 2301 | CA | PRO | 111 | 13.503 | −2.654 | 22.225 | 1 | 17.38 |
| 2302 | CB | PRO | 111 | 13.472 | −1.458 | 23.172 | 1 | 17.04 |
| 2303 | CG | PRO | 111 | 12.149 | −0.831 | 22.879 | 1 | 19.66 |
| 2304 | C | PRO | 111 | 14.212 | −3.852 | 22.846 | 1 | 17.45 |
| 2305 | O | PRO | 111 | 13.682 | −4.498 | 23.757 | 1 | 17.26 |
| 2306 | N | GLU | 112 | 15.415 | −4.131 | 22.363 | 1 | 15.51 |
| 2307 | CA | GLU | 112 | 16.192 | −5.262 | 22.83 | 1 | 16.57 |
| 2308 | CB | GLU | 112 | 16.094 | −6.365 | 21.775 | 1 | 18.19 |
| 2309 | CG | GLU | 112 | 16.601 | −7.718 | 22.167 | 1 | 21.34 |
| 2310 | CD | GLU | 112 | 16.472 | −8.696 | 21.019 | 1 | 18.43 |
| 2311 | OE1 | GLU | 112 | 17.515 | −9.156 | 20.517 | 1 | 19.19 |
| 2312 | OE2 | GLU | 112 | 15.326 | −8.993 | 20.61 | 1 | 16.1 |
| 2313 | C | GLU | 112 | 17.643 | −4.819 | 23.011 | 1 | 15.63 |
| 2314 | O | GLU | 112 | 18.125 | −3.95 | 22.283 | 1 | 15.14 |
| 2315 | N | GLY | 113 | 18.325 | −5.406 | 23.988 | 1 | 15.13 |
| 2316 | CA | GLY | 113 | 19.715 | −5.067 | 24.233 | 1 | 14.82 |
| 2317 | C | GLY | 113 | 20.583 | −6.311 | 24.16 | 1 | 13.27 |
| 2318 | O | GLY | 113 | 20.083 | −7.4 | 23.885 | 1 | 14.28 |
| 2319 | N | CYS | 114 | 21.88 | −6.154 | 24.408 | 1 | 12.66 |
| 2320 | CA | CYS | 114 | 22.804 | −7.281 | 24.372 | 1 | 11.46 |
| 2321 | CB | CYS | 114 | 23.282 | −7.528 | 22.936 | 1 | 11.36 |
| 2322 | SG | CYS | 114 | 24.434 | −8.905 | 22.731 | 1 | 10.73 |
| 2323 | C | CYS | 114 | 23.999 | −6.996 | 25.268 | 1 | 11.62 |
| 2324 | O | CYS | 114 | 24.614 | −5.931 | 25.175 | 1 | 11.2 |
| 2325 | N | GLU | 115 | 24.322 | −7.946 | 26.137 | 1 | 11.39 |
| 2326 | CA | GLU | 115 | 25.454 | −7.79 | 27.042 | 1 | 11.6 |
| 2327 | CB | GLU | 115 | 25.569 | −9.013 | 27.959 | 1 | 12.85 |
| 2328 | CG | GLU | 115 | 24.533 | −9.077 | 29.08 | 1 | 14.49 |
| 2329 | CD | GLU | 115 | 24.744 | −8.01 | 30.145 | 1 | 17.46 |
| 2330 | OE1 | GLU | 115 | 25.898 | −7.836 | 30.598 | 1 | 19.68 |
| 2331 | OE2 | GLU | 115 | 23.757 | −7.354 | 30.54 | 1 | 20.82 |
| 2332 | C | GLU | 115 | 26.751 | −7.606 | 26.254 | 1 | 11.54 |
| 2333 | O | GLU | 115 | 27.717 | −7.039 | 26.767 | 1 | 11.37 |
| 2334 | N | SER | 116 | 26.77 | −8.081 | 25.009 | 1 | 10.98 |
| 2335 | CA | SER | 116 | 27.957 | −7.958 | 24.158 | 1 | 11.15 |
| 2336 | CB | SER | 116 | 28.069 | −9.163 | 23.218 | 1 | 10.72 |
| 2337 | OG | SER | 116 | 28.379 | −10.34 | 23.954 | 1 | 12.43 |
| 2338 | C | SER | 116 | 28.015 | −6.654 | 23.354 | 1 | 11.18 |
| 2339 | O | SER | 116 | 28.949 | −6.435 | 22.582 | 1 | 12.54 |
| 2340 | N | VAL | 117 | 27.006 | −5.805 | 23.526 | 1 | 11.78 |
| 2341 | CA | VAL | 117 | 26.959 | −4.485 | 22.888 | 1 | 12.08 |
| 2342 | CB | VAL | 117 | 25.984 | −4.432 | 21.687 | 1 | 12.95 |
| 2343 | CG1 | VAL | 117 | 26.14 | −3.095 | 20.96 | 1 | 14.65 |
| 2344 | CG2 | VAL | 117 | 26.261 | −5.58 | 20.724 | 1 | 13.06 |
| 2345 | C | VAL | 117 | 26.438 | −3.603 | 24.021 | 1 | 13.14 |
| 2346 | O | VAL | 117 | 25.411 | −2.929 | 23.91 | 1 | 12.26 |
| 2347 | N | ALA | 118 | 27.173 | −3.643 | 25.128 | 1 | 14.66 |
| 2348 | CA | ALA | 118 | 26.831 | −2.928 | 26.351 | 1 | 15.43 |
| 2349 | CB | ALA | 118 | 27.999 | −3.021 | 27.331 | 1 | 17.48 |
| 2350 | C | ALA | 118 | 26.399 | −1.473 | 26.214 | 1 | 15.62 |
| 2351 | O | ALA | 118 | 27.056 | −0.68 | 25.542 | 1 | 16.19 |
| 2352 | N | GLY | 119 | 25.277 | −1.144 | 26.851 | 1 | 15.46 |
| 2353 | CA | GLY | 119 | 24.787 | 0.222 | 26.853 | 1 | 15.48 |
| 2354 | C | GLY | 119 | 23.88 | 0.697 | 25.737 | 1 | 14.75 |
| 2355 | O | GLY | 119 | 23.58 | 1.889 | 25.663 | 1 | 14.07 |
| 2356 | N | PHE | 120 | 23.426 | −0.212 | 24.88 | 1 | 14.17 |
| 2357 | CA | PHE | 120 | 22.555 | 0.174 | 23.774 | 1 | 14.29 |
| 2358 | CB | PHE | 120 | 23.322 | 0.089 | 22.451 | 1 | 14.46 |
| 2359 | CG | PHE | 120 | 24.463 | 1.057 | 22.345 | 1 | 16.03 |
| 2360 | CD1 | PHE | 120 | 24.247 | 2.363 | 21.915 | 1 | 14.87 |
| 2361 | CD2 | PHE | 120 | 25.75 | 0.669 | 22.692 | 1 | 15.97 |
| 2362 | CE1 | PHE | 120 | 25.3 | 3.27 | 21.83 | 1 | 17.92 |
| 2363 | CE2 | PHE | 120 | 26.813 | 1.568 | 22.613 | 1 | 18.59 |
| 2364 | CZ | PHE | 120 | 26.586 | 2.871 | 22.181 | 1 | 19.64 |
| 2365 | C | PHE | 120 | 21.295 | −0.675 | 23.668 | 1 | 15.24 |
| 2366 | O | PHE | 120 | 21.248 | −1.81 | 24.141 | 1 | 16.83 |
| 2367 | N | LEU | 121 | 20.271 | −0.096 | 23.053 | 1 | 13.72 |
| 2368 | CA | LEU | 121 | 19.001 | −0.771 | 22.824 | 1 | 14.87 |
| 2369 | CB | LEU | 121 | 17.932 | −0.291 | 23.807 | 1 | 16.78 |
| 2370 | CG | LEU | 121 | 18.012 | −0.701 | 25.276 | 1 | 18.04 |
| 2371 | CD1 | LEU | 121 | 16.885 | −0.009 | 26.037 | 1 | 19.1 |
| 2372 | CD2 | LEU | 121 | 17.896 | −2.213 | 25.405 | 1 | 20.06 |
| 2373 | C | LEU | 121 | 18.544 | −0.427 | 21.415 | 1 | 15.27 |
| 2374 | O | LEU | 121 | 18.928 | 0.606 | 20.869 | 1 | 14.36 |
| 2375 | N | ALA | 122 | 17.737 | −1.303 | 20.875 | 1 | 14.35 |
| 2376 | CA | ALA | 122 | 17.186 | −1.074 | 19.494 | 1 | 14.63 |
| 2377 | CB | ALA | 122 | 18.219 | −1.365 | 18.42 | 1 | 15.5 |
| 2378 | C | ALA | 122 | 15.997 | −2.001 | 19.329 | 1 | 14.58 |
| 2379 | O | ALA | 122 | 15.99 | −3.106 | 19.872 | 1 | 15.67 |
| 2380 | N | CYS | 123 | 14.985 | −1.549 | 18.599 | 1 | 14.03 |

TABLE 1-continued

| Atom | Atom Type | Residue | # | X | Y | Z | OCC | B |
|---|---|---|---|---|---|---|---|---|
| 2381 | CA | CYS | 123 | 13.818 | −2.387 | 18.368 | 1 | 15.2 |
| 2382 | CB | CYS | 123 | 12.676 | −1.568 | 17.774 | 1 | 16.19 |
| 2383 | SG | CYS | 123 | 11.913 | −0.478 | 18.964 | 1 | 21.64 |
| 2384 | C | CYS | 123 | 14.186 | −3.514 | 17.416 | 1 | 14.88 |
| 2385 | O | CYS | 123 | 14.84 | −3.292 | 16.398 | 1 | 14.29 |
| 2386 | N | VAL | 124 | 13.762 | −4.726 | 17.75 | 1 | 13.48 |
| 2387 | CA | VAL | 124 | 14.053 | −5.882 | 16.915 | 1 | 13.44 |
| 2388 | CB | VAL | 124 | 15.155 | −6.773 | 17.533 | 1 | 13.76 |
| 2389 | CG1 | VAL | 124 | 15.425 | −7.976 | 16.623 | 1 | 12.5 |
| 2390 | CG2 | VAL | 124 | 16.428 | −5.966 | 17.755 | 1 | 13.31 |
| 2391 | C | VAL | 124 | 12.812 | −6.743 | 16.761 | 1 | 14.14 |
| 2392 | O | VAL | 124 | 12.172 | −7.101 | 17.747 | 1 | 14.14 |
| 2393 | N | PRO | 125 | 12.446 | −7.073 | 15.517 | 1 | 15.02 |
| 2394 | CD | PRO | 125 | 12.962 | −6.544 | 14.245 | 1 | 15.31 |
| 2395 | CA | PRO | 125 | 11.267 | −7.91 | 15.293 | 1 | 15.06 |
| 2396 | CB | PRO | 125 | 11.01 | −7.759 | 13.796 | 1 | 16.19 |
| 2397 | CG | PRO | 125 | 11.716 | −6.474 | 13.428 | 1 | 19.7 |
| 2398 | C | PRO | 125 | 11.654 | −9.346 | 15.646 | 1 | 14.54 |
| 2399 | O | PRO | 125 | 12.731 | −9.808 | 15.264 | 1 | 14.86 |
| 2400 | N | ARG | 126 | 10.786 | −10.041 | 16.373 | 1 | 14.09 |
| 2401 | CA | ARG | 126 | 11.038 | −11.429 | 16.765 | 1 | 13.11 |
| 2402 | CB | ARG | 126 | 11.418 | −11.521 | 18.244 | 1 | 13.69 |
| 2403 | CG | ARG | 126 | 12.728 | −10.859 | 18.611 | 1 | 13.09 |
| 2404 | CD | ARG | 126 | 13.901 | −11.586 | 17.978 | 1 | 15.06 |
| 2405 | NE | ARG | 126 | 15.174 | −11.074 | 18.48 | 1 | 13.9 |
| 2406 | CZ | ARG | 126 | 16.364 | −11.495 | 18.065 | 1 | 12.88 |
| 2407 | NH1 | ARG | 126 | 16.451 | −12.44 | 17.138 | 1 | 11.87 |
| 2408 | NH2 | ARG | 126 | 17.469 | −10.968 | 18.579 | 1 | 15.01 |
| 2409 | C | ARG | 126 | 9.768 | −12.234 | 16.557 | 1 | 12.98 |
| 2410 | O | ARG | 126 | 8.673 | −11.681 | 16.588 | 1 | 14.01 |
| 2411 | N | PHE | 127 | 9.915 | −13.539 | 16.365 | 1 | 13.51 |
| 2412 | CA | PHE | 127 | 8.753 | −14.402 | 16.186 | 1 | 14.08 |
| 2413 | CB | PHE | 127 | 9.19 | −15.787 | 15.717 | 1 | 14.4 |
| 2414 | CG | PHE | 127 | 9.853 | −15.79 | 14.373 | 1 | 15.88 |
| 2415 | CD1 | PHE | 127 | 11.158 | −16.252 | 14.23 | 1 | 16.71 |
| 2416 | CD2 | PHE | 127 | 9.168 | −15.348 | 13.244 | 1 | 16.77 |
| 2417 | CE1 | PHE | 127 | 11.775 | −16.279 | 12.977 | 1 | 17.46 |
| 2418 | CE2 | PHE | 127 | 9.772 | −15.37 | 11.99 | 1 | 18.18 |
| 2419 | CZ | PHE | 127 | 11.079 | −15.838 | 11.857 | 1 | 18.66 |
| 2420 | C | PHE | 127 | 8.004 | −14.517 | 17.513 | 1 | 15.42 |
| 2421 | O | PHE | 127 | 8.611 | −14.546 | 18.581 | 1 | 15.24 |
| 2422 | N | GLN | 128 | 6.68 | −14.585 | 17.434 | 1 | 15.05 |
| 2423 | CA | GLN | 128 | 5.829 | −14.689 | 18.613 | 1 | 15.46 |
| 2424 | CB | GLN | 128 | 4.365 | −14.538 | 18.185 | 1 | 16.26 |
| 2425 | CG | GLN | 128 | 3.319 | −14.973 | 19.204 | 1 | 18.34 |
| 2426 | CD | GLN | 128 | 3.38 | −14.205 | 20.512 | 1 | 19.64 |
| 2427 | OE1 | GLN | 128 | 3.955 | −13.117 | 20.59 | 1 | 21.62 |
| 2428 | NE2 | GLN | 128 | 2.77 | −14.766 | 21.548 | 1 | 18.95 |
| 2429 | C | GLN | 128 | 6.008 | −15.979 | 19.418 | 1 | 14.88 |
| 2430 | O | GLN | 128 | 5.926 | −15.957 | 20.646 | 1 | 15.75 |
| 2431 | N | ALA | 129 | 6.242 | −17.099 | 18.739 | 1 | 14.51 |
| 2432 | CA | ALA | 129 | 6.41 | −18.375 | 19.433 | 1 | 14.12 |
| 2433 | CB | ALA | 129 | 5.058 | −19.075 | 19.583 | 1 | 14.55 |
| 2434 | C | ALA | 129 | 7.396 | −19.303 | 18.744 | 1 | 15.04 |
| 2435 | O | ALA | 129 | 7.392 | −19.452 | 17.518 | 1 | 15.12 |
| 2436 | N | VAL | 130 | 8.24 | −19.935 | 19.548 | 1 | 15.12 |
| 2437 | CA | VAL | 130 | 9.243 | −20.842 | 19.029 | 1 | 15.57 |
| 2438 | CB | VAL | 130 | 10.631 | −20.16 | 18.938 | 1 | 16.15 |
| 2439 | CG1 | VAL | 130 | 10.548 | −18.915 | 18.072 | 1 | 15.04 |
| 2440 | CG2 | VAL | 130 | 11.128 | −19.798 | 20.337 | 1 | 16.57 |
| 2441 | C | VAL | 130 | 9.384 | −22.06 | 19.922 | 1 | 15.69 |
| 2442 | O | VAL | 130 | 8.876 | −22.096 | 21.041 | 1 | 16.58 |
| 2443 | N | GLN | 131 | 10.086 | −23.057 | 19.407 | 1 | 15.35 |
| 2444 | CA | GLN | 131 | 10.338 | −24.277 | 20.143 | 1 | 17.23 |
| 2445 | CB | GLN | 131 | 9.639 | −25.454 | 19.46 | 1 | 19.03 |
| 2446 | CG | GLN | 131 | 10.085 | −26.815 | 19.959 | 1 | 20.89 |
| 2447 | CD | GLN | 131 | 9.48 | −27.941 | 19.153 | 1 | 21.76 |
| 2448 | OE1 | GLN | 131 | 8.297 | −28.25 | 19.288 | 1 | 21.92 |
| 2449 | NE2 | GLN | 131 | 10.287 | −28.552 | 18.295 | 1 | 21.67 |
| 2450 | C | GLN | 131 | 11.838 | −24.51 | 20.147 | 1 | 17.18 |
| 2451 | O | GLN | 131 | 12.453 | −24.609 | 19.086 | 1 | 17.43 |
| 2452 | N | ILE | 132 | 12.44 | −24.565 | 21.329 | 1 | 15.91 |
| 2453 | CA | ILE | 132 | 13.864 | −24.84 | 21.391 | 1 | 15.33 |
| 2454 | CB | ILE | 132 | 14.628 | −23.839 | 22.302 | 1 | 14.32 |
| 2455 | CG2 | ILE | 132 | 14.007 | −23.796 | 23.689 | 1 | 14.11 |
| 2456 | CG1 | ILE | 132 | 16.111 | −24.227 | 22.353 | 1 | 14.58 |
| 2457 | CD1 | ILE | 132 | 17.017 | −23.196 | 23.037 | 1 | 15.15 |
| 2458 | C | ILE | 132 | 14.038 | −26.263 | 21.9 | 1 | 16.54 |
| 2459 | O | ILE | 132 | 13.512 | −26.633 | 22.957 | 1 | 17.12 |
| 2460 | N | SER | 133 | 14.753 | −27.063 | 21.117 | 1 | 15.59 |
| 2461 | CA | SER | 133 | 15.013 | −28.457 | 21.446 | 1 | 17.59 |
| 2462 | CB | SER | 133 | 14.468 | −29.372 | 20.344 | 1 | 18.07 |
| 2463 | OG | SER | 133 | 13.093 | −29.134 | 20.107 | 1 | 20.7 |
| 2464 | C | SER | 133 | 16.515 | −28.671 | 21.577 | 1 | 18.63 |
| 2465 | O | SER | 133 | 17.287 | −28.271 | 20.705 | 1 | 18.97 |
| 2466 | N | GLY | 134 | 16.927 | −29.305 | 22.667 | 1 | 18.77 |
| 2467 | CA | GLY | 134 | 18.335 | −29.554 | 22.87 | 1 | 21.2 |
| 2468 | C | GLY | 134 | 18.563 | −30.523 | 24.005 | 1 | 22.52 |
| 2469 | O | GLY | 134 | 17.626 | −31.149 | 24.503 | 1 | 23.78 |
| 2470 | N | LEU | 135 | 19.815 | −30.654 | 24.414 | 1 | 21.12 |
| 2471 | CA | LEU | 135 | 20.155 | −31.555 | 25.502 | 1 | 22.06 |
| 2472 | CB | LEU | 135 | 21.374 | −32.4 | 25.124 | 1 | 23 |
| 2473 | CG | LEU | 135 | 21.364 | −33.128 | 23.777 | 1 | 24.23 |
| 2474 | CD1 | LEU | 135 | 22.705 | −33.819 | 23.565 | 1 | 26.41 |
| 2475 | CD2 | LEU | 135 | 20.229 | −34.137 | 23.74 | 1 | 25.8 |
| 2476 | C | LEU | 135 | 20.495 | −30.723 | 26.723 | 1 | 22.65 |
| 2477 | O | LEU | 135 | 21.015 | −29.613 | 26.589 | 1 | 19.69 |
| 2478 | N | ASP | 136 | 20.177 | −31.223 | 27.913 | 1 | 22.25 |
| 2479 | CA | ASP | 136 | 20.56 | −30.488 | 29.102 | 1 | 24.7 |
| 2480 | CB | ASP | 136 | 19.688 | −30.843 | 30.32 | 1 | 25.52 |
| 2481 | CG | ASP | 136 | 19.713 | −32.316 | 30.671 | 1 | 27.9 |
| 2482 | OD1 | ASP | 136 | 20.705 | −33.005 | 30.364 | 1 | 29.92 |
| 2483 | OD2 | ASP | 136 | 18.727 | −32.78 | 31.281 | 1 | 31.3 |
| 2484 | C | ASP | 136 | 22.005 | −30.933 | 29.289 | 1 | 26.2 |
| 2485 | O | ASP | 136 | 22.472 | −31.822 | 28.576 | 1 | 26.09 |
| 2486 | N | PRO | 137 | 22.738 | −30.321 | 30.226 | 1 | 28.19 |
| 2487 | CD | PRO | 137 | 22.36 | −29.21 | 31.118 | 1 | 28.47 |
| 2488 | CA | PRO | 137 | 24.135 | −30.708 | 30.439 | 1 | 29.97 |
| 2489 | CB | PRO | 137 | 24.511 | −29.932 | 31.695 | 1 | 29.5 |
| 2490 | CG | PRO | 137 | 23.708 | −28.671 | 31.543 | 1 | 29.45 |
| 2491 | C | PRO | 137 | 24.396 | −32.21 | 30.578 | 1 | 31.42 |
| 2492 | O | PRO | 137 | 25.493 | −32.68 | 30.272 | 1 | 30.76 |
| 2493 | N | ASN | 138 | 23.394 | −32.962 | 31.023 | 1 | 32.62 |
| 2494 | CA | ASN | 138 | 23.558 | −34.403 | 31.204 | 1 | 33.57 |
| 2495 | CB | ASN | 138 | 22.78 | −34.864 | 32.437 | 1 | 35.71 |
| 2496 | CG | ASN | 138 | 23.379 | −34.341 | 33.724 | 1 | 38.49 |
| 2497 | OD1 | ASN | 138 | 24.58 | −34.486 | 33.963 | 1 | 41.61 |
| 2498 | ND2 | ASN | 138 | 22.549 | −33.733 | 34.563 | 1 | 40.76 |
| 2499 | C | ASN | 138 | 23.183 | −35.269 | 30.006 | 1 | 32.63 |
| 2500 | O | ASN | 138 | 23.192 | −36.499 | 30.096 | 1 | 32.71 |
| 2501 | N | GLY | 139 | 22.856 | −34.635 | 28.885 | 1 | 29.97 |
| 2502 | CA | GLY | 139 | 22.508 | −35.39 | 27.697 | 1 | 28.81 |
| 2503 | C | GLY | 139 | 21.037 | −35.715 | 27.526 | 1 | 27.42 |
| 2504 | O | GLY | 139 | 20.655 | −36.324 | 26.528 | 1 | 28.58 |
| 2505 | N | GLU | 140 | 20.206 | −35.319 | 28.485 | 1 | 26.8 |
| 2506 | CA | GLU | 140 | 18.774 | −35.585 | 28.388 | 1 | 25.97 |
| 2507 | CB | GLU | 140 | 18.107 | −35.453 | 29.758 | 1 | 28.14 |
| 2508 | CG | GLU | 140 | 16.585 | −35.566 | 29.709 | 1 | 33.85 |
| 2509 | CD | GLU | 140 | 15.952 | −35.648 | 31.087 | 1 | 36.71 |
| 2510 | OE1 | GLU | 140 | 16.242 | −34.775 | 31.933 | 1 | 40.64 |
| 2511 | OE2 | GLU | 140 | 15.157 | −36.583 | 31.32 | 1 | 38.43 |
| 2512 | C | GLU | 140 | 18.111 | −34.626 | 27.403 | 1 | 24.82 |
| 2513 | O | GLU | 140 | 18.397 | −33.428 | 27.402 | 1 | 23.53 |
| 2514 | N | GLN | 141 | 17.223 | −35.163 | 26.572 | 1 | 23.21 |
| 2515 | CA | GLN | 141 | 16.515 | −34.365 | 25.575 | 1 | 23.42 |
| 2516 | CB | GLN | 141 | 15.871 | −35.276 | 24.526 | 1 | 26.24 |
| 2517 | CG | GLN | 141 | 16.866 | −35.996 | 23.635 | 1 | 32.62 |
| 2518 | CD | GLN | 141 | 16.198 | −36.985 | 22.696 | 1 | 36.99 |
| 2519 | OE1 | GLN | 141 | 15.295 | −36.628 | 21.937 | 1 | 39.26 |
| 2520 | NE2 | GLN | 141 | 16.642 | −38.236 | 22.743 | 1 | 38.51 |
| 2521 | C | GLN | 141 | 15.442 | −33.493 | 26.206 | 1 | 21.98 |
| 2522 | O | GLN | 141 | 14.546 | −33.985 | 26.894 | 1 | 21.31 |
| 2523 | N | VAL | 142 | 15.534 | −32.191 | 25.964 | 1 | 19.73 |
| 2524 | CA | VAL | 142 | 14.564 | −31.25 | 26.5 | 1 | 18.19 |
| 2525 | CB | VAL | 142 | 15.205 | −30.34 | 27.567 | 1 | 19.21 |
| 2526 | CG1 | VAL | 142 | 14.196 | −29.311 | 28.056 | 1 | 20.11 |
| 2527 | CG2 | VAL | 142 | 15.71 | −31.188 | 28.732 | 1 | 20.27 |
| 2528 | C | VAL | 142 | 13.999 | −30.386 | 25.381 | 1 | 18.27 |
| 2529 | O | VAL | 142 | 14.735 | −29.929 | 24.506 | 1 | 16.76 |
| 2530 | N | VAL | 143 | 12.684 | −30.191 | 25.405 | 1 | 16.76 |
| 2531 | CA | VAL | 143 | 12.004 | −29.367 | 24.417 | 1 | 17.45 |
| 2532 | CB | VAL | 143 | 11.062 | −30.202 | 23.527 | 1 | 18.1 |

TABLE 1-continued

| Atom | Atom Type | Residue | # | X | Y | Z | OCC | B |
|---|---|---|---|---|---|---|---|---|
| 2533 | CG1 | VAL | 143 | 10.368 | −29.295 | 22.514 | 1 | 19.3 |
| 2534 | CG2 | VAL | 143 | 11.847 | −31.284 | 22.813 | 1 | 17.91 |
| 2535 | C | VAL | 143 | 11.176 | −28.335 | 25.165 | 1 | 17.87 |
| 2536 | O | VAL | 143 | 10.382 | −28.674 | 26.043 | 1 | 18.68 |
| 2537 | N | TRP | 144 | 11.369 | −27.069 | 24.825 | 1 | 15.04 |
| 2538 | CA | TRP | 144 | 10.63 | −26.006 | 25.477 | 1 | 14.88 |
| 2539 | CB | TRP | 144 | 11.584 | −25.167 | 26.342 | 1 | 15.43 |
| 2540 | CG | TRP | 144 | 10.98 | −23.938 | 26.967 | 1 | 14.98 |
| 2541 | CD2 | TRP | 144 | 11.693 | −22.788 | 27.446 | 1 | 16.32 |
| 2542 | CE2 | TRP | 144 | 10.737 | −21.894 | 27.979 | 1 | 16.44 |
| 2543 | CE3 | TRP | 144 | 13.047 | −22.429 | 27.477 | 1 | 19.58 |
| 2544 | CD1 | TRP | 144 | 9.659 | −23.701 | 27.224 | 1 | 15.93 |
| 2545 | NE1 | TRP | 144 | 9.504 | −22.475 | 27.832 | 1 | 16.34 |
| 2546 | CZ2 | TRP | 144 | 11.092 | −20.66 | 28.536 | 1 | 18.74 |
| 2547 | CZ3 | TRP | 144 | 13.401 | −21.199 | 28.033 | 1 | 17.99 |
| 2548 | CH2 | TRP | 144 | 12.426 | −20.332 | 28.554 | 1 | 18.14 |
| 2549 | C | TRP | 144 | 9.931 | −25.135 | 24.445 | 1 | 15.84 |
| 2550 | O | TRP | 144 | 10.572 | −24.574 | 23.558 | 1 | 15.42 |
| 2551 | N | GLN | 145 | 8.607 | −25.066 | 24.542 | 1 | 15.5 |
| 2552 | CA | GLN | 145 | 7.827 | −24.232 | 23.649 | 1 | 16.51 |
| 2553 | CB | GLN | 145 | 6.503 | −24.894 | 23.267 | 1 | 18.66 |
| 2554 | CG | GLN | 145 | 5.656 | −23.993 | 22.382 | 1 | 22.1 |
| 2555 | CD | GLN | 145 | 4.458 | −24.697 | 21.793 | 1 | 24.4 |
| 2556 | OE1 | GLN | 145 | 4.541 | −25.864 | 21.418 | 1 | 27.98 |
| 2557 | NE2 | GLN | 145 | 3.341 | −23.984 | 21.685 | 1 | 22.75 |
| 2558 | C | GLN | 145 | 7.545 | −22.95 | 24.407 | 1 | 17.04 |
| 2559 | O | GLN | 145 | 6.948 | −22.975 | 25.489 | 1 | 15.57 |
| 2560 | N | ALA | 146 | 7.989 | −21.833 | 23.842 | 1 | 15.3 |
| 2561 | CA | ALA | 146 | 7.806 | −20.539 | 24.476 | 1 | 15.93 |
| 2562 | CB | ALA | 146 | 9.134 | −20.052 | 25.049 | 1 | 17.43 |
| 2563 | C | ALA | 146 | 7.249 | −19.499 | 23.518 | 1 | 15.18 |
| 2564 | O | ALA | 146 | 7.385 | −19.614 | 22.299 | 1 | 16.11 |
| 2565 | N | SER | 147 | 6.618 | −18.482 | 24.087 | 1 | 15.24 |
| 2566 | CA | SER | 147 | 6.055 | −17.396 | 23.304 | 1 | 17.15 |
| 2567 | CB | SER | 147 | 4.534 | −17.554 | 23.189 | 1 | 21.64 |
| 2568 | OG | SER | 147 | 3.918 | −17.547 | 24.464 | 1 | 26.07 |
| 2569 | C | SER | 147 | 6.397 | −16.086 | 23.999 | 1 | 17.81 |
| 2570 | O | SER | 147 | 6.992 | −16.085 | 25.077 | 1 | 18.42 |
| 2571 | N | GLY | 148 | 6.042 | −14.973 | 23.371 | 1 | 18.24 |
| 2572 | CA | GLY | 148 | 6.303 | −13.677 | 23.969 | 1 | 17.33 |
| 2573 | C | GLY | 148 | 7.759 | −13.4 | 24.282 | 1 | 16.33 |
| 2574 | O | GLY | 148 | 8.652 | −13.789 | 23.531 | 1 | 15.64 |
| 2575 | N | TRP | 149 | 8.002 | −12.734 | 25.406 | 1 | 16.8 |
| 2576 | CA | TRP | 149 | 9.363 | −12.378 | 25.785 | 1 | 15.5 |
| 2577 | CB | TRP | 149 | 9.358 | −11.603 | 27.104 | 1 | 16.82 |
| 2578 | CG | TRP | 149 | 10.553 | −10.724 | 27.236 | 1 | 16.74 |
| 2579 | CD2 | TRP | 149 | 10.8 | −9.511 | 26.516 | 1 | 17.3 |
| 2580 | CE2 | TRP | 149 | 12.068 | −9.038 | 26.917 | 1 | 17 |
| 2581 | CE3 | TRP | 149 | 10.072 | −8.778 | 25.567 | 1 | 17.56 |
| 2582 | CD1 | TRP | 149 | 11.648 | −10.932 | 28.024 | 1 | 17.75 |
| 2583 | NE1 | TRP | 149 | 12.564 | −9.923 | 27.838 | 1 | 18.11 |
| 2584 | CZ2 | TRP | 149 | 12.628 | −7.86 | 26.402 | 1 | 17.17 |
| 2585 | CZ3 | TRP | 149 | 10.628 | −7.606 | 25.055 | 1 | 17.86 |
| 2586 | CH2 | TRP | 149 | 11.895 | −7.161 | 25.476 | 1 | 18.01 |
| 2587 | C | TRP | 149 | 10.324 | −13.561 | 25.88 | 1 | 14.87 |
| 2588 | O | TRP | 149 | 11.48 | −13.455 | 25.466 | 1 | 14.23 |
| 2589 | N | ALA | 150 | 9.863 | −14.684 | 26.424 | 1 | 15.08 |
| 2590 | CA | ALA | 150 | 10.718 | −15.861 | 26.537 | 1 | 14.43 |
| 2591 | CB | ALA | 150 | 9.958 | −17.01 | 27.205 | 1 | 16.11 |
| 2592 | C | ALA | 150 | 11.194 | −16.282 | 25.15 | 1 | 13.58 |
| 2593 | O | ALA | 150 | 12.36 | −16.631 | 24.96 | 1 | 12.38 |
| 2594 | N | ALA | 151 | 10.282 | −16.257 | 24.183 | 1 | 13.23 |
| 2595 | CA | ALA | 151 | 10.619 | −16.624 | 22.817 | 1 | 12.21 |
| 2596 | CB | ALA | 151 | 9.364 | −16.594 | 21.938 | 1 | 13.05 |
| 2597 | C | ALA | 151 | 11.67 | −15.659 | 22.272 | 1 | 12.39 |
| 2598 | O | ALA | 151 | 12.574 | −16.063 | 21.541 | 1 | 12.69 |
| 2599 | N | ARG | 152 | 11.548 | −14.385 | 22.636 | 1 | 12.83 |
| 2600 | CA | ARG | 152 | 12.5 | −13.375 | 22.187 | 1 | 11.58 |
| 2601 | CB | ARG | 152 | 12.087 | −11.987 | 22.683 | 1 | 11.58 |
| 2602 | CG | ARG | 152 | 13.139 | −10.899 | 22.458 | 1 | 11.65 |
| 2603 | CD | ARG | 152 | 12.582 | −9.525 | 22.82 | 1 | 13.13 |
| 2604 | NE | ARG | 152 | 11.432 | −9.187 | 21.985 | 1 | 13.75 |
| 2605 | CZ | ARG | 152 | 11.501 | −8.503 | 20.846 | 1 | 15.37 |
| 2606 | NH1 | ARG | 152 | 12.67 | −8.06 | 20.395 | 1 | 14.86 |
| 2607 | NH2 | ARG | 152 | 10.399 | −8.286 | 20.14 | 1 | 13.94 |
| 2608 | C | ARG | 152 | 13.903 | −13.693 | 22.686 | 1 | 12.93 |
| 2609 | O | ARG | 152 | 14.856 | −13.686 | 21.909 | 1 | 11.63 |
| 2610 | N | ILE | 153 | 14.029 | −13.969 | 23.982 | 1 | 11.9 |
| 2611 | CA | ILE | 153 | 15.333 | −14.281 | 24.557 | 1 | 12.92 |
| 2612 | CB | ILE | 153 | 15.245 | −14.48 | 26.088 | 1 | 13.63 |
| 2613 | CG2 | ILE | 153 | 16.646 | −14.68 | 26.664 | 1 | 15.78 |
| 2614 | CG1 | ILE | 153 | 14.58 | −13.26 | 26.736 | 1 | 17.8 |
| 2615 | CD1 | ILE | 153 | 15.27 | −11.938 | 26.443 | 1 | 20.9 |
| 2616 | C | ILE | 153 | 15.916 | −15.534 | 23.914 | 1 | 11.72 |
| 2617 | O | ILE | 153 | 17.106 | −15.583 | 23.605 | 1 | 12.4 |
| 2618 | N | ILE | 154 | 15.081 | −16.549 | 23.704 | 1 | 11.25 |
| 2619 | CA | ILE | 154 | 15.547 | −17.773 | 23.067 | 1 | 12.2 |
| 2620 | CB | ILE | 154 | 14.396 | −18.797 | 22.927 | 1 | 11.74 |
| 2621 | CG2 | ILE | 154 | 14.79 | −19.906 | 21.951 | 1 | 13.45 |
| 2622 | CG1 | ILE | 154 | 14.073 | −19.385 | 24.305 | 1 | 13.79 |
| 2623 | CD1 | ILE | 154 | 12.806 | −20.215 | 24.34 | 1 | 15.07 |
| 2624 | C | ILE | 154 | 16.125 | −17.457 | 21.685 | 1 | 10.02 |
| 2625 | O | ILE | 154 | 17.2 | −17.937 | 21.333 | 1 | 11.94 |
| 2626 | N | GLN | 155 | 15.413 | −16.647 | 20.909 | 1 | 11.08 |
| 2627 | CA | GLN | 155 | 15.878 | −16.277 | 19.573 | 1 | 10.47 |
| 2628 | CB | GLN | 155 | 14.801 | −15.466 | 18.852 | 1 | 13.17 |
| 2629 | CG | GLN | 155 | 13.571 | −16.292 | 18.506 | 1 | 13.32 |
| 2630 | CD | GLN | 155 | 12.406 | −15.445 | 18.042 | 1 | 14.6 |
| 2631 | OE1 | GLN | 155 | 12.453 | −14.826 | 16.976 | 1 | 14.78 |
| 2632 | NE2 | GLN | 155 | 11.351 | −15.406 | 18.847 | 1 | 13.27 |
| 2633 | C | GLN | 155 | 17.181 | −15.482 | 19.636 | 1 | 10.65 |
| 2634 | O | GLN | 155 | 18.077 | −15.672 | 18.811 | 1 | 11.71 |
| 2635 | N | HIS | 156 | 17.281 | −14.597 | 20.62 | 1 | 11.58 |
| 2636 | CA | HIS | 156 | 18.479 | −13.786 | 20.791 | 1 | 11.03 |
| 2637 | CB | HIS | 156 | 18.279 | −12.793 | 21.949 | 1 | 11.99 |
| 2638 | CG | HIS | 156 | 19.433 | −11.861 | 22.155 | 1 | 12.02 |
| 2639 | CD2 | HIS | 156 | 20.622 | −12.037 | 22.778 | 1 | 13.99 |
| 2640 | ND1 | HIS | 156 | 19.436 | −10.564 | 21.684 | 1 | 13.73 |
| 2641 | CE1 | HIS | 156 | 20.577 | −9.982 | 22.012 | 1 | 15.17 |
| 2642 | NE2 | HIS | 156 | 21.315 | −10.854 | 22.675 | 1 | 10.4 |
| 2643 | C | HIS | 156 | 19.688 | −14.682 | 21.073 | 1 | 10.68 |
| 2644 | O | HIS | 156 | 20.748 | −14.522 | 20.463 | 1 | 11.67 |
| 2645 | N | GLU | 157 | 19.535 | −15.635 | 21.992 | 1 | 11.36 |
| 2646 | CA | GLU | 157 | 20.645 | −16.518 | 22.33 | 1 | 11.26 |
| 2647 | CB | GLU | 157 | 20.348 | −17.3 | 23.62 | 1 | 12.64 |
| 2648 | GG | GLU | 157 | 19.963 | −16.456 | 24.849 | 1 | 13.99 |
| 2649 | CD | GLU | 157 | 20.763 | −15.164 | 25.02 | 1 | 15.11 |
| 2650 | OE1 | GLU | 157 | 21.944 | −15.105 | 24.62 | 1 | 15.76 |
| 2651 | OE2 | GLU | 157 | 20.199 | −14.202 | 25.585 | 1 | 15.81 |
| 2652 | C | GLU | 157 | 20.982 | −17.484 | 21.19 | 1 | 11.87 |
| 2653 | O | GLU | 157 | 22.151 | −17.796 | 20.961 | 1 | 11.24 |
| 2654 | N | MET | 158 | 19.966 | −17.974 | 20.48 | 1 | 11.99 |
| 2655 | CA | MET | 158 | 20.228 | −18.87 | 19.359 | 1 | 12.4 |
| 2656 | CB | MET | 158 | 18.921 | −19.415 | 18.773 | 1 | 13.47 |
| 2657 | CG | MET | 158 | 18.28 | −20.53 | 19.592 | 1 | 14.54 |
| 2658 | SD | MET | 158 | 19.327 | −21.998 | 19.755 | 1 | 16.93 |
| 2659 | CE | MET | 158 | 19.493 | −22.486 | 18.051 | 1 | 17.55 |
| 2660 | C | MET | 158 | 21.004 | −18.092 | 18.296 | 1 | 12.67 |
| 2661 | O | MET | 158 | 21.913 | −18.628 | 17.665 | 1 | 12.75 |
| 2662 | N | ASP | 159 | 20.654 | −16.822 | 18.107 | 1 | 12.81 |
| 2663 | CA | ASP | 159 | 21.363 | −15.996 | 17.132 | 1 | 11.65 |
| 2664 | CB | ASP | 159 | 20.784 | −14.579 | 17.078 | 1 | 13.76 |
| 2665 | CG | ASP | 159 | 19.552 | −14.479 | 16.199 | 1 | 17.18 |
| 2666 | OD1 | ASP | 159 | 19.198 | −15.478 | 15.531 | 1 | 16.91 |
| 2667 | OD2 | ASP | 159 | 18.941 | −13.39 | 16.172 | 1 | 15.27 |
| 2668 | C | ASP | 159 | 22.841 | −15.922 | 17.511 | 1 | 11.51 |
| 2669 | O | ASP | 159 | 23.709 | −15.997 | 16.647 | 1 | 11.91 |
| 2670 | N | HIS | 160 | 23.128 | −15.779 | 18.804 | 1 | 11.43 |
| 2671 | CA | HIS | 160 | 24.519 | −15.716 | 19.256 | 1 | 11.63 |
| 2672 | CB | HIS | 160 | 24.603 | −15.584 | 20.779 | 1 | 11.71 |
| 2673 | CG | HIS | 160 | 24.551 | −14.17 | 21.27 | 1 | 12.08 |
| 2674 | CD2 | HIS | 160 | 23.699 | −13.552 | 22.122 | 1 | 11.74 |
| 2675 | ND1 | HIS | 160 | 25.478 | −13.22 | 20.898 | 1 | 11.72 |
| 2676 | CE1 | HIS | 160 | 25.199 | −12.077 | 21.502 | 1 | 10.3 |
| 2677 | NE2 | HIS | 160 | 24.124 | −12.252 | 22.25 | 1 | 11.34 |
| 2678 | C | HIS | 160 | 25.294 | −16.954 | 18.828 | 1 | 11.47 |
| 2679 | O | HIS | 160 | 26.469 | −16.867 | 18.472 | 1 | 13.24 |
| 2680 | N | LEU | 161 | 24.644 | −18.115 | 18.875 | 1 | 12.65 |
| 2681 | CA | LEU | 161 | 25.313 | −19.348 | 18.472 | 1 | 11.32 |
| 2682 | CB | LEU | 161 | 24.499 | −20.571 | 18.909 | 1 | 11.5 |
| 2683 | GG | LEU | 161 | 24.32 | −20.73 | 20.422 | 1 | 12.87 |
| 2684 | CD1 | LEU | 161 | 23.694 | −22.092 | 20.705 | 1 | 14.56 |

TABLE 1-continued

| Atom | Atom Type | Residue | # | X | Y | Z | OCC | B |
|---|---|---|---|---|---|---|---|---|
| 2685 | CD2 | LEU | 161 | 25.666 | −20.615 | 21.136 | 1 | 14.25 |
| 2686 | C | LEU | 161 | 25.558 | −19.404 | 16.968 | 1 | 11.22 |
| 2687 | O | LEU | 161 | 26.364 | −20.208 | 16.504 | 1 | 12.65 |
| 2688 | N | GLN | 162 | 24.871 | −18.547 | 16.213 | 1 | 11.61 |
| 2689 | CA | GLN | 162 | 25.032 | −18.5 | 14.756 | 1 | 12.89 |
| 2690 | CB | GLN | 162 | 23.686 | −18.279 | 14.058 | 1 | 16.24 |
| 2691 | CG | GLN | 162 | 22.53 | −19.102 | 14.578 | 1 | 23.6 |
| 2692 | CD | GLN | 162 | 22.861 | −20.564 | 14.7 | 1 | 27.29 |
| 2693 | OE1 | GLN | 162 | 23.427 | −21.164 | 13.786 | 1 | 30.32 |
| 2694 | NE2 | GLN | 162 | 22.499 | −21.155 | 15.833 | 1 | 30.78 |
| 2695 | C | GLN | 162 | 25.964 | −17.36 | 14.345 | 1 | 13.18 |
| 2696 | O | GLN | 162 | 26.243 | −17.177 | 13.153 | 1 | 14.65 |
| 2697 | N | GLY | 163 | 26.434 | −16.592 | 15.325 | 1 | 12.04 |
| 2698 | CA | GLY | 163 | 27.321 | −15.475 | 15.035 | 1 | 12.13 |
| 2699 | C | GLY | 163 | 26.545 | −14.241 | 14.621 | 1 | 11.72 |
| 2700 | O | GLY | 163 | 27.078 | −13.341 | 13.969 | 1 | 12.84 |
| 2701 | N | CYS | 164 | 25.275 | −14.206 | 15.009 | 1 | 11.92 |
| 2702 | CA | CYS | 164 | 24.378 | −13.107 | 14.686 | 1 | 13.36 |
| 2703 | CB | CYS | 164 | 23.075 | −13.687 | 14.118 | 1 | 14.57 |
| 2704 | SG | CYS | 164 | 21.768 | −12.498 | 13.787 | 1 | 18.36 |
| 2705 | C | CYS | 164 | 24.081 | −12.252 | 15.918 | 1 | 13.27 |
| 2706 | O | CYS | 164 | 23.785 | −12.782 | 16.991 | 1 | 12.01 |
| 2707 | N | LEU | 165 | 24.181 | −10.931 | 15.762 | 1 | 11.91 |
| 2708 | CA | LEU | 165 | 23.905 | −9.992 | 16.85 | 1 | 12.1 |
| 2709 | CB | LEU | 165 | 25.084 | −9.03 | 17.038 | 1 | 10.91 |
| 2710 | CG | LEU | 165 | 26.423 | −9.691 | 17.378 | 1 | 13.87 |
| 2711 | CD1 | LEU | 165 | 27.484 | −8.615 | 17.583 | 1 | 14.64 |
| 2712 | CD2 | LEU | 165 | 26.277 | −10.534 | 18.639 | 1 | 14.94 |
| 2713 | C | LEU | 165 | 22.634 | −9.211 | 16.523 | 1 | 11.68 |
| 2714 | O | LEU | 165 | 22.245 | −9.1 | 15.354 | 1 | 13.25 |
| 2715 | N | PHE | 166 | 21.989 | −8.651 | 17.542 | 1 | 11.96 |
| 2716 | CA | PHE | 166 | 20.74 | −7.931 | 17.316 | 1 | 13.02 |
| 2717 | CB | PHE | 166 | 20.114 | −7.506 | 18.658 | 1 | 12.84 |
| 2718 | CG | PHE | 166 | 20.692 | −6.251 | 19.248 | 1 | 12.73 |
| 2719 | CD1 | PHE | 166 | 19.99 | −5.051 | 19.173 | 1 | 14.61 |
| 2720 | CD2 | PHE | 166 | 21.923 | −6.267 | 19.898 | 1 | 13.78 |
| 2721 | CE1 | PHE | 166 | 20.504 | −3.878 | 19.741 | 1 | 15.71 |
| 2722 | CE2 | PHE | 166 | 22.448 | −5.099 | 20.471 | 1 | 14.24 |
| 2723 | CZ | PHE | 166 | 21.737 | −3.904 | 20.393 | 1 | 14.34 |
| 2724 | C | PHE | 166 | 20.884 | −6.742 | 16.374 | 1 | 13.13 |
| 2725 | O | PHE | 166 | 19.918 | −6.347 | 15.719 | 1 | 14.87 |
| 2726 | N | ILE | 167 | 22.086 | −6.177 | 16.285 | 1 | 11.61 |
| 2727 | CA | ILE | 167 | 22.305 | −5.05 | 15.389 | 1 | 12.04 |
| 2728 | CB | ILE | 167 | 23.69 | −4.405 | 15.616 | 1 | 11.73 |
| 2729 | CG2 | ILE | 167 | 23.737 | −3.774 | 16.999 | 1 | 13.02 |
| 2730 | CG1 | ILE | 167 | 24.799 | −5.45 | 15.456 | 1 | 14.17 |
| 2731 | CD1 | ILE | 167 | 26.197 | −4.844 | 15.357 | 1 | 13.63 |
| 2732 | C | ILE | 167 | 22.181 | −5.468 | 13.922 | 1 | 11.85 |
| 2733 | O | ILE | 167 | 22.124 | −4.616 | 13.035 | 1 | 13.57 |
| 2734 | N | ASP | 168 | 22.143 | −6.775 | 13.667 | 1 | 11.95 |
| 2735 | CA | ASP | 168 | 22.007 | −7.28 | 12.3 | 1 | 13.37 |
| 2736 | CB | ASP | 168 | 22.558 | −8.707 | 12.154 | 1 | 13.17 |
| 2737 | CG | ASP | 168 | 24.017 | −8.835 | 12.535 | 1 | 14.18 |
| 2738 | OD1 | ASP | 168 | 24.779 | −7.852 | 12.401 | 1 | 15.22 |
| 2739 | OD2 | ASP | 168 | 24.403 | −9.95 | 12.947 | 1 | 13.94 |
| 2740 | C | ASP | 168 | 20.537 | −7.335 | 11.892 | 1 | 14.5 |
| 2741 | O | ASP | 168 | 20.221 | −7.422 | 10.705 | 1 | 15.79 |
| 2742 | N | LYS | 169 | 19.644 | −7.292 | 12.876 | 1 | 14.37 |
| 2743 | CA | LYS | 169 | 18.211 | −7.401 | 12.612 | 1 | 15.49 |
| 2744 | CB | LYS | 169 | 17.685 | −8.677 | 13.27 | 1 | 17.52 |
| 2745 | CG | LYS | 169 | 18.313 | −9.956 | 12.761 | 1 | 17.97 |
| 2746 | CD | LYS | 169 | 17.764 | −11.154 | 13.524 | 1 | 15.91 |
| 2747 | CE | LYS | 169 | 18.179 | −12.457 | 12.871 | 1 | 17.47 |
| 2748 | NZ | LYS | 169 | 17.667 | −13.638 | 13.624 | 1 | 17.66 |
| 2749 | C | LYS | 169 | 17.365 | −6.229 | 13.092 | 1 | 14.88 |
| 2750 | O | LYS | 169 | 16.155 | −6.193 | 12.873 | 1 | 15.83 |
| 2751 | N | MET | 170 | 18.004 | −5.267 | 13.737 | 1 | 14.94 |
| 2752 | CA | MET | 170 | 17.306 | −4.116 | 14.289 | 1 | 13.71 |
| 2753 | CB | MET | 170 | 18.25 | −3.356 | 15.214 | 1 | 14.01 |
| 2754 | CG | MET | 170 | 19.409 | −2.72 | 14.449 | 1 | 13.85 |
| 2755 | SD | MET | 170 | 20.399 | −1.633 | 15.468 | 1 | 14.82 |
| 2756 | CE | MET | 170 | 21.662 | −1.123 | 14.314 | 1 | 14.73 |
| 2757 | C | MET | 170 | 16.75 | −3.102 | 13.302 | 1 | 14.36 |
| 2758 | O | MET | 170 | 17.092 | −3.096 | 12.119 | 1 | 14.71 |
| 2759 | N | ASP | 171 | 15.873 | −2.25 | 13.824 | 1 | 14.76 |
| 2760 | CA | ASP | 171 | 15.33 | −1.123 | 13.076 | 1 | 14.85 |
| 2761 | CB | ASP | 171 | 13.972 | −0.692 | 13.628 | 1 | 16.63 |
| 2762 | CG | ASP | 171 | 13.491 | 0.623 | 13.03 | 1 | 19.23 |
| 2763 | OD1 | ASP | 171 | 14.313 | 1.353 | 12.426 | 1 | 20.23 |
| 2764 | OD2 | ASP | 171 | 12.291 | 0.938 | 13.173 | 1 | 22 |
| 2765 | C | ASP | 171 | 16.394 | −0.124 | 13.517 | 1 | 14.76 |
| 2766 | O | ASP | 171 | 16.342 | 0.386 | 14.638 | 1 | 13.88 |
| 2767 | N | SER | 172 | 17.37 | 0.134 | 12.655 | 1 | 15.04 |
| 2768 | CA | SER | 172 | 18.479 | 1.016 | 13.006 | 1 | 14.05 |
| 2769 | CB | SER | 172 | 19.462 | 1.119 | 11.836 | 1 | 14.54 |
| 2770 | OG | SER | 172 | 18.877 | 1.771 | 10.728 | 1 | 14.91 |
| 2771 | C | SER | 172 | 18.108 | 2.413 | 13.489 | 1 | 13.02 |
| 2772 | O | SER | 172 | 18.849 | 3.012 | 14.268 | 1 | 13.24 |
| 2773 | N | ARG | 173 | 16.968 | 2.936 | 13.051 | 1 | 13.22 |
| 2774 | CA | ARG | 173 | 16.579 | 4.272 | 13.484 | 1 | 12.62 |
| 2775 | CB | ARG | 173 | 15.474 | 4.829 | 12.584 | 1 | 13.96 |
| 2776 | CG | ARG | 173 | 15.961 | 5.15 | 11.172 | 1 | 16.13 |
| 2777 | CD | ARG | 173 | 14.859 | 5.772 | 10.338 | 1 | 16.5 |
| 2778 | NE | ARG | 173 | 14.387 | 7.023 | 10.919 | 1 | 18.92 |
| 2779 | CZ | ARG | 173 | 15.05 | 8.176 | 10.876 | 1 | 19.02 |
| 2780 | NH1 | ARG | 173 | 16.227 | 8.25 | 10.271 | 1 | 18.49 |
| 2781 | NH2 | ARG | 173 | 14.533 | 9.257 | 11.445 | 1 | 19.82 |
| 2782 | C | ARG | 173 | 16.152 | 4.323 | 14.948 | 1 | 13.39 |
| 2783 | O | ARG | 173 | 15.969 | 5.409 | 15.499 | 1 | 13.92 |
| 2784 | N | THR | 174 | 16.014 | 3.158 | 15.58 | 1 | 12.97 |
| 2785 | CA | THR | 174 | 15.626 | 3.098 | 16.992 | 1 | 13.12 |
| 2786 | CB | THR | 174 | 14.517 | 2.043 | 17.247 | 1 | 13.79 |
| 2787 | OG1 | THR | 174 | 15.031 | 0.732 | 16.987 | 1 | 13.77 |
| 2788 | CG2 | THR | 174 | 13.306 | 2.309 | 16.352 | 1 | 14.5 |
| 2789 | C | THR | 174 | 16.812 | 2.774 | 17.91 | 1 | 12.75 |
| 2790 | O | THR | 174 | 16.649 | 2.651 | 19.133 | 1 | 12.23 |
| 2791 | N | PHE | 175 | 17.997 | 2.627 | 17.322 | 1 | 12.82 |
| 2792 | CA | PHE | 175 | 19.213 | 2.335 | 18.086 | 1 | 12.2 |
| 2793 | CB | PHE | 175 | 20.403 | 2.197 | 17.136 | 1 | 12.24 |
| 2794 | CG | PHE | 175 | 21.656 | 1.681 | 17.786 | 1 | 12.88 |
| 2795 | CD1 | PHE | 175 | 21.769 | 0.339 | 18.148 | 1 | 13.45 |
| 2796 | CD2 | PHE | 175 | 22.74 | 2.529 | 17.999 | 1 | 12.49 |
| 2797 | CE1 | PHE | 175 | 22.949 | −0.152 | 18.709 | 1 | 13.21 |
| 2798 | CE2 | PHE | 175 | 23.922 | 2.049 | 18.559 | 1 | 14.8 |
| 2799 | CZ | PHE | 175 | 24.025 | 0.706 | 18.912 | 1 | 14.29 |
| 2800 | C | PHE | 175 | 19.434 | 3.513 | 19.031 | 1 | 12.52 |
| 2801 | O | PHE | 175 | 19.332 | 4.67 | 18.623 | 1 | 12.19 |
| 2802 | N | THR | 176 | 19.748 | 3.229 | 20.29 | 1 | 13.15 |
| 2803 | CA | THR | 176 | 19.929 | 4.309 | 21.25 | 1 | 13.04 |
| 2804 | CB | THR | 176 | 18.549 | 4.771 | 21.798 | 1 | 14.61 |
| 2805 | OG1 | THR | 176 | 18.721 | 5.826 | 22.754 | 1 | 15.79 |
| 2806 | CG2 | THR | 176 | 17.834 | 3.606 | 22.484 | 1 | 15.78 |
| 2807 | C | THR | 176 | 20.803 | 3.957 | 22.442 | 1 | 12.58 |
| 2808 | O | THR | 176 | 20.879 | 2.796 | 22.857 | 1 | 11.62 |
| 2809 | N | ASN | 177 | 21.488 | 4.967 | 22.971 | 1 | 11.82 |
| 2810 | CA | ASN | 177 | 22.279 | 4.788 | 24.184 | 1 | 12.73 |
| 2811 | CB | ASN | 177 | 23.074 | 6.058 | 24.493 | 1 | 12.68 |
| 2812 | CG | ASN | 177 | 24.424 | 6.075 | 23.825 | 1 | 12.14 |
| 2813 | OD1 | ASN | 177 | 25.382 | 5.482 | 24.329 | 1 | 13.8 |
| 2814 | ND2 | ASN | 177 | 24.514 | 6.749 | 22.681 | 1 | 11.74 |
| 2815 | C | ASN | 177 | 21.195 | 4.606 | 25.243 | 1 | 13.35 |
| 2816 | O | ASN | 177 | 20.122 | 5.207 | 25.14 | 1 | 13.76 |
| 2817 | N | VAL | 178 | 21.458 | 3.794 | 26.26 | 1 | 14.11 |
| 2818 | CA | VAL | 178 | 20.458 | 3.566 | 27.291 | 1 | 15.97 |
| 2819 | CB | VAL | 178 | 20.903 | 2.464 | 28.273 | 1 | 18.67 |
| 2820 | CG1 | VAL | 178 | 20.935 | 1.121 | 27.556 | 1 | 19.81 |
| 2821 | CG2 | VAL | 178 | 22.267 | 2.799 | 28.844 | 1 | 21.97 |
| 2822 | C | VAL | 178 | 20.106 | 4.825 | 28.082 | 1 | 15.06 |
| 2823 | O | VAL | 178 | 19.032 | 4.895 | 28.676 | 1 | 15.85 |
| 2824 | N | TYR | 179 | 20.99 | 5.821 | 28.08 | 1 | 12.99 |
| 2825 | CA | TYR | 179 | 20.707 | 7.045 | 28.821 | 1 | 14.1 |
| 2826 | CB | TYR | 179 | 22.01 | 7.742 | 29.245 | 1 | 13.13 |
| 2827 | CG | TYR | 179 | 22.992 | 8.048 | 28.144 | 1 | 13.68 |
| 2828 | CD1 | TYR | 179 | 22.787 | 9.119 | 27.274 | 1 | 15.07 |
| 2829 | CE1 | TYR | 179 | 23.725 | 9.436 | 26.288 | 1 | 16.95 |
| 2830 | CD2 | TYR | 179 | 24.157 | 7.294 | 28 | 1 | 14.53 |
| 2831 | CE2 | TYR | 179 | 25.098 | 7.598 | 27.023 | 1 | 14.23 |
| 2832 | CZ | TYR | 179 | 24.876 | 8.671 | 26.171 | 1 | 15.46 |
| 2833 | OH | TYR | 179 | 25.804 | 8.976 | 25.205 | 1 | 16.37 |
| 2834 | C | TYR | 179 | 19.763 | 8.007 | 28.095 | 1 | 13.58 |
| 2835 | O | TYR | 179 | 19.476 | 9.098 | 28.584 | 1 | 13.99 |
| 2836 | N | TRP | 180 | 19.291 | 7.592 | 26.92 | 1 | 12.8 |

TABLE 1-continued

| Atom | Atom Type | Residue | # | X | Y | Z | OCC | B |
|---|---|---|---|---|---|---|---|---|
| 2837 | CA | TRP | 180 | 18.312 | 8.358 | 26.152 | 1 | 13.26 |
| 2838 | CB | TRP | 180 | 18.765 | 8.577 | 24.708 | 1 | 11.78 |
| 2839 | CG | TRP | 180 | 19.482 | 9.864 | 24.51 | 1 | 12.92 |
| 2840 | CD2 | TRP | 180 | 18.892 | 11.168 | 24.446 | 1 | 11.93 |
| 2841 | CE2 | TRP | 180 | 19.944 | 12.093 | 24.285 | 1 | 11.74 |
| 2842 | CE3 | TRP | 180 | 17.575 | 11.844 | 24.511 | 1 | 11.05 |
| 2843 | CD1 | TRP | 180 | 20.825 | 10.043 | 24.388 | 1 | 13.2 |
| 2844 | NE1 | TRP | 180 | 21.114 | 11.379 | 24.251 | 1 | 12.36 |
| 2845 | CZ2 | TRP | 180 | 19.724 | 13.469 | 24.187 | 1 | 13.45 |
| 2846 | CZ3 | TRP | 180 | 17.354 | 13.016 | 24.412 | 1 | 13.37 |
| 2847 | CH2 | TRP | 180 | 18.425 | 13.913 | 24.252 | 1 | 13.19 |
| 2848 | C | TRP | 180 | 17.059 | 7.49 | 26.149 | 1 | 14.53 |
| 2849 | O | TRP | 180 | 17.133 | 6.305 | 25.829 | 1 | 15.38 |
| 2850 | N | MET | 181 | 15.911 | 8.065 | 26.491 | 1 | 14.98 |
| 2851 | CA | MET | 181 | 14.689 | 7.275 | 26.527 | 1 | 17.58 |
| 2852 | CB | MET | 181 | 14.578 | 6.591 | 27.893 | 1 | 18.73 |
| 2853 | CG | MET | 181 | 14.486 | 7.57 | 29.053 | 1 | 20.52 |
| 2854 | SD | MET | 181 | 15.085 | 6.897 | 30.621 | 1 | 22.31 |
| 2855 | CE | MET | 181 | 16.819 | 7.312 | 30.501 | 1 | 20.14 |
| 2856 | C | MET | 181 | 13.433 | 8.097 | 26.263 | 1 | 19.38 |
| 2857 | O | MET | 181 | 13.425 | 9.312 | 26.446 | 1 | 17.08 |
| 2858 | N | LYS | 182 | 12.378 | 7.422 | 25.814 | 1 | 22.45 |
| 2859 | CA | LYS | 182 | 11.102 | 8.081 | 25.563 | 1 | 28.27 |
| 2860 | CB | LYS | 182 | 10.326 | 7.386 | 24.441 | 1 | 30.45 |
| 2861 | CG | LYS | 182 | 10.589 | 7.942 | 23.054 | 1 | 34.18 |
| 2862 | CD | LYS | 182 | 9.598 | 7.376 | 22.044 | 1 | 37 |
| 2863 | CE | LYS | 182 | 9.781 | 8.004 | 20.671 | 1 | 39.08 |
| 2864 | NZ | LYS | 182 | 8.792 | 7.49 | 19.683 | 1 | 41.86 |
| 2865 | C | LYS | 182 | 10.293 | 8.01 | 26.847 | 1 | 30.01 |
| 2866 | O | LYS | 182 | 10.275 | 6.98 | 27.521 | 1 | 31.56 |
| 2867 | N | VAL | 183 | 9.628 | 9.106 | 27.189 | 1 | 32.18 |
| 2868 | CA | VAL | 183 | 8.827 | 9.149 | 28.403 | 1 | 34.79 |
| 2869 | CB | VAL | 183 | 9.526 | 9.98 | 29.498 | 1 | 35.23 |
| 2870 | CG1 | VAL | 183 | 10.849 | 9.331 | 29.874 | 1 | 35.42 |
| 2871 | CG2 | VAL | 183 | 9.752 | 11.402 | 29.01 | 1 | 35 |
| 2872 | C | VAL | 183 | 7.449 | 9.74 | 28.139 | 1 | 36.54 |
| 2873 | O | VAL | 183 | 7.269 | 10.541 | 27.221 | 1 | 36.4 |
| 2874 | N | ASN | 184 | 6.477 | 9.334 | 28.948 | 1 | 38.91 |
| 2875 | CA | ASN | 184 | 5.114 | 9.826 | 28.809 | 1 | 41.1 |
| 2876 | CB | ASN | 184 | 4.121 | 8.795 | 29.346 | 1 | 41.72 |
| 2877 | CG | ASN | 184 | 4.143 | 7.504 | 28.557 | 1 | 42.17 |
| 2878 | OD1 | ASN | 184 | 3.908 | 7.499 | 27.348 | 1 | 42.99 |
| 2879 | ND2 | ASN | 184 | 4.427 | 6.398 | 29.236 | 1 | 43.73 |
| 2880 | C | ASN | 184 | 4.951 | 11.138 | 29.559 | 1 | 42.46 |
| 2881 | O | ASN | 184 | 5.437 | 11.289 | 30.679 | 1 | 42.94 |
| 2882 | N | ASP | 185 | 4.267 | 12.088 | 28.932 | 1 | 44.09 |
| 2883 | CA | ASP | 185 | 4.045 | 13.39 | 29.541 | 1 | 45.85 |
| 2884 | CB | ASP | 185 | 4.089 | 14.479 | 28.468 | 1 | 46.83 |
| 2885 | CG | ASP | 185 | 5.379 | 14.456 | 27.673 | 1 | 47.93 |
| 2886 | OD1 | ASP | 185 | 6.459 | 14.574 | 28.29 | 1 | 48.44 |
| 2887 | OD2 | ASP | 185 | 5.313 | 14.319 | 26.433 | 1 | 49.4 |
| 2888 | C | ASP | 185 | 2.705 | 13.427 | 30.267 | 1 | 46.52 |
| 2889 | O | ASP | 185 | 2.005 | 12.391 | 30.26 | 1 | 46.69 |
| 2890 | OXT | ASP | 185 | 2.375 | 14.489 | 30.838 | 1 | 47.17 |
| 2891 | CB | HIS | 3 | 11.596 | −54.205 | −6.596 | 1 | 45.69 |
| 2892 | CG | HIS | 3 | 12.296 | −55.167 | −7.505 | 1 | 46.28 |
| 2893 | CD2 | HIS | 3 | 11.871 | −55.821 | −8.612 | 1 | 46.5 |
| 2894 | ND1 | HIS | 3 | 13.6 | −55.567 | −7.302 | 1 | 47.12 |
| 2895 | CE1 | HIS | 3 | 13.947 | −56.426 | −8.243 | 1 | 46.9 |
| 2896 | NE2 | HIS | 3 | 12.915 | −56.598 | −9.051 | 1 | 47.01 |
| 2897 | C | HIS | 3 | 12.009 | −52.033 | −7.771 | 1 | 44.7 |
| 2898 | O | HIS | 3 | 11.222 | −52.445 | −8.626 | 1 | 45.24 |
| 2899 | N | HIS | 3 | 11.745 | −52.086 | −5.324 | 1 | 45.69 |
| 2900 | CA | HIS | 3 | 12.274 | −52.834 | −6.5 | 1 | 45.08 |
| 2901 | N | MET | 4 | 12.671 | −50.885 | −7.882 | 1 | 43.59 |
| 2902 | CA | MET | 4 | 12.517 | −50.001 | −9.035 | 1 | 42.55 |
| 2903 | CB | MET | 4 | 13.217 | −48.668 | −8.767 | 1 | 43.76 |
| 2904 | CG | MET | 4 | 12.641 | −47.891 | −7.597 | 1 | 44.99 |
| 2905 | SD | MET | 4 | 13.572 | −46.389 | −7.254 | 1 | 48.83 |
| 2906 | CE | MET | 4 | 12.732 | −45.209 | −8.316 | 1 | 46.48 |
| 2907 | C | MET | 4 | 13.062 | −50.607 | −10.322 | 1 | 40.62 |
| 2908 | O | MET | 4 | 13.671 | −51.677 | −10.313 | 1 | 41.25 |
| 2909 | N | SER | 5 | 12.839 | −49.908 | −11.431 | 1 | 38.64 |
| 2910 | CA | SER | 5 | 13.298 | −50.365 | −12.736 | 1 | 35.89 |
| 2911 | CB | SER | 5 | 12.127 | −50.958 | −13.522 | 1 | 37.32 |
| 2912 | OG | SER | 5 | 12.535 | −51.36 | −14.818 | 1 | 42.17 |
| 2913 | C | SER | 5 | 13.911 | −49.21 | −13.52 | 1 | 33.21 |
| 2914 | O | SER | 5 | 13.681 | −48.043 | −13.202 | 1 | 33.03 |
| 2915 | N | PHE | 6 | 14.693 | −49.537 | −14.542 | 1 | 29.26 |
| 2916 | CA | PHE | 6 | 15.321 | −48.507 | −15.36 | 1 | 26.46 |
| 2917 | CB | PHE | 6 | 16.743 | −48.906 | −15.767 | 1 | 26.45 |
| 2918 | CG | PHE | 6 | 17.733 | −48.887 | −14.643 | 1 | 26.23 |
| 2919 | CD1 | PHE | 6 | 17.872 | −49.984 | −13.802 | 1 | 28.11 |
| 2920 | CD2 | PHE | 6 | 18.54 | −47.774 | −14.434 | 1 | 27.67 |
| 2921 | CE1 | PHE | 6 | 18.804 | −49.976 | −12.769 | 1 | 27.11 |
| 2922 | CE2 | PHE | 6 | 19.474 | −47.755 | −13.403 | 1 | 28.09 |
| 2923 | CZ | PHE | 6 | 19.606 | −48.859 | −12.57 | 1 | 28.14 |
| 2924 | C | PHE | 6 | 14.532 | −48.236 | −16.629 | 1 | 23.9 |
| 2925 | O | PHE | 6 | 13.96 | −49.146 | −17.227 | 1 | 24.47 |
| 2926 | N | SER | 7 | 14.507 | −46.971 | −17.027 | 1 | 21.21 |
| 2927 | CA | SER | 7 | 13.841 | −46.555 | −18.252 | 1 | 19.64 |
| 2928 | CB | SER | 7 | 12.559 | −45.769 | −17.957 | 1 | 22.79 |
| 2929 | OG | SER | 7 | 11.53 | −46.624 | −17.488 | 1 | 28.67 |
| 2930 | C | SER | 7 | 14.83 | −45.657 | −18.966 | 1 | 17.25 |
| 2931 | O | SER | 7 | 15.669 | −45.013 | −18.334 | 1 | 15.05 |
| 2932 | N | HIS | 8 | 14.756 | −45.621 | −20.287 | 1 | 16.84 |
| 2933 | CA | HIS | 8 | 15.66 | −44.765 | −21.026 | 1 | 16.62 |
| 2934 | CB | HIS | 8 | 16.884 | −45.554 | −21.492 | 1 | 20.1 |
| 2935 | CG | HIS | 8 | 16.598 | −46.537 | −22.582 | 1 | 22.69 |
| 2936 | CD2 | HIS | 8 | 16.089 | −47.791 | −22.542 | 1 | 26.02 |
| 2937 | ND1 | HIS | 8 | 16.838 | −46.264 | −23.911 | 1 | 25.67 |
| 2938 | CE1 | HIS | 8 | 16.491 | −47.307 | −24.643 | 1 | 26.84 |
| 2939 | NE2 | HIS | 8 | 16.033 | −48.248 | −23.836 | 1 | 29.04 |
| 2940 | C | HIS | 8 | 14.949 | −44.149 | −22.209 | 1 | 15.15 |
| 2941 | O | HIS | 8 | 14.041 | −44.751 | −22.786 | 1 | 16.06 |
| 2942 | N | VAL | 9 | 15.341 | −42.926 | −22.539 | 1 | 13.97 |
| 2943 | CA | VAL | 9 | 14.764 | −42.236 | −23.679 | 1 | 13.28 |
| 2944 | CB | VAL | 9 | 14.701 | −40.716 | −23.442 | 1 | 14.06 |
| 2945 | CG1 | VAL | 9 | 14.199 | −40.013 | −24.7 | 1 | 12.38 |
| 2946 | CG2 | VAL | 9 | 13.785 | −40.418 | −22.258 | 1 | 14.46 |
| 2947 | C | VAL | 9 | 15.682 | −42.531 | −24.856 | 1 | 13.49 |
| 2948 | O | VAL | 9 | 16.872 | −42.202 | −24.823 | 1 | 13.46 |
| 2949 | N | CYS | 10 | 15.131 | −43.173 | −25.881 | 1 | 12.24 |
| 2950 | CA | CYS | 10 | 15.895 | −43.531 | −27.069 | 1 | 12.6 |
| 2951 | CB | CYS | 10 | 15.006 | −44.31 | −28.039 | 1 | 14.12 |
| 2952 | SG | CYS | 10 | 14.312 | −45.797 | −27.299 | 1 | 16.49 |
| 2953 | C | CYS | 10 | 16.455 | −42.287 | −27.747 | 1 | 11.99 |
| 2954 | O | CYS | 10 | 15.784 | −41.26 | −27.815 | 1 | 12.41 |
| 2955 | N | GLN | 11 | 17.69 | −42.387 | −28.238 | 1 | 11.67 |
| 2956 | CA | GLN | 11 | 18.359 | −41.262 | −28.889 | 1 | 11.79 |
| 2957 | CB | GLN | 11 | 19.781 | −41.122 | −28.34 | 1 | 12.17 |
| 2958 | CG | GLN | 11 | 19.826 | −40.802 | −26.853 | 1 | 10.01 |
| 2959 | CD | GLN | 11 | 19.091 | −39.517 | −26.519 | 1 | 10.9 |
| 2960 | OE1 | GLN | 11 | 19.434 | −38.442 | −27.02 | 1 | 12.2 |
| 2961 | NE2 | GLN | 11 | 18.069 | −39.621 | −25.676 | 1 | 11.41 |
| 2962 | C | GLN | 11 | 18.392 | −41.397 | −30.403 | 1 | 11.41 |
| 2963 | O | GLN | 11 | 18.368 | −42.509 | −30.933 | 1 | 13.02 |
| 2964 | N | VAL | 12 | 18.453 | −40.261 | −31.094 | 1 | 11.46 |
| 2965 | CA | VAL | 12 | 18.451 | −40.265 | −32.551 | 1 | 11.73 |
| 2966 | CB | VAL | 12 | 18.621 | −38.831 | −33.127 | 1 | 12.72 |
| 2967 | CG1 | VAL | 12 | 19.973 | −38.243 | −32.752 | 1 | 12.94 |
| 2968 | CG2 | VAL | 12 | 18.425 | −38.866 | −34.638 | 1 | 13.26 |
| 2969 | C | VAL | 12 | 19.488 | −41.231 | −33.116 | 1 | 12.78 |
| 2970 | O | VAL | 12 | 20.671 | −41.207 | −32.755 | 1 | 12.39 |
| 2971 | N | GLY | 13 | 19.006 | −42.096 | −34 | 1 | 13.28 |
| 2972 | CA | GLY | 13 | 19.826 | −43.133 | −34.595 | 1 | 13.42 |
| 2973 | C | GLY | 13 | 19.035 | −44.416 | −34.405 | 1 | 13.88 |
| 2974 | O | GLY | 13 | 19.091 | −45.329 | −35.23 | 1 | 13.91 |
| 2975 | N | ASP | 14 | 18.297 | −44.485 | −33.299 | 1 | 12.99 |
| 2976 | CA | ASP | 14 | 17.453 | −45.642 | −33.001 | 1 | 12.5 |
| 2977 | CB | ASP | 14 | 16.871 | −45.528 | −31.589 | 1 | 12.83 |
| 2978 | CG | ASP | 14 | 16.112 | −46.775 | −31.162 | 1 | 12.35 |
| 2979 | OD1 | ASP | 14 | 15.6 | −47.503 | −32.035 | 1 | 13.3 |
| 2980 | OD2 | ASP | 14 | 16.012 | −47.021 | −29.94 | 1 | 14.01 |
| 2981 | C | ASP | 14 | 16.315 | −45.598 | −34.02 | 1 | 13.4 |
| 2982 | O | ASP | 14 | 15.542 | −44.642 | −34.048 | 1 | 13.64 |
| 2983 | N | PRO | 15 | 16.185 | −46.64 | −34.859 | 1 | 13.94 |
| 2984 | CD | PRO | 15 | 16.91 | −47.923 | −34.834 | 1 | 15.14 |
| 2985 | CA | PRO | 15 | 15.121 | −46.663 | −35.868 | 1 | 15.16 |
| 2986 | CB | PRO | 15 | 15.355 | −47.992 | −36.583 | 1 | 15.55 |
| 2987 | CG | PRO | 15 | 15.927 | −48.856 | −35.503 | 1 | 16.22 |
| 2988 | C | PRO | 15 | 13.694 | −46.526 | −35.341 | 1 | 14.27 |

TABLE 1-continued

| Atom | Atom Type | Residue | # | X | Y | Z | OCC | B |
|---|---|---|---|---|---|---|---|---|
| 2989 | O | PRO | 15 | 12.79 | −46.134 | −36.084 | 1 | 14.42 |
| 2990 | N | VAL | 16 | 13.484 | −46.846 | −34.069 | 1 | 13.77 |
| 2991 | CA | VAL | 16 | 12.145 | −46.745 | −33.506 | 1 | 14.75 |
| 2992 | CB | VAL | 16 | 12.104 | −47.251 | −32.042 | 1 | 14.24 |
| 2993 | CG1 | VAL | 16 | 12.781 | −46.254 | −31.11 | 1 | 14.59 |
| 2994 | CG2 | VAL | 16 | 10.665 | −47.499 | −31.626 | 1 | 16.32 |
| 2995 | C | VAL | 16 | 11.648 | −45.299 | −33.57 | 1 | 14.52 |
| 2996 | O | VAL | 16 | 10.446 | −45.054 | −33.658 | 1 | 14.62 |
| 2997 | N | LEU | 17 | 12.573 | −44.342 | −33.559 | 1 | 13.62 |
| 2998 | CA | LEU | 17 | 12.206 | −42.927 | −33.612 | 1 | 13.72 |
| 2999 | CB | LEU | 17 | 13.358 | −42.067 | −33.09 | 1 | 13.76 |
| 3000 | CG | LEU | 17 | 13.759 | −42.279 | −31.627 | 1 | 14 |
| 3001 | CD1 | LEU | 17 | 15.043 | −41.529 | −31.354 | 1 | 12.28 |
| 3002 | CD2 | LEU | 17 | 12.646 | −41.802 | −30.699 | 1 | 13.08 |
| 3003 | C | LEU | 17 | 11.817 | −42.438 | −35.006 | 1 | 13.23 |
| 3004 | O | LEU | 17 | 11.256 | −41.35 | −35.148 | 1 | 13.37 |
| 3005 | N | ARG | 18 | 12.109 | −43.234 | −36.03 | 1 | 12.89 |
| 3006 | CA | ARG | 18 | 11.801 | −42.841 | −37.402 | 1 | 12.69 |
| 3007 | CB | ARG | 18 | 13.071 | −42.903 | −38.256 | 1 | 14.01 |
| 3008 | CG | ARG | 18 | 13.742 | −41.543 | −38.479 | 1 | 12.69 |
| 3009 | CD | ARG | 18 | 14.061 | −40.816 | −37.171 | 1 | 14.11 |
| 3010 | NE | ARG | 18 | 14.882 | −39.629 | −37.407 | 1 | 13.62 |
| 3011 | CZ | ARG | 18 | 14.439 | −38.489 | −37.933 | 1 | 13.58 |
| 3012 | NH1 | ARG | 18 | 13.163 | −38.353 | −38.278 | 1 | 12.88 |
| 3013 | NH2 | ARG | 18 | 15.282 | −37.489 | −38.141 | 1 | 11.36 |
| 3014 | C | ARG | 18 | 10.691 | −43.65 | −38.067 | 1 | 13.36 |
| 3015 | O | ARG | 18 | 10.316 | −43.376 | −39.208 | 1 | 15.34 |
| 3016 | N | GLY | 19 | 10.165 | −44.639 | −37.358 | 1 | 14.69 |
| 3017 | CA | GLY | 19 | 9.094 | −45.438 | −37.922 | 1 | 14.66 |
| 3018 | C | GLY | 19 | 7.746 | −44.817 | −37.617 | 1 | 16.42 |
| 3019 | O | GLY | 19 | 7.662 | −43.82 | −36.897 | 1 | 16.79 |
| 3020 | N | VAL | 20 | 6.687 | −45.392 | −38.176 | 1 | 16.11 |
| 3021 | CA | VAL | 20 | 5.343 | −44.89 | −37.92 | 1 | 17.38 |
| 3022 | CB | VAL | 20 | 4.47 | −44.934 | −39.194 | 1 | 17.1 |
| 3023 | CG1 | VAL | 20 | 3.069 | −44.427 | −38.881 | 1 | 19 |
| 3024 | CG2 | VAL | 20 | 5.105 | −44.088 | −40.286 | 1 | 18.7 |
| 3025 | C | VAL | 20 | 4.738 | −45.789 | −36.849 | 1 | 16.86 |
| 3026 | O | VAL | 20 | 4.511 | −46.978 | −37.082 | 1 | 17.77 |
| 3027 | N | ALA | 21 | 4.498 | −45.228 | −35.667 | 1 | 17.17 |
| 3028 | CA | ALA | 21 | 3.939 | −45.996 | −34.559 | 1 | 17.06 |
| 3029 | CB | ALA | 21 | 3.711 | −45.085 | −33.357 | 1 | 18.11 |
| 3030 | C | ALA | 21 | 2.639 | −46.706 | −34.933 | 1 | 18.23 |
| 3031 | O | ALA | 21 | 1.789 | −46.149 | −35.624 | 1 | 17.79 |
| 3032 | N | ALA | 22 | 2.494 | −47.94 | −34.466 | 1 | 18.51 |
| 3033 | CA | ALA | 22 | 1.298 | −48.723 | −34.748 | 1 | 19.53 |
| 3034 | CB | ALA | 22 | 1.6 | −50.208 | −34.605 | 1 | 20.32 |
| 3035 | C | ALA | 22 | 0.18 | −48.328 | −33.795 | 1 | 18.98 |
| 3036 | O | ALA | 22 | 0.428 | −47.959 | −32.648 | 1 | 17.97 |
| 3037 | N | PRO | 23 | −1.074 | −48.399 | −34.258 | 1 | 20.92 |
| 3038 | CD | PRO | 23 | −1.571 | −48.772 | −35.593 | 1 | 21.03 |
| 3039 | CA | PRO | 23 | −2.176 | −48.03 | −33.371 | 1 | 21.4 |
| 3040 | CB | PRO | 23 | −3.373 | −47.981 | −34.318 | 1 | 22.57 |
| 3041 | CG | PRO | 23 | −3.038 | −49.042 | −35.323 | 1 | 22.52 |
| 3042 | C | PRO | 23 | −2.36 | −49.051 | −32.258 | 1 | 21.63 |
| 3043 | O | PRO | 23 | −1.933 | −50.204 | −32.377 | 1 | 22.05 |
| 3044 | N | VAL | 24 | −2.98 | −48.618 | −31.167 | 1 | 21.39 |
| 3045 | CA | VAL | 24 | −3.257 | −49.504 | −30.047 | 1 | 22.09 |
| 3046 | CB | VAL | 24 | −3.429 | −48.714 | −28.732 | 1 | 21.08 |
| 3047 | CG1 | VAL | 24 | −3.88 | −49.644 | −27.618 | 1 | 21.01 |
| 3048 | CG2 | VAL | 24 | −2.117 | −48.042 | −28.358 | 1 | 21 |
| 3049 | C | VAL | 24 | −4.565 | −50.221 | −30.375 | 1 | 23.89 |
| 3050 | O | VAL | 24 | −5.544 | −49.585 | −30.77 | 1 | 24.38 |
| 3051 | N | GLU | 25 | −4.578 | −51.54 | −30.222 | 1 | 26.33 |
| 3052 | CA | GLU | 25 | −5.773 | −52.328 | −30.515 | 1 | 30.9 |
| 3053 | CB | GLU | 25 | −5.42 | −53.818 | −30.56 | 1 | 33.68 |
| 3054 | CG | GLU | 25 | −4.322 | −54.176 | −31.556 | 1 | 38.26 |
| 3055 | CD | GLU | 25 | −4.738 | −53.971 | −33.004 | 1 | 41.66 |
| 3056 | OE1 | GLU | 25 | −5.027 | −52.819 | −33.392 | 1 | 44.17 |
| 3057 | OE2 | GLU | 25 | −4.774 | −54.969 | −33.756 | 1 | 43.69 |
| 3058 | C | GLU | 25 | −6.868 | −52.09 | −29.477 | 1 | 31.46 |
| 3059 | O | GLU | 25 | −6.583 | −51.88 | −28.297 | 1 | 31.4 |
| 3060 | N | ARG | 26 | −8.119 | −52.126 | −29.927 | 1 | 34.02 |
| 3061 | CA | ARG | 26 | −9.271 | −51.912 | −29.054 | 1 | 36.05 |
| 3062 | CB | ARG | 26 | −10.566 | −52.242 | −29.803 | 1 | 37.59 |
| 3063 | CG | ARG | 26 | −10.938 | −51.253 | −30.895 | 1 | 40.33 |
| 3064 | CD | ARG | 26 | −11.366 | −49.915 | −30.311 | 1 | 42.64 |
| 3065 | NE | ARG | 26 | −11.761 | −48.969 | −31.352 | 1 | 44.58 |
| 3066 | CZ | ARG | 26 | −12.182 | −47.73 | −31.117 | 1 | 45.78 |
| 3067 | NH1 | ARG | 26 | −12.268 | −47.279 | −29.872 | 1 | 46.31 |
| 3068 | NH2 | ARG | 26 | −12.515 | −46.939 | −32.129 | 1 | 47 |
| 3069 | C | ARG | 26 | −9.221 | −52.733 | −27.769 | 1 | 36.01 |
| 3070 | O | ARG | 26 | −9.429 | −52.203 | −26.678 | 1 | 37.02 |
| 3071 | N | ALA | 27 | −8.945 | −54.025 | −27.902 | 1 | 36.94 |
| 3072 | CA | ALA | 27 | −8.89 | −54.922 | −26.752 | 1 | 36.4 |
| 3073 | CB | ALA | 27 | −8.649 | −56.345 | −27.219 | 1 | 37.3 |
| 3074 | C | ALA | 27 | −7.844 | −54.541 | −25.714 | 1 | 36.97 |
| 3075 | O | ALA | 27 | −7.936 | −54.957 | −24.559 | 1 | 36.96 |
| 3076 | N | GLN | 28 | −6.849 | −53.759 | −26.118 | 1 | 36.45 |
| 3077 | CA | GLN | 28 | −5.795 | −53.348 | −25.197 | 1 | 36.35 |
| 3078 | CB | GLN | 28 | −4.508 | −53.047 | −25.967 | 1 | 37.11 |
| 3079 | CG | GLN | 28 | −3.931 | −54.256 | −26.681 | 1 | 40.3 |
| 3080 | CD | GLN | 28 | −3.727 | −55.434 | −25.747 | 1 | 43.12 |
| 3081 | OE1 | GLN | 28 | −3.002 | −55.338 | −24.754 | 1 | 45.16 |
| 3082 | NE2 | GLN | 28 | −4.368 | −56.556 | −26.06 | 1 | 44.43 |
| 3083 | C | GLN | 28 | −6.193 | −52.137 | −24.364 | 1 | 35.51 |
| 3084 | O | GLN | 28 | −5.607 | −51.88 | −23.312 | 1 | 34.91 |
| 3085 | N | LEU | 29 | −7.19 | −51.397 | −24.835 | 1 | 35.31 |
| 3086 | CA | LEU | 29 | −7.661 | −50.217 | −24.122 | 1 | 35.54 |
| 3087 | CB | LEU | 29 | −8.8 | −49.549 | −24.898 | 1 | 35.82 |
| 3088 | CG | LEU | 29 | −8.448 | −48.979 | −26.276 | 1 | 36.56 |
| 3089 | CD1 | LEU | 29 | −9.708 | −48.471 | −26.964 | 1 | 36.77 |
| 3090 | CD2 | LEU | 29 | −7.434 | −47.856 | −26.12 | 1 | 35.77 |
| 3091 | C | LEU | 29 | −8.14 | −50.59 | −22.723 | 1 | 36.36 |
| 3092 | O | LEU | 29 | −8.987 | −51.47 | −22.562 | 1 | 36.41 |
| 3093 | N | GLY | 30 | −7.59 | −49.922 | −21.714 | 1 | 36.26 |
| 3094 | CA | GLY | 30 | −7.978 | −50.2 | −20.343 | 1 | 36.32 |
| 3095 | C | GLY | 30 | −7.24 | −51.381 | −19.743 | 1 | 36.81 |
| 3096 | O | GLY | 30 | −7.388 | −51.674 | −18.555 | 1 | 37.87 |
| 3097 | N | GLY | 31 | −6.443 | −52.06 | −20.565 | 1 | 36.05 |
| 3098 | CA | GLY | 31 | −5.689 | −53.209 | −20.096 | 1 | 35.36 |
| 3099 | C | GLY | 31 | −4.484 | −52.828 | −19.255 | 1 | 35.67 |
| 3100 | O | GLY | 31 | −4.077 | −51.665 | −19.245 | 1 | 34.74 |
| 3101 | N | PRO | 32 | −3.886 | −53.791 | −18.535 | 1 | 35.58 |
| 3102 | CD | PRO | 32 | −4.275 | −55.211 | −18.471 | 1 | 35.7 |
| 3103 | CA | PRO | 32 | −2.718 | −53.536 | −17.686 | 1 | 35.08 |
| 3104 | CB | PRO | 32 | −2.556 | −54.851 | −16.928 | 1 | 35.42 |
| 3105 | CG | PRO | 32 | −3.024 | −55.861 | −17.926 | 1 | 35.92 |
| 3106 | C | PRO | 32 | −1.461 | −53.153 | −18.464 | 1 | 34.52 |
| 3107 | O | PRO | 32 | −0.687 | −52.305 | −18.022 | 1 | 34.87 |
| 3108 | N | GLU | 33 | −1.263 | −53.781 | −19.619 | 1 | 33.63 |
| 3109 | CA | GLU | 33 | −0.096 | −53.506 | −20.452 | 1 | 32.78 |
| 3110 | CB | GLU | 33 | −0.111 | −54.406 | −21.689 | 1 | 35.2 |
| 3111 | CG | GLU | 33 | 1.122 | −54.285 | −22.568 | 1 | 38.96 |
| 3112 | CD | GLU | 33 | 1.123 | −55.288 | −23.706 | 1 | 41.77 |
| 3113 | OE1 | GLU | 33 | 0.193 | −55.25 | −24.54 | 1 | 44.08 |
| 3114 | OE2 | GLU | 33 | 2.055 | −56.119 | −23.765 | 1 | 44.13 |
| 3115 | C | GLU | 33 | −0.066 | −52.04 | −20.874 | 1 | 31.2 |
| 3116 | O | GLU | 33 | 0.987 | −51.4 | −20.851 | 1 | 29.66 |
| 3117 | N | LEU | 34 | −1.221 | −51.511 | −21.263 | 1 | 29.32 |
| 3118 | CA | LEU | 34 | −1.308 | −50.115 | −21.672 | 1 | 28.89 |
| 3119 | CB | LEU | 34 | −2.65 | −49.834 | −22.353 | 1 | 27.53 |
| 3120 | CG | LEU | 34 | −2.86 | −48.4 | −22.852 | 1 | 26.39 |
| 3121 | CD1 | LEU | 34 | −1.762 | −48.03 | −23.839 | 1 | 26.18 |
| 3122 | CD2 | LEU | 34 | −4.226 | −48.28 | −23.51 | 1 | 25.83 |
| 3123 | C | LEU | 34 | −1.156 | −49.234 | −20.437 | 1 | 29.69 |
| 3124 | O | LEU | 34 | −0.596 | −48.139 | −20.51 | 1 | 29.94 |
| 3125 | N | GLN | 35 | −1.66 | −49.716 | −19.303 | 1 | 29.21 |
| 3126 | CA | GLN | 35 | −1.557 | −48.974 | −18.051 | 1 | 30.61 |
| 3127 | CB | GLN | 35 | −2.282 | −49.711 | −16.924 | 1 | 32.58 |
| 3128 | CG | GLN | 35 | −3.794 | −49.742 | −17.055 | 1 | 38.37 |
| 3129 | CD | GLN | 35 | −4.462 | −50.462 | −15.895 | 1 | 40.93 |
| 3130 | OE1 | GLN | 35 | −4.323 | −50.061 | −14.737 | 1 | 42.8 |
| 3131 | NE2 | GLN | 35 | −5.19 | −51.532 | −16.201 | 1 | 42.8 |
| 3132 | C | GLN | 35 | −0.09 | −48.796 | −17.673 | 1 | 29.42 |
| 3133 | O | GLN | 35 | 0.329 | −47.709 | −17.274 | 1 | 29.86 |
| 3134 | N | ARG | 36 | 0.684 | −49.87 | −17.796 | 1 | 28.44 |
| 3135 | CA | ARG | 36 | 2.106 | −49.825 | −17.471 | 1 | 27.87 |
| 3136 | CB | ARG | 36 | 2.747 | −51.203 | −17.662 | 1 | 30.18 |
| 3137 | CG | ARG | 36 | 4.267 | −51.191 | −17.535 | 1 | 34.29 |
| 3138 | CD | ARG | 36 | 4.883 | −52.527 | −17.92 | 1 | 38.27 |
| 3139 | NE | ARG | 36 | 6.34 | −52.445 | −18.009 | 1 | 41.73 |
| 3140 | CZ | ARG | 36 | 7.126 | −53.453 | −18.375 | 1 | 43.36 |

TABLE 1-continued

| Atom | Atom Type | Residue | # | X | Y | Z | OCC | B |
|---|---|---|---|---|---|---|---|---|
| 3141 | NH1 | ARG | 36 | 6.599 | −54.631 | −18.688 | 1 | 44.48 |
| 3142 | NH2 | ARG | 36 | 8.441 | −53.284 | −18.433 | 1 | 44.31 |
| 3143 | C | ARG | 36 | 2.822 | −48.813 | −18.358 | 1 | 26.48 |
| 3144 | O | ARG | 36 | 3.665 | −48.051 | −17.887 | 1 | 25.9 |
| 3145 | N | LEU | 37 | 2.483 | −48.814 | −19.643 | 1 | 23.8 |
| 3146 | CA | LEU | 37 | 3.098 | −47.897 | −20.593 | 1 | 23.41 |
| 3147 | CB | LEU | 37 | 2.627 | −48.212 | −22.017 | 1 | 22.12 |
| 3148 | CG | LEU | 37 | 3.149 | −47.277 | −23.113 | 1 | 21.92 |
| 3149 | CD1 | LEU | 37 | 4.678 | −47.259 | −23.107 | 1 | 22.28 |
| 3150 | CD2 | LEU | 37 | 2.631 | −47.736 | −24.464 | 1 | 19.55 |
| 3151 | C | LEU | 37 | 2.8 | −46.435 | −20.269 | 1 | 23.55 |
| 3152 | O | LEU | 37 | 3.715 | −45.616 | −20.18 | 1 | 22.01 |
| 3153 | N | THR | 38 | 1.523 | −46.106 | −20.095 | 1 | 22.99 |
| 3154 | CA | THR | 38 | 1.142 | −44.732 | −19.789 | 1 | 24.12 |
| 3155 | CB | THR | 38 | −0.394 | −44.571 | −19.741 | 1 | 25.45 |
| 3156 | OG1 | THR | 38 | −0.933 | −45.382 | −18.692 | 1 | 28.12 |
| 3157 | CG2 | THR | 38 | −1.006 | −44.998 | −21.067 | 1 | 24.67 |
| 3158 | C | THR | 38 | 1.744 | −44.287 | −18.461 | 1 | 24.01 |
| 3159 | O | THR | 38 | 2.181 | −43.145 | −18.316 | 1 | 23.25 |
| 3160 | N | GLN | 39 | 1.775 | −45.199 | −17.495 | 1 | 24.14 |
| 3161 | CA | GLN | 39 | 2.34 | −44.904 | −16.186 | 1 | 25.9 |
| 3162 | CB | GLN | 39 | 2.172 | −46.114 | −15.263 | 1 | 29.49 |
| 3163 | CG | GLN | 39 | 2.721 | −45.928 | −13.858 | 1 | 35.5 |
| 3164 | CD | GLN | 39 | 2.44 | −47.126 | −12.965 | 1 | 38.91 |
| 3165 | OE1 | GLN | 39 | 2.857 | −48.248 | −13.262 | 1 | 42.31 |
| 3166 | NE2 | GLN | 39 | 1.729 | −46.894 | −11.867 | 1 | 40.83 |
| 3167 | C | GLN | 39 | 3.822 | −44.563 | −16.338 | 1 | 24.77 |
| 3168 | O | GLN | 39 | 4.314 | −43.601 | −15.748 | 1 | 25.24 |
| 3169 | N | ARG | 40 | 4.527 | −45.349 | −17.145 | 1 | 24.6 |
| 3170 | CA | ARG | 40 | 5.951 | −45.128 | −17.363 | 1 | 23.51 |
| 3171 | CB | ARG | 40 | 6.562 | −46.317 | −18.113 | 1 | 26.72 |
| 3172 | CG | ARG | 40 | 8.08 | −46.278 | −18.195 | 1 | 30.97 |
| 3173 | CD | ARG | 40 | 8.701 | −46.048 | −16.819 | 1 | 35.71 |
| 3174 | NE | ARG | 40 | 8.397 | −47.118 | −15.869 | 1 | 39.37 |
| 3175 | CZ | ARG | 40 | 8.956 | −48.325 | −15.89 | 1 | 41.1 |
| 3176 | NH1 | ARG | 40 | 9.858 | −48.63 | −16.815 | 1 | 41.14 |
| 3177 | NH2 | ARG | 40 | 8.616 | −49.229 | −14.979 | 1 | 41.67 |
| 3178 | C | ARG | 40 | 6.212 | −43.829 | −18.125 | 1 | 21.59 |
| 3179 | O | ARG | 40 | 7.169 | −43.115 | −17.829 | 1 | 20.5 |
| 3180 | N | LEU | 41 | 5.364 | −43.521 | −19.103 | 1 | 20.45 |
| 3181 | CA | LEU | 41 | 5.52 | −42.29 | −19.873 | 1 | 20.27 |
| 3182 | CB | LEU | 41 | 4.425 | −42.172 | −20.936 | 1 | 21.98 |
| 3183 | CG | LEU | 41 | 4.633 | −42.813 | −22.305 | 1 | 22.83 |
| 3184 | CD1 | LEU | 41 | 3.342 | −42.674 | −23.11 | 1 | 22.92 |
| 3185 | CD2 | LEU | 41 | 5.791 | −42.137 | −23.036 | 1 | 21.08 |
| 3186 | C | LEU | 41 | 5.445 | −41.07 | −18.963 | 1 | 20 |
| 3187 | O | LEU | 41 | 6.299 | −40.185 | −19.016 | 1 | 20.37 |
| 3188 | N | VAL | 42 | 4.405 | −41.025 | −18.136 | 1 | 21.04 |
| 3189 | CA | VAL | 42 | 4.205 | −39.912 | −17.22 | 1 | 21.62 |
| 3190 | CB | VAL | 42 | 2.857 | −40.046 | −16.477 | 1 | 23.43 |
| 3191 | CG1 | VAL | 42 | 2.693 | −38.911 | −15.48 | 1 | 22.81 |
| 3192 | CG2 | VAL | 42 | 1.715 | −40.032 | −17.48 | 1 | 22.5 |
| 3193 | C | VAL | 42 | 5.332 | −39.823 | −16.2 | 1 | 21.97 |
| 3194 | O | VAL | 42 | 5.777 | −38.734 | −15.844 | 1 | 21.53 |
| 3195 | N | GLN | 43 | 5.799 | −40.974 | −15.738 | 1 | 21.97 |
| 3196 | CA | GLN | 43 | 6.872 | −41.008 | −14.758 | 1 | 22.85 |
| 3197 | CB | GLN | 43 | 7.11 | −42.453 | −14.324 | 1 | 25.54 |
| 3198 | CG | GLN | 43 | 7.865 | −42.613 | −13.025 | 1 | 32.72 |
| 3199 | CD | GLN | 43 | 7.715 | −44.01 | −12.463 | 1 | 36.63 |
| 3200 | OE1 | GLN | 43 | 8.007 | −44.996 | −13.14 | 1 | 39.56 |
| 3201 | NE2 | GLN | 43 | 7.248 | −44.104 | −11.223 | 1 | 39.55 |
| 3202 | C | GLN | 43 | 8.148 | −40.394 | −15.339 | 1 | 20.78 |
| 3203 | O | GLN | 43 | 8.786 | −39.555 | −14.705 | 1 | 19.68 |
| 3204 | N | VAL | 44 | 8.51 | −40.8 | −16.552 | 1 | 20.26 |
| 3205 | CA | VAL | 44 | 9.707 | −40.272 | −17.2 | 1 | 20.43 |
| 3206 | CB | VAL | 44 | 10.032 | −41.056 | −18.491 | 1 | 20.49 |
| 3207 | CG1 | VAL | 44 | 11.191 | −40.401 | −19.229 | 1 | 21.36 |
| 3208 | CG2 | VAL | 44 | 10.376 | −42.492 | −18.141 | 1 | 20.99 |
| 3209 | C | VAL | 44 | 9.536 | −38.799 | −17.544 | 1 | 20.86 |
| 3210 | O | VAL | 44 | 10.45 | −37.994 | −17.376 | 1 | 19.99 |
| 3211 | N | MET | 45 | 8.352 | −38.45 | −18.028 | 1 | 21.86 |
| 3212 | CA | MET | 45 | 8.067 | −37.074 | −18.394 | 1 | 23.49 |
| 3213 | CB | MET | 45 | 6.632 | −36.968 | −18.904 | 1 | 24.09 |
| 3214 | CG | MET | 45 | 6.316 | −35.679 | −19.63 | 1 | 25.55 |
| 3215 | SD | MET | 45 | 4.559 | −35.56 | −20.015 | 1 | 28.2 |
| 3216 | CE | MET | 45 | 4.135 | −37.259 | −20.015 | 1 | 23.4 |
| 3217 | C | MET | 45 | 8.261 | −36.161 | −17.188 | 1 | 24.29 |
| 3218 | O | MET | 45 | 8.893 | −35.112 | −17.289 | 1 | 25.14 |
| 3219 | N | ARG | 46 | 7.728 | −36.57 | −16.042 | 1 | 25.24 |
| 3220 | CA | ARG | 46 | 7.842 | −35.775 | −14.826 | 1 | 25.61 |
| 3221 | CB | ARG | 46 | 6.853 | −36.292 | −13.779 | 1 | 27.07 |
| 3222 | CG | ARG | 46 | 5.408 | −35.991 | −14.159 | 1 | 26.65 |
| 3223 | CD | ARG | 46 | 4.405 | −36.646 | −13.227 | 1 | 28.34 |
| 3224 | NE | ARG | 46 | 3.049 | −36.179 | −13.512 | 1 | 29.15 |
| 3225 | CZ | ARG | 46 | 1.946 | −36.709 | −12.991 | 1 | 29.87 |
| 3226 | NH1 | ARG | 46 | 2.031 | −37.734 | −12.155 | 1 | 30.91 |
| 3227 | NH2 | ARG | 46 | 0.758 | −36.21 | −13.304 | 1 | 29.97 |
| 3228 | C | ARG | 46 | 9.259 | −35.724 | −14.257 | 1 | 25.46 |
| 3229 | O | ARG | 46 | 9.689 | −34.687 | −13.753 | 1 | 25.09 |
| 3230 | N | ARG | 47 | 9.986 | −36.835 | −14.344 | 1 | 23.97 |
| 3231 | CA | ARG | 47 | 11.357 | −36.88 | −13.844 | 1 | 23.94 |
| 3232 | CB | ARG | 47 | 11.89 | −38.315 | −13.875 | 1 | 25.69 |
| 3233 | CG | ARG | 47 | 11.333 | −39.216 | −12.784 | 1 | 30.76 |
| 3234 | CD | ARG | 47 | 11.886 | −40.629 | −12.907 | 1 | 33.52 |
| 3235 | NE | ARG | 47 | 11.431 | −41.506 | −11.83 | 1 | 38.09 |
| 3236 | CZ | ARG | 47 | 11.836 | −41.42 | −10.566 | 1 | 39.34 |
| 3237 | NH1 | ARG | 47 | 12.714 | −40.491 | −10.208 | 1 | 40.8 |
| 3238 | NH2 | ARG | 47 | 11.364 | −42.265 | −9.658 | 1 | 40.79 |
| 3239 | C | ARG | 47 | 12.271 | −35.98 | −14.67 | 1 | 22.84 |
| 3240 | O | ARG | 47 | 13.162 | −35.317 | −14.135 | 1 | 23.43 |
| 3241 | N | ARG | 48 | 12.047 | −35.963 | −15.979 | 1 | 21.63 |
| 3242 | CA | ARG | 48 | 12.848 | −35.152 | −16.89 | 1 | 20.49 |
| 3243 | CB | ARG | 48 | 12.928 | −35.835 | −18.258 | 1 | 20.2 |
| 3244 | CG | ARG | 48 | 13.865 | −37.039 | −18.289 | 1 | 21.97 |
| 3245 | CD | ARG | 48 | 15.295 | −36.59 | −18.022 | 1 | 22.9 |
| 3246 | NE | ARG | 48 | 15.685 | −35.532 | −18.95 | 1 | 25.16 |
| 3247 | CZ | ARG | 48 | 16.378 | −34.452 | −18.61 | 1 | 26.28 |
| 3248 | NH1 | ARG | 48 | 16.77 | −34.278 | −17.355 | 1 | 29.07 |
| 3249 | NH2 | ARG | 48 | 16.665 | −33.535 | −19.523 | 1 | 30.19 |
| 3250 | C | ARG | 48 | 12.281 | −33.749 | −17.038 | 1 | 21.47 |
| 3251 | O | ARG | 48 | 12.899 | −32.872 | −17.645 | 1 | 20.43 |
| 3252 | N | ARG | 49 | 11.097 | −33.546 | −16.472 | 1 | 22.06 |
| 3253 | CA | ARG | 49 | 10.427 | −32.258 | −16.522 | 1 | 23.74 |
| 3254 | CB | ARG | 49 | 11.259 | −31.215 | −15.779 | 1 | 26.16 |
| 3255 | CG | ARG | 49 | 11.505 | −31.593 | −14.328 | 1 | 29.22 |
| 3256 | CD | ARG | 49 | 12.339 | −30.562 | −13.61 | 1 | 33.7 |
| 3257 | NE | ARG | 49 | 12.666 | −30.994 | −12.255 | 1 | 35.83 |
| 3258 | CZ | ARG | 49 | 13.378 | −30.274 | −11.396 | 1 | 37.7 |
| 3259 | NH1 | ARG | 49 | 13.836 | −29.081 | −11.755 | 1 | 38.39 |
| 3260 | NH2 | ARG | 49 | 13.633 | −30.746 | −10.183 | 1 | 37.95 |
| 3261 | C | ARG | 49 | 10.133 | −31.791 | −17.941 | 1 | 22.78 |
| 3262 | O | ARG | 49 | 10.123 | −30.594 | −18.221 | 1 | 24.4 |
| 3263 | N | CYS | 50 | 9.907 | −32.74 | −18.844 | 1 | 22.37 |
| 3264 | CA | CYS | 50 | 9.569 | −32.382 | −20.214 | 1 | 21.64 |
| 3265 | CB | CYS | 50 | 10.095 | −33.43 | −21.207 | 1 | 23.13 |
| 3266 | SG | CYS | 50 | 9.774 | −35.157 | −20.811 | 1 | 25.36 |
| 3267 | C | CYS | 50 | 8.044 | −32.265 | −20.27 | 1 | 20.98 |
| 3268 | O | CYS | 50 | 7.33 | −33.003 | −19.592 | 1 | 22.83 |
| 3269 | N | VAL | 51 | 7.557 | −31.317 | −21.058 | 1 | 19.32 |
| 3270 | CA | VAL | 51 | 6.127 | −31.057 | −21.182 | 1 | 18.21 |
| 3271 | CB | VAL | 51 | 5.903 | −29.707 | −21.896 | 1 | 18.23 |
| 3272 | CG1 | VAL | 51 | 4.419 | −29.392 | −21.992 | 1 | 19.45 |
| 3273 | CG2 | VAL | 51 | 6.624 | −28.605 | −21.13 | 1 | 21.71 |
| 3274 | C | VAL | 51 | 5.345 | −32.155 | −21.902 | 1 | 18.39 |
| 3275 | O | VAL | 51 | 4.134 | −32.28 | −21.732 | 1 | 19.08 |
| 3276 | N | GLY | 52 | 6.036 | −32.95 | −22.707 | 1 | 16.74 |
| 3277 | CA | GLY | 52 | 5.369 | −34.025 | −23.419 | 1 | 15.38 |
| 3278 | C | GLY | 52 | 6.339 | −35.158 | −23.673 | 1 | 15.13 |
| 3279 | O | GLY | 52 | 7.548 | −34.975 | −23.542 | 1 | 15.11 |
| 3280 | N | LEU | 53 | 5.814 | −36.327 | −24.022 | 1 | 13.94 |
| 3281 | CA | LEU | 53 | 6.649 | −37.492 | −24.309 | 1 | 14.33 |
| 3282 | CB | LEU | 53 | 7.184 | −38.093 | −23.005 | 1 | 14.08 |
| 3283 | CG | LEU | 53 | 8.225 | −39.211 | −23.11 | 1 | 14.01 |
| 3284 | CD1 | LEU | 53 | 9.47 | −38.685 | −23.797 | 1 | 15.16 |
| 3285 | CD2 | LEU | 53 | 8.568 | −39.726 | −21.715 | 1 | 13.37 |
| 3286 | C | LEU | 53 | 5.797 | −38.515 | −25.051 | 1 | 13.53 |
| 3287 | O | LEU | 53 | 4.59 | −38.613 | −24.809 | 1 | 14.85 |
| 3288 | N | SER | 54 | 6.421 | −39.271 | −25.952 | 1 | 12.96 |
| 3289 | CA | SER | 54 | 5.713 | −40.282 | −26.739 | 1 | 13.32 |
| 3290 | CB | SER | 54 | 5.808 | −39.95 | −28.23 | 1 | 13.69 |
| 3291 | OG | SER | 54 | 7.149 | −40.029 | −28.684 | 1 | 15.88 |
| 3292 | C | SER | 54 | 6.262 | −41.688 | −26.502 | 1 | 14.49 |

TABLE 1-continued

| Atom | Atom Type | Residue | # | X | Y | Z | OCC | B |
|---|---|---|---|---|---|---|---|---|
| 3293 | O | SER | 54 | 7.428 | −41.858 | −26.139 | 1 | 14.62 |
| 3294 | N | ALA | 55 | 5.421 | −42.695 | −26.73 | 1 | 14.64 |
| 3295 | CA | ALA | 55 | 5.819 | −44.088 | −26.531 | 1 | 15.67 |
| 3296 | CB | ALA | 55 | 4.65 | −45.019 | −26.857 | 1 | 15.6 |
| 3297 | C | ALA | 55 | 7.058 | −44.504 | −27.327 | 1 | 14.59 |
| 3298 | O | ALA | 55 | 7.919 | −45.214 | −26.804 | 1 | 14.39 |
| 3299 | N | PRO | 56 | 7.168 | −44.08 | −28.601 | 1 | 14.14 |
| 3300 | CD | PRO | 56 | 6.177 | −43.41 | −29.465 | 1 | 13.59 |
| 3301 | CA | PRO | 56 | 8.353 | −44.47 | −29.376 | 1 | 13.31 |
| 3302 | CB | PRO | 56 | 8.148 | −43.746 | −30.704 | 1 | 14.03 |
| 3303 | CG | PRO | 56 | 6.654 | −43.78 | −30.856 | 1 | 14.08 |
| 3304 | C | PRO | 56 | 9.667 | −44.082 | −28.694 | 1 | 13.76 |
| 3305 | O | PRO | 56 | 10.681 | −44.762 | −28.846 | 1 | 14.22 |
| 3306 | N | GLN | 57 | 9.642 | −42.992 | −27.936 | 1 | 12.7 |
| 3307 | CA | GLN | 57 | 10.838 | −42.533 | −27.243 | 1 | 13.82 |
| 3308 | CB | GLN | 57 | 10.622 | −41.114 | −26.733 | 1 | 13.3 |
| 3309 | CG | GLN | 57 | 10.511 | −40.107 | −27.857 | 1 | 12.62 |
| 3310 | CD | GLN | 57 | 10.119 | −38.747 | −27.355 | 1 | 14.72 |
| 3311 | OE1 | GLN | 57 | 8.933 | −38.457 | −27.168 | 1 | 13.92 |
| 3312 | NE2 | GLN | 57 | 11.114 | −37.902 | −27.107 | 1 | 13.5 |
| 3313 | C | GLN | 57 | 11.243 | −43.465 | −26.106 | 1 | 14.33 |
| 3314 | O | GLN | 57 | 12.376 | −43.402 | −25.617 | 1 | 14.82 |
| 3315 | N | LEU | 58 | 10.319 | −44.321 | −25.677 | 1 | 14.82 |
| 3316 | CA | LEU | 58 | 10.623 | −45.29 | −24.628 | 1 | 16.87 |
| 3317 | CB | LEU | 58 | 9.496 | −45.366 | −23.596 | 1 | 17.78 |
| 3318 | CG | LEU | 58 | 9.316 | −44.121 | −22.723 | 1 | 18.33 |
| 3319 | CD1 | LEU | 58 | 8.317 | −44.419 | −21.612 | 1 | 21.61 |
| 3320 | CD2 | LEU | 58 | 10.66 | −43.706 | −22.124 | 1 | 18.51 |
| 3321 | C | LEU | 58 | 10.841 | −46.655 | −25.276 | 1 | 17.87 |
| 3322 | O | LEU | 58 | 10.885 | −47.681 | −24.596 | 1 | 20.19 |
| 3323 | N | GLY | 59 | 10.975 | −46.651 | −26.599 | 1 | 16.17 |
| 3324 | CA | GLY | 59 | 11.21 | −47.878 | −27.341 | 1 | 16.45 |
| 3325 | C | GLY | 59 | 9.971 | −48.672 | −27.706 | 1 | 17.45 |
| 3326 | O | GLY | 59 | 10.074 | −49.81 | −28.167 | 1 | 18.1 |
| 3327 | N | VAL | 60 | 8.8 | −48.075 | −27.51 | 1 | 17.35 |
| 3328 | CA | VAL | 60 | 7.533 | −48.736 | −27.81 | 1 | 17.62 |
| 3329 | CB | VAL | 60 | 6.592 | −48.659 | −26.596 | 1 | 18.53 |
| 3330 | CG1 | VAL | 60 | 5.291 | −49.38 | −26.891 | 1 | 19.77 |
| 3331 | CG2 | VAL | 60 | 7.275 | −49.269 | −25.381 | 1 | 21.11 |
| 3332 | C | VAL | 60 | 6.872 | −48.068 | −29.013 | 1 | 17.94 |
| 3333 | O | VAL | 60 | 6.344 | −46.96 | −28.904 | 1 | 16.96 |
| 3334 | N | PRO | 61 | 6.894 | −48.737 | −30.182 | 1 | 17.54 |
| 3335 | CD | PRO | 61 | 7.52 | −50.051 | −30.427 | 1 | 18.94 |
| 3336 | CA | PRO | 61 | 6.304 | −48.209 | −31.415 | 1 | 16.98 |
| 3337 | CB | PRO | 61 | 6.943 | −49.077 | −32.493 | 1 | 18.48 |
| 3338 | CG | PRO | 61 | 7.014 | −50.406 | −31.817 | 1 | 18.86 |
| 3339 | C | PRO | 61 | 4.779 | −48.271 | −31.443 | 1 | 17.96 |
| 3340 | O | PRO | 61 | 4.187 | −48.927 | −32.304 | 1 | 18.47 |
| 3341 | N | ARG | 62 | 4.152 | −47.578 | −30.499 | 1 | 17.39 |
| 3342 | CA | ARG | 62 | 2.697 | −47.546 | −30.408 | 1 | 16.98 |
| 3343 | CB | ARG | 62 | 2.232 | −48.315 | −29.17 | 1 | 18.54 |
| 3344 | CG | ARG | 62 | 2.712 | −49.761 | −29.137 | 1 | 22.52 |
| 3345 | CD | ARG | 62 | 2.27 | −50.476 | −27.869 | 1 | 26.74 |
| 3346 | NE | ARG | 62 | 0.851 | −50.822 | −27.885 | 1 | 30.82 |
| 3347 | CZ | ARG | 62 | 0.188 | −51.307 | −26.838 | 1 | 32.94 |
| 3348 | NH1 | ARG | 62 | 0.814 | −51.5 | −25.684 | 1 | 33.39 |
| 3349 | NH2 | ARG | 62 | −1.099 | −51.609 | −26.947 | 1 | 33.69 |
| 3350 | C | ARG | 62 | 2.221 | −46.1 | −30.338 | 1 | 16.42 |
| 3351 | O | ARG | 62 | 2.929 | −45.222 | −29.838 | 1 | 15.38 |
| 3352 | N | GLN | 63 | 1.017 | −45.856 | −30.839 | 1 | 15.23 |
| 3353 | CA | GLN | 63 | 0.461 | −44.51 | −30.853 | 1 | 15.5 |
| 3354 | CB | GLN | 63 | −0.656 | −44.426 | −31.891 | 1 | 15.25 |
| 3355 | CG | GLN | 63 | −0.154 | −44.489 | −33.323 | 1 | 16.53 |
| 3356 | CD | GLN | 63 | −1.286 | −44.618 | −34.32 | 1 | 18.56 |
| 3357 | OE1 | GLN | 63 | −2.345 | −44.021 | −34.145 | 1 | 19.53 |
| 3358 | NE2 | GLN | 63 | −1.064 | −45.393 | −35.377 | 1 | 18.69 |
| 3359 | C | GLN | 63 | −0.047 | −44.061 | −29.491 | 1 | 15.89 |
| 3360 | O | GLN | 63 | −1.248 | −44.067 | −29.221 | 1 | 15.35 |
| 3361 | N | VAL | 64 | 0.886 | −43.665 | −28.633 | 1 | 14.99 |
| 3362 | CA | VAL | 64 | 0.549 | −43.198 | −27.299 | 1 | 15.08 |
| 3363 | CB | VAL | 64 | 0.754 | −44.306 | −26.241 | 1 | 15.6 |
| 3364 | CG1 | VAL | 64 | 0.306 | −43.809 | −24.875 | 1 | 16.02 |
| 3365 | CG2 | VAL | 64 | −0.02 | −45.558 | −26.638 | 1 | 15.79 |
| 3366 | C | VAL | 64 | 1.458 | −42.031 | −26.947 | 1 | 15.92 |
| 3367 | O | VAL | 64 | 2.667 | −42.089 | −27.172 | 1 | 15.04 |
| 3368 | N | LEU | 65 | 0.874 | −40.967 | −26.409 | 1 | 14.51 |
| 3369 | CA | LEU | 65 | 1.654 | −39.806 | −26.016 | 1 | 15.05 |
| 3370 | CB | LEU | 65 | 1.759 | −38.804 | −27.182 | 1 | 15.11 |
| 3371 | CG | LEU | 65 | 0.497 | −38.156 | −27.761 | 1 | 14.62 |
| 3372 | CD1 | LEU | 65 | 0.004 | −37.058 | −26.828 | 1 | 16.36 |
| 3373 | CD2 | LEU | 65 | 0.812 | −37.567 | −29.13 | 1 | 16.18 |
| 3374 | C | LEU | 65 | 1.008 | −39.161 | −24.802 | 1 | 14.96 |
| 3375 | O | LEU | 65 | −0.176 | −39.371 | −24.532 | 1 | 16.1 |
| 3376 | N | ALA | 66 | 1.793 | −38.391 | −24.061 | 1 | 14.33 |
| 3377 | CA | ALA | 66 | 1.29 | −37.721 | −22.872 | 1 | 15.08 |
| 3378 | CB | ALA | 66 | 1.773 | −38.437 | −21.633 | 1 | 15.69 |
| 3379 | C | ALA | 66 | 1.76 | −36.277 | −22.873 | 1 | 15.5 |
| 3380 | O | ALA | 66 | 2.833 | −35.962 | −23.392 | 1 | 14.52 |
| 3381 | N | LEU | 67 | 0.951 | −35.4 | −22.286 | 1 | 15.81 |
| 3382 | CA | LEU | 67 | 1.262 | −33.981 | −22.242 | 1 | 17.79 |
| 3383 | CB | LEU | 67 | 0.464 | −33.254 | −23.332 | 1 | 21.65 |
| 3384 | CG | LEU | 67 | 0.394 | −33.936 | −24.704 | 1 | 23.34 |
| 3385 | CD1 | LEU | 67 | −0.859 | −33.499 | −25.443 | 1 | 24.68 |
| 3386 | CD2 | LEU | 67 | 1.641 | −33.606 | −25.502 | 1 | 26.44 |
| 3387 | C | LEU | 67 | 0.866 | −33.423 | −20.88 | 1 | 17.03 |
| 3388 | O | LEU | 67 | −0.186 | −33.77 | −20.351 | 1 | 16.97 |
| 3389 | N | GLU | 68 | 1.711 | −32.568 | −20.313 | 1 | 16.63 |
| 3390 | CA | GLU | 68 | 1.417 | −31.945 | −19.027 | 1 | 17.21 |
| 3391 | CB | GLU | 68 | 1.567 | −32.947 | −17.879 | 1 | 18.97 |
| 3392 | CG | GLU | 68 | 1.315 | −32.329 | −16.505 | 1 | 22.43 |
| 3393 | CD | GLU | 68 | 1.564 | −33.298 | −15.366 | 1 | 25.25 |
| 3394 | OE1 | GLU | 68 | 2.64 | −33.933 | −15.35 | 1 | 27.52 |
| 3395 | OE2 | GLU | 68 | 0.689 | −33.419 | −14.484 | 1 | 27.07 |
| 3396 | C | GLU | 68 | 2.342 | −30.761 | −18.786 | 1 | 18.08 |
| 3397 | O | GLU | 68 | 3.564 | −30.881 | −18.895 | 1 | 16.87 |
| 3398 | N | LEU | 69 | 1.758 | −29.614 | −18.462 | 1 | 16.5 |
| 3399 | CA | LEU | 69 | 2.553 | −28.426 | −18.204 | 1 | 17.6 |
| 3400 | CB | LEU | 69 | 2.374 | −27.407 | −19.335 | 1 | 19.32 |
| 3401 | CG | LEU | 69 | 3.109 | −26.07 | −19.199 | 1 | 20.81 |
| 3402 | CD1 | LEU | 69 | 4.581 | −26.307 | −18.879 | 1 | 23.84 |
| 3403 | CD2 | LEU | 69 | 2.956 | −25.279 | −20.489 | 1 | 21.27 |
| 3404 | C | LEU | 69 | 2.159 | −27.814 | −16.868 | 1 | 19.6 |
| 3405 | O | LEU | 69 | 1.197 | −27.048 | −16.781 | 1 | 18.09 |
| 3406 | N | PRO | 70 | 2.891 | −28.167 | −15.8 | 1 | 20.21 |
| 3407 | CD | PRO | 70 | 3.912 | −29.227 | −15.745 | 1 | 20.98 |
| 3408 | CA | PRO | 70 | 2.616 | −27.646 | −14.458 | 1 | 21.18 |
| 3409 | CB | PRO | 70 | 3.6 | −28.42 | −13.577 | 1 | 21.64 |
| 3410 | CG | PRO | 70 | 3.778 | −29.713 | −14.323 | 1 | 22.75 |
| 3411 | C | PRO | 70 | 2.849 | −26.143 | −14.39 | 1 | 21.43 |
| 3412 | O | PRO | 70 | 3.671 | −25.593 | −15.123 | 1 | 20.87 |
| 3413 | N | GLU | 71 | 2.115 | −25.482 | −13.504 | 1 | 22.28 |
| 3414 | CA | GLU | 71 | 2.24 | −24.045 | −13.335 | 1 | 24.58 |
| 3415 | CB | GLU | 71 | 1.298 | −23.583 | −12.225 | 1 | 27.96 |
| 3416 | CG | GLU | 71 | 1.367 | −22.106 | −11.916 | 1 | 34.5 |
| 3417 | CD | GLU | 71 | 0.345 | −21.701 | −10.875 | 1 | 38 |
| 3418 | OE1 | GLU | 71 | 0.358 | −22.291 | −9.773 | 1 | 40.95 |
| 3419 | OE2 | GLU | 71 | −0.47 | −20.798 | −11.16 | 1 | 41.26 |
| 3420 | C | GLU | 71 | 3.682 | −23.67 | −12.993 | 1 | 23.44 |
| 3421 | O | GLU | 71 | 4.21 | −22.678 | −13.493 | 1 | 23.49 |
| 3422 | N | ALA | 72 | 4.314 | −24.477 | −12.147 | 1 | 23.58 |
| 3423 | CA | ALA | 72 | 5.691 | −24.231 | −11.733 | 1 | 24.93 |
| 3424 | CB | ALA | 72 | 6.173 | −25.361 | −10.834 | 1 | 25.67 |
| 3425 | C | ALA | 72 | 6.627 | −24.077 | −12.926 | 1 | 26 |
| 3426 | O | ALA | 72 | 7.474 | −23.186 | −12.945 | 1 | 25.29 |
| 3427 | N | LEU | 73 | 6.468 | −24.94 | −13.926 | 1 | 27.07 |
| 3428 | CA | LEU | 73 | 7.316 | −24.886 | −15.109 | 1 | 28.26 |
| 3429 | CB | LEU | 73 | 7.01 | −26.07 | −16.032 | 1 | 29.52 |
| 3430 | CG | LEU | 73 | 8.074 | −26.388 | −17.085 | 1 | 31.6 |
| 3431 | CD1 | LEU | 73 | 9.406 | −26.674 | −16.399 | 1 | 30.95 |
| 3432 | CD2 | LEU | 73 | 7.637 | −27.588 | −17.909 | 1 | 31.75 |
| 3433 | C | LEU | 73 | 7.138 | −23.57 | −15.861 | 1 | 29.17 |
| 3434 | O | LEU | 73 | 8.11 | −22.985 | −16.337 | 1 | 29.23 |
| 3435 | N | CYS | 74 | 5.897 | −23.104 | −15.97 | 1 | 28.67 |
| 3436 | CA | CYS | 74 | 5.618 | −21.845 | −16.653 | 1 | 28.85 |
| 3437 | CB | CYS | 74 | 4.112 | −21.59 | −16.729 | 1 | 29.78 |
| 3438 | SG | CYS | 74 | 3.239 | −22.641 | −17.87 | 1 | 29.51 |
| 3439 | C | CYS | 74 | 6.258 | −20.678 | −15.92 | 1 | 29.77 |
| 3440 | O | CYS | 74 | 6.875 | −19.806 | −16.534 | 1 | 30.8 |
| 3441 | N | ARG | 75 | 6.095 | −20.666 | −14.602 | 1 | 30.34 |
| 3442 | CA | ARG | 75 | 6.633 | −19.598 | −13.773 | 1 | 32.11 |
| 3443 | CB | ARG | 75 | 6.12 | −19.742 | −12.339 | 1 | 32.57 |
| 3444 | CG | ARG | 75 | 4.623 | −19.517 | −12.218 | 1 | 33.76 |

TABLE 1-continued

| Atom | Atom Type | Residue | # | X | Y | Z | OCC | B |
|---|---|---|---|---|---|---|---|---|
| 3445 | CD | ARG | 75 | 4.166 | −19.519 | −10.768 | 1 | 35.52 |
| 3446 | NE | ARG | 75 | 2.754 | −19.163 | −10.659 | 1 | 38.28 |
| 3447 | CZ | ARG | 75 | 2.09 | −19.069 | −9.512 | 1 | 39.77 |
| 3448 | NH1 | ARG | 75 | 2.708 | −19.305 | −8.361 | 1 | 39.97 |
| 3449 | NH2 | ARG | 75 | 0.806 | −18.734 | −9.514 | 1 | 40.22 |
| 3450 | C | ARG | 75 | 8.153 | −19.527 | −13.782 | 1 | 33.05 |
| 3451 | O | ARG | 75 | 8.73 | −18.479 | −13.486 | 1 | 33.5 |
| 3452 | N | GLU | 76 | 8.803 | −20.635 | −14.123 | 1 | 33.82 |
| 3453 | CA | GLU | 76 | 10.258 | −20.657 | −14.175 | 1 | 35.58 |
| 3454 | CB | GLU | 76 | 10.774 | −22.096 | −14.17 | 1 | 37.32 |
| 3455 | CG | GLU | 76 | 12.286 | −22.196 | −14.064 | 1 | 40.9 |
| 3456 | CD | GLU | 76 | 12.854 | −21.294 | −12.979 | 1 | 42.19 |
| 3457 | OE1 | GLU | 76 | 12.371 | −21.364 | −11.828 | 1 | 43.51 |
| 3458 | OE2 | GLU | 76 | 13.785 | −20.515 | −13.277 | 1 | 43.77 |
| 3459 | C | GLU | 76 | 10.723 | −19.933 | −15.434 | 1 | 36.13 |
| 3460 | O | GLU | 76 | 11.875 | −19.509 | −15.533 | 1 | 36.35 |
| 3461 | N | CYS | 77 | 9.813 | −19.796 | −16.394 | 1 | 35.88 |
| 3462 | CA | CYS | 77 | 10.105 | −19.106 | −17.644 | 1 | 36.95 |
| 3463 | CB | CYS | 77 | 9.201 | −19.635 | −18.763 | 1 | 36.21 |
| 3464 | SG | CYS | 77 | 9.457 | −18.865 | −20.382 | 1 | 39.22 |
| 3465 | C | CYS | 77 | 9.847 | −17.616 | −17.426 | 1 | 37.1 |
| 3466 | O | CYS | 77 | 8.766 | −17.227 | −16.981 | 1 | 37.95 |
| 3467 | N | PRO | 78 | 10.84 | −16.764 | −17.731 | 1 | 37.32 |
| 3468 | CD | PRO | 78 | 12.145 | −17.107 | −18.323 | 1 | 36.95 |
| 3469 | CA | PRO | 78 | 10.713 | −15.313 | −17.566 | 1 | 37.36 |
| 3470 | CB | PRO | 78 | 11.887 | −14.778 | −18.376 | 1 | 37.77 |
| 3471 | CG | PRO | 78 | 12.927 | −15.822 | −18.146 | 1 | 37.25 |
| 3472 | C | PRO | 78 | 9.37 | −14.781 | −18.06 | 1 | 37.87 |
| 3473 | O | PRO | 78 | 8.897 | −15.163 | −19.129 | 1 | 37.6 |
| 3474 | N | PRO | 79 | 8.743 | −13.883 | −17.283 | 1 | 37.73 |
| 3475 | CD | PRO | 79 | 9.272 | −13.3 | −16.037 | 1 | 38.43 |
| 3476 | CA | PRO | 79 | 7.447 | −13.286 | −17.621 | 1 | 37.19 |
| 3477 | CB | PRO | 79 | 7.356 | −12.109 | −16.656 | 1 | 37.87 |
| 3478 | CG | PRO | 79 | 8.043 | −12.646 | −15.442 | 1 | 38.33 |
| 3479 | C | PRO | 79 | 7.312 | −12.854 | −19.079 | 1 | 36.49 |
| 3480 | O | PRO | 79 | 6.301 | −13.138 | −19.724 | 1 | 36.02 |
| 3481 | N | ARG | 80 | 8.326 | −12.168 | −19.595 | 1 | 35.94 |
| 3482 | CA | ARG | 80 | 8.287 | −11.706 | −20.976 | 1 | 35.75 |
| 3483 | CB | ARG | 80 | 9.429 | −10.724 | −21.253 | 1 | 37.43 |
| 3484 | CG | ARG | 80 | 9.413 | −10.178 | −22.675 | 1 | 41.34 |
| 3485 | CD | ARG | 80 | 8.029 | −9.644 | −23.024 | 1 | 44.08 |
| 3486 | NE | ARG | 80 | 7.882 | −9.337 | −24.444 | 1 | 47.02 |
| 3487 | CZ | ARG | 80 | 6.739 | −8.955 | −25.008 | 1 | 47.8 |
| 3488 | NH1 | ARG | 80 | 5.643 | −8.833 | −24.269 | 1 | 47.84 |
| 3489 | NH2 | ARG | 80 | 6.69 | −8.697 | −26.308 | 1 | 47.98 |
| 3490 | C | ARG | 80 | 8.356 | −12.868 | −21.962 | 1 | 34.22 |
| 3491 | O | ARG | 80 | 7.628 | −12.889 | −22.956 | 1 | 33.25 |
| 3492 | N | GLN | 81 | 9.233 | −13.829 | −21.689 | 1 | 33.34 |
| 3493 | CA | GLN | 81 | 9.368 | −14.992 | −22.557 | 1 | 32.13 |
| 3494 | CB | GLN | 81 | 10.529 | −15.878 | −22.099 | 1 | 34.37 |
| 3495 | CG | GLN | 81 | 11.907 | −15.284 | −22.337 | 1 | 38.08 |
| 3496 | CD | GLN | 81 | 13.025 | −16.231 | −21.943 | 1 | 40.39 |
| 3497 | OE1 | GLN | 81 | 13.089 | −17.369 | −22.415 | 1 | 42.61 |
| 3498 | NE2 | GLN | 81 | 13.917 | −15.765 | −21.076 | 1 | 42.12 |
| 3499 | C | GLN | 81 | 8.074 | −15.791 | −22.527 | 1 | 30.82 |
| 3500 | O | GLN | 81 | 7.563 | −16.206 | −23.566 | 1 | 29.01 |
| 3501 | N | ARG | 82 | 7.546 | −16.002 | −21.326 | 1 | 28.96 |
| 3502 | CA | ARG | 82 | 6.306 | −16.748 | −21.158 | 1 | 27.75 |
| 3503 | CB | ARG | 82 | 5.894 | −16.77 | −19.682 | 1 | 28.15 |
| 3504 | CG | ARG | 82 | 4.568 | −17.464 | −19.441 | 1 | 29.71 |
| 3505 | CD | ARG | 82 | 4.162 | −17.451 | −17.977 | 1 | 31.49 |
| 3506 | NE | ARG | 82 | 2.871 | −18.107 | −17.791 | 1 | 32.29 |
| 3507 | CZ | ARG | 82 | 2.286 | −18.297 | −16.614 | 1 | 33.37 |
| 3508 | NH1 | ARG | 82 | 2.875 | −17.88 | −15.5 | 1 | 34.04 |
| 3509 | NH2 | ARG | 82 | 1.11 | −18.906 | −16.551 | 1 | 33.89 |
| 3510 | C | ARG | 82 | 5.181 | −16.144 | −21.994 | 1 | 26.95 |
| 3511 | O | ARG | 82 | 4.46 | −16.859 | −22.688 | 1 | 26.31 |
| 3512 | N | ALA | 83 | 5.035 | −14.824 | −21.925 | 1 | 25.74 |
| 3513 | CA | ALA | 83 | 3.996 | −14.129 | −22.673 | 1 | 25.72 |
| 3514 | CB | ALA | 83 | 3.952 | −12.663 | −22.26 | 1 | 25.8 |
| 3515 | C | ALA | 83 | 4.244 | −14.24 | −24.172 | 1 | 24.67 |
| 3516 | O | ALA | 83 | 3.322 | −14.48 | −24.949 | 1 | 24.25 |
| 3517 | N | LEU | 84 | 5.499 | −14.061 | −24.568 | 1 | 23.32 |
| 3518 | CA | LEU | 84 | 5.886 | −14.133 | −25.972 | 1 | 23.73 |
| 3519 | CB | LEU | 84 | 7.385 | −13.856 | −26.102 | 1 | 26.14 |
| 3520 | CG | LEU | 84 | 7.944 | −13.457 | −27.467 | 1 | 30.07 |
| 3521 | CD1 | LEU | 84 | 7.47 | −12.05 | −27.823 | 1 | 30.26 |
| 3522 | CD2 | LEU | 84 | 9.467 | −13.502 | −27.423 | 1 | 31.9 |
| 3523 | C | LEU | 84 | 5.56 | −15.513 | −26.543 | 1 | 21.81 |
| 3524 | O | LEU | 84 | 5.069 | −15.634 | −27.666 | 1 | 20.89 |
| 3525 | N | ARG | 85 | 5.826 | −16.551 | −25.757 | 1 | 20.37 |
| 3526 | CA | ARG | 85 | 5.576 | −17.924 | −26.182 | 1 | 18.98 |
| 3527 | CB | ARG | 85 | 6.569 | −18.865 | −25.498 | 1 | 19.49 |
| 3528 | CG | ARG | 85 | 8.014 | −18.543 | −25.831 | 1 | 20.8 |
| 3529 | CD | ARG | 85 | 8.989 | −19.503 | −25.178 | 1 | 22.72 |
| 3530 | NE | ARG | 85 | 10.354 | −19.184 | −25.581 | 1 | 23.87 |
| 3531 | CZ | ARG | 85 | 11.409 | −19.959 | −25.357 | 1 | 26.73 |
| 3532 | NH1 | ARG | 85 | 11.269 | −21.117 | −24.725 | 1 | 26.71 |
| 3533 | NH2 | ARG | 85 | 12.606 | −19.576 | −25.778 | 1 | 27.75 |
| 3534 | C | ARG | 85 | 4.153 | −18.393 | −25.904 | 1 | 18.91 |
| 3535 | O | ARG | 85 | 3.791 | −19.52 | −26.244 | 1 | 18.71 |
| 3536 | N | GLN | 86 | 3.346 | −17.525 | −25.297 | 1 | 19 |
| 3537 | CA | GLN | 86 | 1.966 | −17.864 | −24.965 | 1 | 19.85 |
| 3538 | CB | GLN | 86 | 1.121 | −17.968 | −26.235 | 1 | 22.32 |
| 3539 | CG | GLN | 86 | 0.873 | −16.631 | −26.911 | 1 | 25.16 |
| 3540 | CD | GLN | 86 | 0.132 | −16.774 | −28.222 | 1 | 26.87 |
| 3541 | OE1 | GLN | 86 | −0.866 | −17.488 | −28.308 | 1 | 28.04 |
| 3542 | NE2 | GLN | 86 | 0.613 | −16.089 | −29.252 | 1 | 32.58 |
| 3543 | C | GLN | 86 | 1.947 | −19.183 | −24.213 | 1 | 19.65 |
| 3544 | O | GLN | 86 | 1.23 | −20.122 | −24.569 | 1 | 20.3 |
| 3545 | N | MET | 87 | 2.758 | −19.24 | −23.165 | 1 | 18.87 |
| 3546 | CA | MET | 87 | 2.874 | −20.422 | −22.338 | 1 | 18.49 |
| 3547 | CB | MET | 87 | 4.297 | −20.513 | −21.788 | 1 | 20.41 |
| 3548 | CG | MET | 87 | 4.674 | −21.853 | −21.208 | 1 | 24.45 |
| 3549 | SD | MET | 87 | 6.387 | −21.823 | −20.646 | 1 | 28.78 |
| 3550 | CE | MET | 87 | 7.205 | −21.28 | −22.11 | 1 | 27.14 |
| 3551 | C | MET | 87 | 1.875 | −20.335 | −21.192 | 1 | 18.94 |
| 3552 | O | MET | 87 | 1.906 | −19.396 | −20.395 | 1 | 21.56 |
| 3553 | N | GLU | 88 | 0.978 | −21.308 | −21.131 | 1 | 16.61 |
| 3554 | CA | GLU | 88 | −0.024 | −21.375 | −20.078 | 1 | 18.17 |
| 3555 | CB | GLU | 88 | −1.403 | −20.982 | −20.617 | 1 | 18.24 |
| 3556 | CG | GLU | 88 | −1.485 | −19.56 | −21.148 | 1 | 20.56 |
| 3557 | CD | GLU | 88 | −1.353 | −18.51 | −20.062 | 1 | 21.7 |
| 3558 | OE1 | GLU | 88 | −1.338 | −17.309 | −20.402 | 1 | 24.69 |
| 3559 | OE2 | GLU | 88 | −1.266 | −18.882 | −18.872 | 1 | 23.5 |
| 3560 | C | GLU | 88 | −0.049 | −22.815 | −19.597 | 1 | 18.23 |
| 3561 | O | GLU | 88 | 0.096 | −23.747 | −20.389 | 1 | 19.4 |
| 3562 | N | PRO | 89 | −0.228 | −23.023 | −18.29 | 1 | 18.89 |
| 3563 | CD | PRO | 89 | −0.37 | −22.059 | −17.185 | 1 | 18.71 |
| 3564 | CA | PRO | 89 | −0.254 | −24.399 | −17.799 | 1 | 17.71 |
| 3565 | CB | PRO | 89 | −0.189 | −24.222 | −16.284 | 1 | 20.22 |
| 3566 | CG | PRO | 89 | −0.897 | −22.928 | −16.071 | 1 | 19.82 |
| 3567 | C | PRO | 89 | −1.485 | −25.178 | −18.237 | 1 | 18.69 |
| 3568 | O | PRO | 89 | −2.522 | −24.597 | −18.563 | 1 | 19.36 |
| 3569 | N | PHE | 90 | −1.346 | −26.498 | −18.278 | 1 | 16.9 |
| 3570 | CA | PHE | 90 | −2.453 | −27.38 | −18.613 | 1 | 16.91 |
| 3571 | CB | PHE | 90 | −2.62 | −27.571 | −20.133 | 1 | 17.76 |
| 3572 | CG | PHE | 90 | −1.375 | −27.998 | −20.861 | 1 | 16.32 |
| 3573 | CD1 | PHE | 90 | −0.568 | −27.055 | −21.491 | 1 | 16.94 |
| 3574 | CD2 | PHE | 90 | −1.04 | −29.347 | −20.967 | 1 | 17.99 |
| 3575 | CE1 | PHE | 90 | 0.555 | −27.446 | −22.225 | 1 | 17.31 |
| 3576 | CE2 | PHE | 90 | 0.08 | −29.75 | −21.697 | 1 | 16.79 |
| 3577 | CZ | PHE | 90 | 0.878 | −28.799 | −22.328 | 1 | 17.37 |
| 3578 | C | PHE | 90 | −2.264 | −28.717 | −17.912 | 1 | 17.85 |
| 3579 | O | PHE | 90 | −1.132 | −29.161 | −17.682 | 1 | 17.93 |
| 3580 | N | PRO | 91 | −3.375 | −29.369 | −17.542 | 1 | 16.93 |
| 3581 | CD | PRO | 91 | −4.764 | −28.923 | −17.764 | 1 | 17.89 |
| 3582 | CA | PRO | 91 | −3.353 | −30.66 | −16.853 | 1 | 17.19 |
| 3583 | CB | PRO | 91 | −4.795 | −30.82 | −16.389 | 1 | 18.39 |
| 3584 | CG | PRO | 91 | −5.554 | −30.186 | −17.503 | 1 | 16.38 |
| 3585 | C | PRO | 91 | −2.893 | −31.832 | −17.707 | 1 | 17.63 |
| 3586 | O | PRO | 91 | −2.911 | −31.778 | −18.939 | 1 | 16.64 |
| 3587 | N | LEU | 92 | −2.492 | −32.899 | −17.029 | 1 | 16.54 |
| 3588 | CA | LEU | 92 | −2.024 | −34.1 | −17.696 | 1 | 17.76 |
| 3589 | CB | LEU | 92 | −1.554 | −35.126 | −16.661 | 1 | 18.29 |
| 3590 | CG | LEU | 92 | −1.278 | −36.528 | −17.214 | 1 | 18.87 |
| 3591 | CD1 | LEU | 92 | −0.062 | −36.488 | −18.129 | 1 | 19.31 |
| 3592 | CD2 | LEU | 92 | −1.052 | −37.502 | −16.063 | 1 | 20.56 |
| 3593 | C | LEU | 92 | −3.092 | −34.74 | −18.572 | 1 | 18.37 |
| 3594 | O | LEU | 92 | −4.25 | −34.887 | −18.17 | 1 | 17.62 |
| 3595 | N | ARG | 93 | −2.69 | −35.116 | −19.778 | 1 | 18.09 |
| 3596 | CA | ARG | 93 | −3.579 | −35.79 | −20.704 | 1 | 18.33 |

TABLE 1-continued

| Atom | Atom Type | Residue | # | X | Y | Z | OCC | B |
|---|---|---|---|---|---|---|---|---|
| 3597 | CB | ARG | 93 | −4.234 | −34.81 | −21.677 | 1 | 20.35 |
| 3598 | CG | ARG | 93 | −5.331 | −33.976 | −21.047 | 1 | 20.25 |
| 3599 | CD | ARG | 93 | −6.27 | −33.405 | −22.1 | 1 | 22.78 |
| 3600 | NE | ARG | 93 | −7.339 | −32.634 | −21.473 | 1 | 25.81 |
| 3601 | CZ | ARG | 93 | −7.171 | −31.43 | −20.939 | 1 | 25.55 |
| 3602 | NH1 | ARG | 93 | −5.977 | −30.852 | −20.967 | 1 | 28.7 |
| 3603 | NH2 | ARG | 93 | −8.191 | −30.818 | −20.35 | 1 | 27.28 |
| 3604 | C | ARG | 93 | −2.781 | −36.814 | −21.476 | 1 | 17.79 |
| 3605 | O | ARG | 93 | −1.676 | −36.536 | −21.944 | 1 | 18.03 |
| 3606 | N | VAL | 94 | −3.342 | −38.009 | −21.581 | 1 | 17.08 |
| 3607 | CA | VAL | 94 | −2.704 | −39.092 | −22.306 | 1 | 16.93 |
| 3608 | CB | VAL | 94 | −2.559 | −40.343 | −21.421 | 1 | 17.65 |
| 3609 | CG1 | VAL | 94 | −1.936 | −41.478 | −22.222 | 1 | 17.93 |
| 3610 | CG2 | VAL | 94 | −1.708 | −40.012 | −20.201 | 1 | 19.18 |
| 3611 | C | VAL | 94 | −3.589 | −39.421 | −23.492 | 1 | 18.34 |
| 3612 | O | VAL | 94 | −4.788 | −39.652 | −23.333 | 1 | 18.94 |
| 3613 | N | PHE | 95 | −3.001 | −39.431 | −24.683 | 1 | 16.39 |
| 3614 | CA | PHE | 95 | −3.76 | −39.734 | −25.886 | 1 | 16.95 |
| 3615 | CB | PHE | 95 | −3.629 | −38.606 | −26.911 | 1 | 16.86 |
| 3616 | CG | PHE | 95 | −4.422 | −37.384 | −26.565 | 1 | 19.77 |
| 3617 | CD1 | PHE | 95 | −3.918 | −36.439 | −25.677 | 1 | 19.27 |
| 3618 | CD2 | PHE | 95 | −5.688 | −37.189 | −27.111 | 1 | 20.48 |
| 3619 | CE1 | PHE | 95 | −4.667 | −35.313 | −25.335 | 1 | 21.75 |
| 3620 | CE2 | PHE | 95 | −6.447 | −36.066 | −26.776 | 1 | 21 |
| 3621 | CZ | PHE | 95 | −5.936 | −35.128 | −25.886 | 1 | 21.41 |
| 3622 | C | PHE | 95 | −3.336 | −41.034 | −26.539 | 1 | 18.35 |
| 3623 | O | PHE | 95 | −2.147 | −41.315 | −26.668 | 1 | 16.66 |
| 3624 | N | VAL | 96 | −4.328 | −41.817 | −26.949 | 1 | 17.85 |
| 3625 | CA | VAL | 96 | −4.103 | −43.088 | −27.623 | 1 | 19.04 |
| 3626 | CB | VAL | 96 | −4.792 | −44.25 | −26.866 | 1 | 20.53 |
| 3627 | CG1 | VAL | 96 | −4.655 | −45.547 | −27.656 | 1 | 20.54 |
| 3628 | CG2 | VAL | 96 | −4.168 | −44.406 | −25.485 | 1 | 21.15 |
| 3629 | C | VAL | 96 | −4.693 | −42.96 | −29.027 | 1 | 19.23 |
| 3630 | O | VAL | 96 | −5.807 | −42.456 | −29.194 | 1 | 18.3 |
| 3631 | N | ASN | 97 | −3.937 | −43.402 | −30.029 | 1 | 17.73 |
| 3632 | CA | ASN | 97 | −4.358 | −43.321 | −31.429 | 1 | 17.98 |
| 3633 | CB | ASN | 97 | −5.451 | −44.35 | −31.721 | 1 | 18.74 |
| 3634 | CG | ASN | 97 | −5.003 | −45.77 | −31.456 | 1 | 20.82 |
| 3635 | OD1 | ASN | 97 | −3.806 | −46.056 | −31.387 | 1 | 19.74 |
| 3636 | ND2 | ASN | 97 | −5.966 | −46.677 | −31.319 | 1 | 20.29 |
| 3637 | C | ASN | 97 | −4.866 | −41.925 | −31.792 | 1 | 18.74 |
| 3638 | O | ASN | 97 | −5.945 | −41.773 | −32.373 | 1 | 18.56 |
| 3639 | N | PRO | 98 | −4.089 | −40.881 | −31.467 | 1 | 17.36 |
| 3640 | CD | PRO | 98 | −2.814 | −40.871 | −30.721 | 1 | 16.03 |
| 3641 | CA | PRO | 98 | −4.517 | −39.518 | −31.781 | 1 | 16.56 |
| 3642 | CB | PRO | 98 | −3.63 | −38.671 | −30.879 | 1 | 15.61 |
| 3643 | CG | PRO | 98 | −2.34 | −39.441 | −30.896 | 1 | 16.26 |
| 3644 | C | PRO | 98 | −4.383 | −39.11 | −33.244 | 1 | 18.1 |
| 3645 | O | PRO | 98 | −3.625 | −39.703 | −34.013 | 1 | 16.56 |
| 3646 | N | SER | 99 | −5.151 | −38.094 | −33.616 | 1 | 17.16 |
| 3647 | CA | SER | 99 | −5.115 | −37.53 | −34.955 | 1 | 18.61 |
| 3648 | CB | SER | 99 | −6.374 | −37.906 | −35.744 | 1 | 20.89 |
| 3649 | OG | SER | 99 | −7.548 | −37.462 | −35.089 | 1 | 27.32 |
| 3650 | C | SER | 99 | −5.052 | −36.028 | −34.71 | 1 | 17.97 |
| 3651 | O | SER | 99 | −5.593 | −35.536 | −33.717 | 1 | 18.59 |
| 3652 | N | LEU | 100 | −4.377 | −35.303 | −35.589 | 1 | 16.9 |
| 3653 | CA | LEU | 100 | −4.245 | −33.865 | −35.415 | 1 | 16.93 |
| 3654 | CB | LEU | 100 | −2.765 | −33.492 | −35.266 | 1 | 19.29 |
| 3655 | CG | LEU | 100 | −2.42 | −32.021 | −35.002 | 1 | 22.23 |
| 3656 | CD1 | LEU | 100 | −1.089 | −31.93 | −34.277 | 1 | 26.29 |
| 3657 | CD2 | LEU | 100 | −2.371 | −31.249 | −36.31 | 1 | 25.53 |
| 3658 | C | LEU | 100 | −4.852 | −33.07 | −36.555 | 1 | 17.28 |
| 3659 | O | LEU | 100 | −4.758 | −33.458 | −37.72 | 1 | 16.76 |
| 3660 | N | ARG | 101 | −5.48 | −31.952 | −36.207 | 1 | 16.75 |
| 3661 | CA | ARG | 101 | −6.069 | −31.065 | −37.201 | 1 | 17.11 |
| 3662 | CB | ARG | 101 | −7.596 | −31.062 | −37.107 | 1 | 21.13 |
| 3663 | CG | ARG | 101 | −8.259 | −30.169 | −38.15 | 1 | 25.71 |
| 3664 | CD | ARG | 101 | −9.757 | −30.039 | −37.922 | 1 | 29.45 |
| 3665 | NE | ARG | 101 | −10.442 | −31.326 | −37.972 | 1 | 35.13 |
| 3666 | CZ | ARG | 101 | −11.746 | −31.486 | −37.767 | 1 | 37.75 |
| 3667 | NH1 | ARG | 101 | −12.511 | −30.435 | −37.5 | 1 | 39.59 |
| 3668 | NH2 | ARG | 101 | −12.286 | −32.696 | −37.826 | 1 | 40.16 |
| 3669 | C | ARG | 101 | −5.543 | −29.664 | −36.922 | 1 | 16.05 |
| 3670 | O | ARG | 101 | −5.603 | −29.19 | −35.785 | 1 | 15.75 |
| 3671 | N | VAL | 102 | −5.012 | −29.013 | −37.954 | 1 | 15.35 |
| 3672 | CA | VAL | 102 | −4.488 | −27.66 | −37.818 | 1 | 15.3 |
| 3673 | CB | VAL | 102 | −3.475 | −27.336 | −38.937 | 1 | 15.96 |
| 3674 | CG1 | VAL | 102 | −2.959 | −25.909 | −38.779 | 1 | 15.84 |
| 3675 | CG2 | VAL | 102 | −2.313 | −28.328 | −38.887 | 1 | 15.89 |
| 3676 | C | VAL | 102 | −5.661 | −26.684 | −37.892 | 1 | 16.53 |
| 3677 | O | VAL | 102 | −6.463 | −26.734 | −38.832 | 1 | 16.09 |
| 3678 | N | LEU | 103 | −5.764 | −25.808 | −36.897 | 1 | 15.86 |
| 3679 | CA | LEU | 103 | −6.852 | −24.833 | −36.835 | 1 | 17.62 |
| 3680 | CB | LEU | 103 | −7.434 | −24.795 | −35.418 | 1 | 17.6 |
| 3681 | CG | LEU | 103 | −7.987 | −26.129 | −34.91 | 1 | 17.27 |
| 3682 | CD1 | LEU | 103 | −8.538 | −25.953 | −33.507 | 1 | 19.48 |
| 3683 | CD2 | LEU | 103 | −9.071 | −26.64 | −35.855 | 1 | 19.94 |
| 3684 | C | LEU | 103 | −6.406 | −23.438 | −37.266 | 1 | 18.91 |
| 3685 | O | LEU | 103 | −7.176 | −22.689 | −37.869 | 1 | 20.86 |
| 3686 | N | ASP | 104 | −5.169 | −23.081 | −36.936 | 1 | 18.26 |
| 3687 | CA | ASP | 104 | −4.601 | −21.798 | −37.334 | 1 | 18.05 |
| 3688 | CB | ASP | 104 | −4.454 | −20.845 | −36.143 | 1 | 19.34 |
| 3689 | CG | ASP | 104 | −4.041 | −19.443 | −36.569 | 1 | 20.69 |
| 3690 | OD1 | ASP | 104 | −3.393 | −19.303 | −37.628 | 1 | 20.71 |
| 3691 | OD2 | ASP | 104 | −4.353 | −18.477 | −35.842 | 1 | 23 |
| 3692 | C | ASP | 104 | −3.229 | −22.154 | −37.882 | 1 | 19.35 |
| 3693 | O | ASP | 104 | −2.324 | −22.517 | −37.123 | 1 | 17.93 |
| 3694 | N | SER | 105 | −3.083 | −22.069 | −39.2 | 1 | 18.62 |
| 3695 | CA | SER | 105 | −1.831 | −22.422 | −39.852 | 1 | 20.27 |
| 3696 | CB | SER | 105 | −2.095 | −22.836 | −41.305 | 1 | 20.44 |
| 3697 | OG | SER | 105 | −2.815 | −21.838 | −42.003 | 1 | 24.65 |
| 3698 | C | SER | 105 | −0.733 | −21.368 | −39.804 | 1 | 18.47 |
| 3699 | O | SER | 105 | 0.334 | −21.565 | −40.386 | 1 | 18.35 |
| 3700 | N | ARG | 106 | −0.98 | −20.252 | −39.12 | 1 | 16.94 |
| 3701 | CA | ARG | 106 | 0.046 | −19.223 | −39 | 1 | 18.36 |
| 3702 | CB | ARG | 106 | −0.464 | −18.034 | −38.181 | 1 | 20.41 |
| 3703 | CG | ARG | 106 | 0.587 | −16.958 | −37.928 | 1 | 24.14 |
| 3704 | CD | ARG | 106 | −0.033 | −15.691 | −37.338 | 1 | 27.83 |
| 3705 | NE | ARG | 106 | −0.532 | −15.879 | −35.977 | 1 | 30.66 |
| 3706 | CZ | ARG | 106 | 0.225 | −15.835 | −34.883 | 1 | 31.81 |
| 3707 | NH1 | ARG | 106 | 1.528 | −15.606 | −34.977 | 1 | 33.06 |
| 3708 | NH2 | ARG | 106 | −0.324 | −16.017 | −33.691 | 1 | 33.4 |
| 3709 | C | ARG | 106 | 1.214 | −19.885 | −38.275 | 1 | 17.91 |
| 3710 | O | ARG | 106 | 1.007 | −20.624 | −37.311 | 1 | 19.37 |
| 3711 | N | LEU | 107 | 2.431 | −19.623 | −38.738 | 1 | 17.57 |
| 3712 | CA | LEU | 107 | 3.613 | −20.225 | −38.135 | 1 | 17.12 |
| 3713 | CB | LEU | 107 | 4.628 | −20.58 | −39.223 | 1 | 18.07 |
| 3714 | CG | LEU | 107 | 4.185 | −21.648 | −40.224 | 1 | 18.78 |
| 3715 | CD1 | LEU | 107 | 5.243 | −21.808 | −41.301 | 1 | 19.71 |
| 3716 | CD2 | LEU | 107 | 3.947 | −22.97 | −39.502 | 1 | 18.12 |
| 3717 | C | LEU | 107 | 4.288 | −19.348 | −37.092 | 1 | 17.52 |
| 3718 | O | LEU | 107 | 4.514 | −18.158 | −37.312 | 1 | 16.81 |
| 3719 | N | VAL | 108 | 4.607 | −19.958 | −35.956 | 1 | 16.61 |
| 3720 | CA | VAL | 108 | 5.281 | −19.28 | −34.857 | 1 | 17.05 |
| 3721 | CB | VAL | 108 | 4.446 | −19.352 | −33.565 | 1 | 18.5 |
| 3722 | CG1 | VAL | 108 | 5.172 | −18.649 | −32.44 | 1 | 22.98 |
| 3723 | CG2 | VAL | 108 | 3.084 | −18.704 | −33.793 | 1 | 22.24 |
| 3724 | C | VAL | 108 | 6.607 | −20.014 | −34.659 | 1 | 14.99 |
| 3725 | O | VAL | 108 | 6.639 | −21.242 | −34.632 | 1 | 15.21 |
| 3726 | N | THR | 109 | 7.695 | −19.263 | −34.522 | 1 | 15.14 |
| 3727 | CA | THR | 109 | 9.019 | −19.867 | −34.372 | 1 | 16.6 |
| 3728 | CB | THR | 109 | 9.946 | −19.419 | −35.524 | 1 | 17.23 |
| 3729 | OG1 | THR | 109 | 9.375 | −19.822 | −36.776 | 1 | 18.2 |
| 3730 | CG2 | THR | 109 | 11.333 | −20.039 | −35.379 | 1 | 19.46 |
| 3731 | C | THR | 109 | 9.715 | −19.562 | −33.048 | 1 | 16.18 |
| 3732 | O | THR | 109 | 9.904 | −18.401 | −32.687 | 1 | 16.69 |
| 3733 | N | PHE | 110 | 10.104 | −20.623 | −32.346 | 1 | 15.64 |
| 3734 | CA | PHE | 110 | 10.8 | −20.524 | −31.065 | 1 | 15.86 |
| 3735 | CB | PHE | 110 | 9.81 | −20.569 | −29.901 | 1 | 17.21 |
| 3736 | CG | PHE | 110 | 9.027 | −19.307 | −29.717 | 1 | 17.34 |
| 3737 | CD1 | PHE | 110 | 9.663 | −18.128 | −29.343 | 1 | 19.52 |
| 3738 | CD2 | PHE | 110 | 7.651 | −19.297 | −29.908 | 1 | 19.71 |
| 3739 | CE1 | PHE | 110 | 8.937 | −16.955 | −29.161 | 1 | 19.58 |
| 3740 | CE2 | PHE | 110 | 6.917 | −18.128 | −29.728 | 1 | 20.73 |
| 3741 | CZ | PHE | 110 | 7.562 | −16.953 | −29.354 | 1 | 20.41 |
| 3742 | C | PHE | 110 | 11.754 | −21.704 | −30.919 | 1 | 15.72 |
| 3743 | O | PHE | 110 | 11.583 | −22.733 | −31.579 | 1 | 14.58 |
| 3744 | N | PRO | 111 | 12.772 | −21.569 | −30.05 | 1 | 16.09 |
| 3745 | CD | PRO | 111 | 13.225 | −20.353 | −29.354 | 1 | 16.95 |
| 3746 | CA | PRO | 111 | 13.724 | −22.664 | −29.848 | 1 | 17.18 |
| 3747 | CB | PRO | 111 | 14.731 | −22.075 | −28.863 | 1 | 17.02 |
| 3748 | CG | PRO | 111 | 14.708 | −20.618 | −29.196 | 1 | 16.96 |

TABLE 1-continued

| Atom | Atom Type | Residue | # | X | Y | Z | OCC | B |
|---|---|---|---|---|---|---|---|---|
| 3749 | C | PRO | 111 | 12.978 | −23.852 | −29.261 | 1 | 16.73 |
| 3750 | O | PRO | 111 | 12.12 | −23.698 | −28.391 | 1 | 16.69 |
| 3751 | N | GLU | 112 | 13.323 | −25.04 | −29.737 | 1 | 15.3 |
| 3752 | CA | GLU | 112 | 12.679 | −26.259 | −29.296 | 1 | 15.76 |
| 3753 | CB | GLU | 112 | 11.68 | −26.68 | −30.376 | 1 | 19.01 |
| 3754 | CG | GLU | 112 | 10.695 | −27.737 | −29.984 | 1 | 21.1 |
| 3755 | CD | GLU | 112 | 9.756 | −28.062 | −31.126 | 1 | 20.75 |
| 3756 | OE1 | GLU | 112 | 8.993 | −27.164 | −31.551 | 1 | 18.04 |
| 3757 | OE2 | GLU | 112 | 9.791 | −29.213 | −31.604 | 1 | 20.47 |
| 3758 | C | GLU | 112 | 13.742 | −27.338 | −29.1 | 1 | 14.42 |
| 3759 | O | GLU | 112 | 14.743 | −27.359 | −29.81 | 1 | 14.71 |
| 3760 | N | GLY | 113 | 13.531 | −28.213 | −28.123 | 1 | 14.74 |
| 3761 | CA | GLY | 113 | 14.473 | −29.29 | −27.871 | 1 | 16.46 |
| 3762 | C | GLY | 113 | 13.758 | −30.627 | −27.938 | 1 | 15.61 |
| 3763 | O | GLY | 113 | 12.56 | −30.675 | −28.206 | 1 | 15.19 |
| 3764 | N | CYS | 114 | 14.486 | −31.712 | −27.69 | 1 | 15.14 |
| 3765 | CA | CYS | 114 | 13.904 | −33.051 | −27.723 | 1 | 12.76 |
| 3766 | CB | CYS | 114 | 13.904 | −33.609 | −29.151 | 1 | 11.84 |
| 3767 | SG | CYS | 114 | 13.135 | −35.244 | −29.312 | 1 | 12.46 |
| 3768 | C | CYS | 114 | 14.704 | −33.987 | −26.831 | 1 | 11.51 |
| 3769 | O | CYS | 114 | 15.928 | −34.065 | −26.945 | 1 | 13.02 |
| 3770 | N | GLU | 115 | 14.012 | −34.696 | −25.949 | 1 | 12.73 |
| 3771 | CA | GLU | 115 | 14.667 | −35.635 | −25.047 | 1 | 12.13 |
| 3772 | CB | GLU | 115 | 13.638 | −36.288 | −24.119 | 1 | 13.65 |
| 3773 | CG | GLU | 115 | 13.107 | −35.381 | −23.018 | 1 | 16.32 |
| 3774 | CD | GLU | 115 | 14.173 | −34.992 | −22.006 | 1 | 18.9 |
| 3775 | OE1 | GLU | 115 | 14.876 | −35.893 | −21.498 | 1 | 20.03 |
| 3776 | OE2 | GLU | 115 | 14.301 | −33.786 | −21.708 | 1 | 22.18 |
| 3777 | C | GLU | 115 | 15.408 | −36.719 | −25.827 | 1 | 12.45 |
| 3778 | O | GLU | 115 | 16.331 | −37.341 | −25.299 | 1 | 12.86 |
| 3779 | N | SER | 116 | 15.007 | −36.933 | −27.08 | 1 | 12.32 |
| 3780 | CA | SER | 116 | 15.635 | −37.945 | −27.933 | 1 | 11.42 |
| 3781 | CB | SER | 116 | 14.588 | −38.594 | −28.843 | 1 | 12.46 |
| 3782 | OG | SER | 116 | 13.731 | −39.441 | −28.091 | 1 | 13.94 |
| 3783 | C | SER | 116 | 16.812 | −37.425 | −28.765 | 1 | 12.54 |
| 3784 | O | SER | 116 | 17.393 | −38.159 | −29.569 | 1 | 12.89 |
| 3785 | N | VAL | 117 | 17.142 | −36.152 | −28.582 | 1 | 12.16 |
| 3786 | CA | VAL | 117 | 18.287 | −35.526 | −29.234 | 1 | 13.85 |
| 3787 | CB | VAL | 117 | 17.884 | −34.622 | −30.419 | 1 | 13.88 |
| 3788 | CG1 | VAL | 117 | 19.136 | −34.182 | −31.172 | 1 | 14.22 |
| 3789 | CG2 | VAL | 117 | 16.946 | −35.367 | −31.356 | 1 | 14.37 |
| 3790 | C | VAL | 117 | 18.83 | −34.666 | −28.098 | 1 | 14.57 |
| 3791 | O | VAL | 117 | 18.942 | −33.446 | −28.203 | 1 | 14.83 |
| 3792 | N | ALA | 118 | 19.145 | −35.339 | −26.997 | 1 | 15.34 |
| 3793 | CA | ALA | 118 | 19.623 | −34.696 | −25.782 | 1 | 15.83 |
| 3794 | CB | ALA | 118 | 20.054 | −35.767 | −24.779 | 1 | 18.33 |
| 3795 | C | ALA | 118 | 20.731 | −33.66 | −25.932 | 1 | 16.1 |
| 3796 | O | ALA | 118 | 21.72 | −33.884 | −26.628 | 1 | 16.27 |
| 3797 | N | GLY | 119 | 20.539 | −32.521 | −25.272 | 1 | 15.78 |
| 3798 | CA | GLY | 119 | 21.537 | −31.464 | −25.274 | 1 | 15.88 |
| 3799 | C | GLY | 119 | 21.534 | −30.448 | −26.396 | 1 | 15.68 |
| 3800 | O | GLY | 119 | 22.448 | −29.626 | −26.478 | 1 | 14.73 |
| 3801 | N | PHE | 120 | 20.518 | −30.481 | −27.251 | 1 | 15.59 |
| 3802 | CA | PHE | 120 | 20.447 | −29.546 | −28.368 | 1 | 15.3 |
| 3803 | CB | PHE | 120 | 20.727 | −30.288 | −29.676 | 1 | 15.32 |
| 3804 | CG | PHE | 120 | 22.113 | −30.855 | −29.764 | 1 | 16.98 |
| 3805 | CD1 | PHE | 120 | 23.174 | −30.068 | −30.195 | 1 | 16.33 |
| 3806 | CD2 | PHE | 120 | 22.361 | −32.169 | −29.389 | 1 | 17.87 |
| 3807 | CE1 | PHE | 120 | 24.466 | −30.581 | −30.252 | 1 | 17.82 |
| 3808 | CE2 | PHE | 120 | 23.652 | −32.698 | −29.439 | 1 | 20.53 |
| 3809 | CZ | PHE | 120 | 24.707 | −31.901 | −29.873 | 1 | 20.13 |
| 3810 | C | PHE | 120 | 19.104 | −28.832 | −28.477 | 1 | 16.26 |
| 3811 | O | PHE | 120 | 18.075 | −29.33 | −28.019 | 1 | 19.04 |
| 3812 | N | LEU | 121 | 19.135 | −27.659 | −29.096 | 1 | 15.09 |
| 3813 | CA | LEU | 121 | 17.947 | −26.846 | −29.32 | 1 | 15.81 |
| 3814 | CB | LEU | 121 | 17.869 | −25.7 | −28.305 | 1 | 18.64 |
| 3815 | CG | LEU | 121 | 17.574 | −25.975 | −26.832 | 1 | 20.9 |
| 3816 | CD1 | LEU | 121 | 17.726 | −24.675 | −26.037 | 1 | 21.11 |
| 3817 | CD2 | LEU | 121 | 16.158 | −26.52 | −26.684 | 1 | 22.59 |
| 3818 | C | LEU | 121 | 18.056 | −26.241 | −30.713 | 1 | 15.2 |
| 3819 | O | LEU | 121 | 19.151 | −26.105 | −31.254 | 1 | 14.59 |
| 3820 | N | ALA | 122 | 16.917 | −25.883 | −31.293 | 1 | 13.59 |
| 3821 | CA | ALA | 122 | 16.898 | −25.241 | −32.599 | 1 | 13.49 |
| 3822 | CB | ALA | 122 | 17.114 | −26.264 | −33.711 | 1 | 14.51 |
| 3823 | C | ALA | 122 | 15.541 | −24.58 | −32.757 | 1 | 13.24 |
| 3824 | O | ALA | 122 | 14.547 | −25.067 | −32.22 | 1 | 13.58 |
| 3825 | N | CYS | 123 | 15.502 | −23.46 | −33.469 | 1 | 13.75 |
| 3826 | CA | CYS | 123 | 14.232 | −22.785 | −33.698 | 1 | 14.55 |
| 3827 | CB | CYS | 123 | 14.457 | −21.399 | −34.301 | 1 | 15.52 |
| 3828 | SG | CYS | 123 | 15.087 | −20.205 | −33.102 | 1 | 22.68 |
| 3829 | C | CYS | 123 | 13.418 | −23.648 | −34.652 | 1 | 14.51 |
| 3830 | O | CYS | 123 | 13.941 | −24.156 | −35.65 | 1 | 16.29 |
| 3831 | N | VAL | 124 | 12.141 | −23.821 | −34.339 | 1 | 13.19 |
| 3832 | CA | VAL | 124 | 11.265 | −24.634 | −35.168 | 1 | 13.71 |
| 3833 | CB | VAL | 124 | 10.978 | −26.008 | −34.515 | 1 | 14.19 |
| 3834 | CG1 | VAL | 124 | 10.057 | −26.829 | −35.414 | 1 | 13.26 |
| 3835 | CG2 | VAL | 124 | 12.285 | −26.754 | −34.259 | 1 | 14.65 |
| 3836 | C | VAL | 124 | 9.927 | −23.948 | −35.385 | 1 | 13.68 |
| 3837 | O | VAL | 124 | 9.277 | −23.53 | −34.427 | 1 | 13.77 |
| 3838 | N | PRO | 125 | 9.51 | −23.805 | −36.65 | 1 | 14.33 |
| 3839 | CD | PRO | 125 | 10.304 | −23.993 | −37.875 | 1 | 15.4 |
| 3840 | CA | PRO | 125 | 8.226 | −23.169 | −36.956 | 1 | 14.03 |
| 3841 | CB | PRO | 125 | 8.3 | −22.938 | −38.467 | 1 | 14.3 |
| 3842 | CG | PRO | 125 | 9.768 | −22.9 | −38.757 | 1 | 19.23 |
| 3843 | C | PRO | 125 | 7.107 | −24.15 | −36.603 | 1 | 13.64 |
| 3844 | O | PRO | 125 | 7.183 | −25.327 | −36.959 | 1 | 14.26 |
| 3845 | N | ARG | 126 | 6.081 | −23.675 | −35.902 | 1 | 11.74 |
| 3846 | CA | ARG | 126 | 4.952 | −24.521 | −35.528 | 1 | 11.82 |
| 3847 | CB | ARG | 126 | 5.016 | −24.908 | −34.045 | 1 | 11.79 |
| 3848 | CG | ARG | 126 | 6.204 | −25.774 | −33.66 | 1 | 11.88 |
| 3849 | CD | ARG | 126 | 6.124 | −27.161 | −34.292 | 1 | 14.68 |
| 3850 | NE | ARG | 126 | 7.141 | −28.053 | −33.735 | 1 | 13.11 |
| 3851 | CZ | ARG | 126 | 7.332 | −29.308 | −34.128 | 1 | 15.29 |
| 3852 | NH1 | ARG | 126 | 6.573 | −29.831 | −35.087 | 1 | 14.33 |
| 3853 | NH2 | ARG | 126 | 8.282 | −30.042 | −33.561 | 1 | 14.83 |
| 3854 | C | ARG | 126 | 3.654 | −23.77 | −35.774 | 1 | 11.45 |
| 3855 | O | ARG | 126 | 3.637 | −22.542 | −35.784 | 1 | 13.97 |
| 3856 | N | PHE | 127 | 2.569 | −24.511 | −35.969 | 1 | 12.21 |
| 3857 | CA | PHE | 127 | 1.271 | −23.889 | −36.189 | 1 | 13.43 |
| 3858 | CB | PHE | 127 | 0.256 | −24.931 | −36.65 | 1 | 12.92 |
| 3859 | CG | PHE | 127 | 0.629 | −25.598 | −37.941 | 1 | 14.05 |
| 3860 | CD1 | PHE | 127 | 0.791 | −26.978 | −38.006 | 1 | 14.53 |
| 3861 | CD2 | PHE | 127 | 0.836 | −24.841 | −39.091 | 1 | 15.22 |
| 3862 | CE1 | PHE | 127 | 1.158 | −27.769 | −39.204 | 1 | 14.2 |
| 3863 | CE2 | PHE | 127 | 1.204 | −25.45 | −40.294 | 1 | 16.86 |
| 3864 | CZ | PHE | 127 | 1.365 | −26.831 | −40.348 | 1 | 16.59 |
| 3865 | C | PHE | 127 | 0.795 | −23.239 | −34.895 | 1 | 14.6 |
| 3866 | O | PHE | 127 | 1.036 | −23.755 | −33.803 | 1 | 13.77 |
| 3867 | N | GLN | 128 | 0.108 | −22.112 | −35.029 | 1 | 14.66 |
| 3868 | CA | GLN | 128 | −0.403 | −21.367 | −33.879 | 1 | 14.54 |
| 3869 | CB | GLN | 128 | −0.947 | −20.015 | −34.351 | 1 | 15.92 |
| 3870 | CG | GLN | 128 | −1.708 | −19.2 | −33.302 | 1 | 18.29 |
| 3871 | CD | GLN | 128 | −0.893 | −18.905 | −32.056 | 1 | 20.85 |
| 3872 | OE1 | GLN | 128 | 0.338 | −18.861 | −32.097 | 1 | 21.6 |
| 3873 | NE2 | GLN | 128 | −1.581 | −18.68 | −30.94 | 1 | 21.01 |
| 3874 | C | GLN | 128 | −1.473 | −22.111 | −33.089 | 1 | 14.21 |
| 3875 | O | GLN | 128 | −1.503 | −22.04 | −31.861 | 1 | 14.54 |
| 3876 | N | ALA | 129 | −2.356 | −22.822 | −33.779 | 1 | 13.11 |
| 3877 | CA | ALA | 129 | −3.414 | −23.546 | −33.092 | 1 | 12.43 |
| 3878 | CB | ALA | 129 | −4.665 | −22.674 | −32.993 | 1 | 14.26 |
| 3879 | C | ALA | 129 | −3.75 | −24.856 | −33.781 | 1 | 13.87 |
| 3880 | O | ALA | 129 | −3.795 | −24.937 | −35.011 | 1 | 15.33 |
| 3881 | N | VAL | 130 | −3.992 | −25.878 | −32.971 | 1 | 14.42 |
| 3882 | CA | VAL | 130 | −4.32 | −27.201 | −33.474 | 1 | 15.84 |
| 3883 | CB | VAL | 130 | −3.056 | −28.095 | −33.57 | 1 | 14.86 |
| 3884 | CG1 | VAL | 130 | −1.976 | −27.395 | −34.372 | 1 | 16.2 |
| 3885 | CG2 | VAL | 130 | −2.553 | −28.442 | −32.167 | 1 | 17.93 |
| 3886 | C | VAL | 130 | −5.28 | −27.876 | −32.511 | 1 | 15.93 |
| 3887 | O | VAL | 130 | −5.561 | −27.364 | −31.428 | 1 | 16.08 |
| 3888 | N | GLN | 131 | −5.793 | −29.026 | −32.918 | 1 | 16.21 |
| 3889 | CA | GLN | 131 | −6.665 | −29.797 | −32.056 | 1 | 17.95 |
| 3890 | CB | GLN | 131 | −8.139 | −29.637 | −32.439 | 1 | 21.95 |
| 3891 | CG | GLN | 131 | −8.534 | −30.244 | −33.766 | 1 | 24.37 |
| 3892 | CD | GLN | 131 | −10.022 | −30.545 | −33.833 | 1 | 28.21 |
| 3893 | OE1 | GLN | 131 | −10.855 | −29.682 | −33.555 | 1 | 28.8 |
| 3894 | NE2 | GLN | 131 | −10.361 | −31.777 | −34.202 | 1 | 28.15 |
| 3895 | C | GLN | 131 | −6.235 | −31.242 | −32.21 | 1 | 17.78 |
| 3896 | O | GLN | 131 | −5.979 | −31.71 | −33.319 | 1 | 17.92 |
| 3897 | N | ILE | 132 | −6.121 | −31.936 | −31.089 | 1 | 15.74 |
| 3898 | CA | ILE | 132 | −5.732 | −33.332 | −31.112 | 1 | 16.62 |
| 3899 | CB | ILE | 132 | −4.486 | −33.583 | −30.222 | 1 | 16 |
| 3900 | CG2 | ILE | 132 | −4.734 | −33.074 | −28.81 | 1 | 17.5 |

TABLE 1-continued

| Atom | Atom Type | Residue | # | X | Y | Z | OCC | B |
|---|---|---|---|---|---|---|---|---|
| 3901 | CG1 | ILE | 132 | -4.138 | -35.072 | -30.22 | 1 | 16.46 |
| 3902 | CD1 | ILE | 132 | -2.832 | -35.392 | -29.516 | 1 | 18.14 |
| 3903 | C | ILE | 132 | -6.912 | -34.145 | -30.61 | 1 | 17.29 |
| 3904 | O | ILE | 132 | -7.5 | -33.832 | -29.577 | 1 | 17.39 |
| 3905 | N | SER | 133 | -7.28 | -35.171 | -31.365 | 1 | 18.13 |
| 3906 | CA | SER | 133 | -8.396 | -36.018 | -30.982 | 1 | 19.7 |
| 3907 | CB | SER | 133 | -9.519 | -35.916 | -32.019 | 1 | 22 |
| 3908 | OG | SER | 133 | -9.063 | -36.302 | -33.303 | 1 | 29.23 |
| 3909 | C | SER | 133 | -7.909 | -37.453 | -30.871 | 1 | 20.57 |
| 3910 | O | SER | 133 | -7.124 | -37.917 | -31.694 | 1 | 20.62 |
| 3911 | N | GLY | 134 | -8.369 | -38.149 | -29.842 | 1 | 20.77 |
| 3912 | CA | GLY | 134 | -7.957 | -39.524 | -29.654 | 1 | 22.38 |
| 3913 | C | GLY | 134 | -8.69 | -40.153 | -28.494 | 1 | 24.16 |
| 3914 | O | GLY | 134 | -9.706 | -39.631 | -28.037 | 1 | 25.62 |
| 3915 | N | LEU | 135 | -8.169 | -41.273 | -28.011 | 1 | 23.06 |
| 3916 | CA | LEU | 135 | -8.778 | -41.984 | -26.897 | 1 | 25.71 |
| 3917 | CB | LEU | 135 | -8.914 | -43.47 | -27.239 | 1 | 24.24 |
| 3918 | CG | LEU | 135 | -9.674 | -43.836 | -28.516 | 1 | 25.26 |
| 3919 | CD1 | LEU | 135 | -9.531 | -45.328 | -28.786 | 1 | 25.3 |
| 3920 | CD2 | LEU | 135 | -11.139 | -43.451 | -28.366 | 1 | 24.84 |
| 3921 | C | LEU | 135 | -7.918 | -41.848 | -25.65 | 1 | 28.29 |
| 3922 | O | LEU | 135 | -6.708 | -41.657 | -25.742 | 1 | 26.8 |
| 3923 | N | ASP | 136 | -8.546 | -41.94 | -24.484 | 1 | 32.05 |
| 3924 | CA | ASP | 136 | -7.803 | -41.874 | -23.233 | 1 | 35.62 |
| 3925 | CB | ASP | 136 | -8.69 | -41.353 | -22.099 | 1 | 38.09 |
| 3926 | CG | ASP | 136 | -9.652 | -42.403 | -21.58 | 1 | 41.64 |
| 3927 | OD1 | ASP | 136 | -10.475 | -42.899 | -22.373 | 1 | 44.06 |
| 3928 | OD2 | ASP | 136 | -9.583 | -42.735 | -20.378 | 1 | 44.39 |
| 3929 | C | ASP | 136 | -7.399 | -43.323 | -22.964 | 1 | 36.79 |
| 3930 | O | ASP | 136 | -7.843 | -44.231 | -23.668 | 1 | 36.63 |
| 3931 | N | PRO | 137 | -6.553 | -43.563 | -21.951 | 1 | 38.13 |
| 3932 | CD | PRO | 137 | -6.025 | -42.638 | -20.932 | 1 | 38.82 |
| 3933 | CA | PRO | 137 | -6.142 | -44.941 | -21.664 | 1 | 39.12 |
| 3934 | CB | PRO | 137 | -5.259 | -44.785 | -20.426 | 1 | 39.93 |
| 3935 | CG | PRO | 137 | -5.824 | -43.557 | -19.757 | 1 | 40.12 |
| 3936 | C | PRO | 137 | -7.315 | -45.895 | -21.43 | 1 | 40.2 |
| 3937 | O | PRO | 137 | -7.174 | -47.11 | -21.581 | 1 | 40.15 |
| 3938 | N | ASN | 138 | -8.471 | -45.34 | -21.073 | 1 | 40.37 |
| 3939 | CA | ASN | 138 | -9.657 | -46.15 | -20.819 | 1 | 40.78 |
| 3940 | CB | ASN | 138 | -10.536 | -45.483 | -19.756 | 1 | 42.09 |
| 3941 | CG | ASN | 138 | -9.887 | -45.478 | -18.383 | 1 | 43.95 |
| 3942 | OD1 | ASN | 138 | -9.51 | -46.529 | -17.859 | 1 | 45.36 |
| 3943 | ND2 | ASN | 138 | -9.756 | -44.295 | -17.791 | 1 | 44.52 |
| 3944 | C | ASN | 138 | -10.485 | -46.434 | -22.072 | 1 | 40.25 |
| 3945 | O | ASN | 138 | -11.13 | -47.479 | -22.165 | 1 | 40.69 |
| 3946 | N | GLY | 139 | -10.48 | -45.508 | -23.029 | 1 | 39.31 |
| 3947 | CA | GLY | 139 | -11.235 | -45.724 | -24.254 | 1 | 37.57 |
| 3948 | C | GLY | 139 | -12.196 | -44.62 | -24.66 | 1 | 36.69 |
| 3949 | O | GLY | 139 | -12.857 | -44.722 | -25.694 | 1 | 35.34 |
| 3950 | N | GLU | 140 | -12.281 | -43.568 | -23.853 | 1 | 36.07 |
| 3951 | CA | GLU | 140 | -13.164 | -42.443 | -24.142 | 1 | 36.83 |
| 3952 | CB | GLU | 140 | -13.454 | -41.659 | -22.86 | 1 | 39.01 |
| 3953 | CG | GLU | 140 | -14.543 | -42.264 | -21.989 | 1 | 41.92 |
| 3954 | CD | GLU | 140 | -15.808 | -41.427 | -21.987 | 1 | 43.92 |
| 3955 | OE1 | GLU | 140 | -15.781 | -40.312 | -21.422 | 1 | 45.08 |
| 3956 | OE2 | GLU | 140 | -16.827 | -41.876 | -22.555 | 1 | 46.42 |
| 3957 | C | GLU | 140 | -12.571 | -41.502 | -25.188 | 1 | 35.86 |
| 3958 | O | GLU | 140 | -11.378 | -41.198 | -25.159 | 1 | 35.8 |
| 3959 | N | GLN | 141 | -13.415 | -41.041 | -26.105 | 1 | 35.28 |
| 3960 | CA | GLN | 141 | -12.987 | -40.132 | -27.162 | 1 | 34.61 |
| 3961 | CB | GLN | 141 | -13.995 | -40.157 | -28.313 | 1 | 36.87 |
| 3962 | CG | GLN | 141 | -13.631 | -39.256 | -29.485 | 1 | 40.18 |
| 3963 | CD | GLN | 141 | -12.324 | -39.655 | -30.144 | 1 | 42.25 |
| 3964 | OE1 | GLN | 141 | -12.146 | -40.805 | -30.547 | 1 | 44.46 |
| 3965 | NE2 | GLN | 141 | -11.405 | -38.705 | -30.263 | 1 | 43.12 |
| 3966 | C | GLN | 141 | -12.857 | -38.708 | -26.628 | 1 | 34.41 |
| 3967 | O | GLN | 141 | -13.808 | -38.152 | -26.078 | 1 | 33.44 |
| 3968 | N | VAL | 142 | -11.676 | -38.121 | -26.798 | 1 | 31.39 |
| 3969 | CA | VAL | 142 | -11.423 | -36.764 | -26.33 | 1 | 30.47 |
| 3970 | CB | VAL | 142 | -10.406 | -36.755 | -25.162 | 1 | 31.71 |
| 3971 | CG1 | VAL | 142 | -10.133 | -35.323 | -24.716 | 1 | 33.27 |
| 3972 | CG2 | VAL | 142 | -10.939 | -37.578 | -24 | 1 | 33.9 |
| 3973 | C | VAL | 142 | -10.871 | -35.888 | -27.448 | 1 | 27.71 |
| 3974 | O | VAL | 142 | -10.082 | -36.341 | -28.276 | 1 | 25.74 |
| 3975 | N | VAL | 143 | -11.307 | -34.634 | -27.472 | 1 | 24.33 |
| 3976 | CA | VAL | 143 | -10.844 | -33.67 | -28.459 | 1 | 22.85 |
| 3977 | CB | VAL | 143 | -11.981 | -33.201 | -29.385 | 1 | 24.2 |
| 3978 | CG1 | VAL | 143 | -11.443 | -32.203 | -30.397 | 1 | 25.67 |
| 3979 | CG2 | VAL | 143 | -12.603 | -34.398 | -30.097 | 1 | 26.55 |
| 3980 | C | VAL | 143 | -10.323 | -32.474 | -27.675 | 1 | 22.16 |
| 3981 | O | VAL | 143 | -11.081 | -31.813 | -26.965 | 1 | 21.77 |
| 3982 | N | TRP | 144 | -9.027 | -32.206 | -27.789 | 1 | 19.23 |
| 3983 | CA | TRP | 144 | -8.423 | -31.093 | -27.071 | 1 | 17.87 |
| 3984 | CB | TRP | 144 | -7.282 | -31.599 | -26.181 | 1 | 17.63 |
| 3985 | CG | TRP | 144 | -6.642 | -30.532 | -25.345 | 1 | 18.83 |
| 3986 | CD2 | TRP | 144 | -5.248 | -30.401 | -25.04 | 1 | 19.99 |
| 3987 | CE2 | TRP | 144 | -5.109 | -29.275 | -24.194 | 1 | 20.85 |
| 3988 | CE3 | TRP | 144 | -4.103 | -31.126 | -25.395 | 1 | 22.66 |
| 3989 | CD1 | TRP | 144 | -7.273 | -29.511 | -24.692 | 1 | 20.85 |
| 3990 | NE1 | TRP | 144 | -6.359 | -28.75 | -23.999 | 1 | 22.87 |
| 3991 | CZ2 | TRP | 144 | -3.868 | -28.856 | -23.7 | 1 | 21.67 |
| 3992 | CZ3 | TRP | 144 | -2.866 | -30.707 | -24.9 | 1 | 23.67 |
| 3993 | CH2 | TRP | 144 | -2.763 | -29.583 | -24.062 | 1 | 20.93 |
| 3994 | C | TRP | 144 | -7.911 | -30.038 | -28.04 | 1 | 17.73 |
| 3995 | O | TRP | 144 | -7.082 | -30.323 | -28.908 | 1 | 17.05 |
| 3996 | N | GLN | 145 | -8.429 | -28.821 | -27.893 | 1 | 15.66 |
| 3997 | CA | GLN | 145 | -8.051 | -27.699 | -28.743 | 1 | 15.85 |
| 3998 | CB | GLN | 145 | -9.304 | -26.946 | -29.202 | 1 | 18.36 |
| 3999 | CG | GLN | 145 | -9.032 | -25.764 | -30.118 | 1 | 20.82 |
| 4000 | CD | GLN | 145 | -10.31 | -25.067 | -30.551 | 1 | 23.35 |
| 4001 | OE1 | GLN | 145 | -11.326 | -25.715 | -30.787 | 1 | 28.31 |
| 4002 | NE2 | GLN | 145 | -10.26 | -23.747 | -30.669 | 1 | 23.15 |
| 4003 | C | GLN | 145 | -7.149 | -26.762 | -27.952 | 1 | 15.73 |
| 4004 | O | GLN | 145 | -7.492 | -26.35 | -26.839 | 1 | 13.81 |
| 4005 | N | ALA | 146 | -6 | -26.423 | -28.527 | 1 | 15.59 |
| 4006 | CA | ALA | 146 | -5.05 | -25.544 | -27.856 | 1 | 15.95 |
| 4007 | CB | ALA | 146 | -4.103 | -26.376 | -26.987 | 1 | 18.02 |
| 4008 | C | ALA | 146 | -4.253 | -24.704 | -28.842 | 1 | 16.81 |
| 4009 | O | ALA | 146 | -4.213 | -24.996 | -30.041 | 1 | 17.34 |
| 4010 | N | SER | 147 | -3.619 | -23.656 | -28.328 | 1 | 16.37 |
| 4011 | CA | SER | 147 | -2.819 | -22.755 | -29.146 | 1 | 16.69 |
| 4012 | CB | SER | 147 | -3.599 | -21.463 | -29.419 | 1 | 20.08 |
| 4013 | OG | SER | 147 | -3.936 | -20.804 | -28.206 | 1 | 26.03 |
| 4014 | C | SER | 147 | -1.51 | -22.421 | -28.435 | 1 | 15.74 |
| 4015 | O | SER | 147 | -1.263 | -22.882 | -27.319 | 1 | 15.59 |
| 4016 | N | GLY | 148 | -0.674 | -21.624 | -29.088 | 1 | 15.43 |
| 4017 | CA | GLY | 148 | 0.586 | -21.229 | -28.486 | 1 | 14.73 |
| 4018 | C | GLY | 148 | 1.498 | -22.382 | -28.118 | 1 | 14.05 |
| 4019 | O | GLY | 148 | 1.617 | -23.356 | -28.862 | 1 | 12.69 |
| 4020 | N | TRP | 149 | 2.134 | -22.281 | -26.953 | 1 | 14.12 |
| 4021 | CA | TRP | 149 | 3.062 | -23.319 | -26.517 | 1 | 13.95 |
| 4022 | CB | TRP | 149 | 3.69 | -22.947 | -25.167 | 1 | 14.14 |
| 4023 | CG | TRP | 149 | 5.044 | -23.571 | -24.996 | 1 | 14.81 |
| 4024 | CD2 | TRP | 149 | 6.233 | -23.235 | -25.721 | 1 | 15.27 |
| 4025 | CE2 | TRP | 149 | 7.252 | -24.115 | -25.287 | 1 | 16.97 |
| 4026 | CE3 | TRP | 149 | 6.538 | -22.276 | -26.697 | 1 | 14.2 |
| 4027 | CD1 | TRP | 149 | 5.377 | -24.611 | -24.172 | 1 | 17.56 |
| 4028 | NE1 | TRP | 149 | 6.703 | -24.944 | -24.342 | 1 | 16.93 |
| 4029 | CZ2 | TRP | 149 | 8.556 | -24.063 | -25.797 | 1 | 17.73 |
| 4030 | CZ3 | TRP | 149 | 7.835 | -22.223 | -27.205 | 1 | 16.15 |
| 4031 | CH2 | TRP | 149 | 8.827 | -23.111 | -26.752 | 1 | 15.84 |
| 4032 | C | TRP | 149 | 2.447 | -24.713 | -26.437 | 1 | 14.46 |
| 4033 | O | TRP | 149 | 3.079 | -25.692 | -26.835 | 1 | 14.3 |
| 4034 | N | ALA | 150 | 1.222 | -24.816 | -25.928 | 1 | 14.31 |
| 4035 | CA | ALA | 150 | 0.573 | -26.121 | -25.832 | 1 | 13.66 |
| 4036 | CB | ALA | 150 | -0.802 | -25.982 | -25.195 | 1 | 14.09 |
| 4037 | C | ALA | 150 | 0.452 | -26.735 | -27.227 | 1 | 13.38 |
| 4038 | O | ALA | 150 | 0.683 | -27.93 | -27.411 | 1 | 12.94 |
| 4039 | N | ALA | 151 | 0.088 | -25.913 | -28.207 | 1 | 12.37 |
| 4040 | CA | ALA | 151 | -0.046 | -26.384 | -29.583 | 1 | 12.82 |
| 4041 | CB | ALA | 151 | -0.557 | -25.261 | -30.475 | 1 | 12.92 |
| 4042 | C | ALA | 151 | 1.307 | -26.884 | -30.089 | 1 | 13.33 |
| 4043 | O | ALA | 151 | 1.377 | -27.855 | -30.845 | 1 | 12.71 |
| 4044 | N | ARG | 152 | 2.379 | -26.215 | -29.671 | 1 | 12.74 |
| 4045 | CA | ARG | 152 | 3.726 | -26.61 | -30.073 | 1 | 13.16 |
| 4046 | CB | ARG | 152 | 4.757 | -25.611 | -29.553 | 1 | 13 |
| 4047 | CG | ARG | 152 | 6.21 | -26.07 | -29.721 | 1 | 12.46 |
| 4048 | CD | ARG | 152 | 7.175 | -24.949 | -29.361 | 1 | 12.94 |
| 4049 | NE | ARG | 152 | 7.002 | -23.8 | -30.245 | 1 | 12.68 |
| 4050 | CZ | ARG | 152 | 7.637 | -23.62 | -31.4 | 1 | 14.63 |
| 4051 | NH1 | ARG | 152 | 8.519 | -24.514 | -31.832 | 1 | 13.63 |
| 4052 | NH2 | ARG | 152 | 7.379 | -22.541 | -32.132 | 1 | 13.08 |

TABLE 1-continued

| Atom | Atom Type | Residue | # | X | Y | Z | OCC | B |
|---|---|---|---|---|---|---|---|---|
| 4053 | C | ARG | 152 | 4.066 | −27.998 | −29.546 | 1 | 12.97 |
| 4054 | O | ARG | 152 | 4.544 | −28.853 | −30.292 | 1 | 12.07 |
| 4055 | N | ILE | 153 | 3.821 | −28.223 | −28.26 | 1 | 12.75 |
| 4056 | CA | ILE | 153 | 4.122 | −29.521 | −27.669 | 1 | 13.19 |
| 4057 | CB | ILE | 153 | 3.881 | −29.518 | −26.15 | 1 | 15.87 |
| 4058 | CG2 | ILE | 153 | 4.291 | −30.861 | −25.56 | 1 | 17.21 |
| 4059 | CG1 | ILE | 153 | 4.687 | −28.388 | −25.499 | 1 | 18.53 |
| 4060 | CD1 | ILE | 153 | 6.18 | −28.437 | −25.785 | 1 | 20.71 |
| 4061 | C | ILE | 153 | 3.282 | −30.615 | −28.318 | 1 | 12.96 |
| 4062 | O | ILE | 153 | 3.777 | −31.708 | −28.583 | 1 | 12.65 |
| 4063 | N | ILE | 154 | 2.013 | −30.323 | −28.583 | 1 | 12.88 |
| 4064 | CA | ILE | 154 | 1.15 | −31.306 | −29.228 | 1 | 12.68 |
| 4065 | CB | ILE | 154 | −0.268 | −30.739 | −29.478 | 1 | 11.42 |
| 4066 | CG2 | ILE | 154 | −1.046 | −31.673 | −30.398 | 1 | 14.12 |
| 4067 | CG1 | ILE | 154 | −0.999 | −30.553 | −28.146 | 1 | 14.42 |
| 4068 | CD1 | ILE | 154 | −2.344 | −29.836 | −28.277 | 1 | 14.86 |
| 4069 | C | ILE | 154 | 1.75 | −31.722 | −30.57 | 1 | 11.66 |
| 4070 | O | ILE | 154 | 1.826 | −32.91 | −30.886 | 1 | 12.48 |
| 4071 | N | GLN | 155 | 2.175 | −30.738 | −31.356 | 1 | 12.02 |
| 4072 | CA | GLN | 155 | 2.761 | −31.002 | −32.668 | 1 | 11.05 |
| 4073 | CB | GLN | 155 | 3.018 | −29.687 | −33.4 | 1 | 11.82 |
| 4074 | CG | GLN | 155 | 1.73 | −28.978 | −33.807 | 1 | 13.23 |
| 4075 | CD | GLN | 155 | 1.97 | −27.563 | −34.277 | 1 | 13.71 |
| 4076 | OE1 | GLN | 155 | 2.594 | −27.335 | −35.313 | 1 | 15.8 |
| 4077 | NE2 | GLN | 155 | 1.481 | −26.597 | −33.506 | 1 | 12.46 |
| 4078 | C | GLN | 155 | 4.054 | −31.795 | −32.557 | 1 | 11.83 |
| 4079 | O | GLN | 155 | 4.317 | −32.683 | −33.368 | 1 | 12.5 |
| 4080 | N | HIS | 156 | 4.857 | −31.467 | −31.552 | 1 | 11.54 |
| 4081 | CA | HIS | 156 | 6.125 | −32.152 | −31.333 | 1 | 12.33 |
| 4082 | CB | HIS | 156 | 6.876 | −31.499 | −30.168 | 1 | 11.59 |
| 4083 | CG | HIS | 156 | 8.23 | −32.087 | −29.917 | 1 | 12.51 |
| 4084 | CD2 | HIS | 156 | 8.599 | −33.241 | −29.313 | 1 | 14.78 |
| 4085 | ND1 | HIS | 156 | 9.396 | −31.477 | −30.327 | 1 | 13.88 |
| 4086 | CE1 | HIS | 156 | 10.427 | −32.231 | −29.984 | 1 | 14.8 |
| 4087 | NE2 | HIS | 156 | 9.97 | −33.307 | −29.368 | 1 | 10.34 |
| 4088 | C | HIS | 156 | 5.901 | −33.635 | −31.036 | 1 | 11.67 |
| 4089 | O | HIS | 156 | 6.569 | −34.496 | −31.608 | 1 | 11.66 |
| 4090 | N | GLU | 157 | 4.957 | −33.942 | −30.15 | 1 | 13.01 |
| 4091 | CA | GLU | 157 | 4.704 | −35.336 | −29.809 | 1 | 13.71 |
| 4092 | CB | GLU | 157 | 3.874 | −35.437 | −28.526 | 1 | 14.81 |
| 4093 | CG | GLU | 157 | 4.399 | −34.577 | −27.376 | 1 | 15.36 |
| 4094 | CD | GLU | 157 | 5.885 | −34.765 | −27.098 | 1 | 17.36 |
| 4095 | OE1 | GLU | 157 | 6.484 | −33.855 | −26.49 | 1 | 15.9 |
| 4096 | OE2 | GLU | 157 | 6.455 | −35.81 | −27.472 | 1 | 16.92 |
| 4097 | C | GLU | 157 | 4.016 | −36.076 | −30.95 | 1 | 14 |
| 4098 | O | GLU | 157 | 4.302 | −37.251 | −31.195 | 1 | 13.54 |
| 4099 | N | MET | 158 | 3.105 | −35.403 | −31.65 | 1 | 13.67 |
| 4100 | CA | MET | 158 | 2.436 | −36.048 | −32.774 | 1 | 14.04 |
| 4101 | CB | MET | 158 | 1.362 | −35.131 | −33.362 | 1 | 14.23 |
| 4102 | CG | MET | 158 | 0.085 | −35.087 | −32.535 | 1 | 14.69 |
| 4103 | SD | MET | 158 | −0.721 | −36.707 | −32.404 | 1 | 17.84 |
| 4104 | CE | MET | 158 | −1.349 | −36.885 | −34.061 | 1 | 18.56 |
| 4105 | C | MET | 158 | 3.481 | −36.405 | −33.828 | 1 | 14.29 |
| 4106 | O | MET | 158 | 3.421 | −37.479 | −34.436 | 1 | 14.59 |
| 4107 | N | ASP | 159 | 4.442 | −35.51 | −34.039 | 1 | 13.55 |
| 4108 | CA | ASP | 159 | 5.508 | −35.77 | −35.002 | 1 | 13.33 |
| 4109 | CB | ASP | 159 | 6.503 | −34.605 | −35.04 | 1 | 13.39 |
| 4110 | CG | ASP | 159 | 6.057 | −33.483 | −35.963 | 1 | 16.76 |
| 4111 | OD1 | ASP | 159 | 4.959 | −33.586 | −36.555 | 1 | 17.75 |
| 4112 | OD2 | ASP | 159 | 6.809 | −32.495 | −36.102 | 1 | 16.04 |
| 4113 | C | ASP | 159 | 6.238 | −37.059 | −34.625 | 1 | 13.41 |
| 4114 | O | ASP | 159 | 6.577 | −37.861 | −35.495 | 1 | 12.97 |
| 4115 | N | HIS | 160 | 6.477 | −37.26 | −33.331 | 1 | 13.17 |
| 4116 | CA | HIS | 160 | 7.159 | −38.475 | −32.87 | 1 | 12.52 |
| 4117 | CB | HIS | 160 | 7.287 | −38.483 | −31.343 | 1 | 12.54 |
| 4118 | CG | HIS | 160 | 8.507 | −37.78 | −30.833 | 1 | 13.83 |
| 4119 | CD2 | HIS | 160 | 8.648 | −36.758 | −29.956 | 1 | 14.91 |
| 4120 | ND1 | HIS | 160 | 9.782 | −38.136 | −31.216 | 1 | 14.08 |
| 4121 | CE1 | HIS | 160 | 10.657 | −37.363 | −30.597 | 1 | 15.13 |
| 4122 | NE2 | HIS | 160 | 9.995 | −36.518 | −29.826 | 1 | 13.26 |
| 4123 | C | HIS | 160 | 6.428 | −39.745 | −33.301 | 1 | 13.63 |
| 4124 | O | HIS | 160 | 7.055 | −40.758 | −33.608 | 1 | 13.24 |
| 4125 | N | LEU | 161 | 5.101 | −39.693 | −33.322 | 1 | 13.06 |
| 4126 | CA | LEU | 161 | 4.32 | −40.861 | −33.703 | 1 | 14 |
| 4127 | CB | LEU | 161 | 2.867 | −40.704 | −33.249 | 1 | 14.53 |
| 4128 | CG | LEU | 161 | 2.64 | −40.538 | −31.742 | 1 | 15.19 |
| 4129 | CD1 | LEU | 161 | 1.15 | −40.626 | −31.465 | 1 | 17.11 |
| 4130 | CD2 | LEU | 161 | 3.38 | −41.62 | −30.958 | 1 | 14.4 |
| 4131 | C | LEU | 161 | 4.376 | −41.129 | −35.2 | 1 | 14.43 |
| 4132 | O | LEU | 161 | 4.019 | −42.216 | −35.656 | 1 | 15.23 |
| 4133 | N | GLN | 162 | 4.831 | −40.139 | −35.961 | 1 | 14.41 |
| 4134 | CA | GLN | 162 | 4.955 | −40.284 | −37.404 | 1 | 16.92 |
| 4135 | CB | GLN | 162 | 4.424 | −39.037 | −38.111 | 1 | 19.65 |
| 4136 | CG | GLN | 162 | 2.92 | −38.899 | −38.043 | 1 | 26.6 |
| 4137 | CD | GLN | 162 | 2.217 | −40.123 | −38.591 | 1 | 30.85 |
| 4138 | OE1 | GLN | 162 | 2.531 | −40.595 | −39.687 | 1 | 34.57 |
| 4139 | NE2 | GLN | 162 | 1.258 | −40.646 | −37.835 | 1 | 33.15 |
| 4140 | C | GLN | 162 | 6.409 | −40.518 | −37.803 | 1 | 16.78 |
| 4141 | O | GLN | 162 | 6.73 | −40.565 | −38.991 | 1 | 18.18 |
| 4142 | N | GLY | 163 | 7.28 | −40.658 | −36.807 | 1 | 14.98 |
| 4143 | CA | GLY | 163 | 8.69 | −40.887 | −37.072 | 1 | 14.23 |
| 4144 | C | GLY | 163 | 9.441 | −39.623 | −37.443 | 1 | 13.08 |
| 4145 | O | GLY | 163 | 10.497 | −39.684 | −38.072 | 1 | 13.78 |
| 4146 | N | CYS | 164 | 8.894 | −38.477 | −37.046 | 1 | 11.91 |
| 4147 | CA | CYS | 164 | 9.488 | −37.178 | −37.34 | 1 | 13.86 |
| 4148 | CB | CYS | 164 | 8.412 | −36.255 | −37.924 | 1 | 14.9 |
| 4149 | SG | CYS | 164 | 8.942 | −34.573 | −38.279 | 1 | 21.67 |
| 4150 | C | CYS | 164 | 10.102 | −36.53 | −36.097 | 1 | 13.12 |
| 4151 | O | CYS | 164 | 9.517 | −36.574 | −35.014 | 1 | 13.05 |
| 4152 | N | LEU | 165 | 11.288 | −35.944 | −36.26 | 1 | 12.76 |
| 4153 | CA | LEU | 165 | 11.984 | −35.266 | −35.166 | 1 | 13.07 |
| 4154 | CB | LEU | 165 | 13.382 | −35.859 | −34.954 | 1 | 12.59 |
| 4155 | CG | LEU | 165 | 13.452 | −37.34 | −34.57 | 1 | 14.34 |
| 4156 | CD1 | LEU | 165 | 14.904 | −37.743 | −34.37 | 1 | 12.92 |
| 4157 | CD2 | LEU | 165 | 12.661 | −37.58 | −33.295 | 1 | 13.91 |
| 4158 | C | LEU | 165 | 12.106 | −33.79 | −35.521 | 1 | 12.73 |
| 4159 | O | LEU | 165 | 12.021 | −33.417 | −36.693 | 1 | 14.97 |
| 4160 | N | PHE | 166 | 12.334 | −32.946 | −34.52 | 1 | 12.57 |
| 4161 | CA | PHE | 166 | 12.418 | −31.515 | −34.782 | 1 | 12.38 |
| 4162 | CB | PHE | 166 | 12.525 | −30.731 | −33.463 | 1 | 12.66 |
| 4163 | CG | PHE | 166 | 13.906 | −30.694 | −32.874 | 1 | 14.4 |
| 4164 | CD1 | PHE | 166 | 14.735 | −29.596 | −33.082 | 1 | 15.55 |
| 4165 | CD2 | PHE | 166 | 14.367 | −31.739 | −32.083 | 1 | 15.83 |
| 4166 | CE1 | PHE | 166 | 16.005 | −29.537 | −32.506 | 1 | 16.23 |
| 4167 | CE2 | PHE | 166 | 15.634 | −31.691 | −31.502 | 1 | 15.55 |
| 4168 | CZ | PHE | 166 | 16.454 | −30.588 | −31.714 | 1 | 16.53 |
| 4169 | C | PHE | 166 | 13.54 | −31.126 | −35.737 | 1 | 13.17 |
| 4170 | O | PHE | 166 | 13.447 | −30.101 | −36.413 | 1 | 13.3 |
| 4171 | N | ILE | 167 | 14.594 | −31.938 | −35.81 | 1 | 12.93 |
| 4172 | CA | ILE | 167 | 15.695 | −31.627 | −36.713 | 1 | 13.15 |
| 4173 | CB | ILE | 167 | 16.917 | −32.549 | −36.478 | 1 | 12.56 |
| 4174 | CG2 | ILE | 167 | 17.508 | −32.272 | −35.104 | 1 | 12.96 |
| 4175 | CG1 | ILE | 167 | 16.512 | −34.017 | −36.626 | 1 | 13.92 |
| 4176 | CD1 | ILE | 167 | 17.695 | −34.98 | −36.599 | 1 | 13.26 |
| 4177 | C | ILE | 167 | 15.268 | −31.734 | −38.178 | 1 | 13.46 |
| 4178 | O | ILE | 167 | 15.988 | −31.286 | −39.069 | 1 | 14.88 |
| 4179 | N | ASP | 168 | 14.097 | −32.322 | −38.422 | 1 | 12.99 |
| 4180 | CA | ASP | 168 | 13.58 | −32.457 | −39.785 | 1 | 13.92 |
| 4181 | CB | ASP | 168 | 12.569 | −33.609 | −39.901 | 1 | 12.41 |
| 4182 | CG | ASP | 168 | 13.136 | −34.953 | −39.492 | 1 | 11.94 |
| 4183 | OD1 | ASP | 168 | 14.352 | −35.179 | −39.651 | 1 | 15.05 |
| 4184 | OD2 | ASP | 168 | 12.337 | −35.796 | −39.029 | 1 | 13.75 |
| 4185 | C | ASP | 168 | 12.847 | −31.188 | −40.221 | 1 | 15.4 |
| 4186 | O | ASP | 168 | 12.584 | −30.998 | −41.409 | 1 | 16.18 |
| 4187 | N | LYS | 169 | 12.508 | −30.328 | −39.264 | 1 | 14.73 |
| 4188 | CA | LYS | 169 | 11.749 | −29.114 | −39.578 | 1 | 16.64 |
| 4189 | CB | LYS | 169 | 10.335 | −29.254 | −39.02 | 1 | 20.43 |
| 4190 | CG | LYS | 169 | 9.569 | −30.443 | −39.549 | 1 | 21.88 |
| 4191 | CD | LYS | 169 | 8.204 | −30.508 | −38.894 | 1 | 24.99 |
| 4192 | CE | LYS | 169 | 7.364 | −31.624 | −39.471 | 1 | 24.69 |
| 4193 | NZ | LYS | 169 | 6.05 | −31.691 | −38.782 | 1 | 27.46 |
| 4194 | C | LYS | 169 | 12.341 | −27.819 | −39.045 | 1 | 16.37 |
| 4195 | O | LYS | 169 | 11.739 | −26.754 | −39.163 | 1 | 17.18 |
| 4196 | N | MET | 170 | 13.528 | −27.908 | −38.471 | 1 | 15.4 |
| 4197 | CA | MET | 170 | 14.18 | −26.75 | −37.878 | 1 | 14.18 |
| 4198 | CB | MET | 170 | 15.274 | −27.233 | −36.936 | 1 | 14.42 |
| 4199 | CG | MET | 170 | 16.42 | −27.893 | −37.703 | 1 | 14.54 |
| 4200 | SD | MET | 170 | 17.786 | −28.37 | −36.648 | 1 | 14.58 |
| 4201 | CE | MET | 170 | 18.721 | −29.437 | −37.721 | 1 | 14.34 |
| 4202 | C | MET | 170 | 14.83 | −25.768 | −38.841 | 1 | 15.15 |
| 4203 | O | MET | 170 | 15.005 | −26.045 | −40.028 | 1 | 15.58 |
| 4204 | N | ASP | 171 | 15.178 | −24.606 | −38.297 | 1 | 15.08 |

TABLE 1-continued

| Atom | Atom Type | Residue | # | X | Y | Z | OCC | B |
|---|---|---|---|---|---|---|---|---|
| 4205 | CA | ASP | 171 | 15.929 | −23.602 | −39.03 | 1 | 15.75 |
| 4206 | CB | ASP | 171 | 15.683 | −22.197 | −38.486 | 1 | 19.76 |
| 4207 | CG | ASP | 171 | 16.586 | −21.161 | −39.135 | 1 | 22.63 |
| 4208 | OD1 | ASP | 171 | 17.645 | −21.547 | −39.685 | 1 | 24.85 |
| 4209 | OD2 | ASP | 171 | 16.248 | −19.96 | −39.087 | 1 | 27.15 |
| 4210 | C | ASP | 171 | 17.308 | −24.075 | −38.585 | 1 | 15.91 |
| 4211 | O | ASP | 171 | 17.753 | −23.757 | −37.476 | 1 | 14.92 |
| 4212 | N | SER | 172 | 17.964 | −24.857 | −39.434 | 1 | 14.93 |
| 4213 | CA | SER | 172 | 19.262 | −25.441 | −39.107 | 1 | 14.08 |
| 4214 | CB | SER | 172 | 19.792 | −26.243 | −40.304 | 1 | 14.81 |
| 4215 | OG | SER | 172 | 20.133 | −25.403 | −41.391 | 1 | 15.74 |
| 4216 | C | SER | 172 | 20.34 | −24.484 | −38.618 | 1 | 15.27 |
| 4217 | O | SER | 172 | 21.198 | −24.874 | −37.822 | 1 | 13.7 |
| 4218 | N | ARG | 173 | 20.306 | −23.236 | −39.074 | 1 | 13.54 |
| 4219 | CA | ARG | 173 | 21.323 | −22.285 | −38.647 | 1 | 14.9 |
| 4220 | CB | ARG | 173 | 21.301 | −21.045 | −39.547 | 1 | 16 |
| 4221 | CG | ARG | 173 | 21.784 | −21.331 | −40.966 | 1 | 16.56 |
| 4222 | CD | ARG | 173 | 21.834 | −20.064 | −41.806 | 1 | 17.41 |
| 4223 | NE | ARG | 173 | 22.671 | −19.042 | −41.183 | 1 | 18.37 |
| 4224 | CZ | ARG | 173 | 24.001 | −19.042 | −41.196 | 1 | 19.48 |
| 4225 | NH1 | ARG | 173 | 24.665 | −20.009 | −41.812 | 1 | 19.72 |
| 4226 | NH2 | ARG | 173 | 24.667 | −18.075 | −40.577 | 1 | 18.3 |
| 4227 | C | ARG | 173 | 21.201 | −21.89 | −37.177 | 1 | 14.67 |
| 4228 | O | ARG | 173 | 22.112 | −21.271 | −36.627 | 1 | 14.78 |
| 4229 | N | THR | 174 | 20.093 | −22.268 | −36.536 | 1 | 14.12 |
| 4230 | CA | THR | 174 | 19.881 | −21.951 | −35.119 | 1 | 14.39 |
| 4231 | CB | THR | 174 | 18.435 | −21.464 | −34.842 | 1 | 15.49 |
| 4232 | OG1 | THR | 174 | 17.509 | −22.519 | −35.127 | 1 | 14.58 |
| 4233 | CG2 | THR | 174 | 18.104 | −20.24 | −35.697 | 1 | 17.04 |
| 4234 | C | THR | 174 | 20.15 | −23.149 | −34.207 | 1 | 14.1 |
| 4235 | O | THR | 174 | 19.989 | −23.055 | −32.985 | 1 | 14.71 |
| 4236 | N | PHE | 175 | 20.54 | −24.275 | −34.801 | 1 | 13.11 |
| 4237 | CA | PHE | 175 | 20.842 | −25.492 | −34.043 | 1 | 12.75 |
| 4238 | CB | PHE | 175 | 21.271 | −26.604 | −35.007 | 1 | 12.43 |
| 4239 | CG | PHE | 175 | 21.385 | −27.965 | −34.369 | 1 | 13.73 |
| 4240 | CD1 | PHE | 175 | 20.247 | −28.684 | −34.018 | 1 | 13.14 |
| 4241 | CD2 | PHE | 175 | 22.634 | −28.543 | −34.15 | 1 | 12.99 |
| 4242 | CE1 | PHE | 175 | 20.349 | −29.966 | −33.461 | 1 | 14.44 |
| 4243 | CE2 | PHE | 175 | 22.748 | −29.821 | −33.595 | 1 | 12.32 |
| 4244 | CZ | PHE | 175 | 21.604 | −30.533 | −33.252 | 1 | 13.98 |
| 4245 | C | PHE | 175 | 21.984 | −25.15 | −33.09 | 1 | 12.86 |
| 4246 | O | PHE | 175 | 22.955 | −24.504 | −33.489 | 1 | 13.86 |
| 4247 | N | THR | 176 | 21.88 | −25.583 | −31.838 | 1 | 12 |
| 4248 | CA | THR | 176 | 22.916 | −25.254 | −30.867 | 1 | 11.88 |
| 4249 | CB | THR | 176 | 22.688 | −23.82 | −30.316 | 1 | 13.59 |
| 4250 | OG1 | THR | 176 | 23.693 | −23.492 | −29.346 | 1 | 14.39 |
| 4251 | CG2 | THR | 176 | 21.318 | −23.722 | −29.646 | 1 | 15.14 |
| 4252 | C | THR | 176 | 22.982 | −26.2 | −29.682 | 1 | 11.16 |
| 4253 | O | THR | 176 | 21.982 | −26.794 | −29.282 | 1 | 12.31 |
| 4254 | N | ASN | 177 | 24.187 | −26.357 | −29.145 | 1 | 12.47 |
| 4255 | CA | ASN | 177 | 24.39 | −27.15 | −27.941 | 1 | 11.91 |
| 4256 | CB | ASN | 177 | 25.882 | −27.265 | −27.634 | 1 | 13.27 |
| 4257 | CG | ASN | 177 | 26.521 | −28.46 | −28.297 | 1 | 11.84 |
| 4258 | OD1 | ASN | 177 | 26.445 | −29.574 | −27.783 | 1 | 14.44 |
| 4259 | ND2 | ASN | 177 | 27.142 | −28.242 | −29.452 | 1 | 12.4 |
| 4260 | C | ASN | 177 | 23.719 | −26.282 | −26.878 | 1 | 12.65 |
| 4261 | O | ASN | 177 | 23.76 | −25.053 | −26.97 | 1 | 13.32 |
| 4262 | N | VAL | 178 | 23.108 | −26.9 | −25.876 | 1 | 13.46 |
| 4263 | CA | VAL | 178 | 22.442 | −26.123 | −24.841 | 1 | 15.3 |
| 4264 | CB | VAL | 178 | 21.69 | −27.031 | −23.846 | 1 | 18.02 |
| 4265 | CG1 | VAL | 178 | 20.531 | −27.717 | −24.553 | 1 | 21.83 |
| 4266 | CG2 | VAL | 178 | 22.644 | −28.052 | −23.248 | 1 | 20.83 |
| 4267 | C | VAL | 178 | 23.403 | −25.228 | −24.064 | 1 | 15.25 |
| 4268 | O | VAL | 178 | 22.979 | −24.223 | −23.491 | 1 | 14.81 |
| 4269 | N | TYR | 179 | 24.691 | −25.569 | −24.053 | 1 | 13.08 |
| 4270 | CA | TYR | 179 | 25.645 | −24.747 | −23.317 | 1 | 14.23 |
| 4271 | CB | TYR | 179 | 26.874 | −25.574 | −22.9 | 1 | 13.87 |
| 4272 | CG | TYR | 179 | 27.613 | −26.295 | −24.004 | 1 | 13.89 |
| 4273 | CD1 | TYR | 179 | 28.442 | −25.602 | −24.889 | 1 | 13.87 |
| 4274 | CE1 | TYR | 179 | 29.178 | −26.275 | −25.864 | 1 | 14.68 |
| 4275 | CD2 | TYR | 179 | 27.53 | −27.682 | −24.128 | 1 | 12.88 |
| 4276 | CE2 | TYR | 179 | 28.262 | −28.363 | −25.104 | 1 | 13.63 |
| 4277 | CZ | TYR | 179 | 29.086 | −27.651 | −25.964 | 1 | 14.54 |
| 4278 | OH | TYR | 179 | 29.844 | −28.314 | −26.904 | 1 | 16.35 |
| 4279 | C | TYR | 179 | 26.05 | −23.454 | −24.032 | 1 | 14.02 |
| 4280 | O | TYR | 179 | 26.859 | −22.679 | −23.522 | 1 | 14.39 |
| 4281 | N | TRP | 180 | 25.481 | −23.227 | −25.213 | 1 | 12.82 |
| 4282 | CA | TRP | 180 | 25.714 | −21.992 | −25.965 | 1 | 13.28 |
| 4283 | CB | TRP | 180 | 26.143 | −22.27 | −27.41 | 1 | 13.89 |
| 4284 | CG | TRP | 180 | 27.622 | −22.311 | −27.586 | 1 | 12.86 |
| 4285 | CD2 | TRP | 180 | 28.51 | −21.189 | −27.622 | 1 | 12.57 |
| 4286 | CE2 | TRP | 180 | 29.818 | −21.696 | −27.774 | 1 | 12.61 |
| 4287 | CE3 | TRP | 180 | 28.327 | −19.801 | −27.538 | 1 | 12.71 |
| 4288 | CD1 | TRP | 180 | 28.402 | −23.422 | −27.717 | 1 | 12.46 |
| 4289 | NE1 | TRP | 180 | 29.724 | −23.062 | −27.83 | 1 | 12.29 |
| 4290 | CZ2 | TRP | 180 | 30.943 | −20.864 | −27.846 | 1 | 14.3 |
| 4291 | CZ3 | TRP | 180 | 29.443 | −18.973 | −27.609 | 1 | 13 |
| 4292 | CH2 | TRP | 180 | 30.736 | −19.509 | −27.762 | 1 | 14.77 |
| 4293 | C | TRP | 180 | 24.364 | −21.294 | −25.975 | 1 | 14.68 |
| 4294 | O | TRP | 180 | 23.349 | −21.924 | −26.263 | 1 | 13.76 |
| 4295 | N | MET | 181 | 24.345 | −20.003 | −25.664 | 1 | 15.54 |
| 4296 | CA | MET | 181 | 23.085 | −19.27 | −25.628 | 1 | 18.05 |
| 4297 | CB | MET | 181 | 22.411 | −19.493 | −24.232 | 1 | 20.69 |
| 4298 | CG | MET | 181 | 23.198 | −18.913 | −23.101 | 1 | 18.75 |
| 4299 | SD | MET | 181 | 22.89 | −19.758 | −21.532 | 1 | 20.13 |
| 4300 | CE | MET | 181 | 24.091 | −21.098 | −21.645 | 1 | 20.88 |
| 4301 | C | MET | 181 | 23.252 | −17.774 | −25.866 | 1 | 20.25 |
| 4302 | O | MET | 181 | 24.338 | −17.221 | −25.693 | 1 | 18.75 |
| 4303 | N | LYS | 182 | 22.162 | −17.128 | −26.267 | 1 | 24.55 |
| 4304 | CA | LYS | 182 | 22.158 | −15.688 | −26.501 | 1 | 28.86 |
| 4305 | CB | LYS | 182 | 21.161 | −15.317 | −27.601 | 1 | 31.36 |
| 4306 | CG | LYS | 182 | 21.46 | −15.919 | −28.959 | 1 | 33.75 |
| 4307 | CD | LYS | 182 | 20.484 | −15.404 | −30.009 | 1 | 36.22 |
| 4308 | CE | LYS | 182 | 20.786 | −15.991 | −31.377 | 1 | 38.18 |
| 4309 | NZ | LYS | 182 | 19.861 | −15.466 | −32.419 | 1 | 40.21 |
| 4310 | C | LYS | 182 | 21.731 | −15.027 | −25.198 | 1 | 30.54 |
| 4311 | O | LYS | 182 | 20.814 | −15.503 | −24.531 | 1 | 31.49 |
| 4312 | N | VAL | 183 | 22.398 | −13.939 | −24.83 | 1 | 32.69 |
| 4313 | CA | VAL | 183 | 22.066 | −13.23 | −23.601 | 1 | 34.79 |
| 4314 | CB | VAL | 183 | 23.084 | −13.539 | −22.482 | 1 | 35.6 |
| 4315 | CG1 | VAL | 183 | 23.03 | −15.018 | −22.118 | 1 | 34.24 |
| 4316 | CG2 | VAL | 183 | 24.483 | −13.154 | −22.936 | 1 | 34.67 |
| 4317 | C | VAL | 183 | 22.045 | −11.727 | −23.842 | 1 | 36.74 |
| 4318 | O | VAL | 183 | 22.566 | −11.246 | −24.848 | 1 | 36.9 |
| 4319 | N | ASN | 184 | 21.437 | −10.992 | −22.916 | 1 | 39.17 |
| 4320 | CA | ASN | 184 | 21.35 | −9.539 | −23.022 | 1 | 41.39 |
| 4321 | CB | ASN | 184 | 20.143 | −9.019 | −22.236 | 1 | 41.35 |
| 4322 | CG | ASN | 184 | 18.833 | −9.56 | −22.729 | 1 | 40.67 |
| 4323 | OD1 | ASN | 184 | 18.481 | −9.455 | −23.9 | 1 | 41.86 |
| 4324 | ND2 | ASN | 184 | 18.099 | −10.247 | −21.834 | 1 | 41.72 |
| 4325 | C | ASN | 184 | 22.618 | −8.898 | −22.471 | 1 | 43.22 |
| 4326 | O | ASN | 184 | 22.952 | −9.079 | −21.3 | 1 | 44.36 |
| 4327 | N | ASP | 185 | 23.321 | −8.151 | −23.316 | 1 | 45.22 |
| 4328 | CA | ASP | 185 | 24.546 | −7.484 | −22.891 | 1 | 46.88 |
| 4329 | CB | ASP | 185 | 25.217 | −6.794 | −24.081 | 1 | 47.83 |
| 4330 | CG | ASP | 185 | 25.969 | −7.765 | −24.968 | 1 | 49.46 |
| 4331 | OD1 | ASP | 185 | 26.96 | −8.357 | −24.49 | 1 | 50.57 |
| 4332 | OD2 | ASP | 185 | 25.569 | −7.938 | −26.139 | 1 | 50.78 |
| 4333 | C | ASP | 185 | 24.255 | −6.461 | −21.802 | 1 | 47.38 |
| 4334 | O | ASP | 185 | 23.067 | −6.295 | −21.451 | 1 | 47.84 |
| 4335 | OXT | ASP | 185 | 25.221 | −5.838 | −21.311 | 1 | 48.17 |
| 4336 | CB | HIS | 3 | 56.782 | −25.605 | −24.896 | 1 | 46.8 |
| 4337 | CG | HIS | 3 | 57.363 | −26.172 | −26.155 | 1 | 48.02 |
| 4338 | CD2 | HIS | 3 | 57.155 | −25.855 | −27.455 | 1 | 48.55 |
| 4339 | ND1 | HIS | 3 | 58.28 | −27.201 | −26.154 | 1 | 49.6 |
| 4340 | CE1 | HIS | 3 | 58.612 | −27.493 | −27.399 | 1 | 48.97 |
| 4341 | NE2 | HIS | 3 | 57.943 | −26.69 | −28.208 | 1 | 49 |
| 4342 | C | HIS | 3 | 54.722 | −27.025 | −24.794 | 1 | 44.05 |
| 4343 | O | HIS | 3 | 54.706 | −27.152 | −26.02 | 1 | 43.6 |
| 4344 | N | HIS | 3 | 56.853 | −27.808 | −23.766 | 1 | 45.49 |
| 4345 | CA | HIS | 3 | 55.998 | −26.623 | −24.06 | 1 | 44.94 |
| 4346 | N | MET | 4 | 53.65 | −27.226 | −24.035 | 1 | 42.81 |
| 4347 | CA | MET | 4 | 52.372 | −27.614 | −24.617 | 1 | 41.5 |
| 4348 | CB | MET | 4 | 51.984 | −29.019 | −24.157 | 1 | 43.17 |
| 4349 | CG | MET | 4 | 52.934 | −30.107 | −24.617 | 1 | 45.78 |
| 4350 | SD | MET | 4 | 52.348 | −31.74 | −24.145 | 1 | 49.81 |
| 4351 | CE | MET | 4 | 51.348 | −32.168 | −25.574 | 1 | 47.46 |
| 4352 | C | MET | 4 | 51.26 | −26.642 | −24.253 | 1 | 39.32 |
| 4353 | O | MET | 4 | 51.308 | −25.981 | −23.213 | 1 | 39.3 |
| 4354 | N | SER | 5 | 50.258 | −26.563 | −25.121 | 1 | 36.7 |
| 4355 | CA | SER | 5 | 49.117 | −25.685 | −24.905 | 1 | 33.88 |
| 4356 | CB | SER | 5 | 49.25 | −24.42 | −25.755 | 1 | 35.01 |

TABLE 1-continued

| Atom | Atom Type | Residue | # | X | Y | Z | OCC | B |
|---|---|---|---|---|---|---|---|---|
| 4357 | OG | SER | 5 | 49.253 | −24.731 | −27.138 | 1 | 37.57 |
| 4358 | C | SER | 5 | 47.847 | −26.433 | −25.288 | 1 | 31.58 |
| 4359 | O | SER | 5 | 47.906 | −27.487 | −25.92 | 1 | 31.96 |
| 4360 | N | PHE | 6 | 46.702 | −25.887 | −24.902 | 1 | 27.67 |
| 4361 | CA | PHE | 6 | 45.421 | −26.511 | −25.207 | 1 | 25.89 |
| 4362 | CB | PHE | 6 | 44.471 | −26.372 | −24.016 | 1 | 25.66 |
| 4363 | CG | PHE | 6 | 44.792 | −27.289 | −22.873 | 1 | 26.88 |
| 4364 | CD1 | PHE | 6 | 44.321 | −28.596 | −22.862 | 1 | 28.2 |
| 4365 | CD2 | PHE | 6 | 45.577 | −26.849 | −21.812 | 1 | 28.69 |
| 4366 | CE1 | PHE | 6 | 44.623 | −29.455 | −21.811 | 1 | 28.84 |
| 4367 | CE2 | PHE | 6 | 45.887 | −27.701 | −20.755 | 1 | 28.25 |
| 4368 | CZ | PHE | 6 | 45.409 | −29.005 | −20.754 | 1 | 28.81 |
| 4369 | C | PHE | 6 | 44.765 | −25.904 | −26.434 | 1 | 24.05 |
| 4370 | O | PHE | 6 | 44.832 | −24.697 | −26.656 | 1 | 24.57 |
| 4371 | N | SER | 7 | 44.142 | −26.761 | −27.233 | 1 | 22.11 |
| 4372 | CA | SER | 7 | 43.428 | −26.334 | −28.427 | 1 | 20.86 |
| 4373 | CB | SER | 7 | 44.166 | −26.753 | −29.7 | 1 | 23.93 |
| 4374 | OG | SER | 7 | 45.366 | −26.021 | −29.856 | 1 | 31.14 |
| 4375 | C | SER | 7 | 42.089 | −27.034 | −28.369 | 1 | 18.8 |
| 4376 | O | SER | 7 | 41.982 | −28.142 | −27.841 | 1 | 17.17 |
| 4377 | N | HIS | 8 | 41.06 | −26.393 | −28.898 | 1 | 16.59 |
| 4378 | CA | HIS | 8 | 39.753 | −27.009 | −28.872 | 1 | 16.41 |
| 4379 | CB | HIS | 8 | 38.959 | −26.52 | −27.659 | 1 | 19.2 |
| 4380 | CG | HIS | 8 | 38.519 | −25.095 | −27.755 | 1 | 22.83 |
| 4381 | CD2 | HIS | 8 | 39.223 | −23.938 | −27.734 | 1 | 24.63 |
| 4382 | ND1 | HIS | 8 | 37.196 | −24.736 | −27.907 | 1 | 24.39 |
| 4383 | CE1 | HIS | 8 | 37.105 | −23.419 | −27.978 | 1 | 26.29 |
| 4384 | NE2 | HIS | 8 | 38.32 | −22.911 | −27.875 | 1 | 28.37 |
| 4385 | C | HIS | 8 | 38.988 | −26.719 | −30.144 | 1 | 16.11 |
| 4386 | O | HIS | 8 | 39.123 | −25.647 | −30.742 | 1 | 16.62 |
| 4387 | N | VAL | 9 | 38.198 | −27.693 | −30.567 | 1 | 13.68 |
| 4388 | CA | VAL | 9 | 37.386 | −27.519 | −31.755 | 1 | 13.48 |
| 4389 | CB | VAL | 9 | 37.179 | −28.851 | −32.492 | 1 | 13.15 |
| 4390 | CG1 | VAL | 9 | 36.222 | −28.658 | −33.657 | 1 | 16.08 |
| 4391 | CG2 | VAL | 9 | 38.522 | −29.369 | −32.992 | 1 | 16.21 |
| 4392 | C | VAL | 9 | 36.046 | −26.971 | −31.286 | 1 | 13.89 |
| 4393 | O | VAL | 9 | 35.341 | −27.618 | −30.505 | 1 | 13.73 |
| 4394 | N | CYS | 10 | 35.717 | −25.765 | −31.743 | 1 | 12.85 |
| 4395 | CA | CYS | 10 | 34.465 | −25.11 | −31.375 | 1 | 13.15 |
| 4396 | CB | CYS | 10 | 34.374 | −23.736 | −32.043 | 1 | 14.05 |
| 4397 | SG | CYS | 10 | 35.737 | −22.63 | −31.613 | 1 | 17.69 |
| 4398 | C | CYS | 10 | 33.274 | −25.965 | −31.788 | 1 | 12.49 |
| 4399 | O | CYS | 10 | 33.282 | −26.566 | −32.863 | 1 | 12.62 |
| 4400 | N | GLN | 11 | 32.259 | −26.018 | −30.93 | 1 | 12.94 |
| 4401 | CA | GLN | 11 | 31.065 | −26.813 | −31.197 | 1 | 12.14 |
| 4402 | CB | GLN | 11 | 30.7 | −27.641 | −29.962 | 1 | 12.13 |
| 4403 | CG | GLN | 11 | 31.784 | −28.632 | −29.562 | 1 | 11.66 |
| 4404 | CD | GLN | 11 | 32.09 | −29.617 | −30.669 | 1 | 12.38 |
| 4405 | OE1 | GLN | 11 | 31.222 | −30.385 | −31.082 | 1 | 13.59 |
| 4406 | NE2 | GLN | 11 | 33.325 | −29.599 | −31.16 | 1 | 11.41 |
| 4407 | C | GLN | 11 | 29.873 | −25.96 | −31.616 | 1 | 13.58 |
| 4408 | O | GLN | 11 | 29.761 | −24.794 | −31.223 | 1 | 13.21 |
| 4409 | N | VAL | 12 | 28.979 | −26.56 | −32.4 | 1 | 13.32 |
| 4410 | CA | VAL | 12 | 27.801 | −25.859 | −32.899 | 1 | 13.6 |
| 4411 | CB | VAL | 12 | 26.843 | −26.834 | −33.645 | 1 | 14.03 |
| 4412 | CG1 | VAL | 12 | 26.324 | −27.914 | −32.703 | 1 | 13.81 |
| 4413 | CG2 | VAL | 12 | 25.699 | −26.049 | −34.284 | 1 | 13.58 |
| 4414 | C | VAL | 12 | 27.083 | −25.105 | −31.781 | 1 | 13.96 |
| 4415 | O | VAL | 12 | 26.758 | −25.653 | −30.723 | 1 | 12.44 |
| 4416 | N | GLY | 13 | 26.86 | −23.823 | −32.034 | 1 | 14.46 |
| 4417 | CA | GLY | 13 | 26.244 | −22.949 | −31.051 | 1 | 14.77 |
| 4418 | C | GLY | 13 | 27.171 | −21.754 | −30.97 | 1 | 13.81 |
| 4419 | O | GLY | 13 | 26.74 | −20.619 | −30.75 | 1 | 13.91 |
| 4420 | N | ASP | 14 | 28.464 | −22.015 | −31.144 | 1 | 13.06 |
| 4421 | CA | ASP | 14 | 29.459 | −20.951 | −31.137 | 1 | 13.89 |
| 4422 | CB | ASP | 14 | 30.871 | −21.546 | −31.164 | 1 | 14.14 |
| 4423 | CG | ASP | 14 | 31.955 | −20.493 | −31.007 | 1 | 14.54 |
| 4424 | OD1 | ASP | 14 | 31.738 | −19.333 | −31.421 | 1 | 15.46 |
| 4425 | OD2 | ASP | 14 | 33.04 | −20.831 | −30.483 | 1 | 14.83 |
| 4426 | C | ASP | 14 | 29.21 | −20.151 | −32.422 | 1 | 14.21 |
| 4427 | O | ASP | 14 | 29.316 | −20.687 | −33.524 | 1 | 14.32 |
| 4428 | N | PRO | 15 | 28.882 | −18.859 | −32.298 | 1 | 14.85 |
| 4429 | CD | PRO | 15 | 28.861 | −18.037 | −31.076 | 1 | 15.38 |
| 4430 | CA | PRO | 15 | 28.624 | −18.038 | −33.488 | 1 | 15.63 |
| 4431 | CB | PRO | 15 | 28.277 | −16.672 | −32.892 | 1 | 16.65 |
| 4432 | CG | PRO | 15 | 29.076 | −16.647 | −31.628 | 1 | 18.23 |
| 4433 | C | PRO | 15 | 29.759 | −17.968 | −34.516 | 1 | 15.06 |
| 4434 | O | PRO | 15 | 29.521 | −17.663 | −35.688 | 1 | 15.91 |
| 4435 | N | VAL | 16 | 30.984 | −18.256 | −34.093 | 1 | 15.2 |
| 4436 | CA | VAL | 16 | 32.112 | −18.206 | −35.012 | 1 | 14.59 |
| 4437 | CB | VAL | 16 | 33.448 | −18.501 | −34.29 | 1 | 15.22 |
| 4438 | CG1 | VAL | 16 | 33.529 | −19.976 | −33.903 | 1 | 14.46 |
| 4439 | CG2 | VAL | 16 | 34.611 | −18.102 | −35.178 | 1 | 16.79 |
| 4440 | C | VAL | 16 | 31.932 | −19.207 | −36.152 | 1 | 13.86 |
| 4441 | O | VAL | 16 | 32.467 | −19.016 | −37.241 | 1 | 15.86 |
| 4442 | N | LEU | 17 | 31.159 | −20.262 | −35.903 | 1 | 12.12 |
| 4443 | CA | LEU | 17 | 30.922 | −21.295 | −36.908 | 1 | 12.65 |
| 4444 | CB | LEU | 17 | 30.471 | −22.588 | −36.229 | 1 | 11.86 |
| 4445 | CG | LEU | 17 | 31.493 | −23.269 | −35.32 | 1 | 13.54 |
| 4446 | CD1 | LEU | 17 | 30.808 | −24.39 | −34.552 | 1 | 13.06 |
| 4447 | CD2 | LEU | 17 | 32.648 | −23.811 | −36.157 | 1 | 14.49 |
| 4448 | C | LEU | 17 | 29.882 | −20.9 | −37.947 | 1 | 13.05 |
| 4449 | O | LEU | 17 | 29.785 | −21.527 | −39.006 | 1 | 13.58 |
| 4450 | N | ARG | 18 | 29.107 | −19.862 | −37.651 | 1 | 14.3 |
| 4451 | CA | ARG | 18 | 28.061 | −19.428 | −38.572 | 1 | 15.2 |
| 4452 | CB | ARG | 18 | 26.724 | −19.347 | −37.831 | 1 | 16.24 |
| 4453 | CG | ARG | 18 | 25.808 | −20.548 | −38.056 | 1 | 17.15 |
| 4454 | CD | ARG | 18 | 26.482 | −21.883 | −37.74 | 1 | 16.19 |
| 4455 | NE | ARG | 18 | 25.509 | −22.974 | −37.743 | 1 | 15.06 |
| 4456 | CZ | ARG | 18 | 24.998 | −23.533 | −38.837 | 1 | 15.81 |
| 4457 | NH1 | ARG | 18 | 25.37 | −23.12 | −40.043 | 1 | 13.09 |
| 4458 | NH2 | ARG | 18 | 24.086 | −24.492 | −38.724 | 1 | 12.42 |
| 4459 | C | ARG | 18 | 28.341 | −18.114 | −39.283 | 1 | 16.9 |
| 4460 | O | ARG | 18 | 27.553 | −17.676 | −40.127 | 1 | 16.11 |
| 4461 | N | GLY | 19 | 29.456 | −17.481 | −38.946 | 1 | 17.05 |
| 4462 | CA | GLY | 19 | 29.794 | −16.232 | −39.597 | 1 | 18.27 |
| 4463 | C | GLY | 19 | 30.533 | −16.509 | −40.891 | 1 | 19.08 |
| 4464 | O | GLY | 19 | 30.905 | −17.65 | −41.168 | 1 | 17.59 |
| 4465 | N | VAL | 20 | 30.727 | −15.475 | −41.7 | 1 | 19.77 |
| 4466 | CA | VAL | 20 | 31.461 | −15.634 | −42.947 | 1 | 20.52 |
| 4467 | CB | VAL | 20 | 30.876 | −14.753 | −44.07 | 1 | 20.61 |
| 4468 | CG1 | VAL | 20 | 31.761 | −14.825 | −45.302 | 1 | 21.81 |
| 4469 | CG2 | VAL | 20 | 29.47 | −15.222 | −44.412 | 1 | 21.45 |
| 4470 | C | VAL | 20 | 32.886 | −15.198 | −42.638 | 1 | 19.76 |
| 4471 | O | VAL | 20 | 33.135 | −14.029 | −42.348 | 1 | 20.73 |
| 4472 | N | ALA | 21 | 33.814 | −16.148 | −42.681 | 1 | 18.81 |
| 4473 | CA | ALA | 21 | 35.214 | −15.868 | −42.381 | 1 | 18.16 |
| 4474 | CB | ALA | 21 | 36.056 | −17.161 | −42.611 | 1 | 17.64 |
| 4475 | C | ALA | 21 | 35.767 | −14.71 | −43.203 | 1 | 18.2 |
| 4476 | O | ALA | 21 | 35.482 | −14.59 | −44.394 | 1 | 17.77 |
| 4477 | N | ALA | 22 | 36.557 | −13.861 | −42.555 | 1 | 19.13 |
| 4478 | CA | ALA | 22 | 37.164 | −12.711 | −43.22 | 1 | 20.86 |
| 4479 | CB | ALA | 22 | 37.437 | −11.608 | −42.211 | 1 | 20.39 |
| 4480 | C | ALA | 22 | 38.463 | −13.136 | −43.89 | 1 | 20.8 |
| 4481 | O | ALA | 22 | 39.148 | −14.048 | −43.425 | 1 | 20.37 |
| 4482 | N | PRO | 23 | 38.82 | −12.48 | −45.002 | 1 | 21.69 |
| 4483 | CD | PRO | 23 | 38.063 | −11.458 | −45.743 | 1 | 22.96 |
| 4484 | CA | PRO | 23 | 40.055 | −12.828 | −45.705 | 1 | 21.38 |
| 4485 | CB | PRO | 23 | 40.022 | −11.922 | −46.937 | 1 | 22.7 |
| 4486 | CG | PRO | 23 | 38.559 | −11.664 | −47.149 | 1 | 23.99 |
| 4487 | C | PRO | 23 | 41.29 | −12.559 | −44.855 | 1 | 21.73 |
| 4488 | O | PRO | 23 | 41.269 | −11.712 | −43.96 | 1 | 21.3 |
| 4489 | N | VAL | 24 | 42.361 | −13.291 | −45.132 | 1 | 22.05 |
| 4490 | CA | VAL | 24 | 43.613 | −13.08 | −44.429 | 1 | 23.68 |
| 4491 | CB | VAL | 24 | 44.548 | −14.296 | −44.558 | 1 | 24.3 |
| 4492 | CG1 | VAL | 24 | 45.927 | −13.946 | −44.02 | 1 | 24.86 |
| 4493 | CG2 | VAL | 24 | 43.97 | −15.479 | −43.79 | 1 | 21.85 |
| 4494 | C | VAL | 24 | 44.252 | −11.885 | −45.129 | 1 | 25.32 |
| 4495 | O | VAL | 24 | 44.329 | −11.853 | −46.358 | 1 | 24.25 |
| 4496 | N | GLU | 25 | 44.688 | −10.9 | −44.351 | 1 | 27.11 |
| 4497 | CA | GLU | 25 | 45.312 | −9.708 | −44.911 | 1 | 30.24 |
| 4498 | CB | GLU | 25 | 45.573 | −8.676 | −43.808 | 1 | 32.96 |
| 4499 | CG | GLU | 25 | 44.422 | −8.475 | −42.831 | 1 | 37.55 |
| 4500 | CD | GLU | 25 | 44.466 | −9.442 | −41.655 | 1 | 40.87 |
| 4501 | OE1 | GLU | 25 | 44.401 | −10.671 | −41.876 | 1 | 40.91 |
| 4502 | OE2 | GLU | 25 | 44.571 | −8.967 | −40.502 | 1 | 42.34 |
| 4503 | C | GLU | 25 | 46.633 | −10.089 | −45.571 | 1 | 29.37 |
| 4504 | O | GLU | 25 | 47.387 | −10.897 | −45.034 | 1 | 28.82 |
| 4505 | N | ARG | 26 | 46.916 | −9.506 | −46.732 | 1 | 30.74 |
| 4506 | CA | ARG | 26 | 48.157 | −9.811 | −47.435 | 1 | 30.83 |
| 4507 | CB | ARG | 26 | 48.269 | −8.982 | −48.716 | 1 | 32.47 |
| 4508 | CG | ARG | 26 | 47.252 | −9.344 | −49.787 | 1 | 34.45 |

TABLE 1-continued

| Atom | Atom Type | Residue | # | X | Y | Z | OCC | B |
|---|---|---|---|---|---|---|---|---|
| 4509 | CD | ARG | 26 | 47.667 | −8.778 | −51.133 | 1 | 37.03 |
| 4510 | NE | ARG | 26 | 48.935 | −9.345 | −51.585 | 1 | 38.55 |
| 4511 | CZ | ARG | 26 | 49.103 | −10.616 | −51.942 | 1 | 39.39 |
| 4512 | NH1 | ARG | 26 | 48.082 | −11.461 | −51.904 | 1 | 41.01 |
| 4513 | NH2 | ARG | 26 | 50.294 | −11.043 | −52.335 | 1 | 40.87 |
| 4514 | C | ARG | 26 | 49.377 | −9.563 | −46.554 | 1 | 30.7 |
| 4515 | O | ARG | 26 | 50.404 | −10.221 | −46.706 | 1 | 30.09 |
| 4516 | N | ALA | 27 | 49.256 | −8.615 | −45.629 | 1 | 31.92 |
| 4517 | CA | ALA | 27 | 50.35 | −8.287 | −44.722 | 1 | 32.16 |
| 4518 | CB | ALA | 27 | 50 | −7.048 | −43.908 | 1 | 33.45 |
| 4519 | C | ALA | 27 | 50.652 | −9.456 | −43.789 | 1 | 32.31 |
| 4520 | O | ALA | 27 | 51.73 | −9.527 | −43.197 | 1 | 32.36 |
| 4521 | N | GLN | 28 | 49.694 | −10.37 | −43.662 | 1 | 31.94 |
| 4522 | CA | GLN | 28 | 49.849 | −11.539 | −42.803 | 1 | 32.7 |
| 4523 | CB | GLN | 28 | 48.49 | −11.951 | −42.232 | 1 | 34.16 |
| 4524 | CG | GLN | 28 | 48.028 | −11.107 | −41.062 | 1 | 36.52 |
| 4525 | CD | GLN | 28 | 48.88 | −11.323 | −39.826 | 1 | 39.12 |
| 4526 | OE1 | GLN | 28 | 48.972 | −12.439 | −39.31 | 1 | 42.25 |
| 4527 | NE2 | GLN | 28 | 49.508 | −10.258 | −39.344 | 1 | 40.74 |
| 4528 | C | GLN | 28 | 50.477 | −12.73 | −43.522 | 1 | 31.91 |
| 4529 | O | GLN | 28 | 50.972 | −13.658 | −42.881 | 1 | 33.19 |
| 4530 | N | LEU | 29 | 50.457 | −12.704 | −44.85 | 1 | 31.01 |
| 4531 | CA | LEU | 29 | 51.023 | −13.792 | −45.642 | 1 | 30.66 |
| 4532 | CB | LEU | 29 | 50.836 | −13.509 | −47.135 | 1 | 30.11 |
| 4533 | CG | LEU | 29 | 49.387 | −13.453 | −47.624 | 1 | 29.29 |
| 4534 | CD1 | LEU | 29 | 49.357 | −13.034 | −49.084 | 1 | 28.43 |
| 4535 | CD2 | LEU | 29 | 48.727 | −14.815 | −47.44 | 1 | 28.85 |
| 4536 | C | LEU | 29 | 52.5 | −14.014 | −45.343 | 1 | 31.57 |
| 4537 | O | LEU | 29 | 53.3 | −13.08 | −45.385 | 1 | 32.15 |
| 4538 | N | GLY | 30 | 52.854 | −15.259 | −45.042 | 1 | 31.77 |
| 4539 | CA | GLY | 30 | 54.235 | −15.584 | −44.737 | 1 | 32.92 |
| 4540 | C | GLY | 30 | 54.641 | −15.153 | −43.34 | 1 | 33.86 |
| 4541 | O | GLY | 30 | 55.777 | −15.386 | −42.918 | 1 | 34.81 |
| 4542 | N | GLY | 31 | 53.713 | −14.529 | −42.621 | 1 | 33.06 |
| 4543 | CA | GLY | 31 | 53.997 | −14.067 | −41.274 | 1 | 32.48 |
| 4544 | C | GLY | 31 | 53.946 | −15.163 | −40.224 | 1 | 32.49 |
| 4545 | O | GLY | 31 | 53.422 | −16.248 | −40.482 | 1 | 32.47 |
| 4546 | N | PRO | 32 | 54.484 | −14.906 | −39.02 | 1 | 31.47 |
| 4547 | CD | PRO | 32 | 55.189 | −13.669 | −38.639 | 1 | 31.96 |
| 4548 | CA | PRO | 32 | 54.503 | −15.875 | −37.918 | 1 | 30.6 |
| 4549 | CB | PRO | 32 | 55.452 | −15.229 | −36.911 | 1 | 30.73 |
| 4550 | CG | PRO | 32 | 55.217 | −13.765 | −37.133 | 1 | 31.86 |
| 4551 | C | PRO | 32 | 53.13 | −16.179 | −37.318 | 1 | 29.96 |
| 4552 | O | PRO | 32 | 52.887 | −17.293 | −36.85 | 1 | 29.11 |
| 4553 | N | GLU | 33 | 52.237 | −15.194 | −37.327 | 1 | 29.82 |
| 4554 | CA | GLU | 33 | 50.897 | −15.388 | −36.781 | 1 | 30.26 |
| 4555 | CB | GLU | 33 | 50.125 | −14.064 | −36.758 | 1 | 32.95 |
| 4556 | CG | GLU | 33 | 50.822 | −12.942 | −35.995 | 1 | 36.41 |
| 4557 | CD | GLU | 33 | 51.557 | −11.971 | −36.907 | 1 | 38.2 |
| 4558 | OE1 | GLU | 33 | 52.357 | −12.423 | −37.755 | 1 | 38.61 |
| 4559 | OE2 | GLU | 33 | 51.336 | −10.749 | −36.772 | 1 | 39.64 |
| 4560 | C | GLU | 33 | 50.137 | −16.411 | −37.623 | 1 | 29.32 |
| 4561 | O | GLU | 33 | 49.547 | −17.356 | −37.093 | 1 | 28.73 |
| 4562 | N | LEU | 34 | 50.155 | −16.218 | −38.937 | 1 | 28.69 |
| 4563 | CA | LEU | 34 | 49.477 | −17.132 | −39.848 | 1 | 27.91 |
| 4564 | CB | LEU | 34 | 49.554 | −16.607 | −41.283 | 1 | 27.03 |
| 4565 | CG | LEU | 34 | 48.949 | −17.494 | −42.377 | 1 | 27.15 |
| 4566 | CD1 | LEU | 34 | 47.475 | −17.759 | −42.088 | 1 | 26.06 |
| 4567 | CD2 | LEU | 34 | 49.113 | −16.807 | −43.725 | 1 | 25.72 |
| 4568 | C | LEU | 34 | 50.127 | −18.508 | −39.772 | 1 | 28.08 |
| 4569 | O | LEU | 34 | 49.452 | −19.534 | −39.857 | 1 | 28.11 |
| 4570 | N | GLN | 35 | 51.445 | −18.521 | −39.611 | 1 | 27.79 |
| 4571 | CA | GLN | 35 | 52.19 | −19.77 | −39.523 | 1 | 27.76 |
| 4572 | CB | GLN | 35 | 53.69 | −19.476 | −39.479 | 1 | 30.01 |
| 4573 | CG | GLN | 35 | 54.569 | −20.707 | −39.405 | 1 | 33.35 |
| 4574 | CD | GLN | 35 | 56.037 | −20.373 | −39.589 | 1 | 36.58 |
| 4575 | OE1 | GLN | 35 | 56.597 | −19.556 | −38.856 | 1 | 38.68 |
| 4576 | NE2 | GLN | 35 | 56.668 | −21.002 | −40.575 | 1 | 37.31 |
| 4577 | C | GLN | 35 | 51.771 | −20.563 | −38.288 | 1 | 27.23 |
| 4578 | O | GLN | 35 | 51.669 | −21.788 | −38.328 | 1 | 27.12 |
| 4579 | N | ARG | 36 | 51.529 | −19.861 | −37.188 | 1 | 26.06 |
| 4580 | CA | ARG | 36 | 51.113 | −20.521 | −35.96 | 1 | 26.67 |
| 4581 | CB | ARG | 36 | 51.096 | −19.531 | −34.799 | 1 | 29.45 |
| 4582 | CG | ARG | 36 | 50.685 | −20.166 | −33.489 | 1 | 35.39 |
| 4583 | CD | ARG | 36 | 50.443 | −19.128 | −32.416 | 1 | 40.14 |
| 4584 | NE | ARG | 36 | 49.949 | −19.744 | −31.19 | 1 | 44.02 |
| 4585 | CZ | ARG | 36 | 49.549 | −19.064 | −30.122 | 1 | 45.8 |
| 4586 | NH1 | ARG | 36 | 49.586 | −17.737 | −30.127 | 1 | 46.09 |
| 4587 | NH2 | ARG | 36 | 49.111 | −19.713 | −29.05 | 1 | 47.68 |
| 4588 | C | ARG | 36 | 49.719 | −21.115 | −36.143 | 1 | 24.72 |
| 4589 | O | ARG | 36 | 49.441 | −22.22 | −35.68 | 1 | 23.92 |
| 4590 | N | LEU | 37 | 48.847 | −20.373 | −36.82 | 1 | 22.09 |
| 4591 | CA | LEU | 37 | 47.486 | −20.831 | −37.07 | 1 | 21.17 |
| 4592 | CB | LEU | 37 | 46.671 | −19.735 | −37.758 | 1 | 21.29 |
| 4593 | CG | LEU | 37 | 45.276 | −20.129 | −38.259 | 1 | 20.46 |
| 4594 | CD1 | LEU | 37 | 44.413 | −20.606 | −37.094 | 1 | 20.36 |
| 4595 | CD2 | LEU | 37 | 44.633 | −18.936 | −38.943 | 1 | 21.05 |
| 4596 | C | LEU | 37 | 47.475 | −22.082 | −37.936 | 1 | 21.45 |
| 4597 | O | LEU | 37 | 46.768 | −23.043 | −37.636 | 1 | 20.42 |
| 4598 | N | THR | 38 | 48.256 | −22.07 | −39.013 | 1 | 22.56 |
| 4599 | CA | THR | 38 | 48.306 | −23.222 | −39.908 | 1 | 22.83 |
| 4600 | CB | THR | 38 | 49.119 | −22.915 | −41.183 | 1 | 24.42 |
| 4601 | OG1 | THR | 38 | 50.479 | −22.628 | −40.835 | 1 | 27.03 |
| 4602 | CG2 | THR | 38 | 48.523 | −21.719 | −41.907 | 1 | 25.06 |
| 4603 | C | THR | 38 | 48.904 | −24.429 | −39.2 | 1 | 23.04 |
| 4604 | O | THR | 38 | 48.452 | −25.559 | −39.392 | 1 | 19.55 |
| 4605 | N | GLN | 39 | 49.92 | −24.19 | −38.377 | 1 | 22.59 |
| 4606 | CA | GLN | 39 | 50.545 | −25.273 | −37.634 | 1 | 24.94 |
| 4607 | CB | GLN | 39 | 51.734 | −24.754 | −36.82 | 1 | 27.95 |
| 4608 | CG | GLN | 39 | 52.309 | −25.783 | −35.855 | 1 | 34.28 |
| 4609 | CD | GLN | 39 | 53.426 | −25.224 | −34.994 | 1 | 37.68 |
| 4610 | OE1 | GLN | 39 | 53.234 | −24.256 | −34.255 | 1 | 40.32 |
| 4611 | NE2 | GLN | 39 | 54.603 | −25.836 | −35.082 | 1 | 39.93 |
| 4612 | C | GLN | 39 | 49.516 | −25.888 | −36.69 | 1 | 24 |
| 4613 | O | GLN | 39 | 49.422 | −27.108 | −36.57 | 1 | 23.51 |
| 4614 | N | ARG | 40 | 48.741 | −25.035 | −36.025 | 1 | 23.61 |
| 4615 | CA | ARG | 40 | 47.728 | −25.504 | −35.088 | 1 | 23.32 |
| 4616 | CB | ARG | 40 | 47.127 | −24.321 | −34.32 | 1 | 26.53 |
| 4617 | CG | ARG | 40 | 46.174 | −24.728 | −33.205 | 1 | 30.87 |
| 4618 | CD | ARG | 40 | 46.795 | −25.782 | −32.295 | 1 | 34.36 |
| 4619 | NE | ARG | 40 | 48.007 | −25.314 | −31.625 | 1 | 38.43 |
| 4620 | CZ | ARG | 40 | 48.03 | −24.43 | −30.631 | 1 | 39.79 |
| 4621 | NH1 | ARG | 40 | 46.903 | −23.903 | −30.173 | 1 | 41.54 |
| 4622 | NH2 | ARG | 40 | 49.189 | −24.074 | −30.091 | 1 | 41.73 |
| 4623 | C | ARG | 40 | 46.629 | −26.292 | −35.796 | 1 | 22.49 |
| 4624 | O | ARG | 40 | 46.166 | −27.315 | −35.29 | 1 | 21.2 |
| 4625 | N | LEU | 41 | 46.211 | −25.819 | −36.967 | 1 | 20.85 |
| 4626 | CA | LEU | 41 | 45.179 | −26.511 | −37.732 | 1 | 20.19 |
| 4627 | CB | LEU | 41 | 44.871 | −25.755 | −39.028 | 1 | 20.58 |
| 4628 | CG | LEU | 41 | 43.903 | −24.575 | −38.959 | 1 | 22.89 |
| 4629 | CD1 | LEU | 41 | 43.926 | −23.814 | −40.281 | 1 | 22.4 |
| 4630 | CD2 | LEU | 41 | 42.503 | −25.088 | −38.657 | 1 | 21.76 |
| 4631 | C | LEU | 41 | 45.634 | −27.921 | −38.079 | 1 | 20.08 |
| 4632 | O | LEU | 41 | 44.914 | −28.894 | −37.852 | 1 | 20.18 |
| 4633 | N | VAL | 42 | 46.841 | −28.025 | −38.627 | 1 | 20.1 |
| 4634 | CA | VAL | 42 | 47.398 | −29.312 | −39.024 | 1 | 20.79 |
| 4635 | CB | VAL | 42 | 48.744 | −29.119 | −39.755 | 1 | 21.6 |
| 4636 | CG1 | VAL | 42 | 49.405 | −30.465 | −40.014 | 1 | 20.49 |
| 4637 | CG2 | VAL | 42 | 48.507 | −28.381 | −41.068 | 1 | 21.71 |
| 4638 | C | VAL | 42 | 47.592 | −30.246 | −37.836 | 1 | 20.66 |
| 4639 | O | VAL | 42 | 47.357 | −31.45 | −37.934 | 1 | 20.96 |
| 4640 | N | GLN | 43 | 48.02 | −29.687 | −36.712 | 1 | 21.19 |
| 4641 | CA | GLN | 43 | 48.237 | −30.472 | −35.508 | 1 | 22.27 |
| 4642 | CB | GLN | 43 | 48.85 | −29.582 | −34.426 | 1 | 25.12 |
| 4643 | CG | GLN | 43 | 49.146 | −30.278 | −33.117 | 1 | 32.15 |
| 4644 | CD | GLN | 43 | 50.005 | −29.423 | −32.209 | 1 | 35.61 |
| 4645 | OE1 | GLN | 43 | 49.738 | −28.234 | −32.024 | 1 | 39.86 |
| 4646 | NE2 | GLN | 43 | 51.041 | −30.023 | −31.634 | 1 | 38.07 |
| 4647 | C | GLN | 43 | 46.928 | −31.092 | −35.014 | 1 | 21.79 |
| 4648 | O | GLN | 43 | 46.88 | −32.277 | −34.681 | 1 | 21.05 |
| 4649 | N | VAL | 44 | 45.864 | −30.295 | −34.975 | 1 | 20.79 |
| 4650 | CA | VAL | 44 | 44.573 | −30.801 | −34.518 | 1 | 20.89 |
| 4651 | CB | VAL | 44 | 43.556 | −29.654 | −34.327 | 1 | 20.55 |
| 4652 | CG1 | VAL | 44 | 42.17 | −30.219 | −34.037 | 1 | 21.94 |
| 4653 | CG2 | VAL | 44 | 44.007 | −28.758 | −33.185 | 1 | 21.42 |
| 4654 | C | VAL | 44 | 44.019 | −31.809 | −35.512 | 1 | 20.43 |
| 4655 | O | VAL | 44 | 43.48 | −32.849 | −35.129 | 1 | 20.64 |
| 4656 | N | MET | 45 | 44.171 | −31.506 | −36.795 | 1 | 21.29 |
| 4657 | CA | MET | 45 | 43.686 | −32.39 | −37.845 | 1 | 23.54 |
| 4658 | CB | MET | 45 | 44.001 | −31.783 | −39.208 | 1 | 24.1 |
| 4659 | CG | MET | 45 | 43.297 | −32.446 | −40.372 | 1 | 26.35 |
| 4660 | SD | MET | 45 | 43.753 | −31.674 | −41.935 | 1 | 30.16 |

TABLE 1-continued

| Atom | Atom Type | Residue | # | X | Y | Z | OCC | B |
|---|---|---|---|---|---|---|---|---|
| 4661 | CE | MET | 45 | 44.208 | −30.079 | −41.35 | 1 | 21.49 |
| 4662 | C | MET | 45 | 44.325 | −33.77 | −37.737 | 1 | 24.03 |
| 4663 | O | MET | 45 | 43.646 | −34.792 | −37.839 | 1 | 25.79 |
| 4664 | N | ARG | 46 | 45.636 | −33.799 | −37.526 | 1 | 24.09 |
| 4665 | CA | ARG | 46 | 46.351 | −35.061 | −37.409 | 1 | 24.39 |
| 4666 | CB | ARG | 46 | 47.853 | −34.816 | −37.557 | 1 | 25.6 |
| 4667 | CG | ARG | 46 | 48.224 | −34.37 | −38.96 | 1 | 26.07 |
| 4668 | CD | ARG | 46 | 49.687 | −34.007 | −39.099 | 1 | 27.94 |
| 4669 | NE | ARG | 46 | 50.013 | −33.758 | −40.5 | 1 | 29.21 |
| 4670 | CZ | ARG | 46 | 51.18 | −33.297 | −40.933 | 1 | 30.61 |
| 4671 | NH1 | ARG | 46 | 52.152 | −33.024 | −40.073 | 1 | 30.77 |
| 4672 | NH2 | ARG | 46 | 51.375 | −33.11 | −42.232 | 1 | 29.16 |
| 4673 | C | ARG | 46 | 46.047 | −35.766 | −36.093 | 1 | 24.43 |
| 4674 | O | ARG | 46 | 46.064 | −36.993 | −36.016 | 1 | 25.31 |
| 4675 | N | ARG | 47 | 45.757 | −34.981 | −35.061 | 1 | 23.9 |
| 4676 | CA | ARG | 47 | 45.437 | −35.522 | −33.747 | 1 | 24.12 |
| 4677 | CB | ARG | 47 | 45.412 | −34.389 | −32.719 | 1 | 25.74 |
| 4678 | CG | ARG | 47 | 45.228 | −34.832 | −31.279 | 1 | 31.44 |
| 4679 | CD | ARG | 47 | 46.45 | −35.581 | −30.774 | 1 | 35.13 |
| 4680 | NE | ARG | 47 | 46.848 | −35.133 | −29.442 | 1 | 39.24 |
| 4681 | CZ | ARG | 47 | 46.084 | −35.223 | −28.358 | 1 | 40.76 |
| 4682 | NH1 | ARG | 47 | 44.867 | −35.75 | −28.432 | 1 | 41.87 |
| 4683 | NH2 | ARG | 47 | 46.538 | −34.783 | −27.194 | 1 | 42.44 |
| 4684 | C | ARG | 47 | 44.073 | −36.209 | −33.781 | 1 | 22.89 |
| 4685 | O | ARG | 47 | 43.904 | −37.319 | −33.275 | 1 | 22.76 |
| 4686 | N | ARG | 48 | 43.102 | −35.533 | −34.388 | 1 | 20.38 |
| 4687 | CA | ARG | 48 | 41.74 | −36.043 | −34.49 | 1 | 21.05 |
| 4688 | CB | ARG | 48 | 40.76 | −34.87 | −34.524 | 1 | 20.03 |
| 4689 | CG | ARG | 48 | 40.654 | −34.124 | −33.201 | 1 | 20.14 |
| 4690 | CD | ARG | 48 | 40.056 | −35.034 | −32.147 | 1 | 20.88 |
| 4691 | NE | ARG | 48 | 38.778 | −35.564 | −32.612 | 1 | 22.41 |
| 4692 | CZ | ARG | 48 | 38.405 | −36.834 | −32.507 | 1 | 24.37 |
| 4693 | NH1 | ARG | 48 | 39.211 | −37.724 | −31.943 | 1 | 26.44 |
| 4694 | NH2 | ARG | 48 | 37.229 | −37.217 | −32.988 | 1 | 25.77 |
| 4695 | C | ARG | 48 | 41.523 | −36.935 | −35.705 | 1 | 21.99 |
| 4696 | O | ARG | 48 | 40.452 | −37.522 | −35.876 | 1 | 21.68 |
| 4697 | N | ARG | 49 | 42.546 | −37.035 | −36.544 | 1 | 23 |
| 4698 | CA | ARG | 49 | 42.484 | −37.855 | −37.745 | 1 | 25.16 |
| 4699 | CB | ARG | 49 | 42.337 | −39.329 | −37.366 | 1 | 28.55 |
| 4700 | CG | ARG | 49 | 43.5 | −39.84 | −36.535 | 1 | 32.54 |
| 4701 | CD | ARG | 49 | 43.308 | −41.282 | −36.127 | 1 | 35.46 |
| 4702 | NE | ARG | 49 | 44.369 | −41.726 | −35.229 | 1 | 38.72 |
| 4703 | CZ | ARG | 49 | 44.435 | −42.94 | −34.692 | 1 | 40.5 |
| 4704 | NH1 | ARG | 49 | 43.497 | −43.839 | −34.963 | 1 | 40.77 |
| 4705 | NH2 | ARG | 49 | 45.437 | −43.253 | −33.882 | 1 | 40.75 |
| 4706 | C | ARG | 49 | 41.363 | −37.441 | −38.684 | 1 | 24.55 |
| 4707 | O | ARG | 49 | 40.787 | −38.273 | −39.387 | 1 | 24.64 |
| 4708 | N | CYS | 50 | 41.037 | −36.153 | −38.686 | 1 | 24.04 |
| 4709 | CA | CYS | 50 | 40.012 | −35.665 | −39.592 | 1 | 22.45 |
| 4710 | CB | CYS | 50 | 39.234 | −34.488 | −38.977 | 1 | 22.11 |
| 4711 | SG | CYS | 50 | 40.19 | −33.16 | −38.232 | 1 | 23.19 |
| 4712 | C | CYS | 50 | 40.751 | −35.265 | −40.866 | 1 | 22.86 |
| 4713 | O | CYS | 50 | 41.88 | −34.781 | −40.815 | 1 | 24.9 |
| 4714 | N | VAL | 51 | 40.12 | −35.5 | −42.006 | 1 | 22.6 |
| 4715 | CA | VAL | 51 | 40.714 | −35.213 | −43.307 | 1 | 20.63 |
| 4716 | CB | VAL | 51 | 39.896 | −35.908 | −44.417 | 1 | 20.34 |
| 4717 | CG1 | VAL | 51 | 40.514 | −35.646 | −45.781 | 1 | 22.14 |
| 4718 | CG2 | VAL | 51 | 39.836 | −37.4 | −44.14 | 1 | 22.33 |
| 4719 | C | VAL | 51 | 40.852 | −33.728 | −43.628 | 1 | 20 |
| 4720 | O | VAL | 51 | 41.665 | −33.34 | −44.462 | 1 | 21 |
| 4721 | N | GLY | 52 | 40.058 | −32.897 | −42.967 | 1 | 18.72 |
| 4722 | CA | GLY | 52 | 40.133 | −31.469 | −43.213 | 1 | 16.28 |
| 4723 | C | GLY | 52 | 39.757 | −30.705 | −41.964 | 1 | 15.77 |
| 4724 | O | GLY | 52 | 39.19 | −31.275 | −41.036 | 1 | 15.87 |
| 4725 | N | LEU | 53 | 40.081 | −29.418 | −41.934 | 1 | 14.91 |
| 4726 | CA | LEU | 53 | 39.762 | −28.574 | −40.786 | 1 | 13.46 |
| 4727 | CB | LEU | 53 | 40.735 | −28.854 | −39.632 | 1 | 15.14 |
| 4728 | CG | LEU | 53 | 40.365 | −28.259 | −38.268 | 1 | 15.21 |
| 4729 | CD1 | LEU | 53 | 39.036 | −28.839 | −37.796 | 1 | 16.11 |
| 4730 | CD2 | LEU | 53 | 41.465 | −28.574 | −37.258 | 1 | 16.34 |
| 4731 | C | LEU | 53 | 39.881 | −27.119 | −41.231 | 1 | 15.44 |
| 4732 | O | LEU | 53 | 40.675 | −26.803 | −42.118 | 1 | 15.36 |
| 4733 | N | SER | 54 | 39.094 | −26.24 | −40.619 | 1 | 14.32 |
| 4734 | CA | SER | 54 | 39.109 | −24.823 | −40.972 | 1 | 14.46 |
| 4735 | CB | SER | 54 | 37.76 | −24.421 | −41.573 | 1 | 15.03 |
| 4736 | OG | SER | 54 | 36.723 | −24.56 | −40.617 | 1 | 16.59 |
| 4737 | C | SER | 54 | 39.401 | −23.945 | −39.761 | 1 | 14.8 |
| 4738 | O | SER | 54 | 39.109 | −24.32 | −38.627 | 1 | 13.32 |
| 4739 | N | ALA | 55 | 39.96 | −22.764 | −40.008 | 1 | 13.37 |
| 4740 | CA | ALA | 55 | 40.293 | −21.836 | −38.932 | 1 | 13.78 |
| 4741 | CB | ALA | 55 | 40.906 | −20.565 | −39.514 | 1 | 13.93 |
| 4742 | C | ALA | 55 | 39.111 | −21.481 | −38.027 | 1 | 14.47 |
| 4743 | O | ALA | 55 | 39.266 | −21.388 | −36.811 | 1 | 14.24 |
| 4744 | N | PRO | 56 | 37.915 | −21.261 | −38.602 | 1 | 14.31 |
| 4745 | CD | PRO | 56 | 37.559 | −21.102 | −40.024 | 1 | 14.48 |
| 4746 | CA | PRO | 56 | 36.778 | −20.924 | −37.742 | 1 | 14.25 |
| 4747 | CB | PRO | 56 | 35.62 | −20.822 | −38.728 | 1 | 15 |
| 4748 | CG | PRO | 56 | 36.293 | −20.267 | −39.948 | 1 | 14.11 |
| 4749 | C | PRO | 56 | 36.528 | −21.971 | −36.661 | 1 | 13.67 |
| 4750 | O | PRO | 56 | 36.047 | −21.645 | −35.578 | 1 | 14.77 |
| 4751 | N | GLN | 57 | 36.866 | −23.223 | −36.958 | 1 | 13.03 |
| 4752 | CA | GLN | 57 | 36.669 | −24.305 | −36.003 | 1 | 12.66 |
| 4753 | CB | GLN | 57 | 36.811 | −25.651 | −36.704 | 1 | 13.39 |
| 4754 | CG | GLN | 57 | 35.654 | −25.936 | −37.64 | 1 | 14.14 |
| 4755 | CD | GLN | 57 | 35.857 | −27.201 | −38.43 | 1 | 14.79 |
| 4756 | OE1 | GLN | 57 | 36.521 | −27.201 | −39.469 | 1 | 16.12 |
| 4757 | NE2 | GLN | 57 | 35.301 | −28.296 | −37.933 | 1 | 13.87 |
| 4758 | C | GLN | 57 | 37.613 | −24.216 | −34.816 | 1 | 13.79 |
| 4759 | O | GLN | 57 | 37.378 | −24.845 | −33.785 | 1 | 14.69 |
| 4760 | N | LEU | 58 | 38.687 | −23.448 | −34.964 | 1 | 13.92 |
| 4761 | CA | LEU | 58 | 39.621 | −23.258 | −33.863 | 1 | 16.87 |
| 4762 | CB | LEU | 58 | 41.071 | −23.398 | −34.34 | 1 | 16.55 |
| 4763 | CG | LEU | 58 | 41.479 | −24.788 | −34.84 | 1 | 18.1 |
| 4764 | CD1 | LEU | 58 | 42.973 | −24.809 | −35.14 | 1 | 22.08 |
| 4765 | CD2 | LEU | 58 | 41.14 | −25.835 | −33.792 | 1 | 19.64 |
| 4766 | C | LEU | 58 | 39.378 | −21.869 | −33.275 | 1 | 17.5 |
| 4767 | O | LEU | 58 | 40.221 | −21.325 | −32.559 | 1 | 20.43 |
| 4768 | N | GLY | 59 | 38.217 | −21.303 | −33.594 | 1 | 16.97 |
| 4769 | CA | GLY | 59 | 37.843 | −19.995 | −33.082 | 1 | 17.04 |
| 4770 | C | GLY | 59 | 38.409 | −18.788 | −33.808 | 1 | 17.57 |
| 4771 | O | GLY | 59 | 38.297 | −17.664 | −33.318 | 1 | 18.3 |
| 4772 | N | VAL | 60 | 39.01 | −19.007 | −34.973 | 1 | 17.01 |
| 4773 | CA | VAL | 60 | 39.596 | −17.913 | −35.745 | 1 | 16.92 |
| 4774 | CB | VAL | 60 | 41.055 | −18.236 | −36.121 | 1 | 18.06 |
| 4775 | CG1 | VAL | 60 | 41.653 | −17.098 | −36.939 | 1 | 19.28 |
| 4776 | CG2 | VAL | 60 | 41.873 | −18.471 | −34.852 | 1 | 18.69 |
| 4777 | C | VAL | 60 | 38.782 | −17.66 | −37.014 | 1 | 18.12 |
| 4778 | O | VAL | 60 | 38.82 | −18.453 | −37.955 | 1 | 17.47 |
| 4779 | N | PRO | 61 | 38.037 | −16.542 | −37.053 | 1 | 18.8 |
| 4780 | CD | PRO | 61 | 37.907 | −15.536 | −35.983 | 1 | 19.59 |
| 4781 | CA | PRO | 61 | 37.205 | −16.184 | −38.207 | 1 | 18.7 |
| 4782 | CB | PRO | 61 | 36.28 | −15.117 | −37.634 | 1 | 19.58 |
| 4783 | CG | PRO | 61 | 37.18 | −14.399 | −36.684 | 1 | 20.25 |
| 4784 | C | PRO | 61 | 37.988 | −15.693 | −39.426 | 1 | 19.66 |
| 4785 | O | PRO | 61 | 37.771 | −14.578 | −39.915 | 1 | 18.59 |
| 4786 | N | ARG | 62 | 38.894 | −16.535 | −39.914 | 1 | 18.82 |
| 4787 | CA | ARG | 62 | 39.705 | −16.201 | −41.08 | 1 | 19.4 |
| 4788 | CB | ARG | 62 | 41.169 | −16.021 | −40.673 | 1 | 20.64 |
| 4789 | CG | ARG | 62 | 41.408 | −14.833 | −39.751 | 1 | 23.78 |
| 4790 | CD | ARG | 62 | 41.154 | −13.513 | −40.468 | 1 | 26.94 |
| 4791 | NE | ARG | 62 | 41.312 | −12.372 | −39.571 | 1 | 28.87 |
| 4792 | CZ | ARG | 62 | 41.223 | −11.101 | −39.95 | 1 | 31.97 |
| 4793 | NH1 | ARG | 62 | 40.976 | −10.798 | −41.219 | 1 | 31.88 |
| 4794 | NH2 | ARG | 62 | 41.378 | −10.13 | −39.058 | 1 | 32.51 |
| 4795 | C | ARG | 62 | 39.591 | −17.287 | −42.144 | 1 | 18.85 |
| 4796 | O | ARG | 62 | 39.371 | −18.461 | −41.833 | 1 | 18.07 |
| 4797 | N | GLN | 63 | 39.748 | −16.887 | −43.4 | 1 | 18.03 |
| 4798 | CA | GLN | 63 | 39.649 | −17.817 | −44.517 | 1 | 17.19 |
| 4799 | CB | GLN | 63 | 39.382 | −17.043 | −45.812 | 1 | 17.86 |
| 4800 | CG | GLN | 63 | 38.083 | −16.25 | −45.76 | 1 | 19.69 |
| 4801 | CD | GLN | 63 | 37.8 | −15.465 | −47.026 | 1 | 21.31 |
| 4802 | OE1 | GLN | 63 | 36.948 | −14.574 | −47.035 | 1 | 24.15 |
| 4803 | NE2 | GLN | 63 | 38.502 | −15.795 | −48.102 | 1 | 20.2 |
| 4804 | C | GLN | 63 | 40.889 | −18.689 | −44.664 | 1 | 17.77 |
| 4805 | O | GLN | 63 | 41.734 | −18.455 | −45.527 | 1 | 18.4 |
| 4806 | N | VAL | 64 | 40.993 | −19.697 | −43.804 | 1 | 17.2 |
| 4807 | CA | VAL | 64 | 42.113 | −20.627 | −43.843 | 1 | 16.28 |
| 4808 | CB | VAL | 64 | 43.174 | −20.299 | −42.763 | 1 | 17.07 |
| 4809 | CG1 | VAL | 64 | 44.337 | −21.273 | −42.864 | 1 | 16.39 |
| 4810 | CG2 | VAL | 64 | 43.664 | −18.867 | −42.922 | 1 | 18.12 |
| 4811 | C | VAL | 64 | 41.591 | −22.038 | −43.593 | 1 | 17.42 |
| 4812 | O | VAL | 64 | 40.777 | −22.261 | −42.693 | 1 | 16.48 |

TABLE 1-continued

| Atom | Atom Type | Residue | # | X | Y | Z | OCC | B |
|---|---|---|---|---|---|---|---|---|
| 4813 | N | LEU | 65 | 42.045 | −22.986 | −44.401 | 1 | 16.12 |
| 4814 | CA | LEU | 65 | 41.626 | −24.371 | −44.235 | 1 | 15.92 |
| 4815 | CB | LEU | 65 | 40.381 | −24.667 | −45.084 | 1 | 15.54 |
| 4816 | CG | LEU | 65 | 40.469 | −24.6 | −46.61 | 1 | 15.16 |
| 4817 | CD1 | LEU | 65 | 41.101 | −25.876 | −47.146 | 1 | 15.07 |
| 4818 | CD2 | LEU | 65 | 39.065 | −24.428 | −47.194 | 1 | 15.9 |
| 4819 | C | LEU | 65 | 42.767 | −25.293 | −44.617 | 1 | 15.38 |
| 4820 | O | LEU | 65 | 43.661 | −24.91 | −45.369 | 1 | 17.06 |
| 4821 | N | ALA | 66 | 42.747 | −26.504 | −44.074 | 1 | 15.68 |
| 4822 | CA | ALA | 66 | 43.78 | −27.482 | −44.371 | 1 | 16.85 |
| 4823 | CB | ALA | 66 | 44.692 | −27.656 | −43.175 | 1 | 17.36 |
| 4824 | C | ALA | 66 | 43.124 | −28.803 | −44.741 | 1 | 17.01 |
| 4825 | O | ALA | 66 | 42.037 | −29.124 | −44.257 | 1 | 16.69 |
| 4826 | N | LEU | 67 | 43.794 | −29.564 | −45.599 | 1 | 17.65 |
| 4827 | CA | LEU | 67 | 43.279 | −30.842 | −46.075 | 1 | 18.88 |
| 4828 | CB | LEU | 67 | 42.654 | −30.655 | −47.461 | 1 | 20.43 |
| 4829 | CG | LEU | 67 | 41.7 | −29.47 | −47.634 | 1 | 22.48 |
| 4830 | CD1 | LEU | 67 | 41.666 | −29.035 | −49.095 | 1 | 23.55 |
| 4831 | CD2 | LEU | 67 | 40.317 | −29.858 | −47.144 | 1 | 24.38 |
| 4832 | C | LEU | 67 | 44.422 | −31.844 | −46.186 | 1 | 18.36 |
| 4833 | O | LEU | 67 | 45.503 | −31.501 | −46.659 | 1 | 19.51 |
| 4834 | N | GLU | 68 | 44.178 | −33.079 | −45.758 | 1 | 18.68 |
| 4835 | CA | GLU | 68 | 45.188 | −34.13 | −45.835 | 1 | 19.88 |
| 4836 | CB | GLU | 68 | 46.279 | −33.908 | −44.782 | 1 | 21.28 |
| 4837 | CG | GLU | 68 | 47.374 | −34.962 | −44.804 | 1 | 25.07 |
| 4838 | CD | GLU | 68 | 48.422 | −34.74 | −43.731 | 1 | 28.55 |
| 4839 | OE1 | GLU | 68 | 48.056 | −34.699 | −42.539 | 1 | 30.31 |
| 4840 | OE2 | GLU | 68 | 49.614 | −34.605 | −44.079 | 1 | 31.26 |
| 4841 | C | GLU | 68 | 44.564 | −35.503 | −45.631 | 1 | 19.61 |
| 4842 | O | GLU | 68 | 43.894 | −35.75 | −44.628 | 1 | 19.52 |
| 4843 | N | LEU | 69 | 44.784 | −36.399 | −46.586 | 1 | 19.13 |
| 4844 | CA | LEU | 69 | 44.238 | −37.744 | −46.479 | 1 | 20.65 |
| 4845 | CB | LEU | 69 | 43.195 | −37.983 | −47.572 | 1 | 20.49 |
| 4846 | CG | LEU | 69 | 42.52 | −39.359 | −47.577 | 1 | 21.73 |
| 4847 | CD1 | LEU | 69 | 42.095 | −39.736 | −46.164 | 1 | 21.7 |
| 4848 | CD2 | LEU | 69 | 41.318 | −39.331 | −48.51 | 1 | 22.75 |
| 4849 | C | LEU | 69 | 45.345 | −38.786 | −46.572 | 1 | 21.88 |
| 4850 | O | LEU | 69 | 45.742 | −39.189 | −47.666 | 1 | 21.48 |
| 4851 | N | PRO | 70 | 45.859 | −39.233 | −45.414 | 1 | 23.42 |
| 4852 | CD | PRO | 70 | 45.556 | −38.724 | −44.066 | 1 | 24.53 |
| 4853 | CA | PRO | 70 | 46.928 | −40.234 | −45.358 | 1 | 24.48 |
| 4854 | CB | PRO | 70 | 47.241 | −40.326 | −43.863 | 1 | 25.5 |
| 4855 | CG | PRO | 70 | 46.855 | −38.965 | −43.345 | 1 | 26.58 |
| 4856 | C | PRO | 70 | 46.489 | −41.573 | −45.931 | 1 | 24.75 |
| 4857 | O | PRO | 70 | 45.318 | −41.949 | −45.846 | 1 | 23.35 |
| 4858 | N | GLU | 71 | 47.444 | −42.287 | −46.514 | 1 | 26.82 |
| 4859 | CA | GLU | 71 | 47.186 | −43.588 | −47.107 | 1 | 28.94 |
| 4860 | CB | GLU | 71 | 48.505 | −44.161 | −47.639 | 1 | 32.81 |
| 4861 | CG | GLU | 71 | 48.361 | −45.244 | −48.691 | 1 | 37.82 |
| 4862 | CD | GLU | 71 | 47.683 | −46.479 | −48.158 | 1 | 41.05 |
| 4863 | OE1 | GLU | 71 | 48.12 | −46.977 | −47.098 | 1 | 43.78 |
| 4864 | OE2 | GLU | 71 | 46.719 | −46.953 | −48.799 | 1 | 44.13 |
| 4865 | C | GLU | 71 | 46.568 | −44.522 | −46.06 | 1 | 28.2 |
| 4866 | O | GLU | 71 | 45.669 | −45.303 | −46.366 | 1 | 27.38 |
| 4867 | N | ALA | 72 | 47.044 | −44.418 | −44.821 | 1 | 28.17 |
| 4868 | CA | ALA | 72 | 46.55 | −45.253 | −43.727 | 1 | 28.65 |
| 4869 | CB | ALA | 72 | 47.266 | −44.886 | −42.428 | 1 | 28.53 |
| 4870 | C | ALA | 72 | 45.037 | −45.158 | −43.537 | 1 | 28.28 |
| 4871 | O | ALA | 72 | 44.361 | −46.178 | −43.397 | 1 | 26.6 |
| 4872 | N | LEU | 73 | 44.506 | −43.937 | −43.528 | 1 | 28.71 |
| 4873 | CA | LEU | 73 | 43.067 | −43.742 | −43.36 | 1 | 28.67 |
| 4874 | CB | LEU | 73 | 42.716 | −42.251 | −43.363 | 1 | 30.11 |
| 4875 | CG | LEU | 73 | 42.843 | −41.5 | −42.035 | 1 | 31.7 |
| 4876 | CD1 | LEU | 73 | 42.443 | −40.046 | −42.232 | 1 | 31.96 |
| 4877 | CD2 | LEU | 73 | 41.947 | −42.155 | −40.991 | 1 | 31.01 |
| 4878 | C | LEU | 73 | 42.277 | −44.445 | −44.455 | 1 | 28.42 |
| 4879 | O | LEU | 73 | 41.247 | −45.064 | −44.19 | 1 | 28.1 |
| 4880 | N | CYS | 74 | 42.761 | −44.346 | −45.688 | 1 | 28.16 |
| 4881 | CA | CYS | 74 | 42.087 | −44.981 | −46.813 | 1 | 29.16 |
| 4882 | CB | CYS | 74 | 42.764 | −44.587 | −48.127 | 1 | 28.38 |
| 4883 | SG | CYS | 74 | 42.639 | −42.833 | −48.519 | 1 | 28.35 |
| 4884 | C | CYS | 74 | 42.079 | −46.499 | −46.679 | 1 | 29.91 |
| 4885 | O | CYS | 74 | 41.082 | −47.15 | −46.998 | 1 | 30.08 |
| 4886 | N | ARG | 75 | 43.188 | −47.061 | −46.207 | 1 | 31.41 |
| 4887 | CA | ARG | 75 | 43.293 | −48.509 | −46.049 | 1 | 32.82 |
| 4888 | CB | ARG | 75 | 44.736 | −48.916 | −45.746 | 1 | 33.17 |
| 4889 | CG | ARG | 75 | 45.65 | −48.859 | −46.947 | 1 | 36.46 |
| 4890 | CD | ARG | 75 | 46.975 | −49.559 | −46.682 | 1 | 38.59 |
| 4891 | NE | ARG | 75 | 47.875 | −49.443 | −47.827 | 1 | 40.87 |
| 4892 | CZ | ARG | 75 | 49.1 | −49.956 | −47.877 | 1 | 41.82 |
| 4893 | NH1 | ARG | 75 | 49.586 | −50.63 | −46.843 | 1 | 42.18 |
| 4894 | NH2 | ARG | 75 | 49.843 | −49.792 | −48.965 | 1 | 42.16 |
| 4895 | C | ARG | 75 | 42.377 | −49.073 | −44.973 | 1 | 32.97 |
| 4896 | O | ARG | 75 | 41.986 | −50.238 | −45.037 | 1 | 32.79 |
| 4897 | N | GLU | 76 | 42.04 | −48.254 | −43.984 | 1 | 33.52 |
| 4898 | CA | GLU | 76 | 41.167 | −48.696 | −42.905 | 1 | 35.18 |
| 4899 | CB | GLU | 76 | 41.239 | −47.712 | −41.733 | 1 | 36.72 |
| 4900 | CG | GLU | 76 | 40.46 | −48.143 | −40.5 | 1 | 40.24 |
| 4901 | CD | GLU | 76 | 40.741 | −49.582 | −40.101 | 1 | 41.11 |
| 4902 | OE1 | GLU | 76 | 41.924 | −49.987 | −40.102 | 1 | 43.53 |
| 4903 | OE2 | GLU | 76 | 39.777 | −50.307 | −39.778 | 1 | 41.95 |
| 4904 | C | GLU | 76 | 39.736 | −48.806 | −43.42 | 1 | 35.51 |
| 4905 | O | GLU | 76 | 38.891 | −49.464 | −42.811 | 1 | 36.67 |
| 4906 | N | CYS | 77 | 39.474 | −48.16 | −44.551 | 1 | 34.32 |
| 4907 | CA | CYS | 77 | 38.153 | −48.185 | −45.167 | 1 | 34.11 |
| 4908 | CB | CYS | 77 | 37.978 | −46.955 | −46.065 | 1 | 33.79 |
| 4909 | SG | CYS | 77 | 36.369 | −46.81 | −46.882 | 1 | 37.49 |
| 4910 | C | CYS | 77 | 38.016 | −49.461 | −45.998 | 1 | 32.87 |
| 4911 | O | CYS | 77 | 38.852 | −49.738 | −46.859 | 1 | 34.23 |
| 4912 | N | PRO | 78 | 36.965 | −50.259 | −45.744 | 1 | 31.57 |
| 4913 | CD | PRO | 78 | 35.882 | −50.046 | −44.766 | 1 | 31.09 |
| 4914 | CA | PRO | 78 | 36.754 | −51.501 | −46.495 | 1 | 30.57 |
| 4915 | CB | PRO | 78 | 35.338 | −51.902 | −46.099 | 1 | 31.39 |
| 4916 | CG | PRO | 78 | 35.253 | −51.421 | −44.678 | 1 | 31.93 |
| 4917 | C | PRO | 78 | 36.893 | −51.247 | −47.997 | 1 | 30.5 |
| 4918 | O | PRO | 78 | 36.414 | −50.236 | −48.507 | 1 | 29.15 |
| 4919 | N | PRO | 79 | 37.547 | −52.169 | −48.721 | 1 | 29.98 |
| 4920 | CD | PRO | 79 | 38.053 | −53.46 | −48.22 | 1 | 30.73 |
| 4921 | CA | PRO | 79 | 37.764 | −52.057 | −50.167 | 1 | 29.39 |
| 4922 | CB | PRO | 79 | 38.214 | −53.464 | −50.552 | 1 | 29.59 |
| 4923 | CG | PRO | 79 | 38.972 | −53.899 | −49.338 | 1 | 30.6 |
| 4924 | C | PRO | 79 | 36.557 | −51.594 | −50.983 | 1 | 29.29 |
| 4925 | O | PRO | 79 | 36.659 | −50.654 | −51.774 | 1 | 29.67 |
| 4926 | N | ARG | 80 | 35.42 | −52.255 | −50.797 | 1 | 28.82 |
| 4927 | CA | ARG | 80 | 34.211 | −51.905 | −51.535 | 1 | 29.13 |
| 4928 | CB | ARG | 80 | 33.09 | −52.894 | −51.215 | 1 | 32.08 |
| 4929 | CG | ARG | 80 | 33.414 | −54.33 | −51.581 | 1 | 36.58 |
| 4930 | CD | ARG | 80 | 32.231 | −55.241 | −51.305 | 1 | 39.84 |
| 4931 | NE | ARG | 80 | 32.539 | −56.638 | −51.596 | 1 | 42.83 |
| 4932 | CZ | ARG | 80 | 31.658 | −57.629 | −51.509 | 1 | 43.73 |
| 4933 | NH1 | ARG | 80 | 30.409 | −57.378 | −51.141 | 1 | 44.48 |
| 4934 | NH2 | ARG | 80 | 32.027 | −58.873 | −51.787 | 1 | 45.55 |
| 4935 | C | ARG | 80 | 33.745 | −50.49 | −51.225 | 1 | 27.34 |
| 4936 | O | ARG | 80 | 33.312 | −49.76 | −52.116 | 1 | 27.04 |
| 4937 | N | GLN | 81 | 33.833 | −50.111 | −49.955 | 1 | 26.27 |
| 4938 | CA | GLN | 81 | 33.423 | −48.781 | −49.522 | 1 | 25.27 |
| 4939 | CB | GLN | 81 | 33.386 | −48.716 | −47.994 | 1 | 27.9 |
| 4940 | CG | GLN | 81 | 33.035 | −47.345 | −47.436 | 1 | 32.19 |
| 4941 | CD | GLN | 81 | 32.934 | −47.34 | −45.922 | 1 | 34.66 |
| 4942 | OE1 | GLN | 81 | 32.134 | −48.071 | −45.34 | 1 | 38.59 |
| 4943 | NE2 | GLN | 81 | 33.748 | −46.512 | −45.276 | 1 | 37.83 |
| 4944 | C | GLN | 81 | 34.384 | −47.729 | −50.06 | 1 | 24.53 |
| 4945 | O | GLN | 81 | 33.969 | −46.657 | −50.503 | 1 | 23.61 |
| 4946 | N | ARG | 82 | 35.674 | −48.043 | −50.024 | 1 | 23.57 |
| 4947 | CA | ARG | 82 | 36.691 | −47.121 | −50.507 | 1 | 23.17 |
| 4948 | CB | ARG | 82 | 38.088 | −47.711 | −50.282 | 1 | 24.03 |
| 4949 | CG | ARG | 82 | 39.21 | −46.804 | −50.74 | 1 | 25.24 |
| 4950 | CD | ARG | 82 | 40.575 | −47.405 | −50.464 | 1 | 25.48 |
| 4951 | NE | ARG | 82 | 41.638 | −46.559 | −50.997 | 1 | 28.01 |
| 4952 | CZ | ARG | 82 | 42.936 | −46.816 | −50.868 | 1 | 27.42 |
| 4953 | NH1 | ARG | 82 | 43.34 | −47.9 | −50.22 | 1 | 27.92 |
| 4954 | NH2 | ARG | 82 | 43.829 | −45.988 | −51.389 | 1 | 28.27 |
| 4955 | C | ARG | 82 | 36.485 | −46.821 | −51.988 | 1 | 22.43 |
| 4956 | O | ARG | 82 | 36.639 | −45.681 | −52.428 | 1 | 22.77 |
| 4957 | N | ALA | 83 | 36.127 | −47.851 | −52.749 | 1 | 21.55 |
| 4958 | CA | ALA | 83 | 35.9 | −47.707 | −54.182 | 1 | 21.34 |
| 4959 | CB | ALA | 83 | 35.791 | −49.082 | −54.828 | 1 | 21.69 |
| 4960 | C | ALA | 83 | 34.643 | −46.896 | −54.475 | 1 | 21.14 |
| 4961 | O | ALA | 83 | 34.648 | −46.018 | −55.335 | 1 | 21.55 |
| 4962 | N | LEU | 84 | 33.567 | −47.196 | −53.755 | 1 | 21.01 |
| 4963 | CA | LEU | 84 | 32.299 | −46.496 | −53.944 | 1 | 21.61 |
| 4964 | CB | LEU | 84 | 31.218 | −47.131 | −53.065 | 1 | 22.92 |

TABLE 1-continued

| Atom | Atom Type | Residue | # | X | Y | Z | OCC | B |
|---|---|---|---|---|---|---|---|---|
| 4965 | CG | LEU | 84 | 29.801 | −46.559 | −53.171 | 1 | 25.84 |
| 4966 | CD1 | LEU | 84 | 29.266 | −46.771 | −54.581 | 1 | 26.86 |
| 4967 | CD2 | LEU | 84 | 28.895 | −47.239 | −52.151 | 1 | 26.63 |
| 4968 | C | LEU | 84 | 32.43 | −45.011 | −53.61 | 1 | 21.01 |
| 4969 | O | LEU | 84 | 31.914 | −44.155 | −54.327 | 1 | 20.55 |
| 4970 | N | ARG | 85 | 33.13 | −44.711 | −52.521 | 1 | 20.46 |
| 4971 | CA | ARG | 85 | 33.323 | −43.33 | −52.092 | 1 | 21.03 |
| 4972 | CB | ARG | 85 | 33.598 | −43.289 | −50.587 | 1 | 21.8 |
| 4973 | CG | ARG | 85 | 32.41 | −43.662 | −49.714 | 1 | 24.38 |
| 4974 | CD | ARG | 85 | 32.841 | −43.787 | −48.259 | 1 | 27.74 |
| 4975 | NE | ARG | 85 | 31.721 | −43.838 | −47.322 | 1 | 31.54 |
| 4976 | CZ | ARG | 85 | 30.74 | −44.734 | −47.358 | 1 | 35.33 |
| 4977 | NH1 | ARG | 85 | 30.72 | −45.675 | −48.293 | 1 | 38.13 |
| 4978 | NH2 | ARG | 85 | 29.777 | −44.693 | −46.445 | 1 | 36.32 |
| 4979 | C | ARG | 85 | 34.465 | −42.639 | −52.833 | 1 | 21.69 |
| 4980 | O | ARG | 85 | 34.73 | −41.456 | −52.611 | 1 | 20.61 |
| 4981 | N | GLN | 86 | 35.133 | −43.375 | −53.719 | 1 | 21.88 |
| 4982 | CA | GLN | 86 | 36.263 | −42.835 | −54.474 | 1 | 22.43 |
| 4983 | CB | GLN | 86 | 35.79 | −41.848 | −55.541 | 1 | 24.03 |
| 4984 | CG | GLN | 86 | 34.871 | −42.459 | −56.576 | 1 | 25.93 |
| 4985 | CD | GLN | 86 | 34.85 | −41.665 | −57.864 | 1 | 28.37 |
| 4986 | OE1 | GLN | 86 | 34.643 | −40.454 | −57.856 | 1 | 27.76 |
| 4987 | NE2 | GLN | 86 | 35.067 | −42.348 | −58.984 | 1 | 32.74 |
| 4988 | C | GLN | 86 | 37.202 | −42.138 | −53.503 | 1 | 23.11 |
| 4989 | O | GLN | 86 | 37.544 | −40.963 | −53.668 | 1 | 22.6 |
| 4990 | N | MET | 87 | 37.61 | −42.884 | −52.486 | 1 | 23.2 |
| 4991 | CA | MET | 87 | 38.493 | −42.373 | −51.455 | 1 | 24.94 |
| 4992 | CB | MET | 87 | 38.082 | −42.962 | −50.109 | 1 | 26.12 |
| 4993 | CG | MET | 87 | 38.706 | −42.298 | −48.906 | 1 | 30.19 |
| 4994 | SD | MET | 87 | 38.295 | −43.228 | −47.427 | 1 | 30.32 |
| 4995 | CE | MET | 87 | 36.523 | −42.983 | −47.362 | 1 | 31.69 |
| 4996 | C | MET | 87 | 39.937 | −42.744 | −51.766 | 1 | 25.29 |
| 4997 | O | MET | 87 | 40.315 | −43.914 | −51.7 | 1 | 26.02 |
| 4998 | N | GLU | 88 | 40.734 | −41.74 | −52.118 | 1 | 24.57 |
| 4999 | CA | GLU | 88 | 42.143 | −41.945 | −52.43 | 1 | 23.76 |
| 5000 | CB | GLU | 88 | 42.389 | −41.809 | −53.934 | 1 | 26.24 |
| 5001 | CG | GLU | 88 | 41.762 | −42.918 | −54.769 | 1 | 30.58 |
| 5002 | CD | GLU | 88 | 42.147 | −44.307 | −54.283 | 1 | 32.28 |
| 5003 | OE1 | GLU | 88 | 43.349 | −44.545 | −54.04 | 1 | 33.95 |
| 5004 | OE2 | GLU | 88 | 41.247 | −45.164 | −54.149 | 1 | 35.09 |
| 5005 | C | GLU | 88 | 42.98 | −40.926 | −51.67 | 1 | 22.57 |
| 5006 | O | GLU | 88 | 42.561 | −39.788 | −51.462 | 1 | 20.53 |
| 5007 | N | PRO | 89 | 44.185 | −41.323 | −51.248 | 1 | 22.02 |
| 5008 | CD | PRO | 89 | 44.838 | −42.626 | −51.469 | 1 | 22.48 |
| 5009 | CA | PRO | 89 | 45.062 | −40.419 | −50.501 | 1 | 21.6 |
| 5010 | CB | PRO | 89 | 46.202 | −41.337 | −50.067 | 1 | 22.47 |
| 5011 | CG | PRO | 89 | 46.293 | −42.302 | −51.205 | 1 | 23.26 |
| 5012 | C | PRO | 89 | 45.573 | −39.206 | −51.265 | 1 | 21.73 |
| 5013 | O | PRO | 89 | 45.752 | −39.249 | −52.482 | 1 | 23.2 |
| 5014 | N | PHE | 90 | 45.781 | −38.114 | −50.536 | 1 | 21.43 |
| 5015 | CA | PHE | 90 | 46.335 | −36.894 | −51.105 | 1 | 21.6 |
| 5016 | CB | PHE | 90 | 45.251 | −35.945 | −51.655 | 1 | 21.23 |
| 5017 | CG | PHE | 90 | 44.169 | −35.58 | −50.671 | 1 | 21.02 |
| 5018 | CD1 | PHE | 90 | 42.951 | −36.254 | −50.678 | 1 | 20.27 |
| 5019 | CD2 | PHE | 90 | 44.342 | −34.521 | −49.781 | 1 | 21.32 |
| 5020 | CE1 | PHE | 90 | 41.916 | −35.877 | −49.818 | 1 | 21.69 |
| 5021 | CE2 | PHE | 90 | 43.315 | −34.138 | −48.917 | 1 | 19.8 |
| 5022 | CZ | PHE | 90 | 42.1 | −34.816 | −48.937 | 1 | 21.2 |
| 5023 | C | PHE | 90 | 47.167 | −36.209 | −50.029 | 1 | 21.93 |
| 5024 | O | PHE | 90 | 46.875 | −36.321 | −48.838 | 1 | 19.91 |
| 5025 | N | PRO | 91 | 48.232 | −35.505 | −50.436 | 1 | 23.18 |
| 5026 | CD | PRO | 91 | 48.684 | −35.283 | −51.821 | 1 | 24.21 |
| 5027 | CA | PRO | 91 | 49.109 | −34.812 | −49.49 | 1 | 22.8 |
| 5028 | CB | PRO | 91 | 50.322 | −34.472 | −50.346 | 1 | 24.32 |
| 5029 | CG | PRO | 91 | 49.694 | −34.155 | −51.658 | 1 | 23.42 |
| 5030 | C | PRO | 91 | 48.49 | −33.575 | −48.855 | 1 | 22.2 |
| 5031 | O | PRO | 91 | 47.488 | −33.039 | −49.336 | 1 | 20.76 |
| 5032 | N | LEU | 92 | 49.106 | −33.127 | −47.768 | 1 | 21.79 |
| 5033 | CA | LEU | 92 | 48.647 | −31.949 | −47.052 | 1 | 21.76 |
| 5034 | CB | LEU | 92 | 49.544 | −31.682 | −45.842 | 1 | 22.18 |
| 5035 | CG | LEU | 92 | 49.339 | −30.328 | −45.154 | 1 | 23.11 |
| 5036 | CD1 | LEU | 92 | 47.954 | −30.284 | −44.516 | 1 | 23.17 |
| 5037 | CD2 | LEU | 92 | 50.417 | −30.116 | −44.103 | 1 | 23.99 |
| 5038 | C | LEU | 92 | 48.646 | −30.712 | −47.936 | 1 | 22.57 |
| 5039 | O | LEU | 92 | 49.617 | −30.435 | −48.646 | 1 | 22.7 |
| 5040 | N | ARG | 93 | 47.541 | −29.978 | −47.894 | 1 | 21.51 |
| 5041 | CA | ARG | 93 | 47.407 | −28.734 | −48.637 | 1 | 22.6 |
| 5042 | CB | ARG | 93 | 46.541 | −28.905 | −49.889 | 1 | 23.21 |
| 5043 | CG | ARG | 93 | 47.244 | −29.514 | −51.097 | 1 | 27.61 |
| 5044 | CD | ARG | 93 | 46.45 | −29.205 | −52.365 | 1 | 29.95 |
| 5045 | NE | ARG | 93 | 47.044 | −29.758 | −53.581 | 1 | 32.35 |
| 5046 | CZ | ARG | 93 | 47.106 | −31.056 | −53.863 | 1 | 35.21 |
| 5047 | NH1 | ARG | 93 | 46.612 | −31.948 | −53.015 | 1 | 36.59 |
| 5048 | NH2 | ARG | 93 | 47.654 | −31.463 | −55.001 | 1 | 36.65 |
| 5049 | C | ARG | 93 | 46.746 | −27.723 | −47.713 | 1 | 22.23 |
| 5050 | O | ARG | 93 | 45.769 | −28.041 | −47.036 | 1 | 21.3 |
| 5051 | N | VAL | 94 | 47.296 | −26.516 | −47.669 | 1 | 20.69 |
| 5052 | CA | VAL | 94 | 46.736 | −25.456 | −46.843 | 1 | 20.29 |
| 5053 | CB | VAL | 94 | 47.759 | −24.938 | −45.808 | 1 | 20.46 |
| 5054 | CG1 | VAL | 94 | 47.185 | −23.737 | −45.061 | 1 | 20.72 |
| 5055 | CG2 | VAL | 94 | 48.107 | −26.048 | −44.83 | 1 | 21.08 |
| 5056 | C | VAL | 94 | 46.329 | −24.314 | −47.763 | 1 | 21.34 |
| 5057 | O | VAL | 94 | 47.142 | −23.811 | −48.545 | 1 | 22.03 |
| 5058 | N | PHE | 95 | 45.063 | −23.917 | −47.682 | 1 | 20.06 |
| 5059 | CA | PHE | 95 | 44.56 | −22.836 | −48.514 | 1 | 18.67 |
| 5060 | CB | PHE | 95 | 43.342 | −23.287 | −49.324 | 1 | 19.07 |
| 5061 | CG | PHE | 95 | 43.67 | −24.223 | −50.452 | 1 | 19.31 |
| 5062 | CD1 | PHE | 95 | 43.841 | −25.582 | −50.22 | 1 | 19.43 |
| 5063 | CD2 | PHE | 95 | 43.802 | −23.741 | −51.751 | 1 | 20.62 |
| 5064 | CE1 | PHE | 95 | 44.136 | −26.454 | −51.268 | 1 | 20.7 |
| 5065 | CE2 | PHE | 95 | 44.098 | −24.603 | −52.806 | 1 | 20.46 |
| 5066 | CZ | PHE | 95 | 44.264 | −25.959 | −52.566 | 1 | 20.95 |
| 5067 | C | PHE | 95 | 44.179 | −21.604 | −47.711 | 1 | 20.4 |
| 5068 | O | PHE | 95 | 43.549 | −21.699 | −46.653 | 1 | 19.31 |
| 5069 | N | VAL | 96 | 44.57 | −20.451 | −48.238 | 1 | 18.75 |
| 5070 | CA | VAL | 96 | 44.277 | −19.159 | −47.639 | 1 | 19.06 |
| 5071 | CB | VAL | 96 | 45.571 | −18.359 | −47.358 | 1 | 19.34 |
| 5072 | CG1 | VAL | 96 | 45.225 | −16.974 | −46.83 | 1 | 20.06 |
| 5073 | CG2 | VAL | 96 | 46.435 | −19.107 | −46.352 | 1 | 19.68 |
| 5074 | C | VAL | 96 | 43.426 | −18.408 | −48.658 | 1 | 18.23 |
| 5075 | O | VAL | 96 | 43.721 | −18.435 | −49.857 | 1 | 18.24 |
| 5076 | N | ASN | 97 | 42.368 | −17.76 | −48.181 | 1 | 17.83 |
| 5077 | CA | ASN | 97 | 41.449 | −17.009 | −49.035 | 1 | 18.77 |
| 5078 | CB | ASN | 97 | 42.075 | −15.668 | −49.435 | 1 | 20.03 |
| 5079 | CG | ASN | 97 | 42.447 | −14.822 | −48.234 | 1 | 21.44 |
| 5080 | OD1 | ASN | 97 | 41.878 | −14.981 | −47.154 | 1 | 20.62 |
| 5081 | ND2 | ASN | 97 | 43.397 | −13.908 | −48.416 | 1 | 21.53 |
| 5082 | C | ASN | 97 | 41.043 | −17.788 | −50.289 | 1 | 19.07 |
| 5083 | O | ASN | 97 | 41.093 | −17.264 | −51.405 | 1 | 19.96 |
| 5084 | N | PRO | 98 | 40.606 | −19.046 | −50.119 | 1 | 18.1 |
| 5085 | CD | PRO | 98 | 40.516 | −19.816 | −48.864 | 1 | 19.39 |
| 5086 | CA | PRO | 98 | 40.201 | −19.869 | −51.261 | 1 | 18.36 |
| 5087 | CB | PRO | 98 | 40.25 | −21.279 | −50.691 | 1 | 18.79 |
| 5088 | CG | PRO | 98 | 39.756 | −21.061 | −49.293 | 1 | 18.4 |
| 5089 | C | PRO | 98 | 38.833 | −19.554 | −51.86 | 1 | 19 |
| 5090 | O | PRO | 98 | 37.968 | −18.962 | −51.213 | 1 | 18.65 |
| 5091 | N | SER | 99 | 38.66 | −19.957 | −53.114 | 1 | 19.33 |
| 5092 | CA | SER | 99 | 37.405 | −19.786 | −53.833 | 1 | 19.89 |
| 5093 | CB | SER | 99 | 37.541 | −18.717 | −54.922 | 1 | 20.68 |
| 5094 | OG | SER | 99 | 38.603 | −19.017 | −55.806 | 1 | 26.15 |
| 5095 | C | SER | 99 | 37.112 | −21.151 | −54.447 | 1 | 18.83 |
| 5096 | O | SER | 99 | 38.035 | −21.909 | −54.756 | 1 | 19.02 |
| 5097 | N | LEU | 100 | 35.837 | −21.474 | −54.62 | 1 | 18.22 |
| 5098 | CA | LEU | 100 | 35.481 | −22.774 | −55.162 | 1 | 19.04 |
| 5099 | CB | LEU | 100 | 34.81 | −23.62 | −54.073 | 1 | 20.23 |
| 5100 | CG | LEU | 100 | 34.366 | −25.052 | −54.408 | 1 | 20.94 |
| 5101 | CD1 | LEU | 100 | 34.172 | −25.831 | −53.119 | 1 | 24.27 |
| 5102 | CD2 | LEU | 100 | 33.073 | −25.041 | −55.219 | 1 | 24.73 |
| 5103 | C | LEU | 100 | 34.577 | −22.706 | −56.38 | 1 | 19.72 |
| 5104 | O | LEU | 100 | 33.672 | −21.873 | −56.456 | 1 | 20.21 |
| 5105 | N | ARG | 101 | 34.833 | −23.6 | −57.329 | 1 | 19.13 |
| 5106 | CA | ARG | 101 | 34.028 | −23.69 | −58.538 | 1 | 19.78 |
| 5107 | CB | ARG | 101 | 34.773 | −23.102 | −59.735 | 1 | 21.76 |
| 5108 | CG | ARG | 101 | 34.919 | −21.594 | −59.648 | 1 | 25.31 |
| 5109 | CD | ARG | 101 | 35.322 | −20.99 | −60.97 | 1 | 28.97 |
| 5110 | NE | ARG | 101 | 35.421 | −19.536 | −60.89 | 1 | 30.87 |
| 5111 | CZ | ARG | 101 | 35.743 | −18.757 | −61.916 | 1 | 32.64 |
| 5112 | NH1 | ARG | 101 | 35.998 | −19.291 | −63.101 | 1 | 32.47 |
| 5113 | NH2 | ARG | 101 | 35.814 | −17.439 | −61.756 | 1 | 34.8 |
| 5114 | C | ARG | 101 | 33.709 | −25.155 | −58.78 | 1 | 17.93 |
| 5115 | O | ARG | 101 | 34.578 | −26.015 | −58.656 | 1 | 19.46 |
| 5116 | N | VAL | 102 | 32.453 | −25.433 | −59.104 | 1 | 18.42 |

TABLE 1-continued

| Atom | Atom Type | Residue | # | X | Y | Z | OCC | B |
|---|---|---|---|---|---|---|---|---|
| 5117 | CA | VAL | 102 | 32.015 | −26.797 | −59.354 | 1 | 18.29 |
| 5118 | CB | VAL | 102 | 30.483 | −26.915 | −59.224 | 1 | 18.63 |
| 5119 | CG1 | VAL | 102 | 30.039 | −28.344 | −59.499 | 1 | 19.05 |
| 5120 | CG2 | VAL | 102 | 30.052 | −26.478 | −57.834 | 1 | 19.03 |
| 5121 | C | VAL | 102 | 32.431 | −27.234 | −60.752 | 1 | 19.68 |
| 5122 | O | VAL | 102 | 32.164 | −26.536 | −61.732 | 1 | 20.39 |
| 5123 | N | LEU | 103 | 33.093 | −28.384 | −60.836 | 1 | 17.29 |
| 5124 | CA | LEU | 103 | 33.544 | −28.921 | −62.119 | 1 | 18.84 |
| 5125 | CB | LEU | 103 | 34.94 | −29.528 | −61.978 | 1 | 18.79 |
| 5126 | CG | LEU | 103 | 36.057 | −28.562 | −61.575 | 1 | 20.11 |
| 5127 | CD1 | LEU | 103 | 37.36 | −29.329 | −61.423 | 1 | 22.01 |
| 5128 | CD2 | LEU | 103 | 36.202 | −27.465 | −62.624 | 1 | 21.43 |
| 5129 | C | LEU | 103 | 32.57 | −29.977 | −62.631 | 1 | 19.24 |
| 5130 | O | LEU | 103 | 32.319 | −30.074 | −63.834 | 1 | 21.11 |
| 5131 | N | ASP | 104 | 32.034 | −30.774 | −61.712 | 1 | 17.82 |
| 5132 | CA | ASP | 104 | 31.067 | −31.817 | −62.05 | 1 | 18.63 |
| 5133 | CB | ASP | 104 | 31.693 | −33.208 | −61.926 | 1 | 18.88 |
| 5134 | CG | ASP | 104 | 30.815 | −34.302 | −62.522 | 1 | 20.53 |
| 5135 | OD1 | ASP | 104 | 29.573 | −34.204 | −62.429 | 1 | 20.97 |
| 5136 | OD2 | ASP | 104 | 31.371 | −35.272 | −63.074 | 1 | 24.64 |
| 5137 | C | ASP | 104 | 29.941 | −31.669 | −61.039 | 1 | 18.28 |
| 5138 | O | ASP | 104 | 30.107 | −31.993 | −59.858 | 1 | 17.65 |
| 5139 | N | SER | 105 | 28.796 | −31.178 | −61.505 | 1 | 18.55 |
| 5140 | CA | SER | 105 | 27.647 | −30.941 | −60.643 | 1 | 17.89 |
| 5141 | CB | SER | 105 | 26.725 | −29.898 | −61.284 | 1 | 19.42 |
| 5142 | OG | SER | 105 | 26.308 | −30.31 | −62.571 | 1 | 20.15 |
| 5143 | C | SER | 105 | 26.831 | −32.168 | −60.245 | 1 | 18.61 |
| 5144 | O | SER | 105 | 25.848 | −32.044 | −59.513 | 1 | 18.96 |
| 5145 | N | ARG | 106 | 27.219 | −33.346 | −60.725 | 1 | 18.57 |
| 5146 | CA | ARG | 106 | 26.505 | −34.567 | −60.356 | 1 | 18.29 |
| 5147 | CB | ARG | 106 | 27.153 | −35.793 | −61.005 | 1 | 19.34 |
| 5148 | CG | ARG | 106 | 26.547 | −37.13 | −60.586 | 1 | 24.15 |
| 5149 | CD | ARG | 106 | 25.086 | −37.261 | −61.011 | 1 | 26.57 |
| 5150 | NE | ARG | 106 | 24.521 | −38.567 | −60.669 | 1 | 28.8 |
| 5151 | CZ | ARG | 106 | 24.83 | −39.707 | −61.282 | 1 | 29.66 |
| 5152 | NH1 | ARG | 106 | 25.701 | −39.713 | −62.282 | 1 | 31.77 |
| 5153 | NH2 | ARG | 106 | 24.272 | −40.846 | −60.89 | 1 | 30.33 |
| 5154 | C | ARG | 106 | 26.593 | −34.687 | −58.838 | 1 | 17.86 |
| 5155 | O | ARG | 106 | 27.657 | −34.476 | −58.258 | 1 | 18.73 |
| 5156 | N | LEU | 107 | 25.476 | −35.016 | −58.2 | 1 | 17.24 |
| 5157 | CA | LEU | 107 | 25.447 | −35.144 | −56.746 | 1 | 17.77 |
| 5158 | CB | LEU | 107 | 24.105 | −34.646 | −56.2 | 1 | 17.86 |
| 5159 | CG | LEU | 107 | 23.8 | −33.164 | −56.428 | 1 | 19.31 |
| 5160 | CD1 | LEU | 107 | 22.403 | −32.845 | −55.923 | 1 | 21.08 |
| 5161 | CD2 | LEU | 107 | 24.833 | −32.307 | −55.716 | 1 | 20.67 |
| 5162 | C | LEU | 107 | 25.69 | −36.57 | −56.272 | 1 | 17.95 |
| 5163 | O | LEU | 107 | 25.164 | −37.529 | −56.839 | 1 | 17.9 |
| 5164 | N | VAL | 108 | 26.509 | −36.697 | −55.234 | 1 | 17.18 |
| 5165 | CA | VAL | 108 | 26.821 | −37.992 | −54.648 | 1 | 18.38 |
| 5166 | CB | VAL | 108 | 28.308 | −38.374 | −54.869 | 1 | 20.25 |
| 5167 | CG1 | VAL | 108 | 29.221 | −37.31 | −54.301 | 1 | 24.09 |
| 5168 | CG2 | VAL | 108 | 28.595 | −39.714 | −54.231 | 1 | 22.18 |
| 5169 | C | VAL | 108 | 26.518 | −37.861 | −53.161 | 1 | 16.32 |
| 5170 | O | VAL | 108 | 26.89 | −36.87 | −52.532 | 1 | 15.41 |
| 5171 | N | THR | 109 | 25.825 | −38.852 | −52.612 | 1 | 16.59 |
| 5172 | CA | THR | 109 | 25.44 | −38.827 | −51.205 | 1 | 15.6 |
| 5173 | CB | THR | 109 | 23.904 | −38.93 | −51.06 | 1 | 18.09 |
| 5174 | OG1 | THR | 109 | 23.288 | −37.825 | −51.733 | 1 | 17.63 |
| 5175 | CG2 | THR | 109 | 23.497 | −38.915 | −49.589 | 1 | 18.62 |
| 5176 | C | THR | 109 | 26.075 | −39.93 | −50.372 | 1 | 15.32 |
| 5177 | O | THR | 109 | 25.99 | −41.109 | −50.713 | 1 | 15.95 |
| 5178 | N | PHE | 110 | 26.702 | −39.522 | −49.27 | 1 | 14.9 |
| 5179 | CA | PHE | 110 | 27.352 | −40.432 | −48.332 | 1 | 15.1 |
| 5180 | CB | PHE | 110 | 28.828 | −40.629 | −48.686 | 1 | 16.22 |
| 5181 | CG | PHE | 110 | 29.059 | −41.526 | −49.864 | 1 | 18.21 |
| 5182 | CD1 | PHE | 110 | 28.7 | −42.872 | −49.813 | 1 | 19.02 |
| 5183 | CD2 | PHE | 110 | 29.634 | −41.026 | −51.028 | 1 | 18.81 |
| 5184 | CE1 | PHE | 110 | 28.91 | −43.709 | −50.91 | 1 | 18.98 |
| 5185 | CE2 | PHE | 110 | 29.848 | −41.854 | −52.128 | 1 | 19.54 |
| 5186 | CZ | PHE | 110 | 29.484 | −43.198 | −52.067 | 1 | 19.74 |
| 5187 | C | PHE | 110 | 27.279 | −39.823 | −46.939 | 1 | 14.82 |
| 5188 | O | PHE | 110 | 27.07 | −38.616 | −46.795 | 1 | 14.23 |
| 5189 | N | PRO | 111 | 27.441 | −40.653 | −45.895 | 1 | 16.82 |
| 5190 | CD | PRO | 111 | 27.426 | −42.126 | −45.906 | 1 | 17.45 |
| 5191 | CA | PRO | 111 | 27.397 | −40.148 | −44.522 | 1 | 16.92 |
| 5192 | CB | PRO | 111 | 27.471 | −41.417 | −43.678 | 1 | 17.49 |
| 5193 | CG | PRO | 111 | 26.829 | −42.443 | −44.553 | 1 | 19.06 |
| 5194 | C | PRO | 111 | 28.597 | −39.238 | −44.289 | 1 | 16.73 |
| 5195 | O | PRO | 111 | 29.718 | −39.528 | −44.73 | 1 | 15.71 |
| 5196 | N | GLU | 112 | 28.356 | −38.147 | −43.577 | 1 | 15.66 |
| 5197 | CA | GLU | 112 | 29.385 | −37.169 | −43.289 | 1 | 16.56 |
| 5198 | CB | GLU | 112 | 29.14 | −35.933 | −44.143 | 1 | 20.98 |
| 5199 | CG | GLU | 112 | 30.308 | −35.46 | −44.951 | 1 | 22.77 |
| 5200 | CD | GLU | 112 | 29.986 | −34.167 | −45.655 | 1 | 19.9 |
| 5201 | OE1 | GLU | 112 | 29.925 | −33.119 | −44.976 | 1 | 19.83 |
| 5202 | OE2 | GLU | 112 | 29.776 | −34.203 | −46.881 | 1 | 17.1 |
| 5203 | C | GLU | 112 | 29.29 | −36.771 | −41.824 | 1 | 16.3 |
| 5204 | O | GLU | 112 | 28.204 | −36.77 | −41.25 | 1 | 16.5 |
| 5205 | N | GLY | 113 | 30.428 | −36.424 | −41.234 | 1 | 15.17 |
| 5206 | CA | GLY | 113 | 30.45 | −35.989 | −39.849 | 1 | 15.65 |
| 5207 | C | GLY | 113 | 31.148 | −34.643 | −39.775 | 1 | 13.9 |
| 5208 | O | GLY | 113 | 31.574 | −34.111 | −40.797 | 1 | 14.02 |
| 5209 | N | CYS | 114 | 31.264 | −34.086 | −38.575 | 1 | 12.71 |
| 5210 | CA | CYS | 114 | 31.927 | −32.799 | −38.403 | 1 | 12.01 |
| 5211 | CB | CYS | 114 | 30.936 | −31.648 | −38.632 | 1 | 13.54 |
| 5212 | SG | CYS | 114 | 31.647 | −29.993 | −38.451 | 1 | 13.95 |
| 5213 | C | CYS | 114 | 32.503 | −32.707 | −36.995 | 1 | 11.59 |
| 5214 | O | CYS | 114 | 31.808 | −32.977 | −36.014 | 1 | 12.04 |
| 5215 | N | GLU | 115 | 33.778 | −32.342 | −36.901 | 1 | 12.59 |
| 5216 | CA | GLU | 115 | 34.437 | −32.211 | −35.605 | 1 | 12.45 |
| 5217 | CB | GLU | 115 | 35.901 | −31.802 | −35.786 | 1 | 14.88 |
| 5218 | CG | GLU | 115 | 36.823 | −32.92 | −36.249 | 1 | 18.43 |
| 5219 | CD | GLU | 115 | 36.972 | −34.021 | −35.214 | 1 | 21.54 |
| 5220 | OE1 | GLU | 115 | 37.254 | −33.7 | −34.04 | 1 | 23.22 |
| 5221 | OE2 | GLU | 115 | 36.818 | −35.207 | −35.573 | 1 | 24.7 |
| 5222 | C | GLU | 115 | 33.731 | −31.181 | −34.73 | 1 | 12.6 |
| 5223 | O | GLU | 115 | 33.837 | −31.233 | −33.502 | 1 | 11.89 |
| 5224 | N | SER | 116 | 33.017 | −30.247 | −35.363 | 1 | 11.71 |
| 5225 | CA | SER | 116 | 32.291 | −29.201 | −34.643 | 1 | 12.11 |
| 5226 | CB | SER | 116 | 32.275 | −27.905 | −35.465 | 1 | 12.33 |
| 5227 | OG | SER | 116 | 33.568 | −27.321 | −35.515 | 1 | 12.91 |
| 5228 | C | SER | 116 | 30.86 | −29.593 | −34.26 | 1 | 12.88 |
| 5229 | O | SER | 116 | 30.116 | −28.784 | −33.707 | 1 | 13.23 |
| 5230 | N | VAL | 117 | 30.473 | −30.825 | −34.585 | 1 | 13.62 |
| 5231 | CA | VAL | 117 | 29.16 | −31.37 | −34.233 | 1 | 14.31 |
| 5232 | CB | VAL | 117 | 28.178 | −31.389 | −35.43 | 1 | 15 |
| 5233 | CG1 | VAL | 117 | 26.78 | −31.769 | −34.943 | 1 | 15.11 |
| 5234 | CG2 | VAL | 117 | 28.145 | −30.022 | −36.105 | 1 | 14.96 |
| 5235 | C | VAL | 117 | 29.511 | −32.799 | −33.833 | 1 | 14.92 |
| 5236 | O | VAL | 117 | 29.028 | −33.778 | −34.407 | 1 | 13.76 |
| 5237 | N | ALA | 118 | 30.386 | −32.886 | −32.837 | 1 | 15.84 |
| 5238 | CA | ALA | 118 | 30.913 | −34.148 | −32.333 | 1 | 17.01 |
| 5239 | CB | ALA | 118 | 31.765 | −33.877 | −31.085 | 1 | 19.03 |
| 5240 | C | ALA | 118 | 29.925 | −35.268 | −32.039 | 1 | 16.71 |
| 5241 | O | ALA | 118 | 28.917 | −35.066 | −31.362 | 1 | 17.28 |
| 5242 | N | GLY | 119 | 30.236 | −36.451 | −32.568 | 1 | 16.64 |
| 5243 | CA | GLY | 119 | 29.427 | −37.633 | −32.321 | 1 | 16.36 |
| 5244 | C | GLY | 119 | 28.241 | −37.932 | −33.207 | 1 | 15.39 |
| 5245 | O | GLY | 119 | 27.476 | −38.849 | −32.908 | 1 | 14.83 |
| 5246 | N | PHE | 120 | 28.087 | −37.192 | −34.299 | 1 | 15.89 |
| 5247 | CA | PHE | 120 | 26.952 | −37.407 | −35.192 | 1 | 16.45 |
| 5248 | CB | PHE | 120 | 25.971 | −36.238 | −35.071 | 1 | 15.91 |
| 5249 | CG | PHE | 120 | 25.334 | −36.119 | −33.718 | 1 | 16.99 |
| 5250 | CD1 | PHE | 120 | 24.227 | −36.893 | −33.385 | 1 | 15.73 |
| 5251 | CD2 | PHE | 120 | 25.848 | −35.241 | −32.769 | 1 | 19.18 |
| 5252 | CE1 | PHE | 120 | 23.639 | −36.794 | −32.126 | 1 | 18.27 |
| 5253 | CE2 | PHE | 120 | 25.268 | −35.135 | −31.506 | 1 | 21.46 |
| 5254 | CZ | PHE | 120 | 24.16 | −35.913 | −31.185 | 1 | 21.13 |
| 5255 | C | PHE | 120 | 27.358 | −37.548 | −36.648 | 1 | 16.45 |
| 5256 | O | PHE | 120 | 28.409 | −37.072 | −37.066 | 1 | 17.83 |
| 5257 | N | LEU | 121 | 26.504 | −38.225 | −37.412 | 1 | 14.64 |
| 5258 | CA | LEU | 121 | 26.715 | −38.432 | −38.839 | 1 | 15.43 |
| 5259 | CB | LEU | 121 | 27.227 | −39.845 | −39.124 | 1 | 17.84 |
| 5260 | CG | LEU | 121 | 28.647 | −40.242 | −38.728 | 1 | 20.91 |
| 5261 | CD1 | LEU | 121 | 28.82 | −41.734 | −38.962 | 1 | 22.07 |
| 5262 | CD2 | LEU | 121 | 29.657 | −39.457 | −39.551 | 1 | 22.41 |
| 5263 | C | LEU | 121 | 25.376 | −38.268 | −39.539 | 1 | 15.23 |
| 5264 | O | LEU | 121 | 24.325 | −38.466 | −38.936 | 1 | 13.47 |
| 5265 | N | ALA | 122 | 25.422 | −37.905 | −40.814 | 1 | 14.26 |
| 5266 | CA | ALA | 122 | 24.214 | −37.764 | −41.607 | 1 | 14.55 |
| 5267 | CB | ALA | 122 | 23.498 | −36.455 | −41.284 | 1 | 13.85 |
| 5268 | C | ALA | 122 | 24.622 | −37.785 | −43.066 | 1 | 14.18 |

TABLE 1-continued

| Atom | Atom Type | Residue | # | X | Y | Z | OCC | B |
|---|---|---|---|---|---|---|---|---|
| 5269 | O | ALA | 122 | 25.732 | −37.376 | −43.415 | 1 | 14.24 |
| 5270 | N | CYS | 123 | 23.734 | −38.281 | −43.915 | 1 | 14.81 |
| 5271 | CA | CYS | 123 | 24.019 | −38.321 | −45.34 | 1 | 15.65 |
| 5272 | CB | CYS | 123 | 23.026 | −39.224 | −46.062 | 1 | 16.71 |
| 5273 | SG | CYS | 123 | 23.334 | −40.958 | −45.761 | 1 | 22.39 |
| 5274 | C | CYS | 123 | 23.924 | −36.911 | −45.893 | 1 | 15.84 |
| 5275 | O | CYS | 123 | 22.981 | −36.175 | −45.586 | 1 | 15.2 |
| 5276 | N | VAL | 124 | 24.908 | −36.539 | −46.703 | 1 | 14.7 |
| 5277 | CA | VAL | 124 | 24.946 | −35.21 | −47.295 | 1 | 14.74 |
| 5278 | CB | VAL | 124 | 26.009 | −34.313 | −46.62 | 1 | 15.27 |
| 5279 | CG1 | VAL | 124 | 26.004 | −32.929 | −47.264 | 1 | 16.03 |
| 5280 | CG2 | VAL | 124 | 25.739 | −34.206 | −45.124 | 1 | 13.93 |
| 5281 | C | VAL | 124 | 25.291 | −35.277 | −48.774 | 1 | 14.6 |
| 5282 | O | VAL | 124 | 26.276 | −35.903 | −49.162 | 1 | 14.24 |
| 5283 | N | PRO | 125 | 24.47 | −34.643 | −49.624 | 1 | 15.17 |
| 5284 | CD | PRO | 125 | 23.153 | −34.045 | −49.343 | 1 | 16.23 |
| 5285 | CA | PRO | 125 | 24.749 | −34.655 | −51.061 | 1 | 14.97 |
| 5286 | CB | PRO | 125 | 23.416 | −34.233 | −51.676 | 1 | 15.24 |
| 5287 | CG | PRO | 125 | 22.839 | −33.328 | −50.64 | 1 | 19.63 |
| 5288 | C | PRO | 125 | 25.876 | −33.668 | −51.358 | 1 | 14.77 |
| 5289 | O | PRO | 125 | 25.883 | −32.55 | −50.834 | 1 | 14.8 |
| 5290 | N | ARG | 126 | 26.831 | −34.087 | −52.185 | 1 | 13.51 |
| 5291 | CA | ARG | 126 | 27.966 | −33.24 | −52.542 | 1 | 13.65 |
| 5292 | CB | ARG | 126 | 29.217 | −33.675 | −51.776 | 1 | 14.53 |
| 5293 | CG | ARG | 126 | 29.129 | −33.531 | −50.267 | 1 | 15.05 |
| 5294 | CD | ARG | 126 | 29.097 | −32.069 | −49.852 | 1 | 14.54 |
| 5295 | NE | ARG | 126 | 29.255 | −31.919 | −48.406 | 1 | 15.2 |
| 5296 | CZ | ARG | 126 | 29.224 | −30.756 | −47.763 | 1 | 16.03 |
| 5297 | NH1 | ARG | 126 | 29.038 | −29.625 | −48.433 | 1 | 13.84 |
| 5298 | NH2 | ARG | 126 | 29.384 | −30.725 | −46.444 | 1 | 15.48 |
| 5299 | C | ARG | 126 | 28.258 | −33.342 | −54.03 | 1 | 13.81 |
| 5300 | O | ARG | 126 | 27.952 | −34.352 | −54.657 | 1 | 14.15 |
| 5301 | N | PHE | 127 | 28.861 | −32.299 | −54.589 | 1 | 14.33 |
| 5302 | CA | PHE | 127 | 29.208 | −32.315 | −56.006 | 1 | 14.96 |
| 5303 | CB | PHE | 127 | 29.666 | −30.93 | −56.465 | 1 | 15.08 |
| 5304 | CG | PHE | 127 | 28.599 | −29.881 | −56.369 | 1 | 16.73 |
| 5305 | CD1 | PHE | 127 | 28.753 | −28.788 | −55.521 | 1 | 17.54 |
| 5306 | CD2 | PHE | 127 | 27.436 | −29.984 | −57.128 | 1 | 18.21 |
| 5307 | CE1 | PHE | 127 | 27.764 | −27.809 | −55.43 | 1 | 19.45 |
| 5308 | CE2 | PHE | 127 | 26.442 | −29.013 | −57.045 | 1 | 19.22 |
| 5309 | CZ | PHE | 127 | 26.607 | −27.923 | −56.193 | 1 | 19.96 |
| 5310 | C | PHE | 127 | 30.33 | −33.327 | −56.225 | 1 | 15.47 |
| 5311 | O | PHE | 127 | 31.211 | −33.484 | −55.38 | 1 | 16.18 |
| 5312 | N | GLN | 128 | 30.288 | −34.006 | −57.365 | 1 | 14.59 |
| 5313 | CA | GLN | 128 | 31.283 | −35.016 | −57.711 | 1 | 15.27 |
| 5314 | CB | GLN | 128 | 30.865 | −35.709 | −59.012 | 1 | 16.11 |
| 5315 | CG | GLN | 128 | 31.914 | −36.612 | −59.646 | 1 | 17.79 |
| 5316 | CD | GLN | 128 | 32.378 | −37.722 | −58.731 | 1 | 19.23 |
| 5317 | OE1 | GLN | 128 | 31.598 | −38.27 | −57.95 | 1 | 22.05 |
| 5318 | NE2 | GLN | 128 | 33.653 | −38.078 | −58.837 | 1 | 21.27 |
| 5319 | C | GLN | 128 | 32.698 | −34.467 | −57.853 | 1 | 14.42 |
| 5320 | O | GLN | 128 | 33.662 | −35.122 | −57.462 | 1 | 16.02 |
| 5321 | N | ALA | 129 | 32.829 | −33.273 | −58.421 | 1 | 14.46 |
| 5322 | CA | ALA | 129 | 34.15 | −32.684 | −58.61 | 1 | 14.55 |
| 5323 | CB | ALA | 129 | 34.708 | −33.083 | −59.985 | 1 | 14.84 |
| 5324 | C | ALA | 129 | 34.111 | −31.172 | −58.48 | 1 | 15.28 |
| 5325 | O | ALA | 129 | 33.173 | −30.519 | −58.934 | 1 | 15.17 |
| 5326 | N | VAL | 130 | 35.138 | −30.618 | −57.847 | 1 | 15.95 |
| 5327 | CA | VAL | 130 | 35.222 | −29.181 | −57.649 | 1 | 15.82 |
| 5328 | CB | VAL | 130 | 34.736 | −28.77 | −56.238 | 1 | 15.78 |
| 5329 | CG1 | VAL | 130 | 33.305 | −29.227 | −56.023 | 1 | 16.92 |
| 5330 | CG2 | VAL | 130 | 35.65 | −29.373 | −55.175 | 1 | 16.52 |
| 5331 | C | VAL | 130 | 36.657 | −28.715 | −57.795 | 1 | 15.72 |
| 5332 | O | VAL | 130 | 37.597 | −29.512 | −57.739 | 1 | 16.4 |
| 5333 | N | GLN | 131 | 36.818 | −27.414 | −57.984 | 1 | 16.37 |
| 5334 | CA | GLN | 131 | 38.139 | −26.834 | −58.102 | 1 | 17.51 |
| 5335 | CB | GLN | 131 | 38.306 | −26.133 | −59.447 | 1 | 18.76 |
| 5336 | CG | GLN | 131 | 39.666 | −25.478 | −59.609 | 1 | 21.3 |
| 5337 | CD | GLN | 131 | 39.756 | −24.641 | −60.863 | 1 | 23.66 |
| 5338 | OE1 | GLN | 131 | 39.35 | −23.476 | −60.882 | 1 | 28.16 |
| 5339 | NE2 | GLN | 131 | 40.277 | −25.233 | −61.925 | 1 | 21.76 |
| 5340 | C | GLN | 131 | 38.295 | −25.811 | −56.994 | 1 | 18.17 |
| 5341 | O | GLN | 131 | 37.478 | −24.898 | −56.872 | 1 | 18.98 |
| 5342 | N | ILE | 132 | 39.326 | −25.972 | −56.175 | 1 | 18.01 |
| 5343 | CA | ILE | 132 | 39.578 | −25.014 | −55.112 | 1 | 18.11 |
| 5344 | CB | ILE | 132 | 39.758 | −25.705 | −53.733 | 1 | 17.46 |
| 5345 | CG2 | ILE | 132 | 40.875 | −26.737 | −53.797 | 1 | 16.73 |
| 5346 | CG1 | ILE | 132 | 40.043 | −24.65 | −52.66 | 1 | 17.07 |
| 5347 | CD1 | ILE | 132 | 39.985 | −25.188 | −51.234 | 1 | 15.69 |
| 5348 | C | ILE | 132 | 40.836 | −24.245 | −55.49 | 1 | 18.84 |
| 5349 | O | ILE | 132 | 41.858 | −24.837 | −55.844 | 1 | 18.89 |
| 5350 | N | SER | 133 | 40.74 | −22.921 | −55.444 | 1 | 19.88 |
| 5351 | CA | SER | 133 | 41.86 | −22.055 | −55.785 | 1 | 20.91 |
| 5352 | CB | SER | 133 | 41.559 | −21.268 | −57.064 | 1 | 22.92 |
| 5353 | OG | SER | 133 | 41.331 | −22.134 | −58.159 | 1 | 27.22 |
| 5354 | C | SER | 133 | 42.107 | −21.076 | −54.651 | 1 | 21.67 |
| 5355 | O | SER | 133 | 41.167 | −20.537 | −54.067 | 1 | 21.97 |
| 5356 | N | GLY | 134 | 43.376 | −20.843 | −54.346 | 1 | 21.66 |
| 5357 | CA | GLY | 134 | 43.707 | −19.918 | −53.281 | 1 | 22.78 |
| 5358 | C | GLY | 134 | 45.196 | −19.682 | −53.191 | 1 | 23.67 |
| 5359 | O | GLY | 134 | 45.934 | −19.895 | −54.156 | 1 | 24.15 |
| 5360 | N | LEU | 135 | 45.641 | −19.242 | −52.022 | 1 | 23.84 |
| 5361 | CA | LEU | 135 | 47.052 | −18.97 | −51.795 | 1 | 25.12 |
| 5362 | CB | LEU | 135 | 47.237 | −17.522 | −51.34 | 1 | 25.86 |
| 5363 | CG | LEU | 135 | 46.627 | −16.41 | −52.192 | 1 | 26.62 |
| 5364 | CD1 | LEU | 135 | 46.739 | −15.084 | −51.453 | 1 | 28.59 |
| 5365 | CD2 | LEU | 135 | 47.337 | −16.345 | −53.532 | 1 | 27.1 |
| 5366 | C | LEU | 135 | 47.562 | −19.885 | −50.698 | 1 | 26.1 |
| 5367 | O | LEU | 135 | 46.798 | −20.285 | −49.821 | 1 | 25.06 |
| 5368 | N | ASP | 136 | 48.842 | −20.241 | −50.749 | 1 | 27.37 |
| 5369 | CA | ASP | 136 | 49.396 | −21.053 | −49.681 | 1 | 27.78 |
| 5370 | CB | ASP | 136 | 50.611 | −21.875 | −50.144 | 1 | 29.9 |
| 5371 | CG | ASP | 136 | 51.728 | −21.025 | −50.716 | 1 | 30.71 |
| 5372 | OD1 | ASP | 136 | 51.977 | −19.914 | −50.205 | 1 | 32 |
| 5373 | OD2 | ASP | 136 | 52.376 | −21.489 | −51.676 | 1 | 33.7 |
| 5374 | C | ASP | 136 | 49.788 | −20.009 | −48.639 | 1 | 27.7 |
| 5375 | O | ASP | 136 | 49.72 | −18.809 | −48.913 | 1 | 26.75 |
| 5376 | N | PRO | 137 | 50.184 | −20.436 | −47.432 | 1 | 27.91 |
| 5377 | CD | PRO | 137 | 50.231 | −21.812 | −46.905 | 1 | 27.48 |
| 5378 | CA | PRO | 137 | 50.563 | −19.469 | −46.397 | 1 | 29.05 |
| 5379 | CB | PRO | 137 | 51.071 | −20.361 | −45.27 | 1 | 29.01 |
| 5380 | CG | PRO | 137 | 50.199 | −21.578 | −45.411 | 1 | 29.13 |
| 5381 | C | PRO | 137 | 51.591 | −18.414 | −46.815 | 1 | 30.5 |
| 5382 | O | PRO | 137 | 51.684 | −17.354 | −46.192 | 1 | 30.97 |
| 5383 | N | ASN | 138 | 52.35 | −18.697 | −47.869 | 1 | 31.82 |
| 5384 | CA | ASN | 138 | 53.37 | −17.763 | −48.338 | 1 | 32.92 |
| 5385 | CB | ASN | 138 | 54.619 | −18.529 | −48.773 | 1 | 34.57 |
| 5386 | CG | ASN | 138 | 55.298 | −19.228 | −47.614 | 1 | 36.19 |
| 5387 | OD1 | ASN | 138 | 55.608 | −18.604 | −46.599 | 1 | 38.58 |
| 5388 | ND2 | ASN | 138 | 55.535 | −20.528 | −47.758 | 1 | 37.34 |
| 5389 | C | ASN | 138 | 52.91 | −16.841 | −49.461 | 1 | 33.34 |
| 5390 | O | ASN | 138 | 53.7 | −16.051 | −49.986 | 1 | 34.22 |
| 5391 | N | GLY | 139 | 51.638 | −16.941 | −49.832 | 1 | 31.9 |
| 5392 | CA | GLY | 139 | 51.109 | −16.082 | −50.877 | 1 | 30.52 |
| 5393 | C | GLY | 139 | 51.2 | −16.621 | −52.291 | 1 | 29.68 |
| 5394 | O | GLY | 139 | 50.829 | −15.932 | −53.239 | 1 | 29.12 |
| 5395 | N | GLU | 140 | 51.694 | −17.844 | −52.445 | 1 | 29.99 |
| 5396 | CA | GLU | 140 | 51.805 | −18.442 | −53.769 | 1 | 31.34 |
| 5397 | CB | GLU | 140 | 52.849 | −19.558 | −53.767 | 1 | 34.82 |
| 5398 | CG | GLU | 140 | 54.21 | −19.126 | −53.249 | 1 | 39.83 |
| 5399 | CD | GLU | 140 | 55.282 | −20.169 | −53.494 | 1 | 43.93 |
| 5400 | OE1 | GLU | 140 | 55.109 | −21.322 | −53.044 | 1 | 46.72 |
| 5401 | OE2 | GLU | 140 | 56.3 | −19.833 | −54.138 | 1 | 46.77 |
| 5402 | C | GLU | 140 | 50.451 | −18.999 | −54.198 | 1 | 31.19 |
| 5403 | O | GLU | 140 | 49.721 | −19.576 | −53.392 | 1 | 31 |
| 5404 | N | GLN | 141 | 50.125 | −18.821 | −55.473 | 1 | 29.98 |
| 5405 | CA | GLN | 141 | 48.858 | −19.288 | −56.02 | 1 | 30.07 |
| 5406 | CB | GLN | 141 | 48.656 | −18.697 | −57.417 | 1 | 31.5 |
| 5407 | CG | GLN | 141 | 47.267 | −18.905 | −57.999 | 1 | 35.05 |
| 5408 | CD | GLN | 141 | 46.189 | −18.221 | −57.182 | 1 | 36.9 |
| 5409 | OE1 | GLN | 141 | 46.305 | −17.041 | −56.845 | 1 | 38.81 |
| 5410 | NE2 | GLN | 141 | 45.128 | −18.957 | −56.864 | 1 | 37.63 |
| 5411 | C | GLN | 141 | 48.808 | −20.811 | −56.093 | 1 | 28.82 |
| 5412 | O | GLN | 141 | 49.756 | −21.452 | −56.543 | 1 | 27.16 |
| 5413 | N | VAL | 142 | 47.702 | −21.388 | −55.638 | 1 | 27.97 |
| 5414 | CA | VAL | 142 | 47.532 | −22.835 | −55.672 | 1 | 27.54 |
| 5415 | CB | VAL | 142 | 47.714 | −23.466 | −54.271 | 1 | 28.78 |
| 5416 | CG1 | VAL | 142 | 47.405 | −24.954 | −54.328 | 1 | 30.82 |
| 5417 | CG2 | VAL | 142 | 49.141 | −23.253 | −53.783 | 1 | 30.69 |
| 5418 | C | VAL | 142 | 46.146 | −23.195 | −56.193 | 1 | 26.71 |
| 5419 | O | VAL | 142 | 45.143 | −22.628 | −55.76 | 1 | 26.24 |
| 5420 | N | VAL | 143 | 46.1 | −24.131 | −57.134 | 1 | 25.48 |

TABLE 1-continued

| Atom | Atom Type | Residue | # | X | Y | Z | OCC | B |
|---|---|---|---|---|---|---|---|---|
| 5421 | CA | VAL | 143 | 44.836 | −24.575 | −57.708 | 1 | 25.08 |
| 5422 | CB | VAL | 143 | 44.671 | −24.101 | −59.169 | 1 | 25.64 |
| 5423 | CG1 | VAL | 143 | 43.309 | −24.534 | −59.703 | 1 | 26.03 |
| 5424 | CG2 | VAL | 143 | 44.813 | −22.588 | −59.245 | 1 | 26.76 |
| 5425 | C | VAL | 143 | 44.791 | −26.093 | −57.681 | 1 | 23.89 |
| 5426 | O | VAL | 143 | 45.756 | −26.763 | −58.054 | 1 | 25.34 |
| 5427 | N | TRP | 144 | 43.669 | −26.638 | −57.233 | 1 | 21.94 |
| 5428 | CA | TRP | 144 | 43.522 | −28.079 | −57.164 | 1 | 21.28 |
| 5429 | CB | TRP | 144 | 43.793 | −28.564 | −55.735 | 1 | 22.1 |
| 5430 | CG | TRP | 144 | 43.657 | −30.047 | −55.544 | 1 | 22.73 |
| 5431 | CD2 | TRP | 144 | 43.312 | −30.725 | −54.33 | 1 | 22.09 |
| 5432 | CE2 | TRP | 144 | 43.359 | −32.111 | −54.595 | 1 | 22.16 |
| 5433 | CE3 | TRP | 144 | 42.97 | −30.294 | −53.041 | 1 | 21.99 |
| 5434 | CD1 | TRP | 144 | 43.891 | −31.025 | −56.474 | 1 | 22.69 |
| 5435 | NE1 | TRP | 144 | 43.714 | −32.267 | −55.91 | 1 | 24.69 |
| 5436 | CZ2 | TRP | 144 | 43.078 | −33.071 | −53.617 | 1 | 21.94 |
| 5437 | CZ3 | TRP | 144 | 42.691 | −31.252 | −52.069 | 1 | 21.89 |
| 5438 | CH2 | TRP | 144 | 42.747 | −32.622 | −52.365 | 1 | 20.55 |
| 5439 | C | TRP | 144 | 42.142 | −28.524 | −57.615 | 1 | 20.3 |
| 5440 | O | TRP | 144 | 41.129 | −28.134 | −57.036 | 1 | 19.72 |
| 5441 | N | GLN | 145 | 42.113 | −29.32 | −58.679 | 1 | 19.82 |
| 5442 | CA | GLN | 145 | 40.861 | −29.852 | −59.192 | 1 | 18.16 |
| 5443 | CB | GLN | 145 | 40.881 | −29.922 | −60.72 | 1 | 18.11 |
| 5444 | CG | GLN | 145 | 41.141 | −28.585 | −61.393 | 1 | 17.65 |
| 5445 | CD | GLN | 145 | 40.862 | −28.627 | −62.883 | 1 | 19.71 |
| 5446 | OE1 | GLN | 145 | 41.154 | −29.618 | −63.55 | 1 | 21.87 |
| 5447 | NE2 | GLN | 145 | 40.306 | −27.544 | −63.413 | 1 | 19.92 |
| 5448 | C | GLN | 145 | 40.771 | −31.249 | −58.6 | 1 | 18.42 |
| 5449 | O | GLN | 145 | 41.652 | −32.084 | −58.826 | 1 | 19.43 |
| 5450 | N | ALA | 146 | 39.717 | −31.499 | −57.831 | 1 | 18.21 |
| 5451 | CA | ALA | 146 | 39.545 | −32.791 | −57.178 | 1 | 18.05 |
| 5452 | CB | ALA | 146 | 39.835 | −32.656 | −55.688 | 1 | 18.81 |
| 5453 | C | ALA | 146 | 38.16 | −33.379 | −57.377 | 1 | 17.81 |
| 5454 | O | ALA | 146 | 37.204 | −32.664 | −57.671 | 1 | 17.21 |
| 5455 | N | SER | 147 | 38.061 | −34.693 | −57.201 | 1 | 18.16 |
| 5456 | CA | SER | 147 | 36.797 | −35.393 | −57.354 | 1 | 19.32 |
| 5457 | CB | SER | 147 | 36.739 | −36.092 | −58.714 | 1 | 21.76 |
| 5458 | OG | SER | 147 | 37.76 | −37.07 | −58.825 | 1 | 24.13 |
| 5459 | C | SER | 147 | 36.638 | −36.424 | −56.245 | 1 | 19.06 |
| 5460 | O | SER | 147 | 37.555 | −36.642 | −55.448 | 1 | 19.09 |
| 5461 | N | GLY | 148 | 35.467 | −37.045 | −56.188 | 1 | 17.07 |
| 5462 | CA | GLY | 148 | 35.22 | −38.06 | −55.184 | 1 | 16.38 |
| 5463 | C | GLY | 148 | 35.282 | −37.562 | −53.754 | 1 | 15.6 |
| 5464 | O | GLY | 148 | 34.86 | −36.446 | −53.455 | 1 | 15.43 |
| 5465 | N | TRP | 149 | 35.824 | −38.391 | −52.867 | 1 | 15.66 |
| 5466 | CA | TRP | 149 | 35.909 | −38.034 | −51.456 | 1 | 15.42 |
| 5467 | CB | TRP | 149 | 36.516 | −39.191 | −50.652 | 1 | 15.67 |
| 5468 | CG | TRP | 149 | 36.095 | −39.168 | −49.211 | 1 | 17.6 |
| 5469 | CD2 | TRP | 149 | 34.784 | −39.44 | −48.701 | 1 | 16.33 |
| 5470 | CE2 | TRP | 149 | 34.836 | −39.269 | −47.299 | 1 | 18.25 |
| 5471 | CE3 | TRP | 149 | 33.569 | −39.81 | −49.293 | 1 | 16 |
| 5472 | CD1 | TRP | 149 | 36.869 | −38.853 | −48.131 | 1 | 19 |
| 5473 | NE1 | TRP | 149 | 36.12 | −38.912 | −46.978 | 1 | 18.77 |
| 5474 | CZ2 | TRP | 149 | 33.718 | −39.456 | −46.478 | 1 | 18.48 |
| 5475 | CZ3 | TRP | 149 | 32.456 | −39.997 | −48.477 | 1 | 15.79 |
| 5476 | CH2 | TRP | 149 | 32.54 | −39.819 | −47.083 | 1 | 16.35 |
| 5477 | C | TRP | 149 | 36.697 | −36.748 | −51.211 | 1 | 15.41 |
| 5478 | O | TRP | 149 | 36.343 | −35.954 | −50.336 | 1 | 14.35 |
| 5479 | N | ALA | 150 | 37.76 | −36.537 | −51.981 | 1 | 14.96 |
| 5480 | CA | ALA | 150 | 38.56 | −35.327 | −51.83 | 1 | 15.96 |
| 5481 | CB | ALA | 150 | 39.722 | −35.334 | −52.817 | 1 | 17.87 |
| 5482 | C | ALA | 150 | 37.68 | −34.102 | −52.06 | 1 | 15.93 |
| 5483 | O | ALA | 150 | 37.755 | −33.125 | −51.314 | 1 | 15.32 |
| 5484 | N | ALA | 151 | 36.837 | −34.162 | −53.088 | 1 | 14.85 |
| 5485 | CA | ALA | 151 | 35.943 | −33.05 | −53.404 | 1 | 14.28 |
| 5486 | CB | ALA | 151 | 35.199 | −33.321 | −54.71 | 1 | 15.37 |
| 5487 | C | ALA | 151 | 34.951 | −32.819 | −52.272 | 1 | 14.3 |
| 5488 | O | ALA | 151 | 34.588 | −31.68 | −51.984 | 1 | 13.79 |
| 5489 | N | ARG | 152 | 34.512 | −33.899 | −51.63 | 1 | 14.05 |
| 5490 | CA | ARG | 152 | 33.572 | −33.785 | −50.516 | 1 | 12.59 |
| 5491 | CB | ARG | 152 | 33.144 | −35.17 | −50.031 | 1 | 12.48 |
| 5492 | CG | ARG | 152 | 32.357 | −35.162 | −48.718 | 1 | 14.59 |
| 5493 | CD | ARG | 152 | 31.838 | −36.555 | −48.394 | 1 | 13.22 |
| 5494 | NE | ARG | 152 | 30.927 | −37.027 | −49.433 | 1 | 14.59 |
| 5495 | CZ | ARG | 152 | 29.608 | −36.855 | −49.416 | 1 | 16.08 |
| 5496 | NH1 | ARG | 152 | 29.019 | −36.227 | −48.403 | 1 | 15.56 |
| 5497 | NH2 | ARG | 152 | 28.877 | −37.294 | −50.432 | 1 | 16.17 |
| 5498 | C | ARG | 152 | 34.199 | −33.013 | −49.36 | 1 | 14.07 |
| 5499 | O | ARG | 152 | 33.579 | −32.111 | −48.803 | 1 | 13.75 |
| 5500 | N | ILE | 153 | 35.429 | −33.368 | −49.002 | 1 | 13.32 |
| 5501 | CA | ILE | 153 | 36.123 | −32.694 | −47.907 | 1 | 14.22 |
| 5502 | CB | ILE | 153 | 37.484 | −33.359 | −47.618 | 1 | 16.63 |
| 5503 | CG2 | ILE | 153 | 38.14 | −32.704 | −46.401 | 1 | 17.32 |
| 5504 | CG1 | ILE | 153 | 37.282 | −34.853 | −47.36 | 1 | 18.15 |
| 5505 | CD1 | ILE | 153 | 36.318 | −35.158 | −46.228 | 1 | 23.61 |
| 5506 | C | ILE | 153 | 36.337 | −31.223 | −48.237 | 1 | 13.97 |
| 5507 | O | ILE | 153 | 36.162 | −30.354 | −47.385 | 1 | 13.48 |
| 5508 | N | ILE | 154 | 36.712 | −30.944 | −49.48 | 1 | 13.6 |
| 5509 | CA | ILE | 154 | 36.916 | −29.566 | −49.899 | 1 | 13.34 |
| 5510 | CB | ILE | 154 | 37.339 | −29.493 | −51.381 | 1 | 13.35 |
| 5511 | CG2 | ILE | 154 | 37.327 | −28.046 | −51.861 | 1 | 14.08 |
| 5512 | CG1 | ILE | 154 | 38.74 | −30.089 | −51.548 | 1 | 14.78 |
| 5513 | CD1 | ILE | 154 | 39.194 | −30.2 | −52.999 | 1 | 16.07 |
| 5514 | C | ILE | 154 | 35.624 | −28.774 | −49.704 | 1 | 13.01 |
| 5515 | O | ILE | 154 | 35.639 | −27.673 | −49.16 | 1 | 13.52 |
| 5516 | N | GLN | 155 | 34.503 | −29.337 | −50.144 | 1 | 12.73 |
| 5517 | CA | GLN | 155 | 33.217 | −28.662 | −50.002 | 1 | 13.11 |
| 5518 | CB | GLN | 155 | 32.126 | −29.455 | −50.728 | 1 | 13.97 |
| 5519 | CG | GLN | 155 | 32.3 | −29.46 | −52.243 | 1 | 14.75 |
| 5520 | CD | GLN | 155 | 31.427 | −30.489 | −52.931 | 1 | 14.79 |
| 5521 | OE1 | GLN | 155 | 30.205 | −30.35 | −52.978 | 1 | 16.13 |
| 5522 | NE2 | GLN | 155 | 32.052 | −31.537 | −53.463 | 1 | 13.29 |
| 5523 | C | GLN | 155 | 32.848 | −28.471 | −48.533 | 1 | 13.51 |
| 5524 | O | GLN | 155 | 32.33 | −27.422 | −48.148 | 1 | 13.83 |
| 5525 | N | HIS | 156 | 33.129 | −29.48 | −47.716 | 1 | 13.58 |
| 5526 | CA | HIS | 156 | 32.832 | −29.412 | −46.29 | 1 | 13.14 |
| 5527 | CB | HIS | 156 | 33.2 | −30.736 | −45.61 | 1 | 13.74 |
| 5528 | CG | HIS | 156 | 32.84 | −30.793 | −44.157 | 1 | 13.43 |
| 5529 | CD2 | HIS | 156 | 33.449 | −30.267 | −43.068 | 1 | 14.38 |
| 5530 | ND1 | HIS | 156 | 31.718 | −31.445 | −43.691 | 1 | 14.4 |
| 5531 | CE1 | HIS | 156 | 31.653 | −31.32 | −42.376 | 1 | 15.27 |
| 5532 | NE2 | HIS | 156 | 32.691 | −30.609 | −41.973 | 1 | 11.3 |
| 5533 | C | HIS | 156 | 33.612 | −28.269 | −45.641 | 1 | 13.46 |
| 5534 | O | HIS | 156 | 33.05 | −27.462 | −44.892 | 1 | 13.38 |
| 5535 | N | GLU | 157 | 34.908 | −28.19 | −45.93 | 1 | 13.58 |
| 5536 | CA | GLU | 157 | 35.724 | −27.137 | −45.344 | 1 | 14.07 |
| 5537 | CB | GLU | 157 | 37.215 | −27.428 | −45.543 | 1 | 14.26 |
| 5538 | CG | GLU | 157 | 37.691 | −28.808 | −45.065 | 1 | 15.37 |
| 5539 | CD | GLU | 157 | 37.115 | −29.248 | −43.723 | 1 | 17.38 |
| 5540 | OE1 | GLU | 157 | 36.874 | −28.395 | −42.844 | 1 | 17.69 |
| 5541 | OE2 | GLU | 157 | 36.923 | −30.468 | −43.543 | 1 | 18.47 |
| 5542 | C | GLU | 157 | 35.376 | −25.76 | −45.905 | 1 | 14.04 |
| 5543 | O | GLU | 157 | 35.368 | −24.775 | −45.166 | 1 | 14.86 |
| 5544 | N | MET | 158 | 35.093 | −25.674 | −47.203 | 1 | 14.43 |
| 5545 | CA | MET | 158 | 34.731 | −24.382 | −47.786 | 1 | 15.42 |
| 5546 | CB | MET | 158 | 34.571 | −24.493 | −49.306 | 1 | 14.86 |
| 5547 | CG | MET | 158 | 35.889 | −24.551 | −50.057 | 1 | 16.22 |
| 5548 | SD | MET | 158 | 36.896 | −23.066 | −49.818 | 1 | 19.76 |
| 5549 | CE | MET | 158 | 36.012 | −21.902 | −50.84 | 1 | 20.88 |
| 5550 | C | MET | 158 | 33.433 | −23.889 | −47.157 | 1 | 14.95 |
| 5551 | O | MET | 158 | 33.259 | −22.688 | −46.925 | 1 | 15.76 |
| 5552 | N | ASP | 159 | 32.522 | −24.819 | −46.877 | 1 | 15.27 |
| 5553 | CA | ASP | 159 | 31.255 | −24.466 | −46.245 | 1 | 14.52 |
| 5554 | CB | ASP | 159 | 30.378 | −25.708 | −46.037 | 1 | 15.46 |
| 5555 | CG | ASP | 159 | 29.556 | −26.073 | −47.267 | 1 | 17.25 |
| 5556 | OD1 | ASP | 159 | 29.646 | −25.374 | −48.299 | 1 | 17.97 |
| 5557 | OD2 | ASP | 159 | 28.813 | −27.071 | −47.195 | 1 | 16.18 |
| 5558 | C | ASP | 159 | 31.544 | −23.821 | −44.891 | 1 | 13.79 |
| 5559 | O | ASP | 159 | 30.905 | −22.842 | −44.519 | 1 | 14.42 |
| 5560 | N | HIS | 160 | 32.51 | −24.37 | −44.156 | 1 | 13.64 |
| 5561 | CA | HIS | 160 | 32.865 | −23.819 | −42.851 | 1 | 14.04 |
| 5562 | CB | HIS | 160 | 34.027 | −24.593 | −42.22 | 1 | 12.53 |
| 5563 | CG | HIS | 160 | 33.603 | −25.774 | −41.433 | 1 | 12.83 |
| 5564 | CD2 | HIS | 160 | 33.971 | −27.094 | −41.522 | 1 | 13.45 |
| 5565 | ND1 | HIS | 160 | 32.72 | −25.715 | −40.378 | 1 | 14.52 |
| 5566 | CE1 | HIS | 160 | 32.561 | −26.917 | −39.851 | 1 | 13.51 |
| 5567 | NE2 | HIS | 160 | 33.309 | −27.771 | −40.527 | 1 | 13.14 |
| 5568 | C | HIS | 160 | 33.261 | −22.35 | −42.942 | 1 | 14.37 |
| 5569 | O | HIS | 160 | 32.923 | −21.562 | −42.06 | 1 | 15.19 |
| 5570 | N | LEU | 161 | 33.982 | −21.986 | −44.002 | 1 | 15.56 |
| 5571 | CA | LEU | 161 | 34.423 | −20.606 | −44.18 | 1 | 15.37 |
| 5572 | CB | LEU | 161 | 35.511 | −20.52 | −45.259 | 1 | 16 |

TABLE 1-continued

| Atom | Atom Type | Residue | # | X | Y | Z | OCC | B |
|---|---|---|---|---|---|---|---|---|
| 5573 | CG | LEU | 161 | 36.796 | −21.32 | −45.001 | 1 | 16.02 |
| 5574 | CD1 | LEU | 161 | 37.84 | −20.962 | −46.056 | 1 | 16.18 |
| 5575 | CD2 | LEU | 161 | 37.336 | −21.016 | −43.602 | 1 | 14.99 |
| 5576 | C | LEU | 161 | 33.257 | −19.699 | −44.547 | 1 | 15.52 |
| 5577 | O | LEU | 161 | 33.366 | −18.479 | −44.469 | 1 | 16.43 |
| 5578 | N | GLN | 162 | 32.143 | −20.301 | −44.95 | 1 | 16.75 |
| 5579 | CA | GLN | 162 | 30.953 | −19.536 | −45.303 | 1 | 18.82 |
| 5580 | CB | GLN | 162 | 30.33 | −20.095 | −46.584 | 1 | 21.81 |
| 5581 | CG | GLN | 162 | 31.226 | −19.932 | −47.799 | 1 | 27.81 |
| 5582 | CD | GLN | 162 | 31.472 | −18.474 | −48.144 | 1 | 31.52 |
| 5583 | OE1 | GLN | 162 | 32.458 | −18.139 | −48.801 | 1 | 35.8 |
| 5584 | NE2 | GLN | 162 | 30.569 | −17.6 | −47.711 | 1 | 32.37 |
| 5585 | C | GLN | 162 | 29.933 | −19.56 | −44.166 | 1 | 18.38 |
| 5586 | O | GLN | 162 | 28.846 | −18.991 | −44.282 | 1 | 19.34 |
| 5587 | N | GLY | 163 | 30.29 | −20.217 | −43.064 | 1 | 16.71 |
| 5588 | CA | GLY | 163 | 29.396 | −20.295 | −41.919 | 1 | 15.08 |
| 5589 | C | GLY | 163 | 28.328 | −21.354 | −42.089 | 1 | 13.77 |
| 5590 | O | GLY | 163 | 27.279 | −21.309 | −41.443 | 1 | 14.43 |
| 5591 | N | CYS | 164 | 28.609 | −22.321 | −42.955 | 1 | 13.03 |
| 5592 | CA | CYS | 164 | 27.681 | −23.403 | −43.255 | 1 | 13.15 |
| 5593 | CB | CYS | 164 | 27.548 | −23.533 | −44.776 | 1 | 14.98 |
| 5594 | SG | CYS | 164 | 26.45 | −24.839 | −45.342 | 1 | 18.65 |
| 5595 | C | CYS | 164 | 28.157 | −24.729 | −42.66 | 1 | 12.84 |
| 5596 | O | CYS | 164 | 29.336 | −25.073 | −42.775 | 1 | 13.23 |
| 5597 | N | LEU | 165 | 27.242 | −25.454 | −42.015 | 1 | 12.58 |
| 5598 | CA | LEU | 165 | 27.553 | −26.752 | −41.415 | 1 | 14 |
| 5599 | CB | LEU | 165 | 27.164 | −26.773 | −39.934 | 1 | 13.6 |
| 5600 | CG | LEU | 165 | 27.872 | −25.754 | −39.037 | 1 | 14.6 |
| 5601 | CD1 | LEU | 165 | 27.424 | −25.947 | −37.592 | 1 | 14.95 |
| 5602 | CD2 | LEU | 165 | 29.38 | −25.929 | −39.153 | 1 | 15.55 |
| 5603 | C | LEU | 165 | 26.788 | −27.836 | −42.167 | 1 | 14.45 |
| 5604 | O | LEU | 165 | 25.756 | −27.558 | −42.785 | 1 | 15.11 |
| 5605 | N | PHE | 166 | 27.279 | −29.07 | −42.107 | 1 | 13.18 |
| 5606 | CA | PHE | 166 | 26.638 | −30.165 | −42.829 | 1 | 14.48 |
| 5607 | CB | PHE | 166 | 27.445 | −31.464 | −42.663 | 1 | 14.23 |
| 5608 | CG | PHE | 166 | 27.168 | −32.216 | −41.389 | 1 | 13.71 |
| 5609 | CD1 | PHE | 166 | 26.351 | −33.341 | −41.396 | 1 | 15.1 |
| 5610 | CD2 | PHE | 166 | 27.751 | −31.823 | −40.189 | 1 | 15.53 |
| 5611 | CE1 | PHE | 166 | 26.12 | −34.07 | −40.229 | 1 | 15.91 |
| 5612 | CE2 | PHE | 166 | 27.524 | −32.545 | −39.016 | 1 | 13.71 |
| 5613 | CZ | PHE | 166 | 26.71 | −33.668 | −39.037 | 1 | 15.04 |
| 5614 | C | PHE | 166 | 25.177 | −30.369 | −42.443 | 1 | 14.52 |
| 5615 | O | PHE | 166 | 24.386 | −30.882 | −43.24 | 1 | 15.38 |
| 5616 | N | ILE | 167 | 24.81 | −29.955 | −41.233 | 1 | 12.83 |
| 5617 | CA | ILE | 167 | 23.426 | −30.098 | −40.796 | 1 | 13.02 |
| 5618 | CB | ILE | 167 | 23.268 | −29.808 | −39.278 | 1 | 13.58 |
| 5619 | CG2 | ILE | 167 | 23.966 | −30.893 | −38.469 | 1 | 13.92 |
| 5620 | CG1 | ILE | 167 | 23.827 | −28.425 | −38.942 | 1 | 14.54 |
| 5621 | CD1 | ILE | 167 | 23.489 | −27.956 | −37.538 | 1 | 15.03 |
| 5622 | C | ILE | 167 | 22.491 | −29.178 | −41.589 | 1 | 13.17 |
| 5623 | O | ILE | 167 | 21.268 | −29.326 | −41.523 | 1 | 14.71 |
| 5624 | N | ASP | 168 | 23.061 | −28.238 | −42.345 | 1 | 13.46 |
| 5625 | CA | ASP | 168 | 22.255 | −27.32 | −43.159 | 1 | 14.09 |
| 5626 | CB | ASP | 168 | 23.002 | −26.007 | −43.445 | 1 | 14.15 |
| 5627 | CG | ASP | 168 | 23.42 | −25.264 | −42.192 | 1 | 13.97 |
| 5628 | OD1 | ASP | 168 | 22.711 | −25.338 | −41.167 | 1 | 15.04 |
| 5629 | OD2 | ASP | 168 | 24.463 | −24.575 | −42.25 | 1 | 14.63 |
| 5630 | C | ASP | 168 | 21.914 | −27.939 | −44.518 | 1 | 15.29 |
| 5631 | O | ASP | 168 | 21.03 | −27.444 | −45.224 | 1 | 16.92 |
| 5632 | N | LYS | 169 | 22.614 | −29.012 | −44.879 | 1 | 14.32 |
| 5633 | CA | LYS | 169 | 22.426 | −29.662 | −46.181 | 1 | 15.24 |
| 5634 | CB | LYS | 169 | 23.688 | −29.482 | −47.022 | 1 | 17.19 |
| 5635 | CG | LYS | 169 | 24.068 | −28.048 | −47.317 | 1 | 18.07 |
| 5636 | CD | LYS | 169 | 25.391 | −27.998 | −48.059 | 1 | 18.17 |
| 5637 | CE | LYS | 169 | 25.656 | −26.603 | −48.598 | 1 | 19.64 |
| 5638 | NZ | LYS | 169 | 26.93 | −26.54 | −49.357 | 1 | 18.89 |
| 5639 | C | LYS | 169 | 22.121 | −31.154 | −46.132 | 1 | 15.16 |
| 5640 | O | LYS | 169 | 21.926 | −31.79 | −47.171 | 1 | 16.95 |
| 5641 | N | MET | 170 | 22.086 | −31.712 | −44.933 | 1 | 14.9 |
| 5642 | CA | MET | 170 | 21.855 | −33.14 | −44.742 | 1 | 14.75 |
| 5643 | CB | MET | 170 | 22.186 | −33.508 | −43.299 | 1 | 14.72 |
| 5644 | CG | MET | 170 | 21.193 | −32.888 | −42.317 | 1 | 13.79 |
| 5645 | SD | MET | 170 | 21.387 | −33.481 | −40.641 | 1 | 14.45 |
| 5646 | CE | MET | 170 | 20.333 | −32.351 | −39.737 | 1 | 15.28 |
| 5647 | C | MET | 170 | 20.445 | −33.652 | −45.008 | 1 | 15.84 |
| 5648 | O | MET | 170 | 19.488 | −32.88 | −45.105 | 1 | 16.28 |
| 5649 | N | ASP | 171 | 20.342 | −34.975 | −45.131 | 1 | 15.11 |
| 5650 | CA | ASP | 171 | 19.051 | −35.641 | −45.253 | 1 | 16.42 |
| 5651 | CB | ASP | 171 | 19.166 | −36.989 | −45.962 | 1 | 18.14 |
| 5652 | CG | ASP | 171 | 17.865 | −37.783 | −45.917 | 1 | 22.22 |
| 5653 | OD1 | ASP | 171 | 16.992 | −37.478 | −45.067 | 1 | 22.11 |
| 5654 | OD2 | ASP | 171 | 17.715 | −38.722 | −46.726 | 1 | 24.37 |
| 5655 | C | ASP | 171 | 18.843 | −35.881 | −43.762 | 1 | 14.64 |
| 5656 | O | ASP | 171 | 19.404 | −36.822 | −43.192 | 1 | 14.77 |
| 5657 | N | SER | 172 | 18.073 | −35.007 | −43.127 | 1 | 14.4 |
| 5658 | CA | SER | 172 | 17.844 | −35.086 | −41.69 | 1 | 13.92 |
| 5659 | CB | SER | 172 | 16.863 | −33.992 | −41.255 | 1 | 15.01 |
| 5660 | OG | SER | 172 | 15.572 | −34.233 | −41.777 | 1 | 15.73 |
| 5661 | C | SER | 172 | 17.376 | −36.436 | −41.153 | 1 | 13.52 |
| 5662 | O | SER | 172 | 17.653 | −36.769 | −40.002 | 1 | 13.95 |
| 5663 | N | ARG | 173 | 16.677 | −37.22 | −41.967 | 1 | 13.46 |
| 5664 | CA | ARG | 173 | 16.205 | −38.513 | −41.489 | 1 | 14.43 |
| 5665 | CB | ARG | 173 | 15.116 | −39.063 | −42.415 | 1 | 15.7 |
| 5666 | CG | ARG | 173 | 13.81 | −38.275 | −42.34 | 1 | 17.8 |
| 5667 | CD | ARG | 173 | 12.725 | −38.917 | −43.186 | 1 | 17.89 |
| 5668 | NE | ARG | 173 | 12.39 | −40.26 | −42.719 | 1 | 19.81 |
| 5669 | CZ | ARG | 173 | 11.651 | −40.521 | −41.645 | 1 | 20.51 |
| 5670 | NH1 | ARG | 173 | 11.156 | −39.531 | −40.917 | 1 | 21.79 |
| 5671 | NH2 | ARG | 173 | 11.415 | −41.776 | −41.293 | 1 | 23.54 |
| 5672 | C | ARG | 173 | 17.332 | −39.53 | −41.318 | 1 | 14.37 |
| 5673 | O | ARG | 173 | 17.122 | −40.603 | −40.754 | 1 | 14.87 |
| 5674 | N | THR | 174 | 18.529 | −39.184 | −41.789 | 1 | 13.7 |
| 5675 | CA | THR | 174 | 19.68 | −40.077 | −41.65 | 1 | 13.71 |
| 5676 | CB | THR | 174 | 20.518 | −40.15 | −42.938 | 1 | 14.81 |
| 5677 | OG1 | THR | 174 | 21.063 | −38.856 | −43.226 | 1 | 13.72 |
| 5678 | CG2 | THR | 174 | 19.664 | −40.628 | −44.105 | 1 | 15.33 |
| 5679 | C | THR | 174 | 20.608 | −39.622 | −40.527 | 1 | 14.01 |
| 5680 | O | THR | 174 | 21.651 | −40.233 | −40.294 | 1 | 13.67 |
| 5681 | N | PHE | 175 | 20.233 | −38.546 | −39.842 | 1 | 13.02 |
| 5682 | CA | PHE | 175 | 21.03 | −38.016 | −38.736 | 1 | 12.54 |
| 5683 | CB | PHE | 175 | 20.352 | −36.773 | −38.163 | 1 | 12.9 |
| 5684 | CG | PHE | 175 | 21.201 | −36.005 | −37.189 | 1 | 11.42 |
| 5685 | CD1 | PHE | 175 | 22.245 | −35.202 | −37.637 | 1 | 12.41 |
| 5686 | CD2 | PHE | 175 | 20.931 | −36.059 | −35.826 | 1 | 12.47 |
| 5687 | CE1 | PHE | 175 | 23.011 | −34.453 | −36.741 | 1 | 12.74 |
| 5688 | CE2 | PHE | 175 | 21.69 | −35.314 | −34.919 | 1 | 13.68 |
| 5689 | CZ | PHE | 175 | 22.732 | −34.508 | −35.381 | 1 | 13.75 |
| 5690 | C | PHE | 175 | 21.1 | −39.106 | −37.671 | 1 | 12.49 |
| 5691 | O | PHE | 175 | 20.085 | −39.724 | −37.349 | 1 | 13.66 |
| 5692 | N | THR | 176 | 22.287 | −39.345 | −37.121 | 1 | 12.56 |
| 5693 | CA | THR | 176 | 22.428 | −40.401 | −36.125 | 1 | 11.61 |
| 5694 | CB | THR | 176 | 22.578 | −41.783 | −36.823 | 1 | 14.4 |
| 5695 | OG1 | THR | 176 | 22.732 | −42.818 | −35.841 | 1 | 14.19 |
| 5696 | CG2 | THR | 176 | 23.807 | −41.787 | −37.742 | 1 | 15.76 |
| 5697 | C | THR | 176 | 23.618 | −40.236 | −35.191 | 1 | 12.04 |
| 5698 | O | THR | 176 | 24.646 | −39.674 | −35.566 | 1 | 12.4 |
| 5699 | N | ASN | 177 | 23.455 | −40.717 | −33.962 | 1 | 12.19 |
| 5700 | CA | ASN | 177 | 24.546 | −40.719 | −32.998 | 1 | 11.91 |
| 5701 | CB | ASN | 177 | 24.056 | −41.197 | −31.635 | 1 | 11.49 |
| 5702 | CG | ASN | 177 | 23.536 | −40.076 | −30.779 | 1 | 11.95 |
| 5703 | OD1 | ASN | 177 | 24.309 | −39.359 | −30.153 | 1 | 14.14 |
| 5704 | ND2 | ASN | 177 | 22.221 | −39.906 | −30.755 | 1 | 11.1 |
| 5705 | C | ASN | 177 | 25.47 | −41.774 | −33.582 | 1 | 12.77 |
| 5706 | O | ASN | 177 | 24.998 | −42.75 | −34.162 | 1 | 13.36 |
| 5707 | N | VAL | 178 | 26.776 | −41.598 | −33.431 | 1 | 12.8 |
| 5708 | CA | VAL | 178 | 27.711 | −42.574 | −33.98 | 1 | 14.83 |
| 5709 | CB | VAL | 178 | 29.172 | −42.098 | −33.831 | 1 | 16.69 |
| 5710 | CG1 | VAL | 178 | 29.416 | −40.892 | −34.728 | 1 | 19.5 |
| 5711 | CG2 | VAL | 178 | 29.463 | −41.753 | −32.385 | 1 | 19.49 |
| 5712 | C | VAL | 178 | 27.576 | −43.962 | −33.354 | 1 | 13.09 |
| 5713 | O | VAL | 178 | 27.97 | −44.957 | −33.968 | 1 | 14.24 |
| 5714 | N | TYR | 179 | 27.016 | −44.044 | −32.148 | 1 | 12.78 |
| 5715 | CA | TYR | 179 | 26.868 | −45.343 | −31.511 | 1 | 12.45 |
| 5716 | CB | TYR | 179 | 26.811 | −45.226 | −29.982 | 1 | 11.65 |
| 5717 | CG | TYR | 179 | 25.774 | −44.287 | −29.42 | 1 | 12.38 |
| 5718 | CD1 | TYR | 179 | 26.142 | −43.042 | −28.909 | 1 | 13.01 |
| 5719 | CE1 | TYR | 179 | 25.202 | −42.186 | −28.331 | 1 | 12.32 |
| 5720 | CD2 | TYR | 179 | 24.434 | −44.662 | −29.347 | 1 | 13.39 |
| 5721 | CE2 | TYR | 179 | 23.486 | −43.824 | −28.771 | 1 | 15.26 |
| 5722 | CZ | TYR | 179 | 23.877 | −42.594 | −28.264 | 1 | 14.06 |
| 5723 | OH | TYR | 179 | 22.949 | −41.77 | −27.677 | 1 | 16.32 |
| 5724 | C | TYR | 179 | 25.688 | −46.16 | −32.044 | 1 | 11.82 |

TABLE 1-continued

| Atom | Atom Type | Residue | # | X | Y | Z | OCC | B |
|---|---|---|---|---|---|---|---|---|
| 5725 | O | TYR | 179 | 25.421 | −47.264 | −31.573 | 1 | 12.8 |
| 5726 | N | TRP | 180 | 24.984 | −45.601 | −33.028 | 1 | 12.53 |
| 5727 | CA | TRP | 180 | 23.886 | −46.298 | −33.698 | 1 | 12.93 |
| 5728 | CB | TRP | 180 | 22.601 | −45.466 | −33.72 | 1 | 12.91 |
| 5729 | CG | TRP | 180 | 21.7 | −45.757 | −32.572 | 1 | 12.68 |
| 5730 | CD2 | TRP | 180 | 20.865 | −46.911 | −32.417 | 1 | 12 |
| 5731 | CE2 | TRP | 180 | 20.223 | −46.794 | −31.166 | 1 | 11.51 |
| 5732 | CE3 | TRP | 180 | 20.601 | −48.034 | −33.213 | 1 | 13.32 |
| 5733 | CD1 | TRP | 180 | 21.535 | −45.008 | −31.447 | 1 | 12.79 |
| 5734 | NE1 | TRP | 180 | 20.649 | −45.623 | −30.594 | 1 | 11.56 |
| 5735 | CZ2 | TRP | 180 | 19.327 | −47.759 | −30.689 | 1 | 11.58 |
| 5736 | CZ3 | TRP | 180 | 19.71 | −48.998 | −32.738 | 1 | 11.36 |
| 5737 | CH2 | TRP | 180 | 19.085 | −48.852 | −31.486 | 1 | 12.25 |
| 5738 | C | TRP | 180 | 24.367 | −46.51 | −35.125 | 1 | 13.51 |
| 5739 | O | TRP | 180 | 24.906 | −45.591 | −35.741 | 1 | 13.45 |
| 5740 | N | MET | 181 | 24.178 | −47.71 | −35.659 | 1 | 13.69 |
| 5741 | CA | MET | 181 | 24.642 | −47.985 | −37.013 | 1 | 16.31 |
| 5742 | CB | MET | 181 | 26.128 | −48.349 | −36.976 | 1 | 17.68 |
| 5743 | CG | MET | 181 | 26.413 | −49.637 | −36.221 | 1 | 17.91 |
| 5744 | SD | MET | 181 | 28.058 | −49.645 | −35.469 | 1 | 20.2 |
| 5745 | CE | MET | 181 | 27.74 | −48.678 | −34.006 | 1 | 19.15 |
| 5746 | C | MET | 181 | 23.866 | −49.109 | −37.676 | 1 | 18.65 |
| 5747 | O | MET | 181 | 23.299 | −49.967 | −37.006 | 1 | 17.77 |
| 5748 | N | LYS | 182 | 23.849 | −49.1 | −39.004 | 1 | 22.61 |
| 5749 | CA | LYS | 182 | 23.155 | −50.135 | −39.752 | 1 | 28.25 |
| 5750 | CB | LYS | 182 | 22.678 | −49.585 | −41.097 | 1 | 30.5 |
| 5751 | CG | LYS | 182 | 21.428 | −50.263 | −41.631 | 1 | 34.55 |
| 5752 | CD | LYS | 182 | 20.828 | −49.486 | −42.795 | 1 | 36.39 |
| 5753 | CE | LYS | 182 | 19.511 | −50.102 | −43.244 | 1 | 37.69 |
| 5754 | NZ | LYS | 182 | 18.86 | −49.312 | −44.329 | 1 | 38.75 |
| 5755 | C | LYS | 182 | 24.156 | −51.266 | −39.95 | 1 | 30.23 |
| 5756 | O | LYS | 182 | 25.332 | −51.022 | −40.225 | 1 | 30.94 |
| 5757 | N | VAL | 183 | 23.696 | −52.501 | −39.79 | 1 | 32.25 |
| 5758 | CA | VAL | 183 | 24.57 | −53.656 | −39.935 | 1 | 34.86 |
| 5759 | CB | VAL | 183 | 24.897 | −54.276 | −38.56 | 1 | 35.2 |
| 5760 | CG1 | VAL | 183 | 25.719 | −53.303 | −37.728 | 1 | 35.25 |
| 5761 | CG2 | VAL | 183 | 23.608 | −54.637 | −37.837 | 1 | 35.86 |
| 5762 | C | VAL | 183 | 23.97 | −54.745 | −40.812 | 1 | 36.6 |
| 5763 | O | VAL | 183 | 22.776 | −54.733 | −41.119 | 1 | 36.41 |
| 5764 | N | ASN | 184 | 24.817 | −55.688 | −41.22 | 1 | 38.98 |
| 5765 | CA | ASN | 184 | 24.396 | −56.805 | −42.057 | 1 | 41.59 |
| 5766 | CB | ASN | 184 | 25.557 | −57.28 | −42.932 | 1 | 41.37 |
| 5767 | CG | ASN | 184 | 26.09 | −56.187 | −43.834 | 1 | 42.06 |
| 5768 | OD1 | ASN | 184 | 25.366 | −55.653 | −44.675 | 1 | 42.52 |
| 5769 | ND2 | ASN | 184 | 27.363 | −55.849 | −43.665 | 1 | 42.1 |
| 5770 | C | ASN | 184 | 23.937 | −57.949 | −41.164 | 1 | 43.13 |
| 5771 | O | ASN | 184 | 24.428 | −58.108 | −40.046 | 1 | 44.27 |
| 5772 | N | ASP | 185 | 22.995 | −58.742 | −41.66 | 1 | 45.15 |
| 5773 | CA | ASP | 185 | 22.477 | −59.872 | −40.902 | 1 | 46.68 |
| 5774 | CB | ASP | 185 | 20.949 | −59.81 | −40.838 | 1 | 47.2 |
| 5775 | CG | ASP | 185 | 20.446 | −58.512 | −40.242 | 1 | 48.01 |
| 5776 | OD1 | ASP | 185 | 20.849 | −58.184 | −39.105 | 1 | 49.15 |
| 5777 | OD2 | ASP | 185 | 19.646 | −57.82 | −40.909 | 1 | 48.44 |
| 5778 | C | ASP | 185 | 22.912 | −61.186 | −41.539 | 1 | 47.77 |
| 5779 | O | ASP | 185 | 23.567 | −61.99 | −40.841 | 1 | 48.77 |
| 5780 | OXT | ASP | 185 | 22.592 | −61.394 | −42.73 | 1 | 48.71 |
| 5781 | OH2 | TIP | 3 | 35.835 | −7.631 | 24.377 | 1 | 8.18 |
| 5782 | OH2 | TIP | 4 | 19.456 | −44.872 | −27.846 | 1 | 11.24 |
| 5783 | OH2 | TIP | 5 | 23.844 | 12.921 | 24.005 | 1 | 9.88 |
| 5784 | OH2 | TIP | 6 | 32.299 | −24.795 | −28.149 | 1 | 10.79 |
| 5785 | OH2 | TIP | 7 | 32.152 | −9.202 | 16.944 | 1 | 13.84 |
| 5786 | OH2 | TIP | 8 | 22.208 | −12.253 | 19.251 | 1 | 12.58 |
| 5787 | OH2 | TIP | 9 | 16.494 | −42.256 | −35.24 | 1 | 13.66 |
| 5788 | OH2 | TIP | 10 | 28.789 | −18.477 | 17.795 | 1 | 13.61 |
| 5789 | OH2 | TIP | 11 | 35.284 | 6.016 | 0.227 | 1 | 13.41 |
| 5790 | OH2 | TIP | 12 | 20.139 | −11.259 | 17.547 | 1 | 14.6 |
| 5791 | OH2 | TIP | 13 | 6.707 | −43.42 | −34.363 | 1 | 13.16 |
| 5792 | OH2 | TIP | 14 | 22.987 | −9.681 | 19.981 | 1 | 13.54 |
| 5793 | OH2 | TIP | 15 | 19.387 | 9.463 | 17.783 | 1 | 13.64 |
| 5794 | OH2 | TIP | 16 | 33.279 | −18.843 | −41.209 | 1 | 14.92 |
| 5795 | OH2 | TIP | 17 | 17.589 | −39.552 | −38.008 | 1 | 15.07 |
| 5796 | OH2 | TIP | 18 | 7.846 | −45.961 | −33.639 | 1 | 13.86 |
| 5797 | OH2 | TIP | 19 | 25.667 | 10.244 | 8.999 | 1 | 12.85 |
| 5798 | OH2 | TIP | 20 | 25.639 | 8.01 | 7.234 | 1 | 16.02 |
| 5799 | OH2 | TIP | 21 | 30.809 | −27.43 | −43.046 | 1 | 14.64 |
| 5800 | OH2 | TIP | 22 | 28.789 | −28.503 | −44.828 | 1 | 15.46 |
| 5801 | OH2 | TIP | 23 | 27.512 | −14.259 | 19.093 | 1 | 13.87 |
| 5802 | OH2 | TIP | 24 | 32.137 | −35.538 | −53.644 | 1 | 17.6 |
| 5803 | OH2 | TIP | 25 | 4.852 | −22.009 | −30.542 | 1 | 13.77 |
| 5804 | OH2 | TIP | 26 | 30.182 | −3.123 | 22.99 | 1 | 15.98 |
| 5805 | OH2 | TIP | 27 | 23.66 | −23.535 | −35.811 | 1 | 17.66 |
| 5806 | OH2 | TIP | 28 | 11.841 | −34.223 | −32.051 | 1 | 14.17 |
| 5807 | OH2 | TIP | 29 | 27.161 | −22.353 | −34.336 | 1 | 14.34 |
| 5808 | OH2 | TIP | 30 | 9.211 | −34.728 | −32.872 | 1 | 13.55 |
| 5809 | OH2 | TIP | 31 | 37.691 | 6.278 | −0.885 | 1 | 17.97 |
| 5810 | OH2 | TIP | 32 | 28.441 | −30.389 | −30.88 | 1 | 16.33 |
| 5811 | OH2 | TIP | 33 | 26.568 | 8.732 | 11.193 | 1 | 13.36 |
| 5812 | OH2 | TIP | 34 | 9.128 | −32.531 | −34.685 | 1 | 16.31 |
| 5813 | OH2 | TIP | 35 | 19.202 | 16.479 | 10.666 | 1 | 15.57 |
| 5814 | OH2 | TIP | 36 | 8.879 | −10.24 | 21.714 | 1 | 15.84 |
| 5815 | OH2 | TIP | 37 | 18.773 | 5.803 | 16.312 | 1 | 15.28 |
| 5816 | OH2 | TIP | 38 | 31.417 | −37.65 | −52.192 | 1 | 16.03 |
| 5817 | OH2 | TIP | 39 | 9.859 | −40.364 | −32.913 | 1 | 13.89 |
| 5818 | OH2 | TIP | 40 | 31.429 | −18.585 | 18.392 | 1 | 15.07 |
| 5819 | OH2 | TIP | 41 | 30.127 | −7.019 | 14.123 | 1 | 15.48 |
| 5820 | OH2 | TIP | 42 | 29.819 | −29.019 | −40.945 | 1 | 14.22 |
| 5821 | OH2 | TIP | 43 | 18.313 | 17.758 | 13.1 | 1 | 14.04 |
| 5822 | OH2 | TIP | 44 | 2.626 | −23.281 | −31.513 | 1 | 13.8 |
| 5823 | OH2 | TIP | 45 | 4.296 | −28.992 | −36.76 | 1 | 14.33 |
| 5824 | OH2 | TIP | 46 | 6.712 | −10.236 | 23.414 | 1 | 16.41 |
| 5825 | OH2 | TIP | 47 | 27.043 | 6.883 | 21.237 | 1 | 17.36 |
| 5826 | OH2 | TIP | 48 | 21.08 | −37.843 | −29.143 | 1 | 17.07 |
| 5827 | OH2 | TIP | 49 | 23.568 | −39.339 | −27.242 | 1 | 21.33 |
| 5828 | OH2 | TIP | 50 | 36.874 | −10.359 | 24.406 | 1 | 21.12 |
| 5829 | OH2 | TIP | 51 | 22.239 | 13.447 | 12.251 | 1 | 15.39 |
| 5830 | OH2 | TIP | 52 | 16.315 | −30.281 | −41.539 | 1 | 20.69 |
| 5831 | OH2 | TIP | 53 | 33.837 | 7.806 | −1.357 | 1 | 14.57 |
| 5832 | OH2 | TIP | 54 | 27.202 | 34.118 | 9.157 | 1 | 22.03 |
| 5833 | OH2 | TIP | 55 | 32.014 | −23.032 | −39.756 | 1 | 16.05 |
| 5834 | OH2 | TIP | 56 | 8.918 | −12.905 | 20.869 | 1 | 16.06 |
| 5835 | OH2 | TIP | 57 | 27.115 | −39.741 | −30.358 | 1 | 22.28 |
| 5836 | OH2 | TIP | 58 | 32.689 | −39.602 | −53.352 | 1 | 17.62 |
| 5837 | OH2 | TIP | 59 | 29.316 | −0.193 | −7.304 | 1 | 16.67 |
| 5838 | OH2 | TIP | 60 | 22.667 | 15.434 | 23.494 | 1 | 21.23 |
| 5839 | OH2 | TIP | 61 | 12.888 | −27.307 | 18.146 | 1 | 17.96 |
| 5840 | OH2 | TIP | 62 | 34.084 | −17.54 | −38.872 | 1 | 16.11 |
| 5841 | OH2 | TIP | 63 | 22.539 | 34.43 | 11.69 | 1 | 23.01 |
| 5842 | OH2 | TIP | 64 | 20.203 | 17.956 | 21.559 | 1 | 21.05 |
| 5843 | OH2 | TIP | 65 | 21.438 | −3.767 | 10.564 | 1 | 18.94 |
| 5844 | OH2 | TIP | 66 | 30.376 | −35.371 | −36.279 | 1 | 35.46 |
| 5845 | OH2 | TIP | 67 | 14.863 | −13.754 | 15.076 | 1 | 19.31 |
| 5846 | OH2 | TIP | 68 | 28.122 | −28.688 | −51.036 | 1 | 22.54 |
| 5847 | OH2 | TIP | 69 | 3.861 | −20.115 | −29.02 | 1 | 17.47 |
| 5848 | OH2 | TIP | 70 | 16.878 | −0.69 | 10.016 | 1 | 22.36 |
| 5849 | OH2 | TIP | 71 | 38.57 | −22.39 | −58.124 | 1 | 23.9 |
| 5850 | OH2 | TIP | 72 | 38.731 | −13.694 | 19.996 | 1 | 23.72 |
| 5851 | OH2 | TIP | 73 | 24.953 | −30.068 | −25.564 | 1 | 20.63 |
| 5852 | OH2 | TIP | 74 | 17.481 | −31.585 | −29.169 | 1 | 47.91 |
| 5853 | OH2 | TIP | 75 | 21.477 | −1.051 | 9.506 | 1 | 17.4 |
| 5854 | OH2 | TIP | 76 | 18.797 | −29.077 | −42.469 | 1 | 20.39 |
| 5855 | OH2 | TIP | 77 | 23.865 | −22.253 | −43.722 | 1 | 22.14 |
| 5856 | OH2 | TIP | 78 | 16.312 | −33.462 | −44.884 | 1 | 24.1 |
| 5857 | OH2 | TIP | 79 | 4.638 | −18.789 | 31.302 | 1 | 21.45 |
| 5858 | OH2 | TIP | 80 | 32.803 | 11.501 | 19.967 | 1 | 19.1 |
| 5859 | OH2 | TIP | 81 | 44.636 | −30.183 | −60.054 | 1 | 23.65 |
| 5860 | OH2 | TIP | 82 | 10.66 | −36.589 | −41.161 | 1 | 19.89 |
| 5861 | OH2 | TIP | 83 | 35.208 | −33.277 | −32.198 | 1 | 20.2 |
| 5862 | OH2 | TIP | 85 | 25.618 | 7.409 | 0.959 | 1 | 17.12 |
| 5863 | OH2 | TIP | 86 | 17.003 | −24.742 | −42.119 | 1 | 21.77 |
| 5864 | OH2 | TIP | 87 | 34.718 | 1.439 | 21.868 | 1 | 19.53 |
| 5865 | OH2 | TIP | 88 | 37.328 | −14.02 | 23.086 | 1 | 22.52 |
| 5866 | OH2 | TIP | 89 | 34.823 | 0.884 | −5.862 | 1 | 24 |
| 5867 | OH2 | TIP | 90 | 6.238 | −27.873 | 21.118 | 1 | 20.16 |
| 5868 | OH2 | TIP | 91 | 17.796 | 6.628 | 8.374 | 1 | 20.77 |
| 5869 | OH2 | TIP | 92 | 29.038 | −30.852 | −27.437 | 1 | 21.62 |
| 5870 | OH2 | TIP | 93 | 24.236 | −5.24 | 7.289 | 1 | 20.75 |
| 5871 | OH2 | TIP | 94 | 26.007 | −22.918 | 16.216 | 1 | 19.42 |
| 5872 | OH2 | TIP | 95 | 25.391 | 19.47 | −5.977 | 1 | 22.13 |
| 5873 | OH2 | TIP | 96 | 30.668 | −24.461 | −62.375 | 1 | 19.04 |
| 5874 | OH2 | TIP | 97 | 29.524 | 12.57 | −13.615 | 1 | 21.97 |
| 5875 | OH2 | TIP | 98 | 24.651 | 37.311 | 3.804 | 1 | 23.16 |
| 5876 | OH2 | TIP | 99 | 34.105 | −22.577 | −28.466 | 1 | 22.07 |

TABLE 1-continued

| Atom | Atom Type | Residue | # | X | Y | Z | OCC | B |
|---|---|---|---|---|---|---|---|---|
| 5877 | OH2 | TIP | 100 | 17.165 | 16.699 | 21.911 | 1 | 24.61 |
| 5878 | OH2 | TIP | 101 | 25.167 | 3.967 | 26.543 | 1 | 25.74 |
| 5879 | OH2 | TIP | 102 | 14.508 | −49.084 | −29.039 | 1 | 25.41 |
| 5880 | OH2 | TIP | 103 | 17.657 | −46.929 | −27.738 | 1 | 22.1 |
| 5881 | OH2 | TIP | 104 | 18.878 | −26.958 | 32.601 | 1 | 24.15 |
| 5882 | OH2 | TIP | 106 | 15.326 | −50.16 | −32.011 | 1 | 24.03 |
| 5883 | OH2 | TIP | 108 | −5.456 | −20.649 | −40.334 | 1 | 29.44 |
| 5884 | OH2 | TIP | 109 | 15.6 | −21.186 | 38.07 | 1 | 26.03 |
| 5885 | OH2 | TIP | 110 | 27.543 | −5.913 | 29.413 | 1 | 20.58 |
| 5886 | OH2 | TIP | 111 | 14.359 | −49.139 | −26.327 | 1 | 28.19 |
| 5887 | OH2 | TIP | 112 | 24.669 | −11.788 | 10.864 | 1 | 26.41 |
| 5888 | OH2 | TIP | 113 | 32.223 | −40.091 | −56.066 | 1 | 30.46 |
| 5889 | OH2 | TIP | 114 | 1.456 | −43.265 | −35.877 | 1 | 25.9 |
| 5890 | OH2 | TIP | 115 | 23.024 | −25.048 | 18.579 | 1 | 19.75 |
| 5891 | OH2 | TIP | 116 | 22.948 | −3.556 | 25.238 | 1 | 19.36 |
| 5892 | OH2 | TIP | 117 | 35.331 | −1.141 | −2.161 | 1 | 21.61 |
| 5893 | OH2 | TIP | 118 | 18.677 | −4.351 | 10.373 | 1 | 23.5 |
| 5894 | OH2 | TIP | 119 | 19.001 | −30.223 | −45.142 | 1 | 23.16 |
| 5895 | OH2 | TIP | 120 | 26.529 | 14.7 | 24.347 | 1 | 26.42 |
| 5896 | OH2 | TIP | 121 | 25.449 | 3.148 | 1.837 | 1 | 21.56 |
| 5897 | OH2 | TIP | 122 | 2.766 | −18.06 | −41.114 | 1 | 25.37 |
| 5898 | OH2 | TIP | 123 | 4.918 | −5.544 | 17.959 | 1 | 26.14 |
| 5899 | OH2 | TIP | 124 | 35.17 | −19.261 | −30.294 | 1 | 21.91 |
| 5900 | OH2 | TIP | 125 | 3.894 | −10.376 | 11.443 | 1 | 26.54 |
| 5901 | OH2 | TIP | 126 | −8.135 | −33.697 | −34.361 | 1 | 23.4 |
| 5902 | OH2 | TIP | 127 | 7.33 | −15.029 | 28.109 | 1 | 26.41 |
| 5903 | OH2 | TIP | 128 | 19.56 | −32.874 | −48.264 | 1 | 29.71 |
| 5904 | OH2 | TIP | 129 | 17.308 | −36.706 | −22.745 | 1 | 18.4 |
| 5905 | OH2 | TIP | 130 | 21.176 | 8.531 | 1.072 | 1 | 32.69 |
| 5906 | OH2 | TIP | 131 | 3.119 | −26.729 | −10.369 | 1 | 27.52 |
| 5907 | OH2 | TIP | 132 | 4.113 | −11.281 | 22.502 | 1 | 30.32 |
| 5908 | OH2 | TIP | 133 | 29.292 | −0.885 | 24.219 | 1 | 23.88 |
| 5909 | OH2 | TIP | 134 | 2.772 | −18.82 | 12.154 | 1 | 32.71 |
| 5910 | OH2 | TIP | 135 | 19.129 | 28.176 | 0.441 | 1 | 26.9 |
| 5911 | OH2 | TIP | 136 | 22.719 | −35.959 | −27.984 | 1 | 26.43 |
| 5912 | OH2 | TIP | 137 | 20.621 | 16.675 | −1.782 | 1 | 23.3 |
| 5913 | OH2 | TIP | 138 | 40.796 | −36.021 | −56.986 | 1 | 28.2 |
| 5914 | OH2 | TIP | 139 | 33.477 | −30.148 | 27.192 | 1 | 29.26 |
| 5915 | OH2 | TIP | 140 | 29.074 | 5.333 | 22.057 | 1 | 22.85 |
| 5916 | OH2 | TIP | 141 | −8.47 | −22.098 | −31.866 | 1 | 27.79 |
| 5917 | OH2 | TIP | 142 | 47.956 | 1.39 | −1.226 | 1 | 33.88 |
| 5918 | OH2 | TIP | 143 | 12.234 | 15.916 | 10.831 | 1 | 29.81 |
| 5919 | OH2 | TIP | 144 | 32.591 | −17.04 | −30.41 | 1 | 24.94 |
| 5920 | OH2 | TIP | 145 | 18.132 | −24.15 | 14.743 | 1 | 24.25 |
| 5921 | OH2 | TIP | 146 | 15.636 | 6.573 | 23.064 | 1 | 28.61 |
| 5922 | OH2 | TIP | 147 | 50.913 | −35.174 | −46.531 | 1 | 33.6 |
| 5923 | OH2 | TIP | 148 | 37.468 | −5.17 | 14.512 | 1 | 35.08 |
| 5924 | OH2 | TIP | 149 | 23.965 | −41.4 | −41.561 | 1 | 25.36 |
| 5925 | OH2 | TIP | 150 | 37.4 | −16.761 | 22.133 | 1 | 27.64 |
| 5926 | OH2 | TIP | 151 | −1.081 | −27.946 | −15.015 | 1 | 29.37 |
| 5927 | OH2 | TIP | 152 | 2.07 | −18.29 | −30.041 | 1 | 22.72 |
| 5928 | OH2 | TIP | 153 | −4.99 | −30.487 | −40.377 | 1 | 22.85 |
| 5929 | OH2 | TIP | 154 | −2.194 | −19.227 | −26.836 | 1 | 36.48 |
| 5930 | OH2 | TIP | 155 | 52.814 | −17.732 | −42.856 | 1 | 28.35 |
| 5931 | OH2 | TIP | 156 | 17.111 | −17.286 | 16.454 | 1 | 21.72 |
| 5932 | OH2 | TIP | 157 | 36.415 | 21.233 | 1.639 | 1 | 26.74 |
| 5933 | OH2 | TIP | 158 | 54.305 | −18.234 | −56.057 | 1 | 37.65 |
| 5934 | OH2 | TIP | 159 | 18.195 | −21.956 | −31.034 | 1 | 25.29 |
| 5935 | OH2 | TIP | 160 | 14.404 | 34.999 | 5.921 | 1 | 30.77 |
| 5936 | OH2 | TIP | 161 | 32.632 | 27.763 | 2.482 | 1 | 31.63 |
| 5937 | OH2 | TIP | 162 | 40.056 | 0.492 | 15.51 | 1 | 20.97 |
| 5938 | OH2 | TIP | 163 | 38.106 | 5.709 | −3.646 | 1 | 24.12 |
| 5939 | OH2 | TIP | 164 | 38.643 | −1.377 | 14.318 | 1 | 27.62 |
| 5940 | OH2 | TIP | 165 | 22.354 | −45.229 | −37.383 | 1 | 28.82 |
| 5941 | OH2 | TIP | 166 | −8.148 | −19.967 | −36.849 | 1 | 30.46 |
| 5942 | OH2 | TIP | 167 | 34.72 | −2.047 | 10.586 | 1 | 23.57 |
| 5943 | OH2 | TIP | 168 | −2.96 | −36.829 | −37.491 | 1 | 24.02 |
| 5944 | OH2 | TIP | 169 | −1.575 | −41.412 | −33.737 | 1 | 25.21 |
| 5945 | OH2 | TIP | 170 | 25.011 | −41.092 | −54.265 | 1 | 29.1 |
| 5946 | OH2 | TIP | 171 | 22.305 | 23.972 | −4.15 | 1 | 35.47 |
| 5947 | OH2 | TIP | 172 | −6.857 | −37.688 | −23.701 | 1 | 27.37 |
| 5948 | OH2 | TIP | 173 | 36.377 | 28.225 | 14.717 | 1 | 38.05 |
| 5949 | OH2 | TIP | 174 | 29.484 | 35.214 | 8.258 | 1 | 30.26 |
| 5950 | OH2 | TIP | 175 | 5.767 | −18.939 | 33.631 | 1 | 24.72 |
| 5951 | OH2 | TIP | 176 | 44.022 | 21.353 | 4.097 | 1 | 32.63 |
| 5952 | OH2 | TIP | 177 | 20.89 | 20.586 | 3.258 | 1 | 24.75 |
| 5953 | OH2 | TIP | 178 | 32.222 | −36.956 | −34.511 | 1 | 33.97 |
| 5954 | OH2 | TIP | 179 | −3.368 | −53.242 | −22.459 | 1 | 31.19 |
| 5955 | OH2 | TIP | 180 | 1.563 | −22.337 | −42.719 | 1 | 23.26 |
| 5956 | OH2 | TIP | 181 | 34.723 | 2.923 | −12.32 | 1 | 27.3 |
| 5957 | OH2 | TIP | 182 | 28.697 | −45.072 | −36.682 | 1 | 29.36 |
| 5958 | OH2 | TIP | 183 | 51.113 | −10.993 | −33.14 | 1 | 39.54 |
| 5959 | OH2 | TIP | 184 | 35.108 | 21.536 | −7.077 | 1 | 23.58 |
| 5960 | OH2 | TIP | 185 | 20.549 | −22.128 | −26.182 | 1 | 23.73 |
| 5961 | OH2 | TIP | 186 | 31.121 | −38.428 | −36.704 | 1 | 37.44 |
| 5962 | OH2 | TIP | 187 | 21.003 | 38.2 | 4.445 | 1 | 34.64 |
| 5963 | OH2 | TIP | 189 | 16.896 | −28.585 | 31.407 | 1 | 29.84 |
| 5964 | OH2 | TIP | 190 | 52.035 | −20.59 | −42.438 | 1 | 38.72 |
| 5965 | OH2 | TIP | 191 | 7.159 | −47.638 | −39.791 | 1 | 29.52 |
| 5966 | OH2 | TIP | 192 | 35.043 | −14.917 | 30.229 | 1 | 27.65 |
| 5967 | OH2 | TIP | 193 | 21.558 | 26.429 | −0.939 | 1 | 31.7 |
| 5968 | OH2 | TIP | 194 | 33.952 | −19.751 | −53.505 | 1 | 27.49 |
| 5969 | OH2 | TIP | 195 | 22.949 | −20.48 | −29.069 | 1 | 28.19 |
| 5970 | OH2 | TIP | 196 | 20.095 | −39.552 | −48.084 | 1 | 29.59 |
| 5971 | OH2 | TIP | 197 | 42.155 | 3.442 | −4.708 | 1 | 40.33 |
| 5972 | OH2 | TIP | 198 | 20.537 | 10.806 | 3.526 | 1 | 29.09 |
| 5973 | OH2 | TIP | 199 | 39.718 | 2.41 | 9.856 | 1 | 29.82 |
| 5974 | OH2 | TIP | 200 | 22.627 | −1.606 | 6.886 | 1 | 21.13 |
| 5975 | OH2 | TIP | 201 | 10.845 | −0.514 | 14.762 | 1 | 25.68 |
| 5976 | OH2 | TIP | 202 | 20.464 | −23.171 | −23.825 | 1 | 24.1 |
| 5977 | OH2 | TIP | 203 | 17.908 | −17.692 | 40.237 | 1 | 34.68 |
| 5978 | OH2 | TIP | 204 | 24.203 | 0.736 | 2.564 | 1 | 24.26 |
| 5979 | OH2 | TIP | 205 | 17.86 | 23.498 | 1.601 | 1 | 25.92 |
| 5980 | OH2 | TIP | 206 | 35.7 | 3.513 | −6.787 | 1 | 31.65 |
| 5981 | OH2 | TIP | 207 | 7.363 | −16.297 | −34.682 | 1 | 26.7 |
| 5982 | OH2 | TIP | 208 | 28.782 | −24.075 | 14.135 | 1 | 55.89 |
| 5983 | OH2 | TIP | 209 | 38.976 | −38.687 | −54.124 | 1 | 33.55 |
| 5984 | OH2 | TIP | 210 | 32.854 | −32.208 | 29.133 | 1 | 31.37 |
| 5985 | OH2 | TIP | 211 | 31.865 | −4.784 | 4.461 | 1 | 30.99 |
| 5986 | OH2 | TIP | 212 | 14.145 | −28.264 | 15.982 | 1 | 27.13 |
| 5987 | OH2 | TIP | 213 | 16.836 | 3.189 | 28.323 | 1 | 25.65 |
| 5988 | OH2 | TIP | 214 | 32.668 | −1.372 | 24.859 | 1 | 24.49 |
| 5989 | OH2 | TIP | 215 | 12.648 | −47.374 | −21.636 | 1 | 25.74 |
| 5990 | OH2 | TIP | 216 | 49.519 | −43.164 | −43.919 | 1 | 31.89 |
| 5991 | OH2 | TIP | 217 | 24.488 | 11.572 | 1.602 | 1 | 22.86 |
| 5992 | OH2 | TIP | 218 | 34.277 | −14.422 | 13.235 | 1 | 34.39 |
| 5993 | OH2 | TIP | 219 | 13.862 | 13.049 | 15.523 | 1 | 32.22 |
| 5994 | OH2 | TIP | 220 | 14.558 | −28.116 | −41.642 | 1 | 22.97 |
| 5995 | OH2 | TIP | 221 | 3.075 | −21.482 | 23.659 | 1 | 36.93 |
| 5996 | OH2 | TIP | 222 | 13.797 | 27.087 | 8.214 | 1 | 34.7 |
| 5997 | OH2 | TIP | 223 | 35.054 | −54.464 | −48.834 | 1 | 39.15 |
| 5998 | OH2 | TIP | 224 | 33.238 | −22.992 | 36.316 | 1 | 25.91 |
| 5999 | OH2 | TIP | 225 | 23.48 | −30.792 | −59.247 | 1 | 30.9 |
| 6000 | OH2 | TIP | 226 | 37.907 | −37.257 | −36.845 | 1 | 39.43 |
| 6001 | OH2 | TIP | 227 | 48.282 | 20.366 | 8.56 | 1 | 35.23 |
| 6002 | OH2 | TIP | 228 | 14.255 | 19.775 | 12.131 | 1 | 28.58 |
| 6003 | OH2 | TIP | 229 | 25.423 | 2.684 | −6.943 | 1 | 24.48 |
| 6004 | OH2 | TIP | 230 | −5.661 | −18.899 | −26.937 | 1 | 28.61 |
| 6005 | OH2 | TIP | 231 | 17.327 | 30.422 | 9.999 | 1 | 32.8 |
| 6006 | OH2 | TIP | 232 | 34.563 | −21.873 | 31.246 | 1 | 46.27 |
| 6007 | OH2 | TIP | 233 | 14.88 | 1.447 | 21.02 | 1 | 21.62 |
| 6008 | OH2 | TIP | 234 | 26.351 | −44.561 | −37.837 | 1 | 28.24 |
| 6009 | OH2 | TIP | 235 | 39.868 | 12.421 | −1.128 | 1 | 32.05 |
| 6010 | OH2 | TIP | 236 | 17.721 | −27.847 | 29 | 1 | 26.47 |
| 6011 | OH2 | TIP | 237 | 20.503 | −2.528 | 27.06 | 1 | 30.05 |
| 6012 | OH2 | TIP | 238 | 22.313 | 12.629 | −7.833 | 1 | 26.04 |
| 6013 | OH2 | TIP | 239 | 17.97 | 18.584 | 5.864 | 1 | 23.23 |
| 6014 | OH2 | TIP | 240 | 26.912 | 14.245 | −13.829 | 1 | 28.41 |
| 6015 | OH2 | TIP | 241 | 41.1 | 18.098 | 26.385 | 1 | 31.3 |
| 6016 | OH2 | TIP | 242 | 19.775 | 18.295 | 3.337 | 1 | 34.93 |
| 6017 | OH2 | TIP | 243 | 12.765 | −46.448 | −38.79 | 1 | 29.2 |
| 6018 | OH2 | TIP | 244 | −4.166 | −17.456 | −39.899 | 1 | 42.25 |
| 6019 | OH2 | TIP | 245 | 29.7 | −37.605 | −63.153 | 1 | 31.6 |
| 6020 | OH2 | TIP | 246 | 0.603 | −10.894 | 28.226 | 1 | 36.79 |
| 6021 | OH2 | TIP | 247 | −16.688 | −37.913 | −26.698 | 1 | 26.72 |
| 6022 | OH2 | TIP | 248 | 34.776 | 9.365 | −10.826 | 1 | 28.72 |
| 6023 | OH2 | TIP | 249 | 4.252 | −22.854 | 25.576 | 1 | 29.38 |
| 6024 | OH2 | TIP | 250 | 12.122 | −24.527 | −40.88 | 1 | 29.88 |
| 6025 | OH2 | TIP | 251 | 31.809 | 34.758 | 1.631 | 1 | 32.16 |
| 6026 | OH2 | TIP | 253 | 40.278 | 13.219 | 1.221 | 1 | 32.38 |
| 6027 | OH2 | TIP | 254 | 9.608 | −26.462 | −40.818 | 1 | 31.22 |
| 6028 | OH2 | TIP | 256 | 47.982 | −17.304 | −34.841 | 1 | 29.14 |

TABLE 1-continued

| Atom | Atom Type | Residue | # | X | Y | Z | OCC | B |
|---|---|---|---|---|---|---|---|---|
| 6029 | OH2 | TIP | 257 | 24.377 | −28.212 | −62.712 | 1 | 28.7 |
| 6030 | OH2 | TIP | 258 | 18.711 | −44.482 | −24.637 | 1 | 27.44 |
| 6031 | OH2 | TIP | 259 | 9.121 | −14.263 | 29.847 | 1 | 33.4 |
| 6032 | OH2 | TIP | 260 | 28.012 | −32.945 | −30.169 | 1 | 24.14 |
| 6033 | OH2 | TIP | 261 | 17.451 | −35.518 | −15.062 | 1 | 25.64 |
| 6034 | OH2 | TIP | 262 | 18.552 | 39.846 | 7.704 | 1 | 34.59 |
| 6035 | OH2 | TIP | 263 | 5.823 | −49.144 | −36.036 | 1 | 33.49 |
| 6036 | OH2 | TIP | 264 | 11.203 | −23.22 | 11.809 | 1 | 26.35 |
| 6037 | OH2 | TIP | 265 | 14.305 | −9.819 | 13.032 | 1 | 23.96 |
| 6038 | OH2 | TIP | 266 | 33.893 | −20.878 | −48.747 | 1 | 30.42 |
| 6039 | OH2 | TIP | 267 | 23.928 | −28.985 | 16.935 | 1 | 25.72 |
| 6040 | OH2 | TIP | 268 | 30.78 | −23.06 | −59.399 | 1 | 31.13 |
| 6041 | OH2 | TIP | 269 | 0.847 | −23.564 | −22.946 | 1 | 30.84 |
| 6042 | OH2 | TIP | 270 | 43.533 | −13.402 | −51.479 | 1 | 34.55 |
| 6043 | OH2 | TIP | 271 | 16.453 | 18.251 | 3.646 | 1 | 38.06 |
| 6044 | OH2 | TIP | 272 | 38.348 | 15.116 | −4.387 | 1 | 33.04 |
| 6045 | OH2 | TIP | 273 | −2.067 | −32.666 | −14.022 | 1 | 30.31 |
| 6046 | OH2 | TIP | 274 | 29.029 | −30.059 | −64.306 | 1 | 25.12 |
| 6047 | OH2 | TIP | 275 | 14.825 | −22.031 | −25.167 | 1 | 36.48 |
| 6048 | OH2 | TIP | 276 | 27.909 | −34.013 | −64.52 | 1 | 33.79 |
| 6049 | OH2 | TIP | 277 | 5.208 | −33.109 | −15.7 | 1 | 39.89 |
| 6050 | OH2 | TIP | 278 | 27.084 | −24.181 | −50.996 | 1 | 36.49 |
| 6051 | OH2 | TIP | 279 | 18.831 | −14.5 | 34.425 | 1 | 33.33 |
| 6052 | OH2 | TIP | 280 | 16.181 | 3.67 | 25.838 | 1 | 25.21 |
| 6053 | OH2 | TIP | 281 | 29.207 | −22.777 | −48.734 | 1 | 30.48 |
| 6054 | OH2 | TIP | 282 | 31.317 | −25.708 | −50.527 | 1 | 25.76 |
| 6055 | OH2 | TIP | 283 | 3.8 | −54.483 | −20.111 | 1 | 49.23 |
| 6056 | OH2 | TIP | 284 | −9.227 | −26.593 | −39.71 | 1 | 28.36 |
| 6057 | OH2 | TIP | 285 | 13.616 | −3.767 | 26.315 | 1 | 48.02 |
| 6058 | OH2 | TIP | 286 | 27.679 | 7.073 | 24.809 | 1 | 27.15 |
| 6059 | OH2 | TIP | 287 | 22.229 | 34.163 | −0.721 | 1 | 32.65 |
| 6060 | OH2 | TIP | 288 | 35.994 | −17.078 | −31.73 | 1 | 29.13 |
| 6061 | OH2 | TIP | 289 | 25.465 | −28.086 | 14.548 | 1 | 27.57 |
| 6062 | OH2 | TIP | 290 | 14.262 | −4.69 | 11.393 | 1 | 34.8 |
| 6063 | OH2 | TIP | 291 | 24.788 | 16.892 | −16.019 | 1 | 31.83 |
| 6064 | OH2 | TIP | 292 | −0.774 | −16.804 | −23.319 | 1 | 26.62 |
| 6065 | OH2 | TIP | 293 | 7.147 | −13.656 | 9.95 | 1 | 29.77 |
| 6066 | OH2 | TIP | 294 | 34.477 | −25.159 | 27.197 | 1 | 29.73 |
| 6067 | OH2 | TIP | 295 | 18.703 | 19.847 | 20.301 | 1 | 29.46 |
| 6068 | OH2 | TIP | 296 | 3.66 | −15.595 | −37.025 | 1 | 36.29 |
| 6069 | OH2 | TIP | 297 | 27.014 | 21.54 | 21.87 | 1 | 25.33 |
| 6070 | OH2 | TIP | 298 | 9.612 | −32.558 | −42.338 | 1 | 28.2 |
| 6071 | OH2 | TIP | 299 | 9.354 | −30.466 | 16.249 | 1 | 31.23 |
| 6072 | OH2 | TIP | 300 | 4.932 | −49.002 | −15.568 | 1 | 38.11 |
| 6073 | OH2 | TIP | 301 | 2.554 | −48.135 | −38.71 | 1 | 32.3 |
| 6074 | OH2 | TIP | 302 | 27.281 | 39.228 | 11.318 | 1 | 29.62 |
| 6075 | OH2 | TIP | 303 | 43.097 | −1.89 | 11.824 | 1 | 41.18 |
| 6076 | OH2 | TIP | 304 | 36.853 | 9.709 | −9.074 | 1 | 35.99 |
| 6077 | OH2 | TIP | 305 | 39.247 | 3.403 | −3.203 | 1 | 39.03 |
| 6078 | OH2 | TIP | 306 | 9.612 | −23.828 | −18.484 | 1 | 44.98 |
| 6079 | OH2 | TIP | 307 | 38.931 | −50.539 | −53.086 | 1 | 30.48 |
| 6080 | OH2 | TIP | 308 | 26.633 | 28.047 | −7.981 | 1 | 38.88 |
| 6081 | OH2 | TIP | 309 | 3.576 | −51.728 | −21.269 | 1 | 37.38 |
| 6082 | OH2 | TIP | 310 | 13.055 | −43.559 | −42.299 | 1 | 41.7 |
| 6083 | CO+2 | CO2 | 1 | 10.944 | −35.021 | −28.781 | 1 | 12.21 |
| 6084 | CO+2 | CO2 | 2 | 33.186 | −29.779 | −40.135 | 1 | 13.01 |
| 6085 | CO+2 | CO2 | 3 | 28.759 | 11.367 | 12.015 | 1 | 11.18 |
| 6086 | CO+2 | CO2 | 4 | 23.253 | −10.765 | 23.301 | 1 | 11.56 |
| 6087 | OH2 | TIP | 311 | 24.003 | 5.211 | 0.444 | 1 | 18.74 |
| 6088 | OH2 | TIP | 312 | 14.756 | −12.68 | 12.586 | 1 | 23.76 |
| 6089 | OH2 | TIP | 313 | 33.287 | −9.052 | 14.441 | 1 | 27.46 |
| 6090 | OH2 | TIP | 314 | 33.268 | −19.282 | 16.534 | 1 | 21.66 |
| 6091 | OH2 | TIP | 315 | 8.118 | −47.734 | −35.576 | 1 | 21.94 |
| 6092 | OH2 | TIP | 316 | 17.049 | −43.287 | −37.672 | 1 | 29.33 |
| 6093 | OH2 | TIP | 317 | 24.967 | 9.711 | −0.169 | 1 | 22.93 |
| 6094 | OH2 | TIP | 318 | 15.647 | 17.848 | 13.48 | 1 | 22.37 |
| 6095 | OH2 | TIP | 319 | 25.57 | −28.254 | −51.696 | 1 | 24.44 |
| 6096 | OH2 | TIP | 320 | −7.529 | −21.227 | −34.201 | 1 | 25.44 |
| 6097 | OH2 | TIP | 321 | 14.878 | −16.5 | 15.15 | 1 | 25.77 |
| 6098 | OH2 | TIP | 322 | 14.795 | 2.275 | 23.82 | 1 | 23.4 |
| 6099 | OH2 | TIP | 323 | 16.752 | 8.472 | 17.991 | 1 | 28.98 |
| 6100 | OH2 | TIP | 324 | 32.771 | −15.194 | −38.445 | 1 | 21.81 |
| 6101 | OH2 | TIP | 325 | 32.491 | 6.163 | 15.937 | 1 | 18.84 |
| 6102 | OH2 | TIP | 326 | 39.355 | −0.112 | 10.644 | 1 | 25.18 |
| 6103 | OH2 | TIP | 327 | 25.15 | −20.615 | −34.221 | 1 | 29.92 |
| 6104 | OH2 | TIP | 328 | 37.301 | −1.455 | 11.773 | 1 | 23.99 |
| 6105 | OH2 | TIP | 329 | 25.509 | 12.159 | 25.96 | 1 | 25.03 |
| 6106 | OH2 | TIP | 330 | 21.277 | −44.056 | −26.087 | 1 | 23.66 |
| 6107 | OH2 | TIP | 331 | 22.981 | −23.625 | 16.475 | 1 | 29.75 |
| 6108 | OH2 | TIP | 332 | 23.86 | 2.649 | −4.657 | 1 | 25.93 |
| 6109 | OH2 | TIP | 333 | 39.376 | 17.067 | 28.282 | 1 | 25.11 |
| 6110 | OH2 | TIP | 334 | −8.522 | −42.605 | −32.026 | 1 | 32.57 |
| 6111 | OH2 | TIP | 335 | 22.398 | 9.523 | −1.434 | 1 | 29.94 |
| 6112 | OH2 | TIP | 336 | 24.213 | −30.421 | −50.372 | 1 | 26.06 |
| 6113 | OH2 | TIP | 337 | 21.881 | 36.224 | 13.961 | 1 | 33.07 |
| 6114 | OH2 | TIP | 338 | 35.226 | −26.388 | −27.868 | 1 | 24.99 |
| 6115 | OH2 | TIP | 339 | 20.61 | −31.372 | 20.27 | 1 | 38.01 |
| 6116 | OH2 | TIP | 340 | 40.863 | −12.684 | 18.468 | 1 | 33.78 |
| 6117 | OH2 | TIP | 341 | −3.343 | −31.827 | −21.636 | 1 | 27.91 |
| 6118 | OH2 | TIP | 342 | 11.474 | −35.037 | −43.21 | 1 | 28.82 |
| 6119 | OH2 | TIP | 343 | 34.552 | −16.797 | −46.098 | 1 | 27.29 |
| 6120 | OH2 | TIP | 344 | 22.296 | 19.575 | 22.503 | 1 | 30.95 |
| 6121 | OH2 | TIP | 345 | 29.883 | −26.894 | −52.376 | 1 | 23.17 |
| 6122 | OH2 | TIP | 346 | 33.869 | −35.707 | −62.921 | 1 | 35.18 |
| 6123 | OH2 | TIP | 347 | −0.646 | −22.298 | −24.606 | 1 | 33.49 |
| 6124 | OH2 | TIP | 348 | −0.386 | −15.041 | 16.791 | 1 | 36.69 |
| 6125 | OH2 | TIP | 349 | 25.237 | 18.778 | −12.479 | 1 | 32.94 |
| 6126 | OH2 | TIP | 350 | 8.705 | −26.641 | −23.289 | 1 | 42.11 |
| 6127 | OH2 | TIP | 351 | 37.515 | −20.359 | −29.379 | 1 | 30.58 |
| 6128 | OH2 | TIP | 352 | 12.985 | −1.32 | 27.05 | 1 | 34.13 |
| 6129 | OH2 | TIP | 353 | −3.475 | −26.756 | −15.178 | 1 | 27.93 |
| 6130 | OH2 | TIP | 354 | 10.203 | −13.259 | 9.42 | 1 | 33.33 |
| 6131 | OH2 | TIP | 355 | 17.167 | 4.139 | 7.663 | 1 | 30.8 |
| 6132 | OH2 | TIP | 356 | 2.429 | −8.522 | 15.93 | 1 | 33.82 |
| 6133 | OH2 | TIP | 357 | 21.276 | −22.671 | −44.388 | 1 | 32.9 |
| 6134 | OH2 | TIP | 358 | 30.812 | −15.605 | −28.707 | 1 | 31.76 |
| 6135 | OH2 | TIP | 359 | 39.822 | −38.943 | −51.835 | 1 | 34.39 |
| 6136 | OH2 | TIP | 360 | 16.99 | −29.081 | −25.033 | 1 | 41.4 |
| 6137 | OH2 | TIP | 361 | 34.95 | −8.219 | 27.424 | 1 | 27.17 |
| 6138 | OH2 | TIP | 362 | 35.514 | 5.729 | 15.308 | 1 | 38.46 |
| 6139 | OH2 | TIP | 363 | 47.043 | 21.162 | 10.857 | 1 | 41.77 |
| 6140 | OH2 | TIP | 364 | 41.654 | 24.986 | 5.839 | 1 | 33.22 |
| 6141 | OH2 | TIP | 365 | 27.966 | −16.1 | 11.361 | 1 | 26.92 |
| 6142 | OH2 | TIP | 366 | −5.745 | −38.308 | −19.991 | 1 | 31.67 |
| 6143 | OH2 | TIP | 367 | 31.951 | 13.132 | −13.241 | 1 | 32.06 |
| 6144 | OH2 | TIP | 368 | 29.809 | −36.315 | 18.881 | 1 | 34.42 |
| 6145 | OH2 | TIP | 369 | 23.772 | −9.919 | 8.739 | 1 | 30.84 |
| 6146 | OH2 | TIP | 370 | 3.647 | −13.1 | −18.722 | 1 | 39.45 |
| 6147 | OH2 | TIP | 371 | 16.098 | −32.246 | −24.073 | 1 | 48.18 |
| 6148 | OH2 | TIP | 372 | 37.449 | −14.193 | 25.811 | 1 | 30.42 |
| 6149 | OH2 | TIP | 373 | 1.054 | −38.169 | −35.705 | 1 | 36.18 |
| 6150 | OH2 | TIP | 374 | 51.218 | −13.855 | −40.014 | 1 | 31.31 |
| 6151 | OH2 | TIP | 375 | 28.428 | −28.338 | −66.203 | 1 | 37.66 |
| 6152 | OH2 | TIP | 376 | 32.726 | −28.38 | 21.254 | 1 | 31.85 |
| 6153 | OH2 | TIP | 377 | −11.286 | −25.413 | −38.39 | 1 | 32.83 |
| 6154 | OH2 | TIP | 378 | 3.595 | −24.24 | 13.835 | 1 | 30.45 |
| 6155 | OH2 | TIP | 379 | 38.791 | −14.291 | −50.194 | 1 | 29.5 |
| 6156 | OH2 | TIP | 380 | 27.659 | −15.844 | −36.396 | 1 | 32.94 |
| 6157 | OH2 | TIP | 381 | 21.656 | −45.01 | −39.819 | 1 | 43.68 |
| 6158 | OH2 | TIP | 382 | 7.476 | −18.204 | −37.851 | 1 | 29.47 |
| 6159 | OH2 | TIP | 383 | −4.623 | −44.374 | −35.446 | 1 | 29.79 |
| 6160 | OH2 | TIP | 384 | −3.267 | −16.209 | −35.497 | 1 | 30.78 |
| 6161 | OH2 | TIP | 385 | 17.336 | −51.635 | −33.777 | 1 | 31.72 |
| 6162 | OH2 | TIP | 386 | 19.105 | −0.947 | 8.468 | 1 | 33.89 |
| 6163 | OH2 | TIP | 387 | 25.075 | −19.687 | 39.921 | 1 | 34.62 |
| 6164 | OH2 | TIP | 388 | 10.444 | −47.564 | −20.172 | 1 | 29.31 |
| 6165 | OH2 | TIP | 389 | 39.449 | 21.297 | −2.26 | 1 | 35.7 |
| 6166 | OH2 | TIP | 390 | 44.812 | −37.74 | −25.89 | 1 | 25.16 |
| 6167 | OH2 | TIP | 391 | 20.556 | −16.652 | 13.413 | 1 | 32.9 |
| 6168 | OH2 | TIP | 392 | 39.709 | −23.546 | −64.345 | 1 | 37.62 |
| 6169 | OH2 | TIP | 393 | 1.258 | −16.445 | −21.66 | 1 | 36.09 |
| 6170 | OH2 | TIP | 394 | 23.04 | −35.237 | −59.668 | 1 | 30.44 |
| 6171 | OH2 | TIP | 395 | 12.53 | −18.942 | 37.763 | 1 | 40.32 |
| 6172 | OH2 | TIP | 396 | 2.573 | −19.767 | −43.419 | 1 | 36.44 |
| 6173 | OH2 | TIP | 397 | 33.293 | −11.685 | −43.695 | 1 | 34.51 |
| 6174 | OH2 | TIP | 398 | 36.517 | −38.272 | −44.067 | 1 | 33.79 |
| 6175 | OH2 | TIP | 399 | 23.117 | −38.012 | −54.521 | 1 | 30.29 |
| 6176 | OH2 | TIP | 400 | 51.662 | −28.98 | −37.298 | 1 | 40.22 |
| 6177 | OH2 | TIP | 401 | −0.622 | −19.737 | −14.527 | 1 | 39.9 |
| 6178 | OH2 | TIP | 402 | 25.22 | −43.498 | −49.791 | 1 | 40.5 |
| 6179 | OH2 | TIP | 403 | 21.218 | −32.605 | −59.418 | 1 | 30.69 |
| 6180 | OH2 | TIP | 404 | 11.994 | −31.395 | 19.041 | 1 | 37.45 |

TABLE 1-continued

| Atom | Atom Type | Residue | # | X | Y | Z | OCC | B |
|---|---|---|---|---|---|---|---|---|
| 6181 | OH2 | TIP | 405 | 17.87 | −15.902 | 12.053 | 1 | 39.89 |
| 6182 | OH2 | TIP | 406 | 7.787 | −42.149 | −41.026 | 1 | 33.75 |
| 6183 | OH2 | TIP | 407 | 17.631 | −49.654 | −27.159 | 1 | 39.21 |
| 6184 | OH2 | TIP | 408 | 25.819 | −43.133 | −40.475 | 1 | 27.99 |
| 6185 | OH2 | TIP | 409 | 32.734 | −31.36 | 23.035 | 1 | 36.52 |
| 6186 | OH2 | TIP | 410 | −2.558 | −52.938 | −29.135 | 1 | 34.56 |
| 6187 | OH2 | TIP | 411 | 37.094 | −5.262 | 12.038 | 1 | 49.39 |
| 6188 | OH2 | TIP | 412 | 37.757 | −19.825 | −58.162 | 1 | 30.94 |
| 6189 | OH2 | TIP | 413 | 9.596 | −49.842 | −8.283 | 1 | 45.14 |
| 6190 | OH2 | TIP | 414 | 15.988 | −40.711 | −45.888 | 1 | 40.94 |
| 6191 | OH2 | TIP | 415 | 38.76 | −39.945 | −40.002 | 1 | 47.1 |
| 6192 | OH2 | TIP | 416 | 9.487 | −26.013 | −20.108 | 1 | 46.55 |
| 6193 | OH2 | TIP | 417 | 23.792 | 38.047 | 18.522 | 1 | 42.86 |
| 6194 | OH2 | TIP | 418 | 26.6 | −21.369 | 38.562 | 1 | 33.92 |
| 6195 | OH2 | TIP | 419 | 32.867 | 36.838 | −3.79 | 1 | 33.51 |
| 6196 | OH2 | TIP | 420 | 15.004 | 15.624 | 23.231 | 1 | 31.77 |
| 6197 | OH2 | TIP | 421 | 24.779 | 30.102 | 17.116 | 1 | 29.59 |
| 6198 | OH2 | TIP | 422 | 3.861 | −32.762 | −39.439 | 1 | 37.9 |
| 6199 | OH2 | TIP | 423 | 13.393 | −31.277 | −20.349 | 1 | 46.5 |
| 6200 | OH2 | TIP | 424 | 4.425 | −11.58 | 34.834 | 1 | 39.44 |
| 6201 | OH2 | TIP | 425 | 22.668 | −37.97 | −58.476 | 1 | 41.4 |
| 6202 | OH2 | TIP | 426 | 18.377 | −18.363 | −38.824 | 1 | 39.97 |
| 6203 | OH2 | TIP | 427 | 2.169 | −52.428 | −30.577 | 1 | 46.58 |
| 6204 | OH2 | TIP | 428 | 25.348 | −7.75 | 7.999 | 1 | 38.28 |
| 6205 | OH2 | TIP | 429 | 12.327 | −50.493 | −29.688 | 1 | 28.46 |
| 6206 | OH2 | TIP | 430 | 24.369 | −4.503 | 4.71 | 1 | 29.05 |
| 6207 | OH2 | TIP | 431 | 28.017 | 7.155 | −12.189 | 1 | 35.79 |
| 6208 | OH2 | TIP | 432 | 7.994 | −26.956 | −38.823 | 1 | 34.15 |
| 6209 | OH2 | TIP | 433 | 33.786 | −13.045 | −39.872 | 1 | 32.42 |
| 6210 | OH2 | TIP | 434 | 34.946 | −20.481 | −26.995 | 1 | 40.88 |
| 6211 | OH2 | TIP | 435 | 19.079 | 39.319 | 3.031 | 1 | 39.96 |
| 6212 | OH2 | TIP | 436 | 43.998 | −23.644 | −31.402 | 1 | 33.49 |
| 6213 | OH2 | TIP | 437 | 11.91 | 6.408 | 11.946 | 1 | 40 |
| 6214 | OH2 | TIP | 438 | 35.588 | −33.111 | 30.474 | 1 | 41.73 |
| 6215 | OH2 | TIP | 439 | 38.094 | 10.402 | 8.257 | 1 | 25.83 |
| 6216 | OH2 | TIP | 440 | 19.636 | −24.907 | −43.981 | 1 | 41.79 |
| 6217 | OH2 | TIP | 441 | 43.16 | −15.787 | −52.87 | 1 | 36.42 |
| 6218 | OH2 | TIP | 442 | −12.441 | −34.956 | −22.104 | 1 | 37.92 |
| 6219 | OH2 | TIP | 443 | 17.861 | −26.892 | −43.674 | 1 | 33.74 |
| 6220 | OH2 | TIP | 444 | 33.406 | −6.708 | 13.633 | 1 | 33.73 |
| 6221 | OH2 | TIP | 445 | −0.26 | −40.45 | −35.725 | 1 | 34.95 |
| 6222 | OH2 | TIP | 446 | 32.237 | −41.261 | −37.068 | 1 | 39.32 |
| 6223 | OH2 | TIP | 447 | 46.436 | −34.627 | −54.835 | 1 | 38.86 |
| 6224 | OH2 | TIP | 448 | 25.801 | −3.92 | 29.667 | 1 | 40.47 |
| 6225 | OH2 | TIP | 449 | 3.302 | −51.477 | −24.589 | 1 | 40.53 |
| 6226 | OH2 | TIP | 450 | 3.777 | −16.256 | −30.345 | 1 | 37.09 |
| 6227 | OH2 | TIP | 451 | 15.034 | −31.314 | −43.617 | 1 | 41.45 |
| 6228 | OH2 | TIP | 452 | 5.163 | −15.824 | −15.186 | 1 | 41.9 |
| 6229 | OH2 | TIP | 453 | 19.217 | −1.679 | 29.278 | 1 | 36.72 |
| 6230 | OH2 | TIP | 454 | 28.3 | −31.747 | 32.198 | 1 | 39.45 |
| 6231 | OH2 | TIP | 455 | 13.083 | −22.182 | −39.967 | 1 | 37.89 |
| 6232 | OH2 | TIP | 456 | 47.198 | 21.662 | 6.137 | 1 | 42.5 |
| 6233 | OH2 | TIP | 457 | 20.756 | −42.258 | −47.904 | 1 | 36.87 |
| 6234 | OH2 | TIP | 458 | 30.811 | −10.279 | 40.418 | 1 | 39.84 |
| 6235 | OH2 | TIP | 459 | 11.15 | −28.268 | −18.862 | 1 | 43.26 |
| 6236 | OH2 | TIP | 460 | −0.002 | −16.512 | 13.641 | 1 | 47.17 |
| 6237 | OH2 | TIP | 461 | 20.924 | −24.85 | 14.864 | 1 | 40.05 |
| 6238 | OH2 | TIP | 462 | 2.519 | −32.703 | −35.796 | 1 | 34.54 |
| 6239 | OH2 | TIP | 463 | 2.03 | −30.71 | −37.367 | 1 | 38.29 |
| 6240 | OH2 | TIP | 464 | 44.984 | −7.6 | −47.822 | 1 | 37.3 |
| 6241 | OH2 | TIP | 465 | 20.694 | 37.461 | 11.992 | 1 | 39.66 |
| 6242 | OH2 | TIP | 466 | 15.012 | −2.602 | 9.668 | 1 | 35.43 |
| 6243 | OH2 | TIP | 467 | 29.475 | −12.934 | −41.108 | 1 | 34.56 |
| 6244 | OH2 | TIP | 468 | −2.067 | −52.359 | −33.956 | 1 | 38.26 |
| 6245 | OH2 | TIP | 469 | −9.901 | −23.036 | −38.138 | 1 | 37.22 |
| 6246 | OH2 | TIP | 470 | 36.382 | −2.638 | 3.27 | 1 | 31.89 |
| 6247 | OH2 | TIP | 471 | −8.543 | −34.909 | −36.638 | 1 | 35 |
| 6248 | OH2 | TIP | 472 | 14.527 | −24.092 | −42.665 | 1 | 42.58 |
| 6249 | OH2 | TIP | 473 | 27.847 | 2.594 | −10.864 | 1 | 36.8 |
| 6250 | OH2 | TIP | 474 | 38.277 | 17.71 | −4.896 | 1 | 38.66 |
| 6251 | OH2 | TIP | 475 | 28.758 | −26.267 | −63.939 | 1 | 35.87 |
| 6252 | OH2 | TIP | 476 | 12.452 | 11.85 | 13.509 | 1 | 34.81 |
| 6253 | OH2 | TIP | 477 | 27.166 | −34.291 | 19.857 | 1 | 38.28 |
| 6254 | OH2 | TIP | 478 | 21.578 | −30.507 | −49.543 | 1 | 33.07 |
| 6255 | OH2 | TIP | 479 | 13.913 | 7.374 | 15.269 | 1 | 36.38 |
| 6256 | OH2 | TIP | 480 | 32.667 | −9.867 | 10.7 | 1 | 38.59 |
| 6257 | OH2 | TIP | 481 | 14.885 | −8.054 | 11.145 | 1 | 31 |
| 6258 | OH2 | TIP | 482 | 41.563 | −23.659 | −30.223 | 1 | 31.92 |
| 6259 | OH2 | TIP | 483 | 15.655 | −25.314 | 36.317 | 1 | 38.23 |
| 6260 | OH2 | TIP | 484 | 5.849 | −11.596 | 8.927 | 1 | 35.32 |
| 6261 | OH2 | TIP | 485 | 15.413 | 1.81 | 9.168 | 1 | 45.21 |
| 6262 | OH2 | TIP | 486 | 12.258 | −17.148 | −32.023 | 1 | 39.14 |
| 6263 | OH2 | TIP | 487 | 32.477 | −20.796 | −51.03 | 1 | 38.13 |
| 6264 | OH2 | TIP | 488 | 25.227 | 19.733 | 21.435 | 1 | 36.17 |
| 6265 | OH2 | TIP | 489 | −7.628 | −40.524 | −34.088 | 1 | 34.49 |
| 6266 | OH2 | TIP | 490 | 17.853 | −19.595 | 14.711 | 1 | 35.16 |
| 6267 | OH2 | TIP | 491 | 2.922 | −42.191 | −13.646 | 1 | 40.13 |
| 6268 | OH2 | TIP | 492 | 21.679 | −7.229 | 8.366 | 1 | 37.2 |
| 6269 | OH2 | TIP | 493 | 13.377 | −47.09 | −24.13 | 1 | 42.01 |
| 6270 | OH2 | TIP | 494 | 34.877 | −25.425 | 30.277 | 1 | 35.69 |
| 6271 | OH2 | TIP | 495 | 44.186 | −35.495 | −41.983 | 1 | 38.87 |
| 6272 | OH2 | TIP | 496 | 12.815 | 4.74 | 25.203 | 1 | 36.67 |
| 6273 | OH2 | TIP | 497 | 22.666 | −18.531 | −36.628 | 1 | 34.83 |
| 6274 | OH2 | TIP | 498 | −2.501 | −56.06 | −21.03 | 1 | 42.74 |
| 6275 | OH2 | TIP | 499 | 33.689 | 11.797 | −11.114 | 1 | 37.93 |
| 6276 | OH2 | TIP | 500 | 30.206 | −43.839 | −42.806 | 1 | 34.08 |
| 6277 | OH2 | TIP | 501 | 35.627 | 29.447 | 12.319 | 1 | 45.17 |
| 6278 | OH2 | TIP | 502 | 25.626 | −20.769 | −45.559 | 1 | 42.79 |
| 6279 | OH2 | TIP | 503 | 13.596 | −41.573 | −44.864 | 1 | 39.87 |
| 6280 | OH2 | TIP | 504 | −8.703 | −45.559 | −32.056 | 1 | 35.68 |
| 6281 | OH2 | TIP | 505 | 23.601 | −3.011 | 28.22 | 1 | 36.8 |
| 6282 | OH2 | TIP | 506 | 20.903 | 23.382 | −2.002 | 1 | 32.51 |
| 6283 | OH2 | TIP | 507 | 32.567 | −50.825 | −54.422 | 1 | 35.92 |
| 6284 | OH2 | TIP | 508 | 7.051 | −2.119 | 26.71 | 1 | 39.86 |
| 6285 | OH2 | TIP | 509 | 40.05 | 11.841 | 11.698 | 1 | 47.35 |
| 6286 | OH2 | TIP | 510 | 28.425 | 37.02 | 17.984 | 1 | 42.79 |
| 6287 | OH2 | TIP | 511 | 51.588 | −31.676 | −37.102 | 1 | 43.16 |
| 6288 | OH2 | TIP | 512 | 0.785 | −27.708 | −10.835 | 1 | 40.26 |
| 6289 | OH2 | TIP | 513 | 23.001 | 14.96 | −17.254 | 1 | 36.3 |
| 6290 | OH2 | TIP | 514 | 30.898 | 30.302 | 18.728 | 1 | 36.98 |
| 6291 | OH2 | TIP | 515 | 55.34 | −21.599 | −50.427 | 1 | 39.75 |
| 6292 | OH2 | TIP | 516 | 16.524 | 19.855 | 18.766 | 1 | 41.74 |
| 6293 | OH2 | TIP | 517 | 34.639 | 9.298 | 19.433 | 1 | 37.76 |
| 6294 | OH2 | TIP | 518 | 8.99 | −44.58 | −41.425 | 1 | 35.73 |
| 6295 | OH2 | TIP | 519 | 32.684 | −30.099 | 17.919 | 1 | 33.22 |
| 6296 | OH2 | TIP | 520 | −0.175 | −51.705 | −30.912 | 1 | 39.61 |
| 6297 | OH2 | TIP | 521 | −9.52 | −31.193 | −41.615 | 1 | 44.11 |
| 6298 | OH2 | TIP | 522 | 39.326 | −11.495 | 24.699 | 1 | 36.98 |
| 6299 | OH2 | TIP | 523 | 31.61 | −16.933 | 10.796 | 1 | 34.6 |
| 6300 | OH2 | TIP | 524 | 14.43 | −36.562 | −45.325 | 1 | 44.5 |
| 6301 | OH2 | TIP | 525 | 37.984 | −20.402 | 24.207 | 1 | 41.21 |
| 6302 | OH2 | TIP | 526 | 44.436 | 21.455 | 1.311 | 1 | 34.06 |
| 6303 | OH2 | TIP | 527 | 25.359 | −47.148 | −40.337 | 1 | 36.22 |
| 6304 | OH2 | TIP | 528 | 35.184 | −37.236 | −61.35 | 1 | 34.52 |
| 6305 | OH2 | TIP | 529 | 8.476 | −15.679 | −32.472 | 1 | 40.92 |
| 6306 | OH2 | TIP | 530 | 29.848 | −48.665 | −48.304 | 1 | 40.51 |
| 6307 | OH2 | TIP | 531 | 9.282 | 0.753 | 16.59 | 1 | 39.42 |
| 6308 | OH2 | TIP | 532 | 33.785 | −35.922 | −32.654 | 1 | 34.85 |
| 6309 | OH2 | TIP | 533 | −1.249 | −52.925 | −24.556 | 1 | 41.44 |
| 6310 | OH2 | TIP | 534 | 43.91 | −10.221 | −48.641 | 1 | 37.63 |
| 6311 | OH2 | TIP | 535 | 5.95 | −46.959 | −14.167 | 1 | 44.94 |
| 6312 | OH2 | TIP | 536 | 52.097 | −18.273 | −57.47 | 1 | 35.04 |
| 6313 | OH2 | TIP | 537 | 26.161 | −43.031 | −53.012 | 1 | 39.95 |
| 6314 | OH2 | TIP | 538 | −0.026 | −42.964 | −38.291 | 1 | 41.27 |
| 6315 | OH2 | TIP | 539 | 30.534 | −42.367 | −55.859 | 1 | 39.65 |
| 6316 | OH2 | TIP | 540 | 7.944 | −1.674 | 20.311 | 1 | 41.46 |
| 6317 | OH2 | TIP | 541 | 19.592 | 29.748 | 11.39 | 1 | 43.83 |
| 6318 | OH2 | TIP | 542 | 17.34 | −8.131 | 32.935 | 1 | 43.71 |
| 6319 | OH2 | TIP | 543 | 45.115 | 6.615 | −4.878 | 1 | 39.23 |
| 6320 | OH2 | TIP | 544 | 50.009 | 7.635 | −0.354 | 1 | 44.25 |
| 6321 | OH2 | TIP | 545 | 34.585 | −17.839 | −27.991 | 1 | 41.58 |
| 6322 | OH2 | TIP | 546 | 37.364 | −39.566 | −57.762 | 1 | 33.74 |
| 6323 | OH2 | TIP | 547 | 24.396 | −3.285 | 34.815 | 1 | 48.93 |
| 6324 | OH2 | TIP | 548 | 39.024 | 25.767 | 18.291 | 1 | 53.34 |
| 6325 | OH2 | TIP | 549 | 40.445 | −3.396 | 11.727 | 1 | 37.86 |
| 6326 | OH2 | TIP | 550 | 29.13 | 25.924 | 28.825 | 1 | 45.04 |
| 6327 | OH2 | TIP | 551 | 39.19 | −43.84 | −43.135 | 1 | 44.5 |
| 6328 | OH2 | TIP | 552 | 43.966 | 10.617 | 9.319 | 1 | 36.99 |
| 6329 | OH2 | TIP | 553 | 11.23 | −20.102 | −38.911 | 1 | 34.82 |
| 6330 | OH2 | TIP | 554 | 44.496 | 9.751 | −3.991 | 1 | 41.92 |
| 6331 | OH2 | TIP | 555 | 21.619 | 28.404 | 15.276 | 1 | 40.59 |
| 6332 | OH2 | TIP | 556 | 35.216 | 5.102 | −10.791 | 1 | 35.55 |

TABLE 1-continued

| Atom | Atom Type | Residue | # | X | Y | Z | OCC | B |
|---|---|---|---|---|---|---|---|---|
| 6333 | OH2 | TIP | 557 | 22.748 | 19.626 | −6.213 | 1 | 39.72 |
| 6334 | OH2 | TIP | 558 | 33.453 | −31.441 | −65.957 | 1 | 41.19 |
| 6335 | OH2 | TIP | 559 | 10.407 | −11.099 | −18.287 | 1 | 41.64 |
| 6336 | OH2 | TIP | 560 | 41.136 | −38.106 | −55.506 | 1 | 46.32 |
| 6337 | OH2 | TIP | 561 | 40.797 | −12.903 | −36.245 | 1 | 42.6 |
| 6338 | OH2 | TIP | 562 | 17.322 | −31.546 | −26.738 | 1 | 23.48 |
| 6339 | OH2 | TIP | 563 | −12.534 | −22.167 | −31.412 | 1 | 23.61 |
| 6340 | OH2 | TIP | 564 | 23.982 | 4.102 | −2.047 | 1 | 24.25 |
| 6341 | OH2 | TIP | 565 | 32.49 | 10.039 | 9.662 | 1 | 24.58 |
| 6342 | OH2 | TIP | 566 | 9.89 | −30.872 | −27.242 | 1 | 25.87 |
| 6343 | OH2 | TIP | 567 | 14.542 | 9.572 | 17.14 | 1 | 27.81 |
| 6344 | OH2 | TIP | 568 | 15.949 | 7.802 | 20.721 | 1 | 29.3 |
| 6345 | OH2 | TIP | 569 | 19.039 | −9.834 | 24.812 | 1 | 24.41 |
| 6346 | OH2 | TIP | 570 | 15.22 | −9.076 | 28.748 | 1 | 27.4 |
| 6347 | OH2 | TIP | 571 | 33.771 | −33.597 | −42.559 | 1 | 25.34 |
| 6348 | OH2 | TIP | 572 | 34.311 | −10.85 | 12.631 | 1 | 33.29 |
| 6349 | OH2 | TIP | 573 | 33.037 | −37.396 | −42.178 | 1 | 27.89 |
| 6350 | OH2 | TIP | 574 | 16.871 | −6.87 | 26 | 1 | 30.05 |
| 6351 | OH2 | TIP | 575 | 37.895 | 4.605 | 9.065 | 1 | 31.12 |
| 6352 | OH2 | TIP | 576 | 33.321 | 15.189 | −13.682 | 1 | 39.84 |
| 6353 | OH2 | TIP | 577 | 34.522 | 7.276 | 17.683 | 1 | 29.11 |
| 6354 | OH2 | TIP | 578 | 15.81 | −44.983 | −39.275 | 1 | 32.28 |
| 6355 | OH2 | TIP | 579 | 40.869 | −38.058 | −29.783 | 1 | 28.42 |
| 6356 | OH2 | TIP | 580 | 15.264 | −17.69 | 12.716 | 1 | 34.74 |
| 6357 | OH2 | TIP | 581 | 23.222 | −33.151 | 20.113 | 1 | 29.85 |
| 6358 | OH2 | TIP | 582 | 27.926 | 39.799 | 17.645 | 1 | 31.51 |
| 6359 | OH2 | TIP | 583 | 12.354 | −12.73 | 11.344 | 1 | 34.42 |
| 6360 | OH2 | TIP | 584 | 38.767 | 18.71 | 10.284 | 1 | 31.01 |
| 6361 | OH2 | TIP | 585 | 20.488 | −19.445 | −28.414 | 1 | 32.99 |
| 6362 | OH2 | TIP | 586 | 25.063 | −17.703 | −35.027 | 1 | 29.13 |
| 6363 | OH2 | TIP | 587 | 18.198 | −33.872 | −22.559 | 1 | 31.35 |
| 6364 | OH2 | TIP | 588 | 32.571 | 20.452 | −10.555 | 1 | 32.75 |
| 6365 | OH2 | TIP | 589 | 2.056 | −24.988 | 11.617 | 1 | 35.89 |
| 6366 | OH2 | TIP | 590 | 27.73 | −44.598 | −41.65 | 1 | 31.16 |
| 6367 | OH2 | TIP | 591 | 41.299 | 11.054 | 9.446 | 1 | 40.41 |
| 6368 | OH2 | TIP | 592 | 48.839 | −38.658 | −48.48 | 1 | 38.08 |
| 6369 | OH2 | TIP | 593 | 23.75 | −20.21 | −31.513 | 1 | 40.74 |
| 6370 | OH2 | TIP | 594 | 37.675 | −18.364 | −48.563 | 1 | 32.83 |
| 6371 | OH2 | TIP | 595 | 14.835 | 18.021 | 16.255 | 1 | 37.43 |
| 6372 | OH2 | TIP | 596 | 30.856 | 8.868 | −13.404 | 1 | 31.14 |
| 6373 | OH2 | TIP | 597 | 39.148 | 20.81 | 24.057 | 1 | 38.22 |
| 6374 | OH2 | TIP | 598 | 22.353 | 12.942 | 0.634 | 1 | 31.33 |
| 6375 | OH2 | TIP | 599 | 12.451 | −23.951 | −25.795 | 1 | 38.94 |
| 6376 | OH2 | TIP | 600 | 34.674 | 13.847 | −9.577 | 1 | 40.17 |
| 6377 | OH2 | TIP | 601 | 21.159 | 16.025 | 3.207 | 1 | 30.47 |
| 6378 | OH2 | TIP | 602 | 18.503 | −24.421 | −22.504 | 1 | 34.89 |
| 6379 | OH2 | TIP | 603 | 12.342 | 2.757 | 20.388 | 1 | 34.07 |
| 6380 | OH2 | TIP | 604 | 36.078 | −13.238 | −49.411 | 1 | 37.51 |
| 6381 | OH2 | TIP | 605 | 29.129 | −39.136 | −59.653 | 1 | 36.87 |
| 6382 | OH2 | TIP | 606 | 35.811 | −7.196 | 14.48 | 1 | 36.01 |
| 6383 | OH2 | TIP | 607 | 45.991 | −39.948 | −34.039 | 1 | 39.46 |
| 6384 | OH2 | TIP | 608 | 19.879 | −44.441 | −37.788 | 1 | 40.11 |
| 6385 | OH2 | TIP | 609 | 35.533 | 7.764 | 9.88 | 1 | 34.46 |
| 6386 | OH2 | TIP | 610 | 43.265 | −21.318 | −32.493 | 1 | 38.8 |
| 6387 | OH2 | TIP | 611 | 21.171 | 13.346 | −3.985 | 1 | 38.74 |
| 6388 | OH2 | TIP | 612 | 3.88 | −8.834 | 22.818 | 1 | 44.38 |
| 6389 | OH2 | TIP | 613 | 11.856 | −27.686 | −25.93 | 1 | 31.01 |
| 6390 | OH2 | TIP | 614 | 11.975 | −33.469 | −11.473 | 1 | 41.47 |
| 6391 | OH2 | TIP | 615 | 35.076 | −18.511 | −48.643 | 1 | 38.72 |
| 6392 | OH2 | TIP | 616 | 19.742 | −43.511 | −40.936 | 1 | 39.95 |
| 6393 | OH2 | TIP | 617 | 13.14 | 20.08 | 7.865 | 1 | 34.48 |
| 6394 | OH2 | TIP | 618 | 25.646 | 26.494 | −5.356 | 1 | 35.66 |
| 6395 | OH2 | TIP | 619 | 39.88 | 10.418 | −5.411 | 1 | 37.9 |
| 6396 | OH2 | TIP | 620 | 40.222 | −16.831 | −54.199 | 1 | 38.58 |
| 6397 | OH2 | TIP | 621 | 21.467 | 4.716 | 0.141 | 1 | 38.9 |
| 6398 | OH2 | TIP | 622 | 22.08 | −43.418 | −43.164 | 1 | 38.22 |
| 6399 | OH2 | TIP | 623 | 31.38 | −23.077 | −51.417 | 1 | 39.14 |
| 6400 | OH2 | TIP | 624 | 24.265 | −24.209 | 36.887 | 1 | 45.77 |
| 6401 | OH2 | TIP | 625 | 21.667 | 29.245 | 12.708 | 1 | 41.04 |
| 6402 | OH2 | TIP | 626 | 27.023 | 0.414 | −8.351 | 1 | 36.72 |
| 6403 | OH2 | TIP | 627 | 33.585 | −15.421 | −48.186 | 1 | 36.23 |
| 6404 | OH2 | TIP | 628 | −6.728 | −21.539 | −27.917 | 1 | 30.77 |
| 6405 | OH2 | TIP | 629 | 27.822 | −42.666 | −55.468 | 1 | 38.25 |
| 6406 | OH2 | TIP | 630 | 21.514 | 11.927 | −1.746 | 1 | 39.24 |
| 6407 | OH2 | TIP | 631 | 26.878 | −17.523 | −43.209 | 1 | 37.25 |
| 6408 | OH2 | TIP | 632 | 32.277 | 27.435 | −5.356 | 1 | 28.69 |
| 6409 | OH2 | TIP | 633 | 35.694 | −18.269 | 17.085 | 1 | 39.12 |
| 6410 | OH2 | TIP | 634 | 0.426 | −50.455 | −38.031 | 1 | 39.75 |
| 6411 | OH2 | TIP | 635 | 29.541 | 36.521 | 15.384 | 1 | 39.7 |
| 6412 | OH2 | TIP | 636 | 18.845 | −15.195 | 36.846 | 1 | 34.23 |
| 6413 | OH2 | TIP | 637 | 31.478 | −41.232 | −43.35 | 1 | 38.75 |
| 6414 | OH2 | TIP | 638 | 17.332 | −27.051 | −23.04 | 1 | 36.37 |
| 6415 | OH2 | TIP | 639 | 34.258 | −16.997 | 31.826 | 1 | 36.27 |
| 6416 | OH2 | TIP | 640 | 15.423 | 21.679 | 2.544 | 1 | 42.79 |
| 6417 | OH2 | TIP | 641 | 9.036 | −52.251 | −27.693 | 1 | 37.05 |
| 6418 | OH2 | TIP | 642 | 52.59 | 10.06 | 10.376 | 1 | 45.28 |
| 6419 | OH2 | TIP | 643 | 31.12 | −44.216 | −37.292 | 1 | 36.56 |
| 6420 | OH2 | TIP | 644 | 41.322 | −0.169 | 12.689 | 1 | 42.51 |
| 6421 | OH2 | TIP | 645 | 35.506 | 23.961 | −5.455 | 1 | 40.98 |
| 6422 | OH2 | TIP | 646 | 32.96 | 31.413 | −0.419 | 1 | 41.32 |
| 6423 | OH2 | TIP | 647 | 21.341 | −27.5 | 15.428 | 1 | 43.96 |
| 6424 | OH2 | TIP | 648 | 3.638 | −17.156 | 27.717 | 1 | 38.75 |
| 6425 | OH2 | TIP | 649 | 18.077 | −19.368 | −31.622 | 1 | 34.18 |
| 6426 | OH2 | TIP | 650 | −6.802 | −18.499 | −39.141 | 1 | 42.83 |
| 6427 | OH2 | TIP | 651 | 9.635 | −22.57 | −23.121 | 1 | 40.03 |
| 6428 | OH2 | TIP | 652 | 26.493 | 28.44 | 18.662 | 1 | 44.4 |
| 6429 | OH2 | TIP | 653 | 4.15 | −39.995 | −12.085 | 1 | 39.19 |
| 6430 | OH2 | TIP | 654 | 6.26 | −6.423 | 14.732 | 1 | 38.64 |
| 6431 | OH2 | TIP | 655 | 42.036 | −50.315 | −49.358 | 1 | 42.09 |
| 6432 | OH2 | TIP | 656 | 38.907 | −53.079 | −39.337 | 1 | 46.9 |
| 6433 | OH2 | TIP | 657 | 32.052 | −37.876 | 21.01 | 1 | 34.39 |
| 6434 | OH2 | TIP | 658 | 11.026 | −17.308 | 39.902 | 1 | 43.59 |
| 6435 | OH2 | TIP | 659 | −0.615 | −12.845 | 26.565 | 1 | 39.22 |
| 6436 | OH2 | TIP | 660 | 38.839 | 18.394 | 24.766 | 1 | 38.99 |
| 6437 | OH2 | TIP | 661 | −15.965 | −42.079 | −26.507 | 1 | 41.15 |
| 6438 | OH2 | TIP | 662 | 26.099 | 9.034 | −11.861 | 1 | 40.67 |
| 6439 | OH2 | TIP | 663 | 32.053 | 3.408 | 23.007 | 1 | 36.22 |
| 6440 | OH2 | TIP | 664 | 45.812 | −40.912 | −54.534 | 1 | 34.04 |
| 6441 | OH2 | TIP | 665 | 40.693 | −1.317 | 8.368 | 1 | 41.01 |
| 6442 | OH2 | TIP | 666 | 39.099 | 26.99 | 14.969 | 1 | 41.93 |
| 6443 | OH2 | TIP | 667 | −1.316 | −30.189 | −13.682 | 1 | 37.7 |
| 6444 | OH2 | TIP | 668 | 18.204 | 9.164 | 4.539 | 1 | 39.96 |
| 6445 | OH2 | TIP | 669 | 38.634 | 28.26 | 19.165 | 1 | 47.88 |
| 6446 | OH2 | TIP | 670 | 43.284 | 18.31 | 18.436 | 1 | 40.12 |
| 6447 | OH2 | TIP | 671 | 35.112 | −14.124 | 27.776 | 1 | 39.59 |
| 6448 | OH2 | TIP | 672 | 34.735 | −6.464 | 11.131 | 1 | 42.97 |
| 6449 | OH2 | TIP | 673 | 48.541 | −25.053 | −58.366 | 1 | 43.6 |
| 6450 | OH2 | TIP | 674 | 15.529 | −43.081 | −41.227 | 1 | 44.74 |
| 6451 | OH2 | TIP | 675 | 5.141 | −4.045 | 20.088 | 1 | 39.36 |
| 6452 | OH2 | TIP | 676 | −2.812 | −45.778 | −37.679 | 1 | 38.07 |
| 6453 | OH2 | TIP | 677 | 12.735 | −14.151 | 42.498 | 1 | 37.53 |
| 6454 | OH2 | TIP | 678 | 39.045 | −22.906 | −30.628 | 1 | 47.35 |
| 6455 | OH2 | TIP | 679 | 16.915 | −31.044 | 32.404 | 1 | 39.02 |
| 6456 | OH2 | TIP | 680 | 19.42 | −35.461 | −48.991 | 1 | 38.72 |
| 6457 | OH2 | TIP | 681 | 24.437 | −1.597 | 1.245 | 1 | 41.26 |
| 6458 | OH2 | TIP | 682 | 11.624 | −45.64 | −41.112 | 1 | 44.94 |
| 6459 | OH2 | TIP | 683 | 0.87 | −14.046 | −24.066 | 1 | 40.27 |
| 6460 | OH2 | TIP | 684 | 30.798 | −11.192 | −45.228 | 1 | 39.22 |
| 6461 | OH2 | TIP | 685 | 16.493 | −23.71 | 38.751 | 1 | 45.24 |
| 6462 | OH2 | TIP | 686 | 32.569 | −15.477 | 8.248 | 1 | 37.24 |
| 6463 | OH2 | TIP | 687 | 40.745 | 19.965 | 11.237 | 1 | 35.35 |
| 6464 | OH2 | TIP | 688 | 31.923 | −20.653 | 37.768 | 1 | 45.66 |
| 6465 | OH2 | TIP | 689 | 8.641 | −0.855 | 25.018 | 1 | 42.26 |
| 6466 | OH2 | TIP | 690 | 36.503 | −21.606 | −25.094 | 1 | 40.61 |
| 6467 | OH2 | TIP | 691 | 40.004 | −9.151 | −43.637 | 1 | 39.92 |
| 6468 | OH2 | TIP | 692 | 24.735 | −26.448 | −60.137 | 1 | 42.15 |
| 6469 | OH2 | TIP | 693 | 21.125 | 31.843 | 12.38 | 1 | 41.28 |
| 6470 | OH2 | TIP | 694 | 18.266 | −21.77 | −42.624 | 1 | 44.31 |
| 6471 | OH2 | TIP | 695 | 25.521 | −15.405 | −38.435 | 1 | 43.37 |
| 6472 | OH2 | TIP | 696 | 35.125 | −17.543 | −51.646 | 1 | 43.4 |
| 6473 | OH2 | TIP | 697 | 15.453 | 17.901 | 20.25 | 1 | 40.82 |
| 6474 | OH2 | TIP | 698 | 12.785 | 12.39 | 10.647 | 1 | 38.61 |
| 6475 | OH2 | TIP | 699 | 34.791 | 25.509 | −3.469 | 1 | 39.14 |
| 6476 | OH2 | TIP | 700 | 25.975 | −39.487 | −58.534 | 1 | 40.88 |
| 6477 | OH2 | TIP | 701 | 26.701 | −21.46 | −47.845 | 1 | 47.35 |
| 6478 | OH2 | TIP | 702 | 7.666 | −18.949 | 30.515 | 1 | 40.96 |
| 6479 | OH2 | TIP | 703 | 36.28 | 11.103 | 14.338 | 1 | 40.73 |
| 6480 | OH2 | TIP | 704 | 36.021 | −3.978 | 9.096 | 1 | 44.57 |
| 6481 | OH2 | TIP | 705 | 36.527 | −2.356 | −0.265 | 1 | 43.02 |
| 6482 | OH2 | TIP | 706 | 24.106 | −12.628 | 7.186 | 1 | 38.7 |
| 6483 | OH2 | TIP | 707 | 27.599 | −37.021 | 34.448 | 1 | 47.36 |
| 6484 | OH2 | TIP | 708 | 18.892 | −7.328 | 30.947 | 1 | 45.14 |

TABLE 1-continued

| Atom | Atom Type | Residue | # | X | Y | Z | OCC | B |
|---|---|---|---|---|---|---|---|---|
| 6485 | OH2 | TIP | 709 | 25.403 | 40.245 | 18.214 | 1 | 48.12 |
| 6486 | OH2 | TIP | 710 | 2.727 | −18.777 | −5.642 | 1 | 46.83 |
| 6487 | OH2 | TIP | 711 | 4.394 | −35.633 | −38.55 | 1 | 37.19 |
| 6488 | OH2 | TIP | 712 | 19.94 | −33.962 | 33.801 | 1 | 41.56 |
| 6489 | OH2 | TIP | 713 | −1.735 | −36.906 | −12.117 | 1 | 47.05 |
| 6490 | OH2 | TIP | 714 | 3.899 | −51.819 | −32.456 | 1 | 45.67 |
| 6491 | OH2 | TIP | 715 | 5.481 | −17.604 | −41.761 | 1 | 39.01 |
| 6492 | OH2 | TIP | 716 | 11.651 | 3.468 | 12.991 | 1 | 38.5 |
| 6493 | OH2 | TIP | 717 | 11.359 | −16.566 | −25.97 | 1 | 45.17 |
| 6494 | OH2 | TIP | 718 | 21.545 | −28.692 | −62.021 | 1 | 42.24 |
| 6495 | OH2 | TIP | 719 | 12.886 | −36.26 | 33.035 | 1 | 38.35 |
| 6496 | OH2 | TIP | 720 | 2.606 | −7.049 | 18.241 | 1 | 42.89 |
| 6497 | OH2 | TIP | 721 | 26.352 | −1.12 | 30.202 | 1 | 42.49 |
| 6498 | OH2 | TIP | 722 | 37.153 | −17.737 | 27.407 | 1 | 45.17 |
| 6499 | OH2 | TIP | 723 | 14.356 | −19.387 | −37.259 | 1 | 44.84 |
| 6500 | P | PO4 | 1 | 35.312 | 11.778 | 10.603 | 1 | 23.61 |
| 6501 | O1 | PO4 | 1 | 34.497 | 12.942 | 10.146 | 1 | 24.54 |
| 6502 | O2 | PO4 | 1 | 34.963 | 11.452 | 12.009 | 1 | 24.19 |
| 6503 | O3 | PO4 | 1 | 35.031 | 10.6 | 9.732 | 1 | 24.02 |
| 6504 | O4 | PO4 | 1 | 36.757 | 12.121 | 10.517 | 1 | 24.38 |
| 6505 | P | PO4 | 2 | 31.591 | 12.853 | 12.152 | 1 | 15.18 |
| 6506 | O1 | PO4 | 2 | 31.799 | 12.863 | 10.683 | 1 | 15.62 |
| 6507 | O2 | PO4 | 2 | 30.169 | 12.554 | 12.451 | 1 | 14.92 |
| 6508 | O3 | PO4 | 2 | 32.457 | 11.808 | 12.768 | 1 | 17.03 |
| 6509 | O4 | PO4 | 2 | 31.947 | 14.185 | 12.715 | 1 | 16.17 |
| 6510 | P | PO4 | 3 | 18.94 | −9.859 | 28.231 | 1 | 26.43 |
| 6511 | O1 | PO4 | 3 | 19.237 | −11.291 | 27.96 | 1 | 27.77 |
| 6512 | O2 | PO4 | 3 | 20.208 | −9.08 | 28.236 | 1 | 26.31 |
| 6513 | O3 | PO4 | 3 | 18.036 | −9.331 | 27.176 | 1 | 28.18 |
| 6514 | O4 | PO4 | 3 | 18.279 | −9.732 | 29.557 | 1 | 26.35 |
| 6515 | P | PO4 | 4 | 22.34 | −11.127 | 26.308 | 1 | 15.06 |
| 6516 | O1 | PO4 | 4 | 21.043 | −11.775 | 25.98 | 1 | 14.35 |
| 6517 | O2 | PO4 | 4 | 23.219 | −11.137 | 25.109 | 1 | 14.36 |
| 6518 | O3 | PO4 | 4 | 22.098 | −9.721 | 26.729 | 1 | 15.58 |
| 6519 | O4 | PO4 | 4 | 23.002 | −11.868 | 27.415 | 1 | 14.36 |
| 6520 | P | PO4 | 5 | 9.711 | −30.619 | −23.897 | 1 | 29.52 |
| 6521 | O1 | PO4 | 5 | 8.582 | −31.564 | −24.116 | 1 | 29.68 |
| 6522 | O2 | PO4 | 5 | 10.993 | −31.373 | −23.908 | 1 | 28.21 |
| 6523 | O3 | PO4 | 5 | 9.722 | −29.598 | −24.982 | 1 | 27.64 |
| 6524 | O4 | PO4 | 5 | 9.547 | −29.942 | −22.584 | 1 | 29.27 |
| 6525 | P | PO4 | 6 | 10.221 | −34.362 | −25.755 | 1 | 16.22 |
| 6526 | O1 | PO4 | 6 | 9.049 | −33.502 | −26.061 | 1 | 17.46 |
| 6527 | O2 | PO4 | 6 | 10.59 | −35.153 | −26.964 | 1 | 15.24 |
| 6528 | O3 | PO4 | 6 | 11.371 | −33.505 | −25.36 | 1 | 17.9 |
| 6529 | O4 | PO4 | 6 | 9.884 | −35.288 | −24.638 | 1 | 15.63 |
| 6530 | P | PO4 | 7 | 36.517 | −35.356 | −41.669 | 1 | 29.64 |
| 6531 | O1 | PO4 | 7 | 37.202 | −34.164 | −42.244 | 1 | 30.25 |
| 6532 | O2 | PO4 | 7 | 36.12 | −35.071 | −40.268 | 1 | 30.01 |
| 6533 | O3 | PO4 | 7 | 35.305 | −35.667 | −42.477 | 1 | 30.19 |
| 6534 | O4 | PO4 | 7 | 37.44 | −36.521 | −41.693 | 1 | 30.13 |
| 6535 | P | PO4 | 8 | 35.785 | −31.587 | −40.045 | 1 | 16.98 |
| 6536 | O1 | PO4 | 8 | 35.846 | −31.763 | −41.52 | 1 | 18.3 |
| 6537 | O2 | PO4 | 8 | 34.893 | −30.444 | −39.713 | 1 | 16.83 |
| 6538 | O3 | PO4 | 8 | 35.249 | −32.828 | −39.424 | 1 | 17.93 |
| 6539 | O4 | PO4 | 8 | 37.149 | −31.316 | −39.52 | 1 | 16.9 |

Appendix B

Table 2, pp. 177-300

TABLE 2

| Atom | Atom Type | Residue | # | X | Y | Z | OCC | B |
|---|---|---|---|---|---|---|---|---|
| 1 | CB | HIS | 3 | 35.504 | 34.325 | 27.68 | 1 | 34.61 |
| 2 | CG | HIS | 3 | 35.27 | 35.007 | 28.991 | 1 | 34.62 |
| 3 | CD2 | HIS | 3 | 34.207 | 34.984 | 29.831 | 1 | 34.36 |
| 4 | ND1 | HIS | 3 | 36.215 | 35.815 | 29.59 | 1 | 35.4 |
| 5 | CE1 | HIS | 3 | 35.744 | 36.258 | 30.742 | 1 | 35.08 |
| 6 | NE2 | HIS | 3 | 34.528 | 35.769 | 30.912 | 1 | 35.14 |

TABLE 2-continued

| Atom | Atom Type | Residue | # | X | Y | Z | OCC | B |
|---|---|---|---|---|---|---|---|---|
| 7 | C | HIS | 3 | 36.343 | 32.062 | 27.046 | 1 | 35.95 |
| 8 | O | HIS | 3 | 36.484 | 31.881 | 25.837 | 1 | 36.52 |
| 9 | N | HIS | 3 | 37.865 | 34.037 | 26.982 | 1 | 34.76 |
| 10 | CA | HIS | 3 | 36.716 | 33.392 | 27.684 | 1 | 35.59 |
| 11 | N | MET | 4 | 35.855 | 31.132 | 27.861 | 1 | 35.31 |
| 12 | CA | MET | 4 | 35.491 | 29.817 | 27.353 | 1 | 35.09 |
| 13 | CB | MET | 4 | 36.611 | 28.819 | 27.658 | 1 | 36.54 |
| 14 | CG | MET | 4 | 37.954 | 29.188 | 27.05 | 1 | 37.66 |
| 15 | SD | MET | 4 | 39.238 | 27.987 | 27.438 | 1 | 43.46 |
| 16 | CE | MET | 4 | 39.161 | 26.922 | 25.997 | 1 | 38.06 |
| 17 | C | MET | 4 | 34.175 | 29.272 | 27.889 | 1 | 33.85 |
| 18 | O | MET | 4 | 33.577 | 29.822 | 28.815 | 1 | 34.87 |
| 19 | N | SER | 5 | 33.736 | 28.174 | 27.283 | 1 | 32.87 |
| 20 | CA | SER | 5 | 32.503 | 27.499 | 27.665 | 1 | 29.99 |
| 21 | CB | SER | 5 | 31.315 | 28.085 | 26.899 | 1 | 30.45 |
| 22 | OG | SER | 5 | 31.524 | 28 | 25.498 | 1 | 33.94 |
| 23 | C | SER | 5 | 32.677 | 26.031 | 27.305 | 1 | 28.06 |
| 24 | O | SER | 5 | 33.789 | 25.587 | 27.026 | 1 | 29.14 |
| 25 | N | PHE | 6 | 31.583 | 25.281 | 27.315 | 1 | 26.42 |
| 26 | CA | PHE | 6 | 31.646 | 23.867 | 26.978 | 1 | 23.75 |
| 27 | CB | PHE | 6 | 31.23 | 22.997 | 28.167 | 1 | 23.58 |
| 28 | CG | PHE | 6 | 32.223 | 22.98 | 29.288 | 1 | 23.41 |
| 29 | CD1 | PHE | 6 | 32.325 | 24.056 | 30.163 | 1 | 24.05 |
| 30 | CD2 | PHE | 6 | 33.055 | 21.881 | 29.475 | 1 | 22.6 |
| 31 | CE1 | PHE | 6 | 33.243 | 24.036 | 31.212 | 1 | 24 |
| 32 | CE2 | PHE | 6 | 33.974 | 21.85 | 30.518 | 1 | 25.18 |
| 33 | CZ | PHE | 6 | 34.068 | 22.93 | 31.389 | 1 | 23 |
| 34 | C | PHE | 6 | 30.74 | 23.538 | 25.809 | 1 | 23.34 |
| 35 | O | PHE | 6 | 29.657 | 24.103 | 25.669 | 1 | 24.13 |
| 36 | N | SER | 7 | 31.199 | 22.618 | 24.969 | 1 | 20.57 |
| 37 | CA | SER | 7 | 30.426 | 22.166 | 23.825 | 1 | 19.54 |
| 38 | CB | SER | 7 | 31.052 | 22.637 | 22.511 | 1 | 22.2 |
| 39 | OG | SER | 7 | 30.835 | 24.023 | 22.308 | 1 | 27.54 |
| 40 | C | SER | 7 | 30.451 | 20.654 | 23.885 | 1 | 17.2 |
| 41 | O | SER | 7 | 31.359 | 20.066 | 24.469 | 1 | 16.31 |
| 42 | N | HIS | 8 | 29.448 | 20.018 | 23.299 | 1 | 15.98 |
| 43 | CA | HIS | 8 | 29.419 | 18.571 | 23.302 | 1 | 15.38 |
| 44 | CB | HIS | 8 | 28.636 | 18.049 | 24.509 | 1 | 18.42 |
| 45 | CG | HIS | 8 | 27.162 | 18.297 | 24.436 | 1 | 20.61 |
| 46 | CD2 | HIS | 8 | 26.432 | 19.41 | 24.681 | 1 | 23.01 |
| 47 | ND1 | HIS | 8 | 26.26 | 17.318 | 24.081 | 1 | 23.87 |
| 48 | CE1 | HIS | 8 | 25.036 | 17.816 | 24.113 | 1 | 24.62 |
| 49 | NE2 | HIS | 8 | 25.113 | 19.084 | 24.475 | 1 | 26.71 |
| 50 | C | HIS | 8 | 28.815 | 18.048 | 22.018 | 1 | 14.18 |
| 51 | O | HIS | 8 | 27.929 | 18.671 | 21.432 | 1 | 15.89 |
| 52 | N | VAL | 9 | 29.327 | 16.911 | 21.572 | 1 | 12.98 |
| 53 | CA | VAL | 9 | 28.821 | 16.275 | 20.369 | 1 | 10.98 |
| 54 | CB | VAL | 9 | 29.921 | 15.479 | 19.654 | 1 | 12.02 |
| 55 | CG1 | VAL | 9 | 29.333 | 14.729 | 18.469 | 1 | 12.34 |
| 56 | CG2 | VAL | 9 | 31.014 | 16.428 | 19.178 | 1 | 14.08 |
| 57 | C | VAL | 9 | 27.729 | 15.325 | 20.831 | 1 | 11.65 |
| 58 | O | VAL | 9 | 27.986 | 14.413 | 21.616 | 1 | 11.09 |
| 59 | N | CYS | 10 | 26.508 | 15.566 | 20.367 | 1 | 10.72 |
| 60 | CA | CYS | 10 | 25.365 | 14.737 | 20.731 | 1 | 11.09 |
| 61 | CB | CYS | 10 | 24.099 | 15.269 | 20.056 | 1 | 10.94 |
| 62 | SG | CYS | 10 | 23.697 | 16.98 | 20.5 | 1 | 14.61 |
| 63 | C | CYS | 10 | 25.604 | 13.288 | 20.314 | 1 | 10.48 |
| 64 | O | CYS | 10 | 26.145 | 13.023 | 19.239 | 1 | 11.1 |
| 65 | N | GLN | 11 | 25.18 | 12.358 | 21.167 | 1 | 9.37 |
| 66 | CA | GLN | 11 | 25.353 | 10.93 | 20.918 | 1 | 10.58 |
| 67 | CB | GLN | 11 | 25.889 | 10.245 | 22.17 | 1 | 10.85 |
| 68 | CG | GLN | 11 | 27.267 | 10.744 | 22.583 | 1 | 9.61 |
| 69 | CD | GLN | 11 | 28.297 | 10.527 | 21.496 | 1 | 10.68 |
| 70 | OE1 | GLN | 11 | 28.56 | 9.39 | 21.093 | 1 | 11.04 |
| 71 | NE2 | GLN | 11 | 28.887 | 11.617 | 21.009 | 1 | 10.08 |
| 72 | C | GLN | 11 | 24.058 | 10.258 | 20.491 | 1 | 10.52 |
| 73 | O | GLN | 11 | 22.969 | 10.715 | 20.846 | 1 | 10.97 |
| 74 | N | VAL | 12 | 24.19 | 9.157 | 19.752 | 1 | 10.44 |
| 75 | CA | VAL | 12 | 23.026 | 8.437 | 19.25 | 1 | 10.58 |
| 76 | CB | VAL | 12 | 23.449 | 7.149 | 18.478 | 1 | 10.34 |
| 77 | CG1 | VAL | 12 | 24.2 | 6.188 | 19.383 | 1 | 11.76 |
| 78 | CG2 | VAL | 12 | 22.22 | 6.495 | 17.859 | 1 | 12.75 |
| 79 | C | VAL | 12 | 22.044 | 8.149 | 20.377 | 1 | 10.46 |
| 80 | O | VAL | 12 | 22.408 | 7.632 | 21.437 | 1 | 11.02 |
| 81 | N | GLY | 13 | 20.793 | 8.525 | 20.129 | 1 | 11.08 |
| 82 | CA | GLY | 13 | 19.739 | 8.403 | 21.118 | 1 | 11.44 |

TABLE 2-continued

| Atom | Atom Type | Residue | # | X | Y | Z | OCC | B |
|---|---|---|---|---|---|---|---|---|
| 83 | C | GLY | 13 | 19.078 | 9.773 | 21.179 | 1 | 11.33 |
| 84 | O | GLY | 13 | 17.87 | 9.894 | 21.395 | 1 | 12.49 |
| 85 | N | ASP | 14 | 19.884 | 10.816 | 20.994 | 1 | 11.27 |
| 86 | CA | ASP | 14 | 19.378 | 12.188 | 20.985 | 1 | 12.03 |
| 87 | CB | ASP | 14 | 20.547 | 13.179 | 20.95 | 1 | 12.46 |
| 88 | CG | ASP | 14 | 20.102 | 14.626 | 21.103 | 1 | 13.44 |
| 89 | OD1 | ASP | 14 | 18.965 | 14.957 | 20.708 | 1 | 12.68 |
| 90 | OD2 | ASP | 14 | 20.904 | 15.444 | 21.61 | 1 | 13.68 |
| 91 | C | ASP | 14 | 18.552 | 12.319 | 19.704 | 1 | 13.49 |
| 92 | O | ASP | 14 | 19.07 | 12.136 | 18.606 | 1 | 12.87 |
| 93 | N | PRO | 15 | 17.258 | 12.644 | 19.824 | 1 | 13.1 |
| 94 | CD | PRO | 15 | 16.503 | 12.982 | 21.044 | 1 | 13.09 |
| 95 | CA | PRO | 15 | 16.414 | 12.776 | 18.633 | 1 | 14.28 |
| 96 | CB | PRO | 15 | 15.037 | 13.093 | 19.22 | 1 | 14.63 |
| 97 | CG | PRO | 15 | 15.367 | 13.816 | 20.488 | 1 | 14.4 |
| 98 | C | PRO | 15 | 16.858 | 13.798 | 17.587 | 1 | 13.97 |
| 99 | O | PRO | 15 | 16.478 | 13.693 | 16.418 | 1 | 14.09 |
| 100 | N | VAL | 16 | 17.664 | 14.776 | 17.989 | 1 | 13.83 |
| 101 | CA | VAL | 16 | 18.119 | 15.792 | 17.043 | 1 | 13.68 |
| 102 | CB | VAL | 16 | 18.949 | 16.889 | 17.759 | 1 | 14.03 |
| 103 | CG1 | VAL | 16 | 20.31 | 16.347 | 18.155 | 1 | 14.41 |
| 104 | CG2 | VAL | 16 | 19.087 | 18.11 | 16.861 | 1 | 14.35 |
| 105 | C | VAL | 16 | 18.947 | 15.174 | 15.91 | 1 | 13.64 |
| 106 | O | VAL | 16 | 19.006 | 15.715 | 14.806 | 1 | 14.68 |
| 107 | N | LEU | 17 | 19.565 | 14.027 | 16.178 | 1 | 13.01 |
| 108 | CA | LEU | 17 | 20.387 | 13.354 | 15.177 | 1 | 11.69 |
| 109 | CB | LEU | 17 | 21.33 | 12.358 | 15.858 | 1 | 11.19 |
| 110 | CG | LEU | 17 | 22.372 | 12.965 | 16.798 | 1 | 10.85 |
| 111 | CD1 | LEU | 17 | 23.089 | 11.849 | 17.548 | 1 | 10.92 |
| 112 | CD2 | LEU | 17 | 23.365 | 13.802 | 15.992 | 1 | 12.46 |
| 113 | C | LEU | 17 | 19.575 | 12.616 | 14.119 | 1 | 11.48 |
| 114 | O | LEU | 17 | 20.103 | 12.258 | 13.064 | 1 | 12.01 |
| 115 | N | ARG | 18 | 18.293 | 12.394 | 14.398 | 1 | 12.9 |
| 116 | CA | ARG | 18 | 17.432 | 11.666 | 13.471 | 1 | 12.01 |
| 117 | CB | ARG | 18 | 16.732 | 10.525 | 14.21 | 1 | 12.46 |
| 118 | CG | ARG | 18 | 17.392 | 9.165 | 14.036 | 1 | 12.16 |
| 119 | CD | ARG | 18 | 18.864 | 9.157 | 14.431 | 1 | 11.81 |
| 120 | NE | ARG | 18 | 19.383 | 7.79 | 14.428 | 1 | 12.34 |
| 121 | CZ | ARG | 18 | 19.706 | 7.102 | 13.335 | 1 | 12.41 |
| 122 | NH1 | ARG | 18 | 19.585 | 7.648 | 12.13 | 1 | 13.18 |
| 123 | NH2 | ARG | 18 | 20.127 | 5.848 | 13.449 | 1 | 12.74 |
| 124 | C | ARG | 18 | 16.395 | 12.506 | 12.745 | 1 | 14.45 |
| 125 | O | ARG | 18 | 15.652 | 11.991 | 11.909 | 1 | 16.27 |
| 126 | N | GLY | 19 | 16.328 | 13.791 | 13.07 | 1 | 14.94 |
| 127 | CA | GLY | 19 | 15.375 | 14.651 | 12.395 | 1 | 16.17 |
| 128 | C | GLY | 19 | 15.968 | 15.199 | 11.109 | 1 | 16.41 |
| 129 | O | GLY | 19 | 17.152 | 15.007 | 10.828 | 1 | 15.56 |
| 130 | N | VAL | 20 | 15.143 | 15.862 | 10.306 | 1 | 16.57 |
| 131 | CA | VAL | 20 | 15.623 | 16.461 | 9.068 | 1 | 16.23 |
| 132 | CB | VAL | 20 | 14.576 | 16.365 | 7.942 | 1 | 17.14 |
| 133 | CG1 | VAL | 20 | 15.104 | 17.045 | 6.689 | 1 | 17.84 |
| 134 | CG2 | VAL | 20 | 14.258 | 14.906 | 7.654 | 1 | 18.82 |
| 135 | C | VAL | 20 | 15.874 | 17.926 | 9.398 | 1 | 15.69 |
| 136 | O | VAL | 20 | 14.94 | 18.668 | 9.705 | 1 | 16.41 |
| 137 | N | ALA | 21 | 17.136 | 18.334 | 9.35 | 1 | 14.8 |
| 138 | CA | ALA | 21 | 17.512 | 19.706 | 9.674 | 1 | 16.4 |
| 139 | CB | ALA | 21 | 19.015 | 19.887 | 9.498 | 1 | 15.39 |
| 140 | C | ALA | 21 | 16.762 | 20.729 | 8.831 | 1 | 16.29 |
| 141 | O | ALA | 21 | 16.531 | 20.517 | 7.643 | 1 | 16.8 |
| 142 | N | ALA | 22 | 16.382 | 21.835 | 9.464 | 1 | 17.15 |
| 143 | CA | ALA | 22 | 15.661 | 22.904 | 8.781 | 1 | 18.18 |
| 144 | CB | ALA | 22 | 14.847 | 23.707 | 9.781 | 1 | 18.76 |
| 145 | C | ALA | 22 | 16.653 | 23.817 | 8.072 | 1 | 18.24 |
| 146 | O | ALA | 22 | 17.782 | 23.994 | 8.524 | 1 | 17.92 |
| 147 | N | PRO | 23 | 16.243 | 24.405 | 6.942 | 1 | 19.16 |
| 148 | CD | PRO | 23 | 14.973 | 24.203 | 6.224 | 1 | 19.66 |
| 149 | CA | PRO | 23 | 17.132 | 25.3 | 6.198 | 1 | 19.27 |
| 150 | CB | PRO | 23 | 16.329 | 25.622 | 4.934 | 1 | 20.38 |
| 151 | CG | PRO | 23 | 15.382 | 24.457 | 4.801 | 1 | 23.84 |
| 152 | C | PRO | 23 | 17.417 | 26.564 | 7.003 | 1 | 18.95 |
| 153 | O | PRO | 23 | 16.637 | 26.936 | 7.88 | 1 | 20.21 |
| 154 | N | VAL | 24 | 18.538 | 27.215 | 6.714 | 1 | 19.93 |
| 155 | CA | VAL | 24 | 18.867 | 28.465 | 7.387 | 1 | 21.53 |
| 156 | CB | VAL | 24 | 20.384 | 28.739 | 7.372 | 1 | 21.15 |
| 157 | CG1 | VAL | 24 | 20.673 | 30.113 | 7.969 | 1 | 22.46 |
| 158 | CG2 | VAL | 24 | 21.111 | 27.654 | 8.162 | 1 | 20.34 |
| 159 | C | VAL | 24 | 18.151 | 29.548 | 6.579 | 1 | 22.76 |
| 160 | O | VAL | 24 | 18.325 | 29.632 | 5.363 | 1 | 23.9 |
| 161 | N | GLU | 25 | 17.33 | 30.352 | 7.25 | 1 | 24.37 |
| 162 | CA | GLU | 25 | 16.583 | 31.417 | 6.585 | 1 | 26.33 |
| 163 | CB | GLU | 25 | 15.598 | 32.06 | 7.566 | 1 | 30 |
| 164 | CG | GLU | 25 | 14.48 | 31.134 | 8.021 | 1 | 34.46 |
| 165 | CD | GLU | 25 | 13.653 | 30.614 | 6.862 | 1 | 36.52 |
| 166 | OE1 | GLU | 25 | 13.12 | 31.442 | 6.094 | 1 | 39.49 |
| 167 | OE2 | GLU | 25 | 13.535 | 29.379 | 6.719 | 1 | 38.67 |
| 168 | C | GLU | 25 | 17.511 | 32.484 | 6.018 | 1 | 26.42 |
| 169 | O | GLU | 25 | 18.557 | 32.777 | 6.595 | 1 | 24.69 |
| 170 | N | ARG | 26 | 17.124 | 33.066 | 4.887 | 1 | 26.73 |
| 171 | CA | ARG | 26 | 17.944 | 34.092 | 4.257 | 1 | 27.86 |
| 172 | CB | ARG | 26 | 17.254 | 34.649 | 3.01 | 1 | 29.6 |
| 173 | CG | ARG | 26 | 18.026 | 35.798 | 2.401 | 1 | 32.06 |
| 174 | CD | ARG | 26 | 17.482 | 36.254 | 1.064 | 1 | 35.11 |
| 175 | NE | ARG | 26 | 18.274 | 37.375 | 0.567 | 1 | 38.36 |
| 176 | CZ | ARG | 26 | 19.586 | 37.326 | 0.354 | 1 | 39.31 |
| 177 | NH1 | ARG | 26 | 20.265 | 36.209 | 0.586 | 1 | 41.88 |
| 178 | NH2 | ARG | 26 | 20.228 | 38.401 | −0.074 | 1 | 39.72 |
| 179 | C | ARG | 26 | 18.263 | 35.237 | 5.213 | 1 | 26.58 |
| 180 | O | ARG | 26 | 19.346 | 35.818 | 5.159 | 1 | 26.13 |
| 181 | N | ALA | 27 | 17.318 | 35.555 | 6.091 | 1 | 26.89 |
| 182 | CA | ALA | 27 | 17.503 | 36.635 | 7.053 | 1 | 26.59 |
| 183 | CB | ALA | 27 | 16.205 | 36.882 | 7.811 | 1 | 27.26 |
| 184 | C | ALA | 27 | 18.633 | 36.343 | 8.035 | 1 | 26.21 |
| 185 | O | ALA | 27 | 19.14 | 37.25 | 8.696 | 1 | 26.46 |
| 186 | N | GLN | 28 | 19.026 | 35.076 | 8.131 | 1 | 24.41 |
| 187 | CA | GLN | 28 | 20.094 | 34.675 | 9.037 | 1 | 23.85 |
| 188 | CB | GLN | 28 | 19.791 | 33.295 | 9.628 | 1 | 25.89 |
| 189 | CG | GLN | 28 | 18.705 | 33.299 | 10.685 | 1 | 30.68 |
| 190 | CD | GLN | 28 | 19.132 | 34.028 | 11.943 | 1 | 33.57 |
| 191 | OE1 | GLN | 28 | 19.393 | 35.231 | 11.92 | 1 | 37.51 |
| 192 | NE2 | GLN | 28 | 19.213 | 33.299 | 13.05 | 1 | 37.82 |
| 193 | C | GLN | 28 | 21.471 | 34.653 | 8.383 | 1 | 21.91 |
| 194 | O | GLN | 28 | 22.489 | 34.664 | 9.074 | 1 | 20.76 |
| 195 | N | LEU | 29 | 21.506 | 34.618 | 7.055 | 1 | 20.45 |
| 196 | CA | LEU | 29 | 22.779 | 34.576 | 6.343 | 1 | 20.24 |
| 197 | CB | LEU | 29 | 22.54 | 34.543 | 4.832 | 1 | 21.19 |
| 198 | CG | LEU | 29 | 21.826 | 33.289 | 4.322 | 1 | 21.86 |
| 199 | CD1 | LEU | 29 | 21.522 | 33.441 | 2.838 | 1 | 22.82 |
| 200 | CD2 | LEU | 29 | 22.696 | 32.062 | 4.574 | 1 | 22.52 |
| 201 | C | LEU | 29 | 23.623 | 35.809 | 6.698 | 1 | 19.73 |
| 202 | O | LEU | 29 | 23.107 | 36.923 | 6.791 | 1 | 20.18 |
| 203 | N | GLY | 30 | 24.919 | 35.58 | 6.9 | 1 | 19.82 |
| 204 | CA | GLY | 30 | 25.833 | 36.654 | 7.248 | 1 | 20.97 |
| 205 | C | GLY | 30 | 25.671 | 37.144 | 8.677 | 1 | 22.06 |
| 206 | O | GLY | 30 | 26.475 | 37.944 | 9.156 | 1 | 22.38 |
| 207 | N | GLY | 31 | 24.639 | 36.649 | 9.356 | 1 | 21.84 |
| 208 | CA | GLY | 31 | 24.359 | 37.06 | 10.724 | 1 | 22.53 |
| 209 | C | GLY | 31 | 25.292 | 36.554 | 11.812 | 1 | 23.75 |
| 210 | O | GLY | 31 | 26.035 | 35.592 | 11.61 | 1 | 22.33 |
| 211 | N | PRO | 32 | 25.267 | 37.197 | 12.993 | 1 | 23.52 |
| 212 | CD | PRO | 32 | 24.516 | 38.439 | 13.244 | 1 | 24.88 |
| 213 | CA | PRO | 32 | 26.092 | 36.857 | 14.156 | 1 | 23.73 |
| 214 | CB | PRO | 32 | 25.73 | 37.946 | 15.167 | 1 | 23.75 |
| 215 | CG | PRO | 32 | 25.356 | 39.101 | 14.3 | 1 | 26.19 |
| 216 | C | PRO | 32 | 25.83 | 35.46 | 14.713 | 1 | 22.79 |
| 217 | O | PRO | 32 | 26.765 | 34.745 | 15.075 | 1 | 22.57 |
| 218 | N | GLU | 33 | 24.558 | 35.08 | 14.787 | 1 | 22.88 |
| 219 | CA | GLU | 33 | 24.189 | 33.769 | 15.311 | 1 | 24.47 |
| 220 | CB | GLU | 33 | 22.667 | 33.629 | 15.383 | 1 | 27.61 |
| 221 | CG | GLU | 33 | 22.181 | 32.89 | 16.622 | 1 | 34.64 |
| 222 | CD | GLU | 33 | 20.686 | 32.632 | 16.608 | 1 | 37.13 |
| 223 | OE1 | GLU | 33 | 19.918 | 33.576 | 16.32 | 1 | 39.73 |
| 224 | OE2 | GLU | 33 | 20.279 | 31.485 | 16.893 | 1 | 38.51 |
| 225 | C | GLU | 33 | 24.772 | 32.658 | 14.441 | 1 | 23 |
| 226 | O | GLU | 33 | 25.37 | 31.708 | 14.95 | 1 | 21.91 |
| 227 | N | LEU | 34 | 24.596 | 32.776 | 13.128 | 1 | 21.71 |
| 228 | CA | LEU | 34 | 25.125 | 31.779 | 12.205 | 1 | 21.03 |
| 229 | CB | LEU | 34 | 24.696 | 32.097 | 10.77 | 1 | 19.67 |
| 230 | CG | LEU | 34 | 25.263 | 31.184 | 9.679 | 1 | 18.95 |
| 231 | CD1 | LEU | 34 | 24.868 | 29.74 | 9.96 | 1 | 21.73 |
| 232 | CD2 | LEU | 34 | 24.743 | 31.627 | 8.316 | 1 | 19.14 |
| 233 | C | LEU | 34 | 26.647 | 31.779 | 12.298 | 1 | 21.66 |
| 234 | O | LEU | 34 | 27.298 | 30.74 | 12.17 | 1 | 20.35 |

TABLE 2-continued

| Atom | Atom Type | Residue | # | X | Y | Z | OCC | B |
|---|---|---|---|---|---|---|---|---|
| 235 | N | GLN | 35 | 27.209 | 32.959 | 12.528 | 1 | 22.05 |
| 236 | CA | GLN | 35 | 28.65 | 33.103 | 12.644 | 1 | 24.17 |
| 237 | CB | GLN | 35 | 29.009 | 34.585 | 12.773 | 1 | 26.61 |
| 238 | CG | GLN | 35 | 30.246 | 34.985 | 12.006 | 1 | 33.36 |
| 239 | CD | GLN | 35 | 31.46 | 34.206 | 12.439 | 1 | 34.71 |
| 240 | OE1 | GLN | 35 | 31.841 | 34.236 | 13.608 | 1 | 39.21 |
| 241 | NE2 | GLN | 35 | 32.078 | 33.498 | 11.501 | 1 | 37.45 |
| 242 | C | GLN | 35 | 29.155 | 32.331 | 13.865 | 1 | 22.83 |
| 243 | O | GLN | 35 | 30.17 | 31.634 | 13.796 | 1 | 22.64 |
| 244 | N | ARG | 36 | 28.444 | 32.452 | 14.981 | 1 | 22.36 |
| 245 | CA | ARG | 36 | 28.842 | 31.749 | 16.194 | 1 | 22.5 |
| 246 | CB | ARG | 36 | 28.004 | 32.213 | 17.39 | 1 | 23.28 |
| 247 | CG | ARG | 36 | 28.302 | 33.645 | 17.84 | 1 | 26.24 |
| 248 | CD | ARG | 36 | 27.736 | 33.919 | 19.23 | 1 | 28.22 |
| 249 | NE | ARG | 36 | 26.277 | 33.907 | 19.254 | 1 | 29.6 |
| 250 | CZ | ARG | 36 | 25.513 | 34.894 | 18.796 | 1 | 31.5 |
| 251 | NH1 | ARG | 36 | 26.068 | 35.982 | 18.278 | 1 | 31.08 |
| 252 | NH2 | ARG | 36 | 24.191 | 34.794 | 18.856 | 1 | 31.98 |
| 253 | C | ARG | 36 | 28.706 | 30.239 | 16.015 | 1 | 20.57 |
| 254 | O | ARG | 36 | 29.511 | 29.468 | 16.539 | 1 | 20.35 |
| 255 | N | LEU | 37 | 27.691 | 29.82 | 15.267 | 1 | 19.96 |
| 256 | CA | LEU | 37 | 27.478 | 28.395 | 15.031 | 1 | 18.52 |
| 257 | CB | LEU | 37 | 26.129 | 28.161 | 14.347 | 1 | 18.43 |
| 258 | CG | LEU | 37 | 25.849 | 26.729 | 13.872 | 1 | 17.96 |
| 259 | CD1 | LEU | 37 | 25.913 | 25.758 | 15.048 | 1 | 17.79 |
| 260 | CD2 | LEU | 37 | 24.483 | 26.683 | 13.206 | 1 | 17.59 |
| 261 | C | LEU | 37 | 28.59 | 27.788 | 14.183 | 1 | 18.47 |
| 262 | O | LEU | 37 | 29.12 | 26.726 | 14.516 | 1 | 16.91 |
| 263 | N | THR | 38 | 28.945 | 28.454 | 13.087 | 1 | 18.09 |
| 264 | CA | THR | 38 | 29.995 | 27.938 | 12.217 | 1 | 18.7 |
| 265 | CB | THR | 38 | 30.088 | 28.737 | 10.89 | 1 | 19.41 |
| 266 | OG1 | THR | 38 | 30.358 | 30.116 | 11.164 | 1 | 22.54 |
| 267 | CG2 | THR | 38 | 28.784 | 28.62 | 10.113 | 1 | 16.97 |
| 268 | C | THR | 38 | 31.354 | 27.935 | 12.91 | 1 | 18.83 |
| 269 | O | THR | 38 | 32.161 | 27.03 | 12.697 | 1 | 17.99 |
| 270 | N | GLN | 39 | 31.607 | 28.939 | 13.744 | 1 | 20.32 |
| 271 | CA | GLN | 39 | 32.873 | 29 | 14.461 | 1 | 21.75 |
| 272 | CB | GLN | 39 | 33.009 | 30.327 | 15.214 | 1 | 24.28 |
| 273 | CG | GLN | 39 | 33.762 | 31.399 | 14.441 | 1 | 31.32 |
| 274 | CD | GLN | 39 | 34.087 | 32.614 | 15.294 | 1 | 33.5 |
| 275 | OE1 | GLN | 39 | 34.527 | 32.483 | 16.438 | 1 | 36.82 |
| 276 | NE2 | GLN | 39 | 33.886 | 33.801 | 14.737 | 1 | 35.68 |
| 277 | C | GLN | 39 | 32.966 | 27.84 | 15.442 | 1 | 20.38 |
| 278 | O | GLN | 39 | 34.017 | 27.214 | 15.579 | 1 | 19.73 |
| 279 | N | ARG | 40 | 31.858 | 27.551 | 16.116 | 1 | 20.73 |
| 280 | CA | ARG | 40 | 31.821 | 26.459 | 17.081 | 1 | 20.97 |
| 281 | CB | ARG | 40 | 30.489 | 26.454 | 17.837 | 1 | 23.75 |
| 282 | CG | ARG | 40 | 30.507 | 25.595 | 19.089 | 1 | 27.92 |
| 283 | CD | ARG | 40 | 31.442 | 26.188 | 20.135 | 1 | 32.48 |
| 284 | NE | ARG | 40 | 30.896 | 27.408 | 20.725 | 1 | 35.52 |
| 285 | CZ | ARG | 40 | 31.588 | 28.252 | 21.485 | 1 | 36.95 |
| 286 | NH1 | ARG | 40 | 32.863 | 28.017 | 21.749 | 1 | 38.82 |
| 287 | NH2 | ARG | 40 | 30.999 | 29.329 | 21.987 | 1 | 38.15 |
| 288 | C | ARG | 40 | 32.017 | 25.122 | 16.369 | 1 | 19.78 |
| 289 | O | ARG | 40 | 32.737 | 24.251 | 16.854 | 1 | 17.3 |
| 290 | N | LEU | 41 | 31.372 | 24.957 | 15.218 | 1 | 18.17 |
| 291 | CA | LEU | 41 | 31.516 | 23.723 | 14.456 | 1 | 16.98 |
| 292 | CB | LEU | 41 | 30.685 | 23.771 | 13.171 | 1 | 18.13 |
| 293 | CG | LEU | 41 | 29.212 | 23.367 | 13.226 | 1 | 20.38 |
| 294 | CD1 | LEU | 41 | 28.569 | 23.628 | 11.87 | 1 | 20.91 |
| 295 | CD2 | LEU | 41 | 29.096 | 21.888 | 13.589 | 1 | 18.45 |
| 296 | C | LEU | 41 | 32.974 | 23.484 | 14.092 | 1 | 17.41 |
| 297 | O | LEU | 41 | 33.499 | 22.39 | 14.294 | 1 | 17.13 |
| 298 | N | VAL | 42 | 33.632 | 24.509 | 13.554 | 1 | 15.72 |
| 299 | CA | VAL | 42 | 35.028 | 24.374 | 13.167 | 1 | 17.73 |
| 300 | CB | VAL | 42 | 35.528 | 25.628 | 12.417 | 1 | 17.46 |
| 301 | CG1 | VAL | 42 | 37.021 | 25.513 | 12.142 | 1 | 18 |
| 302 | CG2 | VAL | 42 | 34.767 | 25.78 | 11.106 | 1 | 19.56 |
| 303 | C | VAL | 42 | 35.918 | 24.112 | 14.379 | 1 | 17.18 |
| 304 | O | VAL | 42 | 36.834 | 23.299 | 14.31 | 1 | 17.76 |
| 305 | N | GLN | 43 | 35.64 | 24.791 | 15.489 | 1 | 17.76 |
| 306 | CA | GLN | 43 | 36.43 | 24.604 | 16.706 | 1 | 19.33 |
| 307 | CB | GLN | 43 | 35.94 | 25.53 | 17.822 | 1 | 22.44 |
| 308 | CG | GLN | 43 | 36.397 | 26.969 | 17.716 | 1 | 30.29 |
| 309 | CD | GLN | 43 | 35.995 | 27.779 | 18.933 | 1 | 33.56 |
| 310 | OE1 | GLN | 43 | 36.307 | 27.41 | 20.068 | 1 | 36.65 |
| 311 | NE2 | GLN | 43 | 35.299 | 28.887 | 18.705 | 1 | 37.16 |
| 312 | C | GLN | 43 | 36.361 | 23.169 | 17.211 | 1 | 18.71 |
| 313 | O | GLN | 43 | 37.383 | 22.559 | 17.527 | 1 | 18.27 |
| 314 | N | VAL | 44 | 35.146 | 22.636 | 17.295 | 1 | 16.8 |
| 315 | CA | VAL | 44 | 34.956 | 21.273 | 17.773 | 1 | 17.04 |
| 316 | CB | VAL | 44 | 33.461 | 20.961 | 17.977 | 1 | 16.42 |
| 317 | CG1 | VAL | 44 | 33.282 | 19.503 | 18.371 | 1 | 19.39 |
| 318 | CG2 | VAL | 44 | 32.887 | 21.871 | 19.051 | 1 | 19.42 |
| 319 | C | VAL | 44 | 35.555 | 20.267 | 16.803 | 1 | 16.13 |
| 320 | O | VAL | 44 | 36.196 | 19.3 | 17.213 | 1 | 17.47 |
| 321 | N | MET | 45 | 35.352 | 20.496 | 15.511 | 1 | 17.61 |
| 322 | CA | MET | 45 | 35.892 | 19.603 | 14.5 | 1 | 17.96 |
| 323 | CB | MET | 45 | 35.503 | 20.097 | 13.101 | 1 | 17.81 |
| 324 | CG | MET | 45 | 36.032 | 19.235 | 11.966 | 1 | 19.99 |
| 325 | SD | MET | 45 | 35.476 | 19.81 | 10.338 | 1 | 21.95 |
| 326 | CE | MET | 45 | 36.391 | 21.346 | 10.178 | 1 | 23.49 |
| 327 | C | MET | 45 | 37.412 | 19.509 | 14.625 | 1 | 18.92 |
| 328 | O | MET | 45 | 37.979 | 18.421 | 14.575 | 1 | 21.48 |
| 329 | N | ARG | 46 | 38.069 | 20.651 | 14.807 | 1 | 19.71 |
| 330 | CA | ARG | 46 | 39.523 | 20.678 | 14.932 | 1 | 21.2 |
| 331 | CB | ARG | 46 | 40.032 | 22.11 | 14.741 | 1 | 22.38 |
| 332 | CG | ARG | 46 | 39.887 | 22.601 | 13.304 | 1 | 21.44 |
| 333 | CD | ARG | 46 | 40.241 | 24.069 | 13.155 | 1 | 22.68 |
| 334 | NE | ARG | 46 | 40.265 | 24.466 | 11.75 | 1 | 20.78 |
| 335 | CZ | ARG | 46 | 40.302 | 25.725 | 11.326 | 1 | 21.97 |
| 336 | NH1 | ARG | 46 | 40.316 | 26.723 | 12.202 | 1 | 23.33 |
| 337 | NH2 | ARG | 46 | 40.328 | 25.986 | 10.025 | 1 | 21.64 |
| 338 | C | ARG | 46 | 40.023 | 20.106 | 16.258 | 1 | 21.36 |
| 339 | O | ARG | 46 | 41.067 | 19.452 | 16.305 | 1 | 22.93 |
| 340 | N | ARG | 47 | 39.275 | 20.344 | 17.329 | 1 | 21.01 |
| 341 | CA | ARG | 47 | 39.644 | 19.838 | 18.649 | 1 | 21.8 |
| 342 | CB | ARG | 47 | 38.677 | 20.381 | 19.703 | 1 | 23.15 |
| 343 | CG | ARG | 47 | 38.941 | 19.904 | 21.124 | 1 | 28.25 |
| 344 | CD | ARG | 47 | 40.165 | 20.579 | 21.726 | 1 | 31.26 |
| 345 | NE | ARG | 47 | 39.859 | 21.198 | 23.015 | 1 | 35.88 |
| 346 | CZ | ARG | 47 | 39.507 | 20.527 | 24.108 | 1 | 35.94 |
| 347 | NH1 | ARG | 47 | 39.416 | 19.203 | 24.083 | 1 | 37.64 |
| 348 | NH2 | ARG | 47 | 39.239 | 21.183 | 25.229 | 1 | 37.58 |
| 349 | C | ARG | 47 | 39.605 | 18.312 | 18.662 | 1 | 21.15 |
| 350 | O | ARG | 47 | 40.479 | 17.658 | 19.234 | 1 | 21.99 |
| 351 | N | ARG | 48 | 38.585 | 17.753 | 18.019 | 1 | 19.63 |
| 352 | CA | ARG | 48 | 38.401 | 16.308 | 17.955 | 1 | 20.96 |
| 353 | CB | ARG | 48 | 36.91 | 15.988 | 17.822 | 1 | 20.96 |
| 354 | CG | ARG | 48 | 36.102 | 16.247 | 19.086 | 1 | 23.58 |
| 355 | CD | ARG | 48 | 36.589 | 15.341 | 20.197 | 1 | 26.36 |
| 356 | NE | ARG | 48 | 36.601 | 13.953 | 19.753 | 1 | 28.57 |
| 357 | CZ | ARG | 48 | 37.369 | 13.005 | 20.275 | 1 | 31.59 |
| 358 | NH1 | ARG | 48 | 38.198 | 13.292 | 21.27 | 1 | 34.58 |
| 359 | NH2 | ARG | 48 | 37.315 | 11.771 | 19.793 | 1 | 31.45 |
| 360 | C | ARG | 48 | 39.167 | 15.645 | 16.815 | 1 | 21.78 |
| 361 | O | ARG | 48 | 39.105 | 14.43 | 16.64 | 1 | 22.18 |
| 362 | N | ARG | 49 | 39.892 | 16.448 | 16.047 | 1 | 22.31 |
| 363 | CA | ARG | 49 | 40.66 | 15.943 | 14.919 | 1 | 23.86 |
| 364 | CB | ARG | 49 | 41.861 | 15.119 | 15.397 | 1 | 26.74 |
| 365 | CG | ARG | 49 | 43.004 | 15.937 | 15.997 | 1 | 31.9 |
| 366 | CD | ARG | 49 | 42.888 | 16.053 | 17.507 | 1 | 35.66 |
| 367 | NE | ARG | 49 | 44.057 | 16.7 | 18.101 | 1 | 38.6 |
| 368 | CZ | ARG | 49 | 44.295 | 18.008 | 18.067 | 1 | 38.49 |
| 369 | NH1 | ARG | 49 | 43.442 | 18.827 | 17.468 | 1 | 39.34 |
| 370 | NH2 | ARG | 49 | 45.388 | 18.499 | 18.637 | 1 | 40.6 |
| 371 | C | ARG | 49 | 39.829 | 15.112 | 13.943 | 1 | 22.96 |
| 372 | O | ARG | 49 | 40.303 | 14.105 | 13.414 | 1 | 24.34 |
| 373 | N | CYS | 50 | 38.582 | 15.516 | 13.719 | 1 | 21.35 |
| 374 | CA | CYS | 50 | 37.745 | 14.811 | 12.758 | 1 | 20.8 |
| 375 | CB | CYS | 50 | 36.33 | 14.566 | 13.304 | 1 | 21.25 |
| 376 | SG | CYS | 50 | 35.412 | 15.982 | 13.895 | 1 | 20.78 |
| 377 | C | CYS | 50 | 37.733 | 15.675 | 11.499 | 1 | 20.4 |
| 378 | O | CYS | 50 | 38.155 | 16.832 | 11.534 | 1 | 22.25 |
| 379 | N | VAL | 51 | 37.261 | 15.125 | 10.39 | 1 | 18.11 |
| 380 | CA | VAL | 51 | 37.288 | 15.853 | 9.128 | 1 | 15.54 |
| 381 | CB | VAL | 51 | 37.794 | 14.931 | 8.013 | 1 | 16.9 |
| 382 | CG1 | VAL | 51 | 39.237 | 14.532 | 8.29 | 1 | 18.06 |
| 383 | CG2 | VAL | 51 | 36.934 | 13.692 | 7.942 | 1 | 18.36 |
| 384 | C | VAL | 51 | 35.986 | 16.508 | 8.69 | 1 | 15.5 |
| 385 | O | VAL | 51 | 35.938 | 17.171 | 7.655 | 1 | 15.19 |
| 386 | N | GLY | 52 | 34.937 | 16.329 | 9.481 | 1 | 14.28 |

TABLE 2-continued

| Atom | Atom Type | Residue | # | X | Y | Z | OCC | B |
|---|---|---|---|---|---|---|---|---|
| 387 | CA | GLY | 52 | 33.656 | 16.93 | 9.155 | 1 | 14.19 |
| 388 | C | GLY | 52 | 32.762 | 16.954 | 10.379 | 1 | 12.82 |
| 389 | O | GLY | 52 | 32.939 | 16.15 | 11.291 | 1 | 14.14 |
| 390 | N | LEU | 53 | 31.815 | 17.883 | 10.413 | 1 | 12.85 |
| 391 | CA | LEU | 53 | 30.89 | 17.983 | 11.535 | 1 | 12.35 |
| 392 | CB | LEU | 53 | 31.566 | 18.681 | 12.716 | 1 | 12.69 |
| 393 | CG | LEU | 53 | 30.891 | 18.554 | 14.083 | 1 | 14.76 |
| 394 | CD1 | LEU | 53 | 30.829 | 17.087 | 14.504 | 1 | 15.29 |
| 395 | CD2 | LEU | 53 | 31.685 | 19.35 | 15.11 | 1 | 14.25 |
| 396 | C | LEU | 53 | 29.661 | 18.764 | 11.084 | 1 | 13.28 |
| 397 | O | LEU | 53 | 29.773 | 19.685 | 10.277 | 1 | 14.23 |
| 398 | N | SER | 54 | 28.493 | 18.393 | 11.6 | 1 | 11.71 |
| 399 | CA | SER | 54 | 27.251 | 19.061 | 11.221 | 1 | 12.14 |
| 400 | CB | SER | 54 | 26.301 | 18.052 | 10.571 | 1 | 12.57 |
| 401 | OG | SER | 54 | 25.871 | 17.088 | 11.516 | 1 | 14.49 |
| 402 | C | SER | 54 | 26.563 | 19.722 | 12.413 | 1 | 13.2 |
| 403 | O | SER | 54 | 26.753 | 19.314 | 13.559 | 1 | 13.09 |
| 404 | N | ALA | 55 | 25.75 | 20.737 | 12.136 | 1 | 12.83 |
| 405 | CA | ALA | 55 | 25.049 | 21.457 | 13.189 | 1 | 13.42 |
| 406 | CB | ALA | 55 | 24.176 | 22.562 | 12.578 | 1 | 14.23 |
| 407 | C | ALA | 55 | 24.212 | 20.559 | 14.103 | 1 | 12.75 |
| 408 | O | ALA | 55 | 24.219 | 20.738 | 15.32 | 1 | 12.79 |
| 409 | N | PRO | 56 | 23.471 | 19.59 | 13.535 | 1 | 12.73 |
| 410 | CD | PRO | 56 | 23.196 | 19.325 | 12.11 | 1 | 12.32 |
| 411 | CA | PRO | 56 | 22.663 | 18.714 | 14.393 | 1 | 12.23 |
| 412 | CB | PRO | 56 | 22.079 | 17.709 | 13.403 | 1 | 13.26 |
| 413 | CG | PRO | 56 | 21.89 | 18.548 | 12.169 | 1 | 12.52 |
| 414 | C | PRO | 56 | 23.488 | 18.029 | 15.486 | 1 | 12.77 |
| 415 | O | PRO | 56 | 22.981 | 17.733 | 16.572 | 1 | 13.56 |
| 416 | N | GLN | 57 | 24.759 | 17.776 | 15.193 | 1 | 12.03 |
| 417 | CA | GLN | 57 | 25.637 | 17.121 | 16.155 | 1 | 12.89 |
| 418 | CB | GLN | 57 | 26.905 | 16.634 | 15.459 | 1 | 12.31 |
| 419 | CG | GLN | 57 | 26.647 | 15.434 | 14.565 | 1 | 13.9 |
| 420 | CD | GLN | 57 | 27.837 | 15.093 | 13.712 | 1 | 13.5 |
| 421 | OE1 | GLN | 57 | 28.081 | 15.726 | 12.683 | 1 | 13.68 |
| 422 | NE2 | GLN | 57 | 28.602 | 14.097 | 14.14 | 1 | 12.71 |
| 423 | C | GLN | 57 | 25.983 | 18.022 | 17.333 | 1 | 13.21 |
| 424 | O | GLN | 57 | 26.472 | 17.55 | 18.359 | 1 | 13.19 |
| 425 | N | LEU | 58 | 25.735 | 19.319 | 17.184 | 1 | 12.82 |
| 426 | CA | LEU | 58 | 25.98 | 20.256 | 18.273 | 1 | 15.2 |
| 427 | CB | LEU | 58 | 26.762 | 21.481 | 17.785 | 1 | 15.57 |
| 428 | CG | LEU | 58 | 28.193 | 21.226 | 17.303 | 1 | 16.9 |
| 429 | CD1 | LEU | 58 | 28.863 | 22.565 | 17.008 | 1 | 19.82 |
| 430 | CD2 | LEU | 58 | 28.982 | 20.457 | 18.361 | 1 | 18.36 |
| 431 | C | LEU | 58 | 24.624 | 20.674 | 18.836 | 1 | 16.63 |
| 432 | O | LEU | 58 | 24.5 | 21.692 | 19.525 | 1 | 18.26 |
| 433 | N | GLY | 59 | 23.607 | 19.874 | 18.519 | 1 | 14.85 |
| 434 | CA | GLY | 59 | 22.262 | 20.122 | 19.006 | 1 | 14.64 |
| 435 | C | GLY | 59 | 21.455 | 21.169 | 18.262 | 1 | 14.7 |
| 436 | O | GLY | 59 | 20.399 | 21.583 | 18.736 | 1 | 17.16 |
| 437 | N | VAL | 60 | 21.941 | 21.596 | 17.101 | 1 | 14 |
| 438 | CA | VAL | 60 | 21.246 | 22.612 | 16.312 | 1 | 15.2 |
| 439 | CB | VAL | 60 | 22.199 | 23.776 | 15.979 | 1 | 16.8 |
| 440 | CG1 | VAL | 60 | 21.462 | 24.849 | 15.192 | 1 | 16.39 |
| 441 | CG2 | VAL | 60 | 22.766 | 24.356 | 17.271 | 1 | 18.95 |
| 442 | C | VAL | 60 | 20.69 | 22.002 | 15.026 | 1 | 14.72 |
| 443 | O | VAL | 60 | 21.44 | 21.677 | 14.103 | 1 | 14.49 |
| 444 | N | PRO | 61 | 19.357 | 21.843 | 14.95 | 1 | 15.66 |
| 445 | CD | PRO | 61 | 18.382 | 22.163 | 16.011 | 1 | 16.3 |
| 446 | CA | PRO | 61 | 18.685 | 21.263 | 13.783 | 1 | 16.17 |
| 447 | CB | PRO | 61 | 17.309 | 20.9 | 14.333 | 1 | 16.52 |
| 448 | CG | PRO | 61 | 17.048 | 22.025 | 15.291 | 1 | 17.99 |
| 449 | C | PRO | 61 | 18.607 | 22.179 | 12.566 | 1 | 15.92 |
| 450 | O | PRO | 61 | 17.519 | 22.476 | 12.069 | 1 | 17.63 |
| 451 | N | ARG | 62 | 19.768 | 22.613 | 12.089 | 1 | 14.88 |
| 452 | CA | ARG | 62 | 19.843 | 23.496 | 10.929 | 1 | 15.01 |
| 453 | CB | ARG | 62 | 20.322 | 24.887 | 11.355 | 1 | 17.43 |
| 454 | CG | ARG | 62 | 19.47 | 25.51 | 12.454 | 1 | 22.1 |
| 455 | CD | ARG | 62 | 20.024 | 26.852 | 12.917 | 1 | 27.02 |
| 456 | NE | ARG | 62 | 19.697 | 27.942 | 12.002 | 1 | 31.02 |
| 457 | CZ | ARG | 62 | 20.19 | 29.172 | 12.105 | 1 | 33.19 |
| 458 | NH1 | ARG | 62 | 21.038 | 29.469 | 13.081 | 1 | 34.7 |
| 459 | NH2 | ARG | 62 | 19.829 | 30.109 | 11.238 | 1 | 32.64 |
| 460 | C | ARG | 62 | 20.798 | 22.905 | 9.902 | 1 | 14.71 |
| 461 | O | ARG | 62 | 21.742 | 22.189 | 10.257 | 1 | 15.25 |
| 462 | N | GLN | 63 | 20.556 | 23.216 | 8.63 | 1 | 14.38 |
| 463 | CA | GLN | 63 | 21.374 | 22.701 | 7.539 | 1 | 15.07 |
| 464 | CB | GLN | 63 | 20.59 | 22.761 | 6.222 | 1 | 16.46 |
| 465 | CG | GLN | 63 | 19.266 | 22.021 | 6.275 | 1 | 18.17 |
| 466 | CD | GLN | 63 | 18.481 | 22.104 | 4.976 | 1 | 20.24 |
| 467 | OE1 | GLN | 63 | 17.308 | 21.732 | 4.924 | 1 | 23.21 |
| 468 | NE2 | GLN | 63 | 19.126 | 22.583 | 3.92 | 1 | 18.38 |
| 469 | C | GLN | 63 | 22.697 | 23.436 | 7.387 | 1 | 15.2 |
| 470 | O | GLN | 63 | 22.855 | 24.286 | 6.513 | 1 | 15.94 |
| 471 | N | VAL | 64 | 23.646 | 23.094 | 8.252 | 1 | 14.32 |
| 472 | CA | VAL | 64 | 24.973 | 23.69 | 8.234 | 1 | 13.57 |
| 473 | CB | VAL | 64 | 25.126 | 24.787 | 9.31 | 1 | 15.42 |
| 474 | CG1 | VAL | 64 | 26.496 | 25.434 | 9.193 | 1 | 15.03 |
| 475 | CG2 | VAL | 64 | 24.033 | 25.828 | 9.162 | 1 | 16.15 |
| 476 | C | VAL | 64 | 25.988 | 22.6 | 8.543 | 1 | 13.95 |
| 477 | O | VAL | 64 | 25.78 | 21.792 | 9.45 | 1 | 14.14 |
| 478 | N | LEU | 65 | 27.076 | 22.569 | 7.787 | 1 | 13.09 |
| 479 | CA | LEU | 65 | 28.119 | 21.581 | 8.021 | 1 | 13.57 |
| 480 | CB | LEU | 65 | 27.817 | 20.285 | 7.248 | 1 | 13.51 |
| 481 | CG | LEU | 65 | 27.746 | 20.301 | 5.717 | 1 | 13.34 |
| 482 | CD1 | LEU | 65 | 29.152 | 20.3 | 5.127 | 1 | 16.72 |
| 483 | CD2 | LEU | 65 | 26.986 | 19.063 | 5.236 | 1 | 15.76 |
| 484 | C | LEU | 65 | 29.474 | 22.149 | 7.622 | 1 | 14.81 |
| 485 | O | LEU | 65 | 29.554 | 23.098 | 6.84 | 1 | 14.59 |
| 486 | N | ALA | 66 | 30.535 | 21.574 | 8.178 | 1 | 14.34 |
| 487 | CA | ALA | 66 | 31.895 | 22.009 | 7.885 | 1 | 14.64 |
| 488 | CB | ALA | 66 | 32.501 | 22.696 | 9.102 | 1 | 16.02 |
| 489 | C | ALA | 66 | 32.727 | 20.794 | 7.497 | 1 | 14.24 |
| 490 | O | ALA | 66 | 32.48 | 19.679 | 7.973 | 1 | 14.21 |
| 491 | N | LEU | 67 | 33.713 | 21.016 | 6.635 | 1 | 13.49 |
| 492 | CA | LEU | 67 | 34.58 | 19.954 | 6.148 | 1 | 15.16 |
| 493 | CB | LEU | 67 | 34.138 | 19.533 | 4.744 | 1 | 16.41 |
| 494 | CG | LEU | 67 | 32.653 | 19.214 | 4.565 | 1 | 18.56 |
| 495 | CD1 | LEU | 67 | 32.298 | 19.189 | 3.083 | 1 | 20.83 |
| 496 | CD2 | LEU | 67 | 32.337 | 17.885 | 5.227 | 1 | 20.37 |
| 497 | C | LEU | 67 | 36.012 | 20.468 | 6.076 | 1 | 14.93 |
| 498 | O | LEU | 67 | 36.244 | 21.58 | 5.608 | 1 | 15.14 |
| 499 | N | GLU | 68 | 36.965 | 19.659 | 6.527 | 1 | 14.66 |
| 500 | CA | GLU | 68 | 38.369 | 20.052 | 6.484 | 1 | 16.57 |
| 501 | CB | GLU | 68 | 38.647 | 21.18 | 7.484 | 1 | 18.98 |
| 502 | CG | GLU | 68 | 40.118 | 21.588 | 7.55 | 1 | 20.55 |
| 503 | CD | GLU | 68 | 40.391 | 22.647 | 8.601 | 1 | 23.37 |
| 504 | OE1 | GLU | 68 | 39.962 | 22.462 | 9.76 | 1 | 25 |
| 505 | OE2 | GLU | 68 | 41.044 | 23.661 | 8.272 | 1 | 24.79 |
| 506 | C | GLU | 68 | 39.299 | 18.886 | 6.782 | 1 | 17.57 |
| 507 | O | GLU | 68 | 39.073 | 18.125 | 7.722 | 1 | 15.9 |
| 508 | N | LEU | 69 | 40.34 | 18.742 | 5.97 | 1 | 17.16 |
| 509 | CA | LEU | 69 | 41.322 | 17.687 | 6.176 | 1 | 18.24 |
| 510 | CB | LEU | 69 | 41.118 | 16.54 | 5.181 | 1 | 18.05 |
| 511 | CG | LEU | 69 | 42.134 | 15.395 | 5.278 | 1 | 19.57 |
| 512 | CD1 | LEU | 69 | 42.316 | 14.975 | 6.728 | 1 | 21.29 |
| 513 | CD2 | LEU | 69 | 41.66 | 14.222 | 4.435 | 1 | 21.34 |
| 514 | C | LEU | 69 | 42.725 | 18.263 | 6.028 | 1 | 19.81 |
| 515 | O | LEU | 69 | 43.281 | 18.311 | 4.928 | 1 | 19.04 |
| 516 | N | PRO | 70 | 43.31 | 18.721 | 7.144 | 1 | 20.29 |
| 517 | CD | PRO | 70 | 42.683 | 18.845 | 8.47 | 1 | 20.67 |
| 518 | CA | PRO | 70 | 44.656 | 19.301 | 7.154 | 1 | 21.82 |
| 519 | CB | PRO | 70 | 44.839 | 19.722 | 8.61 | 1 | 21.7 |
| 520 | CG | PRO | 70 | 43.439 | 20.007 | 9.061 | 1 | 23.09 |
| 521 | C | PRO | 70 | 45.713 | 18.297 | 6.714 | 1 | 22.14 |
| 522 | O | PRO | 70 | 45.518 | 17.088 | 6.818 | 1 | 21.77 |
| 523 | N | GLU | 71 | 46.836 | 18.812 | 6.226 | 1 | 23.65 |
| 524 | CA | GLU | 71 | 47.933 | 17.973 | 5.767 | 1 | 25.57 |
| 525 | CB | GLU | 71 | 49.079 | 18.85 | 5.254 | 1 | 27.88 |
| 526 | CG | GLU | 71 | 50.251 | 18.075 | 4.671 | 1 | 33.51 |
| 527 | CD | GLU | 71 | 51.357 | 18.984 | 4.16 | 1 | 35.71 |
| 528 | OE1 | GLU | 71 | 51.957 | 19.714 | 4.977 | 1 | 38.73 |
| 529 | OE2 | GLU | 71 | 51.626 | 18.97 | 2.939 | 1 | 38.89 |
| 530 | C | GLU | 71 | 48.447 | 17.059 | 6.876 | 1 | 24.74 |
| 531 | O | GLU | 71 | 48.692 | 15.877 | 6.647 | 1 | 25.4 |
| 532 | N | ALA | 72 | 48.608 | 17.615 | 8.074 | 1 | 25.44 |
| 533 | CA | ALA | 72 | 49.11 | 16.857 | 9.216 | 1 | 25.36 |
| 534 | CB | ALA | 72 | 49.255 | 17.771 | 10.424 | 1 | 25.38 |
| 535 | C | ALA | 72 | 48.208 | 15.682 | 9.561 | 1 | 24.97 |
| 536 | O | ALA | 72 | 48.673 | 14.549 | 9.693 | 1 | 24.08 |
| 537 | N | LEU | 73 | 46.917 | 15.958 | 9.711 | 1 | 25.13 |
| 538 | CA | LEU | 73 | 45.953 | 14.917 | 10.043 | 1 | 26.13 |

TABLE 2-continued

| Atom | Atom Type | Residue | # | X | Y | Z | OCC | B |
|---|---|---|---|---|---|---|---|---|
| 539 | CB | LEU | 73 | 44.556 | 15.525 | 10.186 | 1 | 24.71 |
| 540 | CG | LEU | 73 | 43.431 | 14.56 | 10.558 | 1 | 24.5 |
| 541 | CD1 | LEU | 73 | 43.76 | 13.872 | 11.876 | 1 | 25.01 |
| 542 | CD2 | LEU | 73 | 42.124 | 15.324 | 10.666 | 1 | 23.6 |
| 543 | C | LEU | 73 | 45.947 | 13.852 | 8.956 | 1 | 26.1 |
| 544 | O | LEU | 73 | 45.846 | 12.656 | 9.234 | 1 | 27.19 |
| 545 | N | CYS | 74 | 46.066 | 14.299 | 7.712 | 1 | 27.26 |
| 546 | CA | CYS | 74 | 46.077 | 13.402 | 6.571 | 1 | 28.15 |
| 547 | CB | CYS | 74 | 46.032 | 14.217 | 5.277 | 1 | 28.71 |
| 548 | SG | CYS | 74 | 45.763 | 13.243 | 3.785 | 1 | 30.48 |
| 549 | C | CYS | 74 | 47.321 | 12.515 | 6.586 | 1 | 30.64 |
| 550 | O | CYS | 74 | 47.282 | 11.368 | 6.141 | 1 | 30.48 |
| 551 | N | ARG | 75 | 48.422 | 13.046 | 7.107 | 1 | 31.93 |
| 552 | CA | ARG | 75 | 49.67 | 12.295 | 7.163 | 1 | 33.7 |
| 553 | CB | ARG | 75 | 50.859 | 13.251 | 7.304 | 1 | 34.5 |
| 554 | CG | ARG | 75 | 51.121 | 14.082 | 6.054 | 1 | 36.12 |
| 555 | CD | ARG | 75 | 52.396 | 14.901 | 6.179 | 1 | 38.28 |
| 556 | NE | ARG | 75 | 52.708 | 15.617 | 4.944 | 1 | 39.94 |
| 557 | CZ | ARG | 75 | 53.803 | 16.349 | 4.758 | 1 | 40.85 |
| 558 | NH1 | ARG | 75 | 54.698 | 16.467 | 5.73 | 1 | 40.89 |
| 559 | NH2 | ARG | 75 | 54.004 | 16.965 | 3.6 | 1 | 41.82 |
| 560 | C | ARG | 75 | 49.718 | 11.233 | 8.259 | 1 | 34.53 |
| 561 | O | ARG | 75 | 50.649 | 10.427 | 8.298 | 1 | 35.15 |
| 562 | N | GLU | 76 | 48.73 | 11.229 | 9.151 | 1 | 35.15 |
| 563 | CA | GLU | 76 | 48.686 | 10.22 | 10.21 | 1 | 36.41 |
| 564 | CB | GLU | 76 | 47.49 | 10.425 | 11.136 | 1 | 37.83 |
| 565 | CG | GLU | 76 | 47.573 | 11.593 | 12.073 | 1 | 40.93 |
| 566 | CD | GLU | 76 | 46.427 | 11.589 | 13.068 | 1 | 42.64 |
| 567 | OE1 | GLU | 76 | 45.261 | 11.533 | 12.628 | 1 | 43.8 |
| 568 | OE2 | GLU | 76 | 46.688 | 11.636 | 14.287 | 1 | 46.39 |
| 569 | C | GLU | 76 | 48.512 | 8.873 | 9.535 | 1 | 36.32 |
| 570 | O | GLU | 76 | 49.081 | 7.866 | 9.952 | 1 | 37.05 |
| 571 | N | CYS | 77 | 47.696 | 8.877 | 8.489 | 1 | 35.24 |
| 572 | CA | CYS | 77 | 47.398 | 7.68 | 7.726 | 1 | 34.86 |
| 573 | CB | CYS | 77 | 46.177 | 7.939 | 6.842 | 1 | 35.88 |
| 574 | SG | CYS | 77 | 45.574 | 6.507 | 5.945 | 1 | 39 |
| 575 | C | CYS | 77 | 48.596 | 7.29 | 6.868 | 1 | 34.14 |
| 576 | O | CYS | 77 | 49.131 | 8.114 | 6.127 | 1 | 34 |
| 577 | N | PRO | 78 | 49.04 | 6.026 | 6.968 | 1 | 33.53 |
| 578 | CD | PRO | 78 | 48.519 | 4.962 | 7.844 | 1 | 33.41 |
| 579 | CA | PRO | 78 | 50.183 | 5.543 | 6.187 | 1 | 33.41 |
| 580 | CB | PRO | 78 | 50.208 | 4.05 | 6.503 | 1 | 33.72 |
| 581 | CG | PRO | 78 | 49.683 | 4.001 | 7.901 | 1 | 34.3 |
| 582 | C | PRO | 78 | 49.972 | 5.813 | 4.7 | 1 | 33.27 |
| 583 | O | PRO | 78 | 48.849 | 5.741 | 4.204 | 1 | 32.56 |
| 584 | N | PRO | 79 | 51.054 | 6.118 | 3.967 | 1 | 32.8 |
| 585 | CD | PRO | 79 | 52.464 | 6.003 | 4.379 | 1 | 33.93 |
| 586 | CA | PRO | 79 | 50.954 | 6.398 | 2.532 | 1 | 32.71 |
| 587 | CB | PRO | 79 | 52.417 | 6.533 | 2.104 | 1 | 33.04 |
| 588 | CG | PRO | 79 | 53.139 | 5.645 | 3.08 | 1 | 33.57 |
| 589 | C | PRO | 79 | 50.207 | 5.326 | 1.741 | 1 | 32.44 |
| 590 | O | PRO | 79 | 49.391 | 5.642 | 0.874 | 1 | 32.15 |
| 591 | N | ARG | 80 | 50.482 | 4.062 | 2.042 | 1 | 32.27 |
| 592 | CA | ARG | 80 | 49.828 | 2.96 | 1.346 | 1 | 32.36 |
| 593 | CB | ARG | 80 | 50.407 | 1.622 | 1.811 | 1 | 34.09 |
| 594 | CG | ARG | 80 | 49.833 | 0.416 | 1.086 | 1 | 37.31 |
| 595 | CD | ARG | 80 | 50.533 | −0.864 | 1.513 | 1 | 40.3 |
| 596 | NE | ARG | 80 | 50.054 | −2.028 | 0.772 | 1 | 42.63 |
| 597 | CZ | ARG | 80 | 50.547 | −3.255 | 0.912 | 1 | 43.08 |
| 598 | NH1 | ARG | 80 | 51.536 | −3.48 | 1.767 | 1 | 43.48 |
| 599 | NH2 | ARG | 80 | 50.053 | −4.257 | 0.196 | 1 | 43.72 |
| 600 | C | ARG | 80 | 48.326 | 2.989 | 1.599 | 1 | 31.54 |
| 601 | O | ARG | 80 | 47.524 | 2.761 | 0.689 | 1 | 30.35 |
| 602 | N | GLN | 81 | 47.952 | 3.273 | 2.841 | 1 | 30.64 |
| 603 | CA | GLN | 81 | 46.548 | 3.34 | 3.218 | 1 | 30.23 |
| 604 | CB | GLN | 81 | 46.422 | 3.361 | 4.743 | 1 | 31.95 |
| 605 | CG | GLN | 81 | 44.996 | 3.319 | 5.253 | 1 | 35.4 |
| 606 | CD | GLN | 81 | 44.927 | 3.194 | 6.763 | 1 | 37.5 |
| 607 | OE1 | GLN | 81 | 45.453 | 4.035 | 7.492 | 1 | 40.13 |
| 608 | NE2 | GLN | 81 | 44.279 | 2.137 | 7.24 | 1 | 38.91 |
| 609 | C | GLN | 81 | 45.907 | 4.587 | 2.612 | 1 | 28.65 |
| 610 | O | GLN | 81 | 44.738 | 4.566 | 2.221 | 1 | 26.9 |
| 611 | N | ARG | 82 | 46.676 | 5.67 | 2.537 | 1 | 28.19 |
| 612 | CA | ARG | 82 | 46.185 | 6.917 | 1.961 | 1 | 28.33 |
| 613 | CB | ARG | 82 | 47.21 | 8.041 | 2.141 | 1 | 30.73 |
| 614 | CG | ARG | 82 | 47.02 | 8.882 | 3.387 | 1 | 32.5 |
| 615 | CD | ARG | 82 | 48.047 | 10.003 | 3.439 | 1 | 36.03 |
| 616 | NE | ARG | 82 | 49.396 | 9.495 | 3.669 | 1 | 38.23 |
| 617 | CZ | ARG | 82 | 50.492 | 10.246 | 3.657 | 1 | 39.84 |
| 618 | NH1 | ARG | 82 | 50.405 | 11.549 | 3.422 | 1 | 41.37 |
| 619 | NH2 | ARG | 82 | 51.676 | 9.696 | 3.888 | 1 | 40.32 |
| 620 | C | ARG | 82 | 45.912 | 6.729 | 0.476 | 1 | 27.27 |
| 621 | O | ARG | 82 | 44.907 | 7.206 | −0.048 | 1 | 26.24 |
| 622 | N | ALA | 83 | 46.818 | 6.032 | −0.2 | 1 | 25.88 |
| 623 | CA | ALA | 83 | 46.67 | 5.782 | −1.627 | 1 | 25.53 |
| 624 | CB | ALA | 83 | 47.917 | 5.086 | −2.166 | 1 | 26.57 |
| 625 | C | ALA | 83 | 45.437 | 4.927 | −1.891 | 1 | 25.26 |
| 626 | O | ALA | 83 | 44.647 | 5.216 | −2.791 | 1 | 25.28 |
| 627 | N | LEU | 84 | 45.278 | 3.875 | −1.096 | 1 | 24.5 |
| 628 | CA | LEU | 84 | 44.147 | 2.966 | −1.24 | 1 | 23.96 |
| 629 | CB | LEU | 84 | 44.256 | 1.84 | −0.209 | 1 | 25.91 |
| 630 | CG | LEU | 84 | 43.218 | 0.721 | −0.303 | 1 | 29.28 |
| 631 | CD1 | LEU | 84 | 43.317 | 0.04 | −1.667 | 1 | 30.58 |
| 632 | CD2 | LEU | 84 | 43.452 | −0.287 | 0.814 | 1 | 29.54 |
| 633 | C | LEU | 84 | 42.811 | 3.687 | −1.072 | 1 | 22.67 |
| 634 | O | LEU | 84 | 41.876 | 3.474 | −1.845 | 1 | 22.32 |
| 635 | N | ARG | 85 | 42.725 | 4.541 | −0.059 | 1 | 20.55 |
| 636 | CA | ARG | 85 | 41.496 | 5.279 | 0.214 | 1 | 21.24 |
| 637 | CB | ARG | 85 | 41.415 | 5.615 | 1.705 | 1 | 22.09 |
| 638 | CG | ARG | 85 | 41.239 | 4.409 | 2.619 | 1 | 23.78 |
| 639 | CD | ARG | 85 | 41.399 | 4.82 | 4.079 | 1 | 25.02 |
| 640 | NE | ARG | 85 | 40.955 | 3.789 | 5.015 | 1 | 27.86 |
| 641 | CZ | ARG | 85 | 41.465 | 2.565 | 5.098 | 1 | 29.01 |
| 642 | NH1 | ARG | 85 | 42.453 | 2.192 | 4.295 | 1 | 32.2 |
| 643 | NH2 | ARG | 85 | 40.99 | 1.711 | 5.994 | 1 | 30.1 |
| 644 | C | ARG | 85 | 41.368 | 6.567 | −0.596 | 1 | 20.53 |
| 645 | O | ARG | 85 | 40.375 | 7.28 | −0.468 | 1 | 19.43 |
| 646 | N | GLN | 86 | 42.363 | 6.857 | −1.434 | 1 | 20.94 |
| 647 | CA | GLN | 86 | 42.351 | 8.077 | −2.24 | 1 | 21.47 |
| 648 | CB | GLN | 86 | 41.246 | 8.015 | −3.3 | 1 | 23.15 |
| 649 | CG | GLN | 86 | 41.422 | 6.864 | −4.281 | 1 | 24.86 |
| 650 | CD | GLN | 86 | 40.403 | 6.872 | −5.405 | 1 | 26.16 |
| 651 | OE1 | GLN | 86 | 40.345 | 5.939 | −6.206 | 1 | 32.1 |
| 652 | NE2 | GLN | 86 | 39.602 | 7.927 | −5.477 | 1 | 26.55 |
| 653 | C | GLN | 86 | 42.129 | 9.258 | −1.304 | 1 | 21.06 |
| 654 | O | GLN | 86 | 41.254 | 10.099 | −1.518 | 1 | 21.17 |
| 655 | N | MET | 87 | 42.946 | 9.298 | −0.259 | 1 | 21.19 |
| 656 | CA | MET | 87 | 42.878 | 10.334 | 0.754 | 1 | 22.04 |
| 657 | CB | MET | 87 | 43.172 | 9.722 | 2.123 | 1 | 23.36 |
| 658 | CG | MET | 87 | 42.884 | 10.628 | 3.298 | 1 | 24.79 |
| 659 | SD | MET | 87 | 43.415 | 9.864 | 4.84 | 1 | 28.09 |
| 660 | CE | MET | 87 | 42.391 | 8.402 | 4.863 | 1 | 28.31 |
| 661 | C | MET | 87 | 43.876 | 11.451 | 0.475 | 1 | 23.5 |
| 662 | O | MET | 87 | 45.083 | 11.216 | 0.4 | 1 | 23.63 |
| 663 | N | GLU | 88 | 43.361 | 12.664 | 0.325 | 1 | 22.59 |
| 664 | CA | GLU | 88 | 44.199 | 13.826 | 0.074 | 1 | 23.01 |
| 665 | CB | GLU | 88 | 44.165 | 14.198 | −1.411 | 1 | 26.68 |
| 666 | CG | GLU | 88 | 44.857 | 13.185 | −2.308 | 1 | 32.9 |
| 667 | CD | GLU | 88 | 44.797 | 13.56 | −3.776 | 1 | 37.97 |
| 668 | OE1 | GLU | 88 | 45.259 | 14.666 | −4.129 | 1 | 41.13 |
| 669 | OE2 | GLU | 88 | 44.291 | 12.745 | −4.577 | 1 | 40.19 |
| 670 | C | GLU | 88 | 43.697 | 14.986 | 0.917 | 1 | 21.21 |
| 671 | O | GLU | 88 | 42.503 | 15.094 | 1.199 | 1 | 19.87 |
| 672 | N | PRO | 89 | 44.605 | 15.87 | 1.348 | 1 | 21 |
| 673 | CD | PRO | 89 | 46.072 | 15.89 | 1.205 | 1 | 21.17 |
| 674 | CA | PRO | 89 | 44.14 | 16.991 | 2.16 | 1 | 20.06 |
| 675 | CB | PRO | 89 | 45.442 | 17.597 | 2.684 | 1 | 20.54 |
| 676 | CG | PRO | 89 | 46.406 | 17.313 | 1.587 | 1 | 23.54 |
| 677 | C | PRO | 89 | 43.31 | 17.993 | 1.366 | 1 | 19.21 |
| 678 | O | PRO | 89 | 43.426 | 18.083 | 0.143 | 1 | 21.03 |
| 679 | N | PHE | 90 | 42.441 | 18.712 | 2.068 | 1 | 17.44 |
| 680 | CA | PHE | 90 | 41.624 | 19.749 | 1.456 | 1 | 17.57 |
| 681 | CB | PHE | 90 | 40.312 | 19.198 | 0.866 | 1 | 17.4 |
| 682 | CG | PHE | 90 | 39.484 | 18.381 | 1.824 | 1 | 17 |
| 683 | CD1 | PHE | 90 | 39.533 | 16.992 | 1.788 | 1 | 15.97 |
| 684 | CD2 | PHE | 90 | 38.611 | 18.998 | 2.714 | 1 | 16.86 |
| 685 | CE1 | PHE | 90 | 38.717 | 16.224 | 2.622 | 1 | 16.56 |
| 686 | CE2 | PHE | 90 | 37.791 | 18.24 | 3.553 | 1 | 16.95 |
| 687 | CZ | PHE | 90 | 37.846 | 16.85 | 3.503 | 1 | 14.51 |
| 688 | C | PHE | 90 | 41.338 | 20.827 | 2.487 | 1 | 18.13 |
| 689 | O | PHE | 90 | 41.268 | 20.556 | 3.688 | 1 | 18.19 |
| 690 | N | PRO | 91 | 41.185 | 22.077 | 2.031 | 1 | 18.05 |

TABLE 2-continued

| Atom | Atom Type | Residue | # | X | Y | Z | OCC | B |
|---|---|---|---|---|---|---|---|---|
| 691 | CD | PRO | 91 | 41.308 | 22.52 | 0.629 | 1 | 19.01 |
| 692 | CA | PRO | 91 | 40.914 | 23.21 | 2.917 | 1 | 18.6 |
| 693 | CB | PRO | 91 | 41.183 | 24.413 | 2.019 | 1 | 19.03 |
| 694 | CG | PRO | 91 | 40.73 | 23.918 | 0.679 | 1 | 19.37 |
| 695 | C | PRO | 91 | 39.515 | 23.229 | 3.51 | 1 | 17.99 |
| 696 | O | PRO | 91 | 38.62 | 22.508 | 3.065 | 1 | 18.28 |
| 697 | N | LEU | 92 | 39.342 | 24.066 | 4.526 | 1 | 17.49 |
| 698 | CA | LEU | 92 | 38.065 | 24.209 | 5.195 | 1 | 16.6 |
| 699 | CB | LEU | 92 | 38.208 | 25.102 | 6.432 | 1 | 17.6 |
| 700 | CG | LEU | 92 | 36.882 | 25.572 | 7.045 | 1 | 16.35 |
| 701 | CD1 | LEU | 92 | 36.152 | 24.389 | 7.679 | 1 | 17.8 |
| 702 | CD2 | LEU | 92 | 37.147 | 26.648 | 8.082 | 1 | 18.71 |
| 703 | C | LEU | 92 | 36.994 | 24.805 | 4.293 | 1 | 18.08 |
| 704 | O | LEU | 92 | 37.219 | 25.806 | 3.608 | 1 | 18.44 |
| 705 | N | ARG | 93 | 35.83 | 24.169 | 4.295 | 1 | 17.69 |
| 706 | CA | ARG | 93 | 34.681 | 24.643 | 3.543 | 1 | 18.6 |
| 707 | CB | ARG | 93 | 34.438 | 23.805 | 2.283 | 1 | 19.56 |
| 708 | CG | ARG | 93 | 35.374 | 24.087 | 1.112 | 1 | 19.24 |
| 709 | CD | ARG | 93 | 34.833 | 23.406 | −0.145 | 1 | 21.39 |
| 710 | NE | ARG | 93 | 35.621 | 23.683 | −1.345 | 1 | 22.15 |
| 711 | CZ | ARG | 93 | 36.801 | 23.136 | −1.618 | 1 | 22.79 |
| 712 | NH1 | ARG | 93 | 37.35 | 22.27 | −0.777 | 1 | 25.29 |
| 713 | NH2 | ARG | 93 | 37.429 | 23.449 | −2.743 | 1 | 25.99 |
| 714 | C | ARG | 93 | 33.488 | 24.502 | 4.471 | 1 | 17.86 |
| 715 | O | ARG | 93 | 33.338 | 23.484 | 5.147 | 1 | 18.44 |
| 716 | N | VAL | 94 | 32.658 | 25.537 | 4.522 | 1 | 16.46 |
| 717 | CA | VAL | 94 | 31.459 | 25.529 | 5.349 | 1 | 16.3 |
| 718 | CB | VAL | 94 | 31.453 | 26.703 | 6.354 | 1 | 15.7 |
| 719 | CG1 | VAL | 94 | 30.151 | 26.708 | 7.141 | 1 | 15.73 |
| 720 | CG2 | VAL | 94 | 32.644 | 26.586 | 7.295 | 1 | 16.51 |
| 721 | C | VAL | 94 | 30.268 | 25.677 | 4.409 | 1 | 16.76 |
| 722 | O | VAL | 94 | 30.217 | 26.611 | 3.601 | 1 | 16.72 |
| 723 | N | PHE | 95 | 29.32 | 24.751 | 4.504 | 1 | 15.61 |
| 724 | CA | PHE | 95 | 28.135 | 24.789 | 3.656 | 1 | 15.83 |
| 725 | CB | PHE | 95 | 27.968 | 23.479 | 2.876 | 1 | 16.24 |
| 726 | CG | PHE | 95 | 28.955 | 23.295 | 1.764 | 1 | 16.36 |
| 727 | CD1 | PHE | 95 | 30.219 | 22.777 | 2.015 | 1 | 15.73 |
| 728 | CD2 | PHE | 95 | 28.616 | 23.636 | 0.458 | 1 | 18.33 |
| 729 | CE1 | PHE | 95 | 31.137 | 22.595 | 0.981 | 1 | 17.7 |
| 730 | CE2 | PHE | 95 | 29.523 | 23.461 | −0.584 | 1 | 18.92 |
| 731 | CZ | PHE | 95 | 30.786 | 22.939 | −0.322 | 1 | 18.48 |
| 732 | C | PHE | 95 | 26.849 | 25.043 | 4.429 | 1 | 16.42 |
| 733 | O | PHE | 95 | 26.634 | 24.495 | 5.512 | 1 | 16.49 |
| 734 | N | VAL | 96 | 25.994 | 25.875 | 3.845 | 1 | 14.3 |
| 735 | CA | VAL | 96 | 24.698 | 26.21 | 4.413 | 1 | 14.78 |
| 736 | CB | VAL | 96 | 24.593 | 27.729 | 4.676 | 1 | 13.99 |
| 737 | CG1 | VAL | 96 | 23.205 | 28.086 | 5.177 | 1 | 15.8 |
| 738 | CG2 | VAL | 96 | 25.65 | 28.145 | 5.693 | 1 | 15.25 |
| 739 | C | VAL | 96 | 23.664 | 25.776 | 3.371 | 1 | 15.07 |
| 740 | O | VAL | 96 | 23.842 | 26.031 | 2.179 | 1 | 14.42 |
| 741 | N | ASN | 97 | 22.605 | 25.109 | 3.825 | 1 | 15.5 |
| 742 | CA | ASN | 97 | 21.541 | 24.604 | 2.949 | 1 | 16.15 |
| 743 | CB | ASN | 97 | 20.625 | 25.744 | 2.488 | 1 | 16.97 |
| 744 | CG | ASN | 97 | 20.044 | 26.529 | 3.641 | 1 | 17.27 |
| 745 | OD1 | ASN | 97 | 19.908 | 26.019 | 4.753 | 1 | 16.67 |
| 746 | ND2 | ASN | 97 | 19.681 | 27.779 | 3.376 | 1 | 20.03 |
| 747 | C | ASN | 97 | 22.096 | 23.889 | 1.719 | 1 | 17.56 |
| 748 | O | ASN | 97 | 21.692 | 24.172 | 0.589 | 1 | 17.44 |
| 749 | N | PRO | 98 | 23.013 | 22.931 | 1.923 | 1 | 17.05 |
| 750 | CD | PRO | 98 | 23.638 | 22.512 | 3.193 | 1 | 18.84 |
| 751 | CA | PRO | 98 | 23.597 | 22.206 | 0.795 | 1 | 17.01 |
| 752 | CB | PRO | 98 | 24.863 | 21.612 | 1.399 | 1 | 17.6 |
| 753 | CG | PRO | 98 | 24.413 | 21.274 | 2.787 | 1 | 17.42 |
| 754 | C | PRO | 98 | 22.715 | 21.138 | 0.168 | 1 | 17.04 |
| 755 | O | PRO | 98 | 21.749 | 20.668 | 0.769 | 1 | 17.41 |
| 756 | N | SER | 99 | 23.059 | 20.784 | −1.064 | 1 | 17.46 |
| 757 | CA | SER | 99 | 22.362 | 19.744 | −1.804 | 1 | 17.71 |
| 758 | CB | SER | 99 | 21.509 | 20.342 | −2.927 | 1 | 20.97 |
| 759 | OG | SER | 99 | 22.3 | 21.065 | −3.847 | 1 | 26.88 |
| 760 | C | SER | 99 | 23.472 | 18.869 | −2.373 | 1 | 17.23 |
| 761 | O | SER | 99 | 24.589 | 19.34 | −2.598 | 1 | 15.39 |
| 762 | N | LEU | 100 | 23.17 | 17.598 | −2.6 | 1 | 17.11 |
| 763 | CA | LEU | 100 | 24.171 | 16.671 | −3.107 | 1 | 15.96 |
| 764 | CB | LEU | 100 | 24.397 | 15.557 | −2.08 | 1 | 19.14 |
| 765 | CG | LEU | 100 | 25.457 | 14.494 | −2.373 | 1 | 20.08 |
| 766 | CD1 | LEU | 100 | 26.843 | 15.108 | −2.303 | 1 | 23.02 |
| 767 | CD2 | LEU | 100 | 25.332 | 13.37 | −1.35 | 1 | 23.75 |
| 768 | C | LEU | 100 | 23.796 | 16.047 | −4.442 | 1 | 17.49 |
| 769 | O | LEU | 100 | 22.643 | 15.683 | −4.663 | 1 | 17.3 |
| 770 | N | ARG | 101 | 24.781 | 15.937 | −5.328 | 1 | 17.49 |
| 771 | CA | ARG | 101 | 24.591 | 15.315 | −6.634 | 1 | 18.53 |
| 772 | CB | ARG | 101 | 24.744 | 16.33 | −7.774 | 1 | 22.16 |
| 773 | CG | ARG | 101 | 23.463 | 17.065 | −8.143 | 1 | 28.34 |
| 774 | CD | ARG | 101 | 23.5 | 17.523 | −9.6 | 1 | 32.7 |
| 775 | NE | ARG | 101 | 22.225 | 18.09 | −10.035 | 1 | 37.93 |
| 776 | CZ | ARG | 101 | 21.931 | 18.398 | −11.296 | 1 | 39.06 |
| 777 | NH1 | ARG | 101 | 22.821 | 18.194 | −12.259 | 1 | 41.07 |
| 778 | NH2 | ARG | 101 | 20.746 | 18.913 | −11.596 | 1 | 40.31 |
| 779 | C | ARG | 101 | 25.644 | 14.229 | −6.789 | 1 | 17.74 |
| 780 | O | ARG | 101 | 26.826 | 14.462 | −6.54 | 1 | 17.69 |
| 781 | N | VAL | 102 | 25.213 | 13.039 | −7.189 | 1 | 17.77 |
| 782 | CA | VAL | 102 | 26.139 | 11.928 | −7.38 | 1 | 17.96 |
| 783 | CB | VAL | 102 | 25.407 | 10.575 | −7.258 | 1 | 17.78 |
| 784 | CG1 | VAL | 102 | 26.388 | 9.43 | −7.454 | 1 | 18.39 |
| 785 | CG2 | VAL | 102 | 24.731 | 10.477 | −5.898 | 1 | 20.35 |
| 786 | C | VAL | 102 | 26.764 | 12.044 | −8.767 | 1 | 17.92 |
| 787 | O | VAL | 102 | 26.05 | 12.111 | −9.769 | 1 | 20.03 |
| 788 | N | LEU | 103 | 28.093 | 12.072 | −8.818 | 1 | 16.85 |
| 789 | CA | LEU | 103 | 28.812 | 12.199 | −10.085 | 1 | 18.14 |
| 790 | CB | LEU | 103 | 30 | 13.147 | −9.917 | 1 | 17.76 |
| 791 | CG | LEU | 103 | 29.632 | 14.532 | −9.372 | 1 | 19.1 |
| 792 | CD1 | LEU | 103 | 30.876 | 15.399 | −9.295 | 1 | 18.07 |
| 793 | CD2 | LEU | 103 | 28.581 | 15.18 | −10.272 | 1 | 18.23 |
| 794 | C | LEU | 103 | 29.3 | 10.858 | −10.62 | 1 | 19.04 |
| 795 | O | LEU | 103 | 29.336 | 10.64 | −11.831 | 1 | 19.25 |
| 796 | N | ASP | 104 | 29.69 | 9.974 | −9.677 | 1 | 18.73 |
| 797 | CA | ASP | 104 | 30.161 | 8.635 | −10.051 | 1 | 18.48 |
| 798 | CB | ASP | 104 | 31.683 | 8.539 | −9.913 | 1 | 19.75 |
| 799 | CG | ASP | 104 | 32.236 | 7.221 | −10.428 | 1 | 20.84 |
| 800 | OD1 | ASP | 104 | 31.496 | 6.213 | −10.402 | 1 | 19.9 |
| 801 | OD2 | ASP | 104 | 33.415 | 7.187 | −10.847 | 1 | 21.99 |
| 802 | C | ASP | 104 | 29.492 | 7.738 | −9.018 | 1 | 18.7 |
| 803 | O | ASP | 104 | 29.852 | 7.771 | −7.838 | 1 | 16.91 |
| 804 | N | SER | 105 | 28.514 | 6.95 | −9.456 | 1 | 18.32 |
| 805 | CA | SER | 105 | 27.774 | 6.083 | −8.546 | 1 | 18.52 |
| 806 | CB | SER | 105 | 26.386 | 5.775 | −9.118 | 1 | 20.33 |
| 807 | OG | SER | 105 | 26.474 | 5.117 | −10.369 | 1 | 23.19 |
| 808 | C | SER | 105 | 28.465 | 4.784 | −8.185 | 1 | 16.98 |
| 809 | O | SER | 105 | 27.887 | 3.978 | −7.423 | 1 | 17.82 |
| 810 | N | ARG | 106 | 29.69 | 4.572 | −8.622 | 1 | 16.64 |
| 811 | CA | ARG | 106 | 30.424 | 3.366 | −8.254 | 1 | 16.07 |
| 812 | CB | ARG | 106 | 31.8 | 3.348 | −8.922 | 1 | 16.6 |
| 813 | CG | ARG | 106 | 32.697 | 2.224 | −8.441 | 1 | 18.35 |
| 814 | CD | ARG | 106 | 33.925 | 2.06 | −9.323 | 1 | 19.83 |
| 815 | NE | ARG | 106 | 34.772 | 0.974 | −8.84 | 1 | 18.45 |
| 816 | CZ | ARG | 106 | 35.765 | 0.426 | −9.533 | 1 | 21.85 |
| 817 | NH1 | ARG | 106 | 36.049 | 0.858 | −10.756 | 1 | 22.26 |
| 818 | NH2 | ARG | 106 | 36.472 | −0.561 | −9 | 1 | 20.83 |
| 819 | C | ARG | 106 | 30.583 | 3.373 | −6.738 | 1 | 15.29 |
| 820 | O | ARG | 106 | 30.871 | 4.411 | −6.147 | 1 | 16.07 |
| 821 | N | LEU | 107 | 30.392 | 2.215 | −6.11 | 1 | 15.5 |
| 822 | CA | LEU | 107 | 30.499 | 2.114 | −4.66 | 1 | 14.65 |
| 823 | CB | LEU | 107 | 29.439 | 1.142 | −4.126 | 1 | 13.48 |
| 824 | CG | LEU | 107 | 27.99 | 1.602 | −4.293 | 1 | 14.62 |
| 825 | CD1 | LEU | 107 | 27.046 | 0.513 | −3.815 | 1 | 17.02 |
| 826 | CD2 | LEU | 107 | 27.769 | 2.888 | −3.504 | 1 | 15.89 |
| 827 | C | LEU | 107 | 31.879 | 1.681 | −4.18 | 1 | 13.23 |
| 828 | O | LEU | 107 | 32.509 | 0.797 | −4.764 | 1 | 14.14 |
| 829 | N | VAL | 108 | 32.335 | 2.318 | −3.106 | 1 | 13.76 |
| 830 | CA | VAL | 108 | 33.631 | 2.028 | −2.504 | 1 | 13.69 |
| 831 | CB | VAL | 108 | 34.576 | 3.243 | −2.606 | 1 | 16.75 |
| 832 | CG1 | VAL | 108 | 35.955 | 2.878 | −2.088 | 1 | 16.63 |
| 833 | CG2 | VAL | 108 | 34.658 | 3.716 | −4.047 | 1 | 19.89 |
| 834 | C | VAL | 108 | 33.342 | 1.736 | −1.037 | 1 | 14.19 |
| 835 | O | VAL | 108 | 32.62 | 2.489 | −0.389 | 1 | 13.38 |
| 836 | N | THR | 109 | 33.904 | 0.65 | −0.516 | 1 | 12.79 |
| 837 | CA | THR | 109 | 33.644 | 0.266 | 0.867 | 1 | 13.3 |
| 838 | CB | THR | 109 | 32.998 | −1.136 | 0.91 | 1 | 14.17 |
| 839 | OG1 | THR | 109 | 31.788 | −1.122 | 0.141 | 1 | 15.61 |
| 840 | CG2 | THR | 109 | 32.671 | −1.539 | 2.344 | 1 | 16.97 |
| 841 | C | THR | 109 | 34.867 | 0.289 | 1.771 | 1 | 13.56 |
| 842 | O | THR | 109 | 35.859 | −0.393 | 1.514 | 1 | 14.87 |

TABLE 2-continued

| Atom | Atom Type | Residue | # | X | Y | Z | OCC | B |
|---|---|---|---|---|---|---|---|---|
| 843 | N | PHE | 110 | 34.77 | 1.075 | 2.84 | 1 | 13.78 |
| 844 | CA | PHE | 110 | 35.839 | 1.227 | 3.823 | 1 | 13.27 |
| 845 | CB | PHE | 110 | 36.729 | 2.428 | 3.488 | 1 | 15.69 |
| 846 | CG | PHE | 110 | 37.717 | 2.182 | 2.387 | 1 | 15.46 |
| 847 | CD1 | PHE | 110 | 38.767 | 1.285 | 2.562 | 1 | 17.2 |
| 848 | CD2 | PHE | 110 | 37.63 | 2.89 | 1.191 | 1 | 16.32 |
| 849 | CE1 | PHE | 110 | 39.722 | 1.098 | 1.563 | 1 | 18.59 |
| 850 | CE2 | PHE | 110 | 38.581 | 2.711 | 0.183 | 1 | 16.44 |
| 851 | CZ | PHE | 110 | 39.628 | 1.815 | 0.371 | 1 | 17.55 |
| 852 | C | PHE | 110 | 35.225 | 1.493 | 5.191 | 1 | 13.45 |
| 853 | O | PHE | 110 | 34.064 | 1.893 | 5.296 | 1 | 13.56 |
| 854 | N | PRO | 111 | 36.004 | 1.283 | 6.259 | 1 | 14 |
| 855 | CD | PRO | 111 | 37.275 | 0.541 | 6.325 | 1 | 14.28 |
| 856 | CA | PRO | 111 | 35.48 | 1.531 | 7.601 | 1 | 14.57 |
| 857 | CB | PRO | 111 | 36.507 | 0.857 | 8.514 | 1 | 15.81 |
| 858 | CG | PRO | 111 | 37.145 | −0.18 | 7.637 | 1 | 16.72 |
| 859 | C | PRO | 111 | 35.426 | 3.03 | 7.872 | 1 | 14.56 |
| 860 | O | PRO | 111 | 36.292 | 3.787 | 7.425 | 1 | 15.45 |
| 861 | N | GLU | 112 | 34.399 | 3.46 | 8.591 | 1 | 14.4 |
| 862 | CA | GLU | 112 | 34.289 | 4.859 | 8.97 | 1 | 13.98 |
| 863 | CB | GLU | 112 | 33.496 | 5.676 | 7.93 | 1 | 16.92 |
| 864 | CG | GLU | 112 | 32.035 | 5.311 | 7.744 | 1 | 15.7 |
| 865 | CD | GLU | 112 | 31.306 | 6.283 | 6.813 | 1 | 15.61 |
| 866 | OE1 | GLU | 112 | 31.562 | 6.273 | 5.588 | 1 | 15.41 |
| 867 | OE2 | GLU | 112 | 30.471 | 7.064 | 7.312 | 1 | 15.85 |
| 868 | C | GLU | 112 | 33.631 | 4.896 | 10.342 | 1 | 12.72 |
| 869 | O | GLU | 112 | 33.045 | 3.903 | 10.787 | 1 | 12.38 |
| 870 | N | GLY | 113 | 33.769 | 6.025 | 11.024 | 1 | 11.87 |
| 871 | CA | GLY | 113 | 33.188 | 6.169 | 12.342 | 1 | 12.86 |
| 872 | C | GLY | 113 | 32.503 | 7.51 | 12.436 | 1 | 14.31 |
| 873 | O | GLY | 113 | 32.623 | 8.335 | 11.532 | 1 | 17.32 |
| 874 | N | CYS | 114 | 31.805 | 7.742 | 13.537 | 1 | 12.01 |
| 875 | CA | CYS | 114 | 31.084 | 8.99 | 13.716 | 1 | 11.4 |
| 876 | CB | CYS | 114 | 29.591 | 8.747 | 13.488 | 1 | 12.08 |
| 877 | SG | CYS | 114 | 28.55 | 10.211 | 13.624 | 1 | 11.8 |
| 878 | C | CYS | 114 | 31.303 | 9.531 | 15.119 | 1 | 10.8 |
| 879 | O | CYS | 114 | 31.292 | 8.774 | 16.089 | 1 | 11.17 |
| 880 | N | GLU | 115 | 31.491 | 10.842 | 15.226 | 1 | 11.38 |
| 881 | CA | GLU | 115 | 31.694 | 11.457 | 16.531 | 1 | 12.15 |
| 882 | CB | GLU | 115 | 32.013 | 12.946 | 16.377 | 1 | 14.25 |
| 883 | CG | GLU | 115 | 33.416 | 13.238 | 15.866 | 1 | 19.21 |
| 884 | CD | GLU | 115 | 34.496 | 12.846 | 16.86 | 1 | 23.24 |
| 885 | OE1 | GLU | 115 | 34.354 | 13.174 | 18.057 | 1 | 23.93 |
| 886 | OE2 | GLU | 115 | 35.493 | 12.22 | 16.444 | 1 | 27.03 |
| 887 | C | GLU | 115 | 30.455 | 11.296 | 17.401 | 1 | 11.63 |
| 888 | O | GLU | 115 | 30.536 | 11.39 | 18.623 | 1 | 12.29 |
| 889 | N | SER | 116 | 29.311 | 11.059 | 16.762 | 1 | 10.49 |
| 890 | CA | SER | 116 | 28.047 | 10.88 | 17.469 | 1 | 10.64 |
| 891 | CB | SER | 116 | 26.899 | 11.44 | 16.633 | 1 | 10 |
| 892 | OG | SER | 116 | 26.991 | 12.854 | 16.542 | 1 | 12.26 |
| 893 | C | SER | 116 | 27.753 | 9.429 | 17.87 | 1 | 9.57 |
| 894 | O | SER | 116 | 26.709 | 9.139 | 18.447 | 1 | 10.97 |
| 895 | N | VAL | 117 | 28.671 | 8.523 | 17.542 | 1 | 10.6 |
| 896 | CA | VAL | 117 | 28.562 | 7.115 | 17.93 | 1 | 10.75 |
| 897 | CB | VAL | 117 | 28.146 | 6.204 | 16.755 | 1 | 10.3 |
| 898 | CG1 | VAL | 117 | 27.847 | 4.803 | 17.28 | 1 | 13.3 |
| 899 | CG2 | VAL | 117 | 26.914 | 6.772 | 16.062 | 1 | 12.94 |
| 900 | C | VAL | 117 | 29.985 | 6.793 | 18.365 | 1 | 10.93 |
| 901 | O | VAL | 117 | 30.657 | 5.922 | 17.814 | 1 | 11.73 |
| 902 | N | ALA | 118 | 30.434 | 7.537 | 19.369 | 1 | 12.31 |
| 903 | CA | ALA | 118 | 31.789 | 7.437 | 19.887 | 1 | 12.8 |
| 904 | CB | ALA | 118 | 31.924 | 8.315 | 21.133 | 1 | 15.77 |
| 905 | C | ALA | 118 | 32.322 | 6.043 | 20.188 | 1 | 13.08 |
| 906 | O | ALA | 118 | 31.67 | 5.244 | 20.863 | 1 | 14.52 |
| 907 | N | GLY | 119 | 33.513 | 5.769 | 19.663 | 1 | 14.21 |
| 908 | CA | GLY | 119 | 34.189 | 4.509 | 19.918 | 1 | 14.54 |
| 909 | C | GLY | 119 | 33.949 | 3.32 | 19.013 | 1 | 13.27 |
| 910 | O | GLY | 119 | 34.419 | 2.225 | 19.318 | 1 | 12.79 |
| 911 | N | PHE | 120 | 33.246 | 3.517 | 17.905 | 1 | 12.31 |
| 912 | CA | PHE | 120 | 32.962 | 2.413 | 16.996 | 1 | 12.1 |
| 913 | CB | PHE | 120 | 31.477 | 2.048 | 17.077 | 1 | 11.53 |
| 914 | CG | PHE | 120 | 31.053 | 1.532 | 18.418 | 1 | 12.9 |
| 915 | CD1 | PHE | 120 | 31.266 | 0.202 | 18.765 | 1 | 13.54 |
| 916 | CD2 | PHE | 120 | 30.46 | 2.381 | 19.346 | 1 | 14.62 |
| 917 | CE1 | PHE | 120 | 30.895 | −0.276 | 20.019 | 1 | 15.12 |
| 918 | CE2 | PHE | 120 | 30.084 | 1.911 | 20.609 | 1 | 17.95 |
| 919 | CZ | PHE | 120 | 30.304 | 0.579 | 20.943 | 1 | 16.46 |
| 920 | C | PHE | 120 | 33.306 | 2.726 | 15.548 | 1 | 13.53 |
| 921 | O | PHE | 120 | 33.404 | 3.891 | 15.156 | 1 | 14.16 |
| 922 | N | LEU | 121 | 33.486 | 1.665 | 14.768 | 1 | 11.94 |
| 923 | CA | LEU | 121 | 33.776 | 1.765 | 13.34 | 1 | 13.34 |
| 924 | CB | LEU | 121 | 35.266 | 1.543 | 13.067 | 1 | 14.38 |
| 925 | CG | LEU | 121 | 36.268 | 2.595 | 13.539 | 1 | 16.19 |
| 926 | CD1 | LEU | 121 | 37.679 | 2.049 | 13.372 | 1 | 18.28 |
| 927 | CD2 | LEU | 121 | 36.091 | 3.874 | 12.733 | 1 | 19.79 |
| 928 | C | LEU | 121 | 32.995 | 0.669 | 12.626 | 1 | 12.36 |
| 929 | O | LEU | 121 | 32.639 | −0.343 | 13.228 | 1 | 11.94 |
| 930 | N | ALA | 122 | 32.718 | 0.877 | 11.346 | 1 | 11.96 |
| 931 | CA | ALA | 122 | 32.028 | −0.13 | 10.548 | 1 | 11.12 |
| 932 | CB | ALA | 122 | 30.549 | −0.184 | 10.899 | 1 | 10.89 |
| 933 | C | ALA | 122 | 32.202 | 0.226 | 9.082 | 1 | 11.49 |
| 934 | O | ALA | 122 | 32.31 | 1.398 | 8.732 | 1 | 12.09 |
| 935 | N | CYS | 123 | 32.253 | −0.785 | 8.227 | 1 | 10.9 |
| 936 | CA | CYS | 123 | 32.395 | −0.534 | 6.8 | 1 | 12.16 |
| 937 | CB | CYS | 123 | 32.759 | −1.82 | 6.069 | 1 | 13.43 |
| 938 | SG | CYS | 123 | 34.431 | −2.352 | 6.392 | 1 | 18.43 |
| 939 | C | CYS | 123 | 31.093 | 0.011 | 6.238 | 1 | 12.65 |
| 940 | O | CYS | 123 | 30.01 | −0.461 | 6.583 | 1 | 12.45 |
| 941 | N | VAL | 124 | 31.205 | 1.012 | 5.374 | 1 | 11.35 |
| 942 | CA | VAL | 124 | 30.036 | 1.623 | 4.758 | 1 | 12.66 |
| 943 | CB | VAL | 124 | 29.707 | 3.002 | 5.388 | 1 | 12.43 |
| 944 | CG1 | VAL | 124 | 28.467 | 3.596 | 4.726 | 1 | 12.99 |
| 945 | CG2 | VAL | 124 | 29.5 | 2.867 | 6.888 | 1 | 13.17 |
| 946 | C | VAL | 124 | 30.329 | 1.862 | 3.287 | 1 | 11.96 |
| 947 | O | VAL | 124 | 31.374 | 2.414 | 2.941 | 1 | 13.03 |
| 948 | N | PRO | 125 | 29.424 | 1.429 | 2.398 | 1 | 12.68 |
| 949 | CD | PRO | 125 | 28.254 | 0.557 | 2.617 | 1 | 12.97 |
| 950 | CA | PRO | 125 | 29.66 | 1.654 | 0.97 | 1 | 12.6 |
| 951 | CB | PRO | 125 | 28.726 | 0.644 | 0.303 | 1 | 13.54 |
| 952 | CG | PRO | 125 | 27.577 | 0.564 | 1.262 | 1 | 16.61 |
| 953 | C | PRO | 125 | 29.286 | 3.107 | 0.663 | 1 | 12.92 |
| 954 | O | PRO | 125 | 28.26 | 3.598 | 1.136 | 1 | 12.87 |
| 955 | N | ARG | 126 | 30.124 | 3.79 | −0.112 | 1 | 12.97 |
| 956 | CA | ARG | 126 | 29.891 | 5.191 | −0.467 | 1 | 12.42 |
| 957 | CB | ARG | 126 | 30.834 | 6.109 | 0.321 | 1 | 13.25 |
| 958 | CG | ARG | 126 | 30.634 | 6.125 | 1.829 | 1 | 13.74 |
| 959 | CD | ARG | 126 | 29.335 | 6.806 | 2.221 | 1 | 12.75 |
| 960 | NE | ARG | 126 | 29.254 | 6.982 | 3.671 | 1 | 10.9 |
| 961 | CZ | ARG | 126 | 28.198 | 7.474 | 4.306 | 1 | 11.12 |
| 962 | NH1 | ARG | 126 | 27.121 | 7.839 | 3.624 | 1 | 12.42 |
| 963 | NH2 | ARG | 126 | 28.218 | 7.605 | 5.625 | 1 | 11.98 |
| 964 | C | ARG | 126 | 30.162 | 5.405 | −1.948 | 1 | 13.08 |
| 965 | O | ARG | 126 | 30.922 | 4.659 | −2.554 | 1 | 13.79 |
| 966 | N | PHE | 127 | 29.547 | 6.436 | −2.519 | 1 | 12.76 |
| 967 | CA | PHE | 127 | 29.756 | 6.752 | −3.929 | 1 | 12.85 |
| 968 | CB | PHE | 127 | 28.778 | 7.842 | −4.378 | 1 | 13.69 |
| 969 | CG | PHE | 127 | 27.337 | 7.427 | −4.322 | 1 | 13.72 |
| 970 | CD1 | PHE | 127 | 26.414 | 8.175 | −3.6 | 1 | 15.66 |
| 971 | CD2 | PHE | 127 | 26.892 | 6.306 | −5.017 | 1 | 15.47 |
| 972 | CE1 | PHE | 127 | 25.068 | 7.816 | −3.571 | 1 | 16.98 |
| 973 | CE2 | PHE | 127 | 25.547 | 5.94 | −4.995 | 1 | 18.45 |
| 974 | CZ | PHE | 127 | 24.636 | 6.697 | −4.271 | 1 | 16.94 |
| 975 | C | PHE | 127 | 31.192 | 7.236 | −4.133 | 1 | 13.42 |
| 976 | O | PHE | 127 | 31.77 | 7.879 | −3.261 | 1 | 15.4 |
| 977 | N | GLN | 128 | 31.759 | 6.927 | −5.293 | 1 | 14.05 |
| 978 | CA | GLN | 128 | 33.125 | 7.317 | −5.628 | 1 | 14.27 |
| 979 | CB | GLN | 128 | 33.55 | 6.601 | −6.916 | 1 | 15.04 |
| 980 | CG | GLN | 128 | 34.868 | 7.062 | −7.531 | 1 | 15.58 |
| 981 | CD | GLN | 128 | 36.049 | 6.924 | −6.593 | 1 | 17.32 |
| 982 | OE1 | GLN | 128 | 36.079 | 6.042 | −5.735 | 1 | 18.73 |
| 983 | NE2 | GLN | 128 | 37.04 | 7.79 | −6.765 | 1 | 18.13 |
| 984 | C | GLN | 128 | 33.306 | 8.827 | −5.789 | 1 | 14.94 |
| 985 | O | GLN | 128 | 34.36 | 9.367 | −5.45 | 1 | 16.06 |
| 986 | N | ALA | 129 | 32.289 | 9.506 | −6.311 | 1 | 14.73 |
| 987 | CA | ALA | 129 | 32.388 | 10.952 | −6.509 | 1 | 14.84 |
| 988 | CB | ALA | 129 | 33.036 | 11.25 | −7.862 | 1 | 15.32 |
| 989 | C | ALA | 129 | 31.047 | 11.662 | −6.408 | 1 | 13.38 |
| 990 | O | ALA | 129 | 30.024 | 11.162 | −6.877 | 1 | 13.49 |
| 991 | N | VAL | 130 | 31.062 | 12.839 | −5.789 | 1 | 14.29 |
| 992 | CA | VAL | 130 | 29.852 | 13.632 | −5.619 | 1 | 13.71 |
| 993 | CB | VAL | 130 | 29.199 | 13.399 | −4.23 | 1 | 13.78 |
| 994 | CG1 | VAL | 130 | 28.818 | 11.939 | −4.061 | 1 | 14.74 |

TABLE 2-continued

| Atom | Atom Type | Residue | # | X | Y | Z | OCC | B |
|---|---|---|---|---|---|---|---|---|
| 995 | CG2 | VAL | 130 | 30.164 | 13.841 | -3.121 | 1 | 14.96 |
| 996 | C | VAL | 130 | 30.177 | 15.113 | -5.7 | 1 | 14.15 |
| 997 | O | VAL | 130 | 31.341 | 15.511 | -5.657 | 1 | 15.53 |
| 998 | N | GLN | 131 | 29.131 | 15.92 | -5.82 | 1 | 16.28 |
| 999 | CA | GLN | 131 | 29.284 | 17.363 | -5.837 | 1 | 16.62 |
| 1000 | CB | GLN | 131 | 28.894 | 17.966 | -7.188 | 1 | 19.75 |
| 1001 | CG | GLN | 131 | 29.013 | 19.49 | -7.196 | 1 | 20.88 |
| 1002 | CD | GLN | 131 | 28.31 | 20.137 | -8.373 | 1 | 23.4 |
| 1003 | OE1 | GLN | 131 | 27.089 | 20.06 | -8.499 | 1 | 27.86 |
| 1004 | NE2 | GLN | 131 | 29.078 | 20.779 | -9.239 | 1 | 24.39 |
| 1005 | C | GLN | 131 | 28.354 | 17.918 | -4.777 | 1 | 16.57 |
| 1006 | O | GLN | 131 | 27.156 | 17.617 | -4.768 | 1 | 17.02 |
| 1007 | N | ILE | 132 | 28.904 | 18.705 | -3.863 | 1 | 15.49 |
| 1008 | CA | ILE | 132 | 28.076 | 19.326 | -2.851 | 1 | 14.61 |
| 1009 | CB | ILE | 132 | 28.684 | 19.182 | -1.432 | 1 | 14.74 |
| 1010 | CG2 | ILE | 132 | 30.12 | 19.686 | -1.42 | 1 | 16.93 |
| 1011 | CG1 | ILE | 132 | 27.807 | 19.923 | -0.42 | 1 | 14.76 |
| 1012 | CD1 | ILE | 132 | 28.165 | 19.646 | 1.032 | 1 | 15.24 |
| 1013 | C | ILE | 132 | 27.984 | 20.79 | -3.25 | 1 | 15.61 |
| 1014 | O | ILE | 132 | 28.983 | 21.406 | -3.62 | 1 | 16.2 |
| 1015 | N | SER | 133 | 26.775 | 21.331 | -3.211 | 1 | 15.98 |
| 1016 | CA | SER | 133 | 26.559 | 22.725 | -3.569 | 1 | 18.09 |
| 1017 | CB | SER | 133 | 25.873 | 22.823 | -4.935 | 1 | 19.98 |
| 1018 | OG | SER | 133 | 24.608 | 22.187 | -4.909 | 1 | 25.54 |
| 1019 | C | SER | 133 | 25.687 | 23.37 | -2.512 | 1 | 17.78 |
| 1020 | O | SER | 133 | 24.761 | 22.753 | -1.991 | 1 | 18.71 |
| 1021 | N | GLY | 134 | 25.988 | 24.62 | -2.192 | 1 | 18.02 |
| 1022 | CA | GLY | 134 | 25.205 | 25.315 | -1.195 | 1 | 18.74 |
| 1023 | C | GLY | 134 | 25.645 | 26.756 | -1.119 | 1 | 18.63 |
| 1024 | O | GLY | 134 | 26.109 | 27.324 | -2.105 | 1 | 18.82 |
| 1025 | N | LEU | 135 | 25.497 | 27.348 | 0.055 | 1 | 18.62 |
| 1026 | CA | LEU | 135 | 25.892 | 28.731 | 0.261 | 1 | 19.72 |
| 1027 | CB | LEU | 135 | 24.687 | 29.562 | 0.705 | 1 | 20.44 |
| 1028 | CG | LEU | 135 | 23.452 | 29.572 | -0.192 | 1 | 22.45 |
| 1029 | CD1 | LEU | 135 | 22.327 | 30.322 | 0.5 | 1 | 23.22 |
| 1030 | CD2 | LEU | 135 | 23.798 | 30.215 | -1.521 | 1 | 24.99 |
| 1031 | C | LEU | 135 | 26.927 | 28.764 | 1.367 | 1 | 20.08 |
| 1032 | O | LEU | 135 | 26.942 | 27.882 | 2.226 | 1 | 19.06 |
| 1033 | N | ASP | 136 | 27.818 | 29.748 | 1.344 | 1 | 19.41 |
| 1034 | CA | ASP | 136 | 28.759 | 29.85 | 2.443 | 1 | 19.49 |
| 1035 | CB | ASP | 136 | 30.083 | 30.517 | 2.027 | 1 | 21.51 |
| 1036 | CG | ASP | 136 | 29.91 | 31.93 | 1.507 | 1 | 23.51 |
| 1037 | OD1 | ASP | 136 | 28.924 | 32.602 | 1.863 | 1 | 23.04 |
| 1038 | OD2 | ASP | 136 | 30.796 | 32.373 | 0.748 | 1 | 27.87 |
| 1039 | C | ASP | 136 | 27.989 | 30.685 | 3.464 | 1 | 19.71 |
| 1040 | O | ASP | 136 | 26.881 | 31.144 | 3.179 | 1 | 19.8 |
| 1041 | N | PRO | 137 | 28.538 | 30.871 | 4.67 | 1 | 20.28 |
| 1042 | CD | PRO | 137 | 29.756 | 30.242 | 5.213 | 1 | 20.28 |
| 1043 | CA | PRO | 137 | 27.852 | 31.656 | 5.703 | 1 | 20.72 |
| 1044 | CB | PRO | 137 | 28.874 | 31.688 | 6.834 | 1 | 21.67 |
| 1045 | CG | PRO | 137 | 29.527 | 30.343 | 6.709 | 1 | 21.88 |
| 1046 | C | PRO | 137 | 27.389 | 33.056 | 5.292 | 1 | 21.47 |
| 1047 | O | PRO | 137 | 26.477 | 33.615 | 5.904 | 1 | 22.43 |
| 1048 | N | ASN | 138 | 28.007 | 33.615 | 4.257 | 1 | 21.28 |
| 1049 | CA | ASN | 138 | 27.649 | 34.953 | 3.794 | 1 | 21.89 |
| 1050 | CB | ASN | 138 | 28.913 | 35.714 | 3.389 | 1 | 22.16 |
| 1051 | CG | ASN | 138 | 29.768 | 36.085 | 4.582 | 1 | 23.26 |
| 1052 | OD1 | ASN | 138 | 30.997 | 36.068 | 4.509 | 1 | 25.82 |
| 1053 | ND2 | ASN | 138 | 29.121 | 36.434 | 5.687 | 1 | 20.48 |
| 1054 | C | ASN | 138 | 26.646 | 34.958 | 2.643 | 1 | 22.18 |
| 1055 | O | ASN | 138 | 26.352 | 36.007 | 2.07 | 1 | 22.37 |
| 1056 | N | GLY | 139 | 26.124 | 33.784 | 2.306 | 1 | 21.77 |
| 1057 | CA | GLY | 139 | 25.145 | 33.695 | 1.238 | 1 | 22.34 |
| 1058 | C | GLY | 139 | 25.697 | 33.574 | -0.168 | 1 | 21.9 |
| 1059 | O | GLY | 139 | 24.954 | 33.741 | -1.136 | 1 | 23.04 |
| 1060 | N | GLU | 140 | 26.99 | 33.293 | -0.296 | 1 | 21.63 |
| 1061 | CA | GLU | 140 | 27.598 | 33.143 | -1.612 | 1 | 24.19 |
| 1062 | CB | GLU | 140 | 29.039 | 33.654 | -1.604 | 1 | 24.63 |
| 1063 | CG | GLU | 140 | 29.149 | 35.165 | -1.497 | 1 | 27.86 |
| 1064 | CD | GLU | 140 | 30.521 | 35.673 | -1.881 | 1 | 30.16 |
| 1065 | OE1 | GLU | 140 | 31.45 | 35.596 | -1.049 | 1 | 31.16 |
| 1066 | OE2 | GLU | 140 | 30.671 | 36.14 | -3.028 | 1 | 31.64 |
| 1067 | C | GLU | 140 | 27.579 | 31.688 | -2.063 | 1 | 25.02 |
| 1068 | O | GLU | 140 | 27.792 | 30.778 | -1.262 | 1 | 24.88 |
| 1069 | N | GLN | 141 | 27.323 | 31.481 | -3.352 | 1 | 27.76 |
| 1070 | CA | GLN | 141 | 27.277 | 30.144 | -3.935 | 1 | 28.93 |
| 1071 | CB | GLN | 141 | 26.913 | 30.217 | -5.42 | 1 | 31.4 |
| 1072 | CG | GLN | 141 | 25.497 | 30.669 | -5.705 | 1 | 33.42 |
| 1073 | CD | GLN | 141 | 24.462 | 29.648 | -5.284 | 1 | 35.27 |
| 1074 | OE1 | GLN | 141 | 24.53 | 28.481 | -5.675 | 1 | 36.49 |
| 1075 | NE2 | GLN | 141 | 23.491 | 30.082 | -4.491 | 1 | 36.22 |
| 1076 | C | GLN | 141 | 28.608 | 29.424 | -3.792 | 1 | 28.75 |
| 1077 | O | GLN | 141 | 29.66 | 29.946 | -4.168 | 1 | 29.12 |
| 1078 | N | VAL | 142 | 28.553 | 28.216 | -3.248 | 1 | 27.16 |
| 1079 | CA | VAL | 142 | 29.742 | 27.409 | -3.06 | 1 | 26.59 |
| 1080 | CB | VAL | 142 | 30.085 | 27.245 | -1.563 | 1 | 28.06 |
| 1081 | CG1 | VAL | 142 | 31.306 | 26.35 | -1.403 | 1 | 30.72 |
| 1082 | CG2 | VAL | 142 | 30.348 | 28.608 | -0.939 | 1 | 31.35 |
| 1083 | C | VAL | 142 | 29.48 | 26.033 | -3.654 | 1 | 25.38 |
| 1084 | O | VAL | 142 | 28.433 | 25.436 | -3.418 | 1 | 24.94 |
| 1085 | N | VAL | 143 | 30.431 | 25.543 | -4.436 | 1 | 23.41 |
| 1086 | CA | VAL | 143 | 30.301 | 24.231 | -5.047 | 1 | 23.08 |
| 1087 | CB | VAL | 143 | 29.891 | 24.34 | -6.535 | 1 | 24.05 |
| 1088 | CG1 | VAL | 143 | 29.846 | 22.96 | -7.169 | 1 | 26.67 |
| 1089 | CG2 | VAL | 143 | 28.529 | 25.004 | -6.645 | 1 | 26.03 |
| 1090 | C | VAL | 143 | 31.632 | 23.514 | -4.938 | 1 | 22 |
| 1091 | O | VAL | 143 | 32.69 | 24.127 | -5.075 | 1 | 23.62 |
| 1092 | N | TRP | 144 | 31.579 | 22.215 | -4.67 | 1 | 19.62 |
| 1093 | CA | TRP | 144 | 32.786 | 21.419 | -4.547 | 1 | 19.22 |
| 1094 | CB | TRP | 144 | 33.23 | 21.35 | -3.077 | 1 | 18.94 |
| 1095 | CG | TRP | 144 | 34.491 | 20.556 | -2.851 | 1 | 18.56 |
| 1096 | CD2 | TRP | 144 | 34.845 | 19.817 | -1.673 | 1 | 18.6 |
| 1097 | CE2 | TRP | 144 | 36.128 | 19.268 | -1.894 | 1 | 18.27 |
| 1098 | CE3 | TRP | 144 | 34.203 | 19.567 | -0.452 | 1 | 16.01 |
| 1099 | CD1 | TRP | 144 | 35.543 | 20.426 | -3.71 | 1 | 20.24 |
| 1100 | NE1 | TRP | 144 | 36.53 | 19.655 | -3.145 | 1 | 20.88 |
| 1101 | CZ2 | TRP | 144 | 36.785 | 18.481 | -0.937 | 1 | 16.94 |
| 1102 | CZ3 | TRP | 144 | 34.858 | 18.783 | 0.5 | 1 | 17.77 |
| 1103 | CH2 | TRP | 144 | 36.135 | 18.251 | 0.248 | 1 | 17.1 |
| 1104 | C | TRP | 144 | 32.553 | 20.017 | -5.09 | 1 | 19.73 |
| 1105 | O | TRP | 144 | 31.68 | 19.292 | -4.614 | 1 | 19.69 |
| 1106 | N | GLN | 145 | 33.324 | 19.659 | -6.111 | 1 | 19.68 |
| 1107 | CA | GLN | 145 | 33.244 | 18.338 | -6.715 | 1 | 20.78 |
| 1108 | CB | GLN | 145 | 33.427 | 18.432 | -8.232 | 1 | 22.49 |
| 1109 | CG | GLN | 145 | 32.466 | 19.396 | -8.897 | 1 | 27.5 |
| 1110 | CD | GLN | 145 | 32.717 | 19.542 | -10.382 | 1 | 29.71 |
| 1111 | OE1 | GLN | 145 | 32.202 | 20.46 | -11.018 | 1 | 31.77 |
| 1112 | NE2 | GLN | 145 | 33.505 | 18.63 | -10.948 | 1 | 30.15 |
| 1113 | C | GLN | 145 | 34.403 | 17.576 | -6.095 | 1 | 20.17 |
| 1114 | O | GLN | 145 | 35.534 | 18.061 | -6.091 | 1 | 20.79 |
| 1115 | N | ALA | 146 | 34.126 | 16.392 | -5.561 | 1 | 18.57 |
| 1116 | CA | ALA | 146 | 35.172 | 15.606 | -4.921 | 1 | 17.55 |
| 1117 | CB | ALA | 146 | 35.173 | 15.88 | -3.42 | 1 | 18.86 |
| 1118 | C | ALA | 146 | 35.014 | 14.114 | -5.17 | 1 | 17.15 |
| 1119 | O | ALA | 146 | 33.925 | 13.634 | -5.475 | 1 | 16.73 |
| 1120 | N | SER | 147 | 36.115 | 13.387 | -5.04 | 1 | 17.68 |
| 1121 | CA | SER | 147 | 36.098 | 11.945 | -5.235 | 1 | 17.9 |
| 1122 | CB | SER | 147 | 36.705 | 11.585 | -6.594 | 1 | 18.81 |
| 1123 | OG | SER | 147 | 38.048 | 12.024 | -6.685 | 1 | 23.77 |
| 1124 | C | SER | 147 | 36.894 | 11.281 | -4.122 | 1 | 18.41 |
| 1125 | O | SER | 147 | 37.531 | 11.955 | -3.31 | 1 | 19.13 |
| 1126 | N | GLY | 148 | 36.842 | 9.957 | -4.08 | 1 | 17.9 |
| 1127 | CA | GLY | 148 | 37.578 | 9.225 | -3.071 | 1 | 16.59 |
| 1128 | C | GLY | 148 | 37.148 | 9.526 | -1.65 | 1 | 14.96 |
| 1129 | O | GLY | 148 | 35.959 | 9.693 | -1.367 | 1 | 14.69 |
| 1130 | N | TRP | 149 | 38.125 | 9.615 | -0.755 | 1 | 14.87 |
| 1131 | CA | TRP | 149 | 37.841 | 9.865 | 0.652 | 1 | 13.42 |
| 1132 | CB | TRP | 149 | 39.141 | 9.852 | 1.461 | 1 | 13.79 |
| 1133 | CG | TRP | 149 | 38.908 | 9.513 | 2.895 | 1 | 13.84 |
| 1134 | CD2 | TRP | 149 | 38.536 | 8.232 | 3.418 | 1 | 14.95 |
| 1135 | CE2 | TRP | 149 | 38.372 | 8.382 | 4.813 | 1 | 15.7 |
| 1136 | CE3 | TRP | 149 | 38.326 | 6.971 | 2.842 | 1 | 15.44 |
| 1137 | CD1 | TRP | 149 | 38.955 | 10.364 | 3.962 | 1 | 15.24 |
| 1138 | NE1 | TRP | 149 | 38.633 | 9.692 | 5.12 | 1 | 17.89 |
| 1139 | CZ2 | TRP | 149 | 38.005 | 7.316 | 5.645 | 1 | 17.02 |
| 1140 | CZ3 | TRP | 149 | 37.959 | 5.907 | 3.672 | 1 | 16 |
| 1141 | CH2 | TRP | 149 | 37.804 | 6.092 | 5.058 | 1 | 14.97 |
| 1142 | C | TRP | 149 | 37.077 | 11.159 | 0.906 | 1 | 13.1 |
| 1143 | O | TRP | 149 | 36.193 | 11.205 | 1.764 | 1 | 12.23 |
| 1144 | N | ALA | 150 | 37.405 | 12.214 | 0.164 | 1 | 14.05 |
| 1145 | CA | ALA | 150 | 36.712 | 13.484 | 0.344 | 1 | 13.34 |
| 1146 | CB | ALA | 150 | 37.312 | 14.55 | -0.572 | 1 | 14.48 |

TABLE 2-continued

| Atom | Atom Type | Residue | # | X | Y | Z | OCC | B |
|---|---|---|---|---|---|---|---|---|
| 1147 | C | ALA | 150 | 35.221 | 13.307 | 0.055 | 1 | 13.24 |
| 1148 | O | ALA | 150 | 34.37 | 13.864 | 0.752 | 1 | 12.58 |
| 1149 | N | ALA | 151 | 34.911 | 12.525 | −0.975 | 1 | 12.77 |
| 1150 | CA | ALA | 151 | 33.522 | 12.272 | −1.333 | 1 | 12.27 |
| 1151 | CB | ALA | 151 | 33.447 | 11.462 | −2.622 | 1 | 11.9 |
| 1152 | C | ALA | 151 | 32.819 | 11.526 | −0.201 | 1 | 12.71 |
| 1153 | O | ALA | 151 | 31.649 | 11.769 | 0.066 | 1 | 10.38 |
| 1154 | N | ARG | 152 | 33.537 | 10.616 | 0.454 | 1 | 11.86 |
| 1155 | CA | ARG | 152 | 32.967 | 9.854 | 1.568 | 1 | 13.06 |
| 1156 | CB | ARG | 152 | 33.962 | 8.791 | 2.049 | 1 | 11.71 |
| 1157 | CG | ARG | 152 | 33.596 | 8.129 | 3.384 | 1 | 12.21 |
| 1158 | CD | ARG | 152 | 34.589 | 7.024 | 3.729 | 1 | 11.99 |
| 1159 | NE | ARG | 152 | 34.592 | 5.979 | 2.709 | 1 | 11.91 |
| 1160 | CZ | ARG | 152 | 33.809 | 4.904 | 2.726 | 1 | 12.11 |
| 1161 | NH1 | ARG | 152 | 32.955 | 4.71 | 3.721 | 1 | 13.55 |
| 1162 | NH2 | ARG | 152 | 33.864 | 4.036 | 1.727 | 1 | 13.61 |
| 1163 | C | ARG | 152 | 32.605 | 10.776 | 2.729 | 1 | 12.47 |
| 1164 | O | ARG | 152 | 31.535 | 10.657 | 3.322 | 1 | 11.69 |
| 1165 | N | ILE | 153 | 33.51 | 11.693 | 3.054 | 1 | 12.9 |
| 1166 | CA | ILE | 153 | 33.286 | 12.632 | 4.146 | 1 | 13.09 |
| 1167 | CB | ILE | 153 | 34.536 | 13.515 | 4.357 | 1 | 14.07 |
| 1168 | CG2 | ILE | 153 | 34.281 | 14.53 | 5.456 | 1 | 16.1 |
| 1169 | CG1 | ILE | 153 | 35.73 | 12.628 | 4.725 | 1 | 14.51 |
| 1170 | CD1 | ILE | 153 | 37.082 | 13.314 | 4.583 | 1 | 18.15 |
| 1171 | C | ILE | 153 | 32.067 | 13.506 | 3.85 | 1 | 11.54 |
| 1172 | O | ILE | 153 | 31.247 | 13.76 | 4.728 | 1 | 12.58 |
| 1173 | N | ILE | 154 | 31.95 | 13.958 | 2.605 | 1 | 12.92 |
| 1174 | CA | ILE | 154 | 30.815 | 14.781 | 2.203 | 1 | 11.91 |
| 1175 | CB | ILE | 154 | 30.938 | 15.213 | 0.725 | 1 | 12.08 |
| 1176 | CG2 | ILE | 154 | 29.632 | 15.85 | 0.252 | 1 | 12.23 |
| 1177 | CG1 | ILE | 154 | 32.098 | 16.198 | 0.567 | 1 | 12.93 |
| 1178 | CD1 | ILE | 154 | 32.481 | 16.448 | −0.883 | 1 | 13.93 |
| 1179 | C | ILE | 154 | 29.505 | 14.017 | 2.389 | 1 | 12.23 |
| 1180 | O | ILE | 154 | 28.532 | 14.554 | 2.918 | 1 | 12.17 |
| 1181 | N | GLN | 155 | 29.478 | 12.76 | 1.957 | 1 | 11.93 |
| 1182 | CA | GLN | 155 | 28.267 | 11.959 | 2.086 | 1 | 10.62 |
| 1183 | CB | GLN | 155 | 28.43 | 10.63 | 1.352 | 1 | 12.06 |
| 1184 | CG | GLN | 155 | 28.546 | 10.795 | −0.158 | 1 | 12.43 |
| 1185 | CD | GLN | 155 | 29.057 | 9.548 | −0.84 | 1 | 12.45 |
| 1186 | OE1 | GLN | 155 | 28.375 | 8.522 | −0.878 | 1 | 13.41 |
| 1187 | NE2 | GLN | 155 | 30.271 | 9.624 | −1.377 | 1 | 12.47 |
| 1188 | C | GLN | 155 | 27.909 | 11.706 | 3.543 | 1 | 10.4 |
| 1189 | O | GLN | 155 | 26.735 | 11.709 | 3.907 | 1 | 11.51 |
| 1190 | N | HIS | 156 | 28.924 | 11.484 | 4.372 | 1 | 10.21 |
| 1191 | CA | HIS | 156 | 28.7 | 11.247 | 5.793 | 1 | 11.48 |
| 1192 | CB | HIS | 156 | 30.031 | 10.929 | 6.484 | 1 | 11.15 |
| 1193 | CG | HIS | 156 | 29.908 | 10.704 | 7.96 | 1 | 10.16 |
| 1194 | CD2 | HIS | 156 | 29.671 | 11.567 | 8.975 | 1 | 12.23 |
| 1195 | ND1 | HIS | 156 | 30.026 | 9.457 | 8.535 | 1 | 12.26 |
| 1196 | CE1 | HIS | 156 | 29.865 | 9.562 | 9.842 | 1 | 12.72 |
| 1197 | NE2 | HIS | 156 | 29.647 | 10.831 | 10.134 | 1 | 10.55 |
| 1198 | C | HIS | 156 | 28.061 | 12.481 | 6.433 | 1 | 11.48 |
| 1199 | O | HIS | 156 | 27.088 | 12.366 | 7.173 | 1 | 11.48 |
| 1200 | N | GLU | 157 | 28.594 | 13.667 | 6.146 | 1 | 11.27 |
| 1201 | CA | GLU | 157 | 28.03 | 14.879 | 6.733 | 1 | 13.6 |
| 1202 | CB | GLU | 157 | 28.949 | 16.083 | 6.522 | 1 | 15.68 |
| 1203 | CG | GLU | 157 | 30.31 | 15.984 | 7.185 | 1 | 18.95 |
| 1204 | CD | GLU | 157 | 30.276 | 15.392 | 8.589 | 1 | 16.42 |
| 1205 | OE1 | GLU | 157 | 29.377 | 15.729 | 9.394 | 1 | 21.48 |
| 1206 | OE2 | GLU | 157 | 31.177 | 14.59 | 8.886 | 1 | 21.09 |
| 1207 | C | GLU | 157 | 26.65 | 15.215 | 6.185 | 1 | 10.93 |
| 1208 | O | GLU | 157 | 25.766 | 15.635 | 6.929 | 1 | 13.9 |
| 1209 | N | MET | 158 | 26.461 | 15.044 | 4.88 | 1 | 11.15 |
| 1210 | CA | MET | 158 | 25.162 | 15.329 | 4.289 | 1 | 12.96 |
| 1211 | CB | MET | 158 | 25.219 | 15.16 | 2.769 | 1 | 14.69 |
| 1212 | CG | MET | 158 | 25.904 | 16.313 | 2.048 | 1 | 15.47 |
| 1213 | SD | MET | 158 | 25.01 | 17.874 | 2.237 | 1 | 17.78 |
| 1214 | CE | MET | 158 | 23.616 | 17.609 | 1.141 | 1 | 18.66 |
| 1215 | C | MET | 158 | 24.096 | 14.416 | 4.895 | 1 | 13.23 |
| 1216 | O | MET | 158 | 22.963 | 14.842 | 5.115 | 1 | 15.08 |
| 1217 | N | ASP | 159 | 24.462 | 13.166 | 5.176 | 1 | 12.27 |
| 1218 | CA | ASP | 159 | 23.522 | 12.222 | 5.782 | 1 | 12.41 |
| 1219 | CB | ASP | 159 | 24.179 | 10.853 | 6.015 | 1 | 12.55 |
| 1220 | CG | ASP | 159 | 24.184 | 9.976 | 4.777 | 1 | 14.86 |
| 1221 | OD1 | ASP | 159 | 23.556 | 10.348 | 3.763 | 1 | 18.14 |
| 1222 | OD2 | ASP | 159 | 24.811 | 8.898 | 4.827 | 1 | 14.86 |
| 1223 | C | ASP | 159 | 23.029 | 12.77 | 7.121 | 1 | 11.56 |
| 1224 | O | ASP | 159 | 21.854 | 12.65 | 7.453 | 1 | 10.99 |
| 1225 | N | HIS | 160 | 23.932 | 13.377 | 7.888 | 1 | 11.97 |
| 1226 | CA | HIS | 160 | 23.566 | 13.936 | 9.186 | 1 | 11.94 |
| 1227 | CB | HIS | 160 | 24.766 | 14.618 | 9.85 | 1 | 11.83 |
| 1228 | CG | HIS | 160 | 25.633 | 13.691 | 10.647 | 1 | 10.61 |
| 1229 | CD2 | HIS | 160 | 26.928 | 13.333 | 10.49 | 1 | 13.25 |
| 1230 | ND1 | HIS | 160 | 25.189 | 13.04 | 11.779 | 1 | 11.48 |
| 1231 | CE1 | HIS | 160 | 26.175 | 12.321 | 12.285 | 1 | 10.27 |
| 1232 | NE2 | HIS | 160 | 27.242 | 12.481 | 11.521 | 1 | 10.07 |
| 1233 | C | HIS | 160 | 22.438 | 14.948 | 9.069 | 1 | 12.2 |
| 1234 | O | HIS | 160 | 21.578 | 15.028 | 9.944 | 1 | 12.08 |
| 1235 | N | LEU | 161 | 22.443 | 15.728 | 7.994 | 1 | 12.81 |
| 1236 | CA | LEU | 161 | 21.403 | 16.735 | 7.812 | 1 | 12.51 |
| 1237 | CB | LEU | 161 | 21.832 | 17.756 | 6.753 | 1 | 11.98 |
| 1238 | CG | LEU | 161 | 23.113 | 18.529 | 7.092 | 1 | 11.82 |
| 1239 | CD1 | LEU | 161 | 23.308 | 19.636 | 6.066 | 1 | 13.67 |
| 1240 | CD2 | LEU | 161 | 23.024 | 19.131 | 8.494 | 1 | 11.44 |
| 1241 | C | LEU | 161 | 20.055 | 16.128 | 7.455 | 1 | 14.13 |
| 1242 | O | LEU | 161 | 19.027 | 16.805 | 7.539 | 1 | 13.62 |
| 1243 | N | GLN | 162 | 20.063 | 14.856 | 7.06 | 1 | 13.99 |
| 1244 | CA | GLN | 162 | 18.837 | 14.142 | 6.723 | 1 | 16.1 |
| 1245 | CB | GLN | 162 | 19.036 | 13.293 | 5.466 | 1 | 17.95 |
| 1246 | CG | GLN | 162 | 19.235 | 14.095 | 4.195 | 1 | 24.06 |
| 1247 | CD | GLN | 162 | 18.068 | 15.019 | 3.907 | 1 | 27.04 |
| 1248 | OE1 | GLN | 162 | 16.909 | 14.597 | 3.91 | 1 | 29.86 |
| 1249 | NE2 | GLN | 162 | 18.369 | 16.285 | 3.648 | 1 | 29.81 |
| 1250 | C | GLN | 162 | 18.401 | 13.234 | 7.873 | 1 | 15.67 |
| 1251 | O | GLN | 162 | 17.415 | 12.504 | 7.753 | 1 | 16.46 |
| 1252 | N | GLY | 163 | 19.141 | 13.28 | 8.979 | 1 | 13.38 |
| 1253 | CA | GLY | 163 | 18.817 | 12.454 | 10.133 | 1 | 14.13 |
| 1254 | C | GLY | 163 | 19.323 | 11.029 | 9.993 | 1 | 13.03 |
| 1255 | O | GLY | 163 | 18.845 | 10.117 | 10.671 | 1 | 14.41 |
| 1256 | N | CYS | 164 | 20.302 | 10.842 | 9.115 | 1 | 12.46 |
| 1257 | CA | CYS | 164 | 20.878 | 9.527 | 8.849 | 1 | 12.5 |
| 1258 | CB | CYS | 164 | 20.944 | 9.309 | 7.335 | 1 | 13.4 |
| 1259 | SG | CYS | 164 | 21.676 | 7.751 | 6.792 | 1 | 17.2 |
| 1260 | C | CYS | 164 | 22.271 | 9.367 | 9.455 | 1 | 12.95 |
| 1261 | O | CYS | 164 | 23.125 | 10.249 | 9.313 | 1 | 12.5 |
| 1262 | N | LEU | 165 | 22.491 | 8.244 | 10.135 | 1 | 11.24 |
| 1263 | CA | LEU | 165 | 23.784 | 7.943 | 10.746 | 1 | 12.35 |
| 1264 | CB | LEU | 165 | 23.614 | 7.592 | 12.228 | 1 | 11.88 |
| 1265 | CG | LEU | 165 | 23.003 | 8.678 | 13.123 | 1 | 12.11 |
| 1266 | CD1 | LEU | 165 | 22.932 | 8.184 | 14.556 | 1 | 13.37 |
| 1267 | CD2 | LEU | 165 | 23.841 | 9.951 | 13.047 | 1 | 12.72 |
| 1268 | C | LEU | 165 | 24.4 | 6.771 | 9.991 | 1 | 12.28 |
| 1269 | O | LEU | 165 | 23.683 | 5.991 | 9.347 | 1 | 12.56 |
| 1270 | N | PHE | 166 | 25.72 | 6.632 | 10.068 | 1 | 11.14 |
| 1271 | CA | PHE | 166 | 26.383 | 5.562 | 9.332 | 1 | 11.87 |
| 1272 | CB | PHE | 166 | 27.915 | 5.669 | 9.463 | 1 | 12.95 |
| 1273 | CG | PHE | 166 | 28.476 | 5.099 | 10.737 | 1 | 11.28 |
| 1274 | CD1 | PHE | 166 | 29.17 | 3.892 | 10.722 | 1 | 13.66 |
| 1275 | CD2 | PHE | 166 | 28.34 | 5.778 | 11.94 | 1 | 13.23 |
| 1276 | CE1 | PHE | 166 | 29.725 | 3.37 | 11.888 | 1 | 13.26 |
| 1277 | CE2 | PHE | 166 | 28.892 | 5.267 | 13.118 | 1 | 13.57 |
| 1278 | CZ | PHE | 166 | 29.586 | 4.061 | 13.093 | 1 | 13.02 |
| 1279 | C | PHE | 166 | 25.894 | 4.173 | 9.708 | 1 | 12.48 |
| 1280 | O | PHE | 166 | 25.978 | 3.248 | 8.897 | 1 | 12.24 |
| 1281 | N | ILE | 167 | 25.365 | 4.021 | 10.919 | 1 | 12.21 |
| 1282 | CA | ILE | 167 | 24.86 | 2.719 | 11.342 | 1 | 11.31 |
| 1283 | CB | ILE | 167 | 24.554 | 2.686 | 12.859 | 1 | 12.05 |
| 1284 | CG2 | ILE | 167 | 25.849 | 2.853 | 13.646 | 1 | 12.32 |
| 1285 | CG1 | ILE | 167 | 23.551 | 3.781 | 13.227 | 1 | 12.19 |
| 1286 | CD1 | ILE | 167 | 23.009 | 3.653 | 14.646 | 1 | 13.65 |
| 1287 | C | ILE | 167 | 23.607 | 2.318 | 10.559 | 1 | 12.81 |
| 1288 | O | ILE | 167 | 23.165 | 1.165 | 10.63 | 1 | 13.65 |
| 1289 | N | ASP | 168 | 23.037 | 3.259 | 9.808 | 1 | 10.99 |
| 1290 | CA | ASP | 168 | 21.848 | 2.959 | 9.007 | 1 | 11.58 |
| 1291 | CB | ASP | 168 | 21.012 | 4.219 | 8.728 | 1 | 12.24 |
| 1292 | CG | ASP | 168 | 20.538 | 4.918 | 9.986 | 1 | 13.34 |
| 1293 | OD1 | ASP | 168 | 20.292 | 4.244 | 11.009 | 1 | 12.17 |
| 1294 | OD2 | ASP | 168 | 20.388 | 6.161 | 9.937 | 1 | 14 |
| 1295 | C | ASP | 168 | 22.237 | 2.369 | 7.652 | 1 | 13.22 |
| 1296 | O | ASP | 168 | 21.399 | 1.778 | 6.966 | 1 | 14.31 |
| 1297 | N | LYS | 169 | 23.499 | 2.543 | 7.265 | 1 | 12.26 |
| 1298 | CA | LYS | 169 | 23.99 | 2.072 | 5.967 | 1 | 13.97 |

TABLE 2-continued

| Atom | Atom Type | Residue | # | X | Y | Z | OCC | B |
|---|---|---|---|---|---|---|---|---|
| 1299 | CB | LYS | 169 | 24.428 | 3.269 | 5.121 | 1 | 13.98 |
| 1300 | CG | LYS | 169 | 23.331 | 4.261 | 4.784 | 1 | 14.33 |
| 1301 | CD | LYS | 169 | 23.903 | 5.419 | 3.977 | 1 | 15.03 |
| 1302 | CE | LYS | 169 | 22.803 | 6.317 | 3.449 | 1 | 14.21 |
| 1303 | NZ | LYS | 169 | 23.359 | 7.454 | 2.658 | 1 | 16.66 |
| 1304 | C | LYS | 169 | 25.169 | 1.11 | 6.053 | 1 | 13.91 |
| 1305 | O | LYS | 169 | 25.672 | 0.64 | 5.033 | 1 | 15.23 |
| 1306 | N | MET | 170 | 25.613 | 0.821 | 7.266 | 1 | 14.23 |
| 1307 | CA | MET | 170 | 26.767 | -0.043 | 7.461 | 1 | 13.23 |
| 1308 | CB | MET | 170 | 27.234 | 0.053 | 8.91 | 1 | 12.97 |
| 1309 | CG | MET | 170 | 26.266 | -0.63 | 9.864 | 1 | 12.27 |
| 1310 | SD | MET | 170 | 26.851 | -0.672 | 11.556 | 1 | 12.28 |
| 1311 | CE | MET | 170 | 25.379 | -1.191 | 12.416 | 1 | 10.33 |
| 1312 | C | MET | 170 | 26.568 | -1.517 | 7.157 | 1 | 13.44 |
| 1313 | O | MET | 170 | 25.442 | -2.007 | 7.032 | 1 | 13.72 |
| 1314 | N | ASP | 171 | 27.697 | -2.205 | 7.033 | 1 | 13.45 |
| 1315 | CA | ASP | 171 | 27.733 | -3.652 | 6.861 | 1 | 13.99 |
| 1316 | CB | ASP | 171 | 29.019 | -4.065 | 6.146 | 1 | 17.64 |
| 1317 | CG | ASP | 171 | 29.197 | -5.568 | 6.083 | 1 | 22.01 |
| 1318 | OD1 | ASP | 171 | 28.577 | -6.282 | 6.899 | 1 | 22.14 |
| 1319 | OD2 | ASP | 171 | 29.975 | -6.032 | 5.223 | 1 | 27.04 |
| 1320 | C | ASP | 171 | 27.821 | -3.999 | 8.351 | 1 | 14.59 |
| 1321 | O | ASP | 171 | 28.894 | -3.911 | 8.947 | 1 | 14.41 |
| 1322 | N | SER | 172 | 26.695 | -4.364 | 8.958 | 1 | 14.13 |
| 1323 | CA | SER | 172 | 26.667 | -4.634 | 10.394 | 1 | 13.07 |
| 1324 | CB | SER | 172 | 25.252 | -5.017 | 10.839 | 1 | 14.79 |
| 1325 | OG | SER | 172 | 24.861 | -6.26 | 10.288 | 1 | 16.34 |
| 1326 | C | SER | 172 | 27.658 | -5.66 | 10.927 | 1 | 12.71 |
| 1327 | O | SER | 172 | 28.078 | -5.571 | 12.081 | 1 | 11.69 |
| 1328 | N | ARG | 173 | 28.049 | -6.626 | 10.104 | 1 | 13.63 |
| 1329 | CA | ARG | 173 | 28.995 | -7.629 | 10.578 | 1 | 13.78 |
| 1330 | CB | ARG | 173 | 29.035 | -8.827 | 9.621 | 1 | 15.94 |
| 1331 | CG | ARG | 173 | 27.774 | -9.683 | 9.678 | 1 | 18.62 |
| 1332 | CD | ARG | 173 | 27.901 | -10.926 | 8.815 | 1 | 16.91 |
| 1333 | NE | ARG | 173 | 28.98 | -11.804 | 9.259 | 1 | 15.72 |
| 1334 | CZ | ARG | 173 | 28.883 | -12.676 | 10.259 | 1 | 17.15 |
| 1335 | NH1 | ARG | 173 | 27.75 | -12.802 | 10.934 | 1 | 18.74 |
| 1336 | NH2 | ARG | 173 | 29.927 | -13.425 | 10.579 | 1 | 17.57 |
| 1337 | C | ARG | 173 | 30.4 | -7.068 | 10.789 | 1 | 12.72 |
| 1338 | O | ARG | 173 | 31.249 | -7.732 | 11.384 | 1 | 13.53 |
| 1339 | N | THR | 174 | 30.638 | -5.841 | 10.328 | 1 | 11.81 |
| 1340 | CA | THR | 174 | 31.949 | -5.211 | 10.486 | 1 | 10.94 |
| 1341 | CB | THR | 174 | 32.412 | -4.511 | 9.181 | 1 | 11.41 |
| 1342 | OG1 | THR | 174 | 31.543 | -3.41 | 8.886 | 1 | 12.76 |
| 1343 | CG2 | THR | 174 | 32.392 | -5.491 | 8.015 | 1 | 13.49 |
| 1344 | C | THR | 174 | 31.964 | -4.176 | 11.618 | 1 | 11.2 |
| 1345 | O | THR | 174 | 32.986 | -3.531 | 11.87 | 1 | 12.01 |
| 1346 | N | PHE | 175 | 30.832 | -4.02 | 12.298 | 1 | 10.15 |
| 1347 | CA | PHE | 175 | 30.731 | -3.068 | 13.403 | 1 | 10.6 |
| 1348 | CB | PHE | 175 | 29.308 | -3.071 | 13.954 | 1 | 10.37 |
| 1349 | CG | PHE | 175 | 29.023 | -1.974 | 14.934 | 1 | 9.51 |
| 1350 | CD1 | PHE | 175 | 28.849 | -0.661 | 14.505 | 1 | 9.78 |
| 1351 | CD2 | PHE | 175 | 28.876 | -2.261 | 16.287 | 1 | 9.53 |
| 1352 | CE1 | PHE | 175 | 28.524 | 0.347 | 15.409 | 1 | 10.84 |
| 1353 | CE2 | PHE | 175 | 28.551 | -1.261 | 17.199 | 1 | 9.76 |
| 1354 | CZ | PHE | 175 | 28.373 | 0.048 | 16.761 | 1 | 11.77 |
| 1355 | C | PHE | 175 | 31.713 | -3.526 | 14.474 | 1 | 11.19 |
| 1356 | O | PHE | 175 | 31.747 | -4.71 | 14.828 | 1 | 10.86 |
| 1357 | N | THR | 176 | 32.51 | -2.599 | 14.997 | 1 | 10 |
| 1358 | CA | THR | 176 | 33.502 | -2.973 | 15.991 | 1 | 10.67 |
| 1359 | CB | THR | 176 | 34.789 | -3.481 | 15.286 | 1 | 10.49 |
| 1360 | OG1 | THR | 176 | 35.765 | -3.87 | 16.259 | 1 | 12.58 |
| 1361 | CG2 | THR | 176 | 35.385 | -2.38 | 14.412 | 1 | 12.49 |
| 1362 | C | THR | 176 | 33.909 | -1.85 | 16.938 | 1 | 9.84 |
| 1363 | O | THR | 176 | 33.911 | -0.676 | 16.569 | 1 | 10.8 |
| 1364 | N | ASN | 177 | 34.222 | -2.224 | 18.174 | 1 | 10.32 |
| 1365 | CA | ASN | 177 | 34.735 | -1.263 | 19.142 | 1 | 9.15 |
| 1366 | CB | ASN | 177 | 34.927 | -1.928 | 20.504 | 1 | 11.4 |
| 1367 | CG | ASN | 177 | 33.695 | -1.838 | 21.375 | 1 | 9.82 |
| 1368 | OD1 | ASN | 177 | 33.459 | -0.822 | 22.033 | 1 | 12.56 |
| 1369 | ND2 | ASN | 177 | 32.892 | -2.899 | 21.378 | 1 | 11.98 |
| 1370 | C | ASN | 177 | 36.101 | -0.921 | 18.558 | 1 | 10.71 |
| 1371 | O | ASN | 177 | 36.743 | -1.781 | 17.958 | 1 | 10.59 |
| 1372 | N | VAL | 178 | 36.553 | 0.316 | 18.736 | 1 | 11.19 |
| 1373 | CA | VAL | 178 | 37.841 | 0.716 | 18.187 | 1 | 14.2 |
| 1374 | CB | VAL | 178 | 38.066 | 2.234 | 18.335 | 1 | 15.78 |
| 1375 | CG1 | VAL | 178 | 37.079 | 2.979 | 17.459 | 1 | 18 |
| 1376 | CG2 | VAL | 178 | 37.914 | 2.648 | 19.788 | 1 | 16.94 |
| 1377 | C | VAL | 178 | 39.022 | -0.025 | 18.796 | 1 | 12.65 |
| 1378 | O | VAL | 178 | 40.084 | -0.105 | 18.18 | 1 | 13.18 |
| 1379 | N | TYR | 179 | 38.843 | -0.574 | 19.994 | 1 | 11.92 |
| 1380 | CA | TYR | 179 | 39.927 | -1.307 | 20.63 | 1 | 11.56 |
| 1381 | CB | TYR | 179 | 39.774 | -1.29 | 22.159 | 1 | 11.06 |
| 1382 | CG | TYR | 179 | 38.456 | -1.777 | 22.713 | 1 | 12.02 |
| 1383 | CD1 | TYR | 179 | 38.15 | -3.136 | 22.749 | 1 | 13.04 |
| 1384 | CE1 | TYR | 179 | 36.956 | -3.59 | 23.323 | 1 | 14.11 |
| 1385 | CD2 | TYR | 179 | 37.538 | -0.876 | 23.257 | 1 | 11.84 |
| 1386 | CE2 | TYR | 179 | 36.347 | -1.316 | 23.831 | 1 | 11.59 |
| 1387 | CZ | TYR | 179 | 36.067 | -2.673 | 23.861 | 1 | 14.19 |
| 1388 | OH | TYR | 179 | 34.9 | -3.101 | 24.446 | 1 | 14.82 |
| 1389 | C | TYR | 179 | 40.113 | -2.73 | 20.084 | 1 | 12.05 |
| 1390 | O | TYR | 179 | 40.972 | -3.475 | 20.557 | 1 | 12.33 |
| 1391 | N | TRP | 180 | 39.306 | -3.097 | 19.087 | 1 | 9.99 |
| 1392 | CA | TRP | 180 | 39.442 | -4.382 | 18.397 | 1 | 10.75 |
| 1393 | CB | TRP | 180 | 38.126 | -5.169 | 18.36 | 1 | 11.1 |
| 1394 | CG | TRP | 180 | 37.97 | -6.117 | 19.508 | 1 | 11.03 |
| 1395 | CD2 | TRP | 180 | 38.626 | -7.379 | 19.67 | 1 | 10.85 |
| 1396 | CE2 | TRP | 180 | 38.22 | -7.903 | 20.918 | 1 | 10.5 |
| 1397 | CE3 | TRP | 180 | 39.52 | -8.119 | 18.883 | 1 | 11.01 |
| 1398 | CD1 | TRP | 180 | 37.213 | -5.932 | 20.627 | 1 | 11.38 |
| 1399 | NE1 | TRP | 180 | 37.358 | -7 | 21.481 | 1 | 10.93 |
| 1400 | CZ2 | TRP | 180 | 38.678 | -9.135 | 21.399 | 1 | 10.89 |
| 1401 | CZ3 | TRP | 180 | 39.975 | -9.348 | 19.363 | 1 | 11.79 |
| 1402 | CH2 | TRP | 180 | 39.551 | -9.84 | 20.61 | 1 | 12.38 |
| 1403 | C | TRP | 180 | 39.843 | -4.021 | 16.97 | 1 | 12.84 |
| 1404 | O | TRP | 180 | 39.248 | -3.129 | 16.371 | 1 | 14.24 |
| 1405 | N | MET | 181 | 40.839 | -4.705 | 16.421 | 1 | 12.86 |
| 1406 | CA | MET | 181 | 41.279 | -4.385 | 15.067 | 1 | 15.62 |
| 1407 | CB | MET | 181 | 42.214 | -3.17 | 15.106 | 1 | 18.59 |
| 1408 | CG | MET | 181 | 43.525 | -3.425 | 15.838 | 1 | 18.02 |
| 1409 | SD | MET | 181 | 44.227 | -1.933 | 16.603 | 1 | 20.53 |
| 1410 | CE | MET | 181 | 43.322 | -1.918 | 18.17 | 1 | 18.41 |
| 1411 | C | MET | 181 | 41.984 | -5.544 | 14.384 | 1 | 18.15 |
| 1412 | O | MET | 181 | 42.469 | -6.464 | 15.036 | 1 | 17.82 |
| 1413 | N | LYS | 182 | 42.025 | -5.497 | 13.056 | 1 | 21.45 |
| 1414 | CA | LYS | 182 | 42.703 | -6.529 | 12.287 | 1 | 25.95 |
| 1415 | CB | LYS | 182 | 42.036 | -6.73 | 10.924 | 1 | 27.97 |
| 1416 | CG | LYS | 182 | 40.64 | -7.313 | 10.987 | 1 | 31.06 |
| 1417 | CD | LYS | 182 | 40.141 | -7.709 | 9.601 | 1 | 33.8 |
| 1418 | CE | LYS | 182 | 40.064 | -6.513 | 8.665 | 1 | 34.66 |
| 1419 | NZ | LYS | 182 | 39.571 | -6.902 | 7.311 | 1 | 37.31 |
| 1420 | C | LYS | 182 | 44.133 | -6.058 | 12.085 | 1 | 27.31 |
| 1421 | O | LYS | 182 | 44.371 | -4.888 | 11.787 | 1 | 29.04 |
| 1422 | N | VAL | 183 | 45.082 | -6.968 | 12.261 | 1 | 28.71 |
| 1423 | CA | VAL | 183 | 46.488 | -6.635 | 12.1 | 1 | 30.74 |
| 1424 | CB | VAL | 183 | 47.21 | -6.633 | 13.458 | 1 | 31.16 |
| 1425 | CG1 | VAL | 183 | 46.688 | -5.495 | 14.322 | 1 | 31.61 |
| 1426 | CG2 | VAL | 183 | 46.994 | -7.965 | 14.158 | 1 | 31.2 |
| 1427 | C | VAL | 183 | 47.171 | -7.639 | 11.183 | 1 | 32.37 |
| 1428 | O | VAL | 183 | 46.66 | -8.736 | 10.961 | 1 | 31.79 |
| 1429 | N | ASN | 184 | 48.324 | -7.254 | 10.646 | 1 | 35.24 |
| 1430 | CA | ASN | 184 | 49.084 | -8.127 | 9.759 | 1 | 38.19 |
| 1431 | CB | ASN | 184 | 49.915 | -7.295 | 8.779 | 1 | 38.85 |
| 1432 | CG | ASN | 184 | 49.059 | -6.433 | 7.875 | 1 | 39.51 |
| 1433 | OD1 | ASN | 184 | 48.256 | -6.94 | 7.092 | 1 | 40.82 |
| 1434 | ND2 | ASN | 184 | 49.226 | -5.119 | 7.979 | 1 | 40.77 |
| 1435 | C | ASN | 184 | 50.007 | -9.007 | 10.59 | 1 | 39.85 |
| 1436 | O | ASN | 184 | 50.67 | -8.527 | 11.51 | 1 | 41.26 |
| 1437 | N | ASP | 185 | 50.046 | -10.295 | 10.269 | 1 | 41.27 |
| 1438 | CA | ASP | 185 | 50.896 | -11.227 | 10.998 | 1 | 42.82 |
| 1439 | CB | ASP | 185 | 50.33 | -12.646 | 10.901 | 1 | 43.64 |
| 1440 | CG | ASP | 185 | 48.944 | -12.762 | 11.504 | 1 | 44.51 |
| 1441 | OD1 | ASP | 185 | 48.797 | -12.493 | 12.715 | 1 | 46.11 |
| 1442 | OD2 | ASP | 185 | 48 | -13.12 | 10.767 | 1 | 45.32 |
| 1443 | C | ASP | 185 | 52.315 | -11.2 | 10.442 | 1 | 43.61 |
| 1444 | O | ASP | 185 | 52.528 | -10.528 | 9.411 | 1 | 44.14 |
| 1445 | OXT | ASP | 185 | 53.194 | -11.855 | 11.042 | 1 | 44.99 |
| 1446 | CB | HIS | 3 | 39.183 | -19.483 | 45.224 | 1 | 34.34 |
| 1447 | CG | HIS | 3 | 39.609 | -18.63 | 46.379 | 1 | 33.69 |
| 1448 | CD2 | HIS | 3 | 40.553 | -17.663 | 46.472 | 1 | 33.23 |
| 1449 | ND1 | HIS | 3 | 39.054 | -18.746 | 47.636 | 1 | 33.53 |
| 1450 | CE1 | HIS | 3 | 39.639 | -17.889 | 48.454 | 1 | 33.47 |

TABLE 2-continued

| Atom | Atom Type | Residue | # | X | Y | Z | OCC | B |
|---|---|---|---|---|---|---|---|---|
| 1451 | NE2 | HIS | 3 | 40.553 | −17.22 | 47.773 | 1 | 33.64 |
| 1452 | C | HIS | 3 | 37.364 | −17.997 | 44.351 | 1 | 36.05 |
| 1453 | O | HIS | 3 | 36.232 | −17.524 | 44.465 | 1 | 35.8 |
| 1454 | N | HIS | 3 | 37.312 | −20.442 | 43.914 | 1 | 35.61 |
| 1455 | CA | HIS | 3 | 37.687 | −19.386 | 44.897 | 1 | 35.74 |
| 1456 | N | MET | 4 | 38.359 | −17.345 | 43.756 | 1 | 35.43 |
| 1457 | CA | MET | 4 | 38.166 | −16.007 | 43.207 | 1 | 36.06 |
| 1458 | CB | MET | 4 | 38.574 | −14.957 | 44.247 | 1 | 39.25 |
| 1459 | CG | MET | 4 | 37.802 | −15.06 | 45.56 | 1 | 41.9 |
| 1460 | SD | MET | 4 | 38.354 | −13.898 | 46.83 | 1 | 42.28 |
| 1461 | CE | MET | 4 | 37.22 | −12.524 | 46.538 | 1 | 42.21 |
| 1462 | C | MET | 4 | 38.97 | −15.816 | 41.923 | 1 | 34.57 |
| 1463 | O | MET | 4 | 40.188 | −15.997 | 41.907 | 1 | 36.11 |
| 1464 | N | SER | 5 | 38.275 | −15.458 | 40.846 | 1 | 33.83 |
| 1465 | CA | SER | 5 | 38.906 | −15.236 | 39.549 | 1 | 30.09 |
| 1466 | CB | SER | 5 | 38.886 | −16.522 | 38.722 | 1 | 30.09 |
| 1467 | OG | SER | 5 | 39.558 | −16.349 | 37.487 | 1 | 35.5 |
| 1468 | C | SER | 5 | 38.15 | −14.141 | 38.807 | 1 | 27.52 |
| 1469 | O | SER | 5 | 37.256 | −13.51 | 39.367 | 1 | 28.8 |
| 1470 | N | PHE | 6 | 38.509 | −13.916 | 37.547 | 1 | 24.98 |
| 1471 | CA | PHE | 6 | 37.851 | −12.892 | 36.744 | 1 | 21.47 |
| 1472 | CB | PHE | 6 | 38.832 | −11.766 | 36.402 | 1 | 21.18 |
| 1473 | CG | PHE | 6 | 39.139 | −10.858 | 37.556 | 1 | 21.22 |
| 1474 | CD1 | PHE | 6 | 38.329 | −9.76 | 37.832 | 1 | 21.42 |
| 1475 | CD2 | PHE | 6 | 40.224 | −11.115 | 38.386 | 1 | 22.12 |
| 1476 | CE1 | PHE | 6 | 38.594 | −8.933 | 38.92 | 1 | 23.63 |
| 1477 | CE2 | PHE | 6 | 40.497 | −10.295 | 39.477 | 1 | 21.92 |
| 1478 | CZ | PHE | 6 | 39.682 | −9.201 | 39.745 | 1 | 23.9 |
| 1479 | C | PHE | 6 | 37.281 | −13.457 | 35.452 | 1 | 20.94 |
| 1480 | O | PHE | 6 | 37.855 | −14.36 | 34.841 | 1 | 21.95 |
| 1481 | N | SER | 7 | 36.141 | −12.916 | 35.045 | 1 | 18.13 |
| 1482 | CA | SER | 7 | 35.499 | −13.333 | 33.812 | 1 | 17.78 |
| 1483 | CB | SER | 7 | 34.314 | −14.253 | 34.102 | 1 | 21.45 |
| 1484 | OG | SER | 7 | 33.727 | −14.703 | 32.895 | 1 | 27.77 |
| 1485 | C | SER | 7 | 35.012 | −12.075 | 33.115 | 1 | 14.01 |
| 1486 | O | SER | 7 | 34.784 | −11.051 | 33.757 | 1 | 14.09 |
| 1487 | N | HIS | 8 | 34.858 | −12.14 | 31.8 | 1 | 14.22 |
| 1488 | CA | HIS | 8 | 34.39 | −10.974 | 31.075 | 1 | 14.6 |
| 1489 | CB | HIS | 8 | 35.582 | −10.158 | 30.575 | 1 | 17.33 |
| 1490 | CG | HIS | 8 | 36.358 | −10.831 | 29.489 | 1 | 19.66 |
| 1491 | CD2 | HIS | 8 | 37.198 | −11.891 | 29.519 | 1 | 21.78 |
| 1492 | ND1 | HIS | 8 | 36.295 | −10.43 | 28.172 | 1 | 23.19 |
| 1493 | CE1 | HIS | 8 | 37.065 | −11.213 | 27.438 | 1 | 23.83 |
| 1494 | NE2 | HIS | 8 | 37.624 | −12.109 | 28.232 | 1 | 25.5 |
| 1495 | C | HIS | 8 | 33.518 | −11.367 | 29.901 | 1 | 13.08 |
| 1496 | O | HIS | 8 | 33.677 | −12.445 | 29.324 | 1 | 14.1 |
| 1497 | N | VAL | 9 | 32.582 | −10.49 | 29.564 | 1 | 12.03 |
| 1498 | CA | VAL | 9 | 31.707 | −10.725 | 28.427 | 1 | 10.7 |
| 1499 | CB | VAL | 9 | 30.317 | −10.112 | 28.645 | 1 | 9.61 |
| 1500 | CG1 | VAL | 9 | 29.458 | −10.306 | 27.396 | 1 | 11.81 |
| 1501 | CG2 | VAL | 9 | 29.652 | −10.761 | 29.852 | 1 | 13.01 |
| 1502 | C | VAL | 9 | 32.366 | −10.044 | 27.239 | 1 | 10.29 |
| 1503 | O | VAL | 9 | 32.58 | −8.828 | 27.252 | 1 | 10.96 |
| 1504 | N | CYS | 10 | 32.703 | −10.832 | 26.221 | 1 | 9.8 |
| 1505 | CA | CYS | 10 | 33.345 | −10.307 | 25.021 | 1 | 10 |
| 1506 | CB | CYS | 10 | 33.603 | −11.441 | 24.033 | 1 | 11.71 |
| 1507 | SG | CYS | 10 | 34.661 | −12.743 | 24.697 | 1 | 15.01 |
| 1508 | C | CYS | 10 | 32.491 | −9.232 | 24.358 | 1 | 10.73 |
| 1509 | O | CYS | 10 | 31.266 | −9.357 | 24.284 | 1 | 10.37 |
| 1510 | N | GLN | 11 | 33.144 | −8.175 | 23.881 | 1 | 9.51 |
| 1511 | CA | GLN | 11 | 32.45 | −7.064 | 23.239 | 1 | 10.13 |
| 1512 | CB | GLN | 11 | 32.981 | −5.737 | 23.786 | 1 | 8.96 |
| 1513 | CG | GLN | 11 | 32.723 | −5.557 | 25.274 | 1 | 9.81 |
| 1514 | CD | GLN | 11 | 31.247 | −5.588 | 25.612 | 1 | 9.76 |
| 1515 | OE1 | GLN | 11 | 30.466 | −4.766 | 25.124 | 1 | 10.97 |
| 1516 | NE2 | GLN | 11 | 30.853 | −6.541 | 26.45 | 1 | 8.42 |
| 1517 | C | GLN | 11 | 32.583 | −7.093 | 21.718 | 1 | 9.32 |
| 1518 | O | GLN | 11 | 33.56 | −7.615 | 21.183 | 1 | 10.46 |
| 1519 | N | VAL | 12 | 31.603 | −6.504 | 21.032 | 1 | 10.43 |
| 1520 | CA | VAL | 12 | 31.586 | −6.498 | 19.574 | 1 | 10.03 |
| 1521 | CB | VAL | 12 | 30.357 | −5.7 | 19.037 | 1 | 10.63 |
| 1522 | CG1 | VAL | 12 | 30.444 | −4.237 | 19.426 | 1 | 9.79 |
| 1523 | CG2 | VAL | 12 | 30.231 | −5.889 | 17.525 | 1 | 9.64 |
| 1524 | C | VAL | 12 | 32.905 | −6.002 | 18.99 | 1 | 10.78 |
| 1525 | O | VAL | 12 | 33.428 | −4.941 | 19.357 | 1 | 10.72 |
| 1526 | N | GLY | 13 | 33.44 | −6.816 | 18.088 | 1 | 10.55 |
| 1527 | CA | GLY | 13 | 34.726 | −6.548 | 17.477 | 1 | 12.37 |
| 1528 | C | GLY | 13 | 35.537 | −7.82 | 17.675 | 1 | 11.35 |
| 1529 | O | GLY | 13 | 36.407 | −8.15 | 16.873 | 1 | 11.3 |
| 1530 | N | ASP | 14 | 35.248 | −8.538 | 18.759 | 1 | 10.88 |
| 1531 | CA | ASP | 14 | 35.926 | −9.801 | 19.049 | 1 | 10.24 |
| 1532 | CB | ASP | 14 | 35.569 | −10.285 | 20.459 | 1 | 10.46 |
| 1533 | CG | ASP | 14 | 36.34 | −11.527 | 20.868 | 1 | 10.46 |
| 1534 | OD1 | ASP | 14 | 36.755 | −12.3 | 19.98 | 1 | 12.5 |
| 1535 | OD2 | ASP | 14 | 36.52 | −11.739 | 22.085 | 1 | 13.27 |
| 1536 | C | ASP | 14 | 35.387 | −10.793 | 18.02 | 1 | 11.93 |
| 1537 | O | ASP | 14 | 34.192 | −11.077 | 17.996 | 1 | 12.33 |
| 1538 | N | PRO | 15 | 36.26 | −11.342 | 17.163 | 1 | 11.72 |
| 1539 | CD | PRO | 15 | 37.729 | −11.215 | 17.133 | 1 | 11.54 |
| 1540 | CA | PRO | 15 | 35.792 | −12.294 | 16.15 | 1 | 13.59 |
| 1541 | CB | PRO | 15 | 37.076 | −12.66 | 15.4 | 1 | 12.53 |
| 1542 | CG | PRO | 15 | 38.143 | −12.501 | 16.451 | 1 | 15.02 |
| 1543 | C | PRO | 15 | 35.026 | −13.523 | 16.646 | 1 | 13.19 |
| 1544 | O | PRO | 15 | 34.274 | −14.132 | 15.887 | 1 | 12.74 |
| 1545 | N | VAL | 16 | 35.196 | −13.882 | 17.911 | 1 | 13.3 |
| 1546 | CA | VAL | 16 | 34.506 | −15.055 | 18.44 | 1 | 12.43 |
| 1547 | CB | VAL | 16 | 34.953 | −15.362 | 19.892 | 1 | 10.98 |
| 1548 | CG1 | VAL | 16 | 34.378 | −14.32 | 20.855 | 1 | 13.51 |
| 1549 | CG2 | VAL | 16 | 34.52 | −16.776 | 20.286 | 1 | 13.98 |
| 1550 | C | VAL | 16 | 32.989 | −14.863 | 18.402 | 1 | 12.67 |
| 1551 | O | VAL | 16 | 32.227 | −15.831 | 18.324 | 1 | 12.63 |
| 1552 | N | LEU | 17 | 32.552 | −13.609 | 18.436 | 1 | 10.77 |
| 1553 | CA | LEU | 17 | 31.124 | −13.31 | 18.423 | 1 | 10.75 |
| 1554 | CB | LEU | 17 | 30.877 | −11.892 | 18.945 | 1 | 11 |
| 1555 | CG | LEU | 17 | 31.252 | −11.625 | 20.406 | 1 | 10.36 |
| 1556 | CD1 | LEU | 17 | 31.176 | −10.122 | 20.678 | 1 | 9.98 |
| 1557 | CD2 | LEU | 17 | 30.308 | −12.389 | 21.343 | 1 | 13.28 |
| 1558 | C | LEU | 17 | 30.498 | −13.455 | 17.042 | 1 | 11.86 |
| 1559 | O | LEU | 17 | 29.276 | −13.518 | 16.92 | 1 | 12.15 |
| 1560 | N | ARG | 18 | 31.33 | −13.511 | 16.005 | 1 | 10.26 |
| 1561 | CA | ARG | 18 | 30.824 | −13.634 | 14.642 | 1 | 11.57 |
| 1562 | CB | ARG | 18 | 31.409 | −12.526 | 13.758 | 1 | 12.23 |
| 1563 | CG | ARG | 18 | 30.47 | −11.342 | 13.532 | 1 | 11.43 |
| 1564 | CD | ARG | 18 | 30 | −10.722 | 14.84 | 1 | 12.37 |
| 1565 | NE | ARG | 18 | 29.326 | −9.447 | 14.606 | 1 | 11.55 |
| 1566 | CZ | ARG | 18 | 28.097 | −9.315 | 14.115 | 1 | 12.69 |
| 1567 | NH1 | ARG | 18 | 27.372 | −10.384 | 13.802 | 1 | 13.01 |
| 1568 | NH2 | ARG | 18 | 27.597 | −8.103 | 13.918 | 1 | 12.27 |
| 1569 | C | ARG | 18 | 31.08 | −14.991 | 14 | 1 | 12.48 |
| 1570 | O | ARG | 18 | 30.74 | −15.21 | 12.836 | 1 | 13.99 |
| 1571 | N | GLY | 19 | 31.681 | −15.901 | 14.756 | 1 | 12.66 |
| 1572 | CA | GLY | 19 | 31.937 | −17.228 | 14.228 | 1 | 14.88 |
| 1573 | C | GLY | 19 | 30.732 | −18.106 | 14.5 | 1 | 14.76 |
| 1574 | O | GLY | 19 | 29.793 | −17.687 | 15.177 | 1 | 15.49 |
| 1575 | N | VAL | 20 | 30.736 | −19.317 | 13.957 | 1 | 14.61 |
| 1576 | CA | VAL | 20 | 29.631 | −20.242 | 14.195 | 1 | 14.64 |
| 1577 | CB | VAL | 20 | 29.221 | −20.996 | 12.911 | 1 | 14.62 |
| 1578 | CG1 | VAL | 20 | 28.071 | −21.948 | 13.221 | 1 | 15.12 |
| 1579 | CG2 | VAL | 20 | 28.806 | −20.007 | 11.832 | 1 | 15.27 |
| 1580 | C | VAL | 20 | 30.125 | −21.244 | 15.229 | 1 | 13.74 |
| 1581 | O | VAL | 20 | 31.063 | −21.997 | 14.972 | 1 | 15.7 |
| 1582 | N | ALA | 21 | 29.502 | −21.238 | 16.402 | 1 | 13.36 |
| 1583 | CA | ALA | 21 | 29.897 | −22.129 | 17.486 | 1 | 14.68 |
| 1584 | CB | ALA | 21 | 28.967 | −21.93 | 18.677 | 1 | 13.75 |
| 1585 | C | ALA | 21 | 29.897 | −23.592 | 17.063 | 1 | 14.24 |
| 1586 | O | ALA | 21 | 28.998 | −24.04 | 16.359 | 1 | 14.09 |
| 1587 | N | ALA | 22 | 30.913 | −24.327 | 17.504 | 1 | 14.6 |
| 1588 | CA | ALA | 22 | 31.034 | −25.746 | 17.182 | 1 | 15.92 |
| 1589 | CB | ALA | 22 | 32.49 | −26.176 | 17.26 | 1 | 16.65 |
| 1590 | C | ALA | 22 | 30.199 | −26.569 | 18.155 | 1 | 15.85 |
| 1591 | O | ALA | 22 | 29.995 | −26.177 | 19.299 | 1 | 14.36 |
| 1592 | N | PRO | 23 | 29.706 | −27.733 | 17.71 | 1 | 16.31 |
| 1593 | CD | PRO | 23 | 29.801 | −28.356 | 16.377 | 1 | 17.93 |
| 1594 | CA | PRO | 23 | 28.901 | −28.547 | 18.62 | 1 | 17.23 |
| 1595 | CB | PRO | 23 | 28.254 | −29.563 | 17.682 | 1 | 18.31 |
| 1596 | CG | PRO | 23 | 29.314 | −29.764 | 16.641 | 1 | 19.58 |
| 1597 | C | PRO | 23 | 29.75 | −29.209 | 19.699 | 1 | 17.13 |
| 1598 | O | PRO | 23 | 30.963 | −29.366 | 19.546 | 1 | 17.25 |
| 1599 | N | VAL | 24 | 29.109 | −29.564 | 20.806 | 1 | 17.96 |
| 1600 | CA | VAL | 24 | 29.792 | −30.25 | 21.891 | 1 | 19.6 |
| 1601 | CB | VAL | 24 | 29.059 | −30.055 | 23.235 | 1 | 19.72 |
| 1602 | CG1 | VAL | 24 | 29.722 | −30.898 | 24.314 | 1 | 20.95 |

TABLE 2-continued

| Atom | Atom Type | Residue | # | X | Y | Z | OCC | B |
|---|---|---|---|---|---|---|---|---|
| 1603 | CG2 | VAL | 24 | 29.076 | −28.583 | 23.631 | 1 | 19.8 |
| 1604 | C | VAL | 24 | 29.741 | −31.726 | 21.502 | 1 | 20.48 |
| 1605 | O | VAL | 24 | 28.672 | −32.25 | 21.193 | 1 | 21.11 |
| 1606 | N | GLU | 25 | 30.893 | −32.385 | 21.496 | 1 | 22.61 |
| 1607 | CA | GLU | 25 | 30.949 | −33.797 | 21.132 | 1 | 25.42 |
| 1608 | CB | GLU | 25 | 32.403 | −34.222 | 20.931 | 1 | 27.87 |
| 1609 | CG | GLU | 25 | 33.064 | −33.57 | 19.728 | 1 | 32.43 |
| 1610 | CD | GLU | 25 | 34.557 | −33.823 | 19.672 | 1 | 36.37 |
| 1611 | OE1 | GLU | 25 | 34.963 | −35.004 | 19.717 | 1 | 39.14 |
| 1612 | OE2 | GLU | 25 | 35.327 | −32.842 | 19.579 | 1 | 39.82 |
| 1613 | C | GLU | 25 | 30.27 | −34.683 | 22.175 | 1 | 26.71 |
| 1614 | O | GLU | 25 | 30.331 | −34.418 | 23.375 | 1 | 26.1 |
| 1615 | N | ARG | 26 | 29.618 | −35.738 | 21.695 | 1 | 28.24 |
| 1616 | CA | ARG | 26 | 28.9 | −36.679 | 22.545 | 1 | 29.56 |
| 1617 | CB | ARG | 26 | 28.454 | −37.877 | 21.698 | 1 | 31.11 |
| 1618 | CG | ARG | 26 | 27.69 | −38.96 | 22.438 | 1 | 32.49 |
| 1619 | CD | ARG | 26 | 27.023 | −39.902 | 21.44 | 1 | 34.25 |
| 1620 | NE | ARG | 26 | 26.416 | −41.066 | 22.08 | 1 | 36.06 |
| 1621 | CZ | ARG | 26 | 27.106 | −42.065 | 22.622 | 1 | 36.12 |
| 1622 | NH1 | ARG | 26 | 28.432 | −42.046 | 22.602 | 1 | 38.31 |
| 1623 | NH2 | ARG | 26 | 26.47 | −43.084 | 23.185 | 1 | 38.55 |
| 1624 | C | ARG | 26 | 29.723 | −37.149 | 23.74 | 1 | 30.25 |
| 1625 | O | ARG | 26 | 29.195 | −37.32 | 24.839 | 1 | 30.65 |
| 1626 | N | ALA | 27 | 31.02 | −37.339 | 23.523 | 1 | 30.19 |
| 1627 | CA | ALA | 27 | 31.923 | −37.799 | 24.57 | 1 | 31.39 |
| 1628 | CB | ALA | 27 | 33.257 | −38.2 | 23.956 | 1 | 31.82 |
| 1629 | C | ALA | 27 | 32.15 | −36.77 | 25.677 | 1 | 31.41 |
| 1630 | O | ALA | 27 | 32.654 | −37.108 | 26.749 | 1 | 30.57 |
| 1631 | N | GLN | 28 | 31.781 | −35.519 | 25.423 | 1 | 31.47 |
| 1632 | CA | GLN | 28 | 31.964 | −34.465 | 26.417 | 1 | 31.86 |
| 1633 | CB | GLN | 28 | 32.348 | −33.146 | 25.735 | 1 | 33.2 |
| 1634 | CG | GLN | 28 | 33.843 | −32.975 | 25.481 | 1 | 36.17 |
| 1635 | CD | GLN | 28 | 34.402 | −33.994 | 24.508 | 1 | 39.04 |
| 1636 | OE1 | GLN | 28 | 33.99 | −34.055 | 23.351 | 1 | 41.07 |
| 1637 | NE2 | GLN | 28 | 35.352 | −34.8 | 24.974 | 1 | 39.92 |
| 1638 | C | GLN | 28 | 30.741 | −34.243 | 27.298 | 1 | 31.18 |
| 1639 | O | GLN | 28 | 30.831 | −33.593 | 28.338 | 1 | 31.11 |
| 1640 | N | LEU | 29 | 29.6 | −34.783 | 26.884 | 1 | 31.09 |
| 1641 | CA | LEU | 29 | 28.368 | −34.632 | 27.65 | 1 | 31.25 |
| 1642 | CB | LEU | 29 | 27.214 | −35.341 | 26.937 | 1 | 30.81 |
| 1643 | CG | LEU | 29 | 26.882 | −34.821 | 25.535 | 1 | 30.41 |
| 1644 | CD1 | LEU | 29 | 25.83 | −35.713 | 24.894 | 1 | 29.77 |
| 1645 | CD2 | LEU | 29 | 26.389 | −33.381 | 25.62 | 1 | 30.8 |
| 1646 | C | LEU | 29 | 28.535 | −35.197 | 29.057 | 1 | 32.13 |
| 1647 | O | LEU | 29 | 28.999 | −36.324 | 29.233 | 1 | 33.21 |
| 1648 | N | GLY | 30 | 28.159 | −34.403 | 30.055 | 1 | 31.89 |
| 1649 | CA | GLY | 30 | 28.28 | −34.839 | 31.435 | 1 | 32.21 |
| 1650 | C | GLY | 30 | 29.714 | −34.835 | 31.935 | 1 | 31.92 |
| 1651 | O | GLY | 30 | 29.994 | −35.335 | 33.025 | 1 | 33.15 |
| 1652 | N | GLY | 31 | 30.622 | −34.267 | 31.146 | 1 | 31.36 |
| 1653 | CA | GLY | 31 | 32.024 | −34.22 | 31.531 | 1 | 31.28 |
| 1654 | C | GLY | 31 | 32.409 | −33.027 | 32.393 | 1 | 31.29 |
| 1655 | O | GLY | 31 | 31.663 | −32.051 | 32.472 | 1 | 30.6 |
| 1656 | N | PRO | 32 | 33.582 | −33.073 | 33.05 | 1 | 30.92 |
| 1657 | CD | PRO | 32 | 34.562 | −34.174 | 33.02 | 1 | 31.58 |
| 1658 | CA | PRO | 32 | 34.053 | −31.982 | 33.911 | 1 | 30.13 |
| 1659 | CB | PRO | 32 | 35.33 | −32.555 | 34.527 | 1 | 30.64 |
| 1660 | CG | PRO | 32 | 35.829 | −33.483 | 33.465 | 1 | 30.76 |
| 1661 | C | PRO | 32 | 34.295 | −30.659 | 33.186 | 1 | 29.16 |
| 1662 | O | PRO | 32 | 33.945 | −29.596 | 33.7 | 1 | 27.68 |
| 1663 | N | GLU | 33 | 34.894 | −30.722 | 32 | 1 | 28 |
| 1664 | CA | GLU | 33 | 35.167 | −29.515 | 31.227 | 1 | 27.69 |
| 1665 | CB | GLU | 33 | 35.908 | −29.863 | 29.934 | 1 | 30.11 |
| 1666 | CG | GLU | 33 | 36.287 | −28.652 | 29.093 | 1 | 34.11 |
| 1667 | CD | GLU | 33 | 37.035 | −29.026 | 27.826 | 1 | 37.31 |
| 1668 | OE1 | GLU | 33 | 36.471 | −29.774 | 26.997 | 1 | 39.02 |
| 1669 | OE2 | GLU | 33 | 38.187 | −28.572 | 27.657 | 1 | 39.02 |
| 1670 | C | GLU | 33 | 33.865 | −28.789 | 30.898 | 1 | 26.35 |
| 1671 | O | GLU | 33 | 33.767 | −27.572 | 31.053 | 1 | 24.41 |
| 1672 | N | LEU | 34 | 32.866 | −29.54 | 30.443 | 1 | 24.61 |
| 1673 | CA | LEU | 34 | 31.575 | −28.951 | 30.11 | 1 | 22.69 |
| 1674 | CB | LEU | 34 | 30.651 | −30 | 29.484 | 1 | 21.97 |
| 1675 | CG | LEU | 34 | 29.252 | −29.513 | 29.096 | 1 | 20.97 |
| 1676 | CD1 | LEU | 34 | 29.369 | −28.397 | 28.068 | 1 | 20.5 |
| 1677 | CD2 | LEU | 34 | 28.436 | −30.669 | 28.532 | 1 | 22.16 |
| 1678 | C | LEU | 34 | 30.93 | −28.388 | 31.372 | 1 | 22.8 |
| 1679 | O | LEU | 34 | 30.253 | −27.362 | 31.331 | 1 | 21.96 |
| 1680 | N | GLN | 35 | 31.147 | −29.061 | 32.497 | 1 | 22.93 |
| 1681 | CA | GLN | 35 | 30.576 | −28.612 | 33.76 | 1 | 23.64 |
| 1682 | CB | GLN | 35 | 30.867 | −29.625 | 34.872 | 1 | 26.47 |
| 1683 | CG | GLN | 35 | 30.171 | −29.303 | 36.188 | 1 | 31.37 |
| 1684 | CD | GLN | 35 | 30.486 | −30.306 | 37.284 | 1 | 33.98 |
| 1685 | OE1 | GLN | 35 | 30.318 | −31.513 | 37.105 | 1 | 37.64 |
| 1686 | NE2 | GLN | 35 | 30.939 | −29.808 | 38.43 | 1 | 36.04 |
| 1687 | C | GLN | 35 | 31.133 | −27.248 | 34.152 | 1 | 22.89 |
| 1688 | O | GLN | 35 | 30.393 | −26.37 | 34.598 | 1 | 22.42 |
| 1689 | N | ARG | 36 | 32.44 | −27.07 | 33.986 | 1 | 22.61 |
| 1690 | CA | ARG | 36 | 33.065 | −25.8 | 34.326 | 1 | 22.82 |
| 1691 | CB | ARG | 36 | 34.585 | −25.874 | 34.131 | 1 | 25.18 |
| 1692 | CG | ARG | 36 | 35.289 | −26.839 | 35.083 | 1 | 29.92 |
| 1693 | CD | ARG | 36 | 36.788 | −26.561 | 35.153 | 1 | 32.62 |
| 1694 | NE | ARG | 36 | 37.482 | −26.839 | 33.898 | 1 | 35.76 |
| 1695 | CZ | ARG | 36 | 37.745 | −28.059 | 33.438 | 1 | 37.39 |
| 1696 | NH1 | ARG | 36 | 37.373 | −29.129 | 34.129 | 1 | 37.45 |
| 1697 | NH2 | ARG | 36 | 38.387 | −28.21 | 32.287 | 1 | 37.48 |
| 1698 | C | ARG | 36 | 32.485 | −24.677 | 33.472 | 1 | 21.48 |
| 1699 | O | ARG | 36 | 32.215 | −23.583 | 33.969 | 1 | 20.84 |
| 1700 | N | LEU | 37 | 32.285 | −24.957 | 32.189 | 1 | 20.17 |
| 1701 | CA | LEU | 37 | 31.74 | −23.959 | 31.272 | 1 | 19.24 |
| 1702 | CB | LEU | 37 | 31.783 | −24.481 | 29.834 | 1 | 18.37 |
| 1703 | CG | LEU | 37 | 31.089 | −23.603 | 28.785 | 1 | 16.98 |
| 1704 | CD1 | LEU | 37 | 31.703 | −22.205 | 28.778 | 1 | 19.48 |
| 1705 | CD2 | LEU | 37 | 31.221 | −24.251 | 27.416 | 1 | 18.75 |
| 1706 | C | LEU | 37 | 30.31 | −23.564 | 31.621 | 1 | 17.72 |
| 1707 | O | LEU | 37 | 29.978 | −22.38 | 31.658 | 1 | 16.49 |
| 1708 | N | THR | 38 | 29.458 | −24.553 | 31.867 | 1 | 17.3 |
| 1709 | CA | THR | 38 | 28.071 | −24.259 | 32.197 | 1 | 17.87 |
| 1710 | CB | THR | 38 | 27.224 | −25.55 | 32.23 | 1 | 18.74 |
| 1711 | OG1 | THR | 38 | 27.767 | −26.463 | 33.189 | 1 | 21.62 |
| 1712 | CG2 | THR | 38 | 27.23 | −26.211 | 30.863 | 1 | 18.77 |
| 1713 | C | THR | 38 | 27.944 | −23.511 | 33.523 | 1 | 17.67 |
| 1714 | O | THR | 38 | 27.13 | −22.598 | 33.65 | 1 | 17.98 |
| 1715 | N | GLN | 39 | 28.753 | −23.885 | 34.508 | 1 | 19.28 |
| 1716 | CA | GLN | 39 | 28.709 | −23.216 | 35.807 | 1 | 19.93 |
| 1717 | CB | GLN | 39 | 29.621 | −23.934 | 36.807 | 1 | 23.4 |
| 1718 | CG | GLN | 39 | 29.109 | −25.296 | 37.249 | 1 | 30.8 |
| 1719 | CD | GLN | 39 | 27.847 | −25.198 | 38.086 | 1 | 33.22 |
| 1720 | OE1 | GLN | 39 | 27.846 | −24.598 | 39.162 | 1 | 37.41 |
| 1721 | NE2 | GLN | 39 | 26.762 | −25.788 | 37.594 | 1 | 36.24 |
| 1722 | C | GLN | 39 | 29.151 | −21.761 | 35.665 | 1 | 18.99 |
| 1723 | O | GLN | 39 | 28.565 | −20.86 | 36.262 | 1 | 17.23 |
| 1724 | N | ARG | 40 | 30.19 | −21.55 | 34.865 | 1 | 19.25 |
| 1725 | CA | ARG | 40 | 30.745 | −20.226 | 34.617 | 1 | 19.05 |
| 1726 | CB | ARG | 40 | 32.017 | −20.386 | 33.78 | 1 | 23.01 |
| 1727 | CG | ARG | 40 | 32.792 | −19.127 | 33.448 | 1 | 28.32 |
| 1728 | CD | ARG | 40 | 33.969 | −19.519 | 32.556 | 1 | 31.53 |
| 1729 | NE | ARG | 40 | 34.709 | −18.382 | 32.02 | 1 | 37.27 |
| 1730 | CZ | ARG | 40 | 35.662 | −18.489 | 31.099 | 1 | 38.55 |
| 1731 | NH1 | ARG | 40 | 35.985 | −19.681 | 30.613 | 1 | 40.8 |
| 1732 | NH2 | ARG | 40 | 36.295 | −17.407 | 30.664 | 1 | 41.18 |
| 1733 | C | ARG | 40 | 29.717 | −19.363 | 33.884 | 1 | 17.73 |
| 1734 | O | ARG | 40 | 29.5 | −18.199 | 34.224 | 1 | 16.39 |
| 1735 | N | LEU | 41 | 29.079 | −19.951 | 32.879 | 1 | 17.12 |
| 1736 | CA | LEU | 41 | 28.073 | −19.254 | 32.093 | 1 | 15.46 |
| 1737 | CB | LEU | 41 | 27.569 | −20.181 | 30.981 | 1 | 17.31 |
| 1738 | CG | LEU | 41 | 26.726 | −19.615 | 29.841 | 1 | 17.61 |
| 1739 | CD1 | LEU | 41 | 27.509 | −18.55 | 29.078 | 1 | 16.01 |
| 1740 | CD2 | LEU | 41 | 26.348 | −20.762 | 28.905 | 1 | 18.88 |
| 1741 | C | LEU | 41 | 26.913 | −18.809 | 32.983 | 1 | 15.03 |
| 1742 | O | LEU | 41 | 26.476 | −17.659 | 32.93 | 1 | 14.75 |
| 1743 | N | VAL | 42 | 26.42 | −19.718 | 33.82 | 1 | 14.75 |
| 1744 | CA | VAL | 42 | 25.314 | −19.385 | 34.705 | 1 | 14.73 |
| 1745 | CB | VAL | 42 | 24.799 | −20.65 | 35.432 | 1 | 15.3 |
| 1746 | CG1 | VAL | 42 | 23.744 | −20.279 | 36.461 | 1 | 16.8 |
| 1747 | CG2 | VAL | 42 | 24.22 | −21.617 | 34.41 | 1 | 18.06 |
| 1748 | C | VAL | 42 | 25.706 | −18.32 | 35.73 | 1 | 14.45 |
| 1749 | O | VAL | 42 | 24.93 | −17.405 | 36.013 | 1 | 14.1 |
| 1750 | N | GLN | 43 | 26.918 | −18.425 | 36.269 | 1 | 15.78 |
| 1751 | CA | GLN | 43 | 27.385 | −17.462 | 37.262 | 1 | 17.49 |
| 1752 | CB | GLN | 43 | 28.766 | −17.866 | 37.785 | 1 | 19.98 |
| 1753 | CG | GLN | 43 | 29.116 | −17.228 | 39.116 | 1 | 26.24 |
| 1754 | CD | GLN | 43 | 30.584 | −17.351 | 39.463 | 1 | 28.43 |

TABLE 2-continued

| Atom | Atom Type | Residue | # | X | Y | Z | OCC | B |
|---|---|---|---|---|---|---|---|---|
| 1755 | OE1 | GLN | 43 | 31.217 | −18.373 | 39.198 | 1 | 32.06 |
| 1756 | NE2 | GLN | 43 | 31.132 | −16.307 | 40.073 | 1 | 29.15 |
| 1757 | C | GLN | 43 | 27.456 | −16.043 | 36.694 | 1 | 16.17 |
| 1758 | O | GLN | 43 | 27.022 | −15.084 | 37.335 | 1 | 16.53 |
| 1759 | N | VAL | 44 | 28.009 | −15.91 | 35.491 | 1 | 14.92 |
| 1760 | CA | VAL | 44 | 28.128 | −14.601 | 34.858 | 1 | 15.31 |
| 1761 | CB | VAL | 44 | 28.985 | −14.673 | 33.576 | 1 | 15.42 |
| 1762 | CG1 | VAL | 44 | 28.956 | −13.33 | 32.853 | 1 | 16.36 |
| 1763 | CG2 | VAL | 44 | 30.414 | −15.051 | 33.938 | 1 | 16 |
| 1764 | C | VAL | 44 | 26.757 | −14.042 | 34.514 | 1 | 14.22 |
| 1765 | O | VAL | 44 | 26.49 | −12.857 | 34.705 | 1 | 15.62 |
| 1766 | N | MET | 45 | 25.882 | −14.898 | 34.004 | 1 | 14.86 |
| 1767 | CA | MET | 45 | 24.538 | −14.46 | 33.662 | 1 | 14.57 |
| 1768 | CB | MET | 45 | 23.736 | −15.63 | 33.076 | 1 | 14.22 |
| 1769 | CG | MET | 45 | 22.291 | −15.279 | 32.776 | 1 | 16.34 |
| 1770 | SD | MET | 45 | 21.396 | −16.652 | 32.017 | 1 | 17.92 |
| 1771 | CE | MET | 45 | 21.244 | −17.766 | 33.409 | 1 | 19.61 |
| 1772 | C | MET | 45 | 23.827 | −13.909 | 34.899 | 1 | 15.93 |
| 1773 | O | MET | 45 | 23.179 | −12.864 | 34.843 | 1 | 16.81 |
| 1774 | N | ARG | 46 | 23.96 | −14.607 | 36.021 | 1 | 16.06 |
| 1775 | CA | ARG | 46 | 23.31 | −14.178 | 37.254 | 1 | 17.11 |
| 1776 | CB | ARG | 46 | 23.329 | −15.318 | 38.276 | 1 | 18.57 |
| 1777 | CG | ARG | 46 | 22.327 | −16.416 | 37.946 | 1 | 19.6 |
| 1778 | CD | ARG | 46 | 22.46 | −17.627 | 38.854 | 1 | 20.28 |
| 1779 | NE | ARG | 46 | 21.36 | −18.565 | 38.636 | 1 | 18.66 |
| 1780 | CZ | ARG | 46 | 21.31 | −19.796 | 39.131 | 1 | 20.88 |
| 1781 | NH1 | ARG | 46 | 22.304 | −20.26 | 39.88 | 1 | 22.28 |
| 1782 | NH2 | ARG | 46 | 20.261 | −20.566 | 38.879 | 1 | 19.86 |
| 1783 | C | ARG | 46 | 23.912 | −12.913 | 37.855 | 1 | 18.83 |
| 1784 | O | ARG | 46 | 23.19 | −12.064 | 38.376 | 1 | 19.2 |
| 1785 | N | ARG | 47 | 25.231 | −12.78 | 37.778 | 1 | 18.95 |
| 1786 | CA | ARG | 47 | 25.88 | −11.595 | 38.319 | 1 | 20.94 |
| 1787 | CB | ARG | 47 | 27.398 | −11.785 | 38.352 | 1 | 24.48 |
| 1788 | CG | ARG | 47 | 27.847 | −12.888 | 39.301 | 1 | 28.87 |
| 1789 | CD | ARG | 47 | 29.305 | −12.726 | 39.69 | 1 | 31.48 |
| 1790 | NE | ARG | 47 | 29.724 | −13.733 | 40.661 | 1 | 34.8 |
| 1791 | CZ | ARG | 47 | 30.53 | −13.485 | 41.687 | 1 | 37.53 |
| 1792 | NH1 | ARG | 47 | 31.001 | −12.26 | 41.875 | 1 | 39.08 |
| 1793 | NH2 | ARG | 47 | 30.866 | −14.457 | 42.525 | 1 | 37.61 |
| 1794 | C | ARG | 47 | 25.521 | −10.356 | 37.507 | 1 | 20.25 |
| 1795 | O | ARG | 47 | 25.357 | −9.27 | 38.061 | 1 | 21.34 |
| 1796 | N | ARG | 48 | 25.39 | −10.525 | 36.194 | 1 | 18.88 |
| 1797 | CA | ARG | 48 | 25.044 | −9.42 | 35.309 | 1 | 19.82 |
| 1798 | CB | ARG | 48 | 25.529 | −9.712 | 33.883 | 1 | 19.31 |
| 1799 | CG | ARG | 48 | 27.035 | −9.585 | 33.701 | 1 | 20.72 |
| 1800 | CD | ARG | 48 | 27.48 | −8.179 | 34.057 | 1 | 24.1 |
| 1801 | NE | ARG | 48 | 26.717 | −7.189 | 33.304 | 1 | 24.96 |
| 1802 | CZ | ARG | 48 | 26.354 | −6.003 | 33.779 | 1 | 27.1 |
| 1803 | NH1 | ARG | 48 | 26.686 | −5.65 | 35.014 | 1 | 27.33 |
| 1804 | NH2 | ARG | 48 | 25.65 | −5.175 | 33.022 | 1 | 26.57 |
| 1805 | C | ARG | 48 | 23.543 | −9.171 | 35.291 | 1 | 21.05 |
| 1806 | O | ARG | 48 | 23.073 | −8.175 | 34.743 | 1 | 20.77 |
| 1807 | N | ARG | 49 | 22.792 | −10.086 | 35.894 | 1 | 21.45 |
| 1808 | CA | ARG | 49 | 21.345 | −9.961 | 35.938 | 1 | 23.52 |
| 1809 | CB | ARG | 49 | 20.951 | −8.706 | 36.724 | 1 | 27.6 |
| 1810 | CG | ARG | 49 | 21.105 | −8.849 | 38.233 | 1 | 31.54 |
| 1811 | CD | ARG | 49 | 21.548 | −7.544 | 38.877 | 1 | 35.15 |
| 1812 | NE | ARG | 49 | 20.761 | −6.397 | 38.431 | 1 | 38.21 |
| 1813 | CZ | ARG | 49 | 19.477 | −6.203 | 38.717 | 1 | 39.39 |
| 1814 | NH1 | ARG | 49 | 18.812 | −7.081 | 39.457 | 1 | 38.76 |
| 1815 | NH2 | ARG | 49 | 18.855 | −5.125 | 38.255 | 1 | 40.24 |
| 1816 | C | ARG | 49 | 20.728 | −9.924 | 34.544 | 1 | 22.07 |
| 1817 | O | ARG | 49 | 19.703 | −9.277 | 34.328 | 1 | 24.3 |
| 1818 | N | CYS | 50 | 21.361 | −10.59 | 33.584 | 1 | 19.5 |
| 1819 | CA | CYS | 50 | 20.79 | −10.635 | 32.246 | 1 | 18.63 |
| 1820 | CB | CYS | 50 | 21.879 | −10.617 | 31.163 | 1 | 18.58 |
| 1821 | SG | CYS | 50 | 23.188 | −11.839 | 31.291 | 1 | 18.34 |
| 1822 | C | CYS | 50 | 19.971 | −11.921 | 32.217 | 1 | 18.16 |
| 1823 | O | CYS | 50 | 20.109 | −12.763 | 33.105 | 1 | 19.18 |
| 1824 | N | VAL | 51 | 19.106 | −12.075 | 31.224 | 1 | 17.84 |
| 1825 | CA | VAL | 51 | 18.253 | −13.256 | 31.173 | 1 | 15.68 |
| 1826 | CB | VAL | 51 | 16.836 | −12.864 | 30.73 | 1 | 16.18 |
| 1827 | CG1 | VAL | 51 | 16.23 | −11.897 | 31.735 | 1 | 19.54 |
| 1828 | CG2 | VAL | 51 | 16.882 | −12.221 | 29.37 | 1 | 18.46 |
| 1829 | C | VAL | 51 | 18.755 | −14.406 | 30.306 | 1 | 15.35 |
| 1830 | O | VAL | 51 | 18.141 | −15.471 | 30.26 | 1 | 15.5 |
| 1831 | N | GLY | 52 | 19.874 | −14.195 | 29.624 | 1 | 14.16 |
| 1832 | CA | GLY | 52 | 20.428 | −15.239 | 28.784 | 1 | 13 |
| 1833 | C | GLY | 52 | 21.884 | −14.949 | 28.493 | 1 | 12.18 |
| 1834 | O | GLY | 52 | 22.312 | −13.798 | 28.565 | 1 | 13.73 |
| 1835 | N | LEU | 53 | 22.651 | −15.988 | 28.185 | 1 | 11.36 |
| 1836 | CA | LEU | 53 | 24.064 | −15.811 | 27.87 | 1 | 11.9 |
| 1837 | CB | LEU | 53 | 24.881 | −15.613 | 29.155 | 1 | 13.12 |
| 1838 | CG | LEU | 53 | 26.295 | −15.058 | 28.945 | 1 | 14.26 |
| 1839 | CD1 | LEU | 53 | 26.203 | −13.668 | 28.324 | 1 | 13.65 |
| 1840 | CD2 | LEU | 53 | 27.037 | −14.991 | 30.28 | 1 | 12.59 |
| 1841 | C | LEU | 53 | 24.561 | −17.029 | 27.107 | 1 | 13.36 |
| 1842 | O | LEU | 53 | 24.121 | −18.15 | 27.364 | 1 | 14.21 |
| 1843 | N | SER | 54 | 25.476 | −16.813 | 26.168 | 1 | 11.74 |
| 1844 | CA | SER | 54 | 26.008 | −17.91 | 25.364 | 1 | 12.64 |
| 1845 | CB | SER | 54 | 25.706 | −17.67 | 23.888 | 1 | 12.57 |
| 1846 | OG | SER | 54 | 26.436 | −16.559 | 23.405 | 1 | 13.52 |
| 1847 | C | SER | 54 | 27.509 | −18.081 | 25.543 | 1 | 12.23 |
| 1848 | O | SER | 54 | 28.217 | −17.129 | 25.863 | 1 | 10.7 |
| 1849 | N | ALA | 55 | 27.993 | −19.296 | 25.313 | 1 | 11.07 |
| 1850 | CA | ALA | 55 | 29.414 | −19.589 | 25.454 | 1 | 11.53 |
| 1851 | CB | ALA | 55 | 29.678 | −21.057 | 25.102 | 1 | 14.69 |
| 1852 | C | ALA | 55 | 30.338 | −18.674 | 24.634 | 1 | 12.81 |
| 1853 | O | ALA | 55 | 31.395 | −18.277 | 25.116 | 1 | 12.82 |
| 1854 | N | PRO | 56 | 29.961 | −18.338 | 23.386 | 1 | 11.45 |
| 1855 | CD | PRO | 56 | 28.909 | −18.92 | 22.53 | 1 | 9.97 |
| 1856 | CA | PRO | 56 | 30.841 | −17.461 | 22.601 | 1 | 11.07 |
| 1857 | CB | PRO | 56 | 30.087 | −17.308 | 21.286 | 1 | 11.62 |
| 1858 | CG | PRO | 56 | 29.451 | −18.667 | 21.133 | 1 | 10.5 |
| 1859 | C | PRO | 56 | 31.095 | −16.125 | 23.289 | 1 | 10.76 |
| 1860 | O | PRO | 56 | 32.158 | −15.515 | 23.12 | 1 | 11.72 |
| 1861 | N | GLN | 57 | 30.126 | −15.678 | 24.077 | 1 | 10.55 |
| 1862 | CA | GLN | 57 | 30.264 | −14.41 | 24.785 | 1 | 11.4 |
| 1863 | CB | GLN | 57 | 28.91 | −13.968 | 25.322 | 1 | 11.81 |
| 1864 | CG | GLN | 57 | 27.952 | −13.584 | 24.211 | 1 | 12.23 |
| 1865 | CD | GLN | 57 | 26.571 | −13.292 | 24.728 | 1 | 13.47 |
| 1866 | OE1 | GLN | 57 | 25.753 | −14.2 | 24.895 | 1 | 12.63 |
| 1867 | NE2 | GLN | 57 | 26.299 | −12.02 | 24.999 | 1 | 12.13 |
| 1868 | C | GLN | 57 | 31.295 | −14.479 | 25.904 | 1 | 13.67 |
| 1869 | O | GLN | 57 | 31.733 | −13.449 | 26.424 | 1 | 12.54 |
| 1870 | N | LEU | 58 | 31.685 | −15.696 | 26.272 | 1 | 13.27 |
| 1871 | CA | LEU | 58 | 32.703 | −15.89 | 27.296 | 1 | 15.66 |
| 1872 | CB | LEU | 58 | 32.263 | −16.938 | 28.325 | 1 | 15.79 |
| 1873 | CG | LEU | 58 | 31.092 | −16.54 | 29.228 | 1 | 16.5 |
| 1874 | CD1 | LEU | 58 | 30.911 | −17.595 | 30.32 | 1 | 18.51 |
| 1875 | CD2 | LEU | 58 | 31.362 | −15.178 | 29.857 | 1 | 18.52 |
| 1876 | C | LEU | 58 | 33.991 | −16.357 | 26.614 | 1 | 15.85 |
| 1877 | O | LEU | 58 | 34.912 | −16.83 | 27.263 | 1 | 18.82 |
| 1878 | N | GLY | 59 | 34.031 | −16.172 | 25.294 | 1 | 14.26 |
| 1879 | CA | GLY | 59 | 35.207 | −16.531 | 24.52 | 1 | 14.63 |
| 1880 | C | GLY | 59 | 35.319 | −17.989 | 24.125 | 1 | 14.85 |
| 1881 | O | GLY | 59 | 36.345 | −18.406 | 23.589 | 1 | 16.52 |
| 1882 | N | VAL | 60 | 34.262 | −18.759 | 24.367 | 1 | 14.84 |
| 1883 | CA | VAL | 60 | 34.253 | −20.19 | 24.052 | 1 | 15.68 |
| 1884 | CB | VAL | 60 | 33.78 | −20.999 | 25.279 | 1 | 15.09 |
| 1885 | CG1 | VAL | 60 | 33.786 | −22.485 | 24.965 | 1 | 16.79 |
| 1886 | CG2 | VAL | 60 | 34.685 | −20.705 | 26.464 | 1 | 18.07 |
| 1887 | C | VAL | 60 | 33.336 | −20.477 | 22.86 | 1 | 15.21 |
| 1888 | O | VAL | 60 | 32.116 | −20.411 | 22.979 | 1 | 14.01 |
| 1889 | N | PRO | 61 | 33.92 | −20.818 | 21.696 | 1 | 14.59 |
| 1890 | CD | PRO | 61 | 35.366 | −20.91 | 21.416 | 1 | 15.65 |
| 1891 | CA | PRO | 61 | 33.14 | −21.103 | 20.487 | 1 | 15.28 |
| 1892 | CB | PRO | 61 | 34.17 | −20.937 | 19.378 | 1 | 15.58 |
| 1893 | CG | PRO | 61 | 35.397 | −21.505 | 20.008 | 1 | 16.19 |
| 1894 | C | PRO | 61 | 32.47 | −22.471 | 20.463 | 1 | 14.32 |
| 1895 | O | PRO | 61 | 32.756 | −23.296 | 19.596 | 1 | 15.77 |
| 1896 | N | ARG | 62 | 31.57 | −22.695 | 21.414 | 1 | 14.61 |
| 1897 | CA | ARG | 62 | 30.853 | −23.961 | 21.521 | 1 | 14.7 |
| 1898 | CB | ARG | 62 | 31.366 | −24.756 | 22.723 | 1 | 17.44 |
| 1899 | CG | ARG | 62 | 32.868 | −24.994 | 22.703 | 1 | 20.32 |
| 1900 | CD | ARG | 62 | 33.333 | −25.744 | 23.939 | 1 | 25.53 |
| 1901 | NE | ARG | 62 | 32.985 | −27.161 | 23.885 | 1 | 26.71 |
| 1902 | CZ | ARG | 62 | 33.128 | −28.005 | 24.901 | 1 | 27.83 |
| 1903 | NH1 | ARG | 62 | 33.61 | −27.579 | 26.061 | 1 | 29.59 |
| 1904 | NH2 | ARG | 62 | 32.791 | −29.279 | 24.756 | 1 | 29.31 |
| 1905 | C | ARG | 62 | 29.357 | −23.71 | 21.661 | 1 | 14.03 |
| 1906 | O | ARG | 62 | 28.931 | −22.684 | 22.197 | 1 | 13.09 |

TABLE 2-continued

| Atom | Atom Type | Residue | # | X | Y | Z | OCC | B |
|---|---|---|---|---|---|---|---|---|
| 1907 | N | GLN | 63 | 28.558 | −24.659 | 21.188 | 1 | 14.35 |
| 1908 | CA | GLN | 63 | 27.109 | −24.527 | 21.233 | 1 | 13.55 |
| 1909 | CB | GLN | 63 | 26.48 | −25.446 | 20.185 | 1 | 13.32 |
| 1910 | CG | GLN | 63 | 26.98 | −25.133 | 18.774 | 1 | 12.6 |
| 1911 | CD | GLN | 63 | 26.463 | −26.093 | 17.718 | 1 | 14.78 |
| 1912 | OE1 | GLN | 63 | 26.999 | −26.155 | 16.61 | 1 | 18.18 |
| 1913 | NE2 | GLN | 63 | 25.416 | −26.837 | 18.05 | 1 | 14.58 |
| 1914 | C | GLN | 63 | 26.514 | −24.798 | 22.605 | 1 | 14.64 |
| 1915 | O | GLN | 63 | 25.959 | −25.868 | 22.863 | 1 | 15.48 |
| 1916 | N | VAL | 64 | 26.637 | −23.811 | 23.483 | 1 | 12.53 |
| 1917 | CA | VAL | 64 | 26.105 | −23.905 | 24.833 | 1 | 12.88 |
| 1918 | CB | VAL | 64 | 27.196 | −24.264 | 25.857 | 1 | 12.33 |
| 1919 | CG1 | VAL | 64 | 26.572 | −24.431 | 27.24 | 1 | 13.64 |
| 1920 | CG2 | VAL | 64 | 27.915 | −25.541 | 25.437 | 1 | 13.99 |
| 1921 | C | VAL | 64 | 25.542 | −22.545 | 25.208 | 1 | 12.71 |
| 1922 | O | VAL | 64 | 26.187 | −21.521 | 24.981 | 1 | 13.35 |
| 1923 | N | LEU | 65 | 24.338 | −22.538 | 25.767 | 1 | 12.86 |
| 1924 | CA | LEU | 65 | 23.703 | −21.299 | 26.189 | 1 | 13.23 |
| 1925 | CB | LEU | 65 | 22.82 | −20.731 | 25.065 | 1 | 15.13 |
| 1926 | CG | LEU | 65 | 21.658 | −21.548 | 24.485 | 1 | 14.9 |
| 1927 | CD1 | LEU | 65 | 20.501 | −21.55 | 25.464 | 1 | 16.04 |
| 1928 | CD2 | LEU | 65 | 21.203 | −20.944 | 23.16 | 1 | 17.94 |
| 1929 | C | LEU | 65 | 22.885 | −21.53 | 27.455 | 1 | 13.72 |
| 1930 | O | LEU | 65 | 22.498 | −22.66 | 27.766 | 1 | 13.66 |
| 1931 | N | ALA | 66 | 22.649 | −20.455 | 28.195 | 1 | 13.07 |
| 1932 | CA | ALA | 66 | 21.88 | −20.525 | 29.429 | 1 | 13.72 |
| 1933 | CB | ALA | 66 | 22.785 | −20.28 | 30.627 | 1 | 13.5 |
| 1934 | C | ALA | 66 | 20.785 | −19.474 | 29.373 | 1 | 13.63 |
| 1935 | O | ALA | 66 | 20.965 | −18.414 | 28.773 | 1 | 13.07 |
| 1936 | N | LEU | 67 | 19.655 | −19.775 | 30.008 | 1 | 13.17 |
| 1937 | CA | LEU | 67 | 18.498 | −18.887 | 30.025 | 1 | 14.54 |
| 1938 | CB | LEU | 67 | 17.48 | −19.353 | 28.974 | 1 | 16.7 |
| 1939 | CG | LEU | 67 | 18.006 | −19.618 | 27.56 | 1 | 18.07 |
| 1940 | CD1 | LEU | 67 | 17.049 | −20.522 | 26.8 | 1 | 20.42 |
| 1941 | CD2 | LEU | 67 | 18.199 | −18.294 | 26.837 | 1 | 20.95 |
| 1942 | C | LEU | 67 | 17.847 | −18.952 | 31.402 | 1 | 13.89 |
| 1943 | O | LEU | 67 | 17.689 | −20.039 | 31.959 | 1 | 15.43 |
| 1944 | N | GLU | 68 | 17.469 | −17.8 | 31.947 | 1 | 13.86 |
| 1945 | CA | GLU | 68 | 16.817 | −17.762 | 33.253 | 1 | 13.84 |
| 1946 | CB | GLU | 68 | 17.819 | −18.092 | 34.368 | 1 | 15.08 |
| 1947 | CG | GLU | 68 | 17.207 | −18.092 | 35.768 | 1 | 16.99 |
| 1948 | CD | GLU | 68 | 18.24 | −18.317 | 36.86 | 1 | 21.39 |
| 1949 | OE1 | GLU | 68 | 19.313 | −17.681 | 36.804 | 1 | 22.91 |
| 1950 | OE2 | GLU | 68 | 17.976 | −19.118 | 37.781 | 1 | 23.38 |
| 1951 | C | GLU | 68 | 16.195 | −16.401 | 33.527 | 1 | 14.58 |
| 1952 | O | GLU | 68 | 16.831 | −15.365 | 33.328 | 1 | 15.7 |
| 1953 | N | LEU | 69 | 14.944 | −16.4 | 33.971 | 1 | 14.76 |
| 1954 | CA | LEU | 69 | 14.273 | −15.153 | 34.295 | 1 | 16.59 |
| 1955 | CB | LEU | 69 | 13.259 | −14.769 | 33.212 | 1 | 17.96 |
| 1956 | CG | LEU | 69 | 12.479 | −13.478 | 33.494 | 1 | 19.6 |
| 1957 | CD1 | LEU | 69 | 13.435 | −12.36 | 33.907 | 1 | 20.56 |
| 1958 | CD2 | LEU | 69 | 11.694 | −13.082 | 32.258 | 1 | 21.77 |
| 1959 | C | LEU | 69 | 13.577 | −15.274 | 35.641 | 1 | 18.37 |
| 1960 | O | LEU | 69 | 12.431 | −15.723 | 35.729 | 1 | 18.07 |
| 1961 | N | PRO | 70 | 14.276 | −14.884 | 36.717 | 1 | 20.55 |
| 1962 | CD | PRO | 70 | 15.689 | −14.471 | 36.739 | 1 | 21.03 |
| 1963 | CA | PRO | 70 | 13.735 | −14.943 | 38.077 | 1 | 22.6 |
| 1964 | CB | PRO | 70 | 14.92 | −14.508 | 38.941 | 1 | 23.04 |
| 1965 | CG | PRO | 70 | 16.109 | −14.898 | 38.117 | 1 | 22.22 |
| 1966 | C | PRO | 70 | 12.545 | −14.004 | 38.226 | 1 | 23.46 |
| 1967 | O | PRO | 70 | 12.446 | −12.996 | 37.527 | 1 | 23.05 |
| 1968 | N | GLU | 71 | 11.649 | −14.338 | 39.146 | 1 | 25.49 |
| 1969 | CA | GLU | 71 | 10.464 | −13.529 | 39.391 | 1 | 27.92 |
| 1970 | CB | GLU | 71 | 9.633 | −14.171 | 40.503 | 1 | 30.58 |
| 1971 | CG | GLU | 71 | 8.318 | −13.474 | 40.798 | 1 | 34.27 |
| 1972 | CD | GLU | 71 | 7.512 | −14.206 | 41.853 | 1 | 36.78 |
| 1973 | OE1 | GLU | 71 | 7.141 | −15.374 | 41.612 | 1 | 39.21 |
| 1974 | OE2 | GLU | 71 | 7.254 | −13.617 | 42.925 | 1 | 38.97 |
| 1975 | C | GLU | 71 | 10.826 | −12.092 | 39.766 | 1 | 27.01 |
| 1976 | O | GLU | 71 | 10.261 | −11.142 | 39.224 | 1 | 26.58 |
| 1977 | N | ALA | 72 | 11.775 | −11.939 | 40.686 | 1 | 28 |
| 1978 | CA | ALA | 72 | 12.21 | −10.619 | 41.14 | 1 | 28.86 |
| 1979 | CB | ALA | 72 | 13.331 | −10.764 | 42.16 | 1 | 29.57 |
| 1980 | C | ALA | 72 | 12.675 | −9.751 | 39.978 | 1 | 29.06 |
| 1981 | O | ALA | 72 | 12.168 | −8.648 | 39.77 | 1 | 28.5 |
| 1982 | N | LEU | 73 | 13.647 | −10.249 | 39.223 | 1 | 30.46 |
| 1983 | CA | LEU | 73 | 14.163 | −9.509 | 38.081 | 1 | 30.69 |
| 1984 | CB | LEU | 73 | 15.232 | −10.331 | 37.356 | 1 | 30.39 |
| 1985 | CG | LEU | 73 | 15.863 | −9.675 | 36.126 | 1 | 30.21 |
| 1986 | CD1 | LEU | 73 | 16.539 | −8.373 | 36.531 | 1 | 30.08 |
| 1987 | CD2 | LEU | 73 | 16.865 | −10.629 | 35.497 | 1 | 30.04 |
| 1988 | C | LEU | 73 | 13.011 | −9.21 | 37.133 | 1 | 31.08 |
| 1989 | O | LEU | 73 | 12.981 | −8.17 | 36.475 | 1 | 32.12 |
| 1990 | N | CYS | 74 | 12.054 | −10.129 | 37.086 | 1 | 31.96 |
| 1991 | CA | CYS | 74 | 10.894 | −9.991 | 36.219 | 1 | 31.69 |
| 1992 | CB | CYS | 74 | 10.162 | −11.331 | 36.131 | 1 | 32.35 |
| 1993 | SG | CYS | 74 | 9.009 | −11.463 | 34.752 | 1 | 29.04 |
| 1994 | C | CYS | 74 | 9.938 | −8.9 | 36.703 | 1 | 33.53 |
| 1995 | O | CYS | 74 | 9.396 | −8.143 | 35.898 | 1 | 33.91 |
| 1996 | N | ARG | 75 | 9.73 | −8.821 | 38.015 | 1 | 34.33 |
| 1997 | CA | ARG | 75 | 8.839 | −7.814 | 38.586 | 1 | 35.26 |
| 1998 | CB | ARG | 75 | 8.479 | −8.174 | 40.03 | 1 | 36.7 |
| 1999 | CG | ARG | 75 | 7.575 | −9.387 | 40.155 | 1 | 38.51 |
| 2000 | CD | ARG | 75 | 7.182 | −9.633 | 41.602 | 1 | 40.3 |
| 2001 | NE | ARG | 75 | 6.26 | −10.759 | 41.734 | 1 | 41.93 |
| 2002 | CZ | ARG | 75 | 5.765 | −11.186 | 42.891 | 1 | 42.52 |
| 2003 | NH1 | ARG | 75 | 6.104 | −10.582 | 44.023 | 1 | 43.56 |
| 2004 | NH2 | ARG | 75 | 4.932 | −12.218 | 42.919 | 1 | 43.59 |
| 2005 | C | ARG | 75 | 9.479 | −6.431 | 38.548 | 1 | 35.89 |
| 2006 | O | ARG | 75 | 8.839 | −5.424 | 38.857 | 1 | 35.47 |
| 2007 | N | GLU | 76 | 10.75 | −6.395 | 38.167 | 1 | 36 |
| 2008 | CA | GLU | 76 | 11.493 | −5.148 | 38.07 | 1 | 36.6 |
| 2009 | CB | GLU | 76 | 12.953 | −5.459 | 37.732 | 1 | 37.78 |
| 2010 | CG | GLU | 76 | 13.93 | −4.329 | 37.972 | 1 | 40.59 |
| 2011 | CD | GLU | 76 | 15.372 | −4.769 | 37.791 | 1 | 40.73 |
| 2012 | OE1 | GLU | 76 | 15.804 | −5.7 | 38.505 | 1 | 42.16 |
| 2013 | OE2 | GLU | 76 | 16.073 | −4.188 | 36.937 | 1 | 43.22 |
| 2014 | C | GLU | 76 | 10.843 | −4.315 | 36.966 | 1 | 36.35 |
| 2015 | O | GLU | 76 | 10.922 | −3.087 | 36.961 | 1 | 36.77 |
| 2016 | N | CYS | 77 | 10.188 | −5.005 | 36.037 | 1 | 35.81 |
| 2017 | CA | CYS | 77 | 9.503 | −4.367 | 34.919 | 1 | 35.44 |
| 2018 | CB | CYS | 77 | 9.536 | −5.294 | 33.698 | 1 | 35.64 |
| 2019 | SG | CYS | 77 | 8.744 | −4.645 | 32.21 | 1 | 38.39 |
| 2020 | C | CYS | 77 | 8.055 | −4.083 | 35.313 | 1 | 34.61 |
| 2021 | O | CYS | 77 | 7.356 | −4.969 | 35.8 | 1 | 34.48 |
| 2022 | N | PRO | 78 | 7.585 | −2.841 | 35.104 | 1 | 34.97 |
| 2023 | CD | PRO | 78 | 8.267 | −1.74 | 34.404 | 1 | 34.41 |
| 2024 | CA | PRO | 78 | 6.209 | −2.464 | 35.449 | 1 | 34.23 |
| 2025 | CB | PRO | 78 | 6.111 | −1.02 | 34.951 | 1 | 35.3 |
| 2026 | CG | PRO | 78 | 7.109 | −0.973 | 33.83 | 1 | 35.98 |
| 2027 | C | PRO | 78 | 5.144 | −3.378 | 34.835 | 1 | 33.99 |
| 2028 | O | PRO | 78 | 5.324 | −3.909 | 33.741 | 1 | 33.45 |
| 2029 | N | PRO | 79 | 4.017 | −3.566 | 35.544 | 1 | 33.49 |
| 2030 | CD | PRO | 79 | 3.739 | −2.951 | 36.855 | 1 | 33.4 |
| 2031 | CA | PRO | 79 | 2.89 | −4.408 | 35.123 | 1 | 33.4 |
| 2032 | CB | PRO | 79 | 1.808 | −4.062 | 36.143 | 1 | 33.62 |
| 2033 | CG | PRO | 79 | 2.606 | −3.807 | 37.38 | 1 | 33.77 |
| 2034 | C | PRO | 79 | 2.413 | −4.206 | 33.687 | 1 | 32.79 |
| 2035 | O | PRO | 79 | 2.23 | −5.174 | 32.948 | 1 | 32.74 |
| 2036 | N | ARG | 80 | 2.204 | −2.952 | 33.3 | 1 | 32.51 |
| 2037 | CA | ARG | 80 | 1.737 | −2.635 | 31.956 | 1 | 32.71 |
| 2038 | CB | ARG | 80 | 1.497 | −1.13 | 31.819 | 1 | 34.37 |
| 2039 | CG | ARG | 80 | 1.007 | −0.71 | 30.441 | 1 | 37.88 |
| 2040 | CD | ARG | 80 | 0.734 | 0.785 | 30.373 | 1 | 40.69 |
| 2041 | NE | ARG | 80 | 0.34 | 1.207 | 29.031 | 1 | 42.24 |
| 2042 | CZ | ARG | 80 | −0.008 | 2.45 | 28.71 | 1 | 43.12 |
| 2043 | NH1 | ARG | 80 | −0.014 | 3.4 | 29.637 | 1 | 43.32 |
| 2044 | NH2 | ARG | 80 | −0.347 | 2.747 | 27.462 | 1 | 44 |
| 2045 | C | ARG | 80 | 2.721 | −3.097 | 30.885 | 1 | 32.02 |
| 2046 | O | ARG | 80 | 2.316 | −3.616 | 29.845 | 1 | 30.38 |
| 2047 | N | GLN | 81 | 4.011 | −2.905 | 31.142 | 1 | 31.45 |
| 2048 | CA | GLN | 81 | 5.04 | −3.31 | 30.19 | 1 | 31.23 |
| 2049 | CB | GLN | 81 | 6.382 | −2.665 | 30.539 | 1 | 32.68 |
| 2050 | CG | GLN | 81 | 6.475 | −1.191 | 30.199 | 1 | 35.87 |
| 2051 | CD | GLN | 81 | 7.87 | −0.637 | 30.413 | 1 | 37.56 |
| 2052 | OE1 | GLN | 81 | 8.845 | −1.153 | 29.863 | 1 | 39.12 |
| 2053 | NE2 | GLN | 81 | 7.973 | 0.419 | 31.212 | 1 | 39.11 |
| 2054 | C | GLN | 81 | 5.207 | −4.824 | 30.127 | 1 | 29.81 |
| 2055 | O | GLN | 81 | 5.43 | −5.38 | 29.051 | 1 | 28.85 |
| 2056 | N | ARG | 82 | 5.116 | −5.489 | 31.276 | 1 | 28.89 |
| 2057 | CA | ARG | 82 | 5.252 | −6.94 | 31.311 | 1 | 28.73 |
| 2058 | CB | ARG | 82 | 5.196 | −7.471 | 32.747 | 1 | 30.44 |

TABLE 2-continued

| Atom | Atom Type | Residue | # | X | Y | Z | OCC | B |
|---|---|---|---|---|---|---|---|---|
| 2059 | CG | ARG | 82 | 6.36 | −7.065 | 33.628 | 1 | 33.18 |
| 2060 | CD | ARG | 82 | 6.618 | −8.125 | 34.693 | 1 | 34.97 |
| 2061 | NE | ARG | 82 | 5.426 | −8.443 | 35.474 | 1 | 36.75 |
| 2062 | CZ | ARG | 82 | 4.889 | −7.645 | 36.393 | 1 | 39.05 |
| 2063 | NH1 | ARG | 82 | 5.437 | −6.466 | 36.659 | 1 | 40.15 |
| 2064 | NH2 | ARG | 82 | 3.801 | −8.026 | 37.048 | 1 | 38.83 |
| 2065 | C | ARG | 82 | 4.126 | −7.57 | 30.507 | 1 | 27.43 |
| 2066 | O | ARG | 82 | 4.328 | −8.552 | 29.795 | 1 | 26.28 |
| 2067 | N | ALA | 83 | 2.934 | −6.996 | 30.633 | 1 | 26.63 |
| 2068 | CA | ALA | 83 | 1.771 | −7.498 | 29.919 | 1 | 25.66 |
| 2069 | CB | ALA | 83 | 0.518 | −6.753 | 30.37 | 1 | 25.22 |
| 2070 | C | ALA | 83 | 1.965 | −7.338 | 28.415 | 1 | 24.73 |
| 2071 | O | ALA | 83 | 1.749 | −8.277 | 27.654 | 1 | 24.74 |
| 2072 | N | LEU | 84 | 2.378 | −6.146 | 27.995 | 1 | 24.04 |
| 2073 | CA | LEU | 84 | 2.593 | −5.871 | 26.579 | 1 | 24.43 |
| 2074 | CB | LEU | 84 | 2.992 | −4.406 | 26.377 | 1 | 25.62 |
| 2075 | CG | LEU | 84 | 1.872 | −3.373 | 26.511 | 1 | 28.57 |
| 2076 | CD1 | LEU | 84 | 2.441 | −1.97 | 26.389 | 1 | 29.41 |
| 2077 | CD2 | LEU | 84 | 0.825 | −3.62 | 25.433 | 1 | 30.02 |
| 2078 | C | LEU | 84 | 3.663 | −6.771 | 25.975 | 1 | 23.25 |
| 2079 | O | LEU | 84 | 3.52 | −7.248 | 24.849 | 1 | 23.22 |
| 2080 | N | ARG | 85 | 4.732 | −7 | 26.728 | 1 | 22.08 |
| 2081 | CA | ARG | 85 | 5.833 | −7.83 | 26.255 | 1 | 22.17 |
| 2082 | CB | ARG | 85 | 7.148 | −7.348 | 26.872 | 1 | 22.13 |
| 2083 | CG | ARG | 85 | 7.487 | −5.909 | 26.529 | 1 | 24.31 |
| 2084 | CD | ARG | 85 | 8.826 | −5.478 | 27.103 | 1 | 25.95 |
| 2085 | NE | ARG | 85 | 9.113 | −4.087 | 26.766 | 1 | 28.95 |
| 2086 | CZ | ARG | 85 | 10.25 | −3.463 | 27.05 | 1 | 31.29 |
| 2087 | NH1 | ARG | 85 | 11.224 | −4.105 | 27.682 | 1 | 31.06 |
| 2088 | NH2 | ARG | 85 | 10.415 | −2.195 | 26.699 | 1 | 33.58 |
| 2089 | C | ARG | 85 | 5.645 | −9.31 | 26.552 | 1 | 21.65 |
| 2090 | O | ARG | 85 | 6.467 | −10.134 | 26.156 | 1 | 21.89 |
| 2091 | N | GLN | 86 | 4.56 | −9.644 | 27.245 | 1 | 22.57 |
| 2092 | CA | GLN | 86 | 4.282 | −11.028 | 27.603 | 1 | 23.04 |
| 2093 | CB | GLN | 86 | 4.001 | −11.853 | 26.348 | 1 | 24.78 |
| 2094 | CG | GLN | 86 | 3.222 | −13.127 | 26.61 | 1 | 28.92 |
| 2095 | CD | GLN | 86 | 2.991 | −13.93 | 25.348 | 1 | 30.65 |
| 2096 | OE1 | GLN | 86 | 2.629 | −13.381 | 24.304 | 1 | 30.96 |
| 2097 | NE2 | GLN | 86 | 3.19 | −15.239 | 25.437 | 1 | 31.18 |
| 2098 | C | GLN | 86 | 5.509 | −11.572 | 28.324 | 1 | 22.51 |
| 2099 | O | GLN | 86 | 6.028 | −12.634 | 27.988 | 1 | 22.37 |
| 2100 | N | MET | 87 | 5.971 | −10.812 | 29.311 | 1 | 22.6 |
| 2101 | CA | MET | 87 | 7.143 | −11.174 | 30.093 | 1 | 22.09 |
| 2102 | CB | MET | 87 | 7.913 | −9.911 | 30.477 | 1 | 23.83 |
| 2103 | CG | MET | 87 | 9.24 | −10.165 | 31.165 | 1 | 22.12 |
| 2104 | SD | MET | 87 | 9.977 | −8.61 | 31.703 | 1 | 25.29 |
| 2105 | CE | MET | 87 | 10.477 | −7.921 | 30.125 | 1 | 26.28 |
| 2106 | C | MET | 87 | 6.741 | −11.936 | 31.349 | 1 | 22.57 |
| 2107 | O | MET | 87 | 6.043 | −11.409 | 32.217 | 1 | 22.12 |
| 2108 | N | GLU | 88 | 7.186 | −13.182 | 31.433 | 1 | 21.53 |
| 2109 | CA | GLU | 88 | 6.877 | −14.032 | 32.571 | 1 | 22.35 |
| 2110 | CB | GLU | 88 | 5.809 | −15.049 | 32.174 | 1 | 25.71 |
| 2111 | CG | GLU | 88 | 4.579 | −14.394 | 31.561 | 1 | 30.93 |
| 2112 | CD | GLU | 88 | 3.648 | −15.387 | 30.902 | 1 | 34.28 |
| 2113 | OE1 | GLU | 88 | 4.118 | −16.162 | 30.042 | 1 | 37.45 |
| 2114 | OE2 | GLU | 88 | 2.445 | −15.387 | 31.236 | 1 | 36.77 |
| 2115 | C | GLU | 88 | 8.136 | −14.746 | 33.036 | 1 | 20.47 |
| 2116 | O | GLU | 88 | 9.036 | −15.029 | 32.245 | 1 | 19.75 |
| 2117 | N | PRO | 89 | 8.218 | −15.047 | 34.334 | 1 | 19.14 |
| 2118 | CD | PRO | 89 | 7.259 | −14.795 | 35.424 | 1 | 20.43 |
| 2119 | CA | PRO | 89 | 9.409 | −15.733 | 34.83 | 1 | 18.45 |
| 2120 | CB | PRO | 89 | 9.239 | −15.655 | 36.345 | 1 | 19.8 |
| 2121 | CG | PRO | 89 | 7.748 | −15.735 | 36.504 | 1 | 21.12 |
| 2122 | C | PRO | 89 | 9.506 | −17.17 | 34.331 | 1 | 17.97 |
| 2123 | O | PRO | 89 | 8.503 | −17.786 | 33.966 | 1 | 19.07 |
| 2124 | N | PHE | 90 | 10.729 | −17.684 | 34.291 | 1 | 16.62 |
| 2125 | CA | PHE | 90 | 10.971 | −19.058 | 33.893 | 1 | 15.64 |
| 2126 | CB | PHE | 90 | 11.013 | −19.23 | 32.362 | 1 | 15.3 |
| 2127 | CG | PHE | 90 | 11.985 | −18.324 | 31.646 | 1 | 14.86 |
| 2128 | CD1 | PHE | 90 | 11.533 | −17.181 | 30.992 | 1 | 15.1 |
| 2129 | CD2 | PHE | 90 | 13.334 | −18.648 | 31.569 | 1 | 14.31 |
| 2130 | CE1 | PHE | 90 | 12.41 | −16.376 | 30.264 | 1 | 15.29 |
| 2131 | CE2 | PHE | 90 | 14.221 | −17.849 | 30.844 | 1 | 14.49 |
| 2132 | CZ | PHE | 90 | 13.758 | −16.714 | 30.19 | 1 | 14.67 |
| 2133 | C | PHE | 90 | 12.259 | −19.535 | 34.537 | 1 | 16.38 |
| 2134 | O | PHE | 90 | 13.194 | −18.754 | 34.733 | 1 | 14.96 |
| 2135 | N | PRO | 91 | 12.314 | −20.824 | 34.905 | 1 | 15.95 |
| 2136 | CD | PRO | 91 | 11.249 | −21.828 | 34.719 | 1 | 17.13 |
| 2137 | CA | PRO | 91 | 13.483 | −21.43 | 35.543 | 1 | 15.99 |
| 2138 | CB | PRO | 91 | 12.955 | −22.783 | 36.004 | 1 | 17.86 |
| 2139 | CG | PRO | 91 | 11.997 | −23.13 | 34.913 | 1 | 18.57 |
| 2140 | C | PRO | 91 | 14.691 | −21.567 | 34.633 | 1 | 14.35 |
| 2141 | O | PRO | 91 | 14.584 | −21.509 | 33.408 | 1 | 16 |
| 2142 | N | LEU | 92 | 15.842 | −21.759 | 35.259 | 1 | 14.73 |
| 2143 | CA | LEU | 92 | 17.098 | −21.908 | 34.55 | 1 | 14.67 |
| 2144 | CB | LEU | 92 | 18.243 | −22.043 | 35.555 | 1 | 15.33 |
| 2145 | CG | LEU | 92 | 19.606 | −22.415 | 34.97 | 1 | 16.22 |
| 2146 | CD1 | LEU | 92 | 20.159 | −21.231 | 34.178 | 1 | 15.42 |
| 2147 | CD2 | LEU | 92 | 20.556 | −22.797 | 36.091 | 1 | 17.33 |
| 2148 | C | LEU | 92 | 17.131 | −23.104 | 33.609 | 1 | 16 |
| 2149 | O | LEU | 92 | 16.729 | −24.211 | 33.969 | 1 | 16.89 |
| 2150 | N | ARG | 93 | 17.606 | −22.861 | 32.394 | 1 | 15.76 |
| 2151 | CA | ARG | 93 | 17.768 | −23.907 | 31.4 | 1 | 16.7 |
| 2152 | CB | ARG | 93 | 16.715 | −23.833 | 30.294 | 1 | 18.82 |
| 2153 | CG | ARG | 93 | 15.443 | −24.605 | 30.552 | 1 | 20.17 |
| 2154 | CD | ARG | 93 | 14.417 | −23.742 | 31.222 | 1 | 24.82 |
| 2155 | NE | ARG | 93 | 13.065 | −24.21 | 30.936 | 1 | 27.07 |
| 2156 | CZ | ARG | 93 | 11.972 | −23.489 | 31.157 | 1 | 28.22 |
| 2157 | NH1 | ARG | 93 | 12.088 | −22.27 | 31.667 | 1 | 27.79 |
| 2158 | NH2 | ARG | 93 | 10.774 | −23.979 | 30.859 | 1 | 23.3 |
| 2159 | C | ARG | 93 | 19.12 | −23.709 | 30.752 | 1 | 16.79 |
| 2160 | O | ARG | 93 | 19.473 | −22.595 | 30.365 | 1 | 17.05 |
| 2161 | N | VAL | 94 | 19.882 | −24.788 | 30.658 | 1 | 15.04 |
| 2162 | CA | VAL | 94 | 21.172 | −24.746 | 29.996 | 1 | 15.34 |
| 2163 | CB | VAL | 94 | 22.312 | −25.203 | 30.926 | 1 | 14.45 |
| 2164 | CG1 | VAL | 94 | 23.619 | −25.272 | 30.149 | 1 | 17.25 |
| 2165 | CG2 | VAL | 94 | 22.45 | −24.228 | 32.089 | 1 | 15.54 |
| 2166 | C | VAL | 94 | 21.016 | −25.727 | 28.842 | 1 | 15.76 |
| 2167 | O | VAL | 94 | 20.668 | −26.891 | 29.058 | 1 | 16.88 |
| 2168 | N | PHE | 95 | 21.228 | −25.246 | 27.62 | 1 | 14.84 |
| 2169 | CA | PHE | 95 | 21.109 | −26.088 | 26.435 | 1 | 14.68 |
| 2170 | CB | PHE | 95 | 20.16 | −25.47 | 25.401 | 1 | 15.05 |
| 2171 | CG | PHE | 95 | 18.707 | −25.594 | 25.748 | 1 | 15.46 |
| 2172 | CD1 | PHE | 95 | 18.061 | −24.601 | 26.472 | 1 | 14.68 |
| 2173 | CD2 | PHE | 95 | 17.981 | −26.714 | 25.348 | 1 | 16.69 |
| 2174 | CE1 | PHE | 95 | 16.709 | −24.715 | 26.795 | 1 | 16.46 |
| 2175 | CE2 | PHE | 95 | 16.628 | −26.839 | 25.666 | 1 | 16.52 |
| 2176 | CZ | PHE | 95 | 15.992 | −25.835 | 26.391 | 1 | 16.67 |
| 2177 | C | PHE | 95 | 22.44 | −26.333 | 25.752 | 1 | 16.53 |
| 2178 | O | PHE | 95 | 23.258 | −25.423 | 25.601 | 1 | 16.8 |
| 2179 | N | VAL | 96 | 22.639 | −27.574 | 25.33 | 1 | 15.06 |
| 2180 | CA | VAL | 96 | 23.84 | −27.954 | 24.614 | 1 | 17.21 |
| 2181 | CB | VAL | 96 | 24.553 | −29.138 | 25.325 | 1 | 18.09 |
| 2182 | CG1 | VAL | 96 | 25.719 | −29.63 | 24.48 | 1 | 18.81 |
| 2183 | CG2 | VAL | 96 | 25.045 | −28.682 | 26.694 | 1 | 18.41 |
| 2184 | C | VAL | 96 | 23.371 | −28.416 | 23.231 | 1 | 16.94 |
| 2185 | O | VAL | 96 | 22.394 | −29.152 | 23.11 | 1 | 16.81 |
| 2186 | N | ASN | 97 | 24.057 | −27.944 | 22.194 | 1 | 15.82 |
| 2187 | CA | ASN | 97 | 23.718 | −28.262 | 20.81 | 1 | 16.43 |
| 2188 | CB | ASN | 97 | 24.116 | −29.707 | 20.488 | 1 | 17.69 |
| 2189 | CG | ASN | 97 | 25.577 | −29.979 | 20.768 | 1 | 20.04 |
| 2190 | OD1 | ASN | 97 | 26.409 | −29.071 | 20.717 | 1 | 17.53 |
| 2191 | ND2 | ASN | 97 | 25.906 | −31.237 | 21.051 | 1 | 19.54 |
| 2192 | C | ASN | 97 | 22.237 | −28.052 | 20.483 | 1 | 17.18 |
| 2193 | O | ASN | 97 | 21.599 | −28.908 | 19.869 | 1 | 16.43 |
| 2194 | N | PRO | 98 | 21.675 | −26.894 | 20.865 | 1 | 15.55 |
| 2195 | CD | PRO | 98 | 22.278 | −25.775 | 21.618 | 1 | 16.35 |
| 2196 | CA | PRO | 98 | 20.26 | −26.628 | 20.591 | 1 | 16.84 |
| 2197 | CB | PRO | 98 | 19.951 | −25.46 | 21.518 | 1 | 15.79 |
| 2198 | CG | PRO | 98 | 21.233 | −24.684 | 21.479 | 1 | 14.34 |
| 2199 | C | PRO | 98 | 19.904 | −26.308 | 19.143 | 1 | 16.96 |
| 2200 | O | PRO | 98 | 20.736 | −25.843 | 18.363 | 1 | 17.9 |
| 2201 | N | SER | 99 | 18.65 | −26.578 | 18.797 | 1 | 17.37 |
| 2202 | CA | SER | 99 | 18.129 | −26.291 | 17.471 | 1 | 18.19 |
| 2203 | CB | SER | 99 | 17.835 | −27.583 | 16.703 | 1 | 21.12 |
| 2204 | OG | SER | 99 | 16.82 | −28.334 | 17.342 | 1 | 25.81 |
| 2205 | C | SER | 99 | 16.844 | −25.507 | 17.703 | 1 | 18.27 |
| 2206 | O | SER | 99 | 16.172 | −25.687 | 18.726 | 1 | 18.33 |
| 2207 | N | LEU | 100 | 16.503 | −24.635 | 16.766 | 1 | 17.41 |
| 2208 | CA | LEU | 100 | 15.307 | −23.82 | 16.907 | 1 | 18.56 |
| 2209 | CB | LEU | 100 | 15.697 | −22.335 | 16.96 | 1 | 20.64 |
| 2210 | CG | LEU | 100 | 14.632 | −21.266 | 17.237 | 1 | 22.3 |

TABLE 2-continued

| Atom | Atom Type | Residue | # | X | Y | Z | OCC | B |
|---|---|---|---|---|---|---|---|---|
| 2211 | CD1 | LEU | 100 | 15.325 | −19.939 | 17.488 | 1 | 27.33 |
| 2212 | CD2 | LEU | 100 | 13.667 | −21.135 | 16.071 | 1 | 25.58 |
| 2213 | C | LEU | 100 | 14.305 | −24.049 | 15.788 | 1 | 18.83 |
| 2214 | O | LEU | 100 | 14.675 | −24.213 | 14.624 | 1 | 20.64 |
| 2215 | N | ARG | 101 | 13.03 | −24.065 | 16.16 | 1 | 18.22 |
| 2216 | CA | ARG | 101 | 11.942 | −24.235 | 15.212 | 1 | 19.2 |
| 2217 | CB | ARG | 101 | 11.298 | −25.615 | 15.374 | 1 | 21.01 |
| 2218 | CG | ARG | 101 | 10.085 | −25.841 | 14.485 | 1 | 27.53 |
| 2219 | CD | ARG | 101 | 9.564 | −27.265 | 14.621 | 1 | 30.58 |
| 2220 | NE | ARG | 101 | 10.582 | −28.25 | 14.264 | 1 | 35.89 |
| 2221 | CZ | ARG | 101 | 11.095 | −28.389 | 13.045 | 1 | 37.46 |
| 2222 | NH1 | ARG | 101 | 10.685 | −27.607 | 12.054 | 1 | 39.02 |
| 2223 | NH2 | ARG | 101 | 12.023 | −29.31 | 12.814 | 1 | 38.26 |
| 2224 | C | ARG | 101 | 10.919 | −23.142 | 15.5 | 1 | 19.02 |
| 2225 | O | ARG | 101 | 10.524 | −22.94 | 16.649 | 1 | 18.95 |
| 2226 | N | VAL | 102 | 10.506 | −22.426 | 14.461 | 1 | 17.33 |
| 2227 | CA | VAL | 102 | 9.529 | −21.354 | 14.615 | 1 | 18.86 |
| 2228 | CB | VAL | 102 | 9.66 | −20.316 | 13.478 | 1 | 19.06 |
| 2229 | CG1 | VAL | 102 | 8.661 | −19.187 | 13.681 | 1 | 19.63 |
| 2230 | CG2 | VAL | 102 | 11.08 | −19.769 | 13.441 | 1 | 22.05 |
| 2231 | C | VAL | 102 | 8.12 | −21.94 | 14.594 | 1 | 19.04 |
| 2232 | O | VAL | 102 | 7.748 | −22.64 | 13.651 | 1 | 19.44 |
| 2233 | N | LEU | 103 | 7.346 | −21.656 | 15.637 | 1 | 18.41 |
| 2234 | CA | LEU | 103 | 5.98 | −22.162 | 15.736 | 1 | 19.14 |
| 2235 | CB | LEU | 103 | 5.722 | −22.68 | 17.156 | 1 | 19.74 |
| 2236 | CG | LEU | 103 | 6.671 | −23.789 | 17.628 | 1 | 21.32 |
| 2237 | CD1 | LEU | 103 | 6.308 | −24.194 | 19.045 | 1 | 22.57 |
| 2238 | CD2 | LEU | 103 | 6.583 | −24.992 | 16.697 | 1 | 23.35 |
| 2239 | C | LEU | 103 | 4.943 | −21.103 | 15.359 | 1 | 19.6 |
| 2240 | O | LEU | 103 | 3.865 | −21.428 | 14.863 | 1 | 20.21 |
| 2241 | N | ASP | 104 | 5.269 | −19.836 | 15.596 | 1 | 18.74 |
| 2242 | CA | ASP | 104 | 4.382 | −18.725 | 15.26 | 1 | 19.33 |
| 2243 | CB | ASP | 104 | 3.693 | −18.176 | 16.511 | 1 | 20.08 |
| 2244 | CG | ASP | 104 | 2.571 | −17.212 | 16.183 | 1 | 19.96 |
| 2245 | OD1 | ASP | 104 | 2.644 | −16.526 | 15.14 | 1 | 21.32 |
| 2246 | OD2 | ASP | 104 | 1.617 | −17.122 | 16.98 | 1 | 19.62 |
| 2247 | C | ASP | 104 | 5.281 | −17.649 | 14.662 | 1 | 19.98 |
| 2248 | O | ASP | 104 | 6.036 | −16.997 | 15.383 | 1 | 18.73 |
| 2249 | N | SER | 105 | 5.192 | −17.466 | 13.349 | 1 | 19.24 |
| 2250 | CA | SER | 105 | 6.034 | −16.498 | 12.655 | 1 | 19.28 |
| 2251 | CB | SER | 105 | 6.181 | −16.906 | 11.186 | 1 | 20.75 |
| 2252 | OG | SER | 105 | 4.919 | −16.976 | 10.549 | 1 | 24.56 |
| 2253 | C | SER | 105 | 5.602 | −15.037 | 12.743 | 1 | 18.6 |
| 2254 | O | SER | 105 | 6.242 | −14.171 | 12.144 | 1 | 18.69 |
| 2255 | N | ARG | 106 | 4.528 | −14.751 | 13.474 | 1 | 17.59 |
| 2256 | CA | ARG | 106 | 4.084 | −13.368 | 13.614 | 1 | 18.51 |
| 2257 | CB | ARG | 106 | 2.842 | −13.285 | 14.507 | 1 | 20.92 |
| 2258 | CG | ARG | 106 | 2.367 | −11.863 | 14.772 | 1 | 25.21 |
| 2259 | CD | ARG | 106 | 0.947 | −11.841 | 15.325 | 1 | 28.38 |
| 2260 | NE | ARG | 106 | 0.832 | −12.495 | 16.627 | 1 | 31.15 |
| 2261 | CZ | ARG | 106 | 1.176 | −11.938 | 17.784 | 1 | 33.1 |
| 2262 | NH1 | ARG | 106 | 1.664 | −10.705 | 17.815 | 1 | 33.71 |
| 2263 | NH2 | ARG | 106 | 1.018 | −12.613 | 18.915 | 1 | 34.07 |
| 2264 | C | ARG | 106 | 5.232 | −12.58 | 14.242 | 1 | 17.91 |
| 2265 | O | ARG | 106 | 5.856 | −13.049 | 15.187 | 1 | 18.57 |
| 2266 | N | LEU | 107 | 5.51 | −11.393 | 13.711 | 1 | 17.99 |
| 2267 | CA | LEU | 107 | 6.603 | −10.571 | 14.223 | 1 | 17.71 |
| 2268 | CB | LEU | 107 | 7.291 | −9.838 | 13.069 | 1 | 18.5 |
| 2269 | CG | LEU | 107 | 7.995 | −10.721 | 12.039 | 1 | 19.17 |
| 2270 | CD1 | LEU | 107 | 8.5 | −9.851 | 10.898 | 1 | 21.99 |
| 2271 | CD2 | LEU | 107 | 9.146 | −11.476 | 12.694 | 1 | 21.14 |
| 2272 | C | LEU | 107 | 6.202 | −9.561 | 15.293 | 1 | 18.57 |
| 2273 | O | LEU | 107 | 5.223 | −8.822 | 15.149 | 1 | 17.35 |
| 2274 | N | VAL | 108 | 6.985 | −9.534 | 16.367 | 1 | 16.46 |
| 2275 | CA | VAL | 108 | 6.756 | −8.63 | 17.483 | 1 | 17.1 |
| 2276 | CB | VAL | 108 | 6.491 | −9.414 | 18.784 | 1 | 19.35 |
| 2277 | CG1 | VAL | 108 | 6.321 | −8.454 | 19.944 | 1 | 21.58 |
| 2278 | CG2 | VAL | 108 | 5.244 | −10.274 | 18.625 | 1 | 21.97 |
| 2279 | C | VAL | 108 | 8.02 | −7.797 | 17.644 | 1 | 16.29 |
| 2280 | O | VAL | 108 | 9.118 | −8.339 | 17.662 | 1 | 16.09 |
| 2281 | N | THR | 109 | 7.864 | −6.484 | 17.761 | 1 | 16.35 |
| 2282 | CA | THR | 109 | 9.018 | −5.599 | 17.89 | 1 | 16.68 |
| 2283 | CB | THR | 109 | 9.032 | −4.563 | 16.75 | 1 | 16.68 |
| 2284 | OG1 | THR | 109 | 9.083 | −5.242 | 15.491 | 1 | 18.58 |
| 2285 | CG2 | THR | 109 | 10.242 | −3.637 | 16.875 | 1 | 18.95 |
| 2286 | C | THR | 109 | 9.072 | −4.853 | 19.218 | 1 | 16.16 |
| 2287 | O | THR | 109 | 8.111 | −4.191 | 19.609 | 1 | 17.16 |
| 2288 | N | PHE | 110 | 10.215 | −4.963 | 19.894 | 1 | 16.78 |
| 2289 | CA | PHE | 110 | 10.462 | −4.298 | 21.172 | 1 | 14.81 |
| 2290 | CB | PHE | 110 | 10.102 | −5.203 | 22.352 | 1 | 16.56 |
| 2291 | CG | PHE | 110 | 8.635 | −5.303 | 22.625 | 1 | 16.93 |
| 2292 | CD1 | PHE | 110 | 7.921 | −4.193 | 23.061 | 1 | 18.65 |
| 2293 | CD2 | PHE | 110 | 7.968 | −6.511 | 22.464 | 1 | 20.3 |
| 2294 | CE1 | PHE | 110 | 6.559 | −4.284 | 23.336 | 1 | 21.6 |
| 2295 | CE2 | PHE | 110 | 6.604 | −6.613 | 22.737 | 1 | 20.04 |
| 2296 | CZ | PHE | 110 | 5.901 | −5.497 | 23.174 | 1 | 20.54 |
| 2297 | C | PHE | 110 | 11.948 | −3.997 | 21.269 | 1 | 15.28 |
| 2298 | O | PHE | 110 | 12.753 | −4.616 | 20.573 | 1 | 14.52 |
| 2299 | N | PRO | 111 | 12.33 | −3.038 | 22.131 | 1 | 15.63 |
| 2300 | CD | PRO | 111 | 11.472 | −2.034 | 22.784 | 1 | 16.47 |
| 2301 | CA | PRO | 111 | 13.742 | −2.689 | 22.302 | 1 | 16.32 |
| 2302 | CB | PRO | 111 | 13.692 | −1.487 | 23.239 | 1 | 16.46 |
| 2303 | CG | PRO | 111 | 12.401 | −0.842 | 22.878 | 1 | 18.99 |
| 2304 | C | PRO | 111 | 14.466 | −3.874 | 22.925 | 1 | 16.66 |
| 2305 | O | PRO | 111 | 13.938 | −4.547 | 23.816 | 1 | 17.46 |
| 2306 | N | GLU | 112 | 15.686 | −4.104 | 22.462 | 1 | 16.2 |
| 2307 | CA | GLU | 112 | 16.491 | −5.219 | 22.625 | 1 | 17.42 |
| 2308 | CB | GLU | 112 | 16.49 | −6.273 | 21.815 | 1 | 19.62 |
| 2309 | CG | GLU | 112 | 16.655 | −7.68 | 22.263 | 1 | 22.58 |
| 2310 | CD | GLU | 112 | 16.632 | −8.622 | 21.086 | 1 | 17.29 |
| 2311 | OE1 | GLU | 112 | 17.723 | −9.024 | 20.637 | 1 | 16.98 |
| 2312 | OE2 | GLU | 112 | 15.524 | −8.939 | 20.598 | 1 | 16.3 |
| 2313 | C | GLU | 112 | 17.915 | −4.728 | 23.151 | 1 | 15.9 |
| 2314 | O | GLU | 112 | 18.362 | −3.79 | 22.495 | 1 | 15.54 |
| 2315 | N | GLY | 113 | 18.616 | −5.367 | 24.082 | 1 | 14.72 |
| 2316 | CA | GLY | 113 | 19.992 | −4.998 | 24.368 | 1 | 15.46 |
| 2317 | C | GLY | 113 | 20.849 | −6.251 | 24.438 | 1 | 15.4 |
| 2318 | O | GLY | 113 | 20.322 | −7.352 | 24.598 | 1 | 19.21 |
| 2319 | N | CYS | 114 | 22.165 | −6.098 | 24.327 | 1 | 11.72 |
| 2320 | CA | CYS | 114 | 23.066 | −7.249 | 24.382 | 1 | 10.9 |
| 2321 | CB | CYS | 114 | 23.599 | −7.565 | 22.98 | 1 | 11.18 |
| 2322 | SG | CYS | 114 | 24.696 | −9.008 | 22.893 | 1 | 12.18 |
| 2323 | C | CYS | 114 | 24.239 | −6.963 | 25.31 | 1 | 10.42 |
| 2324 | O | CYS | 114 | 24.801 | −5.872 | 25.28 | 1 | 12.75 |
| 2325 | N | GLU | 115 | 24.614 | −7.939 | 26.131 | 1 | 10.47 |
| 2326 | CA | GLU | 115 | 25.743 | −7.758 | 27.044 | 1 | 10.44 |
| 2327 | CB | GLU | 115 | 25.871 | −8.969 | 27.973 | 1 | 12.57 |
| 2328 | CG | GLU | 115 | 24.821 | −9.04 | 29.075 | 1 | 16.92 |
| 2329 | CD | GLU | 115 | 25.018 | −7.972 | 30.133 | 1 | 19.95 |
| 2330 | OE1 | GLU | 115 | 26.169 | −7.793 | 30.588 | 1 | 21.32 |
| 2331 | OE2 | GLU | 115 | 24.025 | −7.318 | 30.517 | 1 | 23.75 |
| 2332 | C | GLU | 115 | 27.047 | −7.569 | 26.263 | 1 | 11.87 |
| 2333 | O | GLU | 115 | 28.015 | −7.018 | 26.789 | 1 | 10.56 |
| 2334 | N | SER | 116 | 27.064 | −8.023 | 25.01 | 1 | 10.55 |
| 2335 | CA | SER | 116 | 28.246 | −7.901 | 24.156 | 1 | 9.9 |
| 2336 | CB | SER | 116 | 28.343 | −9.094 | 23.205 | 1 | 10.07 |
| 2337 | OG | SER | 116 | 28.667 | −10.27 | 23.927 | 1 | 12.32 |
| 2338 | C | SER | 116 | 28.3 | −6.598 | 23.361 | 1 | 10.51 |
| 2339 | O | SER | 116 | 29.226 | −6.379 | 22.582 | 1 | 10.42 |
| 2340 | N | VAL | 117 | 27.295 | −5.75 | 23.546 | 1 | 11.08 |
| 2341 | CA | VAL | 117 | 27.257 | −4.43 | 22.91 | 1 | 11.87 |
| 2342 | CB | VAL | 117 | 26.268 | −4.367 | 21.72 | 1 | 11.19 |
| 2343 | CG1 | VAL | 117 | 26.424 | −3.032 | 20.991 | 1 | 13.5 |
| 2344 | CG2 | VAL | 117 | 26.527 | −5.515 | 20.756 | 1 | 11.59 |
| 2345 | C | VAL | 117 | 26.763 | −3.538 | 24.05 | 1 | 11.81 |
| 2346 | O | VAL | 117 | 25.716 | −2.891 | 23.966 | 1 | 12.62 |
| 2347 | N | ALA | 118 | 27.543 | −3.543 | 25.128 | 1 | 13.38 |
| 2348 | CA | ALA | 118 | 27.241 | −2.816 | 26.356 | 1 | 13.37 |
| 2349 | CB | ALA | 118 | 28.452 | −2.874 | 27.289 | 1 | 16.83 |
| 2350 | C | ALA | 118 | 26.776 | −1.372 | 26.223 | 1 | 13.73 |
| 2351 | O | ALA | 118 | 27.401 | −0.567 | 25.541 | 1 | 15.13 |
| 2352 | N | GLY | 119 | 25.657 | −1.063 | 26.875 | 1 | 14.31 |
| 2353 | CA | GLY | 119 | 25.144 | 0.297 | 26.877 | 1 | 14.96 |
| 2354 | C | GLY | 119 | 24.202 | 0.764 | 25.786 | 1 | 13.97 |
| 2355 | O | GLY | 119 | 23.856 | 1.944 | 25.747 | 1 | 13.26 |
| 2356 | N | PHE | 120 | 23.765 | −0.135 | 24.913 | 1 | 12.09 |
| 2357 | CA | PHE | 120 | 22.864 | 0.259 | 23.838 | 1 | 12.52 |
| 2358 | CB | PHE | 120 | 23.583 | 0.173 | 22.491 | 1 | 12.67 |
| 2359 | CG | PHE | 120 | 24.738 | 1.115 | 22.364 | 1 | 13.16 |
| 2360 | CD1 | PHE | 120 | 24.541 | 2.424 | 21.935 | 1 | 12.25 |
| 2361 | CD2 | PHE | 120 | 26.02 | 0.701 | 22.691 | 1 | 14.03 |
| 2362 | CE1 | PHE | 120 | 25.608 | 3.309 | 21.832 | 1 | 14.38 |

TABLE 2-continued

| Atom | Atom Type | Residue | # | X | Y | Z | OCC | B |
|---|---|---|---|---|---|---|---|---|
| 2363 | CE2 | PHE | 120 | 27.098 | 1.581 | 22.594 | 1 | 16.73 |
| 2364 | CZ | PHE | 120 | 26.888 | 2.886 | 22.163 | 1 | 16.78 |
| 2365 | C | PHE | 120 | 21.604 | -0.587 | 23.772 | 1 | 13 |
| 2366 | O | PHE | 120 | 21.554 | -1.7 | 24.301 | 1 | 14.73 |
| 2367 | N | LEU | 121 | 20.587 | -0.031 | 23.123 | 1 | 12.66 |
| 2368 | CA | LEU | 121 | 19.311 | -0.706 | 22.916 | 1 | 13.86 |
| 2369 | CB | LEU | 121 | 18.253 | -0.213 | 23.903 | 1 | 15.05 |
| 2370 | CG | LEU | 121 | 18.38 | -0.558 | 25.386 | 1 | 17.41 |
| 2371 | CD1 | LEU | 121 | 17.263 | 0.138 | 26.15 | 1 | 18.88 |
| 2372 | CD2 | LEU | 121 | 18.308 | -2.065 | 25.583 | 1 | 19.13 |
| 2373 | C | LEU | 121 | 18.836 | -0.381 | 21.507 | 1 | 13.68 |
| 2374 | O | LEU | 121 | 19.226 | 0.637 | 20.933 | 1 | 13.83 |
| 2375 | N | ALA | 122 | 17.996 | -1.25 | 20.953 | 1 | 13.06 |
| 2376 | CA | ALA | 122 | 17.431 | -1.031 | 19.627 | 1 | 12.35 |
| 2377 | CB | ALA | 122 | 18.465 | -1.301 | 18.542 | 1 | 13.41 |
| 2378 | C | ALA | 122 | 16.25 | -1.965 | 19.446 | 1 | 13.77 |
| 2379 | O | ALA | 122 | 16.242 | -3.071 | 19.989 | 1 | 14.81 |
| 2380 | N | CYS | 123 | 15.254 | -1.521 | 18.688 | 1 | 14.13 |
| 2381 | CA | CYS | 123 | 14.089 | -2.357 | 18.433 | 1 | 15.42 |
| 2382 | CB | CYS | 123 | 12.956 | -1.53 | 17.838 | 1 | 15.42 |
| 2383 | SG | CYS | 123 | 12.193 | -0.45 | 19.041 | 1 | 21.55 |
| 2384 | C | CYS | 123 | 14.462 | -3.476 | 17.477 | 1 | 14.83 |
| 2385 | O | CYS | 123 | 15.16 | -3.257 | 16.485 | 1 | 14.08 |
| 2386 | N | VAL | 124 | 14.002 | -4.683 | 17.781 | 1 | 13.82 |
| 2387 | CA | VAL | 124 | 14.297 | -5.83 | 16.939 | 1 | 13.88 |
| 2388 | CB | VAL | 124 | 15.396 | -6.727 | 17.556 | 1 | 14 |
| 2389 | CG1 | VAL | 124 | 15.67 | -7.916 | 16.642 | 1 | 14.23 |
| 2390 | CG2 | VAL | 124 | 16.675 | -5.925 | 17.774 | 1 | 13.5 |
| 2391 | C | VAL | 124 | 13.054 | -6.69 | 16.765 | 1 | 14.5 |
| 2392 | O | VAL | 124 | 12.397 | -7.043 | 17.741 | 1 | 14.33 |
| 2393 | N | PRO | 125 | 12.696 | -7.009 | 15.515 | 1 | 14.36 |
| 2394 | CD | PRO | 125 | 13.166 | -6.456 | 14.232 | 1 | 15.72 |
| 2395 | CA | PRO | 125 | 11.512 | -7.849 | 15.327 | 1 | 14.77 |
| 2396 | CB | PRO | 125 | 11.16 | -7.624 | 13.86 | 1 | 16.34 |
| 2397 | CG | PRO | 125 | 12.496 | -7.363 | 13.228 | 1 | 18.92 |
| 2398 | C | PRO | 125 | 11.887 | -9.301 | 15.63 | 1 | 14.4 |
| 2399 | O | PRO | 125 | 12.944 | -9.778 | 15.215 | 1 | 14.5 |
| 2400 | N | ARG | 126 | 11.025 | -9.991 | 16.367 | 1 | 13.87 |
| 2401 | CA | ARG | 126 | 11.269 | -11.383 | 16.728 | 1 | 13.3 |
| 2402 | CB | ARG | 126 | 11.658 | -11.501 | 18.203 | 1 | 13.24 |
| 2403 | CG | ARG | 126 | 12.959 | -10.82 | 18.586 | 1 | 12.85 |
| 2404 | CD | ARG | 126 | 14.154 | -11.534 | 17.979 | 1 | 13.44 |
| 2405 | NE | ARG | 126 | 15.41 | -11.014 | 18.521 | 1 | 12.75 |
| 2406 | CZ | ARG | 126 | 16.615 | -11.421 | 18.137 | 1 | 12.11 |
| 2407 | NH1 | ARG | 126 | 16.738 | -12.358 | 17.207 | 1 | 12.74 |
| 2408 | NH2 | ARG | 126 | 17.7 | -10.889 | 18.686 | 1 | 13.66 |
| 2409 | C | ARG | 126 | 9.999 | -12.182 | 16.514 | 1 | 13.58 |
| 2410 | O | ARG | 126 | 8.903 | -11.626 | 16.527 | 1 | 14.28 |
| 2411 | N | PHE | 127 | 10.153 | -13.488 | 16.337 | 1 | 14.31 |
| 2412 | CA | PHE | 127 | 8.997 | -14.357 | 16.151 | 1 | 14.08 |
| 2413 | CB | PHE | 127 | 9.448 | -15.74 | 15.689 | 1 | 15.62 |
| 2414 | CG | PHE | 127 | 10.109 | -15.745 | 14.341 | 1 | 17.22 |
| 2415 | CD1 | PHE | 127 | 11.39 | -16.262 | 14.185 | 1 | 17.04 |
| 2416 | CD2 | PHE | 127 | 9.44 | -15.256 | 13.221 | 1 | 17.5 |
| 2417 | CE1 | PHE | 127 | 11.999 | -16.3 | 12.93 | 1 | 19.38 |
| 2418 | CE2 | PHE | 127 | 10.038 | -15.287 | 11.961 | 1 | 19.08 |
| 2419 | CZ | PHE | 127 | 11.321 | -15.811 | 11.817 | 1 | 19.36 |
| 2420 | C | PHE | 127 | 8.236 | -14.47 | 17.47 | 1 | 15.35 |
| 2421 | O | PHE | 127 | 8.833 | -14.477 | 18.543 | 1 | 15.65 |
| 2422 | N | GLN | 128 | 6.914 | -14.56 | 17.375 | 1 | 15.64 |
| 2423 | CA | GLN | 128 | 6.044 | -14.664 | 18.543 | 1 | 16.14 |
| 2424 | CB | GLN | 128 | 4.585 | -14.522 | 18.088 | 1 | 15.8 |
| 2425 | CG | GLN | 128 | 3.522 | -14.39 | 19.102 | 1 | 18.56 |
| 2426 | CD | GLN | 128 | 3.595 | -14.173 | 20.411 | 1 | 19.77 |
| 2427 | OE1 | GLN | 128 | 4.139 | -13.07 | 20.479 | 1 | 21.2 |
| 2428 | NE2 | GLN | 128 | 3.024 | -14.754 | 21.462 | 1 | 19.18 |
| 2429 | C | GLN | 128 | 6.216 | -15.948 | 19.362 | 1 | 15.74 |
| 2430 | O | GLN | 128 | 6.12 | -15.917 | 20.588 | 1 | 16.58 |
| 2431 | N | ALA | 129 | 6.465 | -17.072 | 18.698 | 1 | 14.71 |
| 2432 | CA | ALA | 129 | 6.627 | -18.339 | 19.411 | 1 | 14.55 |
| 2433 | CB | ALA | 129 | 5.269 | -19.03 | 19.57 | 1 | 14.57 |
| 2434 | C | ALA | 129 | 7.609 | -19.275 | 18.729 | 1 | 14.77 |
| 2435 | O | ALA | 129 | 7.609 | -19.421 | 17.504 | 1 | 15.25 |
| 2436 | N | VAL | 130 | 8.446 | -19.918 | 19.534 | 1 | 14.13 |
| 2437 | CA | VAL | 130 | 9.449 | -20.83 | 19.019 | 1 | 14.56 |
| 2438 | CB | VAL | 130 | 10.836 | -20.148 | 18.917 | 1 | 14.68 |
| 2439 | CG1 | VAL | 130 | 10.758 | -18.938 | 17.999 | 1 | 14.78 |
| 2440 | CG2 | VAL | 130 | 11.318 | -19.722 | 20.31 | 1 | 14.45 |
| 2441 | C | VAL | 130 | 9.603 | -22.04 | 19.92 | 1 | 14 |
| 2442 | O | VAL | 130 | 9.089 | -22.074 | 21.04 | 1 | 15.78 |
| 2443 | N | GLN | 131 | 10.326 | -23.028 | 19.415 | 1 | 15.13 |
| 2444 | CA | GLN | 131 | 10.602 | -24.25 | 20.148 | 1 | 16.59 |
| 2445 | CB | GLN | 131 | 9.908 | -25.436 | 19.468 | 1 | 18.48 |
| 2446 | CG | GLN | 131 | 10.348 | -26.795 | 19.982 | 1 | 21.9 |
| 2447 | CD | GLN | 131 | 9.752 | -27.934 | 19.182 | 1 | 21.02 |
| 2448 | OE1 | GLN | 131 | 8.562 | -28.235 | 19.298 | 1 | 21.64 |
| 2449 | NE2 | GLN | 131 | 10.575 | -28.568 | 18.356 | 1 | 22.56 |
| 2450 | C | GLN | 131 | 12.108 | -24.474 | 20.147 | 1 | 16.61 |
| 2451 | O | GLN | 131 | 12.72 | -24.554 | 19.082 | 1 | 17.54 |
| 2452 | N | ILE | 132 | 12.715 | -24.546 | 21.327 | 1 | 15.08 |
| 2453 | CA | ILE | 132 | 14.147 | -24.81 | 21.388 | 1 | 15.17 |
| 2454 | CB | ILE | 132 | 14.906 | -23.8 | 22.299 | 1 | 14.16 |
| 2455 | CG2 | ILE | 132 | 14.282 | -23.755 | 23.686 | 1 | 14.44 |
| 2456 | CG1 | ILE | 132 | 16.388 | -24.188 | 22.363 | 1 | 13.77 |
| 2457 | CD1 | ILE | 132 | 17.292 | -23.126 | 22.984 | 1 | 14.46 |
| 2458 | C | ILE | 132 | 14.343 | -26.231 | 21.897 | 1 | 16.94 |
| 2459 | O | ILE | 132 | 13.849 | -26.603 | 22.966 | 1 | 18.09 |
| 2460 | N | SER | 133 | 15.048 | -27.03 | 21.104 | 1 | 16.52 |
| 2461 | CA | SER | 133 | 15.315 | -28.419 | 21.447 | 1 | 18.39 |
| 2462 | CB | SER | 133 | 14.778 | -29.35 | 20.357 | 1 | 17.34 |
| 2463 | OG | SER | 133 | 13.411 | -29.105 | 20.093 | 1 | 19.72 |
| 2464 | C | SER | 133 | 16.813 | -28.626 | 21.581 | 1 | 19.62 |
| 2465 | O | SER | 133 | 17.588 | -28.198 | 20.727 | 1 | 20.72 |
| 2466 | N | GLY | 134 | 17.219 | -29.293 | 22.651 | 1 | 19.88 |
| 2467 | CA | GLY | 134 | 18.629 | -29.538 | 22.855 | 1 | 21.58 |
| 2468 | C | GLY | 134 | 18.848 | -30.522 | 23.976 | 1 | 22.85 |
| 2469 | O | GLY | 134 | 17.912 | -31.174 | 24.436 | 1 | 24.03 |
| 2470 | N | LEU | 135 | 20.09 | -30.629 | 24.421 | 1 | 21.73 |
| 2471 | CA | LEU | 135 | 20.425 | -31.541 | 25.499 | 1 | 22.52 |
| 2472 | CB | LEU | 135 | 21.616 | -32.415 | 25.097 | 1 | 23.99 |
| 2473 | CG | LEU | 135 | 21.54 | -33.16 | 23.761 | 1 | 24.52 |
| 2474 | CD1 | LEU | 135 | 22.853 | -33.882 | 23.507 | 1 | 26.87 |
| 2475 | CD2 | LEU | 135 | 20.381 | -34.147 | 23.785 | 1 | 26.02 |
| 2476 | C | LEU | 135 | 20.802 | -30.724 | 26.722 | 1 | 23.28 |
| 2477 | O | LEU | 135 | 21.357 | -29.634 | 26.589 | 1 | 20.24 |
| 2478 | N | ASP | 136 | 20.476 | -31.219 | 27.911 | 1 | 22.2 |
| 2479 | CA | ASP | 136 | 20.886 | -30.502 | 29.104 | 1 | 25.13 |
| 2480 | CB | ASP | 136 | 20.032 | -30.875 | 30.327 | 1 | 26.43 |
| 2481 | CG | ASP | 136 | 20.003 | -32.365 | 30.606 | 1 | 28.68 |
| 2482 | OD1 | ASP | 136 | 21.011 | -33.055 | 30.348 | 1 | 27.81 |
| 2483 | OD2 | ASP | 136 | 18.963 | -32.84 | 31.108 | 1 | 31.93 |
| 2484 | C | ASP | 136 | 22.334 | -30.945 | 29.279 | 1 | 26.65 |
| 2485 | O | ASP | 136 | 22.802 | -31.82 | 28.552 | 1 | 26.3 |
| 2486 | N | PRO | 137 | 23.07 | -30.341 | 30.22 | 1 | 28.82 |
| 2487 | CD | PRO | 137 | 22.698 | -29.232 | 31.116 | 1 | 29.64 |
| 2488 | CA | PRO | 137 | 24.469 | -30.729 | 30.424 | 1 | 30.46 |
| 2489 | CB | PRO | 137 | 24.846 | -29.972 | 31.692 | 1 | 30.71 |
| 2490 | CG | PRO | 137 | 24.05 | -28.707 | 31.553 | 1 | 30.24 |
| 2491 | C | PRO | 137 | 24.717 | -32.235 | 30.544 | 1 | 31.65 |
| 2492 | O | PRO | 137 | 25.804 | -32.715 | 30.223 | 1 | 31.12 |
| 2493 | N | ASN | 138 | 23.707 | -32.976 | 30.991 | 1 | 33.15 |
| 2494 | CA | ASN | 138 | 23.837 | -34.423 | 31.163 | 1 | 34.34 |
| 2495 | CB | ASN | 138 | 22.932 | -34.9 | 32.299 | 1 | 36.1 |
| 2496 | CG | ASN | 138 | 23.339 | -34.331 | 33.639 | 1 | 38.39 |
| 2497 | OD1 | ASN | 138 | 24.496 | -34.443 | 34.046 | 1 | 40.92 |
| 2498 | ND2 | ASN | 138 | 22.39 | -33.718 | 34.338 | 1 | 39.95 |
| 2499 | C | ASN | 138 | 23.546 | -35.243 | 29.909 | 1 | 33.59 |
| 2500 | O | ASN | 138 | 23.78 | -36.455 | 29.884 | 1 | 34.21 |
| 2501 | N | GLY | 139 | 23.034 | -34.592 | 28.873 | 1 | 31.96 |
| 2502 | CA | GLY | 139 | 22.74 | -35.302 | 27.643 | 1 | 29.96 |
| 2503 | C | GLY | 139 | 21.285 | -35.688 | 27.466 | 1 | 28.8 |
| 2504 | O | GLY | 139 | 20.936 | -36.345 | 26.486 | 1 | 28.92 |
| 2505 | N | GLU | 140 | 20.429 | -35.295 | 28.405 | 1 | 27.1 |
| 2506 | CA | GLU | 140 | 19.013 | -35.617 | 28.291 | 1 | 26.11 |
| 2507 | CB | GLU | 140 | 18.318 | -35.528 | 29.651 | 1 | 28.43 |
| 2508 | CG | GLU | 140 | 16.828 | -35.854 | 29.584 | 1 | 32.82 |
| 2509 | CD | GLU | 140 | 16.132 | -35.751 | 30.929 | 1 | 35.37 |
| 2510 | OE1 | GLU | 140 | 16.118 | -34.646 | 31.512 | 1 | 38.65 |
| 2511 | OE2 | GLU | 140 | 15.595 | -36.776 | 31.401 | 1 | 37.27 |
| 2512 | C | GLU | 140 | 18.349 | -34.648 | 27.321 | 1 | 24.18 |
| 2513 | O | GLU | 140 | 18.666 | -33.458 | 27.309 | 1 | 23.34 |
| 2514 | N | GLN | 141 | 17.43 | -35.164 | 26.512 | 1 | 23.53 |

TABLE 2-continued

| Atom | Atom Type | Residue | # | X | Y | Z | OCC | B |
|---|---|---|---|---|---|---|---|---|
| 2515 | CA | GLN | 141 | 16.716 | −34.351 | 25.531 | 1 | 23.17 |
| 2516 | CB | GLN | 141 | 16.028 | −35.241 | 24.496 | 1 | 25.71 |
| 2517 | CG | GLN | 141 | 16.969 | −36.006 | 23.596 | 1 | 31.29 |
| 2518 | CD | GLN | 141 | 16.227 | −36.894 | 22.617 | 1 | 34.95 |
| 2519 | OE1 | GLN | 141 | 15.393 | −36.423 | 21.841 | 1 | 35.53 |
| 2520 | NE2 | GLN | 141 | 16.526 | −38.189 | 22.648 | 1 | 36.51 |
| 2521 | C | GLN | 141 | 15.668 | −33.47 | 26.188 | 1 | 21.61 |
| 2522 | O | GLN | 141 | 14.789 | −33.956 | 26.898 | 1 | 21.37 |
| 2523 | N | VAL | 142 | 15.762 | −32.169 | 25.94 | 1 | 18.89 |
| 2524 | CA | VAL | 142 | 14.815 | −31.22 | 26.5 | 1 | 17.72 |
| 2525 | CB | VAL | 142 | 15.455 | −30.322 | 27.563 | 1 | 17.72 |
| 2526 | CG1 | VAL | 142 | 14.498 | −29.279 | 28.063 | 1 | 19.56 |
| 2527 | CG2 | VAL | 142 | 15.987 | −31.176 | 28.719 | 1 | 20.9 |
| 2528 | C | VAL | 142 | 14.251 | −30.337 | 25.397 | 1 | 17.76 |
| 2529 | O | VAL | 142 | 14.992 | −29.812 | 24.567 | 1 | 17.97 |
| 2530 | N | VAL | 143 | 12.932 | −30.19 | 25.383 | 1 | 16.59 |
| 2531 | CA | VAL | 143 | 12.271 | −29.353 | 24.396 | 1 | 16.87 |
| 2532 | CB | VAL | 143 | 11.341 | −30.177 | 23.485 | 1 | 17.11 |
| 2533 | CG1 | VAL | 143 | 10.668 | −29.264 | 22.467 | 1 | 17.91 |
| 2534 | CG2 | VAL | 143 | 12.133 | −31.257 | 22.783 | 1 | 16.62 |
| 2535 | C | VAL | 143 | 11.444 | −28.324 | 25.144 | 1 | 17.48 |
| 2536 | O | VAL | 143 | 10.649 | −28.666 | 26.02 | 1 | 19.11 |
| 2537 | N | TRP | 144 | 11.651 | −27.057 | 24.818 | 1 | 15.38 |
| 2538 | CA | TRP | 144 | 10.912 | −25.99 | 25.465 | 1 | 15.42 |
| 2539 | CB | TRP | 144 | 11.864 | −25.14 | 26.325 | 1 | 15.66 |
| 2540 | CG | TRP | 144 | 11.245 | −23.922 | 26.958 | 1 | 14.91 |
| 2541 | CD2 | TRP | 144 | 11.94 | −22.761 | 27.434 | 1 | 14.67 |
| 2542 | CE2 | TRP | 144 | 10.971 | −21.888 | 27.981 | 1 | 15.83 |
| 2543 | CE3 | TRP | 144 | 13.288 | −22.375 | 27.453 | 1 | 17.65 |
| 2544 | CD1 | TRP | 144 | 9.921 | −23.711 | 27.229 | 1 | 15.18 |
| 2545 | NE1 | TRP | 144 | 9.749 | −22.491 | 27.843 | 1 | 16.97 |
| 2546 | CZ2 | TRP | 144 | 11.307 | −20.649 | 28.541 | 1 | 17.72 |
| 2547 | CZ3 | TRP | 144 | 13.622 | −21.139 | 28.013 | 1 | 16.07 |
| 2548 | CH2 | TRP | 144 | 12.633 | −20.294 | 28.547 | 1 | 17.05 |
| 2549 | C | TRP | 144 | 10.209 | −25.125 | 24.432 | 1 | 16 |
| 2550 | O | TRP | 144 | 10.842 | −24.582 | 23.526 | 1 | 16.09 |
| 2551 | N | GLN | 145 | 8.888 | −25.039 | 24.553 | 1 | 15.87 |
| 2552 | CA | GLN | 145 | 8.094 | −24.206 | 23.667 | 1 | 16.14 |
| 2553 | CB | GLN | 145 | 6.773 | −24.88 | 23.294 | 1 | 18.93 |
| 2554 | CG | GLN | 145 | 5.928 | −24.01 | 22.379 | 1 | 21.34 |
| 2555 | CD | GLN | 145 | 4.711 | −24.723 | 21.848 | 1 | 23.61 |
| 2556 | OE1 | GLN | 145 | 4.774 | −25.902 | 21.506 | 1 | 27.12 |
| 2557 | NE2 | GLN | 145 | 3.595 | −24.006 | 21.754 | 1 | 22.35 |
| 2558 | C | GLN | 145 | 7.807 | −22.92 | 24.422 | 1 | 16.68 |
| 2559 | O | GLN | 145 | 7.222 | −22.941 | 25.511 | 1 | 15.28 |
| 2560 | N | ALA | 146 | 8.224 | −21.799 | 23.844 | 1 | 15.45 |
| 2561 | CA | ALA | 146 | 8.031 | −20.504 | 24.476 | 1 | 16.03 |
| 2562 | CB | ALA | 146 | 9.36 | −20.005 | 25.037 | 1 | 17.52 |
| 2563 | C | ALA | 146 | 7.461 | −19.474 | 23.513 | 1 | 15.88 |
| 2564 | O | ALA | 146 | 7.635 | −19.575 | 22.3 | 1 | 16.55 |
| 2565 | N | SER | 147 | 6.775 | −18.483 | 24.068 | 1 | 16.36 |
| 2566 | CA | SER | 147 | 6.195 | −17.413 | 23.273 | 1 | 19.12 |
| 2567 | CB | SER | 147 | 4.677 | −17.591 | 23.149 | 1 | 21.82 |
| 2568 | OG | SER | 147 | 4.042 | −17.499 | 24.412 | 1 | 25.03 |
| 2569 | C | SER | 147 | 6.511 | −16.088 | 23.95 | 1 | 18.98 |
| 2570 | O | SER | 147 | 7.085 | −16.06 | 25.039 | 1 | 19.4 |
| 2571 | N | GLY | 148 | 6.157 | −14.989 | 23.295 | 1 | 19.09 |
| 2572 | CA | GLY | 148 | 6.4 | −13.684 | 23.876 | 1 | 16.67 |
| 2573 | C | GLY | 148 | 7.85 | −13.399 | 24.218 | 1 | 15.29 |
| 2574 | O | GLY | 148 | 8.757 | −13.755 | 23.468 | 1 | 14.35 |
| 2575 | N | TRP | 149 | 8.072 | −12.764 | 25.364 | 1 | 15.63 |
| 2576 | CA | TRP | 149 | 9.422 | −12.395 | 25.776 | 1 | 15.14 |
| 2577 | CB | TRP | 149 | 9.379 | −11.633 | 27.101 | 1 | 17.01 |
| 2578 | CG | TRP | 149 | 10.552 | −10.721 | 27.262 | 1 | 17.03 |
| 2579 | CD2 | TRP | 149 | 10.804 | −9.519 | 26.523 | 1 | 18.66 |
| 2580 | CE2 | TRP | 149 | 12.035 | −8.998 | 26.979 | 1 | 18.21 |
| 2581 | CE3 | TRP | 149 | 10.11 | −8.832 | 25.518 | 1 | 18.67 |
| 2582 | CD1 | TRP | 149 | 11.607 | −10.877 | 28.113 | 1 | 18.71 |
| 2583 | NE1 | TRP | 149 | 12.503 | −9.846 | 27.95 | 1 | 19.34 |
| 2584 | CZ2 | TRP | 149 | 12.588 | −7.82 | 26.465 | 1 | 18.71 |
| 2585 | CZ3 | TRP | 149 | 10.661 | −7.657 | 25.006 | 1 | 18.99 |
| 2586 | CH2 | TRP | 149 | 11.889 | −7.165 | 25.482 | 1 | 19.51 |
| 2587 | C | TRP | 149 | 10.407 | −13.556 | 25.873 | 1 | 15.12 |
| 2588 | O | TRP | 149 | 11.567 | −13.421 | 25.481 | 1 | 14.88 |
| 2589 | N | ALA | 150 | 9.957 | −14.696 | 26.39 | 1 | 14.68 |
| 2590 | CA | ALA | 150 | 10.835 | −15.856 | 26.505 | 1 | 14.47 |
| 2591 | CB | ALA | 150 | 10.097 | −17.011 | 27.184 | 1 | 15.13 |
| 2592 | C | ALA | 150 | 11.326 | −16.281 | 25.12 | 1 | 12.94 |
| 2593 | O | ALA | 150 | 12.489 | −16.644 | 24.948 | 1 | 13.24 |
| 2594 | N | ALA | 151 | 10.433 | −16.239 | 24.135 | 1 | 13.81 |
| 2595 | CA | ALA | 151 | 10.794 | −16.608 | 22.772 | 1 | 12.65 |
| 2596 | CB | ALA | 151 | 9.559 | −16.577 | 21.873 | 1 | 13.61 |
| 2597 | C | ALA | 151 | 11.856 | −15.652 | 22.233 | 1 | 12.22 |
| 2598 | O | ALA | 151 | 12.764 | −16.063 | 21.511 | 1 | 11.58 |
| 2599 | N | ARG | 152 | 11.736 | −14.377 | 22.593 | 1 | 13.23 |
| 2600 | CA | ARG | 152 | 12.69 | −13.366 | 22.152 | 1 | 12 |
| 2601 | CB | ARG | 152 | 12.241 | −11.974 | 22.608 | 1 | 11.95 |
| 2602 | CG | ARG | 152 | 13.294 | −10.877 | 22.439 | 1 | 11.89 |
| 2603 | CD | ARG | 152 | 12.714 | −9.518 | 22.826 | 1 | 11.94 |
| 2604 | NE | ARG | 152 | 11.589 | −9.16 | 21.968 | 1 | 13.7 |
| 2605 | CZ | ARG | 152 | 11.695 | −8.488 | 20.827 | 1 | 14.05 |
| 2606 | NH1 | ARG | 152 | 12.883 | −8.076 | 20.396 | 1 | 14.23 |
| 2607 | NH2 | ARG | 152 | 10.612 | −8.256 | 20.099 | 1 | 14.48 |
| 2608 | C | ARG | 152 | 14.072 | −13.673 | 22.714 | 1 | 12.75 |
| 2609 | O | ARG | 152 | 15.062 | −13.65 | 21.987 | 1 | 10.39 |
| 2610 | N | ILE | 153 | 14.134 | −13.963 | 24.009 | 1 | 12.92 |
| 2611 | CA | ILE | 153 | 15.406 | −14.278 | 24.651 | 1 | 13.35 |
| 2612 | CB | ILE | 153 | 15.21 | −14.556 | 26.157 | 1 | 13.6 |
| 2613 | CG2 | ILE | 153 | 16.555 | −14.853 | 26.813 | 1 | 17.07 |
| 2614 | CG1 | ILE | 153 | 14.552 | −13.343 | 26.823 | 1 | 16.51 |
| 2615 | CD1 | ILE | 153 | 14.035 | −13.615 | 28.226 | 1 | 19.74 |
| 2616 | C | ILE | 153 | 16.032 | −15.499 | 23.979 | 1 | 11.58 |
| 2617 | O | ILE | 153 | 17.222 | −15.514 | 23.676 | 1 | 11.86 |
| 2618 | N | ILE | 154 | 15.221 | −16.525 | 23.735 | 1 | 11.23 |
| 2619 | CA | ILE | 154 | 15.711 | −17.728 | 23.085 | 1 | 10.71 |
| 2620 | CB | ILE | 154 | 14.573 | −18.775 | 22.95 | 1 | 10.42 |
| 2621 | CG2 | ILE | 154 | 14.981 | −19.889 | 21.99 | 1 | 12.8 |
| 2622 | CG1 | ILE | 154 | 14.256 | −19.354 | 24.332 | 1 | 13.16 |
| 2623 | CD1 | ILE | 154 | 12.969 | −20.148 | 24.377 | 1 | 14.52 |
| 2624 | C | ILE | 154 | 16.296 | −17.404 | 21.708 | 1 | 10.46 |
| 2625 | O | ILE | 154 | 17.372 | −17.886 | 21.355 | 1 | 11.64 |
| 2626 | N | GLN | 155 | 15.594 | −16.579 | 20.939 | 1 | 10.85 |
| 2627 | CA | GLN | 155 | 16.069 | −16.21 | 19.607 | 1 | 10.38 |
| 2628 | CB | GLN | 155 | 14.998 | −15.396 | 18.877 | 1 | 11.72 |
| 2629 | CG | GLN | 155 | 13.791 | −16.24 | 18.49 | 1 | 13.02 |
| 2630 | CD | GLN | 155 | 12.621 | −15.412 | 18.024 | 1 | 14.73 |
| 2631 | OE1 | GLN | 155 | 12.668 | −14.782 | 16.967 | 1 | 16.39 |
| 2632 | NE2 | GLN | 155 | 11.556 | −15.401 | 18.819 | 1 | 13.11 |
| 2633 | C | GLN | 155 | 17.373 | −15.423 | 19.673 | 1 | 10.56 |
| 2634 | O | GLN | 155 | 18.275 | −15.636 | 18.861 | 1 | 11.31 |
| 2635 | N | HIS | 156 | 17.466 | −14.515 | 20.639 | 1 | 12.16 |
| 2636 | CA | HIS | 156 | 18.668 | −13.707 | 20.819 | 1 | 10.44 |
| 2637 | CB | HIS | 156 | 18.453 | −12.709 | 21.969 | 1 | 10.37 |
| 2638 | CG | HIS | 156 | 19.638 | −11.835 | 22.249 | 1 | 10.07 |
| 2639 | CD2 | HIS | 156 | 20.806 | −12.094 | 22.885 | 1 | 13.69 |
| 2640 | ND1 | HIS | 156 | 19.694 | −10.513 | 21.865 | 1 | 12.29 |
| 2641 | CE1 | HIS | 156 | 20.846 | −9.993 | 22.256 | 1 | 12.76 |
| 2642 | NE2 | HIS | 156 | 21.538 | −10.931 | 22.876 | 1 | 10.07 |
| 2643 | C | HIS | 156 | 19.867 | −14.612 | 21.121 | 1 | 11.53 |
| 2644 | O | HIS | 156 | 20.934 | −14.463 | 20.521 | 1 | 11.13 |
| 2645 | N | GLU | 157 | 19.694 | −15.56 | 22.039 | 1 | 11.04 |
| 2646 | CA | GLU | 157 | 20.796 | −16.453 | 22.392 | 1 | 12.2 |
| 2647 | CB | GLU | 157 | 20.472 | −17.269 | 23.647 | 1 | 14.54 |
| 2648 | CG | GLU | 157 | 20.263 | −16.464 | 24.923 | 1 | 18.16 |
| 2649 | CD | GLU | 157 | 21.241 | −15.308 | 25.103 | 1 | 18.33 |
| 2650 | OE1 | GLU | 157 | 22.448 | −15.457 | 24.808 | 1 | 22.57 |
| 2651 | OE2 | GLU | 157 | 20.786 | −14.245 | 25.564 | 1 | 19.51 |
| 2652 | C | GLU | 157 | 21.169 | −17.402 | 21.261 | 1 | 12.51 |
| 2653 | O | GLU | 157 | 22.348 | −17.659 | 21.032 | 1 | 11.77 |
| 2654 | N | MET | 158 | 20.169 | −17.942 | 20.564 | 1 | 12.62 |
| 2655 | CA | MET | 158 | 20.45 | −18.835 | 19.451 | 1 | 14.05 |
| 2656 | CB | MET | 158 | 19.153 | −19.391 | 18.855 | 1 | 14.23 |
| 2657 | CG | MET | 158 | 18.514 | −20.51 | 19.672 | 1 | 15.5 |
| 2658 | SD | MET | 158 | 19.585 | −21.956 | 19.832 | 1 | 18.33 |
| 2659 | CE | MET | 158 | 19.702 | −22.482 | 18.118 | 1 | 18.97 |
| 2660 | C | MET | 158 | 21.234 | −18.079 | 18.381 | 1 | 12.9 |
| 2661 | O | MET | 158 | 22.147 | −18.632 | 17.777 | 1 | 13.21 |
| 2662 | N | ASP | 159 | 20.883 | −16.813 | 18.15 | 1 | 11.68 |
| 2663 | CA | ASP | 159 | 21.604 | −16.015 | 17.155 | 1 | 11.82 |
| 2664 | CB | ASP | 159 | 21.044 | −14.588 | 17.062 | 1 | 11.5 |
| 2665 | CG | ASP | 159 | 19.806 | −14.49 | 16.186 | 1 | 15.54 |
| 2666 | OD1 | ASP | 159 | 19.449 | −15.488 | 15.525 | 1 | 15.91 |

TABLE 2-continued

| Atom | Atom Type | Residue | # | X | Y | Z | OCC | B |
|---|---|---|---|---|---|---|---|---|
| 2667 | OD2 | ASP | 159 | 19.194 | −13.401 | 16.151 | 1 | 14.42 |
| 2668 | C | ASP | 159 | 23.089 | −15.946 | 17.509 | 1 | 10.88 |
| 2669 | O | ASP | 159 | 23.94 | −16.017 | 16.627 | 1 | 10.55 |
| 2670 | N | HIS | 160 | 23.403 | −15.808 | 18.798 | 1 | 11.29 |
| 2671 | CA | HIS | 160 | 24.803 | −15.75 | 19.227 | 1 | 11.7 |
| 2672 | CB | HIS | 160 | 24.911 | −15.619 | 20.753 | 1 | 10.2 |
| 2673 | CG | HIS | 160 | 24.842 | −14.209 | 21.254 | 1 | 10.08 |
| 2674 | CD2 | HIS | 160 | 23.963 | −13.604 | 22.085 | 1 | 11.79 |
| 2675 | ND1 | HIS | 160 | 25.781 | −13.252 | 20.925 | 1 | 10.27 |
| 2676 | CE1 | HIS | 160 | 25.48 | −12.118 | 21.535 | 1 | 9.29 |
| 2677 | NE2 | HIS | 160 | 24.381 | −12.306 | 22.244 | 1 | 10.35 |
| 2678 | C | HIS | 160 | 25.575 | −16.989 | 18.794 | 1 | 13.12 |
| 2679 | O | HIS | 160 | 26.755 | −16.905 | 18.451 | 1 | 12.96 |
| 2680 | N | LEU | 161 | 24.916 | −18.146 | 18.819 | 1 | 11.2 |
| 2681 | CA | LEU | 161 | 25.584 | −19.38 | 18.425 | 1 | 11.23 |
| 2682 | CB | LEU | 161 | 24.769 | −20.601 | 18.875 | 1 | 10.75 |
| 2683 | CG | LEU | 161 | 24.627 | −20.763 | 20.393 | 1 | 12.13 |
| 2684 | CD1 | LEU | 161 | 24.009 | −22.132 | 20.692 | 1 | 12.24 |
| 2685 | CD2 | LEU | 161 | 25.984 | −20.646 | 21.073 | 1 | 12.83 |
| 2686 | C | LEU | 161 | 25.834 | −19.442 | 16.923 | 1 | 11.87 |
| 2687 | O | LEU | 161 | 26.612 | −20.275 | 16.458 | 1 | 12.06 |
| 2688 | N | GLN | 162 | 25.176 | −18.557 | 16.173 | 1 | 11.81 |
| 2689 | CA | GLN | 162 | 25.333 | −18.503 | 14.718 | 1 | 13.33 |
| 2690 | CB | GLN | 162 | 23.979 | −18.314 | 14.027 | 1 | 15.8 |
| 2691 | CG | GLN | 162 | 22.866 | −19.215 | 14.529 | 1 | 22.99 |
| 2692 | CD | GLN | 162 | 23.288 | −20.657 | 14.643 | 1 | 26.9 |
| 2693 | OE1 | GLN | 162 | 23.793 | −21.248 | 13.69 | 1 | 29.58 |
| 2694 | NE2 | GLN | 162 | 23.079 | −21.238 | 15.818 | 1 | 30.64 |
| 2695 | C | GLN | 162 | 26.24 | −17.344 | 14.309 | 1 | 13 |
| 2696 | O | GLN | 162 | 26.467 | −17.118 | 13.118 | 1 | 15 |
| 2697 | N | GLY | 163 | 26.746 | −16.607 | 15.294 | 1 | 12.32 |
| 2698 | CA | GLY | 163 | 27.613 | −15.474 | 15.004 | 1 | 11.7 |
| 2699 | C | GLY | 163 | 26.823 | −14.237 | 14.615 | 1 | 12.1 |
| 2700 | O | GLY | 163 | 27.346 | −13.333 | 13.954 | 1 | 12.23 |
| 2701 | N | CYS | 164 | 25.561 | −14.2 | 15.033 | 1 | 11.36 |
| 2702 | CA | CYS | 164 | 24.659 | −13.092 | 14.731 | 1 | 11.58 |
| 2703 | CB | CYS | 164 | 23.349 | −13.652 | 14.162 | 1 | 14.47 |
| 2704 | SG | CYS | 164 | 22.046 | −12.448 | 13.821 | 1 | 16.51 |
| 2705 | C | CYS | 164 | 24.364 | −12.248 | 15.973 | 1 | 11.79 |
| 2706 | O | CYS | 164 | 24.067 | −12.784 | 17.04 | 1 | 10.79 |
| 2707 | N | LEU | 165 | 24.462 | −10.928 | 15.826 | 1 | 9.99 |
| 2708 | CA | LEU | 165 | 24.186 | −9.994 | 16.916 | 1 | 10.9 |
| 2709 | CB | LEU | 165 | 25.361 | −9.032 | 17.102 | 1 | 9.66 |
| 2710 | CG | LEU | 165 | 26.694 | −9.684 | 17.472 | 1 | 11 |
| 2711 | CD1 | LEU | 165 | 27.758 | −8.602 | 17.596 | 1 | 13.6 |
| 2712 | CD2 | LEU | 165 | 26.565 | −10.439 | 18.787 | 1 | 11.98 |
| 2713 | C | LEU | 165 | 22.919 | −9.209 | 16.586 | 1 | 10.98 |
| 2714 | O | LEU | 165 | 22.557 | −9.061 | 15.416 | 1 | 11.7 |
| 2715 | N | PHE | 166 | 22.253 | −8.683 | 17.609 | 1 | 11.36 |
| 2716 | CA | PHE | 166 | 21.006 | −7.961 | 17.38 | 1 | 12.83 |
| 2717 | CB | PHE | 166 | 20.365 | −7.547 | 18.717 | 1 | 12.32 |
| 2718 | CG | PHE | 166 | 20.922 | −6.282 | 19.312 | 1 | 11.82 |
| 2719 | CD1 | PHE | 166 | 20.228 | −5.082 | 19.192 | 1 | 13.23 |
| 2720 | CD2 | PHE | 166 | 22.122 | −6.294 | 20.015 | 1 | 12.95 |
| 2721 | CE1 | PHE | 166 | 20.72 | −3.905 | 19.769 | 1 | 13.97 |
| 2722 | CE2 | PHE | 166 | 22.625 | −5.127 | 20.595 | 1 | 12.47 |
| 2723 | CZ | PHE | 166 | 21.919 | −3.928 | 20.472 | 1 | 13.71 |
| 2724 | C | PHE | 166 | 21.14 | −6.763 | 16.442 | 1 | 13.22 |
| 2725 | O | PHE | 166 | 20.172 | −6.38 | 15.786 | 1 | 14.72 |
| 2726 | N | ILE | 167 | 22.335 | −6.184 | 16.359 | 1 | 12.01 |
| 2727 | CA | ILE | 167 | 22.554 | −5.049 | 15.466 | 1 | 12.61 |
| 2728 | CB | ILE | 167 | 23.926 | −4.391 | 15.715 | 1 | 10.7 |
| 2729 | CG2 | ILE | 167 | 23.947 | −3.769 | 17.103 | 1 | 13.33 |
| 2730 | CG1 | ILE | 167 | 25.045 | −5.427 | 15.57 | 1 | 13.11 |
| 2731 | CD1 | ILE | 167 | 26.431 | −4.805 | 15.478 | 1 | 13.08 |
| 2732 | C | ILE | 167 | 22.456 | −5.453 | 13.99 | 1 | 12.74 |
| 2733 | O | ILE | 167 | 22.419 | −4.595 | 13.106 | 1 | 14.18 |
| 2734 | N | ASP | 168 | 22.42 | −6.759 | 13.726 | 1 | 12.79 |
| 2735 | CA | ASP | 168 | 22.294 | −7.255 | 12.354 | 1 | 12.46 |
| 2736 | CB | ASP | 168 | 22.844 | −8.682 | 12.212 | 1 | 12.81 |
| 2737 | CG | ASP | 168 | 24.308 | −8.803 | 12.576 | 1 | 14.72 |
| 2738 | OD1 | ASP | 168 | 25.059 | −7.814 | 12.428 | 1 | 14.58 |
| 2739 | OD2 | ASP | 168 | 24.712 | −9.909 | 12.991 | 1 | 13.74 |
| 2740 | C | ASP | 168 | 20.821 | −7.304 | 11.941 | 1 | 13.66 |
| 2741 | O | ASP | 168 | 20.503 | −7.392 | 10.753 | 1 | 14.55 |
| 2742 | N | LYS | 169 | 19.928 | −7.253 | 12.924 | 1 | 13.79 |
| 2743 | CA | LYS | 169 | 18.494 | −7.354 | 12.661 | 1 | 14.88 |
| 2744 | CB | LYS | 169 | 17.954 | −8.63 | 13.311 | 1 | 17.19 |
| 2745 | CG | LYS | 169 | 18.515 | −9.922 | 12.75 | 1 | 17.68 |
| 2746 | CD | LYS | 169 | 18.003 | −11.116 | 13.548 | 1 | 17.04 |
| 2747 | CE | LYS | 169 | 18.389 | −12.425 | 12.89 | 1 | 16.68 |
| 2748 | NZ | LYS | 169 | 17.894 | −13.597 | 13.667 | 1 | 18.6 |
| 2749 | C | LYS | 169 | 17.652 | −6.179 | 13.149 | 1 | 14.24 |
| 2750 | O | LYS | 169 | 16.44 | −6.151 | 12.943 | 1 | 15.15 |
| 2751 | N | MET | 170 | 18.294 | −5.208 | 13.784 | 1 | 13.48 |
| 2752 | CA | MET | 170 | 17.599 | −4.053 | 14.342 | 1 | 12.97 |
| 2753 | CB | MET | 170 | 18.547 | −3.295 | 15.266 | 1 | 13.04 |
| 2754 | CG | MET | 170 | 19.67 | −2.621 | 14.489 | 1 | 13.06 |
| 2755 | SD | MET | 170 | 20.705 | −1.615 | 15.54 | 1 | 13.34 |
| 2756 | CE | MET | 170 | 22.016 | −1.15 | 14.424 | 1 | 10.24 |
| 2757 | C | MET | 170 | 17.053 | −3.033 | 13.357 | 1 | 13.7 |
| 2758 | O | MET | 170 | 17.41 | −3.018 | 12.179 | 1 | 13.27 |
| 2759 | N | ASP | 171 | 16.167 | −2.185 | 13.876 | 1 | 14.5 |
| 2760 | CA | ASP | 171 | 15.629 | −1.052 | 13.13 | 1 | 14.42 |
| 2761 | CB | ASP | 171 | 14.273 | −0.618 | 13.684 | 1 | 16.17 |
| 2762 | CG | ASP | 171 | 13.786 | 0.695 | 13.078 | 1 | 18.65 |
| 2763 | OD1 | ASP | 171 | 14.618 | 1.46 | 12.537 | 1 | 20.31 |
| 2764 | OD2 | ASP | 171 | 12.571 | 0.97 | 13.155 | 1 | 21.71 |
| 2765 | C | ASP | 171 | 16.697 | −0.056 | 13.578 | 1 | 14.94 |
| 2766 | O | ASP | 171 | 16.639 | 0.45 | 14.698 | 1 | 14.21 |
| 2767 | N | SER | 172 | 17.68 | 0.2 | 12.723 | 1 | 14.66 |
| 2768 | CA | SER | 172 | 18.788 | 1.081 | 13.085 | 1 | 13.6 |
| 2769 | CB | SER | 172 | 19.772 | 1.198 | 11.918 | 1 | 14.27 |
| 2770 | OG | SER | 172 | 19.173 | 1.845 | 10.816 | 1 | 15.6 |
| 2771 | C | SER | 172 | 18.415 | 2.475 | 13.568 | 1 | 13.47 |
| 2772 | O | SER | 172 | 19.155 | 3.072 | 14.349 | 1 | 13.16 |
| 2773 | N | ARG | 173 | 17.286 | 3.003 | 13.113 | 1 | 12.69 |
| 2774 | CA | ARG | 173 | 16.886 | 4.336 | 13.546 | 1 | 12.94 |
| 2775 | CB | ARG | 173 | 15.788 | 4.896 | 12.629 | 1 | 12.36 |
| 2776 | CG | ARG | 173 | 16.29 | 5.216 | 11.22 | 1 | 14.9 |
| 2777 | CD | ARG | 173 | 15.19 | 5.823 | 10.361 | 1 | 14.61 |
| 2778 | NE | ARG | 173 | 14.667 | 7.055 | 10.94 | 1 | 16.18 |
| 2779 | CZ | ARG | 173 | 15.298 | 8.226 | 10.92 | 1 | 17.39 |
| 2780 | NH1 | ARG | 173 | 16.485 | 8.337 | 10.34 | 1 | 17.44 |
| 2781 | NH2 | ARG | 173 | 14.741 | 9.284 | 11.495 | 1 | 18.09 |
| 2782 | C | ARG | 173 | 16.44 | 4.373 | 15.007 | 1 | 13.32 |
| 2783 | O | ARG | 173 | 16.226 | 5.455 | 15.562 | 1 | 14.41 |
| 2784 | N | THR | 174 | 16.322 | 3.203 | 15.636 | 1 | 12.68 |
| 2785 | CA | THR | 174 | 15.918 | 3.133 | 17.043 | 1 | 11.68 |
| 2786 | CB | THR | 174 | 14.83 | 2.053 | 17.286 | 1 | 13.41 |
| 2787 | OG1 | THR | 174 | 15.378 | 0.753 | 17.042 | 1 | 12.63 |
| 2788 | CG2 | THR | 174 | 13.633 | 2.279 | 16.371 | 1 | 13.63 |
| 2789 | C | THR | 174 | 17.098 | 2.819 | 17.971 | 1 | 12.19 |
| 2790 | O | THR | 174 | 16.926 | 2.721 | 19.192 | 1 | 11.19 |
| 2791 | N | PHE | 175 | 18.283 | 2.645 | 17.389 | 1 | 11.38 |
| 2792 | CA | PHE | 175 | 19.502 | 2.354 | 18.152 | 1 | 10.63 |
| 2793 | CB | PHE | 175 | 20.676 | 2.195 | 17.181 | 1 | 11.46 |
| 2794 | CG | PHE | 175 | 21.945 | 1.706 | 17.819 | 1 | 11.47 |
| 2795 | CD1 | PHE | 175 | 22.087 | 0.376 | 18.2 | 1 | 11.63 |
| 2796 | CD2 | PHE | 175 | 23.014 | 2.578 | 18.014 | 1 | 10.74 |
| 2797 | CE1 | PHE | 175 | 23.276 | −0.081 | 18.762 | 1 | 11.7 |
| 2798 | CE2 | PHE | 175 | 24.205 | 2.133 | 18.573 | 1 | 11.46 |
| 2799 | CZ | PHE | 175 | 24.339 | 0.801 | 18.947 | 1 | 12.43 |
| 2800 | C | PHE | 175 | 19.735 | 3.54 | 19.091 | 1 | 12.09 |
| 2801 | O | PHE | 175 | 19.647 | 4.688 | 18.669 | 1 | 12 |
| 2802 | N | THR | 176 | 20.036 | 3.269 | 20.359 | 1 | 11.76 |
| 2803 | CA | THR | 176 | 20.213 | 4.356 | 21.317 | 1 | 12.09 |
| 2804 | CB | THR | 176 | 18.824 | 4.808 | 21.865 | 1 | 13.6 |
| 2805 | OG1 | THR | 176 | 18.978 | 5.883 | 22.803 | 1 | 13.86 |
| 2806 | CG2 | THR | 176 | 18.138 | 3.645 | 22.575 | 1 | 15.57 |
| 2807 | C | THR | 176 | 21.085 | 4.023 | 22.516 | 1 | 11.73 |
| 2808 | O | THR | 176 | 21.138 | 2.878 | 22.968 | 1 | 11.28 |
| 2809 | N | ASN | 177 | 21.781 | 5.037 | 23.025 | 1 | 10.47 |
| 2810 | CA | ASN | 177 | 22.563 | 4.87 | 24.24 | 1 | 10.28 |
| 2811 | CB | ASN | 177 | 23.37 | 6.137 | 24.53 | 1 | 11.11 |
| 2812 | CG | ASN | 177 | 24.727 | 6.121 | 23.874 | 1 | 11.93 |
| 2813 | OD1 | ASN | 177 | 25.665 | 5.518 | 24.395 | 1 | 12.09 |
| 2814 | ND2 | ASN | 177 | 24.844 | 6.777 | 22.719 | 1 | 11.69 |
| 2815 | C | ASN | 177 | 21.483 | 4.7 | 25.312 | 1 | 11.63 |
| 2816 | O | ASN | 177 | 20.414 | 5.308 | 25.216 | 1 | 11.08 |
| 2817 | N | VAL | 178 | 21.753 | 3.894 | 26.331 | 1 | 11.98 |
| 2818 | CA | VAL | 178 | 20.763 | 3.67 | 27.376 | 1 | 13.98 |

TABLE 2-continued

| Atom | Atom Type | Residue | # | X | Y | Z | OCC | B |
|---|---|---|---|---|---|---|---|---|
| 2819 | CB | VAL | 178 | 21.214 | 2.566 | 28.357 | 1 | 17.33 |
| 2820 | CG1 | VAL | 178 | 21.216 | 1.217 | 27.648 | 1 | 19.49 |
| 2821 | CG2 | VAL | 178 | 22.595 | 2.886 | 28.903 | 1 | 18.95 |
| 2822 | C | VAL | 178 | 20.417 | 4.926 | 28.166 | 1 | 13.12 |
| 2823 | O | VAL | 178 | 19.359 | 4.985 | 28.789 | 1 | 14.42 |
| 2824 | N | TYR | 179 | 21.289 | 5.932 | 28.138 | 1 | 12.08 |
| 2825 | CA | TYR | 179 | 21.007 | 7.157 | 28.876 | 1 | 12.11 |
| 2826 | CB | TYR | 179 | 22.308 | 7.853 | 29.299 | 1 | 11.78 |
| 2827 | CG | TYR | 179 | 23.291 | 8.145 | 28.195 | 1 | 11.41 |
| 2828 | CD1 | TYR | 179 | 23.081 | 9.198 | 27.306 | 1 | 13.73 |
| 2829 | CE1 | TYR | 179 | 24.018 | 9.501 | 26.32 | 1 | 15.11 |
| 2830 | CD2 | TYR | 179 | 24.461 | 7.396 | 28.069 | 1 | 11.84 |
| 2831 | CE2 | TYR | 179 | 25.402 | 7.69 | 27.09 | 1 | 12.91 |
| 2832 | CZ | TYR | 179 | 25.174 | 8.744 | 26.221 | 1 | 14.82 |
| 2833 | OH | TYR | 179 | 26.101 | 9.033 | 25.252 | 1 | 15.93 |
| 2834 | C | TYR | 179 | 20.065 | 8.118 | 28.146 | 1 | 12.7 |
| 2835 | O | TYR | 179 | 19.788 | 9.216 | 28.625 | 1 | 13.88 |
| 2836 | N | TRP | 180 | 19.575 | 7.688 | 26.984 | 1 | 12.21 |
| 2837 | CA | TRP | 180 | 18.591 | 8.447 | 26.214 | 1 | 11.96 |
| 2838 | CB | TRP | 180 | 19.043 | 8.663 | 24.768 | 1 | 11.58 |
| 2839 | CG | TRP | 180 | 19.758 | 9.955 | 24.567 | 1 | 11.65 |
| 2840 | CD2 | TRP | 180 | 19.167 | 11.258 | 24.52 | 1 | 11.71 |
| 2841 | CE2 | TRP | 180 | 20.216 | 12.187 | 24.356 | 1 | 11.37 |
| 2842 | CE3 | TRP | 180 | 17.851 | 11.731 | 24.604 | 1 | 11.02 |
| 2843 | CD1 | TRP | 180 | 21.101 | 10.136 | 24.429 | 1 | 12.34 |
| 2844 | NE1 | TRP | 180 | 21.387 | 11.476 | 24.302 | 1 | 11.88 |
| 2845 | CZ2 | TRP | 180 | 19.992 | 13.564 | 24.274 | 1 | 13.3 |
| 2846 | CZ3 | TRP | 180 | 17.626 | 13.1 | 24.522 | 1 | 12.55 |
| 2847 | CH2 | TRP | 180 | 18.694 | 14.002 | 24.359 | 1 | 13.14 |
| 2848 | C | TRP | 180 | 17.345 | 7.571 | 26.219 | 1 | 14 |
| 2849 | O | TRP | 180 | 17.427 | 6.378 | 25.924 | 1 | 15.41 |
| 2850 | N | MET | 181 | 16.195 | 8.15 | 26.542 | 1 | 14.27 |
| 2851 | CA | MET | 181 | 14.973 | 7.361 | 26.589 | 1 | 16.8 |
| 2852 | CB | MET | 181 | 14.864 | 6.686 | 27.961 | 1 | 17.94 |
| 2853 | CG | MET | 181 | 14.685 | 7.655 | 29.121 | 1 | 19.04 |
| 2854 | SD | MET | 181 | 15.407 | 7.05 | 30.675 | 1 | 21.22 |
| 2855 | CE | MET | 181 | 17.118 | 7.583 | 30.457 | 1 | 17.1 |
| 2856 | C | MET | 181 | 13.713 | 8.174 | 26.316 | 1 | 19.11 |
| 2857 | O | MET | 181 | 13.685 | 9.388 | 26.51 | 1 | 17.31 |
| 2858 | N | LYS | 182 | 12.676 | 7.489 | 25.844 | 1 | 22.75 |
| 2859 | CA | LYS | 182 | 11.393 | 8.128 | 25.58 | 1 | 27.46 |
| 2860 | CB | LYS | 182 | 10.61 | 7.375 | 24.502 | 1 | 30.15 |
| 2861 | CG | LYS | 182 | 10.725 | 7.969 | 23.112 | 1 | 33.23 |
| 2862 | CD | LYS | 182 | 9.711 | 7.334 | 22.17 | 1 | 35.5 |
| 2863 | CE | LYS | 182 | 9.74 | 7.986 | 20.798 | 1 | 36.78 |
| 2864 | NZ | LYS | 182 | 8.721 | 7.397 | 19.884 | 1 | 39.39 |
| 2865 | C | LYS | 182 | 10.612 | 8.089 | 26.881 | 1 | 28.92 |
| 2866 | O | LYS | 182 | 10.646 | 7.09 | 27.601 | 1 | 30.4 |
| 2867 | N | VAL | 183 | 9.911 | 9.172 | 27.188 | 1 | 30.34 |
| 2868 | CA | VAL | 183 | 9.136 | 9.236 | 28.417 | 1 | 32.64 |
| 2869 | CB | VAL | 183 | 9.887 | 10.038 | 29.498 | 1 | 33.09 |
| 2870 | CG1 | VAL | 183 | 11.186 | 9.334 | 29.861 | 1 | 33.8 |
| 2871 | CG2 | VAL | 183 | 10.168 | 11.448 | 29 | 1 | 33.08 |
| 2872 | C | VAL | 183 | 7.767 | 9.869 | 28.199 | 1 | 34.34 |
| 2873 | O | VAL | 183 | 7.567 | 10.634 | 27.255 | 1 | 34.2 |
| 2874 | N | ASN | 184 | 6.827 | 9.537 | 29.078 | 1 | 36.63 |
| 2875 | CA | ASN | 184 | 5.476 | 10.074 | 29.002 | 1 | 38.46 |
| 2876 | CB | ASN | 184 | 4.472 | 9.074 | 29.58 | 1 | 39.33 |
| 2877 | CG | ASN | 184 | 4.509 | 7.735 | 28.871 | 1 | 39.34 |
| 2878 | OD1 | ASN | 184 | 4.308 | 7.654 | 27.659 | 1 | 41.17 |
| 2879 | ND2 | ASN | 184 | 4.769 | 6.674 | 29.627 | 1 | 42.72 |
| 2880 | C | ASN | 184 | 5.416 | 11.371 | 29.796 | 1 | 39.61 |
| 2881 | O | ASN | 184 | 5.917 | 11.444 | 30.918 | 1 | 40.51 |
| 2882 | N | ASP | 185 | 4.804 | 12.394 | 29.213 | 1 | 40.84 |
| 2883 | CA | ASP | 185 | 4.692 | 13.683 | 29.881 | 1 | 42.19 |
| 2884 | CB | ASP | 185 | 4.542 | 14.797 | 28.845 | 1 | 43.27 |
| 2885 | CG | ASP | 185 | 5.641 | 14.769 | 27.805 | 1 | 43.86 |
| 2886 | OD1 | ASP | 185 | 6.827 | 14.832 | 28.194 | 1 | 45.39 |
| 2887 | OD2 | ASP | 185 | 5.321 | 14.683 | 26.6 | 1 | 44.7 |
| 2888 | C | ASP | 185 | 3.502 | 13.692 | 30.833 | 1 | 43.02 |
| 2889 | O | ASP | 185 | 2.84 | 12.639 | 30.952 | 1 | 43.78 |
| 2890 | OXT | ASP | 185 | 3.251 | 14.749 | 31.451 | 1 | 44.03 |
| 2891 | CB | HIS | 3 | 11.765 | −54.433 | −6.414 | 1 | 34.84 |
| 2892 | CG | HIS | 3 | 12.484 | −55.275 | −7.422 | 1 | 34.45 |
| 2893 | CD2 | HIS | 3 | 12.035 | −55.933 | −8.517 | 1 | 34.54 |
| 2894 | ND1 | HIS | 3 | 13.836 | −55.532 | −7.348 | 1 | 34.98 |
| 2895 | CE1 | HIS | 3 | 14.189 | −56.313 | −8.354 | 1 | 35.18 |
| 2896 | NE2 | HIS | 3 | 13.114 | −56.571 | −9.078 | 1 | 34.8 |
| 2897 | C | HIS | 3 | 11.972 | −52.208 | −7.545 | 1 | 36.47 |
| 2898 | O | HIS | 3 | 11.047 | −52.555 | −8.284 | 1 | 37.78 |
| 2899 | N | HIS | 3 | 11.728 | −52.341 | −5.089 | 1 | 35.32 |
| 2900 | CA | HIS | 3 | 12.313 | −53.007 | −6.29 | 1 | 35.81 |
| 2901 | N | MET | 4 | 12.724 | −51.137 | −7.779 | 1 | 36.35 |
| 2902 | CA | MET | 4 | 12.508 | −50.278 | −8.94 | 1 | 35.83 |
| 2903 | CB | MET | 4 | 13.141 | −48.905 | −8.695 | 1 | 36.84 |
| 2904 | CG | MET | 4 | 12.514 | −48.125 | −7.55 | 1 | 36.66 |
| 2905 | SD | MET | 4 | 13.368 | −46.568 | −7.223 | 1 | 41.25 |
| 2906 | CE | MET | 4 | 12.537 | −45.463 | −8.37 | 1 | 37.41 |
| 2907 | C | MET | 4 | 13.072 | −50.879 | −10.222 | 1 | 34.51 |
| 2908 | O | MET | 4 | 13.66 | −51.962 | −10.209 | 1 | 35.69 |
| 2909 | N | SER | 5 | 12.885 | −50.166 | −11.328 | 1 | 33.88 |
| 2910 | CA | SER | 5 | 13.37 | −50.613 | −12.627 | 1 | 31.3 |
| 2911 | CB | SER | 5 | 12.221 | −51.223 | −13.433 | 1 | 31.35 |
| 2912 | OG | SER | 5 | 12.663 | −51.65 | −14.71 | 1 | 37.63 |
| 2913 | C | SER | 5 | 13.962 | −49.433 | −13.39 | 1 | 28.53 |
| 2914 | O | SER | 5 | 13.849 | −48.286 | −12.958 | 1 | 29.56 |
| 2915 | N | PHE | 6 | 14.599 | −49.712 | −14.521 | 1 | 26.05 |
| 2916 | CA | PHE | 6 | 15.193 | −48.649 | −15.322 | 1 | 23.36 |
| 2917 | CB | PHE | 6 | 16.643 | −48.981 | −15.695 | 1 | 23.82 |
| 2918 | CG | PHE | 6 | 17.598 | −48.941 | −14.541 | 1 | 24.29 |
| 2919 | CD1 | PHE | 6 | 17.695 | −50.013 | −13.661 | 1 | 25.4 |
| 2920 | CD2 | PHE | 6 | 18.41 | −47.83 | −14.335 | 1 | 25.37 |
| 2921 | CE1 | PHE | 6 | 18.589 | −49.98 | −12.593 | 1 | 25.31 |
| 2922 | CE2 | PHE | 6 | 19.305 | −47.786 | −13.271 | 1 | 26.09 |
| 2923 | CZ | PHE | 6 | 19.395 | −48.866 | −12.397 | 1 | 26.67 |
| 2924 | C | PHE | 6 | 14.414 | −48.402 | −16.604 | 1 | 21.86 |
| 2925 | O | PHE | 6 | 13.861 | −49.328 | −17.198 | 1 | 22.41 |
| 2926 | N | SER | 7 | 14.374 | −47.14 | −17.015 | 1 | 19.4 |
| 2927 | CA | SER | 7 | 13.709 | −46.738 | −18.246 | 1 | 18.5 |
| 2928 | CB | SER | 7 | 12.398 | −45.998 | −17.958 | 1 | 21.64 |
| 2929 | OG | SER | 7 | 11.415 | −46.877 | −17.444 | 1 | 27.84 |
| 2930 | C | SER | 7 | 14.663 | −45.802 | −18.961 | 1 | 15.6 |
| 2931 | O | SER | 7 | 15.476 | −45.125 | −18.33 | 1 | 14.79 |
| 2932 | N | HIS | 8 | 14.579 | −45.761 | −20.281 | 1 | 15.95 |
| 2933 | CA | HIS | 8 | 15.455 | −44.879 | −21.026 | 1 | 14.44 |
| 2934 | CB | HIS | 8 | 16.673 | −45.647 | −21.534 | 1 | 18.33 |
| 2935 | CG | HIS | 8 | 16.354 | −46.652 | −22.595 | 1 | 22.4 |
| 2936 | CD2 | HIS | 8 | 15.828 | −47.897 | −22.513 | 1 | 23.72 |
| 2937 | ND1 | HIS | 8 | 16.557 | −46.409 | −23.936 | 1 | 26.15 |
| 2938 | CE1 | HIS | 8 | 16.172 | −47.461 | −24.636 | 1 | 25.59 |
| 2939 | NE2 | HIS | 8 | 15.726 | −48.379 | −23.796 | 1 | 28.15 |
| 2940 | C | HIS | 8 | 14.725 | −44.248 | −22.192 | 1 | 12.84 |
| 2941 | O | HIS | 8 | 13.827 | −44.854 | −22.779 | 1 | 13.87 |
| 2942 | N | VAL | 9 | 15.094 | −43.013 | −22.502 | 1 | 11.57 |
| 2943 | CA | VAL | 9 | 14.501 | −42.317 | −23.632 | 1 | 11.99 |
| 2944 | CB | VAL | 9 | 14.425 | −40.802 | −23.383 | 1 | 12.2 |
| 2945 | CG1 | VAL | 9 | 13.892 | −40.097 | −24.626 | 1 | 11.75 |
| 2946 | CG2 | VAL | 9 | 13.517 | −40.525 | −22.19 | 1 | 13.72 |
| 2947 | C | VAL | 9 | 15.405 | −42.592 | −24.828 | 1 | 12.21 |
| 2948 | O | VAL | 9 | 16.593 | −42.252 | −24.812 | 1 | 11.77 |
| 2949 | N | CYS | 10 | 14.841 | −43.229 | −25.849 | 1 | 11.48 |
| 2950 | CA | CYS | 10 | 15.58 | −43.576 | −27.062 | 1 | 10.45 |
| 2951 | CB | CYS | 10 | 14.659 | −44.32 | −28.032 | 1 | 12.13 |
| 2952 | SG | CYS | 10 | 14.009 | −45.87 | −27.36 | 1 | 15.44 |
| 2953 | C | CYS | 10 | 16.158 | −42.337 | −27.739 | 1 | 10.5 |
| 2954 | O | CYS | 10 | 15.495 | −41.307 | −27.813 | 1 | 11.31 |
| 2955 | N | GLN | 11 | 17.389 | −42.448 | −28.238 | 1 | 10.13 |
| 2956 | CA | GLN | 11 | 18.06 | −41.327 | −28.888 | 1 | 10.1 |
| 2957 | CB | GLN | 11 | 19.479 | −41.189 | −28.338 | 1 | 10.06 |
| 2958 | CG | GLN | 11 | 19.512 | −40.877 | −26.85 | 1 | 9.34 |
| 2959 | CD | GLN | 11 | 18.791 | −39.584 | −26.517 | 1 | 10.01 |
| 2960 | OE1 | GLN | 11 | 19.159 | −38.511 | −27.003 | 1 | 12.92 |
| 2961 | NE2 | GLN | 11 | 17.756 | −39.678 | −25.683 | 1 | 10.08 |
| 2962 | C | GLN | 11 | 18.097 | −41.45 | −30.402 | 1 | 9.74 |
| 2963 | O | GLN | 11 | 18.06 | −42.555 | −30.94 | 1 | 11.76 |
| 2964 | N | VAL | 12 | 18.181 | −40.31 | −31.081 | 1 | 10.22 |
| 2965 | CA | VAL | 12 | 18.181 | −40.297 | −32.535 | 1 | 10.67 |
| 2966 | CB | VAL | 12 | 18.348 | −38.849 | −33.086 | 1 | 10.84 |
| 2967 | CG1 | VAL | 12 | 19.697 | −38.261 | −32.696 | 1 | 12.58 |
| 2968 | CG2 | VAL | 12 | 18.155 | −38.858 | −34.591 | 1 | 12.55 |
| 2969 | C | VAL | 12 | 19.22 | −41.258 | −33.107 | 1 | 11.41 |
| 2970 | O | VAL | 12 | 20.404 | −41.231 | −32.753 | 1 | 11.2 |

TABLE 2-continued

| Atom | Atom Type | Residue | # | X | Y | Z | OCC | B |
|---|---|---|---|---|---|---|---|---|
| 2971 | N | GLY | 13 | 18.738 | −42.126 | −33.988 | 1 | 11.24 |
| 2972 | CA | GLY | 13 | 19.566 | −43.157 | −34.584 | 1 | 12.48 |
| 2973 | C | GLY | 13 | 18.786 | −44.45 | −34.403 | 1 | 12.76 |
| 2974 | O | GLY | 13 | 18.874 | −45.365 | −35.216 | 1 | 12.49 |
| 2975 | N | ASP | 14 | 18.022 | −44.523 | −33.314 | 1 | 11.6 |
| 2976 | CA | ASP | 14 | 17.187 | −45.69 | −33.033 | 1 | 11.19 |
| 2977 | CB | ASP | 14 | 16.612 | −45.592 | −31.617 | 1 | 11.15 |
| 2978 | CG | ASP | 14 | 15.86 | −46.839 | −31.197 | 1 | 11.34 |
| 2979 | OD1 | ASP | 14 | 15.338 | −47.556 | −32.074 | 1 | 11.95 |
| 2980 | OD2 | ASP | 14 | 15.773 | −47.093 | −29.977 | 1 | 12.62 |
| 2981 | C | ASP | 14 | 16.047 | −45.641 | −34.054 | 1 | 12.43 |
| 2982 | O | ASP | 14 | 15.278 | −44.682 | −34.082 | 1 | 11.39 |
| 2983 | N | PRO | 15 | 15.912 | −46.678 | −34.898 | 1 | 11.09 |
| 2984 | CD | PRO | 15 | 16.695 | −47.928 | −34.934 | 1 | 12.08 |
| 2985 | CA | PRO | 15 | 14.85 | −46.698 | −35.908 | 1 | 12.53 |
| 2986 | CB | PRO | 15 | 15.084 | −48.028 | −36.633 | 1 | 13.61 |
| 2987 | CG | PRO | 15 | 15.722 | −48.887 | −35.578 | 1 | 13.47 |
| 2988 | C | PRO | 15 | 13.417 | −46.551 | −35.394 | 1 | 12.41 |
| 2989 | O | PRO | 15 | 12.531 | −46.129 | −36.139 | 1 | 13.66 |
| 2990 | N | VAL | 16 | 13.188 | −46.891 | −34.132 | 1 | 11.34 |
| 2991 | CA | VAL | 16 | 11.845 | −46.79 | −33.57 | 1 | 13.05 |
| 2992 | CB | VAL | 16 | 11.804 | −47.322 | −32.109 | 1 | 12.53 |
| 2993 | CG1 | VAL | 16 | 12.469 | −46.333 | −31.155 | 1 | 13.48 |
| 2994 | CG2 | VAL | 16 | 10.364 | −47.593 | −31.695 | 1 | 13.51 |
| 2995 | C | VAL | 16 | 11.342 | −45.342 | −33.614 | 1 | 13.07 |
| 2996 | O | VAL | 16 | 10.14 | −45.099 | −33.677 | 1 | 14.34 |
| 2997 | N | LEU | 17 | 12.263 | −44.384 | −33.604 | 1 | 12.06 |
| 2998 | CA | LEU | 17 | 11.883 | −42.971 | −33.633 | 1 | 11.76 |
| 2999 | CB | LEU | 17 | 13.033 | −42.107 | −33.117 | 1 | 11.49 |
| 3000 | CG | LEU | 17 | 13.442 | −42.321 | −31.66 | 1 | 13.08 |
| 3001 | CD1 | LEU | 17 | 14.746 | −41.596 | −31.392 | 1 | 10.59 |
| 3002 | CD2 | LEU | 17 | 12.345 | −41.822 | −30.738 | 1 | 14.06 |
| 3003 | C | LEU | 17 | 11.486 | −42.47 | −35.013 | 1 | 11.87 |
| 3004 | O | LEU | 17 | 10.9 | −41.391 | −35.14 | 1 | 12.75 |
| 3005 | N | ARG | 18 | 11.802 | −43.242 | −36.049 | 1 | 10.73 |
| 3006 | CA | ARG | 18 | 11.488 | −42.828 | −37.412 | 1 | 11.62 |
| 3007 | CB | ARG | 18 | 12.754 | −42.869 | −38.272 | 1 | 12.61 |
| 3008 | CG | ARG | 18 | 13.442 | −41.518 | −38.444 | 1 | 12.24 |
| 3009 | CD | ARG | 18 | 13.789 | −40.852 | −37.113 | 1 | 11.55 |
| 3010 | NE | ARG | 18 | 14.61 | −39.664 | −37.331 | 1 | 10.6 |
| 3011 | CZ | ARG | 18 | 14.156 | −38.52 | −37.831 | 1 | 10.5 |
| 3012 | NH1 | ARG | 18 | 12.873 | −38.391 | −38.156 | 1 | 11.81 |
| 3013 | NH2 | ARG | 18 | 14.994 | −37.517 | −38.049 | 1 | 10.53 |
| 3014 | C | ARG | 18 | 10.387 | −43.63 | −38.091 | 1 | 12.74 |
| 3015 | O | ARG | 18 | 10.027 | −43.351 | −39.233 | 1 | 15.33 |
| 3016 | N | GLY | 19 | 9.859 | −44.627 | −37.395 | 1 | 14.03 |
| 3017 | CA | GLY | 19 | 8.793 | −45.425 | −37.972 | 1 | 14.14 |
| 3018 | C | GLY | 19 | 7.441 | −44.814 | −37.659 | 1 | 15.54 |
| 3019 | O | GLY | 19 | 7.352 | −43.837 | −36.912 | 1 | 15.67 |
| 3020 | N | VAL | 20 | 6.387 | −45.373 | −38.243 | 1 | 15.45 |
| 3021 | CA | VAL | 20 | 5.036 | −44.883 | −37.987 | 1 | 16.55 |
| 3022 | CB | VAL | 20 | 4.169 | −44.907 | −39.265 | 1 | 17.42 |
| 3023 | CG1 | VAL | 20 | 2.755 | −44.442 | −38.941 | 1 | 19.41 |
| 3024 | CG2 | VAL | 20 | 4.785 | −44.008 | −40.329 | 1 | 19.97 |
| 3025 | C | VAL | 20 | 4.427 | −45.805 | −36.937 | 1 | 15.55 |
| 3026 | O | VAL | 20 | 4.207 | −46.99 | −37.189 | 1 | 17.06 |
| 3027 | N | ALA | 21 | 4.175 | −45.261 | −35.752 | 1 | 15.6 |
| 3028 | CA | ALA | 21 | 3.613 | −46.04 | −34.655 | 1 | 16.08 |
| 3029 | CB | ALA | 21 | 3.367 | −45.138 | −33.455 | 1 | 16.99 |
| 3030 | C | ALA | 21 | 2.324 | −46.756 | −35.039 | 1 | 16.4 |
| 3031 | O | ALA | 21 | 1.494 | −46.215 | −35.766 | 1 | 17.08 |
| 3032 | N | ALA | 22 | 2.167 | −47.977 | −34.541 | 1 | 17.45 |
| 3033 | CA | ALA | 22 | 0.977 | −48.77 | −34.818 | 1 | 18.81 |
| 3034 | CB | ALA | 22 | 1.293 | −50.252 | −34.674 | 1 | 18.82 |
| 3035 | C | ALA | 22 | −0.135 | −48.384 | −33.856 | 1 | 19.67 |
| 3036 | O | ALA | 22 | 0.119 | −48.007 | −32.716 | 1 | 18.41 |
| 3037 | N | PRO | 23 | −1.392 | −48.473 | −34.306 | 1 | 20.88 |
| 3038 | CD | PRO | 23 | −1.875 | −48.846 | −35.647 | 1 | 21.66 |
| 3039 | CA | PRO | 23 | −2.506 | −48.119 | −33.428 | 1 | 20.98 |
| 3040 | CB | PRO | 23 | −3.691 | −48.066 | −34.389 | 1 | 21.5 |
| 3041 | CG | PRO | 23 | −3.341 | −49.121 | −35.393 | 1 | 22.64 |
| 3042 | C | PRO | 23 | −2.693 | −49.156 | −32.328 | 1 | 20.56 |
| 3043 | O | PRO | 23 | −2.276 | −50.31 | −32.469 | 1 | 19.41 |
| 3044 | N | VAL | 24 | −3.301 | −48.736 | −31.225 | 1 | 20.39 |
| 3045 | CA | VAL | 24 | −3.57 | −49.637 | −30.116 | 1 | 22.23 |
| 3046 | CB | VAL | 24 | −3.712 | −48.865 | −28.784 | 1 | 20.61 |
| 3047 | CG1 | VAL | 24 | −4.17 | −49.802 | −27.682 | 1 | 21.18 |
| 3048 | CG2 | VAL | 24 | −2.377 | −48.234 | −28.406 | 1 | 20.27 |
| 3049 | C | VAL | 24 | −4.883 | −50.347 | −30.433 | 1 | 24.34 |
| 3050 | O | VAL | 24 | −5.859 | −49.708 | −30.826 | 1 | 25.46 |
| 3051 | N | GLU | 25 | −4.9 | −51.666 | −30.272 | 1 | 26.9 |
| 3052 | CA | GLU | 25 | −6.095 | −52.457 | −30.553 | 1 | 30.68 |
| 3053 | CB | GLU | 25 | −5.738 | −53.946 | −30.608 | 1 | 33.53 |
| 3054 | CG | GLU | 25 | −4.825 | −54.336 | −31.763 | 1 | 37.74 |
| 3055 | CD | GLU | 25 | −5.506 | −54.226 | −33.115 | 1 | 40.73 |
| 3056 | OE1 | GLU | 25 | −5.857 | −53.097 | −33.521 | 1 | 42.3 |
| 3057 | OE2 | GLU | 25 | −5.694 | −55.273 | −33.772 | 1 | 42.94 |
| 3058 | C | GLU | 25 | −7.185 | −52.233 | −29.509 | 1 | 31 |
| 3059 | O | GLU | 25 | −6.898 | −51.968 | −28.342 | 1 | 30.83 |
| 3060 | N | ARG | 26 | −8.438 | −52.348 | −29.939 | 1 | 32.76 |
| 3061 | CA | ARG | 26 | −9.581 | −52.157 | −29.052 | 1 | 34.32 |
| 3062 | CB | ARG | 26 | −10.882 | −52.471 | −29.797 | 1 | 35.86 |
| 3063 | CG | ARG | 26 | −11.218 | −51.495 | −30.911 | 1 | 37.62 |
| 3064 | CD | ARG | 26 | −11.582 | −50.128 | −30.353 | 1 | 40.51 |
| 3065 | NE | ARG | 26 | −11.879 | −49.166 | −31.411 | 1 | 41.73 |
| 3066 | CZ | ARG | 26 | −12.254 | −47.909 | −31.195 | 1 | 42.77 |
| 3067 | NH1 | ARG | 26 | −12.383 | −47.454 | −29.955 | 1 | 42.82 |
| 3068 | NH2 | ARG | 26 | −12.499 | −47.105 | −32.222 | 1 | 43.26 |
| 3069 | C | ARG | 26 | −9.51 | −53.007 | −27.786 | 1 | 34.11 |
| 3070 | O | ARG | 26 | −9.675 | −52.498 | −26.679 | 1 | 34.55 |
| 3071 | N | ALA | 27 | −9.263 | −54.301 | −27.953 | 1 | 34.85 |
| 3072 | CA | ALA | 27 | −9.193 | −55.215 | −26.82 | 1 | 34.47 |
| 3073 | CB | ALA | 27 | −8.991 | −56.637 | −27.312 | 1 | 35.09 |
| 3074 | C | ALA | 27 | −8.11 | −54.862 | −25.808 | 1 | 34.76 |
| 3075 | O | ALA | 27 | −8.079 | −55.422 | −24.713 | 1 | 35.34 |
| 3076 | N | GLN | 28 | −7.221 | −53.94 | −26.164 | 1 | 33.9 |
| 3077 | CA | GLN | 28 | −6.154 | −53.542 | −25.253 | 1 | 33.72 |
| 3078 | CB | GLN | 28 | −4.864 | −53.261 | −26.028 | 1 | 34.98 |
| 3079 | CG | GLN | 28 | −4.247 | −54.499 | −26.652 | 1 | 37.45 |
| 3080 | CD | GLN | 28 | −3.993 | −55.595 | −25.633 | 1 | 39.79 |
| 3081 | OE1 | GLN | 28 | −3.241 | −55.407 | −24.673 | 1 | 42.05 |
| 3082 | NE2 | GLN | 28 | −4.623 | −56.748 | −25.834 | 1 | 41.55 |
| 3083 | C | GLN | 28 | −6.535 | −52.319 | −24.429 | 1 | 33.05 |
| 3084 | O | GLN | 28 | −5.925 | −52.041 | −23.397 | 1 | 32.54 |
| 3085 | N | LEU | 29 | −7.549 | −51.594 | −24.887 | 1 | 32.78 |
| 3086 | CA | LEU | 29 | −8.009 | −50.402 | −24.185 | 1 | 33.37 |
| 3087 | CB | LEU | 29 | −9.193 | −49.778 | −24.928 | 1 | 33.51 |
| 3088 | CG | LEU | 29 | −8.907 | −49.226 | −26.328 | 1 | 34.32 |
| 3089 | CD1 | LEU | 29 | −10.204 | −48.754 | −26.971 | 1 | 34.34 |
| 3090 | CD2 | LEU | 29 | −7.909 | −48.08 | −26.234 | 1 | 33.91 |
| 3091 | C | LEU | 29 | −8.417 | −50.742 | −22.756 | 1 | 34.52 |
| 3092 | O | LEU | 29 | −9.185 | −51.676 | −22.527 | 1 | 35.52 |
| 3093 | N | GLY | 30 | −7.895 | −49.98 | −21.8 | 1 | 34.48 |
| 3094 | CA | GLY | 30 | −8.216 | −50.215 | −20.403 | 1 | 34.38 |
| 3095 | C | GLY | 30 | −7.519 | −51.434 | −19.829 | 1 | 34.66 |
| 3096 | O | GLY | 30 | −7.701 | −51.76 | −18.655 | 1 | 35.14 |
| 3097 | N | GLY | 31 | −6.72 | −52.105 | −20.655 | 1 | 34.44 |
| 3098 | CA | GLY | 31 | −6.006 | −53.288 | −20.208 | 1 | 33.98 |
| 3099 | C | GLY | 31 | −4.765 | −52.979 | −19.388 | 1 | 34.31 |
| 3100 | O | GLY | 31 | −4.262 | −51.855 | −19.427 | 1 | 34.08 |
| 3101 | N | PRO | 32 | −4.247 | −53.961 | −18.63 | 1 | 34.15 |
| 3102 | CD | PRO | 32 | −4.857 | −55.286 | −18.422 | 1 | 34.09 |
| 3103 | CA | PRO | 32 | −3.055 | −53.807 | −17.788 | 1 | 33.82 |
| 3104 | CB | PRO | 32 | −2.883 | −55.198 | −17.181 | 1 | 34.39 |
| 3105 | CG | PRO | 32 | −4.289 | −55.69 | −17.08 | 1 | 34.88 |
| 3106 | C | PRO | 32 | −1.81 | −53.359 | −18.553 | 1 | 33.34 |
| 3107 | O | PRO | 32 | −1.088 | −52.466 | −18.11 | 1 | 33.7 |
| 3108 | N | GLU | 33 | −1.562 | −53.984 | −19.7 | 1 | 32.43 |
| 3109 | CA | GLU | 33 | −0.399 | −53.65 | −20.515 | 1 | 31.77 |
| 3110 | CB | GLU | 33 | −0.372 | −54.517 | −21.775 | 1 | 33.62 |
| 3111 | CG | GLU | 33 | 0.808 | −54.243 | −22.691 | 1 | 36.83 |
| 3112 | CD | GLU | 33 | 0.879 | −55.212 | −23.855 | 1 | 39.57 |
| 3113 | OE1 | GLU | 33 | −0.102 | −55.297 | −24.625 | 1 | 41.13 |
| 3114 | OE2 | GLU | 33 | 1.918 | −55.89 | −23.999 | 1 | 40.6 |
| 3115 | C | GLU | 33 | −0.386 | −52.174 | −20.899 | 1 | 30.18 |
| 3116 | O | GLU | 33 | 0.64 | −51.503 | −20.778 | 1 | 29.16 |
| 3117 | N | LEU | 34 | −1.524 | −51.671 | −21.364 | 1 | 28.58 |
| 3118 | CA | LEU | 34 | −1.621 | −50.27 | −21.75 | 1 | 27.18 |
| 3119 | CB | LEU | 34 | −2.968 | −49.99 | −22.422 | 1 | 27.47 |
| 3120 | CG | LEU | 34 | −3.208 | −48.541 | −22.86 | 1 | 26.78 |
| 3121 | CD1 | LEU | 34 | −2.134 | −48.111 | −23.85 | 1 | 26.82 |
| 3122 | CD2 | LEU | 34 | −4.588 | −48.423 | −23.489 | 1 | 28.35 |

TABLE 2-continued

| Atom | Atom Type | Residue | # | X | Y | Z | OCC | B |
|---|---|---|---|---|---|---|---|---|
| 3123 | C | LEU | 34 | −1.466 | −49.387 | −20.517 | 1 | 27.29 |
| 3124 | O | LEU | 34 | −0.871 | −48.313 | −20.586 | 1 | 26.58 |
| 3125 | N | GLN | 35 | −2.004 | −49.843 | −19.389 | 1 | 27.42 |
| 3126 | CA | GLN | 35 | −1.906 | −49.085 | −18.147 | 1 | 28.81 |
| 3127 | CB | GLN | 35 | −2.719 | −49.759 | −17.038 | 1 | 31.14 |
| 3128 | CG | GLN | 35 | −4.221 | −49.571 | −17.171 | 1 | 36.22 |
| 3129 | CD | GLN | 35 | −4.987 | −50.173 | −16.008 | 1 | 39 |
| 3130 | OE1 | GLN | 35 | −4.727 | −49.854 | −14.846 | 1 | 41.53 |
| 3131 | NE2 | GLN | 35 | −5.941 | −51.045 | −16.315 | 1 | 40.86 |
| 3132 | C | GLN | 35 | −0.454 | −48.93 | −17.704 | 1 | 28.14 |
| 3133 | O | GLN | 35 | −0.058 | −47.867 | −17.226 | 1 | 29.17 |
| 3134 | N | ARG | 36 | 0.336 | −49.989 | −17.86 | 1 | 27.88 |
| 3135 | CA | ARG | 36 | 1.744 | −49.939 | −17.482 | 1 | 26.94 |
| 3136 | CB | ARG | 36 | 2.382 | −51.333 | −17.546 | 1 | 29.47 |
| 3137 | CG | ARG | 36 | 1.943 | −52.281 | −16.437 | 1 | 33.6 |
| 3138 | CD | ARG | 36 | 2.863 | −53.498 | −16.353 | 1 | 35.38 |
| 3139 | NE | ARG | 36 | 2.728 | −54.391 | −17.501 | 1 | 37.03 |
| 3140 | CZ | ARG | 36 | 1.697 | −55.209 | −17.698 | 1 | 38.55 |
| 3141 | NH1 | ARG | 36 | 0.703 | −55.252 | −16.82 | 1 | 38.16 |
| 3142 | NH2 | ARG | 36 | 1.659 | −55.986 | −18.772 | 1 | 38.44 |
| 3143 | C | ARG | 36 | 2.504 | −48.988 | −18.401 | 1 | 25.23 |
| 3144 | O | ARG | 36 | 3.399 | −48.268 | −17.96 | 1 | 25.27 |
| 3145 | N | LEU | 37 | 2.144 | −48.986 | −19.68 | 1 | 22.77 |
| 3146 | CA | LEU | 37 | 2.801 | −48.112 | −20.644 | 1 | 21.36 |
| 3147 | CB | LEU | 37 | 2.346 | −48.444 | −22.069 | 1 | 20.06 |
| 3148 | CG | LEU | 37 | 2.844 | −47.499 | −23.169 | 1 | 19.89 |
| 3149 | CD1 | LEU | 37 | 4.37 | −47.445 | −23.161 | 1 | 21.21 |
| 3150 | CD2 | LEU | 37 | 2.332 | −47.971 | −24.52 | 1 | 20.03 |
| 3151 | C | LEU | 37 | 2.508 | −46.644 | −20.345 | 1 | 21.94 |
| 3152 | O | LEU | 37 | 3.422 | −45.819 | −20.294 | 1 | 21.51 |
| 3153 | N | THR | 38 | 1.235 | −46.317 | −20.147 | 1 | 21.8 |
| 3154 | CA | THR | 38 | 0.856 | −44.938 | −19.862 | 1 | 22.74 |
| 3155 | CB | THR | 38 | −0.68 | −44.772 | −19.844 | 1 | 24.04 |
| 3156 | OG1 | THR | 38 | −1.254 | −45.675 | −18.893 | 1 | 26.44 |
| 3157 | CG2 | THR | 38 | −1.253 | −45.065 | −21.218 | 1 | 23.11 |
| 3158 | C | THR | 38 | 1.442 | −44.471 | −18.534 | 1 | 22.71 |
| 3159 | O | THR | 38 | 1.874 | −43.326 | −18.404 | 1 | 22.33 |
| 3160 | N | GLN | 39 | 1.466 | −45.365 | −17.554 | 1 | 23.06 |
| 3161 | CA | GLN | 39 | 2.014 | −45.039 | −16.246 | 1 | 24.18 |
| 3162 | CB | GLN | 39 | 1.836 | −46.224 | −15.293 | 1 | 28.01 |
| 3163 | CG | GLN | 39 | 2.41 | −46.011 | −13.904 | 1 | 33.61 |
| 3164 | CD | GLN | 39 | 2.132 | −47.182 | −12.979 | 1 | 36.23 |
| 3165 | OE1 | GLN | 39 | 2.547 | −48.31 | −13.244 | 1 | 40 |
| 3166 | NE2 | GLN | 39 | 1.419 | −46.919 | −11.888 | 1 | 38.01 |
| 3167 | C | GLN | 39 | 3.495 | −44.696 | −16.38 | 1 | 22.84 |
| 3168 | O | GLN | 39 | 3.977 | −43.74 | −15.774 | 1 | 22.61 |
| 3169 | N | ARG | 40 | 4.21 | −45.472 | −17.189 | 1 | 22.39 |
| 3170 | CA | ARG | 40 | 5.639 | −45.253 | −17.395 | 1 | 21.23 |
| 3171 | CB | ARG | 40 | 6.253 | −46.452 | −18.129 | 1 | 25.03 |
| 3172 | CG | ARG | 40 | 7.765 | −46.381 | −18.286 | 1 | 28.35 |
| 3173 | CD | ARG | 40 | 8.456 | −46.175 | −16.942 | 1 | 33.23 |
| 3174 | NE | ARG | 40 | 8.169 | −47.25 | −15.994 | 1 | 36.1 |
| 3175 | CZ | ARG | 40 | 8.592 | −48.503 | −16.129 | 1 | 38.42 |
| 3176 | NH1 | ARG | 40 | 9.327 | −48.851 | −17.177 | 1 | 40.06 |
| 3177 | NH2 | ARG | 40 | 8.282 | −49.411 | −15.212 | 1 | 39.14 |
| 3178 | C | ARG | 40 | 5.906 | −43.965 | −18.174 | 1 | 20.8 |
| 3179 | O | ARG | 40 | 6.835 | −43.223 | −17.86 | 1 | 18.81 |
| 3180 | N | LEU | 41 | 5.095 | −43.703 | −19.195 | 1 | 19.17 |
| 3181 | CA | LEU | 41 | 5.259 | −42.488 | −19.986 | 1 | 19.21 |
| 3182 | CB | LEU | 41 | 4.18 | −42.395 | −21.069 | 1 | 20.49 |
| 3183 | CG | LEU | 41 | 4.432 | −43.097 | −22.4 | 1 | 22.15 |
| 3184 | CD1 | LEU | 41 | 3.168 | −43.029 | −23.253 | 1 | 23.01 |
| 3185 | CD2 | LEU | 41 | 5.599 | −42.429 | −23.12 | 1 | 19.91 |
| 3186 | C | LEU | 41 | 5.163 | −41.264 | −19.089 | 1 | 18.42 |
| 3187 | O | LEU | 41 | 6.007 | −40.373 | −19.141 | 1 | 18.24 |
| 3188 | N | VAL | 42 | 4.122 | −41.223 | −18.264 | 1 | 18.91 |
| 3189 | CA | VAL | 42 | 3.921 | −40.098 | −17.366 | 1 | 19.31 |
| 3190 | CB | VAL | 42 | 2.575 | −40.217 | −16.627 | 1 | 20.25 |
| 3191 | CG1 | VAL | 42 | 2.424 | −39.079 | −15.628 | 1 | 20.88 |
| 3192 | CG2 | VAL | 42 | 1.435 | −40.188 | −17.634 | 1 | 19.8 |
| 3193 | C | VAL | 42 | 5.049 | −39.995 | −16.348 | 1 | 18.8 |
| 3194 | O | VAL | 42 | 5.529 | −38.903 | −16.046 | 1 | 19.68 |
| 3195 | N | GLN | 43 | 5.482 | −41.138 | −15.828 | 1 | 19.52 |
| 3196 | CA | GLN | 43 | 6.554 | −41.15 | −14.844 | 1 | 19.78 |
| 3197 | CB | GLN | 43 | 6.765 | −42.572 | −14.317 | 1 | 22.49 |
| 3198 | CG | GLN | 43 | 7.941 | −42.712 | −13.37 | 1 | 27.96 |
| 3199 | CD | GLN | 43 | 7.902 | −44.007 | −12.587 | 1 | 30.44 |
| 3200 | OE1 | GLN | 43 | 7.673 | −45.079 | −13.147 | 1 | 33.52 |
| 3201 | NE2 | GLN | 43 | 8.131 | −43.914 | −11.284 | 1 | 35.39 |
| 3202 | C | GLN | 43 | 7.858 | −40.598 | −15.414 | 1 | 18.13 |
| 3203 | O | GLN | 43 | 8.531 | −39.793 | −14.772 | 1 | 17.93 |
| 3204 | N | VAL | 44 | 8.213 | −41.027 | −16.622 | 1 | 18.6 |
| 3205 | CA | VAL | 44 | 9.441 | −40.556 | −17.249 | 1 | 17.87 |
| 3206 | CB | VAL | 44 | 9.776 | −41.378 | −18.512 | 1 | 17.97 |
| 3207 | CG1 | VAL | 44 | 10.999 | −40.795 | −19.21 | 1 | 18.58 |
| 3208 | CG2 | VAL | 44 | 10.038 | −42.82 | −18.124 | 1 | 19.02 |
| 3209 | C | VAL | 44 | 9.323 | −39.085 | −17.615 | 1 | 17.04 |
| 3210 | O | VAL | 44 | 10.257 | −38.31 | −17.422 | 1 | 16.88 |
| 3211 | N | MET | 45 | 8.166 | −38.698 | −18.142 | 1 | 16.19 |
| 3212 | CA | MET | 45 | 7.941 | −37.311 | −18.512 | 1 | 18.22 |
| 3213 | CB | MET | 45 | 6.528 | −37.137 | −19.08 | 1 | 18.44 |
| 3214 | CG | MET | 45 | 6.159 | −35.695 | −19.391 | 1 | 20.19 |
| 3215 | SD | MET | 45 | 4.502 | −35.535 | −20.105 | 1 | 21.34 |
| 3216 | CE | MET | 45 | 3.484 | −35.88 | −18.679 | 1 | 21.79 |
| 3217 | C | MET | 45 | 8.128 | −36.41 | −17.295 | 1 | 17.86 |
| 3218 | O | MET | 45 | 8.829 | −35.404 | −17.358 | 1 | 18.5 |
| 3219 | N | ARG | 46 | 7.513 | −36.785 | −16.178 | 1 | 19.33 |
| 3220 | CA | ARG | 46 | 7.617 | −35.987 | −14.964 | 1 | 20.33 |
| 3221 | CB | ARG | 46 | 6.584 | −36.463 | −13.941 | 1 | 21.32 |
| 3222 | CG | ARG | 46 | 5.162 | −36.087 | −14.337 | 1 | 22.03 |
| 3223 | CD | ARG | 46 | 4.128 | −36.692 | −13.408 | 1 | 23.52 |
| 3224 | NE | ARG | 46 | 2.793 | −36.167 | −13.687 | 1 | 23.29 |
| 3225 | CZ | ARG | 46 | 1.673 | −36.647 | −13.156 | 1 | 24.61 |
| 3226 | NH1 | ARG | 46 | 1.72 | −37.671 | −12.316 | 1 | 26.4 |
| 3227 | NH2 | ARG | 46 | 0.506 | −36.097 | −13.46 | 1 | 23.7 |
| 3228 | C | ARG | 46 | 9.019 | −35.982 | −14.357 | 1 | 21.43 |
| 3229 | O | ARG | 46 | 9.482 | −34.948 | −13.879 | 1 | 21.33 |
| 3230 | N | ARG | 47 | 9.696 | −37.126 | −14.381 | 1 | 20.61 |
| 3231 | CA | ARG | 47 | 11.049 | −37.202 | −13.836 | 1 | 21.28 |
| 3232 | CB | ARG | 47 | 11.55 | −38.652 | −13.835 | 1 | 22.93 |
| 3233 | CG | ARG | 47 | 10.987 | −39.503 | −12.704 | 1 | 28.64 |
| 3234 | CD | ARG | 47 | 11.518 | −40.93 | −12.767 | 1 | 31.82 |
| 3235 | NE | ARG | 47 | 11.026 | −41.751 | −11.663 | 1 | 35.78 |
| 3236 | CZ | ARG | 47 | 11.432 | −41.636 | −10.402 | 1 | 38.25 |
| 3237 | NH1 | ARG | 47 | 12.347 | −40.732 | −10.076 | 1 | 38.81 |
| 3238 | NH2 | ARG | 47 | 10.921 | −42.425 | −9.465 | 1 | 39.66 |
| 3239 | C | ARG | 47 | 12.01 | −36.325 | −14.632 | 1 | 20.31 |
| 3240 | O | ARG | 47 | 12.93 | −35.728 | −14.075 | 1 | 21.57 |
| 3241 | N | ARG | 48 | 11.79 | −36.245 | −15.94 | 1 | 20.22 |
| 3242 | CA | ARG | 48 | 12.639 | −35.441 | −16.811 | 1 | 20.38 |
| 3243 | CB | ARG | 48 | 12.655 | −36.039 | −18.219 | 1 | 20.91 |
| 3244 | CG | ARG | 48 | 13.435 | −37.341 | −18.317 | 1 | 22.47 |
| 3245 | CD | ARG | 48 | 14.9 | −37.096 | −18.005 | 1 | 25.38 |
| 3246 | NE | ARG | 48 | 15.457 | −36.083 | −18.895 | 1 | 28.21 |
| 3247 | CZ | ARG | 48 | 16.26 | −35.102 | −18.502 | 1 | 28.15 |
| 3248 | NH1 | ARG | 48 | 16.608 | −34.998 | −17.227 | 1 | 31.8 |
| 3249 | NH2 | ARG | 48 | 16.706 | −34.219 | −19.382 | 1 | 30.68 |
| 3250 | C | ARG | 48 | 12.195 | −33.984 | −16.866 | 1 | 21.11 |
| 3251 | O | ARG | 48 | 12.859 | −33.144 | −17.474 | 1 | 20.86 |
| 3252 | N | ARG | 49 | 11.069 | −33.69 | −16.228 | 1 | 21.44 |
| 3253 | CA | ARG | 49 | 10.546 | −32.332 | −16.192 | 1 | 23.17 |
| 3254 | CB | ARG | 49 | 11.566 | −31.395 | −15.534 | 1 | 25.82 |
| 3255 | CG | ARG | 49 | 12.027 | −31.827 | −14.145 | 1 | 29.55 |
| 3256 | CD | ARG | 49 | 10.912 | −31.725 | −13.119 | 1 | 32.65 |
| 3257 | NE | ARG | 49 | 11.366 | −32.099 | −11.781 | 1 | 36 |
| 3258 | CZ | ARG | 49 | 11.687 | −33.337 | −11.415 | 1 | 36.09 |
| 3259 | NH1 | ARG | 49 | 11.603 | −34.332 | −12.285 | 1 | 38.89 |
| 3260 | NH2 | ARG | 49 | 12.093 | −33.58 | −10.176 | 1 | 39.93 |
| 3261 | C | ARG | 49 | 10.191 | −31.798 | −17.581 | 1 | 22.34 |
| 3262 | O | ARG | 49 | 10.291 | −30.596 | −17.828 | 1 | 24.34 |
| 3263 | N | CYS | 50 | 9.796 | −32.68 | −18.494 | 1 | 21.33 |
| 3264 | CA | CYS | 50 | 9.414 | −32.22 | −19.824 | 1 | 20.74 |
| 3265 | CB | CYS | 50 | 9.981 | −33.134 | −20.919 | 1 | 21.05 |
| 3266 | SG | CYS | 50 | 9.552 | −34.867 | −20.828 | 1 | 21.31 |
| 3267 | C | CYS | 50 | 7.891 | −32.139 | −19.883 | 1 | 19.2 |
| 3268 | O | CYS | 50 | 7.208 | −32.584 | −18.96 | 1 | 18.99 |
| 3269 | N | VAL | 51 | 7.357 | −31.576 | −20.959 | 1 | 17.39 |
| 3270 | CA | VAL | 51 | 5.913 | −31.386 | −21.063 | 1 | 15.23 |
| 3271 | CB | VAL | 51 | 5.61 | −29.95 | −21.508 | 1 | 16.1 |
| 3272 | CG1 | VAL | 51 | 6.105 | −28.972 | −20.449 | 1 | 18.4 |
| 3273 | CG2 | VAL | 51 | 6.296 | −29.663 | −22.823 | 1 | 17.3 |
| 3274 | C | VAL | 51 | 5.141 | −32.353 | −21.951 | 1 | 14.86 |

TABLE 2-continued

| Atom | Atom Type | Residue | # | X | Y | Z | OCC | B |
|---|---|---|---|---|---|---|---|---|
| 3275 | O | VAL | 51 | 3.922 | −32.237 | −22.093 | 1 | 15.66 |
| 3276 | N | GLY | 52 | 5.845 | −33.312 | −22.537 | 1 | 14.22 |
| 3277 | CA | GLY | 52 | 5.185 | −34.285 | −23.384 | 1 | 13.24 |
| 3278 | C | GLY | 52 | 6.131 | −35.43 | −23.662 | 1 | 13.28 |
| 3279 | O | GLY | 52 | 7.344 | −35.254 | −23.604 | 1 | 14.38 |
| 3280 | N | LEU | 53 | 5.578 | −36.605 | −23.936 | 1 | 12.45 |
| 3281 | CA | LEU | 53 | 6.396 | −37.774 | −24.243 | 1 | 13.62 |
| 3282 | CB | LEU | 53 | 6.945 | −38.397 | −22.955 | 1 | 14.56 |
| 3283 | CG | LEU | 53 | 8.107 | −39.38 | −23.12 | 1 | 15.39 |
| 3284 | CD1 | LEU | 53 | 9.309 | −38.658 | −23.716 | 1 | 16.97 |
| 3285 | CD2 | LEU | 53 | 8.469 | −39.967 | −21.76 | 1 | 17.24 |
| 3286 | C | LEU | 53 | 5.538 | −38.781 | −24.997 | 1 | 13.92 |
| 3287 | O | LEU | 53 | 4.339 | −38.904 | −24.733 | 1 | 14.24 |
| 3288 | N | SER | 54 | 6.149 | −39.499 | −25.936 | 1 | 12.02 |
| 3289 | CA | SER | 54 | 5.426 | −40.484 | −26.741 | 1 | 12.86 |
| 3290 | CB | SER | 54 | 5.499 | −40.102 | −28.219 | 1 | 14.2 |
| 3291 | OG | SER | 54 | 6.829 | −40.213 | −28.699 | 1 | 16.7 |
| 3292 | C | SER | 54 | 5.988 | −41.891 | −26.554 | 1 | 13.85 |
| 3293 | O | SER | 54 | 7.165 | −42.058 | −26.234 | 1 | 14.13 |
| 3294 | N | ALA | 55 | 5.144 | −42.898 | −26.772 | 1 | 13.44 |
| 3295 | CA | ALA | 55 | 5.548 | −44.291 | −26.609 | 1 | 13.82 |
| 3296 | CB | ALA | 55 | 4.383 | −45.216 | −26.964 | 1 | 14.51 |
| 3297 | C | ALA | 55 | 6.796 | −44.681 | −27.407 | 1 | 13.82 |
| 3298 | O | ALA | 55 | 7.657 | −45.399 | −26.897 | 1 | 13.73 |
| 3299 | N | PRO | 56 | 6.911 | −44.226 | −28.669 | 1 | 13.12 |
| 3300 | CD | PRO | 56 | 5.917 | −43.553 | −29.528 | 1 | 11.79 |
| 3301 | CA | PRO | 56 | 8.103 | −44.592 | −29.442 | 1 | 12.96 |
| 3302 | CB | PRO | 56 | 7.894 | −43.852 | −30.762 | 1 | 13.44 |
| 3303 | CG | PRO | 56 | 6.398 | −43.912 | −30.925 | 1 | 11.86 |
| 3304 | C | PRO | 56 | 9.409 | −44.199 | −28.752 | 1 | 13.29 |
| 3305 | O | PRO | 56 | 10.442 | −44.851 | −28.929 | 1 | 13.64 |
| 3306 | N | GLN | 57 | 9.359 | −43.138 | −27.953 | 1 | 12.69 |
| 3307 | CA | GLN | 57 | 10.545 | −42.67 | −27.25 | 1 | 12.9 |
| 3308 | CB | GLN | 57 | 10.316 | −41.25 | −26.74 | 1 | 13.39 |
| 3309 | CG | GLN | 57 | 10.249 | −40.225 | −27.862 | 1 | 13.99 |
| 3310 | CD | GLN | 57 | 9.818 | −38.869 | −27.368 | 1 | 14.08 |
| 3311 | OE1 | GLN | 57 | 8.626 | −38.608 | −27.207 | 1 | 15.21 |
| 3312 | NE2 | GLN | 57 | 10.786 | −38 | −27.104 | 1 | 14.21 |
| 3313 | C | GLN | 57 | 10.958 | −43.598 | −26.115 | 1 | 13.68 |
| 3314 | O | GLN | 57 | 12.067 | −43.487 | −25.586 | 1 | 14.09 |
| 3315 | N | LEU | 58 | 10.063 | −44.508 | −25.737 | 1 | 13.64 |
| 3316 | CA | LEU | 58 | 10.37 | −45.487 | −24.702 | 1 | 14.88 |
| 3317 | CB | LEU | 58 | 9.244 | −45.578 | −23.666 | 1 | 15.44 |
| 3318 | CG | LEU | 58 | 9.059 | −44.323 | −22.806 | 1 | 16.74 |
| 3319 | CD1 | LEU | 58 | 8.017 | −44.59 | −21.729 | 1 | 20.12 |
| 3320 | CD2 | LEU | 58 | 10.388 | −43.932 | −22.171 | 1 | 18.72 |
| 3321 | C | LEU | 58 | 10.577 | −46.84 | −25.379 | 1 | 15.69 |
| 3322 | O | LEU | 58 | 10.601 | −47.881 | −24.721 | 1 | 19.6 |
| 3323 | N | GLY | 59 | 10.715 | −46.807 | −26.703 | 1 | 14.8 |
| 3324 | CA | GLY | 59 | 10.946 | −48.018 | −27.477 | 1 | 15.3 |
| 3325 | C | GLY | 59 | 9.71 | −48.817 | −27.842 | 1 | 16.22 |
| 3326 | O | GLY | 59 | 9.813 | −49.96 | −28.29 | 1 | 17.14 |
| 3327 | N | VAL | 60 | 8.541 | −48.212 | −27.665 | 1 | 16.53 |
| 3328 | CA | VAL | 60 | 7.276 | −48.877 | −27.96 | 1 | 16.44 |
| 3329 | CB | VAL | 60 | 6.349 | −48.815 | −26.734 | 1 | 16.46 |
| 3330 | CG1 | VAL | 60 | 5.052 | −49.546 | −27.018 | 1 | 18.3 |
| 3331 | CG2 | VAL | 60 | 7.054 | −49.425 | −25.529 | 1 | 19.66 |
| 3332 | C | VAL | 60 | 6.607 | −48.201 | −29.152 | 1 | 17.27 |
| 3333 | O | VAL | 60 | 6.078 | −47.095 | −29.033 | 1 | 16.09 |
| 3334 | N | PRO | 61 | 6.62 | −48.861 | −30.322 | 1 | 15.27 |
| 3335 | CD | PRO | 61 | 7.241 | −50.172 | −30.597 | 1 | 17.58 |
| 3336 | CA | PRO | 61 | 6.018 | −48.309 | −31.539 | 1 | 16.11 |
| 3337 | CB | PRO | 61 | 6.648 | −49.153 | −32.637 | 1 | 16.21 |
| 3338 | CG | PRO | 61 | 6.725 | −50.495 | −31.989 | 1 | 16.18 |
| 3339 | C | PRO | 61 | 4.495 | −48.362 | −31.562 | 1 | 17.36 |
| 3340 | O | PRO | 61 | 3.9 | −49.015 | −32.423 | 1 | 17.03 |
| 3341 | N | ARG | 62 | 3.877 | −47.66 | −30.616 | 1 | 17.11 |
| 3342 | CA | ARG | 62 | 2.422 | −47.612 | −30.508 | 1 | 17.09 |
| 3343 | CB | ARG | 62 | 1.96 | −48.395 | −29.274 | 1 | 18.58 |
| 3344 | CG | ARG | 62 | 2.417 | −49.85 | −29.268 | 1 | 22.26 |
| 3345 | CD | ARG | 62 | 1.969 | −50.585 | −28.013 | 1 | 25.92 |
| 3346 | NE | ARG | 62 | 0.546 | −50.916 | −28.038 | 1 | 28.93 |
| 3347 | CZ | ARG | 62 | −0.111 | −51.458 | −27.017 | 1 | 29.17 |
| 3348 | NH1 | ARG | 62 | 0.524 | −51.729 | −25.885 | 1 | 31.05 |
| 3349 | NH2 | ARG | 62 | −1.402 | −51.741 | −27.132 | 1 | 30.54 |
| 3350 | C | ARG | 62 | 1.945 | −46.167 | −30.415 | 1 | 16.95 |
| 3351 | O | ARG | 62 | 2.653 | −45.3 | −29.9 | 1 | 16.56 |
| 3352 | N | GLN | 63 | 0.738 | −45.913 | −30.911 | 1 | 15.46 |
| 3353 | CA | GLN | 63 | 0.171 | −44.568 | −30.898 | 1 | 15.44 |
| 3354 | CB | GLN | 63 | −0.958 | −44.476 | −31.927 | 1 | 13.81 |
| 3355 | CG | GLN | 63 | −0.462 | −44.527 | −33.362 | 1 | 16.56 |
| 3356 | CD | GLN | 63 | −1.59 | −44.648 | −34.365 | 1 | 18.1 |
| 3357 | OE1 | GLN | 63 | −2.651 | −44.05 | −34.194 | 1 | 19.57 |
| 3358 | NE2 | GLN | 63 | −1.359 | −45.413 | −35.429 | 1 | 19.39 |
| 3359 | C | GLN | 63 | −0.334 | −44.144 | −29.524 | 1 | 15.82 |
| 3360 | O | GLN | 63 | −1.54 | −44.144 | −29.256 | 1 | 14.45 |
| 3361 | N | VAL | 64 | 0.603 | −43.772 | −28.656 | 1 | 14.5 |
| 3362 | CA | VAL | 64 | 0.277 | −43.338 | −27.304 | 1 | 14.46 |
| 3363 | CB | VAL | 64 | 0.5 | −44.474 | −26.282 | 1 | 15.41 |
| 3364 | CG1 | VAL | 64 | 0.081 | −44.016 | −24.89 | 1 | 15.52 |
| 3365 | CG2 | VAL | 64 | −0.275 | −45.715 | −26.702 | 1 | 15.55 |
| 3366 | C | VAL | 64 | 1.189 | −42.176 | −26.931 | 1 | 15.2 |
| 3367 | O | VAL | 64 | 2.391 | −42.228 | −27.172 | 1 | 15.24 |
| 3368 | N | LEU | 65 | 0.617 | −41.121 | −26.363 | 1 | 14.42 |
| 3369 | CA | LEU | 65 | 1.413 | −39.976 | −25.95 | 1 | 14.58 |
| 3370 | CB | LEU | 65 | 1.558 | −38.969 | −27.102 | 1 | 14.29 |
| 3371 | CG | LEU | 65 | 0.318 | −38.315 | −27.719 | 1 | 14.02 |
| 3372 | CD1 | LEU | 65 | −0.207 | −37.245 | −26.783 | 1 | 15.78 |
| 3373 | CD2 | LEU | 65 | 0.677 | −37.696 | −29.066 | 1 | 15.34 |
| 3374 | C | LEU | 65 | 0.773 | −39.328 | −24.734 | 1 | 15.14 |
| 3375 | O | LEU | 65 | −0.42 | −39.505 | −24.481 | 1 | 16.18 |
| 3376 | N | ALA | 66 | 1.583 | −38.605 | −23.971 | 1 | 14.13 |
| 3377 | CA | ALA | 66 | 1.118 | −37.921 | −22.769 | 1 | 14.79 |
| 3378 | CB | ALA | 66 | 1.716 | −38.575 | −21.533 | 1 | 14.78 |
| 3379 | C | ALA | 66 | 1.551 | −36.468 | −22.858 | 1 | 14.78 |
| 3380 | O | ALA | 66 | 2.603 | −36.162 | −23.42 | 1 | 14.5 |
| 3381 | N | LEU | 67 | 0.733 | −35.575 | −22.306 | 1 | 15.17 |
| 3382 | CA | LEU | 67 | 1.018 | −34.147 | −22.339 | 1 | 16.55 |
| 3383 | CB | LEU | 67 | 0.176 | −33.474 | −23.428 | 1 | 18.1 |
| 3384 | CG | LEU | 67 | 0.18 | −34.089 | −24.831 | 1 | 18.58 |
| 3385 | CD1 | LEU | 67 | −0.986 | −33.532 | −25.635 | 1 | 21.68 |
| 3386 | CD2 | LEU | 67 | 1.503 | −33.806 | −25.522 | 1 | 22.2 |
| 3387 | C | LEU | 67 | 0.661 | −33.532 | −20.992 | 1 | 15.79 |
| 3388 | O | LEU | 67 | −0.386 | −33.835 | −20.431 | 1 | 16.38 |
| 3389 | N | GLU | 68 | 1.527 | −32.67 | −20.475 | 1 | 15.29 |
| 3390 | CA | GLU | 68 | 1.257 | −32.017 | −19.199 | 1 | 16.04 |
| 3391 | CB | GLU | 68 | 1.434 | −33.005 | −18.041 | 1 | 17.14 |
| 3392 | CG | GLU | 68 | 1.243 | −32.373 | −16.666 | 1 | 19.23 |
| 3393 | CD | GLU | 68 | 1.523 | −33.338 | −15.529 | 1 | 23.31 |
| 3394 | OE1 | GLU | 68 | 2.586 | −33.991 | −15.551 | 1 | 24.81 |
| 3395 | OE2 | GLU | 68 | 0.684 | −33.437 | −14.61 | 1 | 26.31 |
| 3396 | C | GLU | 68 | 2.168 | −30.82 | −18.981 | 1 | 17.11 |
| 3397 | O | GLU | 68 | 3.381 | −30.91 | −19.17 | 1 | 17.04 |
| 3398 | N | LEU | 69 | 1.582 | −29.697 | −18.577 | 1 | 16.67 |
| 3399 | CA | LEU | 69 | 2.362 | −28.498 | −18.324 | 1 | 16.87 |
| 3400 | CB | LEU | 69 | 2.158 | −27.478 | −19.449 | 1 | 17.79 |
| 3401 | CG | LEU | 69 | 2.872 | −26.131 | −19.301 | 1 | 19.12 |
| 3402 | CD1 | LEU | 69 | 4.35 | −26.344 | −18.991 | 1 | 21.85 |
| 3403 | CD2 | LEU | 69 | 2.704 | −25.328 | −20.58 | 1 | 19.18 |
| 3404 | C | LEU | 69 | 1.98 | −27.884 | −16.985 | 1 | 18.66 |
| 3405 | O | LEU | 69 | 1.058 | −27.071 | −16.899 | 1 | 17.72 |
| 3406 | N | PRO | 70 | 2.679 | −28.282 | −15.911 | 1 | 20.01 |
| 3407 | CD | PRO | 70 | 3.726 | −29.316 | −15.844 | 1 | 20.56 |
| 3408 | CA | PRO | 70 | 2.386 | −27.743 | −14.58 | 1 | 21.06 |
| 3409 | CB | PRO | 70 | 3.289 | −28.57 | −13.66 | 1 | 22.58 |
| 3410 | CG | PRO | 70 | 4.427 | −28.971 | −14.556 | 1 | 23.83 |
| 3411 | C | PRO | 70 | 2.658 | −26.245 | −14.488 | 1 | 20.85 |
| 3412 | O | PRO | 70 | 3.504 | −25.706 | −15.199 | 1 | 20.7 |
| 3413 | N | GLU | 71 | 1.919 | −25.577 | −13.612 | 1 | 22.37 |
| 3414 | CA | GLU | 71 | 2.062 | −24.141 | −13.422 | 1 | 23.8 |
| 3415 | CB | GLU | 71 | 1.112 | −23.678 | −12.317 | 1 | 26.51 |
| 3416 | CG | GLU | 71 | 1.225 | −22.211 | −11.96 | 1 | 31.64 |
| 3417 | CD | GLU | 71 | 0.227 | −21.806 | −10.893 | 1 | 35.36 |
| 3418 | OE1 | GLU | 71 | 0.226 | −22.434 | −9.811 | 1 | 37.93 |
| 3419 | OE2 | GLU | 71 | −0.555 | −20.864 | −11.136 | 1 | 38.03 |
| 3420 | C | GLU | 71 | 3.495 | −23.729 | −13.084 | 1 | 22.89 |
| 3421 | O | GLU | 71 | 3.987 | −22.717 | −13.581 | 1 | 22.94 |
| 3422 | N | ALA | 72 | 4.156 | −24.516 | −12.242 | 1 | 23.4 |
| 3423 | CA | ALA | 72 | 5.53 | −24.225 | −11.836 | 1 | 24.62 |
| 3424 | CB | ALA | 72 | 6.05 | −25.332 | −10.929 | 1 | 25.54 |
| 3425 | C | ALA | 72 | 6.459 | −24.055 | −13.036 | 1 | 25.43 |
| 3426 | O | ALA | 72 | 7.309 | −23.164 | −13.054 | 1 | 24.27 |

TABLE 2-continued

| Atom | Atom Type | Residue | # | X | Y | Z | OCC | B |
|---|---|---|---|---|---|---|---|---|
| 3427 | N | LEU | 73 | 6.294 | −24.907 | −14.042 | 1 | 26.6 |
| 3428 | CA | LEU | 73 | 7.134 | −24.838 | −15.229 | 1 | 27.67 |
| 3429 | CB | LEU | 73 | 6.874 | −26.055 | −16.121 | 1 | 29.69 |
| 3430 | CG | LEU | 73 | 7.975 | −26.426 | −17.115 | 1 | 31.72 |
| 3431 | CD1 | LEU | 73 | 9.315 | −26.53 | −16.398 | 1 | 31.54 |
| 3432 | CD2 | LEU | 73 | 7.627 | −27.749 | −17.775 | 1 | 31.05 |
| 3433 | C | LEU | 73 | 6.905 | −23.541 | −16.006 | 1 | 28.33 |
| 3434 | O | LEU | 73 | 7.843 | −22.976 | −16.569 | 1 | 28.74 |
| 3435 | N | CYS | 74 | 5.662 | −23.066 | −16.041 | 1 | 26.84 |
| 3436 | CA | CYS | 74 | 5.353 | −21.821 | −16.739 | 1 | 27.07 |
| 3437 | CB | CYS | 74 | 3.84 | −21.611 | −16.847 | 1 | 26.76 |
| 3438 | SG | CYS | 74 | 2.988 | −22.74 | −17.945 | 1 | 26.24 |
| 3439 | C | CYS | 74 | 5.947 | −20.642 | −15.984 | 1 | 27.53 |
| 3440 | O | CYS | 74 | 6.401 | −19.669 | −16.587 | 1 | 28.43 |
| 3441 | N | ARG | 75 | 5.932 | −20.733 | −14.657 | 1 | 28.17 |
| 3442 | CA | ARG | 75 | 6.452 | −19.667 | −13.813 | 1 | 29.42 |
| 3443 | CB | ARG | 75 | 5.978 | −19.86 | −12.371 | 1 | 29.75 |
| 3444 | CG | ARG | 75 | 4.486 | −19.624 | −12.201 | 1 | 31.28 |
| 3445 | CD | ARG | 75 | 4.057 | −19.665 | −10.744 | 1 | 32.65 |
| 3446 | NE | ARG | 75 | 2.648 | −19.306 | −10.604 | 1 | 35.47 |
| 3447 | CZ | ARG | 75 | 1.989 | −19.275 | −9.449 | 1 | 36.74 |
| 3448 | NH1 | ARG | 75 | 2.607 | −19.582 | −8.316 | 1 | 36.55 |
| 3449 | NH2 | ARG | 75 | 0.707 | −18.932 | −9.428 | 1 | 36.96 |
| 3450 | C | ARG | 75 | 7.969 | −19.532 | −13.858 | 1 | 30.75 |
| 3451 | O | ARG | 75 | 8.509 | −18.483 | −13.509 | 1 | 30.25 |
| 3452 | N | GLU | 76 | 8.654 | −20.588 | −14.286 | 1 | 31.62 |
| 3453 | CA | GLU | 76 | 10.11 | −20.549 | −14.394 | 1 | 33.07 |
| 3454 | CB | GLU | 76 | 10.669 | −21.945 | −14.663 | 1 | 33.74 |
| 3455 | CG | GLU | 76 | 10.596 | −22.889 | −13.487 | 1 | 36.55 |
| 3456 | CD | GLU | 76 | 10.968 | −24.304 | −13.866 | 1 | 37.51 |
| 3457 | OE1 | GLU | 76 | 12.092 | −24.521 | −14.364 | 1 | 38.83 |
| 3458 | OE2 | GLU | 76 | 10.126 | −25.201 | −13.671 | 1 | 41.1 |
| 3459 | C | GLU | 76 | 10.483 | −19.633 | −15.55 | 1 | 34.08 |
| 3460 | O | GLU | 76 | 11.509 | −18.954 | −15.518 | 1 | 35.19 |
| 3461 | N | CYS | 77 | 9.636 | −19.629 | −16.574 | 1 | 34.02 |
| 3462 | CA | CYS | 77 | 9.846 | −18.808 | −17.758 | 1 | 34.8 |
| 3463 | CB | CYS | 77 | 8.928 | −19.288 | −18.888 | 1 | 33.88 |
| 3464 | SG | CYS | 77 | 9.154 | −18.444 | −20.468 | 1 | 39.25 |
| 3465 | C | CYS | 77 | 9.548 | −17.347 | −17.434 | 1 | 35.03 |
| 3466 | O | CYS | 77 | 8.476 | −17.025 | −16.92 | 1 | 35.88 |
| 3467 | N | PRO | 78 | 10.499 | −16.444 | −17.728 | 1 | 34.67 |
| 3468 | CD | PRO | 78 | 11.811 | −16.708 | −18.344 | 1 | 35.02 |
| 3469 | CA | PRO | 78 | 10.332 | −15.011 | −17.467 | 1 | 34.09 |
| 3470 | CB | PRO | 78 | 11.519 | −14.393 | −18.198 | 1 | 34.97 |
| 3471 | CG | PRO | 78 | 12.569 | −15.436 | −18.036 | 1 | 34.85 |
| 3472 | C | PRO | 78 | 8.993 | −14.49 | −17.983 | 1 | 33.98 |
| 3473 | O | PRO | 78 | 8.528 | −14.896 | −19.046 | 1 | 32.61 |
| 3474 | N | PRO | 79 | 8.364 | −13.573 | −17.233 | 1 | 34.42 |
| 3475 | CD | PRO | 79 | 8.898 | −12.96 | −16.003 | 1 | 35.12 |
| 3476 | CA | PRO | 79 | 7.072 | −12.977 | −17.584 | 1 | 33.72 |
| 3477 | CB | PRO | 79 | 7.006 | −11.756 | −16.674 | 1 | 34.52 |
| 3478 | CG | PRO | 79 | 7.683 | −12.251 | −15.441 | 1 | 35.02 |
| 3479 | C | PRO | 79 | 6.889 | −12.615 | −19.057 | 1 | 33.13 |
| 3480 | O | PRO | 79 | 5.917 | −13.037 | −19.685 | 1 | 31.93 |
| 3481 | N | ARG | 80 | 7.812 | −11.836 | −19.611 | 1 | 32.3 |
| 3482 | CA | ARG | 80 | 7.686 | −11.442 | −21.007 | 1 | 32.26 |
| 3483 | CB | ARG | 80 | 8.686 | −10.341 | −21.367 | 1 | 33.95 |
| 3484 | CG | ARG | 80 | 8.539 | −9.87 | −22.811 | 1 | 36.88 |
| 3485 | CD | ARG | 80 | 7.067 | −9.622 | −23.14 | 1 | 40.12 |
| 3486 | NE | ARG | 80 | 6.826 | −9.37 | −24.559 | 1 | 41.92 |
| 3487 | CZ | ARG | 80 | 5.616 | −9.225 | −25.091 | 1 | 42.7 |
| 3488 | NH1 | ARG | 80 | 4.539 | −9.309 | −24.322 | 1 | 44.66 |
| 3489 | NH2 | ARG | 80 | 5.479 | −8.993 | −26.39 | 1 | 44.01 |
| 3490 | C | ARG | 80 | 7.85 | −12.613 | −21.967 | 1 | 30.9 |
| 3491 | O | ARG | 80 | 7.14 | −12.701 | −22.967 | 1 | 30.95 |
| 3492 | N | GLN | 81 | 8.788 | −13.507 | −21.668 | 1 | 29.81 |
| 3493 | CA | GLN | 81 | 9.012 | −14.669 | −22.518 | 1 | 29.01 |
| 3494 | CB | GLN | 81 | 10.204 | −15.485 | −22.015 | 1 | 31.64 |
| 3495 | CG | GLN | 81 | 11.546 | −14.799 | −22.185 | 1 | 36.1 |
| 3496 | CD | GLN | 81 | 12.705 | −15.689 | −21.778 | 1 | 37.54 |
| 3497 | OE1 | GLN | 81 | 12.85 | −16.805 | −22.279 | 1 | 40.7 |
| 3498 | NE2 | GLN | 81 | 13.54 | −15.198 | −20.869 | 1 | 39.83 |
| 3499 | C | GLN | 81 | 7.767 | −15.544 | −22.52 | 1 | 27.35 |
| 3500 | O | GLN | 81 | 7.358 | −16.064 | −23.558 | 1 | 26.51 |
| 3501 | N | ARG | 82 | 7.171 | −15.705 | −21.345 | 1 | 26.02 |
| 3502 | CA | ARG | 82 | 5.969 | −16.512 | −21.201 | 1 | 24.76 |
| 3503 | CB | ARG | 82 | 5.564 | −16.589 | −19.726 | 1 | 24.99 |
| 3504 | CG | ARG | 82 | 4.297 | −17.376 | −19.49 | 1 | 26.72 |
| 3505 | CD | ARG | 82 | 3.891 | −17.376 | −18.027 | 1 | 26.51 |
| 3506 | NE | ARG | 82 | 2.632 | −18.088 | −17.841 | 1 | 27.66 |
| 3507 | CZ | ARG | 82 | 2.054 | −18.302 | −16.665 | 1 | 27.93 |
| 3508 | NH1 | ARG | 82 | 2.621 | −17.856 | −15.551 | 1 | 30.12 |
| 3509 | NH2 | ARG | 82 | 0.906 | −18.963 | −16.605 | 1 | 27.48 |
| 3510 | C | ARG | 82 | 4.83 | −15.915 | −22.021 | 1 | 24.78 |
| 3511 | O | ARG | 82 | 4.074 | −16.637 | −22.671 | 1 | 24.16 |
| 3512 | N | ALA | 83 | 4.714 | −14.592 | −21.986 | 1 | 23.66 |
| 3513 | CA | ALA | 83 | 3.667 | −13.9 | −22.726 | 1 | 24.34 |
| 3514 | CB | ALA | 83 | 3.642 | −12.427 | −22.336 | 1 | 23.79 |
| 3515 | C | ALA | 83 | 3.889 | −14.045 | −24.228 | 1 | 24.41 |
| 3516 | O | ALA | 83 | 2.948 | −14.308 | −24.979 | 1 | 24.39 |
| 3517 | N | LEU | 84 | 5.135 | −13.874 | −24.658 | 1 | 23.64 |
| 3518 | CA | LEU | 84 | 5.483 | −13.993 | −26.07 | 1 | 24.49 |
| 3519 | CB | LEU | 84 | 6.976 | −13.724 | −26.274 | 1 | 26.64 |
| 3520 | CG | LEU | 84 | 7.451 | −12.275 | −26.172 | 1 | 30.43 |
| 3521 | CD1 | LEU | 84 | 8.971 | −12.235 | −26.183 | 1 | 31.93 |
| 3522 | CD2 | LEU | 84 | 6.88 | −11.471 | −27.332 | 1 | 30.76 |
| 3523 | C | LEU | 84 | 5.147 | −15.379 | −26.608 | 1 | 22.95 |
| 3524 | O | LEU | 84 | 4.599 | −15.516 | −27.704 | 1 | 22.63 |
| 3525 | N | ARG | 85 | 5.477 | −16.404 | −25.83 | 1 | 21.16 |
| 3526 | CA | ARG | 85 | 5.228 | −17.779 | −26.237 | 1 | 19.16 |
| 3527 | CB | ARG | 85 | 6.234 | −18.709 | −25.553 | 1 | 19.94 |
| 3528 | CG | ARG | 85 | 7.671 | −18.374 | −25.907 | 1 | 22.59 |
| 3529 | CD | ARG | 85 | 8.673 | −19.316 | −25.265 | 1 | 23.42 |
| 3530 | NE | ARG | 85 | 10.028 | −18.967 | −25.684 | 1 | 24.23 |
| 3531 | CZ | ARG | 85 | 11.113 | −19.68 | −25.404 | 1 | 27.04 |
| 3532 | NH1 | ARG | 85 | 11.016 | −20.799 | −24.698 | 1 | 28.59 |
| 3533 | NH2 | ARG | 85 | 12.299 | −19.271 | −25.836 | 1 | 27.63 |
| 3534 | C | ARG | 85 | 3.809 | −18.254 | −25.952 | 1 | 18.31 |
| 3535 | O | ARG | 85 | 3.445 | −19.373 | −26.311 | 1 | 18.21 |
| 3536 | N | GLN | 86 | 3.006 | −17.399 | −25.322 | 1 | 19.03 |
| 3537 | CA | GLN | 86 | 1.629 | −17.751 | −24.986 | 1 | 20.06 |
| 3538 | CB | GLN | 86 | 0.783 | −17.867 | −26.257 | 1 | 22.8 |
| 3539 | CG | GLN | 86 | 0.58 | −16.549 | −26.982 | 1 | 25.09 |
| 3540 | CD | GLN | 86 | −0.135 | −16.724 | −28.306 | 1 | 27.43 |
| 3541 | OE1 | GLN | 86 | −1.156 | −17.405 | −28.386 | 1 | 27.5 |
| 3542 | NE2 | GLN | 86 | 0.398 | −16.106 | −29.352 | 1 | 31.32 |
| 3543 | C | GLN | 86 | 1.629 | −19.072 | −24.232 | 1 | 19.85 |
| 3544 | O | GLN | 86 | 0.913 | −20.016 | −24.575 | 1 | 19.94 |
| 3545 | N | MET | 87 | 2.451 | −19.123 | −23.194 | 1 | 19.48 |
| 3546 | CA | MET | 87 | 2.594 | −20.31 | −22.372 | 1 | 18.13 |
| 3547 | CB | MET | 87 | 4.041 | −20.394 | −21.879 | 1 | 20.86 |
| 3548 | CG | MET | 87 | 4.386 | −21.618 | −21.069 | 1 | 23.38 |
| 3549 | SD | MET | 87 | 6.161 | −21.646 | −20.706 | 1 | 25.41 |
| 3550 | CE | MET | 87 | 6.546 | −23.36 | −21.028 | 1 | 27.31 |
| 3551 | C | MET | 87 | 1.62 | −20.259 | −21.2 | 1 | 18.3 |
| 3552 | O | MET | 87 | 1.65 | −19.331 | −20.391 | 1 | 19.32 |
| 3553 | N | GLU | 88 | 0.743 | −21.253 | −21.137 | 1 | 15.88 |
| 3554 | CA | GLU | 88 | −0.249 | −21.363 | −20.075 | 1 | 17.78 |
| 3555 | CB | GLU | 88 | −1.634 | −20.954 | −20.589 | 1 | 17.83 |
| 3556 | CG | GLU | 88 | −1.725 | −19.512 | −21.051 | 1 | 19.4 |
| 3557 | CD | GLU | 88 | −1.582 | −18.519 | −19.916 | 1 | 19.35 |
| 3558 | OE1 | GLU | 88 | −1.506 | −17.306 | −20.201 | 1 | 23.5 |
| 3559 | OE2 | GLU | 88 | −1.55 | −18.948 | −18.743 | 1 | 20.8 |
| 3560 | C | GLU | 88 | −0.274 | −22.815 | −19.63 | 1 | 18.19 |
| 3561 | O | GLU | 88 | −0.141 | −23.727 | −20.448 | 1 | 19.09 |
| 3562 | N | PRO | 89 | −0.446 | −23.057 | −18.326 | 1 | 18.19 |
| 3563 | CD | PRO | 89 | −0.604 | −22.107 | −17.209 | 1 | 17.9 |
| 3564 | CA | PRO | 89 | −0.473 | −24.439 | −17.849 | 1 | 17.44 |
| 3565 | CB | PRO | 89 | −0.41 | −24.276 | −16.333 | 1 | 19.83 |
| 3566 | CG | PRO | 89 | −1.16 | −22.991 | −16.115 | 1 | 20.14 |
| 3567 | C | PRO | 89 | −1.702 | −25.217 | −18.289 | 1 | 17.67 |
| 3568 | O | PRO | 89 | −2.721 | −24.635 | −18.658 | 1 | 17.63 |
| 3569 | N | PHE | 90 | −1.58 | −26.538 | −18.279 | 1 | 16.64 |
| 3570 | CA | PHE | 90 | −2.688 | −27.42 | −18.606 | 1 | 16.16 |
| 3571 | CB | PHE | 90 | −2.872 | −27.602 | −20.125 | 1 | 16.31 |
| 3572 | CG | PHE | 90 | −1.656 | −28.099 | −20.855 | 1 | 15.23 |
| 3573 | CD1 | PHE | 90 | −0.837 | −27.212 | −21.542 | 1 | 16.47 |
| 3574 | CD2 | PHE | 90 | −1.362 | −29.461 | −20.901 | 1 | 16.32 |
| 3575 | CE1 | PHE | 90 | 0.26 | −27.669 | −22.274 | 1 | 16.53 |
| 3576 | CE2 | PHE | 90 | −0.267 | −29.931 | −21.628 | 1 | 15.98 |
| 3577 | CZ | PHE | 90 | 0.545 | −29.032 | −22.317 | 1 | 16.26 |
| 3578 | C | PHE | 90 | −2.481 | −28.76 | −17.915 | 1 | 17.36 |

TABLE 2-continued

| Atom | Atom Type | Residue | # | X | Y | Z | OCC | B |
|---|---|---|---|---|---|---|---|---|
| 3579 | O | PHE | 90 | −1.344 | −29.206 | −17.722 | 1 | 17.29 |
| 3580 | N | PRO | 91 | −3.582 | −29.41 | −17.509 | 1 | 16.57 |
| 3581 | CD | PRO | 91 | −4.976 | −28.969 | −17.712 | 1 | 18.43 |
| 3582 | CA | PRO | 91 | −3.545 | −30.702 | −16.824 | 1 | 16.97 |
| 3583 | CB | PRO | 91 | −4.983 | −30.873 | −16.344 | 1 | 18.94 |
| 3584 | CG | PRO | 91 | −5.758 | −30.238 | −17.453 | 1 | 17.16 |
| 3585 | C | PRO | 91 | −3.086 | −31.863 | −17.693 | 1 | 17.35 |
| 3586 | O | PRO | 91 | −3.133 | −31.798 | −18.921 | 1 | 16.85 |
| 3587 | N | LEU | 92 | −2.651 | −32.928 | −17.031 | 1 | 17.24 |
| 3588 | CA | LEU | 92 | −2.182 | −34.123 | −17.712 | 1 | 18.89 |
| 3589 | CB | LEU | 92 | −1.684 | −35.149 | −16.692 | 1 | 18.19 |
| 3590 | CG | LEU | 92 | −1.467 | −36.561 | −17.248 | 1 | 18.2 |
| 3591 | CD1 | LEU | 92 | −0.285 | −36.548 | −18.208 | 1 | 18.04 |
| 3592 | CD2 | LEU | 92 | −1.219 | −37.54 | −16.108 | 1 | 18.9 |
| 3593 | C | LEU | 92 | −3.266 | −34.77 | −18.564 | 1 | 19.14 |
| 3594 | O | LEU | 92 | −4.406 | −34.935 | −18.129 | 1 | 18.18 |
| 3595 | N | ARG | 93 | −2.897 | −35.132 | −19.785 | 1 | 18.79 |
| 3596 | CA | ARG | 93 | −3.805 | −35.81 | −20.692 | 1 | 19.16 |
| 3597 | CB | ARG | 93 | −4.456 | −34.834 | −21.672 | 1 | 21.19 |
| 3598 | CG | ARG | 93 | −5.519 | −33.957 | −21.04 | 1 | 21.62 |
| 3599 | CD | ARG | 93 | −6.524 | −33.474 | −22.072 | 1 | 22.35 |
| 3600 | NE | ARG | 93 | −7.592 | −32.715 | −21.43 | 1 | 24.95 |
| 3601 | CZ | ARG | 93 | −7.439 | −31.498 | −20.925 | 1 | 25.03 |
| 3602 | NH1 | ARG | 93 | −6.261 | −30.893 | −20.994 | 1 | 28.18 |
| 3603 | NH2 | ARG | 93 | −8.458 | −30.897 | −20.325 | 1 | 26.36 |
| 3604 | C | ARG | 93 | −3.023 | −36.856 | −21.461 | 1 | 18.56 |
| 3605 | O | ARG | 93 | −1.912 | −36.598 | −21.922 | 1 | 18.59 |
| 3606 | N | VAL | 94 | −3.603 | −38.043 | −21.569 | 1 | 17.16 |
| 3607 | CA | VAL | 94 | −2.978 | −39.14 | −22.291 | 1 | 16.36 |
| 3608 | CB | VAL | 94 | −2.81 | −40.384 | −21.396 | 1 | 16.56 |
| 3609 | CG1 | VAL | 94 | −2.218 | −41.527 | −22.208 | 1 | 16.05 |
| 3610 | CG2 | VAL | 94 | −1.915 | −40.053 | −20.211 | 1 | 17.26 |
| 3611 | C | VAL | 94 | −3.868 | −39.5 | −23.466 | 1 | 18.4 |
| 3612 | O | VAL | 94 | −5.064 | −39.742 | −23.299 | 1 | 18.96 |
| 3613 | N | PHE | 95 | −3.286 | −39.533 | −24.66 | 1 | 16.23 |
| 3614 | CA | PHE | 95 | −4.055 | −39.862 | −25.849 | 1 | 16.78 |
| 3615 | CB | PHE | 95 | −3.949 | −38.748 | −26.89 | 1 | 17.03 |
| 3616 | CG | PHE | 95 | −4.704 | −37.506 | −26.528 | 1 | 17.55 |
| 3617 | CD1 | PHE | 95 | −4.159 | −36.572 | −25.654 | 1 | 18.93 |
| 3618 | CD2 | PHE | 95 | −5.965 | −37.267 | −27.069 | 1 | 18.16 |
| 3619 | CE1 | PHE | 95 | −4.86 | −35.41 | −25.323 | 1 | 19.31 |
| 3620 | CE2 | PHE | 95 | −6.673 | −36.11 | −26.745 | 1 | 18.38 |
| 3621 | CZ | PHE | 95 | −6.119 | −35.181 | −25.871 | 1 | 19.93 |
| 3622 | C | PHE | 95 | −3.625 | −41.163 | −26.5 | 1 | 17.74 |
| 3623 | O | PHE | 95 | −2.434 | −41.44 | −26.626 | 1 | 17.29 |
| 3624 | N | VAL | 96 | −4.615 | −41.95 | −26.908 | 1 | 16.85 |
| 3625 | CA | VAL | 96 | −4.39 | −43.216 | −27.592 | 1 | 17.64 |
| 3626 | CB | VAL | 96 | −5.092 | −44.384 | −26.862 | 1 | 18.77 |
| 3627 | CG1 | VAL | 96 | −4.931 | −45.674 | −27.662 | 1 | 18.9 |
| 3628 | CG2 | VAL | 96 | −4.508 | −44.547 | −25.47 | 1 | 19.9 |
| 3629 | C | VAL | 96 | −4.981 | −43.058 | −28.992 | 1 | 17.71 |
| 3630 | O | VAL | 96 | −6.09 | −42.537 | −29.148 | 1 | 17.68 |
| 3631 | N | ASN | 97 | −4.229 | −43.49 | −30.002 | 1 | 16.02 |
| 3632 | CA | ASN | 97 | −4.651 | −43.393 | −31.401 | 1 | 17.28 |
| 3633 | CB | ASN | 97 | −5.745 | −44.422 | −31.706 | 1 | 18.53 |
| 3634 | CG | ASN | 97 | −5.302 | −45.845 | −31.434 | 1 | 20.68 |
| 3635 | OD1 | ASN | 97 | −4.107 | −46.14 | −31.383 | 1 | 19.52 |
| 3636 | ND2 | ASN | 97 | −6.271 | −46.745 | −31.269 | 1 | 19.41 |
| 3637 | C | ASN | 97 | −5.16 | −41.998 | −31.763 | 1 | 17.09 |
| 3638 | O | ASN | 97 | −6.249 | −41.851 | −32.323 | 1 | 17.38 |
| 3639 | N | PRO | 98 | −4.37 | −40.955 | −31.469 | 1 | 16.4 |
| 3640 | CD | PRO | 98 | −3.086 | −40.95 | −30.741 | 1 | 15.49 |
| 3641 | CA | PRO | 98 | −4.735 | −39.589 | −31.78 | 1 | 15.74 |
| 3642 | CB | PRO | 98 | −3.92 | −38.746 | −30.862 | 1 | 14.57 |
| 3643 | CG | PRO | 98 | −2.626 | −39.507 | −30.878 | 1 | 14.47 |
| 3644 | C | PRO | 98 | −4.653 | −39.16 | −33.233 | 1 | 16.54 |
| 3645 | O | PRO | 98 | −3.895 | −39.745 | −34.009 | 1 | 16.7 |
| 3646 | N | SER | 99 | −5.406 | −38.124 | −33.581 | 1 | 16.23 |
| 3647 | CA | SER | 99 | −5.374 | −37.533 | −34.908 | 1 | 17.93 |
| 3648 | CB | SER | 99 | −6.64 | −37.89 | −35.694 | 1 | 21.33 |
| 3649 | OG | SER | 99 | −7.808 | −37.537 | −34.975 | 1 | 26.95 |
| 3650 | C | SER | 99 | −5.294 | −36.031 | −34.669 | 1 | 17.97 |
| 3651 | O | SER | 99 | −5.835 | −35.525 | −33.681 | 1 | 17.79 |
| 3652 | N | LEU | 100 | −4.606 | −35.32 | −35.553 | 1 | 17.43 |
| 3653 | CA | LEU | 100 | −4.455 | −33.882 | −35.401 | 1 | 18.38 |
| 3654 | CB | LEU | 100 | −2.972 | −33.515 | −35.303 | 1 | 20.07 |
| 3655 | CG | LEU | 100 | −2.683 | −32.017 | −35.168 | 1 | 23.65 |
| 3656 | CD1 | LEU | 100 | −1.924 | −31.761 | −33.883 | 1 | 25.31 |
| 3657 | CD2 | LEU | 100 | −1.893 | −31.53 | −36.369 | 1 | 26.81 |
| 3658 | C | LEU | 100 | −5.081 | −33.088 | −36.534 | 1 | 17.05 |
| 3659 | O | LEU | 100 | −4.994 | −33.471 | −37.702 | 1 | 17.04 |
| 3660 | N | ARG | 101 | −5.71 | −31.974 | −36.176 | 1 | 16.27 |
| 3661 | CA | ARG | 101 | −6.32 | −31.092 | −37.162 | 1 | 17.41 |
| 3662 | CB | ARG | 101 | −7.845 | −31.133 | −37.056 | 1 | 19.85 |
| 3663 | CG | ARG | 101 | −8.554 | −30.33 | −38.14 | 1 | 24.9 |
| 3664 | CD | ARG | 101 | −10.065 | −30.51 | −38.082 | 1 | 28.56 |
| 3665 | NE | ARG | 101 | −10.735 | −29.815 | −39.178 | 1 | 34.92 |
| 3666 | CZ | ARG | 101 | −12.049 | −29.838 | −39.388 | 1 | 36.16 |
| 3667 | NH1 | ARG | 101 | −12.843 | −30.523 | −38.575 | 1 | 37.6 |
| 3668 | NH2 | ARG | 101 | −12.569 | −29.178 | −40.415 | 1 | 37.64 |
| 3669 | C | ARG | 101 | −5.814 | −29.677 | −36.902 | 1 | 15.9 |
| 3670 | O | ARG | 101 | −5.867 | −29.193 | −35.771 | 1 | 16.69 |
| 3671 | N | VAL | 102 | −5.296 | −29.031 | −37.944 | 1 | 15.38 |
| 3672 | CA | VAL | 102 | −4.785 | −27.667 | −37.83 | 1 | 14.94 |
| 3673 | CB | VAL | 102 | −3.775 | −27.353 | −38.959 | 1 | 16.03 |
| 3674 | CG1 | VAL | 102 | −3.28 | −25.915 | −38.842 | 1 | 15.51 |
| 3675 | CG2 | VAL | 102 | −2.594 | −28.327 | −38.885 | 1 | 16.18 |
| 3676 | C | VAL | 102 | −5.96 | −26.691 | −37.912 | 1 | 16.69 |
| 3677 | O | VAL | 102 | −6.758 | −26.748 | −38.852 | 1 | 16.33 |
| 3678 | N | LEU | 103 | −6.061 | −25.806 | −36.92 | 1 | 16.11 |
| 3679 | CA | LEU | 103 | −7.148 | −24.824 | −36.854 | 1 | 17.87 |
| 3680 | CB | LEU | 103 | −7.706 | −24.771 | −35.43 | 1 | 18.83 |
| 3681 | CG | LEU | 103 | −8.178 | −26.114 | −34.869 | 1 | 17.46 |
| 3682 | CD1 | LEU | 103 | −8.65 | −25.939 | −33.435 | 1 | 18.49 |
| 3683 | CD2 | LEU | 103 | −9.299 | −26.676 | −35.738 | 1 | 19.65 |
| 3684 | C | LEU | 103 | −6.716 | −23.428 | −37.3 | 1 | 19.06 |
| 3685 | O | LEU | 103 | −7.5 | −22.687 | −37.896 | 1 | 20.86 |
| 3686 | N | ASP | 104 | −5.477 | −23.061 | −36.984 | 1 | 17.49 |
| 3687 | CA | ASP | 104 | −4.916 | −21.777 | −37.39 | 1 | 18.06 |
| 3688 | CB | ASP | 104 | −4.77 | −20.824 | −36.198 | 1 | 19.44 |
| 3689 | CG | ASP | 104 | −4.346 | −19.419 | −36.62 | 1 | 20.07 |
| 3690 | OD1 | ASP | 104 | −3.708 | −19.273 | −37.684 | 1 | 19.78 |
| 3691 | OD2 | ASP | 104 | −4.637 | −18.456 | −35.879 | 1 | 21.58 |
| 3692 | C | ASP | 104 | −3.541 | −22.133 | −37.935 | 1 | 19.32 |
| 3693 | O | ASP | 104 | −2.638 | −22.483 | −37.17 | 1 | 18 |
| 3694 | N | SER | 105 | −3.387 | −22.057 | −39.253 | 1 | 18.65 |
| 3695 | CA | SER | 105 | −2.123 | −22.411 | −39.888 | 1 | 19.02 |
| 3696 | CB | SER | 105 | −2.372 | −22.864 | −41.332 | 1 | 19.59 |
| 3697 | OG | SER | 105 | −3.176 | −21.933 | −42.03 | 1 | 22.62 |
| 3698 | C | SER | 105 | −1.039 | −21.341 | −39.855 | 1 | 18 |
| 3699 | O | SER | 105 | 0.02 | −21.514 | −40.461 | 1 | 18.62 |
| 3700 | N | ARG | 106 | −1.295 | −20.235 | −39.162 | 1 | 17.23 |
| 3701 | CA | ARG | 106 | −0.288 | −19.19 | −39.045 | 1 | 17.72 |
| 3702 | CB | ARG | 106 | −0.833 | −18.002 | −38.247 | 1 | 20.04 |
| 3703 | CG | ARG | 106 | 0.232 | −17.044 | −37.739 | 1 | 24.82 |
| 3704 | CD | ARG | 106 | −0.387 | −15.759 | −37.194 | 1 | 28.22 |
| 3705 | NE | ARG | 106 | 0.492 | −15.097 | −36.233 | 1 | 33.41 |
| 3706 | CZ | ARG | 106 | 0.585 | −15.439 | −34.951 | 1 | 33.31 |
| 3707 | NH1 | ARG | 106 | −0.153 | −16.43 | −34.473 | 1 | 35.69 |
| 3708 | NH2 | ARG | 106 | 1.42 | −14.796 | −34.147 | 1 | 35.93 |
| 3709 | C | ARG | 106 | 0.886 | −19.832 | −38.305 | 1 | 17.19 |
| 3710 | O | ARG | 106 | 0.686 | −20.568 | −37.34 | 1 | 18.31 |
| 3711 | N | LEU | 107 | 2.1 | −19.56 | −38.767 | 1 | 16.71 |
| 3712 | CA | LEU | 107 | 3.293 | −20.139 | −38.158 | 1 | 16.43 |
| 3713 | CB | LEU | 107 | 4.302 | −20.518 | −39.246 | 1 | 16.9 |
| 3714 | CG | LEU | 107 | 3.88 | −21.584 | −40.257 | 1 | 16.36 |
| 3715 | CD1 | LEU | 107 | 4.935 | −21.675 | −41.349 | 1 | 19.7 |
| 3716 | CD2 | LEU | 107 | 3.7 | −22.932 | −39.565 | 1 | 16.7 |
| 3717 | C | LEU | 107 | 3.98 | −19.235 | −37.147 | 1 | 16.75 |
| 3718 | O | LEU | 107 | 4.142 | −18.035 | −37.374 | 1 | 17 |
| 3719 | N | VAL | 108 | 4.376 | −19.83 | −36.026 | 1 | 15.85 |
| 3720 | CA | VAL | 108 | 5.084 | −19.114 | −34.973 | 1 | 16.8 |
| 3721 | CB | VAL | 108 | 4.24 | −19.023 | −33.68 | 1 | 19.42 |
| 3722 | CG1 | VAL | 108 | 3.046 | −18.11 | −33.914 | 1 | 21.93 |
| 3723 | CG2 | VAL | 108 | 3.761 | −20.396 | −33.265 | 1 | 22.34 |
| 3724 | C | VAL | 108 | 6.371 | −19.894 | −34.719 | 1 | 16.07 |
| 3725 | O | VAL | 108 | 6.353 | −21.12 | −34.627 | 1 | 14.86 |
| 3726 | N | THR | 109 | 7.485 | −19.18 | −34.623 | 1 | 15.57 |
| 3727 | CA | THR | 109 | 8.781 | −19.82 | −34.431 | 1 | 16.2 |
| 3728 | CB | THR | 109 | 9.739 | −19.42 | −35.569 | 1 | 16.65 |
| 3729 | OG1 | THR | 109 | 9.156 | −19.785 | −36.824 | 1 | 18.11 |
| 3730 | CG2 | THR | 109 | 11.084 | −20.12 | −35.42 | 1 | 19.53 |

TABLE 2-continued

| Atom | Atom Type | Residue | # | X | Y | Z | OCC | B |
|---|---|---|---|---|---|---|---|---|
| 3731 | C | THR | 109 | 9.446 | −19.514 | −33.095 | 1 | 15.77 |
| 3732 | O | THR | 109 | 9.641 | −18.354 | −32.731 | 1 | 15.35 |
| 3733 | N | PHE | 110 | 9.8 | −20.578 | −32.381 | 1 | 15.31 |
| 3734 | CA | PHE | 110 | 10.467 | −20.485 | −31.087 | 1 | 15.31 |
| 3735 | CB | PHE | 110 | 9.459 | −20.523 | −29.944 | 1 | 15.7 |
| 3736 | CG | PHE | 110 | 8.7 | −19.247 | −29.762 | 1 | 17.45 |
| 3737 | CD1 | PHE | 110 | 9.362 | −18.076 | −29.408 | 1 | 19.63 |
| 3738 | CD2 | PHE | 110 | 7.323 | −19.216 | −29.938 | 1 | 19.6 |
| 3739 | CE1 | PHE | 110 | 8.66 | −16.887 | −29.23 | 1 | 20.63 |
| 3740 | CE2 | PHE | 110 | 6.611 | −18.032 | −29.763 | 1 | 20.49 |
| 3741 | CZ | PHE | 110 | 7.28 | −16.867 | −29.408 | 1 | 21.83 |
| 3742 | C | PHE | 110 | 11.384 | −21.683 | −30.939 | 1 | 15.28 |
| 3743 | O | PHE | 110 | 11.194 | −22.701 | −31.601 | 1 | 14.62 |
| 3744 | N | PRO | 111 | 12.392 | −21.577 | −30.063 | 1 | 15.27 |
| 3745 | CD | PRO | 111 | 12.921 | −20.369 | −29.411 | 1 | 17.1 |
| 3746 | CA | PRO | 111 | 13.301 | −22.707 | −29.877 | 1 | 15.77 |
| 3747 | CB | PRO | 111 | 14.446 | −22.108 | −29.057 | 1 | 17.18 |
| 3748 | CG | PRO | 111 | 14.403 | −20.646 | −29.401 | 1 | 18.46 |
| 3749 | C | PRO | 111 | 12.616 | −23.836 | −29.118 | 1 | 16.02 |
| 3750 | O | PRO | 111 | 11.816 | −23.597 | −28.214 | 1 | 16.38 |
| 3751 | N | GLU | 112 | 12.919 | −25.068 | −29.5 | 1 | 14.82 |
| 3752 | CA | GLU | 112 | 12.377 | −26.214 | −28.798 | 1 | 15.43 |
| 3753 | CB | GLU | 112 | 11.046 | −26.684 | −29.409 | 1 | 18.63 |
| 3754 | CG | GLU | 112 | 11.105 | −27.229 | −30.818 | 1 | 18.44 |
| 3755 | CD | GLU | 112 | 9.766 | −27.816 | −31.262 | 1 | 18.55 |
| 3756 | OE1 | GLU | 112 | 8.812 | −27.044 | −31.506 | 1 | 16.3 |
| 3757 | OE2 | GLU | 112 | 9.665 | −29.058 | −31.359 | 1 | 16.49 |
| 3758 | C | GLU | 112 | 13.429 | −27.311 | −28.844 | 1 | 13.72 |
| 3759 | O | GLU | 112 | 14.353 | −27.265 | −29.656 | 1 | 13.68 |
| 3760 | N | GLY | 113 | 13.304 | −28.269 | −27.939 | 1 | 12.87 |
| 3761 | CA | GLY | 113 | 14.251 | −29.365 | −27.886 | 1 | 14.21 |
| 3762 | C | GLY | 113 | 13.501 | −30.667 | −27.758 | 1 | 13.65 |
| 3763 | O | GLY | 113 | 12.277 | −30.668 | −27.609 | 1 | 17.74 |
| 3764 | N | CYS | 114 | 14.229 | −31.778 | −27.805 | 1 | 11.67 |
| 3765 | CA | CYS | 114 | 13.609 | −33.096 | −27.715 | 1 | 9.08 |
| 3766 | CB | CYS | 114 | 13.54 | −33.729 | −29.105 | 1 | 7.84 |
| 3767 | SG | CYS | 114 | 12.711 | −35.332 | −29.157 | 1 | 12.41 |
| 3768 | C | CYS | 114 | 14.401 | −34.014 | −26.79 | 1 | 8.78 |
| 3769 | O | CYS | 114 | 15.628 | −34.039 | −26.838 | 1 | 11.03 |
| 3770 | N | GLU | 115 | 13.696 | −34.772 | −25.959 | 1 | 11.44 |
| 3771 | CA | GLU | 115 | 14.349 | −35.699 | −25.043 | 1 | 11.64 |
| 3772 | CB | GLU | 115 | 13.311 | −36.35 | −24.124 | 1 | 13.79 |
| 3773 | CG | GLU | 115 | 12.772 | −35.428 | −23.046 | 1 | 17.98 |
| 3774 | CD | GLU | 115 | 13.843 | −35.014 | −22.05 | 1 | 20.79 |
| 3775 | OE1 | GLU | 115 | 14.54 | −35.904 | −21.52 | 1 | 22.37 |
| 3776 | OE2 | GLU | 115 | 13.982 | −33.801 | −21.793 | 1 | 25.86 |
| 3777 | C | GLU | 115 | 15.11 | −36.777 | −25.814 | 1 | 12.99 |
| 3778 | O | GLU | 115 | 16.012 | −37.414 | −25.269 | 1 | 13.25 |
| 3779 | N | SER | 116 | 14.751 | −36.963 | −27.083 | 1 | 12.55 |
| 3780 | CA | SER | 116 | 15.399 | −37.957 | −27.932 | 1 | 10.19 |
| 3781 | CB | SER | 116 | 14.375 | −38.62 | −28.853 | 1 | 11.17 |
| 3782 | OG | SER | 116 | 13.483 | −39.426 | −28.103 | 1 | 12.52 |
| 3783 | C | SER | 116 | 16.574 | −37.426 | −28.753 | 1 | 11.3 |
| 3784 | O | SER | 116 | 17.155 | −38.154 | −29.554 | 1 | 10.89 |
| 3785 | N | VAL | 117 | 16.899 | −36.151 | −28.569 | 1 | 10.85 |
| 3786 | CA | VAL | 117 | 18.049 | −35.523 | −29.223 | 1 | 11.2 |
| 3787 | CB | VAL | 117 | 17.642 | −34.598 | −30.393 | 1 | 11.46 |
| 3788 | CG1 | VAL | 117 | 18.887 | −34.147 | −31.143 | 1 | 13.85 |
| 3789 | CG2 | VAL | 117 | 16.7 | −35.324 | −31.336 | 1 | 12.76 |
| 3790 | C | VAL | 117 | 18.616 | −34.689 | −28.075 | 1 | 12.17 |
| 3791 | O | VAL | 117 | 18.704 | −33.464 | −28.139 | 1 | 12.49 |
| 3792 | N | ALA | 118 | 18.979 | −35.395 | −27.009 | 1 | 13.2 |
| 3793 | CA | ALA | 118 | 19.482 | −34.789 | −25.785 | 1 | 12.76 |
| 3794 | CB | ALA | 118 | 19.944 | −35.888 | −24.822 | 1 | 15.21 |
| 3795 | C | ALA | 118 | 20.579 | −33.749 | −25.931 | 1 | 13.32 |
| 3796 | O | ALA | 118 | 21.58 | −33.97 | −26.611 | 1 | 14.98 |
| 3797 | N | GLY | 119 | 20.36 | −32.605 | −25.286 | 1 | 13.15 |
| 3798 | CA | GLY | 119 | 21.347 | −31.54 | −25.276 | 1 | 14.08 |
| 3799 | C | GLY | 119 | 21.326 | −30.497 | −26.372 | 1 | 12.71 |
| 3800 | O | GLY | 119 | 22.25 | −29.687 | −26.45 | 1 | 11.78 |
| 3801 | N | PHE | 120 | 20.289 | −30.491 | −27.203 | 1 | 12.39 |
| 3802 | CA | PHE | 120 | 20.215 | −29.523 | −28.292 | 1 | 11.81 |
| 3803 | CB | PHE | 120 | 20.46 | −30.228 | −29.629 | 1 | 11.03 |
| 3804 | CG | PHE | 120 | 21.84 | −30.803 | −29.768 | 1 | 12.51 |
| 3805 | CD1 | PHE | 120 | 22.902 | −30.008 | −30.186 | 1 | 12.82 |
| 3806 | CD2 | PHE | 120 | 22.078 | −32.139 | −29.468 | 1 | 14.6 |
| 3807 | CE1 | PHE | 120 | 24.183 | −30.536 | −30.305 | 1 | 14.78 |
| 3808 | CE2 | PHE | 120 | 23.361 | −32.68 | −29.581 | 1 | 18.18 |
| 3809 | CZ | PHE | 120 | 24.414 | −31.876 | −30.001 | 1 | 17.5 |
| 3810 | C | PHE | 120 | 18.887 | −28.783 | −28.361 | 1 | 12.75 |
| 3811 | O | PHE | 120 | 17.872 | −29.236 | −27.83 | 1 | 14.81 |
| 3812 | N | LEU | 121 | 18.919 | −27.636 | −29.028 | 1 | 13.03 |
| 3813 | CA | LEU | 121 | 17.745 | −26.801 | −29.232 | 1 | 13.13 |
| 3814 | CB | LEU | 121 | 17.711 | −25.647 | −28.225 | 1 | 15.45 |
| 3815 | CG | LEU | 121 | 17.454 | −25.926 | −26.744 | 1 | 17.17 |
| 3816 | CD1 | LEU | 121 | 17.574 | −24.62 | −25.963 | 1 | 19.48 |
| 3817 | CD2 | LEU | 121 | 16.066 | −26.524 | −26.557 | 1 | 19.71 |
| 3818 | C | LEU | 121 | 17.824 | −26.215 | −30.637 | 1 | 12.74 |
| 3819 | O | LEU | 121 | 18.906 | −26.097 | −31.213 | 1 | 13.15 |
| 3820 | N | ALA | 122 | 16.675 | −25.859 | −31.195 | 1 | 12.21 |
| 3821 | CA | ALA | 122 | 16.638 | −25.232 | −32.51 | 1 | 12.3 |
| 3822 | CB | ALA | 122 | 16.851 | −26.265 | −33.611 | 1 | 14.3 |
| 3823 | C | ALA | 122 | 15.282 | −24.569 | −32.677 | 1 | 12.48 |
| 3824 | O | ALA | 122 | 14.288 | −25.039 | −32.131 | 1 | 12.39 |
| 3825 | N | CYS | 123 | 15.243 | −23.47 | −33.421 | 1 | 12.49 |
| 3826 | CA | CYS | 123 | 13.976 | −22.789 | −33.667 | 1 | 13.9 |
| 3827 | CB | CYS | 123 | 14.213 | −21.405 | −34.264 | 1 | 14.48 |
| 3828 | SG | CYS | 123 | 14.84 | −20.205 | −33.073 | 1 | 21.1 |
| 3829 | C | CYS | 123 | 13.162 | −23.635 | −34.635 | 1 | 12.87 |
| 3830 | O | CYS | 123 | 13.688 | −24.133 | −35.633 | 1 | 13.92 |
| 3831 | N | VAL | 124 | 11.88 | −23.795 | −34.336 | 1 | 11.58 |
| 3832 | CA | VAL | 124 | 10.997 | −24.593 | −35.171 | 1 | 13.15 |
| 3833 | CB | VAL | 124 | 10.707 | −25.972 | −34.53 | 1 | 13.6 |
| 3834 | CG1 | VAL | 124 | 9.781 | −26.783 | −35.433 | 1 | 12.64 |
| 3835 | CG2 | VAL | 124 | 12.01 | −26.722 | −34.285 | 1 | 14.81 |
| 3836 | C | VAL | 124 | 9.661 | −23.899 | −35.374 | 1 | 13.61 |
| 3837 | O | VAL | 124 | 9.007 | −23.509 | −34.406 | 1 | 13.39 |
| 3838 | N | PRO | 125 | 9.249 | −23.716 | −36.636 | 1 | 12.89 |
| 3839 | CD | PRO | 125 | 10.012 | −23.885 | −37.886 | 1 | 14.92 |
| 3840 | CA | PRO | 125 | 7.961 | −23.067 | −36.892 | 1 | 14.06 |
| 3841 | CB | PRO | 125 | 8.044 | −22.704 | −38.374 | 1 | 15.66 |
| 3842 | CG | PRO | 125 | 8.936 | −23.752 | −38.937 | 1 | 17.95 |
| 3843 | C | PRO | 125 | 6.843 | −24.063 | −36.593 | 1 | 13.23 |
| 3844 | O | PRO | 125 | 6.929 | −25.231 | −36.976 | 1 | 13.12 |
| 3845 | N | ARG | 126 | 5.807 | −23.604 | −35.895 | 1 | 10.71 |
| 3846 | CA | ARG | 126 | 4.675 | −24.45 | −35.538 | 1 | 10.78 |
| 3847 | CB | ARG | 126 | 4.715 | −24.825 | −34.052 | 1 | 11.9 |
| 3848 | CG | ARG | 126 | 5.89 | −25.698 | −33.637 | 1 | 11.71 |
| 3849 | CD | ARG | 126 | 5.805 | −27.095 | −34.24 | 1 | 14.03 |
| 3850 | NE | ARG | 126 | 6.83 | −27.973 | −33.673 | 1 | 13.75 |
| 3851 | CZ | ARG | 126 | 7.024 | −29.234 | −34.045 | 1 | 14.96 |
| 3852 | NH1 | ARG | 126 | 6.262 | −29.779 | −34.989 | 1 | 14.47 |
| 3853 | NH2 | ARG | 126 | 7.983 | −29.951 | −33.473 | 1 | 14.6 |
| 3854 | C | ARG | 126 | 3.387 | −23.693 | −35.799 | 1 | 11.59 |
| 3855 | O | ARG | 126 | 3.387 | −22.468 | −35.84 | 1 | 13.39 |
| 3856 | N | PHE | 127 | 2.295 | −24.429 | −35.97 | 1 | 11.69 |
| 3857 | CA | PHE | 127 | 0.996 | −23.811 | −36.201 | 1 | 12.81 |
| 3858 | CB | PHE | 127 | −0.016 | −24.859 | −36.666 | 1 | 12.28 |
| 3859 | CG | PHE | 127 | 0.355 | −25.519 | −37.964 | 1 | 14.08 |
| 3860 | CD1 | PHE | 127 | 0.542 | −26.897 | −38.029 | 1 | 14.14 |
| 3861 | CD2 | PHE | 127 | 0.537 | −24.76 | −39.116 | 1 | 14.51 |
| 3862 | CE1 | PHE | 127 | 0.909 | −27.51 | −39.233 | 1 | 14.4 |
| 3863 | CE2 | PHE | 127 | 0.904 | −25.361 | −40.321 | 1 | 15.72 |
| 3864 | CZ | PHE | 127 | 1.09 | −26.738 | −40.377 | 1 | 15.71 |
| 3865 | C | PHE | 127 | 0.499 | −23.156 | −34.916 | 1 | 14.46 |
| 3866 | O | PHE | 127 | 0.711 | −23.674 | −33.821 | 1 | 13.9 |
| 3867 | N | GLN | 128 | −0.17 | −22.017 | −35.066 | 1 | 14.12 |
| 3868 | CA | GLN | 128 | −0.71 | −21.266 | −33.934 | 1 | 15.24 |
| 3869 | CB | GLN | 128 | −1.287 | −19.936 | −34.434 | 1 | 16.66 |
| 3870 | CG | GLN | 128 | −2.044 | −19.112 | −33.389 | 1 | 20.11 |
| 3871 | CD | GLN | 128 | −1.208 | −18.778 | −32.169 | 1 | 21.62 |
| 3872 | OE1 | GLN | 128 | 0.009 | −18.628 | −32.258 | 1 | 22.51 |
| 3873 | NE2 | GLN | 128 | −1.865 | −18.641 | −31.021 | 1 | 22.27 |
| 3874 | C | GLN | 128 | −1.776 | −22.015 | −33.143 | 1 | 15.45 |
| 3875 | O | GLN | 128 | −1.831 | −21.909 | −31.919 | 1 | 14.75 |
| 3876 | N | ALA | 129 | −2.631 | −22.768 | −33.828 | 1 | 13.56 |
| 3877 | CA | ALA | 129 | −3.687 | −23.492 | −33.135 | 1 | 14.26 |
| 3878 | CB | ALA | 129 | −4.94 | −22.618 | −33.043 | 1 | 16.12 |
| 3879 | C | ALA | 129 | −4.031 | −24.821 | −33.787 | 1 | 14.25 |
| 3880 | O | ALA | 129 | −4.092 | −24.93 | −35.012 | 1 | 15.09 |
| 3881 | N | VAL | 130 | −4.267 | −25.828 | −32.955 | 1 | 13.81 |
| 3882 | CA | VAL | 130 | −4.6 | −27.161 | −33.434 | 1 | 15.67 |

TABLE 2-continued

| Atom | Atom Type | Residue | # | X | Y | Z | OCC | B |
|---|---|---|---|---|---|---|---|---|
| 3883 | CB | VAL | 130 | −3.335 | −28.052 | −33.543 | 1 | 14.12 |
| 3884 | CG1 | VAL | 130 | −2.285 | −27.38 | −34.412 | 1 | 15.4 |
| 3885 | CG2 | VAL | 130 | −2.785 | −28.34 | −32.141 | 1 | 16.12 |
| 3886 | C | VAL | 130 | −5.549 | −27.854 | −32.474 | 1 | 16.47 |
| 3887 | O | VAL | 130 | −5.846 | −27.348 | −31.39 | 1 | 16.66 |
| 3888 | N | GLN | 131 | −6.036 | −29.016 | −32.887 | 1 | 16.72 |
| 3889 | CA | GLN | 131 | −6.898 | −29.81 | −32.033 | 1 | 18 |
| 3890 | CB | GLN | 131 | −8.377 | −29.657 | −32.411 | 1 | 21.69 |
| 3891 | CG | GLN | 131 | −8.766 | −30.215 | −33.759 | 1 | 24.96 |
| 3892 | CD | GLN | 131 | −10.242 | −30.569 | −33.824 | 1 | 28.56 |
| 3893 | OE1 | GLN | 131 | −11.105 | −29.753 | −33.495 | 1 | 28.44 |
| 3894 | NE2 | GLN | 131 | −10.539 | −31.792 | −34.248 | 1 | 27.34 |
| 3895 | C | GLN | 131 | −6.464 | −31.258 | −32.178 | 1 | 18.13 |
| 3896 | O | GLN | 131 | −6.211 | −31.737 | −33.284 | 1 | 18.99 |
| 3897 | N | ILE | 132 | −6.338 | −31.941 | −31.05 | 1 | 15.28 |
| 3898 | CA | ILE | 132 | −5.943 | −33.339 | −31.058 | 1 | 15.72 |
| 3899 | CB | ILE | 132 | −4.703 | −33.571 | −30.144 | 1 | 14.64 |
| 3900 | CG2 | ILE | 132 | −4.965 | −33.028 | −28.748 | 1 | 16.19 |
| 3901 | CG1 | ILE | 132 | −4.341 | −35.058 | −30.111 | 1 | 13.77 |
| 3902 | CD1 | ILE | 132 | −3.043 | −35.351 | −29.367 | 1 | 14.54 |
| 3903 | C | ILE | 132 | −7.137 | −34.16 | −30.588 | 1 | 16.54 |
| 3904 | O | ILE | 132 | −7.748 | −33.859 | −29.564 | 1 | 17.01 |
| 3905 | N | SER | 133 | −7.488 | −35.181 | −31.36 | 1 | 17.28 |
| 3906 | CA | SER | 133 | −8.619 | −36.034 | −31.02 | 1 | 18.24 |
| 3907 | CB | SER | 133 | −9.682 | −35.97 | −32.119 | 1 | 20.37 |
| 3908 | OG | SER | 133 | −9.99 | −34.629 | −32.446 | 1 | 25.9 |
| 3909 | C | SER | 133 | −8.134 | −37.464 | −30.872 | 1 | 19.17 |
| 3910 | O | SER | 133 | −7.321 | −37.932 | −31.664 | 1 | 20 |
| 3911 | N | GLY | 134 | −8.637 | −38.156 | −29.859 | 1 | 19.73 |
| 3912 | CA | GLY | 134 | −8.231 | −39.531 | −29.648 | 1 | 21.34 |
| 3913 | C | GLY | 134 | −8.953 | −40.158 | −28.476 | 1 | 22.6 |
| 3914 | O | GLY | 134 | −9.936 | −39.611 | −27.976 | 1 | 24.46 |
| 3915 | N | LEU | 135 | −8.46 | −41.307 | −28.033 | 1 | 22.63 |
| 3916 | CA | LEU | 135 | −9.055 | −42.017 | −26.911 | 1 | 24.92 |
| 3917 | CB | LEU | 135 | −9.2 | −43.503 | −27.241 | 1 | 23.22 |
| 3918 | CG | LEU | 135 | −9.972 | −43.881 | −28.504 | 1 | 23.67 |
| 3919 | CD1 | LEU | 135 | −9.852 | −45.379 | −28.741 | 1 | 23.22 |
| 3920 | CD2 | LEU | 135 | −11.426 | −43.47 | −28.356 | 1 | 24.34 |
| 3921 | C | LEU | 135 | −8.18 | −41.884 | −25.677 | 1 | 27.84 |
| 3922 | O | LEU | 135 | −6.976 | −41.674 | −25.782 | 1 | 27.47 |
| 3923 | N | ASP | 136 | −8.793 | −42.004 | −24.506 | 1 | 31.36 |
| 3924 | CA | ASP | 136 | −8.048 | −41.944 | −23.254 | 1 | 34.42 |
| 3925 | CB | ASP | 136 | −8.871 | −41.273 | −22.153 | 1 | 35.73 |
| 3926 | CG | ASP | 136 | −9.602 | −40.036 | −22.633 | 1 | 39.42 |
| 3927 | OD1 | ASP | 136 | −8.938 | −39.09 | −23.102 | 1 | 43.96 |
| 3928 | OD2 | ASP | 136 | −10.849 | −40.008 | −22.531 | 1 | 41.2 |
| 3929 | C | ASP | 136 | −7.854 | −43.409 | −22.884 | 1 | 35.41 |
| 3930 | O | ASP | 136 | −8.437 | −44.291 | −23.517 | 1 | 36.78 |
| 3931 | N | PRO | 137 | −7.02 | −43.698 | −21.875 | 1 | 36.32 |
| 3932 | CD | PRO | 137 | −6.215 | −42.848 | −20.98 | 1 | 36.35 |
| 3933 | CA | PRO | 137 | −6.872 | −45.116 | −21.538 | 1 | 37.8 |
| 3934 | CB | PRO | 137 | −5.752 | −45.105 | −20.505 | 1 | 37.15 |
| 3935 | CG | PRO | 137 | −5.95 | −43.779 | −19.817 | 1 | 38.09 |
| 3936 | C | PRO | 137 | −8.222 | −45.53 | −20.946 | 1 | 38.82 |
| 3937 | O | PRO | 137 | −8.475 | −46.701 | −20.662 | 1 | 40.89 |
| 3938 | N | ASN | 138 | −9.079 | −44.524 | −20.78 | 1 | 39.95 |
| 3939 | CA | ASN | 138 | −10.423 | −44.675 | −20.241 | 1 | 39.96 |
| 3940 | CB | ASN | 138 | −10.877 | −43.336 | −19.646 | 1 | 40.71 |
| 3941 | CG | ASN | 138 | −12.129 | −43.458 | −18.801 | 1 | 40.85 |
| 3942 | OD1 | ASN | 138 | −12.152 | −44.178 | −17.8 | 1 | 42.56 |
| 3943 | ND2 | ASN | 138 | −13.179 | −42.745 | −19.195 | 1 | 40.64 |
| 3944 | C | ASN | 138 | −11.363 | −45.105 | −21.369 | 1 | 39.69 |
| 3945 | O | ASN | 138 | −12.572 | −45.246 | −21.173 | 1 | 39.88 |
| 3946 | N | GLY | 139 | −10.791 | −45.303 | −22.554 | 1 | 38.61 |
| 3947 | CA | GLY | 139 | −11.565 | −45.73 | −23.706 | 1 | 37.11 |
| 3948 | C | GLY | 139 | −12.476 | −44.684 | −24.318 | 1 | 36.08 |
| 3949 | O | GLY | 139 | −13.025 | −44.894 | −25.4 | 1 | 35.31 |
| 3950 | N | GLU | 140 | −12.644 | −43.555 | −23.639 | 1 | 35.72 |
| 3951 | CA | GLU | 140 | −13.511 | −42.504 | −24.152 | 1 | 35.88 |
| 3952 | CB | GLU | 140 | −14.068 | −41.654 | −23.01 | 1 | 37.49 |
| 3953 | CG | GLU | 140 | −15.202 | −42.309 | −22.247 | 1 | 39.89 |
| 3954 | CD | GLU | 140 | −16.167 | −41.292 | −21.673 | 1 | 41.3 |
| 3955 | OE1 | GLU | 140 | −15.736 | −40.45 | −20.857 | 1 | 42.56 |
| 3956 | OE2 | GLU | 140 | −17.36 | −41.333 | −22.044 | 1 | 43.5 |
| 3957 | C | GLU | 140 | −12.852 | −41.589 | −25.171 | 1 | 35.4 |
| 3958 | O | GLU | 140 | −11.648 | −41.337 | −25.123 | 1 | 34.31 |
| 3959 | N | GLN | 141 | −13.668 | −41.093 | −26.093 | 1 | 34.69 |
| 3960 | CA | GLN | 141 | −13.215 | −40.19 | −27.137 | 1 | 34.29 |
| 3961 | CB | GLN | 141 | −14.198 | −40.221 | −28.309 | 1 | 36.46 |
| 3962 | CG | GLN | 141 | −13.839 | −39.307 | −29.47 | 1 | 38.38 |
| 3963 | CD | GLN | 141 | −12.502 | −39.649 | −30.094 | 1 | 39.89 |
| 3964 | OE1 | GLN | 141 | −12.227 | −40.808 | −30.408 | 1 | 41.06 |
| 3965 | NE2 | GLN | 141 | −11.664 | −38.638 | −30.287 | 1 | 40.29 |
| 3966 | C | GLN | 141 | −13.145 | −38.781 | −26.559 | 1 | 33.88 |
| 3967 | O | GLN | 141 | −14 | −38.384 | −25.767 | 1 | 33.78 |
| 3968 | N | VAL | 142 | −12.12 | −38.032 | −26.946 | 1 | 31.4 |
| 3969 | CA | VAL | 142 | −11.967 | −36.67 | −26.461 | 1 | 30.39 |
| 3970 | CB | VAL | 142 | −11.182 | −36.625 | −25.129 | 1 | 31.78 |
| 3971 | CG1 | VAL | 142 | −9.812 | −37.25 | −25.312 | 1 | 33.32 |
| 3972 | CG2 | VAL | 142 | −11.048 | −35.185 | −24.653 | 1 | 33.7 |
| 3973 | C | VAL | 142 | −11.253 | −35.799 | −27.481 | 1 | 28.13 |
| 3974 | O | VAL | 142 | −10.331 | −36.245 | −28.164 | 1 | 28.03 |
| 3975 | N | VAL | 143 | −11.703 | −34.558 | −27.589 | 1 | 24.96 |
| 3976 | CA | VAL | 143 | −11.108 | −33.605 | −28.504 | 1 | 23.07 |
| 3977 | CB | VAL | 143 | −12.144 | −33.056 | −29.511 | 1 | 24.29 |
| 3978 | CG1 | VAL | 143 | −11.489 | −32.039 | −30.429 | 1 | 25.09 |
| 3979 | CG2 | VAL | 143 | −12.734 | −34.199 | −30.321 | 1 | 27.44 |
| 3980 | C | VAL | 143 | −10.587 | −32.455 | −27.66 | 1 | 22.46 |
| 3981 | O | VAL | 143 | −11.337 | −31.85 | −26.893 | 1 | 22.68 |
| 3982 | N | TRP | 144 | −9.295 | −32.177 | −27.78 | 1 | 18.43 |
| 3983 | CA | TRP | 144 | −8.69 | −31.086 | −27.032 | 1 | 17.59 |
| 3984 | CB | TRP | 144 | −7.561 | −31.606 | −26.138 | 1 | 16.68 |
| 3985 | CG | TRP | 144 | −6.938 | −30.538 | −25.285 | 1 | 18.72 |
| 3986 | CD2 | TRP | 144 | −5.547 | −30.381 | −24.985 | 1 | 18.53 |
| 3987 | CE3 | TRP | 144 | −5.426 | −29.26 | −24.131 | 1 | 19.4 |
| 3988 | CE3 | TRP | 144 | −4.389 | −31.078 | −25.354 | 1 | 20.47 |
| 3989 | CD1 | TRP | 144 | −7.588 | −29.536 | −24.62 | 1 | 20.51 |
| 3990 | NE1 | TRP | 144 | −6.687 | −28.763 | −23.925 | 1 | 21.59 |
| 3991 | CZ2 | TRP | 144 | −4.194 | −28.819 | −23.638 | 1 | 19.66 |
| 3992 | CZ3 | TRP | 144 | −3.16 | −30.638 | −24.863 | 1 | 20.23 |
| 3993 | CH2 | TRP | 144 | −3.075 | −29.518 | −24.015 | 1 | 19.34 |
| 3994 | C | TRP | 144 | −8.154 | −30.056 | −28.014 | 1 | 18.19 |
| 3995 | O | TRP | 144 | −7.326 | −30.366 | −28.872 | 1 | 18.06 |
| 3996 | N | GLN | 145 | −8.647 | −28.828 | −27.891 | 1 | 17.2 |
| 3997 | CA | GLN | 145 | −8.237 | −27.742 | −28.767 | 1 | 17.6 |
| 3998 | CB | GLN | 145 | −9.478 | −27.049 | −29.343 | 1 | 20.4 |
| 3999 | CG | GLN | 145 | −10.49 | −28.031 | −29.925 | 1 | 25.46 |
| 4000 | CD | GLN | 145 | −11.779 | −27.363 | −30.363 | 1 | 27.72 |
| 4001 | OE1 | GLN | 145 | −12.355 | −26.561 | −29.627 | 1 | 29.07 |
| 4002 | NE2 | GLN | 145 | −12.248 | −27.703 | −31.562 | 1 | 29.01 |
| 4003 | C | GLN | 145 | −7.394 | −26.753 | −27.968 | 1 | 16.83 |
| 4004 | O | GLN | 145 | −7.765 | −26.358 | −26.861 | 1 | 14.2 |
| 4005 | N | ALA | 146 | −6.256 | −26.358 | −28.529 | 1 | 16.33 |
| 4006 | CA | ALA | 146 | −5.368 | −25.427 | −27.849 | 1 | 16.62 |
| 4007 | CB | ALA | 146 | −4.417 | −26.195 | −26.935 | 1 | 17.53 |
| 4008 | C | ALA | 146 | −4.581 | −24.584 | −28.838 | 1 | 16.48 |
| 4009 | O | ALA | 146 | −4.541 | −24.881 | −30.034 | 1 | 17.21 |
| 4010 | N | SER | 147 | −3.952 | −23.529 | −28.332 | 1 | 15.3 |
| 4011 | CA | SER | 147 | −3.168 | −22.63 | −29.164 | 1 | 16.29 |
| 4012 | CB | SER | 147 | −3.948 | −21.335 | −29.417 | 1 | 18.78 |
| 4013 | OG | SER | 147 | −4.257 | −20.688 | −28.191 | 1 | 23.99 |
| 4014 | C | SER | 147 | −1.846 | −22.298 | −28.482 | 1 | 15.38 |
| 4015 | O | SER | 147 | −1.58 | −22.746 | −27.367 | 1 | 16.32 |
| 4016 | N | GLY | 148 | −1.022 | −21.514 | −29.165 | 1 | 15.29 |
| 4017 | CA | GLY | 148 | 0.251 | −21.105 | −28.605 | 1 | 14.62 |
| 4018 | C | GLY | 148 | 1.172 | −22.235 | −28.199 | 1 | 13.99 |
| 4019 | O | GLY | 148 | 1.32 | −23.222 | −28.918 | 1 | 14.17 |
| 4020 | N | TRP | 149 | 1.79 | −22.095 | −27.031 | 1 | 12.49 |
| 4021 | CA | TRP | 149 | 2.729 | −23.105 | −26.566 | 1 | 12.89 |
| 4022 | CB | TRP | 149 | 3.333 | −22.69 | −25.221 | 1 | 13.23 |
| 4023 | CG | TRP | 149 | 4.67 | −23.319 | −24.99 | 1 | 12.98 |
| 4024 | CD2 | TRP | 149 | 5.886 | −23.019 | −25.688 | 1 | 13.59 |
| 4025 | CE2 | TRP | 149 | 6.883 | −23.879 | −25.179 | 1 | 15.43 |
| 4026 | CE3 | TRP | 149 | 6.228 | −22.107 | −26.696 | 1 | 13.12 |
| 4027 | CD1 | TRP | 149 | 4.969 | −24.319 | −24.11 | 1 | 16.13 |
| 4028 | NE1 | TRP | 149 | 6.298 | −24.662 | −24.218 | 1 | 16.64 |
| 4029 | CZ2 | TRP | 149 | 8.203 | −23.853 | −25.644 | 1 | 16.86 |
| 4030 | CZ3 | TRP | 149 | 7.542 | −22.081 | −27.16 | 1 | 16.19 |
| 4031 | CH2 | TRP | 149 | 8.512 | −22.951 | −26.631 | 1 | 13.91 |
| 4032 | C | TRP | 149 | 2.13 | −24.502 | −26.465 | 1 | 14.15 |
| 4033 | O | TRP | 149 | 2.772 | −25.48 | −26.845 | 1 | 14.08 |
| 4034 | N | ALA | 150 | 0.904 | −24.609 | −25.963 | 1 | 13.69 |

TABLE 2-continued

| Atom | Atom Type | Residue | # | X | Y | Z | OCC | B |
|---|---|---|---|---|---|---|---|---|
| 4035 | CA | ALA | 150 | 0.266 | −25.917 | −25.844 | 1 | 12.64 |
| 4036 | CB | ALA | 150 | −1.108 | −25.784 | −25.195 | 1 | 12.67 |
| 4037 | C | ALA | 150 | 0.138 | −26.559 | −27.225 | 1 | 13.13 |
| 4038 | O | ALA | 150 | 0.339 | −27.764 | −27.378 | 1 | 13.25 |
| 4039 | N | ALA | 151 | −0.204 | −25.751 | −28.225 | 1 | 13.19 |
| 4040 | CA | ALA | 151 | −0.342 | −26.251 | −29.592 | 1 | 11.85 |
| 4041 | CB | ALA | 151 | −0.861 | −25.145 | −30.513 | 1 | 12.8 |
| 4042 | C | ALA | 151 | 1.006 | −26.764 | −30.095 | 1 | 12.13 |
| 4043 | O | ALA | 151 | 1.069 | −27.748 | −30.834 | 1 | 12.36 |
| 4044 | N | ARG | 152 | 2.082 | −26.089 | −29.697 | 1 | 12.53 |
| 4045 | CA | ARG | 152 | 3.425 | −26.5 | −30.095 | 1 | 12.91 |
| 4046 | CB | ARG | 152 | 4.463 | −25.486 | −29.617 | 1 | 13.14 |
| 4047 | CG | ARG | 152 | 5.913 | −25.968 | −29.74 | 1 | 11.69 |
| 4048 | CD | ARG | 152 | 6.886 | −24.858 | −29.368 | 1 | 12.46 |
| 4049 | NE | ARG | 152 | 6.739 | −23.705 | −30.252 | 1 | 12.96 |
| 4050 | CZ | ARG | 152 | 7.392 | −23.531 | −31.397 | 1 | 14.19 |
| 4051 | NH1 | ARG | 152 | 8.268 | −24.437 | −31.821 | 1 | 14.16 |
| 4052 | NH2 | ARG | 152 | 7.157 | −22.448 | −32.128 | 1 | 14.42 |
| 4053 | C | ARG | 152 | 3.747 | −27.866 | −29.508 | 1 | 12.5 |
| 4054 | O | ARG | 152 | 4.269 | −28.742 | −30.199 | 1 | 11.15 |
| 4055 | N | ILE | 153 | 3.439 | −28.05 | −28.229 | 1 | 11.69 |
| 4056 | CA | ILE | 153 | 3.698 | −29.328 | −27.568 | 1 | 12.3 |
| 4057 | CB | ILE | 153 | 3.334 | −29.246 | −26.074 | 1 | 12.72 |
| 4058 | CG2 | ILE | 153 | 3.58 | −30.594 | −25.401 | 1 | 15.96 |
| 4059 | CG1 | ILE | 153 | 4.163 | −28.141 | −25.413 | 1 | 16.12 |
| 4060 | CD1 | ILE | 153 | 3.707 | −27.766 | −24.006 | 1 | 16.14 |
| 4061 | C | ILE | 153 | 2.906 | −30.456 | −28.237 | 1 | 12.36 |
| 4062 | O | ILE | 153 | 3.429 | −31.545 | −28.467 | 1 | 12.53 |
| 4063 | N | ILE | 154 | 1.642 | −30.197 | −28.547 | 1 | 11.88 |
| 4064 | CA | ILE | 154 | 0.814 | −31.199 | −29.203 | 1 | 11.58 |
| 4065 | CB | ILE | 154 | −0.61 | −30.659 | −29.465 | 1 | 10.27 |
| 4066 | CG2 | ILE | 154 | −1.373 | −31.619 | −30.369 | 1 | 13.57 |
| 4067 | CG1 | ILE | 154 | −1.345 | −30.469 | −28.134 | 1 | 12.37 |
| 4068 | CD1 | ILE | 154 | −2.692 | −29.761 | −28.273 | 1 | 14.53 |
| 4069 | C | ILE | 154 | 1.435 | −31.619 | −30.536 | 1 | 11.19 |
| 4070 | O | ILE | 154 | 1.515 | −32.81 | −30.847 | 1 | 11.97 |
| 4071 | N | GLN | 155 | 1.877 | −30.635 | −31.316 | 1 | 11.07 |
| 4072 | CA | GLN | 155 | 2.484 | −30.901 | −32.622 | 1 | 11.41 |
| 4073 | CB | GLN | 155 | 2.755 | −29.587 | −33.354 | 1 | 11.12 |
| 4074 | CG | GLN | 155 | 1.484 | −28.887 | −33.815 | 1 | 12.34 |
| 4075 | CD | GLN | 155 | 1.734 | −27.47 | −34.275 | 1 | 13.32 |
| 4076 | OE1 | GLN | 155 | 2.38 | −27.237 | −35.3 | 1 | 14.45 |
| 4077 | NE2 | GLN | 155 | 1.233 | −26.506 | −33.508 | 1 | 13.59 |
| 4078 | C | GLN | 155 | 3.773 | −31.701 | −32.51 | 1 | 12.5 |
| 4079 | O | GLN | 155 | 4 | −32.628 | −33.284 | 1 | 13.62 |
| 4080 | N | HIS | 156 | 4.614 | −31.331 | −31.55 | 1 | 11.66 |
| 4081 | CA | HIS | 156 | 5.88 | −32.025 | −31.336 | 1 | 11.72 |
| 4082 | CB | HIS | 156 | 6.639 | −31.362 | −30.186 | 1 | 10.17 |
| 4083 | CG | HIS | 156 | 7.943 | −32.021 | −29.86 | 1 | 11.47 |
| 4084 | CD2 | HIS | 156 | 8.218 | −33.188 | −29.232 | 1 | 13.73 |
| 4085 | ND1 | HIS | 156 | 9.16 | −31.465 | −30.19 | 1 | 11.19 |
| 4086 | CE1 | HIS | 156 | 10.13 | −32.262 | −29.776 | 1 | 12.5 |
| 4087 | NE2 | HIS | 156 | 9.586 | −33.314 | −29.193 | 1 | 10.12 |
| 4088 | C | HIS | 156 | 5.623 | −33.493 | −31.002 | 1 | 12.38 |
| 4089 | O | HIS | 156 | 6.239 | −34.399 | −31.573 | 1 | 11.62 |
| 4090 | N | GLU | 157 | 4.708 | −33.733 | −30.071 | 1 | 12.25 |
| 4091 | CA | GLU | 157 | 4.403 | −35.093 | −29.666 | 1 | 13.32 |
| 4092 | CB | GLU | 157 | 3.537 | −35.072 | −28.402 | 1 | 15.77 |
| 4093 | CG | GLU | 157 | 4.125 | −35.874 | −27.25 | 1 | 20.56 |
| 4094 | CD | GLU | 157 | 5.622 | −35.638 | −27.068 | 1 | 18.03 |
| 4095 | OE1 | GLU | 157 | 6.03 | −34.528 | −26.654 | 1 | 17.51 |
| 4096 | OE2 | GLU | 157 | 6.391 | −36.579 | −27.347 | 1 | 20.71 |
| 4097 | C | GLU | 157 | 3.733 | −35.89 | −30.785 | 1 | 12.95 |
| 4098 | O | GLU | 157 | 4.06 | −37.06 | −31.003 | 1 | 13.07 |
| 4099 | N | MET | 158 | 2.805 | −35.267 | −31.507 | 1 | 12.52 |
| 4100 | CA | MET | 158 | 2.147 | −35.966 | −32.603 | 1 | 13.38 |
| 4101 | CB | MET | 158 | 1.025 | −35.111 | −33.195 | 1 | 13.07 |
| 4102 | CG | MET | 158 | −0.234 | −35.097 | −32.344 | 1 | 14.3 |
| 4103 | SD | MET | 158 | −1 | −36.729 | −32.214 | 1 | 16.96 |
| 4104 | CE | MET | 158 | −1.739 | −36.87 | −33.837 | 1 | 18.94 |
| 4105 | C | MET | 158 | 3.162 | −36.336 | −33.684 | 1 | 13.5 |
| 4106 | O | MET | 158 | 3.074 | −37.41 | −34.282 | 1 | 14.71 |
| 4107 | N | ASP | 159 | 4.13 | −35.455 | −33.926 | 1 | 12.83 |
| 4108 | CA | ASP | 159 | 5.155 | −35.733 | −34.933 | 1 | 12.19 |
| 4109 | CB | ASP | 159 | 6.171 | −34.586 | −35.016 | 1 | 12.13 |
| 4110 | CG | ASP | 159 | 5.705 | −33.452 | −35.912 | 1 | 15 |
| 4111 | OD1 | ASP | 159 | 4.634 | −33.588 | −36.542 | 1 | 16.97 |
| 4112 | OD2 | ASP | 159 | 6.416 | −32.426 | −35.996 | 1 | 14.67 |
| 4113 | C | ASP | 159 | 5.881 | −37.035 | −34.601 | 1 | 11.9 |
| 4114 | O | ASP | 159 | 6.203 | −37.816 | −35.494 | 1 | 11.84 |
| 4115 | N | HIS | 160 | 6.132 | −37.268 | −33.317 | 1 | 11.8 |
| 4116 | CA | HIS | 160 | 6.818 | −38.49 | −32.893 | 1 | 12.07 |
| 4117 | CB | HIS | 160 | 6.953 | −38.537 | −31.366 | 1 | 11.52 |
| 4118 | CG | HIS | 160 | 8.151 | −37.813 | −30.836 | 1 | 12 |
| 4119 | CD2 | HIS | 160 | 8.254 | −36.752 | −30.001 | 1 | 13.2 |
| 4120 | ND1 | HIS | 160 | 9.444 | −38.192 | −31.135 | 1 | 12.57 |
| 4121 | CE1 | HIS | 160 | 10.29 | −37.395 | −30.505 | 1 | 12.53 |
| 4122 | NE2 | HIS | 160 | 9.593 | −36.512 | −29.81 | 1 | 10.85 |
| 4123 | C | HIS | 160 | 6.093 | −39.752 | −33.353 | 1 | 13.34 |
| 4124 | O | HIS | 160 | 6.732 | −40.749 | −33.693 | 1 | 13.08 |
| 4125 | N | LEU | 161 | 4.763 | −39.712 | −33.364 | 1 | 12.62 |
| 4126 | CA | LEU | 161 | 3.984 | −40.877 | −33.764 | 1 | 12.75 |
| 4127 | CB | LEU | 161 | 2.531 | −40.734 | −33.29 | 1 | 13.26 |
| 4128 | CG | LEU | 161 | 2.351 | −40.597 | −31.772 | 1 | 13.06 |
| 4129 | CD1 | LEU | 161 | 0.867 | −40.678 | −31.435 | 1 | 14.01 |
| 4130 | CD2 | LEU | 161 | 3.11 | −41.699 | −31.042 | 1 | 12.68 |
| 4131 | C | LEU | 161 | 4.033 | −41.131 | −35.266 | 1 | 14.62 |
| 4132 | O | LEU | 161 | 3.635 | −42.2 | −35.73 | 1 | 14.45 |
| 4133 | N | GLN | 162 | 4.521 | −40.149 | −36.017 | 1 | 13.8 |
| 4134 | CA | GLN | 162 | 4.658 | −40.277 | −37.463 | 1 | 17.25 |
| 4135 | CB | GLN | 162 | 4.114 | −39.033 | −38.167 | 1 | 19.83 |
| 4136 | CG | GLN | 162 | 2.601 | −38.906 | −38.108 | 1 | 26.01 |
| 4137 | CD | GLN | 162 | 1.901 | −40.113 | −38.699 | 1 | 28.9 |
| 4138 | OE1 | GLN | 162 | 2.193 | −40.525 | −39.823 | 1 | 33.33 |
| 4139 | NE2 | GLN | 162 | 0.971 | −40.685 | −37.945 | 1 | 31.21 |
| 4140 | C | GLN | 162 | 6.126 | −40.479 | −37.833 | 1 | 16.51 |
| 4141 | O | GLN | 162 | 6.486 | −40.461 | −39.012 | 1 | 17.46 |
| 4142 | N | GLY | 163 | 6.968 | −40.665 | −36.818 | 1 | 15.36 |
| 4143 | CA | GLY | 163 | 8.389 | −40.875 | −37.051 | 1 | 14.12 |
| 4144 | C | GLY | 163 | 9.14 | −39.604 | −37.403 | 1 | 13.74 |
| 4145 | O | GLY | 163 | 10.202 | −39.653 | −38.025 | 1 | 13.31 |
| 4146 | N | CYS | 164 | 8.587 | −38.466 | −36.993 | 1 | 11.72 |
| 4147 | CA | CYS | 164 | 9.174 | −37.162 | −37.271 | 1 | 12.92 |
| 4148 | CB | CYS | 164 | 8.09 | −36.244 | −37.853 | 1 | 13.21 |
| 4149 | SG | CYS | 164 | 8.603 | −34.554 | −38.22 | 1 | 19.86 |
| 4150 | C | CYS | 164 | 9.787 | −36.511 | −36.028 | 1 | 12.27 |
| 4151 | O | CYS | 164 | 9.178 | −36.503 | −34.958 | 1 | 13.04 |
| 4152 | N | LEU | 165 | 10.999 | −35.978 | −36.179 | 1 | 11.31 |
| 4153 | CA | LEU | 165 | 11.691 | −35.301 | −35.083 | 1 | 11.63 |
| 4154 | CB | LEU | 165 | 13.091 | −35.894 | −34.87 | 1 | 11.51 |
| 4155 | CG | LEU | 165 | 13.142 | −37.379 | −34.488 | 1 | 11.61 |
| 4156 | CD1 | LEU | 165 | 14.589 | −37.81 | −34.241 | 1 | 11.23 |
| 4157 | CD2 | LEU | 165 | 12.364 | −37.619 | −33.206 | 1 | 12.23 |
| 4158 | C | LEU | 165 | 11.8 | −33.824 | −35.45 | 1 | 11.78 |
| 4159 | O | LEU | 165 | 11.747 | −33.466 | −36.627 | 1 | 12.61 |
| 4160 | N | PHE | 166 | 11.975 | −32.964 | −34.452 | 1 | 12.38 |
| 4161 | CA | PHE | 166 | 12.041 | −31.531 | −34.72 | 1 | 12.32 |
| 4162 | CB | PHE | 166 | 12.125 | −30.74 | −33.401 | 1 | 11.9 |
| 4163 | CG | PHE | 166 | 13.503 | −30.679 | −32.801 | 1 | 12.16 |
| 4164 | CD1 | PHE | 166 | 14.322 | −29.573 | −33.015 | 1 | 14.37 |
| 4165 | CD2 | PHE | 166 | 13.977 | −31.718 | −32.016 | 1 | 12.33 |
| 4166 | CE1 | PHE | 166 | 15.594 | −29.504 | −32.45 | 1 | 13.55 |
| 4167 | CE2 | PHE | 166 | 15.247 | −31.661 | −31.446 | 1 | 12.7 |
| 4168 | CZ | PHE | 166 | 16.056 | −30.553 | −31.662 | 1 | 13.51 |
| 4169 | C | PHE | 166 | 13.179 | −31.139 | −35.658 | 1 | 12.85 |
| 4170 | O | PHE | 166 | 13.103 | −30.115 | −36.335 | 1 | 12.87 |
| 4171 | N | ILE | 167 | 14.232 | −31.949 | −35.714 | 1 | 11.85 |
| 4172 | CA | ILE | 167 | 15.345 | −31.632 | −36.6 | 1 | 12.5 |
| 4173 | CB | ILE | 167 | 16.561 | −32.556 | −36.359 | 1 | 13.06 |
| 4174 | CG2 | ILE | 167 | 17.129 | −32.307 | −34.971 | 1 | 15.05 |
| 4175 | CG1 | ILE | 167 | 16.155 | −34.021 | −36.539 | 1 | 15.43 |
| 4176 | CD1 | ILE | 167 | 17.337 | −34.984 | −36.528 | 1 | 15.46 |
| 4177 | C | ILE | 167 | 14.935 | −31.731 | −38.067 | 1 | 12.18 |
| 4178 | O | ILE | 167 | 15.659 | −31.272 | −38.943 | 1 | 13.82 |
| 4179 | N | ASP | 168 | 13.773 | −32.328 | −38.33 | 1 | 11.09 |
| 4180 | CA | ASP | 168 | 13.279 | −32.462 | −39.701 | 1 | 12.7 |
| 4181 | CB | ASP | 168 | 12.263 | −33.612 | −39.83 | 1 | 11.97 |
| 4182 | CG | ASP | 168 | 12.822 | −34.97 | −39.429 | 1 | 11.4 |
| 4183 | OD1 | ASP | 168 | 14.034 | −35.21 | −39.598 | 1 | 13.56 |
| 4184 | OD2 | ASP | 168 | 12.023 | −35.814 | −38.967 | 1 | 12.41 |
| 4185 | C | ASP | 168 | 12.562 | −31.186 | −40.158 | 1 | 13.05 |
| 4186 | O | ASP | 168 | 12.326 | −30.999 | −41.353 | 1 | 14.94 |

TABLE 2-continued

| Atom | Atom Type | Residue | # | X | Y | Z | OCC | B |
|---|---|---|---|---|---|---|---|---|
| 4187 | N | LYS | 169 | 12.206 | −30.317 | −39.213 | 1 | 13.74 |
| 4188 | CA | LYS | 169 | 11.466 | −29.097 | −39.543 | 1 | 15.46 |
| 4189 | CB | LYS | 169 | 10.051 | −29.201 | −38.978 | 1 | 20.66 |
| 4190 | CG | LYS | 169 | 9.25 | −30.38 | −39.481 | 1 | 22.72 |
| 4191 | CD | LYS | 169 | 7.928 | −30.454 | −38.741 | 1 | 24.1 |
| 4192 | CE | LYS | 169 | 7.004 | −31.483 | −39.35 | 1 | 23.8 |
| 4193 | NZ | LYS | 169 | 5.721 | −31.523 | −38.607 | 1 | 26.32 |
| 4194 | C | LYS | 169 | 12.084 | −27.801 | −39.033 | 1 | 15.49 |
| 4195 | O | LYS | 169 | 11.519 | −26.722 | −39.208 | 1 | 16.88 |
| 4196 | N | MET | 170 | 13.246 | −27.91 | −38.412 | 1 | 14.71 |
| 4197 | CA | MET | 170 | 13.93 | −26.76 | −37.835 | 1 | 14.52 |
| 4198 | CB | MET | 170 | 15.021 | −27.256 | −36.894 | 1 | 13.95 |
| 4199 | CG | MET | 170 | 16.192 | −27.867 | −37.661 | 1 | 13.97 |
| 4200 | SD | MET | 170 | 17.544 | −28.383 | −36.597 | 1 | 12.97 |
| 4201 | CE | MET | 170 | 18.46 | −29.47 | −37.699 | 1 | 10.41 |
| 4202 | C | MET | 170 | 14.594 | −25.799 | −38.81 | 1 | 14.69 |
| 4203 | O | MET | 170 | 14.758 | −26.09 | −39.995 | 1 | 15.38 |
| 4204 | N | ASP | 171 | 14.965 | −24.638 | −38.278 | 1 | 15.86 |
| 4205 | CA | ASP | 171 | 15.732 | −23.649 | −39.02 | 1 | 15.06 |
| 4206 | CB | ASP | 171 | 15.495 | −22.235 | −38.487 | 1 | 19.51 |
| 4207 | CG | ASP | 171 | 16.411 | −21.211 | −39.136 | 1 | 21.13 |
| 4208 | OD1 | ASP | 171 | 17.426 | −21.614 | −39.751 | 1 | 23.52 |
| 4209 | OD2 | ASP | 171 | 16.126 | −20.001 | −39.023 | 1 | 25.52 |
| 4210 | C | ASP | 171 | 17.11 | −24.137 | −38.579 | 1 | 15.76 |
| 4211 | O | ASP | 171 | 17.557 | −23.838 | −37.469 | 1 | 14.7 |
| 4212 | N | SER | 172 | 17.767 | −24.909 | −39.435 | 1 | 14.03 |
| 4213 | CA | SER | 172 | 19.059 | −25.495 | −39.093 | 1 | 14.14 |
| 4214 | CB | SER | 172 | 19.593 | −26.319 | −40.271 | 1 | 14.82 |
| 4215 | OG | SER | 172 | 19.926 | −25.498 | −41.372 | 1 | 16.27 |
| 4216 | C | SER | 172 | 20.131 | −24.522 | −38.618 | 1 | 14.49 |
| 4217 | O | SER | 172 | 21.002 | −24.897 | −37.835 | 1 | 13.26 |
| 4218 | N | ARG | 173 | 20.076 | −23.274 | −39.07 | 1 | 13.6 |
| 4219 | CA | ARG | 173 | 21.089 | −22.318 | −38.647 | 1 | 13.16 |
| 4220 | CB | ARG | 173 | 21.076 | −21.087 | −39.556 | 1 | 14.38 |
| 4221 | CG | ARG | 173 | 21.573 | −21.383 | −40.964 | 1 | 15.28 |
| 4222 | CD | ARG | 173 | 21.596 | −20.126 | −41.823 | 1 | 16.25 |
| 4223 | NE | ARG | 173 | 22.429 | −19.083 | −41.232 | 1 | 17.6 |
| 4224 | CZ | ARG | 173 | 23.76 | −19.101 | −41.239 | 1 | 18.84 |
| 4225 | NH1 | ARG | 173 | 24.432 | −20.068 | −41.817 | 1 | 18.71 |
| 4226 | NH2 | ARG | 173 | 24.42 | −18.091 | −40.652 | 1 | 19.78 |
| 4227 | C | ARG | 173 | 20.943 | −21.907 | −37.185 | 1 | 12.78 |
| 4228 | O | ARG | 173 | 21.82 | −21.235 | −36.642 | 1 | 15.59 |
| 4229 | N | THR | 174 | 19.85 | −22.325 | −36.545 | 1 | 13.28 |
| 4230 | CA | THR | 174 | 19.621 | −21.993 | −35.137 | 1 | 12.66 |
| 4231 | CB | THR | 174 | 18.171 | −21.506 | −34.882 | 1 | 13.13 |
| 4232 | OG1 | THR | 174 | 17.254 | −22.578 | −35.125 | 1 | 13.46 |
| 4233 | CG2 | THR | 174 | 17.83 | −20.332 | −35.793 | 1 | 15.12 |
| 4234 | C | THR | 174 | 19.884 | −23.182 | −34.216 | 1 | 12.52 |
| 4235 | O | THR | 174 | 19.717 | −23.081 | −33 | 1 | 13.84 |
| 4236 | N | PHE | 175 | 20.283 | −24.309 | −34.802 | 1 | 12.71 |
| 4237 | CA | PHE | 175 | 20.577 | −25.52 | −34.035 | 1 | 12.31 |
| 4238 | CB | PHE | 175 | 20.976 | −26.645 | −34.999 | 1 | 11.07 |
| 4239 | CG | PHE | 175 | 21.11 | −28 | −34.353 | 1 | 11.89 |
| 4240 | CD1 | PHE | 175 | 19.984 | −28.708 | −33.942 | 1 | 11.71 |
| 4241 | CD2 | PHE | 175 | 22.364 | −28.588 | −34.193 | 1 | 11.39 |
| 4242 | CE1 | PHE | 175 | 20.101 | −29.983 | −33.387 | 1 | 11.84 |
| 4243 | CE2 | PHE | 175 | 22.492 | −29.862 | −33.639 | 1 | 10.41 |
| 4244 | CZ | PHE | 175 | 21.36 | −30.561 | −33.237 | 1 | 11.45 |
| 4245 | C | PHE | 175 | 21.729 | −25.176 | −33.094 | 1 | 11.07 |
| 4246 | O | PHE | 175 | 22.704 | −24.544 | −33.506 | 1 | 12.9 |
| 4247 | N | THR | 176 | 21.627 | −25.589 | −31.835 | 1 | 11.96 |
| 4248 | CA | THR | 176 | 22.671 | −25.255 | −30.868 | 1 | 11.7 |
| 4249 | CB | THR | 176 | 22.44 | −23.832 | −30.304 | 1 | 12.64 |
| 4250 | OG1 | THR | 176 | 23.473 | −23.497 | −29.368 | 1 | 13.49 |
| 4251 | CG2 | THR | 176 | 21.091 | −23.763 | −29.584 | 1 | 14.38 |
| 4252 | C | THR | 176 | 22.767 | −26.188 | −29.672 | 1 | 11.81 |
| 4253 | O | THR | 176 | 21.768 | −26.746 | −29.222 | 1 | 10.35 |
| 4254 | N | ASN | 177 | 23.988 | −26.377 | −29.175 | 1 | 10.78 |
| 4255 | CA | ASN | 177 | 24.188 | −27.159 | −27.958 | 1 | 10.89 |
| 4256 | CB | ASN | 177 | 25.683 | −27.301 | −27.658 | 1 | 11.31 |
| 4257 | CG | ASN | 177 | 26.308 | −28.508 | −28.332 | 1 | 10.89 |
| 4258 | OD1 | ASN | 177 | 26.195 | −29.632 | −27.84 | 1 | 12.29 |
| 4259 | ND2 | ASN | 177 | 26.965 | −28.284 | −29.469 | 1 | 11.83 |
| 4260 | C | ASN | 177 | 23.54 | −26.278 | −26.881 | 1 | 12.48 |
| 4261 | O | ASN | 177 | 23.598 | −25.054 | −26.976 | 1 | 11.98 |
| 4262 | N | VAL | 178 | 22.932 | −26.882 | −25.865 | 1 | 11.95 |
| 4263 | CA | VAL | 178 | 22.288 | −26.099 | −24.818 | 1 | 14.24 |
| 4264 | CB | VAL | 178 | 21.542 | −26.997 | −23.809 | 1 | 15.44 |
| 4265 | CG1 | VAL | 178 | 20.392 | −27.708 | −24.506 | 1 | 18.89 |
| 4266 | CG2 | VAL | 178 | 22.502 | −28.001 | −23.19 | 1 | 16.86 |
| 4267 | C | VAL | 178 | 23.255 | −25.208 | −24.044 | 1 | 14 |
| 4268 | O | VAL | 178 | 22.836 | −24.213 | −23.447 | 1 | 14.48 |
| 4269 | N | TYR | 179 | 24.543 | −25.546 | −24.055 | 1 | 12.72 |
| 4270 | CA | TYR | 179 | 25.511 | −24.731 | −23.328 | 1 | 12.6 |
| 4271 | CB | TYR | 179 | 26.735 | −25.568 | −22.911 | 1 | 12.94 |
| 4272 | CG | TYR | 179 | 27.463 | −26.3 | −24.016 | 1 | 12.88 |
| 4273 | CD1 | TYR | 179 | 28.289 | −25.621 | −24.909 | 1 | 13.21 |
| 4274 | CE1 | TYR | 179 | 29.005 | −26.303 | −25.886 | 1 | 14.95 |
| 4275 | CD2 | TYR | 179 | 27.364 | −27.686 | −24.136 | 1 | 12.57 |
| 4276 | CE2 | TYR | 179 | 28.075 | −28.378 | −25.114 | 1 | 13.26 |
| 4277 | CZ | TYR | 179 | 28.894 | −27.679 | −25.982 | 1 | 13.49 |
| 4278 | OH | TYR | 179 | 29.612 | −28.355 | −26.939 | 1 | 17.18 |
| 4279 | C | TYR | 179 | 25.921 | −23.45 | −24.06 | 1 | 12.85 |
| 4280 | O | TYR | 179 | 26.756 | −22.687 | −23.576 | 1 | 13.89 |
| 4281 | N | TRP | 180 | 25.329 | −23.224 | −25.232 | 1 | 12.01 |
| 4282 | CA | TRP | 180 | 25.559 | −21.993 | −25.991 | 1 | 11.89 |
| 4283 | CB | TRP | 180 | 25.982 | −22.278 | −27.436 | 1 | 11.98 |
| 4284 | CG | TRP | 180 | 27.46 | −22.326 | −27.627 | 1 | 11.11 |
| 4285 | CD2 | TRP | 180 | 28.354 | −21.209 | −27.667 | 1 | 11.62 |
| 4286 | CE2 | TRP | 180 | 29.657 | −21.723 | −27.847 | 1 | 11.93 |
| 4287 | CE3 | TRP | 180 | 28.18 | −19.821 | −27.567 | 1 | 12.29 |
| 4288 | CD1 | TRP | 180 | 28.234 | −23.442 | −27.781 | 1 | 10.27 |
| 4289 | NE1 | TRP | 180 | 29.555 | −23.089 | −27.913 | 1 | 11.17 |
| 4290 | CZ2 | TRP | 180 | 30.785 | −20.897 | −27.931 | 1 | 12.81 |
| 4291 | CZ3 | TRP | 180 | 29.299 | −19.001 | −27.651 | 1 | 12.84 |
| 4292 | CH2 | TRP | 180 | 30.586 | −19.543 | −27.831 | 1 | 13.31 |
| 4293 | C | TRP | 180 | 24.21 | −21.287 | −25.999 | 1 | 13.28 |
| 4294 | O | TRP | 180 | 23.183 | −21.92 | −26.248 | 1 | 13.89 |
| 4295 | N | MET | 181 | 24.199 | −19.986 | −25.727 | 1 | 13.15 |
| 4296 | CA | MET | 181 | 22.936 | −19.251 | −25.703 | 1 | 16.16 |
| 4297 | CB | MET | 181 | 22.259 | −19.445 | −24.343 | 1 | 18.01 |
| 4298 | CG | MET | 181 | 23.051 | −18.861 | −23.182 | 1 | 17.45 |
| 4299 | SD | MET | 181 | 22.773 | −19.726 | −21.618 | 1 | 19.18 |
| 4300 | CE | MET | 181 | 23.972 | −21.074 | −21.773 | 1 | 20.14 |
| 4301 | C | MET | 181 | 23.11 | −17.762 | −25.968 | 1 | 18.12 |
| 4302 | O | MET | 181 | 24.181 | −17.201 | −25.747 | 1 | 16.85 |
| 4303 | N | LYS | 182 | 22.044 | −17.129 | −26.45 | 1 | 22.03 |
| 4304 | CA | LYS | 182 | 22.063 | −15.695 | −26.714 | 1 | 26.45 |
| 4305 | CB | LYS | 182 | 21.062 | −15.329 | −27.814 | 1 | 29.2 |
| 4306 | CG | LYS | 182 | 21.292 | −16.045 | −29.129 | 1 | 32.28 |
| 4307 | CD | LYS | 182 | 20.358 | −15.536 | −30.218 | 1 | 34.43 |
| 4308 | CE | LYS | 182 | 20.59 | −16.28 | −31.525 | 1 | 36.41 |
| 4309 | NZ | LYS | 182 | 19.763 | −15.743 | −32.643 | 1 | 38.17 |
| 4310 | C | LYS | 182 | 21.661 | −15.01 | −25.415 | 1 | 27.79 |
| 4311 | O | LYS | 182 | 20.732 | −15.452 | −24.739 | 1 | 28.99 |
| 4312 | N | VAL | 183 | 22.363 | −13.939 | −25.062 | 1 | 29.09 |
| 4313 | CA | VAL | 183 | 22.062 | −13.214 | −23.834 | 1 | 30.92 |
| 4314 | CB | VAL | 183 | 23.119 | −13.499 | −22.747 | 1 | 31.4 |
| 4315 | CG1 | VAL | 183 | 22.976 | −14.929 | −22.242 | 1 | 31.01 |
| 4316 | CG2 | VAL | 183 | 24.51 | −13.28 | −23.314 | 1 | 30.85 |
| 4317 | C | VAL | 183 | 22.002 | −11.711 | −24.072 | 1 | 32.36 |
| 4318 | O | VAL | 183 | 22.489 | −11.215 | −25.086 | 1 | 32 |
| 4319 | N | ASN | 184 | 21.392 | −10.996 | −23.132 | 1 | 34.84 |
| 4320 | CA | ASN | 184 | 21.27 | −9.546 | −23.225 | 1 | 36.95 |
| 4321 | CB | ASN | 184 | 20.175 | −9.038 | −22.285 | 1 | 37.31 |
| 4322 | CG | ASN | 184 | 18.81 | −9.602 | −22.619 | 1 | 37.13 |
| 4323 | OD1 | ASN | 184 | 18.3 | −9.413 | −23.723 | 1 | 38.39 |
| 4324 | ND2 | ASN | 184 | 18.209 | −10.298 | −21.663 | 1 | 38.37 |
| 4325 | C | ASN | 184 | 22.598 | −8.915 | −22.833 | 1 | 38.8 |
| 4326 | O | ASN | 184 | 23.062 | −9.077 | −21.711 | 1 | 39.71 |
| 4327 | N | ASP | 185 | 23.205 | −8.193 | −23.774 | 1 | 40.71 |
| 4328 | CA | ASP | 185 | 24.487 | −7.547 | −23.524 | 1 | 42.35 |
| 4329 | CB | ASP | 185 | 24.952 | −6.8 | −24.776 | 1 | 43.47 |
| 4330 | CG | ASP | 185 | 26.257 | −7.342 | −25.326 | 1 | 44.68 |
| 4331 | OD1 | ASP | 185 | 27.256 | −7.368 | −24.575 | 1 | 46.49 |
| 4332 | OD2 | ASP | 185 | 26.287 | −7.742 | −26.51 | 1 | 45.69 |
| 4333 | C | ASP | 185 | 24.415 | −6.581 | −22.344 | 1 | 42.85 |
| 4334 | O | ASP | 185 | 23.311 | −6.407 | −21.787 | 1 | 43.85 |
| 4335 | OXT | ASP | 185 | 25.468 | −6.01 | −21.99 | 1 | 43.39 |
| 4336 | CB | HIS | 3 | 56.449 | −25.756 | −25.218 | 1 | 41.59 |
| 4337 | CG | HIS | 3 | 56.743 | −26.197 | −26.618 | 1 | 42.15 |
| 4338 | CD2 | HIS | 3 | 56.207 | −25.82 | −27.803 | 1 | 42.52 |

TABLE 2-continued

| Atom | Atom Type | Residue | # | X | Y | Z | OCC | B |
|---|---|---|---|---|---|---|---|---|
| 4339 | ND1 | HIS | 3 | 57.68 | −27.166 | −26.912 | 1 | 42.87 |
| 4340 | CE1 | HIS | 3 | 57.707 | −27.366 | −28.218 | 1 | 42.67 |
| 4341 | NE2 | HIS | 3 | 56.823 | −26.562 | −28.781 | 1 | 42.62 |
| 4342 | C | HIS | 3 | 54.562 | −27.363 | −24.929 | 1 | 40.5 |
| 4343 | O | HIS | 3 | 54.53 | −27.866 | −26.053 | 1 | 41.32 |
| 4344 | N | HIS | 3 | 56.853 | −27.981 | −24.204 | 1 | 40.94 |
| 4345 | CA | HIS | 3 | 55.873 | −26.864 | −24.331 | 1 | 40.95 |
| 4346 | N | MET | 4 | 53.48 | −27.224 | −24.173 | 1 | 39.96 |
| 4347 | CA | MET | 4 | 52.174 | −27.666 | −24.642 | 1 | 38.85 |
| 4348 | CB | MET | 4 | 51.849 | −29.052 | −24.083 | 1 | 40.55 |
| 4349 | CG | MET | 4 | 52.809 | −30.141 | −24.521 | 1 | 42.9 |
| 4350 | SD | MET | 4 | 52.304 | −31.768 | −23.935 | 1 | 48.13 |
| 4351 | CE | MET | 4 | 51.396 | −32.375 | −25.362 | 1 | 45 |
| 4352 | C | MET | 4 | 51.066 | −26.699 | −24.257 | 1 | 37.16 |
| 4353 | O | MET | 4 | 51.1 | −26.086 | −23.189 | 1 | 37.59 |
| 4354 | N | SER | 5 | 50.084 | −26.567 | −25.142 | 1 | 34.74 |
| 4355 | CA | SER | 5 | 48.944 | −25.695 | −24.905 | 1 | 32.21 |
| 4356 | CB | SER | 5 | 49.026 | −24.449 | −25.79 | 1 | 33.46 |
| 4357 | OG | SER | 5 | 48.965 | −24.787 | −27.164 | 1 | 36.63 |
| 4358 | C | SER | 5 | 47.681 | −26.482 | −25.231 | 1 | 29.81 |
| 4359 | O | SER | 5 | 47.754 | −27.62 | −25.692 | 1 | 30.46 |
| 4360 | N | PHE | 6 | 46.526 | −25.876 | −24.987 | 1 | 26.38 |
| 4361 | CA | PHE | 6 | 45.256 | −26.532 | −25.262 | 1 | 24.1 |
| 4362 | CB | PHE | 6 | 44.335 | −26.43 | −24.045 | 1 | 24.87 |
| 4363 | CG | PHE | 6 | 44.706 | −27.354 | −22.924 | 1 | 25.19 |
| 4364 | CD1 | PHE | 6 | 44.257 | −28.67 | −22.915 | 1 | 25.79 |
| 4365 | CD2 | PHE | 6 | 45.513 | −26.913 | −21.882 | 1 | 27.73 |
| 4366 | CE1 | PHE | 6 | 44.606 | −29.536 | −21.882 | 1 | 27.23 |
| 4367 | CE2 | PHE | 6 | 45.869 | −27.772 | −20.843 | 1 | 26.43 |
| 4368 | CZ | PHE | 6 | 45.414 | −29.086 | −20.844 | 1 | 26.82 |
| 4369 | C | PHE | 6 | 44.565 | −25.914 | −26.465 | 1 | 23.16 |
| 4370 | O | PHE | 6 | 44.593 | −24.699 | −26.659 | 1 | 24.37 |
| 4371 | N | SER | 7 | 43.958 | −26.767 | −27.28 | 1 | 20.73 |
| 4372 | CA | SER | 7 | 43.222 | −26.326 | −28.455 | 1 | 19.81 |
| 4373 | CB | SER | 7 | 43.943 | −26.731 | −29.743 | 1 | 23.18 |
| 4374 | OG | SER | 7 | 45.133 | −25.985 | −29.925 | 1 | 28.72 |
| 4375 | C | SER | 7 | 41.876 | −27.02 | −28.392 | 1 | 18.47 |
| 4376 | O | SER | 7 | 41.759 | −28.1 | −27.817 | 1 | 17.16 |
| 4377 | N | HIS | 8 | 40.856 | −26.402 | −28.969 | 1 | 16.73 |
| 4378 | CA | HIS | 8 | 39.545 | −27.017 | −28.957 | 1 | 16.18 |
| 4379 | CB | HIS | 8 | 38.74 | −26.545 | −27.743 | 1 | 19.35 |
| 4380 | CG | HIS | 8 | 38.316 | −25.113 | −27.817 | 1 | 23.77 |
| 4381 | CD2 | HIS | 8 | 39.029 | −23.966 | −27.722 | 1 | 25.74 |
| 4382 | ND1 | HIS | 8 | 37.007 | −24.735 | −28.023 | 1 | 25.87 |
| 4383 | CE1 | HIS | 8 | 36.93 | −23.417 | −28.051 | 1 | 27.55 |
| 4384 | NE2 | HIS | 8 | 38.143 | −22.925 | −27.871 | 1 | 29.34 |
| 4385 | C | HIS | 8 | 38.783 | −26.71 | −30.23 | 1 | 14.51 |
| 4386 | O | HIS | 8 | 38.922 | −25.632 | −30.814 | 1 | 15.29 |
| 4387 | N | VAL | 9 | 37.992 | −27.68 | −30.666 | 1 | 12.63 |
| 4388 | CA | VAL | 9 | 37.176 | −27.501 | −31.852 | 1 | 12.1 |
| 4389 | CB | VAL | 9 | 36.94 | −28.832 | −32.579 | 1 | 12.29 |
| 4390 | CG1 | VAL | 9 | 36.006 | −28.62 | −33.762 | 1 | 14.09 |
| 4391 | CG2 | VAL | 9 | 38.27 | −29.398 | −33.055 | 1 | 15.25 |
| 4392 | C | VAL | 9 | 35.848 | −26.944 | −31.373 | 1 | 12.91 |
| 4393 | O | VAL | 9 | 35.172 | −27.562 | −30.546 | 1 | 12.06 |
| 4394 | N | CYS | 10 | 35.492 | −25.765 | −31.872 | 1 | 11.31 |
| 4395 | CA | CYS | 10 | 34.243 | −25.12 | −31.489 | 1 | 12.01 |
| 4396 | CB | CYS | 10 | 34.138 | −23.749 | −32.156 | 1 | 12.98 |
| 4397 | SG | CYS | 10 | 35.511 | −22.639 | −31.732 | 1 | 16.99 |
| 4398 | C | CYS | 10 | 33.057 | −25.987 | −31.89 | 1 | 11.61 |
| 4399 | O | CYS | 10 | 33.052 | −26.582 | −32.969 | 1 | 11.44 |
| 4400 | N | GLN | 11 | 32.054 | −26.052 | −31.018 | 1 | 12.26 |
| 4401 | CA | GLN | 11 | 30.864 | −26.856 | −31.28 | 1 | 11.87 |
| 4402 | CB | GLN | 11 | 30.504 | −27.674 | −30.042 | 1 | 12.45 |
| 4403 | CG | GLN | 11 | 31.589 | −28.665 | −29.641 | 1 | 10.37 |
| 4404 | CD | GLN | 11 | 31.882 | −29.666 | −30.736 | 1 | 10.04 |
| 4405 | OE1 | GLN | 11 | 31.005 | −30.432 | −31.137 | 1 | 12.67 |
| 4406 | NE2 | GLN | 11 | 33.116 | −29.663 | −31.232 | 1 | 9.67 |
| 4407 | C | GLN | 11 | 29.672 | −26.007 | −31.708 | 1 | 12.77 |
| 4408 | O | GLN | 11 | 29.585 | −24.827 | −31.366 | 1 | 11.4 |
| 4409 | N | VAL | 12 | 28.748 | −26.625 | −32.441 | 1 | 11.78 |
| 4410 | CA | VAL | 12 | 27.578 | −25.916 | −32.946 | 1 | 11.46 |
| 4411 | CB | VAL | 12 | 26.63 | −26.889 | −33.707 | 1 | 11.79 |
| 4412 | CG1 | VAL | 12 | 26.114 | −27.975 | −32.781 | 1 | 12.12 |
| 4413 | CG2 | VAL | 12 | 25.494 | −26.109 | −34.36 | 1 | 12.08 |
| 4414 | C | VAL | 12 | 26.865 | −25.158 | −31.826 | 1 | 12.32 |
| 4415 | O | VAL | 12 | 26.561 | −25.7 | −30.762 | 1 | 10.75 |
| 4416 | N | GLY | 13 | 26.631 | −23.877 | −32.085 | 1 | 13 |
| 4417 | CA | GLY | 13 | 26.025 | −22.999 | −31.1 | 1 | 13.26 |
| 4418 | C | GLY | 13 | 26.942 | −21.792 | −31.015 | 1 | 12.98 |
| 4419 | O | GLY | 13 | 26.493 | −20.668 | −30.778 | 1 | 13.02 |
| 4420 | N | ASP | 14 | 28.237 | −22.03 | −31.212 | 1 | 11.62 |
| 4421 | CA | ASP | 14 | 29.235 | −20.963 | −31.202 | 1 | 12.65 |
| 4422 | CB | ASP | 14 | 30.649 | −21.553 | −31.244 | 1 | 12.48 |
| 4423 | CG | ASP | 14 | 31.733 | −20.499 | −31.099 | 1 | 13.31 |
| 4424 | OD1 | ASP | 14 | 31.497 | −19.329 | −31.473 | 1 | 14.32 |
| 4425 | OD2 | ASP | 14 | 32.837 | −20.843 | −30.623 | 1 | 15.01 |
| 4426 | C | ASP | 14 | 28.983 | −20.167 | −32.483 | 1 | 13.42 |
| 4427 | O | ASP | 14 | 29.074 | −20.708 | −33.58 | 1 | 12.86 |
| 4428 | N | PRO | 15 | 28.671 | −18.873 | −32.362 | 1 | 12.92 |
| 4429 | CD | PRO | 15 | 28.617 | −18.046 | −31.143 | 1 | 12.33 |
| 4430 | CA | PRO | 15 | 28.413 | −18.064 | −33.559 | 1 | 13.49 |
| 4431 | CB | PRO | 15 | 28.072 | −16.693 | −32.975 | 1 | 14.88 |
| 4432 | CG | PRO | 15 | 28.858 | −16.663 | −31.699 | 1 | 14.94 |
| 4433 | C | PRO | 15 | 29.532 | −17.999 | −34.602 | 1 | 13.42 |
| 4434 | O | PRO | 15 | 29.271 | −17.721 | −35.776 | 1 | 14.83 |
| 4435 | N | VAL | 16 | 30.77 | −18.249 | −34.191 | 1 | 12.93 |
| 4436 | CA | VAL | 16 | 31.882 | −18.197 | −35.133 | 1 | 13.66 |
| 4437 | CB | VAL | 16 | 33.239 | −18.473 | −34.43 | 1 | 13.49 |
| 4438 | CG1 | VAL | 16 | 33.35 | −19.944 | −34.034 | 1 | 14.89 |
| 4439 | CG2 | VAL | 16 | 34.39 | −18.065 | −35.347 | 1 | 15.48 |
| 4440 | C | VAL | 16 | 31.681 | −19.202 | −36.268 | 1 | 13.61 |
| 4441 | O | VAL | 16 | 32.158 | −18.992 | −37.385 | 1 | 14.05 |
| 4442 | N | LEU | 17 | 30.949 | −20.276 | −35.987 | 1 | 11.86 |
| 4443 | CA | LEU | 17 | 30.702 | −21.311 | −36.988 | 1 | 11.88 |
| 4444 | CB | LEU | 17 | 30.254 | −22.608 | −36.309 | 1 | 11.58 |
| 4445 | CG | LEU | 17 | 31.27 | −23.276 | −35.381 | 1 | 11.56 |
| 4446 | CD1 | LEU | 17 | 30.599 | −24.429 | −34.647 | 1 | 12.01 |
| 4447 | CD2 | LEU | 17 | 32.463 | −23.769 | −36.187 | 1 | 13.7 |
| 4448 | C | LEU | 17 | 29.657 | −20.917 | −38.023 | 1 | 12.71 |
| 4449 | O | LEU | 17 | 29.553 | −21.548 | −39.074 | 1 | 13.06 |
| 4450 | N | ARG | 18 | 28.882 | −19.877 | −37.732 | 1 | 13.86 |
| 4451 | CA | ARG | 18 | 27.838 | −19.448 | −38.656 | 1 | 14.02 |
| 4452 | CB | ARG | 18 | 26.496 | −19.367 | −37.924 | 1 | 15.12 |
| 4453 | CG | ARG | 18 | 25.601 | −20.586 | −38.12 | 1 | 14.99 |
| 4454 | CD | ARG | 18 | 26.296 | −21.898 | −37.77 | 1 | 13.19 |
| 4455 | NE | ARG | 18 | 25.335 | −22.996 | −37.76 | 1 | 12.07 |
| 4456 | CZ | ARG | 18 | 24.844 | −23.582 | −38.848 | 1 | 12.77 |
| 4457 | NH1 | ARG | 18 | 25.231 | −23.193 | −40.057 | 1 | 11.51 |
| 4458 | NH2 | ARG | 18 | 23.931 | −24.537 | −38.728 | 1 | 11.34 |
| 4459 | C | ARG | 18 | 28.112 | −18.137 | −39.383 | 1 | 14.9 |
| 4460 | O | ARG | 18 | 27.319 | −17.711 | −40.224 | 1 | 15.67 |
| 4461 | N | GLY | 19 | 29.228 | −17.496 | −39.064 | 1 | 16.41 |
| 4462 | CA | GLY | 19 | 29.551 | −16.252 | −39.735 | 1 | 17.65 |
| 4463 | C | GLY | 19 | 30.3 | −16.522 | −41.025 | 1 | 18.79 |
| 4464 | O | GLY | 19 | 30.697 | −17.656 | −41.292 | 1 | 18.36 |
| 4465 | N | VAL | 20 | 30.476 | −15.487 | −41.839 | 1 | 19.96 |
| 4466 | CA | VAL | 20 | 31.214 | −15.621 | −43.088 | 1 | 20.35 |
| 4467 | CB | VAL | 20 | 30.627 | −14.716 | −44.194 | 1 | 21.01 |
| 4468 | CG1 | VAL | 20 | 31.446 | −14.851 | −45.466 | 1 | 21.57 |
| 4469 | CG2 | VAL | 20 | 29.177 | −15.096 | −44.458 | 1 | 23.36 |
| 4470 | C | VAL | 20 | 32.639 | −15.184 | −42.772 | 1 | 19.19 |
| 4471 | O | VAL | 20 | 32.886 | −14.013 | −42.481 | 1 | 20.84 |
| 4472 | N | ALA | 21 | 33.572 | −16.13 | −42.814 | 1 | 17.38 |
| 4473 | CA | ALA | 21 | 34.969 | −15.843 | −42.505 | 1 | 17.72 |
| 4474 | CB | ALA | 21 | 35.815 | −17.089 | −42.719 | 1 | 15.83 |
| 4475 | C | ALA | 21 | 35.524 | −14.692 | −43.331 | 1 | 19.38 |
| 4476 | O | ALA | 21 | 35.273 | −14.597 | −44.53 | 1 | 19.52 |
| 4477 | N | ALA | 22 | 36.277 | −13.817 | −42.675 | 1 | 20.23 |
| 4478 | CA | ALA | 22 | 36.879 | −12.674 | −43.347 | 1 | 22.15 |
| 4479 | CB | ALA | 22 | 37.186 | −11.575 | −42.334 | 1 | 23.24 |
| 4480 | C | ALA | 22 | 38.16 | −13.12 | −44.041 | 1 | 21.74 |
| 4481 | O | ALA | 22 | 38.827 | −14.054 | −43.599 | 1 | 22.13 |
| 4482 | N | PRO | 23 | 38.517 | −12.466 | −45.152 | 1 | 23.32 |
| 4483 | CD | PRO | 23 | 37.815 | −11.393 | −45.875 | 1 | 24.87 |
| 4484 | CA | PRO | 23 | 39.74 | −12.856 | −45.852 | 1 | 23.51 |
| 4485 | CB | PRO | 23 | 39.659 | −12.057 | −47.152 | 1 | 25.07 |
| 4486 | CG | PRO | 23 | 38.918 | −10.826 | −46.739 | 1 | 26.16 |
| 4487 | C | PRO | 23 | 40.996 | −12.53 | −45.054 | 1 | 23.82 |
| 4488 | O | PRO | 23 | 40.987 | −11.661 | −44.177 | 1 | 22.62 |
| 4489 | N | VAL | 24 | 42.069 | −13.252 | −45.349 | 1 | 24.39 |
| 4490 | CA | VAL | 24 | 43.347 | −13.017 | −44.7 | 1 | 26.03 |

TABLE 2-continued

| Atom | Atom Type | Residue | # | X | Y | Z | OCC | B |
|---|---|---|---|---|---|---|---|---|
| 4491 | CB | VAL | 24 | 44.266 | −14.249 | −44.801 | 1 | 25.85 |
| 4492 | CG1 | VAL | 24 | 45.653 | −13.908 | −44.282 | 1 | 26.89 |
| 4493 | CG2 | VAL | 24 | 43.677 | −15.403 | −44.004 | 1 | 25.06 |
| 4494 | C | VAL | 24 | 43.976 | −11.864 | −45.471 | 1 | 27.66 |
| 4495 | O | VAL | 24 | 44.048 | −11.901 | −46.698 | 1 | 26.1 |
| 4496 | N | GLU | 25 | 44.412 | −10.834 | −44.757 | 1 | 30.32 |
| 4497 | CA | GLU | 25 | 45.028 | −9.686 | −45.406 | 1 | 32.7 |
| 4498 | CB | GLU | 25 | 45.108 | −8.515 | −44.426 | 1 | 35.74 |
| 4499 | CG | GLU | 25 | 43.742 | −8.048 | −43.942 | 1 | 39.43 |
| 4500 | CD | GLU | 25 | 43.821 | −6.885 | −42.975 | 1 | 42.07 |
| 4501 | OE1 | GLU | 25 | 44.428 | −7.046 | −41.894 | 1 | 43.7 |
| 4502 | OE2 | GLU | 25 | 43.274 | −5.808 | −43.297 | 1 | 43.94 |
| 4503 | C | GLU | 25 | 46.416 | −10.067 | −45.903 | 1 | 32.6 |
| 4504 | O | GLU | 25 | 47.158 | −10.761 | −45.21 | 1 | 32.7 |
| 4505 | N | ARG | 26 | 46.759 | −9.623 | −47.109 | 1 | 33.23 |
| 4506 | CA | ARG | 26 | 48.06 | −9.939 | −47.692 | 1 | 33.47 |
| 4507 | CB | ARG | 26 | 48.271 | −9.158 | −48.99 | 1 | 34.49 |
| 4508 | CG | ARG | 26 | 47.402 | −9.617 | −50.15 | 1 | 36.34 |
| 4509 | CD | ARG | 26 | 47.936 | −9.12 | −51.492 | 1 | 36.81 |
| 4510 | NE | ARG | 26 | 49.21 | −9.738 | −51.869 | 1 | 38.73 |
| 4511 | CZ | ARG | 26 | 50.394 | −9.418 | −51.351 | 1 | 39.31 |
| 4512 | NH1 | ARG | 26 | 50.492 | −8.479 | −50.422 | 1 | 41.1 |
| 4513 | NH2 | ARG | 26 | 51.49 | −10.036 | −51.766 | 1 | 40.61 |
| 4514 | C | ARG | 26 | 49.213 | −9.655 | −46.737 | 1 | 33.11 |
| 4515 | O | ARG | 26 | 50.263 | −10.293 | −46.815 | 1 | 32.69 |
| 4516 | N | ALA | 27 | 49.012 | −8.699 | −45.837 | 1 | 34.52 |
| 4517 | CA | ALA | 27 | 50.036 | −8.335 | −44.865 | 1 | 34.83 |
| 4518 | CB | ALA | 27 | 49.569 | −7.14 | −44.041 | 1 | 35.24 |
| 4519 | C | ALA | 27 | 50.345 | −9.514 | −43.948 | 1 | 34.99 |
| 4520 | O | ALA | 27 | 51.413 | −9.577 | −43.338 | 1 | 35.69 |
| 4521 | N | GLN | 28 | 49.404 | −10.449 | −43.861 | 1 | 34.64 |
| 4522 | CA | GLN | 28 | 49.554 | −11.631 | −43.02 | 1 | 34.79 |
| 4523 | CB | GLN | 28 | 48.185 | −12.062 | −42.489 | 1 | 35.73 |
| 4524 | CG | GLN | 28 | 47.688 | −11.245 | −41.31 | 1 | 37.84 |
| 4525 | CD | GLN | 28 | 48.39 | −11.618 | −40.02 | 1 | 39.17 |
| 4526 | OE1 | GLN | 28 | 48.316 | −12.765 | −39.572 | 1 | 40.65 |
| 4527 | NE2 | GLN | 28 | 49.076 | −10.655 | −39.415 | 1 | 39.15 |
| 4528 | C | GLN | 28 | 50.21 | −12.806 | −43.74 | 1 | 33.56 |
| 4529 | O | GLN | 28 | 50.742 | −13.713 | −43.099 | 1 | 33.92 |
| 4530 | N | LEU | 29 | 50.173 | −12.788 | −45.068 | 1 | 32.9 |
| 4531 | CA | LEU | 29 | 50.754 | −13.865 | −45.861 | 1 | 32.42 |
| 4532 | CB | LEU | 29 | 50.565 | −13.576 | −47.353 | 1 | 31.55 |
| 4533 | CG | LEU | 29 | 49.113 | −13.427 | −47.82 | 1 | 31.21 |
| 4534 | CD1 | LEU | 29 | 49.085 | −13.03 | −49.287 | 1 | 31.11 |
| 4535 | CD2 | LEU | 29 | 48.359 | −14.732 | −47.602 | 1 | 30.28 |
| 4536 | C | LEU | 29 | 52.234 | −14.079 | −45.555 | 1 | 32.67 |
| 4537 | O | LEU | 29 | 53.035 | −13.146 | −45.618 | 1 | 32.82 |
| 4538 | N | GLY | 30 | 52.589 | −15.316 | −45.221 | 1 | 33.1 |
| 4539 | CA | GLY | 30 | 53.97 | −15.635 | −44.908 | 1 | 33.53 |
| 4540 | C | GLY | 30 | 54.367 | −15.216 | −43.505 | 1 | 34.13 |
| 4541 | O | GLY | 30 | 55.466 | −15.528 | −43.045 | 1 | 34.69 |
| 4542 | N | GLY | 31 | 53.468 | −14.514 | −42.822 | 1 | 33.95 |
| 4543 | CA | GLY | 31 | 53.748 | −14.054 | −41.473 | 1 | 33.81 |
| 4544 | C | GLY | 31 | 53.737 | −15.151 | −40.424 | 1 | 33.75 |
| 4545 | O | GLY | 31 | 53.249 | −16.253 | −40.681 | 1 | 34.6 |
| 4546 | N | PRO | 32 | 54.271 | −14.877 | −39.223 | 1 | 32.77 |
| 4547 | CD | PRO | 32 | 54.931 | −13.616 | −38.837 | 1 | 33.24 |
| 4548 | CA | PRO | 32 | 54.324 | −15.849 | −38.125 | 1 | 32.26 |
| 4549 | CB | PRO | 32 | 55.262 | −15.18 | −37.123 | 1 | 33.07 |
| 4550 | CG | PRO | 32 | 54.978 | −13.724 | −37.331 | 1 | 33.11 |
| 4551 | C | PRO | 32 | 52.962 | −16.188 | −37.518 | 1 | 31.28 |
| 4552 | O | PRO | 32 | 52.739 | −17.316 | −37.076 | 1 | 31.32 |
| 4553 | N | GLU | 33 | 52.055 | −15.216 | −37.492 | 1 | 30.79 |
| 4554 | CA | GLU | 33 | 50.725 | −15.445 | −36.936 | 1 | 30.72 |
| 4555 | CB | GLU | 33 | 49.943 | −14.132 | −36.854 | 1 | 33.37 |
| 4556 | CG | GLU | 33 | 48.57 | −14.277 | −36.216 | 1 | 37.54 |
| 4557 | CD | GLU | 33 | 47.852 | −12.951 | −36.056 | 1 | 39.99 |
| 4558 | OE1 | GLU | 33 | 47.598 | −12.279 | −37.08 | 1 | 42.59 |
| 4559 | OE2 | GLU | 33 | 47.539 | −12.582 | −34.904 | 1 | 40.9 |
| 4560 | C | GLU | 33 | 49.963 | −16.448 | −37.797 | 1 | 29.78 |
| 4561 | O | GLU | 33 | 49.379 | −17.404 | −37.284 | 1 | 29.15 |
| 4562 | N | LEU | 34 | 49.969 | −16.223 | −39.107 | 1 | 28.88 |
| 4563 | CA | LEU | 34 | 49.289 | −17.125 | −40.03 | 1 | 28.38 |
| 4564 | CB | LEU | 34 | 49.378 | −16.596 | −41.463 | 1 | 27.65 |
| 4565 | CG | LEU | 34 | 48.827 | −17.516 | −42.56 | 1 | 28.1 |
| 4566 | CD1 | LEU | 34 | 47.359 | −17.821 | −42.297 | 1 | 26.38 |
| 4567 | CD2 | LEU | 34 | 49.002 | −16.849 | −43.917 | 1 | 27.28 |
| 4568 | C | LEU | 34 | 49.938 | −18.501 | −39.956 | 1 | 27.8 |
| 4569 | O | LEU | 34 | 49.263 | −19.523 | −40.055 | 1 | 26.26 |
| 4570 | N | GLN | 35 | 51.255 | −18.518 | −39.78 | 1 | 28.37 |
| 4571 | CA | GLN | 35 | 51.994 | −19.77 | −39.692 | 1 | 28.62 |
| 4572 | CB | GLN | 35 | 53.494 | −19.487 | −39.631 | 1 | 30.3 |
| 4573 | CG | GLN | 35 | 54.359 | −20.73 | −39.57 | 1 | 33.87 |
| 4574 | CD | GLN | 35 | 55.837 | −20.402 | −39.626 | 1 | 36.48 |
| 4575 | OE1 | GLN | 35 | 56.356 | −19.677 | −38.776 | 1 | 38 |
| 4576 | NE2 | GLN | 35 | 56.524 | −20.932 | −40.631 | 1 | 39.07 |
| 4577 | C | GLN | 35 | 51.564 | −20.561 | −38.461 | 1 | 28.33 |
| 4578 | O | GLN | 35 | 51.493 | −21.79 | −38.493 | 1 | 28.21 |
| 4579 | N | ARG | 36 | 51.278 | −19.855 | −37.374 | 1 | 27.37 |
| 4580 | CA | ARG | 36 | 50.848 | −20.513 | −36.149 | 1 | 27.26 |
| 4581 | CB | ARG | 36 | 50.827 | −19.523 | −34.988 | 1 | 29.11 |
| 4582 | CG | ARG | 36 | 50.453 | −20.173 | −33.675 | 1 | 33.23 |
| 4583 | CD | ARG | 36 | 50.344 | −19.164 | −32.557 | 1 | 37.22 |
| 4584 | NE | ARG | 36 | 50.023 | −19.827 | −31.299 | 1 | 41.82 |
| 4585 | CZ | ARG | 36 | 49.833 | −19.195 | −30.148 | 1 | 42.51 |
| 4586 | NH1 | ARG | 36 | 49.931 | −17.873 | −30.091 | 1 | 43.57 |
| 4587 | NH2 | ARG | 36 | 49.55 | −19.89 | −29.054 | 1 | 43.8 |
| 4588 | C | ARG | 36 | 49.453 | −21.099 | −36.34 | 1 | 25.94 |
| 4589 | O | ARG | 36 | 49.162 | −22.202 | −35.878 | 1 | 26.23 |
| 4590 | N | LEU | 37 | 48.594 | −20.348 | −37.02 | 1 | 24.14 |
| 4591 | CA | LEU | 37 | 47.231 | −20.793 | −37.28 | 1 | 22.09 |
| 4592 | CB | LEU | 37 | 46.429 | −19.682 | −37.964 | 1 | 21.58 |
| 4593 | CG | LEU | 37 | 45.018 | −20.053 | −38.434 | 1 | 19.25 |
| 4594 | CD1 | LEU | 37 | 44.186 | −20.531 | −37.245 | 1 | 21.01 |
| 4595 | CD2 | LEU | 37 | 44.368 | −18.85 | −39.095 | 1 | 18.02 |
| 4596 | C | LEU | 37 | 47.215 | −22.044 | −38.151 | 1 | 22.31 |
| 4597 | O | LEU | 37 | 46.519 | −23.01 | −37.841 | 1 | 21.28 |
| 4598 | N | THR | 38 | 47.98 | −22.032 | −39.24 | 1 | 22.56 |
| 4599 | CA | THR | 38 | 48.016 | −23.186 | −40.132 | 1 | 22.66 |
| 4600 | CB | THR | 38 | 48.827 | −22.888 | −41.413 | 1 | 23.35 |
| 4601 | OG1 | THR | 38 | 50.203 | −22.674 | −41.079 | 1 | 25.2 |
| 4602 | CG2 | THR | 38 | 48.278 | −21.652 | −42.106 | 1 | 24.49 |
| 4603 | C | THR | 38 | 48.611 | −24.395 | −39.426 | 1 | 22.39 |
| 4604 | O | THR | 38 | 48.142 | −25.521 | −39.597 | 1 | 20.78 |
| 4605 | N | GLN | 39 | 49.644 | −24.164 | −38.623 | 1 | 21.95 |
| 4606 | CA | GLN | 39 | 50.277 | −25.251 | −37.896 | 1 | 23.26 |
| 4607 | CB | GLN | 39 | 51.499 | −24.733 | −37.132 | 1 | 26.59 |
| 4608 | CG | GLN | 39 | 52.202 | −25.789 | −36.295 | 1 | 32.48 |
| 4609 | CD | GLN | 39 | 53.47 | −25.263 | −35.649 | 1 | 36.2 |
| 4610 | OE1 | GLN | 39 | 53.443 | −24.278 | −34.91 | 1 | 38.73 |
| 4611 | NE2 | GLN | 39 | 54.59 | −25.921 | −35.925 | 1 | 37.53 |
| 4612 | C | GLN | 39 | 49.284 | −25.879 | −36.924 | 1 | 21.77 |
| 4613 | O | GLN | 39 | 49.208 | −27.102 | −36.805 | 1 | 20.84 |
| 4614 | N | ARG | 40 | 48.516 | −25.036 | −36.237 | 1 | 21.66 |
| 4615 | CA | ARG | 40 | 47.532 | −25.516 | −35.275 | 1 | 20.52 |
| 4616 | CB | ARG | 40 | 46.96 | −24.342 | −34.473 | 1 | 23.6 |
| 4617 | CG | ARG | 40 | 46.07 | −24.755 | −33.308 | 1 | 27.44 |
| 4618 | CD | ARG | 40 | 46.767 | −25.764 | −32.403 | 1 | 31.69 |
| 4619 | NE | ARG | 40 | 48.003 | −25.244 | −31.819 | 1 | 35.07 |
| 4620 | CZ | ARG | 40 | 48.055 | −24.331 | −30.854 | 1 | 35.84 |
| 4621 | NH1 | ARG | 40 | 46.938 | −23.824 | −30.349 | 1 | 37.53 |
| 4622 | NH2 | ARG | 40 | 49.229 | −23.929 | −30.386 | 1 | 37.72 |
| 4623 | C | ARG | 40 | 46.408 | −26.282 | −35.974 | 1 | 19.6 |
| 4624 | O | ARG | 40 | 45.956 | −27.317 | −35.482 | 1 | 18.07 |
| 4625 | N | LEU | 41 | 45.962 | −25.777 | −37.121 | 1 | 19.05 |
| 4626 | CA | LEU | 41 | 44.906 | −26.445 | −37.878 | 1 | 18.85 |
| 4627 | CB | LEU | 41 | 44.571 | −25.661 | −39.15 | 1 | 19.19 |
| 4628 | CG | LEU | 41 | 43.624 | −24.469 | −39.017 | 1 | 20.99 |
| 4629 | CD1 | LEU | 41 | 43.604 | −23.68 | −40.318 | 1 | 19.27 |
| 4630 | CD2 | LEU | 41 | 42.225 | −24.969 | −38.674 | 1 | 18.36 |
| 4631 | C | LEU | 41 | 45.343 | −27.852 | −38.258 | 1 | 18.38 |
| 4632 | O | LEU | 41 | 44.614 | −28.817 | −38.039 | 1 | 17.87 |
| 4633 | N | VAL | 42 | 46.54 | −27.967 | −38.826 | 1 | 18.35 |
| 4634 | CA | VAL | 42 | 47.066 | −29.264 | −39.235 | 1 | 19.17 |
| 4635 | CB | VAL | 42 | 48.406 | −29.104 | −39.987 | 1 | 20.3 |
| 4636 | CG1 | VAL | 42 | 49.018 | −30.469 | −40.265 | 1 | 21.27 |
| 4637 | CG2 | VAL | 42 | 48.175 | −28.367 | −41.297 | 1 | 20.82 |
| 4638 | C | VAL | 42 | 47.266 | −30.191 | −38.039 | 1 | 19.43 |
| 4639 | O | VAL | 42 | 46.971 | −31.383 | −38.109 | 1 | 19.57 |
| 4640 | N | GLN | 43 | 47.761 | −29.638 | −36.939 | 1 | 19.82 |
| 4641 | CA | GLN | 43 | 47.995 | −30.424 | −35.734 | 1 | 20.62 |
| 4642 | CB | GLN | 43 | 48.66 | −29.547 | −34.671 | 1 | 24.45 |

TABLE 2-continued

| Atom | Atom Type | Residue | # | X | Y | Z | OCC | B |
|---|---|---|---|---|---|---|---|---|
| 4643 | CG | GLN | 43 | 48.963 | −30.257 | −33.37 | 1 | 29.55 |
| 4644 | CD | GLN | 43 | 49.746 | −29.381 | −32.413 | 1 | 33.67 |
| 4645 | OE1 | GLN | 43 | 49.337 | −28.26 | −32.107 | 1 | 36.97 |
| 4646 | NE2 | GLN | 43 | 50.877 | −29.886 | −31.936 | 1 | 36.75 |
| 4647 | C | GLN | 43 | 46.701 | −31.026 | −35.182 | 1 | 20.07 |
| 4648 | O | GLN | 43 | 46.655 | −32.207 | −34.836 | 1 | 18.52 |
| 4649 | N | VAL | 44 | 45.652 | −30.212 | −35.101 | 1 | 18.74 |
| 4650 | CA | VAL | 44 | 44.369 | −30.681 | −34.586 | 1 | 18.84 |
| 4651 | CB | VAL | 44 | 43.395 | −29.502 | −34.364 | 1 | 18.75 |
| 4652 | CG1 | VAL | 44 | 42.021 | −30.022 | −33.961 | 1 | 18.8 |
| 4653 | CG2 | VAL | 44 | 43.945 | −28.582 | −33.283 | 1 | 20.9 |
| 4654 | C | VAL | 44 | 43.739 | −31.678 | −35.546 | 1 | 18.32 |
| 4655 | O | VAL | 44 | 43.195 | −32.702 | −35.127 | 1 | 17.96 |
| 4656 | N | MET | 45 | 43.822 | −31.384 | −36.838 | 1 | 18.55 |
| 4657 | CA | MET | 45 | 43.257 | −32.273 | −37.839 | 1 | 19.53 |
| 4658 | CB | MET | 45 | 43.505 | −31.715 | −39.243 | 1 | 19.5 |
| 4659 | CG | MET | 45 | 42.999 | −32.611 | −40.355 | 1 | 20.35 |
| 4660 | SD | MET | 45 | 43.255 | −31.884 | −41.983 | 1 | 22.7 |
| 4661 | CE | MET | 45 | 45.04 | −32.01 | −42.129 | 1 | 23.56 |
| 4662 | C | MET | 45 | 43.868 | −33.665 | −37.72 | 1 | 19.72 |
| 4663 | O | MET | 45 | 43.158 | −34.667 | −37.736 | 1 | 20.88 |
| 4664 | N | ARG | 46 | 45.19 | −33.724 | −37.589 | 1 | 20.75 |
| 4665 | CA | ARG | 46 | 45.879 | −35.001 | −37.474 | 1 | 21.32 |
| 4666 | CB | ARG | 46 | 47.383 | −34.8 | −37.676 | 1 | 22.33 |
| 4667 | CG | ARG | 46 | 47.735 | −34.457 | −39.116 | 1 | 23.95 |
| 4668 | CD | ARG | 46 | 49.198 | −34.099 | −39.297 | 1 | 24.68 |
| 4669 | NE | ARG | 46 | 49.517 | −33.93 | −40.713 | 1 | 26.05 |
| 4670 | CZ | ARG | 46 | 50.664 | −33.443 | −41.175 | 1 | 26.42 |
| 4671 | NH1 | ARG | 46 | 51.62 | −33.068 | −40.334 | 1 | 28.53 |
| 4672 | NH2 | ARG | 46 | 50.856 | −33.331 | −42.483 | 1 | 25.8 |
| 4673 | C | ARG | 46 | 45.608 | −35.716 | −36.153 | 1 | 21.59 |
| 4674 | O | ARG | 46 | 45.506 | −36.941 | −36.119 | 1 | 23.12 |
| 4675 | N | ARG | 47 | 45.486 | −34.959 | −35.068 | 1 | 21.81 |
| 4676 | CA | ARG | 47 | 45.215 | −35.567 | −33.77 | 1 | 21.87 |
| 4677 | CB | ARG | 47 | 45.36 | −34.53 | −32.65 | 1 | 23.36 |
| 4678 | CG | ARG | 47 | 46.803 | −34.117 | −32.375 | 1 | 27.69 |
| 4679 | CD | ARG | 47 | 46.886 | −33.107 | −31.239 | 1 | 30.2 |
| 4680 | NE | ARG | 47 | 48.26 | −32.678 | −30.982 | 1 | 32.89 |
| 4681 | CZ | ARG | 47 | 49.194 | −33.438 | −30.419 | 1 | 35.6 |
| 4682 | NH1 | ARG | 47 | 48.91 | −34.68 | −30.044 | 1 | 36.53 |
| 4683 | NH2 | ARG | 47 | 50.417 | −32.956 | −30.23 | 1 | 37.57 |
| 4684 | C | ARG | 47 | 43.82 | −36.182 | −33.731 | 1 | 20.46 |
| 4685 | O | ARG | 47 | 43.616 | −37.235 | −33.128 | 1 | 21.75 |
| 4686 | N | ARG | 48 | 42.863 | −35.529 | −34.384 | 1 | 19.29 |
| 4687 | CA | ARG | 48 | 41.488 | −36.021 | −34.414 | 1 | 20.3 |
| 4688 | CB | ARG | 48 | 40.513 | −34.851 | −34.554 | 1 | 20.29 |
| 4689 | CG | ARG | 48 | 40.401 | −34.003 | −33.293 | 1 | 22.18 |
| 4690 | CD | ARG | 48 | 39.864 | −34.841 | −32.151 | 1 | 24.48 |
| 4691 | NE | ARG | 48 | 38.57 | −35.421 | −32.5 | 1 | 28.01 |
| 4692 | CZ | ARG | 48 | 38.212 | −36.672 | −32.235 | 1 | 29.87 |
| 4693 | NH1 | ARG | 48 | 39.049 | −37.49 | −31.612 | 1 | 31.62 |
| 4694 | NH2 | ARG | 48 | 37.016 | −37.109 | −32.605 | 1 | 31 |
| 4695 | C | ARG | 48 | 41.251 | −37.029 | −35.531 | 1 | 20.94 |
| 4696 | O | ARG | 48 | 40.148 | −37.553 | −35.687 | 1 | 20.21 |
| 4697 | N | ARG | 49 | 42.291 | −37.296 | −36.31 | 1 | 21.11 |
| 4698 | CA | ARG | 49 | 42.19 | −38.256 | −37.4 | 1 | 23.99 |
| 4699 | CB | ARG | 49 | 41.885 | −39.651 | −36.844 | 1 | 26.97 |
| 4700 | CG | ARG | 49 | 42.887 | −40.16 | −35.817 | 1 | 31.85 |
| 4701 | CD | ARG | 49 | 44.27 | −40.339 | −36.423 | 1 | 35.59 |
| 4702 | NE | ARG | 49 | 45.166 | −41.069 | −35.529 | 1 | 39.8 |
| 4703 | CZ | ARG | 49 | 45.573 | −40.627 | −34.344 | 1 | 40.29 |
| 4704 | NH1 | ARG | 49 | 45.169 | −39.446 | −33.896 | 1 | 41.36 |
| 4705 | NH2 | ARG | 49 | 46.385 | −41.368 | −33.602 | 1 | 41.5 |
| 4706 | C | ARG | 49 | 41.12 | −37.881 | −38.42 | 1 | 22.39 |
| 4707 | O | ARG | 49 | 40.489 | −38.759 | −39.006 | 1 | 24.15 |
| 4708 | N | CYS | 50 | 40.896 | −36.586 | −38.622 | 1 | 21.05 |
| 4709 | CA | CYS | 50 | 39.912 | −36.165 | −39.612 | 1 | 20 |
| 4710 | CB | CYS | 50 | 39.002 | −35.056 | −39.071 | 1 | 20.5 |
| 4711 | SG | CYS | 50 | 39.791 | −33.546 | −38.552 | 1 | 21.66 |
| 4712 | C | CYS | 50 | 40.654 | −35.721 | −40.866 | 1 | 19.06 |
| 4713 | O | CYS | 50 | 41.881 | −35.606 | −40.859 | 1 | 19.46 |
| 4714 | N | VAL | 51 | 39.923 | −35.465 | −41.943 | 1 | 18.06 |
| 4715 | CA | VAL | 51 | 40.563 | −35.122 | −43.209 | 1 | 16.03 |
| 4716 | CB | VAL | 51 | 40.007 | −36.016 | −44.329 | 1 | 16.84 |
| 4717 | CG1 | VAL | 51 | 40.303 | −37.474 | −44.013 | 1 | 18.52 |
| 4718 | CG2 | VAL | 51 | 38.516 | −35.812 | −44.466 | 1 | 18.12 |
| 4719 | C | VAL | 51 | 40.496 | −33.67 | −43.658 | 1 | 15.86 |
| 4720 | O | VAL | 51 | 40.936 | −33.33 | −44.758 | 1 | 15.88 |
| 4721 | N | GLY | 52 | 39.957 | −32.812 | −42.806 | 1 | 15.85 |
| 4722 | CA | GLY | 52 | 39.871 | −31.408 | −43.147 | 1 | 15.34 |
| 4723 | C | GLY | 52 | 39.486 | −30.614 | −41.92 | 1 | 14.63 |
| 4724 | O | GLY | 52 | 38.851 | −31.141 | −41.009 | 1 | 15.54 |
| 4725 | N | LEU | 53 | 39.886 | −29.35 | −41.885 | 1 | 15.23 |
| 4726 | CA | LEU | 53 | 39.558 | −28.485 | −40.762 | 1 | 14.69 |
| 4727 | CB | LEU | 53 | 40.492 | −28.762 | −39.58 | 1 | 14.98 |
| 4728 | CG | LEU | 53 | 40.01 | −28.225 | −38.228 | 1 | 14.38 |
| 4729 | CD1 | LEU | 53 | 38.712 | −28.924 | −37.83 | 1 | 17.58 |
| 4730 | CD2 | LEU | 53 | 41.082 | −28.461 | −37.17 | 1 | 14.72 |
| 4731 | C | LEU | 53 | 39.696 | −27.04 | −41.218 | 1 | 15.16 |
| 4732 | O | LEU | 53 | 40.542 | −26.727 | −42.056 | 1 | 16.53 |
| 4733 | N | SER | 54 | 38.859 | −26.165 | −40.673 | 1 | 14.5 |
| 4734 | CA | SER | 54 | 38.885 | −24.756 | −41.046 | 1 | 14.74 |
| 4735 | CB | SER | 54 | 37.545 | −24.353 | −41.659 | 1 | 14.93 |
| 4736 | OG | SER | 54 | 36.516 | −24.435 | −40.691 | 1 | 15.69 |
| 4737 | C | SER | 54 | 39.163 | −23.874 | −39.837 | 1 | 14.66 |
| 4738 | O | SER | 54 | 38.863 | −24.246 | −38.704 | 1 | 13.79 |
| 4739 | N | ALA | 55 | 39.718 | −22.693 | −40.088 | 1 | 14.62 |
| 4740 | CA | ALA | 55 | 40.04 | −21.759 | −39.015 | 1 | 13.83 |
| 4741 | CB | ALA | 55 | 40.654 | −20.486 | −39.6 | 1 | 14.23 |
| 4742 | C | ALA | 55 | 38.849 | −21.409 | −38.113 | 1 | 14.43 |
| 4743 | O | ALA | 55 | 39.009 | −21.274 | −36.905 | 1 | 14.21 |
| 4744 | N | PRO | 56 | 37.642 | −21.243 | −38.684 | 1 | 13.88 |
| 4745 | CD | PRO | 56 | 37.264 | −21.097 | −40.102 | 1 | 13.33 |
| 4746 | CA | PRO | 56 | 36.51 | −20.911 | −37.809 | 1 | 13.16 |
| 4747 | CB | PRO | 56 | 35.34 | −20.832 | −38.779 | 1 | 13.96 |
| 4748 | CG | PRO | 56 | 35.989 | −20.281 | −40.014 | 1 | 13.06 |
| 4749 | C | PRO | 56 | 36.282 | −21.951 | −36.717 | 1 | 13.22 |
| 4750 | O | PRO | 56 | 35.813 | −21.627 | −35.624 | 1 | 13.39 |
| 4751 | N | GLN | 57 | 36.621 | −23.199 | −37.02 | 1 | 13.02 |
| 4752 | CA | GLN | 57 | 36.452 | −24.286 | −36.069 | 1 | 13.11 |
| 4753 | CB | GLN | 57 | 36.6 | −25.623 | −36.789 | 1 | 12.81 |
| 4754 | CG | GLN | 57 | 35.402 | −25.937 | −37.672 | 1 | 14.64 |
| 4755 | CD | GLN | 57 | 35.622 | −27.151 | −38.537 | 1 | 14.27 |
| 4756 | OE1 | GLN | 57 | 36.308 | −27.088 | −39.561 | 1 | 14.22 |
| 4757 | NE2 | GLN | 57 | 35.046 | −28.275 | −38.126 | 1 | 15.1 |
| 4758 | C | GLN | 57 | 37.417 | −24.182 | −34.896 | 1 | 13.93 |
| 4759 | O | GLN | 57 | 37.232 | −24.838 | −33.871 | 1 | 13.72 |
| 4760 | N | LEU | 58 | 38.454 | −23.366 | −35.048 | 1 | 14.32 |
| 4761 | CA | LEU | 58 | 39.402 | −23.15 | −33.962 | 1 | 17.4 |
| 4762 | CB | LEU | 58 | 40.846 | −23.266 | −34.457 | 1 | 17.55 |
| 4763 | CG | LEU | 58 | 41.296 | −24.655 | −34.911 | 1 | 19.73 |
| 4764 | CD1 | LEU | 58 | 42.788 | −24.621 | −35.229 | 1 | 22 |
| 4765 | CD2 | LEU | 58 | 41.012 | −25.679 | −33.816 | 1 | 19.93 |
| 4766 | C | LEU | 58 | 39.15 | −21.763 | −33.375 | 1 | 18.08 |
| 4767 | O | LEU | 58 | 40 | −21.205 | −32.681 | 1 | 20.93 |
| 4768 | N | GLY | 59 | 37.974 | −21.211 | −33.672 | 1 | 16.57 |
| 4769 | CA | GLY | 59 | 37.594 | −19.906 | −33.157 | 1 | 16.98 |
| 4770 | C | GLY | 59 | 38.139 | −18.692 | −33.893 | 1 | 17.75 |
| 4771 | O | GLY | 59 | 38.014 | −17.567 | −33.408 | 1 | 18.38 |
| 4772 | N | VAL | 60 | 38.731 | −18.908 | −35.061 | 1 | 16.41 |
| 4773 | CA | VAL | 60 | 39.305 | −17.813 | −35.847 | 1 | 16.88 |
| 4774 | CB | VAL | 60 | 40.767 | −18.132 | −36.233 | 1 | 17.47 |
| 4775 | CG1 | VAL | 60 | 41.367 | −16.981 | −37.025 | 1 | 17.82 |
| 4776 | CG2 | VAL | 60 | 41.59 | −18.404 | −34.974 | 1 | 19.54 |
| 4777 | C | VAL | 60 | 38.491 | −17.581 | −37.121 | 1 | 17.7 |
| 4778 | O | VAL | 60 | 38.537 | −18.387 | −38.052 | 1 | 17.36 |
| 4779 | N | PRO | 61 | 37.743 | −16.467 | −37.183 | 1 | 18.29 |
| 4780 | CD | PRO | 61 | 37.547 | −15.463 | −36.119 | 1 | 18.38 |
| 4781 | CA | PRO | 61 | 36.919 | −16.149 | −38.353 | 1 | 17.38 |
| 4782 | CB | PRO | 61 | 35.957 | −15.098 | −37.811 | 1 | 18.32 |
| 4783 | CG | PRO | 61 | 36.814 | −14.35 | −36.85 | 1 | 18.51 |
| 4784 | C | PRO | 61 | 37.703 | −15.661 | −39.571 | 1 | 18.15 |
| 4785 | O | PRO | 61 | 37.484 | −14.55 | −40.06 | 1 | 17.8 |
| 4786 | N | ARG | 62 | 38.603 | −16.507 | −40.061 | 1 | 18.18 |
| 4787 | CA | ARG | 62 | 39.424 | −16.178 | −41.223 | 1 | 18.66 |
| 4788 | CB | ARG | 62 | 40.881 | −15.98 | −40.797 | 1 | 20.32 |
| 4789 | CG | ARG | 62 | 41.096 | −14.784 | −39.88 | 1 | 24.16 |
| 4790 | CD | ARG | 62 | 40.85 | −13.47 | −40.612 | 1 | 27.68 |
| 4791 | NE | ARG | 62 | 40.964 | −12.321 | −39.717 | 1 | 29.47 |
| 4792 | CZ | ARG | 62 | 40.902 | −11.054 | −40.112 | 1 | 31.58 |
| 4793 | NH1 | ARG | 62 | 40.729 | −10.763 | −41.395 | 1 | 32.95 |
| 4794 | NH2 | ARG | 62 | 41.009 | −10.075 | −39.223 | 1 | 33.72 |

TABLE 2-continued

| Atom | Atom Type | Residue | # | X | Y | Z | OCC | B |
|---|---|---|---|---|---|---|---|---|
| 4795 | C | ARG | 62 | 39.336 | −17.276 | −42.279 | 1 | 18.03 |
| 4796 | O | ARG | 62 | 39.13 | −18.449 | −41.959 | 1 | 17.58 |
| 4797 | N | GLN | 63 | 39.503 | −16.891 | −43.539 | 1 | 17.71 |
| 4798 | CA | GLN | 63 | 39.417 | −17.839 | −44.642 | 1 | 17.8 |
| 4799 | CB | GLN | 63 | 39.119 | −17.089 | −45.944 | 1 | 17.29 |
| 4800 | CG | GLN | 63 | 37.808 | −16.311 | −45.891 | 1 | 18.97 |
| 4801 | CD | GLN | 63 | 37.531 | −15.508 | −47.149 | 1 | 20.12 |
| 4802 | OE1 | GLN | 63 | 36.663 | −14.63 | −47.16 | 1 | 23.88 |
| 4803 | NE2 | GLN | 63 | 38.258 | −15.806 | −48.217 | 1 | 19.33 |
| 4804 | C | GLN | 63 | 40.666 | −18.7 | −44.794 | 1 | 17.67 |
| 4805 | O | GLN | 63 | 41.494 | −18.477 | −45.678 | 1 | 18.44 |
| 4806 | N | VAL | 64 | 40.793 | −19.688 | −43.914 | 1 | 17.3 |
| 4807 | CA | VAL | 64 | 41.92 | −20.61 | −43.943 | 1 | 17.53 |
| 4808 | CB | VAL | 64 | 42.973 | −20.263 | −42.86 | 1 | 18.16 |
| 4809 | CG1 | VAL | 64 | 44.157 | −21.209 | −42.962 | 1 | 17.13 |
| 4810 | CG2 | VAL | 64 | 43.437 | −18.828 | −43.023 | 1 | 17.95 |
| 4811 | C | VAL | 64 | 41.393 | −22.015 | −43.674 | 1 | 18.32 |
| 4812 | O | VAL | 64 | 40.528 | −22.208 | −42.817 | 1 | 17.6 |
| 4813 | N | LEU | 65 | 41.901 | −22.992 | −44.415 | 1 | 17.16 |
| 4814 | CA | LEU | 65 | 41.478 | −24.372 | −44.227 | 1 | 16.82 |
| 4815 | CB | LEU | 65 | 40.195 | −24.658 | −45.029 | 1 | 17.22 |
| 4816 | CG | LEU | 65 | 40.183 | −24.544 | −46.557 | 1 | 17 |
| 4817 | CD1 | LEU | 65 | 40.807 | −25.781 | −47.18 | 1 | 16.72 |
| 4818 | CD2 | LEU | 65 | 38.74 | −24.403 | −47.039 | 1 | 18.96 |
| 4819 | C | LEU | 65 | 42.591 | −25.322 | −44.636 | 1 | 16.24 |
| 4820 | O | LEU | 65 | 43.472 | −24.961 | −45.423 | 1 | 17.17 |
| 4821 | N | ALA | 66 | 42.56 | −26.526 | −44.076 | 1 | 14.86 |
| 4822 | CA | ALA | 66 | 43.556 | −27.547 | −44.379 | 1 | 16.89 |
| 4823 | CB | ALA | 66 | 44.423 | −27.816 | −43.156 | 1 | 18.24 |
| 4824 | C | ALA | 66 | 42.837 | −28.818 | −44.804 | 1 | 17.4 |
| 4825 | O | ALA | 66 | 41.745 | −29.112 | −44.315 | 1 | 17.67 |
| 4826 | N | LEU | 67 | 43.454 | −29.562 | −45.717 | 1 | 16.87 |
| 4827 | CA | LEU | 67 | 42.88 | −30.797 | −46.24 | 1 | 17.46 |
| 4828 | CB | LEU | 67 | 42.309 | −30.548 | −47.641 | 1 | 18.97 |
| 4829 | CG | LEU | 67 | 41.343 | −29.371 | −47.808 | 1 | 20.27 |
| 4830 | CD1 | LEU | 67 | 41.234 | −28.998 | −49.281 | 1 | 22.41 |
| 4831 | CD2 | LEU | 67 | 39.985 | −29.74 | −47.241 | 1 | 21.96 |
| 4832 | C | LEU | 67 | 43.969 | −31.859 | −46.333 | 1 | 17.84 |
| 4833 | O | LEU | 67 | 45.08 | −31.57 | −46.77 | 1 | 18.27 |
| 4834 | N | GLU | 68 | 43.65 | −33.086 | −45.932 | 1 | 17.73 |
| 4835 | CA | GLU | 68 | 44.62 | −34.175 | −45.995 | 1 | 18.99 |
| 4836 | CB | GLU | 68 | 45.711 | −33.989 | −44.933 | 1 | 21.08 |
| 4837 | CG | GLU | 68 | 46.75 | −35.101 | −44.924 | 1 | 22.95 |
| 4838 | CD | GLU | 68 | 47.814 | −34.912 | −43.858 | 1 | 27.01 |
| 4839 | OE1 | GLU | 68 | 47.451 | −34.704 | −42.681 | 1 | 27.47 |
| 4840 | OE2 | GLU | 68 | 49.015 | −34.851 | −44.195 | 1 | 28.37 |
| 4841 | C | GLU | 68 | 43.966 | −35.537 | −45.81 | 1 | 19.38 |
| 4842 | O | GLU | 68 | 43.215 | −35.754 | −44.862 | 1 | 19.97 |
| 4843 | N | LEU | 69 | 44.263 | −36.459 | −46.719 | 1 | 19.45 |
| 4844 | CA | LEU | 69 | 43.71 | −37.803 | −46.638 | 1 | 20.07 |
| 4845 | CB | LEU | 69 | 42.668 | −38.012 | −47.738 | 1 | 20.31 |
| 4846 | CG | LEU | 69 | 41.985 | −39.382 | −47.778 | 1 | 21.79 |
| 4847 | CD1 | LEU | 69 | 41.509 | −39.766 | −46.386 | 1 | 22.94 |
| 4848 | CD2 | LEU | 69 | 40.816 | −39.338 | −48.752 | 1 | 23.25 |
| 4849 | C | LEU | 69 | 44.813 | −38.849 | −46.753 | 1 | 21.3 |
| 4850 | O | LEU | 69 | 45.176 | −39.268 | −47.853 | 1 | 19.73 |
| 4851 | N | PRO | 70 | 45.366 | −39.28 | −45.606 | 1 | 22.25 |
| 4852 | CD | PRO | 70 | 45.108 | −38.724 | −44.266 | 1 | 23.96 |
| 4853 | CA | PRO | 70 | 46.436 | −40.283 | −45.551 | 1 | 23.89 |
| 4854 | CB | PRO | 70 | 46.783 | −40.338 | −44.063 | 1 | 24.29 |
| 4855 | CG | PRO | 70 | 46.423 | −38.967 | −43.572 | 1 | 25.72 |
| 4856 | C | PRO | 70 | 45.983 | −41.641 | −46.077 | 1 | 24.67 |
| 4857 | O | PRO | 70 | 44.804 | −41.986 | −45.996 | 1 | 23.38 |
| 4858 | N | GLU | 71 | 46.927 | −42.413 | −46.609 | 1 | 26.18 |
| 4859 | CA | GLU | 71 | 46.622 | −43.735 | −47.143 | 1 | 27.97 |
| 4860 | CB | GLU | 71 | 47.895 | −44.394 | −47.683 | 1 | 32.24 |
| 4861 | CG | GLU | 71 | 47.672 | −45.748 | −48.349 | 1 | 35.64 |
| 4862 | CD | GLU | 71 | 46.869 | −45.65 | −49.636 | 1 | 38.33 |
| 4863 | OE1 | GLU | 71 | 45.704 | −45.2 | −49.586 | 1 | 40.33 |
| 4864 | OE2 | GLU | 71 | 47.404 | −46.024 | −50.702 | 1 | 41.38 |
| 4865 | C | GLU | 71 | 46.008 | −44.618 | −46.062 | 1 | 27.04 |
| 4866 | O | GLU | 71 | 45.084 | −45.385 | −46.326 | 1 | 26.54 |
| 4867 | N | ALA | 72 | 46.523 | −44.497 | −44.842 | 1 | 27.29 |
| 4868 | CA | ALA | 72 | 46.032 | −45.289 | −43.72 | 1 | 28.52 |
| 4869 | CB | ALA | 72 | 46.739 | −44.87 | −42.436 | 1 | 29.09 |
| 4870 | C | ALA | 72 | 44.52 | −45.171 | −43.549 | 1 | 28.09 |
| 4871 | O | ALA | 72 | 43.828 | −46.177 | −43.396 | 1 | 27.77 |
| 4872 | N | LEU | 73 | 44.005 | −43.944 | −43.572 | 1 | 28.12 |
| 4873 | CA | LEU | 73 | 42.569 | −43.733 | −43.42 | 1 | 28.09 |
| 4874 | CB | LEU | 73 | 42.243 | −42.235 | −43.381 | 1 | 29.43 |
| 4875 | CG | LEU | 73 | 42.509 | −41.526 | −42.049 | 1 | 30.04 |
| 4876 | CD1 | LEU | 73 | 42.159 | −40.053 | −42.169 | 1 | 30.82 |
| 4877 | CD2 | LEU | 73 | 41.679 | −42.174 | −40.948 | 1 | 29.93 |
| 4878 | C | LEU | 73 | 41.778 | −44.41 | −44.533 | 1 | 27.94 |
| 4879 | O | LEU | 73 | 40.731 | −45.005 | −44.281 | 1 | 28.1 |
| 4880 | N | CYS | 74 | 42.278 | −44.323 | −45.763 | 1 | 26.93 |
| 4881 | CA | CYS | 74 | 41.601 | −44.949 | −46.893 | 1 | 27.86 |
| 4882 | CB | CYS | 74 | 42.305 | −44.6 | −48.205 | 1 | 27.36 |
| 4883 | SG | CYS | 74 | 42.177 | −42.875 | −48.686 | 1 | 28.55 |
| 4884 | C | CYS | 74 | 41.583 | −46.46 | −46.727 | 1 | 28.63 |
| 4885 | O | CYS | 74 | 40.584 | −47.114 | −47.023 | 1 | 28.92 |
| 4886 | N | ARG | 75 | 42.695 | −47.011 | −46.248 | 1 | 29.72 |
| 4887 | CA | ARG | 75 | 42.804 | −48.451 | −46.058 | 1 | 31.27 |
| 4888 | CB | ARG | 75 | 44.255 | −48.84 | −45.762 | 1 | 31.59 |
| 4889 | CG | ARG | 75 | 45.199 | −48.604 | −46.928 | 1 | 34.61 |
| 4890 | CD | ARG | 75 | 46.581 | −49.186 | −46.668 | 1 | 36.83 |
| 4891 | NE | ARG | 75 | 47.49 | −48.936 | −47.784 | 1 | 39.28 |
| 4892 | CZ | ARG | 75 | 48.74 | −49.383 | −47.849 | 1 | 40.09 |
| 4893 | NH1 | ARG | 75 | 49.242 | −50.11 | −46.86 | 1 | 40.7 |
| 4894 | NH2 | ARG | 75 | 49.492 | −49.1 | −48.905 | 1 | 41.15 |
| 4895 | C | ARG | 75 | 41.889 | −48.978 | −44.959 | 1 | 31.52 |
| 4896 | O | ARG | 75 | 41.549 | −50.16 | −44.946 | 1 | 31.18 |
| 4897 | N | GLU | 76 | 41.488 | −48.106 | −44.039 | 1 | 32.47 |
| 4898 | CA | GLU | 76 | 40.6 | −48.523 | −42.962 | 1 | 33.92 |
| 4899 | CB | GLU | 76 | 40.65 | −47.525 | −41.803 | 1 | 35.01 |
| 4900 | CG | GLU | 76 | 41.484 | −48.021 | −40.636 | 1 | 37.77 |
| 4901 | CD | GLU | 76 | 40.999 | −49.368 | −40.121 | 1 | 39.31 |
| 4902 | OE1 | GLU | 76 | 39.869 | −49.433 | −39.592 | 1 | 39.78 |
| 4903 | OE2 | GLU | 76 | 41.744 | −50.365 | −40.253 | 1 | 38.24 |
| 4904 | C | GLU | 76 | 39.173 | −48.668 | −43.464 | 1 | 33.63 |
| 4905 | O | GLU | 76 | 38.312 | −49.213 | −42.774 | 1 | 35.02 |
| 4906 | N | CYS | 77 | 38.93 | −48.182 | −44.675 | 1 | 32.92 |
| 4907 | CA | CYS | 77 | 37.61 | −48.266 | −45.284 | 1 | 31.57 |
| 4908 | CB | CYS | 77 | 37.369 | −47.046 | −46.176 | 1 | 31.18 |
| 4909 | SG | CYS | 77 | 35.773 | −47.027 | −47.018 | 1 | 33.53 |
| 4910 | C | CYS | 77 | 37.522 | −49.541 | −46.119 | 1 | 30.5 |
| 4911 | O | CYS | 77 | 38.385 | −49.799 | −46.956 | 1 | 31.24 |
| 4912 | N | PRO | 78 | 36.484 | −50.363 | −45.892 | 1 | 29.75 |
| 4913 | CD | PRO | 78 | 35.387 | −50.207 | −44.92 | 1 | 29.77 |
| 4914 | CA | PRO | 78 | 36.332 | −51.604 | −46.658 | 1 | 28.98 |
| 4915 | CB | PRO | 78 | 34.935 | −52.073 | −46.273 | 1 | 29.49 |
| 4916 | CG | PRO | 78 | 34.819 | −51.609 | −44.851 | 1 | 30.81 |
| 4917 | C | PRO | 78 | 36.463 | −51.321 | −48.155 | 1 | 28.45 |
| 4918 | O | PRO | 78 | 35.959 | −50.313 | −48.65 | 1 | 27.02 |
| 4919 | N | PRO | 79 | 37.131 | −52.216 | −48.897 | 1 | 27.86 |
| 4920 | CD | PRO | 79 | 37.559 | −53.561 | −48.477 | 1 | 28.59 |
| 4921 | CA | PRO | 79 | 37.323 | −52.039 | −50.34 | 1 | 27.18 |
| 4922 | CB | PRO | 79 | 37.938 | −53.372 | −50.775 | 1 | 27.97 |
| 4923 | CG | PRO | 79 | 37.419 | −54.341 | −49.757 | 1 | 29.5 |
| 4924 | C | PRO | 79 | 36.083 | −51.666 | −51.157 | 1 | 27.04 |
| 4925 | O | PRO | 79 | 36.132 | −50.74 | −51.965 | 1 | 27.11 |
| 4926 | N | ARG | 80 | 34.979 | −52.379 | −50.961 | 1 | 27.29 |
| 4927 | CA | ARG | 80 | 33.764 | −52.08 | −51.715 | 1 | 27.56 |
| 4928 | CB | ARG | 80 | 32.666 | −53.095 | −51.391 | 1 | 30.49 |
| 4929 | CG | ARG | 80 | 32.994 | −54.515 | −51.812 | 1 | 34.4 |
| 4930 | CD | ARG | 80 | 31.805 | −55.432 | −51.593 | 1 | 37.34 |
| 4931 | NE | ARG | 80 | 32.102 | −56.813 | −51.958 | 1 | 39.63 |
| 4932 | CZ | ARG | 80 | 31.211 | −57.798 | −51.941 | 1 | 40.42 |
| 4933 | NH1 | ARG | 80 | 29.958 | −57.556 | −51.577 | 1 | 41.52 |
| 4934 | NH2 | ARG | 80 | 31.572 | −59.028 | −52.285 | 1 | 41.55 |
| 4935 | C | ARG | 80 | 33.26 | −50.673 | −51.414 | 1 | 25.93 |
| 4936 | O | ARG | 80 | 32.838 | −49.947 | −52.314 | 1 | 24.48 |
| 4937 | N | GLN | 81 | 33.306 | −50.301 | −50.142 | 1 | 25.73 |
| 4938 | CA | GLN | 81 | 32.864 | −48.983 | −49.704 | 1 | 25.38 |
| 4939 | CB | GLN | 81 | 32.843 | −48.932 | −48.175 | 1 | 28.01 |
| 4940 | CG | GLN | 81 | 32.464 | −47.584 | −47.587 | 1 | 32.79 |
| 4941 | CD | GLN | 81 | 32.466 | −47.595 | −46.069 | 1 | 35.75 |
| 4942 | OE1 | GLN | 81 | 31.769 | −48.394 | −45.442 | 1 | 38.05 |
| 4943 | NE2 | GLN | 81 | 33.25 | −46.705 | −45.47 | 1 | 38.81 |
| 4944 | C | GLN | 81 | 33.809 | −47.918 | −50.249 | 1 | 23.6 |
| 4945 | O | GLN | 81 | 33.378 | −46.865 | −50.721 | 1 | 22.32 |
| 4946 | N | ARG | 82 | 35.105 | −48.204 | −50.186 | 1 | 21.64 |

TABLE 2-continued

| Atom | Atom Type | Residue | # | X | Y | Z | OCC | B |
|---|---|---|---|---|---|---|---|---|
| 4947 | CA | ARG | 82 | 36.117 | −47.276 | −50.667 | 1 | 21.62 |
| 4948 | CB | ARG | 82 | 37.516 | −47.843 | −50.404 | 1 | 22.31 |
| 4949 | CG | ARG | 82 | 38.639 | −46.941 | −50.877 | 1 | 23.01 |
| 4950 | CD | ARG | 82 | 40.01 | −47.527 | −50.579 | 1 | 24.71 |
| 4951 | NE | ARG | 82 | 41.072 | −46.708 | −51.158 | 1 | 25.19 |
| 4952 | CZ | ARG | 82 | 42.371 | −46.928 | −50.981 | 1 | 26.86 |
| 4953 | NH1 | ARG | 82 | 42.781 | −47.946 | −50.238 | 1 | 27.24 |
| 4954 | NH2 | ARG | 82 | 43.261 | −46.126 | −51.55 | 1 | 27.61 |
| 4955 | C | ARG | 82 | 35.944 | −46.998 | −52.156 | 1 | 20.89 |
| 4956 | O | ARG | 82 | 36.103 | −45.863 | −52.61 | 1 | 21.61 |
| 4957 | N | ALA | 83 | 35.61 | −48.039 | −52.913 | 1 | 20.85 |
| 4958 | CA | ALA | 83 | 35.42 | −47.904 | −54.351 | 1 | 20.71 |
| 4959 | CB | ALA | 83 | 35.326 | −49.283 | −54.997 | 1 | 21.54 |
| 4960 | C | ALA | 83 | 34.167 | −47.093 | −54.666 | 1 | 19.94 |
| 4961 | O | ALA | 83 | 34.175 | −46.248 | −55.558 | 1 | 20.74 |
| 4962 | N | LEU | 84 | 33.092 | −47.355 | −53.931 | 1 | 20.63 |
| 4963 | CA | LEU | 84 | 31.837 | −46.642 | −54.147 | 1 | 21.91 |
| 4964 | CB | LEU | 84 | 30.732 | −47.236 | −53.268 | 1 | 23.53 |
| 4965 | CG | LEU | 84 | 30.257 | −48.65 | −53.607 | 1 | 26.67 |
| 4966 | CD1 | LEU | 84 | 29.219 | −49.102 | −52.587 | 1 | 28.91 |
| 4967 | CD2 | LEU | 84 | 29.669 | −48.67 | −55.012 | 1 | 29.66 |
| 4968 | C | LEU | 84 | 31.977 | −45.152 | −53.853 | 1 | 21.71 |
| 4969 | O | LEU | 84 | 31.409 | −44.314 | −54.555 | 1 | 22.22 |
| 4970 | N | ARG | 85 | 32.742 | −44.826 | −52.817 | 1 | 22.29 |
| 4971 | CA | ARG | 85 | 32.944 | −43.435 | −52.425 | 1 | 22.16 |
| 4972 | CB | ARG | 85 | 33.265 | −43.358 | −50.93 | 1 | 24.05 |
| 4973 | CG | ARG | 85 | 32.1 | −43.706 | −50.024 | 1 | 26.54 |
| 4974 | CD | ARG | 85 | 32.539 | −43.786 | −48.571 | 1 | 29.45 |
| 4975 | NE | ARG | 85 | 31.409 | −43.888 | −47.652 | 1 | 31.17 |
| 4976 | CZ | ARG | 85 | 30.471 | −44.828 | −47.707 | 1 | 33.41 |
| 4977 | NH1 | ARG | 85 | 30.513 | −45.763 | −48.646 | 1 | 34.28 |
| 4978 | NH2 | ARG | 85 | 29.489 | −44.837 | −46.814 | 1 | 33.24 |
| 4979 | C | ARG | 85 | 34.053 | −42.748 | −53.213 | 1 | 22.39 |
| 4980 | O | ARG | 85 | 34.246 | −41.537 | −53.093 | 1 | 21.24 |
| 4981 | N | GLN | 86 | 34.771 | −43.518 | −54.027 | 1 | 23.09 |
| 4982 | CA | GLN | 86 | 35.877 | −42.977 | −54.81 | 1 | 24.13 |
| 4983 | CB | GLN | 86 | 35.375 | −41.986 | −55.862 | 1 | 26.11 |
| 4984 | CG | GLN | 86 | 34.466 | −42.603 | −56.905 | 1 | 29.6 |
| 4985 | CD | GLN | 86 | 34.374 | −41.759 | −58.159 | 1 | 31.61 |
| 4986 | OE1 | GLN | 86 | 34.06 | −40.571 | −58.099 | 1 | 30.3 |
| 4987 | NE2 | GLN | 86 | 34.652 | −42.371 | −59.306 | 1 | 32.53 |
| 4988 | C | GLN | 86 | 36.819 | −42.278 | −53.844 | 1 | 24.4 |
| 4989 | O | GLN | 86 | 37.19 | −41.116 | −54.031 | 1 | 24.8 |
| 4990 | N | MET | 87 | 37.188 | −43.01 | −52.8 | 1 | 23.8 |
| 4991 | CA | MET | 87 | 38.068 | −42.508 | −51.761 | 1 | 24.77 |
| 4992 | CB | MET | 87 | 37.665 | −43.124 | −50.424 | 1 | 26.15 |
| 4993 | CG | MET | 87 | 38.338 | −42.52 | −49.211 | 1 | 27.24 |
| 4994 | SD | MET | 87 | 37.848 | −43.402 | −47.72 | 1 | 27.45 |
| 4995 | CE | MET | 87 | 36.149 | −42.862 | −47.545 | 1 | 29.56 |
| 4996 | C | MET | 87 | 39.522 | −42.844 | −52.073 | 1 | 25.01 |
| 4997 | O | MET | 87 | 39.92 | −44.01 | −52.042 | 1 | 25.51 |
| 4998 | N | GLU | 88 | 40.302 | −41.813 | −52.382 | 1 | 23.99 |
| 4999 | CA | GLU | 88 | 41.717 | −41.973 | −52.694 | 1 | 24.75 |
| 5000 | CB | GLU | 88 | 41.962 | −41.763 | −54.188 | 1 | 26.87 |
| 5001 | CG | GLU | 88 | 41.368 | −42.86 | −55.052 | 1 | 30.67 |
| 5002 | CD | GLU | 88 | 41.819 | −44.241 | −54.611 | 1 | 33.09 |
| 5003 | OE1 | GLU | 88 | 43.043 | −44.485 | −54.575 | 1 | 35.75 |
| 5004 | OE2 | GLU | 88 | 40.951 | −45.081 | −54.297 | 1 | 35.9 |
| 5005 | C | GLU | 88 | 42.539 | −40.976 | −51.891 | 1 | 23.48 |
| 5006 | O | GLU | 88 | 42.123 | −39.839 | −51.677 | 1 | 23.08 |
| 5007 | N | PRO | 89 | 43.726 | −41.393 | −51.437 | 1 | 22.68 |
| 5008 | CD | PRO | 89 | 44.359 | −42.712 | −51.616 | 1 | 22.31 |
| 5009 | CA | PRO | 89 | 44.582 | −40.503 | −50.652 | 1 | 21.36 |
| 5010 | CB | PRO | 89 | 45.695 | −41.434 | −50.175 | 1 | 22.92 |
| 5011 | CG | PRO | 89 | 45.809 | −42.415 | −51.301 | 1 | 23.97 |
| 5012 | C | PRO | 89 | 45.126 | −39.301 | −51.413 | 1 | 21.71 |
| 5013 | O | PRO | 89 | 45.315 | −39.346 | −52.629 | 1 | 21.91 |
| 5014 | N | PHE | 90 | 45.35 | −38.214 | −50.683 | 1 | 20.55 |
| 5015 | CA | PHE | 90 | 45.928 | −37.008 | −51.256 | 1 | 21.12 |
| 5016 | CB | PHE | 90 | 44.862 | −36.06 | −51.842 | 1 | 20.27 |
| 5017 | CG | PHE | 90 | 43.798 | −35.625 | −50.869 | 1 | 18.81 |
| 5018 | CD1 | PHE | 90 | 42.556 | −36.251 | −50.853 | 1 | 20.28 |
| 5019 | CD2 | PHE | 90 | 44.02 | −34.557 | −50.005 | 1 | 19.76 |
| 5020 | CE1 | PHE | 90 | 41.546 | −35.817 | −49.992 | 1 | 19.59 |
| 5021 | CE2 | PHE | 90 | 43.017 | −34.116 | −49.139 | 1 | 17.99 |
| 5022 | CZ | PHE | 90 | 41.779 | −34.747 | −49.135 | 1 | 20.58 |
| 5023 | C | PHE | 90 | 46.748 | −36.31 | −50.18 | 1 | 21.98 |
| 5024 | O | PHE | 90 | 46.426 | −36.381 | −48.993 | 1 | 20.14 |
| 5025 | N | PRO | 91 | 47.837 | −35.644 | −50.582 | 1 | 23.06 |
| 5026 | CD | PRO | 91 | 48.334 | −35.496 | −51.963 | 1 | 24.42 |
| 5027 | CA | PRO | 91 | 48.709 | −34.941 | −49.64 | 1 | 22.95 |
| 5028 | CB | PRO | 91 | 49.931 | −34.618 | −50.492 | 1 | 24.88 |
| 5029 | CG | PRO | 91 | 49.321 | −34.352 | −51.828 | 1 | 24.74 |
| 5030 | C | PRO | 91 | 48.098 | −33.693 | −49.014 | 1 | 22.57 |
| 5031 | O | PRO | 91 | 47.117 | −33.136 | −49.515 | 1 | 21.33 |
| 5032 | N | LEU | 92 | 48.698 | −33.261 | −47.911 | 1 | 21.8 |
| 5033 | CA | LEU | 92 | 48.248 | −32.076 | −47.199 | 1 | 22.17 |
| 5034 | CB | LEU | 92 | 49.139 | −31.823 | −45.982 | 1 | 21.5 |
| 5035 | CG | LEU | 92 | 48.983 | −30.454 | −45.312 | 1 | 22.69 |
| 5036 | CD1 | LEU | 92 | 47.612 | −30.348 | −44.65 | 1 | 21.34 |
| 5037 | CD2 | LEU | 92 | 50.087 | −30.266 | −44.286 | 1 | 22.45 |
| 5038 | C | LEU | 92 | 48.266 | −30.836 | −48.08 | 1 | 22.79 |
| 5039 | O | LEU | 92 | 49.237 | −30.573 | −48.796 | 1 | 23.61 |
| 5040 | N | ARG | 93 | 47.176 | −30.082 | −48.026 | 1 | 21.4 |
| 5041 | CA | ARG | 93 | 47.048 | −28.838 | −48.768 | 1 | 22.34 |
| 5042 | CB | ARG | 93 | 46.156 | −29.007 | −50.003 | 1 | 24.06 |
| 5043 | CG | ARG | 93 | 46.833 | −29.6 | −51.236 | 1 | 28.83 |
| 5044 | CD | ARG | 93 | 45.981 | −29.315 | −52.47 | 1 | 31.53 |
| 5045 | NE | ARG | 93 | 46.565 | −29.8 | −53.72 | 1 | 34.26 |
| 5046 | CZ | ARG | 93 | 46.623 | −31.08 | −54.076 | 1 | 36.5 |
| 5047 | NH1 | ARG | 93 | 46.134 | −32.019 | −53.277 | 1 | 37.24 |
| 5048 | NH2 | ARG | 93 | 47.161 | −31.421 | −55.24 | 1 | 36.68 |
| 5049 | C | ARG | 93 | 46.416 | −27.812 | −47.84 | 1 | 21.38 |
| 5050 | O | ARG | 93 | 45.435 | −28.107 | −47.155 | 1 | 21.25 |
| 5051 | N | VAL | 94 | 46.987 | −26.614 | −47.805 | 1 | 20.44 |
| 5052 | CA | VAL | 94 | 46.451 | −25.544 | −46.974 | 1 | 19.44 |
| 5053 | CB | VAL | 94 | 47.491 | −25.044 | −45.946 | 1 | 18.76 |
| 5054 | CG1 | VAL | 94 | 46.948 | −23.834 | −45.199 | 1 | 19.8 |
| 5055 | CG2 | VAL | 94 | 47.823 | −26.158 | −44.967 | 1 | 20.55 |
| 5056 | C | VAL | 94 | 46.056 | −24.398 | −47.896 | 1 | 19.93 |
| 5057 | O | VAL | 94 | 46.876 | −23.913 | −48.681 | 1 | 21.25 |
| 5058 | N | PHE | 95 | 44.796 | −23.98 | −47.813 | 1 | 19.53 |
| 5059 | CA | PHE | 95 | 44.292 | −22.895 | −48.648 | 1 | 18.98 |
| 5060 | CB | PHE | 95 | 43.043 | −23.333 | −49.422 | 1 | 19.01 |
| 5061 | CG | PHE | 95 | 43.322 | −24.287 | −50.546 | 1 | 19.91 |
| 5062 | CD1 | PHE | 95 | 43.518 | −25.64 | −50.299 | 1 | 20.52 |
| 5063 | CD2 | PHE | 95 | 43.379 | −23.83 | −51.862 | 1 | 21 |
| 5064 | CE1 | PHE | 95 | 43.765 | −26.53 | −51.345 | 1 | 22.44 |
| 5065 | CE2 | PHE | 95 | 43.626 | −24.71 | −52.915 | 1 | 21.17 |
| 5066 | CZ | PHE | 95 | 43.818 | −26.061 | −52.658 | 1 | 22.26 |
| 5067 | C | PHE | 95 | 43.945 | −21.641 | −47.86 | 1 | 20.67 |
| 5068 | O | PHE | 95 | 43.363 | −21.712 | −46.776 | 1 | 20.66 |
| 5069 | N | VAL | 96 | 44.306 | −20.494 | −48.427 | 1 | 19.19 |
| 5070 | CA | VAL | 96 | 44.026 | −19.196 | −47.83 | 1 | 19.68 |
| 5071 | CB | VAL | 96 | 45.324 | −18.405 | −47.563 | 1 | 19.93 |
| 5072 | CG1 | VAL | 96 | 44.988 | −17.008 | −47.059 | 1 | 20.74 |
| 5073 | CG2 | VAL | 96 | 46.183 | −19.143 | −46.544 | 1 | 19.51 |
| 5074 | C | VAL | 96 | 43.163 | −18.434 | −48.833 | 1 | 19.06 |
| 5075 | O | VAL | 96 | 43.444 | −18.447 | −50.033 | 1 | 18.75 |
| 5076 | N | ASN | 97 | 42.114 | −17.785 | −48.34 | 1 | 18.42 |
| 5077 | CA | ASN | 97 | 41.19 | −17.03 | −49.188 | 1 | 19.61 |
| 5078 | CB | ASN | 97 | 41.818 | −15.697 | −49.608 | 1 | 21.06 |
| 5079 | CG | ASN | 97 | 42.232 | −14.85 | −48.422 | 1 | 21.47 |
| 5080 | OD1 | ASN | 97 | 41.688 | −14.991 | −47.325 | 1 | 21.01 |
| 5081 | ND2 | ASN | 97 | 43.191 | −13.954 | −48.637 | 1 | 23.01 |
| 5082 | C | ASN | 97 | 40.781 | −17.819 | −50.433 | 1 | 19.54 |
| 5083 | O | ASN | 97 | 40.877 | −17.322 | −51.558 | 1 | 20.97 |
| 5084 | N | PRO | 98 | 40.308 | −19.062 | −50.246 | 1 | 18.47 |
| 5085 | CD | PRO | 98 | 40.214 | −19.801 | −48.973 | 1 | 19.47 |
| 5086 | CA | PRO | 98 | 39.892 | −19.908 | −51.368 | 1 | 18.4 |
| 5087 | CB | PRO | 98 | 39.937 | −21.305 | −50.768 | 1 | 18.64 |
| 5088 | CG | PRO | 98 | 39.452 | −21.056 | −49.373 | 1 | 17.6 |
| 5089 | C | PRO | 98 | 38.519 | −19.596 | −51.958 | 1 | 18.16 |
| 5090 | O | PRO | 98 | 37.667 | −18.984 | −51.314 | 1 | 18.45 |
| 5091 | N | SER | 99 | 38.327 | −20.032 | −53.198 | 1 | 18.77 |
| 5092 | CA | SER | 99 | 37.068 | −19.862 | −53.91 | 1 | 19.71 |
| 5093 | CB | SER | 99 | 37.194 | −18.774 | −54.983 | 1 | 22.26 |
| 5094 | OG | SER | 99 | 38.234 | −19.073 | −55.891 | 1 | 26.81 |
| 5095 | C | SER | 99 | 36.77 | −21.216 | −54.546 | 1 | 18.71 |
| 5096 | O | SER | 99 | 37.692 | −21.953 | −54.905 | 1 | 19.06 |
| 5097 | N | LEU | 100 | 35.491 | −21.549 | −54.679 | 1 | 18.31 |
| 5098 | CA | LEU | 100 | 35.11 | −22.834 | −55.244 | 1 | 19.04 |

TABLE 2-continued

| Atom | Atom Type | Residue | # | X | Y | Z | OCC | B |
|---|---|---|---|---|---|---|---|---|
| 5099 | CB | LEU | 100 | 34.415 | −23.684 | −54.171 | 1 | 20.98 |
| 5100 | CG | LEU | 100 | 33.923 | −25.098 | −54.521 | 1 | 21.7 |
| 5101 | CD1 | LEU | 100 | 33.702 | −25.881 | −53.237 | 1 | 25.82 |
| 5102 | CD2 | LEU | 100 | 32.63 | −25.036 | −55.329 | 1 | 23.8 |
| 5103 | C | LEU | 100 | 34.206 | −22.727 | −56.462 | 1 | 19.17 |
| 5104 | O | LEU | 100 | 33.343 | −21.852 | −56.543 | 1 | 20.13 |
| 5105 | N | ARG | 101 | 34.423 | −23.631 | −57.412 | 1 | 19.8 |
| 5106 | CA | ARG | 101 | 33.614 | −23.692 | −58.621 | 1 | 19.87 |
| 5107 | CB | ARG | 101 | 34.367 | −23.111 | −59.821 | 1 | 22.24 |
| 5108 | CG | ARG | 101 | 34.552 | −21.603 | −59.742 | 1 | 25.46 |
| 5109 | CD | ARG | 101 | 34.893 | −21.005 | −61.092 | 1 | 29.38 |
| 5110 | NE | ARG | 101 | 35.017 | −19.552 | −61.024 | 1 | 31.66 |
| 5111 | CZ | ARG | 101 | 35.24 | −18.771 | −62.077 | 1 | 32.42 |
| 5112 | NH1 | ARG | 101 | 35.363 | −19.303 | −63.284 | 1 | 32.74 |
| 5113 | NH2 | ARG | 101 | 35.344 | −17.458 | −61.922 | 1 | 34.92 |
| 5114 | C | ARG | 101 | 33.269 | −25.151 | −58.878 | 1 | 18.65 |
| 5115 | O | ARG | 101 | 34.123 | −26.028 | −58.768 | 1 | 19.63 |
| 5116 | N | VAL | 102 | 32.008 | −25.407 | −59.201 | 1 | 19.17 |
| 5117 | CA | VAL | 102 | 31.554 | −26.764 | −59.466 | 1 | 19.26 |
| 5118 | CB | VAL | 102 | 30.02 | −26.864 | −59.338 | 1 | 18.9 |
| 5119 | CG1 | VAL | 102 | 29.559 | −28.284 | −59.63 | 1 | 20.37 |
| 5120 | CG2 | VAL | 102 | 29.596 | −26.441 | −57.944 | 1 | 18.79 |
| 5121 | C | VAL | 102 | 31.964 | −27.2 | −60.869 | 1 | 20.01 |
| 5122 | O | VAL | 102 | 31.738 | −26.474 | −61.837 | 1 | 20.26 |
| 5123 | N | LEU | 103 | 32.572 | −28.38 | −60.966 | 1 | 18.6 |
| 5124 | CA | LEU | 103 | 33.011 | −28.925 | −62.252 | 1 | 19.15 |
| 5125 | CB | LEU | 103 | 34.394 | −29.565 | −62.108 | 1 | 18.69 |
| 5126 | CG | LEU | 103 | 35.538 | −28.631 | −61.701 | 1 | 19.52 |
| 5127 | CD1 | LEU | 103 | 36.819 | −29.432 | −61.555 | 1 | 20.9 |
| 5128 | CD2 | LEU | 103 | 35.713 | −27.261 | −62.743 | 1 | 23.2 |
| 5129 | C | LEU | 103 | 32.014 | −29.957 | −62.777 | 1 | 20.08 |
| 5130 | O | LEU | 103 | 31.713 | −29.993 | −63.972 | 1 | 22.01 |
| 5131 | N | ASP | 104 | 31.517 | −30.804 | −61.88 | 1 | 19 |
| 5132 | CA | ASP | 104 | 30.533 | −31.826 | −62.235 | 1 | 18.05 |
| 5133 | CB | ASP | 104 | 31.139 | −33.229 | −62.134 | 1 | 18.75 |
| 5134 | CG | ASP | 104 | 30.224 | −34.308 | −62.701 | 1 | 18.8 |
| 5135 | OD1 | ASP | 104 | 28.988 | −34.139 | −62.652 | 1 | 19.33 |
| 5136 | OD2 | ASP | 104 | 30.742 | −35.338 | −63.183 | 1 | 22.7 |
| 5137 | C | ASP | 104 | 29.412 | −31.68 | −61.217 | 1 | 18.53 |
| 5138 | O | ASP | 104 | 29.594 | −31.998 | −60.041 | 1 | 17.71 |
| 5139 | N | SER | 105 | 28.256 | −31.202 | −61.672 | 1 | 18.39 |
| 5140 | CA | SER | 105 | 27.114 | −30.974 | −60.791 | 1 | 18.48 |
| 5141 | CB | SER | 105 | 26.173 | −29.946 | −61.424 | 1 | 21.45 |
| 5142 | OG | SER | 105 | 25.699 | −30.396 | −62.681 | 1 | 21.24 |
| 5143 | C | SER | 105 | 26.308 | −32.201 | −60.374 | 1 | 18.69 |
| 5144 | O | SER | 105 | 25.343 | −32.073 | −59.615 | 1 | 18.53 |
| 5145 | N | ARG | 106 | 26.682 | −33.38 | −60.864 | 1 | 17.49 |
| 5146 | CA | ARG | 106 | 25.976 | −34.606 | −60.493 | 1 | 18.04 |
| 5147 | CB | ARG | 106 | 26.644 | −35.828 | −61.136 | 1 | 18.69 |
| 5148 | CG | ARG | 106 | 26.039 | −37.179 | −60.745 | 1 | 23.49 |
| 5149 | CD | ARG | 106 | 24.602 | −37.328 | −61.239 | 1 | 27.18 |
| 5150 | NE | ARG | 106 | 23.993 | −38.597 | −60.833 | 1 | 28.69 |
| 5151 | CZ | ARG | 106 | 24.279 | −39.78 | −61.37 | 1 | 30.42 |
| 5152 | NH1 | ARG | 106 | 25.171 | −39.876 | −62.347 | 1 | 32.33 |
| 5153 | NH2 | ARG | 106 | 23.67 | −40.874 | −60.928 | 1 | 31.27 |
| 5154 | C | ARG | 106 | 26.05 | −34.721 | −58.973 | 1 | 17.3 |
| 5155 | O | ARG | 106 | 27.104 | −34.49 | −58.386 | 1 | 17.98 |
| 5156 | N | LEU | 107 | 24.938 | −35.072 | −58.34 | 1 | 17.17 |
| 5157 | CA | LEU | 107 | 24.916 | −35.195 | −56.886 | 1 | 16.59 |
| 5158 | CB | LEU | 107 | 23.58 | −34.687 | −56.334 | 1 | 17.24 |
| 5159 | CG | LEU | 107 | 23.292 | −33.195 | −56.522 | 1 | 18.32 |
| 5160 | CD1 | LEU | 107 | 21.906 | −32.87 | −55.985 | 1 | 19.46 |
| 5161 | CD2 | LEU | 107 | 24.348 | −32.371 | −55.806 | 1 | 20.2 |
| 5162 | C | LEU | 107 | 25.166 | −36.622 | −56.411 | 1 | 17.39 |
| 5163 | O | LEU | 107 | 24.66 | −37.587 | −56.987 | 1 | 17.13 |
| 5164 | N | VAL | 108 | 25.963 | −36.739 | −55.354 | 1 | 16 |
| 5165 | CA | VAL | 108 | 26.303 | −38.027 | −54.764 | 1 | 16.75 |
| 5166 | CB | VAL | 108 | 27.793 | −38.359 | −54.986 | 1 | 18.19 |
| 5167 | CG1 | VAL | 108 | 28.131 | −39.688 | −54.353 | 1 | 21.07 |
| 5168 | CG2 | VAL | 108 | 28.098 | −38.392 | −56.481 | 1 | 22.45 |
| 5169 | C | VAL | 108 | 26.029 | −37.91 | −53.27 | 1 | 15 |
| 5170 | O | VAL | 108 | 26.422 | −36.928 | −52.647 | 1 | 13.95 |
| 5171 | N | THR | 109 | 25.354 | −38.908 | −52.707 | 1 | 14.82 |
| 5172 | CA | THR | 109 | 25.009 | −38.888 | −51.289 | 1 | 14.61 |
| 5173 | CB | THR | 109 | 23.483 | −38.99 | −51.098 | 1 | 15.93 |
| 5174 | OG1 | THR | 109 | 22.849 | −37.876 | −51.736 | 1 | 16.92 |
| 5175 | CG2 | THR | 109 | 23.126 | −38.991 | −49.612 | 1 | 18.03 |
| 5176 | C | THR | 109 | 25.666 | −39.988 | −50.464 | 1 | 14.87 |
| 5177 | O | THR | 109 | 25.573 | −41.171 | −50.792 | 1 | 15.15 |
| 5178 | N | PHE | 110 | 26.319 | −39.573 | −49.381 | 1 | 13.12 |
| 5179 | CA | PHE | 110 | 26.996 | −40.477 | −48.455 | 1 | 14.03 |
| 5180 | CB | PHE | 110 | 28.465 | −40.672 | −48.842 | 1 | 15.52 |
| 5181 | CG | PHE | 110 | 28.672 | −41.573 | −50.024 | 1 | 17.46 |
| 5182 | CD1 | PHE | 110 | 28.337 | −42.921 | −49.955 | 1 | 19.93 |
| 5183 | CD2 | PHE | 110 | 29.209 | −41.074 | −51.206 | 1 | 18.31 |
| 5184 | CE1 | PHE | 110 | 28.534 | −43.764 | −51.049 | 1 | 21.01 |
| 5185 | CE2 | PHE | 110 | 29.41 | −41.909 | −52.306 | 1 | 19.08 |
| 5186 | CZ | PHE | 110 | 29.071 | −43.254 | −52.225 | 1 | 20.3 |
| 5187 | C | PHE | 110 | 26.953 | −39.856 | −47.068 | 1 | 13.49 |
| 5188 | O | PHE | 110 | 26.719 | −38.658 | −46.929 | 1 | 13 |
| 5189 | N | PRO | 111 | 27.179 | −40.666 | −46.022 | 1 | 15.32 |
| 5190 | CD | PRO | 111 | 27.151 | −42.138 | −45.989 | 1 | 16.69 |
| 5191 | CA | PRO | 111 | 27.16 | −40.122 | −44.663 | 1 | 15.4 |
| 5192 | CB | PRO | 111 | 27.148 | −41.373 | −43.784 | 1 | 16.14 |
| 5193 | CG | PRO | 111 | 26.498 | −42.401 | −44.654 | 1 | 18.08 |
| 5194 | C | PRO | 111 | 28.393 | −39.265 | −44.406 | 1 | 16.13 |
| 5195 | O | PRO | 111 | 29.497 | −39.574 | −44.875 | 1 | 15.78 |
| 5196 | N | GLU | 112 | 28.187 | −38.193 | −43.65 | 1 | 14.64 |
| 5197 | CA | GLU | 112 | 29.235 | −37.252 | −43.285 | 1 | 15.79 |
| 5198 | CB | GLU | 112 | 29.057 | −35.937 | −44.035 | 1 | 19.25 |
| 5199 | CG | GLU | 112 | 29.817 | −35.791 | −45.307 | 1 | 20.83 |
| 5200 | CD | GLU | 112 | 29.609 | −34.415 | −45.896 | 1 | 16.71 |
| 5201 | OE1 | GLU | 112 | 29.702 | −33.419 | −45.137 | 1 | 17.95 |
| 5202 | OE2 | GLU | 112 | 29.357 | −34.329 | −47.107 | 1 | 17.33 |
| 5203 | C | GLU | 112 | 29.115 | −36.928 | −41.807 | 1 | 14.58 |
| 5204 | O | GLU | 112 | 28.027 | −36.997 | −41.243 | 1 | 14.69 |
| 5205 | N | GLY | 113 | 30.238 | −36.556 | −41.203 | 1 | 13.72 |
| 5206 | CA | GLY | 113 | 30.253 | −36.157 | −39.807 | 1 | 14.94 |
| 5207 | C | GLY | 113 | 31.089 | −34.89 | −39.722 | 1 | 15.18 |
| 5208 | O | GLY | 113 | 31.874 | −34.617 | −40.629 | 1 | 17.39 |
| 5209 | N | CYS | 114 | 30.93 | −34.11 | −38.657 | 1 | 12.63 |
| 5210 | CA | CYS | 114 | 31.699 | −32.874 | −38.498 | 1 | 11.25 |
| 5211 | CB | CYS | 114 | 30.8 | −31.652 | −38.75 | 1 | 11.45 |
| 5212 | SG | CYS | 114 | 31.634 | −30.037 | −38.609 | 1 | 12.49 |
| 5213 | C | CYS | 114 | 32.29 | −32.787 | −37.094 | 1 | 11.5 |
| 5214 | O | CYS | 114 | 31.616 | −33.096 | −36.113 | 1 | 11.22 |
| 5215 | N | GLU | 115 | 33.552 | −32.375 | −37.002 | 1 | 12.95 |
| 5216 | CA | GLU | 115 | 34.209 | −32.24 | −35.703 | 1 | 13.21 |
| 5217 | CB | GLU | 115 | 35.667 | −31.801 | −35.876 | 1 | 15.39 |
| 5218 | CG | GLU | 115 | 36.589 | −32.855 | −36.465 | 1 | 18.73 |
| 5219 | CD | GLU | 115 | 36.706 | −34.081 | −35.582 | 1 | 21.61 |
| 5220 | OE1 | GLU | 115 | 36.901 | −33.915 | −34.36 | 1 | 24.66 |
| 5221 | OE2 | GLU | 115 | 36.61 | −35.208 | −36.11 | 1 | 25.37 |
| 5222 | C | GLU | 115 | 33.487 | −31.219 | −34.83 | 1 | 13.3 |
| 5223 | O | GLU | 115 | 33.608 | −31.249 | −33.605 | 1 | 12.51 |
| 5224 | N | SER | 116 | 32.738 | −30.32 | −35.466 | 1 | 11.83 |
| 5225 | CA | SER | 116 | 32.002 | −29.281 | −34.75 | 1 | 10.91 |
| 5226 | CB | SER | 116 | 31.961 | −27.994 | −35.582 | 1 | 10.58 |
| 5227 | OG | SER | 116 | 33.244 | −27.393 | −35.633 | 1 | 12.93 |
| 5228 | C | SER | 116 | 30.59 | −29.679 | −34.335 | 1 | 11.45 |
| 5229 | O | SER | 116 | 29.863 | −28.879 | −33.75 | 1 | 11.46 |
| 5230 | N | VAL | 117 | 30.196 | −30.906 | −34.668 | 1 | 11.63 |
| 5231 | CA | VAL | 117 | 28.9 | −31.453 | −34.267 | 1 | 12.66 |
| 5232 | CB | VAL | 117 | 27.89 | −31.515 | −35.434 | 1 | 12.26 |
| 5233 | CG1 | VAL | 117 | 26.513 | −31.898 | −34.898 | 1 | 13.5 |
| 5234 | CG2 | VAL | 117 | 27.825 | −30.172 | −36.147 | 1 | 14.16 |
| 5235 | C | VAL | 117 | 29.283 | −32.868 | −33.84 | 1 | 12.91 |
| 5236 | O | VAL | 117 | 28.817 | −33.863 | −34.389 | 1 | 12.93 |
| 5237 | N | ALA | 118 | 30.164 | −32.929 | −32.849 | 1 | 14.84 |
| 5238 | CA | ALA | 118 | 30.697 | −34.186 | −32.339 | 1 | 14.14 |
| 5239 | CB | ALA | 118 | 31.56 | −33.906 | −31.107 | 1 | 16.69 |
| 5240 | C | ALA | 118 | 29.711 | −35.309 | −32.026 | 1 | 14.15 |
| 5241 | O | ALA | 118 | 28.701 | −35.105 | −31.344 | 1 | 14.66 |
| 5242 | N | GLY | 119 | 30.026 | −36.495 | −32.546 | 1 | 14.56 |
| 5243 | CA | GLY | 119 | 29.226 | −37.681 | −32.289 | 1 | 14.75 |
| 5244 | C | GLY | 119 | 28.049 | −37.999 | −33.182 | 1 | 12.69 |
| 5245 | O | GLY | 119 | 27.274 | −38.901 | −32.869 | 1 | 13.18 |
| 5246 | N | PHE | 120 | 27.91 | −37.29 | −34.294 | 1 | 12.59 |
| 5247 | CA | PHE | 120 | 26.784 | −37.532 | −35.19 | 1 | 12.07 |
| 5248 | CB | PHE | 120 | 25.793 | −36.366 | −35.114 | 1 | 12.17 |
| 5249 | CG | PHE | 120 | 25.14 | −36.21 | −33.774 | 1 | 12.14 |
| 5250 | CD1 | PHE | 120 | 24.019 | −36.96 | −33.442 | 1 | 12.68 |

TABLE 2-continued

| Atom | Atom Type | Residue | # | X | Y | Z | OCC | B |
|---|---|---|---|---|---|---|---|---|
| 5251 | CD2 | PHE | 120 | 25.658 | −35.326 | −32.834 | 1 | 14.82 |
| 5252 | CE1 | PHE | 120 | 23.419 | −36.835 | −32.192 | 1 | 14.96 |
| 5253 | CE2 | PHE | 120 | 25.07 | −35.191 | −31.58 | 1 | 16.66 |
| 5254 | CZ | PHE | 120 | 23.945 | −35.95 | −31.258 | 1 | 17.63 |
| 5255 | C | PHE | 120 | 27.205 | −37.709 | −36.634 | 1 | 12.49 |
| 5256 | O | PHE | 120 | 28.299 | −37.311 | −37.029 | 1 | 14.45 |
| 5257 | N | LEU | 121 | 26.31 | −38.312 | −37.411 | 1 | 12.33 |
| 5258 | CA | LEU | 121 | 26.514 | −38.54 | −38.836 | 1 | 12.95 |
| 5259 | CB | LEU | 121 | 26.986 | −39.972 | −39.101 | 1 | 14.96 |
| 5260 | CG | LEU | 121 | 28.361 | −40.405 | −38.596 | 1 | 17.45 |
| 5261 | CD1 | LEU | 121 | 28.519 | −41.898 | −38.824 | 1 | 19.06 |
| 5262 | CD2 | LEU | 121 | 29.453 | −39.639 | −39.324 | 1 | 17.91 |
| 5263 | C | LEU | 121 | 25.176 | −38.342 | −39.539 | 1 | 12.09 |
| 5264 | O | LEU | 121 | 24.118 | −38.5 | −38.932 | 1 | 11.67 |
| 5265 | N | ALA | 122 | 25.226 | −37.986 | −40.818 | 1 | 12.04 |
| 5266 | CA | ALA | 122 | 24.012 | −37.825 | −41.609 | 1 | 12.17 |
| 5267 | CB | ALA | 122 | 23.316 | −36.508 | −41.28 | 1 | 11.33 |
| 5268 | C | ALA | 122 | 24.395 | −37.855 | −43.078 | 1 | 12.1 |
| 5269 | O | ALA | 122 | 25.504 | −37.459 | −43.447 | 1 | 13.93 |
| 5270 | N | CYS | 123 | 23.487 | −38.348 | −43.912 | 1 | 12.19 |
| 5271 | CA | CYS | 123 | 23.742 | −38.391 | −45.345 | 1 | 13.62 |
| 5272 | CB | CYS | 123 | 22.74 | −39.3 | −46.047 | 1 | 15.25 |
| 5273 | SG | CYS | 123 | 23.068 | −41.034 | −45.763 | 1 | 20.81 |
| 5274 | C | CYS | 123 | 23.622 | −36.983 | −45.898 | 1 | 13.37 |
| 5275 | O | CYS | 123 | 22.703 | −36.244 | −45.542 | 1 | 14.09 |
| 5276 | N | VAL | 124 | 24.558 | −36.619 | −46.767 | 1 | 13.54 |
| 5277 | CA | VAL | 124 | 24.578 | −35.291 | −47.363 | 1 | 13.02 |
| 5278 | CB | VAL | 124 | 25.664 | −34.395 | −46.714 | 1 | 12.51 |
| 5279 | CG1 | VAL | 124 | 25.629 | −33.003 | −47.332 | 1 | 12.28 |
| 5280 | CG2 | VAL | 124 | 25.457 | −34.315 | −45.202 | 1 | 12.48 |
| 5281 | C | VAL | 124 | 24.892 | −35.371 | −48.851 | 1 | 13 |
| 5282 | O | VAL | 124 | 25.848 | −36.029 | −49.255 | 1 | 12.78 |
| 5283 | N | PRO | 125 | 24.075 | −34.715 | −49.688 | 1 | 13.3 |
| 5284 | CD | PRO | 125 | 22.789 | −34.064 | −49.381 | 1 | 13.7 |
| 5285 | CA | PRO | 125 | 24.322 | −34.733 | −51.132 | 1 | 13.34 |
| 5286 | CB | PRO | 125 | 22.981 | −34.301 | −51.715 | 1 | 14.5 |
| 5287 | CG | PRO | 125 | 22.467 | −33.355 | −50.681 | 1 | 17.96 |
| 5288 | C | PRO | 125 | 25.441 | −33.743 | −51.442 | 1 | 13.54 |
| 5289 | O | PRO | 125 | 25.46 | −32.631 | −50.905 | 1 | 13.33 |
| 5290 | N | ARG | 126 | 26.375 | −34.151 | −52.296 | 1 | 12.7 |
| 5291 | CA | ARG | 126 | 27.499 | −33.298 | −52.669 | 1 | 13.44 |
| 5292 | CB | ARG | 126 | 28.767 | −33.742 | −51.938 | 1 | 13.77 |
| 5293 | CG | ARG | 126 | 28.711 | −33.617 | −50.423 | 1 | 13.16 |
| 5294 | CD | ARG | 126 | 28.735 | −32.167 | −49.985 | 1 | 13.08 |
| 5295 | NE | ARG | 126 | 28.872 | −32.058 | −48.534 | 1 | 14.55 |
| 5296 | CZ | ARG | 126 | 28.878 | −30.908 | −47.868 | 1 | 13.76 |
| 5297 | NH1 | ARG | 126 | 28.753 | −29.758 | −48.52 | 1 | 14.43 |
| 5298 | NH2 | ARG | 126 | 29.004 | −30.906 | −46.546 | 1 | 14.45 |
| 5299 | C | ARG | 126 | 27.757 | −33.393 | −54.162 | 1 | 13.45 |
| 5300 | O | ARG | 126 | 27.374 | −34.37 | −54.8 | 1 | 14.44 |
| 5301 | N | PHE | 127 | 28.419 | −32.38 | −54.712 | 1 | 14.09 |
| 5302 | CA | PHE | 127 | 28.751 | −32.382 | −56.133 | 1 | 14.55 |
| 5303 | CB | PHE | 127 | 29.211 | −30.99 | −56.574 | 1 | 15.2 |
| 5304 | CG | PHE | 127 | 28.139 | −29.943 | −56.484 | 1 | 16.87 |
| 5305 | CD1 | PHE | 127 | 28.322 | −28.806 | −55.703 | 1 | 18.46 |
| 5306 | CD2 | PHE | 127 | 26.946 | −30.089 | −57.187 | 1 | 18.42 |
| 5307 | CE1 | PHE | 127 | 27.335 | −27.826 | −55.623 | 1 | 19.81 |
| 5308 | CE2 | PHE | 127 | 25.951 | −29.114 | −57.114 | 1 | 19.33 |
| 5309 | CZ | PHE | 127 | 26.147 | −27.979 | −56.33 | 1 | 19.93 |
| 5310 | C | PHE | 127 | 29.861 | −33.399 | −56.388 | 1 | 15.29 |
| 5311 | O | PHE | 127 | 30.755 | −33.58 | −55.562 | 1 | 16.33 |
| 5312 | N | GLN | 128 | 29.801 | −34.057 | −57.541 | 1 | 15.22 |
| 5313 | CA | GLN | 128 | 30.788 | −35.066 | −57.916 | 1 | 15.35 |
| 5314 | CB | GLN | 128 | 30.342 | −35.745 | −59.216 | 1 | 16.2 |
| 5315 | CG | GLN | 128 | 31.357 | −36.681 | −59.863 | 1 | 18.33 |
| 5316 | CD | GLN | 128 | 31.842 | −37.78 | −58.941 | 1 | 19.84 |
| 5317 | OE1 | GLN | 128 | 31.09 | −38.295 | −58.112 | 1 | 20.93 |
| 5318 | NE2 | GLN | 128 | 33.104 | −38.163 | −59.096 | 1 | 21.38 |
| 5319 | C | GLN | 128 | 32.202 | −34.516 | −58.074 | 1 | 14.78 |
| 5320 | O | GLN | 128 | 33.173 | −35.189 | −57.725 | 1 | 15.93 |
| 5321 | N | ALA | 129 | 32.325 | −33.302 | −58.604 | 1 | 13.79 |
| 5322 | CA | ALA | 129 | 33.641 | −32.708 | −58.802 | 1 | 14.45 |
| 5323 | CB | ALA | 129 | 34.18 | −33.09 | −60.183 | 1 | 15.14 |
| 5324 | C | ALA | 129 | 33.614 | −31.194 | −58.651 | 1 | 14.81 |
| 5325 | O | ALA | 129 | 32.663 | −30.533 | −59.064 | 1 | 14.8 |
| 5326 | N | VAL | 130 | 34.669 | −30.653 | −58.051 | 1 | 14.95 |
| 5327 | CA | VAL | 130 | 34.776 | −29.219 | −57.832 | 1 | 15.2 |
| 5328 | CB | VAL | 130 | 34.297 | −28.815 | −56.413 | 1 | 14.79 |
| 5329 | CG1 | VAL | 130 | 32.854 | −29.249 | −56.199 | 1 | 16.06 |
| 5330 | CG2 | VAL | 130 | 35.205 | −29.446 | −55.36 | 1 | 16.76 |
| 5331 | C | VAL | 130 | 36.215 | −28.765 | −57.971 | 1 | 15.68 |
| 5332 | O | VAL | 130 | 37.143 | −29.576 | −57.978 | 1 | 17.93 |
| 5333 | N | GLN | 131 | 36.389 | −27.455 | −58.076 | 1 | 14.97 |
| 5334 | CA | GLN | 131 | 37.711 | −26.868 | −58.191 | 1 | 16.86 |
| 5335 | CB | GLN | 131 | 37.865 | −26.153 | −59.53 | 1 | 18.85 |
| 5336 | CG | GLN | 131 | 39.216 | −25.491 | −59.707 | 1 | 20.61 |
| 5337 | CD | GLN | 131 | 39.276 | −24.643 | −60.959 | 1 | 22.69 |
| 5338 | OE1 | GLN | 131 | 38.831 | −23.493 | −60.971 | 1 | 26.45 |
| 5339 | NE2 | GLN | 131 | 39.812 | −25.213 | −62.026 | 1 | 21.07 |
| 5340 | C | GLN | 131 | 37.884 | −25.854 | −57.078 | 1 | 16.2 |
| 5341 | O | GLN | 131 | 37.054 | −24.962 | −56.914 | 1 | 17.32 |
| 5342 | N | ILE | 132 | 38.952 | −25.998 | −56.304 | 1 | 16.77 |
| 5343 | CA | ILE | 132 | 39.217 | −25.048 | −55.238 | 1 | 17.58 |
| 5344 | CB | ILE | 132 | 39.385 | −25.752 | −53.859 | 1 | 16.35 |
| 5345 | CG2 | ILE | 132 | 40.448 | −26.836 | −53.943 | 1 | 15.87 |
| 5346 | CG1 | ILE | 132 | 39.721 | −24.715 | −52.783 | 1 | 17.4 |
| 5347 | CD1 | ILE | 132 | 39.71 | −25.266 | −51.358 | 1 | 15.53 |
| 5348 | C | ILE | 132 | 40.483 | −24.29 | −55.62 | 1 | 18.34 |
| 5349 | O | ILE | 132 | 41.509 | −24.888 | −55.949 | 1 | 17.88 |
| 5350 | N | SER | 133 | 40.386 | −22.965 | −55.611 | 1 | 19.8 |
| 5351 | CA | SER | 133 | 41.509 | −22.107 | −55.958 | 1 | 21.28 |
| 5352 | CB | SER | 133 | 41.203 | −21.322 | −57.236 | 1 | 23.07 |
| 5353 | OG | SER | 133 | 40.95 | −22.19 | −58.325 | 1 | 27.31 |
| 5354 | C | SER | 133 | 41.757 | −21.134 | −54.819 | 1 | 21.84 |
| 5355 | O | SER | 133 | 40.818 | −20.633 | −54.205 | 1 | 22.33 |
| 5356 | N | GLY | 134 | 43.026 | −20.871 | −54.541 | 1 | 21.76 |
| 5357 | CA | GLY | 134 | 43.361 | −19.95 | −53.476 | 1 | 22.56 |
| 5358 | C | GLY | 134 | 44.853 | −19.727 | −53.407 | 1 | 22.45 |
| 5359 | O | GLY | 134 | 45.571 | −19.955 | −54.381 | 1 | 22.51 |
| 5360 | N | LEU | 135 | 45.321 | −19.285 | −52.249 | 1 | 23.84 |
| 5361 | CA | LEU | 135 | 46.738 | −19.029 | −52.044 | 1 | 25.59 |
| 5362 | CB | LEU | 135 | 46.947 | −17.588 | −51.576 | 1 | 26.32 |
| 5363 | CG | LEU | 135 | 46.315 | −16.462 | −52.395 | 1 | 28.29 |
| 5364 | CD1 | LEU | 135 | 46.489 | −15.137 | −51.669 | 1 | 30.03 |
| 5365 | CD2 | LEU | 135 | 46.957 | −16.412 | −53.769 | 1 | 27.73 |
| 5366 | C | LEU | 135 | 47.252 | −19.964 | −50.966 | 1 | 26.72 |
| 5367 | O | LEU | 135 | 46.492 | −20.373 | −50.087 | 1 | 27.11 |
| 5368 | N | ASP | 136 | 48.529 | −20.326 | −51.036 | 1 | 27.84 |
| 5369 | CA | ASP | 136 | 49.095 | −21.157 | −49.985 | 1 | 28.65 |
| 5370 | CB | ASP | 136 | 50.29 | −21.986 | −50.483 | 1 | 30.14 |
| 5371 | CG | ASP | 136 | 51.414 | −21.138 | −51.05 | 1 | 29.5 |
| 5372 | OD1 | ASP | 136 | 51.634 | −20.007 | −50.571 | 1 | 30.68 |
| 5373 | OD2 | ASP | 136 | 52.098 | −21.628 | −51.972 | 1 | 33.42 |
| 5374 | C | ASP | 136 | 49.527 | −20.132 | −48.939 | 1 | 29 |
| 5375 | O | ASP | 136 | 49.477 | −18.93 | −49.2 | 1 | 28.6 |
| 5376 | N | PRO | 137 | 49.939 | −20.578 | −47.744 | 1 | 29.7 |
| 5377 | CD | PRO | 137 | 49.997 | −21.96 | −47.232 | 1 | 29.75 |
| 5378 | CA | PRO | 137 | 50.355 | −19.623 | −46.711 | 1 | 30.91 |
| 5379 | CB | PRO | 137 | 50.932 | −20.528 | −45.629 | 1 | 30.74 |
| 5380 | CG | PRO | 137 | 50.058 | −21.744 | −45.733 | 1 | 30.92 |
| 5381 | C | PRO | 137 | 51.341 | −18.538 | −47.155 | 1 | 31.85 |
| 5382 | O | PRO | 137 | 51.417 | −17.474 | −46.536 | 1 | 32.35 |
| 5383 | N | ASN | 138 | 52.084 | −18.799 | −48.227 | 1 | 32.89 |
| 5384 | CA | ASN | 138 | 53.065 | −17.836 | −48.721 | 1 | 33.47 |
| 5385 | CB | ASN | 138 | 54.321 | −18.566 | −49.199 | 1 | 35.22 |
| 5386 | CG | ASN | 138 | 55.071 | −19.228 | −48.062 | 1 | 36.46 |
| 5387 | OD1 | ASN | 138 | 55.379 | −18.589 | −47.056 | 1 | 38.35 |
| 5388 | ND2 | ASN | 138 | 55.373 | −20.512 | −48.215 | 1 | 37.82 |
| 5389 | C | ASN | 138 | 52.557 | −16.911 | −49.823 | 1 | 33.38 |
| 5390 | O | ASN | 138 | 53.319 | −16.108 | −50.365 | 1 | 34.01 |
| 5391 | N | GLY | 139 | 51.275 | −17.024 | −50.156 | 1 | 32.55 |
| 5392 | CA | GLY | 139 | 50.702 | −16.166 | −51.177 | 1 | 31.54 |
| 5393 | C | GLY | 139 | 50.786 | −16.683 | −52.6 | 1 | 30.83 |
| 5394 | O | GLY | 139 | 50.407 | −15.981 | −53.538 | 1 | 30.28 |
| 5395 | N | GLU | 140 | 51.281 | −17.903 | −52.771 | 1 | 30.96 |
| 5396 | CA | GLU | 140 | 51.395 | −18.485 | −54.102 | 1 | 31.77 |
| 5397 | CB | GLU | 140 | 52.451 | −19.589 | −54.11 | 1 | 34.85 |
| 5398 | CG | GLU | 140 | 53.788 | −19.171 | −53.522 | 1 | 38.84 |
| 5399 | CD | GLU | 140 | 54.852 | −20.238 | −53.686 | 1 | 41.93 |
| 5400 | OE1 | GLU | 140 | 54.633 | −21.377 | −53.22 | 1 | 43.95 |
| 5401 | OE2 | GLU | 140 | 55.909 | −19.935 | −54.281 | 1 | 44.2 |
| 5402 | C | GLU | 140 | 50.05 | −19.062 | −54.529 | 1 | 31.32 |

TABLE 2-continued

| Atom | Atom Type | Residue | # | X | Y | Z | OCC | B |
|---|---|---|---|---|---|---|---|---|
| 5403 | O | GLU | 140 | 49.337 | −19.658 | −53.721 | 1 | 29.56 |
| 5404 | N | GLN | 141 | 49.706 | −18.877 | −55.799 | 1 | 30.17 |
| 5405 | CA | GLN | 141 | 48.447 | −19.386 | −56.33 | 1 | 31.46 |
| 5406 | CB | GLN | 141 | 48.227 | −18.884 | −57.759 | 1 | 32.94 |
| 5407 | CG | GLN | 141 | 47.93 | −17.399 | −57.889 | 1 | 36.61 |
| 5408 | CD | GLN | 141 | 46.61 | −17.008 | −57.255 | 1 | 38.02 |
| 5409 | OE1 | GLN | 141 | 45.614 | −17.726 | −57.37 | 1 | 39.07 |
| 5410 | NE2 | GLN | 141 | 46.589 | −15.856 | −56.597 | 1 | 39.69 |
| 5411 | C | GLN | 141 | 48.432 | −20.909 | −56.335 | 1 | 30.34 |
| 5412 | O | GLN | 141 | 49.435 | −21.549 | −56.655 | 1 | 31.03 |
| 5413 | N | VAL | 142 | 47.292 | −21.487 | −55.974 | 1 | 29 |
| 5414 | CA | VAL | 142 | 47.139 | −22.937 | −55.963 | 1 | 28.22 |
| 5415 | CB | VAL | 142 | 47.338 | −23.529 | −54.546 | 1 | 28.19 |
| 5416 | CG1 | VAL | 142 | 47.098 | −25.031 | −54.573 | 1 | 29.6 |
| 5417 | CG2 | VAL | 142 | 48.748 | −23.239 | −54.05 | 1 | 29.41 |
| 5418 | C | VAL | 142 | 45.742 | −23.298 | −56.453 | 1 | 26.79 |
| 5419 | O | VAL | 142 | 44.748 | −22.74 | −55.988 | 1 | 26.16 |
| 5420 | N | VAL | 143 | 45.677 | −24.221 | −57.405 | 1 | 25.58 |
| 5421 | CA | VAL | 143 | 44.403 | −24.663 | −57.956 | 1 | 24.42 |
| 5422 | CB | VAL | 143 | 44.221 | −24.193 | −59.415 | 1 | 24.52 |
| 5423 | CG1 | VAL | 143 | 42.883 | −24.682 | −59.954 | 1 | 23.78 |
| 5424 | CG2 | VAL | 143 | 44.298 | −22.677 | −59.486 | 1 | 25.98 |
| 5425 | C | VAL | 143 | 44.357 | −26.182 | −57.926 | 1 | 23.48 |
| 5426 | O | VAL | 143 | 45.313 | −26.848 | −58.325 | 1 | 24.31 |
| 5427 | N | TRP | 144 | 43.247 | −26.727 | −57.445 | 1 | 21.43 |
| 5428 | CA | TRP | 144 | 43.089 | −28.171 | −57.371 | 1 | 20.43 |
| 5429 | CB | TRP | 144 | 43.356 | −28.653 | −55.936 | 1 | 20.97 |
| 5430 | CG | TRP | 144 | 43.18 | −30.138 | −55.722 | 1 | 21.42 |
| 5431 | CD2 | TRP | 144 | 42.843 | −30.795 | −54.491 | 1 | 21.12 |
| 5432 | CE2 | TRP | 144 | 42.843 | −32.185 | −54.743 | 1 | 20.71 |
| 5433 | CE3 | TRP | 144 | 42.545 | −30.343 | −53.199 | 1 | 22.75 |
| 5434 | CD1 | TRP | 144 | 43.362 | −31.133 | −56.644 | 1 | 19.92 |
| 5435 | NE1 | TRP | 144 | 43.161 | −32.363 | −56.054 | 1 | 21.61 |
| 5436 | CZ2 | TRP | 144 | 42.555 | −33.129 | −53.751 | 1 | 20.01 |
| 5437 | CZ3 | TRP | 144 | 42.259 | −31.283 | −52.211 | 1 | 21.86 |
| 5438 | CH2 | TRP | 144 | 42.267 | −32.659 | −52.494 | 1 | 20.57 |
| 5439 | C | TRP | 144 | 41.699 | −28.597 | −57.822 | 1 | 19.54 |
| 5440 | O | TRP | 144 | 40.696 | −28.187 | −57.242 | 1 | 19 |
| 5441 | N | GLN | 145 | 41.65 | −29.393 | −58.886 | 1 | 18.92 |
| 5442 | CA | GLN | 145 | 40.388 | −29.912 | −59.399 | 1 | 17.77 |
| 5443 | CB | GLN | 145 | 40.385 | −29.939 | −60.932 | 1 | 17.76 |
| 5444 | CG | GLN | 145 | 40.654 | −28.591 | −61.582 | 1 | 19.73 |
| 5445 | CD | GLN | 145 | 40.413 | −28.609 | −63.082 | 1 | 20.44 |
| 5446 | OE1 | GLN | 145 | 40.715 | −29.593 | −63.754 | 1 | 22.1 |
| 5447 | NE2 | GLN | 145 | 39.879 | −27.514 | −63.614 | 1 | 20.29 |
| 5448 | C | GLN | 145 | 40.296 | −31.33 | −58.85 | 1 | 18.05 |
| 5449 | O | GLN | 145 | 41.175 | −32.158 | −59.098 | 1 | 19.53 |
| 5450 | N | ALA | 146 | 39.239 | −31.608 | −58.097 | 1 | 17.65 |
| 5451 | CA | ALA | 146 | 39.076 | −32.924 | −57.492 | 1 | 18.53 |
| 5452 | CB | ALA | 146 | 39.406 | −32.848 | −56.007 | 1 | 18.47 |
| 5453 | C | ALA | 146 | 37.679 | −33.486 | −57.676 | 1 | 17.21 |
| 5454 | O | ALA | 146 | 36.725 | −32.747 | −57.901 | 1 | 17.42 |
| 5455 | N | SER | 147 | 37.569 | −34.805 | −57.568 | 1 | 18.27 |
| 5456 | CA | SER | 147 | 36.289 | −35.479 | −57.711 | 1 | 18.54 |
| 5457 | CB | SER | 147 | 36.196 | −36.154 | −59.082 | 1 | 20.33 |
| 5458 | OG | SER | 147 | 37.2 | −37.144 | −59.228 | 1 | 24.74 |
| 5459 | C | SER | 147 | 36.13 | −36.524 | −56.614 | 1 | 18.83 |
| 5460 | O | SER | 147 | 37.046 | −36.759 | −55.824 | 1 | 19.94 |
| 5461 | N | GLY | 148 | 34.958 | −37.141 | −56.563 | 1 | 18.02 |
| 5462 | CA | GLY | 148 | 34.711 | −38.166 | −55.568 | 1 | 15.83 |
| 5463 | C | GLY | 148 | 34.78 | −37.688 | −54.132 | 1 | 15.03 |
| 5464 | O | GLY | 148 | 34.314 | −36.596 | −53.799 | 1 | 15.29 |
| 5465 | N | TRP | 149 | 35.382 | −38.509 | −53.279 | 1 | 15.18 |
| 5466 | CA | TRP | 149 | 35.487 | −38.194 | −51.86 | 1 | 13.76 |
| 5467 | CB | TRP | 149 | 36.113 | −39.372 | −51.112 | 1 | 14.82 |
| 5468 | CG | TRP | 149 | 35.748 | −39.397 | −49.661 | 1 | 15.18 |
| 5469 | CD2 | TRP | 149 | 34.447 | −39.643 | −49.108 | 1 | 16 |
| 5470 | CE2 | TRP | 149 | 34.566 | −39.549 | −47.704 | 1 | 16.19 |
| 5471 | CE3 | TRP | 149 | 33.193 | −39.935 | −49.662 | 1 | 14.21 |
| 5472 | CD1 | TRP | 149 | 36.577 | −39.168 | −48.603 | 1 | 17.68 |
| 5473 | NE1 | TRP | 149 | 35.876 | −39.259 | −47.422 | 1 | 17 |
| 5474 | CZ2 | TRP | 149 | 33.478 | −39.736 | −46.842 | 1 | 16.73 |
| 5475 | CZ3 | TRP | 149 | 32.107 | −40.122 | −48.802 | 1 | 15.77 |
| 5476 | CH2 | TRP | 149 | 32.261 | −40.021 | −47.407 | 1 | 15.45 |
| 5477 | C | TRP | 149 | 36.274 | −36.913 | −51.588 | 1 | 13.8 |
| 5478 | O | TRP | 149 | 35.918 | −36.137 | −50.701 | 1 | 13.43 |
| 5479 | N | ALA | 150 | 37.34 | −36.688 | −52.349 | 1 | 14.42 |
| 5480 | CA | ALA | 150 | 38.14 | −35.478 | −52.177 | 1 | 14.4 |
| 5481 | CB | ALA | 150 | 39.31 | −35.479 | −53.154 | 1 | 15.86 |
| 5482 | C | ALA | 150 | 37.27 | −34.239 | −52.399 | 1 | 13.83 |
| 5483 | O | ALA | 150 | 37.392 | −33.243 | −51.68 | 1 | 14.88 |
| 5484 | N | ALA | 151 | 36.394 | −34.302 | −53.399 | 1 | 14.26 |
| 5485 | CA | ALA | 151 | 35.505 | −33.184 | −53.702 | 1 | 13.62 |
| 5486 | CB | ALA | 151 | 34.715 | −33.47 | −54.974 | 1 | 14.38 |
| 5487 | C | ALA | 151 | 34.55 | −32.943 | −52.538 | 1 | 13.03 |
| 5488 | O | ALA | 151 | 34.229 | −31.799 | −52.211 | 1 | 12.16 |
| 5489 | N | ARG | 152 | 34.097 | −34.027 | −51.918 | 1 | 12.56 |
| 5490 | CA | ARG | 152 | 33.186 | −33.925 | −50.778 | 1 | 12.6 |
| 5491 | CB | ARG | 152 | 32.742 | −35.316 | −50.321 | 1 | 11.78 |
| 5492 | CG | ARG | 152 | 31.998 | −35.329 | −48.983 | 1 | 12.43 |
| 5493 | CD | ARG | 152 | 31.453 | −36.719 | −48.672 | 1 | 12.89 |
| 5494 | NE | ARG | 152 | 30.513 | −37.169 | −49.699 | 1 | 13.33 |
| 5495 | CZ | ARG | 152 | 29.197 | −36.976 | −49.661 | 1 | 14.99 |
| 5496 | NH1 | ARG | 152 | 28.636 | −36.344 | −48.638 | 1 | 15.56 |
| 5497 | NH2 | ARG | 152 | 28.442 | −37.405 | −50.663 | 1 | 15.3 |
| 5498 | C | ARG | 152 | 33.865 | −33.203 | −49.622 | 1 | 13.38 |
| 5499 | O | ARG | 152 | 33.273 | −32.326 | −48.997 | 1 | 13.1 |
| 5500 | N | ILE | 153 | 35.106 | −33.586 | −49.332 | 1 | 13.29 |
| 5501 | CA | ILE | 153 | 35.864 | −32.964 | −48.254 | 1 | 14.38 |
| 5502 | CB | ILE | 153 | 37.242 | −33.632 | −48.093 | 1 | 14.82 |
| 5503 | CG2 | ILE | 153 | 38.032 | −32.943 | −46.987 | 1 | 16.77 |
| 5504 | CG1 | ILE | 153 | 37.052 | −35.114 | −47.77 | 1 | 15.75 |
| 5505 | CD1 | ILE | 153 | 38.327 | −35.931 | −47.821 | 1 | 16.26 |
| 5506 | C | ILE | 153 | 36.051 | −31.477 | −48.526 | 1 | 13.5 |
| 5507 | O | ILE | 153 | 35.882 | −30.647 | −47.633 | 1 | 14.38 |
| 5508 | N | ILE | 154 | 36.397 | −31.14 | −49.763 | 1 | 12.4 |
| 5509 | CA | ILE | 154 | 36.582 | −29.744 | −50.137 | 1 | 12.79 |
| 5510 | CB | ILE | 154 | 36.994 | −29.627 | −51.619 | 1 | 12.04 |
| 5511 | CG2 | ILE | 154 | 36.938 | −28.171 | −52.069 | 1 | 14.81 |
| 5512 | CG1 | ILE | 154 | 38.402 | −30.198 | −51.808 | 1 | 13.78 |
| 5513 | CD1 | ILE | 154 | 38.803 | −30.366 | −53.268 | 1 | 14.36 |
| 5514 | C | ILE | 154 | 35.294 | −28.948 | −49.905 | 1 | 12.15 |
| 5515 | O | ILE | 154 | 35.327 | −27.856 | −49.339 | 1 | 13.45 |
| 5516 | N | GLN | 155 | 34.163 | −29.496 | −50.34 | 1 | 12.73 |
| 5517 | CA | GLN | 155 | 32.885 | −28.812 | −50.174 | 1 | 12.17 |
| 5518 | CB | GLN | 155 | 31.774 | −29.584 | −50.887 | 1 | 12.25 |
| 5519 | CG | GLN | 155 | 31.918 | −29.558 | −52.403 | 1 | 12.7 |
| 5520 | CD | GLN | 155 | 31.013 | −30.557 | −53.096 | 1 | 13.93 |
| 5521 | OE1 | GLN | 155 | 29.792 | −30.407 | −53.106 | 1 | 16.17 |
| 5522 | NE2 | GLN | 155 | 31.613 | −31.594 | −53.673 | 1 | 13.36 |
| 5523 | C | GLN | 155 | 32.531 | −28.626 | −48.703 | 1 | 12.42 |
| 5524 | O | GLN | 155 | 32.03 | −27.578 | −48.313 | 1 | 14.07 |
| 5525 | N | HIS | 156 | 32.794 | −29.649 | −47.897 | 1 | 12.49 |
| 5526 | CA | HIS | 156 | 32.511 | −29.587 | −46.465 | 1 | 13.02 |
| 5527 | CB | HIS | 156 | 32.876 | −30.922 | −45.806 | 1 | 13.26 |
| 5528 | CG | HIS | 156 | 32.617 | −30.964 | −44.329 | 1 | 11.72 |
| 5529 | CD2 | HIS | 156 | 33.306 | −30.441 | −43.288 | 1 | 14.19 |
| 5530 | ND1 | HIS | 156 | 31.53 | −31.613 | −43.782 | 1 | 12.92 |
| 5531 | CE1 | HIS | 156 | 31.562 | −31.488 | −42.466 | 1 | 13.14 |
| 5532 | NE2 | HIS | 156 | 32.629 | −30.781 | −42.141 | 1 | 11.83 |
| 5533 | C | HIS | 156 | 33.32 | −28.455 | −45.824 | 1 | 13.45 |
| 5534 | O | HIS | 156 | 32.776 | −27.635 | −45.078 | 1 | 13.07 |
| 5535 | N | GLU | 157 | 34.616 | −28.405 | −46.117 | 1 | 13.56 |
| 5536 | CA | GLU | 157 | 35.465 | −27.367 | −45.538 | 1 | 14.32 |
| 5537 | CB | GLU | 157 | 36.947 | −27.649 | −45.803 | 1 | 16.92 |
| 5538 | CG | GLU | 157 | 37.502 | −28.892 | −45.136 | 1 | 20.56 |
| 5539 | CD | GLU | 157 | 37.04 | −29.068 | −43.698 | 1 | 20.37 |
| 5540 | OE1 | GLU | 157 | 36.977 | −28.073 | −42.939 | 1 | 24.26 |
| 5541 | OE2 | GLU | 157 | 36.755 | −30.218 | −43.326 | 1 | 23.26 |
| 5542 | C | GLU | 157 | 35.129 | −25.976 | −46.05 | 1 | 16.2 |
| 5543 | O | GLU | 157 | 35.12 | −25.014 | −45.282 | 1 | 15.71 |
| 5544 | N | MET | 158 | 34.869 | −25.857 | −47.349 | 1 | 15.82 |
| 5545 | CA | MET | 158 | 34.524 | −24.557 | −47.913 | 1 | 16.19 |
| 5546 | CB | MET | 158 | 34.388 | −24.647 | −49.437 | 1 | 16.39 |
| 5547 | CG | MET | 158 | 35.722 | −24.704 | −50.169 | 1 | 17.51 |
| 5548 | SD | MET | 158 | 36.72 | −23.205 | −49.934 | 1 | 18.6 |
| 5549 | CE | MET | 158 | 35.952 | −22.108 | −51.1 | 1 | 20.14 |
| 5550 | C | MET | 158 | 33.227 | −24.038 | −47.293 | 1 | 15.27 |
| 5551 | O | MET | 158 | 33.084 | −22.835 | −47.055 | 1 | 16.32 |
| 5552 | N | ASP | 159 | 32.285 | −24.943 | −47.031 | 1 | 14.6 |
| 5553 | CA | ASP | 159 | 31.019 | −24.553 | −46.414 | 1 | 13.53 |
| 5554 | CB | ASP | 159 | 30.111 | −25.769 | −46.193 | 1 | 13.32 |

TABLE 2-continued

| Atom | Atom Type | Residue | # | X | Y | Z | OCC | B |
|---|---|---|---|---|---|---|---|---|
| 5555 | CG | ASP | 159 | 29.298 | −26.134 | −47.426 | 1 | 15.52 |
| 5556 | OD1 | ASP | 159 | 29.369 | −25.404 | −48.436 | 1 | 17.49 |
| 5557 | OD2 | ASP | 159 | 28.578 | −27.153 | −47.376 | 1 | 14.85 |
| 5558 | C | ASP | 159 | 31.29 | −23.885 | −45.069 | 1 | 13.08 |
| 5559 | O | ASP | 159 | 30.639 | −22.906 | −44.719 | 1 | 14.23 |
| 5560 | N | HIS | 160 | 32.25 | −24.421 | −44.317 | 1 | 13.27 |
| 5561 | CA | HIS | 160 | 32.597 | −23.854 | −43.015 | 1 | 13.18 |
| 5562 | CB | HIS | 160 | 33.769 | −24.617 | −42.376 | 1 | 12.79 |
| 5563 | CG | HIS | 160 | 33.358 | −25.821 | −41.584 | 1 | 12.02 |
| 5564 | CD2 | HIS | 160 | 33.675 | −27.13 | −41.724 | 1 | 12.62 |
| 5565 | ND1 | HIS | 160 | 32.551 | −25.74 | −40.47 | 1 | 13 |
| 5566 | CE1 | HIS | 160 | 32.388 | −26.949 | −39.958 | 1 | 12.97 |
| 5567 | NE2 | HIS | 160 | 33.059 | −27.809 | −40.701 | 1 | 10.87 |
| 5568 | C | HIS | 160 | 32.974 | −22.379 | −43.116 | 1 | 14.52 |
| 5569 | O | HIS | 160 | 32.64 | −21.59 | −42.232 | 1 | 14.59 |
| 5570 | N | LEU | 161 | 33.672 | −22.007 | −44.188 | 1 | 14.1 |
| 5571 | CA | LEU | 161 | 34.092 | −20.621 | −44.363 | 1 | 15.06 |
| 5572 | CB | LEU | 161 | 35.187 | −20.526 | −45.433 | 1 | 14.51 |
| 5573 | CG | LEU | 161 | 36.471 | −21.313 | −45.139 | 1 | 15.52 |
| 5574 | CD1 | LEU | 161 | 37.531 | −20.958 | −46.174 | 1 | 16.61 |
| 5575 | CD2 | LEU | 161 | 36.979 | −20.989 | −43.735 | 1 | 16.39 |
| 5576 | C | LEU | 161 | 32.931 | −19.701 | −44.718 | 1 | 15.83 |
| 5577 | O | LEU | 161 | 33.061 | −18.478 | −44.659 | 1 | 16.29 |
| 5578 | N | GLN | 162 | 31.799 | −20.29 | −45.086 | 1 | 16.69 |
| 5579 | CA | GLN | 162 | 30.61 | −19.515 | −45.42 | 1 | 17.48 |
| 5580 | CB | GLN | 162 | 29.973 | −20.055 | −46.703 | 1 | 19.55 |
| 5581 | CG | GLN | 162 | 30.895 | −19.968 | −47.904 | 1 | 23.77 |
| 5582 | CD | GLN | 162 | 31.268 | −18.537 | −48.249 | 1 | 27.47 |
| 5583 | OE1 | GLN | 162 | 32.349 | −18.276 | −48.779 | 1 | 31.2 |
| 5584 | NE2 | GLN | 162 | 30.367 | −17.604 | −47.961 | 1 | 27.38 |
| 5585 | C | GLN | 162 | 29.604 | −19.57 | −44.272 | 1 | 16.44 |
| 5586 | O | GLN | 162 | 28.493 | −19.051 | −44.379 | 1 | 18.16 |
| 5587 | N | GLY | 163 | 30.006 | −20.202 | −43.173 | 1 | 14.53 |
| 5588 | CA | GLY | 163 | 29.137 | −20.313 | −42.013 | 1 | 13.44 |
| 5589 | C | GLY | 163 | 28.088 | −21.396 | −42.165 | 1 | 12.9 |
| 5590 | O | GLY | 163 | 27.047 | −21.372 | −41.498 | 1 | 13.17 |
| 5591 | N | CYS | 164 | 28.376 | −22.355 | −43.039 | 1 | 12.42 |
| 5592 | CA | CYS | 164 | 27.468 | −23.46 | −43.323 | 1 | 12.45 |
| 5593 | CB | CYS | 164 | 27.31 | −23.595 | −44.843 | 1 | 14.38 |
| 5594 | SG | CYS | 164 | 26.232 | −24.931 | −45.401 | 1 | 17.81 |
| 5595 | C | CYS | 164 | 27.965 | −24.782 | −42.735 | 1 | 12.12 |
| 5596 | O | CYS | 164 | 29.137 | −25.132 | −42.886 | 1 | 13.27 |
| 5597 | N | LEU | 165 | 27.071 | −25.496 | −42.054 | 1 | 12.56 |
| 5598 | CA | LEU | 165 | 27.391 | −26.793 | −41.461 | 1 | 12.45 |
| 5599 | CB | LEU | 165 | 27.013 | −26.812 | −39.979 | 1 | 12.51 |
| 5600 | CG | LEU | 165 | 27.741 | −25.806 | −39.084 | 1 | 11.56 |
| 5601 | CD1 | LEU | 165 | 27.28 | −26 | −37.643 | 1 | 12.01 |
| 5602 | CD2 | LEU | 165 | 29.245 | −26.003 | −39.187 | 1 | 14.93 |
| 5603 | C | LEU | 165 | 26.615 | −27.874 | −42.21 | 1 | 13.49 |
| 5604 | O | LEU | 165 | 25.57 | −27.598 | −42.799 | 1 | 14.42 |
| 5605 | N | PHE | 166 | 27.114 | −29.107 | −42.179 | 1 | 12.17 |
| 5606 | CA | PHE | 166 | 26.459 | −30.188 | −42.908 | 1 | 13.63 |
| 5607 | CB | PHE | 166 | 27.273 | −31.487 | −42.781 | 1 | 13.92 |
| 5608 | CG | PHE | 166 | 27.008 | −32.268 | −41.524 | 1 | 12.8 |
| 5609 | CD1 | PHE | 166 | 26.175 | −33.378 | −41.549 | 1 | 13.73 |
| 5610 | CD2 | PHE | 166 | 27.615 | −31.914 | −40.326 | 1 | 13.35 |
| 5611 | CE1 | PHE | 166 | 25.953 | −34.132 | −40.398 | 1 | 14.43 |
| 5612 | CE2 | PHE | 166 | 27.398 | −32.66 | −39.168 | 1 | 13.24 |
| 5613 | CZ | PHE | 166 | 26.566 | −33.773 | −39.207 | 1 | 13.88 |
| 5614 | C | PHE | 166 | 25.006 | −30.411 | −42.501 | 1 | 12.8 |
| 5615 | O | PHE | 166 | 24.213 | −30.927 | −43.29 | 1 | 13.8 |
| 5616 | N | ILE | 167 | 24.643 | −30.007 | −41.284 | 1 | 11.81 |
| 5617 | CA | ILE | 167 | 23.267 | −30.182 | −40.836 | 1 | 12.11 |
| 5618 | CB | ILE | 167 | 23.12 | −29.93 | −39.317 | 1 | 11.82 |
| 5619 | CG2 | ILE | 167 | 23.886 | −30.994 | −38.536 | 1 | 14.37 |
| 5620 | CG1 | ILE | 167 | 23.623 | −28.53 | −38.969 | 1 | 13.2 |
| 5621 | CD1 | ILE | 167 | 23.295 | −28.103 | −37.554 | 1 | 12.69 |
| 5622 | C | ILE | 167 | 22.307 | −29.256 | −41.588 | 1 | 12.13 |
| 5623 | O | ILE | 167 | 21.089 | −29.395 | −41.464 | 1 | 14.63 |
| 5624 | N | ASP | 168 | 22.856 | −28.319 | −42.365 | 1 | 12.68 |
| 5625 | CA | ASP | 168 | 22.039 | −27.388 | −43.152 | 1 | 12.92 |
| 5626 | CB | ASP | 168 | 22.784 | −26.075 | −43.449 | 1 | 11.69 |
| 5627 | CG | ASP | 168 | 23.207 | −25.324 | −42.205 | 1 | 13.04 |
| 5628 | OD1 | ASP | 168 | 22.496 | −25.39 | −41.183 | 1 | 13.78 |
| 5629 | OD2 | ASP | 168 | 24.253 | −24.643 | −42.27 | 1 | 13.95 |
| 5630 | C | ASP | 168 | 21.67 | −27.995 | −44.509 | 1 | 14.06 |
| 5631 | O | ASP | 168 | 20.774 | −27.492 | −45.191 | 1 | 16.33 |
| 5632 | N | LYS | 169 | 22.365 | −29.064 | −44.898 | 1 | 13.72 |
| 5633 | CA | LYS | 169 | 22.147 | −29.705 | −46.199 | 1 | 15.1 |
| 5634 | CB | LYS | 169 | 23.393 | −29.527 | −47.07 | 1 | 16.26 |
| 5635 | CG | LYS | 169 | 23.774 | −28.089 | −47.363 | 1 | 17.14 |
| 5636 | CD | LYS | 169 | 25.087 | −28.032 | −48.134 | 1 | 18.73 |
| 5637 | CE | LYS | 169 | 25.361 | −26.629 | −48.638 | 1 | 18.66 |
| 5638 | NZ | LYS | 169 | 26.639 | −26.556 | −49.392 | 1 | 17.73 |
| 5639 | C | LYS | 169 | 21.842 | −31.197 | −46.135 | 1 | 14.2 |
| 5640 | O | LYS | 169 | 21.624 | −31.842 | −47.164 | 1 | 16.07 |
| 5641 | N | MET | 170 | 21.831 | −31.745 | −44.932 | 1 | 13.69 |
| 5642 | CA | MET | 170 | 21.603 | −33.171 | −44.735 | 1 | 13.5 |
| 5643 | CB | MET | 170 | 21.945 | −33.537 | −43.294 | 1 | 13.14 |
| 5644 | CG | MET | 170 | 20.949 | −32.95 | −42.295 | 1 | 13.73 |
| 5645 | SD | MET | 170 | 21.208 | −33.53 | −40.618 | 1 | 14.36 |
| 5646 | CE | MET | 170 | 20.1 | −32.445 | −39.694 | 1 | 13.88 |
| 5647 | C | MET | 170 | 20.192 | −33.673 | −44.987 | 1 | 13.69 |
| 5648 | O | MET | 170 | 19.237 | −32.896 | −45.06 | 1 | 14.42 |
| 5649 | N | ASP | 171 | 20.084 | −34.995 | −45.123 | 1 | 13.81 |
| 5650 | CA | ASP | 171 | 18.791 | −35.657 | −45.229 | 1 | 14.26 |
| 5651 | CB | ASP | 171 | 18.899 | −37.004 | −45.942 | 1 | 16.89 |
| 5652 | CG | ASP | 171 | 17.595 | −37.79 | −45.902 | 1 | 20.8 |
| 5653 | OD1 | ASP | 171 | 16.729 | −37.483 | −45.048 | 1 | 21.45 |
| 5654 | OD2 | ASP | 171 | 17.438 | −38.726 | −46.716 | 1 | 25.2 |
| 5655 | C | ASP | 171 | 18.581 | −35.897 | −43.734 | 1 | 14.15 |
| 5656 | O | ASP | 171 | 19.13 | −36.844 | −43.166 | 1 | 14.05 |
| 5657 | N | SER | 172 | 17.814 | −35.022 | −43.095 | 1 | 13.3 |
| 5658 | CA | SER | 172 | 17.594 | −35.104 | −41.658 | 1 | 12.85 |
| 5659 | CB | SER | 172 | 16.624 | −34.002 | −41.216 | 1 | 13.76 |
| 5660 | OG | SER | 172 | 15.333 | −34.233 | −41.739 | 1 | 14.54 |
| 5661 | C | SER | 172 | 17.119 | −36.451 | −41.119 | 1 | 12.83 |
| 5662 | O | SER | 172 | 17.399 | −36.787 | −39.97 | 1 | 12.96 |
| 5663 | N | ARG | 173 | 16.41 | −37.231 | −41.929 | 1 | 12.61 |
| 5664 | CA | ARG | 173 | 15.929 | −38.519 | −41.442 | 1 | 12.9 |
| 5665 | CB | ARG | 173 | 14.811 | −39.052 | −42.347 | 1 | 14.09 |
| 5666 | CG | ARG | 173 | 13.503 | −38.262 | −42.222 | 1 | 16.25 |
| 5667 | CD | ARG | 173 | 12.387 | −38.87 | −43.069 | 1 | 16.47 |
| 5668 | NE | ARG | 173 | 12.104 | −40.248 | −42.681 | 1 | 17.64 |
| 5669 | CZ | ARG | 173 | 11.39 | −40.601 | −41.616 | 1 | 17.81 |
| 5670 | NH1 | ARG | 173 | 10.862 | −39.677 | −40.823 | 1 | 18.24 |
| 5671 | NH2 | ARG | 173 | 11.228 | −41.884 | −41.329 | 1 | 20.45 |
| 5672 | C | ARG | 173 | 17.048 | −39.551 | −41.292 | 1 | 12.64 |
| 5673 | O | ARG | 173 | 16.829 | −40.633 | −40.744 | 1 | 14.94 |
| 5674 | N | THR | 174 | 18.248 | −39.205 | −41.758 | 1 | 12.98 |
| 5675 | CA | THR | 174 | 19.396 | −40.105 | −41.638 | 1 | 11.92 |
| 5676 | CB | THR | 174 | 20.215 | −40.184 | −42.948 | 1 | 12.4 |
| 5677 | OG1 | THR | 174 | 20.803 | −38.909 | −43.224 | 1 | 12.87 |
| 5678 | CG2 | THR | 174 | 19.325 | −40.597 | −44.112 | 1 | 12.02 |
| 5679 | C | THR | 174 | 20.341 | −39.664 | −40.517 | 1 | 13.45 |
| 5680 | O | THR | 174 | 21.367 | −40.305 | −40.278 | 1 | 12.08 |
| 5681 | N | PHE | 175 | 19.995 | −38.575 | −39.831 | 1 | 12.82 |
| 5682 | CA | PHE | 175 | 20.812 | −38.056 | −38.729 | 1 | 11.72 |
| 5683 | CB | PHE | 175 | 20.162 | −36.791 | −38.156 | 1 | 11.86 |
| 5684 | CG | PHE | 175 | 21.029 | −36.031 | −37.186 | 1 | 11.14 |
| 5685 | CD1 | PHE | 175 | 22.116 | −35.283 | −37.636 | 1 | 10.79 |
| 5686 | CD2 | PHE | 175 | 20.726 | −36.021 | −35.827 | 1 | 10.48 |
| 5687 | CE1 | PHE | 175 | 22.884 | −34.53 | −36.747 | 1 | 12.1 |
| 5688 | CE2 | PHE | 175 | 21.489 | −35.271 | −34.929 | 1 | 11.56 |
| 5689 | CZ | PHE | 175 | 22.566 | −34.525 | −35.388 | 1 | 11.65 |
| 5690 | C | PHE | 175 | 20.874 | −39.139 | −37.654 | 1 | 11.74 |
| 5691 | O | PHE | 175 | 19.845 | −39.711 | −37.293 | 1 | 12.13 |
| 5692 | N | THR | 176 | 22.069 | −39.416 | −37.136 | 1 | 11.15 |
| 5693 | CA | THR | 176 | 22.206 | −40.467 | −36.131 | 1 | 11.28 |
| 5694 | CB | THR | 176 | 22.371 | −41.849 | −36.82 | 1 | 12.9 |
| 5695 | OG1 | THR | 176 | 22.478 | −42.882 | −35.832 | 1 | 13.21 |
| 5696 | CG2 | THR | 176 | 23.637 | −41.865 | −37.687 | 1 | 13.62 |
| 5697 | C | THR | 176 | 23.389 | −40.306 | −35.183 | 1 | 10.91 |
| 5698 | O | THR | 176 | 24.429 | −39.761 | −35.556 | 1 | 10.3 |
| 5699 | N | ASN | 177 | 23.208 | −40.765 | −33.946 | 1 | 10.97 |
| 5700 | CA | ASN | 177 | 24.297 | −40.771 | −32.976 | 1 | 9.63 |
| 5701 | CB | ASN | 177 | 23.803 | −41.242 | −31.609 | 1 | 9.35 |
| 5702 | CG | ASN | 177 | 23.306 | −40.11 | −30.746 | 1 | 10.14 |
| 5703 | OD1 | ASN | 177 | 24.092 | −39.417 | −30.104 | 1 | 12.28 |
| 5704 | ND2 | ASN | 177 | 21.992 | −39.912 | −30.725 | 1 | 10.54 |
| 5705 | C | ASN | 177 | 25.211 | −41.841 | −33.557 | 1 | 11.02 |
| 5706 | O | ASN | 177 | 24.728 | −42.811 | −34.141 | 1 | 11.4 |

TABLE 2-continued

| Atom | Atom Type | Residue | # | X | Y | Z | OCC | B |
|---|---|---|---|---|---|---|---|---|
| 5707 | N | VAL | 178 | 26.519 | −41.678 | −33.402 | 1 | 11.07 |
| 5708 | CA | VAL | 178 | 27.45 | −42.658 | −33.949 | 1 | 12.32 |
| 5709 | CB | VAL | 178 | 28.917 | −42.182 | −33.816 | 1 | 14.24 |
| 5710 | CG1 | VAL | 178 | 29.156 | −40.985 | −34.73 | 1 | 15.91 |
| 5711 | CG2 | VAL | 178 | 29.224 | −41.826 | −32.37 | 1 | 15 |
| 5712 | C | VAL | 178 | 27.325 | −44.044 | −33.325 | 1 | 12 |
| 5713 | O | VAL | 178 | 27.727 | −45.035 | −33.942 | 1 | 13.38 |
| 5714 | N | TYR | 179 | 26.77 | −44.132 | −32.118 | 1 | 11.39 |
| 5715 | CA | TYR | 179 | 26.627 | −45.439 | −31.489 | 1 | 12.21 |
| 5716 | CB | TYR | 179 | 26.55 | −45.328 | −29.959 | 1 | 11.71 |
| 5717 | CG | TYR | 179 | 25.509 | −44.389 | −29.407 | 1 | 11.14 |
| 5718 | CD1 | TYR | 179 | 25.873 | −43.139 | −28.905 | 1 | 11.45 |
| 5719 | CE1 | TYR | 179 | 24.928 | −42.29 | −28.334 | 1 | 11.2 |
| 5720 | CD2 | TYR | 179 | 24.17 | −44.768 | −29.333 | 1 | 12.73 |
| 5721 | CE2 | TYR | 179 | 23.217 | −43.926 | −28.766 | 1 | 14.09 |
| 5722 | CZ | TYR | 179 | 23.604 | −42.692 | −28.268 | 1 | 13.19 |
| 5723 | OH | TYR | 179 | 22.675 | −41.858 | −27.692 | 1 | 16.39 |
| 5724 | C | TYR | 179 | 25.452 | −46.245 | −32.038 | 1 | 11.09 |
| 5725 | O | TYR | 179 | 25.199 | −47.365 | −31.594 | 1 | 12.71 |
| 5726 | N | TRP | 180 | 24.731 | −45.668 | −32.999 | 1 | 10.79 |
| 5727 | CA | TRP | 180 | 23.639 | −46.371 | −33.675 | 1 | 11.34 |
| 5728 | CB | TRP | 180 | 22.348 | −45.546 | −33.701 | 1 | 11.13 |
| 5729 | CG | TRP | 180 | 21.437 | −45.845 | −32.559 | 1 | 10.58 |
| 5730 | CD2 | TRP | 180 | 20.6 | −47.001 | −32.41 | 1 | 9.55 |
| 5731 | CE2 | TRP | 180 | 19.944 | −46.883 | −31.165 | 1 | 9.78 |
| 5732 | CE3 | TRP | 180 | 20.346 | −48.125 | −33.206 | 1 | 11.92 |
| 5733 | CD1 | TRP | 180 | 21.256 | −45.095 | −31.434 | 1 | 10.8 |
| 5734 | NE1 | TRP | 180 | 20.362 | −45.711 | −30.591 | 1 | 10.95 |
| 5735 | CZ2 | TRP | 180 | 19.047 | −47.848 | −30.694 | 1 | 11.24 |
| 5736 | CZ3 | TRP | 180 | 19.455 | −49.157 | −32.738 | 1 | 10.49 |
| 5737 | CH2 | TRP | 180 | 18.816 | −48.942 | −31.493 | 1 | 10.91 |
| 5738 | C | TRP | 180 | 24.121 | −46.584 | −35.103 | 1 | 12.2 |
| 5739 | O | TRP | 180 | 24.667 | −45.667 | −35.712 | 1 | 13.34 |
| 5740 | N | MET | 181 | 23.921 | −47.782 | −35.64 | 1 | 12.59 |
| 5741 | CA | MET | 181 | 24.375 | −48.056 | −36.998 | 1 | 14.48 |
| 5742 | CB | MET | 181 | 25.861 | −48.428 | −36.977 | 1 | 15.75 |
| 5743 | CG | MET | 181 | 26.154 | −49.739 | −36.268 | 1 | 17.57 |
| 5744 | SD | MET | 181 | 27.788 | −49.744 | −35.497 | 1 | 18.59 |
| 5745 | CE | MET | 181 | 27.414 | −48.832 | −33.976 | 1 | 19.02 |
| 5746 | C | MET | 181 | 23.583 | −49.167 | −37.663 | 1 | 15.96 |
| 5747 | O | MET | 181 | 22.993 | −50.015 | −36.996 | 1 | 15.45 |
| 5748 | N | LYS | 182 | 23.574 | −49.157 | −38.991 | 1 | 20.25 |
| 5749 | CA | LYS | 182 | 22.87 | −50.184 | −39.736 | 1 | 25.16 |
| 5750 | CB | LYS | 182 | 22.405 | −49.637 | −41.088 | 1 | 27.97 |
| 5751 | CG | LYS | 182 | 21.186 | −50.353 | −41.654 | 1 | 32.06 |
| 5752 | CD | LYS | 182 | 20.609 | −49.607 | −42.848 | 1 | 34.84 |
| 5753 | CE | LYS | 182 | 19.327 | −50.262 | −43.343 | 1 | 36.81 |
| 5754 | NZ | LYS | 182 | 18.739 | −49.527 | −44.5 | 1 | 38.68 |
| 5755 | C | LYS | 182 | 23.869 | −51.318 | −39.92 | 1 | 26.82 |
| 5756 | O | LYS | 182 | 25.057 | −51.076 | −40.139 | 1 | 28.25 |
| 5757 | N | VAL | 183 | 23.395 | −52.552 | −39.806 | 1 | 28.3 |
| 5758 | CA | VAL | 183 | 24.264 | −53.712 | −39.944 | 1 | 30.36 |
| 5759 | CB | VAL | 183 | 24.561 | −54.343 | −38.569 | 1 | 30.95 |
| 5760 | CG1 | VAL | 183 | 25.39 | −53.388 | −37.726 | 1 | 29.97 |
| 5761 | CG2 | VAL | 183 | 23.256 | −54.681 | −37.862 | 1 | 30.47 |
| 5762 | C | VAL | 183 | 23.658 | −54.785 | −40.841 | 1 | 32.06 |
| 5763 | O | VAL | 183 | 22.467 | −54.75 | −41.152 | 1 | 31.93 |
| 5764 | N | ASN | 184 | 24.492 | −55.737 | −41.25 | 1 | 34.51 |
| 5765 | CA | ASN | 184 | 24.055 | −56.835 | −42.106 | 1 | 37.27 |
| 5766 | CB | ASN | 184 | 25.207 | −57.307 | −42.997 | 1 | 38.61 |
| 5767 | CG | ASN | 184 | 25.711 | −56.221 | −43.924 | 1 | 39.21 |
| 5768 | OD1 | ASN | 184 | 24.961 | −55.691 | −44.744 | 1 | 41.34 |
| 5769 | ND2 | ASN | 184 | 26.989 | −55.885 | −43.801 | 1 | 39.45 |
| 5770 | C | ASN | 184 | 23.581 | −57.995 | −41.244 | 1 | 38.94 |
| 5771 | O | ASN | 184 | 24.197 | −58.313 | −40.226 | 1 | 39.76 |
| 5772 | N | ASP | 185 | 22.486 | −58.628 | −41.653 | 1 | 40.67 |
| 5773 | CA | ASP | 185 | 21.939 | −59.757 | −40.911 | 1 | 42.37 |
| 5774 | CB | ASP | 185 | 20.413 | −59.78 | −41.029 | 1 | 43.02 |
| 5775 | CG | ASP | 185 | 19.775 | −58.485 | −40.574 | 1 | 43.38 |
| 5776 | OD1 | ASP | 185 | 20.05 | −58.06 | −39.432 | 1 | 44.61 |
| 5777 | OD2 | ASP | 185 | 18.998 | −57.896 | −41.354 | 1 | 44.11 |
| 5778 | C | ASP | 185 | 22.511 | −61.068 | −41.436 | 1 | 43.35 |
| 5779 | O | ASP | 185 | 23.146 | −61.794 | −40.642 | 1 | 44.43 |
| 5780 | OXT | ASP | 185 | 22.315 | −61.351 | −42.637 | 1 | 44.8 |
| 5781 | C5 | BB2 | | 33.344 | 12.895 | 11.885 | 1 | 22.57 |
| 5782 | C3 | BB2 | | 31.844 | 12.933 | 12.037 | 1 | 17.17 |
| 5783 | O4 | BB2 | | 31.28 | 12.103 | 12.714 | 1 | 22.78 |
| 5784 | N1 | BB2 | | 31.15 | 13.962 | 11.53 | 1 | 24.26 |
| 5785 | O2 | BB2 | | 29.746 | 13.872 | 11.4 | 1 | 21.76 |
| 5786 | C6 | BB2 | | 33.755 | 11.849 | 10.836 | 1 | 21.64 |
| 5787 | C12 | BB2 | | 35.177 | 11.402 | 11.117 | 1 | 23.1 |
| 5788 | O13 | BB2 | | 36.112 | 12.16 | 10.9 | 1 | 20.74 |
| 5789 | C7 | BB2 | | 33.595 | 12.428 | 9.4 | 1 | 21.07 |
| 5790 | C8 | BB2 | | 34.185 | 11.502 | 8.303 | 1 | 21.8 |
| 5791 | C9 | BB2 | | 33.398 | 10.182 | 8.179 | 1 | 20.75 |
| 5792 | C10 | BB2 | | 33.729 | 9.498 | 6.843 | 1 | 19.52 |
| 5793 | C11 | BB2 | | 35.135 | 8.88 | 6.895 | 1 | 19.13 |
| 5794 | N14 | BB2 | | 35.395 | 10.101 | 11.453 | 1 | 25.02 |
| 5795 | C15 | BB2 | | 36.757 | 9.537 | 11.561 | 1 | 26.43 |
| 5796 | C16 | BB2 | | 37.051 | 9.072 | 13.009 | 1 | 27.55 |
| 5797 | C18 | BB2 | | 35.87 | 8.285 | 13.6 | 1 | 28.89 |
| 5798 | C17 | BB2 | | 37.354 | 10.286 | 13.894 | 1 | 28.75 |
| 5799 | C19 | BB2 | | 36.936 | 8.386 | 10.573 | 1 | 27.95 |
| 5800 | O20 | BB2 | | 35.947 | 7.8 | 10.146 | 1 | 23.21 |
| 5801 | N21 | BB2 | | 38.193 | 7.993 | 10.177 | 1 | 31.09 |
| 5802 | C22 | BB2 | | 38.497 | 6.813 | 9.329 | 1 | 32.57 |
| 5803 | C23 | BB2 | | 39.397 | 8.869 | 10.16 | 1 | 32.03 |
| 5804 | C24 | BB2 | | 40.585 | 7.926 | 9.863 | 1 | 33.52 |
| 5805 | C25 | BB2 | | 39.953 | 6.962 | 8.826 | 1 | 32.64 |
| 5806 | C26 | BB2 | | 38.341 | 5.5 | 10.114 | 1 | 33.48 |
| 5807 | O27 | BB2 | | 38.289 | 4.403 | 9.195 | 1 | 33.42 |
| 5808 | C5 | BB2 | | 21.637 | −10.64 | 27.501 | 1 | 22.45 |
| 5809 | C3 | BB2 | | 22.506 | −11.089 | 26.343 | 1 | 17.29 |
| 5810 | O4 | BB2 | | 23.034 | −10.266 | 25.628 | 1 | 24.3 |
| 5811 | N1 | BB2 | | 22.505 | −12.38 | 25.98 | 1 | 24.72 |
| 5812 | O2 | BB2 | | 23.343 | −12.826 | 24.933 | 1 | 24.97 |
| 5813 | C6 | BB2 | | 20.235 | −10.226 | 27.004 | 1 | 24.5 |
| 5814 | C12 | BB2 | | 19.575 | −9.334 | 28.04 | 1 | 25.49 |
| 5815 | O13 | BB2 | | 19.221 | −9.795 | 29.119 | 1 | 24.65 |
| 5816 | C7 | BB2 | | 19.375 | −11.482 | 26.688 | 1 | 24.62 |
| 5817 | C8 | BB2 | | 17.915 | −11.126 | 26.322 | 1 | 24.88 |
| 5818 | C9 | BB2 | | 17.819 | −10.443 | 24.949 | 1 | 26.32 |
| 5819 | C10 | BB2 | | 16.366 | −10.481 | 24.457 | 1 | 26.16 |
| 5820 | C11 | BB2 | | 15.535 | −9.409 | 25.179 | 1 | 25.72 |
| 5821 | N14 | BB2 | | 19.393 | −8.019 | 27.747 | 1 | 28.39 |
| 5822 | C15 | BB2 | | 18.536 | −7.142 | 28.573 | 1 | 31.31 |
| 5823 | C16 | BB2 | | 19.33 | −5.917 | 29.091 | 1 | 32.58 |
| 5824 | C18 | BB2 | | 20.219 | −6.334 | 30.269 | 1 | 34.98 |
| 5825 | C17 | BB2 | | 20.2 | −5.305 | 27.983 | 1 | 33.17 |
| 5826 | C19 | BB2 | | 17.304 | −6.695 | 27.791 | 1 | 32.18 |
| 5827 | O20 | BB2 | | 17.341 | −6.651 | 26.567 | 1 | 27.9 |
| 5828 | N21 | BB2 | | 16.2 | −6.237 | 28.458 | 1 | 34.06 |
| 5829 | C22 | BB2 | | 15.187 | −5.299 | 27.917 | 1 | 35.15 |
| 5830 | C23 | BB2 | | 15.652 | −6.819 | 29.711 | 1 | 35.42 |
| 5831 | C24 | BB2 | | 14.114 | −6.719 | 29.56 | 1 | 34.72 |
| 5832 | C25 | BB2 | | 13.963 | −5.347 | 28.857 | 1 | 34.81 |
| 5833 | C26 | BB2 | | 15.735 | −3.869 | 27.854 | 1 | 36.26 |
| 5834 | O27 | BB2 | | 15.089 | −3.169 | 26.788 | 1 | 41.71 |
| 5835 | C5 | BB2 | | 9.875 | −33.235 | −24.623 | 1 | 19.37 |
| 5836 | C3 | BB2 | | 9.964 | −34.25 | −25.73 | 1 | 19.3 |
| 5837 | O4 | BB2 | | 10.968 | −34.313 | −26.409 | 1 | 21.09 |
| 5838 | N1 | BB2 | | 8.852 | −34.9 | −26.112 | 1 | 21.65 |
| 5839 | O2 | BB2 | | 8.905 | −35.83 | −27.172 | 1 | 23.95 |
| 5840 | C6 | BB2 | | 9.65 | −31.826 | −25.199 | 1 | 21.02 |
| 5841 | C12 | BB2 | | 10.141 | −30.803 | −24.19 | 1 | 21.38 |
| 5842 | O13 | BB2 | | 9.617 | −30.727 | −23.086 | 1 | 19.53 |
| 5843 | C7 | BB2 | | 8.149 | −31.621 | −25.566 | 1 | 20.42 |
| 5844 | C8 | BB2 | | 7.798 | −30.147 | −25.896 | 1 | 21 |
| 5845 | C9 | BB2 | | 8.408 | −29.698 | −27.235 | 1 | 21.52 |
| 5846 | C10 | BB2 | | 7.727 | −28.406 | −27.714 | 1 | 20.09 |
| 5847 | C11 | BB2 | | 8.183 | −27.213 | −26.859 | 1 | 21.07 |
| 5848 | N14 | BB2 | | 11.205 | −30.026 | −24.519 | 1 | 23.37 |
| 5849 | C15 | BB2 | | 11.642 | −28.893 | −23.68 | 1 | 26.54 |
| 5850 | C16 | BB2 | | 13.085 | −29.11 | −23.163 | 1 | 28.51 |
| 5851 | C18 | BB2 | | 13.097 | −30.191 | −22.077 | 1 | 31.16 |
| 5852 | C17 | BB2 | | 14.037 | −29.511 | −24.3 | 1 | 28.58 |
| 5853 | C19 | BB2 | | 11.542 | −27.588 | −24.466 | 1 | 27.22 |
| 5854 | O20 | BB2 | | 11.576 | −27.619 | −25.691 | 1 | 20.51 |
| 5855 | N21 | BB2 | | 11.469 | −26.386 | −23.811 | 1 | 29.27 |
| 5856 | C22 | BB2 | | 11.523 | −25.05 | −24.454 | 1 | 32.13 |
| 5857 | C23 | BB2 | | 10.938 | −26.194 | −22.434 | 1 | 31.65 |
| 5858 | C24 | BB2 | | 11.305 | −24.741 | −22.053 | 1 | 33.56 |

TABLE 2-continued

| Atom | Atom Type | Residue | # | X | Y | Z | OCC | B |
|---|---|---|---|---|---|---|---|---|
| 5859 | C25 | BB2 | | 11.085 | −24.005 | −23.401 | 1 | 32.16 |
| 5860 | C26 | BB2 | | 12.937 | −24.727 | −24.962 | 1 | 34 |
| 5861 | O27 | BB2 | | 12.874 | −23.612 | −25.853 | 1 | 36.71 |
| 5862 | C5 | BB2 | | 36.133 | −33.158 | −40.366 | 1 | 20.33 |
| 5863 | C3 | BB2 | | 35.489 | −31.802 | −40.18 | 1 | 18.8 |
| 5864 | O4 | BB2 | | 34.408 | −31.709 | −39.639 | 1 | 19.21 |
| 5865 | N1 | BB2 | | 36.102 | −30.706 | −40.649 | 1 | 21.14 |
| 5866 | O2 | BB2 | | 35.37 | −29.515 | −40.848 | 1 | 20.49 |
| 5867 | C6 | BB2 | | 35.41 | −33.96 | −41.466 | 1 | 21.6 |
| 5868 | C12 | BB2 | | 35.701 | −35.439 | −41.274 | 1 | 21.92 |
| 5869 | O13 | BB2 | | 36.841 | −35.866 | −41.405 | 1 | 21.72 |
| 5870 | C7 | BB2 | | 35.842 | −33.457 | −42.876 | 1 | 18.83 |
| 5871 | C8 | BB2 | | 35.341 | −34.367 | −44.027 | 1 | 19.47 |
| 5872 | C9 | BB2 | | 33.815 | −34.282 | −44.196 | 1 | 20.86 |
| 5873 | C10 | BB2 | | 33.41 | −34.899 | −45.542 | 1 | 19.38 |
| 5874 | C11 | BB2 | | 33.436 | −36.433 | −45.452 | 1 | 21.06 |
| 5875 | N14 | BB2 | | 34.703 | −36.243 | −40.828 | 1 | 23.18 |
| 5876 | C15 | BB2 | | 34.81 | −37.718 | −40.856 | 1 | 24.61 |
| 5877 | C16 | BB2 | | 34.567 | −38.306 | −39.443 | 1 | 26.85 |
| 5878 | C18 | BB2 | | 35.781 | −38.027 | −38.549 | 1 | 29.06 |
| 5879 | C17 | BB2 | | 33.303 | −37.719 | −38.796 | 1 | 27.54 |
| 5880 | C19 | BB2 | | 33.827 | −38.305 | −41.868 | 1 | 24.62 |
| 5881 | O20 | BB2 | | 32.862 | −37.636 | −42.216 | 1 | 17.28 |
| 5882 | N21 | BB2 | | 33.94 | −39.614 | −42.28 | 1 | 27.38 |
| 5883 | C22 | BB2 | | 32.93 | −40.363 | −43.068 | 1 | 29.83 |
| 5884 | C23 | BB2 | | 35.19 | −40.425 | −42.277 | 1 | 29.5 |
| 5885 | C24 | BB2 | | 35.123 | −41.28 | −43.565 | 1 | 30.19 |
| 5886 | C25 | BB2 | | 33.618 | −41.634 | −43.623 | 1 | 29.52 |
| 5887 | C26 | BB2 | | 31.734 | −40.766 | −42.193 | 1 | 31.95 |
| 5888 | O27 | BB2 | | 30.674 | −41.237 | −43.03 | 1 | 33.19 |
| 5889 | OH2 | TIP | 3 | 36.19 | −7.614 | 24.368 | 1 | 7.61 |
| 5890 | OH2 | TIP | 4 | 19.209 | −44.913 | −27.807 | 1 | 9.19 |
| 5891 | OH2 | TIP | 5 | 24.161 | 13.017 | 24.033 | 1 | 7.95 |
| 5892 | OH2 | TIP | 6 | 32.197 | −24.827 | −28.202 | 1 | 11.42 |
| 5893 | OH2 | TIP | 7 | 32.44 | −9.147 | 16.943 | 1 | 13.28 |
| 5894 | OH2 | TIP | 8 | 22.407 | −12.262 | 19.295 | 1 | 13.05 |
| 5895 | OH2 | TIP | 9 | 16.222 | −42.3 | −35.236 | 1 | 12.84 |
| 5896 | OH2 | TIP | 10 | 29.038 | −18.45 | 17.75 | 1 | 13.6 |
| 5897 | OH2 | TIP | 11 | 35.442 | 5.94 | 0.013 | 1 | 14.82 |
| 5898 | OH2 | TIP | 12 | 20.361 | −11.31 | 17.551 | 1 | 13.28 |
| 5899 | OH2 | TIP | 13 | 6.378 | −43.426 | −34.462 | 1 | 13.9 |
| 5900 | OH2 | TIP | 14 | 23.211 | −9.758 | 20.094 | 1 | 13.26 |
| 5901 | OH2 | TIP | 15 | 19.619 | 9.539 | 17.826 | 1 | 13.4 |
| 5902 | OH2 | TIP | 16 | 33.07 | −18.875 | −41.4 | 1 | 15.81 |
| 5903 | OH2 | TIP | 17 | 17.296 | −39.562 | −38.003 | 1 | 12.93 |
| 5904 | OH2 | TIP | 18 | 7.501 | −45.976 | −33.699 | 1 | 14.53 |
| 5905 | OH2 | TIP | 19 | 25.902 | 10.384 | 8.962 | 1 | 11.88 |
| 5906 | OH2 | TIP | 20 | 25.883 | 8.122 | 7.181 | 1 | 14.73 |
| 5907 | OH2 | TIP | 21 | 30.567 | −27.509 | −43.218 | 1 | 13.25 |
| 5908 | OH2 | TIP | 22 | 28.538 | −28.571 | −44.976 | 1 | 13.98 |
| 5909 | OH2 | TIP | 23 | 27.766 | −14.285 | 19.186 | 1 | 14.24 |
| 5910 | OH2 | TIP | 24 | 31.675 | −35.645 | −53.861 | 1 | 15.97 |
| 5911 | OH2 | TIP | 25 | 4.591 | −21.805 | −30.614 | 1 | 13.83 |
| 5912 | OH2 | TIP | 26 | 30.57 | −3.054 | 23.032 | 1 | 14.37 |
| 5913 | OH2 | TIP | 27 | 23.404 | −23.598 | −35.839 | 1 | 15.93 |
| 5914 | OH2 | TIP | 28 | 11.426 | −34.182 | −31.961 | 1 | 12.96 |
| 5915 | OH2 | TIP | 29 | 26.942 | −22.386 | −34.425 | 1 | 13.31 |
| 5916 | OH2 | TIP | 30 | 8.824 | −34.717 | −32.783 | 1 | 12.96 |
| 5917 | OH2 | TIP | 31 | 37.761 | 6.197 | −1.159 | 1 | 18.64 |
| 5918 | OH2 | TIP | 32 | 28.269 | −30.434 | −30.897 | 1 | 16 |
| 5919 | OH2 | TIP | 33 | 26.913 | 8.948 | 11.12 | 1 | 13.05 |
| 5920 | OH2 | TIP | 34 | 8.741 | −32.459 | −34.58 | 1 | 14.19 |
| 5921 | OH2 | TIP | 35 | 19.37 | 16.606 | 10.742 | 1 | 16.62 |
| 5922 | OH2 | TIP | 36 | 8.953 | −10.173 | 21.712 | 1 | 14.21 |
| 5923 | OH2 | TIP | 37 | 19.064 | 5.941 | 16.354 | 1 | 13.9 |
| 5924 | OH2 | TIP | 38 | 30.913 | −37.806 | −52.456 | 1 | 16.11 |
| 5925 | OH2 | TIP | 39 | 9.531 | −40.494 | −32.872 | 1 | 14.7 |
| 5926 | OH2 | TIP | 40 | 31.747 | −18.584 | 18.345 | 1 | 14.2 |
| 5927 | OH2 | TIP | 41 | 30.485 | −6.941 | 14.146 | 1 | 14.63 |
| 5928 | OH2 | TIP | 42 | 29.797 | −29.115 | −41.112 | 1 | 13.97 |
| 5929 | OH2 | TIP | 43 | 18.472 | 17.82 | 13.131 | 1 | 15.23 |
| 5930 | OH2 | TIP | 44 | 2.296 | −23.138 | −31.554 | 1 | 14.94 |
| 5931 | OH2 | TIP | 45 | 4.055 | −28.874 | −36.691 | 1 | 16.91 |
| 5932 | OH2 | TIP | 46 | 6.766 | −10.196 | 23.323 | 1 | 18.93 |
| 5933 | OH2 | TIP | 47 | 27.344 | 6.952 | 21.342 | 1 | 16.14 |
| 5934 | OH2 | TIP | 48 | 20.774 | −37.866 | −29.074 | 1 | 15.36 |
| 5935 | OH2 | TIP | 49 | 23.319 | −39.362 | −27.273 | 1 | 21.65 |
| 5936 | OH2 | TIP | 50 | 37.188 | −10.391 | 24.314 | 1 | 17.49 |
| 5937 | OH2 | TIP | 51 | 22.494 | 13.564 | 12.31 | 1 | 15.13 |
| 5938 | OH2 | TIP | 52 | 16.007 | −30.282 | −41.401 | 1 | 21.15 |
| 5939 | OH2 | TIP | 53 | 33.963 | 7.726 | −1.527 | 1 | 15.09 |
| 5940 | OH2 | TIP | 54 | 27.381 | 34.293 | 9.223 | 1 | 22.41 |
| 5941 | OH2 | TIP | 55 | 31.84 | −23.033 | −39.862 | 1 | 16.72 |
| 5942 | OH2 | TIP | 56 | 9.028 | −12.876 | 20.844 | 1 | 17.76 |
| 5943 | OH2 | TIP | 57 | 26.847 | −39.883 | −30.3 | 1 | 18.91 |
| 5944 | OH2 | TIP | 58 | 32.156 | −39.77 | −53.697 | 1 | 18 |
| 5945 | OH2 | TIP | 59 | 29.378 | −0.171 | −7.399 | 1 | 16.84 |
| 5946 | OH2 | TIP | 60 | 22.848 | 15.566 | 23.513 | 1 | 20.62 |
| 5947 | OH2 | TIP | 61 | 13.161 | −27.237 | 18.186 | 1 | 19.26 |
| 5948 | OH2 | TIP | 62 | 33.752 | −17.525 | −39.026 | 1 | 15.53 |
| 5949 | OH2 | TIP | 63 | 22.554 | 34.547 | 11.792 | 1 | 21.72 |
| 5950 | OH2 | TIP | 64 | 20.411 | 18.019 | 21.742 | 1 | 20.41 |
| 5951 | OH2 | TIP | 65 | 21.699 | −3.701 | 10.598 | 1 | 20.44 |
| 5952 | OH2 | TIP | 66 | 28.823 | −34.662 | −37.015 | 1 | 19.49 |
| 5953 | OH2 | TIP | 67 | 15.075 | −13.715 | 15.191 | 1 | 20.33 |
| 5954 | OH2 | TIP | 68 | 27.861 | −28.754 | −51.103 | 1 | 20.54 |
| 5955 | OH2 | TIP | 69 | 3.548 | −19.908 | −29.117 | 1 | 18.24 |
| 5956 | OH2 | TIP | 70 | 17.282 | −0.625 | 10.037 | 1 | 22.01 |
| 5957 | OH2 | TIP | 71 | 38.081 | −22.362 | −58.152 | 1 | 22.71 |
| 5958 | OH2 | TIP | 72 | 39.126 | −13.698 | 19.824 | 1 | 19.66 |
| 5959 | OH2 | TIP | 73 | 24.782 | −30.09 | −25.497 | 1 | 19.01 |
| 5960 | OH2 | TIP | 74 | 16.923 | −31.58 | −28.749 | 1 | 19.93 |
| 5961 | OH2 | TIP | 75 | 21.777 | −0.959 | 9.556 | 1 | 21.9 |
| 5962 | OH2 | TIP | 76 | 18.604 | −29.115 | −42.53 | 1 | 21.26 |
| 5963 | OH2 | TIP | 77 | 23.718 | −22.333 | −43.727 | 1 | 20.56 |
| 5964 | OH2 | TIP | 78 | 16.03 | −33.444 | −44.797 | 1 | 20.8 |
| 5965 | OH2 | TIP | 79 | 5.045 | −18.802 | 31.291 | 1 | 24.26 |
| 5966 | OH2 | TIP | 80 | 33.111 | 11.554 | 20.084 | 1 | 20.97 |
| 5967 | OH2 | TIP | 81 | 44.237 | −30.315 | −60.161 | 1 | 24.21 |
| 5968 | OH2 | TIP | 82 | 10.429 | −36.633 | −41.029 | 1 | 20.07 |
| 5969 | OH2 | TIP | 83 | 34.963 | −33.228 | −32.179 | 1 | 21.23 |
| 5970 | OH2 | TIP | 85 | 25.855 | 7.496 | 0.957 | 1 | 18.88 |
| 5971 | OH2 | TIP | 86 | 16.799 | −24.808 | −42.199 | 1 | 21.74 |
| 5972 | OH2 | TIP | 87 | 35.158 | 1.48 | 21.915 | 1 | 19.73 |
| 5973 | OH2 | TIP | 88 | 37.681 | −14.04 | 23 | 1 | 18.72 |
| 5974 | OH2 | TIP | 89 | 35.003 | 0.852 | −5.943 | 1 | 21.97 |
| 5975 | OH2 | TIP | 90 | 6.577 | −27.87 | 21.073 | 1 | 18.57 |
| 5976 | OH2 | TIP | 91 | 18.082 | 6.755 | 8.453 | 1 | 20.62 |
| 5977 | OH2 | TIP | 92 | 28.89 | −30.822 | −27.518 | 1 | 22.38 |
| 5978 | OH2 | TIP | 93 | 24.498 | −5.196 | 7.301 | 1 | 21.39 |
| 5979 | OH2 | TIP | 94 | 26.274 | −22.946 | 16.11 | 1 | 20.39 |
| 5980 | OH2 | TIP | 95 | 25.437 | 19.582 | −5.923 | 1 | 21.71 |
| 5981 | OH2 | TIP | 96 | 30.143 | −24.399 | −62.407 | 1 | 21.21 |
| 5982 | OH2 | TIP | 97 | 29.431 | 12.846 | −13.63 | 1 | 19.25 |
| 5983 | OH2 | TIP | 98 | 24.818 | 37.36 | 3.776 | 1 | 22.9 |
| 5984 | OH2 | TIP | 99 | 33.9 | −22.527 | −28.571 | 1 | 20.97 |
| 5985 | OH2 | TIP | 100 | 17.287 | 16.741 | 21.922 | 1 | 22.42 |
| 5986 | OH2 | TIP | 101 | 25.364 | 4.116 | 26.719 | 1 | 20.44 |
| 5987 | OH2 | TIP | 102 | 14.359 | −49.141 | −29.046 | 1 | 23.07 |
| 5988 | OH2 | TIP | 103 | 17.356 | −47.043 | −27.767 | 1 | 21.31 |
| 5989 | OH2 | TIP | 104 | 19.252 | −26.958 | 32.508 | 1 | 23.03 |
| 5990 | OH2 | TIP | 106 | 15.049 | −50.273 | −32.167 | 1 | 23.05 |
| 5991 | OH2 | TIP | 108 | −5.774 | −20.631 | −40.439 | 1 | 26.98 |
| 5992 | OH2 | TIP | 109 | 15.931 | −20.987 | 38.058 | 1 | 26.59 |
| 5993 | OH2 | TIP | 110 | 27.907 | −5.912 | 29.359 | 1 | 21.69 |
| 5994 | OH2 | TIP | 111 | 14.042 | −49.249 | −26.315 | 1 | 27.31 |
| 5995 | OH2 | TIP | 112 | 24.896 | −11.713 | 10.908 | 1 | 23.85 |
| 5996 | OH2 | TIP | 113 | 31.597 | −40.206 | −56.328 | 1 | 23.67 |
| 5997 | OH2 | TIP | 114 | 1.198 | −43.23 | −35.955 | 1 | 26.59 |
| 5998 | OH2 | TIP | 115 | 23.406 | −25.035 | 18.576 | 1 | 21.69 |
| 5999 | OH2 | TIP | 116 | 23.21 | −3.651 | 23.558 | 1 | 20.78 |
| 6000 | OH2 | TIP | 117 | 35.384 | −1.123 | −2.215 | 1 | 18.91 |
| 6001 | OH2 | TIP | 118 | 18.991 | −4.329 | 10.389 | 1 | 24.67 |
| 6002 | OH2 | TIP | 119 | 18.566 | −30.267 | −45.012 | 1 | 23.57 |
| 6003 | OH2 | TIP | 120 | 26.749 | 14.837 | 24.369 | 1 | 23.36 |
| 6004 | OH2 | TIP | 121 | 25.609 | 3.189 | 1.8 | 1 | 19.64 |
| 6005 | OH2 | TIP | 122 | 2.464 | −17.959 | −41.193 | 1 | 25.55 |
| 6006 | OH2 | TIP | 123 | 5.125 | −5.444 | 17.866 | 1 | 25.18 |
| 6007 | OH2 | TIP | 124 | 34.955 | −19.253 | −30.44 | 1 | 20.25 |
| 6008 | OH2 | TIP | 125 | 4.129 | −10.372 | 11.359 | 1 | 26.95 |
| 6009 | OH2 | TIP | 126 | −8.458 | −33.739 | −34.374 | 1 | 24.68 |
| 6010 | OH2 | TIP | 127 | 7.402 | −15.004 | 28.024 | 1 | 25.21 |

TABLE 2-continued

| Atom | Atom Type | Residue | # | X | Y | Z | OCC | B |
|---|---|---|---|---|---|---|---|---|
| 6011 | OH2 | TIP | 128 | 19.2 | −33.003 | −48.31 | 1 | 26.59 |
| 6012 | OH2 | TIP | 129 | 17.082 | −36.811 | −22.711 | 1 | 18.8 |
| 6013 | OH2 | TIP | 130 | 21.455 | 8.577 | 0.96 | 1 | 26.6 |
| 6014 | OH2 | TIP | 131 | 3.061 | −26.823 | −10.461 | 1 | 27.84 |
| 6015 | OH2 | TIP | 132 | 4.192 | −11.152 | 22.451 | 1 | 32.41 |
| 6016 | OH2 | TIP | 133 | 29.616 | −0.801 | 24.104 | 1 | 22.64 |
| 6017 | OH2 | TIP | 134 | 3.053 | −18.897 | 11.993 | 1 | 28.56 |
| 6018 | OH2 | TIP | 135 | 19.146 | 28.227 | 0.374 | 1 | 27.67 |
| 6019 | OH2 | TIP | 136 | 22.46 | −36.037 | −28.046 | 1 | 25.56 |
| 6020 | OH2 | TIP | 137 | 20.775 | 16.676 | −1.573 | 1 | 25.09 |
| 6021 | OH2 | TIP | 138 | 40.311 | −36.145 | −57.302 | 1 | 29.36 |
| 6022 | OH2 | TIP | 139 | 33.859 | −30.227 | 27.169 | 1 | 30.83 |
| 6023 | OH2 | TIP | 140 | 29.3 | 5.423 | 22.128 | 1 | 23.55 |
| 6024 | OH2 | TIP | 141 | −8.742 | −22.09 | −31.825 | 1 | 28.16 |
| 6025 | OH2 | TIP | 142 | 48.106 | 1.399 | −1.478 | 1 | 35.62 |
| 6026 | OH2 | TIP | 143 | 12.327 | 16.023 | 10.98 | 1 | 30.37 |
| 6027 | OH2 | TIP | 144 | 32.325 | −17.003 | −30.403 | 1 | 24.58 |
| 6028 | OH2 | TIP | 145 | 18.416 | −24.167 | 14.753 | 1 | 25.31 |
| 6029 | OH2 | TIP | 146 | 16.473 | 7.573 | 22.404 | 1 | 27.42 |
| 6030 | OH2 | TIP | 147 | 50.424 | −35.334 | −46.577 | 1 | 35.23 |
| 6031 | OH2 | TIP | 148 | 37.297 | −5.91 | 14.966 | 1 | 28.05 |
| 6032 | OH2 | TIP | 149 | 23.688 | −41.443 | −41.615 | 1 | 28.07 |
| 6033 | OH2 | TIP | 150 | 37.86 | −16.761 | 22.054 | 1 | 24.43 |
| 6034 | OH2 | TIP | 151 | −1.276 | −28.056 | −15.007 | 1 | 32.21 |
| 6035 | OH2 | TIP | 152 | 1.802 | −18.162 | −30.154 | 1 | 22.68 |
| 6036 | OH2 | TIP | 153 | −5.126 | −30.368 | −40.429 | 1 | 22.47 |
| 6037 | OH2 | TIP | 154 | −2.433 | −19.248 | −26.798 | 1 | 37.41 |
| 6038 | OH2 | TIP | 155 | 52.549 | −17.739 | −42.977 | 1 | 28.97 |
| 6039 | OH2 | TIP | 156 | 17.335 | −17.301 | 16.432 | 1 | 20.67 |
| 6040 | OH2 | TIP | 157 | 36.396 | 21.259 | 1.706 | 1 | 24.51 |
| 6041 | OH2 | TIP | 158 | 54.123 | −18.406 | −56.292 | 1 | 35.7 |
| 6042 | OH2 | TIP | 159 | 17.94 | −21.988 | −31.063 | 1 | 22.34 |
| 6043 | OH2 | TIP | 160 | 14.419 | 34.99 | 5.874 | 1 | 31.83 |
| 6044 | OH2 | TIP | 161 | 32.539 | 27.938 | 2.578 | 1 | 29.65 |
| 6045 | OH2 | TIP | 162 | 40.475 | 0.493 | 15.502 | 1 | 25.69 |
| 6046 | OH2 | TIP | 163 | 38.133 | 5.718 | −3.8 | 1 | 23.24 |
| 6047 | OH2 | TIP | 164 | 38.981 | −1.367 | 14.265 | 1 | 28.75 |
| 6048 | OH2 | TIP | 165 | 21.283 | −45.199 | −37.052 | 1 | 21.52 |
| 6049 | OH2 | TIP | 166 | −8.489 | −20.126 | −36.728 | 1 | 28.76 |
| 6050 | OH2 | TIP | 167 | 34.944 | −2.012 | 10.519 | 1 | 23.53 |
| 6051 | OH2 | TIP | 168 | −3.171 | −36.87 | −37.487 | 1 | 24.22 |
| 6052 | OH2 | TIP | 169 | −1.906 | −41.475 | −33.687 | 1 | 22.44 |
| 6053 | OH2 | TIP | 170 | 24.279 | −41.058 | −54.489 | 1 | 30.02 |
| 6054 | OH2 | TIP | 171 | 22.447 | 23.889 | −4.261 | 1 | 33.31 |
| 6055 | OH2 | TIP | 172 | −7.008 | −37.606 | −23.584 | 1 | 27.29 |
| 6056 | OH2 | TIP | 173 | 36.52 | 28.331 | 14.52 | 1 | 36.77 |
| 6057 | OH2 | TIP | 174 | 29.688 | 35.312 | 8.231 | 1 | 28.68 |
| 6058 | OH2 | TIP | 175 | 6.12 | −18.842 | 33.677 | 1 | 27.25 |
| 6059 | OH2 | TIP | 176 | 44.11 | 21.367 | 4.346 | 1 | 34.05 |
| 6060 | OH2 | TIP | 177 | 20.972 | 20.578 | 3.343 | 1 | 31.14 |
| 6061 | OH2 | TIP | 178 | 31.605 | −35.978 | −35.325 | 1 | 27.53 |
| 6062 | OH2 | TIP | 179 | −3.652 | −53.405 | −22.488 | 1 | 32.05 |
| 6063 | OH2 | TIP | 180 | 1.186 | −22.323 | −42.746 | 1 | 24.31 |
| 6064 | OH2 | TIP | 181 | 34.668 | 2.899 | −12.435 | 1 | 27.83 |
| 6065 | OH2 | TIP | 182 | 28.538 | −45.171 | −36.531 | 1 | 29.39 |
| 6066 | OH2 | TIP | 183 | 52.047 | −12.149 | −38.112 | 1 | 35.58 |
| 6067 | OH2 | TIP | 184 | 35.311 | 21.617 | −7.114 | 1 | 23.83 |
| 6068 | OH2 | TIP | 185 | 20.4 | −22.205 | −26.171 | 1 | 25.27 |
| 6069 | OH2 | TIP | 186 | 30.914 | −38.338 | −36.524 | 1 | 27.3 |
| 6070 | OH2 | TIP | 187 | 20.834 | 38.279 | 4.501 | 1 | 30.94 |
| 6071 | OH2 | TIP | 189 | 17.162 | −28.455 | 31.417 | 1 | 26.71 |
| 6072 | OH2 | TIP | 190 | 51.627 | −20.618 | −42.74 | 1 | 32.59 |
| 6073 | OH2 | TIP | 191 | 6.936 | −47.512 | −40.092 | 1 | 33.62 |
| 6074 | OH2 | TIP | 192 | 35.541 | −14.815 | 30.191 | 1 | 29.51 |
| 6075 | OH2 | TIP | 193 | 21.707 | 26.586 | −0.894 | 1 | 30.96 |
| 6076 | OH2 | TIP | 194 | 33.635 | −19.781 | −53.489 | 1 | 27.63 |
| 6077 | OH2 | TIP | 195 | 23.374 | −20.615 | −29.488 | 1 | 28.69 |
| 6078 | OH2 | TIP | 196 | 19.662 | −39.679 | −48.018 | 1 | 32.39 |
| 6079 | OH2 | TIP | 197 | 42.293 | 3.493 | −5.095 | 1 | 35.29 |
| 6080 | OH2 | TIP | 198 | 20.789 | 10.89 | 3.486 | 1 | 33.5 |
| 6081 | OH2 | TIP | 199 | 40.22 | 2.501 | 9.693 | 1 | 28.59 |
| 6082 | OH2 | TIP | 200 | 22.864 | −1.486 | 6.95 | 1 | 21.8 |
| 6083 | OH2 | TIP | 201 | 11.1 | −0.389 | 14.845 | 1 | 26.95 |
| 6084 | OH2 | TIP | 202 | 20.294 | −23.211 | −23.713 | 1 | 24.07 |
| 6085 | OH2 | TIP | 203 | 18.267 | −17.503 | 40.17 | 1 | 35.67 |
| 6086 | OH2 | TIP | 204 | 24.448 | 0.816 | 2.541 | 1 | 28.92 |
| 6087 | OH2 | TIP | 205 | 17.85 | 23.615 | 1.702 | 1 | 27.89 |
| 6088 | OH2 | TIP | 206 | 35.806 | 3.397 | −7.048 | 1 | 34.22 |
| 6089 | OH2 | TIP | 207 | 7.132 | −16.248 | −34.686 | 1 | 24.75 |
| 6090 | OH2 | TIP | 208 | 30.963 | −24.547 | 13.757 | 1 | 23.43 |
| 6091 | OH2 | TIP | 209 | 38.575 | −38.863 | −54.215 | 1 | 29.05 |
| 6092 | OH2 | TIP | 210 | 33.162 | −32.167 | 29.133 | 1 | 31.59 |
| 6093 | OH2 | TIP | 211 | 32.489 | −4.889 | 4.388 | 1 | 28.73 |
| 6094 | OH2 | TIP | 212 | 14.505 | −28.221 | 16.037 | 1 | 29.32 |
| 6095 | OH2 | TIP | 213 | 17.215 | 3.144 | 28.528 | 1 | 30.28 |
| 6096 | OH2 | TIP | 214 | 33.001 | −1.314 | 24.867 | 1 | 23.65 |
| 6097 | OH2 | TIP | 215 | 12.447 | −47.456 | −21.715 | 1 | 24.93 |
| 6098 | OH2 | TIP | 216 | 49.112 | −43.089 | −44.133 | 1 | 35.86 |
| 6099 | OH2 | TIP | 217 | 24.74 | 11.687 | 1.565 | 1 | 20.61 |
| 6100 | OH2 | TIP | 218 | 34.589 | −14.271 | 13.003 | 1 | 31.76 |
| 6101 | OH2 | TIP | 219 | 14.106 | 12.772 | 15.637 | 1 | 31.43 |
| 6102 | OH2 | TIP | 220 | 14.29 | −28.126 | −41.679 | 1 | 25.23 |
| 6103 | OH2 | TIP | 221 | 3.356 | −21.56 | 23.613 | 1 | 34.48 |
| 6104 | OH2 | TIP | 222 | 13.8 | 27.18 | 8.344 | 1 | 33.06 |
| 6105 | OH2 | TIP | 223 | 34.468 | −54.717 | −48.993 | 1 | 37.19 |
| 6106 | OH2 | TIP | 224 | 33.55 | −22.824 | 36.22 | 1 | 27.37 |
| 6107 | OH2 | TIP | 225 | 22.967 | −30.805 | −59.471 | 1 | 31.15 |
| 6108 | OH2 | TIP | 226 | 37.601 | −37.473 | −35.67 | 1 | 38.38 |
| 6109 | OH2 | TIP | 227 | 48.423 | 20.499 | 8.745 | 1 | 27.8 |
| 6110 | OH2 | TIP | 228 | 14.333 | 19.855 | 12.204 | 1 | 29.24 |
| 6111 | OH2 | TIP | 229 | 25.471 | 2.681 | −6.971 | 1 | 23.95 |
| 6112 | OH2 | TIP | 230 | −6.18 | −18.947 | −26.97 | 1 | 27.35 |
| 6113 | OH2 | TIP | 231 | 17.268 | 30.437 | 10.034 | 1 | 34.98 |
| 6114 | OH2 | TIP | 232 | 35.319 | −22.433 | 30.771 | 1 | 45.28 |
| 6115 | OH2 | TIP | 233 | 15.177 | 1.493 | 21.132 | 1 | 23.28 |
| 6116 | OH2 | TIP | 234 | 26.142 | −44.65 | −37.782 | 1 | 25.34 |
| 6117 | OH2 | TIP | 235 | 40.062 | 12.571 | −1.295 | 1 | 24.29 |
| 6118 | OH2 | TIP | 236 | 17.922 | −27.762 | 28.951 | 1 | 23.85 |
| 6119 | OH2 | TIP | 237 | 21.288 | −2.405 | 27.163 | 1 | 26.94 |
| 6120 | OH2 | TIP | 238 | 22.402 | 12.662 | −7.845 | 1 | 29.45 |
| 6121 | OH2 | TIP | 239 | 18.057 | 18.734 | 5.88 | 1 | 25.13 |
| 6122 | OH2 | TIP | 240 | 23.138 | 14.792 | −11.62 | 1 | 40.17 |
| 6123 | OH2 | TIP | 241 | 41.405 | 18.303 | 26.396 | 1 | 25.9 |
| 6124 | OH2 | TIP | 242 | 21.398 | 16.16 | 3.279 | 1 | 29.24 |
| 6125 | OH2 | TIP | 243 | 12.545 | −46.512 | −38.882 | 1 | 26.11 |
| 6126 | OH2 | TIP | 244 | −4.391 | −17.404 | −40.044 | 1 | 40.15 |
| 6127 | OH2 | TIP | 245 | 29.211 | −37.728 | −63.302 | 1 | 30.57 |
| 6128 | OH2 | TIP | 246 | 0.738 | −10.677 | 28.306 | 1 | 38.73 |
| 6129 | OH2 | TIP | 247 | −16.987 | −37.951 | −26.617 | 1 | 25.91 |
| 6130 | OH2 | TIP | 248 | 34.886 | 9.335 | −10.99 | 1 | 31.71 |
| 6131 | OH2 | TIP | 249 | 4.574 | −22.671 | 25.626 | 1 | 29.77 |
| 6132 | OH2 | TIP | 250 | 11.845 | −24.563 | −41.042 | 1 | 28.11 |
| 6133 | OH2 | TIP | 251 | 31.732 | 34.988 | 1.707 | 1 | 31.86 |
| 6134 | OH2 | TIP | 253 | 40.465 | 13.113 | 1.282 | 1 | 26.02 |
| 6135 | OH2 | TIP | 254 | 9.33 | −26.369 | −40.859 | 1 | 32.01 |
| 6136 | OH2 | TIP | 256 | 47.725 | −17.309 | −34.965 | 1 | 29.78 |
| 6137 | OH2 | TIP | 257 | 23.973 | −28.171 | −62.881 | 1 | 29.7 |
| 6138 | OH2 | TIP | 258 | 18.385 | −44.54 | −24.587 | 1 | 28.45 |
| 6139 | OH2 | TIP | 259 | 9.541 | −14.103 | 29.763 | 1 | 26.1 |
| 6140 | OH2 | TIP | 260 | 27.82 | −32.935 | −30.058 | 1 | 21.76 |
| 6141 | OH2 | TIP | 261 | 17.275 | −35.639 | −14.855 | 1 | 32.7 |
| 6142 | OH2 | TIP | 262 | 18.654 | 40.06 | 7.778 | 1 | 36.25 |
| 6143 | OH2 | TIP | 263 | 5.618 | −49.279 | −36.263 | 1 | 33.41 |
| 6144 | OH2 | TIP | 264 | 11.466 | −23.27 | 11.79 | 1 | 30.33 |
| 6145 | OH2 | TIP | 265 | 14.641 | −9.85 | 13.002 | 1 | 24.15 |
| 6146 | OH2 | TIP | 266 | 33.733 | −20.907 | −48.811 | 1 | 25.72 |
| 6147 | OH2 | TIP | 267 | 24.257 | −29.061 | 16.906 | 1 | 30.8 |
| 6148 | OH2 | TIP | 268 | 30.127 | −23.194 | −59.457 | 1 | 33.47 |
| 6149 | OH2 | TIP | 269 | 1.013 | −23.703 | −22.871 | 1 | 35.19 |
| 6150 | OH2 | TIP | 270 | 43.108 | −13.464 | −51.748 | 1 | 33.48 |
| 6151 | OH2 | TIP | 271 | 16.588 | 18.345 | 3.647 | 1 | 38.68 |
| 6152 | OH2 | TIP | 272 | 38.534 | 15.055 | −4.783 | 1 | 33.44 |
| 6153 | OH2 | TIP | 273 | −1.962 | −32.495 | −14.058 | 1 | 32.29 |
| 6154 | OH2 | TIP | 274 | 28.451 | −30.098 | −64.432 | 1 | 29.59 |
| 6155 | OH2 | TIP | 275 | 14.6 | −21.716 | −24.966 | 1 | 37.54 |
| 6156 | OH2 | TIP | 276 | 27.271 | −34.09 | −64.657 | 1 | 35.95 |
| 6157 | OH2 | TIP | 277 | 4.968 | −32.944 | −16.463 | 1 | 35.87 |
| 6158 | OH2 | TIP | 278 | 26.497 | −24.152 | −50.883 | 1 | 38.92 |
| 6159 | OH2 | TIP | 279 | 18.99 | −14.568 | 35.156 | 1 | 42.68 |
| 6160 | OH2 | TIP | 280 | 16.439 | 3.789 | 25.962 | 1 | 29.42 |
| 6161 | OH2 | TIP | 281 | 28.841 | −22.839 | −48.858 | 1 | 30.83 |
| 6162 | OH2 | TIP | 282 | 31.026 | −25.722 | −50.672 | 1 | 29.02 |

TABLE 2-continued

| Atom | Atom Type | Residue | # | X | Y | Z | OCC | B |
|---|---|---|---|---|---|---|---|---|
| 6163 | OH2 | TIP | 283 | 4.09 | −54.383 | −20.123 | 1 | 47.51 |
| 6164 | OH2 | TIP | 284 | −9.391 | −26.636 | −39.717 | 1 | 32.44 |
| 6165 | OH2 | TIP | 285 | 12.388 | −3.334 | 25.362 | 1 | 45.82 |
| 6166 | OH2 | TIP | 286 | 28.035 | 7.238 | 24.836 | 1 | 30.82 |
| 6167 | OH2 | TIP | 287 | 22.228 | 34.244 | −0.812 | 1 | 32.43 |
| 6168 | OH2 | TIP | 288 | 35.652 | −16.97 | −31.745 | 1 | 29.74 |
| 6169 | OH2 | TIP | 289 | 25.867 | −28.147 | 14.629 | 1 | 27.52 |
| 6170 | OH2 | TIP | 290 | 14.58 | −4.494 | 11.469 | 1 | 34.6 |
| 6171 | OH2 | TIP | 291 | 24.633 | 16.965 | −16.019 | 1 | 36.41 |
| 6172 | OH2 | TIP | 292 | −1.044 | −16.835 | −23.285 | 1 | 29 |
| 6173 | OH2 | TIP | 293 | 7.381 | −13.656 | 9.797 | 1 | 29.92 |
| 6174 | OH2 | TIP | 294 | 34.86 | −25.289 | 27.183 | 1 | 29.14 |
| 6175 | OH2 | TIP | 295 | 18.712 | 19.771 | 20.33 | 1 | 32.08 |
| 6176 | OH2 | TIP | 296 | 3.309 | −15.529 | −36.917 | 1 | 34.17 |
| 6177 | OH2 | TIP | 297 | 27.147 | 21.659 | 21.996 | 1 | 29.07 |
| 6178 | OH2 | TIP | 298 | 9.347 | −32.597 | −42.407 | 1 | 32.38 |
| 6179 | OH2 | TIP | 299 | 9.641 | −30.482 | 16.29 | 1 | 32.32 |
| 6180 | OH2 | TIP | 300 | 4.492 | −48.972 | −15.618 | 1 | 31.85 |
| 6181 | OH2 | TIP | 301 | 2.428 | −48.11 | −38.915 | 1 | 35.28 |
| 6182 | OH2 | TIP | 302 | 27.61 | 39.389 | 11.299 | 1 | 34.16 |
| 6183 | OH2 | TIP | 303 | 43.475 | −2.105 | 11.828 | 1 | 35.42 |
| 6184 | OH2 | TIP | 304 | 37.1 | 9.324 | −9.368 | 1 | 35.18 |
| 6185 | OH2 | TIP | 305 | 39.336 | 3.283 | −3.457 | 1 | 36.47 |
| 6186 | OH2 | TIP | 306 | 9.623 | −23.861 | −18.437 | 1 | 37.1 |
| 6187 | OH2 | TIP | 307 | 38.331 | −51.005 | −53.3 | 1 | 33.99 |
| 6188 | OH2 | TIP | 308 | 26.646 | 27.918 | −7.953 | 1 | 37.33 |
| 6189 | OH2 | TIP | 309 | 3.235 | −52.054 | −21.227 | 1 | 43.08 |
| 6190 | OH2 | TIP | 310 | 12.917 | −43.767 | −42.311 | 1 | 38.42 |
| 6191 | CO+2 | CO2 | 1 | 10.453 | −35.078 | −28.536 | 1 | 12.55 |
| 6192 | CO+2 | CO2 | 2 | 33.232 | −29.873 | −40.336 | 1 | 14.1 |
| 6193 | CO+2 | CO2 | 3 | 29.14 | 11.648 | 11.941 | 1 | 13.65 |
| 6194 | CO+2 | CO2 | 4 | 23.496 | −10.893 | 23.463 | 1 | 13.16 |
| 6195 | OH2 | TIP | 311 | 24.069 | 5.26 | 0.455 | 1 | 19.8 |
| 6196 | OH2 | TIP | 312 | 15.011 | −12.627 | 12.588 | 1 | 23.04 |
| 6197 | OH2 | TIP | 313 | 33.458 | −9.072 | 14.135 | 1 | 27.89 |
| 6198 | OH2 | TIP | 314 | 33.596 | −19.267 | 16.443 | 1 | 22.61 |
| 6199 | OH2 | TIP | 315 | 7.78 | −47.75 | −35.711 | 1 | 25.08 |
| 6200 | OH2 | TIP | 316 | 16.837 | −43.284 | −37.926 | 1 | 28.18 |
| 6201 | OH2 | TIP | 317 | 25.174 | 9.751 | −0.193 | 1 | 22.38 |
| 6202 | OH2 | TIP | 318 | 15.816 | 17.896 | 13.53 | 1 | 22.22 |
| 6203 | OH2 | TIP | 319 | 25.219 | −28.262 | −51.865 | 1 | 28.16 |
| 6204 | OH2 | TIP | 320 | −7.844 | −21.106 | −34.149 | 1 | 22.69 |
| 6205 | OH2 | TIP | 321 | 15.148 | −16.403 | 15.129 | 1 | 24.94 |
| 6206 | OH2 | TIP | 322 | 15.066 | 2.165 | 23.971 | 1 | 24.44 |
| 6207 | OH2 | TIP | 323 | 16.932 | 8.506 | 17.851 | 1 | 27.52 |
| 6208 | OH2 | TIP | 324 | 32.429 | −15.189 | −38.635 | 1 | 23.32 |
| 6209 | OH2 | TIP | 325 | 31.347 | 5.597 | 15.281 | 1 | 21.53 |
| 6210 | OH2 | TIP | 326 | 39.575 | 0.082 | 10.613 | 1 | 24.66 |
| 6211 | OH2 | TIP | 327 | 24.812 | −20.391 | −34.361 | 1 | 29.9 |
| 6212 | OH2 | TIP | 328 | 37.61 | −1.417 | 11.747 | 1 | 21.15 |
| 6213 | OH2 | TIP | 329 | 25.727 | 12.249 | 26.276 | 1 | 25.56 |
| 6214 | OH2 | TIP | 330 | 21.034 | −44.157 | −26.104 | 1 | 24.11 |
| 6215 | OH2 | TIP | 331 | 23.218 | −23.646 | 16.483 | 1 | 34.17 |
| 6216 | OH2 | TIP | 332 | 23.881 | 2.726 | −4.561 | 1 | 25.93 |
| 6217 | OH2 | TIP | 333 | 39.707 | 17.266 | 28.282 | 1 | 25.7 |
| 6218 | OH2 | TIP | 334 | −8.807 | −42.728 | −31.847 | 1 | 28 |
| 6219 | OH2 | TIP | 335 | 22.723 | 9.691 | −1.5 | 1 | 27.75 |
| 6220 | OH2 | TIP | 336 | 23.914 | −30.432 | −50.399 | 1 | 28.5 |
| 6221 | OH2 | TIP | 337 | 22.067 | 36.386 | 13.994 | 1 | 37.29 |
| 6222 | OH2 | TIP | 338 | 35.031 | −26.466 | −27.874 | 1 | 27.33 |
| 6223 | OH2 | TIP | 339 | 20.802 | −31.376 | 20.034 | 1 | 35.75 |
| 6224 | OH2 | TIP | 340 | 41.05 | −12.675 | 18.248 | 1 | 28.89 |
| 6225 | OH2 | TIP | 341 | −3.54 | −31.903 | −21.756 | 1 | 25.15 |
| 6226 | OH2 | TIP | 342 | 11.079 | −34.845 | −43.141 | 1 | 29.46 |
| 6227 | OH2 | TIP | 343 | 34.438 | −16.831 | −46.455 | 1 | 28.17 |
| 6228 | OH2 | TIP | 344 | 22.564 | 19.735 | 22.613 | 1 | 28.52 |
| 6229 | OH2 | TIP | 345 | 29.523 | −26.975 | −52.491 | 1 | 25.82 |
| 6230 | OH2 | TIP | 346 | 33.353 | −35.774 | −63.081 | 1 | 35.74 |
| 6231 | OH2 | TIP | 347 | −0.603 | −22.237 | −24.429 | 1 | 29 |
| 6232 | OH2 | TIP | 348 | −0.272 | −15.037 | 16.587 | 1 | 31.32 |
| 6233 | OH2 | TIP | 349 | 25.28 | 18.917 | −12.356 | 1 | 37.31 |
| 6234 | OH2 | TIP | 350 | 7.726 | −26.166 | −22.489 | 1 | 36.69 |
| 6235 | OH2 | TIP | 351 | 37.354 | −20.437 | −29.693 | 1 | 26.36 |
| 6236 | OH2 | TIP | 352 | 13.239 | −1.12 | 27.049 | 1 | 32.98 |
| 6237 | OH2 | TIP | 353 | −3.629 | −26.723 | −15.251 | 1 | 28.65 |
| 6238 | OH2 | TIP | 354 | 10.18 | −13.145 | 9.372 | 1 | 32.44 |
| 6239 | OH2 | TIP | 355 | 17.456 | 4.292 | 7.536 | 1 | 32.05 |
| 6240 | OH2 | TIP | 356 | 2.618 | −8.557 | 16.036 | 1 | 31.28 |
| 6241 | OH2 | TIP | 357 | 21.072 | −22.771 | −44.482 | 1 | 31.94 |
| 6242 | OH2 | TIP | 358 | 30.513 | −15.707 | −28.742 | 1 | 29.4 |
| 6243 | OH2 | TIP | 359 | 39.416 | −39.161 | −51.834 | 1 | 37 |
| 6244 | OH2 | TIP | 360 | 17.366 | −29.421 | −24.951 | 1 | 30.95 |
| 6245 | OH2 | TIP | 361 | 35.407 | −8.202 | 27.283 | 1 | 29.9 |
| 6246 | OH2 | TIP | 362 | 35.516 | 5.746 | 15.737 | 1 | 30.68 |
| 6247 | OH2 | TIP | 363 | 47.201 | 20.934 | 11.176 | 1 | 35.81 |
| 6248 | OH2 | TIP | 364 | 41.796 | 24.969 | 5.811 | 1 | 34.52 |
| 6249 | OH2 | TIP | 365 | 28.286 | −16.142 | 11.345 | 1 | 30.28 |
| 6250 | OH2 | TIP | 366 | −5.972 | −38.333 | −19.935 | 1 | 31.81 |
| 6251 | OH2 | TIP | 367 | 31.863 | 13.711 | −13.406 | 1 | 37.34 |
| 6252 | OH2 | TIP | 368 | 30.284 | −36.549 | 18.879 | 1 | 31.49 |
| 6253 | OH2 | TIP | 369 | 24.13 | −9.964 | 8.772 | 1 | 28.31 |
| 6254 | OH2 | TIP | 370 | 3.392 | −12.97 | −18.713 | 1 | 33.46 |
| 6255 | OH2 | TIP | 371 | 17.121 | −32.015 | −25.126 | 1 | 34.12 |
| 6256 | OH2 | TIP | 372 | 37.691 | −14.248 | 25.719 | 1 | 30.02 |
| 6257 | OH2 | TIP | 373 | 0.72 | −38.18 | −35.508 | 1 | 30.38 |
| 6258 | OH2 | TIP | 374 | 50.953 | −13.891 | −40.245 | 1 | 32.44 |
| 6259 | OH2 | TIP | 375 | 28.004 | −28.392 | −66.359 | 1 | 33.55 |
| 6260 | OH2 | TIP | 376 | 32.972 | −28.472 | 21.216 | 1 | 29.49 |
| 6261 | OH2 | TIP | 377 | −11.563 | −25.346 | −38.467 | 1 | 32.69 |
| 6262 | OH2 | TIP | 378 | 3.812 | −24.175 | 13.801 | 1 | 31.72 |
| 6263 | OH2 | TIP | 379 | 38.633 | −14.223 | −50.332 | 1 | 31.57 |
| 6264 | OH2 | TIP | 380 | 27.33 | −15.943 | −36.507 | 1 | 30.7 |
| 6265 | OH2 | TIP | 381 | 21.697 | −45.242 | −39.738 | 1 | 28.93 |
| 6266 | OH2 | TIP | 382 | 7.162 | −18.189 | −37.95 | 1 | 31.35 |
| 6267 | OH2 | TIP | 383 | −5.001 | −44.473 | −35.282 | 1 | 31.93 |
| 6268 | OH2 | TIP | 384 | −3.595 | −16.088 | −35.317 | 1 | 32.69 |
| 6269 | OH2 | TIP | 385 | 16.977 | −51.597 | −33.702 | 1 | 32.09 |
| 6270 | OH2 | TIP | 386 | 19.355 | −0.712 | 8.555 | 1 | 40.25 |
| 6271 | OH2 | TIP | 387 | 25.325 | −19.536 | 39.952 | 1 | 31.41 |
| 6272 | OH2 | TIP | 388 | 10.165 | −47.761 | −20.162 | 1 | 35.1 |
| 6273 | OH2 | TIP | 389 | 39.646 | 21.287 | −2.286 | 1 | 32.98 |
| 6274 | OH2 | TIP | 390 | 46.649 | −34.544 | −28.408 | 1 | 42.8 |
| 6275 | OH2 | TIP | 391 | 20.598 | −16.68 | 13.443 | 1 | 35.34 |
| 6276 | OH2 | TIP | 392 | 39.071 | −23.8 | −64.488 | 1 | 33.65 |
| 6277 | OH2 | TIP | 393 | 0.997 | −16.347 | −21.644 | 1 | 32.53 |
| 6278 | OH2 | TIP | 394 | 22.349 | −35.125 | −59.795 | 1 | 31.15 |
| 6279 | OH2 | TIP | 395 | 12.687 | −18.215 | 37.796 | 1 | 37 |
| 6280 | OH2 | TIP | 396 | 2.338 | −19.808 | −43.324 | 1 | 37.39 |
| 6281 | OH2 | TIP | 397 | 33.172 | −11.71 | −43.892 | 1 | 36.22 |
| 6282 | OH2 | TIP | 398 | 37.129 | −39.098 | −44.891 | 1 | 28.09 |
| 6283 | OH2 | TIP | 399 | 22.521 | −37.753 | −54.442 | 1 | 32.46 |
| 6284 | OH2 | TIP | 400 | 51.287 | −29.017 | −37.833 | 1 | 34.05 |
| 6285 | OH2 | TIP | 401 | −1.064 | −19.858 | −14.468 | 1 | 32.56 |
| 6286 | OH2 | TIP | 402 | 24.691 | −43.362 | −49.47 | 1 | 38.34 |
| 6287 | OH2 | TIP | 403 | 20.738 | −32.61 | −59.5 | 1 | 32.99 |
| 6288 | OH2 | TIP | 404 | 12.595 | −31.46 | 19.024 | 1 | 33.82 |
| 6289 | OH2 | TIP | 405 | 18.105 | −15.868 | 12.09 | 1 | 34.43 |
| 6290 | OH2 | TIP | 406 | 7.611 | −42.183 | −40.935 | 1 | 32.98 |
| 6291 | OH2 | TIP | 407 | 17.391 | −49.721 | −27.171 | 1 | 36.8 |
| 6292 | OH2 | TIP | 408 | 25.535 | −43.199 | −40.615 | 1 | 31.5 |
| 6293 | OH2 | TIP | 409 | 33.083 | −31.417 | 22.888 | 1 | 33.66 |
| 6294 | OH2 | TIP | 410 | −2.808 | −53.102 | −29.193 | 1 | 34.2 |
| 6295 | OH2 | TIP | 411 | 37.321 | −5.602 | 12.317 | 1 | 34.19 |
| 6296 | OH2 | TIP | 412 | 37.367 | −19.828 | −58.269 | 1 | 36.24 |
| 6297 | OH2 | TIP | 413 | 9.635 | −50.106 | −8.201 | 1 | 40.45 |
| 6298 | OH2 | TIP | 414 | 15.722 | −41.021 | −45.768 | 1 | 42.62 |
| 6299 | OH2 | TIP | 415 | 38.385 | −39.79 | −40.726 | 1 | 34.06 |
| 6300 | OH2 | TIP | 416 | 8.651 | −26.095 | −20.014 | 1 | 35.71 |
| 6301 | OH2 | TIP | 417 | 24.142 | 38.337 | 18.653 | 1 | 40.04 |
| 6302 | OH2 | TIP | 418 | 26.77 | −21.36 | 38.442 | 1 | 32.35 |
| 6303 | OH2 | TIP | 419 | 32.911 | 37.078 | −3.793 | 1 | 38 |
| 6304 | OH2 | TIP | 420 | 15.057 | 15.785 | 23.393 | 1 | 33.26 |
| 6305 | OH2 | TIP | 421 | 24.904 | 30.269 | 17.279 | 1 | 31.4 |
| 6306 | OH2 | TIP | 422 | 3.674 | −32.586 | −39.73 | 1 | 38.36 |
| 6307 | OH2 | TIP | 423 | 14.284 | −32.314 | −19.769 | 1 | 39.22 |
| 6308 | OH2 | TIP | 424 | 4.678 | −11.304 | 34.52 | 1 | 37.7 |
| 6309 | OH2 | TIP | 425 | 22.283 | −37.993 | −58.69 | 1 | 35.34 |
| 6310 | OH2 | TIP | 426 | 18.207 | −18.184 | −38.911 | 1 | 39.78 |
| 6311 | OH2 | TIP | 427 | 1.8 | −52.44 | −30.628 | 1 | 45.89 |
| 6312 | OH2 | TIP | 428 | 25.841 | −7.661 | 8.032 | 1 | 33.37 |
| 6313 | OH2 | TIP | 429 | 12.119 | −50.627 | −29.814 | 1 | 34.36 |
| 6314 | OH2 | TIP | 430 | 24.621 | −4.429 | 4.619 | 1 | 36.43 |

TABLE 2-continued

| Atom | Atom Type | Residue | # | X | Y | Z | OCC | B |
|---|---|---|---|---|---|---|---|---|
| 6315 | OH2 | TIP | 431 | 27.86 | 7.207 | -12.273 | 1 | 34.81 |
| 6316 | OH2 | TIP | 432 | 7.808 | -26.976 | -38.775 | 1 | 37.85 |
| 6317 | OH2 | TIP | 433 | 33.626 | -13.012 | -39.972 | 1 | 30.48 |
| 6318 | OH2 | TIP | 434 | 34.902 | -20.432 | -27.208 | 1 | 41.43 |
| 6319 | OH2 | TIP | 435 | 19.09 | 39.547 | 3.02 | 1 | 34.83 |
| 6320 | OH2 | TIP | 436 | 43.7 | -23.584 | -31.36 | 1 | 35.05 |
| 6321 | OH2 | TIP | 437 | 12.13 | 6.187 | 11.961 | 1 | 36.81 |
| 6322 | OH2 | TIP | 438 | 36.049 | -33.207 | 30.386 | 1 | 41.75 |
| 6323 | OH2 | TIP | 439 | 39.099 | 10.823 | 7.552 | 1 | 34.04 |
| 6324 | OH2 | TIP | 440 | 19.166 | -25.243 | -44.038 | 1 | 41.37 |
| 6325 | OH2 | TIP | 441 | 42.855 | -15.96 | -52.971 | 1 | 38.21 |
| 6326 | OH2 | TIP | 442 | -12.652 | -35.133 | -22.106 | 1 | 39.2 |
| 6327 | OH2 | TIP | 443 | 17.39 | -27.019 | -43.511 | 1 | 37.93 |
| 6328 | OH2 | TIP | 444 | 33.83 | -6.642 | 13.549 | 1 | 34.28 |
| 6329 | OH2 | TIP | 445 | -0.42 | -40.5 | -35.67 | 1 | 36.62 |
| 6330 | OH2 | TIP | 446 | 32.054 | -41.166 | -37.284 | 1 | 38.51 |
| 6331 | OH2 | TIP | 447 | 46.087 | -34.51 | -55.06 | 1 | 35.68 |
| 6332 | OH2 | TIP | 448 | 26.19 | -3.968 | 29.849 | 1 | 34.86 |
| 6333 | OH2 | TIP | 449 | 3.055 | -51.861 | -24.758 | 1 | 41.26 |
| 6334 | OH2 | TIP | 450 | 3.502 | -16.109 | -30.211 | 1 | 33.95 |
| 6335 | OH2 | TIP | 451 | 14.833 | -31.458 | -43.551 | 1 | 38.79 |
| 6336 | OH2 | TIP | 452 | 4.971 | -15.808 | -15.003 | 1 | 37.4 |
| 6337 | OH2 | TIP | 453 | 19.574 | -1.808 | 29.246 | 1 | 35.44 |
| 6338 | OH2 | TIP | 454 | 28.498 | -31.663 | 32.177 | 1 | 33.09 |
| 6339 | OH2 | TIP | 455 | 12.905 | -22.234 | -40.047 | 1 | 36.96 |
| 6340 | OH2 | TIP | 456 | 47.327 | 21.979 | 6.75 | 1 | 39.43 |
| 6341 | OH2 | TIP | 457 | 20.335 | -42.225 | -47.861 | 1 | 38.94 |
| 6342 | OH2 | TIP | 458 | 31.12 | -9.975 | 40.58 | 1 | 36.59 |
| 6343 | OH2 | TIP | 459 | 10.521 | -28.242 | -19.507 | 1 | 35.18 |
| 6344 | OH2 | TIP | 460 | 0.288 | -16.261 | 13.699 | 1 | 42.23 |
| 6345 | OH2 | TIP | 461 | 21.234 | -24.823 | 15.141 | 1 | 42.81 |
| 6346 | OH2 | TIP | 462 | 2.184 | -32.758 | -35.682 | 1 | 31.89 |
| 6347 | OH2 | TIP | 463 | 1.909 | -30.623 | -37.183 | 1 | 39.93 |
| 6348 | OH2 | TIP | 464 | 44.364 | -10.916 | -41.977 | 1 | 41.22 |
| 6349 | OH2 | TIP | 465 | 20.651 | 37.628 | 12.237 | 1 | 41.51 |
| 6350 | OH2 | TIP | 466 | 15.161 | -2.437 | 9.719 | 1 | 37.03 |
| 6351 | OH2 | TIP | 467 | 29.294 | -12.928 | -41.176 | 1 | 36.05 |
| 6352 | OH2 | TIP | 468 | -2.299 | -52.454 | -34.091 | 1 | 34.25 |
| 6353 | OH2 | TIP | 469 | -10.312 | -22.932 | -38.107 | 1 | 35.46 |
| 6354 | OH2 | TIP | 470 | 36.504 | -2.706 | 3.247 | 1 | 36.72 |
| 6355 | OH2 | TIP | 471 | -8.711 | -35.18 | -36.601 | 1 | 35.31 |
| 6356 | OH2 | TIP | 472 | 14.146 | -24.148 | -42.461 | 1 | 39.81 |
| 6357 | OH2 | TIP | 473 | 28.166 | 2.599 | -10.98 | 1 | 41.47 |
| 6358 | OH2 | TIP | 474 | 38.434 | 17.832 | -5.154 | 1 | 40.59 |
| 6359 | OH2 | TIP | 475 | 28.083 | -26.282 | -64.129 | 1 | 38.23 |
| 6360 | OH2 | TIP | 476 | 12.581 | 11.925 | 13.618 | 1 | 35.26 |
| 6361 | OH2 | TIP | 477 | 27.395 | -34.462 | 20.002 | 1 | 35.15 |
| 6362 | OH2 | TIP | 478 | 21.166 | -30.522 | -49.59 | 1 | 32.03 |
| 6363 | OH2 | TIP | 479 | 14.047 | 7.213 | 15.254 | 1 | 33.56 |
| 6364 | OH2 | TIP | 480 | 32.879 | -9.689 | 10.51 | 1 | 37.64 |
| 6365 | OH2 | TIP | 481 | 15.224 | -8.002 | 11.139 | 1 | 30.88 |
| 6366 | OH2 | TIP | 482 | 41.146 | -23.596 | -30.216 | 1 | 35.15 |
| 6367 | OH2 | TIP | 483 | 15.967 | -25.203 | 36.332 | 1 | 35.09 |
| 6368 | OH2 | TIP | 484 | 5.981 | -11.588 | 8.952 | 1 | 36.56 |
| 6369 | OH2 | TIP | 485 | 15.057 | 2.108 | 9.758 | 1 | 45.55 |
| 6370 | OH2 | TIP | 486 | 12.083 | -17.266 | -31.824 | 1 | 41.19 |
| 6371 | OH2 | TIP | 487 | 32.204 | -20.867 | -51.176 | 1 | 42.27 |
| 6372 | OH2 | TIP | 488 | 25.395 | 19.878 | 21.568 | 1 | 36.68 |
| 6373 | OH2 | TIP | 489 | -7.87 | -40.568 | -34.052 | 1 | 33.51 |
| 6374 | OH2 | TIP | 490 | 18.429 | -19.582 | 15.061 | 1 | 38.89 |
| 6375 | OH2 | TIP | 491 | 2.675 | -42.405 | -13.702 | 1 | 32.67 |
| 6376 | OH2 | TIP | 492 | 22.18 | -7.047 | 8.561 | 1 | 38.4 |
| 6377 | OH2 | TIP | 493 | 13.123 | -47.257 | -24.16 | 1 | 41.15 |
| 6378 | OH2 | TIP | 494 | 35.312 | -25.283 | 30.357 | 1 | 40.86 |
| 6379 | OH2 | TIP | 495 | 44.764 | -35.985 | -41.524 | 1 | 43.57 |
| 6380 | OH2 | TIP | 496 | 12.876 | 4.829 | 25.398 | 1 | 34.22 |
| 6381 | OH2 | TIP | 497 | 22.342 | -18.441 | -36.606 | 1 | 33.29 |
| 6382 | OH2 | TIP | 498 | -2.711 | -56.277 | -21.012 | 1 | 43.77 |
| 6383 | OH2 | TIP | 499 | 33.795 | 11.713 | -11.242 | 1 | 38.44 |
| 6384 | OH2 | TIP | 500 | 29.852 | -43.827 | -42.753 | 1 | 35.6 |
| 6385 | OH2 | TIP | 501 | 35.96 | 29.463 | 11.919 | 1 | 42.18 |
| 6386 | OH2 | TIP | 502 | 24.836 | -21.146 | -46.08 | 1 | 37.46 |
| 6387 | OH2 | TIP | 503 | 13.153 | -41.383 | -44.919 | 1 | 38.08 |
| 6388 | OH2 | TIP | 504 | -8.986 | -45.888 | -32.296 | 1 | 36.66 |
| 6389 | OH2 | TIP | 505 | 23.734 | -3.724 | 27.318 | 1 | 39.06 |
| 6390 | OH2 | TIP | 506 | 21.131 | 23.414 | -1.99 | 1 | 31.9 |
| 6391 | OH2 | TIP | 507 | 32.108 | -51.045 | -54.689 | 1 | 33.62 |
| 6392 | OH2 | TIP | 508 | 7.188 | -2.072 | 26.597 | 1 | 38.3 |
| 6393 | OH2 | TIP | 509 | 40.309 | 11.815 | 11.791 | 1 | 37.19 |
| 6394 | OH2 | TIP | 510 | 28.502 | 37.218 | 18.132 | 1 | 41.89 |
| 6395 | OH2 | TIP | 511 | 51.47 | -32.369 | -37.324 | 1 | 41.8 |
| 6396 | OH2 | TIP | 512 | 0.788 | -28.061 | -10.835 | 1 | 40.62 |
| 6397 | OH2 | TIP | 513 | 22.748 | 15.057 | -17.055 | 1 | 38.31 |
| 6398 | OH2 | TIP | 514 | 31.05 | 30.483 | 18.513 | 1 | 33.86 |
| 6399 | OH2 | TIP | 515 | 55.256 | -21.68 | -50.703 | 1 | 40.46 |
| 6400 | OH2 | TIP | 516 | 16.456 | 19.786 | 18.51 | 1 | 38.05 |
| 6401 | OH2 | TIP | 517 | 34.829 | 9.566 | 19.537 | 1 | 45.71 |
| 6402 | OH2 | TIP | 518 | 8.728 | -44.609 | -41.439 | 1 | 35.55 |
| 6403 | OH2 | TIP | 519 | 32.83 | -30.198 | 17.616 | 1 | 34.26 |
| 6404 | OH2 | TIP | 520 | -0.639 | -51.75 | -30.965 | 1 | 36.67 |
| 6405 | OH2 | TIP | 521 | -9.841 | -31.217 | -41.703 | 1 | 46.09 |
| 6406 | OH2 | TIP | 522 | 39.794 | -11.519 | 24.703 | 1 | 36.83 |
| 6407 | OH2 | TIP | 523 | 31.857 | -16.969 | 10.722 | 1 | 35.26 |
| 6408 | OH2 | TIP | 524 | 14.098 | -36.201 | -45.146 | 1 | 39.09 |
| 6409 | OH2 | TIP | 525 | 38.33 | -20.605 | 24.037 | 1 | 37.11 |
| 6410 | OH2 | TIP | 526 | 44.549 | 21.465 | 1.417 | 1 | 39.42 |
| 6411 | OH2 | TIP | 527 | 24.842 | -47.043 | -40.291 | 1 | 39.23 |
| 6412 | OH2 | TIP | 528 | 34.503 | -37.619 | -61.664 | 1 | 40.78 |
| 6413 | OH2 | TIP | 529 | 8.882 | -15.507 | -32.945 | 1 | 41.54 |
| 6414 | OH2 | TIP | 530 | 29.687 | -48.32 | -48.727 | 1 | 38.74 |
| 6415 | OH2 | TIP | 531 | 9.685 | 0.764 | 16.791 | 1 | 37.29 |
| 6416 | OH2 | TIP | 532 | 33.885 | -35.86 | -32.718 | 1 | 41.42 |
| 6417 | OH2 | TIP | 533 | -1.411 | -52.985 | -24.522 | 1 | 41.83 |
| 6418 | OH2 | TIP | 534 | 43.408 | -10.013 | -48.77 | 1 | 41.19 |
| 6419 | OH2 | TIP | 535 | 5.848 | -47.077 | -14.337 | 1 | 37.17 |
| 6420 | OH2 | TIP | 536 | 51.865 | -18.499 | -57.623 | 1 | 39.16 |
| 6421 | OH2 | TIP | 537 | 25.749 | -42.968 | -53.267 | 1 | 36.61 |
| 6422 | OH2 | TIP | 538 | -0.402 | -43.34 | -38.563 | 1 | 37.06 |
| 6423 | OH2 | TIP | 539 | 30.134 | -42.368 | -55.855 | 1 | 40.77 |
| 6424 | OH2 | TIP | 540 | 8.534 | -1.359 | 20.436 | 1 | 46.97 |
| 6425 | OH2 | TIP | 541 | 16.681 | 27.165 | 12.162 | 1 | 47.37 |
| 6426 | OH2 | TIP | 542 | 17.741 | -8.008 | 32.62 | 1 | 36.27 |
| 6427 | OH2 | TIP | 543 | 45.164 | 6.604 | -5.044 | 1 | 39.46 |
| 6428 | OH2 | TIP | 544 | 50.242 | 7.78 | -0.661 | 1 | 38.2 |
| 6429 | OH2 | TIP | 545 | 34.121 | -17.794 | -27.964 | 1 | 40.15 |
| 6430 | OH2 | TIP | 546 | 36.858 | -39.708 | -58.297 | 1 | 39.76 |
| 6431 | OH2 | TIP | 547 | 24.823 | -3.189 | 34.694 | 1 | 46.09 |
| 6432 | OH2 | TIP | 548 | 38.616 | 23.35 | 21.273 | 1 | 44.44 |
| 6433 | OH2 | TIP | 549 | 40.407 | -3.63 | 11.793 | 1 | 35.15 |
| 6434 | OH2 | TIP | 550 | 29.153 | 25.855 | 28.918 | 1 | 38.77 |
| 6435 | OH2 | TIP | 551 | 38.323 | -43.473 | -43.198 | 1 | 37.36 |
| 6436 | OH2 | TIP | 552 | 44.046 | 10.729 | 9.264 | 1 | 38.69 |
| 6437 | OH2 | TIP | 553 | 11.088 | -20.126 | -38.958 | 1 | 37.49 |
| 6438 | OH2 | TIP | 554 | 44.64 | 10.057 | -3.956 | 1 | 44.4 |
| 6439 | OH2 | TIP | 555 | 21.669 | 28.545 | 15.594 | 1 | 35.89 |
| 6440 | OH2 | TIP | 556 | 35.147 | 5.131 | -10.946 | 1 | 35.56 |
| 6441 | OH2 | TIP | 557 | 22.819 | 19.607 | -6.135 | 1 | 39.68 |
| 6442 | OH2 | TIP | 558 | 31.869 | -31.833 | -66.072 | 1 | 42.63 |
| 6443 | OH2 | TIP | 559 | 10.252 | -10.643 | -18.267 | 1 | 40.4 |
| 6444 | OH2 | TIP | 560 | 40.548 | -38.393 | -55.975 | 1 | 42.47 |
| 6445 | OH2 | TIP | 561 | 40.556 | -12.889 | -36.712 | 1 | 39.21 |

OTHER EMBODIMENTS

The foregoing has been a description of certain non-limiting preferred embodiments of the invention. Those of ordinary skill in the art will appreciate that various changes and modifications to this description may be made without departing from the spirit or scope of the present invention, as defined in the following claims.

We claim:

1. A method for the design and identification of a potential binding compound for human peptide deformylase (HsPDF) comprising the steps of:
   (a) generating, on a computer, a three-dimensional structure of HsPDF having the structural coordinates of Tables 1 and/or 2;
   (b) identifying amino acid residues forming an HsPDF active site from the three-dimensional structure of HsPDF from step (a) in order to generate a three-dimensional model of the HsPDF active site, wherein the HsPDF active site comprises amino acids $^{50}$CVGLSAPQ$^{57}$ (SEQ ID NO:10), $^{112}$EGCES$^{116}$ (SEQ ID NO:12), and $^{156}$HEMDHL$^{161}$ (SEQ ID NO:13), and $^{176}$TNVYWMKVND$^{185}$ (SEQ ID NO:8) according to Table 1 and/or 2;
   (c) designing and/or selecting a compound that potentially binds to the HsPDF active site using the three-dimensional model of the HsPDF active site; and
   (d) synthesizing and/or choosing the potential binding compound.

2. The method according to claim 1, the method further comprising the steps of:
   (e) contacting the potential binding compound with HsPDF in the presence of a formylated substrate; and
   (f) determining the percent inhibition of deformylase activity of HsPDF.

3. The method according to claim 1, the method further comprising the steps of:
   (e) contacting the potential binding compound with a cell, virus, bacterium, or parasite; and
   (f) determining the cytotoxicity of the potential binding compound to the cell, virus, bacterium, or parasite.

4. The method of claim 1, wherein the HsPDF active site comprises amino acid residues $^{50}$CVGLSAPQ$^{57}$ (SEQ ID NO:11), $^{69}$LPEALCRECPPRQRALRQMEPF$^{90}$ (SEQ ID NO:7), $^{104}$DSRLVT$^{109}$ (SEQ ID NO:9), $^{112}$EGCES$^{116}$ (SEQ ID NO:12), $^{117}$VAG$^{119}$, $^{149}$WAARIIQ$^{155}$ (SEQ ID NO:10), $^{156}$HEMDHL$^{161}$ (SEQ ID NO:13), and $^{176}$TNVYWMKVND$^{185}$ (SEQ ID NO:8) according to Tables 1 and/or 2.

5. The method of claim 1, wherein the HsPDF active site comprises amino acid residues $^{50}$CVGLSAPQ$^{57}$ (SEQ ID NO:11), $^{104}$DSRLVT$^{109}$ (SEQ ID NO:9), $^{112}$EGCES$^{116}$ (SEQ ID NO:12), $^{117}$VAG$^{119}$, $^{149}$WAARIIQ$^{155}$ (SEQ ID NO:10), and $^{156}$HEMDHL$^{161}$ (SEQ ID NO:13), and $^{176}$TNVYWMKVND$^{185}$ (SEQ ID NO:8) according to Tables 1 and/or 2.

6. A method for the design and identification of a potential binding compound for HsPDF comprising the steps of:
   (a) generating, on a computer, a three-dimensional structure of HsPDF having the structural coordinates of Tables 1 andor 2;
   (b) identifying amino acid residues and a $Co^{2+}$ cation forming an HsPDF active site from the three-dimensional structure of HsPDF from step (a) in order to generate a three-dimensional model of the HsPDF active site, wherein the HsPDF active site comprises amino acids $^{50}$CVGLSAPQ$^{57}$(SEQ ID NO:10), $^{112}$EGCES$^{116}$ (SEQ ID NO:12), $^{156}$HEMDHL$^{161}$ (SEQ ID NO:13) $^{176}$TNVYWMKVND$^{185}$ (SEQ ID NO:8) , and the cation $Co^{2+}$ according to Tables 1 and/or 2;
   (c) designing and/or selecting a compound that potentially binds to at least one amino acid in the active site of HsPDF using the three-dimensional model of the HsPDF active site from step (b); and
   (d) synthesizing and/or choosing the potential binding compound.

7. The method according to claim 6, the method further comprising the steps of:
   (e) contacting the potential binding compound with HsPDF in the presence of a formylated substrate; and
   (f) determining the percent inhibition of deformylase activity of HsPDF.

8. The method according to claim 6, the method further comprising the steps of:
   (e) contacting the potential binding compound with a cell, virus, bacterium, or parasite; and
   (f) determining the cytotoxicity of the potential binding compound to the cell, virus, bacterium, or parasite.

9. The method of claim 6, wherein the HsPDF active site comprises amino acid residues $^{50}$CVGLSAPQ$^{57}$ (SEQ ID NO:11), $^{69}$LPEALCRECPPRQRALRQMEPF$^{90}$ (SEQ ID NO:7), $^{104}$DSRLVT$^{109}$ (SEQ ID NO:9), $^{112}$EGCES$^{116}$ (SEQ ID NO:12), $^{117}$VAG$^{119}$, $^{149}$WAARIIQ$^{155}$ (SEQ ID NO:10), $^{156}$HEMDHL$^{161}$ (SEQ ID NO:13), and $^{176}$TNVYWMKVND$^{185}$ (SEQ ID NO:8) and the cation Co$^{2+}$ according to Tables 1 and/or 2.

10. The method of claim 6, wherein the HsPDF active site comprises amino acid residues $^{50}$CVGLSAPQ$^{57}$ (SEQ ID NO:11), $^{104}$DSRLVT$^{109}$ (SEQ ID NO:9), $^{112}$EGCES$^{116}$ (SEQ ID NO:12), $^{117}$VAG$^{119}$, $^{149}$WAARIIQ$^{155}$ (SEQ ID NO:10), and $^{156}$HEMDHL$^{161}$ (SEQ ID NO:13), and $^{176}$TNVYWMKVND$^{185}$ (SEQ ID NO:8) and the cation Co$^{2+}$ according to Tables 1 and/or 2.

* * * * *

UNITED STATES PATENT AND TRADEMARK OFFICE
CERTIFICATE OF CORRECTION

| | | |
|---|---|---|
| PATENT NO. | : 7,747,395 B2 | Page 1 of 1 |
| APPLICATION NO. | : 11/787237 | |
| DATED | : June 29, 2010 | |
| INVENTOR(S) | : David Scheinberg | |

It is certified that error appears in the above-identified patent and that said Letters Patent is hereby corrected as shown below:

Specification

In column 1, beginning at line 7 and ending at line 10, please delete:

"The work described herein was supported, in part, by a grant from the National Institutes of Health (CA-55349). The United States government may have certain rights in the invention."

and insert:

-- This invention was made with government support under grant number CA055394 awarded by National Institutes of Health. The government has certain rights in the invention. --

Signed and Sealed this
Seventeenth Day of May, 2016

Michelle K. Lee
*Director of the United States Patent and Trademark Office*